United States Patent
Granberg et al.

(10) Patent No.: US 11,667,602 B2
(45) Date of Patent: Jun. 6, 2023

(54) COMPOUNDS AND THEIR USE

(71) Applicants: AstraZeneca AB, Södertälje (SE); MITSUBISHI TANABE PHARMA CORPORATION, Osaka (JP)

(72) Inventors: Kenneth Lars Granberg, Gothenburg (SE); Shigeki Sakamaki, Osaka (JP); Ryuichi Fuchigami, Osaka (JP); Yasuki Niwa, Osaka (JP); Masakazu Fujio, Osaka (JP); Hans Fredrik Bergström, Göthenburg (SE); Stig Jonas Boström, Göthenburg (SE)

(73) Assignees: AstraZeneca AB (SE); MITSUBISHI TANABE PHARMA CORPORATION, Osaka (JP)

( * ) Notice: Subject to any disclaimer, the term of this patent is extended or adjusted under 35 U.S.C. 154(b) by 0 days.

(21) Appl. No.: 17/457,953

(22) Filed: Dec. 7, 2021

(65) Prior Publication Data
US 2023/0078576 A1     Mar. 16, 2023

Related U.S. Application Data

(60) Provisional application No. 63/122,690, filed on Dec. 8, 2020.

(51) Int. Cl.
*C07C 233/81* (2006.01)

(52) U.S. Cl.
CPC ........ *C07C 233/81* (2013.01); *C07B 2200/13* (2013.01)

(58) Field of Classification Search
CPC .......................... C07C 233/81; C07B 2200/13
See application file for complete search history.

(56) References Cited

FOREIGN PATENT DOCUMENTS

WO     2013/165606 A1     7/2012

OTHER PUBLICATIONS

Wilson Kenneth J. et al: "Optimization of the first small-molecule relaxin/insulin-like family peptide receptor (RXFP1) agonists: Activation results in an antifibrotic gene expression profile", European Journal of Medicinal Chemistry, vol. 156, Jun. 7, 2018 (Jun. 7, 2018), pp. 79-92.

Martina Kocan et al: "ML290 is a biased allosteric agonist at the relaxin receptor RXFP1", Scientific Reports, vol. 7, No. 2968, Jun. 7, 2017 (Jun. 7, 2017), pp. 1-14.

Lin Tingting et al: "Design, synthesis, and biological evaluation of 4-benzoylamino-IH-pyrazole-3-carboxamide derivatives as potent CDK2 inhibitors", European Journal of Medicinal Chemistry, vol. 215, 113281, Feb. 11, 2021 (Feb. 11, 2021), pp. 1-12.

McBride Andrew et al: "In search of a small molecule agonist of the relaxin receptor RXFP1 for the treatment of liver fibrosis" Scientific Reports, Sep. 7, 2017 (Sep. 7, 2017), pp. 1-11.

Xiao Jingbo et al: "Identification and optimization of small-molecule agonists of the human relaxin hormone receptor RXFP1" nature communications, Jun. 14, 2013 (Jun. 13, 2013), pp. 1-7.

Agoulnik Alexander I et al: "Synthetic non-peptide low molecular weight agonists of the relaxin receptor 1", British Journal of Pharmacology (2017) 174, pp. 977-989.

*Primary Examiner* — Jeffrey S Lundgren
*Assistant Examiner* — William Y Lee

(57) ABSTRACT

The specification generally relates to compounds of Formula (I), and pharmaceutically acceptable salts thereof, where A, U, V, W, X, Y, Z, $R^1$, $R^2$, $R^3$, $R^4$ and $R^5$ have the meanings defined herein. Such compounds are modulators of RXFP1 and may be useful as therapeutic agents. The specification also relates to the use of such compounds to treat or prevent diseases and conditions including heart failure, heart failure with preserved ejection fraction, heart failure with mid-range ejection fraction, heart failure with reduced ejection fraction, chronic kidney disease and acute kidney injury. The specification further relates to compositions comprising such compounds, intermediates useful in processes for preparing such compounds, and processes for preparing such compounds using such intermediates.

6 Claims, 8 Drawing Sheets

COMPOUNDS AND THEIR USE

RELATED APPLICATIONS

Figure 1:
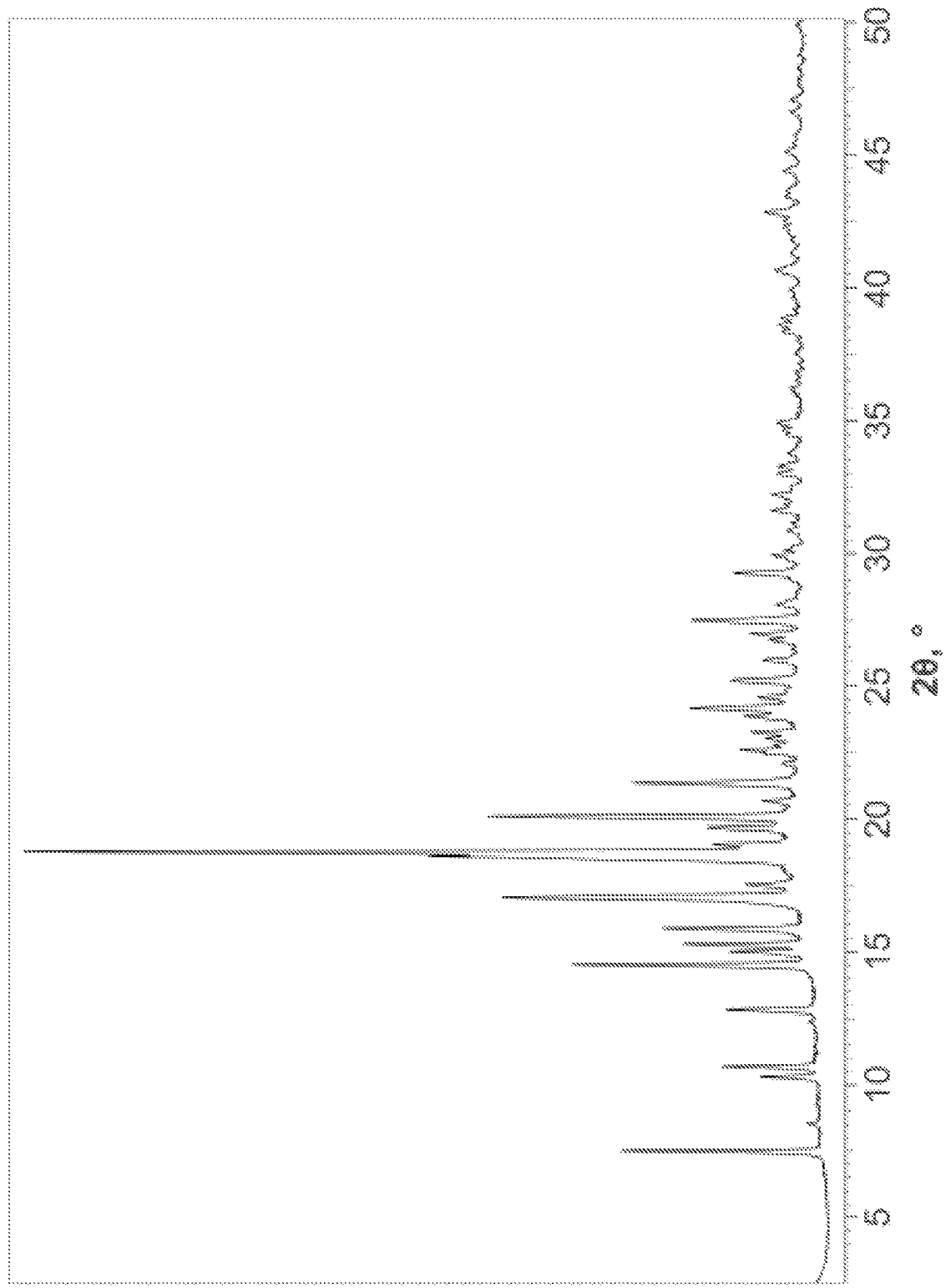

This application claims the benefit of priority under 35 USC 119(e) to U.S. Provisional Application No. 63/122,690, filed on Dec. 8, 2020. The entire contents of the foregoing are hereby incorporated by reference.

FIELD

Described in this specification are compounds (including salts thereof) that are modulators of RXFP1, uses of such compounds, compositions containing such compounds, intermediates useful in processes for preparing such compounds, and processes for preparing such compounds using such intermediates.

BACKGROUND

Relaxin is a pleiotropic hormone known to mediate systemic haemodynamic and renal adaptive changes during pregnancy. Relaxin has also been shown to have anti-fibrotic properties and to have beneficial effects in heart failure e.g. with acute decompensated heart failure (ADHF). Heart failure is associated with significant morbidity and mortality. It is characterized by complex tissue remodelling involving increased cardiomyocyte death and interstitial fibrosis. Relaxin activates a number of signalling cascades which have been shown to be beneficial in the setting of ischemia-reperfusion and heart failure. These signalling pathways include activation of the phosphoinositide 3-kinase pathway and activation of the nitric oxide signalling pathway (Bathgate R A et al. (2013) *Physiol. Rev.* 93(1): 405-480; Mentz R J et al. (2013) *Am. Heart J* 165(2): 193-199; Tietjens J et al. (2016) *Heart* 102: 95-99; Wilson S S et al. (2015) *Pharmacology* 35: 315-327).

Clinical trials have been conducted using unmodified recombinant human Relaxin-2, serelaxin. Continuous intravenous administration of serelaxin to hospitalized patients improved the markers of cardiac, renal and hepatic damage and congestion (Felker G M et al. (2014) *J. Am. Coll. Cardiol.* 64(15): 1591-1598; Metra M et al. (2013) *J. Am. Coll. Cardiol.* 61(2): 196-206; Teerlink J R et al. (2013) *Lancet* 381(9860): 29-39). However, due to the rapid clearance of serelaxin from the patients' circulation, the therapeutic effects were limited and the positive effects rapidly disappeared once intravenous injection stopped. Additionally, approximately one third of the patients experienced a significant blood pressure drop (>40 mm Hg) after receiving serelaxin intravenously, with the consequence that the dose had to be reduced by half or even more.

The cognate receptor for human relaxin is RXFP1 and is a well-validated pharmacologically important GPCR family 1c member whose activation by the hormone relaxin is associated with hemodynamic, anti-fibrotic and anti-inflammatory properties (Halls M L et al., (2015), *Pharmacol Rev.* 67(2): 389-440).

Small-molecule modulators of RXFP1 have been sought as relaxin mimetics. For example, Marugan, J. J., et al., WO2013/165606A1; Xiao J et al. (2013) *Nat. Commun.* 4:1953; and McBride A et al. (2017) *Scientific Reports* 7:10806 discuss small-molecule modulators of RXFP1.

Despite the foregoing, a need continues to exist for further compounds that are modulators of RXFP1 which may make the compounds especially promising for development as therapeutic agents. The compound(s) of the invention may also exhibit improved modulation of RXFP1 in comparison with other known RXFP1 modulators. The compound(s) of the invention is may also exhibit favourable pharmacokinetic profiles (for example, lower intrinsic clearance) and/or advantageous physical properties (for example, higher aqueous solubility) in comparison with other known RXFP1 modulators. Therefore, such compound(s) may be especially useful in the treatment of disease states in which modulation of RXFP1 is beneficial.

SUMMARY

Briefly, this specification describes, in part, a compound of Formula (I):

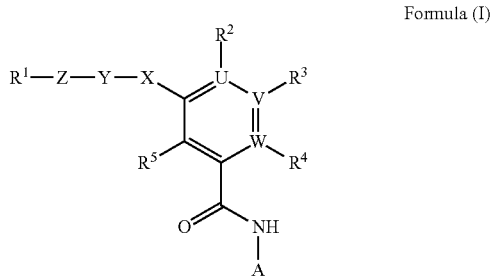

Formula (I)

or a pharmaceutically acceptable salt thereof, wherein

A is

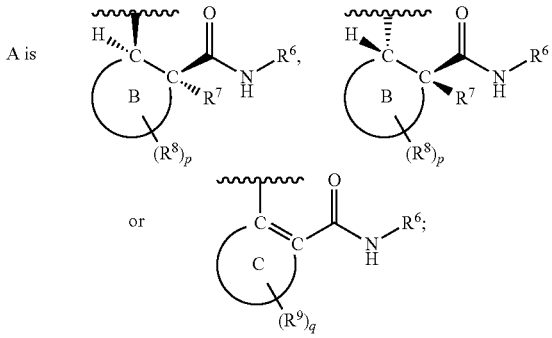

Ring B is a 4- to 10-membered cycloalkyl; a 4- to 10-membered heterocycloalkyl having 1-2 heteroatoms independently selected from nitrogen and oxygen; a 4- to 10-membered heterocycloalkenyl having 1-2 heteroatoms independently selected from nitrogen and oxygen; or a 4- to 10-membered cycloalkenyl;

$R^7$ is selected from —H, —F, —CH$_3$ and —OCH$_3$;

each $R^8$ is independently selected from $C_{1-4}$ alkyl substituted with 0-3 —F substituents; $C_{1-4}$ alkoxy; —OH; —F; and —COO($C_{1-4}$ alkyl);

p is 0, 1 or 2;

Ring C is a 6- to 10-membered aryl; a 5- to 10-membered heteroaryl having 1-4 heteroatoms independently selected from nitrogen, oxygen and sulfur; a 4- to 10-membered cycloalkenyl; or a 4- to 10-membered heterocycloalkenyl having 1-2 heteroatoms independently selected from nitrogen and oxygen;

each $R^9$ is independently selected from $C_{1-4}$ alkyl, $C_{1-4}$ alkoxy, -halo and —OH;

q is 0, 1 or 2;

R¹ is selected from —COOH, —CONH₂, —CONHMe, —CONMe₂, —C(CH₂OH)₂NH₂, —C(NH)NH₂, —SO₂NH₂, —NHSO₂Me,

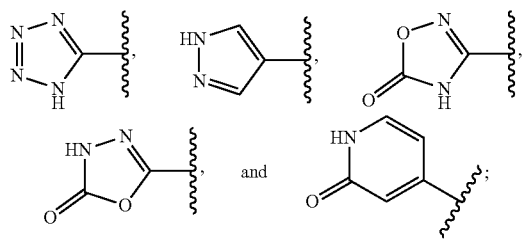

X is selected from a bond, —CH₂—, —O—, —S—, —CH₂O— and —OCH₂—;

Y is selected from $C_{2-6}$ alkylene substituted with 0-2 $R^{14}$ substituents; $C_{3-8}$ cycloalkylene substituted with 0-2 $R^{14}$ substituents; $C_{5-8}$ cycloalkenylene substituted with 0-2 $R^{14}$ substituents; 5- to 8-membered heterocycloalkylene having 1-3 heteroatoms independently selected from oxygen and sulfur and substituted with 0-2 $R^{14}$ substituents; phenylene substituted with 0-2 $R^{14}$ substituents; 5- or 6-membered heteroarylene having 1-3 heteroatoms independently selected from nitrogen, oxygen and sulfur and substituted with 0-2 $R^{14}$ substituents; and

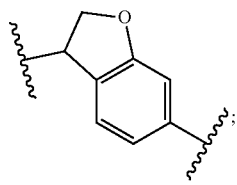 [SMILES: *c1ccc2c(c1)OCC2*]

$R^{14}$ is selected from $C_{1-3}$ alkyl substituted with 0-3 substituents selected from —OH, —OMe, —F and —CN; $C_{1-3}$ alkoxy substituted with 0-3 —F substituents; cyclopropyl substituted with 0-3 substituents selected from —OH, —OMe, —F and —CN; —F; —OH; =O; —CN; —NH₂; —NHMe; and —NMe₂;

Z is selected from a bond; $C_{1-3}$ alkylene substituted with 0-2 substituents selected from -Me, —NH₂, —NHMe and —NMe₂; $C_{2-4}$ heteroalkylene having one heteroatom selected from nitrogen and oxygen and substituted with 0-2 substituents selected from -Me, —NH₂, —NHMe and —NMe₂; $C_{3-4}$ cycloalkylene; and —CH=CH—;

$R^5$ is selected from —H, -Me and —F;

$R^6$ is —$(CR^{10}R^{11})_n R^{12}$;

n is 0, 1 or 2;

$R^{10}$ and $R^{11}$ are each independently selected from —H, -Me and —F, or $R^{10}$ and $R^{11}$ together with the carbon to which they are attached form cyclopropyl;

$R^{12}$ is selected from $C_{3-8}$ alkyl substituted with 0-5 substituents selected from —OH, —F, —CN, and $C_{1-4}$ alkoxy; $C_{3-10}$ cycloalkyl substituted with 0-4 $R^{13}$ substituents; 5- to 10-membered heterocycloalkyl having 1-2 heteroatoms independently selected from oxygen and sulfur and substituted with 0-4 $R^{13}$ substituents; phenyl substituted with 0-3 substituents selected from -halo, $C_{1-4}$ alkyl substituted with 0-3 —F substituents, $C_{3-5}$ cycloalkyl, —CN, —SF₅, —OMe, —OCH₂F, —OCHF₂, —OCF₃ and —SO₂CF₃; 6-membered heteroaryl having 1-2 nitrogen heteroatoms and substituted with 1-3 substituents selected from -halo, —SF₅, —CF₃, —OCF₃ and —SO₂CF₃;

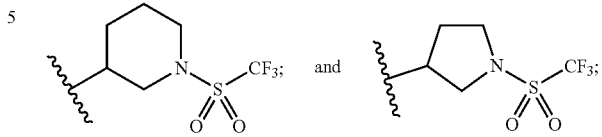

each $R^{13}$ is independently selected from —OH; —F; —CN; $C_{1-4}$ alkoxy substituted with 0-3 substituents selected from —F, —OH, —OMe and —OEt; and $C_{1-4}$ alkyl substituted with 0-3 substituents selected from —F, —OH, —OMe and —OEt;

U, V and W are each independently selected from C and N; provided that when U is N, $R^2$ is absent; when V is N, $R^3$ is absent; and when W is N, $R^4$ is absent;

and wherein (i) $R^2$, $R^3$ and $R^4$ are each independently selected from —H, -halo, —CN, $C_{1-4}$ alkyl substituted with 0-3 substituents selected from —F and —OMe, $C_{1-4}$ alkoxy substituted with 0-3 substituents selected from —F and —OMe, $C_{3-4}$ cycloalkyl substituted with 0-3 substituents selected from —F and —OMe, and $C_{3-4}$ cycloalkoxy substituted with 0-3 substituents selected from —F and -Me; or (ii) U and V are each C;

$R^2$ and $R^3$, together with the atoms to which they are attached, form a 5- or 6-membered heterocyclic ring having 1-3 heteroatoms independently selected from nitrogen, oxygen and sulfur and substituted with 0-3 -Me substituents; and $R^4$ is selected from —H, -halo, —CN, $C_{1-4}$ alkyl substituted with 0-3 substituents selected from —F and —OMe, $C_{1-4}$ alkoxy substituted with 0-3 substituents selected from —F and —OMe, $C_{3-4}$ cycloalkyl substituted with 0-3 substituents selected from —F and —OMe, and $C_{3-4}$ cycloalkoxy substituted with 0-3 substituents selected from —F and -Me; or (iii) V and W are each C;

$R^3$ and $R^4$, together with the atoms to which they are attached, form a 5- or 6-membered heterocyclic ring having 1-3 heteroatoms independently selected from nitrogen, oxygen and sulfur and substituted with 0-3 -Me substituents; and $R^2$ is selected from —H, -halo, —CN, $C_{1-4}$ alkyl substituted with 0-3 substituents selected from —F and —OMe, $C_{1-4}$ alkoxy substituted with 0-3 substituents selected from —F and —OMe, $C_{3-4}$ cycloalkyl substituted with 0-3 substituents selected from —F and —OMe, and $C_{3-4}$ cycloalkoxy substituted with 0-3 substituents selected from —F and -Me.

This specification also describes, in part, a pharmaceutical composition which comprises a compound of Formula (I), or a pharmaceutically acceptable salt thereof, and at least one pharmaceutically acceptable excipient.

This specification also describes, in part, a compound of Formula (I), or a pharmaceutically acceptable salt thereof, for use in therapy.

This specification also describes, in part, a compound of Formula (I), or a pharmaceutically acceptable salt thereof, for use in the treatment of a disease or condition selected from the group consisting of heart failure, heart failure with preserved ejection fraction, heart failure with reduced ejection fraction, chronic kidney disease and acute kidney injury.

This specification also describes, in part, the use of a compound of Formula (I), or a pharmaceutically acceptable salt thereof, in the manufacture of a medicament for the treatment of a disease or condition selected from the group consisting of heart failure, heart failure with preserved ejection fraction, heart failure with reduced ejection fraction, chronic kidney disease and acute kidney injury.

This specification also describes, in part, a method for treating a disease or condition selected from the group consisting of heart failure, heart failure with preserved ejection fraction, heart failure with reduced ejection fraction, chronic kidney disease and acute kidney injury in a subject in need of such treatment, which comprises administering to said subject a therapeutically effective amount of a compound of Formula (I), or a pharmaceutically acceptable salt thereof.

This specification also describes, in part, an Intermediate compound (as described herein), or a salt thereof.

This specification also describes, in part, a process for preparing a compound of Formula (I), or pharmaceutically acceptable salt thereof, using an Intermediate compound (as described herein), or a salt thereof.

Further aspects of Applicant's invention will be apparent to one skilled in the art from reading this specification.

DESCRIPTION OF ILLUSTRATIVE EMBODIMENTS

Many embodiments are detailed throughout the specification and will be apparent to a reader skilled in the art. The specification is not to be interpreted as being limited to any particular embodiment(s) described herein.

In an embodiment there is provided a compound of Formula (I):

Formula (I)

$R^1$—Z—Y—X—[ring with $R^2$, $R^3$, V, W, $R^4$, $R^5$]—C(O)—NH—A or a pharmaceutically acceptable salt thereof, wherein A is

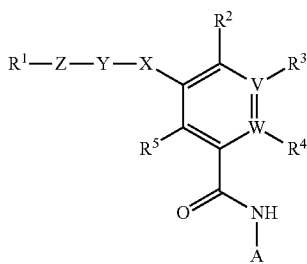

or

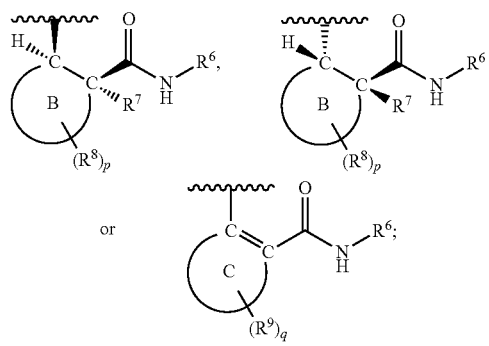

Ring B is a 4- to 10-membered cycloalkyl; a 4- to 10-membered heterocycloalkyl having 1-2 heteroatoms independently selected from nitrogen and oxygen; a 4- to 10-membered heterocycloalkenyl having 1-2 heteroatoms independently selected from nitrogen and oxygen; or a 4- to 10-membered cycloalkenyl;

$R^7$ is selected from —H, —F, —$CH_3$ and —$OCH_3$;

each $R^8$ is independently selected from $C_{1-4}$ alkyl substituted with 0-3 —F substituents; $C_{1-4}$ alkoxy; —OH; —F; and —COO($C_{1-4}$ alkyl);

p is 0, 1 or 2;

Ring C is a 6- to 10-membered aryl; a 5- to 10-membered heteroaryl having 1-4 heteroatoms independently selected from nitrogen, oxygen and sulfur; a 4- to 10-membered cycloalkenyl; or a 4- to 10-membered heterocycloalkenyl having 1-2 heteroatoms independently selected from nitrogen and oxygen;

each $R^9$ is independently selected from $C_{1-4}$ alkyl, $C_{1-4}$ alkoxy, -halo and —OH;

q is 0, 1 or 2;

$R^1$ is selected from —COOH, —$CONH_2$, —CONHMe, —$CONMe_2$, —$C(CH_2OH)_2NH_2$, —$C(NH)NH_2$, —$SO_2NH_2$, —$NHSO_2Me$,

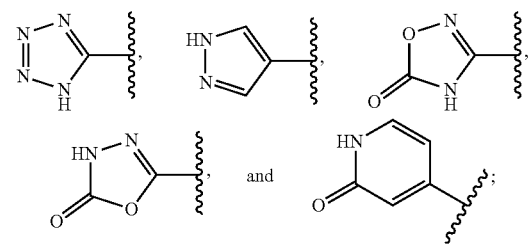

X is selected from a bond, —$CH_2$—, —O—, —S—, —$CH_2O$— and —$OCH_2$—;

Y is selected from $C_{2-6}$ alkylene substituted with 0-2 $R^{14}$ substituents; $C_{3-8}$ cycloalkylene substituted with 0-2 $R^{14}$ substituents; $C_{5-8}$ cycloalkenylene substituted with 0-2 $R^{14}$ substituents; 5- to 8-membered heterocycloalkylene having 1-3 heteroatoms independently selected from oxygen and sulfur and substituted with 0-2 $R^{14}$ substituents; phenylene substituted with 0-2 $R^{14}$ substituents; 5- or 6-membered heteroarylene having 1-3 heteroatoms independently selected from nitrogen, oxygen and sulfur and substituted with 0-2 $R^{14}$ substituents; and

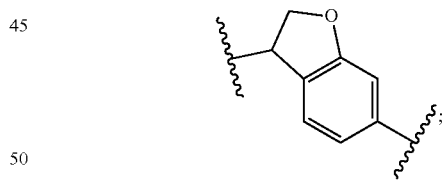

$R^{14}$ is selected from $C_{1-3}$ alkyl substituted with 0-3 substituents selected from —OH, —OMe, —F and —CN; $C_{1-3}$ alkoxy substituted with 0-3 —F substituents; cyclopropyl substituted with 0-3 substituents selected from —OH, —OMe, —F and —CN; —F; —OH; =O; —CN; —$NH_2$; —NHMe; and —$NMe_2$;

Z is selected from a bond; $C_{1-3}$ alkylene substituted with 0-2 substituents selected from -Me, —$NH_2$, —NHMe and —$NMe_2$; $C_{2-4}$ heteroalkylene having one heteroatom selected from nitrogen and oxygen and substituted with 0-2 substituents selected from -Me, —$NH_2$, —NHMe and —$NMe_2$; $C_{3-4}$ cycloalkylene; and —CH=CH—;

$R^5$ is selected from —H, -Me and —F;

$R^6$ is —$(CR^{10}R^{11})_nR^{12}$;

n is 0, 1 or 2;

$R^{10}$ and $R^{11}$ are each independently selected from —H, -Me and —F, or $R^{10}$ and $R^{11}$ together with the carbon to which they are attached form cyclopropyl;

$R^{12}$ is selected from $C_{3-8}$ alkyl substituted with 0-5 substituents selected from —OH, —F, —CN, and $C_{1-4}$ alkoxy; $C_{3-10}$ cycloalkyl substituted with 0-4 $R^{13}$ substituents; 5- to 10-membered heterocycloalkyl having 1-2 heteroatoms independently selected from oxygen and sulfur and substituted with 0-4 $R^{13}$ substituents; phenyl substituted with 0-3 substituents selected from -halo, $C_{1-4}$ alkyl substituted with 0-3 —F substituents, $C_{3-5}$ cycloalkyl, —CN, —SF$_5$, —OMe, —OCH$_2$F, —OCHF$_2$, —OCF$_3$ and —SO$_2$CF$_3$; 6-membered heteroaryl having 1-2 nitrogen heteroatoms and substituted with 1-3 substituents selected from -halo, —SF$_5$, —CF$_3$, —OCF$_3$ and —SO$_2$CF$_3$;

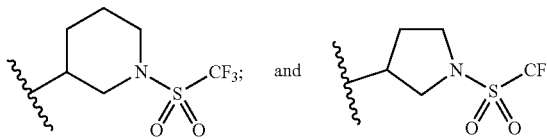

each $R^{13}$ is independently selected from —OH; —F; —CN; $C_{1-4}$ alkoxy substituted with 0-3 substituents selected from —F, —OH, —OMe and —OEt; and $C_{1-4}$ alkyl substituted with 0-3 substituents selected from —F, —OH, —OMe and —OEt;

U, V and W are each independently selected from C and N; provided that when U is N, $R^2$ is absent; when V is N, $R^3$ is absent; and when W is N, $R^4$ is absent;

and wherein (i) $R^2$, $R^3$ and $R^4$ are each independently selected from —H, -halo, —CN, $C_{1-4}$ alkyl substituted with 0-3 substituents selected from —F and —OMe, $C_{1-4}$ alkoxy substituted with 0-3 substituents selected from —F and —OMe, $C_{3-4}$ cycloalkyl substituted with 0-3 substituents selected from —F and —OMe, and $C_{3-4}$ cycloalkoxy substituted with 0-3 substituents selected from —F and -Me; or (ii) U and V are each C;
$R^2$ and $R^3$, together with the atoms to which they are attached, form a 5- or 6-membered heterocyclic ring having 1-3 heteroatoms independently selected from nitrogen, oxygen and sulfur and substituted with 0-3 -Me substituents; and
$R^4$ is selected from —H, -halo, —CN, $C_{1-4}$ alkyl substituted with 0-3 substituents selected from —F and —OMe, $C_{1-4}$ alkoxy substituted with 0-3 substituents selected from —F and —OMe, $C_{3-4}$ cycloalkyl substituted with 0-3 substituents selected from —F and —OMe, and $C_{3-4}$ cycloalkoxy substituted with 0-3 substituents selected from —F and -Me; or (iii) V and W are each C;
$R^3$ and $R^4$, together with the atoms to which they are attached, form a 5- or 6-membered heterocyclic ring having 1-3 heteroatoms independently selected from nitrogen, oxygen and sulfur and substituted with 0-3 -Me substituents; and
$R^2$ is selected from —H, -halo, —CN, $C_{1-4}$ alkyl substituted with 0-3 substituents selected from —F and —OMe, $C_{1-4}$ alkoxy substituted with 0-3 substituents selected from —F and —OMe, $C_{3-4}$ cycloalkyl substituted with 0-3 substituents selected from —F and —OMe, and $C_{3-4}$ cycloalkoxy substituted with 0-3 substituents selected from —F and -Me.

The following embodiments of moieties A, Ring B, Ring C, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, n, p, q, r, U, V, W, X, Y, and Z may be applied, alone or in combination, to the descriptions of the compounds of Formula (I) provided herein.

A is

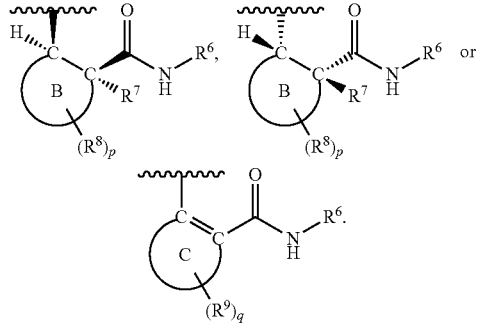

A is

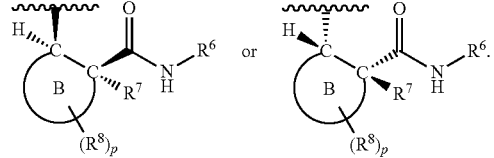

A is

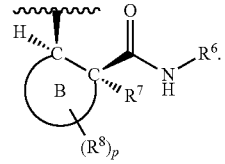

A is selected from

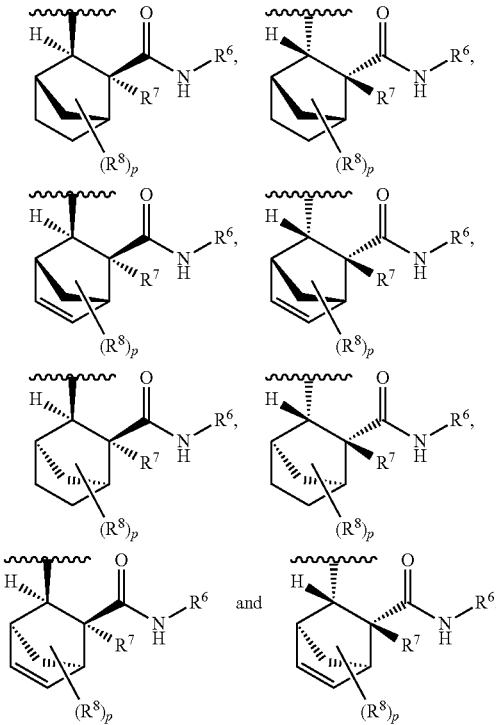

-continued

A is selected from

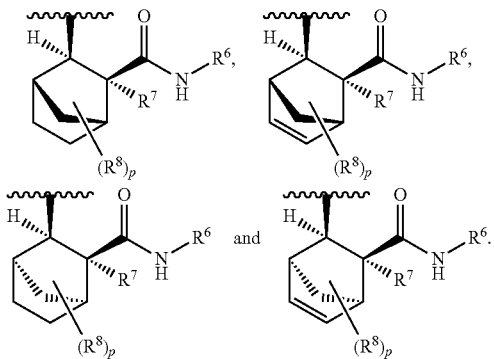

A is selected from

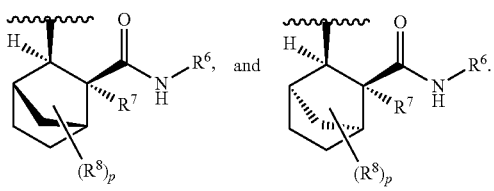

A is

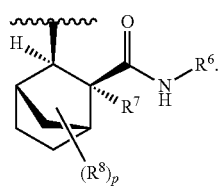

A is selected from

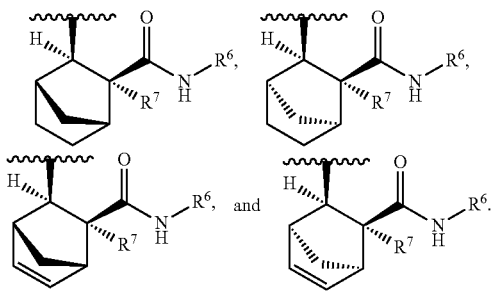

A is

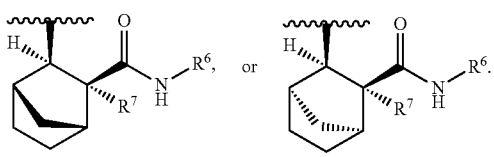

A is

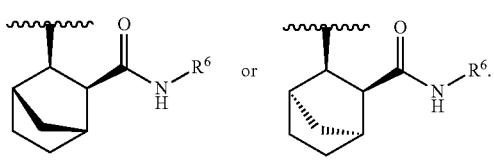

A is

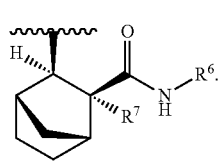

-continued

A is

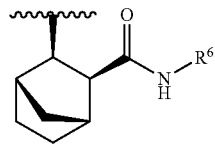

A is

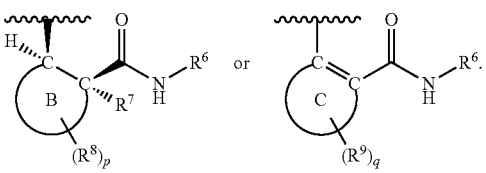

A is

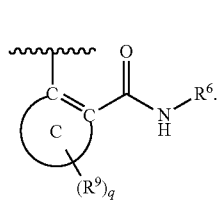

A is

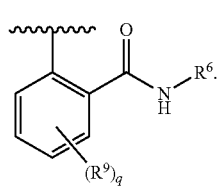

A is

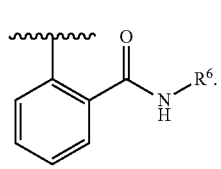

Ring B is a 4- to 10-membered cycloalkyl; a 4- to 10-membered heterocycloalkyl having 1-2 heteroatoms independently selected from nitrogen and oxygen; a 4- to 10-membered heterocycloalkenyl having 1-2 heteroatoms independently selected from nitrogen and oxygen; or a 4- to 10-membered cycloalkenyl.

Ring B is a monocyclic 5- to 7-membered cycloalkyl optionally bridged with $C_{1-3}$ alkylene; a monocyclic 5- to 7-membered heterocycloalkyl having 1-2 heteroatoms independently selected from nitrogen and oxygen and optionally bridged with $C_{1-3}$ alkylene; a monocyclic 5- to 7-membered heterocycloalkenyl having 1-2 heteroatoms independently selected from nitrogen and oxygen and optionally bridged with $C_{1-3}$ alkylene; or a monocyclic 5- to 7-membered cycloalkenyl optionally bridged with $C_{1-3}$ alkylene.

Ring B is a 4- to 10-membered cycloalkyl, or a 4- to 10-membered cycloalkenyl.

Ring B is a 5- to 8-membered cycloalkyl, or a 5- to 8-membered cycloalkenyl.

Ring B is a monocyclic 5- to 7-membered cycloalkyl optionally bridged with $C_{1-3}$ alkylene; or a monocyclic 5- to 7-membered cycloalkenyl optionally bridged with $C_{1-3}$ alkylene.

Ring B is cyclohexyl optionally bridged with $C_{1-2}$ alkylene, or cyclohexenyl optionally bridged with $C_{1-2}$ alkylene.

Ring B is cyclohexyl 1,4-bridged with $C_{1-2}$ alkylene, or cyclohexenyl 1,4-bridged with $C_{1-2}$ alkylene.

Ring B is bicyclo[2.2.1]heptanyl or bicyclo[2.2.1]hept-2-enyl.

Ring B is bicyclo[2.2.1]heptanyl.

$R^7$ is selected from —H, —F, —CH$_3$ and —OCH$_3$.

$R^7$ is selected from —H and —F.

$R^7$ is —H.

each $R^8$ is independently selected from C$_{1-4}$ alkyl substituted with 0-3 —F substituents; C$_{1-4}$ alkoxy; —OH; —F; and —COO(C$_{1-4}$ alkyl).

each $R^8$ is independently selected from C$_{1-2}$ alkyl substituted with 0-3 —F substituents; C$_{1-2}$ alkoxy; —OH; and —F.

each $R^8$ is independently selected from C$_{1-2}$ alkyl substituted with 0-3 —F substituents; and —F.

each $R^8$ is independently selected from -Me and —F.

p is 0, 1 or 2.

p is 0 or 1.

p is 0.

Ring C is a 6- to 10-membered aryl; a 5- to 10-membered heteroaryl having 1-4 heteroatoms independently selected from nitrogen, oxygen and sulfur; a 4- to 10-membered cycloalkenyl; or a 4- to 10-membered heterocycloalkenyl having 1-2 heteroatoms independently selected from nitrogen and oxygen.

Ring C is phenyl; a monocyclic 5- or 6-membered heteroaryl having 1-3 heteroatoms independently selected from nitrogen, oxygen and sulfur; a monocyclic 4- to 7-membered cycloalkenyl optionally bridged with C$_{1-3}$ alkylene; or a monocyclic 4- to 7-membered heterocycloalkenyl having 1-2 heteroatoms independently selected from nitrogen and oxygen and optionally bridged with C$_{1-3}$ alkylene.

Ring C is a monocyclic 5- to 7-membered cycloalkenyl optionally bridged with C$_{1-2}$ alkylene; or a monocyclic 5- to 7-membered heterocycloalkenyl having 1 oxygen heteroatom and optionally bridged with C$_{1-2}$ alkylene.

Ring C is a mono- or poly-cyclic 6- to 10-membered aryl.

Ring C is phenyl.

Ring C is not phenyl.

each $R^9$ is independently selected from C$_{1-4}$ alkyl, C$_{1-4}$ alkoxy, -halo and —OH.

each $R^9$ is independently selected from C$_{1-2}$ alkyl, C$_{1-2}$ alkoxy, -halo and —OH.

q is 0, 1 or 2.

q is 0 or 1.

q is 0.

$R^1$ is selected from —COOH, —CONH$_2$, —CONHMe, —CONMe$_2$, —C(CH$_2$OH)$_2$NH$_2$, —C(NH)NH$_2$, —SO$_2$NH$_2$, —NHSO$_2$Me,

[structures: tetrazolyl, pyrazolyl, oxadiazolone, oxadiazolone, pyridinone]

$R^1$ is —COOH or a bioisotere of a carboxylic acid such as tetrazolyl. Such bioisoteres of carboxylic acids will be apparent to a person of skill in the art.

$R^1$ is selected from —COOH, —CONH$_2$,

[structures: tetrazolyl and oxadiazolone]

$R^1$ is —COOH.

X is selected from a bond, —CH$_2$—, —O—, —S—, —CH$_2$O— and —OCH$_2$—.

X is selected from a bond, —CH$_2$—, —O—, —CH$_2$O— and —OCH$_2$—.

X is selected from a bond, —CH$_2$—, and —O—.

X is selected from —CH$_2$— and —O—.

X is —O—.

Y is selected from C$_{2-6}$ alkylene substituted with 0-2 $R^{14}$ substituents; C$_{3-8}$ cycloalkylene substituted with 0-2 $R^{14}$ substituents; C$_{5-8}$ cycloalkenylene substituted with 0-2 $R^{14}$ substituents; 5- to 8-membered heterocycloalkylene having 1-3 heteroatoms independently selected from oxygen and sulfur and substituted with 0-2 $R^{14}$ substituents; phenylene substituted with 0-2 $R^{14}$ substituents; 5- or 6-membered heteroarylene having 1-3 heteroatoms independently selected from nitrogen, oxygen and sulfur and substituted with 0-2 $R^{14}$ substituents; and

[structure: dihydrobenzofuran]

Y is selected from C$_{2-6}$ alkylene substituted with 0-1 $R^{14}$ substituents; C$_{3-8}$ cycloalkylene substituted with 0-1 $R^{14}$ substituents; C$_{5-8}$ cycloalkenylene substituted with 0-1 $R^{14}$ substituents; 5- to 8-membered heterocycloalkylene having 1-3 heteroatoms independently selected from oxygen and sulfur and substituted with 0-1 $R^{14}$ substituents; phenylene substituted with 0-1 $R^{14}$ substituents; 5- or 6-membered heteroarylene having 1-3 heteroatoms independently selected from nitrogen, oxygen and sulfur and substituted with 0-1 $R^{14}$ substituents; and

[structure: dihydrobenzofuran]

Y is selected from C$_{2-4}$ alkylene substituted with 0-2 $R^{14}$ substituents; C$_{3-8}$ cycloalkylene substituted with 0-2 $R^{14}$ substituents; and 5- to 8-membered heterocycloalkylene having 1-2 heteroatoms independently selected from oxygen and sulfur and substituted with 0-2 $R^{14}$ substituents.

Y is selected from C$_{2-4}$ alkylene substituted with 0-1 $R^{14}$ substituents; C$_{3-8}$ cycloalkylene substituted with 0-1 $R^{14}$ substituents; and 5- to 8-membered heterocycloalkylene having 1-2 heteroatoms independently selected from oxygen and sulfur and substituted with 0-1 $R^{14}$ substituents.

Y is selected from C$_{4-6}$ cycloalkylene substituted with 0-1 $R^{14}$ substituents; and 5- or 6-membered heterocycloalkylene having 1-2 heteroatoms independently selected from oxygen and sulfur and substituted with 0-1 $R^{14}$ substituents.

Y is $C_{3-8}$ cycloalkylene substituted with 0-2 $R^{14}$ substituents.

Y is $C_{4-6}$ cycloalkylene substituted with 0-2 $R^{14}$ substituents.

Y is $C_{3-8}$ cycloalkylene substituted with 0-1 $R^{14}$ substituents.

Y is $C_{4-6}$ cycloalkylene substituted with 0-1 $R^{14}$ substituents.

Y is cyclohexylene substituted with 0-2 $R^{14}$ substituents.

Y is cyclohexylene substituted with 0-1 $R^{14}$ substituents.

Y is cyclohexylene substituted with 1 $R^{14}$ substituent.

Optionally, in any of the embodiments of Y described herein, the X and Z substituents are bonded to Y such that, where there are sufficient ring or chain atoms in Y, the X and Z substituents are not in a geminal or vicinal configuration.

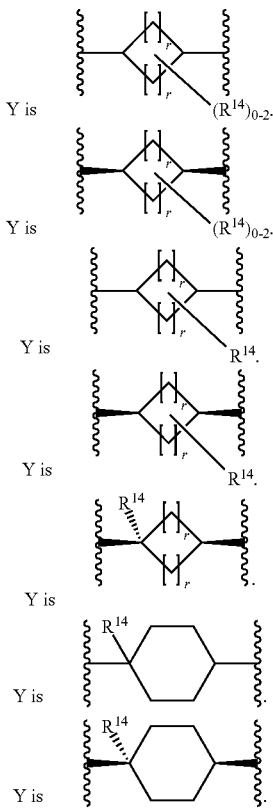

r is 1, 2 or 3.

r is 1 or 2.

r is 2.

$R^{14}$ is selected from $C_{1-3}$ alkyl substituted with 0-1 substituents selected from —OH, —OMe, —F and —CN; $C_{1-3}$ alkoxy substituted with 0-1 —F substituents; cyclopropyl substituted with 0-1 substituents selected from —OH, —OMe, —F and —CN; —F; —OH; =O; —CN; —NH$_2$; —NHMe; and —NMe$_2$.

$R^{14}$ is selected from $C_{1-2}$ alkyl substituted with 0-1 substituents selected from —OH, —OMe, —F and —CN; $C_{1-2}$ alkoxy substituted with 0-1 —F substituents; cyclopropyl substituted with 0-1 substituents selected from —OH, —OMe, —F and —CN; —F; —OH; =O; —CN; —NH$_2$; —NHMe; and —NMe$_2$.

$R^{14}$ is selected from —H, -Me, -Et, —F, —OH, =O, —OMe, —OEt, —CF$_3$, —CH$_2$OH, —CH$_2$OMe, —CN, —CH$_2$CN, —NH$_2$, —NHMe and —NMe$_2$.

$R^{14}$ is —H.

$R^{14}$ is not —H.

$R^{14}$ is -Me.

Z is selected from a bond; $C_{1-3}$ alkylene substituted with 0-2 substituents selected from -Me, —NH$_2$, —NHMe and —NMe$_2$; $C_{2-4}$ heteroalkylene having one heteroatom selected from nitrogen and oxygen and substituted with 0-2 substituents selected from -Me, —NH$_2$, —NHMe and —NMe$_2$; $C_{3-4}$ cycloalkylene; and —CH=CH—.

Z is selected from a bond; $C_{1-2}$ alkylene substituted with 0-1 substituents selected from -Me, —NH$_2$, —NHMe and —NMe$_2$; $C_{2-3}$ heteroalkylene having one heteroatom selected from nitrogen and oxygen and substituted with 0-1 substituents selected from -Me, —NH$_2$, —NHMe and —NMe$_2$; $C_{3-4}$ cycloalkylene; and —CH=CH—.

Z is selected from a bond, —CH$_2$—, —CH$_2$CH$_2$—, —OCH$_2$—, —CH$_2$O—, —C(CH$_3$)$_2$O—, —CH$_2$CH$_2$O—, —CH$_2$CH$_2$CH$_2$O—, —CH$_2$NH—, —CH(NH$_2$)—, —CH(NMe$_2$)-, —CH$_2$CH(NMe$_2$)-, —CH(NMe$_2$)CH$_2$—, —CH$_2$CH(NH$_2$)—, —CH(NH$_2$)CH$_2$—, —CH=CH—,

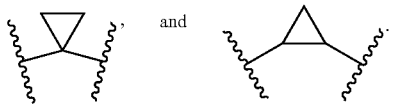 [SMILES: *C1(*)CC1 ; *C1CC1*]

Z is selected from a bond, —CH$_2$—, —CH$_2$CH$_2$—, and —CH$_2$O—.

Z is a bond.

$R^5$ is selected from —H, -Me and —F.

$R^5$ is —H.

$R^6$ is —(CR$^{10}$R$^{11}$)$_n$R$^{12}$.

$R^6$ is —(CR$^{10}$R$^{11}$)R$^{12}$.

$R^6$ is —(CH$_2$)R$^{12}$.

$R^6$ is —R$^{12}$.

$R^6$ is selected from

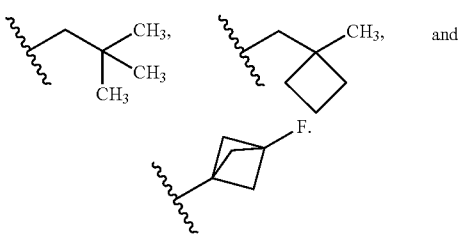

$R^6$ is selected from

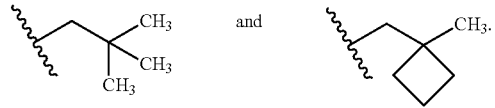

$R^6$ is

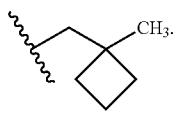

n is 0, 1 or 2.
n is 0 or 1.
n is 0.
n is 1.

$R^{10}$ and $R^{11}$ are each independently selected from —H, -Me and —F, or $R^{10}$ and $R^{11}$ together with the carbon to which they are attached form cyclopropyl.

$R^{10}$ and $R^{11}$ are each independently selected from —H, -Me and —F.

$R^{10}$ and $R^{11}$ are each —H.

$R^{12}$ is selected from $C_{3-8}$ alkyl substituted with 0-5 substituents selected from —OH, —F, —CN, and $C_{1-4}$ alkoxy; $C_{3-10}$ cycloalkyl substituted with 0-4 $R^{13}$ substituents; 5- to 10-membered heterocycloalkyl having 1-2 heteroatoms independently selected from oxygen and sulfur and substituted with 0-4 $R^{13}$ substituents; phenyl substituted with 0-3 substituents selected from -halo, $C_{1-4}$ alkyl substituted with 0-3 —F substituents, $C_{3-5}$ cycloalkyl, —CN, —SF$_5$, —OMe, —OCH$_2$F, —OCHF$_2$, —OCF$_3$ and —SO$_2$CF$_3$; 6-membered heteroaryl having 1-2 nitrogen heteroatoms and substituted with 1-3 substituents selected from -halo, —SF$_5$, —CF$_3$, —OCF$_3$ and —SO$_2$CF$_3$;

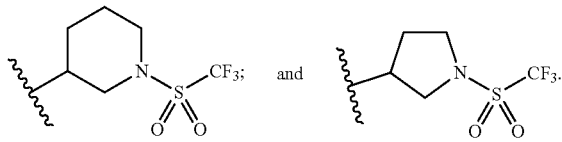 [SMILES: *C1CCCN(S(=O)(=O)C(F)(F)F)C1 ; *C1CCN(S(=O)(=O)C(F)(F)F)C1]

$R^{12}$ is selected from $C_{3-8}$ alkyl substituted with 0-3 substituents selected from —OH, —F, —CN, and $C_{1-4}$ alkoxy; $C_{3-10}$ cycloalkyl substituted with 0-3 $R^{13}$ substituents; and 5- to 10-membered heterocycloalkyl having 1-2 heteroatoms independently selected from oxygen and sulfur and substituted with 0-3 $R^{13}$ substituents.

$R^{12}$ is selected from $C_{4-6}$ alkyl substituted with 0-3 substituents selected from —F, —CN, and $C_{1-2}$ alkoxy; $C_{4-6}$ cycloalkyl substituted with 0-3 $R^{13}$ substituents; and 5- to 6-membered heterocycloalkyl having 1-2 heteroatoms independently selected from oxygen and sulfur and substituted with 0-3 $R^{13}$ substituents.

$R^{12}$ is selected from $C_{4-6}$ alkyl substituted with 0-2 substituents selected from —F, —CN, and $C_{1-2}$ alkoxy; $C_{4-6}$ cycloalkyl substituted with 0-1 $R^{13}$ substituents; and 5- to 6-membered heterocycloalkyl having 1-2 heteroatoms independently selected from oxygen and sulfur and substituted with 0-1 $R^{13}$ substituents.

$R^{12}$ is selected from $C_{4-6}$ alkyl substituted with 0-3 —F substituents; and $C_{4-6}$ cycloalkyl substituted with 0-3 substituents selected from —F and -Me.

$R^{12}$ is selected from $C_{3-6}$ alkyl substituted with 0-3 —F substituents; and $C_{3-6}$ cycloalkyl substituted with 0-3 substituents selected from —F and -Me.

$R^{12}$ is selected from $C_{3-6}$ alkyl substituted with 0-3 —F substituents; and $C_{3-6}$ cycloalkyl substituted with —F or -Me.

$R^{12}$ is selected from tert-butyl substituted with 0-3 —F substituents; cyclobutyl substituted with 0-2 substituents selected from —F and -Me; and bicyclo[1.1.1]pentanyl substituted with 0-2 substituents selected from —F and -Me.

$R^{12}$ is selected from tert-butyl substituted with 0-3 —F substituents; cyclobutyl substituted with 0-2 substituents selected from —F and -Me; and bicyclo[1.1.1]pentanyl substituted with 0-2 substituents selected from —F and -Me.

$R^{12}$ is selected from tert-butyl substituted with 0-3 —F substituents; cyclobutyl substituted with 0-1 substituents selected from —F and -Me; and bicyclo[1.1.1]pentanyl substituted with 0-2 substituents selected from —F and -Me.

$R^{12}$ is selected from

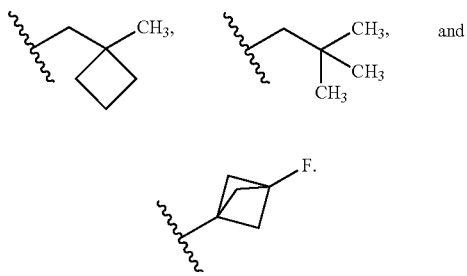

$R^{12}$ is selected from

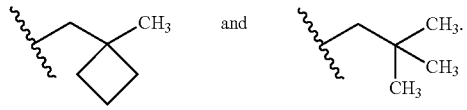

$R^{12}$ is

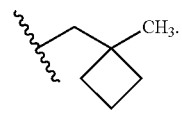

$R^{12}$ is selected from phenyl substituted with 0-3 substituents selected from -halo, $C_{1-4}$ alkyl substituted with 0-3 —F substituents, $C_{3-8}$ cycloalkyl, —CN, —SF$_5$, —OMe, —OCH$_2$F, —OCHF$_2$, —OCF$_3$ and —SO$_2$CF$_3$; 6-membered heteroaryl having 1-2 nitrogen heteroatoms and substituted with 1-3 substituents selected from -halo, —SF$_5$, —CF$_3$, —OCF$_3$ and —SO$_2$CF$_3$;

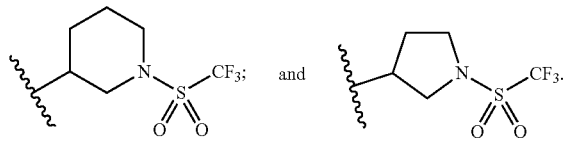 [SMILES: *C1CCCN(S(=O)(=O)C(F)(F)F)C1 ; *C1CCN(S(=O)(=O)C(F)(F)F)C1]

$R^{12}$ is selected from phenyl substituted with 1-2 substituents selected from -halo, $C_{1-4}$ alkyl substituted with 0-3 —F substituents, $C_{3-8}$ cycloalkyl, —CN, —SF$_5$, —OMe, —OCH$_2$F, —OCHF$_2$, —OCF$_3$ and —SO$_2$CF$_3$.

$R^{12}$ is selected from

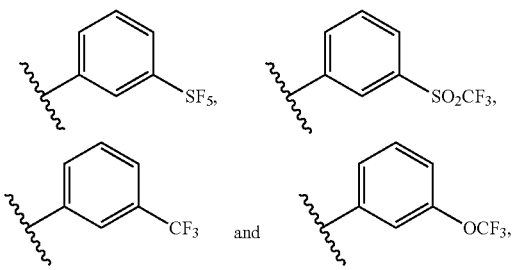

each substituted with 0-1 substituents selected from -halo, -Me, —$CF_3$ and —CN.

$R^{12}$ is selected from

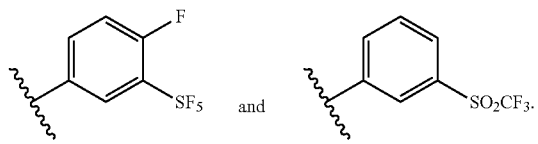

each $R^{13}$ is independently selected from —OH; —F; —CN; $C_{1-4}$ alkoxy substituted with 0-3 substituents selected from —F, —OH, —OMe and —OEt; and $C_{1-4}$ alkyl substituted with 0-3 substituents selected from —F, —OH, —OMe and —OEt.

each $R^{13}$ is independently selected from —F; —CN; $C_{1-2}$ alkoxy substituted with 0-1 substituents selected from —F, —OMe and —OEt; and $C_{1-2}$ alkyl substituted with 0-1 substituents selected from —F, —OMe and —OEt.

each $R^{13}$ is independently selected from —F; —CN; $C_{1-4}$ alkoxy; and $C_{1-4}$ alkyl.

each $R^{13}$ is independently selected from —F; $C_{1-2}$ alkoxy; and $C_{1-2}$ alkyl.

each $R^{13}$ is independently selected from —F; —OMe; and -Me.

each $R^{13}$ is —F.

each $R^{13}$ is -Me.

U, V and W are each independently selected from C and N; provided that when U is N, $R^2$ is absent; when V is N, $R^3$ is absent; and when W is N, $R^4$ is absent.

U, V and W are each C.

$R^2$, $R^3$ and $R^4$ are each independently selected from —H, -halo, —CN, $C_{1-4}$ alkyl substituted with 0-3 substituents selected from —F and —OMe, $C_{1-4}$ alkoxy substituted with 0-3 substituents selected from —F and —OMe, $C_{3-4}$ cycloalkyl substituted with 0-3 substituents selected from —F and —OMe, and $C_{3-4}$ cycloalkoxy substituted with 0-3 substituents selected from —F and -Me.

$R^2$ is selected from —H, -halo, —CN, $C_{1-4}$ alkyl substituted with 0-3 substituents selected from —F and —OMe, $C_{1-4}$ alkoxy substituted with 0-3 substituents selected from —F and —OMe, and $C_{3-4}$ cycloalkyl substituted with 0-3 substituents selected from —F and —OMe.

$R^2$ is selected from —H, -halo, —CN, $C_{1-2}$ alkyl substituted with 0-3 —F substituents, $C_{1-2}$ alkyl substituted with 0-1 —OMe substituents, and $C_{3-4}$ cycloalkyl substituted with 0-1 substituents selected from —F and —OMe.

$R^2$ is selected from —H, -halo, —CN, $C_{1-2}$ alkyl substituted with 0-3 —F substituents, $C_{1-2}$ alkyl substituted with 0-1 —OMe substituents, and cyclopropyl.

$R^2$ is not —H.

$R^2$ is —CN or —F.

$R^2$ is —CN.

$R^2$ is —F.

$R^3$ is selected from —H, -halo, —CN, $C_{1-4}$ alkyl substituted with 0-3 substituents selected from —F and —OMe, $C_{1-4}$ alkoxy substituted with 0-3 substituents selected from —F and —OMe, and $C_{3-4}$ cycloalkyl substituted with 0-3 substituents selected from —F and —OMe.

$R^3$ is selected from —H, -halo, —CN, $C_{1-2}$ alkyl substituted with 0-3 —F substituents, $C_{1-2}$ alkyl substituted with 0-1 —OMe substituents, and $C_{3-4}$ cycloalkyl substituted with 0-1 substituents selected from —F and —OMe.

$R^3$ is selected from —H, -halo, —CN, $C_{1-2}$ alkyl substituted with 0-3 —F substituents, $C_{1-2}$ alkyl substituted with 0-1 —OMe substituents, and cyclopropyl.

$R^3$ is —H.

$R^4$ is selected from —H, —F, $C_{1-4}$ alkoxy substituted with 0-3 substituents selected from —F and —OMe, and $C_{3-4}$ cycloalkoxy substituted with 0-3 substituents selected from —F and -Me.

$R^4$ is selected from —H, —F, and $C_{1-4}$ alkoxy substituted with 0-3 substituents selected from —F and —OMe.

$R^4$ is selected from —F and $C_{1-4}$ alkoxy substituted with 0-3 substituents selected from —F and —OMe.

$R^4$ is selected from —F and $C_{1-3}$ alkoxy substituted with 0-2 substituents selected from —F and —OMe.

$R^4$ is selected from —F and $C_{1-3}$ alkoxy substituted with 0-2 substituents selected from —F and —OMe.

$R^4$ is $C_{1-3}$ alkoxy substituted with 0-2 substituents selected from —F and —OMe.

$R^4$ is —OMe or —OEt.

$R^4$ is not —H.

$R^4$ is selected from —F and —OMe.

$R^4$ is —OMe.

$R^2$ and $R^3$, together with the atoms to which they are attached, form a 5- or 6-membered heterocyclic ring having 1-3 heteroatoms independently selected from nitrogen, oxygen and sulfur and substituted with 0-3 -Me substituents; and U and V are each C.

$R^3$ and $R^4$, together with the atoms to which they are attached, form a 5- or 6-membered heterocyclic ring having 1-3 heteroatoms independently selected from nitrogen, oxygen and sulfur and substituted with 0-3 -Me substituents; and V and W are each C. Optionally, $R^3$ and $R^4$ are selected such that the ring containing $R^3$, $R^4$, V and W is

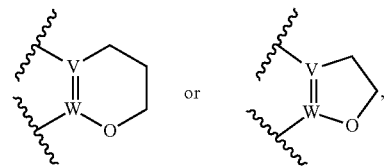

and wherein said ring is optionally substituted with 0-2 -Me substituents. Optionally, $R^3$ and $R^4$ are selected such that the ring containing $R^3$, $R^4$, V and W is or

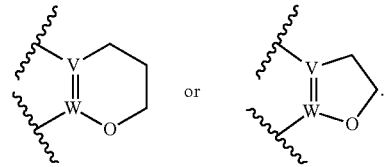

In one embodiment, $R^2$ is —CN; $R^3$ is —H; $R^4$ is —OMe; and $R^5$ is —H.

In one embodiment, $R^2$ is —F; $R^3$ is —H; $R^4$ is —OMe; and $R^5$ is —H.

In one embodiment A is

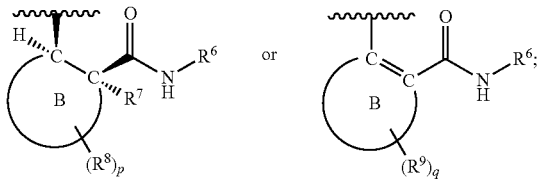

Ring B is a 4- to 10-membered cycloalkyl; a 4- to 10-membered heterocycloalkyl having 1-2 heteroatoms independently selected from nitrogen and oxygen; a 4- to 10-membered heterocycloalkenyl having 1-2 heteroatoms independently selected from nitrogen and oxygen; or a 4- to 10-membered cycloalkenyl;

$R^7$ is selected from —H, —F, —$CH_3$ and —$OCH_3$;

each $R^8$ is independently selected from $C_{1-4}$ alkyl substituted with 0-3 —F substituents; $C_{1-4}$ alkoxy; —OH; —F; and —COO($C_{1-4}$ alkyl);

p is 0, 1 or 2;

Ring C is a 6- to 10-membered aryl; a 5- to 10-membered heteroaryl having 1-4 heteroatoms independently selected from nitrogen, oxygen and sulfur; a 4- to 10-membered cycloalkenyl; or a 4- to 10-membered heterocycloalkenyl having 1-2 heteroatoms independently selected from nitrogen and oxygen;

each $R^9$ is independently selected from $C_{1-4}$ alkyl, $C_{1-4}$ alkoxy, -halo and —OH;

q is 0, 1 or 2;

$R^1$ is selected from —COOH, —$CONH_2$, —CONHMe, —$CONMe_2$, —$C(CH_2OH)_2NH_2$, —$C(NH)NH_2$, —$SO_2NH_2$, —$NHSO_2Me$,

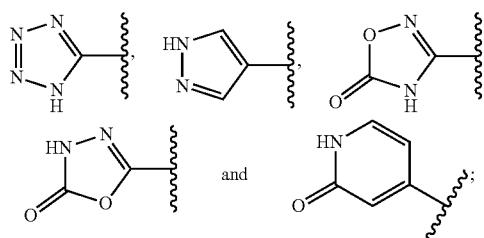

X is selected from a bond, —$CH_2$—, —O—, —S—, —$CH_2O$— and —$OCH_2$—;

Y is selected from $C_{2-6}$ alkylene substituted with 0-2 $R^{14}$ substituents; $C_{3-8}$ cycloalkylene substituted with 0-2 $R^{14}$ substituents; $C_{5-8}$ cycloalkenylene substituted with 0-2 $R^{14}$ substituents; 5- to 8-membered heterocycloalkylene having 1-3 heteroatoms independently selected from oxygen and sulfur and substituted with 0-2 $R^{14}$ substituents; phenylene substituted with 0-2 $R^{14}$ substituents; 5- or 6-membered heteroarylene having 1-3 heteroatoms independently selected from nitrogen, oxygen and sulfur and substituted with 0-2 $R^{14}$ substituents; and

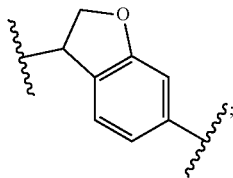 [SMILES: *c1ccc2c(c1)OCC2*]

$R^{14}$ is selected from $C_{1-3}$ alkyl substituted with 0-3 substituents selected from —OH, —OMe, —F and —CN; $C_{1-3}$ alkoxy substituted with 0-3 —F substituents; cyclopropyl substituted with 0-3 substituents selected from —OH, —OMe, —F and —CN; —F; —OH; =O; —CN; —$NH_2$; —NHMe; and —$NMe_2$;

Z is selected from a bond; $C_{1-3}$ alkylene substituted with 0-2 substituents selected from -Me, —$NH_2$, —NHMe and —$NMe_2$; $C_{2-4}$ heteroalkylene having one heteroatom selected from nitrogen and oxygen and substituted with 0-2 substituents selected from -Me, —$NH_2$, —NHMe and —$NMe_2$; $C_{3-4}$ cycloalkylene; and —CH=CH—;

$R^5$ is selected from —H, -Me and —F;

$R^6$ is —$(CR^{10}R^{11})_nR^{12}$;

n is 0, 1 or 2;

$R^{10}$ and $R^{11}$ are each independently selected from —H, -Me and —F, or $R^{10}$ and $R^{11}$ together with the carbon to which they are attached form cyclopropyl;

$R^{12}$ is selected from $C_{3-8}$ alkyl substituted with 0-5 substituents selected from —OH, —F, —CN, and $C_{1-4}$ alkoxy; $C_{3-10}$ cycloalkyl substituted with 0-4 $R^{13}$ substituents; 5- to 10-membered heterocycloalkyl having 1-2 heteroatoms independently selected from oxygen and sulfur and substituted with 0-4 $R^{13}$ substituents; phenyl substituted with 0-3 substituents selected from -halo, $C_{1-4}$ alkyl substituted with 0-3 —F substituents, $C_{3-5}$ cycloalkyl, —CN, —$SF_5$, —OMe, —$OCH_2F$, —$OCHF_2$, —$OCF_3$ and —$SO_2CF_3$; 6-membered heteroaryl having 1-2 nitrogen heteroatoms and substituted with 1-3 substituents selected from -halo, —$SF_5$, —$CF_3$, —$OCF_3$ and —$SO_2CF_3$;

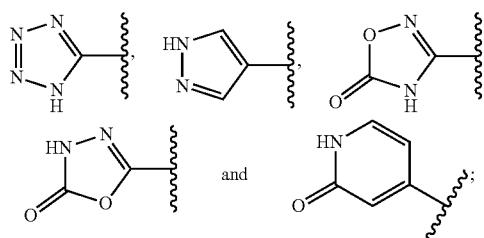

and each $R^{13}$ is independently selected from —OH; —F; —CN; $C_{1-4}$ alkoxy substituted with 0-3 substituents selected from —F, —OH, —OMe and —OEt; and $C_{1-4}$ alkyl substituted with 0-3 substituents selected from —F, —OH, —OMe and —OEt;

U, V and W are each independently selected from C and N; provided that when U is N, $R^2$ is absent; when V is N, $R^3$ is absent; and when W is N, $R^4$ is absent;

$R^2$ and $R^3$ are each independently selected from —H, -halo, —CN, $C_{1-4}$ alkyl substituted with 0-3 substituents selected from —F and —OMe, $C_{1-4}$ alkoxy substituted with 0-3 substituents selected from —F and —OMe, $C_{3-4}$ cycloalkyl substituted with 0-3 substituents selected from —F and —OMe, and $C_{3-4}$ cycloalkoxy substituted with 0-3 substituents selected from —F and -Me; and $R^4$ is selected from —F and $C_{1-4}$ alkoxy substituted with 0-3 substituents selected from —F and —OMe; optionally $R^4$ is $C_{1-4}$ alkoxy substituted with 0-3 substituents selected from —F and —OMe; optionally $R^4$ is —OMe.

In one embodiment A is

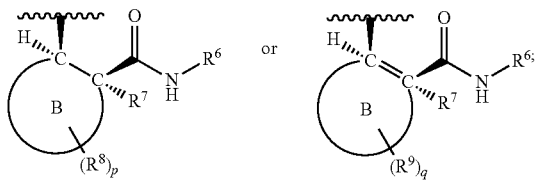

Ring B is a 4- to 10-membered cycloalkyl; a 4- to 10-membered heterocycloalkyl having 1-2 heteroatoms independently selected from nitrogen and oxygen; a 4- to 10-membered heterocycloalkenyl having 1-2 heteroatoms independently selected from nitrogen and oxygen; or a 4- to 10-membered cycloalkenyl;

$R^7$ is —H;

each $R^8$ is independently selected from $C_{1-4}$ alkyl substituted with 0-3 —F substituents; $C_{1-4}$ alkoxy; —OH; —F; and —COO($C_{1-4}$ alkyl);

p is 0, 1 or 2, optionally p is 0;

Ring C is a 6- to 10-membered aryl; a 5- to 10-membered heteroaryl having 1-4 heteroatoms independently selected from nitrogen, oxygen and sulfur; a 4- to 10-membered cycloalkenyl; or a 4- to 10-membered heterocycloalkenyl having 1-2 heteroatoms independently selected from nitrogen and oxygen;

each $R^9$ is independently selected from $C_{1-4}$ alkyl, $C_{1-4}$ alkoxy, -halo and —OH;

q is 0, 1 or 2, optionally q is 0;

$R^1$ is —COOH;

X is selected from a bond, —CH$_2$—, —O—, —S—, —CH$_2$O— and —OCH$_2$—; optionally X is —O—;

Y is

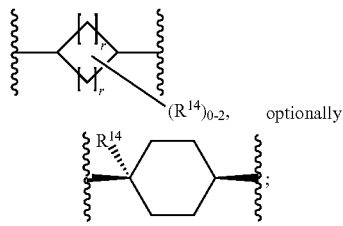

r is 1 or 2;

$R^{14}$ is selected from $C_{1-3}$ alkyl substituted with 0-3 substituents selected from —OH, —OMe, —F and —CN; $C_{1-3}$ alkoxy substituted with 0-3 —F substituents; cyclopropyl substituted with 0-3 substituents selected from —OH, —OMe, —F and —CN; —F; —OH; =O; —CN; —NH$_2$; —NHMe; and —NMe$_2$;

Z is selected from a bond; $C_{1-3}$ alkylene substituted with 0-2 substituents selected from -Me, —NH$_2$, —NHMe and —NMe$_2$; $C_{2-4}$ heteroalkylene having one heteroatom selected from nitrogen and oxygen and substituted with 0-2 substituents selected from -Me, —NH$_2$, —NHMe and —NMe$_2$; $C_{3-4}$ cycloalkylene; and —CH=CH—; optionally Z is a bond;

$R^5$ is selected from —H, -Me and —F, optionally $R^5$ is —H;

$R^6$ is —(CR$^{10}$R$^{11}$)$_n$R$^{12}$;

n is 0, 1 or 2;

$R^{10}$ and $R^{11}$ are each independently selected from —H, -Me and —F, or $R^{10}$ and $R^{11}$ together with the carbon to which they are attached form cyclopropyl;

$R^{12}$ is selected from $C_{4-6}$ alkyl substituted with 0-3 substituents selected from —F, —CN, and $C_{1-2}$ alkoxy; $C_{4-6}$ cycloalkyl substituted with 0-3 $R^{13}$ substituents; and 5- to 6-membered heterocycloalkyl having 1-2 heteroatoms independently selected from oxygen and sulfur and substituted with 0-3 $R^{13}$ substituents; or $R^{12}$ is selected from

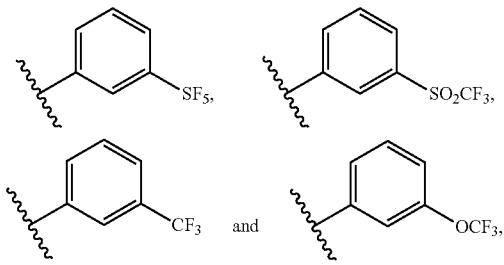

each substituted with 0-1 substituents selected from -halo, -Me, —CF$_3$ and —CN;

each $R^{13}$ is independently selected from —OH; —F; —CN; $C_{1-4}$ alkoxy substituted with 0-3 substituents selected from —F, —OH, —OMe and —OEt; and $C_{1-4}$ alkyl substituted with 0-3 substituents selected from —F, —OH, —OMe and —OEt;

U, V and W are each independently selected from C and N; provided that when U is N, $R^2$ is absent; when V is N, $R^3$ is absent; and when W is N, $R^4$ is absent;

$R^2$ and $R^3$ are each independently selected from —H, -halo, —CN, $C_{1-4}$ alkyl substituted with 0-3 substituents selected from —F and —OMe, $C_{1-4}$ alkoxy substituted with 0-3 substituents selected from —F and —OMe, $C_{3-4}$ cycloalkyl substituted with 0-3 substituents selected from —F and —OMe, and $C_{3-4}$ cycloalkoxy substituted with 0-3 substituents selected from —F and -Me; and $R^4$ is selected from —F and $C_{1-4}$ alkoxy substituted with 0-3 substituents selected from —F and —OMe; optionally $R^4$ is $C_{1-4}$ alkoxy substituted with 0-3 substituents selected from —F and —OMe; optionally $R^4$ is —OMe.

In one embodiment, A is

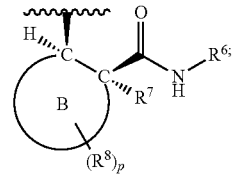

Ring B is a 5- to 8-membered cycloalkyl, or a 5- to 8-membered cycloalkenyl;

$R^7$ is selected from —H and —F;

each $R^8$ is independently selected from $C_{1-2}$ alkyl substituted with 0-3 —F substituents; and —F;

p is 0 or 1; optionally p is 0;

$R^1$ is selected from —COOH, —CONH$_2$,

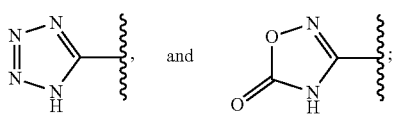 [SMILES: *c1nnn[nH]1 ; *c1noc(=O)[nH]1]

X is —O—;
Y is

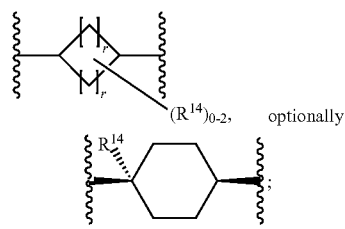

r is 1 or 2;
R$^{14}$ is selected from C$_{1-2}$ alkyl substituted with 0-1 substituents selected from —OH, —OMe, —F and —CN; C$_{1-2}$ alkoxy substituted with 0-1 —F substituents; cyclopropyl substituted with 0-1 substituents selected from —OH, —OMe, —F and —CN; —F; —OH; =O; —CN; —NH$_2$; —NHMe; and —NMe$_2$;
Z is a bond;
R$^5$ is —H;
R$^6$ is —(CR$^{10}$R$^{11}$)$_n$R$^{12}$;
n is 0 or 1; optionally n is 1;
R$^{10}$ and R$^{11}$ are each independently selected from —H, -Me and —F, or R$^{10}$ and R$^{11}$ together with the carbon to which they are attached form cyclopropyl;
R$^{12}$ is selected from C$_{4-6}$ alkyl substituted with 0-3 substituents selected from —F, —CN, and C$_{1-2}$ alkoxy; C$_{4-6}$ cycloalkyl substituted with 0-3 R$^{13}$ substituents; and 5- to 6-membered heterocycloalkyl having 1-2 heteroatoms independently selected from oxygen and sulfur and substituted with 0-3 R$^{13}$ substituents; or
R$^{12}$ is selected from

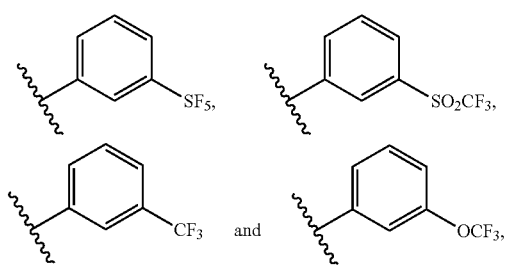

each substituted with 0-1 substituents selected from -halo, -Me, —CF$_3$ and —CN;
each R$^{13}$ is independently selected from —F; —CN; C$_{1-2}$ alkoxy substituted with 0-1 substituents selected from —F, —OMe and —OEt; and C$_{1-2}$ alkyl substituted with 0-1 substituents selected from —F, —OMe and —OEt;
U, V and W are each C;
R$^2$ is selected from —H, -halo, —CN, C$_{1-2}$ alkyl substituted with 0-3 —F substituents, C$_{1-2}$ alkyl substituted with 0-1 —OMe substituents, and cyclopropyl; optionally R$^2$ is —F or —CN;

R$^3$ is selected from —H, -halo, —CN, C$_{1-2}$ alkyl substituted with 0-3 —F substituents, C$_{1-2}$ alkyl substituted with 0-1 —OMe substituents, and cyclopropyl; optionally R$^3$ is —H;

R$^4$ is selected from —F and C$_{1-4}$ alkoxy substituted with 0-3 substituents selected from —F and —OMe; optionally R$^4$ is C$_{1-4}$ alkoxy substituted with 0-3 substituents selected from —F and —OMe; optionally R$^4$ is —OMe.

In an embodiment, there is provided a compound of Formula (IIa) or Formula (IIb):

(Formula IIa)

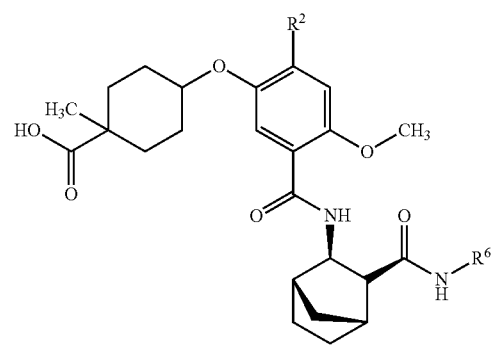

(Formula IIb)

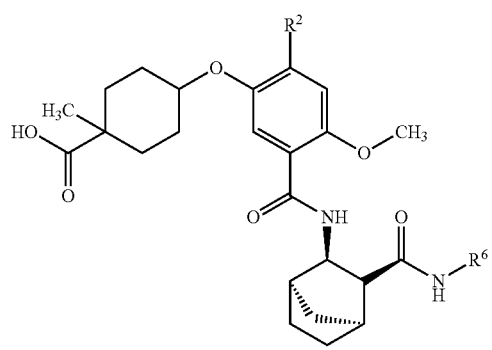

or a pharmaceutically acceptable salt thereof, wherein R$^2$ and R$^6$ are as defined for Formula (I).

In an embodiment, there is provided a compound of Formula (IIa) or Formula (IIb), or a pharmaceutically acceptable salt thereof, wherein R$^2$ is —F or —CN; and R$^6$ is selected from

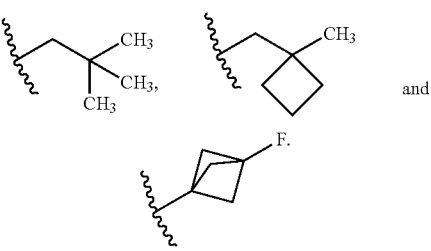

In an embodiment, there is provided a compound of Formula (IIa) or Formula (IIb), or a pharmaceutically acceptable salt thereof, wherein R$^2$ is —F; and R$^6$ is

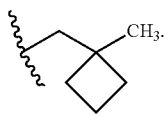 [SMILES: *CC1(C)CCC1]

In an embodiment, there is provided a compound of Formula (IIa) or Formula (IIb), or a pharmaceutically acceptable salt thereof, wherein $R^2$ is —CN; and $R^6$ is

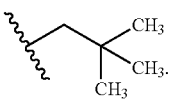

In an embodiment, there is provided a compound of Formula (IIa) or Formula (IIb), or a CH₃ pharmaceutically acceptable salt thereof, wherein $R^2$ is —CN; and $R^6$ is

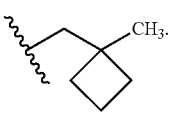 [SMILES: *CC1(C)CCC1]

In an embodiment, there is provided a compound of Formula (IIa) or Formula (IIb), or a pharmaceutically acceptable salt thereof, wherein $R^2$ is —CN; and $R^6$ is

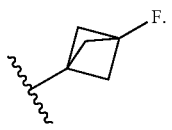 [SMILES: *C12CC(F)(C1)C2]

In an embodiment, there is provided a compound of Formula (IIIa) or Formula (IIIb):

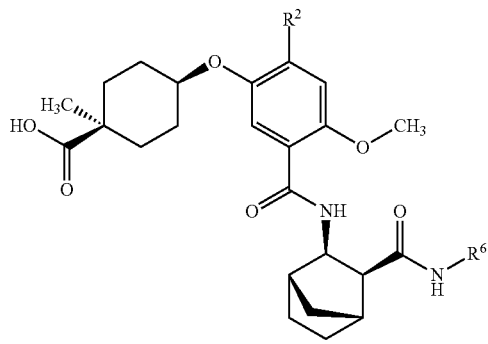

(Formula IIIa)

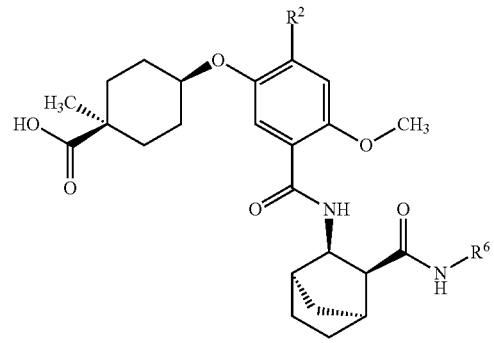

(Formula IIIb)

or a pharmaceutically acceptable salt thereof, wherein $R^2$ and $R^6$ are as defined for Formula (I).

In an embodiment, there is provided a compound of Formula (IIIa) or Formula (IIIb), or a pharmaceutically acceptable salt thereof, wherein $R^2$ is —F or —CN; and $R^6$ is selected from

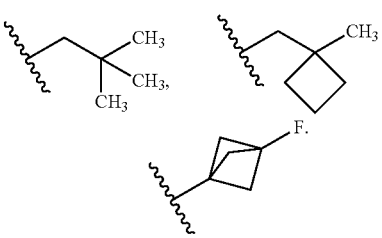

and

In an embodiment, there is provided a compound of Formula (IIIa) or Formula (IIIb), or a pharmaceutically acceptable salt thereof, wherein $R^2$ is —F; and $R^6$ is

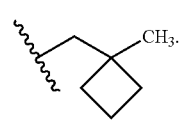

In an embodiment, there is provided a compound of Formula (IIIa) or Formula (IIIb), or a pharmaceutically acceptable salt thereof, wherein $R^2$ is —CN; and $R^6$ is

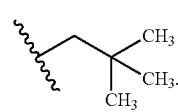

In an embodiment, there is provided a compound of Formula (IIIa) or Formula (IIIb), or a pharmaceutically acceptable salt thereof, wherein $R^2$ is —CN; and $R^6$ is

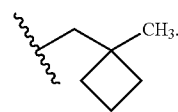

In an embodiment, there is provided a compound of Formula (IIIa) or Formula (IIIb), or a pharmaceutically acceptable salt thereof, wherein R² is —CN; and R⁶ is

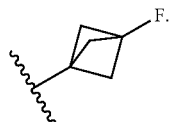 [SMILES: *C12CC(F)(C1)C2]

In an embodiment, there is provided a compound of Formula (IIIa), or a pharmaceutically acceptable salt thereof, wherein R² is —F or —CN; and R⁶ is selected from

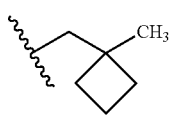 and 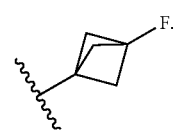

In an embodiment, there is provided a compound of Formula (IVa) or Formula (IVb):

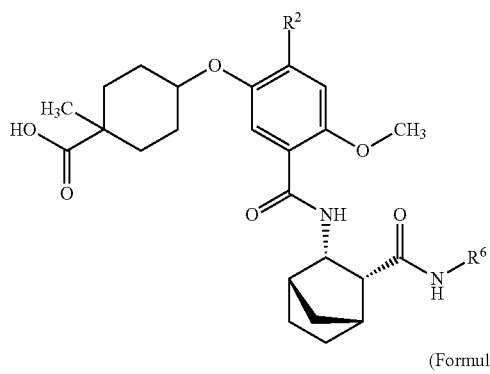

(Formula IVa)

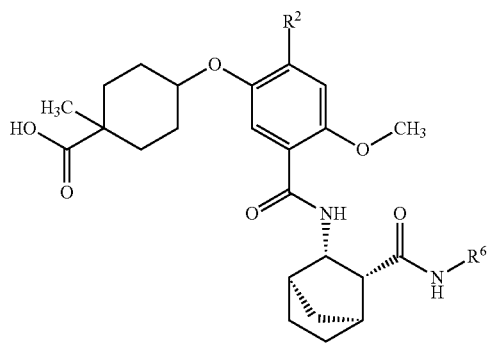

(Formula IVb)

or a pharmaceutically acceptable salt thereof, wherein R² and R⁶ are as defined for Formula (I).

In an embodiment, there is provided a compound of Formula (IVa) or Formula (IVb), or a pharmaceutically acceptable salt thereof, wherein R² is —F or —CN; and R⁶ is selected from

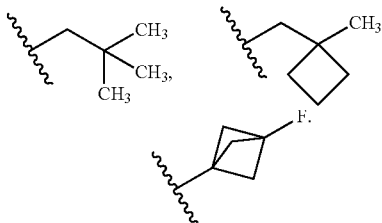 and

In an embodiment, the compound of Formula (I) is

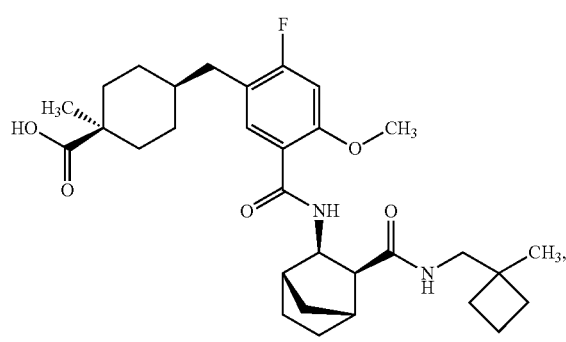 [SMILES: COc1cc(C#N)c(C[C@H]2CC[C@@](C)(C(=O)O)CC2)cc1C(=O)N[C@@H]1[C@H]2CC[C@H](C2)[C@@H]1C(=O)NCC1(C)CCC1]

or a pharmaceutically acceptable salt thereof.

In an embodiment, the compound of Formula (I) is

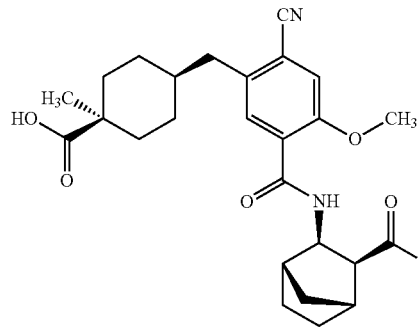

or a pharmaceutically acceptable salt thereof.

In an embodiment, the compound of Formula (I) is

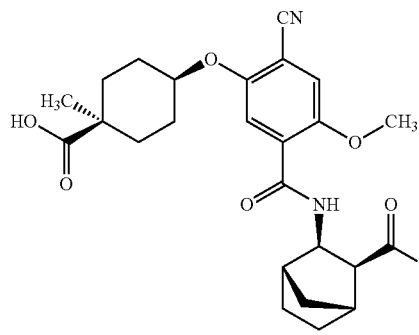

or a pharmaceutically acceptable salt thereof.

In an embodiment, the compound of Formula (I) is

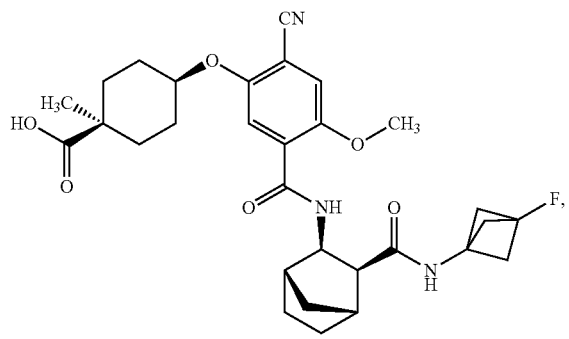 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC12CC(F)(C1)C2]

or a pharmaceutically acceptable salt thereof.

In an embodiment, the compound of Formula (I) is

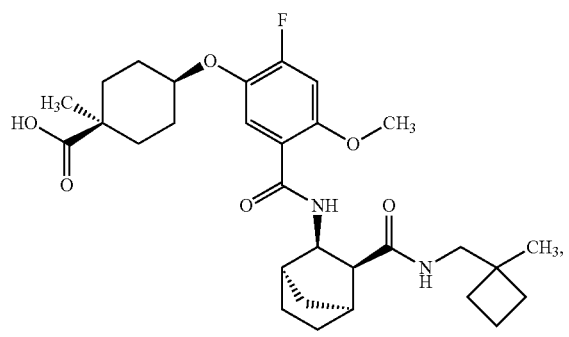 [SMILES: COc1cc(C#N)c(O[C@H]2CC[C@@](C)(C(=O)O)CC2)cc1C(=O)N[C@@H]1[C@@H]2CC[C@@H](C2)[C@@H]1C(=O)NCC1(C)CCC1]

or a pharmaceutically acceptable salt thereof.

In an embodiment, the compound of Formula (I) is

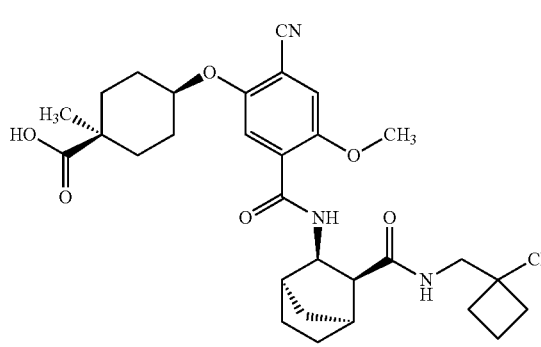

or a pharmaceutically acceptable salt thereof.

In an embodiment, the compound of Formula (I) is

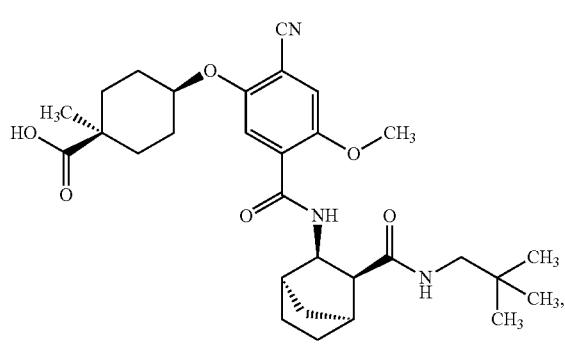 [SMILES: COc1cc(C#N)c(O[C@H]2CC[C@@](C)(C(=O)O)CC2)cc1C(=O)N[C@@H]1[C@@H]2CC[C@@H](C2)[C@@H]1C(=O)NCC(C)(C)C]

or a pharmaceutically acceptable salt thereof.

In an embodiment, the compound of Formula (I) is

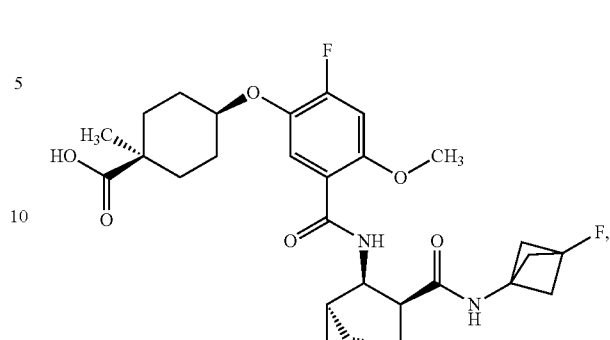

or a pharmaceutically acceptable salt thereof.

In an embodiment, the compound of Formula (I) is

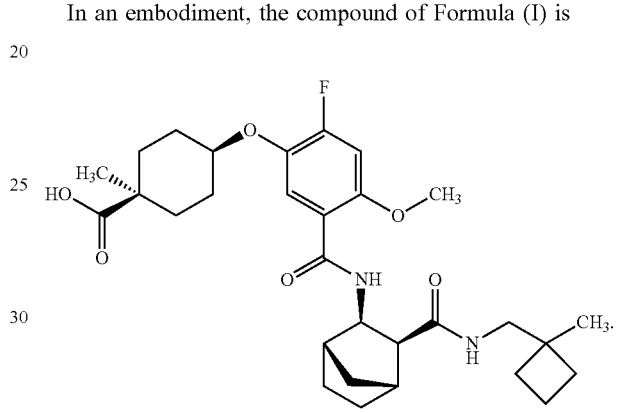

In an embodiment, the compound of Formula (I) is

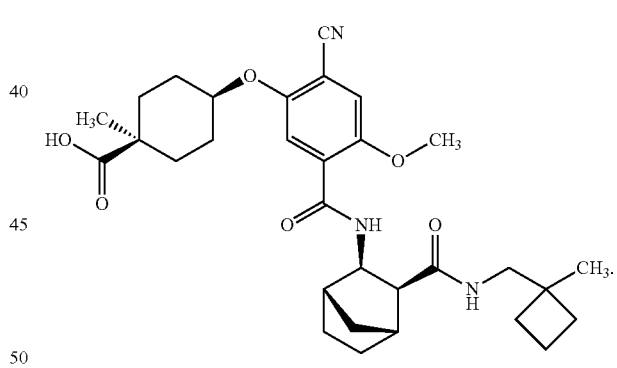

In an embodiment, the compound of Formula (I) is

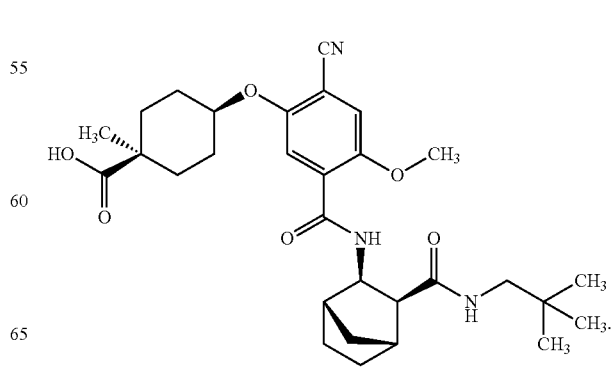

In an embodiment, the compound of Formula (I) is

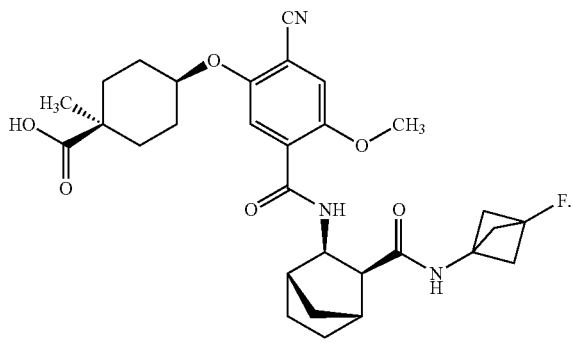 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC12CC(F)(C1)C2]

In an embodiment, a compound is provided that is any one of the compounds from COMPOUND LIST A, or a pharmaceutically acceptable salt thereof.

In an embodiment, a compound is provided that is any one of the compounds from COMPOUND LIST A.

In an embodiment, the compound of Formula (I) is selected from the compounds of COMPOUND LIST A, or pharmaceutically acceptable salts thereof.

In an embodiment, the compound of Formula (I) is selected from the compounds of COMPOUND LIST A.

Compound List a:

4-(2-fluoro-4-methoxy-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(5-((3-((cyclobutylmethyl)carbamoyl)bicyclo[2.2.1]heptan-2-yl)carbamoyl)-2-fluoro-4-methoxyphenoxy)-1-methylcyclohexane-1-carboxylic acid;

4-(2-fluoro-4-(fluoromethoxy)-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(2-fluoro-4-methyl-5-((3-(((1-methylcyclobutyl)methyl)carbamoyl)bicyclo[2.2.1]heptan-2-yl)carbamoyl)phenoxy)-1-methylcyclohexane-1-carboxylic acid;

6-(2-cyano-4-methoxy-5-((3-(((1-methylcyclobutyl)methyl)carbamoyl)bicyclo[2.2.1]heptan-2-yl)carbamoyl)phenoxy)spiro[3.3]heptane-2-carboxylic acid;

4-(2-fluoro-5-((3-(isopropylcarbamoyl)bicyclo[2.2.1]heptan-2-yl)carbamoyl)-4-methoxyphenoxy)cyclohexane-1-carboxylic acid;

4-(5-((3-(cyclohexylcarbamoyl)bicyclo[2.2.1]heptan-2-yl)carbamoyl)-2-fluoro-4-methoxyphenoxy)cyclohexane-1-carboxylic acid;

4-(5-((3-((3-(difluoromethyl)phenyl)carbamoyl)bicyclo[2.2.1]heptan-2-yl)carbamoyl)-2-fluoro-4-methoxyphenoxy)cyclohexane-1-carboxylic acid;

4-(2-fluoro-5-((3-((3-(fluoromethyl)phenyl)carbamoyl)bicyclo[2.2.1]heptan-2-yl)carbamoyl)-4-methoxyphenoxy)cyclohexane-1-carboxylic acid;

4-(2-fluoro-4-methoxy-5-((3-((2-(trifluoromethyl)pyridin-4-yl)carbamoyl)bicyclo[2.2.1]heptan-2-yl)carbamoyl)phenoxy)cyclohexane-1-carboxylic acid;

4-(2-fluoro-4-methoxy-5-((3-((5-(trifluoromethyl)pyridin-2-yl)carbamoyl)bicyclo[2.2.1]heptan-2-yl)carbamoyl)phenoxy)cyclohexane-1-carboxylic acid;

4-(2-fluoro-4-methoxy-5-((3-((4-(trifluoromethyl)pyridin-2-yl)carbamoyl)bicyclo[2.2.1]heptan-2-yl)carbamoyl)phenoxy)cyclohexane-1-carboxylic acid;

4-(2-fluoro-4-methoxy-5-((3-((4-(((trifluoromethyl)sulfonyl)phenyl)carbamoyl)bicyclo[2.2.1]heptan-2-yl)carbamoyl)phenoxy)cyclohexane-1-carboxylic acid;

4-(2-fluoro-4-methoxy-5-((3-((perfluorophenyl)carbamoyl)bicyclo[2.2.1]heptan-2-yl)carbamoyl)phenoxy)cyclohexane-1-carboxylic acid;

4-(2-fluoro-5-((3-((3-fluoro-5-(pentafluoro-$\lambda^6$-sulfaneyl)phenyl)carbamoyl)bicyclo[2.2.1]heptan-2-yl)carbamoyl)-4-methoxyphenoxy)cyclohexane-1-carboxylic acid;

4-(2-fluoro-5-((3-((2-fluoro-3-(trifluoromethoxy)phenyl)carbamoyl)bicyclo[2.2.1]heptan-2-yl)carbamoyl)-4-methoxyphenoxy)cyclohexane-1-carboxylic acid;

4-(5-((3-((3-cyano-4-methylphenyl)carbamoyl)bicyclo[2.2.1]heptan-2-yl)carbamoyl)-2-fluoro-4-methoxyphenoxy)cyclohexane-1-carboxylic acid;

4-(2-fluoro-4-methoxy-5-((3-((3-(trifluoromethoxy)phenyl)carbamoyl)bicyclo[2.2.1]heptan-2-yl)carbamoyl)phenoxy)cyclohexane-1-carboxylic acid;

4-(2-fluoro-5-((3-((4-fluoro-3-(trifluoromethoxy)phenyl)carbamoyl)bicyclo[2.2.1]heptan-2-yl)carbamoyl)-4-methoxyphenoxy)cyclohexane-1-carboxylic acid;

4-(5-((3-((3,5-bis(trifluoromethyl)phenyl)carbamoyl)bicyclo[2.2.1]heptan-2-yl)carbamoyl)-2-fluoro-4-methoxyphenoxy)cyclohexane-1-carboxylic acid;

4-(5-((3-((4-bromo-3-(trifluoromethyl)phenyl)carbamoyl)bicyclo[2.2.1]heptan-2-yl)carbamoyl)-2-fluoro-4-methoxyphenoxy)cyclohexane-1-carboxylic acid;

4-(2-fluoro-4-methoxy-5-((3-((2-methyl-3-(trifluoromethyl)phenyl)carbamoyl)bicyclo[2.2.1]heptan-2-yl)carbamoyl)phenoxy)cyclohexane-1-carboxylic acid;

4-(5-((3-((3-chlorophenyl)carbamoyl)bicyclo[2.2.1]heptan-2-yl)carbamoyl)-2-fluoro-4-methoxyphenoxy)cyclohexane-1-carboxylic acid;

4-(5-((3-((2-chloro-5-(trifluoromethyl)phenyl)carbamoyl)bicyclo[2.2.1]heptan-2-yl)carbamoyl)-2-fluoro-4-methoxyphenoxy)cyclohexane-1-carboxylic acid;

4-(5-((3-((3-bromo-4-cyanophenyl)carbamoyl)bicyclo[2.2.1]heptan-2-yl)carbamoyl)-2-fluoro-4-methoxyphenoxy)cyclohexane-1-carboxylic acid;

4-(5-((3-((4-cyano-3-(trifluoromethyl)phenyl)carbamoyl)bicyclo[2.2.1]heptan-2-yl)carbamoyl)-2-fluoro-4-methoxyphenoxy)cyclohexane-1-carboxylic acid;

4-(2-fluoro-5-((3-((3-fluoro-5-(trifluoromethyl)phenyl)carbamoyl)bicyclo[2.2.1]heptan-2-yl)carbamoyl)-4-methoxyphenoxy)cyclohexane-1-carboxylic acid;

4-(5-((3-((5-chloropyridazin-3-yl)carbamoyl)bicyclo[2.2.1]heptan-2-yl)carbamoyl)-2-fluoro-4-methoxyphenoxy)cyclohexane-1-carboxylic acid;

4-(2-fluoro-4-methoxy-5-((3-((6-(trifluoromethyl)pyrimidin-4-yl)carbamoyl)bicyclo[2.2.1]heptan-2-yl)carbamoyl)phenoxy)cyclohexane-1-carboxylic acid;

4-(2-fluoro-4-methoxy-5-((3-((4-(trifluoromethyl)pyrimidin-2-yl)carbamoyl)bicyclo[2.2.1]heptan-2-yl)carbamoyl)phenoxy)cyclohexane-1-carboxylic acid;

4-(5-((3-((3,3-difluorocyclobutyl)carbamoyl)bicyclo[2.2.1]heptan-2-yl)carbamoyl)-2-fluoro-4-methoxyphenoxy)cyclohexane-1-carboxylic acid;

4-(2-fluoro-5-((3-(isobutylcarbamoyl)bicyclo[2.2.1]heptan-2-yl)carbamoyl)-4-methoxyphenoxy)-1-methylcyclohexane-1-carboxylic acid;

4-(2-fluoro-4-methoxy-5-((3-(neopentylcarbamoyl)bicyclo[2.2.1]heptan-2-yl)carbamoyl)phenoxy)-1-methylcyclohexane-1-carboxylic acid;

4-(5-((3-((3,3-dimethylbutan-2-yl)carbamoyl)bicyclo[2.2.1]heptan-2-yl)carbamoyl)-2-fluoro-4-methoxyphenoxy)-1-methylcyclohexane-1-carboxylic acid;

4-(5-((3-((2,2-dimethylbutyl)carbamoyl)bicyclo[2.2.1]heptan-2-yl)carbamoyl)-2-fluoro-4-methoxyphenoxy)-1-methylcyclohexane-1-carboxylic acid;

4-(2-fluoro-4-methoxy-5-((3-((3,3,3-trifluoro-2,2-dimethylpropyl)carbamoyl)bicyclo[2.2.1]heptan-2-yl)carbamoyl)phenoxy)-1-methylcyclohexane-1-carboxylic acid;

4-(2-fluoro-4-methoxy-5-((3-((1-(1-methylcyclopropyl)ethyl)carbamoyl)bicyclo[2.2.1]heptan-2-yl)carbamoyl)phenoxy)-1-methylcyclohexane-1-carboxylic acid;

4-(5-((3-((2,4-dimethylpentan-3-yl)carbamoyl)bicyclo[2.2.1]heptan-2-yl)carbamoyl)-2-fluoro-4-methoxyphenoxy)-1-methylcyclohexane-1-carboxylic acid;

4-(2-fluoro-4-methoxy-5-((3-(((1-methylcyclopropyl)methyl)carbamoyl)bicyclo[2.2.1]heptan-2-yl)carbamoyl)phenoxy)-1-methylcyclohexane-1-carboxylic acid;

4-(2-fluoro-4-methoxy-5-((3-((3-methylbutan-2-yl)carbamoyl)bicyclo[2.2.1]heptan-2-yl)carbamoyl)phenoxy)-1-methylcyclohexane-1-carboxylic acid;

4-(5-((3-((2-ethylbutyl)carbamoyl)bicyclo[2.2.1]heptan-2-yl)carbamoyl)-2-fluoro-4-methoxyphenoxy)-1-methylcyclohexane-1-carboxylic acid;

4-(2-fluoro-4-methoxy-5-((3-(((1-methylcyclohexyl)methyl)carbamoyl)bicyclo[2.2.1]heptan-2-yl)carbamoyl)phenoxy)-1-methylcyclohexane-1-carboxylic acid;

4-(5-((3-((2-cyano-2-methylpropyl)carbamoyl)bicyclo[2.2.1]heptan-2-yl)carbamoyl)-2-fluoro-4-methoxyphenoxy)-1-methylcyclohexane-1-carboxylic acid;

4-(2-fluoro-5-((3-(((1-(fluoromethyl)cyclopropyl)methyl)carbamoyl)bicyclo[2.2.1]heptan-2-yl)carbamoyl)-4-methoxyphenoxy)-1-methylcyclohexane-1-carboxylic acid;

4-(2-fluoro-5-((3-((4-fluoro-3-(trifluoromethyl)phenyl)carbamoyl)-7-oxabicyclo[2.2.1]heptan-2-yl)carbamoyl)-4-methoxyphenoxy)cyclohexane-1-carboxylic acid;

4-(2-fluoro-5-((2-((4-fluoro-3-(trifluoromethyl)phenyl)carbamoyl)cyclobutyl)carbamoyl)-4-methoxyphenoxy)-1-methylcyclohexane-1-carboxylic acid;

4-(2-fluoro-5-((4-((4-fluoro-3-(trifluoromethyl)phenyl)carbamoyl)tetrahydrofuran-3-yl)carbamoyl)-4-methoxyphenoxy)-1-methylcyclohexane-1-carboxylic acid; 3-(5-((4-carbamoyl-4-methylcyclohexyl)oxy)-4-fluoro-2-methoxybenzamido)-N-neopentylbicyclo[2.2.1]heptane-2-carboxamide;

4-(5-((3-chloro-2-(((1-methylcyclobutyl)methyl)carbamoyl)phenyl)carbamoyl)-2-fluoro-4-methoxyphenoxy)-1-methylcyclohexane-1-carboxylic acid;

4-(2-fluoro-4-methoxy-5-((2-((3-methylbutan-2-yl)carbamoyl)cyclopentyl)carbamoyl)phenoxy)-1-methylcyclohexane-1-carboxylic acid;

4-(2-fluoro-5-((2-(((1-(fluoromethyl)cyclopropyl)methyl)carbamoyl)cyclopentyl)carbamoyl)-4-methoxyphenoxy)-1-methylcyclohexane-1-carboxylic acid;

4-(2-fluoro-4-methoxy-5-((2-(neopentylcarbamoyl)cyclopentyl)carbamoyl)phenoxy)-1-methylcyclohexane-1-carboxylic acid;

4-(5-((2-((2,2-dimethylbutyl)carbamoyl)cyclopentyl)carbamoyl)-2-fluoro-4-methoxyphenoxy)-1-methylcyclohexane-1-carboxylic acid;

4-(5-((2-((2-ethylbutyl)carbamoyl)cyclopentyl)carbamoyl)-2-fluoro-4-methoxyphenoxy)-1-methylcyclohexane-1-carboxylic acid;

4-(5-((2-((3,3-dimethylbutan-2-yl)carbamoyl)cyclopentyl)carbamoyl)-2-fluoro-4-methoxyphenoxy)-1-methylcyclohexane-1-carboxylic acid;

4-(5-((2-((2,4-dimethylpentan-3-yl)carbamoyl)cyclopentyl)carbamoyl)-2-fluoro-4-methoxyphenoxy)-1-methylcyclohexane-1-carboxylic acid;

4-(2-fluoro-4-methoxy-5-((2-((1-(1-methylcyclopropyl)ethyl)carbamoyl)cyclopentyl)carbamoyl)phenoxy)-1-methylcyclohexane-1-carboxylic acid;

4-(2-fluoro-4-methoxy-5-((2-(((1-methylcyclohexyl)methyl)carbamoyl)cyclopentyl)carbamoyl)phenoxy)-1-methylcyclohexane-1-carboxylic acid;

4-(2-fluoro-5-((2-(isobutylcarbamoyl)cyclopentyl)carbamoyl)-4-methoxyphenoxy)-1-methylcyclohexane-1-carboxylic acid;

4-(2-fluoro-4-methoxy-5-((2-(((1-methylcyclobutyl)methyl)carbamoyl)cyclopentyl)carbamoyl)phenoxy)-1-methylcyclohexane-1-carboxylic acid;

4-(2-fluoro-4-methoxy-5-((2-(((1-methylcyclopropyl)methyl)carbamoyl)cyclopentyl)carbamoyl)phenoxy)-1-methylcyclohexane-1-carboxylic acid;

4-(5-((2-((2-cyano-2-methylpropyl)carbamoyl)cyclopentyl)carbamoyl)-2-fluoro-4-methoxyphenoxy)-1-methylcyclohexane-1-carboxylic acid;

4-(2-fluoro-4-methoxy-5-((2-((3,3,3-trifluoro-2,2-dimethylpropyl)carbamoyl)cyclopentyl)carbamoyl)phenoxy)-1-methylcyclohexane-1-carboxylic acid;

4-(2-cyano-5-((3-((cyclopropylmethyl)carbamoyl)bicyclo[2.2.1]heptan-2-yl)carbamoyl)-4-methoxyphenoxy)-1-methylcyclohexane-1-carboxylic acid;

4-(2-cyano-5-((3-((1-cyanocyclopropyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-((3-methylcyclobutyl)carbamoyl)bicyclo[2.2.1]heptan-2-yl)carbamoyl)phenoxy)-1-methylcyclohexane-1-carboxylic acid;

4-(2-cyano-5-((3-(((1-hydroxycyclopentyl)methyl)carbamoyl)bicyclo[2.2.1]heptan-2-yl)carbamoyl)-4-methoxyphenoxy)-1-methylcyclohexane-1-carboxylic acid;

4-(2-cyano-5-((3-(((1-(hydroxymethyl)cyclobutyl)methyl)carbamoyl)bicyclo[2.2.1]heptan-2-yl)carbamoyl)-4-methoxyphenoxy)-1-methylcyclohexane-1-carboxylic acid;

4-(2-cyano-5-((3-((2-hydroxy-2-methylpropyl)carbamoyl)bicyclo[2.2.1]heptan-2-yl)carbamoyl)-4-methoxyphenoxy)-1-methylcyclohexane-1-carboxylic acid;

4-(2-cyano-5-((3-((1-fluoro-2-methylpropan-2-yl)carbamoyl)bicyclo[2.2.1]heptan-2-yl)carbamoyl)-4-methoxyphenoxy)-1-methylcyclohexane-1-carboxylic acid;

4-(2-cyano-5-((3-(((1-isopropylcyclopropyl)methyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-(((1-(methoxymethyl)cyclopropyl)methyl)carbamoyl)bicyclo[2.2.1]heptan-2-yl)carbamoyl)phenoxy)-1-methylcyclohexane-1-carboxylic acid;

4-(2-cyano-4-methoxy-5-((3-(((1-methoxycyclobutyl)methyl)carbamoyl)bicyclo[2.2.1]heptan-2-yl)carbamoyl)phenoxy)-1-methylcyclohexane-1-carboxylic acid;

4-(5-((3-((adamantan-1-yl)carbamoyl)bicyclo[2.2.1]heptan-2-yl)carbamoyl)-2-cyano-4-methoxyphenoxy)-1-methylcyclohexane-1-carboxylic acid;

4-(2-cyano-5-((3-((cycloheptylmethyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-(((1-propylcyclobutyl)methyl)carbamoyl)bicyclo[2.2.1]heptan-2-yl)carbamoyl)phenoxy)-1-methylcyclohexane-1-carboxylic acid;

4-(2-cyano-4-methoxy-5-((3-(((2,2,3,3-tetramethylcyclopropyl)methyl)carbamoyl)bicyclo[2.2.1]heptan-2-yl)carbamoyl)phenoxy)-1-methylcyclohexane-1-carboxylic acid;

4-(2-cyano-5-((3-((2-(isopropylamino)-2-oxoethyl)carbamoyl)bicyclo[2.2.1]heptan-2-yl)carbamoyl)-4-methoxyphenoxy)-1-methylcyclohexane-1-carboxylic acid;

4-(2-cyano-5-((3-(((1-ethylcyclobutyl)methyl)carbamoyl)bicyclo[2.2.1]heptan-2-yl)carbamoyl)-4-methoxyphenoxy)-1-methylcyclohexane-1-carboxylic acid;

4-(2-cyano-5-((3-(((3,3-dimethylcyclobutyl)methyl)carbamoyl)bicyclo[2.2.1]heptan-2-yl)carbamoyl)-4-methoxyphenoxy)-1-methylcyclohexane-1-carboxylic acid;

4-(2-cyano-5-((3-((2-ethylbutyl)carbamoyl)bicyclo[2.2.1]heptan-2-yl)carbamoyl)-4-methoxyphenoxy)-1-methylcyclohexane-1-carboxylic acid;

4-(2-cyano-5-((3-((2-fluoro-3-hydroxypropyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-((1-methylcyclobutyl)carbamoyl)bicyclo[2.2.1]heptan-2-yl)carbamoyl)phenoxy)-1-methylcyclohexane-1-carboxylic acid;

4-(5-((3-(butylcarbamoyl)bicyclo[2.2.1]heptan-2-yl)carbamoyl)-2-cyano-4-methoxyphenoxy)-1-methylcyclohexane-1-carboxylic acid;

4-(2-cyano-5-((3-(((1-fluorocyclopentyl)methyl)carbamoyl)bicyclo[2.2.1]heptan-2-yl)carbamoyl)-4-methoxyphenoxy)-1-methylcyclohexane-1-carboxylic acid;

4-(2-cyano-5-((3-(((1-cyanocyclobutyl)methyl)carbamoyl)bicyclo[2.2.1]heptan-2-yl)carbamoyl)-4-methoxyphenoxy)-1-methylcyclohexane-1-carboxylic acid;

4-(2-cyano-5-((3-(((1-fluorocyclobutyl)methyl)carbamoyl)bicyclo[2.2.1]heptan-2-yl)carbamoyl)-4-methoxyphenoxy)-1-methylcyclohexane-1-carboxylic acid;

4-(2-cyano-5-((3-(((1-(fluoromethyl)cyclopropyl)methyl)carbamoyl)bicyclo[2.2.1]heptan-2-yl)carbamoyl)-4-methoxyphenoxy)-1-methylcyclohexane-1-carboxylic acid;

4-(2-cyano-5-((3-((2,2-difluoropropyl)carbamoyl)bicyclo[2.2.1]heptan-2-yl)carbamoyl)-4-methoxyphenoxy)-1-methylcyclohexane-1-carboxylic acid;

4-(2-cyano-5-((3-((2-fluoro-2-methylpropyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-(((1-methylcyclopropyl)methyl)carbamoyl)bicyclo[2.2.1]heptan-2-yl)carbamoyl)phenoxy)-1-methylcyclohexane-1-carboxylic acid;

4-(5-((3-(tert-butylcarbamoyl)bicyclo[2.2.1]heptan-2-yl)carbamoyl)-2-cyano-4-methoxyphenoxy)-1-methylcyclohexane-1-carboxylic acid;

4-(2-cyano-4-methoxy-5-((3-((1-methylcyclopropyl)carbamoyl)bicyclo[2.2.1]heptan-2-yl)carbamoyl)phenoxy)-1-methylcyclohexane-1-carboxylic acid;

4-(2-cyano-5-((3-(((4,4-difluoro-1-hydroxycyclohexyl)methyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-((2,2,3,3,3-pentafluoropropyl)carbamoyl)bicyclo[2.2.1]heptan-2-yl)carbamoyl)phenoxy)-1-methylcyclohexane-1-carboxylic acid;

4-(2-cyano-5-((3-(((1-hydroxycycloheptyl)methyl)carbamoyl)bicyclo[2.2.1]heptan-2-yl)carbamoyl)-4-methoxyphenoxy)-1-methylcyclohexane-1-carboxylic acid;

4-(2-cyano-5-((3-(((1-(ethoxymethyl)cyclobutyl)methyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-(((1-methylcycloheptyl)methyl)carbamoyl)bicyclo[2.2.1]heptan-2-yl)carbamoyl)phenoxy)-1-methylcyclohexane-1-carboxylic acid;

4-(2-cyano-5-((3-(((1-isobutylcyclobutyl)methyl)carbamoyl)bicyclo[2.2.1]heptan-2-yl)carbamoyl)-4-methoxyphenoxy)-1-methylcyclohexane-1-carboxylic acid;

4-(2-cyano-5-((3-(((4-cyanocyclohexyl)methyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-((2-phenylpropan-2-yl)carbamoyl)bicyclo[2.2.1]heptan-2-yl)carbamoyl)phenoxy)-1-methylcyclohexane-1-carboxylic acid;

4-(2-cyano-5-((3-(((1-(hydroxymethyl)cyclopentyl)methyl)carbamoyl)bicyclo[2.2.1]heptan-2-yl)carbamoyl)-4-methoxyphenoxy)-1-methylcyclohexane-1-carboxylic acid;

4-(2-cyano-5-((3-(((4-fluorotetrahydro-2H-pyran-4-yl)methyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-(((1-methoxycyclopropyl)methyl)carbamoyl)bicyclo[2.2.1]heptan-2-yl)carbamoyl)phenoxy)-1-methylcyclohexane-1-carboxylic acid;

4-(5-((3-(([1,1'-bi(cyclopropan)]-1-ylcarbamoyl)bicyclo[2.2.1]heptan-2-yl)carbamoyl)-2-cyano-4-methoxyphenoxy)-1-methylcyclohexane-1-carboxylic acid;

4-(2-cyano-5-((3-((3-hydroxyadamantan-1-yl)carbamoyl)bicyclo[2.2.1]heptan-2-yl)carbamoyl)-4-methoxyphenoxy)-1-methylcyclohexane-1-carboxylic acid;

4-(2-cyano-5-((3-(((4-(difluoromethyl)pyrimidin-2-yl)methyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-(propylcarbamoyl)bicyclo[2.2.1]heptan-2-yl)carbamoyl)phenoxy)-1-methylcyclohexane-1-carboxylic acid;

4-(2-cyano-5-((3-(hexylcarbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-((2-phenylpropyl)carbamoyl)bicyclo[2.2.1]heptan-2-yl)carbamoyl)phenoxy)-1-methylcyclohexane-1-carboxylic acid;

4-(2-cyano-5-((3-((3,3-dimethylbutan-2-yl)carbamoyl)bicyclo[2.2.1]heptan-2-yl)carbamoyl)-4-methoxyphenoxy)-1-methylcyclohexane-1-carboxylic acid;

4-(2-cyano-5-((3-((1-cyclohexylethyl)carbamoyl)bicyclo[2.2.1]heptan-2-yl)carbamoyl)-4-methoxyphenoxy)-1-methylcyclohexane-1-carboxylic acid;

4-(2-cyano-5-((3-(cyclohexylcarbamoyl)bicyclo[2.2.1]heptan-2-yl)carbamoyl)-4-methoxyphenoxy)-1-methylcyclohexane-1-carboxylic acid;

4-(2-cyano-5-((3-((3-isopropoxypropyl)carbamoyl)bicyclo[2.2.1]heptan-2-yl)carbamoyl)-4-methoxyphenoxy)-1-methylcyclohexane-1-carboxylic acid;

4-(2-cyano-5-((3-((3,4-difluorobenzyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-(((3-methylcyclobutyl)methyl)carbamoyl)bicyclo[2.2.1]heptan-2-yl)carbamoyl)phenoxy)-1-methylcyclohexane-1-carboxylic acid;

4-(2-cyano-4-methoxy-5-((3-(tert-pentylcarbamoyl)bicyclo[2.2.1]heptan-2-yl)carbamoyl)phenoxy)-1-methylcyclohexane-1-carboxylic acid;

4-(2-cyano-4-methoxy-5-((3-((3-methylbutan-2-yl)carbamoyl)bicyclo[2.2.1]heptan-2-yl)carbamoyl)phenoxy)-1-methylcyclohexane-1-carboxylic acid;

4-(2-cyano-5-((3-((4,4-dimethylcyclohexyl)carbamoyl)bicyclo[2.2.1]heptan-2-yl)carbamoyl)-4-methoxyphenoxy)-1-methylcyclohexane-1-carboxylic acid;

4-(2-cyano-4-methoxy-5-((3-((2-methoxy-2-methylpropyl) carbamoyl)bicyclo[2.2.1]heptan-2-yl)carbamoyl)phenoxy)-1-methylcyclohexane-1-carboxylic acid;
4-(2-cyano-5-((3-((3,3-dimethylbutyl)carbamoyl)bicyclo [2.2.1]heptan-2-yl)carbamoyl)-4-methoxyphenoxy)-1-methylcyclohexane-1-carboxylic acid;
4-(2-cyano-5-((3-((2-fluoro-2-phenylethyl)carbamoyl)bicyclo[2.2.1]heptan-2-yl)carbamoyl)-4-methoxyphenoxy)-1-methylcyclohexane-1-carboxylic acid;
4-(2-cyano-5-((3-((3-cyclopropylpropyl)carbamoyl)bicyclo [2.2.1]heptan-2-yl)carbamoyl)-4-methoxyphenoxy)-1-methylcyclohexane-1-carboxylic acid;
4-(2-cyano-5-((3-((2-cyclopropylethyl)carbamoyl)bicyclo [2.2.1]heptan-2-yl)carbamoyl)-4-methoxyphenoxy)-1-methylcyclohexane-1-carboxylic acid;
4-(2-cyano-4-methoxy-5-((3-((2-(2,2,2-trifluoroethyl)cyclohexyl)carbamoyl)bicyclo[2.2.1]heptan-2-yl)carbamoyl)phenoxy)-1-methylcyclohexane-1-carboxylic acid;
4-(2-cyano-5-((3-((3-fluoropropyl)carbamoyl)bicyclo [2.2.1]heptan-2-yl)carbamoyl)-4-methoxyphenoxy)-1-methylcyclohexane-1-carboxylic acid;
4-(2-cyano-5-((3-((2,5-dimethylbenzyl)carbamoyl)bicyclo [2.2.1]heptan-2-yl)carbamoyl)-4-methoxyphenoxy)-1-methylcyclohexane-1-carboxylic acid;
4-(2-cyano-4-methoxy-5-((3-(((tetrahydro-2H-pyran-4-yl) methyl)carbamoyl)bicyclo[2.2.1]heptan-2-yl)carbamoyl) phenoxy)-1-methylcyclohexane-1-carboxylic acid;
4-(2-cyano-5-((3-((3-hydroxy-2,2-dimethylpropyl)carbamoyl)bicyclo[2.2.1]heptan-2-yl)carbamoyl)-4-methoxyphenoxy)-1-methylcyclohexane-1-carboxylic acid;
4-(2-cyano-4-methoxy-5-((3-((3-methylbenzyl)carbamoyl) bicyclo[2.2.1]heptan-2-yl)carbamoyl)phenoxy)-1-methylcyclohexane-1-carboxylic acid;
4-(2-cyano-5-((3-(cyclopentylcarbamoyl)bicyclo[2.2.1]heptan-2-yl)carbamoyl)-4-methoxyphenoxy)-1-methylcyclohexane-1-carboxylic acid;
4-(2-cyano-4-methoxy-5-((3-((1-phenylethyl)carbamoyl)bicyclo[2.2.1]heptan-2-yl)carbamoyl)phenoxy)-1-methylcyclohexane-1-carboxylic acid;
4-(5-((3-(bicyclo[1.1.1]pentan-1-ylcarbamoyl)bicyclo [2.2.1]heptan-2-yl)carbamoyl)-2-cyano-4-methoxyphenoxy)-1-methylcyclohexane-1-carboxylic acid;
4-(2-fluoro-4-methoxy-5-((2-(neopentylcarbamoyl)phenyl) carbamoyl)phenoxy)-1-methylcyclohexane-1-carboxylic acid;
4-(2-fluoro-4-methoxy-5-((2-(((1-methylcyclobutyl) methyl)carbamoyl)phenyl)carbamoyl)phenoxy)-1-methylcyclohexane-1-carboxylic acid;
4-(5-((3-((3-ethylpentan-2-yl)carbamoyl)bicyclo[2.2.1]heptan-2-yl)carbamoyl)-2-fluoro-4-methoxyphenoxy)-1-methylcyclohexane-1-carboxylic acid;
4-(2-fluoro-5-((3-(((4-fluorotetrahydro-2H-pyran-4-yl) methyl)carbamoyl)bicyclo[2.2.1]heptan-2-yl)carbamoyl)-4-methoxyphenoxy)-1-methylcyclohexane-1-carboxylic acid;
3-(5-((4-carbamoyl-4-methylcyclohexyl)oxy)-4-fluoro-2-methoxybenzamido)-N-((4-fluorotetrahydro-2H-pyran-4-yl)methyl)bicyclo[2.2.1]heptane-2-carboxamide;
3-(2-cyano-4-methoxy-5-((3-(((1-methylcyclobutyl)methyl) carbamoyl)bicyclo[2.2.1]heptan-2-yl)carbamoyl)phenoxy)-1-methylcyclobutane-1-carboxylic acid;
3-(2-fluoro-4-methoxy-5-((3-(((1-methylcyclobutyl) methyl)carbamoyl)bicyclo[2.2.1]heptan-2-yl)carbamoyl) phenoxy)-1-methylcyclobutane-1-carboxylic acid;
4-(2-fluoro-4-methoxy-5-((4-(((1-methylcyclobutyl) methyl)carbamoyl)pyridin-3-yl)carbamoyl)phenoxy)-1-methylcyclohexane-1-carboxylic acid;

4-(2-fluoro-4-methoxy-5-((2-(((1-methylcyclobutyl) methyl)carbamoyl)cyclooctyl)carbamoyl)phenoxy)-1-methylcyclohexane-1-carboxylic acid;
4-(2-fluoro-4-methoxy-5-((3-methyl-5-(((1-methylcyclobutyl)methyl)carbamoyl)isothiazol-4-yl)carbamoyl) phenoxy)-1-methylcyclohexane-1-carboxylic acid;
4-(5-((4-chloro-2-(((1-methylcyclobutyl)methyl)carbamoyl)phenyl)carbamoyl)-2-fluoro-4-methoxyphenoxy)-1-methylcyclohexane-1-carboxylic acid;
4-(2-fluoro-4-methoxy-5-((2-(((1-methylcyclobutyl) methyl)carbamoyl)thiophen-3-yl)carbamoyl)phenoxy)-1-methylcyclohexane-1-carboxylic acid;
4-(5-((5-chloro-2-(((1-methylcyclobutyl)methyl)carbamoyl)phenyl)carbamoyl)-2-fluoro-4-methoxyphenoxy)-1-methylcyclohexane-1-carboxylic acid;
4-(2-fluoro-4-methoxy-5-((2-methyl-6-(((1-methylcyclobutyl)methyl)carbamoyl)phenyl)carbamoyl)phenoxy)-1-methylcyclohexane-1-carboxylic acid;
4-(5-((5-chloro-2-((cycloheptylmethyl)carbamoyl)phenyl) carbamoyl)-2-cyano-4-methoxyphenoxy)-1-methylcyclohexane-1-carboxylic acid;
4-(5-((5-chloro-2-(((1-phenylcyclopropyl)methyl)carbamoyl)phenyl)carbamoyl)-2-cyano-4-methoxyphenoxy)-1-methylcyclohexane-1-carboxylic acid;
4-(5-((5-chloro-2-(((3-methylcyclobutyl)methyl)carbamoyl)phenyl)carbamoyl)-2-cyano-4-methoxyphenoxy)-1-methylcyclohexane-1-carboxylic acid;
4-(5-((5-chloro-2-(((1-fluorocyclobutyl)methyl)carbamoyl) phenyl)carbamoyl)-2-cyano-4-methoxyphenoxy)-1-methylcyclohexane-1-carboxylic acid;
4-(5-((2-(bicyclo[1.1.1]pentan-1-ylcarbamoyl)-5-chlorophenyl)carbamoyl)-2-cyano-4-methoxyphenoxy)-1-methylcyclohexane-1-carboxylic acid;
4-(5-((5-chloro-2-((3-fluoro-3-methylbutan-2-yl)carbamoyl)phenyl)carbamoyl)-2-cyano-4-methoxyphenoxy)-1-methylcyclohexane-1-carboxylic acid;
4-(5-((5-chloro-2-(tert-pentylcarbamoyl)phenyl)carbamoyl)-2-cyano-4-methoxyphenoxy)-1-methylcyclohexane-1-carboxylic acid;
4-(5-((5-chloro-2-((2-fluoro-2-methylpropyl)carbamoyl) phenyl)carbamoyl)-2-cyano-4-methoxyphenoxy)-1-methylcyclohexane-1-carboxylic acid;
4-(5-((5-chloro-2-((2-cyclopropylpropan-2-yl)carbamoyl) phenyl)carbamoyl)-2-cyano-4-methoxyphenoxy)-1-methylcyclohexane-1-carboxylic acid;
4-(2-cyano-5-((2-((3-fluorobenzyl)carbamoyl)-5-methylphenyl)carbamoyl)-4-methoxyphenoxy)-1-methylcyclohexane-1-carboxylic acid;
4-(2-cyano-5-((2-((2-ethylbutyl)carbamoyl)-5-methylphenyl)carbamoyl)-4-methoxyphenoxy)-1-methylcyclohexane-1-carboxylic acid;
4-(2-cyano-4-methoxy-5-((5-methyl-2-(pentan-3-ylcarbamoyl)phenyl)carbamoyl)phenoxy)-1-methylcyclohexane-1-carboxylic acid;
4-(2-cyano-4-methoxy-5-((5-methyl-2-((4-methylcyclohexyl)carbamoyl)phenyl)carbamoyl)phenoxy)-1-methylcyclohexane-1-carboxylic acid;
4-(2-cyano-4-methoxy-5-((5-methyl-2-((3-methylbutan-2-yl)carbamoyl)phenyl)carbamoyl)phenoxy)-1-methylcyclohexane-1-carboxylic acid;
4-(2-cyano-4-methoxy-5-((5-methyl-2-((3-methylcyclobutyl)carbamoyl)phenyl)carbamoyl)phenoxy)-1-methylcyclohexane-1-carboxylic acid;
4-(2-cyano-5-((2-(((1-fluorocyclobutyl)methyl)carbamoyl)-5-methylphenyl)carbamoyl)-4-methoxyphenoxy)-1-methylcyclohexane-1-carboxylic acid;

4-(5-((2-(bicyclo[1.1.1]pentan-1-ylcarbamoyl)-5-methylphenyl)carbamoyl)-2-cyano-4-methoxyphenoxy)-1-methylcyclohexane-1-carboxylic acid;

4-(2-cyano-4-methoxy-5-((5-methyl-2-(((1-methylcyclopropyl)methyl)carbamoyl)phenyl)carbamoyl)phenoxy)-1-methylcyclohexane-1-carboxylic acid;

4-(2-fluoro-4-methoxy-5-((3-((4,4,4-trifluorobutyl)carbamoyl)bicyclo[2.2.1]heptan-2-yl)carbamoyl)phenoxy)cyclohexane-1-carboxylic acid;

4-(5-((3-((2-cyclopropylethyl)carbamoyl)bicyclo[2.2.1]heptan-2-yl)carbamoyl)-2-fluoro-4-methoxyphenoxy)cyclohexane-1-carboxylic acid;

4-(5-((3-(cyclobutylcarbamoyl)bicyclo[2.2.1]heptan-2-yl)carbamoyl)-2-fluoro-4-methoxyphenoxy)cyclohexane-1-carboxylic acid;

4-(5-((3-(bicyclo[1.1.1]pentan-1-ylcarbamoyl)bicyclo[2.2.1]heptan-2-yl)carbamoyl)-2-fluoro-4-methoxyphenoxy)cyclohexane-1-carboxylic acid;

4-(2-fluoro-5-((3-((4-fluoro-3-(trifluoromethyl)phenyl)carbamoyl)bicyclo[2.2.1]heptan-2-yl)carbamoyl)-4-methoxyphenoxy)cyclohexane-1-carboxylic acid;

4-(2-fluoro-4-methoxy-5-((3-(neopentylcarbamoyl)bicyclo[2.2.1]heptan-2-yl)carbamoyl)phenoxy)cyclohexane-1-carboxylic acid;

4-(5-((3-((4-(difluoromethyl)phenyl)carbamoyl)bicyclo[2.2.1]heptan-2-yl)carbamoyl)-2-fluoro-4-methoxyphenoxy)cyclohexane-1-carboxylic acid;

4-(2-fluoro-4-methoxy-5-((3-((3-(pentafluoro-$\lambda^6$-sulfaneyl)phenyl)carbamoyl)bicyclo[2.2.1]heptan-2-yl)carbamoyl)phenoxy)cyclohexane-1-carboxylic acid;

4-(2-fluoro-4-methoxy-5-((3-((4-(pentafluoro-$\lambda^6$-sulfaneyl)phenyl)carbamoyl)bicyclo[2.2.1]heptan-2-yl)carbamoyl)phenoxy)cyclohexane-1-carboxylic acid;

4-(5-((3-((2,6-difluorophenyl)carbamoyl)bicyclo[2.2.1]heptan-2-yl)carbamoyl)-2-fluoro-4-methoxyphenoxy)cyclohexane-1-carboxylic acid;

4-(2-fluoro-5-((3-((3-iodophenyl)carbamoyl)bicyclo[2.2.1]heptan-2-yl)carbamoyl)-4-methoxyphenoxy)cyclohexane-1-carboxylic acid;

4-(5-((3-((4-chloro-3-(trifluoromethyl)phenyl)carbamoyl)bicyclo[2.2.1]heptan-2-yl)carbamoyl)-2-fluoro-4-methoxyphenoxy)cyclohexane-1-carboxylic acid;

4-(2-fluoro-4-methoxy-5-((3-((3,4,5-trifluorophenyl)carbamoyl)bicyclo[2.2.1]heptan-2-yl)carbamoyl)phenoxy)cyclohexane-1-carboxylic acid;

4-(2-fluoro-4-methoxy-5-((3-((3-methyl-5-(trifluoromethyl)phenyl)carbamoyl)bicyclo[2.2.1]heptan-2-yl)carbamoyl)phenoxy)cyclohexane-1-carboxylic acid;

4-(5-((3-((3-(tert-butyl)phenyl)carbamoyl)bicyclo[2.2.1]heptan-2-yl)carbamoyl)-2-fluoro-4-methoxyphenoxy)cyclohexane-1-carboxylic acid;

4-(5-((3-((3-cyclopropylphenyl)carbamoyl)bicyclo[2.2.1]heptan-2-yl)carbamoyl)-2-fluoro-4-methoxyphenoxy)cyclohexane-1-carboxylic acid;

4-(5-((3-((3-cyano-5-(trifluoromethyl)phenyl)carbamoyl)bicyclo[2.2.1]heptan-2-yl)carbamoyl)-2-fluoro-4-methoxyphenoxy)cyclohexane-1-carboxylic acid;

4-(2-fluoro-4-methoxy-5-((3-((4-methyl-3-(trifluoromethyl)phenyl)carbamoyl)bicyclo[2.2.1]heptan-2-yl)carbamoyl)phenoxy)cyclohexane-1-carboxylic acid;

4-(2-fluoro-4-methoxy-5-((3-((3-(trifluoromethyl)phenyl)carbamoyl)bicyclo[2.2.1]heptan-2-yl)carbamoyl)phenoxy)cyclohexane-1-carboxylic acid;

4-(2-fluoro-4-methoxy-5-((3-((3-methoxy-5-(trifluoromethyl)phenyl)carbamoyl)bicyclo[2.2.1]heptan-2-yl)carbamoyl)phenoxy)cyclohexane-1-carboxylic acid;

4-(5-((3-((3-(difluoromethoxy)phenyl)carbamoyl)bicyclo[2.2.1]heptan-2-yl)carbamoyl)-2-fluoro-4-methoxyphenoxy)cyclohexane-1-carboxylic acid;

4-(2-fluoro-5-((3-((3-isopropylphenyl)carbamoyl)bicyclo[2.2.1]heptan-2-yl)carbamoyl)-4-methoxyphenoxy)cyclohexane-1-carboxylic acid;

4-(5-((3-((2-ethylbutyl)carbamoyl)bicyclo[2.2.1]heptan-2-yl)carbamoyl)-2-fluoro-4-methoxyphenoxy)cyclohexane-1-carboxylic acid;

4-(2-fluoro-4-methoxy-5-((3-(((1-methylcyclopropyl)methyl)carbamoyl)bicyclo[2.2.1]heptan-2-yl)carbamoyl)phenoxy)cyclohexane-1-carboxylic acid;

4-(5-((3-((3,3-dimethylbutan-2-yl)carbamoyl)bicyclo[2.2.1]heptan-2-yl)carbamoyl)-2-fluoro-4-methoxyphenoxy)cyclohexane-1-carboxylic acid;

4-(2-fluoro-4-methoxy-5-((3-(phenylcarbamoyl)bicyclo[2.2.1]heptan-2-yl)carbamoyl)phenoxy)cyclohexane-1-carboxylic acid;

4-(2-fluoro-4-methoxy-5-((3-((2-methylbutyl)carbamoyl)bicyclo[2.2.1]heptan-2-yl)carbamoyl)phenoxy)cyclohexane-1-carboxylic acid;

4-(2-fluoro-4-methoxy-5-((3-(((1-methylcyclobutyl)methyl)carbamoyl)bicyclo[2.2.1]heptan-2-yl)carbamoyl)benzyl)-1-methylcyclohexane-1-carboxylic acid;

4-(2-fluoro-5-((3-((4-fluoro-3-(pentafluoro-$\lambda^6$-sulfaneyl)phenyl)carbamoyl)bicyclo[2.2.1]heptan-2-yl)carbamoyl)-4-methoxyphenoxy)-1-methylcyclohexane-1-carboxylic acid;

4-(4-(difluoromethoxy)-2-fluoro-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(2-fluoro-4-methoxy-5-((3-((3-((trifluoromethyl)sulfonyl)phenyl)carbamoyl)bicyclo[2.2.1]heptan-2-yl)carbamoyl)phenoxy)-1-methylcyclohexane-1-carboxylic acid;

2'-fluoro-4'-methoxy-5'-((3-((3-(pentafluoro-$\lambda^6$-sulfaneyl)phenyl)carbamoyl)bicyclo[2.2.1]heptan-2-yl)carbamoyl)-[1,1'-biphenyl]-4-carboxylic acid;

2'-fluoro-4'-methoxy-5'-((3-((4-(pentafluoro-$\lambda^6$-sulfaneyl)phenyl)carbamoyl)bicyclo[2.2.1]heptan-2-yl)carbamoyl)-[1,1'-biphenyl]-4-carboxylic acid;

4-(5-((2,4-dimethyl-6-(((1-methylcyclobutyl)methyl)carbamoyl)phenyl)carbamoyl)-2-fluoro-4-methoxyphenoxy)-1-methylcyclohexane-1-carboxylic acid;

4-(5-((4,5-dimethyl-2-(((1-methylcyclobutyl)methyl)carbamoyl)phenyl)carbamoyl)-2-fluoro-4-methoxyphenoxy)-1-methylcyclohexane-1-carboxylic acid;

4-(2-fluoro-5-((2-((4-fluoro-3-(trifluoromethyl)phenyl)carbamoyl)cyclohex-1-en-1-yl)carbamoyl)-4-methoxyphenoxy)cyclohexane-1-carboxylic acid;

4-(2-fluoro-5-((2-((4-fluoro-3-(trifluoromethyl)phenyl)carbamoyl)cyclopent-1-en-1-yl)carbamoyl)-4-methoxyphenoxy)cyclohexane-1-carboxylic acid;

4-(2-fluoro-4-methoxy-5-((3-(((1-methylcyclobutyl)methyl)carbamoyl)naphthalen-2-yl)carbamoyl)phenoxy)-1-methylcyclohexane-1-carboxylic acid;

4-(2-fluoro-4-methoxy-5-((4-methyl-2-(((1-methylcyclobutyl)methyl)carbamoyl)phenyl)carbamoyl)phenoxy)-1-methylcyclohexane-1-carboxylic acid;

4-(2-fluoro-4-methoxy-5-((3-(((1-methylcyclobutyl)methyl)carbamoyl)pyrazolo[1,5-a]pyrimidin-2-yl)carbamoyl)phenoxy)-1-methylcyclohexane-1-carboxylic acid;

3-(4-methoxy-3-((3-((3-((trifluoromethyl)sulfonyl)phenyl)carbamoyl)bicyclo[2.2.1]hept-5-en-2-yl)carbamoyl)phenyl)propanoic acid;

3-(5-((1H-pyrazol-4-yl)methyl)-4-fluoro-2-methoxybenzamido)-N-(3-((trifluoromethyl)sulfonyl)phenyl)bicyclo[2.2.1]heptane-2-carboxamide;
2-(4-(2-fluoro-4-methoxy-5-((3-((3-((trifluoromethyl)sulfonyl)phenyl)carbamoyl)bicyclo[2.2.1]heptan-2-yl)carbamoyl)benzyl)-1H-pyrazol-1-yl)acetic acid;
1-(2-fluoro-4-methoxy-5-((3-((3-((trifluoromethyl)sulfonyl)phenyl)carbamoyl)bicyclo[2.2.1]heptan-2-yl)carbamoyl)benzyl)-1H-pyrazole-5-carboxylic acid;
1-(2-fluoro-4-methoxy-5-((3-((3-((trifluoromethyl)sulfonyl)phenyl)carbamoyl)bicyclo[2.2.1]heptan-2-yl)carbamoyl)benzyl)-1H-pyrazole-3-carboxylic acid;
2-(4-methoxy-3-((3-((3-((trifluoromethyl)sulfonyl)phenyl)carbamoyl)bicyclo[2.2.1]hept-5-en-2-yl)carbamoyl)benzyl)benzoic acid;
2'-fluoro-4'-methoxy-5'-((3-((3-((trifluoromethyl)sulfonyl)phenyl)carbamoyl)bicyclo[2.2.1]hept-5-en-2-yl)carbamoyl)-[1,1'-biphenyl]-4-carboxylic acid;
2'-fluoro-4'-methoxy-5'-((3-((3-((trifluoromethyl)sulfonyl)phenyl)carbamoyl)bicyclo[2.2.1]hept-5-en-2-yl)carbamoyl)-[1,1'-biphenyl]-3-carboxylic acid;
2'-fluoro-3,4'-dimethoxy-5'-((3-((3-((trifluoromethyl)sulfonyl)phenyl)carbamoyl)bicyclo[2.2.1]hept-5-en-2-yl)carbamoyl)-[1,1'-biphenyl]-4-carboxylic acid;
2,2'-difluoro-4'-methoxy-5'-((3-((3-((trifluoromethyl)sulfonyl)phenyl)carbamoyl)bicyclo[2.2.1]hept-5-en-2-yl)carbamoyl)-[1,1'-biphenyl]-4-carboxylic acid;
5-(2-fluoro-4-methoxy-5-((3-((3-((trifluoromethyl)sulfonyl)phenyl)carbamoyl)bicyclo[2.2.1]hept-5-en-2-yl)carbamoyl)phenyl)nicotinic acid;
4-(2-fluoro-4-methoxy-5-((3-((3-((trifluoromethyl)sulfonyl)phenyl)carbamoyl)bicyclo[2.2.1]hept-5-en-2-yl)carbamoyl)phenyl)-1H-pyrrole-2-carboxylic acid;
2'-fluoro-4,4'-dimethoxy-5'-((3-((3-((trifluoromethyl)sulfonyl)phenyl)carbamoyl)bicyclo[2.2.1]hept-5-en-2-yl)carbamoyl)-[1,1'-biphenyl]-3-carboxylic acid;
2',4-difluoro-4'-methoxy-5'-((3-((3-((trifluoromethyl)sulfonyl)phenyl)carbamoyl)bicyclo[2.2.1]hept-5-en-2-yl)carbamoyl)-[1,1'-biphenyl]-3-carboxylic acid;
2',3-difluoro-4'-methoxy-5'-((3-((3-((trifluoromethyl)sulfonyl)phenyl)carbamoyl)bicyclo[2.2.1]hept-5-en-2-yl)carbamoyl)-[1,1'-biphenyl]-4-carboxylic acid;
2,2'-difluoro-4'-methoxy-5'-((3-((3-((trifluoromethyl)sulfonyl)phenyl)carbamoyl)bicyclo[2.2.1]hept-5-en-2-yl)carbamoyl)-[1,1'-biphenyl]-3-carboxylic acid;
2-(2'-fluoro-4'-methoxy-5'-((3-((3-((trifluoromethyl)sulfonyl)phenyl)carbamoyl)bicyclo[2.2.1]hept-5-en-2-yl)carbamoyl)-[1,1'-biphenyl]-4-yl)acetic acid;
2-(2'-fluoro-4'-methoxy-5'-((3-((3-((trifluoromethyl)sulfonyl)phenyl)carbamoyl)bicyclo[2.2.1]hept-5-en-2-yl)carbamoyl)-[1,1'-biphenyl]-2-yl)acetic acid;
2',3-difluoro-4'-methoxy-5'-((3-((3-((trifluoromethyl)sulfonyl)phenyl)carbamoyl)bicyclo[2.2.1]heptan-2-yl)carbamoyl)-[1,1'-biphenyl]-4-carboxylic acid;
3-(5-(2-fluoro-4-methoxy-5-((3-((3-((trifluoromethyl)sulfonyl)phenyl)carbamoyl)bicyclo[2.2.1]heptan-2-yl)carbamoyl)phenyl)pyrimidin-2-yl)propanoic acid;
3-(5-(2-fluoro-4-methoxy-5-((3-((3-((trifluoromethyl)sulfonyl)phenyl)carbamoyl)bicyclo[2.2.1]heptan-2-yl)carbamoyl)phenyl)pyrazin-2-yl)propanoic acid;
3-(dimethylamino)-2'-fluoro-4'-methoxy-5'-((3-((3-((trifluoromethyl)sulfonyl)phenyl)carbamoyl)bicyclo[2.2.1]heptan-2-yl)carbamoyl)-[1,1'-biphenyl]-4-carboxylic acid;
4-((2'-fluoro-4'-methoxy-5'-((3-((3-((trifluoromethyl)sulfonyl)phenyl)carbamoyl)bicyclo[2.2.1]heptan-2-yl)carbamoyl)-[1,1'-biphenyl]-4-yl)oxy)butanoic acid;
2'-fluoro-4'-methoxy-3,5-dimethyl-5'-((3-((3-((trifluoromethyl)sulfonyl)phenyl)carbamoyl)bicyclo[2.2.1]heptan-2-yl)carbamoyl)-[1,1'-biphenyl]-4-carboxylic acid;
2-(6-(2-fluoro-4-methoxy-5-((3-((3-((trifluoromethyl)sulfonyl)phenyl)carbamoyl)bicyclo[2.2.1]heptan-2-yl)carbamoyl)phenyl)-2,3-dihydrobenzofuran-3-yl)acetic acid;
(5-(2-fluoro-4-methoxy-5-((3-((3-((trifluoromethyl)sulfonyl)phenyl)carbamoyl)bicyclo[2.2.1]heptan-2-yl)carbamoyl)phenyl)pyrimidin-2-yl)glycine;
2-((5-(2-fluoro-4-methoxy-5-((3-((3-((trifluoromethyl)sulfonyl)phenyl)carbamoyl)bicyclo[2.2.1]heptan-2-yl)carbamoyl)phenyl)pyridin-2-yl)oxy)acetic acid;
3-(6-(2-fluoro-4-methoxy-5-((3-((3-((trifluoromethyl)sulfonyl)phenyl)carbamoyl)bicyclo[2.2.1]heptan-2-yl)carbamoyl)phenyl)pyridin-3-yl)propanoic acid;
2-((2'-fluoro-4'-methoxy-5'-((3-((3-((trifluoromethyl)sulfonyl)phenyl)carbamoyl)bicyclo[2.2.1]heptan-2-yl)carbamoyl)-[1,1'-biphenyl]-4-yl)oxy)-2-methylpropanoic acid;
2-((2'-fluoro-4'-methoxy-5'-((3-((3-((trifluoromethyl)sulfonyl)phenyl)carbamoyl)bicyclo[2.2.1]heptan-2-yl)carbamoyl)-[1,1'-biphenyl]-4-yl)oxy)acetic acid;
3-(2-(2-fluoro-4-methoxy-5-((3-((3-((trifluoromethyl)sulfonyl)phenyl)carbamoyl)bicyclo[2.2.1]heptan-2-yl)carbamoyl)phenyl)thiazol-5-yl)propanoic acid;
3-(2'-fluoro-4'-methoxy-5'-((3-((3-((trifluoromethyl)sulfonyl)phenyl)carbamoyl)bicyclo[2.2.1]heptan-2-yl)carbamoyl)-[1,1'-biphenyl]-4-yl)propanoic acid;
3-(6-(2-fluoro-4-methoxy-5-((3-((3-((trifluoromethyl)sulfonyl)phenyl)carbamoyl)bicyclo[2.2.1]heptan-2-yl)carbamoyl)phenyl)pyridazin-3-yl)propanoic acid;
2'-fluoro-4'-methoxy-3-methyl-5'-((3-((3-((trifluoromethyl)sulfonyl)phenyl)carbamoyl)bicyclo[2.2.1]heptan-2-yl)carbamoyl)-[1,1'-biphenyl]-4-carboxylic acid;
2'-fluoro-3-hydroxy-4'-methoxy-5'-((3-((3-((trifluoromethyl)sulfonyl)phenyl)carbamoyl)bicyclo[2.2.1]heptan-2-yl)carbamoyl)-[1,1'-biphenyl]-4-carboxylic acid;
3-(5-(2-fluoro-4-methoxy-5-((3-((3-((trifluoromethyl)sulfonyl)phenyl)carbamoyl)bicyclo[2.2.1]heptan-2-yl)carbamoyl)phenyl)pyridin-2-yl)propanoic acid;
3-(2'-fluoro-3,4'-dimethoxy-5'-((3-((3-((trifluoromethyl)sulfonyl)phenyl)carbamoyl)bicyclo[2.2.1]heptan-2-yl)carbamoyl)-[1,1'-biphenyl]-4-yl)propanoic acid;
(E)-3-(5-(2-fluoro-4-methoxy-5-((3-((3-((trifluoromethyl)sulfonyl)phenyl)carbamoyl)bicyclo[2.2.1]heptan-2-yl)carbamoyl)phenyl)pyridin-2-yl)acrylic acid;
2-(5-(2-fluoro-4-methoxy-5-((3-((3-((trifluoromethyl)sulfonyl)phenyl)carbamoyl)bicyclo[2.2.1]heptan-2-yl)carbamoyl)phenyl)pyridin-2-yl)cyclopropane-1-carboxylic acid;
2-(5-(2-fluoro-4-methoxy-5-((3-((3-((trifluoromethyl)sulfonyl)phenyl)carbamoyl)bicyclo[2.2.1]heptan-2-yl)carbamoyl)phenyl)pyrazin-2-yl)cyclopropane-1-carboxylic acid;
3-(6-fluoro-4-methoxy-4'-sulfamoyl-[1,1'-biphenyl]-3-carboxamido)-N-(3-((trifluoromethyl)sulfonyl)phenyl)bicyclo[2.2.1]heptane-2-carboxamide;
3-(4'-(2-amino-1,3-dihydroxypropan-2-yl)-6-fluoro-4-methoxy-[1,1'-biphenyl]-3-carboxamido)-N-(3-((trifluoromethyl)sulfonyl)phenyl)bicyclo[2.2.1]heptane-2-carboxamide;
3-(4'-(3-amino-4-hydroxy-3-(hydroxymethyl)butyl)-3',6-difluoro-4-methoxy-[1,1'-biphenyl]-3-carboxamido)-N-(3-((trifluoromethyl)sulfonyl)phenyl)bicyclo[2.2.1]heptane-2-carboxamide;

3-(4-(2-fluoro-4-methoxy-5-((3-((3-(((trifluoromethyl)sulfonyl)phenyl)carbamoyl)bicyclo[2.2.1]heptan-2-yl)carbamoyl)phenyl)-2-oxopyridin-1(2H)-yl)propanoic acid;

2'-fluoro-4'-methoxy-5'-((3-((3-((trifluoromethyl)sulfonyl)phenyl)carbamoyl)bicyclo[2.2.1]heptan-2-yl)carbamoyl)-[1,1'-biphenyl]-4-carboxylic acid;

3-(4-(2-fluoro-4-methoxy-5-((3-((3-(((trifluoromethyl)sulfonyl)phenyl)carbamoyl)bicyclo[2.2.1]heptan-2-yl)carbamoyl)phenyl)-1H-pyrazol-1-yl)propanoic acid;

2'-fluoro-4'-methoxy-5'-((3-((3-(((trifluoromethyl)sulfonyl)phenyl)carbamoyl)bicyclo[2.2.1]heptan-2-yl)carbamoyl)-2,3,4,5-tetrahydro-[1,1'-biphenyl]-4-carboxylic acid;

4-(2-fluoro-4-methoxy-5-((3-((3-(((trifluoromethyl)sulfonyl)phenyl)carbamoyl)bicyclo[2.2.1]heptan-2-yl)carbamoyl)phenyl)cyclohexane-1-carboxylic acid;

6-fluoro-4-methoxy-N3-(3-((3-(((trifluoromethyl)sulfonyl)phenyl)carbamoyl)bicyclo[2.2.1]hept-5-en-2-yl)-[1,1'-biphenyl]-3,4'-dicarboxamide;

2-(4-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)-1H-pyrazol-1-yl)acetic acid;

4-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)picolinic acid;

2'-fluoro-4'-methoxy-5'-((3-((3-(((trifluoromethyl)sulfonyl)phenyl)carbamoyl)bicyclo[2.2.1]hept-5-en-2-yl)carbamoyl)-[1,1'-biphenyl]-2-carboxylic acid;

5-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)picolinic acid;

2-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)oxazole-4-carboxylic acid;

5-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)pyrazine-2-carboxylic acid;

2-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)isonicotinic acid;

6-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)nicotinic acid;

6-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)picolinic acid;

5-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)pyrimidine-2-carboxylic acid;

2-(2'-fluoro-4'-methoxy-5'-((3-((3-(((trifluoromethyl)sulfonyl)phenyl)carbamoyl)bicyclo[2.2.1]hept-5-en-2-yl)carbamoyl)-[1,1'-biphenyl]-3-yl)acetic acid;

3-(2'-fluoro-4'-methoxy-5'-((3-((3-(((trifluoromethyl)sulfonyl)phenyl)carbamoyl)bicyclo[2.2.1]hept-5-en-2-yl)carbamoyl)-[1,1'-biphenyl]-3-yl)propanoic acid;

3-(2'-fluoro-4'-methoxy-5'-((3-((3-(((trifluoromethyl)sulfonyl)phenyl)carbamoyl)bicyclo[2.2.1]hept-5-en-2-yl)carbamoyl)-[1,1'-biphenyl]-4-yl)propanoic acid;

5-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)thiophene-3-carboxylic acid;

5-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)thiophene-2-carboxylic acid;

2-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)thiazole-4-carboxylic acid;

2-(2-fluoro-4-methoxy-5-((3-((3-(((trifluoromethyl)sulfonyl)phenyl)carbamoyl)bicyclo[2.2.1]hept-5-en-2-yl)carbamoyl)phenyl)thiazole-5-carboxylic acid;

1-(2'-fluoro-4'-methoxy-5'-((3-((3-(((trifluoromethyl)sulfonyl)phenyl)carbamoyl)bicyclo[2.2.1]hept-5-en-2-yl)carbamoyl)-[1,1'-biphenyl]-4-yl)cyclopropane-1-carboxylic acid;

2-(dimethylamino)-3-(2'-fluoro-4'-methoxy-5'-((3-((3-(((trifluoromethyl)sulfonyl)phenyl)carbamoyl)bicyclo[2.2.1]heptan-2-yl)carbamoyl)-[1,1'-biphenyl]-4-yl)propanoic acid;

2-amino-3-(2'-fluoro-4'-methoxy-5'-((3-((3-(((trifluoromethyl)sulfonyl)phenyl)carbamoyl)bicyclo[2.2.1]heptan-2-yl)carbamoyl)-[1,1'-biphenyl]-4-yl)propanoic acid;

2-(dimethylamino)-3-(2'-fluoro-4'-methoxy-5'-((3-((3-(((trifluoromethyl)sulfonyl)phenyl)carbamoyl)bicyclo[2.2.1]heptan-2-yl)carbamoyl)-[1,1'-biphenyl]-3-yl)propanoic acid;

2-(dimethylamino)-2-(2'-fluoro-4'-methoxy-5'-((3-((3-(((trifluoromethyl)sulfonyl)phenyl)carbamoyl)bicyclo[2.2.1]heptan-2-yl)carbamoyl)-[1,1'-biphenyl]-3-yl)acetic acid;

2-(dimethylamino)-2-(2'-fluoro-4'-methoxy-5'-((3-((3-(((trifluoromethyl)sulfonyl)phenyl)carbamoyl)bicyclo[2.2.1]heptan-2-yl)carbamoyl)-[1,1'-biphenyl]-4-yl)acetic acid;

2'-fluoro-5'-((3-((4-fluoro-3-((trifluoromethyl)sulfonyl)phenyl)carbamoyl)bicyclo[2.2.1]hept-5-en-2-yl)carbamoyl)-4'-methoxy-[1,1'-biphenyl]-4-carboxylic acid;

2'-fluoro-5'-((3-((4-fluoro-3-((trifluoromethyl)sulfonyl)phenyl)carbamoyl)bicyclo[2.2.1]hept-5-en-2-yl)carbamoyl)-4'-methoxy-[1,1'-biphenyl]-3-carboxylic acid;

2'-fluoro-5'-((3-((3-fluoro-5-(pentafluoro-$\lambda^6$-sulfaneyl)phenyl)carbamoyl)bicyclo[2.2.1]hept-5-en-2-yl)carbamoyl)-4'-methoxy-[1,1'-biphenyl]-4-carboxylic acid;

2'-fluoro-4'-methoxy-5'-((2-((3-(((trifluoromethyl)sulfonyl)phenyl)carbamoyl)cyclopentyl)carbamoyl)-[1,1'-biphenyl]-4-carboxylic acid;

2'-fluoro-4'-methoxy-5'-((2-((3-(((trifluoromethyl)sulfonyl)phenyl)carbamoyl)cyclopentyl)carbamoyl)-[1,1'-biphenyl]-3-carboxylic acid;

2'-fluoro-4'-methoxy-5'-((2-((3-(((trifluoromethyl)sulfonyl)phenyl)carbamoyl)cyclobutyl)carbamoyl)-[1,1'-biphenyl]-4-carboxylic acid;

2'-fluoro-4'-methoxy-5'-((2-((3-(((trifluoromethyl)sulfonyl)phenyl)carbamoyl)cyclobutyl)carbamoyl)-[1,1'-biphenyl]-3-carboxylic acid;

2'-fluoro-4'-methoxy-5'-((3-(neopentylcarbamoyl)bicyclo[2.2.1]heptan-2-yl)carbamoyl)-[1,1'-biphenyl]-4-carboxylic acid;

2'-fluoro-5'-((3-((3-(((trifluoromethyl)sulfonyl)phenyl)carbamoyl)bicyclo[2.2.1]hept-5-en-2-yl)carbamoyl)-[1,1'-biphenyl]-4-carboxylic acid;

2',4'-difluoro-5'-((3-((3-(((trifluoromethyl)sulfonyl)phenyl)carbamoyl)bicyclo[2.2.1]hept-5-en-2-yl)carbamoyl)-[1,1'-biphenyl]-4-carboxylic acid;

2'-fluoro-5'-((3-((4-fluoro-3-(trifluoromethyl)phenyl)carbamoyl)bicyclo[2.2.1]hept-5-en-2-yl)carbamoyl)-4'-methoxy-[1,1'-biphenyl]-4-carboxylic acid;

2'-fluoro-5'-((3-((3-fluoro-5-(trifluoromethyl)phenyl)carbamoyl)bicyclo[2.2.1]hept-5-en-2-yl)carbamoyl)-4'-methoxy-[1,1'-biphenyl]-4-carboxylic acid;

5'-((3-((3-cyano-4-fluorophenyl)carbamoyl)bicyclo[2.2.1]hept-5-en-2-yl)carbamoyl)-2'-fluoro-4'-methoxy-[1,1'-biphenyl]-4-carboxylic acid;

5'-((3-((3-cyano-5-fluorophenyl)carbamoyl)bicyclo[2.2.1]hept-5-en-2-yl)carbamoyl)-2'-fluoro-4'-methoxy-[1,1'-biphenyl]-4-carboxylic acid;

2'-fluoro-4'-methoxy-5'-((3-((1-(((trifluoromethyl)sulfonyl)
piperidin-3-yl)carbamoyl)bicyclo[2.2.1]hept-5-en-2-yl)
carbamoyl)-[1,1'-biphenyl]-4-carboxylic acid;

2'-fluoro-4'-methoxy-5'-((3-((1-(((trifluoromethyl)sulfonyl)
piperidin-3-yl)carbamoyl)bicyclo[2.2.1]heptan-2-yl)car-
bamoyl)-[1,1'-biphenyl]-4-carboxylic acid;

2'-fluoro-4-hydroxy-4'-methoxy-5'-((3-((3-((trifluorom-
ethyl)sulfonyl)phenyl)carbamoyl)bicyclo[2.2.1]heptan-2-
yl)carbamoyl)-[1,1'-biphenyl]-3-carboxylic acid;

2-(2'-fluoro-4'-methoxy-5'-((2-((3-((trifluoromethyl)sulfo-
nyl)phenyl)carbamoyl)cyclopentyl)carbamoyl)-[1,1'-bi-
phenyl]-3-yl)acetic acid;

3-(2'-fluoro-4'-methoxy-5'-((2-((3-((trifluoromethyl)sulfo-
nyl)phenyl)carbamoyl)cyclopentyl)carbamoyl)-[1,1'-bi-
phenyl]-3-yl)propanoic acid;

2-(2'-fluoro-4'-methoxy-5'-((2-((3-((trifluoromethyl)sulfo-
nyl)phenyl)carbamoyl)cyclopentyl)carbamoyl)-[1,1'-bi-
phenyl]-4-yl)acetic acid;

3-(2'-fluoro-4'-methoxy-5'-((2-((3-((trifluoromethyl)sulfo-
nyl)phenyl)carbamoyl)cyclopentyl)carbamoyl)-[1,1'-bi-
phenyl]-4-yl)propanoic acid;

3-(5-(2-fluoro-4-methoxy-5-((3-((3-((trifluoromethyl)sulfo-
nyl)phenyl)carbamoyl)bicyclo[2.2.1]heptan-2-yl)car-
bamoyl)phenyl)-1,3,4-thiadiazol-2-yl)propanoic acid;

3-(2-(2-fluoro-4-methoxy-5-((3-((3-((trifluoromethyl)sulfo-
nyl)phenyl)carbamoyl)bicyclo[2.2.1]heptan-2-yl)car-
bamoyl)phenyl)pyrimidin-5-yl)propanoic acid;

3-(6-fluoro-4-methoxy-4'-(1H-tetrazol-5-yl)-[1,1'-biphe-
nyl]-3-carboxamido)-N-(3-((trifluoromethyl)sulfonyl)
phenyl)bicyclo[2.2.1]heptane-2-carboxamide;

3-(6-fluoro-4-methoxy-4'-(2-sulfamoylethyl)-[1,1'-biphe-
nyl]-3-carboxamido)-N-(3-((trifluoromethyl)sulfonyl)
phenyl)bicyclo[2.2.1]heptane-2-carboxamide;

2'-fluoro-4'-methoxy-5'-((2-((3-((trifluoromethyl)sulfonyl)
phenyl)carbamoyl)phenyl)carbamoyl)-[1,1'-biphenyl]-4-
carboxylic acid;

2-((2'-cyano-4'-methoxy-5'-((3-((3-((trifluoromethyl)sulfo-
nyl)phenyl)carbamoyl)bicyclo[2.2.1]heptan-2-yl)car-
bamoyl)-[1,1'-biphenyl]-4-yl)oxy)acetic acid;

2-((2'-fluoro-4'-methoxy-5'-((3-(neopentylcarbamoyl)bicy-
clo[2.2.1]heptan-2-yl)carbamoyl)-[1,1'-biphenyl]-4-yl)
oxy)acetic acid;

4-(2-fluoro-4-methoxy-5-((3-(((1-methylcyclobutyl)
methyl)carbamoyl)-7-oxabicyclo[2.2.1]heptan-2-yl)car-
bamoyl)phenoxy)-1-methylcyclohexane-1-carboxylic
acid;

4-(2-fluoro-4-methoxy-5-((3-(((1-methylcyclobutyl)
methyl)carbamoyl)-7-oxabicyclo[2.2.1]heptan-2-yl)car-
bamoyl)phenoxy)-1-(hydroxymethyl)cyclohexane-1-car-
boxylic acid;

4-(2-cyano-4-methoxy-5-((3-(((1-methylcyclobutyl)methyl)
carbamoyl)-7-oxabicyclo[2.2.1]heptan-2-yl)carbamoyl)
phenoxy)-1-methylcyclohexane-1-carboxylic acid;

4-(5-((7-(tert-butoxycarbonyl)-3-(((1-methylcyclobutyl)
methyl)carbamoyl)-7-azabicyclo[2.2.1]heptan-2-yl)car-
bamoyl)-2-cyano-4-methoxyphenoxy)-1-methylcyclo-
hexane-1-carboxylic acid;

4-(2-fluoro-4-methoxy-5-((4-methoxy-2-((3-((trifluorom-
ethyl)sulfonyl)phenyl)carbamoyl)cyclopentyl)carbam-
oyl)phenoxy)-1-methylcyclohexane-1-carboxylic acid;

4-(2-fluoro-4-methoxy-5-((4-methoxy-2-(neopentylcarbam-
oyl)cyclopentyl)carbamoyl)phenoxy)-1-(hydroxymethyl)
cyclohexane-1-carboxylic acid;

4-(2-fluoro-4-methoxy-5-((4-((3-((trifluoromethyl)sulfonyl)
phenyl)carbamoyl)tetrahydro-2H-pyran-3-yl)carbamoyl)
phenoxy)-1-methylcyclohexane-1-carboxylic acid;

4-(2-fluoro-4-methoxy-5-((3-((3-((trifluoromethyl)sulfonyl)
phenyl)carbamoyl)tetrahydro-2H-pyran-4-yl)carbamoyl)
phenoxy)-1-methylcyclohexane-1-carboxylic acid;

4-(2-fluoro-4-methoxy-5-((4-((3-((trifluoromethyl)sulfonyl)
phenyl)carbamoyl)tetrahydrofuran-3-yl)carbamoyl)phe-
noxy)-1-methylcyclohexane-1-carboxylic acid;

4-(2-fluoro-5-((4-((4-fluoro-3-(pentafluoro-$\lambda^6$-sulfaneyl)
phenyl)carbamoyl)tetrahydrofuran-3-yl)carbamoyl)-4-
methoxyphenoxy)-1-methylcyclohexane-1-carboxylic
acid;

4-(2-fluoro-4-methoxy-5-((4-(neopentylcarbamoyl)tetrahy-
drofuran-3-yl)carbamoyl)phenoxy)-1-methylcyclo-
hexane-1-carboxylic acid;

4-(2-fluoro-4-methoxy-5-((2-(neopentylcarbamoyl)cy-
clobutyl)carbamoyl)phenoxy)-1-methylcyclohexane-1-
carboxylic acid;

4-(2-fluoro-5-((2-((4-fluoro-3-(pentafluoro-$\lambda^6$-sulfaneyl)
phenyl)carbamoyl)cyclobutyl)carbamoyl)-4-methoxy-
phenoxy)-1-methylcyclohexane-1-carboxylic acid;

4-(2-cyano-4-methoxy-5-((2-(((1-methylcyclobutyl)methyl)
carbamoyl)cyclobutyl)carbamoyl)phenoxy)-1-methylcy-
clohexane-1-carboxylic acid;

4-(2-fluoro-5-((4-((4-fluoro-3-(pentafluoro-$\lambda^6$-sulfaneyl)
phenyl)carbamoyl)tetrahydro-2H-pyran-3-yl)carbam-
oyl)-4-methoxyphenoxy)-1-methylcyclohexane-1-car-
boxylic acid;

4-(2-fluoro-4-methoxy-5-((4-(((1-methylcyclobutyl)
methyl)carbamoyl)tetrahydrofuran-3-yl)carbamoyl)phe-
noxy)-1-methylcyclohexane-1-carboxylic acid;

4-(2-fluoro-4-methoxy-5-((2-((3-((trifluoromethyl)sulfonyl)
phenyl)carbamoyl)cyclopentyl)carbamoyl)phenoxy)-1-
methylcyclohexane-1-carboxylic acid;

4-(2-fluoro-5-((2-((4-fluoro-3-(pentafluoro-$\lambda^6$-sulfaneyl)
phenyl)carbamoyl)cyclopentyl)carbamoyl)-4-methoxy-
phenoxy)-1-methylcyclohexane-1-carboxylic acid;

4-(2-fluoro-4-methoxy-5-((2-((3-((trifluoromethyl)sulfonyl)
phenyl)carbamoyl)cycloheptyl)carbamoyl)phenoxy)-1-
methylcyclohexane-1-carboxylic acid;

4-(2-fluoro-5-((2-fluoro-2-((3-((trifluoromethyl)sulfonyl)
phenyl)carbamoyl)cyclopentyl)carbamoyl)-4-methoxy-
phenoxy)-1-methylcyclohexane-1-carboxylic acid;

4-(2-fluoro-4-methoxy-5-((2-((3-((trifluoromethyl)sulfonyl)
phenyl)carbamoyl)tetrahydrofuran-3-yl)carbamoyl)phe-
noxy)-1-methylcyclohexane-1-carboxylic acid;

4-(2-fluoro-4-methoxy-5-((2-((3-((trifluoromethyl)sulfonyl)
phenyl)carbamoyl)tetrahydro-2H-pyran-3-yl)carbamoyl)
phenoxy)-1-methylcyclohexane-1-carboxylic acid;

4-(2-fluoro-4-methoxy-5-((2-methoxy-5-((3-((trifluorom-
ethyl)sulfonyl)phenyl)carbamoyl)cyclopentyl)carbam-
oyl)phenoxy)-1-methylcyclohexane-1-carboxylic acid;

4-(2-cyano-4-methoxy-5-((2-(((1-methylcyclobutyl)methyl)
carbamoyl)cyclopentyl)carbamoyl)phenoxy)-1-methyl-
cyclohexane-1-carboxylic acid;

4-(2-cyano-4-methoxy-5-((2-(((1-methylcyclobutyl)methyl)
carbamoyl)cyclohexyl)carbamoyl)phenoxy)-1-methylcy-
clohexane-1-carboxylic acid;

4-(2-fluoro-4-methoxy-5-((3-(((1-methylcyclobutyl)
methyl)carbamoyl)bicyclo[2.2.1]heptan-2-yl)carbamoyl)
phenoxy)-1-(hydroxymethyl)cyclohexane-1-carboxylic
acid;

4-(2-fluoro-4-methoxy-5-((3-(((1-(trifluoromethyl)cy-
clobutyl)methyl)carbamoyl)bicyclo[2.2.1]heptan-2-yl)
carbamoyl)phenoxy)-1-(hydroxymethyl)cyclohexane-1-
carboxylic acid;

4-(2-fluoro-4-methoxy-5-((3-((3-((trifluoromethyl)sulfonyl)phenyl)carbamoyl)bicyclo[2.2.1]heptan-2-yl)carbamoyl)phenoxy)-1-(hydroxymethyl)cyclohexane-1-carboxylic acid;

4-(4-methoxy-5-((3-(((1-methylcyclobutyl)methyl)carbamoyl)bicyclo[2.2.1]heptan-2-yl)carbamoyl)-2-(trifluoromethyl)phenoxy)-1-methylcyclohexane-1-carboxylic acid;

4-(2-(difluoromethyl)-4-methoxy-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(3-fluoro-4-methoxy-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(4-methoxy-2-methyl-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(2-ethyl-4-methoxy-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(4-cyano-2-fluoro-5-((3-(((1-methylcyclobutyl)methyl)carbamoyl)bicyclo[2.2.1]heptan-2-yl)carbamoyl)phenoxy)-1-methylcyclohexane-1-carboxylic acid;

1-methyl-4-((1-methyl-5-((3-(((1-methylcyclobutyl)methyl)carbamoyl)bicyclo[2.2.1]heptan-2-yl)carbamoyl)-1H-indazol-7-yl)oxy)cyclohexane-1-carboxylic acid;

1-methyl-4-((1-methyl-6-((3-(((1-methylcyclobutyl)methyl)carbamoyl)bicyclo[2.2.1]heptan-2-yl)carbamoyl)-1H-indazol-4-yl)oxy)cyclohexane-1-carboxylic acid;

4-(2-fluoro-4-(methoxymethyl)-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(4-methoxy-3-((3-(((1-methylcyclobutyl)methyl)carbamoyl)bicyclo[2.2.1]heptan-2-yl)carbamoyl)phenoxy)-1-methylcyclohexane-1-carboxylic acid;

4-(5-((3-((3-fluorobicyclo[1.1.1]pentan-1-yl)carbamoyl)bicyclo[2.2.1]heptan-2-yl)carbamoyl)-4-methoxy-2-methylphenoxy)-1-methylcyclohexane-1-carboxylic acid;

4-(2-ethyl-5-((3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid;

4-(4-ethoxy-2-fluoro-5-((3-((3-fluorobicyclo[1.1.1]pentan-1-yl)carbamoyl)bicyclo[2.2.1]heptan-2-yl)carbamoyl)phenoxy)-1-methylcyclohexane-1-carboxylic acid;

4-(4-ethoxy-2-fluoro-5-((3-(((1-methylcyclobutyl)methyl)carbamoyl)bicyclo[2.2.1]heptan-2-yl)carbamoyl)phenoxy)-1-methylcyclohexane-1-carboxylic acid;

1-ethyl-4-(2-fluoro-4-methoxy-5-((3-(neopentylcarbamoyl)bicyclo[2.2.1]heptan-2-yl)carbamoyl)phenoxy)cyclohexane-1-carboxylic acid;

4-(2-cyano-4-methoxy-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(2-cyano-4-methoxy-5-((3-(neopentylcarbamoyl)bicyclo[2.2.1]heptan-2-yl)carbamoyl)phenoxy)-1-methylcyclohexane-1-carboxylic acid;

4-(3-fluoro-5-((3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid;

4-(2-fluoro-4-(2-methoxyethoxy)-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(2-chloro-4-methoxy-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(2,4-difluoro-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(5-((2,3-dihydroxy-5-((3-((trifluoromethyl)sulfonyl)phenyl)carbamoyl)cyclopentyl)carbamoyl)-2-fluoro-4-methoxyphenoxy)-1-methylcyclohexane-1-carboxylic acid;

4-(2-fluoro-4-methoxy-5-((5-((3-((trifluoromethyl)sulfonyl)phenyl)carbamoyl)tetrahydro-4H-cyclopenta[d][1,3]dioxol-4-yl)carbamoyl)phenoxy)-1-methylcyclohexane-1-carboxylic acid;

4-(2-fluoro-5-((2-hydroxy-5-((3-((trifluoromethyl)sulfonyl)phenyl)carbamoyl)cyclopentyl)carbamoyl)-4-methoxyphenoxy)-1-methylcyclohexane-1-carboxylic acid;

4-(4-chloro-2-fluoro-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(2-cyclopropyl-4-methoxy-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(2-fluoro-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(2-cyano-4-fluoro-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(4-methoxy-2-(methoxymethyl)-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(3-chloro-4-methoxy-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(3-cyano-4-methoxy-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(4-methoxy-3-methyl-5-((3-(((1-methylcyclobutyl)methyl)carbamoyl)bicyclo[2.2.1]heptan-2-yl)carbamoyl)phenoxy)-1-methylcyclohexane-1-carboxylic acid;

1-methyl-4-((7-((3-(((1-methylcyclobutyl)methyl)carbamoyl)bicyclo[2.2.1]heptan-2-yl)carbamoyl)-2,3-dihydrobenzofuran-5-yl)oxy)cyclohexane-1-carboxylic acid;

1-methyl-4-((8-((3-(((1-methylcyclobutyl)methyl)carbamoyl)bicyclo[2.2.1]heptan-2-yl)carbamoyl)quinolin-6-yl)oxy)cyclohexane-1-carboxylic acid;

4-(2-chloro-4-fluoro-5-((3-(((1-methylcyclobutyl)methyl)carbamoyl)bicyclo[2.2.1]heptan-2-yl)carbamoyl)phenoxy)-1-methylcyclohexane-1-carboxylic acid;

4-(2-chloro-4-methoxy-5-((3-((3,3,3-trifluoro-2,2-dimethylpropyl)carbamoyl)bicyclo[2.2.1]heptan-2-yl)carbamoyl)phenoxy)-1-methylcyclohexane-1-carboxylic acid;

4-(2-chloro-5-((3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid;

4-(2-chloro-4-methoxy-5-((3-(neopentylcarbamoyl)bicyclo[2.2.1]heptan-2-yl)carbamoyl)phenoxy)-1-methylcyclohexane-1-carboxylic acid;

1-fluoro-4-(2-fluoro-4-methoxy-5-((3-(((1-methylcyclobutyl)methyl)carbamoyl)bicyclo[2.2.1]heptan-2-yl)carbamoyl)phenoxy)cyclohexane-1-carboxylic acid;

1-fluoro-4-(2-fluoro-4-methoxy-5-((3-((3-((trifluoromethyl)sulfonyl)phenyl)carbamoyl)bicyclo[2.2.1]heptan-2-yl)carbamoyl)phenoxy)cyclohexane-1-carboxylic acid;

4-(2-fluoro-4-methoxy-5-((3-(((1-methylcyclobutyl)
methyl)carbamoyl)bicyclo[2.2.1]hept-5-en-2-yl)carbamoyl)phenoxy)-1-methylcyclohexane-1-carboxylic acid;

3-(4-fluoro-2-methoxy-5-((4-methyl-4-(5-oxo-4,5-dihydro-1,2,4-oxadiazol-3-yl)cyclohexyl)oxy)benzamido)-N-((1-methylcyclobutyl)methyl)bicyclo[2.2.1]heptane-2-carboxamide;

3-(4-fluoro-2-methoxy-5-((4-methyl-4-(5-oxo-4,5-dihydro-1,3,4-oxadiazol-2-yl)cyclohexyl)oxy)benzamido)-N-((1-methylcyclobutyl)methyl)bicyclo[2.2.1]heptane-2-carboxamide;

3-(4-fluoro-2-methoxy-5-((4-methyl-4-(1H-tetrazol-5-yl)cyclohexyl)oxy)benzamido)-N-((1-methylcyclobutyl)methyl)bicyclo[2.2.1]heptane-2-carboxamide;

3-(5-((4-carbamoyl-4-methylcyclohexyl)oxy)-4-fluoro-2-methoxybenzamido)-N-((1-methylcyclobutyl)methyl)bicyclo[2.2.1]heptane-2-carboxamide;

4-(2-fluoro-4-methoxy-5-((3-((3-((trifluoromethyl)sulfonyl)phenyl)carbamoyl)bicyclo[2.2.1]heptan-2-yl)carbamoyl)phenoxy)-1-hydroxycyclohexane-1-carboxylic acid;

1-(cyanomethyl)-4-(2-fluoro-4-methoxy-5-((3-(((1-methylcyclobutyl)methyl)carbamoyl)bicyclo[2.2.1]heptan-2-yl)carbamoyl)phenoxy)cyclohexane-1-carboxylic acid;

3-(2-fluoro-4-methoxy-5-((3-(((1-methylcyclobutyl)methyl)carbamoyl)bicyclo[2.2.1]heptan-2-yl)carbamoyl)phenoxy)bicyclo[3.1.0]hexane-6-carboxylic acid;

4-(4-methoxy-3-((3-((3-((trifluoromethyl)sulfonyl)phenyl)carbamoyl)bicyclo[2.2.1]hept-5-en-2-yl)carbamoyl)phenoxy)benzoic acid;

3-(4-methoxy-3-((3-((3-((trifluoromethyl)sulfonyl)phenyl)carbamoyl)bicyclo[2.2.1]hept-5-en-2-yl)carbamoyl)phenoxy)benzoic acid;

2-(4-methoxy-3-((3-((3-((trifluoromethyl)sulfonyl)phenyl)carbamoyl)bicyclo[2.2.1]hept-5-en-2-yl)carbamoyl)phenoxy)benzoic acid;

4-(2,4-difluoro-5-((3-((3-((trifluoromethyl)sulfonyl)phenyl)carbamoyl)bicyclo[2.2.1]heptan-2-yl)carbamoyl)phenoxy)cyclohexane-1-carboxylic acid;

5-(2-cyano-4-methoxy-5-((3-(((1-methylcyclobutyl)methyl)carbamoyl)bicyclo[2.2.1]heptan-2-yl)carbamoyl)phenoxy)-2,2-dimethylpentanoic acid;

4-(2-fluoro-5-((3-((4-fluoro-3-(pentafluoro-$\lambda^6$-sulfaneyl)phenyl)carbamoyl)bicyclo[2.2.1]heptan-2-yl)carbamoyl)-4-methoxyphenoxy)cyclohexane-1-carboxylic acid;

3-(5-((4-carbamoylcyclohexyl)oxy)-4-fluoro-2-methoxybenzamido)-N-(3-(pentafluoro-$\lambda^6$-sulfaneyl)phenyl)bicyclo[2.2.1]heptane-2-carboxamide; 6-fluoro-4-methoxy-N3-(3-((3-((trifluoromethyl)sulfonyl)phenyl)carbamoyl)bicyclo[2.2.1]heptan-2-yl)-[1,1'-biphenyl]-3,4'-dicarboxamide;

6-(2-fluoro-4-methoxy-5-((3-((3-((trifluoromethyl)sulfonyl)phenyl)carbamoyl)bicyclo[2.2.1]heptan-2-yl)carbamoyl)phenoxy)hexanoic acid;

7-(2-fluoro-4-methoxy-5-((3-((3-((trifluoromethyl)sulfonyl)phenyl)carbamoyl)bicyclo[2.2.1]heptan-2-yl)carbamoyl)phenoxy)heptanoic acid;

9-(2-fluoro-4-methoxy-5-((3-((3-((trifluoromethyl)sulfonyl)phenyl)carbamoyl)bicyclo[2.2.1]heptan-2-yl)carbamoyl)phenoxy)nonanoic acid;

4-((2-fluoro-4-methoxy-5-((3-((3-((trifluoromethyl)sulfonyl)phenyl)carbamoyl)bicyclo[2.2.1]heptan-2-yl)carbamoyl)phenoxy)methyl)benzoic acid;

4-((2-fluoro-4-methoxy-5-((3-((3-((trifluoromethyl)sulfonyl)phenyl)carbamoyl)bicyclo[2.2.1]heptan-2-yl)carbamoyl)phenoxy)methyl)cyclohexane-1-carboxylic acid;

4-((2-fluoro-4-methoxy-5-((3-((3-((trifluoromethyl)sulfonyl)phenyl)carbamoyl)bicyclo[2.2.1]heptan-2-yl)carbamoyl)phenoxy)methyl)bicyclo[2.2.2]octane-1-carboxylic acid;

5-(2-fluoro-4-methoxy-5-((3-((3-((trifluoromethyl)sulfonyl)phenyl)carbamoyl)bicyclo[2.2.1]heptan-2-yl)carbamoyl)phenoxy)tetrahydro-2H-pyran-2-carboxylic acid;

3-(2-fluoro-4-methoxy-5-((3-((3-((trifluoromethyl)sulfonyl)phenyl)carbamoyl)bicyclo[2.2.1]heptan-2-yl)carbamoyl)phenoxy)cyclobutane-1-carboxylic acid;

3-(2-fluoro-4-methoxy-5-((3-((3-((trifluoromethyl)sulfonyl)phenyl)carbamoyl)bicyclo[2.2.1]heptan-2-yl)carbamoyl)phenoxy)cyclohexane-1-carboxylic acid;

2-((2-fluoro-4-methoxy-5-((3-((3-((trifluoromethyl)sulfonyl)phenyl)carbamoyl)bicyclo[2.2.1]hept-5-en-2-yl)carbamoyl)phenoxy)methyl)benzoic acid;

3-((2-fluoro-4-methoxy-5-((3-((3-((trifluoromethyl)sulfonyl)phenyl)carbamoyl)bicyclo[2.2.1]hept-5-en-2-yl)carbamoyl)phenoxy)methyl)benzoic acid;

4-((2-fluoro-4-methoxy-5-((3-((3-((trifluoromethyl)sulfonyl)phenyl)carbamoyl)bicyclo[2.2.1]hept-5-en-2-yl)carbamoyl)phenoxy)methyl)benzoic acid;

5-(2-fluoro-4-methoxy-5-((3-((3-((trifluoromethyl)sulfonyl)phenyl)carbamoyl)bicyclo[2.2.1]hept-5-en-2-yl)carbamoyl)phenoxy)pentanoic acid;

2-(4-((2-fluoro-4-methoxy-5-((3-((3-((trifluoromethyl)sulfonyl)phenyl)carbamoyl)bicyclo[2.2.1]hept-5-en-2-yl)carbamoyl)phenoxy)methyl)phenyl)-2-methylpropanoic acid;

2-(3-((2-fluoro-4-methoxy-5-((3-((3-((trifluoromethyl)sulfonyl)phenyl)carbamoyl)bicyclo[2.2.1]hept-5-en-2-yl)carbamoyl)phenoxy)methyl)phenyl)acetic acid;

2-(3-((2-fluoro-4-methoxy-5-((3-((3-((trifluoromethyl)sulfonyl)phenyl)carbamoyl)bicyclo[2.2.1]hept-5-en-2-yl)carbamoyl)phenoxy)methyl)phenyl)-2-methylpropanoic acid;

6-(2-fluoro-4-methoxy-5-((3-((3-((trifluoromethyl)sulfonyl)phenyl)carbamoyl)bicyclo[2.2.1]hept-5-en-2-yl)carbamoyl)phenoxy)hexanoic acid;

4-(2-fluoro-4-methoxy-5-((3-((3-((trifluoromethyl)sulfonyl)phenyl)carbamoyl)bicyclo[2.2.1]hept-5-en-2-yl)carbamoyl)phenoxy)butanoic acid;

4-(2-fluoro-4-methoxy-5-((3-((3-((trifluoromethyl)sulfonyl)phenyl)carbamoyl)bicyclo[2.2.1]hept-5-en-2-yl)carbamoyl)phenoxy)cyclohexane-1-carboxylic acid;

1-amino-4-(2-fluoro-4-methoxy-5-((3-((3-((trifluoromethyl)sulfonyl)phenyl)carbamoyl)bicyclo[2.2.1]heptan-2-yl)carbamoyl)phenoxy)cyclohexane-1-carboxylic acid;

3-(4-fluoro-2-methoxy-5-((4-(methylsulfonamido)cyclohexyl)oxy)benzamido)-N-(3-((trifluoromethyl)sulfonyl)phenyl)bicyclo[2.2.1]heptane-2-carboxamide;

4-(2-fluoro-4-methoxy-5-((6-((3-((trifluoromethyl)sulfonyl)phenyl)carbamoyl)hexahydro-4,7-methanobenzo[d][1,3]dioxol-5-yl)carbamoyl)phenoxy)cyclohexane-1-carboxylic acid;

3-(4-fluoro-2-methoxy-5-((4-sulfamoylcyclohexyl)oxy)benzamido)-N-(3-((trifluoromethyl)sulfonyl)phenyl)bicyclo[2.2.1]heptane-2-carboxamide;

4-(2-bromo-4-methoxy-5-((3-((3-((trifluoromethyl)sulfonyl)phenyl)carbamoyl)bicyclo[2.2.1]heptan-2-yl)carbamoyl)phenoxy)cyclohexane-1-carboxylic acid;

4-(4-methoxy-2-methyl-5-((3-((3-((trifluoromethyl)sulfonyl)phenyl)carbamoyl)bicyclo[2.2.1]heptan-2-yl)carbamoyl)phenoxy)cyclohexane-1-carboxylic acid;

4-(4-methoxy-3-((3-((3-((trifluoromethyl)sulfonyl)phenyl)carbamoyl)bicyclo[2.2.1]heptan-2-yl)carbamoyl)phenoxy)cyclohexane-1-carboxylic acid;

4-(2-cyano-4-methoxy-5-((3-((3-((trifluoromethyl)sulfonyl)phenyl)carbamoyl)bicyclo[2.2.1]heptan-2-yl)carbamoyl)phenoxy)cyclohexane-1-carboxylic acid;

4-(2-cyano-4-methoxy-5-((3-(((1-methylcyclobutyl)methyl)carbamoyl)bicyclo[2.2.2]octan-2-yl)carbamoyl)phenoxy)-1-methylcyclohexane-1-carboxylic acid;

4-(2-cyano-4-methoxy-5-((3-(((1-methylcyclobutyl)methyl)carbamoyl)bicyclo[2.2.2]oct-5-en-2-yl)carbamoyl)phenoxy)-1-methylcyclohexane-1-carboxylic acid;

4-(2-fluoro-4-methoxy-5-((3-(((1-methylcyclobutyl)methyl)carbamoyl)bicyclo[2.2.2]octan-2-yl)carbamoyl)phenoxy)-1-methylcyclohexane-1-carboxylic acid;

4-(2-fluoro-4-methoxy-5-((3-(((1-methylcyclobutyl)methyl)carbamoyl)bicyclo[2.2.2]oct-5-en-2-yl)carbamoyl)phenoxy)-1-methylcyclohexane-1-carboxylic acid;

3-((2-fluoro-4-methoxy-5-((3-((3-((trifluoromethyl)sulfonyl)phenyl)carbamoyl)bicyclo[2.2.1]heptan-2-yl)carbamoyl)phenoxy)methyl)cyclobutane-1-carboxylic acid;

2-(3-(2-fluoro-4-methoxy-5-((3-((3-((trifluoromethyl)sulfonyl)phenyl)carbamoyl)bicyclo[2.2.1]heptan-2-yl)carbamoyl)phenoxy)cyclobutyl)acetic acid;

2-(4-(2-fluoro-4-methoxy-5-((3-(((1-methylcyclobutyl)methyl)carbamoyl)bicyclo[2.2.1]heptan-2-yl)carbamoyl)phenoxy)-1-methylcyclohexyl)acetic acid;

4-(2-fluoro-4-methoxy-5-((3-(((1-methylcyclobutyl)methyl)carbamoyl)bicyclo[2.2.1]heptan-2-yl)carbamoyl)phenoxy)-1-(trifluoromethyl)cyclohexane-1-carboxylic acid;

4-(2-fluoro-4-methoxy-5-((3-((3-((trifluoromethyl)sulfonyl)phenyl)carbamoyl)bicyclo[2.2.1]heptan-2-yl)carbamoyl)phenoxy)-1-(methoxymethyl)cyclohexane-1-carboxylic acid;

4-(2-fluoro-4-methoxy-5-((3-(neopentylcarbamoyl)bicyclo[2.2.1]heptan-2-yl)carbamoyl)phenoxy)-1-(methoxymethyl)cyclohexane-1-carboxylic acid;

4-(2-cyano-4-methoxy-5-((3-(((1-methylcyclobutyl)methyl)carbamoyl)bicyclo[2.2.1]heptan-2-yl)carbamoyl)phenoxy)benzoic acid;

4-(2-fluoro-4-methoxy-5-((3-((3-((trifluoromethyl)sulfonyl)phenyl)carbamoyl)bicyclo[2.2.1]hept-5-en-2-yl)carbamoyl)phenoxy)benzoic acid;

4-(2-fluoro-4-isopropoxy-5-((3-(((1-methylcyclobutyl)methyl)carbamoyl)bicyclo[2.2.1]heptan-2-yl)carbamoyl)phenoxy)-1-(methoxycarbonyl)cyclohexane-1-carboxylic acid;

4-(2-fluoro-4-isopropoxy-5-((3-(((1-methylcyclobutyl)methyl)carbamoyl)bicyclo[2.2.1]heptan-2-yl)carbamoyl)phenoxy)-1-(hydroxymethyl)cyclohexane-1-carboxylic acid;

4-(5-((1-acetyl-3-((3-((trifluoromethyl)sulfonyl)phenyl)carbamoyl)piperidin-4-yl)carbamoyl)-2-fluoro-4-methoxyphenoxy)-1-methylcyclohexane-1-carboxylic acid;

4-(2-fluoro-5-((3-((4-fluoro-3-(pentafluoro-λ⁶-sulfaneyl)phenyl)carbamoyl)bicyclo[2.2.1]hept-5-en-2-yl)carbamoyl)-4-methoxyphenoxy)cyclohexane-1-carboxylic acid;

4-(2-fluoro-5-((3-((4-fluoro-3-((trifluoromethyl)sulfonyl)phenyl)carbamoyl)bicyclo[2.2.1]hept-5-en-2-yl)carbamoyl)-4-methoxyphenoxy)cyclohexane-1-carboxylic acid;

4-(2-fluoro-4-methoxy-5-((2-((3-((trifluoromethyl)sulfonyl)phenyl)carbamoyl)cyclopentyl)carbamoyl)phenoxy)cyclohexane-1-carboxylic acid;

4-(2-fluoro-4-methoxy-5-((3-((3-((trifluoromethyl)sulfonyl)phenyl)carbamoyl)bicyclo[2.2.1]heptan-2-yl)carbamoyl)phenoxy)cyclohexane-1-carboxylic acid;

4-(2-fluoro-5-((2-((4-fluoro-3-(trifluoromethyl)phenyl)carbamoyl)cyclopentyl)carbamoyl)-4-methoxyphenoxy)cyclohexane-1-carboxylic acid;

4-(5-((4,4-difluoro-2-((4-fluoro-3-(trifluoromethyl)phenyl)carbamoyl)cyclopentyl)carbamoyl)-2-fluoro-4-methoxyphenoxy)cyclohexane-1-carboxylic acid;

4-(5-((5,6-dihydroxy-3-((3-((trifluoromethyl)sulfonyl)phenyl)carbamoyl)bicyclo[2.2.1]heptan-2-yl)carbamoyl)-2-fluoro-4-methoxyphenoxy)cyclohexane-1-carboxylic acid;

4-(2-fluoro-5-((4-hydroxy-2-((3-((trifluoromethyl)sulfonyl)phenyl)carbamoyl)cyclopentyl)carbamoyl)-4-methoxyphenoxy)cyclohexane-1-carboxylic acid;

4-(2-fluoro-4-methoxy-5-((3-((4-methoxy-3-((trifluoromethyl)sulfonyl)phenyl)carbamoyl)bicyclo[2.2.1]hept-5-en-2-yl)carbamoyl)phenoxy)cyclohexane-1-carboxylic acid;

4-(2-fluoro-5-((3-((4-fluoro-3-(trifluoromethyl)phenyl)carbamoyl)bicyclo[2.2.1]hept-5-en-2-yl)carbamoyl)-4-methoxyphenoxy)cyclohexane-1-carboxylic acid;

3-(5-((4-carbamoylcyclohexyl)oxy)-4-fluoro-2-methoxybenzamido)-N-(4-fluoro-3-(trifluoromethyl)phenyl)bicyclo[2.2.1]hept-5-ene-2-carboxamide;

3-(5-((4-carbamoylcyclohexyl)oxy)-4-fluoro-2-methoxybenzamido)-N-(4-fluoro-3-(trifluoromethyl)phenyl)bicyclo[2.2.1]heptane-2-carboxamide;

4-(2-cyano-4-methoxy-5-((3-((3,3,3-trifluoro-2,2-dimethylpropyl)carbamoyl)bicyclo[2.2.1]heptan-2-yl)carbamoyl)phenoxy)-1-methylcyclohexane-1-carboxylic acid;

4-(5-((3-((2,2-dimethylcyclopentyl)carbamoyl)bicyclo[2.2.1]heptan-2-yl)carbamoyl)-2-fluoro-4-methoxyphenoxy)-1-methylcyclohexane-1-carboxylic acid;

3-(2-fluoro-4-methoxy-5-((3-((3-((trifluoromethyl)sulfonyl)phenyl)carbamoyl)bicyclo[2.2.1]heptan-2-yl)carbamoyl)phenoxy)-1-methylcyclobutane-1-carboxylic acid;

4-(2-fluoro-4-methoxy-5-((3-(((1-methylcyclobutyl)methyl)carbamoyl)bicyclo[2.2.1]heptan-2-yl)carbamoyl)phenoxy)-1-methoxycyclohexane-1-carboxylic acid;

4-(2-fluoro-4-methoxy-5-((3-(((1-methylcyclobutyl)methyl)carbamoyl)bicyclo[2.2.1]heptan-2-yl)carbamoyl)phenoxy)-1-hydroxycyclohexane-1-carboxylic acid;

4-(2-fluoro-4-methoxy-5-((3-((3-((trifluoromethyl)sulfonyl)phenyl)carbamoyl)bicyclo[2.2.1]heptan-2-yl)carbamoyl)phenoxy)-1-methoxycyclohexane-1-carboxylic acid;

4-(2-fluoro-4-methoxy-5-((4-(neopentylcarbamoyl)tetrahydrofuran-3-yl)carbamoyl)phenoxy)-1-(hydroxymethyl)cyclohexane-1-carboxylic acid;

4-(2-fluoro-4-methoxy-5-((4-(((1-methylcyclobutyl)methyl)carbamoyl)tetrahydrofuran-3-yl)carbamoyl)phenoxy)-1-(hydroxymethyl)cyclohexane-1-carboxylic acid;

4-(2-cyano-4-fluoro-5-((3-(((1-methylcyclobutyl)methyl)carbamoyl)bicyclo[2.2.2]octan-2-yl)carbamoyl)phenoxy)-1-methylcyclohexane-1-carboxylic acid;

2'-fluoro-5'-((3-((4-fluoro-3-(trifluoromethyl)phenyl)carbamoyl)bicyclo[2.2.1]heptan-2-yl)carbamoyl)-4'-methoxy-[1,1'-biphenyl]-4-carboxylic acid;

4-(2-fluoro-4-methoxy-5-((3-(((1-methoxycyclobutyl)methyl)carbamoyl)bicyclo[2.2.1]heptan-2-yl)carbamoyl)phenoxy)-1-methylcyclohexane-1-carboxylic acid;

4-(2-fluoro-4-methoxy-5-((3-((1-(methoxymethyl)cyclobutyl)methyl)carbamoyl)bicyclo[2.2.1]heptan-2-yl)carbamoyl)phenoxy)-1-methylcyclohexane-1-carboxylic acid;

4-(5-((3-(((1-cyanocyclobutyl)methyl)carbamoyl)bicyclo[2.2.1]heptan-2-yl)carbamoyl)-2-fluoro-4-methoxyphenoxy)-1-methylcyclohexane-1-carboxylic acid;

4-(2-fluoro-4-methoxy-5-((3-((3,3,3-trifluoropropyl)carbamoyl)bicyclo[2.2.1]heptan-2-yl)carbamoyl)phenoxy)-1-methylcyclohexane-1-carboxylic acid;

4-(2-fluoro-4-methoxy-5-((3-((1,1,1-trifluoropropan-2-yl)carbamoyl)bicyclo[2.2.1]heptan-2-yl)carbamoyl)phenoxy)-1-methylcyclohexane-1-carboxylic acid;

4-(5-((3-(cyclobutylcarbamoyl)bicyclo[2.2.1]heptan-2-yl)carbamoyl)-2-fluoro-4-methoxyphenoxy)-1-methylcyclohexane-1-carboxylic acid;

4-(5-((3-(cyclopentylcarbamoyl)bicyclo[2.2.1]heptan-2-yl)carbamoyl)-2-fluoro-4-methoxyphenoxy)-1-methylcyclohexane-1-carboxylic acid;

4-(5-((3-(bicyclo[1.1.1]pentan-1-ylcarbamoyl)bicyclo[2.2.1]heptan-2-yl)carbamoyl)-2-fluoro-4-methoxyphenoxy)-1-methylcyclohexane-1-carboxylic acid;

4-(5-((3-(tert-butylcarbamoyl)bicyclo[2.2.1]heptan-2-yl)carbamoyl)-2-fluoro-4-methoxyphenoxy)-1-methylcyclohexane-1-carboxylic acid;

4-(2-fluoro-4-methoxy-5-((3-((1,1,1-trifluoro-2-methylpropan-2-yl)carbamoyl)bicyclo[2.2.1]heptan-2-yl)carbamoyl)phenoxy)-1-methylcyclohexane-1-carboxylic acid;

4-(2-fluoro-4-methoxy-5-((3-((1-((trifluoromethyl)sulfonyl)piperidin-3-yl)carbamoyl)bicyclo[2.2.1]heptan-2-yl)carbamoyl)phenoxy)-1-methylcyclohexane-1-carboxylic acid;

4-(2-fluoro-4-methoxy-5-((3-((1-((trifluoromethyl)sulfonyl)pyrrolidin-3-yl)carbamoyl)bicyclo[2.2.1]heptan-2-yl)carbamoyl)phenoxy)-1-methylcyclohexane-1-carboxylic acid;

4-(2-fluoro-5-((3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid;

4-(2-fluoro-5-((3-(((1-fluorocyclobutyl)methyl)carbamoyl)bicyclo[2.2.1]heptan-2-yl)carbamoyl)-4-methoxyphenoxy)-1-methylcyclohexane-1-carboxylic acid;

4-(2-fluoro-4-methoxy-5-((3-((2-methoxy-2-methylpropyl)carbamoyl)bicyclo[2.2.1]heptan-2-yl)carbamoyl)phenoxy)-1-methylcyclohexane-1-carboxylic acid;

4-(2-fluoro-5-((3-((2-hydroxy-2-methylpropyl)carbamoyl)bicyclo[2.2.1]heptan-2-yl)carbamoyl)-4-methoxyphenoxy)-1-methylcyclohexane-1-carboxylic acid;

4-(2-fluoro-5-((3-((3-hydroxy-2,2-dimethylpropyl)carbamoyl)bicyclo[2.2.1]heptan-2-yl)carbamoyl)-4-methoxyphenoxy)-1-methylcyclohexane-1-carboxylic acid;

4-(2-fluoro-4-methoxy-5-((3-(((1-(trifluoromethyl)cyclobutyl)methyl)carbamoyl)bicyclo[2.2.1]heptan-2-yl)carbamoyl)phenoxy)-1-methylcyclohexane-1-carboxylic acid;

4-(2-fluoro-4-methoxy-5-((3-(((1-(trifluoromethyl)cyclopropyl)methyl)carbamoyl)bicyclo[2.2.1]heptan-2-yl)carbamoyl)phenoxy)-1-methylcyclohexane-1-carboxylic acid;

4-(5-((3-((3-cyano-3-methylbutan-2-yl)carbamoyl)bicyclo[2.2.1]heptan-2-yl)carbamoyl)-2-fluoro-4-methoxyphenoxy)-1-methylcyclohexane-1-carboxylic acid;

4-(5-((3-(((1-ethylcyclobutyl)methyl)carbamoyl)bicyclo[2.2.1]heptan-2-yl)carbamoyl)-2-fluoro-4-methoxyphenoxy)-1-methylcyclohexane-1-carboxylic acid;

4-(2-fluoro-4-methoxy-5-((3-((2,2,3,3,3-pentafluoropropyl)carbamoyl)bicyclo[2.2.1]heptan-2-yl)carbamoyl)phenoxy)-1-methylcyclohexane-1-carboxylic acid;

4-(5-((3-((3,3-difluorocyclobutyl)carbamoyl)bicyclo[2.2.1]heptan-2-yl)carbamoyl)-2-fluoro-4-methoxyphenoxy)-1-methylcyclohexane-1-carboxylic acid;

4-(5-((3-(((3,3-difluorocyclobutyl)methyl)carbamoyl)bicyclo[2.2.1]heptan-2-yl)carbamoyl)-2-fluoro-4-methoxyphenoxy)-1-methylcyclohexane-1-carboxylic acid;

4-(2-cyano-5-((3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid; and 4-(2-cyano-5-((3-((3,3-difluorocyclobutyl)carbamoyl)bicyclo[2.2.1]heptan-2-yl)carbamoyl)-4-methoxyphenoxy)-1-methylcyclohexane-1-carboxylic acid.

In a further embodiment there is provided a compound selected from:

(1S,4s)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1R,4s)-4-(2-fluoro-4-methoxy-5-(((1R,2S,3R,4S)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-((cyclobutylmethyl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-fluoro-4-(fluoromethoxy)-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-fluoro-4-methyl-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(2R,4r,6R)-6-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)spiro[3.3]heptane-2-carboxylic acid;

(2S,4s,6S)-6-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)spiro[3.3]heptane-2-carboxylic acid;

(1S,4s)-4-(2-fluoro-5-(((1S,2R,3S,4R)-3-(isopropylcarbamoyl)bicyclo[2.2.1]heptan-2-yl)carbamoyl)-4-methoxyphenoxy)cyclohexane-1-carboxylic acid;

(1S,4s)-4-(5-(((1S,2R,3S,4R)-3-(cyclohexylcarbamoyl)bicyclo[2.2.1]heptan-2-yl)carbamoyl)-2-fluoro-4-methoxyphenoxy)cyclohexane-1-carboxylic acid;

(1S,4s)-4-(5-(((1S,2R,3S,4R)-3-((3-(difluoromethyl)phenyl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-5-(((1S,2R,3S,4R)-3-((3-(fluoromethyl)phenyl)carbamoyl)bicyclo[2.2.1]heptan-2-yl)carbamoyl)-4-methoxyphenoxy)cyclohexane-1-carboxylic acid;

(1S,4s)-4-(2-fluoro-4-methoxy-5-(((1S,2R,3S,4R)-3-((2-(trifluoromethyl)pyridin-4-yl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-((5-(trifluoromethyl)pyridin-2-yl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-((4-(trifluoromethyl)pyridin-2-yl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-((4-((trifluoromethyl)sulfonyl)phenyl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-((perfluorophenyl)carbamoyl)bicyclo[2.2.1]heptan-2-yl)carbamoyl)phenoxy)cyclohexane-1-carboxylic acid;

(1S,4s)-4-(2-fluoro-5-(((1S,2R,3S,4R)-3-((3-fluoro-5-(pentafluoro-λ6-sulfaneyl)phenyl)carbamoyl)bicyclo[2.2.1]heptan-2-yl)carbamoyl)-4-methoxyphenoxy)cyclohexane-1-carboxylic acid;

(1S,4s)-4-(2-fluoro-5-(((1S,2R,3S,4R)-3-((2-fluoro-3-(trifluoromethoxy)phenyl)carbamoyl)bicyclo[2.2.1]heptan-2-yl)carbamoyl)-4-methoxyphenoxy)cyclohexane-1-carboxylic acid;

(1S,4s)-4-(5-(((1S,2R,3S,4R)-3-((3-cyano-4-methylphenyl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-4-methoxy-5-(((1S,2R,3S,4R)-3-((3-(trifluoromethyl)phenyl)carbamoyl)bicyclo[2.2.1]heptan-2-yl)carbamoyl)phenoxy)cyclohexane-1-carboxylic acid;

(1S,4s)-4-(2-fluoro-5-(((1S,2R,3S,4R)-3-((4-fluoro-3-(trifluoromethoxy)phenyl)carbamoyl)bicyclo[2.2.1]heptan-2-yl)carbamoyl)-4-methoxyphenoxy)cyclohexane-1-carboxylic acid;

(1S,4s)-4-(5-(((1S,2R,3S,4R)-3-((3,5-bis(trifluoromethyl)phenyl)carbamoyl)bicyclo[2.2.1]heptan-2-yl)carbamoyl)-2-fluoro-4-methoxyphenoxy)cyclohexane-1-carboxylic acid;

(1S,4s)-4-(5-(((1S,2R,3S,4R)-3-((4-bromo-3-(trifluoromethyl)phenyl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-4-methoxy-5-(((1S,2R,3S,4R)-3-((2-methyl-3-(trifluoromethyl)phenyl)carbamoyl)bicyclo[2.2.1]heptan-2-yl)carbamoyl)phenoxy)cyclohexane-1-carboxylic acid;

(1S,4s)-4-(5-(((1S,2R,3S,4R)-3-((3-chlorophenyl)carbamoyl)bicyclo[2.2.1]heptan-2-yl)carbamoyl)-2-fluoro-4-methoxyphenoxy)cyclohexane-1-carboxylic acid;

(1S,4s)-4-(5-(((1S,2R,3S,4R)-3-((2-chloro-5-(trifluoromethyl)phenyl)carbamoyl)bicyclo[2.2.1]heptan-2-yl)carbamoyl)-2-fluoro-4-methoxyphenoxy)cyclohexane-1-carboxylic acid;

(1S,4s)-4-(5-(((1S,2R,3S,4R)-3-((3-bromo-4-cyanophenyl)carbamoyl)bicyclo[2.2.1]heptan-2-yl)carbamoyl)-2-fluoro-4-methoxyphenoxy)cyclohexane-1-carboxylic acid;

(1S,4s)-4-(5-(((1S,2R,3S,4R)-3-((4-cyano-3-(trifluoromethyl)phenyl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-5-(((1S,2R,3S,4R)-3-((3-fluoro-5-(trifluoromethyl)phenyl)carbamoyl)bicyclo[2.2.1]heptan-2-yl)carbamoyl)-4-methoxyphenoxy)cyclohexane-1-carboxylic acid;

(1S,4s)-4-(5-(((1S,2R,3S,4R)-3-((5-chloropyridazin-3-yl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-4-methoxy-5-(((1S,2R,3S,4R)-3-((6-(trifluoromethyl)pyrimidin-4-yl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-((4-(trifluoromethyl)pyrimidin-2-yl)carbamoyl)bicyclo[2.2.1]heptan-2-yl)carbamoyl)phenoxy)cyclohexane-1-carboxylic acid;

(1S,4s)-4-(5-(((1S,2R,3S,4R)-3-((3,3-difluorocyclobutyl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-5-(((1S,2R,3S,4R)-3-(isobutylcarbamoyl)bicyclo[2.2.1]heptan-2-yl)carbamoyl)-4-methoxyphenoxy)-1-methylcyclohexane-1-carboxylic acid;

(1S,4s)-4-(2-fluoro-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-(((R)-3,3-dimethylbutan-2-yl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(5-(((1S,2R,3S,4R)-3-((2,2-dimethylbutyl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-fluoro-4-methoxy-5-(((1S,2R,3S,4R)-3-((3,3,3-trifluoro-2,2-dimethylpropyl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-(((R)-1-(1-methylcyclopropyl)ethyl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-(((S)-1-(1-methylcyclopropyl)ethyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-((2,4-dimethylpentan-3-yl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-fluoro-4-methoxy-5-(((1S,2R,3S,4R)-3-(((1-methylcyclopropyl)methyl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-(((S)-3-methylbutan-2-yl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-((2-ethylbutyl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-fluoro-4-methoxy-5-(((1S,2R,3S,4R)-3-(((1-methylcyclohexyl)methyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-(((S)-3,3-dimethylbutan-2-yl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-fluoro-4-methoxy-5-(((1S,2R,3S,4R)-3-(((R)-3-methylbutan-2-yl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-((2-cyano-2-methylpropyl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-fluoro-5-(((1S,2R,3S,4R)-3-(((1-(fluoromethyl)cyclopropyl)methyl)carbamoyl)bicyclo[2.2.1]heptan-2-yl)carbamoyl)-4-methoxyphenoxy)-1-methylcyclohexane-1-carboxylic acid;

(1R,4s)-4-(2-fluoro-5-(((1S,2S,3R,4R)-3-((4-fluoro-3-(trifluoromethyl)phenyl)carbamoyl)-7-oxabicyclo[2.2.1]heptan-2-yl)carbamoyl)-4-methoxyphenoxy)cyclohexane-1-carboxylic acid;

(1S,4s)-4-(2-fluoro-5-(((1R,2R,3S,4S)-3-((4-fluoro-3-(trifluoromethyl)phenyl)carbamoyl)-7-oxabicyclo[2.2.1]heptan-2-yl)carbamoyl)-4-methoxyphenoxy)cyclohexane-1-carboxylic acid;

(1S,4s)-4-(2-fluoro-5-(((1R,2S)-2-((4-fluoro-3-(trifluoromethyl)phenyl)carbamoyl)cyclobutyl)carbamoyl)-4-methoxyphenoxy)-1-methylcyclohexane-1-carboxylic acid;

(1R,4s)-4-(2-fluoro-5-(((3S,4R)-4-((4-fluoro-3-(trifluoromethyl)phenyl)carbamoyl)tetrahydrofuran-3-yl)carbamoyl)-4-methoxyphenoxy)-1-methylcyclohexane-1-carboxylic acid;

(1R,2S,3R,4S)-3-(5-(((1s,4S)-4-carbamoyl-4-methylcyclohexyl)oxy)-4-fluoro-2-methoxybenzamido)-N-neopentylbicyclo[2.2.1]heptane-2-carboxamide; (1s,4s)-4-(5-((3-chloro-2-(((1-methylcyclobutyl)methyl)carbamoyl)phenyl)carbamoyl)-2-fluoro-4-methoxyphenoxy)-1-methylcyclohexane-1-carboxylic acid;

(1S,4s)-4-(2-fluoro-4-methoxy-5-(((1R,2S)-2-(((S)-3-methylbutan-2-yl)carbamoyl)cyclopentyl)carbamoyl)phenoxy)-1-methylcyclohexane-1-carboxylic acid;

(1S,4s)-4-(2-fluoro-5-(((1R,2S)-2-(((1-(fluoromethyl)cyclopropyl)methyl)carbamoyl)cyclopentyl)carbamoyl)-4-methoxyphenoxy)-1-methylcyclohexane-1-carboxylic acid;

(1S,4s)-4-(2-fluoro-4-methoxy-5-(((1R,2S)-2-(neopentylcarbamoyl)cyclopentyl)carbamoyl)phenoxy)-1-methylcyclohexane-1-carboxylic acid;

(1S,4s)-4-(5-(((1R,2S)-2-((2,2-dimethylbutyl)carbamoyl)cyclopentyl)carbamoyl)-2-fluoro-4-methoxyphenoxy)-1-methylcyclohexane-1-carboxylic acid;

(1S,4s)-4-(5-(((1R,2S)-2-((2-ethylbutyl)carbamoyl)cyclopentyl)carbamoyl)-2-fluoro-4-methoxyphenoxy)-1-methylcyclohexane-1-carboxylic acid;

(1S,4s)-4-(2-fluoro-4-methoxy-5-(((1R,2S)-2-(((R)-3-methylbutan-2-yl)carbamoyl)cyclopentyl)carbamoyl)phenoxy)-1-methylcyclohexane-1-carboxylic acid;

(1S,4s)-4-(5-(((1R,2S)-2-(((S)-3,3-dimethylbutan-2-yl)carbamoyl)cyclopentyl)carbamoyl)-2-fluoro-4-methoxyphenoxy)-1-methylcyclohexane-1-carboxylic acid;

(1S,4s)-4-(5-(((1R,2S)-2-((2,4-dimethylpentan-3-yl)carbamoyl)cyclopentyl)carbamoyl)-2-fluoro-4-methoxyphenoxy)-1-methylcyclohexane-1-carboxylic acid;

(1S,4s)-4-(2-fluoro-4-methoxy-5-(((1R,2S)-2-(((R)-1-(1-methylcyclopropyl)ethyl)carbamoyl)cyclopentyl)carbamoyl)phenoxy)-1-methylcyclohexane-1-carboxylic acid;

(1S,4s)-4-(2-fluoro-4-methoxy-5-(((1R,2S)-2-(((S)-1-(1-methylcyclopropyl)ethyl)carbamoyl)cyclopentyl)carbamoyl)phenoxy)-1-methylcyclohexane-1-carboxylic acid;

(1S,4s)-4-(2-fluoro-4-methoxy-5-(((1R,2S)-2-(((1-methylcyclohexyl)methyl)carbamoyl)cyclopentyl)carbamoyl)phenoxy)-1-methylcyclohexane-1-carboxylic acid;

(1S,4s)-4-(5-(((1R,2S)-2-(((R)-3,3-dimethylbutan-2-yl)carbamoyl)cyclopentyl)carbamoyl)-2-fluoro-4-methoxyphenoxy)-1-methylcyclohexane-1-carboxylic acid;

(1S,4s)-4-(2-fluoro-5-(((1R,2S)-2-(isobutylcarbamoyl)cyclopentyl)carbamoyl)-4-methoxyphenoxy)-1-methylcyclohexane-1-carboxylic acid;

(1S,4s)-4-(2-fluoro-4-methoxy-5-(((1R,2S)-2-(((1-methylcyclobutyl)methyl)carbamoyl)cyclopentyl)carbamoyl)phenoxy)-1-methylcyclohexane-1-carboxylic acid;

(1S,4s)-4-(2-fluoro-4-methoxy-5-(((1R,2S)-2-(((1-methylcyclopropyl)methyl)carbamoyl)cyclopentyl)carbamoyl)phenoxy)-1-methylcyclohexane-1-carboxylic acid;

(1S,4s)-4-(5-(((1R,2S)-2-((2-cyano-2-methylpropyl)carbamoyl)cyclopentyl)carbamoyl)-2-fluoro-4-methoxyphenoxy)-1-methylcyclohexane-1-carboxylic acid;

(1S,4s)-4-(2-fluoro-4-methoxy-5-(((1R,2S)-2-((3,3,3-trifluoro-2,2-dimethylpropyl)carbamoyl)cyclopentyl)carbamoyl)phenoxy)-1-methylcyclohexane-1-carboxylic acid;

(1S,4s)-4-(2-cyano-5-(((1S,2R,3S,4R)-3-((cyclopropylmethyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((1-cyanocyclopropyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-(((1s,3R)-3-methylcyclobutyl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-(((1-hydroxycyclopentyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((1-(hydroxymethyl)cyclobutyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((2-hydroxy-2-methylpropyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((1-fluoro-2-methylpropan-2-yl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((1-isopropylcyclopropyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-(((1-(methoxymethyl)cyclopropyl)methyl)carbamoyl)bicyclo[2.2.1]heptan-2-yl)carbamoyl)phenoxy)-1-methylcyclohexane-1-carboxylic acid;

(1S,4s)-4-(2-cyano-4-methoxy-5-(((1S,2R,3S,4R)-3-(((1-methoxycyclobutyl)methyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-(((3S,5S)-adamantan-1-yl)carbamoyl)bicyclo[2.2.1]heptan-2-yl)carbamoyl)-2-cyano-4-methoxyphenoxy)-1-methylcyclohexane-1-carboxylic acid;

(1S,4s)-4-(2-cyano-5-(((1S,2R,3S,4R)-3-((cycloheptylmethyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-(((1-propylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-cyano-4-methoxy-5-(((1S,2R,3S,4R)-3-(((2,2,3,3-tetramethylcyclopropyl)methyl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-((2-(isopropylamino)-2-oxoethyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((1-ethylcyclobutyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((3,3-dimethylcyclobutyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((2-ethylbutyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((S)-2-fluoro-3-hydroxypropyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-((1-methylcyclobutyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-(butylcarbamoyl)bicyclo[2.2.1]heptan-2-yl)carbamoyl)-2-cyano-4-methoxyphenoxy)-1-methylcyclohexane-1-carboxylic acid;

(1S,4s)-4-(2-cyano-5-(((1S,2R,3S,4R)-3-(((1-fluorocyclopentyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((1-cyanocyclobutyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((1-fluorocyclobutyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((1-(fluoromethyl)cyclopropyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((2,2-difluoropropyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((2-fluoro-2-methylpropyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-(((1-methylcyclopropyl)methyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-(tert-butylcarbamoyl)bicyclo[2.2.1]heptan-2-yl)carbamoyl)-2-cyano-4-methoxyphenoxy)-1-methylcyclohexane-1-carboxylic acid;

(1S,4s)-4-(2-cyano-4-methoxy-5-(((1S,2R,3S,4R)-3-((1-methylcyclopropyl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-(((4,4-difluoro-1-hydroxycyclohexyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-((2,2,3,3,3-pentafluoropropyl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-(((1-hydroxycycloheptyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((1-(ethoxymethyl)cyclobutyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-(((1-methylcycloheptyl)methyl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-(((1-isobutylcyclobutyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((4-cyanocyclohexyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-((2-phenylpropan-2-yl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-(((1-(hydroxymethyl)cyclopentyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((4-fluorotetrahydro-2H-pyran-4-yl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-(((1-methoxycyclopropyl)methyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-([1,1'-bi(cyclopropan)]-1-ylcarbamoyl)bicyclo[2.2.1]heptan-2-yl)carbamoyl)-2-cyano-4-methoxyphenoxy)-1-methylcyclohexane-1-carboxylic acid;

(1S,4s)-4-(2-cyano-5-(((1S,2R,3S,4R)-3-(((1r,3S)-3-hydroxyadamantan-1-yl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((4-(difluoromethyl)pyrimidin-2-yl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-(propylcarbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-(hexylcarbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-(((R)-2-phenylpropyl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-(((S)-3,3-dimethylbutan-2-yl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((R)-1-cyclohexylethyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(cyclohexylcarbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((3-isopropoxypropyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((3,4-difluorobenzyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-((((1s,3R)-3-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-cyano-4-methoxy-5-(((1S,2R,3S,4R)-3-(((S)-2-phenylpropyl)carbamoyl)bicyclo[2.2.1]heptan-2-yl)carbamoyl)phenoxy)-1-methylcyclohexane-1-carboxylic acid;

(1S,4s)-4-(2-cyano-4-methoxy-5-(((1S,2R,3S,4R)-3-(tert-pentylcarbamoyl)bicyclo[2.2.1]heptan-2-yl)carbamoyl)phenoxy)-1-methylcyclohexane-1-carboxylic acid;

(1S,4s)-4-(2-cyano-4-methoxy-5-(((1S,2R,3S,4R)-3-(((S)-3-methylbutan-2-yl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-((4,4-dimethylcyclohexyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-((2-methoxy-2-methylpropyl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-((3,3-dimethylbutyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-(((S)-2-fluoro-2-phenylethyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((3-cyclopropylpropyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((2-cyclopropylethyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-(((1S,2S)-2-(2,2,2-trifluoroethyl)cyclohexyl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-((3-fluoropropyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((2,5-dimethylbenzyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-(((tetrahydro-2H-pyran-4-yl)methyl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-((3-hydroxy-2,2-dimethylpropyl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-((3-methylbenzyl)carbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-(cyclopentylcarbamoyl)bicyclo[2.2.1]heptan-2-yl)carbamoyl)-4-methoxyphenoxy)-1-methylcyclohexane-1-carboxylic acid;

(1S,4s)-4-(2-cyano-4-methoxy-5-(((1S,2R,3S,4R)-3-(((R)-1-phenylethyl)carbamoyl)bicyclo[2.2.1]heptan-2-yl)carbamoyl)phenoxy)-1-methylcyclohexane-1-carboxylic acid;

(1S,4s)-4-(2-cyano-4-methoxy-5-(((1S,2R,3S,4R)-3-(((S)-1-phenylethyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-(bicyclo[1.1.1]pentan-1-ylcarbamoyl)bicyclo[2.2.1]heptan-2-yl)carbamoyl)-2-cyano-4-methoxyphenoxy)-1-methylcyclohexane-1-carboxylic acid;

(1s,4s)-4-(2-fluoro-4-methoxy-5-((2-(neopentylcarbamoyl)phenyl)carbamoyl)phenoxy)-1-methylcyclohexane-1-carboxylic acid;

(1s,4s)-4-(2-fluoro-4-methoxy-5-((2-(((1-methylcyclobutyl)methyl)carbamoyl)phenyl)carbamoyl)phenoxy)-1-methylcyclohexane-1-carboxylic acid;

(1S,4s)-4-(5-(((1S,2R,3S,4R)-3-(((R)-3-ethylpentan-2-yl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(5-(((1S,2R,3S,4R)-3-(((S)-3-ethylpentan-2-yl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-fluoro-5-(((1S,2R,3S,4R)-3-(((4-fluorotetrahydro-2H-pyran-4-yl)methyl)carbamoyl)bicyclo[2.2.1]heptan-2-yl)carbamoyl)-4-methoxyphenoxy)-1-methylcyclohexane-1-carboxylic acid;

(1R,2S,3R,4S)-3-(5-(((1s,4S)-4-carbamoyl-4-methylcyclohexyl)oxy)-4-fluoro-2-methoxybenzamido)-N-((4-fluorotetrahydro-2H-pyran-4-yl)methyl)bicyclo[2.2.1]heptane-2-carboxamide;

(1S,3s)-3-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclobutane-1-carboxylic acid;

(1S,3s)-3-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclobutane-1-carboxylic acid;

(1s,4s)-4-(2-fluoro-4-methoxy-5-((4-(((1-methylcyclobutyl)methyl)carbamoyl)pyridin-3-yl)carbamoyl)phenoxy)-1-methylcyclohexane-1-carboxylic acid;

(1R,4s)-4-(2-fluoro-4-methoxy-5-(((1S,2R)-2-(((1-methylcyclobutyl)methyl)carbamoyl)cyclooctyl)carbamoyl)phenoxy)-1-methylcyclohexane-1-carboxylic acid;

(1R,4s)-4-(2-fluoro-4-methoxy-5-(((1R,2S)-2-(((1-methylcyclobutyl)methyl)carbamoyl)cyclooctyl)carbamoyl)phenoxy)-1-methylcyclohexane-1-carboxylic acid;

(1s,4s)-4-(2-fluoro-4-methoxy-5-((3-methyl-5-(((1-methyl-cyclobutyl)methyl)carbamoyl)isothiazol-4-yl)carbamoyl)phenoxy)-1-methylcyclohexane-1-carboxylic acid;

(1s,4s)-4-(5-((4-chloro-2-(((1-methylcyclobutyl)methyl)carbamoyl)phenyl)carbamoyl)-2-fluoro-4-methoxyphenoxy)-1-methylcyclohexane-1-carboxylic acid;

(1s,4s)-4-(2-fluoro-4-methoxy-5-((2-(((1-methylcyclobutyl)methyl)carbamoyl)thiophen-3-yl)carbamoyl)phenoxy)-1-methylcyclohexane-1-carboxylic acid;

(1s,4s)-4-(5-((5-chloro-2-(((1-methylcyclobutyl)methyl)carbamoyl)phenyl)carbamoyl)-2-fluoro-4-methoxyphenoxy)-1-methylcyclohexane-1-carboxylic acid;

(1s,4s)-4-(2-fluoro-4-methoxy-5-((2-methyl-6-(((1-methylcyclobutyl)methyl)carbamoyl)phenyl)carbamoyl)phenoxy)-1-methylcyclohexane-1-carboxylic acid;

(1s,4s)-4-(5-((5-chloro-2-((cycloheptylmethyl)carbamoyl)phenyl)carbamoyl)-2-cyano-4-methoxyphenoxy)-1-methylcyclohexane-1-carboxylic acid;

(1s,4s)-4-(5-((5-chloro-2-(((1-phenylcyclopropyl)methyl)carbamoyl)phenyl)carbamoyl)-2-cyano-4-methoxyphenoxy)-1-methylcyclohexane-1-carboxylic acid;

(1s,4s)-4-(5-((5-chloro-2-((((1s,3s)-3-methylcyclobutyl)methyl)carbamoyl)phenyl)carbamoyl)-2-cyano-4-methoxyphenoxy)-1-methylcyclohexane-1-carboxylic acid;

(1s,4s)-4-(5-((5-chloro-2-(((1-fluorocyclobutyl)methyl)carbamoyl)phenyl)carbamoyl)-2-cyano-4-methoxyphenoxy)-1-methylcyclohexane-1-carboxylic acid;

(1s,4s)-4-(5-((2-(bicyclo[1.1.1]pentan-1-ylcarbamoyl)-5-chlorophenyl)carbamoyl)-2-cyano-4-methoxyphenoxy)-1-methylcyclohexane-1-carboxylic acid;

(1S,4s)-4-(5-((5-chloro-2-(((R)-3-fluoro-3-methylbutan-2-yl)carbamoyl)phenyl)carbamoyl)-2-cyano-4-methoxyphenoxy)-1-methylcyclohexane-1-carboxylic acid;

(1s,4s)-4-(5-((5-chloro-2-(tert-pentylcarbamoyl)phenyl)carbamoyl)-2-cyano-4-methoxyphenoxy)-1-methylcyclohexane-1-carboxylic acid;

(1s,4s)-4-(5-((5-chloro-2-((2-fluoro-2-methylpropyl)carbamoyl)phenyl)carbamoyl)-2-cyano-4-methoxyphenoxy)-1-methylcyclohexane-1-carboxylic acid;

(1s,4s)-4-(5-((5-chloro-2-((2-cyclopropylpropan-2-yl)carbamoyl)phenyl)carbamoyl)-2-cyano-4-methoxyphenoxy)-1-methylcyclohexane-1-carboxylic acid;

(1s,4s)-4-(2-cyano-5-((2-((3-fluorobenzyl)carbamoyl)-5-methylphenyl)carbamoyl)-4-methoxyphenoxy)-1-methylcyclohexane-1-carboxylic acid;

(1s,4s)-4-(2-cyano-5-((2-((2-ethylbutyl)carbamoyl)-5-methylphenyl)carbamoyl)-4-methoxyphenoxy)-1-methylcyclohexane-1-carboxylic acid;

(1s,4s)-4-(2-cyano-4-methoxy-5-((5-methyl-2-(pentan-3-ylcarbamoyl)phenyl)carbamoyl)phenoxy)-1-methylcyclohexane-1-carboxylic acid;

(1s,4s)-4-(2-cyano-4-methoxy-5-((5-methyl-2-(((1r,4r)-4-methylcyclohexyl)carbamoyl)phenyl)carbamoyl)phenoxy)-1-methylcyclohexane-1-carboxylic acid;

(1S,4s)-4-(2-cyano-4-methoxy-5-((5-methyl-2-(((R)-3-methylbutan-2-yl)carbamoyl)phenyl)carbamoyl)phenoxy)-1-methylcyclohexane-1-carboxylic acid;

(1s,4s)-4-(2-cyano-4-methoxy-5-((5-methyl-2-(((1s,3s)-3-methylcyclobutyl)carbamoyl)phenyl)carbamoyl)phenoxy)-1-methylcyclohexane-1-carboxylic acid;

(1s,4s)-4-(2-cyano-5-((2-(((1-fluorocyclobutyl)methyl)carbamoyl)-5-methylphenyl)carbamoyl)-4-methoxyphenoxy)-1-methylcyclohexane-1-carboxylic acid;

(1s,4s)-4-(5-((2-(bicyclo[1.1.1]pentan-1-ylcarbamoyl)-5-methylphenyl)carbamoyl)-2-cyano-4-methoxyphenoxy)-1-methylcyclohexane-1-carboxylic acid;

(1s,4s)-4-(2-cyano-4-methoxy-5-((5-methyl-2-(((1-methylcyclopropyl)methyl)carbamoyl)phenyl)carbamoyl)phenoxy)-1-methylcyclohexane-1-carboxylic acid;

(1S,4s)-4-(2-fluoro-4-methoxy-5-(((1S,2R,3S,4R)-3-((4,4,4-trifluorobutyl)carbamoyl)bicyclo[2.2.1]heptan-2-yl)carbamoyl)phenoxy)cyclohexane-1-carboxylic acid;

(1S,4s)-4-(5-(((1S,2R,3S,4R)-3-((2-cyclopropylethyl)carbamoyl)bicyclo[2.2.1]heptan-2-yl)carbamoyl)-2-fluoro-4-methoxyphenoxy)cyclohexane-1-carboxylic acid;

(1S,4s)-4-(5-(((1S,2R,3S,4R)-3-(cyclobutylcarbamoyl)bicyclo[2.2.1]heptan-2-yl)carbamoyl)-2-fluoro-4-methoxyphenoxy)cyclohexane-1-carboxylic acid;

(1S,4s)-4-(5-(((1S,2R,3S,4R)-3-(bicyclo[1.1.1]pentan-1-ylcarbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-5-(((1S,2R,3S,4R)-3-((4-fluoro-3-(trifluoromethyl)phenyl)carbamoyl)bicyclo[2.2.1]heptan-2-yl)carbamoyl)-4-methoxyphenoxy)cyclohexane-1-carboxylic acid;

(1S,4s)-4-(2-fluoro-4-methoxy-5-(((1S,2R,3S,4R)-3-(neopentylcarbamoyl)bicyclo[2.2.1]heptan-2-yl)carbamoyl)phenoxy)cyclohexane-1-carboxylic acid;

(1S,4s)-4-(5-(((1S,2R,3S,4R)-3-((4-(difluoromethyl)phenyl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-4-methoxy-5-(((1S,2R,3S,4R)-3-((3-(pentafluoro-λ6-sulfaneyl)phenyl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-((4-(pentafluoro-λ6-sulfaneyl)phenyl)carbamoyl)bicyclo[2.2.1]heptan-2-yl)carbamoyl)phenoxy)cyclohexane-1-carboxylic acid;

(1S,4s)-4-(5-(((1S,2R,3S,4R)-3-((2,6-difluorophenyl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-5-(((1S,2R,3S,4R)-3-((3-iodophenyl)carbamoyl)bicyclo[2.2.1]heptan-2-yl)carbamoyl)-4-methoxyphenoxy)cyclohexane-1-carboxylic acid;

(1S,4s)-4-(5-(((1S,2R,3S,4R)-3-((4-chloro-3-(trifluoromethyl)phenyl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-4-methoxy-5-(((1S,2R,3S,4R)-3-((3,4,5-trifluorophenyl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-((3-methyl-5-(trifluoromethyl)phenyl)carbamoyl)bicyclo[2.2.1]heptan-2-yl)carbamoyl)phenoxy)cyclohexane-1-carboxylic acid;

(1S,4s)-4-(5-(((1S,2R,3S,4R)-3-((3-(tert-butyl)phenyl)carbamoyl)bicyclo[2.2.1]heptan-2-yl)carbamoyl)-2-fluoro-4-methoxyphenoxy)cyclohexane-1-carboxylic acid;

(1S,4s)-4-(5-(((1S,2R,3S,4R)-3-((3-cyclopropylphenyl)carbamoyl)bicyclo[2.2.1]heptan-2-yl)carbamoyl)-2-fluoro-4-methoxyphenoxy)cyclohexane-1-carboxylic acid;

(1S,4s)-4-(5-(((1S,2R,3S,4R)-3-((3-cyano-5-(trifluoromethyl)phenyl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-4-methoxy-5-(((1S,2R,3S,4R)-3-((4-methyl-3-(trifluoromethyl)phenyl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-((3-(trifluoromethyl)phenyl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-((3-methoxy-5-(trifluoromethyl)phenyl)carbamoyl)bicyclo[2.2.1]heptan-2-yl)carbamoyl)phenoxy)cyclohexane-1-carboxylic acid;

(1S,4s)-4-(5-(((1S,2R,3S,4R)-3-((3-(difluoromethoxy)phenyl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-5-(((1S,2R,3S,4R)-3-((3-isopropylphenyl)carbamoyl)bicyclo[2.2.1]heptan-2-yl)carbamoyl)-4-methoxyphenoxy)cyclohexane-1-carboxylic acid;

(1S,4s)-4-(5-(((1S,2R,3S,4R)-3-((2-ethylbutyl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-4-methoxy-5-(((1S,2R,3S,4R)-3-(((1-methylcyclopropyl)methyl)carbamoyl)bicyclo[2.2.1]heptan-2-yl)carbamoyl)phenoxy)cyclohexane-1-carboxylic acid;

(1S,4s)-4-(5-(((1S,2R,3S,4R)-3-(((S)-3,3-dimethylbutan-2-yl)carbamoyl)bicyclo[2.2.1]heptan-2-yl)carbamoyl)-2-fluoro-4-methoxyphenoxy)cyclohexane-1-carboxylic acid;

(1S,4s)-4-(5-(((1S,2R,3S,4R)-3-(((R)-3,3-dimethylbutan-2-yl)carbamoyl)bicyclo[2.2.1]heptan-2-yl)carbamoyl)-2-fluoro-4-methoxyphenoxy)cyclohexane-1-carboxylic acid;

(1S,4s)-4-(2-fluoro-4-methoxy-5-(((1S,2R,3S,4R)-3-(phenylcarbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-(((R)-2-methylbutyl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-(((S)-2-methylbutyl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)benzyl)-1-methylcyclohexane-1-carboxylic acid;

(1R,4r)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)benzyl)-1-methylcyclohexane-1-carboxylic acid;

(1S,4s)-4-(2-fluoro-4-methoxy-5-(((1S,2R,3R,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1R,4s)-4-(2-fluoro-5-(((1R,2S,3R,4S)-3-((4-fluoro-3-(pentafluoro-λ6-sulfaneyl)phenyl)carbamoyl)bicyclo[2.2.1]heptan-2-yl)carbamoyl)-4-methoxyphenoxy)-1-methylcyclohexane-1-carboxylic acid;

(1S,4s)-4-(4-(difluoromethoxy)-2-fluoro-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)-1-methylcyclohexane-1-carboxylic acid;

2'-fluoro-4'-methoxy-5'-(((1S,2R,3S,4R)-3-((3-(pentafluoro-λ6-sulfaneyl)phenyl)carbamoyl)bicyclo[2.2.1]heptan-2-yl)carbamoyl)-[1,1'-biphenyl]-4-carboxylic acid;

2'-fluoro-4'-methoxy-5'-(((1S,2R,3S,4R)-3-((4-(pentafluoro-λ6-sulfaneyl)phenyl)carbamoyl)bicyclo[2.2.1]heptan-2-yl)carbamoyl)-[1,1'-biphenyl]-4-carboxylic acid;

(1s,4s)-4-(5-((2,4-dimethyl-6-(((1-methylcyclobutyl)methyl)carbamoyl)phenyl)carbamoyl)-2-fluoro-4-methoxyphenoxy)-1-methylcyclohexane-1-carboxylic acid;

(1s,4s)-4-(5-((4,5-dimethyl-2-(((1-methylcyclobutyl)methyl)carbamoyl)phenyl)carbamoyl)-2-fluoro-4-methoxyphenoxy)-1-methylcyclohexane-1-carboxylic acid;

(1s,4s)-4-(2-fluoro-5-((2-((4-fluoro-3-(trifluoromethyl)phenyl)carbamoyl)cyclohex-1-en-1-yl)carbamoyl)-4-methoxyphenoxy)cyclohexane-1-carboxylic acid;

(1s,4s)-4-(2-fluoro-5-((2-((4-fluoro-3-(trifluoromethyl)phenyl)carbamoyl)cyclopent-1-en-1-yl)carbamoyl)-4-methoxyphenoxy)cyclohexane-1-carboxylic acid;

(1s,4s)-4-(2-fluoro-4-methoxy-5-((3-(((1-methylcyclobutyl)methyl)carbamoyl)naphthalen-2-yl)carbamoyl)phenoxy)-1-methylcyclohexane-1-carboxylic acid;

(1s,4s)-4-(2-fluoro-4-methoxy-5-((4-methyl-2-(((1-methylcyclobutyl)methyl)carbamoyl)phenyl)carbamoyl)phenoxy)-1-methylcyclohexane-1-carboxylic acid;

(1s,4s)-4-(2-fluoro-4-methoxy-5-((3-(((1-methylcyclobutyl)methyl)carbamoyl)pyrazolo[1,5-a]pyrimidin-2-yl)carbamoyl)phenoxy)-1-methylcyclohexane-1-carboxylic acid;

3-(4-methoxy-3-((((1R,2R,3S,4S)-3-((3-((trifluoromethyl)sulfonyl)phenyl)carbamoyl)bicyclo[2.2.1]hept-5-en-2-yl)carbamoyl)phenyl)propanoic acid;

3-(4-methoxy-3-((((1S,2S,3R,4R)-3-((3-((trifluoromethyl)sulfonyl)phenyl)carbamoyl)bicyclo[2.2.1]hept-5-en-2-yl)carbamoyl)phenyl)propanoic acid;

(1R,2S,3R,4S)-3-(5-((1H-pyrazol-4-yl)methyl)-4-fluoro-2-methoxybenzamido)-N-(3-((trifluoromethyl)sulfonyl)phenyl)bicyclo[2.2.1]heptane-2-carboxamide;

2-(4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)benzyl)-1H-pyrazol-1-yl)acetic acid;

1-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)benzyl)-1H-pyrazole-5-carboxylic acid;

1-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)benzyl)-1H-pyrazole-3-carboxylic acid;

2-(4-methoxy-3-((((1R,2R,3S,4S)-3-((3-((trifluoromethyl)sulfonyl)phenyl)carbamoyl)bicyclo[2.2.1]hept-5-en-2-yl)carbamoyl)benzyl)benzoic acid;

2-(4-methoxy-3-((((1S,2S,3R,4R)-3-((3-((trifluoromethyl)sulfonyl)phenyl)carbamoyl)bicyclo[2.2.1]hept-5-en-2-yl)carbamoyl)benzyl)benzoic acid;

2'-fluoro-3,4'-dimethoxy-5'-((((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

2'-fluoro-3,4'-dimethoxy-5'-((((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

2,2'-difluoro-4'-methoxy-5'-((((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

2,2'-difluoro-4'-methoxy-5'-((((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

5-(2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenyl)nicotinic acid;

5-(2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenyl)nicotinic acid;

4-(2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenyl)-1H-pyrrole-2-carboxylic acid;

4-(2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenyl)-1H-pyrrole-2-carboxylic acid;

2'-fluoro-4,4'-dimethoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid;

2'-fluoro-4,4'-dimethoxy-5'-(((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid;

2',4-difluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid;

2',4-difluoro-4'-methoxy-5'-(((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid;

2',3-difluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

2',3-difluoro-4'-methoxy-5'-(((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

2,2'-difluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid;

2,2'-difluoro-4'-methoxy-5'-(((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid;

2-(2'-fluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-yl)acetic acid;

2-(2'-fluoro-4'-methoxy-5'-(((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-4-yl)acetic acid;

2-(2'-fluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-2-yl)acetic acid;

2-(2'-fluoro-4'-methoxy-5'-(((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-2-yl)acetic acid;

2',3-difluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-carboxylic acid;

3-(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyrimidin-2-yl)propanoic acid;

3-(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyrazin-2-yl)propanoic acid;

3-(dimethylamino)-2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-carboxylic acid;

4-((2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)oxy)butanoic acid;

2'-fluoro-4'-methoxy-3,5-dimethyl-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-carboxylic acid;

2-((S)-6-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)-2,3-dihydrobenzofuran-3-yl)acetic acid;

2-((R)-6-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)-2,3-dihydrobenzofuran-3-yl)acetic acid;

(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyrimidin-2-yl)glycine;

2-((5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)oxy)acetic acid;

3-(6-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-3-yl)propanoic acid;

2-((2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)oxy)-2-methylpropanoic acid;

2-((2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)oxy)acetic acid;

3-(2-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)thiazol-5-yl)propanoic acid;

3-(2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoic acid;

3-(6-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridazin-3-yl)propanoic acid;

2'-fluoro-4'-methoxy-3-methyl-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-carboxylic acid;

2'-fluoro-3-hydroxy-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-carboxylic acid;

3-(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)propanoic acid;

3-(2'-fluoro-3,4'-dimethoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoic acid;

(E)-3-(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)acrylic acid;

(1R,2R)-2-(5-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)cyclopropane-1-carboxylic acid;

(1S,2S)-2-(5-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)cyclopropane-1-carboxylic acid;

(1R,2R)-2-(5-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)pyrazin-2-yl)cyclopropane-1-carboxylic acid;

(1S,2S)-2-(5-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)pyrazin-2-yl)cyclopropane-1-carboxylic acid;

(1R,2S,3R,4S)-3-(6-fluoro-4-methoxy-4'-sulfamoyl-[1,1'-biphenyl]-3-carboxamido)-N-(3-((trifluoromethyl)sulfonyl)phenyl)bicyclo[2.2.1]heptane-2-carboxamide;

(1R,2S,3R,4S)-3-(4'-(2-amino-1,3-dihydroxypropan-2-yl)-6-fluoro-4-methoxy-[1,1'-biphenyl]-3-carboxamido)-N-(3-((trifluoromethyl)sulfonyl)phenyl)bicyclo[2.2.1]heptane-2-carboxamide;

(1R,2S,3R,4S)-3-(4'-(3-amino-4-hydroxy-3-(hydroxymethyl)butyl)-3',6-difluoro-4-methoxy-[1,1'-biphenyl]-3-carboxamido)-N-(3-((trifluoromethyl)sulfonyl)phenyl)bicyclo[2.2.1]heptane-2-carboxamide;

3-(4-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)-2-oxopyridin-1(2H)-yl)propanoic acid;

2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-carboxylic acid;

3-(4-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)-1H-pyrazol-1-yl)propanoic acid;

(R)-2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-2,3,4,5-tetrahydro-[1,1'-biphenyl]-4-carboxylic acid;

(S)-2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-2,3,4,5-tetrahydro-[1,1'-biphenyl]-4-carboxylic acid;

(1S,4s)-4-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)cyclohexane-1-carboxylic acid;

(1R,4r)-4-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)cyclohexane-1-carboxylic acid;

6-fluoro-4-methoxy-N3-((1R,2R,3S,4S)-3-((3-((trifluoromethyl)sulfonyl)phenyl)carbamoyl)bicyclo[2.2.1]hept-5-en-2-yl)-[1,1'-biphenyl]-3,4'-dicarboxamide;

2-(4-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)-1H-pyrazol-1-yl)acetic acid;

4-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)picolinic acid;

4-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)picolinic acid;

2'-fluoro-4'-methoxy-5'-((((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-2-carboxylic acid;

2'-fluoro-4'-methoxy-5'-((((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-2-carboxylic acid;

5-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)picolinic acid;

5-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)picolinic acid;

2-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)oxazole-4-carboxylic acid;

2-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)oxazole-4-carboxylic acid;

5-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)pyrazine-2-carboxylic acid;

5-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)pyrazine-2-carboxylic acid;

2-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)isonicotinic acid;

2-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)isonicotinic acid;

6-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)nicotinic acid;

6-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)nicotinic acid;

6-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)picolinic acid;

6-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)picolinic acid;

5-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)pyrimidine-2-carboxylic acid;

5-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)pyrimidine-2-carboxylic acid;

2-(2'-fluoro-4'-methoxy-5'-((((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-3-yl)acetic acid;

2-(2'-fluoro-4'-methoxy-5'-((((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-3-yl)acetic acid;

3-(2'-fluoro-4'-methoxy-5'-((((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-3-yl)propanoic acid;

3-(2'-fluoro-4'-methoxy-5'-((((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-3-yl)propanoic acid;

3-(2'-fluoro-4'-methoxy-5'-((((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-yl)propanoic acid;

3-(2'-fluoro-4'-methoxy-5'-((((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-4-yl)propanoic acid;

5-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)thiophene-3-carboxylic acid;

5-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)thiophene-3-carboxylic acid;

5-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)thiophene-2-carboxylic acid;

5-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)thiophene-2-carboxylic acid;

2-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)thiazole-4-carboxylic acid;

2-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)thiazole-4-carboxylic acid;

2-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)thiazole-5-carboxylic acid;

2-(2-fluoro-4-methoxy-5-((((1S,2S,3R,4R)-3-((3-((trifluoromethyl)sulfonyl)phenyl)carbamoyl)bicyclo[2.2.1]hept-5-en-2-yl)carbamoyl)phenyl)thiazole-5-carboxylic acid;

1-(2'-fluoro-4'-methoxy-5'-((((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-yl)cyclopropane-1-carboxylic acid;

1-(2'-fluoro-4'-methoxy-5'-((((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-4-yl)cyclopropane-1-carboxylic acid;

(S)-2-(dimethylamino)-3-(2'-fluoro-4'-methoxy-5'-((((1R,2S,3R,4S)-3-((3-((trifluoromethyl)sulfonyl)phenyl)carbamoyl)bicyclo[2.2.1]heptan-2-yl)carbamoyl)-[1,1'-biphenyl]-4-yl)propanoic acid;

(S)-2-(dimethylamino)-3-(2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoic acid;

(R)-2-(dimethylamino)-3-(2'-fluoro-4'-methoxy-5'-((((1R,2S,3R,4S)-3-((3-((trifluoromethyl)sulfonyl)phenyl)carbamoyl)bicyclo[2.2.1]heptan-2-yl)carbamoyl)-[1,1'-biphenyl]-4-yl)propanoic acid;

(R)-2-amino-3-(2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoic acid;

(R)-2-(dimethylamino)-3-(2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoic acid;

(R)-2-(dimethylamino)-3-(2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-3-yl)propanoic acid;

(S)-2-(dimethylamino)-3-(2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-3-yl)propanoic acid;

(R)-2-(dimethylamino)-2-(2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-3-yl)acetic acid;

(S)-2-(dimethylamino)-2-(2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-3-yl)acetic acid;

(R)-2-(dimethylamino)-2-(2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)acetic acid;

(S)-2-(dimethylamino)-2-(2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)acetic acid;

2'-fluoro-5'-((((1R,2R,3S,4S)-3-((4-fluoro-3-((trifluoromethyl)sulfonyl)phenyl)carbamoyl)bicyclo[2.2.1]hept-5-en-2-yl)carbamoyl)-4'-methoxy-[1,1'-biphenyl]-4-carboxylic acid;

2'-fluoro-5'-((((1S,2S,3R,4R)-3-((4-fluoro-3-((trifluoromethyl)sulfonyl)phenyl)carbamoyl)bicyclo[2.2.1]hept-5-en-2-yl)carbamoyl)-4'-methoxy-[1,1'-biphenyl]-4-carboxylic acid;

2'-fluoro-5'-((((1R,2R,3S,4S)-3-((4-fluoro-3-((trifluoromethyl)sulfonyl)phenyl)carbamoyl)bicyclo[2.2.1]hept-5-en-2-yl)carbamoyl)-4'-methoxy-[1,1'-biphenyl]-3-carboxylic acid;

2'-fluoro-5'-((((1S,2S,3R,4R)-3-((4-fluoro-3-((trifluoromethyl)sulfonyl)phenyl)carbamoyl)bicyclo[2.2.1]hept-5-en-2-yl)carbamoyl)-4'-methoxy-[1,1'-biphenyl]-3-carboxylic acid;

2'-fluoro-5'-((((1R,2R,3S,4S)-3-((3-fluoro-5-(pentafluoro-λ6-sulfaneyl)phenyl)carbamoyl)bicyclo[2.2.1]hept-5-en-2-yl)carbamoyl)-4'-methoxy-[1,1'-biphenyl]-4-carboxylic acid;

2'-fluoro-5'-((((1S,2S,3R,4R)-3-((3-fluoro-5-(pentafluoro-λ6-sulfaneyl)phenyl)carbamoyl)bicyclo[2.2.1]hept-5-en-2-yl)carbamoyl)-4'-methoxy-[1,1'-biphenyl]-4-carboxylic acid;

2'-fluoro-4'-methoxy-5'-((((1R,2S)-2-((3-((trifluoromethyl)sulfonyl)phenyl)carbamoyl)cyclopentyl)carbamoyl)-[1,1'-biphenyl]-4-carboxylic acid;

2'-fluoro-4'-methoxy-5'-((((1S,2R)-2-((3-((trifluoromethyl)sulfonyl)phenyl)carbamoyl)cyclopentyl)carbamoyl)-[1,1'-biphenyl]-4-carboxylic acid;

2'-fluoro-4'-methoxy-5'-((((1R,2S)-2-((3-((trifluoromethyl)sulfonyl)phenyl)carbamoyl)cyclopentyl)carbamoyl)-[1,1'-biphenyl]-3-carboxylic acid;

2'-fluoro-4'-methoxy-5'-((((1S,2R)-2-((3-((trifluoromethyl)sulfonyl)phenyl)carbamoyl)cyclopentyl)carbamoyl)-[1,1'-biphenyl]-3-carboxylic acid;

2'-fluoro-4'-methoxy-5'-((((1R,2S)-2-((3-((trifluoromethyl)sulfonyl)phenyl)carbamoyl)cyclobutyl)carbamoyl)-[1,1'-biphenyl]-4-carboxylic acid;

2'-fluoro-4'-methoxy-5'-((((1S,2R)-2-((3-((trifluoromethyl)sulfonyl)phenyl)carbamoyl)cyclobutyl)carbamoyl)-[1,1'-biphenyl]-4-carboxylic acid;

2'-fluoro-4'-methoxy-5'-((((1R,2S)-2-((3-((trifluoromethyl)sulfonyl)phenyl)carbamoyl)cyclobutyl)carbamoyl)-[1,1'-biphenyl]-3-carboxylic acid;

2'-fluoro-4'-methoxy-5'-(((1S,2R)-2-((3-((trifluoromethyl)sulfonyl)phenyl)carbamoyl)cyclobutyl)carbamoyl)-[1,1'-biphenyl]-3-carboxylic acid;

2'-fluoro-4'-methoxy-5'-(((1R,2R,3S,4S)-3-((3-((trifluoromethyl)sulfonyl)phenyl)carbamoyl)bicyclo[2.2.1]heptan-2-yl)carbamoyl)-[1,1'-biphenyl]-4-carboxylic acid;

2'-fluoro-4'-methoxy-5'-(((1S,2S,3R,4R)-3-((3-((trifluoromethyl)sulfonyl)phenyl)carbamoyl)bicyclo[2.2.1]heptan-2-yl)carbamoyl)-[1,1'-biphenyl]-4-carboxylic acid;

2'-fluoro-4'-methoxy-5'-(((1S,2R,3S,4R)-3-(neopentylcarbamoyl)bicyclo[2.2.1]heptan-2-yl)carbamoyl)-[1,1'-biphenyl]-4-carboxylic acid;

2'-fluoro-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

2'-fluoro-5'-(((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

2',4'-difluoro-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

2',4'-difluoro-5'-(((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

2'-fluoro-5'-(((1R,2R,3S,4S)-3-((4-fluoro-3-(trifluoromethyl)phenyl)carbamoyl)bicyclo[2.2.1]hept-5-en-2-yl)carbamoyl)-4'-methoxy-[1,1'-biphenyl]-4-carboxylic acid;

2'-fluoro-5'-(((1S,2S,3R,4R)-3-((4-fluoro-3-(trifluoromethyl)phenyl)carbamoyl)bicyclo[2.2.1]hept-5-en-2-yl)carbamoyl)-4'-methoxy-[1,1'-biphenyl]-4-carboxylic acid;

2'-fluoro-5'-(((1R,2R,3S,4S)-3-((3-fluoro-5-(trifluoromethyl)phenyl)carbamoyl)bicyclo[2.2.1]hept-5-en-2-yl)carbamoyl)-4'-methoxy-[1,1'-biphenyl]-4-carboxylic acid;

2'-fluoro-5'-(((1S,2S,3R,4R)-3-((3-fluoro-5-(trifluoromethyl)phenyl)carbamoyl)bicyclo[2.2.1]hept-5-en-2-yl)carbamoyl)-4'-methoxy-[1,1'-biphenyl]-4-carboxylic acid;

5'-(((1R,2R,3S,4S)-3-((3-cyano-4-fluorophenyl)carbamoyl)bicyclo[2.2.1]hept-5-en-2-yl)carbamoyl)-2'-fluoro-4'-methoxy-[1,1'-biphenyl]-4-carboxylic acid;

5'-(((1S,2S,3R,4R)-3-((3-cyano-4-fluorophenyl)carbamoyl)bicyclo[2.2.1]hept-5-en-2-yl)carbamoyl)-2'-fluoro-4'-methoxy-[1,1'-biphenyl]-4-carboxylic acid;

5'-(((1R,2R,3S,4S)-3-((3-cyano-5-fluorophenyl)carbamoyl)bicyclo[2.2.1]hept-5-en-2-yl)carbamoyl)-2'-fluoro-4'-methoxy-[1,1'-biphenyl]-4-carboxylic acid;

5'-(((1S,2S,3R,4R)-3-((3-cyano-5-fluorophenyl)carbamoyl)bicyclo[2.2.1]hept-5-en-2-yl)carbamoyl)-2'-fluoro-4'-methoxy-[1,1'-biphenyl]-4-carboxylic acid;

2'-fluoro-4'-methoxy-5'-(((1R,2R,3S,4S)-3-(((S)-1-((trifluoromethyl)sulfonyl)piperidin-3-yl)carbamoyl)bicyclo[2.2.1]hept-5-en-2-yl)carbamoyl)-[1,1'-biphenyl]-4-carboxylic acid;

2'-fluoro-4'-methoxy-5'-(((1S,2S,3R,4R)-3-(((S)-1-((trifluoromethyl)sulfonyl)piperidin-3-yl)carbamoyl)bicyclo[2.2.1]hept-5-en-2-yl)carbamoyl)-[1,1'-biphenyl]-4-carboxylic acid;

2'-fluoro-4'-methoxy-5'-(((1R,2S,3R,4S)-3-(((S)-1-((trifluoromethyl)sulfonyl)piperidin-3-yl)carbamoyl)bicyclo[2.2.1]heptan-2-yl)carbamoyl)-[1,1'-biphenyl]-4-carboxylic acid;

2'-fluoro-4'-methoxy-5'-(((1S,2R,3S,4R)-3-(((S)-1-((trifluoromethyl)sulfonyl)piperidin-3-yl)carbamoyl)bicyclo[2.2.1]heptan-2-yl)carbamoyl)-[1,1'-biphenyl]-4-carboxylic acid;

2'-fluoro-4'-methoxy-5'-(((1R,2R,3S,4S)-3-(((R)-1-((trifluoromethyl)sulfonyl)piperidin-3-yl)carbamoyl)bicyclo[2.2.1]hept-5-en-2-yl)carbamoyl)-[1,1'-biphenyl]-4-carboxylic acid;

2'-fluoro-4'-methoxy-5'-(((1S,2S,3R,4R)-3-(((R)-1-((trifluoromethyl)sulfonyl)piperidin-3-yl)carbamoyl)bicyclo[2.2.1]hept-5-en-2-yl)carbamoyl)-[1,1'-biphenyl]-4-carboxylic acid;

2-(2'-fluoro-4'-methoxy-5'-(((1R,2S)-2-((3-((trifluoromethyl)sulfonyl)phenyl)carbamoyl)cyclopentyl)carbamoyl)-[1,1'-biphenyl]-3-yl)acetic acid;

3-(2'-fluoro-4'-methoxy-5'-(((1R,2S)-2-((3-((trifluoromethyl)sulfonyl)phenyl)carbamoyl)cyclopentyl)carbamoyl)-[1,1'-biphenyl]-3-yl)propanoic acid;

2-(2'-fluoro-4'-methoxy-5'-(((1R,2S)-2-((3-((trifluoromethyl)sulfonyl)phenyl)carbamoyl)cyclopentyl)carbamoyl)-[1,1'-biphenyl]-4-yl)acetic acid;

3-(2'-fluoro-4'-methoxy-5'-(((1R,2S)-2-((3-((trifluoromethyl)sulfonyl)phenyl)carbamoyl)cyclopentyl)carbamoyl)-[1,1'-biphenyl]-4-yl)propanoic acid;

3-(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)-1,3,4-thiadiazol-2-yl)propanoic acid;

3-(2-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyrimidin-5-yl)propanoic acid;

3-(5-(2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenyl)pyrazin-2-yl)propanoic acid;

3-(5-(2-fluoro-4-methoxy-5-(((1S,2S,3R,4R)-3-((3-((trifluoromethyl)sulfonyl)phenyl)carbamoyl)bicyclo[2.2.1]heptan-2-yl)carbamoyl)phenyl)pyrazin-2-yl)propanoic acid;

(1R,2S,3R,4S)-3-(6-fluoro-4-methoxy-4'-(1H-tetrazol-5-yl)-[1,1'-biphenyl]-3-carboxamido)-N-(3-((trifluoromethyl)sulfonyl)phenyl)bicyclo[2.2.1]heptane-2-carboxamide;

(1R,2R,3S,4S)-3-(6-fluoro-4-methoxy-4'-(2-sulfamoylethyl)-[1,1'-biphenyl]-3-carboxamido)-N-(3-((trifluoromethyl)sulfonyl)phenyl)bicyclo[2.2.1]heptane-2-carboxamide;

(1S,2S,3R,4R)-3-(6-fluoro-4-methoxy-4'-(2-sulfamoylethyl)-[1,1'-biphenyl]-3-carboxamido)-N-(3-((trifluoromethyl)sulfonyl)phenyl)bicyclo[2.2.1]heptane-2-carboxamide;

2'-fluoro-4'-methoxy-5'-((2-((3-((trifluoromethyl)sulfonyl)phenyl)carbamoyl)phenyl)carbamoyl)-[1,1'-biphenyl]-4-carboxylic acid;

2-((2'-cyano-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)oxy)acetic acid;

2-((2'-fluoro-4'-methoxy-5'-(((1S,2R,3S,4R)-3-(neopentylcarbamoyl)bicyclo[2.2.1]heptan-2-yl)carbamoyl)-[1,1'-biphenyl]-4-yl)oxy)acetic acid;

(1R,4s)-4-(5-(((1R,2R,3S,4S)-7-(tert-butoxycarbonyl)-3-(((1-methylcyclobutyl)methyl)carbamoyl)-7-azabicyclo[2.2.1]heptan-2-yl)-2-cyano-4-methoxyphenoxy)-1-methylcyclohexane-1-carboxylic acid;

(1R,4s)-4-(5-(((1S,2S,3R,4R)-7-(tert-butoxycarbonyl)-3-(((1-methylcyclobutyl)methyl)carbamoyl)-7-azabicyclo

[2.2.1]heptan-2-yl)carbamoyl)-2-cyano-4-methoxyphenoxy)-1-methylcyclohexane-1-carboxylic acid;

(1S,4s)-4-(2-fluoro-4-methoxy-5-(((1R,2S)-2-((3-((trifluoromethyl)sulfonyl)phenyl)carbamoyl)cyclopentyl)carbamoyl)phenoxy)-1-methylcyclohexane-1-carboxylic acid;

(1S,4s)-4-(2-fluoro-5-(((1R,2S)-2-((4-fluoro-3-(pentafluoro-λ6-sulfaneyl)phenyl)carbamoyl)cyclopentyl)carbamoyl)-4-methoxyphenoxy)-1-methylcyclohexane-1-carboxylic acid;

(1S,4s)-4-(2-fluoro-5-(((1S,2R,3S,4R)-3-((4-fluoro-3-(pentafluoro-λ6-sulfaneyl)phenyl)carbamoyl)bicyclo[2.2.1]heptan-2-yl)carbamoyl)-4-methoxyphenoxy)-1-methylcyclohexane-1-carboxylic acid;

(1S,4s)-4-(2-fluoro-5-(((1R,2R)-2-fluoro-2-((3-((trifluoromethyl)sulfonyl)phenyl)carbamoyl)cyclopentyl)carbamoyl)-4-methoxyphenoxy)-1-methylcyclohexane-1-carboxylic acid;

(1S,4s)-4-(2-fluoro-4-methoxy-5-(((2S,3R)-2-((3-((trifluoromethyl)sulfonyl)phenyl)carbamoyl)tetrahydrofuran-3-yl)carbamoyl)phenoxy)-1-methylcyclohexane-1-carboxylic acid;

(1S,4s)-4-(2-fluoro-4-methoxy-5-(((2S,3R)-2-((3-((trifluoromethyl)sulfonyl)phenyl)carbamoyl)tetrahydro-2H-pyran-3-yl)carbamoyl)phenoxy)-1-methylcyclohexane-1-carboxylic acid;

(1R,4s)-4-(2-fluoro-4-methoxy-5-(((1R,2S,3R,4S)-3-(((1-methylcyclobutyl)methyl)carbamoyl)-7-oxabicyclo[2.2.1]heptan-2-yl)carbamoyl)phenoxy)-1-methylcyclohexane-1-carboxylic acid;

(1R,4s)-4-(2-fluoro-4-methoxy-5-(((1S,2R,3S,4R)-3-(((1-methylcyclobutyl)methyl)carbamoyl)-7-oxabicyclo[2.2.1]heptan-2-yl)carbamoyl)phenoxy)-1-methylcyclohexane-1-carboxylic acid;

(1S,4s)-4-(2-cyano-4-methoxy-5-(((1R,2S)-2-(((1-methylcyclobutyl)methyl)carbamoyl)cyclopentyl)carbamoyl)phenoxy)-1-methylcyclohexane-1-carboxylic acid;

(1S,4s)-4-(2-cyano-4-methoxy-5-(((1R,2S)-2-(((1-methylcyclobutyl)methyl)carbamoyl)cyclohexyl)carbamoyl)phenoxy)-1-methylcyclohexane-1-carboxylic acid;

(1S,4s)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-(hydroxymethyl)cyclohexane-1-carboxylic acid;

(1S,4s)-4-(2-fluoro-4-methoxy-5-(((1S,2R,3S,4R)-3-(((1-(trifluoromethyl)cyclobutyl)methyl)carbamoyl)bicyclo[2.2.1]heptan-2-yl)carbamoyl)phenoxy)-1-(hydroxymethyl)cyclohexane-1-carboxylic acid;

(1S,4s)-4-(2-fluoro-4-methoxy-5-(((1R,2R,3S,4S)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1R,2R,3S,4S)-3-(neopentylcarbamoyl)bicyclo[2.2.1]heptan-2-yl)carbamoyl)phenoxy)-1-methylcyclohexane-1-carboxylic acid;

(1S,4s)-4-(4-methoxy-5-(((1S,2R,3S,4R)-3-(((1-methylcyclobutyl)methyl)carbamoyl)bicyclo[2.2.1]heptan-2-yl)carbamoyl)-2-(trifluoromethyl)phenoxy)-1-methylcyclohexane-1-carboxylic acid;

(1S,4s)-4-(2-(difluoromethyl)-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(3-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(4-methoxy-2-methyl-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-ethyl-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(4-cyano-2-fluoro-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-1-methyl-4-((1-methyl-5-(((1S,2R,3S,4R)-3-(((1-methylcyclobutyl)methyl)carbamoyl)bicyclo[2.2.1]heptan-2-yl)carbamoyl)-1H-indazol-7-yl)oxy)cyclohexane-1-carboxylic acid;

(1S,4s)-1-methyl-4-((1-methyl-6-(((1S,2R,3S,4R)-3-(((1-methylcyclobutyl)methyl)carbamoyl)bicyclo[2.2.1]heptan-2-yl)carbamoyl)-1H-indazol-4-yl)oxy)cyclohexane-1-carboxylic acid;

(1S,4s)-4-(2-fluoro-4-(methoxymethyl)-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(4-methoxy-3-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-((3-fluorobicyclo[1.1.1]pentan-1-yl)carbamoyl)bicyclo[2.2.1]heptan-2-yl)carbamoyl)-4-methoxy-2-methylphenoxy)-1-methylcyclohexane-1-carboxylic acid;

(1S,4s)-4-(2-ethyl-5-(((1S,2R,3S,4R)-3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid;

(1S,4s)-4-(4-ethoxy-2-fluoro-5-(((1S,2R,3S,4R)-3-((3-fluorobicyclo[1.1.1]pentan-1-yl)carbamoyl)bicyclo[2.2.1]heptan-2-yl)carbamoyl)phenoxy)-1-methylcyclohexane-1-carboxylic acid;

(1S,4s)-4-(4-ethoxy-2-fluoro-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-1-ethyl-4-(2-fluoro-4-methoxy-5-(((1S,2R,3S,4R)-3-(neopentylcarbamoyl)bicyclo[2.2.1]heptan-2-yl)carbamoyl)phenoxy)cyclohexane-1-carboxylic acid;

(1R,4s)-4-(2-cyano-4-methoxy-5-(((1R,2S,3R,4S)-3-(((1-methylcyclobutyl)methyl)carbamoyl)bicyclo[2.2.1]heptan-2-yl)carbamoyl)phenoxy)-1-methylcyclohexane-1-carboxylic acid;

(1R,4s)-4-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-cyano-4-methoxy-5-(((1R,2R,3S,4S)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-cyano-4-methoxy-5-(((1R,2R,3S,4S)-3-(neopentylcarbamoyl)bicyclo[2.2.1]heptan-2-yl)carbamoyl)phenoxy)-1-methylcyclohexane-1-carboxylic acid;

(1S,4s)-4-(3-fluoro-5-(((1S,2R,3S,4R)-3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid;

(1S,4s)-4-(2-fluoro-4-(2-methoxyethoxy)-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-chloro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2,4-difluoro-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1R,4s)-4-(2-fluoro-5-(((1S,2R,5S)-2-hydroxy-5-((3-((trifluoromethyl)sulfonyl)phenyl)carbamoyl)cyclopentyl)carbamoyl)-4-methoxyphenoxy)-1-methylcyclohexane-1-carboxylic acid;

(1R,4s)-4-(2-fluoro-5-(((1R,2S,5R)-2-hydroxy-5-((3-((trifluoromethyl)sulfonyl)phenyl)carbamoyl)cyclopentyl)carbamoyl)-4-methoxyphenoxy)-1-methylcyclohexane-1-carboxylic acid;

(1R,4s)-4-(2-fluoro-4-methoxy-5-(((1S,2R,5S)-2-methoxy-5-((3-((trifluoromethyl)sulfonyl)phenyl)carbamoyl)cyclopentyl)carbamoyl)phenoxy)-1-methylcyclohexane-1-carboxylic acid;

(1R,4s)-4-(2-fluoro-4-methoxy-5-(((1R,2S,5R)-2-methoxy-5-((3-((trifluoromethyl)sulfonyl)phenyl)carbamoyl)cyclopentyl)carbamoyl)phenoxy)-1-methylcyclohexane-1-carboxylic acid;

(1S,4s)-4-(4-chloro-2-fluoro-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-cyclopropyl-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-fluoro-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-cyano-4-fluoro-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(4-methoxy-2-(methoxymethyl)-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(3-chloro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(3-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(4-methoxy-3-methyl-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-1-methyl-4-((7-(((1S,2R,3S,4R)-3-(((1-methylcyclobutyl)methyl)carbamoyl)bicyclo[2.2.1]heptan-2-yl)carbamoyl)-2,3-dihydrobenzofuran-5-yl)oxy)cyclohexane-1-carboxylic acid;

(1S,4s)-1-methyl-4-((8-(((1S,2R,3S,4R)-3-(((1-methylcyclobutyl)methyl)carbamoyl)bicyclo[2.2.1]heptan-2-yl)carbamoyl)quinolin-6-yl)oxy)cyclohexane-1-carboxylic acid;

(1S,4s)-4-(2-chloro-4-fluoro-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-chloro-4-methoxy-5-(((1S,2R,3S,4R)-3-((3,3,3-trifluoro-2,2-dimethylpropyl)carbamoyl)bicyclo[2.2.1]heptan-2-yl)carbamoyl)phenoxy)-1-methylcyclohexane-1-carboxylic acid;

(1S,4s)-4-(2-chloro-4-methoxy-5-(((1R,2R,3S,4S)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-chloro-5-(((1S,2R,3S,4R)-3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid;

(1S,4s)-4-(2-chloro-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid;

(1S,4s)-4-(2-cyano-4-fluoro-5-(((1R,2R,3S,4S)-3-(((1-methylcyclobutyl)methyl)carbamoyl)bicyclo[2.2.1]heptan-2-yl)carbamoyl)phenoxy)-1-methylcyclohexane-1-carboxylic acid;

(1R,4s)-4-(2-cyano-4-methoxy-5-(((1S,2S,3R,4R)-3-(neopentylcarbamoyl)bicyclo[2.2.1]heptan-2-yl)carbamoyl)phenoxy)-1-methylcyclohexane-1-carboxylic acid;

(1R,4s)-4-(2-cyano-4-methoxy-5-(((1R,2R,3S,4S)-3-(neopentylcarbamoyl)bicyclo[2.2.1]heptan-2-yl)carbamoyl)phenoxy)-1-methylcyclohexane-1-carboxylic acid;

(1R,4r)-1-fluoro-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)cyclohexane-1-carboxylic acid;

(1R,4r)-1-fluoro-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid;

(1S,4s)-4-(2-fluoro-4-methoxy-5-(((1R,2R,3S,4S)-3-(((1-methylcyclobutyl)methyl)carbamoyl)bicyclo[2.2.1]hept-5-en-2-yl)carbamoyl)phenoxy)-1-methylcyclohexane-1-carboxylic acid;

(1R,2S,3R,4S)-3-(4-fluoro-2-methoxy-5-(((1s,4S)-4-methyl-4-(5-oxo-4,5-dihydro-1,2,4-oxadiazol-3-yl)cyclohexyl)oxy)benzamido)-N-((1-methylcyclobutyl)methyl)bicyclo[2.2.1]heptane-2-carboxamide;

(1R,2S,3R,4S)-3-(4-fluoro-2-methoxy-5-(((1s,4S)-4-methyl-4-(5-oxo-4,5-dihydro-1,3,4-oxadiazol-2-yl)cyclohexyl)oxy)benzamido)-N-((1-methylcyclobutyl)methyl)bicyclo[2.2.1]heptane-2-carboxamide;

(1R,2S,3R,4S)-3-(4-fluoro-2-methoxy-5-(((1s,4S)-4-methyl-4-(1H-tetrazol-5-yl)cyclohexyl)oxy)benzamido)-N-((1-methylcyclobutyl)methyl)bicyclo[2.2.1]heptane-2-carboxamide;

(1S,2S,3R,4R)-3-(5-(((1s,4S)-4-carbamoyl-4-methylcyclohexyl)oxy)-4-fluoro-2-methoxybenzamido)-N-((1-methylcyclobutyl)methyl)bicyclo[2.2.1]heptane-2-carboxamide;

(1R,4r)-1-(cyanomethyl)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)cyclohexane-1-carboxylic acid;

(1S,4s)-1-(cyanomethyl)-4-(2-fluoro-4-methoxy-5-(((1S, 2R,3S,4R)-3-(((1-methylcyclobutyl)methyl)carbamoyl) bicyclo[2.2.1]heptan-2-yl)carbamoyl)phenoxy)cyclohexane-1-carboxylic acid;
(1R,3s,5S,6S)-3-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)bicyclo[3.1.0]hexane-6-carboxylic acid;
(1R,3r,5S,6R)-3-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)bicyclo[3.1.0]hexane-6-carboxylic acid;
(1R,3r,5S,6S)-3-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)bicyclo[3.1.0]hexane-6-carboxylic acid;
(1R,3s,5S,6R)-3-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)bicyclo[3.1.0]hexane-6-carboxylic acid;
4-(4-methoxy-3-(((1R,2R,3S,4S)-3-((3-((trifluoromethyl) sulfonyl)phenyl)carbamoyl)bicyclo[2.2.1]hept-5-en-2-yl) carbamoyl)phenoxy)benzoic acid;
4-(4-methoxy-3-(((1S,2S,3R,4R)-3-((3-((trifluoromethyl) sulfonyl)phenyl)carbamoyl)bicyclo[2.2.1]hept-5-en-2-yl) carbamoyl)phenoxy)benzoic acid;
3-(4-methoxy-3-(((1R,2R,3S,4S)-3-((3-((trifluoromethyl) sulfonyl)phenyl)carbamoyl)bicyclo[2.2.1]hept-5-en-2-yl) carbamoyl)phenoxy)benzoic acid;
3-(4-methoxy-3-(((1S,2S,3R,4R)-3-((3-((trifluoromethyl) sulfonyl)phenyl)carbamoyl)bicyclo[2.2.1]hept-5-en-2-yl) carbamoyl)phenoxy)benzoic acid;
2-(4-methoxy-3-(((1R,2R,3S,4S)-3-((3-((trifluoromethyl) sulfonyl)phenyl)carbamoyl)bicyclo[2.2.1]hept-5-en-2-yl) carbamoyl)phenoxy)benzoic acid;
2-(4-methoxy-3-(((1S,2S,3R,4R)-3-((3-((trifluoromethyl) sulfonyl)phenyl)carbamoyl)bicyclo[2.2.1]hept-5-en-2-yl) carbamoyl)phenoxy)benzoic acid;
(1S,4s)-4-(2,4-difluoro-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid;
5-(2-cyano-4-methoxy-5-(((1S,2R,3S,4R)-3-(((1-methylcyclobutyl)methyl)carbamoyl)bicyclo[2.2.1]heptan-2-yl) carbamoyl)phenoxy)-2,2-dimethylpentanoic acid;
(1S,4s)-4-(2-fluoro-5-(((1S,2R,3S,4R)-3-((4-fluoro-3-(pentafluoro-λ6-sulfaneyl)phenyl)carbamoyl)bicyclo[2.2.1] heptan-2-yl)carbamoyl)-4-methoxyphenoxy)cyclohexane-1-carboxylic acid;
(1S,2S,3R,4R)-3-(5-(((1s,4S)-4-carbamoylcyclohexyl)oxy)-4-fluoro-2-methoxybenzamido)-N-(3-(pentafluoro-λ6-sulfaneyl)phenyl)bicyclo[2.2.1]heptane-2-carboxamide;
6-fluoro-4-methoxy-N3-((1S,2R,3S,4R)-3-((3-((trifluoromethyl)sulfonyl)phenyl)carbamoyl)bicyclo[2.2.1]heptan-2-yl)-[1,1'-biphenyl]-3,4'-dicarboxamide;
6-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)hexanoic acid;
7-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)heptanoic acid;
9-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)nonanoic acid;
4-((2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)methyl)benzoic acid;
(1R,4r)-4-((2-fluoro-4-methoxy-5-(((1S,2R,3S,4R)-3-((3-((trifluoromethyl)sulfonyl)phenyl)carbamoyl)bicyclo [2.2.1]heptan-2-yl)carbamoyl)phenoxy)methyl)cyclohexane-1-carboxylic acid;
(1S,4s)-4-((2-fluoro-4-methoxy-5-(((1S,2R,3S,4R)-3-((3-((trifluoromethyl)sulfonyl)phenyl)carbamoyl)bicyclo [2.2.1]heptan-2-yl)carbamoyl)phenoxy)methyl)cyclohexane-1-carboxylic acid;
4-((2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)methyl)bicyclo[2.2.2]octane-1-carboxylic acid;
(2R,5R)-5-(2-fluoro-4-methoxy-5-(((1S,2R,3S,4R)-3-((3-((trifluoromethyl)sulfonyl)phenyl)carbamoyl)bicyclo [2.2.1]heptan-2-yl)carbamoyl)phenoxy)tetrahydro-2H-pyran-2-carboxylic acid;
(2S,5S)-5-(2-fluoro-4-methoxy-5-(((1S,2R,3S,4R)-3-((3-((trifluoromethyl)sulfonyl)phenyl)carbamoyl)bicyclo [2.2.1]heptan-2-yl)carbamoyl)phenoxy)tetrahydro-2H-pyran-2-carboxylic acid;
(1R,3r)-3-(2-fluoro-4-methoxy-5-(((1S,2R,3S,4R)-3-((3-((trifluoromethyl)sulfonyl)phenyl)carbamoyl)bicyclo [2.2.1]heptan-2-yl)carbamoyl)phenoxy)cyclobutane-1-carboxylic acid;
(1S,3s)-3-(2-fluoro-4-methoxy-5-(((1S,2R,3S,4R)-3-((3-((trifluoromethyl)sulfonyl)phenyl)carbamoyl)bicyclo [2.2.1]heptan-2-yl)carbamoyl)phenoxy)cyclobutane-1-carboxylic acid;
(1R,4r)-4-(2-fluoro-4-methoxy-5-(((1S,2R,3S,4R)-3-((3-((trifluoromethyl)sulfonyl)phenyl)carbamoyl)bicyclo [2.2.1]heptan-2-yl)carbamoyl)phenoxy)-1-methylcyclohexane-1-carboxylic acid;
(1R,3R)-3-(2-fluoro-4-methoxy-5-(((1S,2R,3S,4R)-3-((3-((trifluoromethyl)sulfonyl)phenyl)carbamoyl)bicyclo [2.2.1]heptan-2-yl)carbamoyl)phenoxy)cyclohexane-1-carboxylic acid;
(1R,3S)-3-(2-fluoro-4-methoxy-5-(((1S,2R,3S,4R)-3-((3-((trifluoromethyl)sulfonyl)phenyl)carbamoyl)bicyclo [2.2.1]heptan-2-yl)carbamoyl)phenoxy)cyclohexane-1-carboxylic acid;
(1S,3S)-3-(2-fluoro-4-methoxy-5-(((1S,2R,3S,4R)-3-((3-((trifluoromethyl)sulfonyl)phenyl)carbamoyl)bicyclo [2.2.1]heptan-2-yl)carbamoyl)phenoxy)cyclohexane-1-carboxylic acid;
(1S,3R)-3-(2-fluoro-4-methoxy-5-(((1S,2R,3S,4R)-3-((3-((trifluoromethyl)sulfonyl)phenyl)carbamoyl)bicyclo [2.2.1]heptan-2-yl)carbamoyl)phenoxy)cyclohexane-1-carboxylic acid;
2-((2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)methyl)benzoic acid;
2-((2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)methyl)benzoic acid;
3-((2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)methyl)benzoic acid;
3-((2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)methyl)benzoic acid;
4-((2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)methyl)benzoic acid;
4-((2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)methyl)benzoic acid;

5-(2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)pentanoic acid;

5-(2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)pentanoic acid;

2-(4-((2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)methyl)phenyl)-2-methylpropanoic acid;

2-(4-((2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)methyl)phenyl)-2-methylpropanoic acid;

2-(3-((2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)methyl)phenyl)acetic acid;

2-(3-((2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)methyl)phenyl)acetic acid;

2-(3-((2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)methyl)phenyl)-2-methylpropanoic acid;

2-(3-((2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)methyl)phenyl)-2-methylpropanoic acid;

6-(2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)hexanoic acid;

6-(2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)hexanoic acid;

4-(2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)butanoic acid;

4-(2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)butanoic acid;

(1R,4r)-4-(2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)cyclohexane-1-carboxylic acid;

(1R,4r)-4-(2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)cyclohexane-1-carboxylic acid;

(1R,4r)-1-amino-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid;

(1S,4s)-1-amino-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid;

(1R,2S,3R,4S)-3-(4-fluoro-2-methoxy-5-(((1s,4S)-4-(methylsulfonamido)cyclohexyl)oxy)benzamido)-N-(3-((trifluoromethyl)sulfonyl)phenyl)bicyclo[2.2.1]heptane-2-carboxamide;

(1R,2S,3R,4S)-3-(4-fluoro-2-methoxy-5-(((1r,4R)-4-(methylsulfonamido)cyclohexyl)oxy)benzamido)-N-(3-((trifluoromethyl)sulfonyl)phenyl)bicyclo[2.2.1]heptane-2-carboxamide;

(1S,4s)-4-(2-fluoro-4-methoxy-5-(((3aS,4S,5R,6S,7R,7aR)-6-((3-((trifluoromethyl)sulfonyl)phenyl)carbamoyl)hexahydro-4,7-methanobenzo[d][1,3]dioxol-5-yl)carbamoyl)phenoxy)cyclohexane-1-carboxylic acid;

(1S,2S,3R,4R)-3-(4-fluoro-2-methoxy-5-(((1r,4R)-4-sulfamoylcyclohexyl)oxy)benzamido)-N-(3-((trifluoromethyl)sulfonyl)phenyl)bicyclo[2.2.1]heptane-2-carboxamide;

(1S,2S,3R,4R)-3-(4-fluoro-2-methoxy-5-(((1s,4S)-4-sulfamoylcyclohexyl)oxy)benzamido)-N-(3-((trifluoromethyl)sulfonyl)phenyl)bicyclo[2.2.1]heptane-2-carboxamide;

(1S,4s)-4-(2-bromo-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid;

(1S,4s)-4-(4-methoxy-2-methyl-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid;

(1S,4s)-4-(4-methoxy-3-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid;

(1S,4s)-4-(2-cyano-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid;

(1R,3r)-3-((2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)methyl)cyclobutane-1-carboxylic acid;

(1S,3s)-3-((2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)methyl)cyclobutane-1-carboxylic acid;

2-((1R,3r)-3-(2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)cyclobutyl)acetic acid;

2-((1S,3s)-3-(2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)cyclobutyl)acetic acid;

2-((1S,4s)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexyl)acetic acid;

2-((1R,4r)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexyl)acetic acid;

(1R,4r)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-(trifluoromethyl)cyclohexane-1-carboxylic acid;

(1S,4s)-4-(2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)-1-(methoxymethyl)cyclohexane-1-carboxylic acid;

(1R,4r)-4-(2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)-1-(methoxymethyl)cyclohexane-1-carboxylic acid;

(1S,4s)-4-(2-fluoro-4-methoxy-5-(((1S,2R,3S,4R)-3-(neopentylcarbamoyl)bicyclo[2.2.1]heptan-2-yl)carbamoyl)phenoxy)-1-(methoxymethyl)cyclohexane-1-carboxylic acid;

(1S,4s)-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)-1-(methoxymethyl)cyclohexane-1-carboxylic acid;

4-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)benzoic acid;

4-(2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)benzoic acid;

4-(2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)benzoic acid;

(1R,4r)-4-(2-fluoro-4-isopropoxy-5-(((1S,2R,3S,4R)-3-(((1-methylcyclobutyl)methyl)carbamoyl)bicyclo[2.2.1]heptan-2-yl)carbamoyl)phenoxy)-1-(methoxycarbonyl)cyclohexane-1-carboxylic acid;

(1S,4s)-4-(2-fluoro-4-isopropoxy-5-(((1S,2R,3S,4R)-3-(((1-methylcyclobutyl)methyl)carbamoyl)bicyclo[2.2.1]heptan-2-yl)carbamoyl)phenoxy)-1-(hydroxymethyl)cyclohexane-1-carboxylic acid;

(1S,4s)-4-(2-fluoro-5-(((1R,2R,3S,4S)-3-((4-fluoro-3-(pentafluoro-λ6-sulfaneyl)phenyl)carbamoyl)bicyclo[2.2.1]hept-5-en-2-yl)carbamoyl)-4-methoxyphenoxy)cyclohexane-1-carboxylic acid;

(1S,4s)-4-(2-fluoro-5-(((1R,2R,3S,4S)-3-((4-fluoro-3-((trifluoromethyl)sulfonyl)phenyl)carbamoyl)bicyclo[2.2.1]hept-5-en-2-yl)carbamoyl)-4-methoxyphenoxy)cyclohexane-1-carboxylic acid;

(1S,4s)-4-(2-fluoro-4-methoxy-5-(((1R,2S)-2-((3-((trifluoromethyl)sulfonyl)phenyl)carbamoyl)cyclopentyl)carbamoyl)phenoxy)cyclohexane-1-carboxylic acid;

(1S,4s)-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid;

(1S,4s)-4-(2-fluoro-5-(((1R,2S)-2-((4-fluoro-3-(trifluoromethyl)phenyl)carbamoyl)cyclopentyl)carbamoyl)-4-methoxyphenoxy)cyclohexane-1-carboxylic acid;

(1R,4s)-4-(5-(((1S,2R)-4,4-difluoro-2-((4-fluoro-3-(trifluoromethyl)phenyl)carbamoyl)cyclopentyl)carbamoyl)-2-fluoro-4-methoxyphenoxy)cyclohexane-1-carboxylic acid;

(1R,4s)-4-(5-(((1R,2S)-4,4-difluoro-2-((4-fluoro-3-(trifluoromethyl)phenyl)carbamoyl)cyclopentyl)carbamoyl)-2-fluoro-4-methoxyphenoxy)cyclohexane-1-carboxylic acid;

(1S,4s)-4-(5-(((1S,2R,3S,4R,5R,6S)-5,6-dihydroxy-3-((3-((trifluoromethyl)sulfonyl)phenyl)carbamoyl)bicyclo[2.2.1]heptan-2-yl)carbamoyl)-2-fluoro-4-methoxyphenoxy)cyclohexane-1-carboxylic acid;

(1R,4s)-4-(2-fluoro-4-methoxy-5-(((1S,2S,3R,4R)-3-((3-((trifluoromethyl)sulfonyl)phenyl)carbamoyl)bicyclo[2.2.1]hept-5-en-2-yl)carbamoyl)phenoxy)cyclohexane-1-carboxylic acid;

(1R,4s)-4-(2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)cyclohexane-1-carboxylic acid;

(1R,4s)-4-(2-fluoro-5-(((1S,2R,4S)-4-hydroxy-2-((3-((trifluoromethyl)sulfonyl)phenyl)carbamoyl)cyclopentyl)carbamoyl)-4-methoxyphenoxy)cyclohexane-1-carboxylic acid;

(1R,4s)-4-(2-fluoro-5-(((1R,2S,4R)-4-hydroxy-2-((3-((trifluoromethyl)sulfonyl)phenyl)carbamoyl)cyclopentyl)carbamoyl)-4-methoxyphenoxy)cyclohexane-1-carboxylic acid;

(1S,4s)-4-(2-fluoro-4-methoxy-5-(((1R,2R,3S,4S)-3-((4-methoxy-3-((trifluoromethyl)sulfonyl)phenyl)carbamoyl)bicyclo[2.2.1]hept-5-en-2-yl)carbamoyl)phenoxy)cyclohexane-1-carboxylic acid;

(1S,4s)-4-(2-fluoro-5-(((1R,2R,3S,4S)-3-((4-fluoro-3-(trifluoromethyl)phenyl)carbamoyl)bicyclo[2.2.1]hept-5-en-2-yl)carbamoyl)-4-methoxyphenoxy)cyclohexane-1-carboxylic acid;

(1S,2S,3R,4R)-3-(5-(((1s,4S)-4-carbamoylcyclohexyl)oxy)-4-fluoro-2-methoxybenzamido)-N-(4-fluoro-3-(trifluoromethyl)phenyl)bicyclo[2.2.1]hept-5-ene-2-carboxamide;

(1R,2S,3R,4S)-3-(5-(((1s,4S)-4-carbamoylcyclohexyl)oxy)-4-fluoro-2-methoxybenzamido)-N-(4-fluoro-3-(trifluoromethyl)phenyl)bicyclo[2.2.1]heptane-2-carboxamide;

(1R,4s)-4-(2-fluoro-5-(((1S,2S,3R,4R)-3-((4-fluoro-3-(trifluoromethyl)phenyl)carbamoyl)bicyclo[2.2.1]hept-5-en-2-yl)carbamoyl)-4-methoxyphenoxy)cyclohexane-1-carboxylic acid;

(1S,4s)-4-(2-cyano-4-methoxy-5-(((1R,2R,3S,4S)-3-((3,3,3-trifluoro-2,2-dimethylpropyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-(((R)-2,2-dimethylcyclopentyl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(5-(((1S,2R,3S,4R)-3-(((S)-2,2-dimethylcyclopentyl)carbamoyl)bicyclo[2.2.1]heptan-2-yl)carbamoyl)-2-fluoro-4-methoxyphenoxy)-1-methylcyclohexane-1-carboxylic acid;

(1S,3s)-3-(2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)-1-methylcyclobutane-1-carboxylic acid;

(1R,4r)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methoxycyclohexane-1-carboxylic acid;

(1R,4r)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-hydroxycyclohexane-1-carboxylic acid;

(1R,4r)-4-(2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)-1-methoxycyclohexane-1-carboxylic acid;

(1R,4s)-4-(2-fluoro-4-methoxy-5-(((1S,2S,3R,4R)-3-((3-(pentafluoro-λ6-sulfaneyl)phenyl)carbamoyl)bicyclo[2.2.1]heptan-2-yl)carbamoyl)phenoxy)cyclohexane-1-carboxylic acid;

(1R,4s)-4-(2-fluoro-4-methoxy-5-(((1R,2R,3S,4S)-3-((3-(pentafluoro-λ6-sulfaneyl)phenyl)carbamoyl)bicyclo[2.2.1]heptan-2-yl)carbamoyl)phenoxy)cyclohexane-1-carboxylic acid;

(1R,4s)-4-(2-fluoro-4-methoxy-5-(((3aR,4S,5S,6aS)-5-((3-((trifluoromethyl)sulfonyl)phenyl)carbamoyl)tetrahydro-4H-cyclopenta[d][1,3]dioxol-4-yl)carbamoyl)phenoxy)-1-methylcyclohexane-1-carboxylic acid;

(1R,4s)-4-(2-fluoro-4-methoxy-5-(((3aS,4R,5R,6aR)-5-((3-((trifluoromethyl)sulfonyl)phenyl)carbamoyl)tetrahydro-4H-cyclopenta[d][1,3]dioxol-4-yl)carbamoyl)phenoxy)-1-methylcyclohexane-1-carboxylic acid;

(1R,4s)-4-(5-(((3R,4S)-1-acetyl-3-((3-((trifluoromethyl)sulfonyl)phenyl)carbamoyl)piperidin-4-yl)carbamoyl)-2-fluoro-4-methoxyphenoxy)-1-methylcyclohexane-1-carboxylic acid;

(1R,4s)-4-(5-(((3S,4R)-1-acetyl-3-((3-((trifluoromethyl)sulfonyl)phenyl)carbamoyl)piperidin-4-yl)carbamoyl)-2-fluoro-4-methoxyphenoxy)-1-methylcyclohexane-1-carboxylic acid;

(1R,4s)-4-(2-fluoro-4-methoxy-5-(((1S,2R)-2-((3-((trifluoromethyl)sulfonyl)phenyl)carbamoyl)cycloheptyl)carbamoyl)phenoxy)-1-methylcyclohexane-1-carboxylic acid;

(1R,4s)-4-(2-fluoro-4-methoxy-5-(((1R,2S)-2-((3-((trifluoromethyl)sulfonyl)phenyl)carbamoyl)cycloheptyl)carbamoyl)phenoxy)-1-methylcyclohexane-1-carboxylic acid;

(1R,4s)-4-(2-fluoro-4-methoxy-5-(((3S,4S)-3-((3-((trifluoromethyl)sulfonyl)phenyl)carbamoyl)tetrahydro-2H-pyran-4-yl)carbamoyl)phenoxy)-1-methylcyclohexane-1-carboxylic acid;

(1R,4s)-4-(2-fluoro-4-methoxy-5-(((3R,4R)-3-((3-((trifluoromethyl)sulfonyl)phenyl)carbamoyl)tetrahydro-2H-pyran-4-yl)carbamoyl)phenoxy)-1-methylcyclohexane-1-carboxylic acid;

(1R,4s)-4-(2-fluoro-5-(((1S,2S,3R,4R)-3-((4-fluoro-3-(pentafluoro-λ6-sulfaneyl)phenyl)carbamoyl)bicyclo[2.2.1]heptan-2-yl)carbamoyl)-4-methoxyphenoxy)-1-methylcyclohexane-1-carboxylic acid;

(1R,4s)-4-(2-fluoro-5-(((1R,2R,3S,4S)-3-((4-fluoro-3-(pentafluoro-λ6-sulfaneyl)phenyl)carbamoyl)bicyclo[2.2.1]heptan-2-yl)carbamoyl)-4-methoxyphenoxy)-1-methylcyclohexane-1-carboxylic acid;

(1R,4s)-4-(2-fluoro-4-methoxy-5-(((1S,2R,4S)-4-methoxy-2-((3-((trifluoromethyl)sulfonyl)phenyl)carbamoyl)cyclopentyl)carbamoyl)phenoxy)-1-methylcyclohexane-1-carboxylic acid;

(1R,4s)-4-(2-fluoro-4-methoxy-5-(((1R,2S,4R)-4-methoxy-2-((3-((trifluoromethyl)sulfonyl)phenyl)carbamoyl)cyclopentyl)carbamoyl)phenoxy)-1-methylcyclohexane-1-carboxylic acid;

(1R,4s)-4-(2-fluoro-4-methoxy-5-(((1S,2R,4R)-4-methoxy-2-((3-((trifluoromethyl)sulfonyl)phenyl)carbamoyl)cyclopentyl)carbamoyl)phenoxy)-1-methylcyclohexane-1-carboxylic acid;

(1R,4s)-4-(2-fluoro-4-methoxy-5-(((1R,2S,4S)-4-methoxy-2-((3-((trifluoromethyl)sulfonyl)phenyl)carbamoyl)cyclopentyl)carbamoyl)phenoxy)-1-methylcyclohexane-1-carboxylic acid;

(1R,4s)-4-(2-fluoro-4-methoxy-5-(((1S,2S,5S)-2-methoxy-5-((3-((trifluoromethyl)sulfonyl)phenyl)carbamoyl)cyclopentyl)carbamoyl)phenoxy)-1-methylcyclohexane-1-carboxylic acid;

(1R,4s)-4-(2-fluoro-4-methoxy-5-(((1R,2R,5R)-2-methoxy-5-((3-((trifluoromethyl)sulfonyl)phenyl)carbamoyl)cyclopentyl)carbamoyl)phenoxy)-1-methylcyclohexane-1-carboxylic acid;

(1R,4s)-4-(2-fluoro-5-(((1S,2S,5S)-2-hydroxy-5-((3-((trifluoromethyl)sulfonyl)phenyl)carbamoyl)cyclopentyl)carbamoyl)-4-methoxyphenoxy)-1-methylcyclohexane-1-carboxylic acid;

(1R,4s)-4-(2-fluoro-5-(((1R,2R,5R)-2-hydroxy-5-((3-((trifluoromethyl)sulfonyl)phenyl)carbamoyl)cyclopentyl)carbamoyl)-4-methoxyphenoxy)-1-methylcyclohexane-1-carboxylic acid;

(1R,4s)-4-(2-fluoro-4-methoxy-5-(((1S,2S,3R,4R)-3-(((1-methylcyclobutyl)methyl)carbamoyl)-7-oxabicyclo[2.2.1]heptan-2-yl)carbamoyl)phenoxy)-1-methylcyclohexane-1-carboxylic acid;

(1R,4s)-4-(2-fluoro-4-methoxy-5-(((1R,2R,3S,4S)-3-(((1-methylcyclobutyl)methyl)carbamoyl)-7-oxabicyclo[2.2.1]heptan-2-yl)carbamoyl)phenoxy)-1-methylcyclohexane-1-carboxylic acid;

(1R,4s)-4-(2-fluoro-4-methoxy-5-(((1S,2S,3R,4R)-3-(((1-methylcyclobutyl)methyl)carbamoyl)-7-oxabicyclo[2.2.1]heptan-2-yl)carbamoyl)phenoxy)-1-(hydroxymethyl)cyclohexane-1-carboxylic acid;

(1R,4s)-4-(2-fluoro-4-methoxy-5-(((1R,2R,3S,4S)-3-(((1-methylcyclobutyl)methyl)carbamoyl)-7-oxabicyclo[2.2.1]heptan-2-yl)carbamoyl)phenoxy)-1-(hydroxymethyl)cyclohexane-1-carboxylic acid;

(1R,4s)-4-(2-cyano-4-methoxy-5-(((1S,2S,3R,4R)-3-(((1-methylcyclobutyl)methyl)carbamoyl)-7-oxabicyclo[2.2.1]heptan-2-yl)carbamoyl)phenoxy)-1-methylcyclohexane-1-carboxylic acid;

(1R,4s)-4-(2-cyano-4-methoxy-5-(((1R,2R,3S,4S)-3-(((1-methylcyclobutyl)methyl)carbamoyl)-7-oxabicyclo[2.2.1]heptan-2-yl)carbamoyl)phenoxy)-1-methylcyclohexane-1-carboxylic acid;

(1R,4s)-4-(2-cyano-4-methoxy-5-(((1S,2S,3R,4R)-3-(((1-methylcyclobutyl)methyl)carbamoyl)-7-(3,3,3-trifluoropropyl)-7-azabicyclo[2.2.1]heptan-2-yl)carbamoyl)phenoxy)-1-methylcyclohexane-1-carboxylic acid;

(1R,4s)-4-(2-cyano-4-methoxy-5-(((1R,2R,3S,4S)-3-(((1-methylcyclobutyl)methyl)carbamoyl)-7-(3,3,3-trifluoropropyl)-7-azabicyclo[2.2.1]heptan-2-yl)carbamoyl)phenoxy)-1-methylcyclohexane-1-carboxylic acid;

(1R,4s)-4-(2-cyano-4-methoxy-5-(((2S,3R)-3-(((1-methylcyclobutyl)methyl)carbamoyl)bicyclo[2.2.2]octan-2-yl)carbamoyl)phenoxy)-1-methylcyclohexane-1-carboxylic acid;

(1R,4s)-4-(2-cyano-4-methoxy-5-(((2R,3S)-3-(((1-methylcyclobutyl)methyl)carbamoyl)bicyclo[2.2.2]octan-2-yl)carbamoyl)phenoxy)-1-methylcyclohexane-1-carboxylic acid;

(1R,4s)-4-(2-cyano-4-methoxy-5-(((1R,2S,3R,4S)-3-(((1-methylcyclobutyl)methyl)carbamoyl)bicyclo[2.2.2]oct-5-en-2-yl)carbamoyl)phenoxy)-1-methylcyclohexane-1-carboxylic acid;

(1R,4s)-4-(2-cyano-4-methoxy-5-(((1S,2R,3S,4R)-3-(((1-methylcyclobutyl)methyl)carbamoyl)bicyclo[2.2.2]oct-5-en-2-yl)carbamoyl)phenoxy)-1-methylcyclohexane-1-carboxylic acid;

(1R,4s)-4-(2-fluoro-4-methoxy-5-(((2S,3R)-3-(((1-methylcyclobutyl)methyl)carbamoyl)bicyclo[2.2.2]octan-2-yl)carbamoyl)phenoxy)-1-methylcyclohexane-1-carboxylic acid;

(1R,4s)-4-(2-fluoro-4-methoxy-5-(((2R,3S)-3-(((1-methylcyclobutyl)methyl)carbamoyl)bicyclo[2.2.2]octan-2-yl)carbamoyl)phenoxy)-1-methylcyclohexane-1-carboxylic acid;

(1R,4s)-4-(2-fluoro-4-methoxy-5-(((1R,2S,3R,4S)-3-(((1-methylcyclobutyl)methyl)carbamoyl)bicyclo[2.2.2]oct-5-en-2-yl)carbamoyl)phenoxy)-1-methylcyclohexane-1-carboxylic acid;

(1R,4s)-4-(2-fluoro-4-methoxy-5-(((1S,2R,3S,4R)-3-(((1-methylcyclobutyl)methyl)carbamoyl)bicyclo[2.2.2]oct-5-en-2-yl)carbamoyl)phenoxy)-1-methylcyclohexane-1-carboxylic acid;

(1R,4s)-4-(2-fluoro-4-methoxy-5-(((1S,2R,4R)-4-methoxy-2-(neopentylcarbamoyl)cyclopentyl)carbamoyl)phenoxy)-1-methylcyclohexane-1-carboxylic acid;

(1R,4s)-4-(2-fluoro-4-methoxy-5-(((1R,2S,4S)-4-methoxy-2-(neopentylcarbamoyl)cyclopentyl)carbamoyl)phenoxy)-1-methylcyclohexane-1-carboxylic acid;

(1R,4s)-4-(2-fluoro-4-methoxy-5-(((1S,2R,4R)-4-methoxy-2-(neopentylcarbamoyl)cyclopentyl)carbamoyl)phenoxy)-1-(hydroxymethyl)cyclohexane-1-carboxylic acid;

(1R,4s)-4-(2-fluoro-4-methoxy-5-(((1R,2S,4S)-4-methoxy-2-(neopentylcarbamoyl)cyclopentyl)carbamoyl)phenoxy)-1-(hydroxymethyl)cyclohexane-1-carboxylic acid;

(1R,4s)-4-(2-fluoro-4-methoxy-5-(((1S,2R,4R)-4-methoxy-2-(((1-methylcyclobutyl)methyl)carbamoyl)cyclopentyl)carbamoyl)phenoxy)-1-(hydroxymethyl)cyclohexane-1-carboxylic acid;

(1R,4s)-4-(2-fluoro-4-methoxy-5-(((1R,2S,4S)-4-methoxy-2-(((1-methylcyclobutyl)methyl)carbamoyl)cyclopentyl)carbamoyl)phenoxy)-1-(hydroxymethyl)cyclohexane-1-carboxylic acid;

2'-fluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

2'-fluoro-4'-methoxy-5'-(((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid;

2'-fluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid;

2'-fluoro-4'-methoxy-5'-(((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid;

2'-fluoro-4-hydroxy-4'-methoxy-5'-(((1R,2S,3R,4S)-3-((3-((trifluoromethyl)sulfonyl)phenyl)carbamoyl)bicyclo[2.2.1]heptan-2-yl)carbamoyl)-[1,1'-biphenyl]-3-carboxylic acid;

2'-fluoro-4-hydroxy-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-3-carboxylic acid;

(1R,4s)-4-(2-fluoro-4-methoxy-5-(((3S,4S)-4-((3-((trifluoromethyl)sulfonyl)phenyl)carbamoyl)tetrahydro-2H-pyran-3-yl)carbamoyl)phenoxy)-1-methylcyclohexane-1-carboxylic acid;

(1R,4s)-4-(2-fluoro-4-methoxy-5-(((3R,4R)-4-((3-((trifluoromethyl)sulfonyl)phenyl)carbamoyl)tetrahydro-2H-pyran-3-yl)carbamoyl)phenoxy)-1-methylcyclohexane-1-carboxylic acid;

(1R,4s)-4-(2-fluoro-4-methoxy-5-(((3S,4R)-4-((3-((trifluoromethyl)sulfonyl)phenyl)carbamoyl)tetrahydrofuran-3-yl)carbamoyl)phenoxy)-1-methylcyclohexane-1-carboxylic acid;

(1R,4s)-4-(2-fluoro-4-methoxy-5-(((3R,4S)-4-((3-((trifluoromethyl)sulfonyl)phenyl)carbamoyl)tetrahydrofuran-3-yl)carbamoyl)phenoxy)-1-methylcyclohexane-1-carboxylic acid;

(1R,4s)-4-(5-(((1S,2R,3S,5S)-2,3-dihydroxy-5-((3-((trifluoromethyl)sulfonyl)phenyl)carbamoyl)cyclopentyl)carbamoyl)-2-fluoro-4-methoxyphenoxy)-1-methylcyclohexane-1-carboxylic acid;

(1R,4s)-4-(5-(((1R,2S,3R,5R)-2,3-dihydroxy-5-((3-((trifluoromethyl)sulfonyl)phenyl)carbamoyl)cyclopentyl)carbamoyl)-2-fluoro-4-methoxyphenoxy)-1-methylcyclohexane-1-carboxylic acid;

(1R,4s)-4-(2-fluoro-5-(((3S,4R)-4-((4-fluoro-3-(pentafluoro-λ6-sulfaneyl)phenyl)carbamoyl)tetrahydrofuran-3-yl)carbamoyl)-4-methoxyphenoxy)-1-methylcyclohexane-1-carboxylic acid;

(1R,4s)-4-(2-fluoro-5-(((3R,4S)-4-((4-fluoro-3-(pentafluoro-λ6-sulfaneyl)phenyl)carbamoyl)tetrahydrofuran-3-yl)carbamoyl)-4-methoxyphenoxy)-1-methylcyclohexane-1-carboxylic acid;

(1R,4s)-4-(2-fluoro-4-methoxy-5-(((3S,4R)-4-(neopentylcarbamoyl)tetrahydrofuran-3-yl)carbamoyl)phenoxy)-1-methylcyclohexane-1-carboxylic acid;

(1R,4s)-4-(2-fluoro-4-methoxy-5-(((3R,4S)-4-(neopentylcarbamoyl)tetrahydrofuran-3-yl)carbamoyl)phenoxy)-1-methylcyclohexane-1-carboxylic acid;

(1R,4s)-4-(2-fluoro-4-methoxy-5-(((1S,2R)-2-(neopentylcarbamoyl)cyclobutyl)carbamoyl)phenoxy)-1-methylcyclohexane-1-carboxylic acid;

(1R,4s)-4-(2-fluoro-4-methoxy-5-(((1R,2S)-2-(neopentylcarbamoyl)cyclobutyl)carbamoyl)phenoxy)-1-methylcyclohexane-1-carboxylic acid;

(1R,4s)-4-(2-fluoro-5-(((1S,2R)-2-((4-fluoro-3-(pentafluoro-λ6-sulfaneyl)phenyl)carbamoyl)cyclobutyl)carbamoyl)-4-methoxyphenoxy)-1-methylcyclohexane-1-carboxylic acid;

(1R,4s)-4-(2-fluoro-5-(((1R,2S)-2-((4-fluoro-3-(pentafluoro-λ6-sulfaneyl)phenyl)carbamoyl)cyclobutyl)carbamoyl)-4-methoxyphenoxy)-1-methylcyclohexane-1-carboxylic acid;

(1R,4s)-4-(2-cyano-4-methoxy-5-(((1S,2R)-2-(((1-methylcyclobutyl)methyl)carbamoyl)cyclobutyl)carbamoyl)phenoxy)-1-methylcyclohexane-1-carboxylic acid;

(1R,4s)-4-(2-cyano-4-methoxy-5-(((1R,2S)-2-(((1-methylcyclobutyl)methyl)carbamoyl)cyclobutyl)carbamoyl)phenoxy)-1-methylcyclohexane-1-carboxylic acid;

(1R,4s)-4-(2-fluoro-5-(((3S,4S)-4-((4-fluoro-3-(pentafluoro-λ6-sulfaneyl)phenyl)carbamoyl)tetrahydro-2H-pyran-3-yl)carbamoyl)-4-methoxyphenoxy)-1-methylcyclohexane-1-carboxylic acid;

(1R,4s)-4-(2-fluoro-5-(((3R,4R)-4-((4-fluoro-3-(pentafluoro-λ6-sulfaneyl)phenyl)carbamoyl)tetrahydro-2H-pyran-3-yl)carbamoyl)-4-methoxyphenoxy)-1-methylcyclohexane-1-carboxylic acid;

(1R,4s)-4-(2-fluoro-4-methoxy-5-(((3S,4R)-4-(((1-methylcyclobutyl)methyl)carbamoyl)tetrahydrofuran-3-yl)carbamoyl)phenoxy)-1-methylcyclohexane-1-carboxylic acid;

(1R,4s)-4-(2-fluoro-4-methoxy-5-(((3R,4S)-4-(((1-methylcyclobutyl)methyl)carbamoyl)tetrahydrofuran-3-yl)carbamoyl)phenoxy)-1-methylcyclohexane-1-carboxylic acid;

(1R,4s)-4-(2-fluoro-4-methoxy-5-(((3S,4R)-4-(neopentylcarbamoyl)tetrahydrofuran-3-yl)carbamoyl)phenoxy)-1-(hydroxymethyl)cyclohexane-1-carboxylic acid;

(1R,4s)-4-(2-fluoro-4-methoxy-5-(((3R,4S)-4-(neopentylcarbamoyl)tetrahydrofuran-3-yl)carbamoyl)phenoxy)-1-(hydroxymethyl)cyclohexane-1-carboxylic acid;

(1R,4s)-4-(2-fluoro-4-methoxy-5-(((3S,4R)-4-(((1-methylcyclobutyl)methyl)carbamoyl)tetrahydrofuran-3-yl)carbamoyl)phenoxy)-1-(hydroxymethyl)cyclohexane-1-carboxylic acid;

(1R,4s)-4-(2-fluoro-4-methoxy-5-(((3R,4S)-4-(((1-methylcyclobutyl)methyl)carbamoyl)tetrahydrofuran-3-yl)carbamoyl)phenoxy)-1-(hydroxymethyl)cyclohexane-1-carboxylic acid;

(1R,4r)-4-(2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)-1-hydroxycyclohexane-1-carboxylic acid;

(1R,4r)-4-(2-fluoro-4-methoxy-5-(((1S,2S,3R,4R)-3-((3-((trifluoromethyl)sulfonyl)phenyl)carbamoyl)bicyclo[2.2.1]heptan-2-yl)carbamoyl)phenoxy)-1-hydroxycyclohexane-1-carboxylic acid;

(1R,4s)-4-(2-fluoro-4-methoxy-5-(((1S,2S,3R,4R)-3-((3-((trifluoromethyl)sulfonyl)phenyl)carbamoyl)bicyclo

[2.2.1]heptan-2-yl)carbamoyl)phenoxy)-1-(hydroxymethyl)cyclohexane-1-carboxylic acid;

(1R,4s)-4-(2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)-1-(hydroxymethyl)cyclohexane-1-carboxylic acid;

(1R,4s)-4-(2-fluoro-4-methoxy-5-(((1S,2S,3R,4R)-3-((3-((trifluoromethyl)sulfonyl)phenyl)carbamoyl)bicyclo[2.2.1]heptan-2-yl)carbamoyl)phenoxy)-1-methylcyclohexane-1-carboxylic acid;

(1R,4s)-4-(2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)-1-methylcyclohexane-1-carboxylic acid;

(1R,4s)-4-(2-cyano-4-fluoro-5-(((2S,3R)-3-(((1-methylcyclobutyl)methyl)carbamoyl)bicyclo[2.2.2]octan-2-yl)carbamoyl)phenoxy)-1-methylcyclohexane-1-carboxylic acid;

(1R,4s)-4-(2-cyano-4-fluoro-5-(((2R,3S)-3-(((1-methylcyclobutyl)methyl)carbamoyl)bicyclo[2.2.2]octan-2-yl)carbamoyl)phenoxy)-1-methylcyclohexane-1-carboxylic acid;

2'-fluoro-5'-(((1R,2S,3R,4S)-3-((4-fluoro-3-(trifluoromethyl)phenyl)carbamoyl)bicyclo[2.2.1]heptan-2-yl)carbamoyl)-4'-methoxy-[1,1'-biphenyl]-4-carboxylic acid;

2'-fluoro-5'-(((1S,2R,3S,4R)-3-((4-fluoro-3-(trifluoromethyl)phenyl)carbamoyl)bicyclo[2.2.1]heptan-2-yl)carbamoyl)-4'-methoxy-[1,1'-biphenyl]-4-carboxylic acid;

(1S,4s)-4-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-(((1-methoxycyclobutyl)methyl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-(((1-(methoxymethyl)cyclobutyl)methyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-(((1-cyanocyclobutyl)methyl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-fluoro-4-methoxy-5-(((1S,2R,3S,4R)-3-((3,3,3-trifluoropropyl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-(((R)-1,1,1-trifluoropropan-2-yl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-(cyclobutylcarbamoyl)bicyclo[2.2.1]heptan-2-yl)carbamoyl)-2-fluoro-4-methoxyphenoxy)-1-methylcyclohexane-1-carboxylic acid;

(1S,4s)-4-(5-(((1S,2R,3S,4R)-3-(cyclopentylcarbamoyl)bicyclo[2.2.1]heptan-2-yl)carbamoyl)-2-fluoro-4-methoxyphenoxy)-1-methylcyclohexane-1-carboxylic acid;

(1S,4s)-4-(5-(((1S,2R,3S,4R)-3-(bicyclo[1.1.1]pentan-1-ylcarbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-fluoro-4-methoxy-5-(((1S,2R,3S,4R)-3-(((S)-1,1,1-trifluoropropan-2-yl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-(tert-butylcarbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-fluoro-4-methoxy-5-(((1S,2R,3S,4R)-3-((1,1,1-trifluoro-2-methylpropan-2-yl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-(((R)-1-((trifluoromethyl)sulfonyl)piperidin-3-yl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-(((R)-1-((trifluoromethyl)sulfonyl)pyrrolidin-3-yl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-(((S)-1-((trifluoromethyl)sulfonyl)pyrrolidin-3-yl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-(((S)-1-((trifluoromethyl)sulfonyl)piperidin-3-yl)carbamoyl)bicyclo[2.2.1]heptan-2-yl)carbamoyl)phenoxy)-1-methylcyclohexane-1-carboxylic acid;

(1S,4s)-4-(2-fluoro-5-(((1S,2R,3S,4R)-3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid;

(1S,4s)-4-(2-fluoro-5-(((1S,2R,3S,4R)-3-(((1-fluorocyclobutyl)methyl)carbamoyl)bicyclo[2.2.1]heptan-2-yl)carbamoyl)-4-methoxyphenoxy)-1-methylcyclohexane-1-carboxylic acid;

(1S,4s)-4-(2-fluoro-4-methoxy-5-(((1S,2R,3S,4R)-3-((2-methoxy-2-methylpropyl)carbamoyl)bicyclo[2.2.1]heptan-2-yl)carbamoyl)phenoxy)-1-methylcyclohexane-1-carboxylic acid;

(1S,4s)-4-(2-fluoro-5-(((1S,2R,3S,4R)-3-((2-hydroxy-2-methylpropyl)carbamoyl)bicyclo[2.2.1]heptan-2-yl)carbamoyl)-4-methoxyphenoxy)-1-methylcyclohexane-1-carboxylic acid;

(1S,4s)-4-(2-fluoro-5-(((1S,2R,3S,4R)-3-((3-hydroxy-2,2-dimethylpropyl)carbamoyl)bicyclo[2.2.1]heptan-2-yl)carbamoyl)-4-methoxyphenoxy)-1-methylcyclohexane-1-carboxylic acid;

(1S,4s)-4-(2-fluoro-4-methoxy-5-(((1S,2R,3S,4R)-3-(((1-(trifluoromethyl)cyclobutyl)methyl)carbamoyl)bicyclo[2.2.1]heptan-2-yl)carbamoyl)phenoxy)-1-methylcyclohexane-1-carboxylic acid;

(1S,4s)-4-(2-fluoro-4-methoxy-5-(((1S,2R,3S,4R)-3-(((1-(trifluoromethyl)cyclopropyl)methyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-(((R)-3-cyano-3-methylbutan-2-yl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(5-(((1S,2R,3S,4R)-3-(((S)-3-cyano-3-methylbutan-2-yl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(5-(((1S,2R,3S,4R)-3-(((1-ethylcyclobutyl)methyl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-fluoro-4-methoxy-5-(((1S,2R,3S,4R)-3-((2,2,3,3,3-pentafluoropropyl)carbamoyl)bicyclo[2.2.1]heptan-2-yl)carbamoyl)phenoxy)-1-methylcyclohexane-1-carboxylic acid;

(1S,4s)-4-(5-(((1S,2R,3S,4R)-3-((3,3-difluorocyclobutyl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(5-(((1S,2R,3S,4R)-3-(((3,3-difluorocyclobutyl)methyl)carbamoyl)bicyclo[2.2.1]heptan-2-yl)carbamoyl)-2-fluoro-4-methoxyphenoxy)-1-methylcyclohexane-1-carboxylic acid;

(1S,4s)-4-(2-cyano-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid;

(1S,4s)-4-(2-cyano-5-(((1S,2R,3S,4R)-3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1R,2R,3S,4S)-3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid;

(1S,4s)-4-(2-cyano-5-(((1S,2R,3S,4R)-3-((3,3-difluorocyclobutyl)carbamoyl)bicyclo[2.2.1]heptan-2-yl)carbamoyl)-4-methoxyphenoxy)-1-methylcyclohexane-1-carboxylic acid; and (1S,4s)-4-(2-cyano-4-methoxy-5-(((1S,2R,3S,4R)-3-((3,3,3-trifluoro-2,2-dimethylpropyl)carbamoyl)bicyclo[2.2.1]heptan-2-yl)carbamoyl)phenoxy)-1-methylcyclohexane-1-carboxylic acid;

and pharmaceutically acceptable salts thereof.

In one embodiment there is provided 4-(2-fluoro-4-methoxy-5-((3-(((1-methylcyclobutyl)methyl)carbamoyl)bicyclo[2.2.1]heptan-2-yl)carbamoyl)phenoxy)-1-methylcyclohexane-1-carboxylic acid, or a pharmaceutically acceptable salt thereof.

In one embodiment there is provided 4-(2-cyano-4-methoxy-5-((3-(((1-methylcyclobutyl)methyl)carbamoyl)bicyclo[2.2.1]heptan-2-yl)carbamoyl)phenoxy)-1-methylcyclohexane-1-carboxylic acid, or a pharmaceutically acceptable salt thereof.

In one embodiment there is provided 4-(2-cyano-4-methoxy-5-((3-(neopentylcarbamoyl)bicyclo[2.2.1]heptan-2-yl)carbamoyl)phenoxy)-1-methylcyclohexane-1-carboxylic acid, or a pharmaceutically acceptable salt thereof.

In one embodiment there is provided 4-(2-cyano-5-((3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid, or a pharmaceutically acceptable salt thereof.

In one embodiment there is provided (1S,4s)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid, or a pharmaceutically acceptable salt thereof.

In one embodiment there is provided (1S,4s)-4-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid, or a pharmaceutically acceptable salt thereof.

In one embodiment there is provided (1S,4s)-4-(2-cyano-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid, or a pharmaceutically acceptable salt thereof.

In one embodiment there is provided (1S,4s)-4-(2-cyano-5-(((1S,2R,3S,4R)-3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid, or a pharmaceutically acceptable salt thereof.

In one embodiment there is provided (1S,4s)-4-(2-fluoro-4-methoxy-5-(((1R,2R,3S,4S)-3-(((1-methylcyclobutyl)methyl)carbamoyl)bicyclo[2.2.1]heptan-2-yl)carbamoyl)phenoxy)-1-methylcyclohexane-1-carboxylic acid, or a pharmaceutically acceptable salt thereof.

In one embodiment there is provided (1S,4s)-4-(2-cyano-4-methoxy-5-(((1R,2R,3S,4S)-3-(((1-methylcyclobutyl)methyl)carbamoyl)bicyclo[2.2.1]heptan-2-yl)carbamoyl)phenoxy)-1-methylcyclohexane-1-carboxylic acid, or a pharmaceutically acceptable salt thereof.

In one embodiment there is provided (1S,4s)-4-(2-cyano-4-methoxy-5-(((1R,2R,3S,4S)-3-(neopentylcarbamoyl)bicyclo[2.2.1]heptan-2-yl)carbamoyl)phenoxy)-1-methylcyclohexane-1-carboxylic acid, or a pharmaceutically acceptable salt thereof.

In one embodiment there is provided (1S,4s)-4-(2-cyano-5-(((1R,2R,3S,4S)-3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid, or a pharmaceutically acceptable salt thereof.

In one embodiment there is provided (1S,4s)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid.

In one embodiment there is provided (1S,4s)-4-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid.

In one embodiment there is provided (1S,4s)-4-(2-cyano-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid.

In one embodiment there is provided (1S,4s)-4-(2-cyano-5-(((1S,2R,3S,4R)-3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid.

In further embodiments there is provided any one of the Example compounds (as named hereinafter in the Experimental section), or a pharmaceutically acceptable salt thereof.

In further embodiments there is provided any one of the Example compounds (as named hereinafter in the Experimental section).

The compounds of Formula (I) may be prepared from the Intermediate compounds (as named or shown hereinafter in the Experimental section) using the methods described in the Experimental section. The skilled person will understand that alternative methods may also be used to prepare the compounds of Formula (I) from such Intermediate compounds.

Accordingly, in further embodiments there is provided any one of the Intermediate compounds (as named or shown hereinafter in the Experimental section).

Accordingly, in further embodiments there is provided any one of the Intermediate compounds (as named or shown hereinafter in the Experimental section), or a salt thereof.

Therefore, examples of just some of the above-mentioned embodiments are given below: In one embodiment there is provided Intermediate 75, or a salt thereof.

Therefore, in this case, there is provided (1R,2S,3R,4S)-3-(5-(((1s,4S)-4-(Tert-butoxycarbonyl)-4-methylcyclohexyl)oxy)-4-fluoro-2-methoxybenzamido)bicyclo[2.2.1]heptane-2-carboxylic acid, or a salt thereof.

In one embodiment there is provided Intermediate 68, or a salt thereof.

Therefore, in this case, there is provided (1R,2S,3R,4S)-3-(5-(((1s,4S)-4-Carboxy-4-methylcyclohexyl)oxy)-4- cyano-2-methoxybenzamido)bicyclo[2.2.1]heptane-2-carboxylic acid, or a salt thereof.

In one embodiment there is provided (1R,2S,3R,4S)-3-(5-(((1s,4S)-4-Carboxy-4-methylcyclohexyl)oxy)-4-cyano-2-methoxybenzamido)bicyclo[2.2.1]heptane-2-carboxylic acid, or a salt thereof.

In one embodiment there is provided Intermediate 5, or a salt thereof.

Therefore, in this case, there is provided Methyl 5-(1,3,6,2-dioxazaborocan-2-yl)-4-fluoro-2-methoxybenzoate, or a salt thereof.

In one embodiment there is provided Intermediate 11, or a salt thereof.

Therefore, in this case, there is provided Naphthalen-1-ylmethyl (1r,4r)-4-hydroxy-1-methylcyclohexane-1-carboxylate, or a salt thereof.

In one embodiment there is provided Intermediate 12, or a salt thereof.

Therefore, in this case, there is provided Methyl 4-fluoro-2-methoxy-5-(((1s,4s)-4-methyl-4-((naphthalen-1-ylmethoxy)carbonyl)cyclohexyl)oxy)benzoate, or a salt thereof.

In one embodiment there is provided Intermediate 35, or a salt thereof.

Therefore, in this case, there is provided (1R,2S,3R,4S)-3-(4-Cyano-5-hydroxy-2-methoxybenzamido)-N-((1-methylcyclobutyl)methyl)bicyclo[2.2.1]heptane-2-carboxamide, or a salt thereof.

In one embodiment there is provided (1S,2S,3R,4R)-3-(4-Cyano-5-hydroxy-2-methoxybenzamido)-N-((1-methylcyclobutyl)methyl)bicyclo[2.2.1]heptane-2-carboxamide, or a salt thereof.

In one embodiment there is provided (1R,2S,3R,4S)-3-(4-fluoro-5-hydroxy-2-methoxybenzamido)-N-((1-methylcyclobutyl)methyl)bicyclo[2.2.1]heptane-2-carboxamide, or a salt thereof.

In one embodiment there is provided (1S,2S,3R,4R)-3-(4-fluoro-5-hydroxy-2-methoxybenzamido)-N-((1-methylcyclobutyl)methyl)bicyclo[2.2.1]heptane-2-carboxamide, or a salt thereof.

In one embodiment there is provided Intermediate 13, or a salt thereof.

Therefore, in this case, there is provided 4-Fluoro-2-methoxy-5-(((1s,4s)-4-methyl-4-((naphthalen-1-ylmethoxy)carbonyl)cyclohexyl)oxy)benzoic acid, or a salt thereof.

In one embodiment there is provided Intermediate 15, or a salt thereof.

Therefore, in this case, there is provided Methyl (1S,2S,3R,4R)-3-(4-fluoro-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylate, or a salt thereof.

In one embodiment there is provided Methyl (1R,2S,3R,4S)-3-(4-fluoro-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylate, or a salt thereof.

In one embodiment there is provided Intermediate 16, or a salt thereof.

Therefore, in this case, there is provided (1S,2S,3R,4R)-3-(4-Fluoro-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylic acid, or a salt thereof.

In one embodiment there is provided (1R,2S,3R,4S)-3-(4-Fluoro-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylic acid, or a salt thereof.

In one embodiment there is provided Intermediate 584, or a salt thereof.

Therefore, in this case, there is provided (1S,2S,3R,4R)-3-(4-cyano-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylic acid, or a salt thereof.

In one embodiment there is provided (1R,2S,3R,4S)-3-(4-cyano-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylic acid, or a salt thereof.

In one embodiment there is provided Intermediate 20, or a salt thereof.

Therefore, in this case, there is provided tert-Butyl ((1R,2R,3S,4S)-3-(((1-methylcyclobutyl)methyl)carbamoyl)bicyclo[2.2.1]hept-5-en-2-yl)carbamate, or a salt thereof.

In one embodiment there is provided tert-Butyl ((1R,2R,3S,4S)-3-(((1-methylcyclobutyl)methyl)carbamoyl)bicyclo[2.2.1]hept-5-en-2-yl)carbamate, or a salt thereof.

In one embodiment there is provided Intermediate 21, or the free base or a salt thereof.

Therefore, in this case, there is provided (1R,2S,3R,4S)-3-Amino-N-((1-methylcyclobutyl)methyl)bicyclo[2.2.1]heptane-2-carboxamide hydrochloride, or the free base or a salt thereof.

In one embodiment there is provided (1S,2S,3R,4R)-3-Amino-N-((1-methylcyclobutyl)methyl)bicyclo[2.2.1]heptane-2-carboxamide hydrochloride, or the free base or a salt thereof.

In one embodiment there is provided Intermediate 22, or the free base or a salt thereof.

Therefore, in this case, there is provided (1R,2S,3R,4S)-3-Amino-N-((1-methylcyclobutyl)methyl)bicyclo[2.2.1]heptane-2-carboxamide hydrochloride, or the free base or a salt thereof.

In one embodiment there is provided (1S,2S,3R,4R)-3-Amino-N-((1-methylcyclobutyl)methyl)bicyclo[2.2.1]heptane-2-carboxamide hydrochloride, or the free base or a salt thereof.

In one embodiment there is provided Intermediate 224, or the free base or a salt thereof.

Therefore, in this case, there is provided (1R,2S,3R,4S)-3-amino-N-neopentylbicyclo[2.2.1]heptane-2-carboxamide hydrochloride, or the free base or a salt thereof.

In one embodiment there is provided (1S,2S,3R,4R)-3-amino-N-neopentylbicyclo[2.2.1]heptane-2-carboxamide hydrochloride, or the free base or a salt thereof.

In one embodiment there is provided Intermediate 223, or the free base or a salt thereof.

Therefore, in this case, there is provided (1R,2S,3R,4S)-3-amino-N-(3-fluorobicyclo[1.1.1]pentan-1-yl)bicyclo[2.2.1]heptane-2-carboxamide hydrochloride, or the free base or a salt thereof.

In one embodiment there is provided (1S,2S,3R,4R)-3-amino-N-(3-fluorobicyclo[1.1.1]pentan-1-yl)bicyclo[2.2.1]heptane-2-carboxamide hydrochloride, or the free base or a salt thereof.

In one embodiment there is provided Intermediate 73, or a salt thereof.

Therefore, in this case, there is provided 5-(((1s,4s)-4-(Tert-butoxycarbonyl)-4-methylcyclohexyl)oxy)-4-fluoro-2-methoxybenzoic acid, or a salt thereof.

In one embodiment there is provided Intermediate 69, or a salt thereof.

Therefore, in this case, there is provided Methyl 4-cyano-2-methoxy-5-(((1s,4s)-4-methyl-4-((naphthalen-1-ylmethoxy)carbonyl)cyclohexyl)oxy)benzoate, or a salt thereof.

In one embodiment there is provided Intermediate 70, or a salt thereof.

Therefore, in this case, there is provided 4-Cyano-2-methoxy-5-(((1s,4s)-4-methyl-4-((naphthalen-1-ylmethoxy)carbonyl)cyclohexyl)oxy)benzoic acid, or a salt thereof.

In one embodiment there is provided Intermediate 71, or a salt thereof.

Therefore, in this case, there is provided Methyl (1S,2S,3R,4R)-3-(4-cyano-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylate, or a salt thereof.

In one embodiment there is provided Methyl (1R,2S,3R,4S)-3-(4-cyano-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylate, or a salt thereof.

In one embodiment there is provided Intermediate 72, or a salt thereof.

Therefore, in this case, there is provided (1S,4s)-4-(2-Cyano-4-methoxy-5-(((1S,2R,3S,4R)-3-(methoxycarbonyl)bicyclo[2.2.1]heptan-2-yl)carbamoyl)phenoxy)-1-methylcyclohexane-1-carboxylic acid, or a salt thereof.

In one embodiment there is provided (1S,4s)-4-(2-Cyano-4-methoxy-5-(((1R,2R,3S,4S)-3-(methoxycarbonyl)bicyclo[2.2.1]heptan-2-yl)carbamoyl)phenoxy)-1-methylcyclohexane-1-carboxylic acid, or a salt thereof.

In one embodiment there is provided Intermediate 403, or a salt thereof.

Therefore, in this case, there is provided (1R,2S,3R,4S)-3-(5-(((1s,4S)-4-Carboxy-4-methylcyclohexyl)oxy)-4-fluoro-2-methoxybenzamido)bicyclo[2.2.1]heptane-2-carboxylic acid, or a salt thereof.

In one embodiment there is provided (1S,2S,3R,4R)-3-(5-(((1s,4S)-4-Carboxy-4-methylcyclohexyl)oxy)-4-fluoro-2-methoxybenzamido)bicyclo[2.2.1]heptane-2-carboxylic acid, or a salt thereof.

In one embodiment there is provided Intermediate 127, or a salt thereof.

Therefore, in this case, there is provided Methyl (1R,2S,3R,4S)-3-(5-bromo-4-fluoro-2-methoxybenzamido)bicyclo[2.2.1]heptane-2-carboxylate, or a salt thereof.

In one embodiment there is provided Methyl (1S,2S,3R,4R)-3-(5-bromo-4-fluoro-2-methoxybenzamido)bicyclo[2.2.1]heptane-2-carboxylate, or a salt thereof.

In one embodiment there is provided Intermediate 128, or a salt thereof.

Therefore, in this case, there is provided (1R,2S,3R,4S)-3-(5-Bromo-4-fluoro-2-methoxybenzamido)bicyclo[2.2.1]heptane-2-carboxylic acid, or a salt thereof.

In one embodiment there is provided (1S,2S,3R,4R)-3-(5-Bromo-4-fluoro-2-methoxybenzamido)bicyclo[2.2.1]heptane-2-carboxylic acid, or a salt thereof.

In one embodiment there is provided Intermediate 136, or a salt thereof.

Therefore, in this case, there is provided Benzyl 5-(((1s,4s)-4-(tert-butoxycarbonyl)-4-methylcyclohexyl)oxy)-4-fluoro-2-methoxybenzoate, or a salt thereof.

In one embodiment there is provided Intermediate 521, or a salt thereof.

Therefore, in this case, there is provided (1s,4s)-4-(2-fluoro-4-methoxy-5-(methoxycarbonyl)phenoxy)-1-methylcyclohexane-1-carboxylic acid, or a salt thereof.

In one embodiment there is provided a process for preparing a compound of Formula (I), or pharmaceutically acceptable salt thereof, using an Intermediate compound (as described herein, or named or shown hereinafter in the Experimental section), or a salt thereof.

In one embodiment there is provided a process for preparing (1S,4s)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid, or pharmaceutically acceptable salt thereof, using an Intermediate compound (as described herein, or named or shown hereinafter in the Experimental section), or a salt thereof.

In one embodiment there is provided a process for preparing (1S,4s)-4-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid, or pharmaceutically acceptable salt thereof, using an Intermediate compound (as described herein, or named or shown hereinafter in the Experimental section), or a salt thereof.

In one embodiment there is provided a process for preparing (1S,4s)-4-(2-cyano-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid, or pharmaceutically acceptable salt thereof, using an Intermediate compound (as described herein, or named or shown hereinafter in the Experimental section), or a salt thereof.

In one embodiment there is provided a process for preparing (1S,4s)-4-(2-cyano-5-(((1S,2R,3S,4R)-3-((3-fluorobicyclo[1.1.1]pentan-1-yl)carbamoyl)bicyclo[2.2.1]heptan-2-yl)carbamoyl)-4-methoxyphenoxy)-1-methylcyclohexane-1-carboxylic acid, or pharmaceutically acceptable salt thereof, using an Intermediate compound (as described herein, or named or shown hereinafter in the Experimental section), or a salt thereof.

Terms not specifically defined herein should be understood to have the meanings that would be given to them by one of skill in the art in light of the disclosure and the context. As used in the specification, however, unless specified to the contrary, the following terms have the meaning indicated and the following conventions are adhered to. In the groups defined below, the number of carbon atoms is often specified preceding the group, for example, $C_{1-4}$ alkyl means an alkyl group or radical having 1 to 4 carbon atoms.

"Alkyl" means a saturated aliphatic branched or straight-chain hydrocarbon group having the specified number of carbon atoms. For example, $C_{1-4}$ alkyl means a group having from 1-4 carbon atoms in a linear or branched arrangement, such as —$CH_2CH_2CH_2CH_3$ or —$CH_2CH(CH_3)_2$. An "Alkylene" is a divalent alkyl group.

"Alkoxy" means an alkyl group attached through an oxygen linking atom. For example, $C_{1-3}$ alkoxy includes methoxy, ethoxy and propoxy.

"Aryl" means an aromatic monocyclic or polycyclic hydrocarbon ring system having the specified number of carbon atoms. For example, $C_{6-10}$ aryl includes groups such as phenyl and naphthalenyl. An "Arylene" is a divalent aryl group.

"Cycloalkyl" means a monocyclic, bicyclic, polycyclic, fused, bridged, or spirocyclic saturated aliphatic hydrocarbon group having the specified number of carbon atoms. For example, cycloalkyl includes groups such as cyclohexyl, adamantyl, spiro[3.3]heptanyl, bicyclo[2.2.1]heptanyl and decahydronaphthalenyl. As a further example, monocyclic $C_{3-6}$ cycloalkyl means a group having from 3-6 carbon atoms arranged in a monocyclic ring, such as cyclopropyl and cyclohexyl. A "Cycloalkylene" is a divalent cycloalkyl group.

"Cycloalkoxy" means a cycloalkyl group attached through an oxygen linking atom. For example, $C_{3-4}$ cycloalkoxy includes cyclopropoxy and cyclobutoxy.

"Cycloalkenyl" means a monocyclic, bicyclic, polycyclic, fused, bridged, or spirocyclic unsaturated aliphatic hydrocarbon group having the specified number of carbon atoms. For example, cycloalkenyl includes groups such as cyclohexenyl, spiro[4.4]non-2-enyl, bicyclo[2.2.1]hept-2-enyl and 1,2,3,4,4a,5,8,8a-octahydronaphthalenyl. As a further example, monocyclic $C_{5-6}$ cycloalkenyl means a group having from 3-6 carbon atoms arranged in a monocyclic ring, such as cyclopentenyl and cyclohexenyl. A "Cycloalkenylene" is a divalent cycloalkenyl group.

"Heteroaryl" means an aromatic monocyclic or polycyclic ring system containing carbon atoms and the specified number of heteroatoms (such as O, N or S) in the ring structure, and having the specified total number of atoms in the ring structure. For example, 5- to 10-membered heteroaryl having 1-4 heteroatoms independently selected from nitrogen, oxygen and sulfur includes groups such as indolyl, pyridyl, thiazolyl and oxazolyl. A "Heteroarylene" is a divalent heteroaryl group.

"Heterocycloalkyl" means a monocyclic, bicyclic, polycyclic, fused, bridged, or spirocyclic saturated group containing carbon atoms and the specified number of heteroatoms (such as O, N or S) in the ring structure, and having the specified total number of atoms in the ring structure. For example, 4- to 8-membered heterocycloalkyl having 1-3 heteroatoms independently selected from oxygen, nitrogen and sulfur includes groups such as pyrrolidinyl, oxetanyl, 2-oxa-6-azaspiro[3.3]heptanyl, hexahydro-2H-thieno[2,3-c]pyrrolyl and 7-oxabicyclo[2.2.1]heptanyl. A "Heterocycloalkylene" is a divalent heterocycloalkyl group.

"Heterocycloalkenyl" means a monocyclic, bicyclic, polycyclic, fused, bridged, or spirocyclic unsaturated group containing carbon atoms and the specified number of heteroatoms (such as O, N or S) in the ring structure, and having the specified total number of carbon atoms and heteroatoms in the ring structure. For example, 4- to 8-membered heterocycloalkenyl having 1-3 heteroatoms independently selected from oxygen, nitrogen and sulfur includes groups such as 2,5-dihydro-1H-pyrrolyl, 7-oxabicyclo[2.2.1]hept-2-enyl and 4,5,6,6a-tetrahydro-2H-thieno[2,3-c]pyrrol-3-yl. A "Heterocycloalkenylene" is a divalent heterocycloalkenyl group.

"Heteroalkyl" means an alkyl group, as defined herein, in which one or more of the constituent carbon atoms have been replaced by nitrogen, oxygen, or sulfur. The specified number of members in the heteroalkyl group refers to the total number of carbon atoms and heteroatoms in the chain. For example, —CH$_2$OCH$_2$CH$_3$ and —CH$_2$N(CH$_3$)CH$_2$CH$_3$. As a further example, a 4-membered heteroalkyl group containing one heteroatom selected from oxygen and sulfur includes groups such as —CH$_2$OCH$_2$CH$_3$, —SCH(CH$_3$)$_2$, and —CH(CH$_3$)CH$_2$OH. A "Heteroalkylene" is a divalent heteroalkyl group.

"Halogen" means a fluorine (fluoro), chlorine (chloro), bromine (bromo), or iodine (iodo) radical.

The chemical names of compounds described in this specification were generated using ChemDraw® Professional version 19.0.0.22 from PerkinElmer®. The skilled person will understand that different chemical naming software may generate different chemical names for a particular compound. In case a compound described herein is depicted in form of a chemical name and as a formula, the formula shall prevail in case of any discrepancy.

In substituents such as —OH and —CN, "—" denotes the point of attachment of the substituent to the remainder of the molecule.

In fragments such as

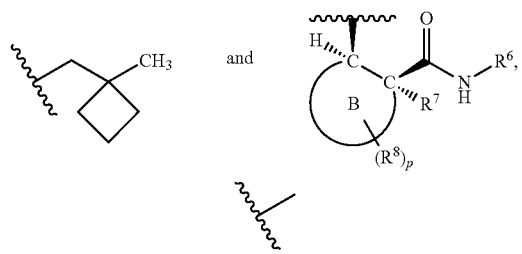

designates the point of attachment of the fragment to the remainder of the molecule.

The term "pharmaceutically acceptable" is used to specify that an object (for example a salt, dosage form or excipient) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich:Wiley-VCH/VHCA, 2002.

A suitable pharmaceutically acceptable salt of a compound of Formula (I) is, for example, an acid-addition salt or a base-addition salt. An acid addition salt of a compound of Formula (I) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid and phosphoric acid. An acid addition salt may also be formed using an organic acid selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

Therefore, in one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid or para-toluenesulfonic acid salt.

Compounds described in this specification may form base addition salts. A base-addition salt of a compound of Formula (I) may be formed by bringing the compound into contact with a suitable inorganic or organic base under conditions known to the skilled person. For example, it may be possible to make an alkali metal (such as sodium, potassium, or lithium) or an alkaline earth metal (such as a calcium) salt by treating a compound with an alkali metal or alkaline earth metal hydroxide or alkoxide (e.g., an ethoxide or methoxide) or a suitably basic organic amine (e.g., a choline or meglumine) in an aqueous medium. Therefore, in one embodiment there is provided a compound of Formula (I) or a pharmaceutically acceptable salt thereof, where the pharmaceutically acceptable salt is a sodium, potassium, lithium, calcium, choline or meglumine salt.

In one embodiment there is provided a compound of Formula (I), or a pharmaceutically acceptable salt thereof.

In one embodiment there is provided a compound of Formula (I).

In one embodiment there is provided a pharmaceutically acceptable salt of a compound of Formula (I).

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. All such solvated and unsolvated forms of compounds of Formula (I) are encompassed herein.

Atoms of the compounds and salts described in this specification may exist as their isotopes. All compounds of Formula (I) where an atom is replaced by one or more of its isotopes (for example a compound of Formula (I) where one or more carbon atom is an $^{11}C$ or $^{13}C$ carbon isotope, or where one or more hydrogen atoms is a 2H or $^{3}H$ isotope) are encompassed herein.

Compounds of the application may exist in one or more geometrical, optical, enantiomeric, and diastereomeric forms, including, but not limited to, cis- and trans-forms, E- and Z-forms, and R-, S- and meso-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods.

The compounds of Formula (I) may include one or more chiral centres. To the extent a structure or chemical name in this specification does not indicate chirality, the structure or name is intended to encompass any single stereoisomer corresponding to that structure or name, as well as any mixture of stereoisomers (e.g. a racemate). Where a structure in this specification includes bonds drawn as solid and hashed wedges (i.e. — and ⋯), it is intended that the solid and hashed wedges indicate the absolute configuration of a chiral centre unless the "or" or "&" chiral flags are present at the chiral centre. Groups of related chiral flags are indicated with the same integer, for example "or1", "&1", "or2", "&2" etc. The skilled person will understand the meaning of chiral flags at a chiral centres. For example, the structure

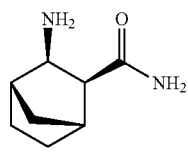 [SMILES: NC(=O)[C@H]1[C@@H]2CC[C@@H](C2)[C@H]1N]

indicates that the compound is a single stereoisomer with the defined absolute configuration. As a further example, the structure

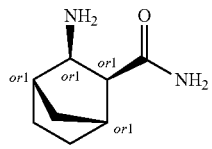 [SMILES: NC(=O)[C@H]1[C@@H]2CC[C@@H](C2)[C@H]1N]

indicates that the compound is a single stereoisomer with the defined relative configuration at the flagged chiral centres, but unknown absolute configuration at the flagged chiral centres. As a further example, the structure

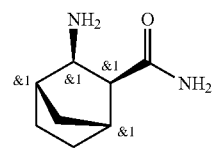 [SMILES: NC(=O)[C@H]1[C@@H]2CC[C@@H](C2)[C@H]1N]

indicates that the compound is a mixture of stereoisomers having the defined relative configuration at the flagged chiral centres.

It is well-known in the art how such optically-active forms can be separated. For example, a single stereoisomer can be obtained by isolating it from a mixtures of isomers (e.g. a racemate) using, for example, chiral chromatographic separation. In other embodiments, a single stereoisomer is obtained through direct synthesis from, for example, a chiral starting material.

According to one embodiment, there is provided a compound of Formula (I), or a pharmaceutically acceptable salt thereof, which is a single enantiomer being in enantiomer excess (% ee) of ≥95%, ≥98%, or ≥99%. Conveniently a single enantiomer is present in an enantiomer excess of ≥99%.

According to one embodiment, there is provided a compound of Formula (I), or a pharmaceutically acceptable salt thereof, which is a single enantiomer being in enantiomer excess (% ee) in the range 95 to 100%.

According to one embodiment, there is provided a pharmaceutical composition, which comprises a compound of Formula (I) which is a single enantiomer being in enantiomer excess (% ee) of ≥95%, ≥98%, or ≥99% or a pharmaceutically acceptable salt thereof, in association with a pharmaceutically acceptable diluent or carrier. Conveniently, the single enantiomer is present in an enantiomer excess of ≥99%.

According to one embodiment, there is provided a pharmaceutical composition, which comprises a compound of Formula (I) which is a single enantiomer being in enantiomer excess (% ee) in the range 95 to 100%, or a pharmaceutically acceptable salt thereof, in association with a pharmaceutically acceptable diluent or carrier.

Compounds of the application may exist in one or more tautomeric forms, including, but not limited to, keto-, and enol-forms. A reference to a particular compound includes all tautomeric forms, including mixtures thereof. Accordingly, a structure depicted herein as one tautomer is intended to also include other tautomers.

The compounds of Formula (I) may be administered in the form of a prodrug, which is a compound which that is broken down in the human or animal body to release the compound of Formula (I). Such, pharmaceutically acceptable, prodrugs of compounds for Formula (I) also form an embodiment. Various forms of prodrugs are known in the art. For example, see a) Design of Pro-drugs, edited by H. Bundgaard, (Elsevier, 1985);

b) A Textbook of Drug Design and Development, edited by Krogsgaard-Larsen and H. Bundgaard, Chapter 5 "Design and Application of Pro-drugs", by H. Bundgaard p. 113-191 (1991);

c) H. Bundgaard, *Advanced Drug Delivery Reviews*, 8, 1-38 (1992);

d) H. Bundgaard, et al., *Journal of Pharmaceutical Sciences*, 77, 285 (1988); and e) N. Kakeya, et al., *Chem. Pharm. Bull.*, 32, 692 (1984).

In one embodiment there is provided a prodrug of a compound of Formula (I) as herein defined, or a pharmaceutically acceptable salt thereof.

In one embodiment there is provided a prodrug of a compound of Formula (I) as herein defined, wherein said prodrug is a compound of Formula (I) as herein defined except that $R^1$ is —COO($C_{1-4}$ alkyl), or a pharmaceutically acceptable salt thereof.

In one embodiment there is provided an N-oxide of a compound of Formula (I) as herein defined, or a prodrug or pharmaceutically acceptable salt thereof.

As a result of their modulation of RXFP1, the compounds of Formula (I), and pharmaceutically acceptable salts thereof are expected to be useful in therapy.

The term "therapy" is intended to have its normal meaning of dealing with a disease or condition in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease or condition and secondary prophylaxis whereby the disease or condition has already developed and the patient is temporarily or permanently protected against exacerbation or worsening of the disease or condition, or the development of new symptoms associated with the disease or condition.

The term "treatment" is used synonymously with "therapy". Similarly the term "treat" can be regarded as "applying therapy" where "therapy" is as defined herein.

Accordingly, the compounds or pharmaceutical compositions described herein may be used in therapy, for example for treating a disease or disorder. Also provided is a method of treating a disease or disorder comprising administering to a subject or patient in need thereof a therapeutically effective amount of the compounds described herein.

It will be understood that the compounds described herein may be used in the treatment of cardiovascular diseases, for example for the treatment of heart failure.

As used herein, the term "heart failure" includes acute heart failure, chronic heart failure (CHF) and acute decompensated heart failure (ADHF). The term "heart failure" may also include more specific diagnoses such as heart failure with preserved ejection fraction (HFpEF), heart failure with mid-range ejection fraction or heart failure with reduced ejection fraction (HFrEF).

The compounds described herein may also be used in the treatment of kidney disease (including chronic kidney disease), acute kidney injury, lung disease and fibrotic disorders, for example fibrotic disorders of the kidney, heart, lung and liver, and in wound healing (Sherwood O D (2004) *Endocrine Reviews* 25(2): 205-234). The compounds described herein may also be used in the reversal of insulin resistance in diabetic patients (Bonner J S et al. (2013) *Diabetes* 62(9):3251-3260). The compounds described herein may also be used in the treatment of various forms of pulmonary hypertension. The compounds described herein may also be used in the treatment of disorders that are a result of or a cause of arterial stiffness, reduced arterial elasticity, reduced arterial compliance and distensibility including hypertension, kidney disease, peripheral arterial disease, carotid and cerebrovascular disease (i.e. stroke and dementia), diabetes, microvascular disease resulting in end organ damage, coronary artery disease, and heart failure. The compounds described herein may also be used in the treatment of pre-eclampsia.

In one embodiment there is provided a compound of Formula (I), or a pharmaceutically acceptable salt thereof, for use in therapy.

In one embodiment there is provided a compound of Formula (I), or a pharmaceutically acceptable salt thereof, for use in the treatment of a disease or condition selected from the group consisting of heart failure, heart failure with preserved ejection fraction, heart failure with mid-range ejection fraction, heart failure with reduced ejection fraction, chronic kidney disease and acute kidney injury.

In one embodiment there is provided a compound of Formula (I), or a pharmaceutically acceptable salt thereof, for use in the treatment of heart failure.

In one embodiment there is provided a compound of Formula (I), or a pharmaceutically acceptable salt thereof, for use in the treatment of heart failure with preserved ejection fraction, heart failure with mid-range ejection fraction, and/or heart failure with reduced ejection fraction.

In one embodiment there is provided a compound of Formula (I), or a pharmaceutically acceptable salt thereof, for use in the treatment of chronic kidney disease and/or acute kidney injury.

In one embodiment there is provided the use of the compound of Formula (I), or a pharmaceutically acceptable salt thereof, for the manufacture of a medicament for the treatment of a disease or condition selected from the group consisting of heart failure, heart failure with preserved ejection fraction, heart failure with mid-range ejection fraction, heart failure with reduced ejection fraction, chronic kidney disease and acute kidney injury.

The term "therapeutically effective amount" refers to an amount of a compound of Formula (I) as described in any of the embodiments herein which is effective to provide "therapy" in a subject, or to "treat" a disease or condition in a subject. The therapeutically effective amount may cause any of the changes observable or measurable in a subject as described in the definition of "therapy", "treatment" and "prophylaxis" above. As recognized by those skilled in the art, effective amounts may vary depending on route of administration, excipient usage, and co-usage with other agents. For example, where a combination therapy is used, the amount of the compound of Formula (I) or pharmaceutically acceptable salt described in this specification and the amount of the other pharmaceutically active agent(s) are, when combined, jointly effective to treat a targeted disorder or condition in the subject. In this context, the combined amounts are in a "therapeutically effective amount" if they are, when combined, sufficient to decrease the symptoms of a disease or condition responsive to modulation and/or agonism of RXFP1 as described above. Typically, such amounts may be determined by one skilled in the art by, for example, starting with the dosage range described in this specification for the compound of Formula (I) or pharmaceutically acceptable salt thereof and an approved or otherwise published dosage range(s) of the other pharmaceutically active compound(s).

"Subjects" include, for example, mammals, for example, humans.

In one embodiment there is provided a method for treating a disease or condition selected from the group consisting of heart failure, heart failure with preserved ejection fraction, heart failure with mid-range ejection fraction, heart failure with reduced ejection fraction, chronic kidney disease and acute kidney injury.

The compounds of Formula (I), and pharmaceutically acceptable salts thereof, may be administered as pharmaceutical compositions, comprising one or more pharmaceutically acceptable excipients.

Therefore, in one embodiment there is provided a pharmaceutical composition comprising a compound of Formula (I), or a pharmaceutically acceptable salt thereof, and at least one pharmaceutically acceptable excipient.

The excipient(s) selected for inclusion in a particular composition will depend on factors such as the mode of administration and the form of the composition provided. Suitable pharmaceutically acceptable excipients are well known to persons skilled in the art and are described, for example, in the *Handbook of Pharmaceutical Excipients*, Sixth edition, Pharmaceutical Press, edited by Rowe, Ray C; Sheskey, Paul J; Quinn, Marian. Pharmaceutically acceptable excipients may function as, for example, adjuvants, diluents, carriers, stabilisers, flavourings, colorants, fillers, binders, disintegrants, lubricants, glidants, thickening agents and coating agents. As persons skilled in the art will appreciate, certain pharmaceutically acceptable excipients may serve more than one function and may serve alternative functions depending on how much of the excipient is present in the composition and what other excipients are present in the composition.

The pharmaceutical compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing), or as a suppository for rectal dosing. The compositions may be obtained by conventional procedures well known in the art. Compositions intended for oral use may contain additional components, for example, one or more colouring, sweetening, flavouring and/or preservative agents.

The compound of Formula (I) will normally be administered to a subject at a unit dose within the range 2.5-5000 mg/m$^2$ body area of the subject, or approximately 0.05-100 mg/kg, and this normally provides a therapeutically-effective dose. A unit dose form such as a tablet or capsule will usually contain, for example 0.1-400 mg of active ingredient. The daily dose will necessarily be varied depending upon the host treated, the particular route of administration, any therapies being co-administered, and the severity of the disease or condition being treated.

The pharmaceutical compositions described herein comprise compounds of Formula (I), or a pharmaceutically acceptable salt thereof, and are therefore expected to be useful in therapy.

As such, in one embodiment there is provided a pharmaceutical composition for use in therapy, comprising a compound of Formula (I), or a pharmaceutically acceptable salt thereof, and at least one pharmaceutically acceptable excipient.

In the formulation of drug compositions, it is important for the drug substance to be in a form in which it can be conveniently handled and processed. This is of importance, not only from the point of view of obtaining a commercially viable manufacturing process, but also from the point of view of subsequent manufacture of pharmaceutical formulations (e.g. oral dosage forms such as tablets) comprising the active compound.

The different physical properties of the crystalline forms with respect to each other and with respect to the non-crystalline state may influence markedly the chemical and pharmaceutical processing of a compound, particularly when the compound is prepared or used on an industrial scale.

Further, in the manufacture of oral drug compositions, it is important that a reliable and reproducible plasma concentration profile of drug is provided following administration to a patient. Inter-patient variability in the absorption profile of a drug within the stomach, intestine or bloodstream can have an effect on drug safety and efficacy.

Chemical stability, solid state stability and "shelf life" of the active ingredients are also very important factors. The drug substance, and compositions containing it, should be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically pure as possible.

Amorphous materials may present problems in this regard. For example, such materials are typically difficult to handle and to formulate, provide for unreliable solubility, and are often found to be unstable and chemically impure.

The skilled person will appreciate that, if a drug can be readily obtained in a stable crystalline form, the above problems may be solved.

Thus, in the manufacture of commercially viable, and pharmaceutically acceptable, drug compositions, it is important, wherever possible, to provide drug in a crystalline, and stable, form.

It is to be noted, however, that this goal is not always achievable. Indeed, typically, it is not possible to predict, from molecular structure alone, what the crystallisation behaviour of a compound, either as such or in the form of a salt, will be. This can only be determined empirically.

In one embodiment, certain compounds and salts thereof may be prepared in crystalline forms. These crystalline forms may be characterised as being a particular polymorphic form. When it is stated that an embodiment relates to a crystalline form, the degree of crystallinity is conveniently greater than about 60%, more conveniently greater than about 80%, preferably greater than about 90% and more preferably greater than about 95%. Most preferably the degree of crystallinity is greater than about 98%.

The specific solid forms described herein provide X-ray powder diffraction patterns substantially the same as the X-ray powder diffraction patterns shown in the Figures and have the various 2-theta values as described herein. It will be understood that the 2-theta values of a X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the solid forms described herein are not limited to the crystals that provide X-ray powder diffraction patterns that are identical to the X-ray powder diffraction pattern shown in the Figures, and any crystals providing X-ray powder diffraction patterns substantially the same as those shown in the Figures fall within the scope of the embodiments described herein. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 μm in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures). The peak intensities are described herein as vs (very strong), s (strong), m (medium) and w (weak) and correspond to % relative intensity (based on the most intense peak) of 25-100%, 10-25%, 3-10% and 1-3%, respectively. The relative intensities are derived from diffractograms measured with fixed slits.

Generally, a measurement error of a diffraction angle in an X-ray powder diffractogram is about 5% or less, in particular plus or minus 0.5° 2-theta, and such degree of a measurement error should be taken into account when considering the X-ray powder diffraction patterns in the Figures herein when reading the data described herein. Furthermore, it should be understood that intensities may fluctuate depending on experimental conditions and sample preparation (preferred orientation).

The X-ray powder diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-ray Diffraction Procedures, John Wiley & Sons, New York.

X-ray powder diffraction data was measured with Corundum as an internal reference. The X-ray powder diffraction (referred to herein as XRPD) pattern was determined by mounting a sample on a zero background holder single silicon crystal and spreading out the sample into a thin layer. The powder X-ray diffraction was recorded with a theta-two theta scan axis and in one dimensional scan with Rigaku Miniflex 600 (wavelength of X-rays 1.5418 Å nickel-filtered Cu $K_\alpha$ radiation, 40 kV, 15 mA) equipped with D/Tex detector. Automatic variable divergence and anti scattering slits were used, and the samples were rotated at 80 revolution per minute during measurement. Samples were scanned from 2.4-50° 2-theta using a 0.01° and 1°/min step width and scan speed respectively.

In this specification (1S,4s)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid (Example 1) is also referred to as "Compound X". Several useful crystalline polymorphic forms have subsequently been produced using the conditions described in Example 1. In all of the embodiments relating to solid forms recited herein, the peaks of the X-ray diffraction patterns are measured using Cu $K_\alpha$ radiation.

Therefore in one embodiment there is provided polymorphic Form A of Compound X. This polymorphic form may be characterised in that it provides at least one of the following 2θ values measured using Cu $K_\alpha$ radiation: 7.5, 10.7, 12.8, 14.5 and 15.8°.

Polymorphic Form A of Compound X is characterised in providing an X-ray powder diffraction pattern, substantially as shown in FIG. 1.

The ten most prominent X-Ray powder diffraction peaks for this polymorphic form [Angle 2-theta (2θ), Intensity] are: 7.5 (s), 10.3 (m), 10.7 (s), 12.8 (s), 14.5 (vs), 15.3 (s), 15.8 (s), 17.5 (m), 19.6 (s) and 21.3 (s).

In one embodiment there is provided the polymorphic Form A of Compound X, which has an X-ray powder diffraction pattern with at least five specific peaks at about 2-theta=7.5, 10.7, 12.8, 14.5 and 15.8°.

In one embodiment there is provided the polymorphic Form A of Compound X, which has an X-ray powder diffraction pattern with specific peaks at about 2-theta=7.5, 10.3, 10.7, 12.8, 14.5, 15.3, 15.8, 17.5, 19.6, and 21.3°.

In one embodiment there is provided polymorphic Form A of Compound X which has an X-ray powder diffraction pattern substantially the same as the X-ray powder diffraction pattern shown in FIG. 1.

In one embodiment there is provided polymorphic Form A of Compound X, which has an X-ray powder diffraction pattern with at least five specific peaks at 2-theta=7.5, 10.7, 12.8, 14.5 and 15.8° wherein said values may be plus or minus 0.2° 2-theta.

In one embodiment there is provided a polymorphic Form A of Compound X, which has an X-ray powder diffraction pattern with specific peaks at 2-theta=7.5, 10.3, 10.7, 12.8, 14.5, 15.3, 15.8, 17.5, 19.6, and 21.3° wherein said values may be plus or minus 0.2° 2-theta.

In one embodiment there is provided polymorphic Form B of Compound X. This polymorphic form may be characterised in that it provides at least one of the following 2θ values measured using Cu $K_\alpha$ radiation: 6.9, 8.2, 9.2, 11.5, and 15.9°.

Figure 2:
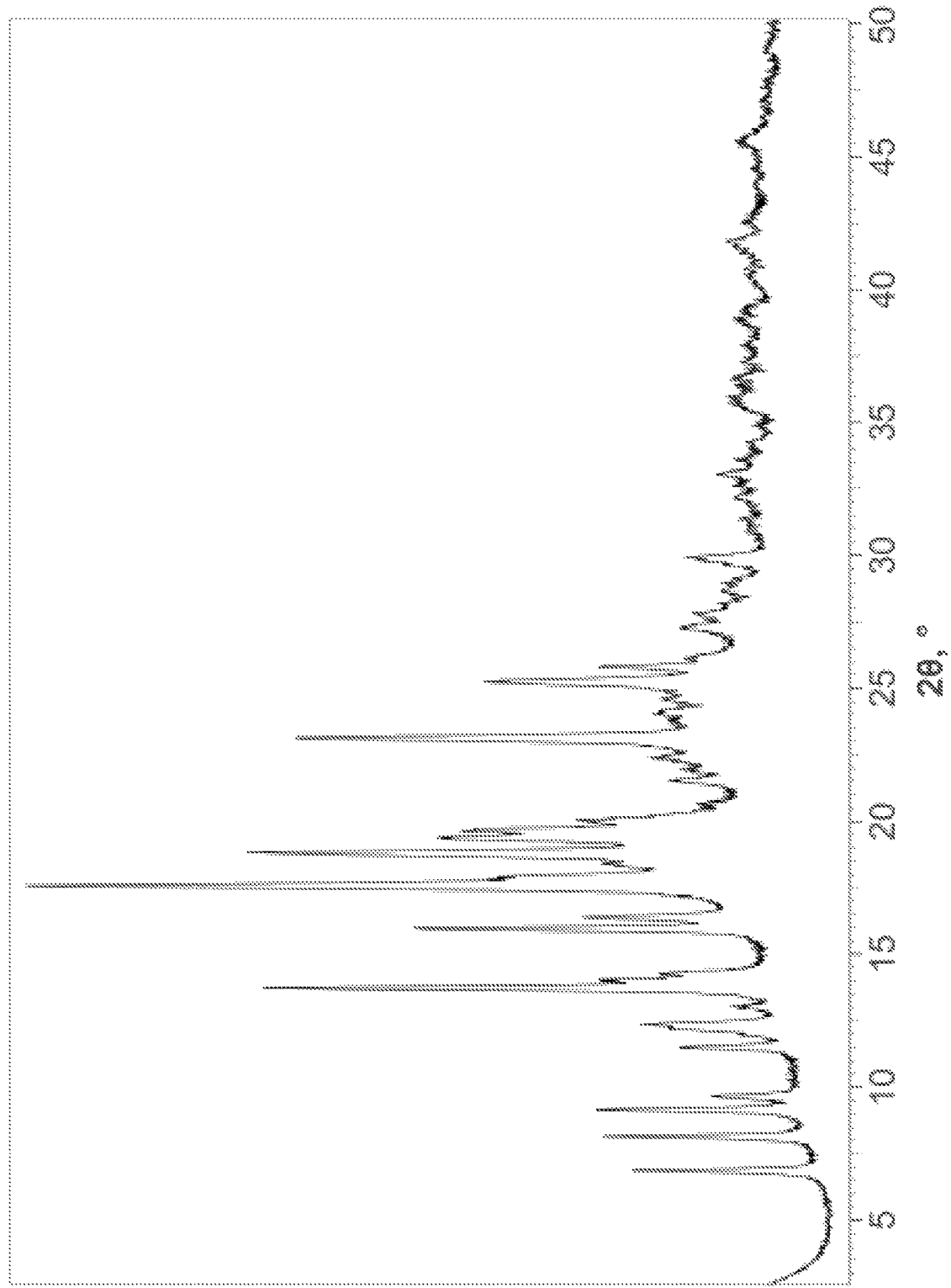

Polymorphic Form B of Compound X is characterised in providing an X-ray powder diffraction pattern, substantially as shown in FIG. 2.

The ten most prominent X-Ray powder diffraction peaks for this polymorphic form [Angle 2-theta (2θ), Intensity] are: 6.9 (vs), 8.2 (vs), 9.2 (vs), 9.6 (s), 11.5 (s), 12.3 (vs), 13.0 (m), 15.9 (vs), 16.3 (s) and 23.1 (vs).

In one embodiment there is provided the polymorphic Form B of Compound X, which has an X-ray powder diffraction pattern with at least five specific peaks at about 2-theta=6.9, 8.2, 9.2, 11.5, and 15.9°.

In one embodiment there is provided the polymorphic Form B of Compound X, which has an X-ray powder diffraction pattern with specific peaks at about 2-theta=6.9, 8.2, 9.2, 9.6, 11.5, 12.3, 13.0, 15.9, 16.3, and 23.1°.

In one embodiment there is provided polymorphic Form B of Compound X which has an X-ray powder diffraction pattern substantially the same as the X-ray powder diffraction pattern shown in FIG. 2.

In one embodiment there is provided polymorphic Form B of Compound X, which has an X-ray powder diffraction pattern with at least five specific peaks at 2-theta=6.9, 8.2, 9.2, 11.5, and 15.9° wherein said values may be plus or minus 0.2° 2-theta.

In one embodiment there is provided a polymorphic Form B of Compound X, which has an X-ray powder diffraction pattern with specific peaks at 2-theta=6.9, 8.2, 9.2, 9.6, 11.5, 12.3, 13.0, 15.9, 16.3, and 23.1° wherein said values may be plus or minus 0.2° 2-theta.

In one embodiment there is provided polymorphic Form D of Compound X. This polymorphic form may be characterised in that it provides at least one of the following 20 values measured using Cu K$_\alpha$ radiation: 7.0, 7.7, 14.0, 16.1 and 16.9°.

Figure 3:
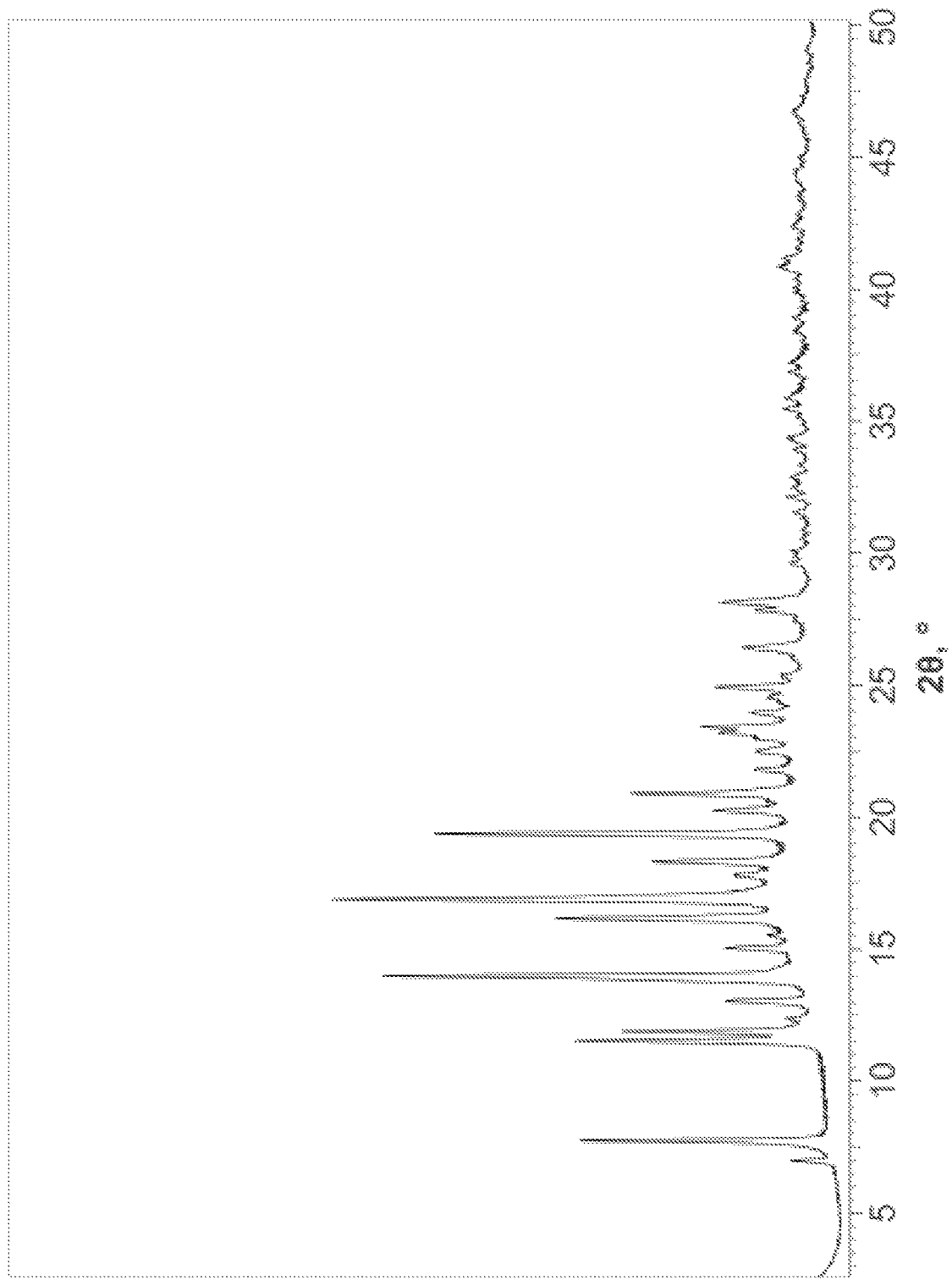

Polymorphic Form D of Compound X is characterised in providing an X-ray powder diffraction pattern, substantially as shown in FIG. 3.

The ten most prominent X-Ray powder diffraction peaks for this polymorphic form [Angle 2-theta (2θ), Intensity] are: 7.0 (m), 7.7 (vs), 14.0 (vs), 15.0 (m), 16.1 (vs), 16.9 (vs), 18.3 (s), 19.4 (vs), 20.2 (s) and 20.9 (vs).

In one embodiment there is provided the polymorphic Form D of Compound X, which has an X-ray powder diffraction pattern with at least five specific peaks at about 2-theta=7.0, 7.7, 14.0, 16.1 and 16.9°.

In one embodiment there is provided the polymorphic Form D of Compound X, which has an X-ray powder diffraction pattern with specific peaks at about 2-theta=7.0, 7.7, 14.0, 15.0, 16.1, 16.9, 18.3, 19.4, 20.2, and 20.9°.

In one embodiment there is provided polymorphic Form D of Compound X which has an X-ray powder diffraction pattern substantially the same as the X-ray powder diffraction pattern shown in FIG. 3.

In one embodiment there is provided polymorphic Form D of Compound X, which has an X-ray powder diffraction pattern with at least five specific peaks at 2-theta=7.0, 7.7, 14.0, 16.1 and 16.9° wherein said values may be plus or minus 0.2° 2-theta.

In one embodiment there is provided a polymorphic Form D of Compound X, which has an X-ray powder diffraction pattern with specific peaks at 2-theta=7.0, 7.7, 14.0, 15.0, 16.1, 16.9, 18.3, 19.4, 20.2, and 20.9° wherein said values may be plus or minus 0.2° 2-theta.

In one embodiment there is provided polymorphic Form E of Compound X. This polymorphic form may be characterised in that it provides at least one of the following 20 values measured using Cu K$_\alpha$ radiation: 6.1, 7.5, 8.2, 14.5 and 15.6°.

Figure 4:
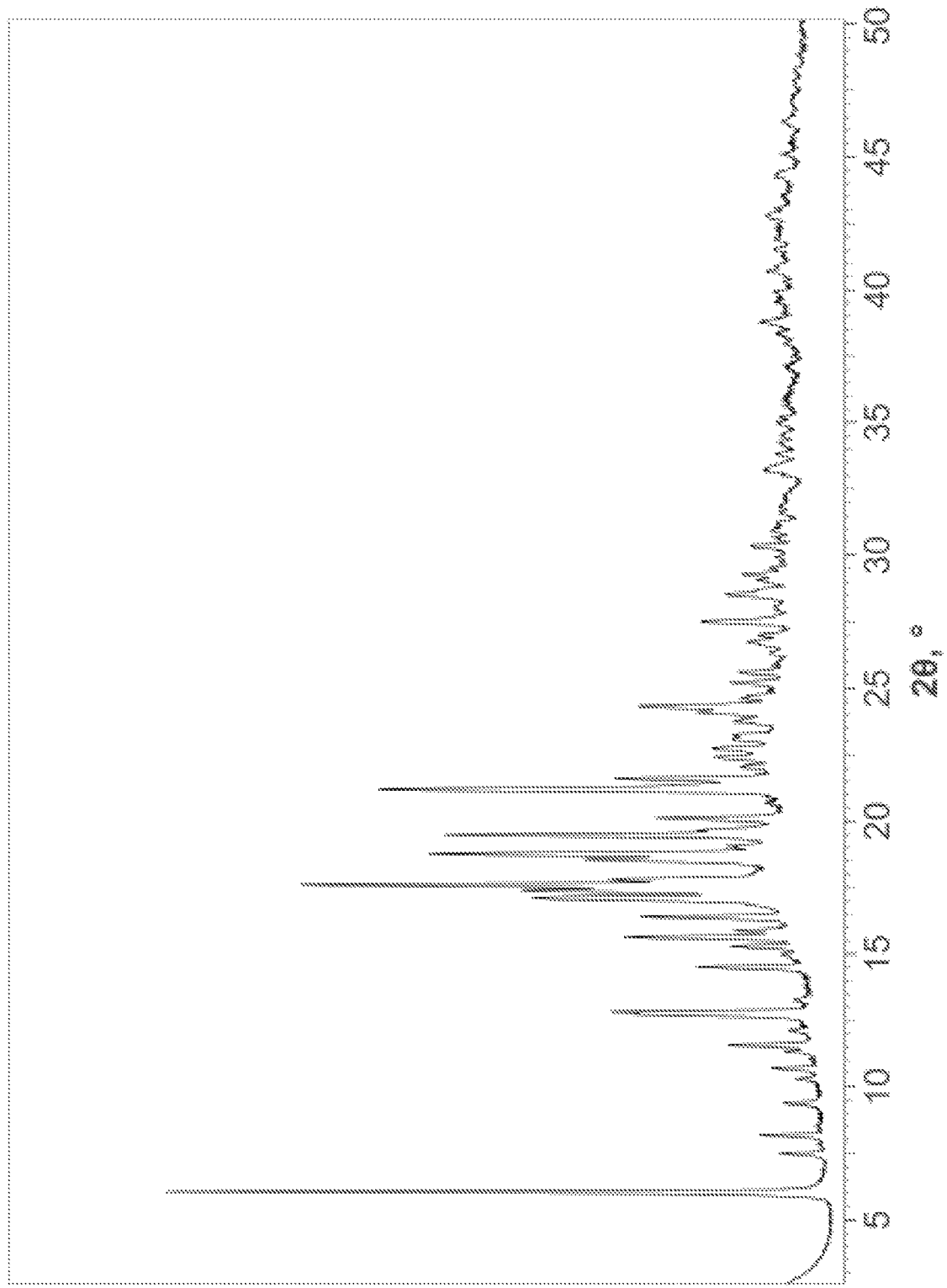

Polymorphic Form E of Compound X is characterised in providing an X-ray powder diffraction pattern, substantially as shown in FIG. 4.

The ten most prominent X-Ray powder diffraction peaks for this polymorphic form [Angle 2-theta (2θ), Intensity] are: 6.1 (vs), 7.5 (m), 8.2 (m), 9.4 (m), 10.3 (m), 10.7 (m), 14.5 (s), 15.6 (vs), 16.4 (s) and 20.1 (s).

In one embodiment there is provided the polymorphic Form E of Compound X, which has an X-ray powder diffraction pattern with at least five specific peaks at about 2-theta=6.1, 7.5, 8.2, 14.5 and 15.6°.

In one embodiment there is provided the polymorphic Form E of Compound X, which has an X-ray powder diffraction pattern with specific peaks at about 2-theta=6.1, 7.5, 8.2, 9.4, 10.3, 10.7, 14.5, 15.6, 16.4, and 20.1°.

In one embodiment there is provided polymorphic Form E of Compound X which has an X-ray powder diffraction pattern substantially the same as the X-ray powder diffraction pattern shown in FIG. 4.

In one embodiment there is provided polymorphic Form E of Compound X, which has an X-ray powder diffraction pattern with at least five specific peaks at 2-theta=6.1, 7.5, 8.2, 14.5 and 15.6° wherein said values may be plus or minus 0.2° 2-theta.

In one embodiment there is provided a polymorphic Form E of Compound X, which has an X-ray powder diffraction pattern with specific peaks at 2-theta=6.1, 7.5, 8.2, 9.4, 10.3, 10.7, 14.5, 15.6, 16.4, and 20.1° wherein said values may be plus or minus 0.2° 2-theta.

In this specification (1S,4s)-4-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid (Example 592) is also referred to as "Compound Y" Several useful crystalline polymorphic forms have subsequently been produced using the conditions described in Example 592. In all of the embodiments relating to solid forms recited herein, the peaks of the X-ray diffraction patterns are measured using Cu K$_\alpha$ radiation.

Therefore in one embodiment there is provided polymorphic Form A of Compound Y. This polymorphic form may be characterised in that it provides at least one of the following 20 values measured using Cu K$_\alpha$ radiation: 6.7, 10.5, 13.5, 15.2 and 18.6°.

Figure 5:
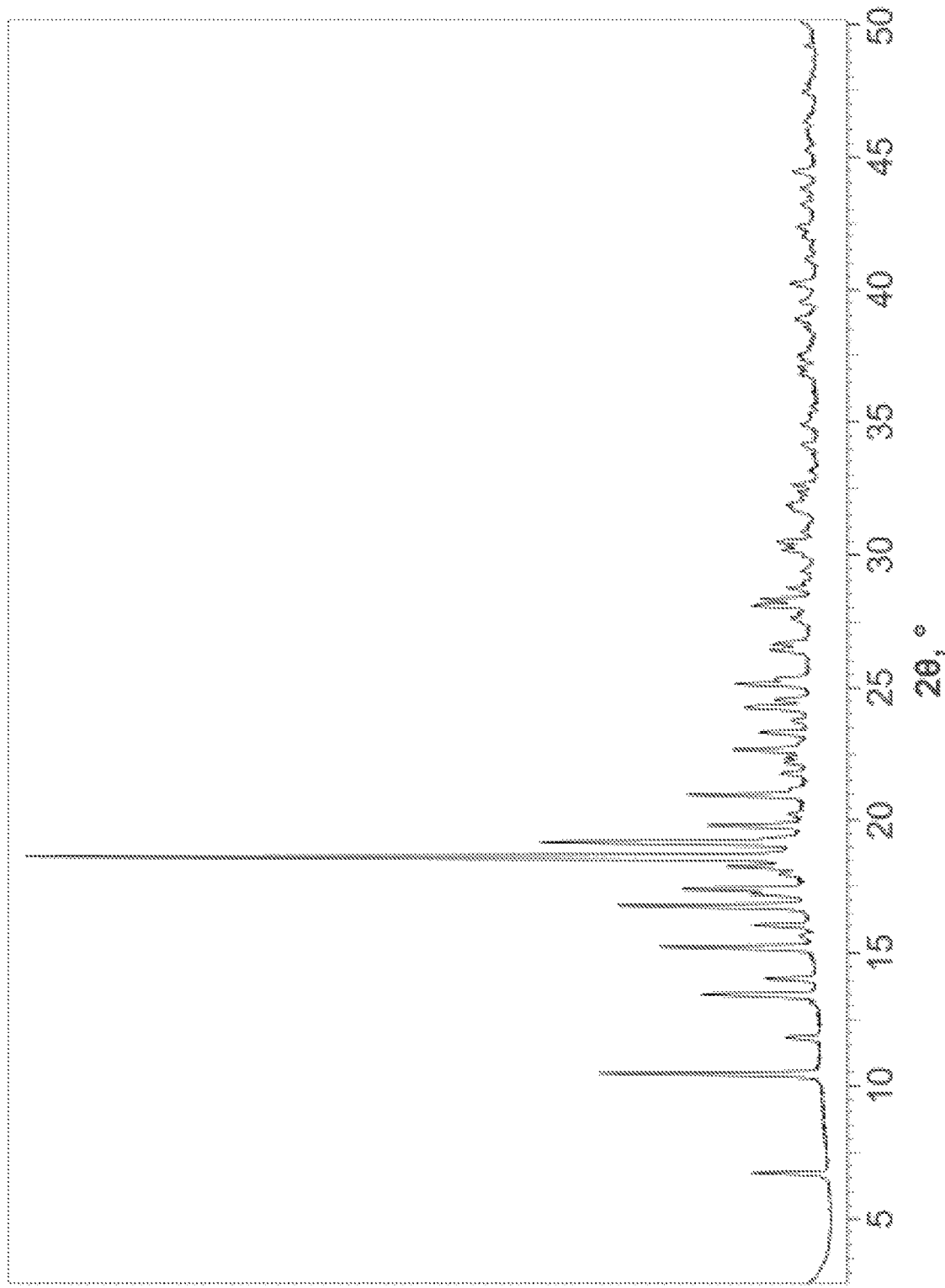

Polymorphic Form A of Compound Y is characterised in providing an X-ray powder diffraction pattern, substantially as shown in FIG. 5.

The ten most prominent X-Ray powder diffraction peaks for this polymorphic form [Angle 2-theta (2θ), Intensity] are: 6.7 (m), 10.5 (vs), 11.8 (m), 13.5 (s), 14.1 (m), 15.2 (s), 16.0 (m), 16.8 (s), 18.6 (vs) and 19.8 (vs).

In one embodiment there is provided the polymorphic Form A of Compound Y, which has an X-ray powder diffraction pattern with at least five specific peaks at about 2-theta=6.7, 10.5, 13.5, 15.2 and 18.6°.

In one embodiment there is provided the polymorphic Form A of Compound Y, which has an X-ray powder diffraction pattern with specific peaks at about 2-theta=6.7, 10.5, 11.8, 13.5, 14.1, 15.2, 16.0, 16.8, 18.6, and 19.8°.

In one embodiment there is provided polymorphic Form A of Compound Y which has an X-ray powder diffraction pattern substantially the same as the X-ray powder diffraction pattern shown in FIG. 5.

In one embodiment there is provided polymorphic Form A of Compound Y, which has an X-ray powder diffraction pattern with at least five specific peaks at 2-theta=6.7, 10.5, 13.5, 15.2 and 18.6° wherein said values may be plus or minus 0.2° 2-theta.

In one embodiment there is provided a polymorphic Form A of Compound Y, which has an X-ray powder diffraction pattern with specific peaks at 2-theta=6.7, 10.5, 11.8, 13.5, 14.1, 15.2, 16.0, 16.8, 18.6, and 19.8° wherein said values may be plus or minus 0.2° 2-theta.

Therefore in one embodiment there is provided polymorphic Form B of Compound Y. This polymorphic form may be characterised in that it provides at least one of the following 20 values measured using Cu K$_\alpha$ radiation: 6.0, 7.6, 8.6, 19.0 and 20.2°.

Figure 6:
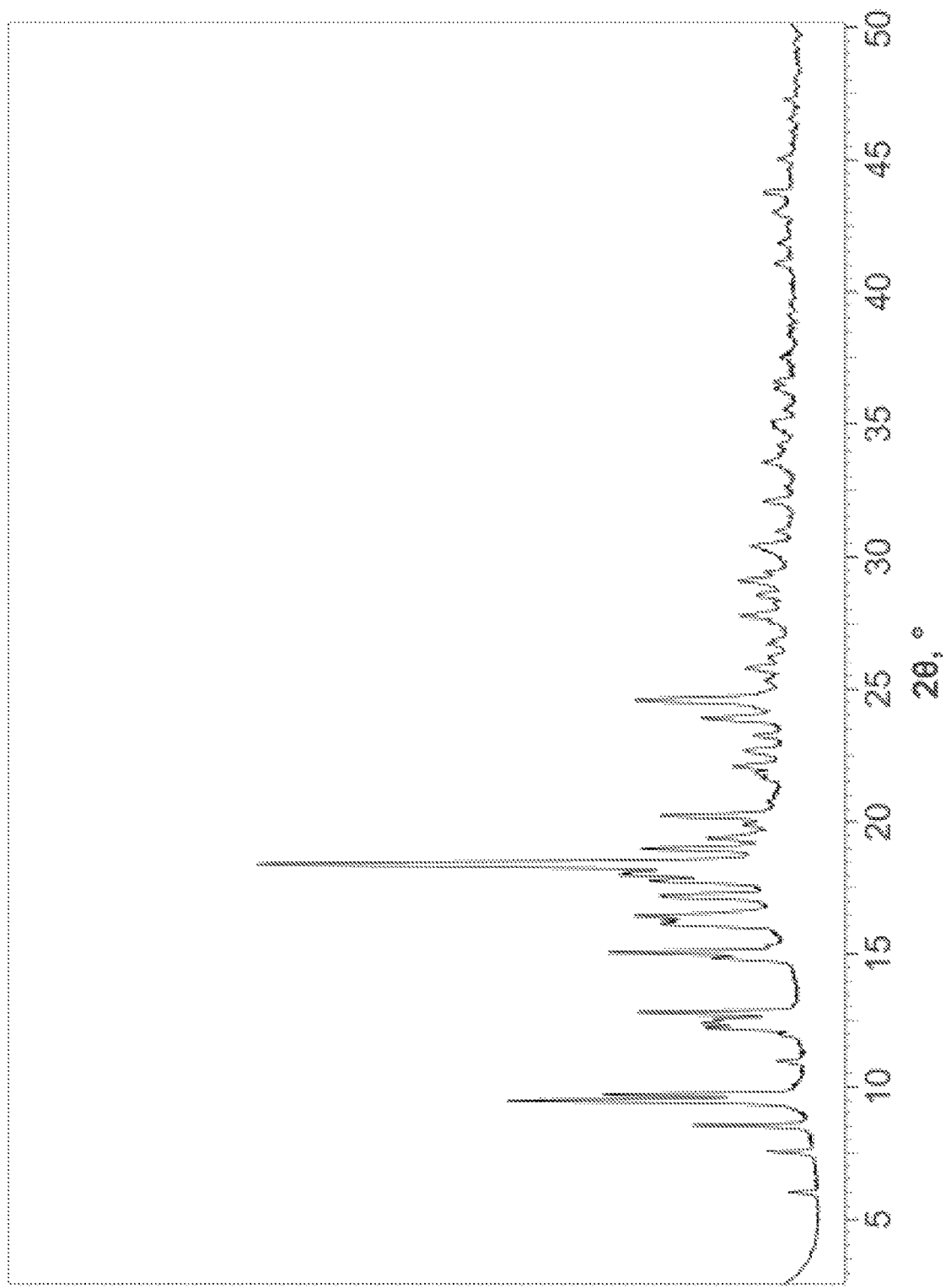

Polymorphic Form B of Compound Y is characterised in providing an X-ray powder diffraction pattern, substantially as shown in FIG. 6.

The ten most prominent X-Ray powder diffraction peaks for this polymorphic form [Angle 2-theta (2θ), Intensity] are: 6.0 (m), 7.6 (m), 8.6 (s), 9.5 (vs), 9.7 (vs), 17.2 (s), 19.0 (s), 20.2 (s), 23.2 (m) and 23.9 (s).

In one embodiment there is provided the polymorphic Form B of Compound Y, which has an X-ray powder diffraction pattern with at least five specific peaks at about 2-theta=6.0, 7.6, 8.6, 19.0 and 20.2°.

In one embodiment there is provided the polymorphic Form B of Compound Y, which has an X-ray powder diffraction pattern with specific peaks at about 2-theta=6.0, 7.6, 8.6, 9.5, 9.7, 17.2, 19.0, 20.2, 23.2, and 23.9°.

In one embodiment there is provided polymorphic Form B of Compound Y which has an X-ray powder diffraction pattern substantially the same as the X-ray powder diffraction pattern shown in FIG. 6.

In one embodiment there is provided polymorphic Form B of Compound Y, which has an X-ray powder diffraction pattern with at least five specific peaks at 2-theta=6.0, 7.6, 8.6, 19.0 and 20.2° wherein said values may be plus or minus 0.2° 2-theta.

In one embodiment there is provided a polymorphic Form B of Compound Y, which has an X-ray powder diffraction pattern with specific peaks at 2-theta=6.0, 7.6, 8.6, 9.5, 9.7, 17.2, 19.0, 20.2, 23.2, and 23.9° wherein said values may be plus or minus 0.2° 2-theta.

In this specification (1S,4s)-4-(2-cyano-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid (Example 621) is also referred to as "Compound Z". Several useful crystalline polymorphic forms have subsequently been produced using the conditions described in Example 621. In all of the embodiments relating to solid forms recited herein, the peaks of the X-ray diffraction patterns are measured using Cu $K_\alpha$ radiation.

Therefore in one embodiment there is provided polymorphic Form A of Compound Z. This polymorphic form may be characterised in that it provides at least one of the following 20 values measured using Cu $K_\alpha$ radiation: 6.0, 7.5, 8.5, 17.5 and 19.4°.

Figure 7:
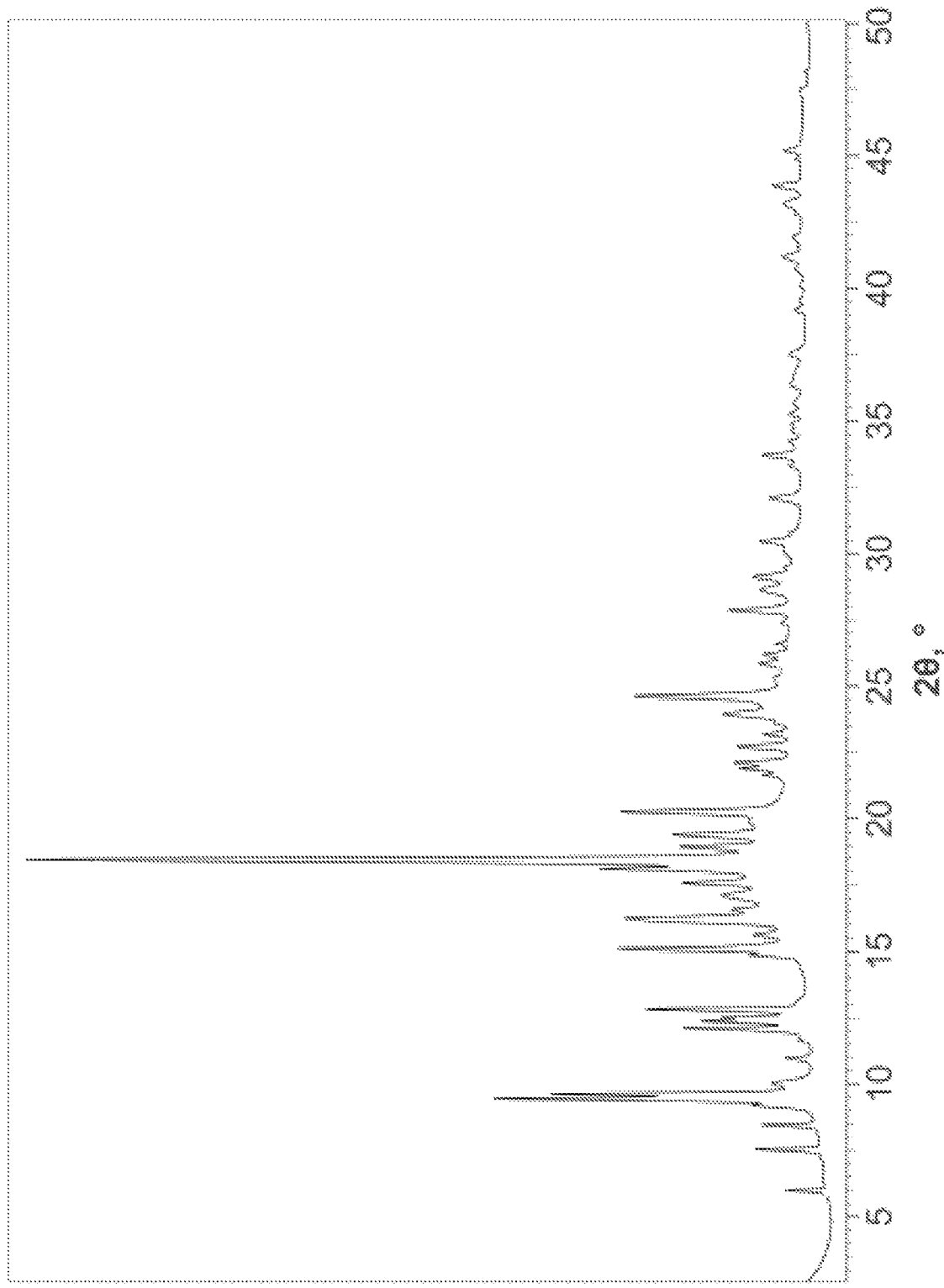

Polymorphic Form A of Compound Z is characterised in providing an X-ray powder diffraction pattern, substantially as shown in FIG. 7.

The ten most prominent X-Ray powder diffraction peaks for this polymorphic form [Angle 2-theta (2θ), Intensity] are: 6.0 (w), 7.5 (m), 8.5 (m), 11.0 (w), 15.6 (w), 17.1 (m), 17.5 (m), 19.4 (s), 22.7 (m) and 23.2 (w).

In one embodiment there is provided the polymorphic Form A of Compound Z, which has an X-ray powder diffraction pattern with at least five specific peaks at about 2-theta=6.0, 7.5, 8.5, 17.5 and 19.4°.

In one embodiment there is provided the polymorphic Form A of Compound Z, which has an X-ray powder diffraction pattern with specific peaks at about 2-theta=6.0, 7.5, 8.5, 11.0, 15.6, 17.1, 17.5, 19.4, 22.7, and 23.2°.

In one embodiment there is provided polymorphic Form A of Compound Z which has an X-ray powder diffraction pattern substantially the same as the X-ray powder diffraction pattern shown in FIG. 7.

In one embodiment there is provided polymorphic Form A of Compound Z, which has an X-ray powder diffraction pattern with at least five specific peaks at 2-theta=6.0, 7.5, 8.5, 17.5 and 19.4° wherein said values may be plus or minus 0.2° 2-theta.

In one embodiment there is provided a polymorphic Form A of Compound Z, which has an X-ray powder diffraction pattern with specific peaks at 2-theta=6.0, 7.5, 8.5, 11.0, 15.6, 17.1, 17.5, 19.4, 22.7, and 23.2° wherein said values may be plus or minus 0.2° 2-theta.

Therefore in one embodiment there is provided polymorphic Form B of Compound Z. This polymorphic form may be characterised in that it provides at least one of the following 20 values measured using Cu $K_\alpha$ radiation: 4.7, 6.1, 7.7, 9.3 and 13.0°.

Figure 8:
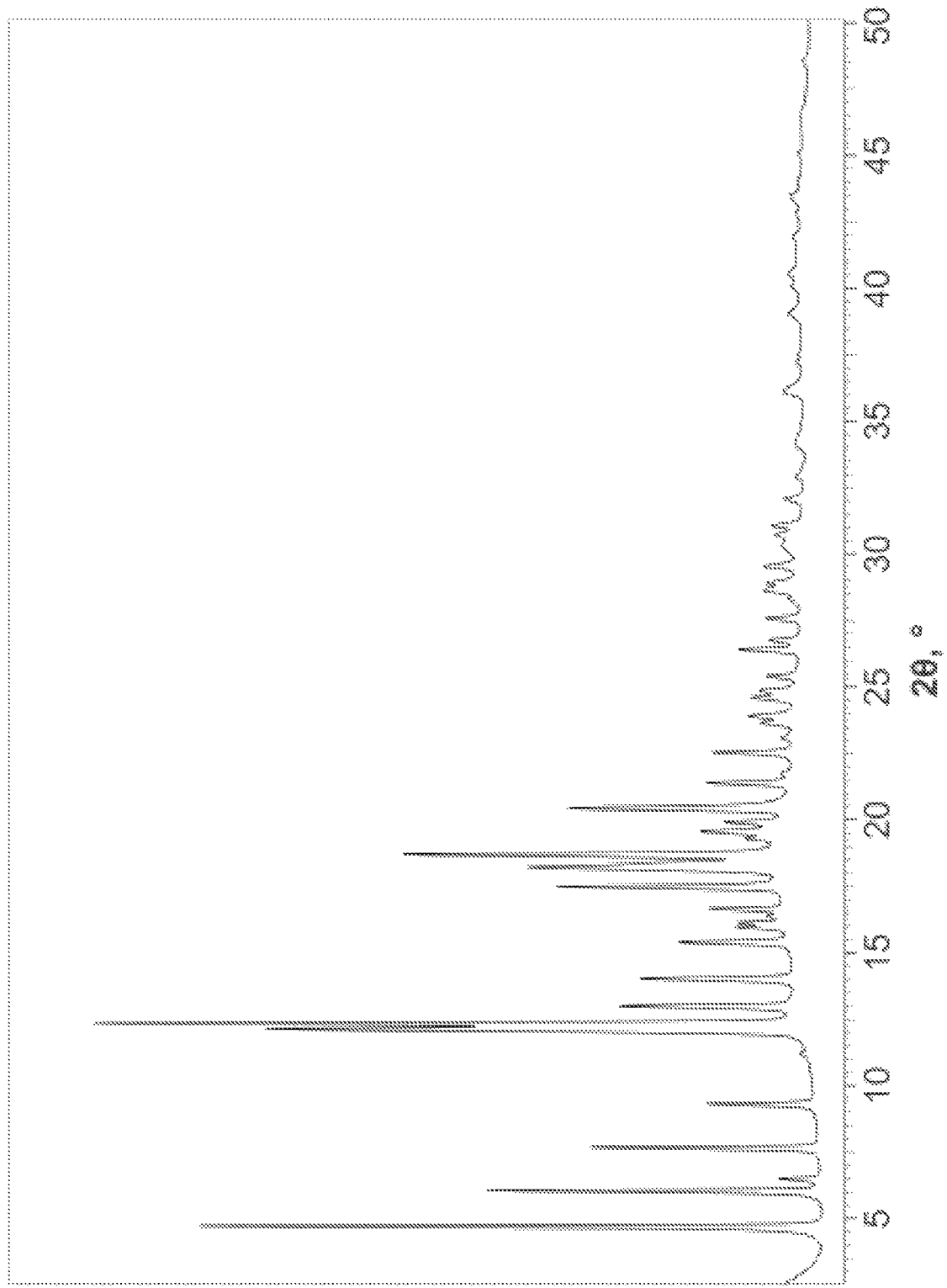

Polymorphic Form B of Compound Z is characterised in providing an X-ray powder diffraction pattern, substantially as shown in FIG. 8.

The ten most prominent X-Ray powder diffraction peaks for this polymorphic form [Angle 2-theta (2θ), Intensity] are: 4.7 (vs), 6.1 (vs), 6.5 (m), 7.7 (vs), 9.3 (s), 13.0 (vs), 14.0 (s), 15.4 (s), 17.5 (vs) and 20.4 (vs).

In one embodiment there is provided the polymorphic Form B of Compound Z, which has an X-ray powder diffraction pattern with at least five specific peaks at about 2-theta=4.7, 6.1, 7.7, 9.3 and 13.0°.

In one embodiment there is provided the polymorphic Form B of Compound Z, which has an X-ray powder diffraction pattern with specific peaks at about 2-theta=4.7, 6.1, 6.5, 7.7, 9.3, 13.0, 14.0, 15.4, 17.5, and 20.4°.

In one embodiment there is provided polymorphic Form B of Compound Z which has an X-ray powder diffraction pattern substantially the same as the X-ray powder diffraction pattern shown in FIG. 8.

In one embodiment there is provided polymorphic Form B of Compound Z, which has an X-ray powder diffraction pattern with at least five specific peaks at 2-theta=4.7, 6.1, 7.7, 9.3 and 13.0° wherein said values may be plus or minus 0.2° 2-theta.

In one embodiment there is provided a polymorphic Form B of Compound Z, which has an X-ray powder diffraction pattern with specific peaks at 2-theta=4.7, 6.1, 6.5, 7.7, 9.3, 13.0, 14.0, 15.4, 17.5, and 20.4° wherein said values may be plus or minus 0.2° 2-theta.

In one embodiment there is provided a pharmaceutical composition comprising a crystalline form as described herein and a pharmaceutically acceptable excipient.

LIST OF FIGURES

The figures relate to solid forms of the compounds: Compound X, Compound Y or Compound Z.

FIG. 1: X-Ray Powder Diffraction Pattern—Form A of Compound X

FIG. 2: X-Ray Powder Diffraction Pattern—Form B of Compound X

FIG. 3: X-Ray Powder Diffraction Pattern—Form D of Compound X

FIG. 4: X-Ray Powder Diffraction Pattern—Form E of Compound X

FIG. 5: X-Ray Powder Diffraction Pattern—Form A of Compound Y

FIG. 6: X-Ray Powder Diffraction Pattern—Form B of Compound Y

FIG. 7: X-Ray Powder Diffraction Pattern—Form A of Compound Z

FIG. 8: X-Ray Powder Diffraction Pattern—Form B of Compound Z

EXAMPLES

The compounds described in this specification are further illustrated in the following Examples. These Examples are given by way of illustration only and are non-limiting.

In the examples, high resolution mass spectra were recorded on a Micromass LCT mass spectrometer equipped with an electrospray interface (LC-HRMS).

$^1$H NMR measurements were performed on Bruker Avance III 300, 400, 500 and 600 spectrometers, operating at $^1$H frequencies of 300, 400, 500 and 600 MHz, respectively. The experiments were typically recorded at 25° C. Chemical shifts are given in ppm with the solvent as internal standard. Protons on heteroatoms such as NH and OH protons are only reported when detected in NMR and can therefore be missing. The following abbreviations have been used (and derivatives thereof, e.g. dd, doublet of doublets, etc.): s, singlet; d, doublet; t, triplet; q, quartet; m, multiplet; br, broad; qn, quintet; p, pentet.

Flash chromatography was performed using either normal phase silica FLASH+® (40M, 25M or 12M), Biotage® SNAP Cartridges KP-Sil (340, 100, 50 or 10), or Agela® Flash Column Silica-CS Cartridges (330, 180, 120, 80) unless otherwise stated.

Reversed phase flash chromatography was performed using Agela® C-18 spherical 20-35 µm 100A cartridges unless otherwise stated.

Purifications were performed by preparative HPLC, preparative SFC or reversed phase flash chromatography on a standard equipment, using MS or UV triggered fraction collection, and using one of the following methods; Method PrepAcidic-A The compound was purified by preparative HPLC on a XSelect CSH Prep C18 OBD column (5 µm 150×19 mm ID) using a gradient of MeCN in a $H_2O$/FA (0.1%) buffer system; Method PrepAcidic-B The compound was purified by preparative HPLC on a Xselect CSH F-Phenyl OBD column (5 µm 250×19 mm ID) using a gradient of MeCN in a $H_2O$/TFA (0.05%) buffer system; Method PrepAcidic-C The compound was purified by preparative HPLC on a XBridge Prep C18 OBD column (5 µm 150×19 mm ID) using a gradient of MeCN in a $H_2O$/TFA (0.05%) buffer system; Method PrepAcidic-D The compound was purified by preparative HPLC on a XBridge Prep C18 OBD column (5 µm 150×19 mm ID) using a gradient of MeCN in a $H_2O$/TFA (0.1%) buffer system; Method PrepAcidic-E The compound was purified by preparative HPLC on a Waters Sunfire C18 OBD column (5 µm 150×30 mm ID) using a gradient of MeCN in a $H_2O$/FA (0.1%) buffer system; Method PrepAcidic-F The compound was purified by preparative HPLC on a Kromasil C18 column (10 µm 250×20 mm ID) using a gradient of MeCN in a $H_2O$/MeCN/FA (95/5/0.2) buffer system; Method PrepAcidic-G The compound was purified by preparative HPLC on a XSelect CSH Prep C18 OBD column (5 µm 150×19 mm ID) using a gradient of MeCN in a $H_2O$/TFA (0.05%) buffer system; Method PrepAcidic-H The compound was purified by preparative HPLC on a Kromasil C18 column (10 µm 250×20 mm ID) using a gradient of MeCN in a $H_2O$/MeCN/Acetic acid (95/5/0.2) buffer system; Method PrepAcidic-I The compound was purified by preparative HPLC on a Waters Sunfire C18 OBD column (5 µm 150×19 mm ID) using a gradient of MeCN in a $H_2O$/FA (0.1%) buffer system; Method PrepAcidic-J The compound was purified by preparative HPLC on a XSelect CSH Prep C18 OBD column (5 µm 150×30 mm ID) using a gradient of MeCN in a $H_2O$/TFA (0.5%) buffer system; Method PrepAcidic-K The compound was purified by preparative HPLC on a XSelect CSH Prep C18 OBD column (5 µm 150×30 mm ID) using a gradient of MeCN in a $H_2O$/TFA (0.05%) buffer system; Method PrepAcidic-L The compound was purified by preparative HPLC on a Waters Sunfire C18 OBD column (5 µm 150×19 mm ID) using a gradient of MeCN in a $H_2O$/FA (0.05%) buffer system; Method PrepAcidic-M The compound was purified by preparative HPLC on a XSelect CSH OBD column (5 µm 150×30 mm ID) using a gradient of MeCN in a $H_2O$/TFA (0.10%) buffer system; Method PrepAcidic-N The compound was purified by preparative HPLC on a Xselect CSH F-Phenyl OBD column (5 µm 250×19 mm ID) using a gradient of MeCN in a $H_2O$/TFA (0.1%) buffer system; Method PrepAcidic-O The compound was purified by preparative HPLC on a Phenomenex Luna C18 column (10 µm 50×100 mm ID) using a gradient of MeCN (40-70% over 25 min) in a $H_2O$ (0.05% HCl) buffer system; Method PrepAcidic-P The compound was purified by preparative HPLC on a Xbridge C18 column (5 µm 150×30 mm ID) using a gradient of 80-95% MeCN in a TFA (0.05%) buffer system as mobile phase; Method PrepBasic-A The compound was purified by preparative HPLC on a XBridge C18 column (10 µm 250×19 mm ID) using a gradient of MeCN in a $H_2O$/MeCN/$NH_3$ (95/5/0.2) buffer system at pH10 as mobile phase; Method PrepBasic-B The compound was purified by preparative HPLC on a Xbridge C18 column (5 µm 50×19 mm ID) using a gradient of MeCN in a $H_2O$/MeCN/$NH_3$ (95/5/0.2) buffer system at pH10 as mobile phase; Method PrepBasic-C The compound was purified by preparative HPLC on a WatersSunfire C18 ODB column (5 µm 150×30 mm ID) using a gradient of MeCN in a $H_2O$/MeCN/$NH_3$ (95/5/0.2) buffer system at pH10 as mobile phase; Method PrepBasic-D The compound was purified by preparative HPLC on a Xbridge C18 column (10 µm 250×19 mm ID) using a gradient of MeCN in a $H_2O$/MeCN/$NH_3$ (95/5/0.2) buffer system at pH10 as mobile phase; Method PrepBasic-E The compound was purified by preparative HPLC on a Xbridge C18 ODB column (5 µm 150×19 mm ID) using a gradient of MeCN in a $H_2O$/MeCN/$NH_3$ (95/5/0.2) buffer system at pH10 as mobile phase; Method PrepBasic-F The compound was purified by preparative HPLC on a XBridge C18 column (10 µm 250×50 mm ID) using a gradient of MeCN in a $H_2O$/MeCN/$NH_3$ (95/5/0.2) buffer system at pH10 as mobile phase; Method PrepBasic-G The compound was purified by preparative HPLC on a Xbridge C18 OBD column (5 µm 150×19 mm ID) using a gradient of MeCN in a $H_2O$/$NH_4HCO_3$ (10 mM) buffer system as mobile phase; Method PrepBasic-H The compound was purified by preparative HPLC on a Xbridge C18 OBD column (5 µm 150×30 mm ID) using a gradient of MeCN in a $H_2O$/$NH_3$ (0.1)/$NH_4HCO_3$ (10 mM) buffer system as mobile phase; Method PrepBasic-I The compound was purified by preparative HPLC on a Xbridge C18 column (5 µm 150×30 mm ID) using a gradient of 20-90% MeCN in a $H_2O$/$NH_4HCO_3$ (10 mM) buffer system as mobile phase; Method PrepBasic-J The compound was purified by preparative HPLC on a Xbridge C18 column (5 µm 150×30 mm ID) using a gradient of 50-70% MeCN in a $H_2O$/$NH_4HCO_3$ (10 mM) buffer system as mobile phase; Method PrepBasic-K The compound was purified by preparative HPLC on a Xbridge C18 column (5 µm 150×30 mm ID) using a gradient of 70-90% MeCN in a $H_2O$/$NH_4HCO_3$ (10 mM) buffer system as mobile phase; Method PrepBasic-L The compound was purified by preparative HPLC on a Xbridge C18 column (5 µm 150×30 mm ID) using a gradient of 30-45% MeCN in a $H_2O$/$NH_4HCO_3$ (10 mM) buffer system as mobile phase; Method PrepBasic-M The compound was purified by preparative HPLC on a Xbridge C18 column (5 µm 150×30 mm ID) using a gradient of 20-70% MeCN in a $H_2O$/$NH_4HCO_3$ (10 mM) buffer system as mobile phase; Method PrepBasic-N The compound was purified by preparative HPLC on a Xbridge C18 column (5 µm 150×30 mm ID) using a gradient of 15-60% MeCN in a $H_2O$/$NH_4HCO_3$ (10 mM) buffer system as mobile phase; Method PrepBasic-O The compound was purified by preparative HPLC on a Ultimate XB-C18 column (11 µm 250×50 mm ID) using a gradient of 30-60% MeCN in a $H_2O$/$NH_4HCO_3$ (10 mM) buffer system as mobile phase; Method PrepBasic-P The compound was purified by preparative HPLC on a Ultimate XB-C18 (11 µm 250×50 mm ID) using a gradient of 45-65% MeCN in a $H_2O$/$NH_4HCO_3$ (10 mM) buffer system as mobile phase; Method PrepBasic-Q The compound was purified by preparative HPLC on a Ultimate XB-C18 column (11 µm 250×50 mm ID) using a gradient of 40-65% MeCN in a H$_2$O/NH$_4$HCO$_3$ (10 mM) buffer system as mobile phase; Method PrepBasic-R The compound was purified by preparative HPLC on a Ultimate XB-C18 column (11 μm 250×50 mm ID) using a gradient of 50-70% MeCN in a H$_2$O/NH$_4$HCO$_3$ (10 mM) buffer system as mobile phase; Method PrepBasic-S The compound was purified by preparative HPLC on a Ultimate XB-C18 column (11 μm 250×50 mm ID) using a gradient of 25-60% MeCN in a H$_2$O/NH$_4$HCO$_3$ (10 mM) buffer system as mobile phase; Method PrepBasic-T The compound was purified by preparative HPLC on a Ultimate XB-C18 column (11 μm 250×50 mm ID) using a gradient of 65-75% MeCN in a H$_2$O/NH$_4$HCO$_3$ (10 mM) buffer system as mobile phase; Method PrepBasic-U The compound was purified by preparative HPLC on a Ultimate XB-C18 column (11 μm 250×50 mm ID) using a gradient of 40-90% MeCN in a H$_2$O/NH$_4$HCO$_3$ (10 mM) buffer system as mobile phase; Method PrepBasic-V The compound was purified by preparative HPLC on a Ultimate XB-C18 column (11 μm 250×50 mm ID) using a gradient of 35-65% MeCN in a H$_2$O/NH$_4$HCO$_3$ (10 mM) buffer system as mobile phase; Method PrepBasic-W The compound was purified by preparative HPLC on a XBridge C18 column (5 μm 150×30 mm ID) using a gradient of 10-50% MeCN in a H$_2$O/NH$_3$ (0.05%) buffer system as mobile phase; Method PrepBasic-X The compound was purified by preparative HPLC on a XBridge C18 column (5 μm 150×30 mm ID) using a gradient of 15-60% MeCN in a H$_2$O/NH$_3$ (0.05%) buffer system as mobile phase; Method PrepBasic-Y The compound was purified by preparative HPLC on a XBridge C18 column (5 μm 150×30 mm ID) using a gradient of 10-70% MeCN in a H$_2$O/NH$_3$ (0.05%) buffer system as mobile phase; Method SFC-A The compound was purified by preparative SFC on a Phenomenex Luna HILIC column (5 μm 250×30 ID mm) using MeOH/20 mM NH$_3$ in CO$_2$ as mobile phase; Method SFC-B The compound was purified by preparative SFC on a Waters BEH 2-EP column (5 μm 250×30 ID mm) using MeOH/20 mM NH$_3$ in CO$_2$ as mobile phase; Method SFC-C The compound was purified by preparative SFC on a Waters BEH 2-EP column (5 μm 250×30 ID mm) using MeOH/H$_2$O (97/3)+50 mM NH$_3$ in CO$_2$ as mobile phase; Method SFC-D The compound was purified by preparative SFC on a Waters BEH column (5 μm 250×30 ID mm) using MeOH/20 mM NH$_3$ in CO$_2$ as mobile phase; Method SFC-E The compound was purified by preparative SFC on a Waters Acquity UPC2 BEH column (3.5 μm 250×30 mm ID) using MeOH/H$_2$O (97/3)+50 mM NH$_3$ in CO$_2$ as mobile phase; Method SFC-F The compound was purified by preparative SFC on a Waters BEH column (5 μm 250×30 ID mm) using MeOH/H$_2$O (97/3)+50 mM NH$_3$ in CO$_2$ as mobile phase; Method SFC-G The compound was purified by chiral preparative SFC on a Chiralpak IC column (5 μm 250×20 ID mm) using IPA in CO$_2$ (g) as mobile phase; Method SFC-H The compound was purified by chiral preparative SFC on a Daicel Chiralpak AD column (10 μm 250×50 ID mm) using 55% 0.1% NH$_4$OH (aq) and 45% IPA as the mobile phase; Method FlashAcid-A The compound was purified by preparative flash chromatography on a WelFlash C18, 120 g column using a gradient of 45-90% MeCN in a FA (0.05%) buffer system as mobile phase; Method FlashBasic-A The compound was purified by preparative flash chromatography on a WelFlash C18, 120 g column using a gradient of 30-80% MeCN in a H$_2$O/NH$_4$HCO$_3$ (10 mM) buffer system as mobile phase;

In general, all solvents used were commercially available and of analytical grade. Anhydrous solvents were routinely used for reactions.

Phase Separators used in the examples are ISOLUTE® Phase Separator columns.

The Intermediates and Examples named below were named using ChemDraw Professional version 19.0.0.22 from PerkinElmer.

The following abbreviations were used

Aq Aq
AIBN 2,2'-Azobis(2-methylpropionitrile)
APCI Atmospheric pressure chemical ionization
Boc$_2$O Di-tert-butyl dicarbonate
B$_2$Pin$_2$ 4,4,5,5-Tetramethyl-2-(4,4,5,5-tetramethyl-1,3,2-dioxaborolan-2-yl)-1,3,2-dioxaborolane
BuOAc n-Butyl acetate
BuOH Butanol
Calcd Calculated
Dba (1E,4E)-1,5-diphenylpenta-1,4-dien-3-one
DBAD Di-tert butyl azodicarboxylate
DCM Dichloromethane
DEA Diethylamine
DIA Diisopropylamine
DIAD Diisopropyl (E)-diazene-1,2-dicarboxylate
DIPEA N-Ethyl-N-isopropyl-propan-2-amine
DMA N,N-dimethylacetamide
DMAP N,N-dimethylpyridin-4-amine
DMF N,N-dimethylformamide
DMSO Dimethylsulfoxide
DPPA Diphenylphosphoryl azide
Dppf 1,1'-bis(diphenylphosphino)ferrocene
DTBBPY 4,4'-Di-tert-butyl-2,2'-dipyridyl
Dtbpf 1,1'-Bis(di-tert-buthylphosphino)ferrocene
EDC 3-(Ethyliminomethyleneamino)-N,N-dimethyl-propan-1-amine; hydrochloride
ESI Electrospray ionization
Et Ethyl
Et$_2$O Diethyl ether
EtOAc Ethylacetate
EtOH Ethanol
FA Formic acid
h/hr Hour(s)
HATU (Dimethylamino)-N,N-dimethyl(3-oxido-1H-[1,2,3]triazolo[4,5-b]pyridinyl)methaniminium hexafluorophosphate
HBTU 2-(1H-Benzo[d][1,2,3]triazol-1-yl)-1,1,3,3-tetramethylisouronium hexafluorophosphate(V)
HOAt 3H-1,2,3-Triazolo[4,5-b]pyridin-3-ol
HOBt 1-Hydroxybenzotriazole; hydrate
HPLC High performance liquid chromatography
HRMS High resolution mass spectrometry
IPA Isopropyl alcohol
IPAC Isopropyl acetate
[Ir(COD)OMe]$_2$ Bis(1,5-cyclooctadiene)di-μ-methoxy-diiridium(I)
L Litre
Me Methyl
MeCN Acetonitrile
mL Millilitre
MeOH Methanol
2-Me-THF 2-Methyltetrahydrofuran
Min Minutes
MS Mass spectrometry
MTBE Methyl tert-butyl ether
NBS 1-Bromopyrrolidine-2,5-dione
NMR Nuclear magnetic resonance
OAc Acetate
OTf Trifluoromethanesulfonate
PE Petroleum ether
Pd—C Palladium on charcoal Rt Room temperature Sat Saturated SM Starting material SFC Supercritical fluid chromatography T3P 2,4,6-tripropyl-1,3,5,2,4,6-trioxatriphosphinane 2,4,6-trioxide TBAF Tetra-n-butylammonium fluoride TCFH N-(Chloro(dimethylamino)methylene)-N-methyl-methanaminium hexafluorophosphate(V)

TEA Triethylamine

TFA Trifluoroacetic acid

THF Tetrahydrofuran

TLC Thin layer chromatography

TCFH N-(Chloro(dimethylamino)methylene)-N-methyl-methanaminium hexafluorophosphate(V)

Xantphos (9,9-Dimethyl-9H-xanthene-4,5-diyl)bis(diphenylphosphane)

INTERMEDIATES

Intermediate 1: Ethyl 8-methyl-1,4-dioxaspiro[4.5]decane-8-carboxylate

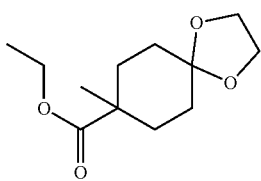 [SMILES: CCOC(=O)C1(C)CCC2(CC1)OCCO2]

A solution of DIA (576 mL, 413 g, 4.08 mol) in THF (3.50 L) was cooled to −50 to −40° C. and a solution of n-BuLi (2.5 M in hexane, 1.09 kg, 3.92 mol) was added over 3 h, maintaining the temperature between −50 to −40° C. The solution was stirred for 3 h at −50 to −40° C., followed by the addition of a solution of ethyl 1,4-dioxaspiro[4.5]decane-8-carboxylate (700 g, 3.27 mol, 2.34 M in THF) over 2 h, maintaining the temperature between −50 to −40° C. The reaction mixture was stirred for 4 h at −50 to −40° C. before the addition of methyl iodide (603 g, 4.25 mol, 3.04 M in THF) over 3 h, maintaining the temperature between −50 to −30° C. The reaction mixture was further stirred for 2 h at −50 to −30° C. followed by the addition of aq NH$_4$Cl (3.50 L, 20% w/w in H$_2$O) over 1 h, maintaining the temperature <0° C. The solution was warmed to between 15 to 25° C., held for 0.5 h then the layers were separated and the organic layer washed with aq NH$_4$Cl (2×3.50 L, 20% w/w in H$_2$O). Exchange of the organic reaction solvent from THF to EtOH under reduced pressure, maintaining the temperature <45° C., gave the title compound as a 27% w/w solution in EtOH (2.51 kg, 2.91 mol, 89%). $^1$H NMR for purified compound (400 MHz CDCl$_3$) δ 1.18 (3H, s), 1.27-1.22 (3H, m), 1.47-1.35 (2H, m), 1.70-1.56 (4H, m), 2.13 (2H, d), 3.92 (4H, s), 4.14 (2H, q), MS (ESI): m/z [M+H]$^+$ 229.2.

Intermediate 2: 8-Methyl-1,4-dioxaspiro[4.5]decane-8-carboxylic acid

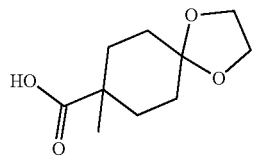

To a solution of Intermediate 1 (1.13 kg, 1.31 mol, 27% w/w in EtOH) was added EtOH (900 mL) followed by aq NaOH (2.63 L, 5.26 mol, 2 M in H$_2$O) maintaining the temperature between 15 to 30° C. The solution was heated to between 50 to 60° C., then held for 6 h before cooling to 15 to 30° C. and concentration of the solution to between 1.8 to 2.4 L under reduced pressure. Hexane (1.50 L) was added and the layers separated. The aq layer was collected and the pH adjusted to between 3 to 4 by the addition of aq HCl (1.30 L, 5.2 mol, 4 M in H$_2$O) maintaining the temperature <20° C. This aq solution was extracted with DCM (2×1.50 L) and the combined organic phases were concentrated under reduced pressure, maintaining the temperature <30° C. to give the title compound as a 17% w/w solution in DCM (1.43 kg, 1.24 mol, 94%). $^1$H NMR for purified compound (500 MHz CDCl$_3$) δ 1.25 (3H, s), 1.53 (2H, dt), 1.62-1.72 (4H, m), 2.05-2.19 (2H, m), 3.93 (4H, s). MS (ESI): m/z [M+Na]$^+$ 223.1.

Intermediate 3: 1-Methyl-4-oxocyclohexane-1-carboxylic acid

Method A

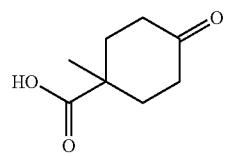

To a solution of Intermediate 2 (367 g, 250 mmol, 14% w/w in DCM) was added TFA (95.3 mL, 142 g, 1.25 mol). The reaction temperature was maintained between 25 to 35° C. for 20 h before cooling to between 0 to 10° C. H$_2$O (250 mL) was added to the reaction solution and the pH of the aq phase adjusted to between 9 and 10 by the addition of aq NaOH (440 mL, 1.76 mol, 4 M in H$_2$O). The layers were separated and the aq layer was retained and cooled to between 0 to 10° C. The pH was adjusted to between 2 and 3 by the addition of aq HCl (73.5 mL, 294 mmol, 4 M in H$_2$O) then extracted with DCM (3×250 mL) and the combined DCM solutions concentrated to between 150 to 200 mL under reduced pressure. Exchange of the organic reaction solvent from DCM to MeCN under reduced pressure, maintaining the temperature <40° C., gave the title compound as a 30% w/w solution in MeCN (119 g, 227 mmol, 91%). $^1$H NMR for purified compound (400 MHz CDCl3) δ 1.39 (3H, s), 1.73 (2H, td), 2.43 (6H, m). MS (ESI): m/z [M+H]$^+$ 157.1.

Method B

To a solution of Intermediate 2 (6.17 kg, 3.83 mol, 12.4% in DCM) was added TFA (1.42 L, 2.18 kg, 19.13 mol). The reaction temperature was maintained between 25 to 35° C.

for 20 h before cooling to between 0 to 10° C. A solution of aq NaOH (918 g, 22.96 mol dissolved in 7.66 L H₂O) was added to the reaction solution and the pH of the aqueous phase was adjusted to between 9 and 11. The layers were separated and the aq layer was retained and cooled to between 0 to 10° C. Addition of DCM (3.83 L) followed by aq HCl (1.52 L, 6.08 mol, 4 M in H₂O) adjusts the pH to between 3 and 4. The organic layer was retained and the aqueous extracted with DCM (2×3.83 L) and the combined organic phase was washed with brine (2.3 L, 15% w/w NaCl). The organic phase was concentrated under reduced pressure to 2.3 to 3.1 L. Exchange of the organic reaction solvent from DCM to MeCN under reduced pressure, maintaining the temperature <45° C., gave the title compound as a 18% solution in MeCN (2.85 kg, 3.32 mol, 87%). ¹H NMR for purified compound (400 MHz CDCl3) δ 1.39 (3H, s), 1.73 (2H, td), 2.43 (6H, m). MS (ESI): m/z [M+H]⁺ 157.1.

Intermediate 4: Naphthalen-1-ylmethyl 1-methyl-4-oxocyclohexane-1-carboxylate

Method A

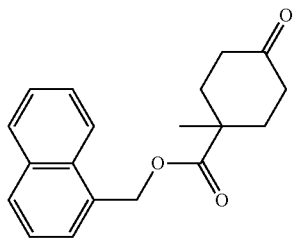 [SMILES: CC1(C(=O)OCc2cccc3ccccc23)CCC(=O)CC1]

To a solution of Intermediate 3 (119 g, 192 mmol, 25% w/w in MeCN) was added 1-chloromethylnaphthalene (32.2 g, 183 mmol) followed by DIPEA (70.0 mL, 49.7 g, 384 mmol) and NaI (2.88 g, 19.2 mmol). The solution was heated to between 50 to 60° C. for 8 h before cooling to between 0 to 10° C. H₂O (240 mL) was added and the pH of the reaction mixture adjusted to between 3 and 4 by the addition of aq HCl (55.0 mL, 220 mmol, 4 M in H₂O). The reaction mixture was extracted with MTBE (2×150 mL) and the combined organic phases washed with aq NaHCO₃ (150 mL, 144 mmol, 8% w/w in H₂O). The organic reaction solvent was exchanged from MTBE to IPA under reduced pressure, maintaining the temperature <40° C. The temperature of the reaction solution was lowered to between −10 to 3° C. and the solution stirred for 2 h, upon which a solid precipitate formed. The solids were filtered and dried under N₂ for 15 h to give the title compound as a white solid (42.8 g, 144 mmol, 74%); ¹H NMR (500 MHz, CDCl₃) 1.30 (3H, s), 1.65 (2H, td), 2.16-2.47 (6H, m), 5.66 (2H, s), 7.46 (1H, dd), 7.51-7.63 (3H, m), 7.78-7.93 (2H, m), 7.93-8.05 (1H, m). MS (ESI): m/z [M+Na]⁺319.1.

Method B

To a solution of Intermediate 3 (2.66 kg, 3.09 mol, 18.2% in MeCN) was added 1-chloromethylnapthalene (535 g, 2.94 mol) followed by potassium carbonate (513 g, 3.71 mol) and a further portion of fresh MeCN (714 mL). The suspension was heated to between 50 to 60° C. for 17 h before cooling to 25 to 30° C. The solid was removed by filtration through a Celite pad, which was washed through with MeCN (2×967 mL). Concentrate the filtrates to 1.45 to 1.93 L under reduced pressure. The MeCN was exchanged to isopropanol under reduced pressure, maintaining the temperature <50° C. The temperature of the mixture was lowered to between 20 to 25° C., upon which a solid precipitate formed. The mixture was cooled further to −10 to 0° C., and the solids were then filtered, washed with isopropanol and dried under N₂ to give the title compound as a white solid (752.6 g, 2.49 mol, 80.5%); ¹H NMR (500 MHz, CDCl₃) 1.30 (3H, s), 1.65 (2H, td), 2.16-2.47 (6H, m), 5.66 (2H, s), 7.46 (1H, dd), 7.51-7.63 (3H, m), 7.78-7.93 (2H, m), 7.93-8.05 (1H, m). MS (ESI): m/z [M+Na]⁺ 319.1.

Intermediate 5: Methyl 5-(1,3,6,2-dioxazaborocan-2-yl)-4-fluoro-2-methoxybenzoate Method A

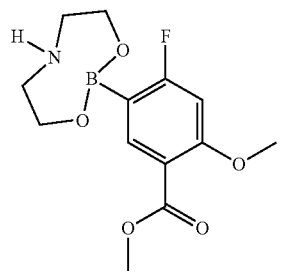 [SMILES: COC(=O)c1cc(B2OCCNCCO2)c(F)cc1OC]

B₂Pin₂ (362 g, 1.43 mol) was added to 2-Me-THF (1.75 L) that had been degassed with N₂ to <1% oxygen. The solution was held between 20 to 30° C. and methyl 4-fluoro-2-methoxybenzoate was added (250 g, 1.36 mol). DTBBPY (1.09 g, 4.10 mmol) was added and the reaction vessel evacuated and re-filled with N₂ until the oxygen level was <0.5%. [Ir(COD)OMe]₂ (1.35 g, 2.04 mmol) was added and the reaction vessel evacuated and re-filled with N₂ until the oxygen level was <0.5%. The reaction mixture was heated to between 80 to 85° C. and held at that temperature for a further 2 h. The reaction mixture was cooled to between 0 to 5° C. followed by the slow addition of diethanolamine (428 g, 4.07 mol, 10.9 M in IPA) over a period of 2.5 h, with the concurrent generation of H₂ gas. The reaction mixture was stirred for 2.5 h between 0 to 5° C., followed by filtration and washing of the solids with 2-Me-THF (3×750 mL). The solid was dried under N₂ for 10 h to give the title compound as a white solid (356 g, 1.20 mol, 88%); ¹H NMR (500 MHz, DMSO-d6) δ 2.81-2.89 (2H, m), 3.14 (2H, dq), 3.71 (2H, ddd), 3.74 (3H, s), 3.78 (3H, s), 3.84 (2H, td), 6.77 (1H, d), 7.10 (1H, s), 7.83 (1H, d). MS (ESI): m/z [M+H]⁺ 297.1.

Method B

B₂Pin₂ (29.0 g, 114 mmol) and methyl 4-fluoro-2-methoxybenzoate (20.6 g, 109 mmol) were added to 2-Me-THF (140 mL) that had been degassed with N₂ to <1% oxygen. The solution was held between 20 to 30° C. then DTBBPY (88 mg, 0.33 mmol) and [Ir(COD)OMe]₂ (108 mg, 0.16 mmol) were added and the reaction vessel evacuated and re-filled with N₂ until the oxygen level was <0.5%. The reaction mixture was heated to between 80 to 85° C. and held at that temperature for a further 3 h. The reaction mixture was cooled to between 0 to 10° C. followed by the slow addition of isopropanol (12.4 mL, 218 mmol), with the concurrent generation of H₂ gas. Addition of seed (100 mg of Intermediate 5) followed by addition of diethanolamine (22.84 g, 218 mmol) dissolved in IPA (20 mL) gave a mobile slurry. The slurry was warmed to 20 to 30° C. and the solid collect by filtration. It was then washed with 2-Me-THF (160 ml) and the solid was dried under N₂ for 10 h to give the title compound as a white solid (29.1 g, 96 mol, 88%); $^1$H NMR (500 MHz, DMSO-d6) δ 2.81-2.89 (2H, m), 3.14 (2H, dq), 3.71 (2H, ddd), 3.74 (3H, s), 3.78 (3H, s), 3.84 (2H, td), 6.77 (1H, d), 7.10 (1H, s), 7.83 (1H, d). MS (ESI): m/z [M+H]$^+$ 297.1.

Intermediate 6: Methyl 4-fluoro-5-hydroxy-2-methoxybenzoate

Method A

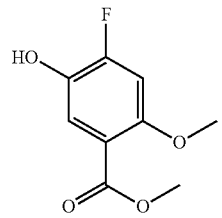

To a suspension of Intermediate 5 (350 g, 1.18 mol) in H$_2$O (1.05 L) was added THF (1.75 L) and the reaction mixture stirred until a clear solution is obtained. (NH$_4$)$_2$CO$_3$ (136 g, 1.41 mol) was added and the heterogenous mixture cooled to between 0 to 10° C. NaBO$_3$.4H$_2$O (217 g, 1.41 mol) was added in 10 equal portions over a period of 2 h maintaining the reaction temperature between 0 to 30° C. The reaction temperature was adjusted to between 20 to 30° C. and held for 1 h. An aq solution of NaHSO$_3$ (1.96 L, 942 mmol, 0.48 M in H$_2$O) was added over 3 h and the reaction mixture stirred for an additional 0.5 h. The reaction mixture was filtered, the solids washed with ethylacetate (700 mL) and the filtrate and wash combined to give a biphasic solution. The solution was separated and the retained organic phase solvent exchanged from THF/ethylacetate to MeOH under reduced pressure, maintaining the temperature <40° C. H$_2$O (3.50 L) was added drop-wise over a period of 4 h and the reaction mixture cooled to between 0 to 5° C. and held for 2 h. The reaction mixture was filtered, the collected solids washed with H$_2$O (3×350 mL) and dried under hot air at <40° C. to give the title compound as a white solid (195 g, 974 mmol, 83% yield); $^1$H NMR (500 MHz, CDCl$_3$) δ 3.82 (3H, s), 3.86 (3H, s), 6.72 (1H, d), 7.54 (1H, d). MS (ESI): m/z [M+H]$^+$ 201.0.

Method B

Intermediate 5 (32.41 g, 67.3 mmol) was dissolved in 2-Me-THF (100 mL) with acetic acid (12.13 g, 202 mmol) and cooled to between 0 to 10° C. Hydrogen peroxide solution (30% w/w, 9.16 g, 80.8 mmol) was added over 2 hours and then the reaction temperature was adjusted to between 20 to 30° C. and held for 18 hours. An aq solution of Na$_2$S$_2$O$_3$.5H$_2$O (20% w/w, 50 mL) quenches the mixture and gives a phase separation. The aqueous is discarded, and the organic washed twice with aq solution of Na$_2$S$_2$O$_3$.5H$_2$O (5% w/w, 100 mL). The organic phase was concentrated to 60 mL under reduced pressure followed by another 2 vacuum distillations with 2-Me-THF (100 mL) to give a dissolved solution at 35 to 45° C. Nucleation was controlled by addition of seed (100 mg of Intermediate 6) followed by slow addition of 300 mL n-heptane over 5 hours. The resulting slurry was adjusted to between 20 to 30° C. and stirred overnight prior to filtration. The collected solid was washed with n-heptane (2×60 mL) and dried to give the title compound as a white solid (12.5 g, 62.5 mmol, 93% yield); $^1$H NMR (500 MHz, CDCl$_3$) δ 3.82 (3H, s), 3.86 (3H, s), 6.72 (1H, d), 7.54 (1H, d). MS (ESI): m/z [M+H]$^+$ 201.0.

Intermediate 7: (1R,2R,3S,4S)-3-(Methoxycarbonyl) bicyclo[2.2.1]hept-5-ene-2-carboxylic acid

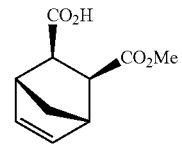 [SMILES: COC(=O)[C@@H]1[C@H](C(=O)O)[C@H]2C=C[C@@H]1C2]

To a solution of (3aR,4R,7S,7aS)-3a,4,7,7a-tetrahydro-4,7-methanoisobenzofuran-1,3-dione (387 g, 2.36 mol) in toluene (4.64 L) was added quinidine (843 g, 2.60 mol) followed by toluene (774 mL). The reaction mixture was cooled to between −10 to −5° C. and MeOH (227 g, 286 mL, 7.08 mol) was added drop-wise over 1.5 h before holding at between −10 to −5° C. for 14 h. The reaction mixture was warmed to between −5 to 5° C., held for 2 h, then filtered. The solids were washed with toluene (3×387 mL), the filtrate and washes combined and cooled to between 0 to 10° C. In a separate vessel an aq solution of HCl (590 mL, 7.08 mol, 12 M in H$_2$O) and NaCl (1.24 kg, 21.2 mol) were added to H$_2$O (6.39 L) and the resulting solution added dropwise to the main reaction vessel, maintaining the reaction solution <10° C. The reaction mixture was warmed to between 10 to 20° C., held for 0.5 h then filtered. The solids were washed with toluene (1.94 L), the filtrate and wash combined, and the biphasic solution separated. The organic phase was washed with aq NaCl (3.87 L, 20% w/w in H$_2$O) and stored at <5° C. to give the title compound as a 5.9% w/w solution in toluene (6.19 kg, 1.83 mol, 78%); $^1$H NMR for purified compound (400 MHz DMSO-d$_6$) δ 1.25-1.32 (1H, m), 1.95 (1H, d), 2.48-2.50 (2H, m), 2.93 (2H, s), 3.51 (3H, s), 6.15-6.22 (2H, m), 12.21 (1H, s). MS (ESI): m/z [M+Na]$^+$ 219.1.

Intermediate 8: Methyl (1S,2S,3R,4R)-3-aminobicyclo[2.2.1]hept-5-ene-2-carboxylate hydrochloride

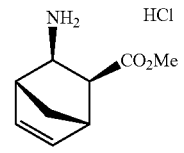 [SMILES: Cl ; COC(=O)[C@@H]1[C@H](N)[C@H]2C=C[C@@H]1C2]

To a solution of Intermediate 7 in toluene (6.19 kg, 5.9% w/w, 1.85 mol) at between −5 to 5° C. was added TEA (307 mL, 223 g, 2.22 mol) followed by DPPA (538 g, 1.94 mol), maintaining the reaction solution <5° C. The reaction mixture was stirred for 4 h at between −5 to 5° C. then TEA was added (767 mL, 557 g, 5.55 mol) followed by citric acid (352 g, 1.85 mol). The reaction mixture was stirred for 6 h at between −5 to 5° C. then H$_2$O (3.6 L) was added maintaining the reaction solution <10° C. The biphasic reaction solution was stirred for 0.5 h, the phases separated and the organic phase washed with H$_2$O (3.6 L) and aq NaCl (3.6 L, 15% w/w in H$_2$O) then stored between 2 to 8° C. to give methyl (1S,2S,3R,4R)-3-(azidocarbonyl)bicyclo[2.2.1] hept-5-ene-2-carboxylate (Intermediate 9) as a solution in toluene that was used directly in the next step. Intermediate 9 as a solution in toluene at between 2 to 8° C. was added over 2 h to a reactor containing toluene (1.80 L) at between 70 to 80° C., maintaining the reaction temperature <80° C. The resulting solution was stirred for 1 h before cooling to between 20 to 30° C. Exchange of the organic reaction solvent from toluene to 1,4-dioxane under reduced pressure, maintaining the temperature <50° C., gave Methyl (1S,2S,3R,4R)-3-isocyanatobicyclo[2.2.1]hept-5-ene-2-carboxylate (Intermediate 10) as a solution in 1,4-dioxane that was used directly in the next step. To a solution of Intermediate 10 in 1,4-dioxane at between 10 to 20° C. was added HCl (420 mL, 1.68 mol, 4 M in 1,4-dioxane) followed by $H_2O$ (360 mL, 1.68 mol, 4.67 M in 1,4-dioxane). The reaction mixture was warmed to between 25 to 35° C. and held for 16 h. MTBE (1.65 L) was added drop-wise and the reaction mixture filtered, the solids washed with MTBE/1,4-dioxane (1:1, 660 mL) and MTBE (660 mL), then dried at between 30 to 40° C. under vacuum to give the title compound as a white solid (258 g, 1.27 mol, >99% ee, 75%); $^1$H NMR (400 MHz, DMSO-d6) δ 1.45 (1H, d), 2.04 (1H, d), 2.52-2.67 (1H, m), 2.94-3.10 (2H, m), 3.19 (1H, d), 3.65 (3H, s), 6.21 (1H, m), 6.30 (1H, m), 8.34 (3H, s). MS (ESI): m/z [M+H]$^+$ 168.1.

Intermediate 11: Naphthalen-1-ylmethyl (1r,4r)-4-hydroxy-1-methylcyclohexane-1-carboxylate

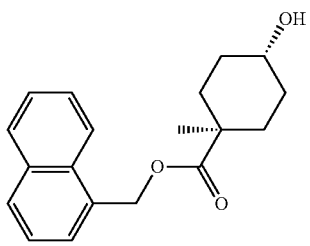 [SMILES: C[C@]1(C(=O)OCc2cccc3ccccc23)CC[C@H](O)CC1]

Route A

To a solution of $Na_2HPO_4.12H_2O$ (8.25 g, 23.0 mmol), $NaH_2PO_4$ (0.55 g, 4.48 mmol) and $MgCl_2$ (0.11 g, 1.10 mmol) in $H_2O$ (550 mL) at 20 to 30° C. was added Intermediate 4 (50.0 g, 169 mmol) as a solution in IPA (450 mL). The pH of the reaction solution was adjusted to between 7.3 to 7.8 using 6 M HCl and NAD+ (0.66 g, 1.00 mmol) was added followed by ADH-230 (7.50 g, 0.15 wt %). ADH-230 is an alcohol dehydrogenase available from Johnson Matthey PLC, UK (catalogue no. ADH-230). The reaction mixture was then held at 33 to 37° C. for 18 h before concentration to between 300 and 400 mL under reduced pressure, maintaining the temperature <45° C. NaCl (150 g), Celite® (20.0 g, 0.4 wt %) and MTBE (500 mL) was added and the reaction held for 0.5 h. The mixture was filtered and the filter cake washed with MTBE (250 mL). The combined filtrate was separated and the aq phase extracted with MTBE (500 mL). The organic phases were combined and washed with $H_2O$ (250 mL) before solvent exchange to THF under reduced pressure, maintaining the temperature <45° C., gave the title compound (138 g, 33% w/w %, >99:1 trans:cis, <0.1% IPA, 92% yield) as a solution in THF that was used directly in the next step. $^1$H NMR for purified compound (500 MHz, CDCl$_3$) δ 1.21 (3H, s), 1.48-1.58 (2H, m), 1.62-1.77 (4H, m), 1.82-1.93 (2H, m), 3.74-3.77 (1H, m), 5.57 (2H, s), 7.41-7.48 (1H, m), 7.48-7.57 (3H, m), 7.85 (1H, d), 7.87-7.91 (1H, m), 7.98 (1H, d). MS (ESI): m/z [M+Na]$^+$321.1.

Route B

A solution of lithium tri-sec-butylborohydride (1.06 g, 5.6 mmol) in THF (5 mL) was added dropwise to a stirred solution of Intermediate 4 (1.00 g, 3.37 mmol) in THF (10 mL) cooled to −78° C., over a period of 1 min under nitrogen. The resulting solution was stirred at −78° C. for 2 h. The reaction mixture was quenched with 0.1 M HCl (10 mL) at −78° C. and then extracted with EtOAc (3×50 mL). The organic layers were pooled and dried over $Na_2SO_4$ filtered and evaporated. The residue was purified by preparative TLC (EtOAc/PE, 1:3), to afford the title compound (0.488 g, 48.5%) as a pale yellow gum. The isolated material had a 3:100 cis/trans ratio. $^1$H NMR (400 MHz, CDCl$_3$) δ1.21-1.25 (s, 3H), 1.37-1.49 (m, 1H), 1.49-1.61 (m, 2H), 1.61-1.74 (m, 4H), 1.83-1.95 (m, 2H), 3.74-3.83 (dq, 1H), 5.57-5.61 (s, 2H), 7.43-7.54 (dd, 1H), 7.50-7.61 (m, 3H), 7.84-7.94 (m, 2H), 7.97-8.04 (m, 1H). MS (ESI): m/z [M+Na]$^+$321.

Intermediate 12: Methyl 4-fluoro-2-methoxy-5-(((1s,4s)-4-methyl-4-((naphthalen-1-ylmethoxy)carbonyl)cyclohexyl)oxy)benzoate

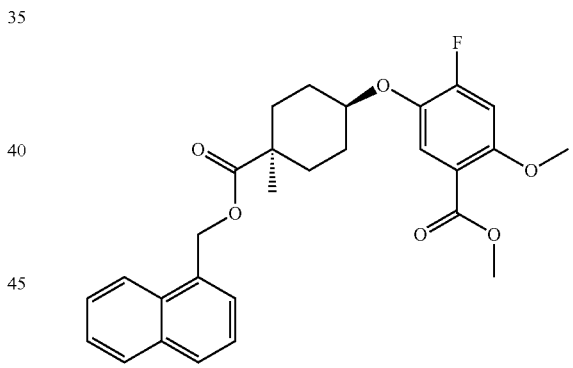

To a solution of Intermediate 11 in THF (736 g, 34% w/w, 839 mmol) was added THF (156 mL), PPh$_3$ (248 g, 944 mmol) and Intermediate 6 (140 g, 699 mmol). The solution was heated to 30° C. prior to the drop-wise addition of DIAD (184 g, 909 mmol) over 1 h maintaining the reaction temperature <40° C. The solution was held at between 30 and 40° C. for 1 h before cooling to between 20 and 30° C. followed by the addition of an aq solution of NaCl (700 mL, 20% w/w in $H_2O$). The layers were separated and the crude solution of the title compound in THF was used directly in the next step. $^1$H NMR for purified compound (500 MHz, CDCl$_3$) δ 1.17 (3H, s), 1.20-1.30 (2H, m), 1.58 (2H, qd), 1.88-1.98 (2H, m), 2.29 (2H, d), 3.84 (3H, s), 3.88 (3H, s), 4.05 (1H, tq), 5.61 (2H, s), 6.72 (1H, d), 7.43-7.58 (5H, m), 7.82-7.94 (2H, m), 8.00 (1H, d). MS (ESI): m/z [M+Na]$^+$ 503.2.

Intermediate 13: 4-Fluoro-2-methoxy-5-(((1s,4s)-4-methyl-4-((naphthalen-1-ylmethoxy)carbonyl)cyclohexyl)oxy)benzoic acid

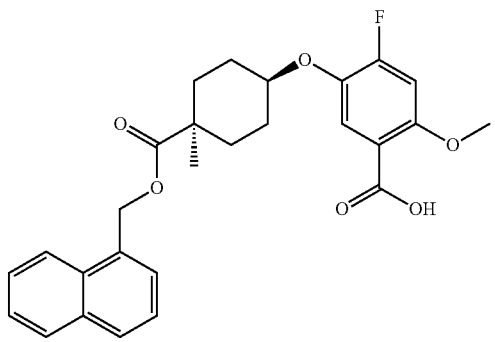 [SMILES: COc1cc(F)c(O[C@H]2CC[C@@](C)(C(=O)OCc3cccc4ccccc34)CC2)cc1C(=O)O]

To the crude solution of Intermediate 12 used directly from the previous step at between 0 and 5° C., was added a aq solution of LiOH.2H$_2$O (88.0 g, 2.10 mol, in 525 mL of H$_2$O) over 1 h maintaining the reaction temperature <10° C. The solution was warmed to between 15 and 30° C. and vigorously stirred for 16 h. IPAC (1.68 L) was added and the solution cooled to between 0 and 10° C. followed by the drop-wise addition of H$_3$PO$_4$ (1.26 L, 2.52 M, 2 M in H$_2$O), maintaining the reaction temperature <10° C., to give a solution pH of between 4.0 and 5.0. The organic layer was separated and washed with of an aq solution of NaCl (700 mL, 20% w/w in H$_2$O). The THF was removed under reduced pressure, maintaining the temperature <50° C. and IPAC (4.20 L) was added to give the title compound in IPAC that was used directly in the next step. $^1$H NMR for purified compound (500 MHz, CDCl$_3$) δ 1.18 (3H, s), 1.22-1.36 (2H, m), 1.58 (2H, qd), 1.95 (2H, dt), 2.29 (2H, d), 4.02 (3H, s), 4.19 (1H, td), 5.60 (2H, s), 6.82 (1H, d), 7.46 (1H, dd), 7.49-7.62 (3H, m), 7.78 (1H, d), 7.82-7.94 (2H, m), 7.99 (1H, d).

Intermediate 14: 4-Fluoro-2-methoxy-5-(((1s,4s)-4-methyl-4-((naphthalen-1-ylmethoxy)carbonyl)cyclohexyl)oxy)benzoate cyclohexanaminium salt

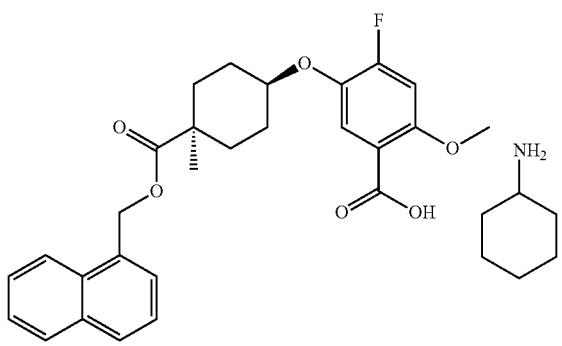

To a crude solution of Intermediate 13 in IPAC used directly from the previous step at between 50 and 55° C., was added a solution of cyclohexylamine (280 mL, 699 mmol, 2.5 M in IPAC) drop-wise over 3 h. The heterogenous slurry was stirred at between 50 and 55° C. for 0.5 h then at between 40 and 45° C. for a further 1 h. The reaction mixture was filtered and the solids washed with IPAC (3×0.98 L) pre warmed to between 40 and 45° C. and dried under a flow of N$_2$ at 45° C. for 16 h. To the dried collected solids was added MeOH (3.64 L) and the mixture heated to between 55 and 56° C. H$_2$O (1.58 L) was added drop-wise over 1 h then the mixture stirred for 1 h before cooling to between 0 and 5° C. over 3 h. The heterogenous slurry was held for a further 1 h then filtered, washed with 5:3 MeOH:H$_2$O at 0° C. (2×750 mL) and the solids dried under N$_2$ at 45° C. for 16 h to give the title compound as a white solid (332 g, 85% from methyl 4-fluoro-5-hydroxy-2-methoxybenzoate); $^1$H NMR (500 MHz, CDCl$_3$) δ 0.96 (1H, ddt), 1.03-1.36 (6H, m), overlapping 1.14 (3H, S), 1.46-1.7 (5H, m), 1.91 (4H, dt), 2.26 (2H, d), 2.81 (1H, t), 3.76 (3H, s), 4.03 (1H, tt), 5.59 (2H, s), 6.65 (1H, d), 7.37-7.49 (2H, m), 7.49-7.6 (3H, m), 7.81-7.93 (2H, m), 7.98 (1H, d). MS (ESI): m/z [M+Na]$^+$489.2.

Intermediate 15: Methyl (1S,2S,3R,4R)-3-(4-fluoro-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylate

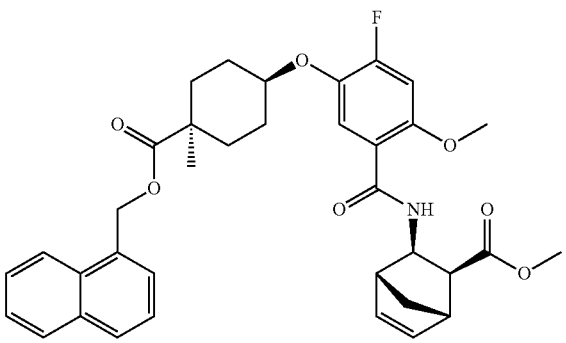 [SMILES: COC(=O)[C@@H]1[C@H](NC(=O)c2cc(O[C@H]3CC[C@@](C)(C(=O)OCc4cccc5ccccc45)CC3)c(F)cc2OC)[C@H]2C=C[C@@H]1C2]

To a solution of Intermediate 14 (149 g, 264 mmol) in DCM (750 mL) at between 15 and 30° C. was added H$_2$O (450 mL) followed by the slow addition of HCL (300 mL, 1 M in H$_2$O). The biphasic solution was stirred for 0.5 h then separated and the organic phased washed with HCl (750 mL, 0.2 M in H$_2$O) then with H$_2$O (3×750 mL). The organic solution was concentrated under reduced pressure, maintaining the temperature below 30° C., to dry to <0.1% H$_2$O. The solution was diluted with DCM (450 mL) to bring the total volume to 750 mL before the addition of Intermediate 8 (59.3 g, 291 mmol) to give a heterogenous slurry. To this mixture was added DIPEA (137 g, 1.06 mol) followed by T3P (252 g, 397 mmol, 50% w/w in EtAOc) and the solution stirred for 1 h. The solution was cooled to between 0 and 10° C. followed by the addition of H$_2$O (750 mL) and subsequently stirred for a further 0.5 h. The biphasic solution was separated and the organic phase washed with H$_2$O (2×750 mL) before solvent exchange to THF under reduced pressure gave the title compound in THF that was used directly in the next step. $^1$H NMR for purified compound (500 MHz, CDCl$_3$) δ1.16 (3H, s), 1.25 (2H, td), 1.49-1.69 (3H, m), 1.92-2.01 (2H, m), 2.04-2.1 (1H, m), 2.28 (2H, d), 2.71 (1H, dd), 2.83 (1H, s), 2.92-3.05 (1H, m), 3.61 (3H, s), 3.93 (3H, s), 4.17 (1H, td), 4.46 (1H, td), 5.60 (2H, s), 6.25 (2H, ddd), 6.72 (1H, d), 7.46 (1H, dd), 7.48-7.6 (3H, m), 7.81-7.95 (3H, m), 7.99 (1H, d), 8.60 (1H, d). MS (ESI): m/z [M+H]$^+$ 616.3.

Intermediate 16: (1S,2S,3R,4R)-3-(4-Fluoro-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylic acid

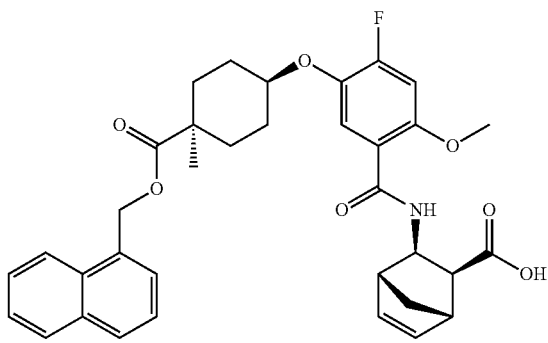 [SMILES: COc1cc(F)c(O[C@H]2CC[C@@](C)(C(=O)OCc3cccc4ccccc34)CC2)cc1C(=O)N[C@H]1[C@@H](C(=O)O)[C@@H]2C=C[C@H]1C2]

A crude solution of Intermediate 15 in THF (750 mL) from the previous step was cooled to between 0 and 5° C. An aq solution of LiOH.2H$_2$O (27.7 g, 661 mmol, in 150 mL of H$_2$O) was added and the solution held for 36 h. The pH of the solution was adjusted to 2 with the portion wise slow addition of HCl (0.5 M, 1.45 L, 2.90 mol) and held for 1 h between 0 and 5° C. The heterogenous slurry was filtered and the solids washed with 1:3 MeOH:H$_2$O at 0° C. (600 mL) and the solids dried under N$_2$ at 45° C. for 16 h to give crude title compound as a white solid (158 g, 99%). The crude (150 g) was slurried in IPAC (1.13 L) at between 60 and 65° C. for 0.5 h. The heterogenous mixture was cooled to between 0 and 5° C. over 3 h then further stirred for 1 h before filtration. The collected solids were with IPAC at between 0 and 5° C. (2×300 mL) then dried under N$_2$ at 45° C. for 12 h to give the title compound as a white solid (127 g, 82% from Intermediate 14); $^1$H NMR (500 MHz, CDCl$_3$) δ1.16 (3H, s), 1.2-1.35 (2H, m), 1.50-1.69 (3H, m), 1.89-2.08 (3H, m), 2.27 (2H, ddd), 2.72 (1H, dd), 2.80 (1H, s), 3.06 (1H, s), 3.75 (3H, s), 4.15 (1H, tt), 4.43-4.54 (1H, m), 5.59 (2H, s), 6.24 (2H, ddd), 6.53 (1H, d), 7.45 (1H, dd), 7.47-7.58 (3H, m), 7.8-7.9 (3H, m), 7.94-8.05 (1H, m), 8.59 (1H, d). MS (ESI): m/z [M+H]$^+$ 602.3.

Intermediate 17: Naphthalen-1-ylmethyl (1S,4s)-4-(2-fluoro-4-methoxy-5-(((1R,2R,3S,4S)-3-(((1-methylcyclobutyl)methyl)carbamoyl)bicyclo[2.2.1]hept-5-en-2-yl)carbamoyl)phenoxy)-1-methylcyclohexane-1-carboxylate

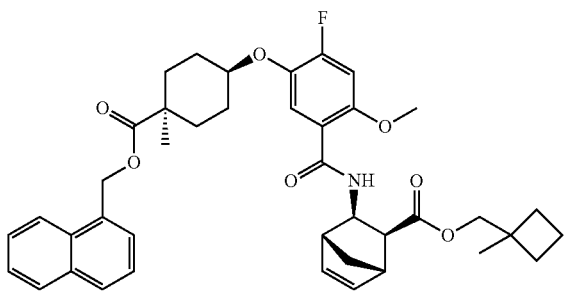 [SMILES: COc1cc(F)c(O[C@H]2CC[C@@](C)(C(=O)OCc3cccc4ccccc34)CC2)cc1C(=O)N[C@H]1[C@@H](C(=O)OCC2(C)CCC2)[C@@H]2C=C[C@H]1C2]

To a solution of DIPEA (6.45 g, 49.9 mmol) in DCM (300 mL) at between 0 and 5° C. was added Intermediate 16 (30.6 g, 49.9 mmol) followed by (1-methylcyclobutyl)methanamine hydrochloride (8.63 g, 62.4 mmol). DIPEA (25.8 g, 200 mmol) was added drop-wise maintaining the temperature between 0 and 5° C., followed by the addition of T3P (50.8 g, 79.8 mmol, 50% w/w in EtAOc) over 0.5 h. The solution was warmed to between 15 and 25° C. and stirred for 1 h followed by the drop-wise addition of H$_2$O (150 mL) maintaining the temperature below 30° C. The biphasic solution was separated and the organic phase washed with H$_2$O (2×150 mL) then the solvent exchanged to EtOH under reduced pressure to give the title compound as a crude solution in EtOH (128 g, 26% w/w, 96% yield) that was used directly in the next step. $^1$H NMR for purified compound (500 MHz, CDCl$_3$) δ 0.98 (3H, s), 1.16 (3H, s), 1.21-1.29 (2H, m), 1.51-1.66 (5H, m), 1.66-1.76 (3H, m), 1.76-1.82 (1H, m), 1.88-2.02 (2H, m), 2.26 (3H, dd), 2.40 (1H, dd), 2.80 (1H, s), 3.00 (1H, s), 3.05 (1H, dd), 3.21 (1H, dd), 3.93 (3H, s), 4.06-4.2 (1H, m), 4.39 (1H, td), 5.60 (2H, s), 5.64 (1H, t), 6.19-6.38 (2H, m), 6.70 (1H, d), 7.46 (1H, dd), 7.49-7.62 (3H, m), 7.75-7.93 (3H, m), 8.00 (1H, d), 8.66 (1H, d). MS (ESI): m/z [M+H]$^+$ 683.3.

Intermediate 19: (1S,2S,3R,4R)-3-((tert-Butoxycarbonyl)amino)bicyclo[2.2.1]hept-5-ene-2-carboxylic acid

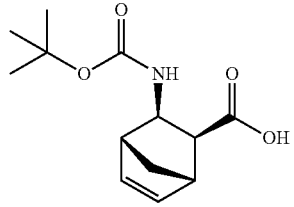 [SMILES: CC(C)(C)OC(=O)N[C@H]1[C@@H](C(=O)O)[C@@H]2C=C[C@H]1C2]

A solution of (1S,2S,3R,4R)-3-aminobicyclo[2.2.1]hept-5-ene-2-carboxylic acid (0.90 g, 5.88 mmol) in H$_2$O (15 mL) was added dropwise to a stirred solution of Boc$_2$O (2.05 mL, 8.8 mmol) and Et$_3$N (2.46 mL, 17.6 mmol) in 1,4-dioxane (20 mL) at 5° C., and under nitrogen atmosphere. The reaction mixture was stirred at 20° C. for 14 h, and then diluted with EtOAc (250 mL). The organic layer was washed sequentially with sat NaHCO$_3$ (100 mL), H$_2$O (100 mL), and sat brine (2×100 mL), dried over Na$_2$SO$_4$, filtered and evaporated. The crude product was precipitated from EtOAc and PE to give the title compound (1.49 g, 100%) as a pale yellow solid; MS (ESI) m/z [M+Na]$^+$276

Intermediate 20: tert-Butyl ((1R,2R,3S,4S)-3-(((1-methylcyclobutyl)methyl)carbamoyl)bicyclo[2.2.1]hept-5-en-2-yl)carbamate

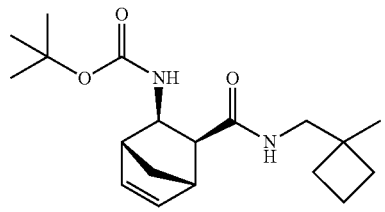 [SMILES: CC1(CNC(=O)[C@@H]2[C@H](NC(=O)OC(C)(C)C)[C@H]3C=C[C@@H]2C3)CCC1]

DIPEA (5.49 mL, 31.4 mmol) was added dropwise to a solution of Intermediate 19 (1.99 g, 7.86 mmol), (1-methylcyclobutyl)methanamine hydrochloride (1.07 g, 7.86 mmol), EDC (3.77 g, 19.64 mmol) and HOBt (3.01 g, 19.64 mmol) in DMF (60 mL) at 20° C. and under nitrogen atmosphere. The reaction mixture was stirred at 20° C. for 14 h and then diluted with EtOAc (125 mL). The organic layer was washed sequentially with sat NH$_4$Cl (125 mL), H$_2$O (125 mL), and sat brine (125 mL), dried over Na$_2$SO$_4$, filtered and evaporated. The crude product was purified by flash chromatography using a gradient of 0-12% EtOAc in PE as mobile phase, to give the title compound (2.5 g, 95%) as a pale yellow solid.

Intermediate 21: (1S,2S,3R,4R)-3-Amino-N-((1-methylcyclobutyl)methyl)bicyclo[2.2.1]hept-5-ene-2-carboxamide hydrochloride

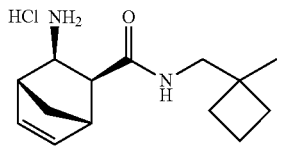 [SMILES: Cl ; CC1(CNC(=O)[C@@H]2[C@H](N)[C@H]3C=C[C@@H]2C3)CCC1]

HCl (25 mL, 100 mmol, 4 M in 1,4-dioxane) was added dropwise to Intermediate 20 (2.5 g, 7.47 mmol) at 0° C., under nitrogen atmosphere, and the reaction mixture was stirred at 20° C. for 14 h. The solvent was removed under reduced pressure, and the crude product was purified by precipitation from EtOAc and diisopropyl ether to give the title compound (1.70 g, 84%) as a white solid.

Intermediate 22: (1R,2S,3R,4S)-3-Amino-N-((1-methylcyclobutyl)methyl)bicyclo[2.2.1]heptane-2-carboxamide hydrochloride

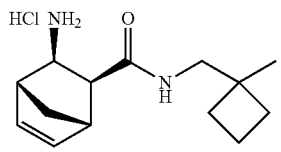 [SMILES: Cl ; CC1(CNC(=O)[C@@H]2[C@H](N)[C@H]3C=C[C@@H]2C3)CCC1]

Pd—C (0.086 g, 0.81 mmol) was added to a solution of Intermediate 21 (1.1 g, 4.06 mmol) in MeOH (30 mL) and the reaction mixture was stirred under an atmosphere of hydrogen (1.5 atm) at 20° C. for 14 h. The reaction mixture was filtered through a pad of Celite® and the solvent was removed under reduced pressure to give the title compound (1.10 g, 99%); MS (ESI) m/z [M+H]$^+$ 237.

Intermediate 23: Methyl 5-bromo-4-fluoro-2-((2-(trimethylsilyl)ethoxy)methoxy)benzoate

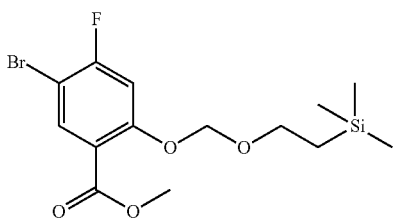 [SMILES: COC(=O)c1cc(Br)c(F)cc1OCOCC[Si](C)(C)C]

(2-(Chloromethoxy)ethyl)trimethylsilane (1.87 g, 11.2 mmol) was added dropwise to a solution of K$_2$CO$_3$ (3.11 g, 22.5 mmol) and methyl 5-bromo-4-fluoro-2-hydroxy-benzoate (2.8 g, 11.2 mmol) in DMF (25 mL) at 20° C. under a nitrogen atmosphere. The reaction mixture was heated at 80° C. for 14 h, and then cooled to rt and diluted with EtOAc (250 mL). The organic layer was washed with sat brine (3×150 mL), dried over Na$_2$SO$_4$, filtered, and evaporated under reduced pressure. The crude product was purified by flash chromatography using a gradient of 0-3% EtOAc in PE as mobile phase, to give the title compound (3.0 g, 70%); MS (ESI) m/z [M+Na]$^+$ 401.4.

Intermediate 24: Methyl 4-fluoro-5-(4,4,5,5-tetramethyl-1,3,2-dioxaborolan-2-yl)-2-((2-(trimethylsilyl)ethoxy)methoxy)benzoate

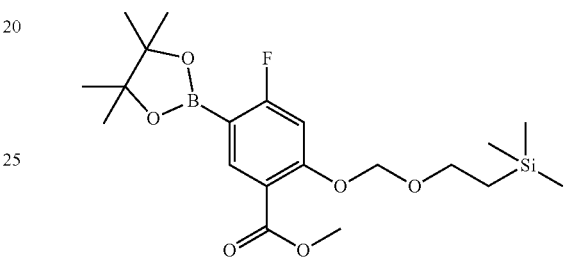

Intermediate 23 (3.0 g, 7.91 mmol) was added to a suspension of B$_2$Pin$_2$ (3.01 g, 11.86 mmol), KOAc (2.33 g, 23.73 mmol) and PdCl$_2$(dppf) (0.58 g, 0.79 mmol) in 1,4-dioxane (50 mL) and the reaction mixture was stirred at 60'° C. for 14 h. The reaction mixture was concentrated under reduced pressure and the crude product was dissolved in EtOAc (20 mL). The organic layer was washed with H$_2$O (3×20 mL), dried over Na$_2$SO$_4$, filtered, and evaporated under reduced pressure. The crude product was purified by flash chromatography using a gradient of 0-10% of EtOAc in PE as mobile phase, to give the title compound (2.5 g, 74%); MS (ESI) m/z [M+Na]$^+$ 449.

Intermediate 25: Methyl 4-fluoro-5-hydroxy-2-((2-(trimethylsilyl)ethoxy)methoxy)benzoate

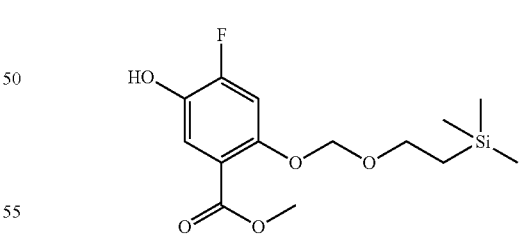

A solution of sodium perborate (2.71 g, 17.59 mmol) in H$_2$O (20 mL) was added slowly to a stirred solution of Intermediate 24 (2.5 g, 5.86 mmol) in THF (40 mL) at 0° C. under a nitrogen atmosphere. The reaction mixture was stirred at 20° C. for 3 h, and then diluted with DCM (50 mL). The organic layer was washed with sat brine (3×50 mL), dried over Na$_2$SO$_4$, filtered, and evaporated under reduced pressure. The crude product was purified by preparative TLC (EtOAc:PE, 1:3) to give the title compound (1.5 g, 81%); MS (ESI) m/z [M+Na]$^+$339.

Intermediate 26: Methyl 4-fluoro-5-(((1s,4s)-4-methyl-4-((naphthalen-1-ylmethoxy)carbonyl)cyclohexyl)oxy)-2-((2-(trimethylsilyl)ethoxy)methoxy)benzoate

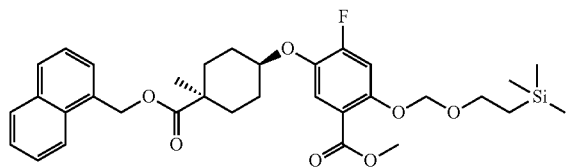 [SMILES: COC(=O)c1cc(O[C@H]2CC[C@@](C)(C(=O)OCc3cccc4ccccc34)CC2)c(F)cc1OCOCC[Si](C)(C)C]

A solution of DBAD (1.74 g, 7.54 mmol) in toluene (10 mL) was added dropwise to a stirred solution of Intermediate 11 (1.5 g, 5.03 mmol), Intermediate 25 (1.75 g, 5.53 mmol) and Ph$_3$P (1.98 g, 7.54 mmol) in DCM (40 mL) at 20° C. and the reaction mixture was stirred at rt for 14 h. The reaction mixture was diluted with EtOAc (200 mL) and the organic layer was washed sequentially with sat NH$_4$Cl (100 mL), sat NaHCO$_3$ (100 mL) and sat brine (100 mL), dried over Na$_2$SO$_4$, filtered, and evaporated. The crude product was purified by preparative TLC (EtOAc:PE, 1:5) to give the title compound (2.50 g, 83%); MS (ESI) m/z [M+Na]$^+$619.

Intermediate 27: Methyl 4-fluoro-2-hydroxy-5-(((1s,4s)-4-methyl-4-((naphthalen-1-ylmethoxy)carbonyl)cyclohexyl)oxy)benzoate

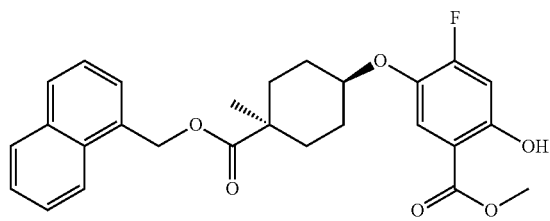 [SMILES: COC(=O)c1cc(O[C@H]2CC[C@@](C)(C(=O)OCc3cccc4ccccc34)CC2)c(F)cc1O]

HCl in 1.4-dioxane (1.27 mL, 4.2 M) was added dropwise to a stirred solution of Intermediate 26 (2.5 g, 4.19 mmol) in THF (40 mL) at 0° C. and under a nitrogen atmosphere, and the reaction mixture was stirred at 0° C. for 3 h. The solvent was removed under reduced pressure and the crude product was purified by precipitation from EtOAc and DCM to give the title compound (1.50 g, 77%); MS (ESI) m/z [M+Na]$^+$ 589.

Intermediate 28: Methyl 4-fluoro-2-(fluoromethoxy)-5-(((1s,4s)-4-methyl-4-((naphthalen-1-ylmethoxy)carbonyl)cyclohexyl)oxy)benzoate

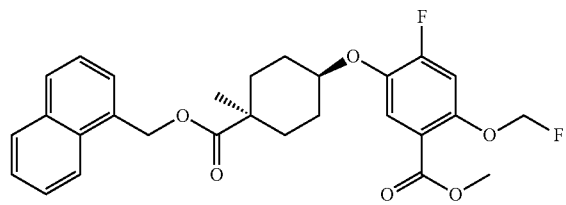 [SMILES: COC(=O)c1cc(O[C@H]2CC[C@@](C)(C(=O)OCc3cccc4ccccc34)CC2)c(F)cc1OCF]

A solution of N-((fluoromethyl)(oxo)(phenyl)-λ$^6$-sulfaneylidene)-4-methylbenzenesulfonamide (351 mg, 1.07 mmol) in DMSO (15 mL) was added dropwise to a stirred solution of Intermediate 27 (500 mg, 1.07 mmol) and NaH (50 mg, 1.25 mmol) in DMSO (10 mL) at 20° C. and under a nitrogen atmosphere. The reaction mixture was stirred at 80° C. for 3 h, and then sat NH$_4$Cl (10 mL) was added. The H$_2$O phase was extracted with EtOAc (3×25 mL) and the combined organic layer was dried over Na$_2$SO$_4$, filtered, and evaporated. The process described above was repeated two more times using in total 1.46 mmol of Intermediate 27. The crude products were combined and purified by preparative TLC (EtOAc:PE, 1:3) to give the title compound (0.52 g, 41%); MS (ESI) m/z [M+Na]$^+$521.

Intermediate 29: 4-Fluoro-2-(fluoromethoxy)-5-(((1s,4s)-4-methyl-4-((naphthalen-1-ylmethoxy)carbonyl)cyclohexyl)oxy)benzoic acid

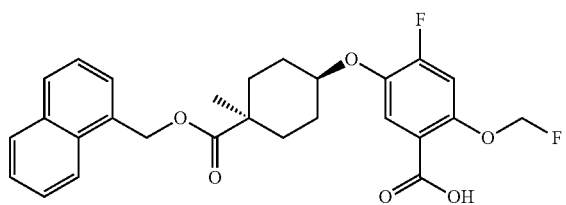 [SMILES: C[C@]1(C(=O)OCc2cccc3ccccc23)CC[C@@H](Oc2cc(C(=O)O)c(OCF)cc2F)CC1]

A solution of LiOH (14.4 mg, 0.60 mmol) in H$_2$O (2.0 mL) was added dropwise to a stirred solution of Intermediate 28 (200 mg, 0.40 mmol) in THF (4 mL) and the reaction mixture was stirred at rt for 3 h. The process was repeated two more times using in total 0.64 mmol of Intermediate 28. The reaction mixtures were combined and pH adjusted to 3 with aq HCl (3 M). The reaction mixture was diluted with EtOAc (250 mL) and the organic layer was washed sequentially with sat brine (200 mL), H$_2$O (200 mL) and sat brine (150 mL), dried over Na$_2$SO$_4$, filtered, and evaporated. The crude product was purified by preparative TLC (MeOH:DCM, 1:5) to give the title compound (310 mg, 60%); MS (ESI) m/z [M+Na]$^+$507.

Intermediate 30: Naphthalen-1-ylmethyl (1S,4s)-4-(2-fluoro-4-(fluoromethoxy)-5-((((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylate

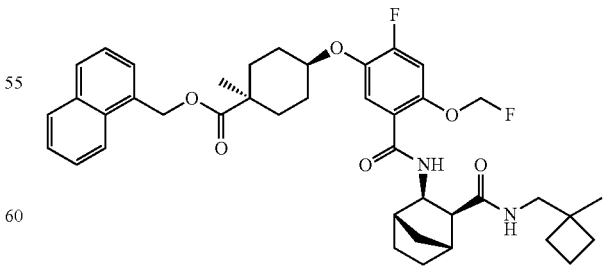

DIPEA (0.56 mL, 3.20 mmol) was added dropwise to a solution of Intermediate 29 (310 mg, 0.64 mmol), Intermediate 22 (302 mg, 1.28 mmol), EDC (368 mg, 1.92 mmol) and HOBt (294 mg, 1.92 mmol) in DMF (10 mL) at 0° C.

and under a nitrogen atmosphere, and the reaction mixture was stirred at 20° C. for 14 h. The reaction mixture was diluted with EtOAc (50 mL), and the organic layer was washed sequentially with sat NH₄Cl (50 mL), sat NaHCO₃ (50 mL), and sat brine (50 mL), dried over Na₂SO₄, filtered, and evaporated under reduced pressure. The crude product was purified by preparative TLC (EtOAc:PE, 1:2), to give the title compound (227 mg, 50%); MS (ESI) m/z [M+H]⁺ 703.

Intermediate 31: Methyl 4-fluoro-2-methyl-5-(((1s,4s)-4-methyl-4-((naphthalen-1-ylmethoxy)carbonyl)cyclohexyl)oxy)benzoate

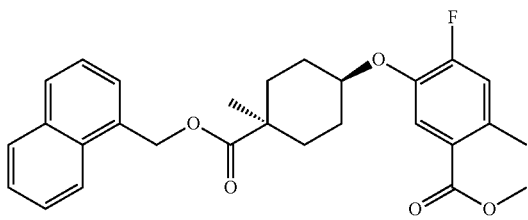 [SMILES: COC(=O)c1cc(O[C@H]2CC[C@@](C)(C(=O)OCc3cccc4ccccc34)CC2)c(F)cc1C]

Intermediate 11 (1.10 g, 3.69 mmol), methyl 4-fluoro-5-hydroxy-2-methylbenzoate (1.02 g, 5.53 mmol), DIAD (1.43 mL, 7.37 mmol) and triphenylphosphine (1.45 g, 5.53 mmol) were dissolved in THF (20 mL) and the reaction mixture was heated at 60° C. for 5 h The reaction mixture was concentrated under reduced pressure and DCM (20 mL) was added to the crude product. The organic layer was washed with H₂O (3×20 mL), dried over Na₂SO₄, filtered, and evaporated. The crude product was purified by reversed phase flash chromatography on a C18 column, using a gradient of 0-70% of MeCN in H₂O as mobile phase, to give the title compound (1.50 g, 88%); MS (ESI) m/z [M+H]⁺ 465.

Intermediate 32: 4-Fluoro-2-methyl-5-(((1s,4s)-4-methyl-4-((naphthalen-1-ylmethoxy)carbonyl)cyclohexyl)oxy)benzoic acid

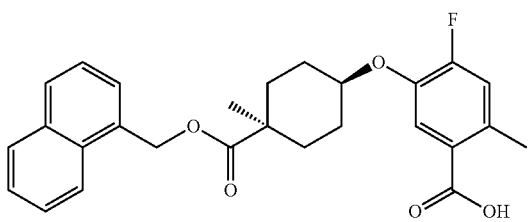 [SMILES: Cc1cc(F)c(O[C@H]2CC[C@@](C)(C(=O)OCc3cccc4ccccc34)CC2)cc1C(=O)O]

Intermediate 31 (1.40 g, 3.01 mmol) and LiOH (217 mg, 9.04 mmol) was dissolved in a mixture of THF (12 mL) and H₂O (3 mL), and the reaction mixture was stirred at rt for 12 h. The reaction mixture was concentrated under reduced pressure and the crude product was dissolved in DCM (10 mL). The organic layer was washed with H₂O (3×5 mL), dried over Na₂SO₄, filtered and evaporated under reduced pressure. The crude product was purified by preparative TLC (PE:EtOAc, 3:1), to give the title compound (800 mg, 59%); MS (ESI) m/z [M+H]⁺ 299.

Intermediate 33: Naphthalen-1-ylmethyl (1S,4s)-4-(2-fluoro-4-methyl-5-(((1R,2R,3S,4S)-3-(((1-methylcyclobutyl)methyl)carbamoyl)bicyclo[2.2.1]hept-5-en-2-yl)carbamoyl)phenoxy)-1-methylcyclohexane-1-carboxylate

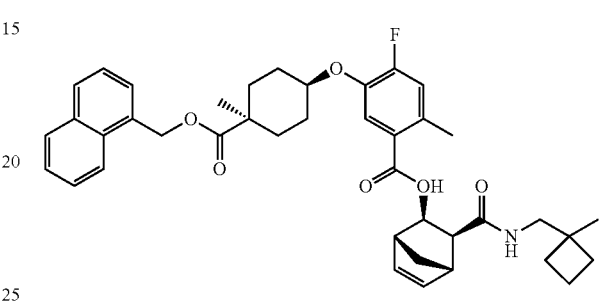

Intermediate 32 (300 mg, 0.67 mmol), Intermediate 21 (156 mg, 0.67 mmol), HATU (380 mg, 1.00 mmol) and DIPEA (0.349 mL, 2.00 mmol) were dissolved in DMF (20 mL), and the reaction mixture was stirred at rt for 5 h. The reaction mixture was concentrated under reduced pressure and the crude product was dissolved in DCM (10 mL). The organic layer was washed with H₂O (3×5 mL), dried over Na₂SO₄, filtered, and evaporated under reduced pressure. The crude product was purified by preparative TLC (PE:EtOAc, 3:1), to give the title compound (300 mg, 68%); MS (ESI) m/z [M+H]⁺ 667.

Intermediate 34: Benzyl (2RS,4r,6R)-6-hydroxyspiro[3.3]heptane-2-carboxylate

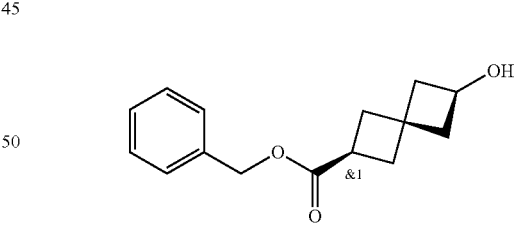

NaBH₄ (46.5 mg, 1.23 mmol) was added slowly to a solution of benzyl 6-oxospiro[3.3]heptane-2-carboxylate (300 mg, 1.23 mmol) in MeOH (2 mL) cooled to 0° C. and under nitrogen. The reaction mixture was stirred at 0° C. for 2 h. The reaction mixture was evaporated to dryness and redissolved in DCM (20 mL). The organic layer was washed with H₂O (3×15 mL), dried over Na₂SO₄, filtered and evaporated. The residue was purified by preparative TLC (PE:EtOAc, 2:1), to give the title compound (230 mg, 76%) as a colourless oil; MS (ESI) m/z [M+H]⁺ 247.

Intermediate 35: (1R,2S,3R,4S)-3-(4-Cyano-5-hydroxy-2-methoxybenzamido)-N-((1-methylcyclobutyl)methyl)bicyclo[2.2.1]heptane-2-carboxamide

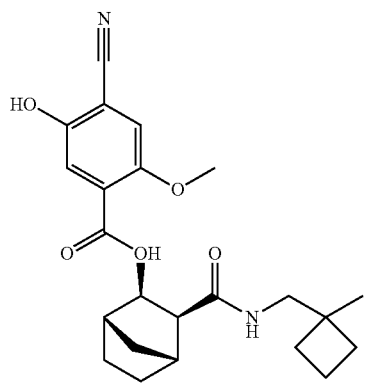 [SMILES: COc1cc(C#N)c(O)cc1C(=O)O[C@@H]1[C@H]2CC[C@H](C2)[C@@H]1C(=O)NCC1(C)CCC1]

4-Cyano-5-hydroxy-2-methoxybenzoic acid (500 mg, 2.59 mmol) was added to a solution of Intermediate 22 (847 mg, 3.11 mmol), EDC (744 mg, 3.88 mmol), HOBt (525 mg, 3.88 mmol) and DIPEA (1.0 g, 7.77 mmol) in DMF (20 mL) and the reaction mixture was stirred at 20° C. for 12 h. The reaction mixture was concentrated under reduced pressure and diluted with EtOAc (150 mL). The organic layer was washed sequentially with sat NaHCO$_3$ (150 mL), H$_2$O (150 mL), and sat brine (150 mL), dried over Na$_2$SO$_4$, filtered, and evaporated. The crude product was purified by preparative TLC (MeOH:DCM, 1:10), to give the title compound (360 mg, 34%); MS (ESI) m/z [M+H]$^+$ 412.3.

Intermediate 36: Benzyl (2RS,4r,6R)-6-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)spiro[3.3]heptane-2-carboxylate

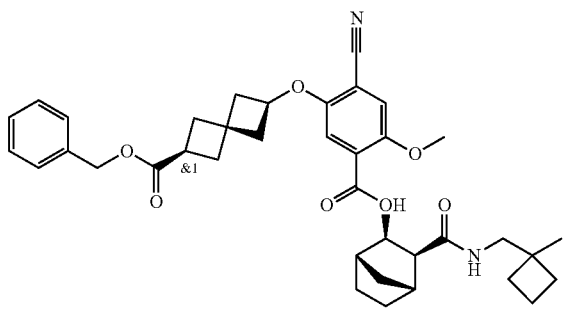

Intermediate 35 (350 mg, 0.85 mmol) was added to a solution of Intermediate 34 (314 mg, 1.28 mmol), Ph$_3$P (335 mg, 1.28 mmol) and DBAD (294 mg, 1.28 mmol) in a mixture of toluene/DCM (16 mL, 1:1) at 20° C. The reaction mixture was stirred at 30° C. for 12 h and then cooled to rt and diluted with DCM (200 mL). The organic layer was washed sequentially with sat NH$_4$Cl (200 mL), H$_2$O (200 mL) and sat brine (200 mL), dried over Na$_2$SO$_4$, filtered, and evaporated. The crude product was purified by preparative TLC (PE:EtOAc, 3:1), to give the title compound (190 mg, 35%); MS (ESI) m/z [M+H]$^+$ 640.4.

Intermediate 37: Benzyl (2R*,4r,6R)-6-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)spiro[3.3]heptane-2-carboxylate Isomer 1

Intermediate 38: Benzyl (2R*,4r,6R)-6-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)spiro[3.3]heptane-2-carboxylate Isomer 2

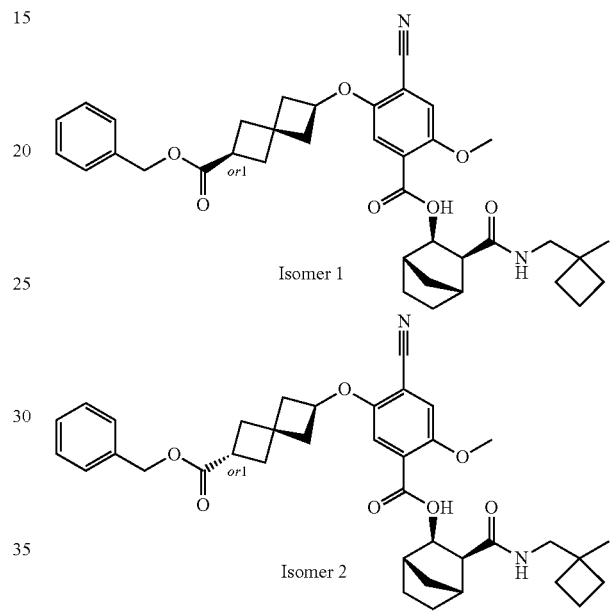

The isomers of Intermediate 36 (200 mg, 0.31 mmol) were separated by preparative chiral HPLC on a Chiralpak IG column (5 µm, 250×20 mm ID) using 10% of EtOH in a hexane:DCM (5:1, 10 mM NH$_3$ in MeOH) buffer system as mobile phase, to give the first eluting compound Isomer 1 Intermediate 37 (60 mg, 30%); MS (ESI) m/z [M+H]$^+$ 640.4, and the second eluting compound Isomer 2 Intermediate 38 (70 mg, 30%); MS (ESI) m/z [M+H]$^+$ 640.4.

Intermediate 39: rac-Methyl (1R,2R,3S,4S)-3-isocyanato-7-oxabicyclo[2.2.1]heptane-2-carboxylate

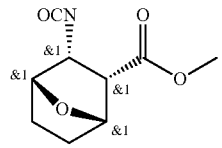

Step A. Intermediate 40: rac-(1R,2R,3S,4S)-3-(Methoxycarbonyl)-7-oxabicyclo[2.2.1]heptane-2-carboxylic acid Pd—C (0.107 g, 1.01 mmol, 10%) was added to a solution of rac-(1R,4S)-3-(methoxycarbonyl)-7-oxabicyclo[2.2.1]hept-2-ene-2-carboxylic acid (2 g, 10.09 mmol) in MeOH (150 mL), and the reaction mixture was stirred under an atmosphere of hydrogen (1.5 atm) at rt for 5h. The reaction mixture was filtered through a pad of Celite® and the solvent was removed under reduced pressure to give the title compound (2 g, 99%). The crude product was used directly without further purification in the next step.

Step B. rac-Methyl (1R,2R,3S,4S)-3-isocyanato-7-oxabicyclo[2.2.1]heptane-2-carboxylate Ethyl chloroformate (1.30 g, 12 mmol) was added dropwise to a solution of Intermediate 40 (2 g, 9.99 mmol) and TEA (1.52 g, 15.0 mmol) in acetone (20 mL) at 0° C., and the reaction mixture was stirred at 0° C. for 30 min. A solution of NaN$_3$ (0.97 g, 15.0 mmol) in H$_2$O (10 mL) was added dropwise over a period of 15 min to the stirred reaction mixture at 0° C., and under a nitrogen atmosphere, and the reaction mixture was stirred at 0° C. overnight. The reaction mixture was diluted with toluene (150 mL), and washed sequentially with sat brine (250 mL), sat NaHCO$_3$ (250 mL), and H$_2$O (200 mL). The organic layer was dried over Na$_2$SO$_4$, and filtered. The filtrate was diluted with toluene (30 mL) and the reaction mixture was stirred at 110° C. overnight. The solvent was removed under reduced pressure to give the title compound (1.7 g, 88%) as a brown oil.

Intermediate 41: rac-Methyl (1R,2R,3S,4S)-3-amino-7-oxabicyclo[2.2.1]heptane-2-carboxylate hydrochloride

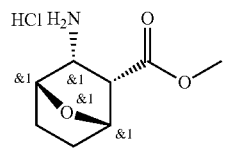

A solution of HCl (2.6 mL, 86.2 mmol, 12 M, aq) in H$_2$O (10 mL) was added to a solution of Intermediate 39 (1.7 g, 8.62 mmol) in THF (20 mL). The reaction mixture was stirred at rt overnight. The solvent was removed under reduced pressure to give the title compound (1.75 g, 98%) as a crude product which was used without further purification.

Intermediate 42: rac-Methyl (1R,2R,3S,4S)-3-((tert-butoxycarbonyl)amino)-7-oxabicyclo[2.2.1]heptane-2-carboxylate

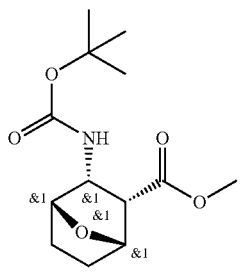 [SMILES: COC(=O)[C@H]1[C@@H](NC(=O)OC(C)(C)C)[C@H]2CC[C@@H]1O2]

Boc$_2$O (3.91 mL, 16.8 mmol) and TEA (5.87 mL, 42.14 mmol) were added to a solution of Intermediate 41 (1.75 g, 8.43 mmol) in THF (20 mL), and the reaction mixture was stirred at rt overnight. The reaction mixture was diluted with EtOAc (50 mL), and washed with sat brine (3×20 mL). The organic layer was dried over Na$_2$SO$_4$, filtered and evaporated to give the title compound (2.1 g, 92%) as a crude product which was used without further purification.

Intermediate 43: rac-(1R,2R,3S,4S)-3-((tert-Butoxycarbonyl)amino)-7-oxabicyclo[2.2.1]heptane-2-carboxylic acid

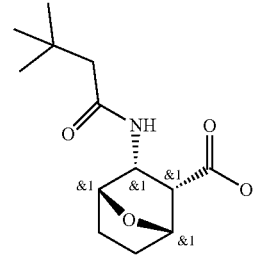 [SMILES: CC(C)(C)CC(=O)N[C@@H]1[C@H](C(=O)O)[C@@H]2CC[C@H]1O2]

LiOH (0.556 g, 23.22 mmol) was added to a solution of Intermediate 42 (2.1 g, 7.74 mmol) in MeOH (8 mL) and H$_2$O (4 mL) and the reaction mixture was stirred at rt for 5h. The reaction mixture was acidified with citric acid (0.5 M, aq), diluted with EtOAc (20 mL), and washed with sat brine (3×2 mL). The organic layer was dried over Na$_2$SO$_4$, filtered and evaporated to give the title compound Intermediate 43 (1.23 g, 62%) as yellow solid, which was used without further purification; MS (ESI) m/z [M+Na]$^+$280.

Intermediate 44: tert-Butyl ((1S,2S,3R,4R)-3-((4-fluoro-3-(trifluoromethyl)phenyl)carbamoyl)-7-oxabicyclo[2.2.1]heptan-2-yl)carbamate Isomer 1

Intermediate 45: tert-Butyl ((1R,2R,3S,4S)-3-((4-fluoro-3-(trifluoromethyl)phenyl)carbamoyl)-7-oxabicyclo[2.2.1]heptan-2-yl)carbamate Isomer 2

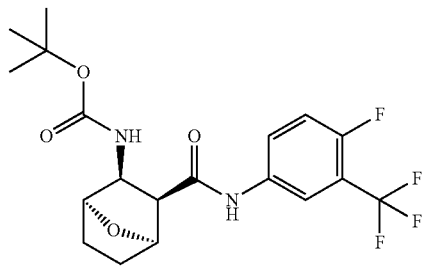

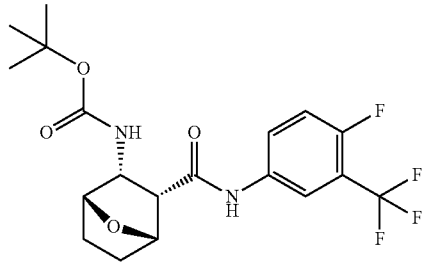

4-Fluoro-3-(trifluoromethyl)aniline (1.028 g, 5.74 mmol), HATU (5.45 g, 14.34 mmol), DIPEA (2.472 g, 19.12 mmol)

and Intermediate 43 (1.23 g, 4.78 mmol) were suspended in DMF (15 mL) and the reaction mixture was stirred at 80° C. for 5h. The reaction mixture was diluted with EtOAc (75 mL), and washed with sat brine (3×20 mL). The organic layer was dried over $Na_2SO_4$, filtered and evaporated. The crude product was purified by flash chromatography using a gradient of 0-40% PE in EtOAc as mobile phase, and then by preparative HPLC, Method PrepBasic-G, using decreasingly polar mixtures of the mobile phase. The enantiomers were separated by preparative chiral HPLC on a Chiralpak IA column (5 μm, 150×4.6 mm ID), using 20% IPA (0.1% DEA) in $CO_2$ (g) as mobile phase, to give the first eluting Isomer 1 Intermediate 44 (170 mg, 8.5%) as a white solid; MS (ESI) m/z [M+H]$^+$ 419, and the second eluting Isomer 2 Intermediate 45 (170 mg, 8.5%) as a white solid, MS (ESI) m/z [M+H]$^+$ 419. The stereochemistry of the two enantiomers were determined using VCD experiments. Experimental VCD spectra of both enantiomers were compared to the DFT calculated spectra. The assignment of the configuration was based of fits of 5 different regions of the spectrum.

Intermediate 46: (1R,2R,3S,4S)-3-Amino-N-(4-fluoro-3-(trifluoromethyl)phenyl)-7-oxabicyclo[2.2.1]heptane-2-carboxamide 2,2,2-trifluoroacetate

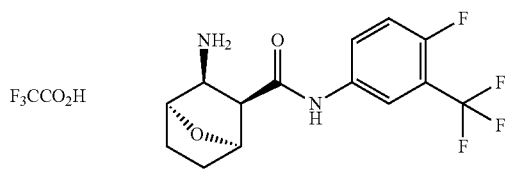 [SMILES: "F3CCO2H" ; N[C@H]1[C@@H](C(=O)Nc2ccc(F)c(C(F)(F)F)c2)[C@H]2CC[C@@H]1O2]

TFA (3 mL) was added to a solution of Intermediate 44 (50 mg, 0.12 mmol) in DCM (3 mL) and the reaction mixture was stirred at 20° C. for 2 h. The solvent was removed under reduced pressure to give the title compound (35 mg, 92%) as a white solid; MS (ESI) m/z [M+H]$^+$ 318.

Intermediate 47: (1S,2S,3R,4R)-3-Amino-N-(4-fluoro-3-(trifluoromethyl)phenyl)-7-oxabicyclo[2.2.1]heptane-2-carboxamide 2,2,2-trifluoroacetate

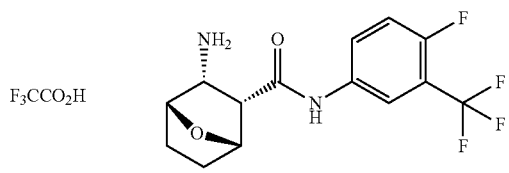 [SMILES: "F3CCO2H" ; N[C@@H]1[C@H](C(=O)Nc2ccc(F)c(C(F)(F)F)c2)[C@@H]2CC[C@H]1O2]

The title compound was prepared from Intermediate 45 in an analogues way as described for Intermediate 46 to give the title compound (35 mg, 92%) as a white solid; MS (ESI) m/z [M+H]$^+$ 319.

Intermediate 48: Benzyl ((1R,2S)-2-((4-fluoro-3-(trifluoromethyl)phenyl)carbamoyl)cyclobutyl)carbamate

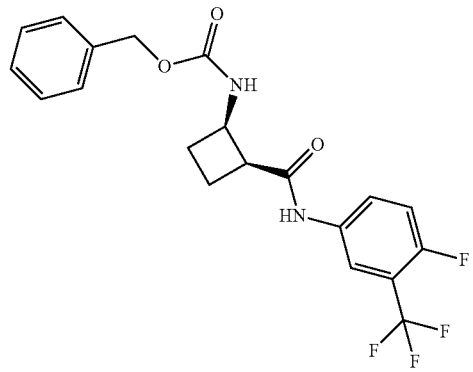 [SMILES: O=C(N[C@@H]1CC[C@@H]1C(=O)Nc1ccc(F)c(C(F)(F)F)c1)OCc1ccccc1]

DIPEA (0.315 mL, 1.81 mmol) was added dropwise to a solution of (1S,2R)-2-(((benzyloxy)carbonyl)amino)cyclobutane-1-carboxylic acid (150 mg, 0.60 mmol), 4-fluoro-3-(trifluoromethyl)aniline (129 mg, 0.72 mmol), and HATU (458 mg, 1.20 mmol) in DMF (10 mL) at 20° C. under a nitrogen atmosphere, and the reaction mixture was stirred at 80° C. for 3 h. The reaction mixture was diluted with EtOAc (100 mL), and washed sequentially with sat brine (150 mL), and $H_2O$ (125 mL). The organic layer was dried over $Na_2SO_4$, filtered and evaporated. The crude product was purified by preparative TLC (EtOAc:PE, 1:2), to give the title compound (196 mg, 79%) as a pale yellow solid; MS (ESI) m/z [M+H]$^+$ 411.

Intermediate 49: (1S,2R)-2-Amino-N-(4-fluoro-3-(trifluoromethyl)phenyl)cyclobutane-1-carboxamide hydrobromide

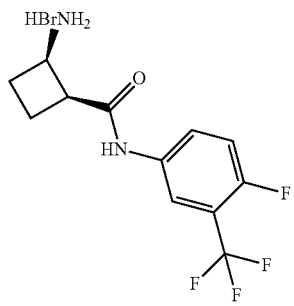

Intermediate 48 (100 mg, 0.24 mmol) was added to a solution of HBr in glacial acetic acid (10 mL, 33%) at 0° C., and the reaction mixture was stirred at 0° C. for 2 h. The solvent was removed under reduced pressure to give the title compound (67 mg) which was used without further purification; MS (ESI) m/z [M+H]$^+$ 277.

Intermediate 50: Methyl (R)-4-((1-phenylethyl)amino)-2,5-dihydrofuran-3-carboxylate

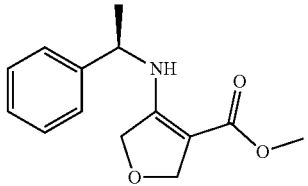 [SMILES: COC(=O)C1=C(N[C@H](C)c2ccccc2)COC1]

(R)-1-Phenylethan-1-amine (920 mg, 7.63 mmol) was added dropwise to a solution of methyl 4-oxotetrahydrofuran-3-carboxylate (1 g, 6.94 mmol), and Yb(OTf)$_3$ (0.129 g, 0.21 mmol) in toluene (50 mL) at 20° C. under a nitrogen atmosphere and the suspension was stirred at 110° C. for 42 h. The reaction mixture was filtered through Celite®, and the solvent was removed under reduced pressure to give the title compound (750 mg, 44%) as a pale yellow oil which solidified on standing.

Intermediate 51: Methyl (3R,4S)-4-(((R)-1-phenylethyl)amino)tetrahydrofuran-3-carboxylate

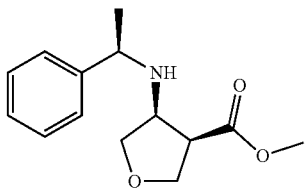 [SMILES: COC(=O)[C@H]1COC[C@H]1N[C@H](C)c1ccccc1]

NaBH$_4$ (320 mg, 8.49 mmol) was added portion wise to acetic acid (25 mL) and the resulting suspension was stirred at 20° C. for 1 h, and then cooled to 0° C. A solution of Intermediate 50 (700 mg, 2.83 mmol) in MeCN (25 mL) was added to the mixture under a nitrogen atmosphere, and the resulting suspension was stirred at 0° C. for 2 h. The reaction mixture was quenched with H$_2$O (125 mL), and concentrated under reduced pressure. The aq phase was extracted with EtOAc (3×150 mL), and the combined organic layer was dried over Na$_2$SO$_4$, filtered and evaporated. The crude product was purified by flash chromatography, using a gradient of 0-30% EtOAc in PE as mobile phase, to give the title compound (410 mg, 58%) as a pale yellow oil which solidified on standing; MS (ESI) m/z [M+H]$^+$ 250.

Intermediate 52: Methyl (3R,4S)-4-aminotetrahydrofuran-3-carboxylate

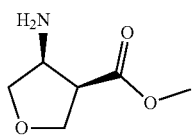

Pd—C (35 mg, 0.33 mmol) was added to a solution of Intermediate 51 (407 mg, 1.63 mmol) in MeOH (20 mL) and the reaction mixture was stirred under an atmosphere of hydrogen (1.5 atm) at 20° C. for 14 h. The reaction mixture was filtered through Celite®, and the filtrate was concentrated under reduced pressure to give the title compound (237 mg, 100%) as a pale yellow solid.

Intermediate 53: Methyl (3R,4S)-4-((tert-butoxycarbonyl)amino)tetrahydrofuran-3-carboxylate

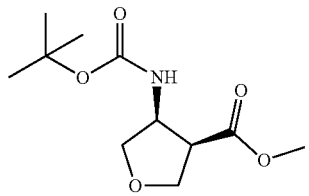 [SMILES: COC(=O)[C@H]1COC[C@H]1NC(=O)OC(C)(C)C]

TEA (0.341 mL, 2.45 mmol) was added dropwise to a solution of Intermediate 52 (237 mg, 1.63 mmol) and Boc$_2$O (0.46 mL, 1.96 mmol) in THF (20 mL) at 20° C. under a nitrogen atmosphere, and the reaction mixture was stirred at 20° C. for 14 h. The reaction mixture was diluted with EtOAc (150 mL), and washed sequentially with sat brine (2×150 mL), H$_2$O (150 mL), and sat NaHCO$_3$ (150 mL). The organic layer was dried over Na$_2$SO$_4$, filtered and evaporated to give the title compound (448 mg) as a yellow gum.

Intermediate 54: (3RS,4S)-4-((tert-Butoxycarbonyl)amino)tetrahydrofuran-3-carboxylic acid

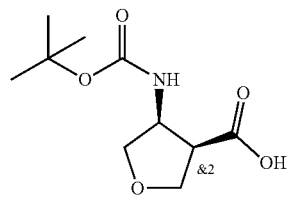 [SMILES: CC(C)(C)OC(=O)N[C@@H]1COC[C@@H]1C(=O)O]

LiOH (219 mg, 9.13 mmol) was added portion wise to a solution of Intermediate 53 (448 mg, 1.83 mmol) in MeOH (10 mL) and H$_2$O (10 mL) at 20° C., and the reaction mixture was stirred at 20° C. for 14 h. The reaction mixture was acidified to pH-3 with citric acid (aq, 0.5 M). The reaction mixture was diluted with EtOAc (200 mL), and washed sequentially with sat brine (2×150 mL), H$_2$O (125 mL), and sat NH$_4$Cl (125 mL). The organic layer was dried over Na$_2$SO$_4$, filtered and evaporated to give a crude containing the title compound (350 mg, 83%) as a yellow gum. The crude product was used without further purification.

Intermediate 55: tert-Butyl ((3S,4R)-4-((4-fluoro-3-(trifluoromethyl)phenyl)carbamoyl)tetrahydrofuran-3-yl)carbamate

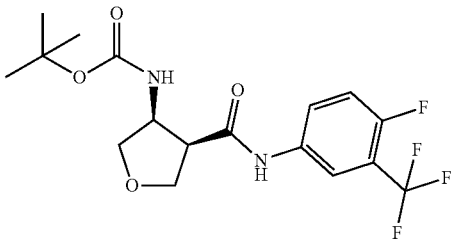 [SMILES: CC(C)(C)OC(=O)N[C@@H]1COC[C@@H]1C(=O)Nc1ccc(F)c(C(F)(F)F)c1]

DIPEA (0.79 mL, 4.54 mmol) was added dropwise to a solution of 4-fluoro-3-(trifluoromethyl)aniline (407 mg, 2.27 mmol), Intermediate 54 (350 mg, 1.51 mmol) and HATU (2.88 g, 7.57 mmol) in DMF (40 mL) and the reaction mixture was stirred at 20° C. for 14 h. The reaction mixture was diluted with EtOAc (100 mL), and washed sequentially with sat brine (100 mL), sat NaHCO₃ (100 mL), and H₂O (100 mL). The organic layer was dried over Na₂SO₄, filtered and evaporated. The crude product was purified by preparative TLC (EtOAc:PE, 1:1), to give the title compound (240 mg, 40%) as a white solid; MS (ESI) m/z [M+H]⁺ 393.

Intermediate 56: (3R,4S)-4-Amino-N-(4-fluoro-3-(trifluoromethyl)phenyl)tetrahydrofuran-3-carboxamide

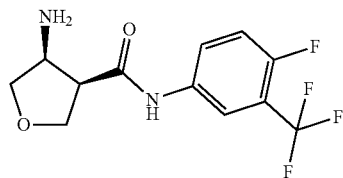 [SMILES: N[C@@H]1COC[C@@H]1C(=O)Nc1ccc(F)c(C(F)(F)F)c1]

The Boc-protecting group of Intermediate 55 (240 mg, 0.61 mmol) was partly deprotected upon standing and the mixture was purified by preparative chiral-HPLC, Method SFC-G, using an isocratic run of 15% of IPA as mobile phase, to give the title compound (40 mg, 22%) as a yellow solid; MS (ESI) m/z [M+Na]⁺293.

Intermediate 57: 2-Chloro-N-((1-methylcyclobutyl)methyl)-6-nitrobenzamide

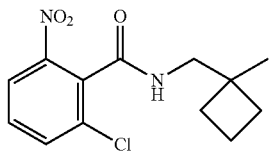 [SMILES: CC1(CNC(=O)c2c(N)cccc2Cl)CCC1]

DIPEA (0.65 mL, 3.72 mmol) was added dropwise to a solution of 2-chloro-6-nitrobenzoic acid (250 mg, 1.24 mmol), (1-methylcyclobutyl)methanamine hydrochloride (168 mg, 1.24 mmol), EDC (476 mg, 2.48 mmol), and HOBt (380 mg, 2.48 mmol) in DMF (5 mL) at 20° C. under a nitrogen atmosphere, and the reaction mixture was stirred at 20° C. for 14 h. The reaction mixture was diluted with EtOAc (100 mL), and washed sequentially with sat NaHCO₃ (100 mL), sat NH₄Cl (150 mL), and sat brine (100 mL). The organic layer was dried over Na₂SO₄, filtered and evaporated. The crude product was purified by preparative TLC (EtOAc:PE, 1:3), to give the title compound (350 mg, 100%) as a white waxy solid; MS (ESI) m/z [M+H]⁺ 283.

Intermediate 58: 2-Amino-6-chloro-N-((1-methylcyclobutyl)methyl)benzamide

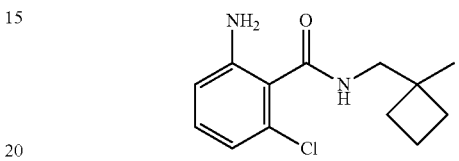

NH₄Cl (662 mg, 12.38 mmol) was added portion wise to a suspension of Intermediate 57 (350 mg, 1.24 mmol) and Fe(s) (346 mg, 6.19 mmol) in H₂O (2 mL) and EtOH (18 mL, 99.5%) at 20° C. and under a nitrogen atmosphere, and the reaction mixture was stirred at 80° C. for 14 h. The reaction mixture was diluted with EtOAc (100 mL), and washed sequentially with sat NaHCO₃ (75 mL), sat brine (75 mL), and H₂O (75 mL). The organic layer was dried over Na₂SO₄, filtered and evaporated. The crude product was purified by precipitation from EtOAc and PE to give the title compound (290 mg, 93%) as a white waxy solid; MS (ESI) m/z [M+H]⁺ 253.

Intermediate 59: Naphthalen-1-ylmethyl (1s,4s)-4-(5-((3-chloro-2-(((1-methylcyclobutyl)methyl)carbamoyl)phenyl)carbamoyl)-2-fluoro-4-methoxyphenoxy)-1-methylcyclohexane-1-carboxylate

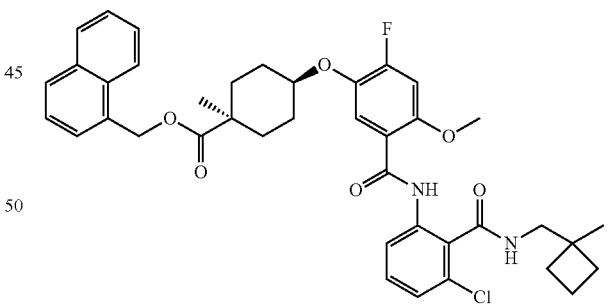

Intermediate 58 (250 mg, 0.99 mmol) was added to a solution of Intermediate 13 (692 mg, 1.48 mmol), T3P (5.9 mL, 9.89 mmol, 50% in EtOAc), and DIPEA (384 mg, 2.97 mmol) in BuOAc (10 mL) at 20° C., and the reaction was stirred at 120° C. for 12 h. The reaction mixture was concentrated and diluted with EtOAc (150 mL). The organic layer was washed sequentially with sat NH₄Cl (250 mL), H₂O (150 mL), and sat brine (250 mL), dried over Na₂SO₄, filtered and evaporated. The crude product was purified by preparative TLC (EtOAc:PE, 1:3), to give the title compound (280 mg, 40%) as a yellow solid; MS (ESI) m/z [M+Na]⁺ 723.3.

Intermediate 60: Benzyl (1S,2R)-2-((tert-butoxycarbonyl)amino)cyclopentane-1-carboxylate

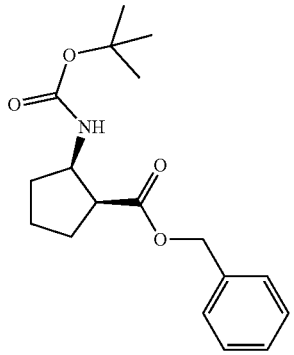 [SMILES: CC(C)(C)OC(=O)N[C@@H]1CCC[C@@H]1C(=O)OCc1ccccc1]

TEA (18.2 mL, 130.8 mmol) was added to a solution of (1S,2R)-2-((tert-butoxycarbonyl)amino)cyclopentane-1-carboxylic acid (5.0 g, 21.8 mmol), phenylmethanol (3.54 g, 32.7 mmol), EDC (12.54 g, 65.42 mmol) and HOBt (10.02 g, 65.42 mmol) in DMF (50 mL) and the reaction mixture was stirred at 20° C. for 15 h. The reaction mixture was concentrated and diluted with EtOAc (125 mL), and washed sequentially with sat NaHCO₃ (125 mL), H₂O (3×125 mL), and sat brine (2×125 mL). The organic layer was dried over Na₂SO₄, filtered and evaporated. The crude product was purified by flash chromatography using a gradient of 10-15% in EtOAc in PE to give the title compound (5.0 g, 72%) as a white solid.

Intermediate 61: Benzyl (1S,2R)-2-aminocyclopentane-1-carboxylate hydrochloride

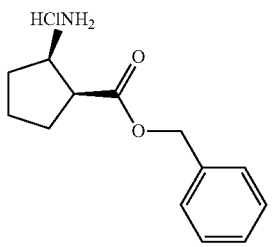

HCl (10 mL, 40.0 mmol, 4 M in 1,4-dioxane) was added to a solution of Intermediate 60 (2 g, 6.26 mmol) in 1,4-dioxane (10 mL) at 20° C. The resulting suspension was stirred at 20° C. for 30 min. The solvent was removed under reduced pressure to give the title compound (2 g) as a yellow oil; MS (ESI) m/z [M+H]⁺ 220.

Intermediate 62: tert-Butyl (1S,4s)-4-(5-(((1R,2S)-2-((benzyloxy)carbonyl)cyclopentyl)carbamoyl)-2-fluoro-4-methoxyphenoxy)-1-methylcyclohexane-1-carboxylate

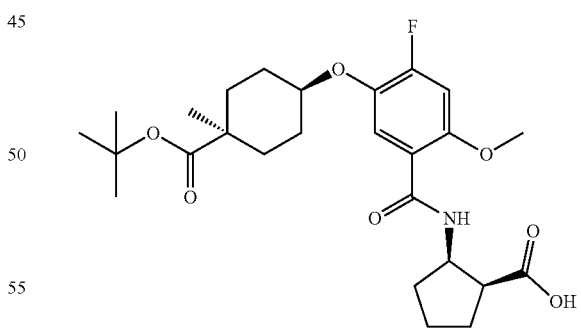

DIPEA (2.28 mL, 13.1 mmol) was added dropwise to a solution of Intermediate 73 (1.0 g, 2.61 mmol), Intermediate 61 (0.67 g, 2.61 mmol) and HATU (2.98 g, 7.84 mmol) in DMF (20 mL) at 20° C. under a nitrogen atmosphere and the reaction mixture was stirred at 30° C. for 4 h. The reaction mixture was diluted with EtOAc (50 mL), and washed sequentially with H₂O (3×50 mL), sat NaHCO₃ (50 mL), and sat brine (50 mL). The organic layer was dried over Na₂SO₄, filtered and evaporated. The crude product was purified by preparative TLC (EtOAc:PE, 1:3), to give the title compound (0.90 g, 59%) as a pale yellow oil which solidified on standing; MS (ESI) m/z [M+H]⁺ 584.

Intermediate 63: (1S,2R)-2-(5-(((1s,4S)-4-(tert-Butoxycarbonyl)-4-methylcyclohexyl)oxy)-4-fluoro-2-methoxybenzamido)cyclopentane-1-carboxylic acid Pd—C (164 mg, 0.15 mmol) was added to a solution of Intermediate 62 (900 mg, 1.54 mmol) in MeOH (20 mL) and the reaction mixture was stirred at 20° C. under an atmosphere of hydrogen (1.3 atm) for 3 h. The reaction mixture was filtered through Celite® and the filtrate was concentrated under reduced pressure to give the title compound (700 mg, 92%) as a white solid; MS (ESI) m/z [M+H]⁺ 494.

Intermediate 64: Benzyl 5-(((1s,4s)-4-(tert-butoxycarbonyl)cyclohexyl)oxy)-4-fluoro-2-methoxybenzoate

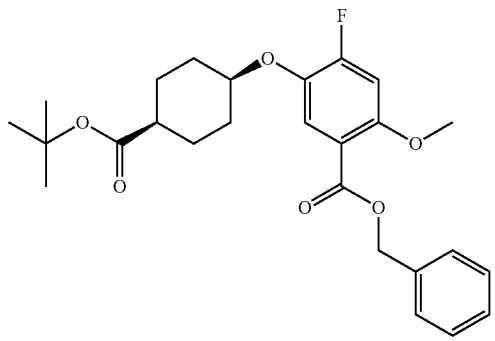 [SMILES: COc1cc(F)c(O[C@H]2CC[C@@H](C(=O)OC(C)(C)C)CC2)cc1C(=O)OCc1ccccc1]

DIAD (1.46 mL, 7.53 mmol) was added dropwise to a solution of Intermediate 117 (1.39 g, 5.02 mmol), tert-butyl (1r,4r)-4-hydroxycyclohexane-1-carboxylate (1.2 g, 6.0 mmol) and PPh$_3$ (1.97 g, 7.53 mmol) in THF (10 mL) at 60° C., and the reaction mixture was stirred at 60° C. for 3 h. The solvent was removed under reduced pressure and the crude product was purified by flash silica chromatography, using a gradient of 0-10% EtOAc in petroleum ether as mobile phase, to give the title compound (1.55 g, 67%) as a white solid; MS (ESI) m/z [M+Na]$^+$ 481.

Intermediate 65: 5-(((1s,4s)-4-(tert-Butoxycarbonyl)cyclohexyl)oxy)-4-fluoro-2-methoxybenzoic acid

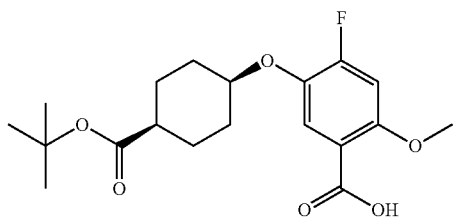 [SMILES: COc1cc(F)c(O[C@H]2CC[C@@H](C(=O)OC(C)(C)C)CC2)cc1C(=O)O]

Pd—C (0.67 g, 0.63 mmol, 10%) was added to a solution of Intermediate 64 (1.45 g, 3.16 mmol) in MeOH (50 mL) at 20° C. The reaction mixture was stirred at 20° C. for 4 h under an atmosphere of hydrogen The reaction mixture was filtered through Celite® and the filtrate was concentrated under reduced pressure to give the title compound (1.10 g, 94%) as a white solid; MS (ESI) m/z [M+Na]$^+$ 368.

Intermediate 66: Methyl (1R,2S,3R,4S)-3-(5-(((1s,4S)-4-(tert-butoxycarbonyl)cyclohexyl)oxy)-4-fluoro-2-methoxybenzamido)bicyclo[2.2.1]heptane-2-carboxylate

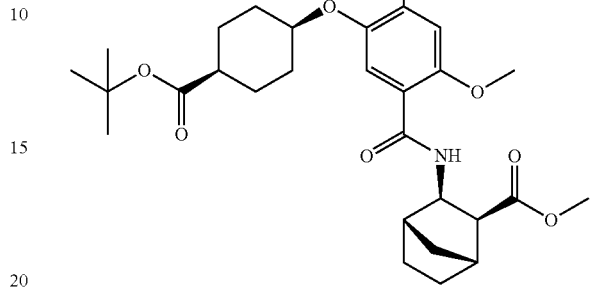

DIPEA (2.61 mL, 14.93 mmol) was added dropwise to a solution of Intermediate 65 (1.1 g, 2.99 mmol), Intermediate 120 (2.8 g, 13.61 mmol) and HATU (3.41 g, 8.96 mmol) in DMF (20 mL) at 20° C., and the reaction mixture was stirred at 20° C. for 14 h. The reaction mixture was diluted with EtOAc (100 mL), and washed with sat brine (3×25 mL). The organic layer was dried over Na$_2$SO$_4$, filtered and evaporated under reduced pressure. The crude product was purified by preparative TLC (petroleum ether:EtOAc, 2:1), to give the title compound (0.56 g, 36%) as a brown yellow oil which solidified on standing; MS (ESI) m/z [M+H]$^+$ 520.

Intermediate 67: (1R,2S,3R,4S)-3-(5-(((1s,4S)-4-(tert-Butoxycarbonyl)cyclohexyl)oxy)-4-fluoro-2-methoxybenzamido)bicyclo[2.2.1]heptane-2-carboxylic acid

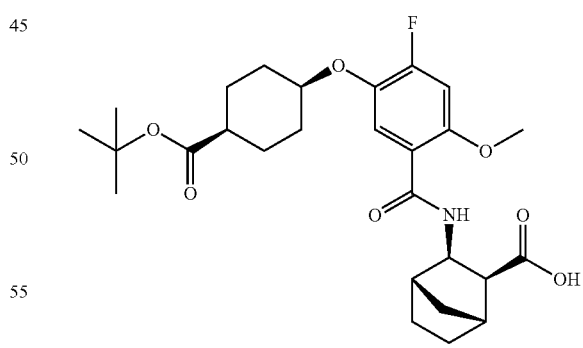

LiOH (106 mg, 4.43 mmol) was added to a solution of Intermediate 66 (460 mg, 0.89 mmol) in MeOH (4 mL) and water (2 mL), and the reaction mixture was stirred at 20° C. for 5 h. The solvent was removed under reduced pressure. The reaction mixture was acidified with citric acid (0.5 M, aq) and the solids were filtered off to give the title compound (385 mg, 86%) as a white solid; MS (ESI) m/z [M+H]$^+$ 506.

Intermediate 68: (1R,2S,3R,4S)-3-(5-(((1s,4S)-4-Carboxy-4-methylcyclohexyl)oxy)-4-cyano-2-methoxybenzamido)bicyclo[2.2.1]heptane-2-carboxylic acid

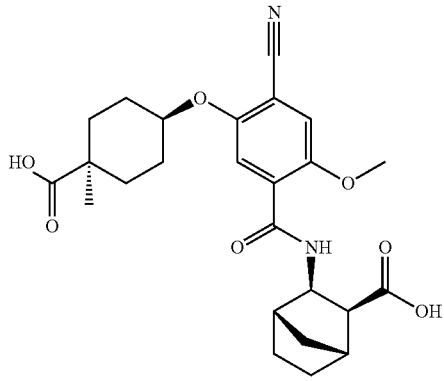 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)O]

Step A. Intermediate 69: Methyl 4-cyano-2-methoxy-5-(((1s,4s)-4-methyl-4-((naphthalen-1-ylmethoxy)carbonyl)cyclohexyl)oxy)benzoate

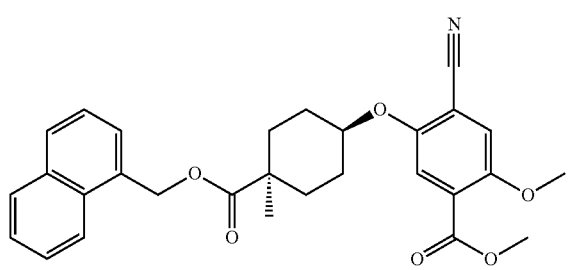 [SMILES: COC(=O)c1cc(O[C@H]2CC[C@@](C)(C(=O)OCc3cccc4ccccc34)CC2)c(C#N)cc1OC]

A solution of methyl 4-cyano-5-hydroxy-2-methoxybenzoate (1.4 g, 6.7 mmol), Intermediate 11 and PPh$_3$ (2.6 g, 10.1 mmol) in THF (30 mL) was stirred at 60° C. for 10 min. After slow addition of DIAD (1.97 mL, 10.1 mmol), the reaction mixture was stirred at 60° C. for 14 h. The solvent was then removed under reduced pressure and the residue redissolved in EtOAc (150 mL), washed sequentially with NaHCO$_3$ (sat, 200 mL), NH$_4$Cl (sat, 250 mL) and brine (sat, 250 mL). The organic layer was separated and dried over Na$_2$SO$_4$, filtered and the solvent removed under reduced pressure. The crude product was purified by flash chromatography using a gradient of 0-18% EtOAc in PE as mobile phase to give the title compound (3.25 g, 99%) as a white solid. MS (ESI): m/z [M+Na]$^+$ 510.3.

Step B. Intermediate 70: 4-Cyano-2-methoxy-5-(((1s,4s)-4-methyl-4-((naphthalen-1-ylmethoxy)carbonyl)cyclohexyl)oxy)benzoic acid

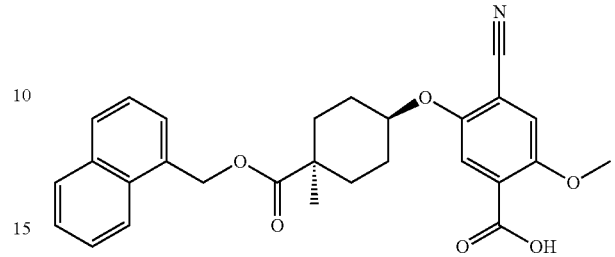

LiOH (1.6 g, 66.7 mmol) was added portionwise to a stirred solution of Intermediate 69 (3.25 g, 6.7 mmol) in H$_2$O:THF 1:3 (80 mL) at 10° C. and the resulting suspension was stirred at 20° C. After 3 h, the pH of the reaction mixture was adjusted to pH 3 by the addition of HCl (2 M). The reaction mixture was diluted with EtOAc (350 mL), and washed sequentially with brine (sat, 350 mL), H$_2$O (350 mL), and brine (350 mL). The organic layer was separated, dried over Na$_2$SO$_4$, filtered and the solvent removed under reduced pressure. The crude product was purified by crystallisation from IPA/EtOAc to afford the title compound (3.16 g, 100%) as a white solid. MS (ESI): m/z [M+Na]$^+$ 496.3.

Step C. Intermediate 71: Methyl (1S,2S,3R,4R)-3-(4-cyano-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylate

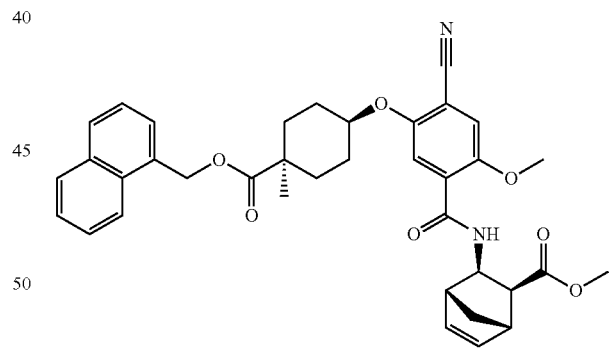

DIPEA (3.5 mL, 20 mmol) was added to a solution of Intermediate 70 (3.16 g, 6.67 mmol), Intermediate 8 (1.291 g, 6.34 mmol), EDC (1.9 g, 10 mmol) and HOBt (1.533 g, 10.01 mmol) in DMF (60 mL) at 10° C. and the resulting suspension was stirred at rt for 13 hours. The reaction mixture was diluted with EtOAc (500 mL) and washed sequentially with NH$_4$Cl (sat, 200 mL), H$_2$O (300 mL), and brine (sat, 250 mL). The organic layer was dried over Na$_2$SO$_4$, filtered and the solvent removed under reduced pressure. The crude product was purified by flash chromatography using a gradient of 0-20% EtOAc in PE as mobile phase to afford the title compound (2.6 g, 62%) as a white solid. MS (ESI): m/z [M+H]$^+$ 623.4.

Step D. Intermediate 72: (1S,4s)-4-(2-Cyano-4-methoxy-5-(((1S,2R,3S,4R)-3-(methoxycarbonyl)bicyclo[2.2.1]heptan-2-yl)carbamoyl)phenoxy)-1-methylcyclohexane-1-carboxylic acid

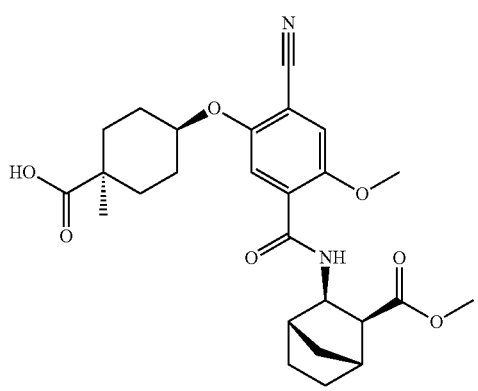 [SMILES: COC(=O)[C@H]1[C@@H]2CC[C@@H](C2)[C@H]1NC(=O)c1cc(O[C@H]2CC[C@@](C)(C(=O)O)CC2)c(C#N)cc1OC]

Intermediate 71 (5.7 g, 9.15 mmol) and Pd/C (0.584 g, 0.55 mmol) in MeOH (100 mL) was stirred at 20° C. under an atmosphere of hydrogen (1.5 atm) for 14 h. The mixture was filtered through a Celite® pad and the solvent was removed under reduced pressure. The crude product was purified by crystallisation from EtOAc/EtOH to afford the title compound (5.1 g) as a pale yellow solid. MS (ESI): m/z [M+H]$^+$ 485.4.

Step E. (1R,2S,3R,4S)-3-(5-(((1s,4S)-4-Carboxy-4-methylcyclohexyl)oxy)-4-cyano-2-methoxybenzamido)bicyclo[2.2.1]heptane-2-carboxylic acid A solution of LiOH (50 mL, 52.6 mmol, 1.05 M in H$_2$O) was added to a stirred solution of Intermediate 72 (5.1 g, 10.5 mmol) in THF (100 mL) at 10° C. The reaction mixture was allowed to warm to rt and stirred for 14 h, then acidified to pH 2 using HCl (1 M, aq). The reaction mixture was diluted with EtOAc (350 mL), and washed sequentially with brine (300 mL, sat), H$_2$O (300 mL) and brine (300 mL, sat). The organic phase was separated and dried over Na$_2$SO$_4$, filtered and the solvent was removed under reduced pressure. The crude product was purified by precipitation from EtOAc/Et$_2$O followed by reversed phase flash chromatography on a C18 column using a gradient of 0-50% MeCN in HCl (0.4%, aq) as mobile phase to afford the title compound (4.00 g, 82%) as a white solid; $^1$H NMR (400 MHz, DMSO-d6) δ 1.13 (s, 3H), 1.20 (s, 1H), 1.23 (s, 2H), 1.33 (t, 2H), 1.46 (q, 4H), 1.84 (d, 1H), 1.92 (d, 2H), 2.03-2.14 (m, 4H), 2.38 (d, 1H), 2.67 (d, 1H), 3.89 (s, 3H), 4.23 (t, 1H), 4.43 (dt, 1H), 7.54 (s, 1H), 7.59 (s, 1H), 8.67 (d, 1H), 12.30 (s, 2H). MS (ESI): m/z [M+H]$^+$ 471.3.

Intermediate 73: 5-(((1s,4s)-4-(Tert-butoxycarbonyl)-4-methylcyclohexyl)oxy)-4-fluoro-2-methoxybenzoic acid

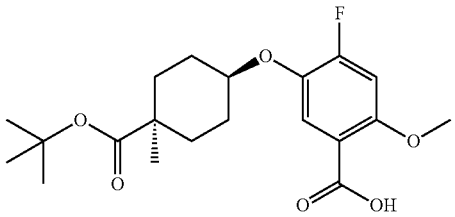 [SMILES: COc1cc(F)c(O[C@H]2CC[C@@](C)(C(=O)OC(C)(C)C)CC2)cc1C(=O)O]

Pd(OH)$_2$/C (20 wt %, 78 mg, 0.11 mmol) was added to a solution of Intermediate 136 (527 mg, 1.12 mmol) in MeOH (11 mL). The reaction suspension was stirred at rt for 3 h under an atmosphere of hydrogen (2 atm). The reaction mixture was filtered through a pad of Celite® and the solvent removed under reduced pressure to afford the title compound (427 mg, 100%) as a colorless thick oil; MS (ESI): m/z [M–H]$^-$ 381.2.

Intermediate 74: tert-Butyl (1s,4s)-4-(2-fluoro-4-methoxy-5-((2-(neopentylcarbamoyl)phenyl)carbamoyl)phenoxy)-1-methylcyclohexane-1-carboxylate

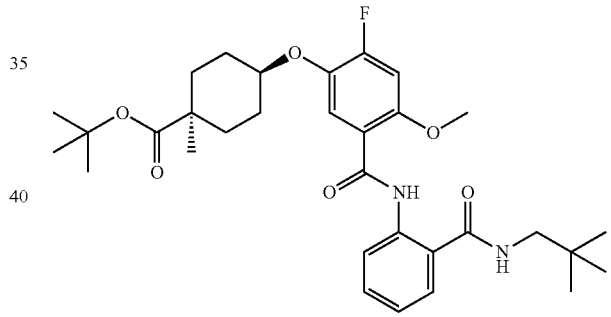

DIPEA (68 μL, 0.39 mmol) was added to a solution of Intermediate 73 (40 mg, 0.1 mmol) in DCM (0.4 mL). HATU (119 mg, 0.31 mmol) was added followed by 2-amino-N-(2,2-dimethylpropyl)benzamide (25.9 mg, 0.13 mmol) and the reaction mixture was stirred at rt overnight. Na$_2$CO$_3$ (sat) was added and the biphasic mixture stirred for 10 min before the two layers were separated. The aq phase was washed with DCM. The combined organic phase was passed through a phase separator and the solvent removed under reduced pressure. The crude product was purified by flash silica chromatography using a gradient of 5-95% EtOAc in heptane as mobile phase to afford the title compound (50.4 mg, 84%) as a white solid; $^1$H NMR (400 MHz, DMSO-d6) δ 0.91 (s, 9H), 1.08 (s, 3H), 1.20-1.34 (m, 3H), 1.42 (s, 11H), 1.92 (d, 2H), 2.05 (d, 2H), 3.12 (d, 2H), 3.98 (s, 3H), 4.20 (t, 1H), 7.15-7.28 (m, 2H), 7.49 (t, 1H), 7.63 (d, 1H), 7.74 (d, 1H), 8.46-8.67 (m, 2H), 11.70 (s, 1H). MS (ESI): m/z [M–H]$^-$ 569.3

Intermediate 75: (1R,2S,3R,4S)-3-(5-(((1s,4S)-4-(tert-Butoxycarbonyl)-4-methylcyclohexyl)oxy)-4-fluoro-2-methoxybenzamido)bicyclo[2.2.1]heptane-2-carboxylic acid

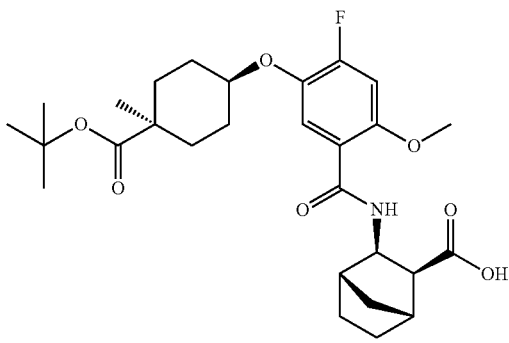 [SMILES: COc1cc(F)c(O[C@H]2CC[C@@](C)(C(=O)OC(C)(C)C)CC2)cc1C(=O)N[C@@H]1[C@H]2CC[C@H](C2)[C@@H]1C(=O)O]

Palladium on carbon (7 mg, 0.07 mmol) was added to a solution of Intermediate 76 (400 mg, 0.66 mmol) in MeOH (30 mL). The reaction suspension was stirred at rt for 3 h under an atmosphere of hydrogen (1.3 atm). The suspension was filtered through Celite®. The solvent was removed under reduced pressure to afford the title compound (208 mg, 60.8%) as a white solid. MS (ESI): m/z [M+H]+ 520.4.

Intermediate 76: Benzyl (1S,2S,3R,4R)-3-(5-(((1s,4S)-4-(tert-butoxycarbonyl)-4-methylcyclohexyl)oxy)-4-fluoro-2-methoxybenzamido)bicyclo[2.2.1]hept-5-ene-2-carboxylate

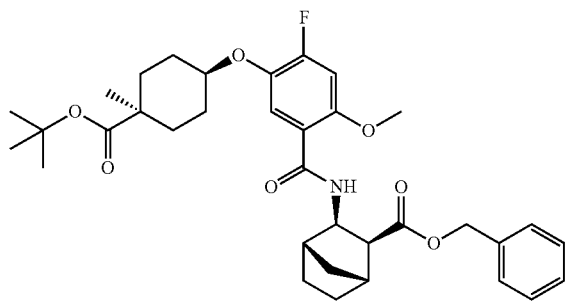 [SMILES: COc1cc(F)c(O[C@H]2CC[C@@](C)(C(=O)OC(C)(C)C)CC2)cc1C(=O)N[C@@H]1[C@H]2CC[C@H](C2)[C@@H]1C(=O)OCc1ccccc1]

Step A. Intermediate 77: Benzyl (1S,2S,3R,4R)-3-aminobicyclo[2.2.1]hept-5-ene-2-carboxylate hydrochloride

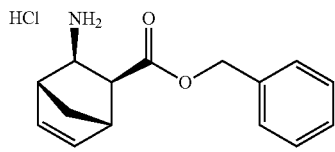 [SMILES: Cl ; N[C@H]1[C@@H](C(=O)OCc2ccccc2)[C@@H]2C=C[C@H]1C2]

HCl (4 M in MeOH, 20 mL, 80 mmol) was added dropwise to a solution of Intermediate 108 (2.0 g, 5.82 mmol) in MeOH (10 mL) at 0° C. The resulting mixture was stirred at 20° C. for 16 h. The solvent was removed under reduced pressure to afford the title compound (1.6 g) as a white solid. ¹H NMR (400 MHz, DMSO-d6) δ 1.48 (d, 1H), 2.06 (d, 1H), 2.65-2.71 (m, 1H), 2.98 (s, 1H), 3.06 (s, 1H), 3.24 (s, 1H), 5.09 (d, 1H), 5.22 (d, 1H), 6.24 (dd, 1H), 6.32 (dd, 1H), 7.29-7.47 (m, 5H), 8.22 (s, 3H).

Step B. Benzyl (1S,2S,3R,4R)-3-(5-(((1s,4S)-4-(tert-butoxycarbonyl)-4-methylcyclohexyl)oxy)-4-fluoro-2-methoxybenzamido)bicyclo[2.2.1]hept-5-ene-2-carboxylate DIPEA (5.1 mL, 29.4 mmol) was added dropwise to a solution of Intermediate 73 (2.25 g, 5.88 mmol), Intermediate 77 (1.88 g, 6.47 mmol) and HATU (6.71 g, 17.65 mmol) in DMF (20 mL) under nitrogen. The reaction mixture was stirred at rt for 14 h after which it was diluted with EtOAc and washed sequentially with NaHCO₃ (sat) and brine (sat). The organic layer was dried over Na₂SO₄, filtered and evaporated under reduce pressure. The crude product was purified by flash silica chromatography using a gradient of 10-15% EtOAc in PE as mobile phase to afford 2.6 g the title compound as a pale yellow oil which solidified on standing. MS (ESI): m/z [M+H]+ 608.4.

Intermediate 78: Tert-butyl (1S,4s)-4-(5-(((1S,2R,3S,4R)-3-(((R*)-3-ethylpentan-2-yl)carbamoyl)bicyclo[2.2.1]heptan-2-yl)carbamoyl)-2-fluoro-4-methoxyphenoxy)-1-methylcyclohexane-1-carboxylate. Isomer 1

Intermediate 79: Tert-butyl (1S,4s)-4-(5-(((1S,2R,3S,4R)-3-(((R*)-3-ethylpentan-2-yl)carbamoyl)bicyclo[2.2.1]heptan-2-yl)carbamoyl)-2-fluoro-4-methoxyphenoxy)-1-methylcyclohexane-1-carboxylate. Isomer 2

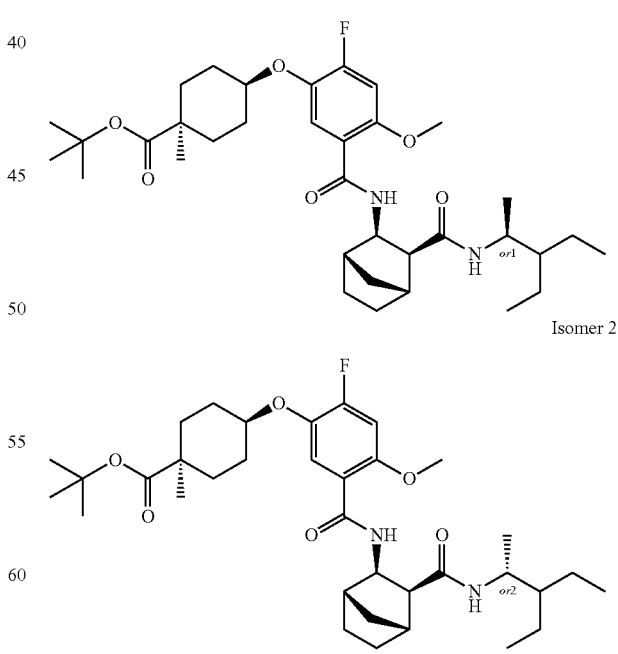

To a solution of Intermediate 75 (138 mg, 0.27 mmol) in DCM (2.7 mL) was added DIPEA (139 μL, 0.8 mmol) followed by HATU (303 mg, 0.8 mmol). 3-Ethylpentan-2- amine (66 µL, 0.4 mmol) was added to the solution and the reaction stirred at rt overnight. Na₂CO₃ (sat) was added and the biphasic mixture stirred for 10 min. The organic layer was separated. The aq phase was washed with DCM twice. The combined organic phase was passed through a phase separator and the solvent removed under reduced pressure. The crude product was purified by flash silica chromatography using a gradient of 10-90% EtOAc in heptane as mobile phase to give the first eluting compound Intermediate 78, isomer 1 (67 mg, 41%); ¹H NMR (400 MHz, CDCl₃) δ 0.75 (d, 3H), 0.89 (td, 6H), 1.16-1.34 (m, 10H), 1.47 (s, 9H), 1.57 (d, 7H), 2.01 (dd, 3H), 2.21 (d, 3H), 2.42 (d, 1H), 2.54 (s, 1H), 3.93 (s, 4H), 4.06-4.23 (m, 1H), 4.41 (t, 1H), 5.40 (d, 1H), 6.71 (d, 1H), 7.88 (d, 1H), 8.53 (d, 1H); MS [ESI] m/z [M+H]⁺ 617.5; and the second eluting compound Intermediate 79, isomer 2 (55 mg, 33%); ¹H NMR (400 MHz, CDCl₃) δ 0.61 (t, 3H), 0.68 (t, 3H), 0.86-0.92 (m, 2H), 1.04 (d, 4H), 1.25 (dd, 8H), 1.47 (s, 9H), 1.51-1.64 (m, 6H), 1.98 (d, 2H), 2.11 (d, 1H), 2.21 (d, 3H), 2.35 (d, 1H), 2.48 (s, 1H), 3.93 (s, 3H), 3.97-4.07 (m, 1H), 4.08-4.18 (m, 1H), 4.43 (t, 1H), 5.35 (d, 1H), 6.69 (d, 1H), 7.90 (d, 1H), 8.78 (d, 1H); MS [ESI] m/z [M+H]⁺ 617.5.

Intermediate 80: (1S,3s)-3-(2-Cyano-4-methoxy-5-(((1R,2R,3S,4S)-3-(((1-methylcyclobutyl)methyl)carbamoyl)bicyclo[2.2.1]hept-5-en-2-yl)carbamoyl)phenoxy)-1-methylcyclobutane-1-carboxylic acid

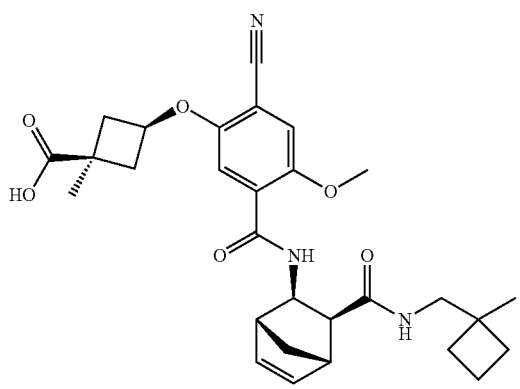 [SMILES: COc1cc(C#N)c(O[C@H]2C[C@@](C)(C(=O)O)C2)cc1C(=O)N[C@H]1[C@@H](C(=O)NCC2(C)CCC2)[C@@H]2C=C[C@H]1C2]

Step A. Intermediate 81: Methyl 4-cyano-2-methoxy-5-((1s,3s)-3-(methoxycarbonyl)-3-methyl-cyclobutoxy)benzoate

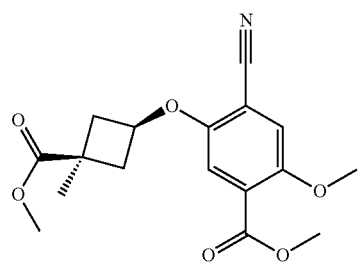 [SMILES: COC(=O)c1cc(O[C@H]2C[C@@](C)(C(=O)OC)C2)c(C#N)cc1OC]

Methyl (1r,3r)-3-hydroxy-1-methylcyclobutane-1-carboxylate (60 mg, 0.42 mmol) was added dropwise to a solution of DIAD (123 µL, 0.62 mmol), PPh₃ (164 mg, 0.62 mmol) and methyl 4-cyano-5-hydroxy-2-methoxybenzoate (86 mg, 0.42 mmol) in THF (13.7 mL) at 50° C. under nitrogen. The resulting solution was stirred at the same temperature for 15 h. The reaction was allowed to cool to rt and it was diluted with EtOAc (150 mL). The organic phase was washed sequentially with H₂O (2×50 mL) and brine (sat, 2×50 mL). The organic layer was separated, dried over a phase separator, filtered and the solvent removed under reduced pressure. The crude material was purified by Method PrepAcidic-F using a gradient of 15-55% followed by flash chromatography using a gradient from of 10-50% of EtOAc in heptane as mobile phase to afford the title compound (0.126 g, 91%) as a white solid. ¹H NMR (400 MHz, CDCl₃) δ 1.48 (s, 3H), 2.47 (ddd, 2H), 2.73 (ddd, 2H), 3.74 (s, 3H), 3.88 (s, 3H), 3.93 (s, 3H), 4.77 (p, 1H), 7.15 (d, 2H). MS [ESI] m/z [M+H]⁺ 334.3.

Step B. Intermediate 82: 5-((1s,3s)-3-Carboxy-3-methylcyclobutoxy)-4-cyano-2-methoxybenzoic acid

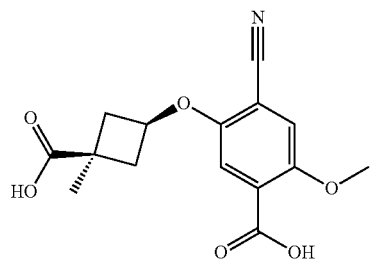 [SMILES: COc1cc(C#N)c(O[C@H]2C[C@@](C)(C(=O)O)C2)cc1C(=O)O]

Cesium hydroxide hydrate (21.9 mg, 0.15 mmol) was added in one portion to a solution of Intermediate 81 (126 mg, 0.38 mmol) in MeOH/H₂O 1:1 (4 mL) at 20° C. The resulting suspension was stirred at 50° C. for 15 h. The reaction was allowed to cool to rt and it was acidified with HCl (aq, 3.8 M). The product was extracted with EtOAc (3×5 mL) and concentrated under reduced pressure to afford the title compound. The product was used in the next step without further purification. ¹H NMR (400 MHz, CDCl₃) δ 1.54 (s, 3H), 2.5-2.63 (m, 3H), 2.76 (ddq, 3H), 4.07 (s, 3H), 4.85 (p, 1H), 7.28 (s, 1H), 7.54 (s, 1H). MS (ESI): m/z [M−H]⁻ 304.3.

Step C. (1S,3s)-3-(2-Cyano-4-methoxy-5-(((1R,2R,3S,4S)-3-(((1-methylcyclobutyl)methyl)carbamoyl)bicyclo[2.2.1]hept-5-en-2-yl)carbamoyl)phenoxy)-1-methylcyclobutane-1-carboxylic acid Intermediate 82 (42 mg, 0.14 mmol) was dissolved in DCM (2.7 mL). DIPEA (28 µL, 0.16 mmol) was added to the solution, followed by HATU (157 mg, 0.41 mmol) and Intermediate 21 (69.6 mg, 0.14 mmol) and the reaction stirred at ambient temperature for 2 h. The reaction was quenched with Na₂CO₃ (sat) and the biphasic mixture stirred for 1 h. The organic layer was separated. The aq phase was washed with DCM. The combined organic phase was passed through a phase separator and the solvent removed under reduced pressure. The crude product was purified by Method PrepAcidic-F using a gradient of 15-55% to afford the title compound (17.5 mg, 24%) as a white solid; ¹H NMR (400 MHz, CD₃OD) δ 1.08 (s, 3H), 1.45 (s, 3H), 1.51 (dt, 1H), 1.59-1.67 (m, 2H), 1.74-1.92 (m, 4H), 2.20 (dt, 1H), 2.42 (dd, 1H), 2.45-2.59 (m, 4H), 2.69 (d, 1H), 2.84 (s, 1H), 3.07

(dd, 1H), 3.21 (dd, 1H), 3.86 (s, 3H), 3.98 (td, 1H), 6.18-6.33 (m, 2H), 7.29 (s, 1H), 7.39 (s, 1H), 7.76 (d, 1H), 7.99 (t, 1H); MS (ESI): m/z [M+H]+ 522.6.

Intermediate 83: (1S,3s)-3-(2-Fluoro-4-methoxy-5-((((1R,2R,3S,4S)-3-(((1-methylcyclobutyl)methyl)carbamoyl)bicyclo[2.2.1]hept-5-en-2-yl)carbamoyl)phenoxy)-1-methylcyclobutane-1-carboxylic acid

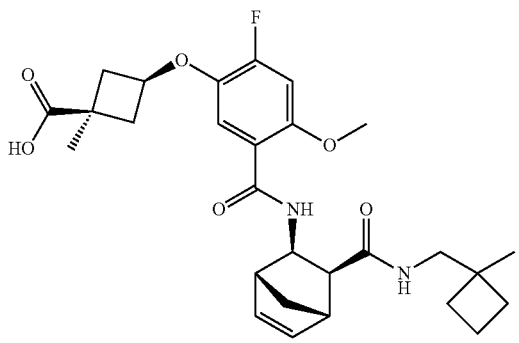 [SMILES: COc1cc(F)c(O[C@H]2C[C@@](C)(C(=O)O)C2)cc1C(=O)N[C@H]1[C@@H](C(=O)NCC2(C)CCC2)[C@@H]2C=C[C@H]1C2]

Step A. Intermediate 84: Methyl 4-fluoro-2-methoxy-5-((1s,3s)-3-(methoxycarbonyl)-3-methyl-cyclobutoxy)benzoate

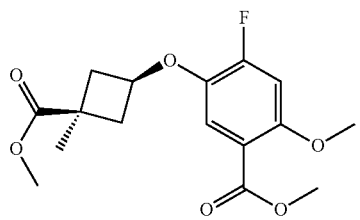 [SMILES: COC(=O)c1cc(O[C@H]2C[C@@](C)(C(=O)OC)C2)c(F)cc1OC]

Methyl (1r,3r)-3-hydroxy-1-methylcyclobutane-1-carboxylate (60 mg, 0.42 mmol) was added dropwise to a solution of DIAD (123 µL, 0.62 mmol), PPh₃ (164 mg, 0.62 mmol) and Intermediate 6 (83 mg, 0.42 mmol) in THF (13.7 mL) at 50° C. under nitrogen. The resulting solution was stirred at the same temperature for 6 h. The reaction was stirred at 30° C. over the weekend. The reaction was diluted with EtOAc (150 mL). The organic phase was washed sequentially with H₂O (2×50 mL) and brine (sat, 2×50 mL). The organic layer was separated, dried over a phase separator, filtered and the solvent removed under reduced pressure. The crude material was purified by flash chromatography using a gradient from of 5-50% of EtOAc in heptane as mobile phase to afford the title compound (102 mg, 75%) as a colorless oil. ¹H NMR (400 MHz, CDCl₃) δ 1.36 (s, 3H), 2.32 (ddd, 2H), 2.58 (ddd, 2H), 3.62 (s, 3H), 3.77 (d, 6H), 4.60 (p, 1H), 6.66 (d, 1H), 7.26 (d, 1H). MS [ESI] m/z [M+H]+ 327.3.

Step B. Intermediate 85: 5-((1s,3s)-3-Carboxy-3-methylcyclobutoxy)-4-fluoro-2-methoxybenzoic acid

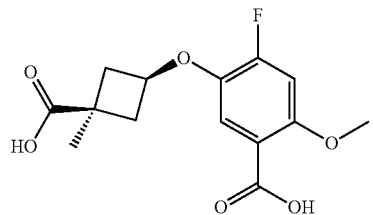 [SMILES: COc1cc(F)c(O[C@H]2C[C@@](C)(C(=O)O)C2)cc1C(=O)O]

Hydrolysis of Intermediate 84 (524 mg, 3.12 mmol) was carried out analogous to the procedure described for Intermediate 81 to afford the title compound. The product was used in the next step directly without further purification. ¹H NMR (400 MHz, CDCl₃) δ 1.51 (s, 3H), 2.51 (ddd, 2H), 2.72 (ddd, 2H), 4.04 (s, 3H), 4.79 (p, 1H), 6.86 (d, 1H), 7.62 (d, 1H). MS (ESI): m/z [M+H]+ 299.3.

Step C. (1S,3s)-3-(2-Fluoro-4-methoxy-5-((((1R,2R,3S,4S)-3-(((1-methylcyclobutyl)-methyl)carbamoyl)bicyclo[2.2.1]hept-5-en-2-yl)carbamoyl)phenoxy)-1-methylcyclobutane-1-carboxylic acid Intermediate 85 (46.5 mg, 0.16 mmol) was dissolved in DCM (2.7 mL). DIPEA (28 µL, 0.16 mmol) was added to the solution, followed by HATU (178 mg, 0.47 mmol) and Intermediate 21 (69.6 mg, 0.14 mmol) and the reaction stirred at ambient temperature for 2 h. The reaction was quenched with Na₂CO₃ (sat) and the biphasic mixture stirred for 1 h. The organic layer was separated. The aq phase was washed with DCM. The combined organic phase was passed through a phase separator and the solvent removed under reduced pressure. The crude product was purified by Method PrepAcidic-F using a gradient of 25-65% to afford the title compound (17.7 mg, 22%) as a white solid; MS (ESI): m/z [M+H]+ 515.6.

Intermediate 86: Naphthalen-1-ylmethyl (1s,4s)-4-(2-fluoro-4-methoxy-5-((4-(((1-methylcyclobutyl)methyl)carbamoyl)pyridin-3-yl)carbamoyl)phenoxy)-1-methylcyclohexane-1-carboxylate

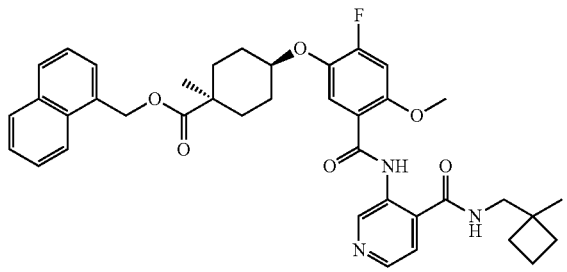 [SMILES: COc1cc(F)c(O[C@H]2CC[C@@](C)(C(=O)OCc3cccc4ccccc34)CC2)cc1C(=O)Nc1cnccc1C(=O)NCC1(C)CCC1]

Step A. Intermediate 87: Tert-butyl (4-(((1-methyl-cyclobutyl)methyl)carbamoyl)pyridin-3-yl)carbamate

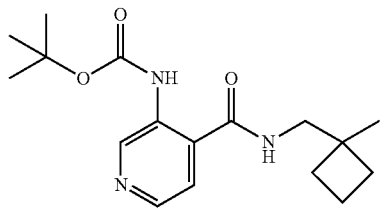 [SMILES: CC1(CNC(=O)c2ccncc2NC(=O)OC(C)(C)C)CCC1]

3-((tert-Butoxycarbonyl)amino)isonicotinic acid (84 mg, 0.35 mmol) and TCFH (124 mg, 0.44 mmol) were added to a solution of 1-methyl-1H-imidazole (82 µL, 1.03 mmol) and (1-methylcyclobutyl)methanamine hydrochloride (40 mg, 0.29 mmol) in MeCN (5.6 mL). The vial was sealed and the reaction was run at 120° C. for 80 min in a microwave reactor. The reaction mixture was then diluted with EtOAc (6 mL) and H₂O (4 mL). The layers were separated, the aq layer was extracted with EtOAc (4 mL) and the combined organic layer was washed with H₂O (4 mL) and passed through a phase separator. After removal of the solvent under reduced pressure, the title compound was progressed to the next step without further purification. MS (ESI): m/z [M+H]$^+$ 320.2.

Step B. Intermediate 88: 3-Amino-N-((1-methylcyclobutyl)methyl)isonicotinamide hydrochloride

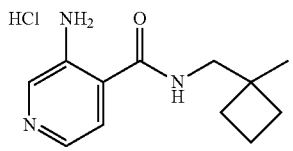 [SMILES: Cl ; CC1(CNC(=O)c2ccncc2N)CCC1]

HCl in 1,4-dioxane (2.9 mL, 11.6 mmol) was added to a solution of Intermediate 87 (93 mg, 0.29 mmol) in 1,4-dioxane (2 mL). After 2 h, few drops of MeOH were added until a clear solution was achieved and the reaction was stirred for additional 5 h. The solvent was removed under reduced pressure and the title compound was progressed to the next step without further purification. MS (ESI): m/z [M+H]$^+$ 220.1.

Step C. Naphthalen-1-ylmethyl (1s,4s)-4-(2-fluoro-4-methoxy-5-((4-(((1-methylcyclobutyl)-methyl)carbamoyl)pyridin-3-yl)carbamoyl)phenoxy)-1-methylcyclohexane-1-carboxylate Intermediate 13 (176 mg, 0.38 mmol) and TCFH (122 mg, 0.44 mmol) were added to a microwave vial followed by a solution of 1-methyl-1H-imidazole (81 µL, 1.02 mmol) in MeCN. After stirring for 1 min, a solution of Intermediate 88 (74.2 mg, 0.29 mmol) in MeCN was added and the vial was sealed. The reaction was stirred at 120° C. for 80 min in a microwave reactor. The reaction was then diluted with EtOAc and H₂O. The layers were separated, the aq layer was extracted with isopropyl acetate and the combined organic layers were washed with H₂O, dried over a phase separator, filtered and concentrated under reduced pressure. The crude product was purified by flash chromatography using a gradient from of 10-60% of EtOAc in heptane as mobile phase to give the title compound (115 mg, 59%) as a white solid; MS (ESI): m/z [M+H]$^+$ 668.4. $^1$H NMR (500 MHz, CDCl₃) δ 1.18 (d, 6H), 1.21-1.38 (m, 3H), 1.60 (q, 2H), 1.72-1.80 (m, 2H), 1.81-2.00 (m, 6H), 2.29 (d, 2H), 3.47 (d, 2H), 4.06 (s, 3H), 4.1-4.26 (m, 1H), 5.61 (s, 2H), 6.78 (d, 1H), 7.37-7.67 (m, 5H), 7.86 (d, 1H), 7.89 (d, 2H), 8.00 (d, 1H), 8.38 (d, 1H), 10.02 (s, 1H), 11.69 (s, 1H).

Intermediate 89: Naphthalen-1-ylmethyl (1R,4s)-4-(2-fluoro-4-methoxy-5-(((1SR,2RS)-2-(((1-methylcyclobutyl)methyl)carbamoyl)cyclooctyl)carbamoyl)phenoxy)-1-methylcyclohexane-1-carboxylate

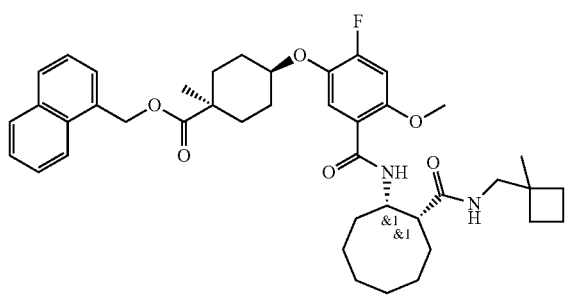 [SMILES: COc1cc(F)c(O[C@H]2CC[C@@](C)(C(=O)OCc3cccc4ccccc34)CC2)cc1C(=O)N[C@H]1CCCCCC[C@H]1C(=O)NCC1(C)CCC1]

Step A. Intermediate 90: rac-tert-Butyl ((1R,2S)-2-(((1-methylcyclobutyl)methyl)carbamoyl)cyclooctyl)carbamate

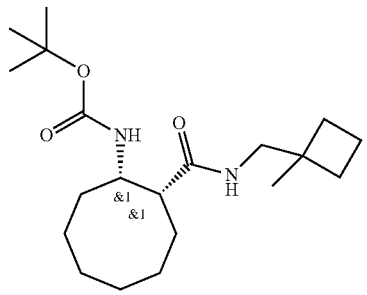 [SMILES: CC1(CNC(=O)[C@@H]2CCCCCC[C@@H]2NC(=O)OC(C)(C)C)CCC1]

Rac-(1R,2S)-2-((tert-Butoxycarbonyl)amino)cyclooctane-1-carboxylic acid (96 mg, 0.35 mmol) and TCFH (124 mg, 0.44 mmol) were added to a microwave vial followed by a solution of 1-methyl-1H-imidazole (82 µL, 1.03 mmol) in MeCN (2.8 mL). After stirring for 1 min, a solution of (1-methylcyclobutyl)methanamine hydrochloride (40 mg, 0.29 mmol) in MeCN (2.8 mL) was added and the vial was sealed. The reaction was stirred at 120° C. for 80 min in a microwave reactor. The reaction was then diluted with EtOAc (6 mL) and H₂O (4 mL). The layers were separated, the aq layer was extracted with iPrOAc and the combined organic layers were washed with H₂O, dried over a phase separator, filtered and concentrated under reduced pressure to afford the title compound. The product was used in the next step without further purification. MS (ESI): m/z [M+H]$^+$ 353.3.

Step B. Intermediate 91: rac-(1R,2S)-2-Amino-N-((1-methylcyclobutyl)methyl)cyclooctane-1-carboxamide

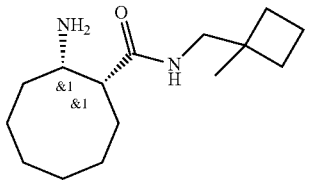 [SMILES: CC1(CNC(=O)[C@@H]2CCCCCC[C@@H]2N)CCC1]

Intermediate 90 was dissolved in 1,4-dioxane (2 mL) and HCl (4 M in dioxane) was added. After stirring at rt for 12 h, the title compound was obtained. The product was used in the next step without further purification. MS (ESI): m/z [M+H]$^+$ 253.1.

Step C. Naphthalen-1-ylmethyl (1R,4s)-4-(2-fluoro-4-methoxy-5-(((1SR,2RS)-2-(((1-methylcyclobutyl)methyl)carbamoyl)cyclooctyl)carbamoyl)phenoxy)-1-methylcyclohexane-1-carboxylate Intermediate 91 was coupled with Intermediate 13 in an analogous procedure for the synthesis of Intermediate 86, to obtain the title compound (75%) as a white solid; MS (ESI): m/z [M+H]$^+$ 701.6.

Intermediate 92: Naphthalen-1-ylmethyl (1s,4s)-4-(2-fluoro-4-methoxy-5-((3-methyl-5-(((1-methylcyclobutyl)methyl)carbamoyl)isothiazol-4-yl)carbamoyl)phenoxy)-1-methylcyclohexane-1-carboxylate

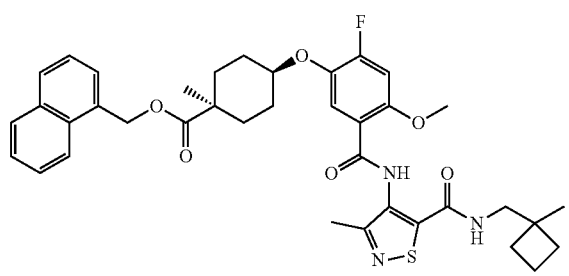 [SMILES: COc1cc(F)c(O[C@H]2CC[C@@](C)(C(=O)OCc3cccc4ccccc34)CC2)cc1C(=O)Nc1c(C)nsc1C(=O)NCC1(C)CCC1]

Step A. Intermediate 93: tert-Butyl (3-methyl-5-(((1-methylcyclobutyl)methyl)carbamoyl)isothiazol-4-yl)carbamate

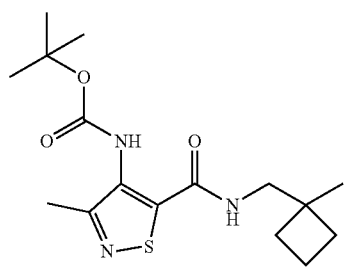 [SMILES: Cc1nsc(C(=O)NCC2(C)CCC2)c1NC(=O)OC(C)(C)C]

4-((tert-Butoxycarbonyl)amino)-3-methylisothiazole-5-carboxylic acid was coupled with (1-methylcyclobutyl)methanamine hydrochloride in an analogous way to Intermediate 90 to afford the title compound. The product was used in the next step without further purification. MS (ESI): m/z [M+H]$^+$ 340.2.

Step B. Intermediate 94: 4-Amino-3-methyl-N-((1-methylcyclobutyl)methyl)isothiazole-5-carboxamide

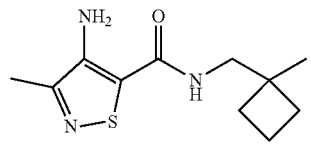

Hydrolysis of Intermediate 93 was carried out in an analogous way to Intermediate 91 to afford the title compound. The product was used in the next step without further purification.

Step C. Naphthalen-1-ylmethyl (1s,4s)-4-(2-fluoro-4-methoxy-5-((3-methyl-5-(((1-methylcyclobutyl)methyl)carbamoyl)isothiazol-4-yl)carbamoyl)phenoxy)-1-methylcyclohexane-1-carboxylate Intermediate 94 was coupled with Intermediate 13 in an analogous procedure for the synthesis of Intermediate 86 to obtain the title compound (46%) as a white solid; $^1$H NMR (500 MHz, CDCl$_3$) δ 1.07 (s, 3H), 1.18 (s, 3H), 1.26 (t, 3H), 1.58-1.65 (m, 4H), 1.81 (d, 3H), 1.96 (d, 2H), 2.29 (d, 2H), 2.44 (s, 3H), 3.36 (d, 2H), 4.04 (s, 3H), 4.16 (d, 1H), 5.61 (s, 2H), 6.84 (d, 1H), 6.94 (s, 1H), 7.46 (t, 1H), 7.54 (dq, 3H), 7.83-7.91 (m, 3H), 8.00 (d, 1H), 9.84 (s, 1H). MS (ESI): m/z [M+H]$^+$ 688.3.

Intermediate 95: Naphthalen-1-ylmethyl (1s,4s)-4-(5-((5-chloro-2-(((1-methylcyclobutyl)methyl)carbamoyl)phenyl)carbamoyl)-2-fluoro-4-methoxyphenoxy)-1-methylcyclohexane-1-carboxylate

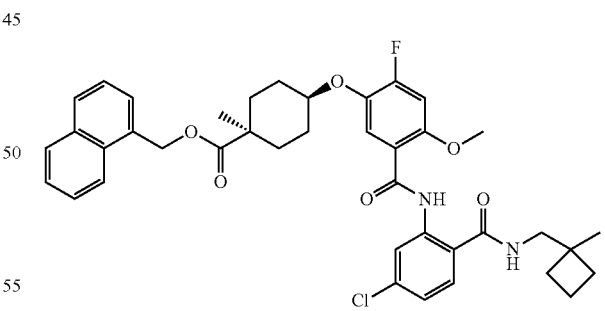

2-Amino-4-chloro-N-((1-methylcyclobutyl)methyl)benzamide was coupled with Intermediate 13 in an analogous procedure for the synthesis of Intermediate 86, to give the title compound (60%) as a white solid; $^1$H NMR (400 MHz, DMSO-d6) δ 1.11 (s, 3H), 1.13 (s, 3H), 1.36 (dt, 4H), 1.53-1.66 (m, 2H), 1.72-2.03 (m, 6H), 2.09 (d, 2H), 3.98 (s, 3H), 4.21 (s, 1H), 5.62 (s, 2H), 7.21 (d, 1H), 7.28 (dd, 1H), 7.48-7.63 (m, 4H), 7.66 (d, 1H), 7.72 (d, 1H), 7.92-8.05 (m, 3H), 8.70 (d, 1H), 8.74 (t, 1H), 11.93 (s, 1H). MS (ESI): m/z [M+H]$^+$ 701.6.

Intermediate 96: Naphthalen-1-ylmethyl (1s,4s)-4-(2-fluoro-4-methoxy-5-((2-methyl-6-(((1-methylcyclobutyl)methyl)carbamoyl)phenyl)carbamoyl)phenoxy)-1-methylcyclohexane-1-carboxylate

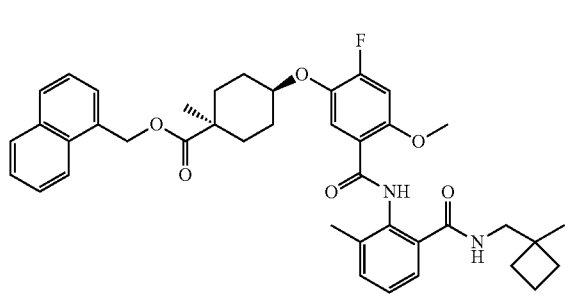 [SMILES: COc1cc(F)c(O[C@H]2CC[C@@](C)(C(=O)OCc3cccc4ccccc34)CC2)cc1C(=O)Nc1c(C)cccc1C(=O)NCC1(C)CCC1]

2-Amino-3-methyl-N-((1-methylcyclobutyl)methyl)benzamide was coupled with Intermediate 13 in an analogous procedure for the synthesis of Intermediate 86, to give the title compound (62%) as a white solid; MS (ESI): m/z [M+H]$^+$ 681.7.

Intermediate 97: Naphthalen-1-ylmethyl (1s,4s)-4-(5-((4-chloro-2-(((1-methylcyclobutyl)methyl)carbamoyl)phenyl)carbamoyl)-2-fluoro-4-methoxyphenoxy)-1-methylcyclohexane-1-carboxylate

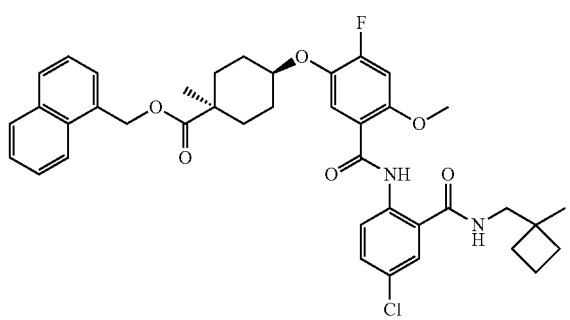 [SMILES: COc1cc(F)c(O[C@H]2CC[C@@](C)(C(=O)OCc3cccc4ccccc34)CC2)cc1C(=O)Nc1ccc(Cl)cc1C(=O)NCC1(C)CCC1]

2-Amino-5-chloro-N-((1-methylcyclobutyl)methyl)benzamide was coupled with Intermediate 13 in an analogous procedure for the synthesis of Intermediate 86 to give the title compound (80%) as a white solid; MS (ESI): m/z [M+H]$^+$ 701.6. $^1$H NMR (400 MHz, DMSO-d6) δ 1.10 (s, 3H), 1.12 (s, 3H), 1.36 (dt, 4H), 1.54-1.65 (m, 2H), 1.73-1.99 (m, 6H), 2.09 (d, 2H), 3.98 (s, 3H), 4.20 (s, 1H), 5.61 (s, 2H), 7.21 (d, 1H), 7.48-7.63 (m, 5H), 7.65 (dd, 1H), 7.72 (d, 1H), 7.86-8.07 (m, 3H), 8.57 (d, 1H), 8.78 (s, 1H), 11.74 (s, 1H).

Intermediate 98: Naphthalen-1-ylmethyl (1s,4s)-4-(2-fluoro-4-methoxy-5-((2-(((1-methylcyclobutyl)methyl)carbamoyl)thiophen-3-yl)carbamoyl)phenoxy)-1-methylcyclohexane-1-carboxylate

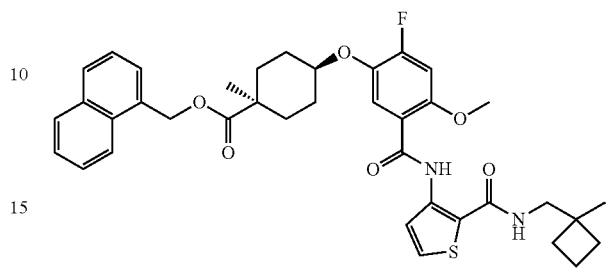

3-Amino-N-((1-methylcyclobutyl)methyl)thiophene-2-carboxamide was coupled with Intermediate 13 in an analogous procedure for the synthesis of Intermediate 86 to give the title compound (96%) as a white solid; MS (ESI): m/z [M+H]$^+$ 673.6. $^1$H NMR (400 MHz, DMSO-d6) δ 1.10 (s, 3H), 1.12 (s, 3H), 1.29-1.47 (m, 4H), 1.55-1.68 (m, 2H), 1.73-1.93 (m, 4H), 1.98 (td, 2H), 2.09 (d, 2H), 3.27 (d, 2H), 4.01 (s, 3H), 4.22 (s, 1H), 5.62 (s, 2H), 7.21 (d, 1H), 7.47-7.66 (m, 4H), 7.7-7.84 (m, 2H), 7.91-8.09 (m, 3H), 8.17-8.28 (m, 2H), 12.51 (s, 1H).

Intermediate 99: ((1s,3s)-3-Methylcyclobutyl)methanamine

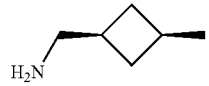

Step A. Intermediate 100: (1s,3s)-3-Methylcyclobutane-1-carboxylic acid

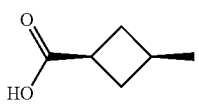

The title compound was obtained from 3-methylcyclobut-1-ene-1-carboxylic acid in 39% yield as colorless oil (Liebigs Ann. Chem. 1990, 411-414). $^1$H NMR (400 MHz, CD$_3$OD): δ 1.06 (dd, 3H), 1.79-1.86 (m, 2H), 2.28-2.39 (m, 3H), 2.89-2.98 (m, 1H).

Step B. Intermediate 101: (1s,3s)-3-Methylcyclobutane-1-carboxamide

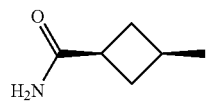

Intermediate 100 (35 g, 0.3 mol) was dissolved in anhydrous THF (500 mL) and N-methyl-morpholine (37.2 g, 0.36 mol) was added. The resulting solution was cooled to 0° C. and isobutyl chloroformate (50 g, 0.36 mol) was added dropwise over 30 min. NH₃ (g) was bubbled through the resulting solution during 30 min, then the resulting mixture was stirred at overnight. The reaction was diluted with HCl (1 M). The organic layer was separated and dried over MgSO₄, filtered and the solvent removed under reduced pressure. The residue was recrystallized from PE and EtOAc to obtain the title compound (15 g, 35%) as a white solid. ¹H NMR (400 MHz, CD₃OD) δ 1.16 (d, 3H), 1.76-1.84 (m, 2H), 2.24-2.37 (m, 3H), 2.87-2.96 (m, 1H).

Step C. ((1s,3s)-3-Methylcyclobutyl)methanamine

Borane dimethylsulfide (30 g, 0.39 mol) was added to a solution of Intermediate 101 (15 g, 0.13 mol) in anhydrous THF (200 mL) at 0° C. After 30 min at rt, the reaction mixture was heated to 80° C. and stirred at the same temperature for 16 h. The reaction was quenched with MeOH at 0° C. and the solvent removed under reduced pressure. A mixture of HCl (4 M)/EtOAc was added and the resulting slurry stirred for 30 min. The solid was filtered and dried under reduced pressure to obtain the HCl salt of the title compound (9 g, 50%) as a white solid. MS (ESI): m/z [M+H]⁺ 100.

Intermediate 102: 4-Chloro-2-(4-cyano-2-methoxy-5-(((1s,4s)-4-methyl-4-((naphthalen-1-ylmethoxy)carbonyl)cyclohexyl)oxy)benzamido)benzoic acid Step A. Intermediate 103: Methyl 4-chloro-2-(4-cyano-2-methoxy-5-(((1s,4s)-4-methyl-4-((naphthalen-1-ylmethoxy)carbonyl)cyclohexyl)oxy)benzamido)benzoate

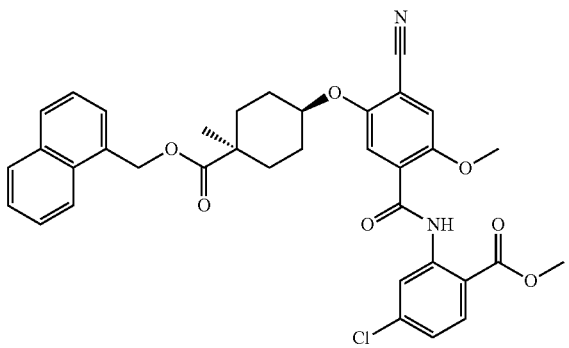 [SMILES: COC(=O)c1ccc(Cl)cc1NC(=O)c1cc(O[C@H]2CC[C@@](C)(C(=O)OCc3cccc4ccccc34)CC2)c(C#N)cc1OC]

Intermediate 70 (1.00 g, 2.09 mmol) was dissolved in MeCN (5.0 mL) and methyl 2-amino-4-chlorobenzoate (0.78 g, 4.18 mmol), was added followed by TCFH (0.89 g, 3.14 mmol) and 1-methyl-1H-imidazole (0.52 g, 6.27 mmol). The mixture was heated to 100° C. and stirred overnight at the same temperature. The reaction was then quenched with H₂O and extracted with EtOAc. The crude material was purified by silica gel column with PE/EA (1:1) to obtain the title compound (187 mg, 13%) as alight yellow solid. MS (ESI): m/z [M+Na]⁺663.1.

Step B. 4-Chloro-2-(4-cyano-2-methoxy-5-(((1s,4s)-4-methyl-4-((naphthalen-1-ylmethoxy)carbonyl)cyclohexyl)oxy)benzamido)benzoic acid LiOH (16.8 mg, 0.69 mmol) was added to a solution of Intermediate 103 (150 mg, 0.23 mol) in THF/H₂O (10 mL) and the mixture was stirred overnight at rt. The mixture was extracted with EtOAc and the organic layer was purified by silica gel column chromatography with PE/EA (1:1) to give the title compound (128 mg, 78.4%) as a light yellow solid. MS (ESI): m/z [M+Na]⁺ 649.1.

Intermediate 104: 2-(4-Cyano-2-methoxy-5-(((1s,4s)-4-methyl-4-((naphthalen-1-ylmethoxy)carbonyl)cyclohexyl)oxy)benzamido)-4-methylbenzoic acid

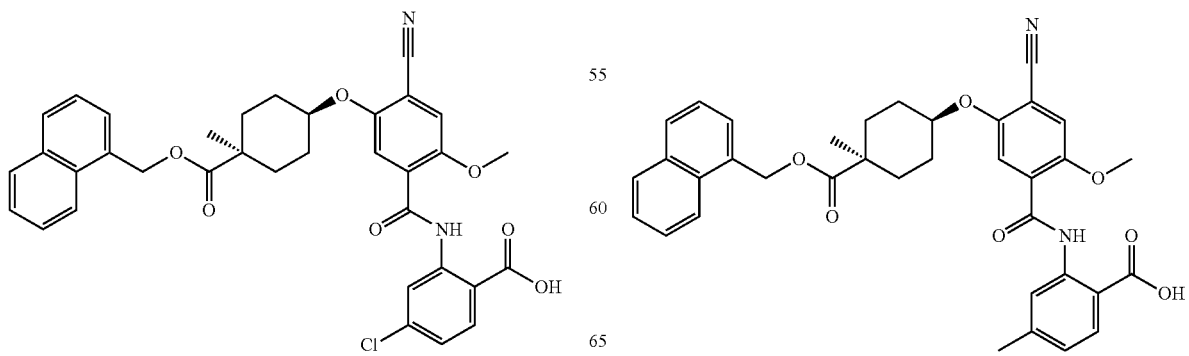

Step A. Intermediate 105: Methyl 2-(4-cyano-2-methoxy-5-(((1s,4s)-4-methyl-4-((naphthalen-1-ylmethoxy)carbonyl)cyclohexyl)oxy)benzamido)-4-methylbenzoate

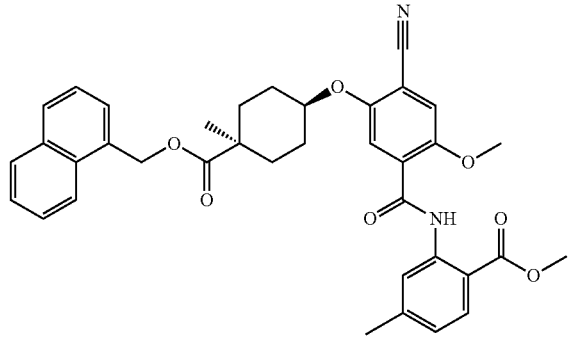 [SMILES: COC(=O)c1ccc(C)cc1NC(=O)c1cc(O[C@H]2CC[C@@](C)(C(=O)OCc3cccc4ccccc34)CC2)c(C#N)cc1OC]

Intermediate 70 (1.00 g, 2.09 mmol) was dissolved in MeCN (5 mL) and methyl 2-amino-4-methylbenzoate (0.698 g, 4.18 mmol) was added followed by TCFH (0.889 g, 3.14 mmol) and 1-methyl-1H-imidazole (0.520 g, 6.27 mmol). The mixture was heated to 100° C. and stirred for 1 h under nitrogen atmosphere. The reaction was then quenched with H$_2$O and extracted with EtOAc. The crude material was purified by silica gel column chromatography and elution with PE/EA (1:1) gave the title compound (220 mg, 14%) as a light yellow solid. MS (ESI): m/z [M+H]$^+$ 621.2.

Step B. 2-(4-Cyano-2-methoxy-5-(((1s,4s)-4-methyl-4-((naphthalen-1-ylmethoxy)carbonyl)cyclohexyl)oxy)benzamido)-4-methylbenzoic acid LiOH (11 mg, 0.45 mmol) was added to a solution of Intermediate 105 (100 mg, 0.16 mol) in THF/H$_2$O (2:1, 30 mL) and the mixture was stirred overnight at rt. The reaction was quenched with H$_2$O and acidified with HCl. Extraction with EtOAc followed by purification by silica gel column chromatography and elution with PE/EA (1:1) gave the title compound (78 mg, 77%) as a yellow solid. MS (ESI): m/z [M+H]$^+$ 607.2

Intermediate 106: (1R,2S,3R,4S)-3-(5-(((1s,4S)-4-(Ethoxycarbonyl)cyclohexyl)oxy)-4-fluoro-2-methoxybenzamido)bicyclo[2.2.1]heptane-2-carboxylic acid

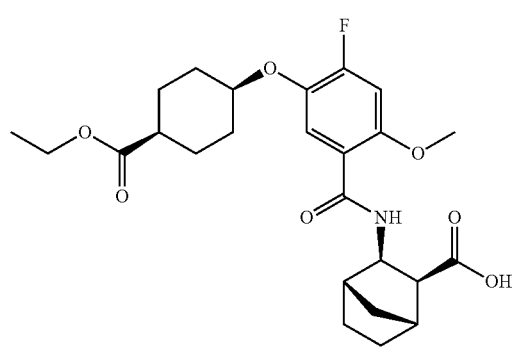 [SMILES: CCOC(=O)[C@H]1CC[C@@H](Oc2cc(C(=O)N[C@@H]3[C@H]4CC[C@H](C4)[C@@H]3C(=O)O)c(OC)cc2F)CC1]

Step A. Intermediate 107: Methyl (1S,2S,3R,4R)-3-((tert-butoxycarbonyl)amino)bicyclo[2.2.1]hept-5-ene-2-carboxylate

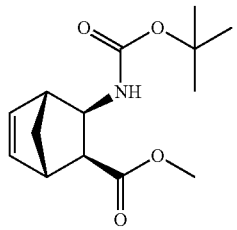 [SMILES: COC(=O)[C@@H]1[C@H](NC(=O)OC(C)(C)C)[C@H]2C=C[C@@H]1C2]

(Boc)$_2$O (22.8 mL, 98.2 mmol) was added to Intermediate 8 (10.0 g, 49.1 mmol) and TEA (34.2 mL, 245.5 mmol) in THF (20 mL) at 20° C. The resulting solution was stirred at 20° C. for 15 h. The reaction mixture was poured into brine (150 mL, sat), extracted with EtOAc (3×50 mL), the organic layer was dried over Na$_2$SO$_4$, filtered and evaporated to afford the title compound (13.0 g, 99%) as a yellow oil. The product was used in the next step directly without further purification.

Step B. Intermediate 19 (1S,2S,3R,4R)-3-((tert-Butoxycarbonyl)amino)bicyclo[2.2.1]hept-5-ene-2-carboxylic acid

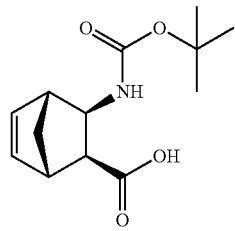 [SMILES: CC(C)(C)OC(=O)N[C@H]1[C@@H](C(=O)O)[C@@H]2C=C[C@H]1C2]

LiOH (6.5 g, 271.4 mmol) was added to Intermediate 107 (13.0 g, 48.63 mmol) in THF (40 mL), MeOH (10 mL) and H$_2$O (10 mL) at 20° C. The resulting solution was stirred at 20° C. for 15 h. The reaction mixture was poured into H$_2$O (300 mL), and acidified with 2 M HCl. The reaction mixture was extracted with EtOAc (3×125 mL), the organic layer was dried over Na$_2$SO$_4$, filtered and evaporated to afford the title compound (12.0 g, 97%) as a colorless gum.

Step C. Intermediate 108: Benzyl (1S,2S,3R,4R)-3-((tert-butoxycarbonyl)amino)bicyclo[2.2.1]hept-5-ene-2-carboxylate

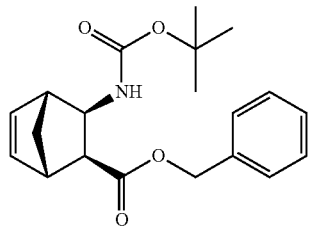 [SMILES: CC(C)(C)OC(=O)N[C@H]1[C@@H](C(=O)OCc2ccccc2)[C@@H]2C=C[C@H]1C2]

TEA (23.11 mL, 165.8 mmol) was added dropwise to Intermediate 19 (12.0 g, 47.38 mmol), phenylmethanol (7.68 g, 71.06 mmol) and EDC (19.98 g, 104.2 mmol), HOBt (15.96 g, 104.2 mmol) in DMF (60 mL) at 20° C. The resulting suspension was stirred at 20° C. for 15 h. The mixture was poured into NaHCO$_3$ (350 mL, sat), extracted with EtOAc (3×150 mL), the organic layer was dried over Na$_2$SO$_4$, filtered and evaporated to afford a pale yellow oil. The crude product was purified by flash chromatography using a gradient of 0-5% EtOAc in heptane as mobile phase to give the title compound (15.0 g, 92%) as a colorless gum. MS (ESI): m/z [M+H-Boc]$^+$244.2.

Step D. Intermediate 109: Benzyl (1S,2S,3R,4R)-3-aminobicyclo[2.2.1]hept-5-ene-2-carboxylate

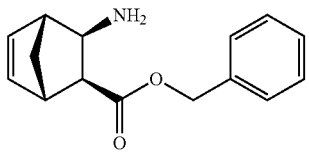 [SMILES: N[C@H]1[C@@H](C(=O)OCc2ccccc2)[C@@H]2C=C[C@H]1C2]

TFA (6.06 mL, 78.6 mmol) was added to Intermediate 108 (5.4 g, 15.7 mmol) in DCM (60 mL) at 20° C. The resulting solution was stirred at 20° C. for 15 h. The reaction mixture was diluted with EtOAc (250 mL), and washed with NaHCO$_3$ (150 mL, sat). The organic layer was dried over Na$_2$SO$_4$, filtered and evaporated to dryness to afford the title compound (3.80 g, 99%) as a pale yellow solid. The product was used in the next step directly without further purification. $^1$H NMR (300 MHz, DMSO-d6): δ 1.44 (m, 1H), 2.00-2.08 (m, 1H), 2.56 (dd, 1H), 2.76 (d, 1H), 2.98 (d, 1H), 3.22 (dd, 1H), 5.06 (d, 1H), 5.19 (d, 1H), 6.05 (s, 2H), 6.16-6.29 (br s, 2H, NH$_2$), 7.32-7.45 (m, 5H). MS (ESI): m/z [M+H]$^+$ 244.5.

Step E. Intermediate 110: Benzyl (1S,2S,3R,4R)-3-(5-(((1s,4S)-4-(ethoxycarbonyl)cyclohexyl)oxy)-4-fluoro-2-methoxybenzamido)bicyclo[2.2.1]hept-5-ene-2-carboxylate

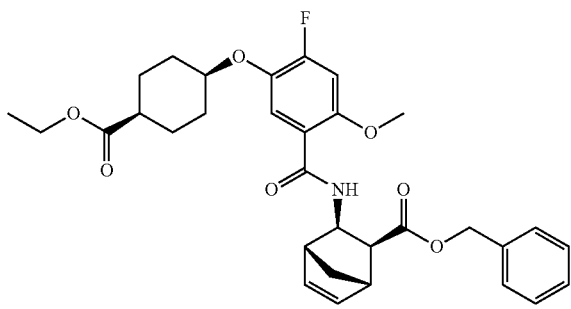 [SMILES: CCOC(=O)[C@H]1CC[C@@H](Oc2cc(C(=O)N[C@H]3[C@@H](C(=O)OCc4ccccc4)[C@@H]4C=C[C@H]3C4)c(OC)cc2F)CC1]

HATU (4.88 g, 12.8 mmol) was added portion wise to Intermediate 111 (3.64 g, 10.69 mmol), Intermediate 109 (2.6 g, 10.7 mmol) and DIPEA (4.14 g, 32.06 mmol) in DMF (50 mL) at Rt. The resulting solution was stirred at 20° C. for 15 h. The reaction mixture was poured into NaHCO$_3$ (200 mL, sat), extracted with EtOAc (3×75 mL), the organic layer was washed with brine (2×100 mL, sat). The organic layer was dried over Na$_2$SO$_4$, filtered and evaporated to afford a brown oil. The crude product was purified by flash chromatography using a gradient of 0-20% EtOAc in heptane as mobile phase to give the title compound (5.50 g, 91%) as a pale yellow gum. $^1$H NMR (300 MHz, CDCl$_3$): δ 1.27-1.30 (m, 3H), 1.69 (dtt, 5H), 2.01 (td, 4H), 2.11 (dt, 1H), 2.41 (tt, 1H), 2.75-2.86 (m, 2H), 3.05 (s, 1H), 3.84 (s, 3H), 4.17 (dd, 2H), 4.45 (tt, 1H), 4.49-4.57 (m, 1H), 5.08 (s, 2H), 6.24 (dd, 1H), 6.30 (dd, 1H), 6.69 (d, 1H), 7.18-7.28 (m, 5H), 7.90 (d, 1H), 8.62 (d, 1H). MS (ESI): m/z [M+H]$^+$ 566.4.

Step F. (1R,2S,3R,4S)-3-(5-(((1s,4S)-4-(Ethoxycarbonyl)cyclohexyl)oxy)-4-fluoro-2-methoxybenzamido)bicyclo[2.2.1]heptane-2-carboxylic acid Pd—C (0.6 g, 5.6 mmol) was added to Intermediate 110 (5.5 g, 9.7 mmol) in MeOH (75 mL) at 20° C. The resulting suspension was stirred at 20° C. for 15 h under an atmosphere of hydrogen. The reaction mixture was filtered through Celite®. The solvent was removed under reduced pressure to give the title compound (4.1 g, 88%) as a white solid. MS (ESI): m/z [M+H]$^+$ 478.4.

Intermediate 111: 5-(((1s,4s)-4-(Ethoxycarbonyl)cyclohexyl)oxy)-4-fluoro-2-methoxybenzoic acid

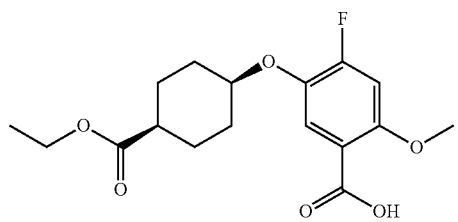 [SMILES: CCOC(=O)[C@H]1CC[C@@H](Oc2cc(C(=O)O)c(OC)cc2F)CC1]

Step A. Intermediate 112: 5-Bromo-4-fluoro-2-hydroxybenzoic acid

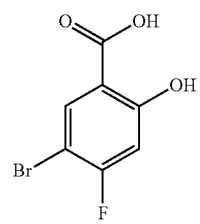 [SMILES: O=C(O)c1cc(Br)c(F)cc1O]

NBS (43.8 g, 246 mmol) was added portion wise to 4-fluoro-2-hydroxybenzoic acid (32 g, 205 mmol) in DMF (250 mL) at 0° C. The resulting solution was stirred at 20° C. for 20 h. The reaction mixture was poured into brine (1 L, sat), extracted with EtOAc (3×500 mL), the organic layer was dried over Na$_2$SO$_4$, filtered and evaporated to afford the title compound (48.0 g, 100%) as a brown solid. The product was used in the next step directly without further purification. $^1$H NMR (300 MHz, CDCl$_3$): δ 6.79 (d, 1H), 8.15 (d, 1H). (ESI): m/z [M−H]$^+$233.

Step B. Intermediate 113: Methyl 5-bromo-4-fluoro-2-methoxybenzoate

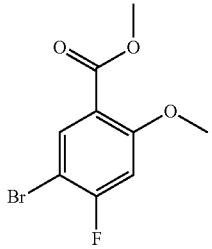

MeI (77 mL, 1225.5 mmol) was added dropwise to Intermediate 112 (48 g, 204.2 mmol) and potassium carbonate (70.6 g, 510.6 mmol) in acetone (400 mL) at 20° C. over a period of 20 Min. The resulting suspension was stirred at 60° C. for 15 h. The reaction mixture was filtered through Celite®. The reaction mixture was diluted with EtOAc (750 mL), the organic layers was washed with brine (2×400 mL, sat). The organic layer was dried over $Na_2SO_4$, filtered and evaporated to afford a brown solid. The dried solid was triturated with EtOAc/PE (1/4) (50 mL) and filtered to afford the tile compound (37.0 g, 68.9%) as a pink solid. $^1$H NMR (300 MHz, $CDCl_3$): δ 3.90 (s, 3H), 3.91 (s, 3H), 6.78 (d, 1H), 8.06 (d, 1H). (ESI): m/z [M+H]$^+$ 262.9.

Step C. Intermediate 114: 5-Bromo-4-fluoro-2-methoxybenzoic acid

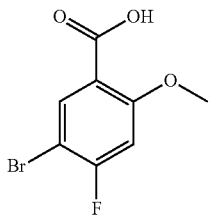

A solution of NaOH (16.88 g, 421.95 mmol) in $H_2O$ (80 mL) was added slowly to a stirred solution of Intermediate 113 (37 g, 140.6 mmol) in MeOH (250 mL) at 20° C. The resulting solution was stirred at 20° C. for 15 h. The reaction mixture was poured into ice/$H_2O$ (2 L), extracted with DCM (3×500 mL), the organic layer was dried over $Na_2SO_4$, filtered and evaporated to afford the title compound (34.0 g, 97%) as a white solid. $^1$H NMR (300 MHz, $CDCl_3$): δ 4.09 (s, 3H), 6.88 (d, 1H), 8.41 (d, 1H). (ESI): m/z [M+H]$^+$ 249.8.

Step D. Intermediate 115: Benzyl 5-bromo-4-fluoro-2-methoxybenzoate

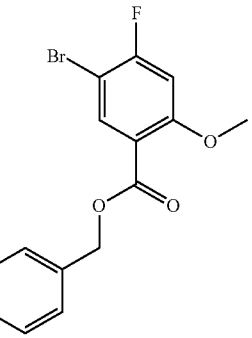

(Bromomethyl)benzene (15.76 mL, 132.51 mmol) was added slowly to Intermediate 114 (30 g, 120.5 mmol) and potassium carbonate (19.98 g, 144.56 mmol) in DMF (200 mL) at 20° C. The resulting suspension was stirred at 20° C. for 15 h. The reaction mixture was poured into brine (1 L, sat), extracted with EtOAc (3×350 mL), the organic layer was dried over $Na_2SO_4$, filtered and evaporated to afford the title compound (38.0 g, 93%) as an orange oil which solidified on standing. $^1$H NMR (300 MHz, $CDCl_3$): δ 3.91 (s, 3H), 5.36 (s, 2H), 6.79 (d, 1H), 7.37-7.50 (m, 5H), 8.08 (dd, 1H). (ESI): m/z [M+H]$^+$ 341.3.

Step E. Intermediate 116: Benzyl 4-fluoro-2-methoxy-5-(4,4,5,5-tetramethyl-1,3,2-dioxaborolan-2-yl)benzoate

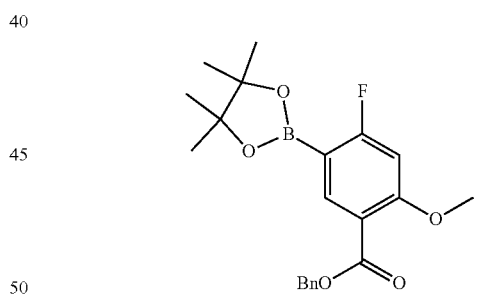

$PdCl_2$(Dppf)-$CH_2Cl_2$ Adduct (4.57 g, 5.60 mmol) was added to Intermediate 115 (38 g, 112.0 mmol), $B_2Pin_2$ (34.1 g, 134.4 mmol) and potassium acetate (27.5 g, 280.1 mmol) in 1,4-dioxane (240 mL) at 20° C. The resulting solution was stirred at 100° C. for 15 h under nitrogen. The solvent was removed under reduced pressure. The crude product was purified by flash chromatography using a gradient of 0-20% EtOAc in heptane as mobile phase to give the title compound (40.0 g, 92%) as a yellow oil which solidified on standing. $^1$H NMR (300 MHz, 23.0° C., CDCl3): δ 1.37 (s, 12H), 3.93 (s, 3H), 5.37 (s, 2H), 6.63-6.70 (m, 1H), 7.36-7.43 (m, 3H), 7.46-7.51 (m, 2H), 8.29 (d, 1H). (ESI): m/z [M+H]$^+$ 387.4.

Step F. Intermediate 117: Benzyl 4-fluoro-5-hydroxy-2-methoxybenzoate

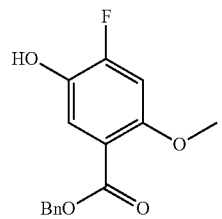 [SMILES: COc1cc(F)c(O)cc1C(=O)OCc1ccccc1]

H₂O₂ (30.0 mL, 30 weight %, 293.7 mmol) was added slowly to Intermediate 116 (44 g, 113.9 mmol) in MeOH (200 mL) at 20° C. The resulting solution was stirred at 25° C. for 5 h. The reaction mixture was poured into ice H₂O. The precipitate was collected by filtration, and dried under vacuum to afford the title compound (20.00 g, 63.5%) as a pale yellow solid. (ESI): m/z [M+H]⁺ 277.1.

Step G. Intermediate 118: Benzyl 5-(((1s,4s)-4-(ethoxycarbonyl)cyclohexyl)oxy)-4-fluoro-2-methoxybenzoate

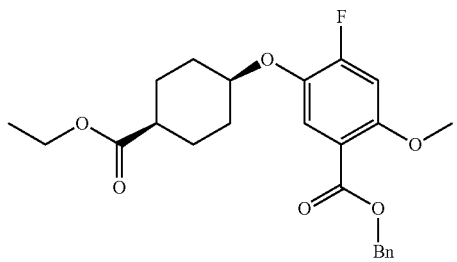 [SMILES: CCOC(=O)[C@H]1CC[C@@H](Oc2cc(C(=O)OCc3ccccc3)c(OC)cc2F)CC1]

DIAD (12.67 mL, 65.16 mmol) was added dropwise to Intermediate 117 (15 g, 54.30 mmol), ethyl (1r,4r)-4-hydroxycyclohexane-1-carboxylate (9.35 g, 54.30 mmol) and triphenylphosphane (17.09 g, 65.16 mmol) in THF (35 mL) at 50° C. The resulting solution was stirred at 60° C. for 15 h. The solvent was removed under reduced pressure. The crude product was purified by flash chromatography using a gradient of 0-10% EtOAc in heptane as mobile phase to give the title compound (17.0 g, 72.7%) as a colorless oil which solidified on standing. ¹H NMR (300 MHz, CDCl₃): δ 1.30 (dd, 3H), 1.59-1.81 (m, 4H), 1.93-2.07 (m, 4H), 2.42 (tt, 1H), 3.88 (s, 3H), 4.15-4.23 (m, 2H), 4.36 (tt, 1H), 5.37 (s, 2H), 6.77 (d, 1H), 7.35-7.44 (m, 3H), 7.45-7.50 (m, 2H), 7.59 (d, 1H). (ESI): m/z [M+Na]⁺ 453.3.

Step H. 5-(((1s,4s)-4-(Ethoxycarbonyl)cyclohexyl)oxy)-4-fluoro-2-methoxybenzoic acid Pd—C (0.20 g, 1.88 mmol) was added to Intermediate 118 (0.5 g, 1.16 mmol) in MeOH (40 mL) at 20° C. The resulting suspension was stirred at 20° C. for 15 h under an atmosphere of hydrogen. The reaction mixture was filtered through Celite®. The solvent was removed under reduced pressure to afford the title compound (0.300 g, 76%) as a white solid which was used in the next step without further purification. ¹H NMR (400 MHz, DMSO-d6): δ 1.20 (d, 3H), 1.67 (dt, 4H), 1.73-1.87 (m, 4H), 2.40-2.49 (m, 1H), 3.78 (s, 3H), 4.08 (2H, d), 4.42 (1H, d), 7.11 (1H, d), 7.46 (1H, d), 12.67 (1H, s). MS (ESI): m/z [M+H]⁺ 341.

Intermediate 119: (1R,2S,3R,4S)-3-Amino-N-(4-fluoro-3-(trifluoromethyl)phenyl)bicyclo[2.2.1]heptane-2-carboxamide

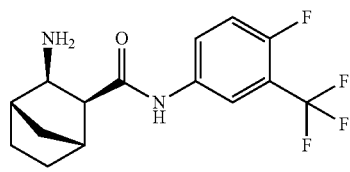 [SMILES: N[C@@H]1[C@H]2CC[C@H](C2)[C@@H]1C(=O)Nc1ccc(F)c(C(F)(F)F)c1]

Step A. Intermediate 120: Methyl (1R,2S,3R,4S)-3-aminobicyclo[2.2.1]heptane-2-carboxylate hydrochloride

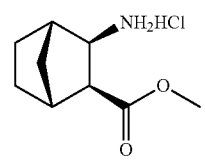

Pd—C (11.9 mg, 0.11 mmol) and Intermediate 8 (228 mg, 1.12 mmol) in MeOH (25 mL) was stirred under an atmosphere of hydrogen at 1.5 atm and 25° C. for 14 h. The mixture was filtered through a Celite® pad. The solvent was removed under reduced pressure to the title compound (230 mg, 100%) as a pale yellow solid. This was used in the next step without further purification.

Step B. Intermediate 121: Methyl (1R,2S,3R,4S)-3-((tert-butoxycarbonyl)amino)bicyclo[2.2.1]heptane-2-carboxylate

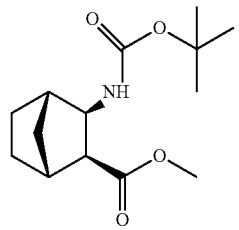 [SMILES: COC(=O)[C@H]1[C@@H]2CC[C@@H](C2)[C@H]1NC(=O)OC(C)(C)C]

Boc₂O (1.81 mL, 7.78 mmol) was added Intermediate 120 (1 g, 4.86 mmol) and TEA (2.71 mL, 19.45 mmol) in THF (20 mL) at 20° C. The resulting solution was stirred at 20° C. for 15 h. The reaction mixture was poured into brine (150 mL, sat), extracted with EtOAc (3×50 mL), the organic layer was dried over Na₂SO₄, filtered and evaporated to afford the title compound (1.20 g, 92%) as a yellow oil. The crude product was used in the next step directly without further purification. ¹H NMR (300 MHz, CDCl₃): δ 1.10-1.36 (m, 4H), 1.43 (s, 9H), 1.56-1.60 (m, 1H), 1.78-1.87 (m, 1H), 2.15 (d, 1H), 2.44 (dd, 1H), 2.64-2.79 (m, 1H), 3.65 (s, 3H), 3.97 (t, 1H), 5.01 (d, 1H).

Step C. Intermediate 122: (1R,2S,3R,4S)-3-((tert-Butoxycarbonyl)amino)bicyclo[2.2.1]heptane-2-carboxylic acid

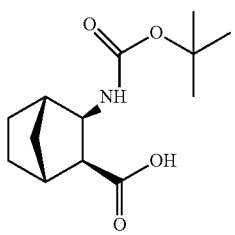 [SMILES: CC(C)(C)OC(=O)N[C@@H]1[C@H]2CC[C@H](C2)[C@@H]1C(=O)O]

LiOH (0.320 g, 13.37 mmol) was added to Intermediate 121 (1.2 g, 4.46 mmol) in THF (12 mL), MeOH (3 mL) and H$_2$O (3 mL) at 20° C. The resulting solution was stirred at 20° C. for 15 h.

The reaction mixture was poured into H$_2$O (150 mL), the reaction mixture was acidified with 2 M HCl. The reaction mixture was extracted with EtOAc (3×50 mL), the organic layer was dried over Na$_2$SO$_4$, filtered and evaporated to afford the title compound (1.100 g, 97%) as a colorless gum. The crude product was used in the next step directly without further purification. $^1$H NMR (300 MHz, CDCl$_3$): δ 1.18 (ddd, 2H), 1.47 (s, 9H), 1.50-1.69 (m, 3H), 1.98 (d, 1H), 2.17-2.22 (m, 1H), 2.51 (d, 1H), 2.61-2.72 (m, 1H), 3.93 (t, 1H), 6.99 (d, 1H).

Step D. Intermediate 123: tert-Butyl ((1S,2R,3S,4R)-3-((4-fluoro-3-(trifluoromethyl)phenyl)carbamoyl)bicyclo[2.2.1]heptan-2-yl)carbamate

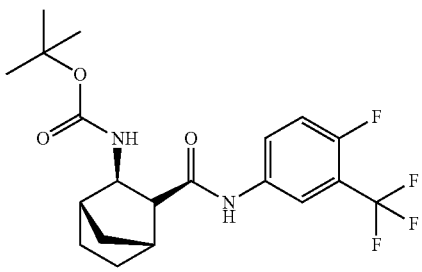

HATU (0.357 g, 0.94 mmol) was added portion wise to 4-fluoro-3-(trifluoromethyl)aniline (0.140 g, 0.78 mmol), Intermediate 122 (0.2 g, 0.78 mmol) and DIPEA (0.304 g, 2.35 mmol) in DMF (10 mL). The resulting solution was stirred at 20° C. for 15 h. The reaction mixture was poured into sat NaHCO$_3$ (200 mL), extracted with EtOAc (3×75 mL), the organic layer was washed with brine (2×100 mL). The organic layer was dried over Na$_2$SO$_4$, filtered and evaporated to afford a yellow oil. The residue was purified by preparative TLC (EtOAc/PE 1/5), to afford the title compound (0.260 g, 80%) as a yellow oil which solidified on standing. MS (ESI): m/z [M+H]$^+$ 417.

Step E. (1R,2S,3R,4S)-3-Amino-N-(4-fluoro-3-(trifluoromethyl)phenyl)bicyclo[2.2.1]heptane-2-carboxamide TFA (0.241 mL, 3.12 mmol) was added to Intermediate 123 (0.26 g, 0.62 mmol) in DCM (20 mL) at 20° C. The resulting solution was stirred at 20° C. for 15 h. The reaction mixture was diluted with EtOAc (150 mL), and washed with sat NaHCO$_3$ (75 mL). The organic layer was dried over Na$_2$SO$_4$, filtered and evaporated to dryness to afford the title compound (0.180 g, 91%) as a yellow gum which was used in the next step without further purification. MS (ESI): m/z [M+H]$^+$ 317.

Intermediate 124: (1R,2S,3R,4S)-3-Amino-N-phenylbicyclo[2.2.1]heptane-2-carboxamide

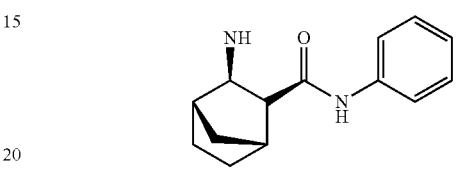

Step A. Intermediate 125: tert-butyl ((1S,2R,3S,4R)-3-(phenylcarbamoyl)bicyclo[2.2.1]heptan-2-yl)carbamate

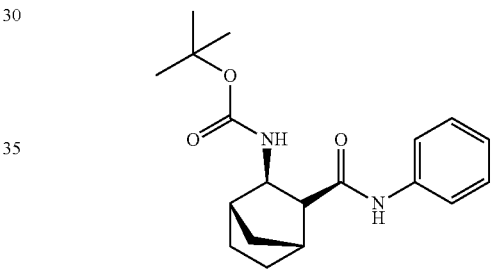

Aniline (82 mg, 0.88 mmol), HATU (402 mg, 1.06 mmol), DIPEA (0.246 mL, 1.41 mmol) and DMAP (8.61 mg, 0.07 mmol) were added to a solution of Intermediate 122 (180 mg, 0.71 mmol) in DMF (5 mL). The reaction mixture was stirred at Rt for 1.5 h. The reaction mixture was diluted with EtOAc (50 mL), and washed sequentially with brine (3×10 mL, sat). The organic layer was dried over Na$_2$SO$_4$, filtered and evaporated to afford crude product. The residue was purified by preparative TLC (PE/EtOAc 1/1), to afford the title compound (187 mg, 80%) as a white solid. MS (ESI): m/z [M+Na]$^+$ 353.

Step B. (1R,2S,3R,4S)-3-Amino-N-phenylbicyclo[2.2.1]heptane-2-carboxamide

A solution of hydrogen chloride (21 mg, 0.57 mmol) was added to Intermediate 125 (187 mg, 0.57 mmol). The reaction mixture was stirred at rt for 2 h. The solvent was removed under reduced pressure. The product was used in the next step directly without further purification. MS (ESI): m/z [M+H]$^+$ 231.

175

Intermediate 126: (1R,2S,3R,4S)-3-(4-Fluoro-2-methoxy-5-((4-methyl-4-((naphthalen-1-ylmethoxy)carbonyl)cyclohexylidene)methyl)benzamido)bicyclo[2.2.1]heptane-2-carboxylic acid

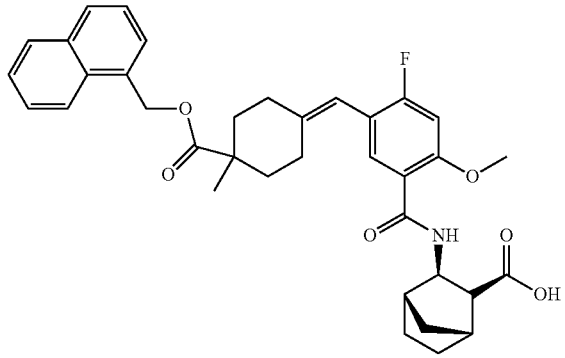

Step A. Intermediate 127: Methyl (1R,2S,3R,4S)-3-(5-bromo-4-fluoro-2-methoxybenzamido)bicyclo[2.2.1]heptane-2-carboxylate

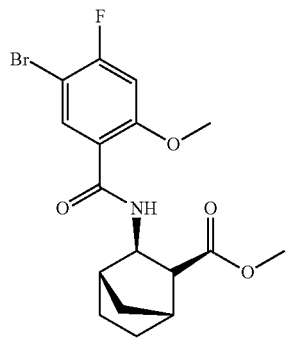

TEA (38.3 mL, 274.7 mmol) was added dropwise to Intermediate 8 (11.3 g, 54.9 mmol), Intermediate 114 (13.68 g, 54.94 mmol) and EDC (21.06 g, 109.88 mmol), HOBt (16.83 g, 109.88 mmol) in CHCl₃ (200 mL) at 20° C. over a period of 1 min under air. The resulting suspension was stirred at 20° C. for 14 h. The reaction mixture was diluted with EtOAc (150 mL), and washed sequentially with (1×150 mL, sat), NaHCO₃ (1×150 mL, sat), and H₂O (1×150 mL). The organic layer was dried over Na₂SO₄, filtered and evaporated to afford crude product. The residue was purified by preparative TLC (PE/EtOAc 5/1), to afford the title compound (13.0 g, 59.1%) as a colorless oil which solidified on standing. MS (ESI): m/z [M+H]⁺ 400.

176

Step B. Intermediate 128: (1R,2S,3R,4S)-3-(5-Bromo-4-fluoro-2-methoxybenzamido)bicyclo[2.2.1]heptane-2-carboxylic acid

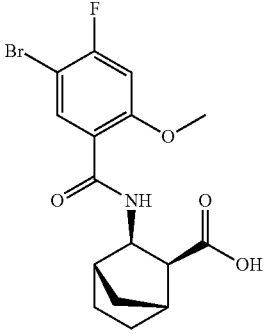 [SMILES: COc1cc(F)c(Br)cc1C(=O)N[C@@H]1[C@H]2CC[C@H](C2)[C@@H]1C(=O)O]

A solution of LiOH (1.256 g, 52.47 mmol) in H₂O (40.0 mL) was added dropwise to a stirred solution of Intermediate 127 (7 g, 17.5 mmol) in methanol (160 mL) cooled to 0° C., over a period of 1 minutes under nitrogen. The resulting solution was stirred at 20° C. for 14 h. The reaction mixture was diluted with EtOAc (100 mL). The H₂O phase was acidified with 2 M HCl to pH 3, diluted with EtOAc (150 mL), and washed sequentially with sat NaHCO₃ (1×150 mL), brine (1×125 mL), and H₂O (1×150 mL). The organic layer was dried over Na₂SO₄, filtered and evaporated to afford the title compound (5.00 g, 74.0%). MS (ESI): m/z [M+H]⁺ 386.

Step C. Intermediate 129: Naphthalen-1-ylmethyl 1-methyl-4-methylenecyclohexane-1-carboxylate

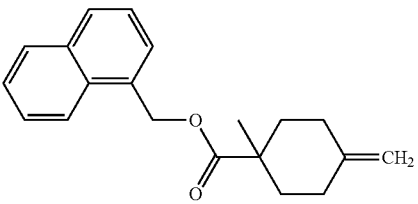 [SMILES: C=C1CCC(C)(C(=O)OCc2cccc3ccccc23)CC1]

Intermediate 4 (1.0 g, 3.37 mmol) was dissolved in THF (10.12 mL) under N2 atmosphere and cooled to 0° C. Tebbe reagent (6.75 mL, 3.37 mmol, 0.5 M in toluene) was added and the reaction was allowed to reach ambient temperature (50 min). Et2O (20 mL) was added followed by 20 drops of NaOH (0.1 M, aq). Gas evolution was observed. Filtered through a phase separator and evaporate the solvents. The crude product was purified by flash chromatography using a gradient of 10-50% EtOAc in heptane as mobile phase to give the title compound (0.479 g, 48.2%) as a yellowish oil. ¹H NMR (400 MHz, CDCl₃) δ 1.19 (s, 3H), 1.28-1.39 (m, 2H), 2.01-2.23 (m, 6H), 4.59 (s, 2H), 5.59 (s, 2H), 7.46 (dd, 1H), 7.49-7.58 (m, 3H), 7.82-7.93 (m, 2H), 7.96-8.03 (m, 1H).

Step D. (1R,2S,3R,4S)-3-(4-Fluoro-2-methoxy-5-((4-methyl-4-((naphthalen-1-ylmethoxy)carbonyl)cyclohexylidene)methyl)benzamido)bicyclo[2.2.1]heptane-2-carboxylic acid Intermediate 128 (628 mg, 1.63 mmol), tetrabutylammonium chloride (45.2 mg, 0.16 mmol) and PdCl₂(dtbpf) (105 mg, 0.16 mmol) was diluted in DMA (7.26 mL) and placed under an N$_2$-atmosphere. Intermediate 129 (479 mg, 1.63 mmol) and N-cyclohexyl-N-methylcyclohexanamine (0.87 mL, 4.07 mmol) was dissolved in small amount of DMA and added to the reaction mixture and the reaction was heated to 80° C. over 2 days. An additional amount of PdCl$_2$ (dtbpf) (105 mg, 0.16 mmol) was added after 24 h. The reaction was diluted with H$_2$O/1 M KHSO$_4$ and EtOAc, rinsed with H$_2$O/1 M KHSO$_4$, filtered through phase separator. The organic phase was evaporated and the crude product was purified by Method PrepBasic-F to give the title compound (148 mg, 15%). $^1$H NMR (400 MHz, CDCl$_3$) δ 1.21 (d, 3H), 1.23-1.46 (m, 5H), 1.51-1.66 (m, 2H), 1.88 (d, 1H), 2.15 (d, 2H), 2.26 (dd, 4H), 2.35-2.46 (m, 1H), 2.54 (s, 1H), 2.81 (d, 1H), 3.78 (s, 3H), 4.46-4.63 (m, 1H), 5.53-5.7 (m, 2H), 6.03 (s, 1H), 6.42 (d, 1H), 7.41-7.6 (m, 4H), 7.87 (dd, 2H), 8.00 (dd, 2H), 8.38 (d, 1H). MS (ESI): m/z [M+H]$^+$ 231.

Intermediate 130: (1S,2R,3S,4R)-3-(5-(((1s,4R)-4-(tert-Butoxycarbonyl)-4-methylcyclohexyl)oxy)-4-fluoro-2-methoxybenzamido)bicyclo[2.2.1]heptane-2-carboxylic acid

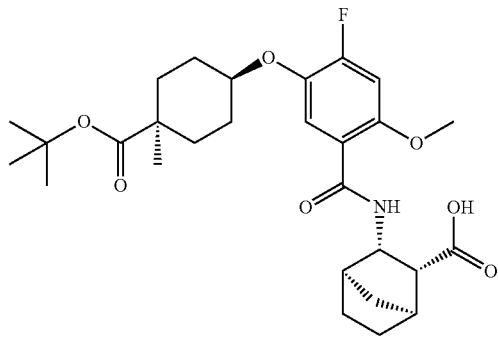 [SMILES: COc1cc(F)c(O[C@H]2CC[C@@](C)(C(=O)OC(C)(C)C)CC2)cc1C(=O)N[C@H]1[C@@H]2CC[C@@H](C2)[C@H]1C(=O)O]

Step A. Intermediate 131: tert-Butyl 4-((tert-butyldimethylsilyl)oxy)-1-methylcyclohexane-1-carboxylate

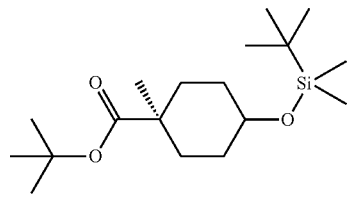

n-Butyllithium (28.6 mL, 71.5 mmol) was added dropwise to DIA (7.24 g, 71.5 mmol) in THF (100 mL) cooled to −78° C. under nitrogen. The resulting solution was stirred at −10° C. for 30 min and tert-butyl 4-((tert-butyldimethylsilyl)oxy)cyclohexane-1-carboxylate (15 g, 47.7 mmol) in THF (40 mL) was added dropwise to the former solution at −78° C. under nitrogen. The resulting solution was stirred at −78° C. for 3 h. Then MeI (4.17 mL, 66.8 mmol) in THF (40 mL) was added dropwise to the stirred mixture at −78° C. The resulting solution was stirred at −78° C. for 2 h. The reaction mixture was poured into NH$_4$Cl (150 mL, sat), extracted with EtOAc (3×150 mL), the organic layer was dried over Na$_2$SO$_4$, filtered and evaporated to the title compound (15.50 g, 99%) as a pale yellow gum. $^1$H NMR (300 MHz, DMSO-d6) δ 0.02 (d, 6H), 0.87 (d, 9H), 1.07 (d, 3H), 1.19 (m, 4H), 1.41 (d, 9H), 1.51 (d, 1H), 1.67 (d, 2H), 1.99 (d, 1H), 3.61 (m, 1H). (Major isomer).

Step B. Intermediate 132: tert-Butyl 4-hydroxy-1-methylcyclohexane-1-carboxylate

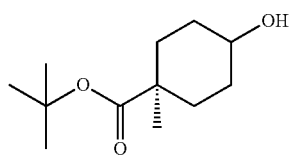

TBAF (13.13 g, 50.22 mmol) was added in one portion to Intermediate 131 (15.0 g, 45.65 mmol) in THF (150 mL) at 20° C. over a period of min under air. The resulting solution was stirred at 20° C. for 20 h. The reaction mixture was evaporated to dryness and dissolved in EtOAc (200 mL), and washed sequentially with NH$_4$Cl (1×100 mL, sat), brine (3×200 mL), and H$_2$O (1×125 mL). The organic layer was dried over Na$_2$SO$_4$, filtered and evaporated to afford crude product. The crude product was purified by flash chromatography using a gradient of 0-10% EtOAc in PE as mobile phase to give the title compound (6.50 g, 66.4%) as a pale yellow gum. $^1$H NMR (300 MHz, DMSO-d6) δ 1.04 (d, 3H), 1.13 (m, 3H), 1.39 (d, 9H), 1.49 (d, 1H), 1.64 (t, 2H), 1.96 (d, 2H), 3.34 (m, 1H), 4.42 (dd, 1H). (Major isomer).

Step C. Intermediate 133: 4-(tert-Butoxycarbonyl)-4-methylcyclohexyl 4-nitrobenzoate

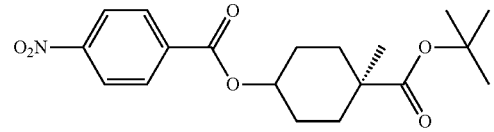

DIAD (13.61 mL, 69.99 mmol) was added dropwise to Intermediate 132 (12 g, 56 mmol), 4-nitrobenzoic acid (12.17 g, 72.79 mmol) and triphenylphosphine (18.36 g, 69.99 mmol) in THF (50 mL) at 50° C. The resulting solution was stirred at 60° C. for 16 h. The reaction mixture was concentrated and diluted with EtOAc (125 mL), and washed sequentially with H$_2$O (2×150 mL), and brine (3×150 mL, sat). The organic layer was dried over Na$_2$SO$_4$, filtered and evaporated to afford the crude product. The crude product was purified by flash chromatography using a gradient of 5-10% EtOAc in PE as mobile phase to give the title compound (13.0 g, 63.9%) as a yellow solid.

Step D. Intermediate 134: (1r,4r)-4-(tert-Butoxycarbonyl)-4-methylcyclohexyl 4-nitrobenzoate

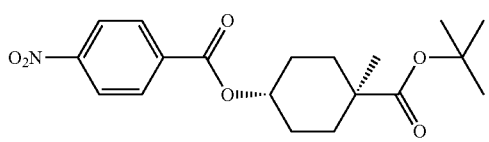 [SMILES: CC(C)(C)OC(=O)[C@]1(C)CC[C@@H](OC(=O)c2ccc([N+](=O)[O-])cc2)CC1]

Intermediate 133 (21 g, 57.8 mmol) was purified by preparative chiral-HPLC on a Chiralpak IB column, isocratic elution with 2% IPA in hexane (modified with 0.1% DEA) as eluent. The fractions containing the desired compound were evaporated to dryness to afford (1s,4s)-4-(tert-butoxycarbonyl)-4-methylcyclohexyl 4-nitrobenzoate (2.30 g, 11.0%) as a yellow oil and Intermediate 134 (11.70 g, 55.7%) as a white solid. $^1$H NMR (300 MHz, DMSO-d6) δ 1.17 (s, 3H), 1.44 (s, 9H), 1.52-1.64 (m, 2H), 1.67-1.95 (m, 6H), 5.14 (s, 1H), 8.20-8.27 (m, 2H), 8.34-8.40 (m, 2H).

Step E. Intermediate 135: tert-Butyl (1r,4r)-4-hydroxy-1-methylcyclohexane-1-carboxylate

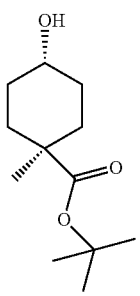

LiOH (2.313 g, 96.59 mmol) was added in one portion to Intermediate 134 (11.7 g, 32.20 mmol) in THF (80 mL) and H$_2$O (40.0 mL) at 20° C. over a period of 1 min under air. The resulting suspension was stirred at 20° C. for 16 h. The reaction mixture was diluted with EtOAc (100 mL), and washed sequentially with brine (2×100 mL, sat), H$_2$O (1×100 mL). The organic layer was dried over Na$_2$SO$_4$, filtered and evaporated to afford the title compound (6.60 g, 96%) as a yellow oil. $^1$H NMR (300 MHz, DMSO-d6) δ 1.06 (s, 3H), 1.38 (s, 9H), 1.47 (dd, 6H), 1.62 (q, 2H), 3.57 (d, 1H), 4.38 (d, 1H).

Step F. Intermediate 136: Benzyl 5-(((1s,4s)-4-(tert-butoxycarbonyl)-4-methylcyclohexyl)oxy)-4-fluoro-2-methoxybenzoate

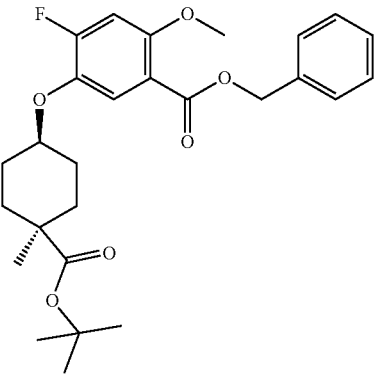 [SMILES: COc1cc(F)c(O[C@H]2CC[C@@](C)(C(=O)OC(C)(C)C)CC2)cc1C(=O)OCc1ccccc1]

DIAD (8.98 mL, 46.20 mmol) was added to Intermediate 135 (6.6 g, 30.8 mmol), Intermediate 117 (8.51 g, 30.80 mmol) and triphenylphosphane (12.12 g, 46.20 mmol) in THF (150 mL) at 60° C. over a period of 5 min under nitrogen. The resulting solution was stirred at 60° C. for 15 h. The reaction mixture was diluted with EtOAc (150 mL), and washed sequentially with H$_2$O (2×150 mL) and brine (2×150 mL, sat). The organic layer was dried over Na$_2$SO$_4$, filtered and evaporated to afford crude product. The crude product was purified by flash chromatography using a gradient of 5-10% EtOAc in PE as mobile phase to give the title compound (12.00 g, 82%) as a yellow solid. MS (ESI): m/z [M+Na]$^+$495.

Step G. Intermediate 137: Benzyl (1R,2R,3S,4S)-3-(5-(((1s,4R)-4-(tert-butoxycarbonyl)-4-methylcyclohexyl)oxy)-4-fluoro-2-methoxybenzamido)bicyclo[2.2.1]hept-5-ene-2-carboxylate

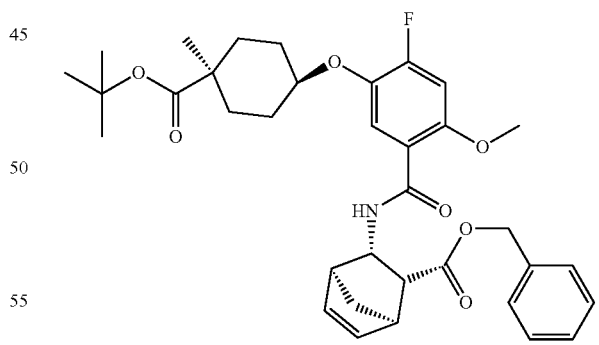

DIPEA (6.17 mL, 35.30 mmol) was added to Intermediate 73 (2.7 g, 7.06 mmol), Intermediate 139 (3.1 g, 11.08 mmol) and HATU (8.05 g, 21.18 mmol) in DMF (150 mL) at 20° C. The resulting mixture was stirred at 20° C. for 16 h. The reaction mixture was diluted with EtOAc (100 mL), and washed sequentially with H$_2$O (3×100 mL), and brine (3×100 mL, sat). The organic layer was dried over Na$_2$SO$_4$, filtered and evaporated to afford the crude product. The crude product was purified by flash chromatography using a gradient of 21-25% EtOAc in PE as mobile phase to give the title compound (3.50 g, 82%) as a yellow solid. MS (ESI): m/z [M+H]⁺ 608.

Step H. (1S,2R,3S,4R)-3-(5-(((1s,4R)-4-(tert-Butoxycarbonyl)-4-methylcyclohexyl)oxy)-4-fluoro-2-methoxybenzamido)bicyclo[2.2.1]heptane-2-carboxylic acid Intermediate 137 (3.5 g, 5.76 mmol) and Pd—C (0.306 g, 0.29 mmol) in MeOH (150 mL) was stirred under an atmosphere of hydrogen at 1.5 atm and 20° C. for 1 h. The reaction mixture was filtered through Celite®. The solvent was removed under reduced pressure to afford the title compound (2.99 g, 100%) as a white solid. MS (ESI): m/z [M+H]⁺ 520.

Intermediate 138: tert-Butyl (1R,4s)-4-(2-fluoro-4-methoxy-5-(((1R,2S,3R,4S)-3-(((1-methylcyclobutyl)methyl)carbamoyl)bicyclo[2.2.1]heptan-2-yl)carbamoyl)phenoxy)-1-methylcyclohexane-1-carboxylate

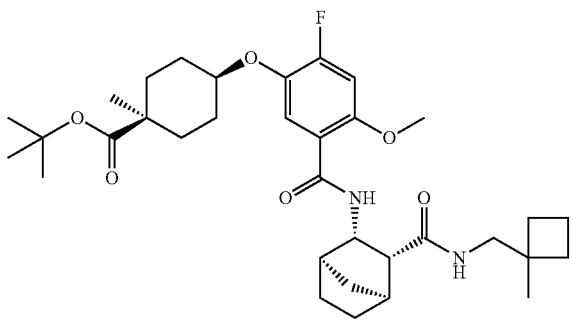 [SMILES: COc1cc(F)c(O[C@H]2CC[C@@](C)(C(=O)OC(C)(C)C)CC2)cc1C(=O)N[C@H]1[C@@H]2CC[C@@H](C2)[C@H]1C(=O)NCC1(C)CCC1]

DIEA (2.52 mL, 14.4 mmol) was added dropwise to Intermediate 130 (2.50 g, 4.81 mmol), (1-methylcyclobutyl)methanamine hydrochloride (0.653 g, 4.81 mmol) and HATU (9.15 g, 24.1 mmol) in DMF (150 mL) cooled to 0° C. in 1 min under nitrogen. The resulting solution was stirred at 20° C. for 14 h. The reaction mixture was diluted with EtOAc (1.0 L) and sequentially washed with saturated NaHCO₃ (250 mL), saturated brine (3×300 mL), and H₂O (2×300 mL).

The organic layers were combined and dried over Na₂SO₄, filtered and evaporated to afford crude product. The crude product was purified by flash silica chromatography, elution gradient 0 to 25% EtOAc in petroleum ether. Pure fractions were pooled and evaporated to dryness to afford the crude title compound, 2.6 g, as a pale yellow solid. The crude product was further purified by C18-flash chromatography, elution gradient 0 to 85% MeCN in H₂O. Fractions containing product were evaporated to dryness to afford 2.1 g of the title compound as a white solid. The material was further purified by preparative chiral SFC (CHIRALPAK IF 20×250 mm ID, 5 μm, 86445S90IF0SCJ-RA002 column) using 70% CO₂ and 30% MeOH as mobile phase. Fractions containing the desired compound were pooled and evaporated to dryness to afford the title compound (1.50 g, 51.9%) as a white solid; MS (ESI): m/z, [M+H]⁺=601.4.

Intermediate 139: Benzyl (1R,2R,3S,4S)-3-aminobicyclo[2.2.1]hept-5-ene-2-carboxylate hydrochloride

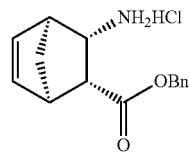

Step A. Intermediate 140: (1S,2S,3R,4R)-3-(methoxycarbonyl)bicyclo[2.2.1]hept-5-ene-2-carboxylic acid

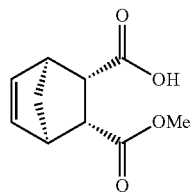 [SMILES: COC(=O)[C@H]1[C@@H](C(=O)O)[C@@H]2C=C[C@H]1C2]

MeOH (18.19 mL, 449.56 mmol) was added dropwise to (3aR,4R,7S,7aS)-3a,4,7,7a-tetrahydro-4,7-methanoisobenzofuran-1,3-dione (24.6 g, 149.85 mmol) and quinine (48.6 g, 149.85 mmol) in toluene (150 mL) and CCl₄ (150 mL) cooled to −55° C. over a period of 1 min under nitrogen. The resulting suspension was stirred at −55° C. for 100 h. The solvent was removed under reduced pressure. The reaction mixture was diluted with EtOAc (1200 mL), and washed sequentially with 2 M HCl (3×500 mL), sat brine (1×500 mL), and H₂O (1×500 mL). The organic layer was dried over Na₂SO₄, filtered and evaporated to afford the desired product (25.7 g, 87%) as a white solid.

Step B. Intermediate 141: Methyl (1R,2R,3S,4S)-3-(azidocarbonyl)bicyclo[2.2.1]hept-5-ene-2-carboxylate

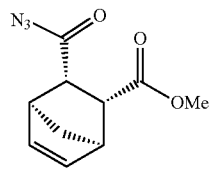 [SMILES: COC(=O)[C@H]1[C@@H](C(=O)N=[N+]=[N-])[C@@H]2C=C[C@H]1C2]

Ethyl carbonochloridate (17.06 g, 157.18 mmol) was added dropwise to Intermediate 140 (25.7 g, 130.99 mmol) and TEA (19.88 g, 196.48 mmol) in acetone (450 mL) at 0° C. over a period of 1 min under nitrogen. The resulting solution was stirred at 0° C. for 2 h. A solution of sodium azide (12.77 g, 196.48 mmol) in H₂O (150 mL) was added dropwise to the stirred suspension of above at 0° C., over a period of 15 min under nitrogen. The resulting solution was stirred at 0° C. for 2 h followed by 14 h at 20° C. The reaction mixture was diluted with toluene (500 mL), and washed sequentially with brine (2×250 mL, sat), NaHCO₃ (2×250 mL, sat), and H₂O (2×200 mL). The organic layer was dried over Na$_2$SO$_4$. The drying agent was filtered off and the solution was used in next step without any purification.

Step C. Intermediate 142: Methyl (1R,2R,3S,4S)-3-isocyanatobicyclo[2.2.1]hept-5-ene-2-carboxylate

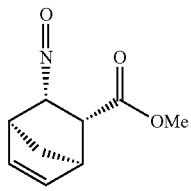 [SMILES: COC(=O)[C@H]1[C@@H](N=O)[C@@H]2C=C[C@H]1C2]

Intermediate 141 (29 g, 131.1 mmol) was added to toluene (500 mL) at 25° C. over a period of 1 min under air. The resulting solution was stirred at 100° C. for 1 h. The solvent was removed under reduced pressure to afford the title compound (25.3 g, 100%) as a yellow oil which was used in next step without further purification.

Step D. Intermediate 143: Methyl (1R,2R,3S,4S)-3-aminobicyclo[2.2.1]hept-5-ene-2-carboxylate hydrochloride

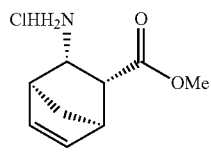

A solution of hydrogen chloride (26.4 g, 724.63 mmol) in H$_2$O (100 mL) was added dropwise to a stirred solution of Intermediate 142 (28 g, 144.93 mmol) in THF (250 mL) at 0° C., over a period of 5 min under air. The resulting solution was stirred at 25° C. for 14 h. The solvent was removed under reduced pressure to afford the title compound (30.0 g, 102%) as a beige oil, which solidified on standing.

Step E. Intermediate 144: Methyl (1R,2R,3S,4S)-3-((tert-butoxycarbonyl)amino)bicyclo[2.2.1]hept-5-ene-2-carboxylate

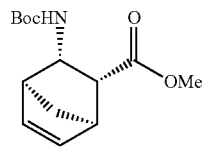

TEA (54.8 mL, 393.3 mmol) was added dropwise to Boc$_2$O (45.7 mL, 196.65 mmol), and Intermediate 143 (26.7 g, 131.1 mmol) in THF (400 mL) at 0° C. over a period of 1 min under nitrogen. The resulting solution was stirred at 20° C. for 14 h. The reaction mixture was diluted with EtOAc (500 mL), and washed sequentially with brine (1×250 mL, sat), H$_2$O (1×200 mL), and NaHCO$_3$ (1×250 mL, sat). The organic layer was dried over Na$_2$SO$_4$, filtered and evaporated and the residue was crystallized from EtOAc/Et$_2$O to afford crude title compound (42 g) as a white solid which was used without further purification.

Step F. Intermediate 145: (1R,2R,3S,4S)-3-((tert-butoxycarbonyl)amino)bicyclo[2.2.1]hept-5-ene-2-carboxylic acid

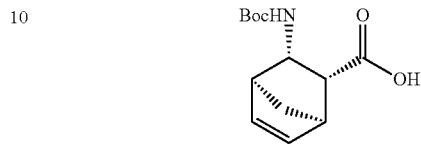

LiOH (9.41 g, 392.78 mmol) in H$_2$O (180 mL) was added dropwise to Intermediate 144 (42.0 g, 157.11 mmol) in MeOH (360 mL) at 20° C. over a period of 10 min under air. The resulting suspension was stirred at 20° C. for 14 h. The solvent was removed under reduced pressure. The reaction mixture was adjusted to pH 2 by 0.5 M citric acid. The reaction mixture was diluted with EtOAc (150 mL), and washed sequentially with brine (1×150 mL, sat), sat NaHCO$_3$ (1×150 mL), and H$_2$O (1×150 mL). The organic layer was dried over Na$_2$SO$_4$, filtered and evaporated to afford pure product. The crude product was purified by crystallization from EtOAc/PE to afford the title compound (21.00 g, 52.8%) as a white solid.

Step G. Intermediate 146: Benzyl (1R,2R,3S,4S)-3-((tert-butoxycarbonyl)amino)bicyclo[2.2.1]hept-5-ene-2-carboxylate

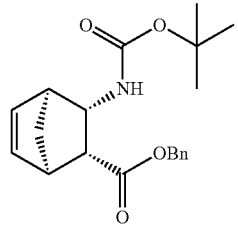 [SMILES: CC(C)(C)OC(=O)N[C@@H]1[C@H](C(=O)OCc2ccccc2)[C@H]2C=C[C@@H]1C2]

TEA (9.63 mL, 69.1 mmol) was added dropwise to Intermediate 145 (5.0 g, 19.7 mmol), phenylmethanol (3.20 g, 29.61 mmol), EDC (8.33 g, 43.43 mmol) and HOBt (6.65 g, 43.43 mmol) in DMF (100 mL) at 20° C. The resulting suspension was stirred at 20° C. for 15 h. The reaction mixture was poured into sat NaHCO$_3$ (350 mL), extracted with EtOAc (3×150 mL), the organic layer was dried over Na$_2$SO$_4$, filtered and evaporated to afford pale yellow oil. The crude product was purified by flash chromatography using a gradient of 0-5% EtOAc in PE as mobile phase to give the title compound (4.50 g, 66%) as a colorless gum. MS (ESI): m/z [M+Na]$^+$366.

Step H. Benzyl (1R,2R,3S,4S)-3-aminobicyclo[2.2.1]hept-5-ene-2-carboxylate hydrochloride Intermediate 146 (3.8 g, 11.07 mmol) was added dropwise to HCl (1.34 mL, 44 mmol) in 1,4-dioxane (100 mL) at 0° C. over a period of 1 min under air. The resulting solution was stirred at 20° C. for 14 h. The solvent was removed under reduced pressure. The crude product was purified by crystallization from EtOAc/PE to afford the title compound (3.10 g, 100%) as a white solid. ¹H NMR (400 MHz, DMSO-d6) δ 1.42-1.52 (m, 1H), 2.03-2.10 (m, 1H), 2.63-2.71 (dd, 1H), 2.95-3.01 (d, 1H), 3.04-3.09 (s, 1H), 3.21-3.26 (s, 1H), 5.04-5.11 (d, 1H), 5.19-5.26 (d, 1H), 6.19-6.27 (dd, 1H), 6.29-6.36 (dd, 1H), 7.29-7.47 (m, 5H), 8.21-8.26 (s, 3H). MS (ESI): m/z [M+H]⁺ 244.

Intermediate 147: 2-(Difluoromethoxy)-4-fluoro-5-(((1s,4s)-4-methyl-4-((naphthalen-1-ylmethoxy)carbonyl)cyclohexyl)oxy)benzoic acid

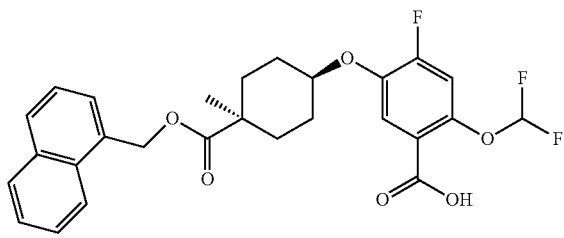 [SMILES: C[C@]1(C(=O)OCc2cccc3ccccc23)CC[C@@H](Oc2cc(C(=O)O)c(OC(F)F)cc2F)CC1]

Step A. Intermediate 148: Methyl 5-bromo-4-fluoro-2-hydroxybenzoate

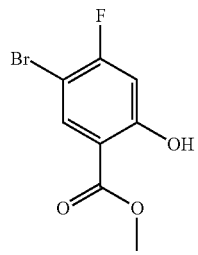

Intermediate 112 (3 g, 12.77 mmol) was added portion wise to HCl (7.29 mL, 240 mmol) in MeOH (60 mL) at 20° C. over a period of 1 min under nitrogen. The resulting solution was stirred at 78° C. for 48 h. The solvent was removed under reduced pressure and the crude product was purified by flash chromatography using a gradient of 0-7% EtOAc in PE as mobile phase to give the title compound (1.50 g, 47.2%) as a white solid. ¹H NMR (300 MHz, DMSO-d6) δ 3.87 (s, 3H), 7.05 (d, 1H), 7.99 (d, 1H), 10.81 (s, 1H).

Step B. Intermediate 149: Methyl 5-bromo-2-(difluoromethoxy)-4-fluorobenzoate

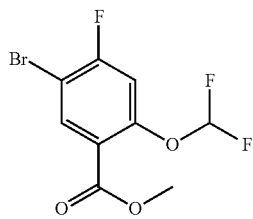 [SMILES: COC(=O)c1cc(Br)c(F)cc1OC(F)F]

(Bromodifluoromethyl)trimethylsilane (3.26 g, 16.06 mmol) in DCM (12 mL) was added slowly to Intermediate 148 (1 g, 4.02 mmol) and KOH (2.253 g, 40.15 mmol) in H₂O (12 mL) at 0° C. over a period of 1 min under nitrogen. The resulting suspension was stirred at 0° C. for 2 h. The reaction mixture was diluted with DCM (100 mL), and washed sequentially with NaHCO₃ (1×100 mL, sat), brine (1×100 mL, sat), and H₂O (1×100 mL). The organic layer was dried over Na₂SO₄, filtered and evaporated to afford the desired product (1.201 g, 100%) as a pale yellow residue. The product was used in the next step directly without further purification. ¹H NMR (400 MHz, DMSO-d6) δ 3.84 (s, 3H), 7.40 (t, 1H), 7.52 (d, 1H), 8.18 (d, 1H).

Step C. Intermediate 150: Methyl 2-(difluoromethoxy)-4-fluoro-5-(4,4,5,5-tetramethyl-1,3,2-dioxaborolan-2-yl)benzoate

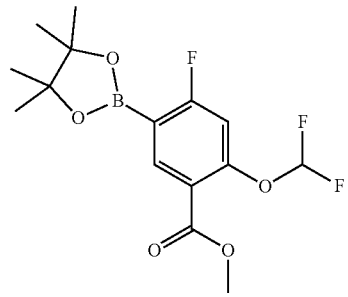 [SMILES: COC(=O)c1cc(B2OC(C)(C)C(C)(C)O2)c(F)cc1OC(F)F]

Potassium acetate (0.985 g, 10.03 mmol) was added slowly to Intermediate 149 (1.2 g, 4.01 mmol)), PdCl₂(dppf)-DCM adduct (0.328 g, 0.40 mmol) and B₂Pin₂ (2.038 g, 8.03 mmol) in 1,4-dioxane (30 mL) at 20° C. over a period of 1 min under nitrogen. The resulting suspension was stirred at 60° C. for 14 h. The reaction mixture was diluted with EtOAc (50 mL), and washed sequentially with brine (3×75 mL, sat). The organic layer was dried over Na₂SO₄, filtered and evaporated to afford crude product. The crude product was purified by preparative TLC (EtOAc/PE1/4), to afford the title compound (0.587 g, 42.3%) as a pale yellow gum.

Step D. Intermediate 151: Methyl 2-(difluoromethoxy)-4-fluoro-5-hydroxybenzoate

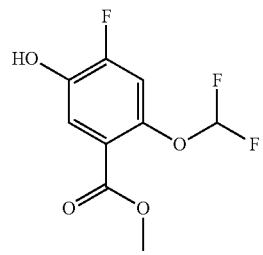 [SMILES: COC(=O)c1cc(O)c(F)cc1OC(F)F]

NaBO₃×4 H₂O (907 mg, 5.89 mmol) was added slowly to Intermediate 150 (510 mg, 1.47 mmol) in THF (20 mL) at 0° C. over a period of 1 min under air. The resulting solution was stirred at 20° C. for 12 h. A solution of ammonium chloride (788 mg, 14.74 mmol) in H₂O (10 mL) was added slowly to the stirred solution obtained above at 0° C., over a period of 1 min under air. The resulting solution was stirred at 20° C. for 4 h. The reaction mixture was diluted with EtOAc (50 mL), and washed sequentially with brine (3×75 mL, sat). The organic layer was dried over Na₂SO₄, filtered and evaporated to afford crude product which was purified by preparative TLC (EtOAc/PE 1/3), to afford the title compound (180 mg, 51.7%) as a white solid. ¹H NMR (300 MHz, DMSO-d6) δ 3.79 (s, 3H), 7.01 (t, 1H), 7.22 (d, 1H), 7.43 (d, 1H), 10.47 (s, 1H).

Step E. Intermediate 152: Methyl 2-(difluoromethoxy)-4-fluoro-5-(((1s,4s)-4-methyl-4-((naphthalen-1-ylmethoxy)carbonyl)cyclohexyl)oxy)benzoate

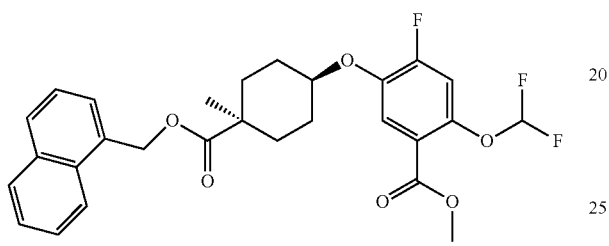

A solution of DBAD (280 mg, 1.22 mmol) in toluene (3 mL) was added dropwise to a stirred solution of triphenylphosphane (287 mg, 1.10 mmol), Intermediate 151 (115 mg, 0.49 mmol) and Intermediate 11 (153 mg, 0.51 mmol) in DCM (3 mL) cooled to 10° C., over a period of 1 min under nitrogen. The resulting solution was stirred at 20° C. for 14 h. The reaction mixture was diluted with EtOAc (150 mL), and washed sequentially with brine (1×150 mL, sat), NaHCO₃ (1×150 mL, sat), and H₂O (1×150 mL). The organic layer was dried over Na₂SO₄, filtered and evaporated to afford crude product. which was purified by preparative TLC (EtOAc/PE 1/4), to afford the title compound (200 mg, 80%) as a pale yellow solid. MS (ESI): m/z [M+Na]⁺ 539.

Step F. 2-(Difluoromethoxy)-4-fluoro-5-(((1s,4s)-4-methyl-4-((naphthalen-1-ylmethoxy)carbonyl)cyclohexyl)oxy)benzoic acid A solution of LiOH (46.4 mg, 1.94 mmol) in H₂O (8 mL) was added dropwise to a stirred solution of Intermediate 152 (200 mg, 0.39 mmol) in THF (10 mL) cooled to 0° C., over a period of 1 min under nitrogen. The resulting solution was stirred at ambient temperature for 2 h. The reaction mixture was adjusted to pH=3 by 0.1 M HCl, diluted with EtOAc (200 mL) and washed sequentially with NH₄Cl (1×150 mL, sat), H₂O (1×200). The organic layer was dried over Na₂SO₄, filtered and evaporated to afford the title compound (195 mg, 100%) as a pale yellow solid. MS (ESI): m/z [M+H]⁺ 503.

Intermediate 153: (1R,2S,3R,4S)-3-Amino-N-(3-((trifluoromethyl)sulfonyl)phenyl)bicyclo[2.2.1]heptane-2-carboxamide

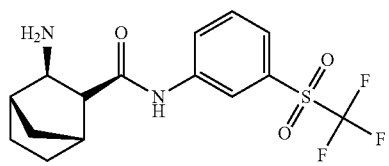

Step A. Intermediate 154: tert-Butyl ((1R,2R,3S,4S)-3-((3-((trifluoromethyl)thio)phenyl)carbamoyl)bicyclo[2.2.1]hept-5-en-2-yl)carbamate

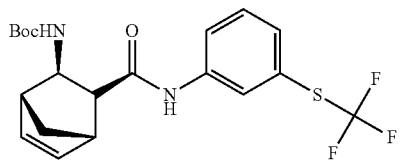

DIPEA (5.52 mL, 31.6 mmol) was added dropwise to Intermediate 19 (4.0 g, 15.8 mmol), 3-((trifluoromethyl)thio)aniline (3.05 g, 15.79 mmol) and T3P (30.1 g, 47.38 mmol) in butyl acetate (100 mL) at 20° C. over a period of 1 min under nitrogen. The resulting solution was stirred at 120° C. for 5 h. The reaction mixture was diluted with EtOAc (100 mL), and washed sequentially with brine (1×200 mL, sat), NaHCO₃ (1×100 mL, sat), and H₂O (1×100 mL). The organic layer was dried over Na₂SO₄, filtered and evaporated to afford crude product which was purified by preparative TLC (EtOAc/PE 1/1), to afford the title compound (3.20 g, 47.3%) as a pale yellow solid. ¹H NMR (400 MHz, DMSO-d6) δ 1.12 (s, 9H), 1.40 (d, 1H), 2.29 (d, 1H), 2.60 (d, 2H), 2.86 (s, 1H), 3.82 (1H, t), 6.21-6.31 (m, 2H), 6.64 d, (1H), 7.34 (d, 1H), 7.42 (t, 1H), 7.68 (m, 1H), 8.12 (s, 1H), 10.10 (s, 1H).

Step B. Intermediate 155: tert-Butyl ((1S,2R,3S,4R)-3-((3-((trifluoromethyl)thio)phenyl)carbamoyl)bicyclo[2.2.1]heptan-2-yl)carbamate

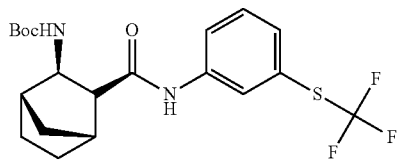

Intermediate 154 (1.8 g, 4.20 mmol) and Pd—C (2.235 g, 2.10 mmol) in MeOH (50 mL) was stirred under an atmosphere of hydrogen at 1.5 atm and 30° C. for 14 h. The reaction mixture was filtered through Celite®. The solvent was removed under reduced pressure to afford the title compound (1.808 g, 100%) as a pale yellow solid. 1H NMR (400 MHz, DMSO-d6) δ 1.07-1.12 (s, 9H), 1.12-1.20 (m, 3H), 1.32-1.39 (m, 1H), 1.42-1.47 (m, 1H), 1.50-1.55 (m, 1H), 2.02 (s, 1H), 2.12 (d, 1H), 2.31-2.36 (m, 1H), 3.86 (t, 1H), 6.62 (d, 1H), 7.32 (d, 1H), 7.42 (t, 1H), 7.66 (d, 1H), 8.08-8.14 (m, 1H), 10.04 (s, 1H). MS (ESI): m/z [M+Na]⁺ 453.

Step C. Intermediate 156: tert-Butyl ((1S,2R,3S,4R)-3-((3-((trifluoromethyl)sulfonyl)phenyl)carbamoyl)bicyclo[2.2.1]heptan-2-yl)carbamate

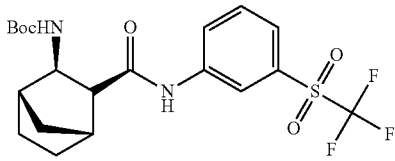

Sodium periodate (1.789 g, 8.36 mmol) was added portion wise to Intermediate 155 (1.8 g, 4.18 mmol) and ruthenium(III) chloride (0.087 g, 0.42 mmol) in MeCN (15 mL) and H₂O (5.00 mL) at 20° C. over a period of 1 min under air. The resulting suspension was stirred at 20° C. for 14 h. The reaction mixture was diluted with EtOAc (150 mL), and washed sequentially with brine (3×25 mL, sat). The organic layer was dried over Na₂SO₄, filtered and evaporated to afford crude product which was purified by C18 flash chromatography using a gradient of 0-90% H₂O in MeCN as mobile phase to give the title compound (1.93 g, 100%) as a yellow solid.

Step D. (1R,2S,3R,4S)-3-Amino-N-(3-((trifluoromethyl)sulfonyl)phenyl)bicyclo[2.2.1]heptane-2-carboxamide TFA (0.045 mL, 0.58 mmol) was added dropwise to Intermediate 156 (180 mg, 0.39 mmol) in DCM (25 mL) at 20° C. over a period of 1 min under nitrogen. The resulting solution was stirred at 20° C. for 14 h. The reaction mixture was diluted with EtOAc (100 mL), and washed sequentially with (1×125 mL, sat), NaHCO₃ (1×125 mL, sat), and H₂O (1×125 mL). The organic layer was dried over Na₂SO₄, filtered and evaporated to the title compound (141 mg, 100%). MS (ESI): m/z [M+H]⁺ 363.

Intermediate 157: (1R,2S,3R,4S)-3-(4'-(Ethoxycarbonyl)-6-fluoro-4-methoxy-[1,1'-biphenyl]-3-carboxamido)bicyclo[2.2.1]heptane-2-carboxylic acid

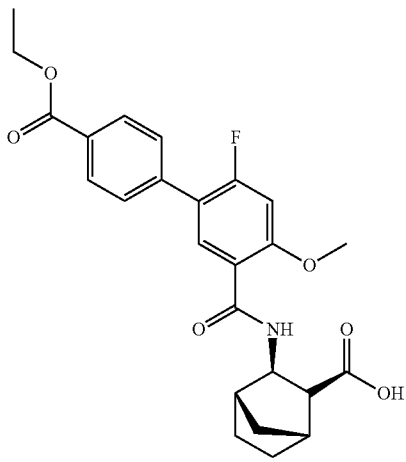

Step A. Intermediate 158: 3-Benzyl 4'-ethyl 6-fluoro-4-methoxy-[1,1'-biphenyl]-3,4'-dicarboxylate

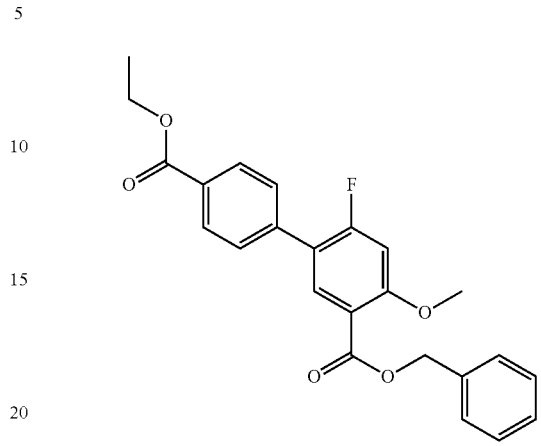

PdCl₂(dppf)-DCM adduct (1.743 g, 2.13 mmol) was added to Intermediate 115 (3.62 g, 10.67 mmol), (4-(ethoxycarbonyl)phenyl)boronic acid (2.485 g, 12.81 mmol) and K₂CO₃ (3.69 g, 26.68 mmol) in 1,4-dioxane (30 mL) and H₂O (7.50 mL). The resulting mixture was stirred at 70° C. for 1.5 h under nitrogen. The reaction mixture was diluted with EtOAc (1 L), and washed sequentially with brine (3×200 mL, sat). The organic layer was dried over Na₂SO₄, filtered and evaporated to afford the crude product which was purified by flash chromatography using a gradient of 0-30% EtOAc in PE as mobile phase to give the title compound (4.20 g, 96%) as a brown oil which solidified on standing. ¹H NMR (300 MHz, DMSO-d6) δ 1.33 (t, 3H), 3.91 (s, 3H), 4.34 (q, 2H), 5.34 (s, 2H), 7.26 (d, 1H), 7.32-7.50 (m, 5H), 7.68 (d, 2H), 7.92 (d, 1H), 8.04 (d, J=8.4 Hz, 2H). MS (ESI): m/z [M+H]⁺ 409.

Step B. Intermediate 159: 4'-(Ethoxycarbonyl)-6-fluoro-4-methoxy-[1,1'-biphenyl]-3-carboxylic acid

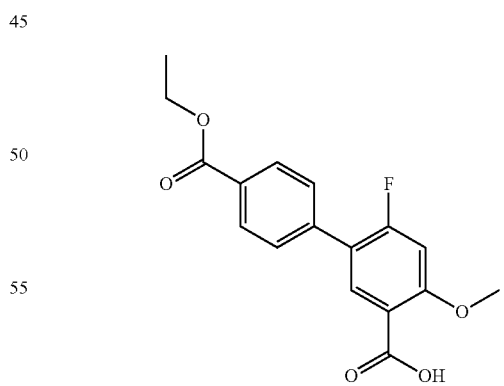

Pd—C (10 mg, 0.09 mmol) was added to Intermediate 158 (4.1 g, 10.04 mmol) in MeOH (150 mL) at 20° C. The resulting suspension was stirred at 20° C. for 15 h. The reaction mixture was filtered through Celite®. The solvent was removed under reduced pressure and the product (0.9 g, 28%) was used in the next step without further purification. MS (ESI): m/z [M+H]⁺ 319.

Step C. Intermediate 160: Benzyl (1S,2S,3R,4R)-3-(4'-(ethoxycarbonyl)-6-fluoro-4-methoxy-[1,1'-biphenyl]-3-carboxamido)bicyclo[2.2.1]hept-5-ene-2-carboxylate

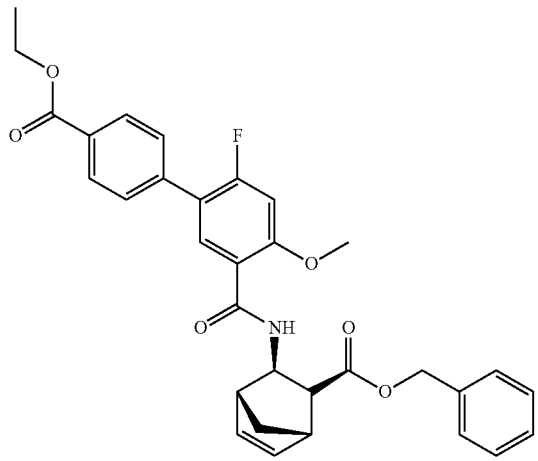

HATU (1.22 g, 3.20 mmol) was added portion wise to Intermediate 109 (0.715 mg, 2.94 mmol), Intermediate 159 (0.850 g, 2.67 mmol) and DIPEA (0.518 g, 4.01 mmol) in DMF (10 mL) at Rt. The resulting solution was stirred at 60° C. for 1.5 h. The reaction mixture was extracted with EtOAc (3×75 mL), the organic layer was washed with brine (2×100 mL, sat). The organic layer was dried over Na₂SO₄, filtered and evaporated to the title compound (3.30 g) as a brown oil. The crude product was used in the next step directly without further purification. MS (ESI): m/z [M+H]⁺ 544.

Step D. (1R,2S,3R,4S)-3-(4'-(Ethoxycarbonyl)-6-fluoro-4-methoxy-[1,1'-biphenyl]-3-carboxamido)bicyclo[2.2.1]heptane-2-carboxylic acid Pd—C (0.626 g, 5.89 mmol) was added to Intermediate 160 (3.2 g, 5.89 mmol) in MeOH (150 mL). The reaction mixture was stirred at 20° C. for 2 h. The reaction mixture was filtered through Celite®. The solvent was removed under reduced pressure to afford the title compound in mixture with the corresponding methyl ester due to some transesterification from the solvent. The crude product was used in the next step directly without purification. MS (ESI): m/z [M+H]⁺ 456.3 (ethyl ester) and MS (ESI): m/z [M+H]⁺ 442.3 (methyl ester).

Intermediate 161: 2-Amino-3,5-dimethyl-N-((1-methylcyclobutyl)methyl)benzamide hydrochloride

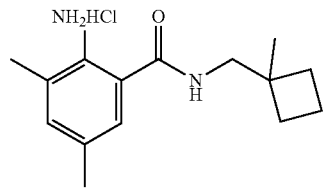

Step A. Intermediate 162: tert-Butyl (2,4-dimethyl-6-(((1-methylcyclobutyl)methyl)carbamoyl)phenyl)carbamate

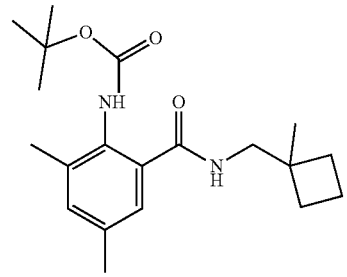 [SMILES: Cc1cc(C)c(NC(=O)OC(C)(C)C)c(C(=O)NCC2(C)CCC2)c1]

2-((tert-Butoxycarbonyl)amino)-3,5-dimethylbenzoic acid (106 mg, 0.4 mmol) and HATU (304 mg, 0.80 mmol) was diluted in DCM (1.79 mL). DIPEA (210 µL, 1.20 mmol) and (1-methylcyclobutyl)methanamine hydrochloride (65.1 mg, 0.48 mmol) was added and the reaction was stirred overnight. DCM (1.79 mL) and NaHCO₃ (aq) was added and the phases was separated and the organic phase was evaporated. The crude product which was purified by flash chromatography using a gradient of 5-50% EtOAc in heptane as mobile phase to give the title compound (100 mg, 72.2%) as a white solid. ¹H NMR (400 MHz, CDCl₃) δ 1.17 (s, 3H), 1.47 (s, 9H), 1.69-1.77 (m, 2H), 1.85-1.96 (m, 4H), 2.27 (s, 3H), 2.31 (s, 3H), 3.41 (d, 2H), 6.16 (s, 1H), 7.07 (s, 1H), 7.12 (s, 1H), 7.36 (s, 1H). MS (ESI): m/z [M+H]⁺ 347.4.

Step B. 2-Amino-3,5-dimethyl-N-((1-methylcyclobutyl)methyl)benzamide hydrochloride Intermediate 162 (100 mg, 0.29 mmol) was diluted in dioxane (1 mL). 4 M HCl in dioxane (1 mL, 4.00 mmol) was added and the reaction was stirred at ambient temperature for 2 h, an additional 4 M HCl in Dioxane (1 mL, 4.00 mmol) was added and the stirring was continued for 2 h. The solvent and excess HCl was evaporated and the crude product was used as such in the next step. MS (ESI): m/z [M+H]⁺ 247.3.

Intermediate 163: 2-Amino-4,5-dimethyl-N-((1-methylcyclobutyl)methyl)benzamide hydrochloride

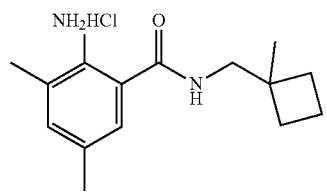

Step A. Intermediate 164: tert-Butyl (4,5-dimethyl-2-(((1-methylcyclobutyl)methyl)carbamoyl)phenyl)carbamate

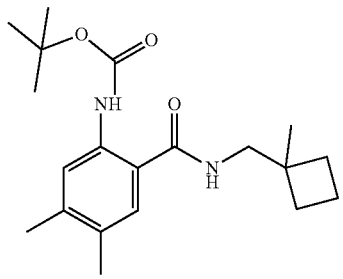 [SMILES: Cc1cc(NC(=O)OC(C)(C)C)c(C(=O)NCC2(C)CCC2)cc1C]

2-((tert-Butoxycarbonyl)amino)-4,5-dimethylbenzoic acid (106 mg, 0.4 mmol) and HATU (304 mg, 0.80 mmol) was diluted in DCM (1790 µL). DIPEA (210 µL, 1.20 mmol and (1-methylcyclobutyl)methanamine hydrochloride (65.1 mg, 0.48 mmol) was added and the reaction was stirred overnight. Diluted with DCM and NaHCO$_3$ (aq) separated the phases and evaporated the organic phase. The crude product was purified by flash chromatography using a gradient of 5-50% EtOAc in heptane as mobile phase to give the title compound (102 mg, 73.6%) as an oil. $^1$H NMR (400 MHz, CDCl$_3$) δ 1.20 (s, 3H), 1.51 (s, 9H), 1.73-1.8 (m, 2H), 1.93 (ddt, 4H), 2.23 (s, 3H), 2.29 (s, 3H), 3.43 (d, 2H), 6.09 (s, 1H), 7.13 (s, 1H), 8.17 (s, 1H), 10.06 (s, 1H). MS (ESI): m/z [M+H]$^+$ 347.4.

Step B. 2-Amino-4,5-dimethyl-N-((1-methylcyclobutyl)methyl)benzamide hydrochloride Intermediate 164 (102 mg, 0.29 mmol) was diluted in dioxane (1 mL). 4 M HCl in Dioxane (1 mL, 4.00 mmol) was added and the reaction was stirred at ambient temperature for 4 h, evaporated with a stream of N$_2$. The solvent and excess HCl was evaporated and the crude product was used as such in the next step. MS (ESI): m/z [M+H]$^+$ 247.3.

Intermediate 165: Ethyl (1s,4s)-4-(5-carbamoyl-2-fluoro-4-methoxyphenoxy)cyclohexane-1-carboxylate

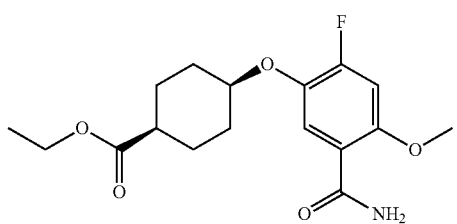 [SMILES: CCOC(=O)[C@H]1CC[C@@H](Oc2cc(C(N)=O)c(OC)cc2F)CC1]

EDC (1.239 g, 6.46 mmol) was added slowly to Intermediate 111 (1 g, 2.94 mmol), NH$_4$Cl (1.572 g, 29.38 mmol), HOBt (0.990 g, 6.46 mmol) and TEA (8.19 mL, 58.76 mmol) in DMF (20 mL) at 20° C. The resulting solution was stirred at 60° C. for 14 h. The reaction mixture was diluted with EtOAc (200 mL), and washed sequentially with brine (2×150 mL, sat), NaHCO$_3$ (1×150 mL, sat), and H$_2$O (1×150 mL). The organic layer was dried over Na$_2$SO$_4$, filtered and evaporated to afford the title compound (0.900 g, 90%) as a yellow oil which solidified on standing. MS (ESI): m/z [M+H]$^+$ 340.2.

Intermediate 166: 2-((4-Fluoro-3-(trifluoromethyl)phenyl)carbamoyl)cyclohex-1-en-1-yl trifluoromethanesulfonate

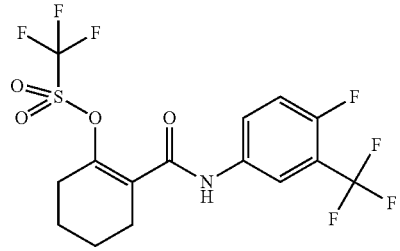 [SMILES: O=C(Nc1ccc(F)c(C(F)(F)F)c1)C1=C(OS(=O)(=O)C(F)(F)F)CCCC1]

Step A. Intermediate 167: N-(4-Fluoro-3-(trifluoromethyl)phenyl)-2-hydroxycyclohex-1-ene-1-carboxamide

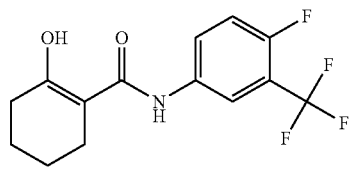 [SMILES: O=C(Nc1ccc(F)c(C(F)(F)F)c1)C1=C(O)CCCC1]

DMAP (0.108 g, 0.88 mmol) was added to 4-fluoro-3-(trifluoromethyl)aniline (1.315 g, 7.34 mmol) and ethyl 2-oxocyclohexane-1-carboxylate (0.5 g, 2.94 mmol) in toluene (20 mL) at 20° C. The resulting solution was stirred at 130° C. for 15 h. The reaction mixture was poured into 2 M HCl (200 mL), extracted with EtOAc (3×75 mL), the organic layer was dried over Na$_2$SO$_4$, filtered and evaporated to afford the crude product as a yellow oil. The residue was purified by preparative TLC (EtOAc/PE 1/2), to afford the title compound (0.500 g, 56.1%) as a yellow gum. MS (ESI): m/z [M+H]$^+$ 304.1.

Step B. 2-((4-Fluoro-3-(trifluoromethyl)phenyl)carbamoyl)cyclohex-1-en-1-yl trifluoromethanesulfonate A solution of trifluoromethanesulfonic anhydride (4.23 g, 15.00 mmol) in DCM (10 mL) was added slowly to a stirred solution of Intermediate 167 (3.5 g, 11.54 mmol) and TEA (5.63 mL, 40.39 mmol) in DCM (10 mL) cooled to −78° C. under nitrogen. The resulting solution was stirred at −78° C. for 30 min. The temperature was increased to Rt and stirred overnight. The reaction mixture was poured into brine (200 mL, sat), extracted with EtOAc (3×75 mL), the organic layer was dried over Na$_2$SO$_4$, filtered and evaporated to afford the crude product as a yellow oil. The crude product which was purified by flash chromatography using a gradient of 0-20% EtOAc in heptane as mobile phase to give the title compound (1.500 g, 29.9%) as an orange oil which solidified on standing. $^1$HNMR (300 MHz, CDCl$_3$): δ 1.68-1.91 (m, 4H), 2.54 (m, 4H), 7.19 (d, 1H), 7.76 (dd, 1H), 7.82-7.86 (m, 1H). MS (ESI): m/z [M+H]+ 436.3.

Intermediate 168: 2-((4-Fluoro-3-(trifluoromethyl)phenyl)carbamoyl)cyclopent-1-en-1-yl trifluoromethanesulfonate

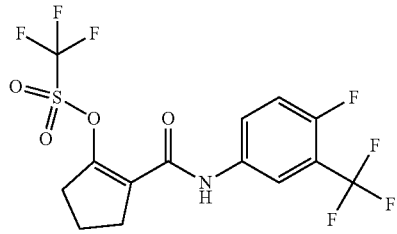 [SMILES: O=C(Nc1ccc(F)c(C(F)(F)F)c1)C1=C(OS(=O)(=O)C(F)(F)F)CCC1]

Step A. Intermediate 169: N-(4-Fluoro-3-(trifluoromethyl)phenyl)-2-hydroxycyclopent-1-ene-1-carboxamide

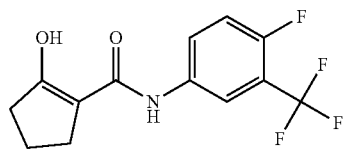 [SMILES: O=C(Nc1ccc(F)c(C(F)(F)F)c1)C1=C(O)CCC1]

DMAP (0.469 g, 3.84 mmol) was added to 4-fluoro-3-(trifluoromethyl)aniline (5.73 g, 32.01 mmol) and ethyl 2-oxocyclopentane-1-carboxylate (2 g, 12.81 mmol) in toluene (25 mL) under nitrogen. The resulting solution was stirred at 130° C. for 18 h. The reaction mixture was poured into 2 M HCl (200 mL), extracted with EtOAc (3×75 mL), the organic layer was dried over Na$_2$SO$_4$, filtered and evaporated to afford the title compound (3.50 g, 94%) as a yellow gum. The product was used in the next step directly without further purification. MS (ESI): m/z [M+H]+ 290.1.

Step B. 2-((4-Fluoro-3-(trifluoromethyl)phenyl)carbamoyl)cyclopent-1-en-1-yl trifluoromethanesulfonate A solution of trifluoromethanesulfonic anhydride (4.10 g, 14.52 mmol) in DCM (10 mL) was added slowly to a stirred solution of Intermediate 169 (3.5 g, 12.10 mmol) and TEA (5.06 mL, 36.30 mmol) in DCM (20 mL) cooled to −78° C. under nitrogen. The resulting solution was stirred at −78° C. for 30 min. The temperature was increased to room temperature. The reaction mixture was poured into brine (200 mL, sat), extracted with EtOAc (3×75 mL), the organic layer was dried over Na$_2$SO$_4$, filtered and evaporated to afford a yellow oil. The crude product which was purified by flash chromatography using a gradient of 0-20% EtOAc in heptane as mobile phase to give the title compound (1.20 g, 24%) as a pale yellow oil which solidified on standing. $^1$H NMR (400 MHz, CDCl$_3$): δ 2.08-2.16 (m, 2H), 2.83 (m, 2H), 2.90 (m, 2H), 7.20 (t, 1H), 7.70-7.76 (m, 1H), 7.78 (s, 1H), 7.87 (dd, 1H). MS (ESI): m/z [M+H]+ 422.0.

Intermediate 170: 3-Amino-N-((1-methylcyclobutyl)methyl)-2-naphthamide 2,2,2-trifluoroacetate

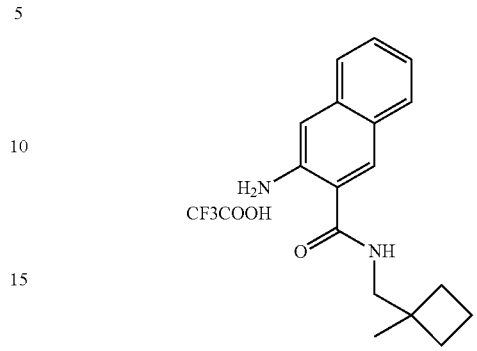

Step A. Intermediate 171: tert-Butyl (3-(((1-methylcyclobutyl)methyl)carbamoyl)naphthalen-2-yl)carbamate

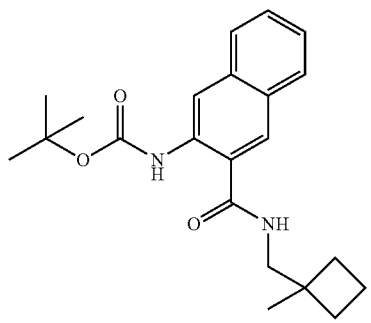 [SMILES: CC1(CNC(=O)c2cc3ccccc3cc2NC(=O)OC(C)(C)C)CCC1]

DIPEA (1.277 mL, 7.31 mmol) was added dropwise to 3-((tert-butoxycarbonyl)amino)-2-naphthoic acid (0.70 g, 2.44 mmol), (1-methylcyclobutyl)methanamine hydrochloride (0.330 g, 2.44 mmol) and HATU (2.78 g, 7.31 mmol) in DMF (20 mL) at 0° C. over a period of 1 min under nitrogen. The resulting solution was stirred at 20° C. for 14 h. The reaction mixture was diluted with EtOAc (100 mL) and washed sequentially with brine (1×100 mL, sat), NH$_4$Cl (1×100 mL, sat) and brine (1×100 mL, sat). The organic layer was dried over Na$_2$SO$_4$, filtered and evaporated to afford crude product which was purified by preparative TLC (EtOAc/PE 1/3), to afford the title compound (0.350 g, 39%) as a white solid. MS (ESI): m/z [M+H]+ 369.3.

Step B. 3-Amino-N-((1-methylcyclobutyl)methyl)-2-naphthamide 2,2,2-trifluoroacetate TFA (0.732 mL, 9.50 mmol) was added dropwise to Intermediate 171 (0.35 g, 0.95 mmol) in DCM (20 mL) at 10° C., over a period of 1 second under nitrogen. The resulting solution was stirred at 20° C. for 14 h. The solvent was removed under reduced pressure. The crude product was purified by crystallization from EtOAc/EtOH to afford the title compound (0.385 g) as a pale yellow solid. MS (ESI): m/z [M+H]+ 269.3.

Intermediate 172: 2-Amino-5-methyl-N-((1-methyl-cyclobutyl)methyl)benzamide hydrochloride

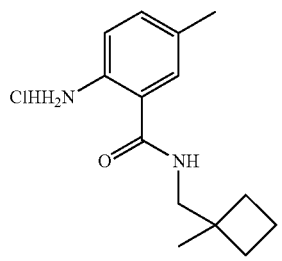

Step A. Intermediate 173: tert-Butyl (4-methyl-2-(((1-methylcyclobutyl)methyl)carbamoyl)phenyl)carbamate

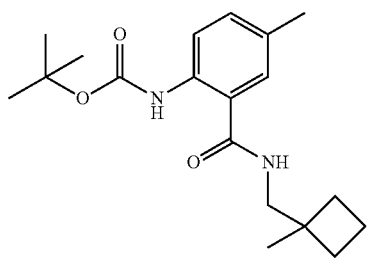 [SMILES: Cc1ccc(NC(=O)OC(C)(C)C)c(C(=O)NCC2(C)CCC2)c1]

2-((tert-Butoxycarbonyl)amino)-5-methylbenzoic acid (300 mg, 1.19 mmol) was added to (1-methylcyclobutyl)methanamine (178 mg, 1.79 mmol), EDC (343 mg, 1.79 mmol), HOBt (242 mg, 1.79 mmol) and DIPEA (463 mg, 3.58 mmol) in DMF (10 mL) at 20° C. The resulting solution was stirred at 30° C. for 12 h. The reaction mixture was concentrated, diluted with EtOAc (150 mL) and washed sequentially with NaHCO$_3$ (1×150 mL, sat), H$_2$O (1×200 mL), and brine (1×200 mL, sat). The organic layer was dried over Na$_2$SO$_4$, filtered and evaporated to afford crude product. The residue was purified by preparative TLC (EtOAc/PE=1/3), to afford the title compound (260 mg, 65%) as a yellow solid. MS (ESI): m/z [M+H]$^+$ 333.3.

Step B. 2-Amino-5-methyl-N-((1-methylcyclobutyl)methyl)benzamide hydrochloride Hydrogen chloride (384 mg, 10.53 mmol) was added to Intermediate 173 (350 mg, 1.05 mmol) in MeOH (6 mL) at 20° C. The resulting solution was stirred at 30° C. for 12 h. The solvent was removed by distillation under vacuum and the residue was purified by preparative TLC (PE/EtOAc 3/1), to afford the title compound (210 mg, 74%) as a yellow solid. MS (ESI): m/z [M+H]$^+$ 233.3.

Intermediate 174: 2-Amino-N-((1-methylcyclobutyl)methyl)pyrazolo[1,5-a]pyrimidine-3-carboxamide hydrochloride

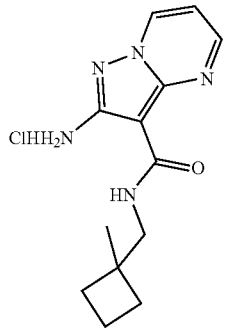

Step A. Intermediate 175: tert-Butyl (3-(((1-methylcyclobutyl)methyl)carbamoyl)pyrazolo[1,5-a]pyrimidin-2-yl)carbamate

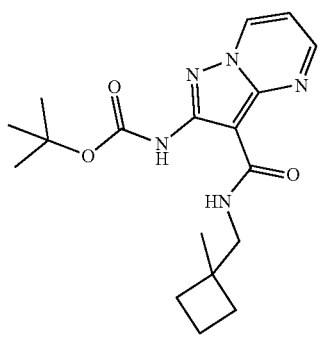 [SMILES: CC1(CNC(=O)c2c(NC(=O)OC(C)(C)C)nn3cccnc23)CCC1]

2-((tert-Butoxycarbonyl)amino)pyrazolo[1,5-a]pyrimidine-3-carboxylic acid (300 mg, 1.08 mmol) was added to (1-methylcyclobutyl)methanamine (160 mg, 1.62 mmol), EDC (310 mg, 1.62 mmol, HOBt (219 mg, 1.62 mmol) and DIPEA (418 mg, 3.23 mmol) in DMF (10 mL) at 20° C. The resulting solution was stirred at 30° C. for 12 h. The reaction mixture was concentrated and diluted with EtOAc (200 mL), and washed sequentially with NaHCO$_3$ (1×200 mL, sat), H$_2$O (1×200 mL) and brine (1×200 mL, sat). The organic layer was dried over Na$_2$SO$_4$, filtered and evaporated to afford crude product which was purified by preparative TLC (PE/EtOAc 3/1), to afford the title compound (280 mg, 72%) as a yellow solid. MS (ESI): m/z [M+H]$^+$ 360.4.

Step B. 2-Amino-N-((1-methylcyclobutyl)methyl)pyrazolo[1,5-a]pyrimidine-3-carboxamide hydrochloride Hydrogen chloride (203 mg, 5.56 mmol) was added to Intermediate 175 (200 mg, 0.56 mmol) in MeOH (6 mL) at 20° C. The resulting solution was stirred at 30° C. for 12 h. The reaction mixture was concentrated and diluted with EtOAc (200 mL), and washed sequentially with H$_2$O (1×200 mL), brine (1×200 mL, sat). The organic layer was dried over Na$_2$SO$_4$, filtered and evaporated to afford crude product which was purified by preparative TLC (EtOAc/PE 1/1), to afford the title compound (130 mg, 79%) as a yellow solid. MS (ESI): m/z [M+H]⁺ 260.3.

Intermediate 176: rac-(1R,2R,3S,4S)-3-Amino-N-((1-methylcyclobutyl)methyl)-7-oxabicyclo[2.2.1]heptane-2-carboxamide

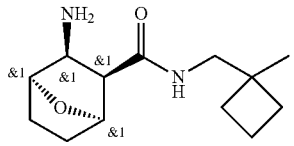 [SMILES: CC1(CNC(=O)[C@@H]2[C@H](N)[C@@H]3CC[C@H]2O3)CCC1]

Step A: Intermediate 177: rac-Methyl (1R,2R,3S,4S)-3-(((benzyloxy)carbonyl)amino)-7-oxabicyclo[2.2.1]heptane-2-carboxylate

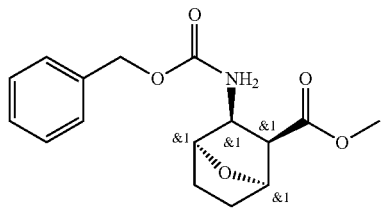 [SMILES: COC(=O)[C@@H]1[C@H](NC(=O)OCc2ccccc2)[C@@H]2CC[C@H]1O2]

DIPEA (1.17 mL, 6.74 mmol) was added to a solution of rac-(1R,2R,3S,4S)-3-(methoxycarbonyl)-7-oxabicyclo[2.2.1]heptane-2-carboxylic acid (900 mg, 4.50 mmol) in toluene and DPPA (1.16 mL, 5.40 mmol) was added dropwise, then the reaction mixture was stirred at rt for 1 hr. The reaction mixture was stirred at 90° C. for 10 min, then benzyl alcohol (0.56 mL, 5.39 mmol) was added and the reaction mixture was stirred for 1.5 hr. The reaction mixture was diluted with EtOAc and washed with H₂O, then the organic layer was concentrated in vacuo. The crude product was purified by flash chromatography using a gradient of 0-35% EtOAc in hexane as mobile phase to give the title compound (1.33 g, 97%). MS (ESI) m/z 306.1 [M+H]⁺

Step B: Intermediate 178: rac-(1R,2R,3S,4S)-3-(((Benzyloxy)carbonyl)amino)-7-oxabicyclo[2.2.1]heptane-2-carboxylic acid

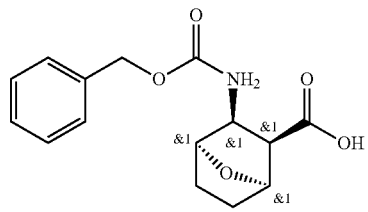 [SMILES: O=C(N[C@H]1[C@@H](C(=O)O)[C@H]2CC[C@@H]1O2)OCc1ccccc1]

Intermediate 177 was dissolved in THF (11 mL) and H₂O (5.5 mL), then the mixture was cooled to 0° C. LiOH was added and the reaction mixture was stirred at 0° C. for 1 h and rt for 3 hr. 1 M aq HCl was added to the reaction mixture until pH<2, then the reaction mixture was extracted with CHCl₃ twice and the combined organic layer was concentrated in vacuo to give titled compound which was used without further purification.

Step C: Intermediate 179: rac-Benzyl ((1R,2R,3S,4S)-3-(((1-methylcyclobutyl)methyl)carbamoyl)-7-oxabicyclo[2.2.1]heptan-2-yl)carbamate

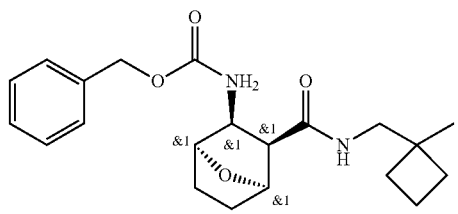 [SMILES: CC1(CNC(=O)[C@@H]2[C@H](NC(=O)OCc3ccccc3)[C@@H]3CC[C@H]2O3)CCC1]

HATU (1.82 g, 4.79 mmol) was added to a solution of Intermediate 178 (1.27 g, 4.35 mmol), (1-methylcyclobutyl)methylamine hydrochloride (708 mg, 5.220 mmol) and DIPEA (1.69 g, 13.05 mmol) in DMF (11 mL) and the reaction mixture was stirred at rt for 1 hr. H₂O was added to the reaction mixture and the mixture was extracted with EtOAc/Hexane (2/1), then the organic layer was concentrated in vacuo. The crude product was purified by flash chromatography using a gradient of 0-40% EtOAc in hexane as mobile phase to give the title compound (671 mg, 41%). MS (ESI) m/z 373.1 [M+H]⁺

Step D: rac-(1R,2R,3S,4S)-3-Amino-N-((1-methylcyclobutyl)methyl)-7-oxabicyclo[2.2.1]heptane-2-carboxamide Palladium (10% Pd/C, moisture by 50% H₂O, 100 mg) was added to a solution of Intermediate 179 (661 mg, 1.77 mmol) in MeOH (8.9 mL). The reaction mixture was stirred under 1 atm of hydrogen atmosphere at rt for 4 hr. The hydrogen in the reaction vessel was replaced with argon and the reaction mixture was filtered with Celite®. The filtrate was concentrated in vacuo to give titled compound (524 mg, 100%). MS (ESI) m/z 239.2 [M+H]⁺

Intermediate 180: rac-(1R,2S,3R,4S)-3-Amino-N-((1-methylcyclobutyl)methyl)-7-oxabicyclo[2.2.1]heptane-2-carboxamide hydrochloride

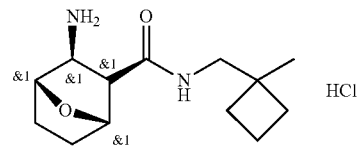

Step A: Intermediate 181: rac-tert-Butyl ((1R,2S,3R,4S)-3-(((1-methylcyclobutyl)methyl)carbamoyl)-7-oxabicyclo[2.2.1]heptan-2-yl)carbamate

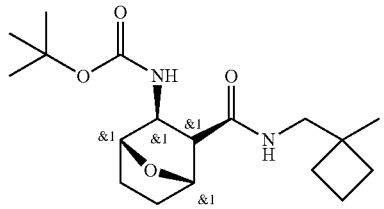

EDC (121 mg, 0.63 mmol) and HOAt (86 mg, 0.63 mmol) were added to a solution of rac-(1R,2S,3R,4S)-3-((tert-butoxycarbonyl)amino)-7-oxabicyclo[2.2.1]heptane-2-carboxylic acid (125 mg, 0.486 mmol), (1-methylcyclobutyl)methylamine hydrochloride (86 mg, 0.634 mmol) and DIPEA (160 mg, 1.20 mmol) in DMF (5 mL) and the reaction mixture was stirred at rt for 12 hr. H$_2$O was added to the reaction mixture and the mixture was extracted with EtOAc, then the organic layer was concentrated in vacuo to give the title compound (169 mg, 100%). MS (ESI) m/z 339.1 [M+H]$^+$ Step B: rac-(1R,2S,3R,4S)-3-Amino-N-((1-methylcyclobutyl)methyl)-7-oxabicyclo[2.2.1]heptane-2-carboxamide hydrochloride

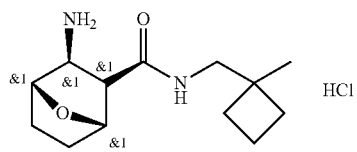

A solution of Intermediate 181 in 4 M HCl in EtOH (2 mL) was stirred at rt for 12 h and the reaction mixture was concentrated in vacuo to give titled compound (144 mg, 100%). MS (ESI) m/z 239.3 [M+H]$^+$ Intermediate 182: rac-tert-Butyl (1R,2R,3S,4S)-2-amino-3-(((1-methylcyclobutyl)methyl)carbamoyl)-7-azabicyclo[2.2.1]heptane-7-carboxylate

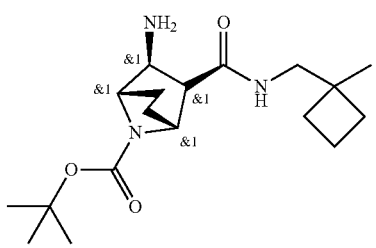

The titled compound was prepared analogous to Intermediate 176, using rac-(1R,2R,3S,4S)-7-(tert-butoxycarbonyl)-3-(methoxycarbonyl)-7-azabicyclo[2.2.1]heptane-2-carboxylic acid instead of rac-(1R,2R,3S,4S)-3-methoxycarbonyl-7-oxabicyclo[2.2.1]heptane-2-carboxylic acid. MS (ESI) m/z 338.2 [M+H]$^+$ Intermediate 183: rac-(1R,2S)-2-Amino-N-(3-((trifluoromethyl)sulfonyl)phenyl)cyclobutane-1-carboxamide

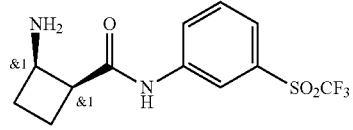

The titled compound was prepared analogous to Intermediate 176 Step C and D, using rac-(1R,2S)-2-(((benzyloxy)carbonyl)amino)cyclobutane-1-carboxylic acid instead of Intermediate 178 and using 3-((trifluoromethyl)sulfonyl)aniline instead of (1-methylcyclobutyl)methylamine hydrochloride.

Intermediate 184: rac-(1R,2S)-2-Amino-N-neopentylcyclobutane-1-carboxamide

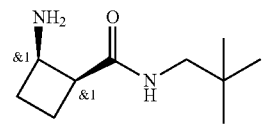

The titled compound was prepared analogous to Intermediate 176 Step C and D, using rac-(1R,2S)-2-(((benzyloxy)carbonyl)amino)cyclobutane-1-carboxylic acid instead of Intermediate 178 and using neopentylamine instead of (1-methylcyclobutyl)methylamine hydrochloride.

Intermediate 185: rac-(1R,2S)-2-Amino-N-(4-fluoro-3-(pentafluoro-λ6-sulfaneyl)phenyl)cyclobutane-1-carboxamide

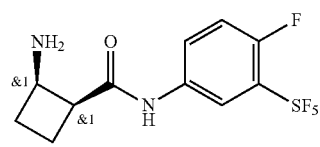

The titled compound was prepared analogous to Intermediate 176 Step C and D, using rac-(1R,2S)-2-(((benzyloxy)carbonyl)amino)cyclobutane-1-carboxylic acid instead of Intermediate 178 and using 4-fluoro-3-(pentafluoro-λ6-sulfaneyl)aniline instead of (1-methylcyclobutyl)methylamine hydrochloride. MS (ESI) m/z 335.0 [M+H]$^+$ Intermediate 186: rac-(1R,2S)-2-Amino-N-((1-methylcyclobutyl)methyl)cyclobutane-1-carboxamide

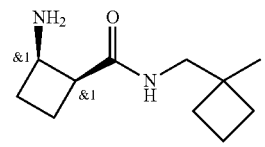

The titled compound was prepared analogous to Intermediate 176 Step C and D, using rac-(1R,2S)-2-(((benzyloxy)carbonyl)amino)cyclobutane-1-carboxylic acid instead of Intermediate 178.

Intermediate 187: rac-(1R,2S,3R,4S)-3-Amino-N-((1-methylcyclobutyl)methyl)bicyclo[2.2.2]oct-5-ene-2-carboxamide hydrochloride

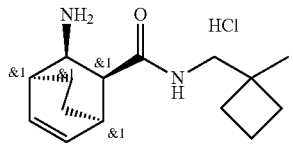 [SMILES: CC1(CNC(=O)[C@@H]2[C@H](N)[C@@H]3C=C[C@H]2CC3)CCC1 ; Cl]

Step A: Intermediate 188: rac-tert-Butyl ((1R,2S,3R,4S)-3-(((1-methylcyclobutyl)methyl)carbamoyl)bicyclo[2.2.2]oct-5-en-2-yl)carbamate

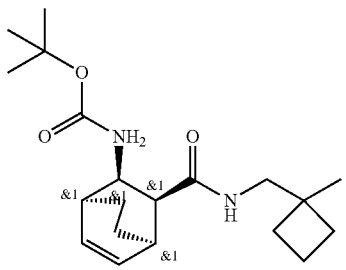 [SMILES: CC1(CNC(=O)[C@@H]2[C@H](NC(=O)OC(C)(C)C)[C@@H]3C=C[C@H]2CC3)CCC1]

HATU (1.91 g, 5.02 mmol) was added to a solution of rac-(1R,2S,3R,4S)-3-(tert-butoxycarbonylamino)bicyclo[2.2.2]oct-5-ene-2-carboxylic acid (Compound 1) (1.22 g, 4.56 mmol), (1-methylcyclobutyl)methylamine hydrochloride (681 mg, 5.02 mmol) and DIPEA (2.37 g, 13.69 mmol) in DMF (11 mL) and the reaction mixture was stirred at rt for 10 min. H$_2$O was added to the reaction mixture and the reaction mixture was stirred vigorously. The precipitate was collected by filtration and the crude material was dried under air to give titled compound (1.56 g, 98%). MS (ESI) m/z 349.3 [M+H]$^+$

Step B: rac-(1R,2S,3R,4S)-3-Amino-N-((1-methylcyclobutyl)methyl)bicyclo[2.2.2]oct-5-ene-2-carboxamide hydrochloride A solution of Intermediate 188 in 4 M HCl in cyclopentyl methyl ether (11 mL) was stirred at rt for 30 min and the reaction mixture was concentrated in vacuo to give titled compound (1.25 g, 98%). MS (ESI) m/z 249.2 [M+H]$^+$

Intermediate 189: (1S,2R)-2-Amino-N-((1-methylcyclobutyl)methyl)cyclohexane-1-carboxamide hydrochloride

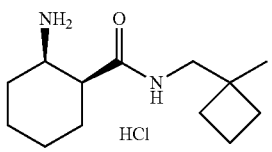 [SMILES: CC1(CNC(=O)[C@H]2CCCC[C@H]2N)CCC1 ; Cl]

The titled compound was prepared analogous to Intermediate 187, using (1S,2R)-2-(tert-butoxycarbonylamino)cyclohexane-1-carboxylic acid instead of Compound 1. MS (ESI) m/z 225.3 [M+H]$^+$.

Intermediate 190: (1S,2R)-2-Amino-N-((1-methylcyclobutyl)methyl)cyclopentane-1-carboxamide hydrochloride

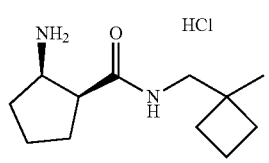

The titled compound was prepared analogous to Intermediate 187, using (1S,2R)-2-(tert-butoxycarbonylamino)cyclopentane-1-carboxylic acid instead of Compound 1. MS (ESI) m/z 211.3 [M+H]$^+$.

Intermediate 191: rac-(1R,2S,4R)-2-Amino-4-methoxy-N-(3-(((trifluoromethyl)sulfonyl)phenyl)cyclopentane-1-carboxamide

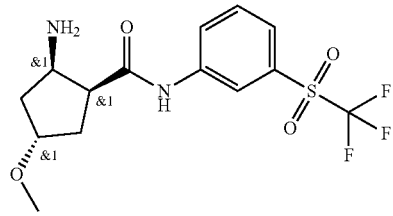 [SMILES: CO[C@@H]1C[C@@H](N)[C@@H](C(=O)Nc2cccc(S(=O)(=O)C(F)(F)F)c2)C1]

Step A: Intermediate 192: rac-Methyl (1R,2S,4R)-2-(((benzyloxy)carbonyl)amino)-4-methoxycyclopentane-1-carboxylate

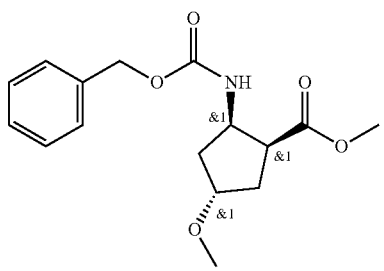 [SMILES: COC(=O)[C@H]1C[C@H](OC)C[C@H]1NC(=O)OCc1ccccc1]

AgO (231 mg, 1.00 mmol) and iodomethane (0.09 mL, 1.36 mmol) were added to a solution of rac-methyl (1S,2R,4S)-2-(((benzyloxy)carbonyl)amino)-4-hydroxy-cyclopentanecarboxylate (Compound 2) (132 mg, 0.453 mmol) in MeCN (5 mL) and the reaction mixture was stirred at 50° C. for 3 hr. Iodomethane (0.38 mL, 6.07 mmol) was added and the reaction mixture was stirred at 40° C. for 20 hr. The reaction mixture was cooled at ambient temperature and filtered with Celite®, then the filtrate was concentrated in vacuo. The crude product was purified by flash chromatography using a gradient of 30-60% EtOAc in hexane as mobile phase to give the title compound (130 mg, 91%). MS (ESI) m/z 308.3 [M+H]⁺.

Step B: Intermediate 193: rac-(1R,2S,4R)-2-(((Benzyloxy)carbonyl)amino)-4-methoxycyclopentane-1-carboxylic acid

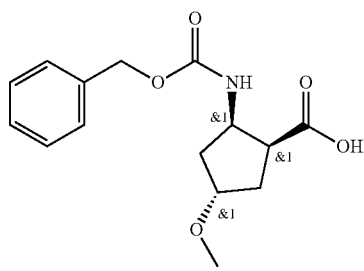 [SMILES: CO[C@H]1C[C@H](C(=O)O)[C@H](NC(=O)OCc2ccccc2)C1]

LiOH (51 mg, 2.11 mmol) was added to a solution of Intermediate 192 (130 mg, 0.42 mmol) in THF (3 mL) and H₂O (1 mL), then the reaction mixture was stirred at rt for 19 hr. 1 M aq HCl was added to a reaction mixture to neutralize and the mixture was extracted with EtOAc three times, then the combined organic layer was concentrated in vacuo to give titled compound (125 mg, 100%). MS (ESI) m/z 294.1 [M+H]⁺.

Step C: Intermediate 194: rac-Benzyl ((1R,2S,4S)-4-methoxy-2-((3-((trifluoromethyl)sulfonyl)phenyl)carbamoyl)cyclopentyl)carbamate

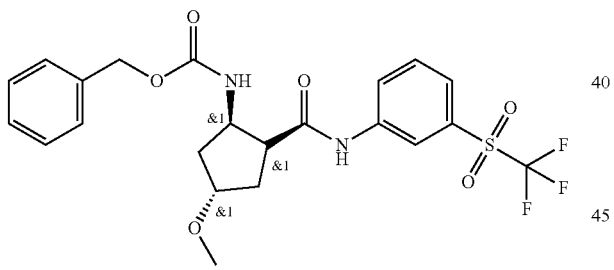

T3P (1.7 M in EtOAc, 0.54 mL, 0.91 mmol) and DIPEA (0.20 mL, 1.13 mmol) were added to a solution of Intermediate 193 (122 mg, 0.42 mmol) and 3-((trifluoromethyl)sulfonyl)aniline (85 mg, 0.38 mmol) in MeCN (4 mL), then the reaction mixture was stirred at rt for 20 hr. Sat aq NaHCO₃ was added to a reaction mixture and the mixture was extracted with EtOAc three times, then the combined organic layer was concentrated in vacuo. The crude product was purified by flash chromatography using a gradient of 0-2% MeOH in CHCl₃ as mobile phase to give the title compound (133 mg, 71%). MS (ESI) m/z 501.1 [M+H]⁺.

Step D: rac-(1R,2S,4R)-2-Amino-4-methoxy-N-(3-((trifluoromethyl)sulfonyl)phenyl)cyclopentane-1-carboxamide Palladium (10% Pd/C, moisture by 50% H₂O, 38 mg) was added to a solution of Intermediate 194 (130 mg, 0.26 mmol) in MeOH (3 mL) and THF (6 mL). The reaction mixture was stirred under 1 atm of hydrogen atmosphere at rt for 5 hr. The hydrogen in the reaction vessel was replaced with argon, and the reaction mixture was filtered with Celite®, then the filtrate was concentrated in vacuo. The crude product was purified by flash chromatography using a gradient of 0-20% MeOH in CHCl₃ as mobile phase to give the title compound (46 mg, 48%). MS (ESI) m/z 367.1 [M+H]⁺.

Intermediate 195: rac-(1R,2S,4S)-2-Amino-4-methoxy-N-(3-((trifluoromethyl)sulfonyl)phenyl)cyclopentane-1-carboxamide

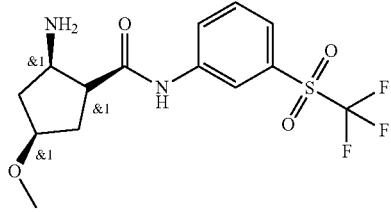

The titled compound was prepared analogous to Intermediate 191, using rac-methyl (1S,2R,4R)-2-(((benzyloxy)carbonyl)amino)-4-hydroxy-cyclopentanecarboxylate instead of Compound 2. MS (ESI) m/z 367.4 [M+H]⁺.

Intermediate 196: rac-(1R,2R)-2-Amino-1-fluoro-N-(3-((trifluoromethyl)sulfonyl)phenyl)cyclopentane-1-carboxamide

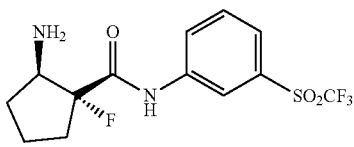

Step A: Intermediate 197: Methyl (1R,2R)-2-(benzyl((R)-1-phenylethyl)amino)-1-fluorocyclopentane-1-carboxylate

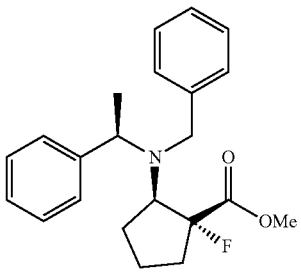

n-BuLi (2.6 M in Hexane, 0.73 mL, 1.90 mmol) was added dropwise to −78° C. cooled solution of (1R)—N-benzyl-1-phenyl-ethanamine (502 mg, 2.38 mmol) in THF (4 mL) and the reaction mixture was stirred at −78° C. for 20 min. Methyl cyclopentene-1-carboxylate (200 mg, 1.59 mmol) was added dropwise to a reaction mixture stirred at −78° C. for 30 min. N-(benzenesulfonyl)-N-fluoro-benzenesulfonamide (1.0 g, 3.17 mmol) in THF (4 mL) was added to a reaction mixture and the mixture was stirred at rt for 30 min. Sat aq NH₄Cl was added to the reaction mixture and the mixture was extracted with EtOAc twice. The combined organic layer was concentrated in vacuo. The crude product was purified by flash chromatography using a gradient of 0-30% EtOAc in hexane as mobile phase to give the title compound (210 mg, 37%). MS (ESI) m/z 356.2 [M+H]⁺.

Step B: Intermediate 198: (1R,2R)-2-(Benzyl((R)-1-phenylethyl)amino)-1-fluorocyclopentane-1-carboxylic acid

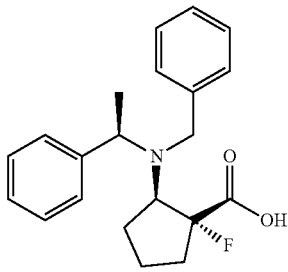

LiOH (142 mg, 5.91 mmol) was added to a solution of Intermediate 197 (210 mg, 0.59 mmol) in THF (3 mL) and H₂O (1.5 mL), then the reaction mixture was stirred at rt for 7 days. 1 M aq HCl was added to a reaction mixture to neutralize and the mixture was extracted with CHCl₃ twice, then the combined organic layer was concentrated in vacuo give titled compound (60 mg, 30%) which was used without further purification.

Step C: Intermediate 199: (1R,2R)-2-(Benzyl((R)-1-phenylethyl)amino)-1-fluoro-N-(3-((trifluoromethyl)sulfonyl)phenyl)cyclopentane-1-carboxamide

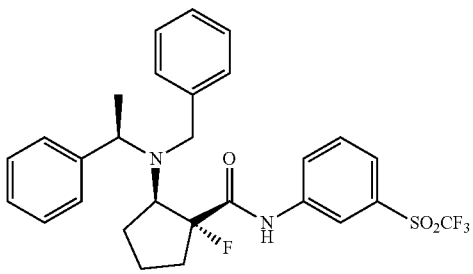

HATU (73 mg, 0.19 mmol) and DIPEA (0.09 mL, 0.53 mmol) were added to a solution of Intermediate 198 (60 mg, 0.18 mmol) and 3-((trifluoromethyl)sulfonyl)aniline (44 mg, 0.19 mmol) in DMF (1 mL), then the reaction mixture was stirred at rt for 24 hr. H₂O was added to a reaction mixture and the mixture was extracted with CHCl₃ twice, then the combined organic layer was concentrated in vacuo. The crude product was purified by flash chromatography using a gradient of 0-25% EtOAc in hexane as mobile phase to give the title compound (43 mg, 45%). MS (ESI) m/z 549.5 [M+H]⁺.

Step D: rac-(1R,2R)-2-Amino-1-fluoro-N-(3-((trifluoromethyl)sulfonyl)phenyl)cyclopentane-1-carboxamide Palladium (10% Pd/C, moisture by 50% H₂O, 10 mg) was added to a solution of Intermediate 199 (43 mg, 0.078 mmol) in MeOH (1.5 mL). The reaction mixture was stirred under 1 atm of hydrogen atmosphere at rt for 20 hr. The hydrogen in the reaction vessel was replaced with argon, and the reaction mixture was filtered with Celite®, then the filtrate was concentrated in vacuo to give titled compound (27 mg, 97%). MS (ESI) m/z 355.3 [M+H]⁺.

Intermediate 200: rac-(1R,2R,3S)-2-Amino-3-hydroxy-N-(3-((trifluoromethyl)sulfonyl)phenyl)cyclopentane-1-carboxamide hydrochloride

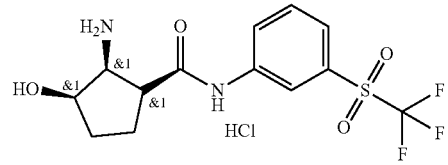

Step A: Intermediate 201: rac-Benzyl (3aR,4R,6R,6aR)-6-bromo-2-oxohexahydro-2H-cyclopenta[d]oxazole-4-carboxylate

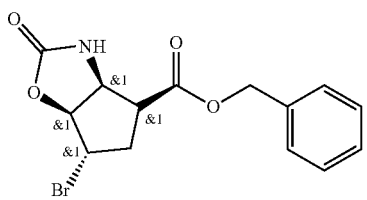

NBS (336 mg, 1.89 mmol) was added to a solution of rac-benzyl (1S,2R)-2-(tert-butoxycarbonylamino)cyclopent-3-ene-1-carboxylate (500 mg, 1.58 mmol) in THF (7.9 mL) and H₂O (0.79 mL), and the reaction mixture was stirred at rt for 3 days. H₂O was added to the reaction mixture and the mixture was extracted with CHCl₃ twice. The combined organic layer was concentrated in vacuo. The crude product was purified by flash chromatography using a gradient of 0-40% EtOAc in hexane as mobile phase to give the title compound (361 mg, 67%). MS (ESI) m/z 340.2/342.2 [M+H]⁺.

Step B: Intermediate 202: rac-Benzyl (3aR,4R,6aS)-2-oxohexahydro-2H-cyclopenta[d]oxazole-4-carboxylate

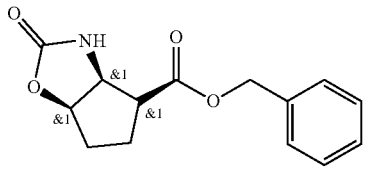

AIBN (17 mg, 0.11 mmol) was added to a solution of Intermediate 201 (359 mg, 1.05 mmol) and tributylstannane (338 mg, 1.16 mmol) in toluene (3 mL), then the reaction mixture was stirred at 80° C. for 2 hr. The reaction mixture was concentrated in vacuo and the crude product was purified by flash chromatography using a gradient of 0-50% EtOAc in hexane as mobile phase to give the title compound (216 mg, 78%). MS (ESI) m/z 262.1 [M+H]+.

Step C: Intermediate 203: rac-4-Benzyl 3-(tert-butyl) (3aR,4R,6aS)-2-oxotetrahydro-2H-cyclopenta[d]oxazole-3,4(3aH)-dicarboxylate

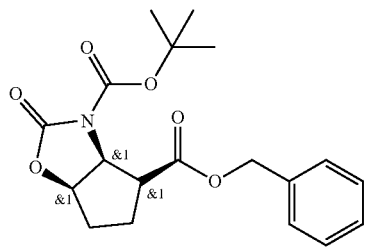

Boc₂O (193 mg, 0.88 mmol) and 4-(dimethylamino)pyridine (10 mg, 0.08 mmol) were added to a solution of Intermediate 202 (210 mg, 0.80 mmol) in MeCN (4 mL), then the reaction mixture was stirred at rt for 30 min. The reaction mixture was concentrated in vacuo to give titled compound (310 mg, 107%) which was used without further purification.

Step D: Intermediate 204: rac-(3aR,4R,6aS)-3-(tert-Butoxycarbonyl)-2-oxohexahydro-2H-cyclopenta[d]oxazole-4-carboxylic acid

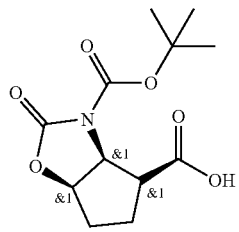

Palladium (10% Pd/C, moisture by 50% H₂O, 30 mg) was added to a solution of Intermediate 203 (262 mg, 0.73 mmol) in MeOH (3.6 mL). The reaction mixture was stirred under 1 atm of hydrogen atmosphere at rt for 4 hr. The hydrogen in the reaction vessel was replaced with argon, and CHCl₃ and MeOH were added to the reaction mixture to dissolve precipitated product. The reaction mixture was filtered with Celite®, then the filtrate was concentrated in vacuo to give titled compound (196 mg, 100%). MS (ESI) m/z 270.3 [M−H]−

Step E: Intermediate 205: rac-tert-Butyl (3aR,4R,6aS)-2-oxo-4-((3-((trifluoromethyl)sulfonyl)phenyl)carbamoyl)tetrahydro-2H-cyclopenta[d]oxazole-3(3aH)-carboxylate

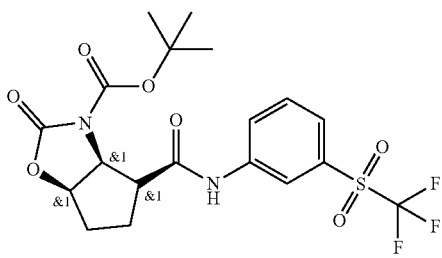

T3P (1.7 M in EtOAc, 910 mg, 1.43 mmol) and pyridine (113 mg, 1.43 mmol) were added to a solution of Intermediate 204 (194 mg, 0.72 mmol) and 3-((trifluoromethyl)sulfonyl)aniline (177 mg, 0.79 mmol) in EtOAc (1.8 mL), then the reaction mixture was stirred at rt for 15 h. CHCl₃ and H₂O were added to a reaction mixture and the mixture was extracted with EtOAc twice, then the combined organic layer was concentrated in vacuo. The crude product was triturated with IPA to give titled compound (164 mg, 48%). MS (ESI) m/z 477.4 [M−H]−

Step F: Intermediate 206: rac-tert-Butyl ((1R,2S,5R)-2-hydroxy-5-((3-((trifluoromethyl)sulfonyl)phenyl)carbamoyl)cyclopentyl)carbamate hydrochloride

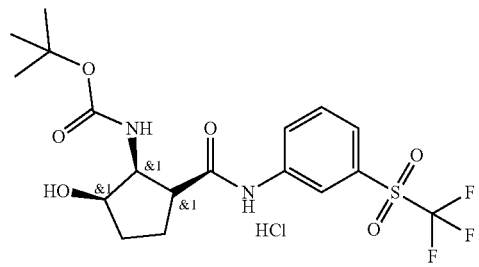

LiOH (80 mg, 3.34 mmol) was added to a solution of Intermediate 205 (160 mg, 0.33 mmol) in THF (3.3 mL) and H₂O (0.84 mL), and the reaction mixture was stirred at rt for 3 hr. H₂O was added to the reaction mixture and the reaction mixture was extracted with EtOAc twice and the combined organic layer was concentrated in vacuo to give titled compound (116 mg, 77%). MS (ESI) m/z 451.3 [M−H]−

Step G: rac-(1R,2R,3S)-2-Amino-3-hydroxy-N-(3-((trifluoromethyl)sulfonyl)phenyl)cyclopentane-1-carboxamide hydrochloride Intermediate 206 (70 mg, 0.15 mmol) was dissolved in 2 M HCl in EtOH (1.6 mL) and the reaction mixture was stirred at rt for 5 hr. The reaction mixture was concentrated in vacuo to give titled compound (62 mg, 103%). MS (ESI) m/z 353.1 [M+H]+.

Intermediate 207: rac-(1R,2R,3R)-2-Amino-3-hydroxy-N-(3-((trifluoromethyl)sulfonyl)phenyl)cyclopentane-1-carboxamide hydrochloride

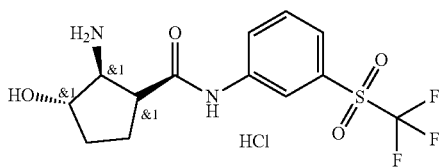

Step A: Intermediate 208: rac-tert-Butyl ((1R,2S,3S,5S)-3-((3-((trifluoromethyl)sulfonyl)phenyl)carbamoyl)-6-oxabicyclo[3.1.0]hexan-2-yl)carbamate

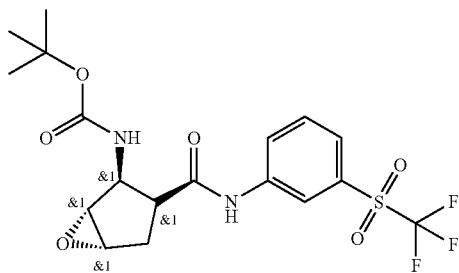

3-((Trifluoromethyl)sulfonyl)aniline (1.33 g, 5.91 mmol) was added to a suspension of NaH (60% in oil suspension, 236 mg, 5.91 mmol) in THF (7.9 mL), then the reaction mixture was stirred at rt for 10 min. The reaction mixture was cooled to 0° C. and rac-tert-butyl (1R,2S,4R,6R)-7-oxo-3-oxa-8-azatricyclo[4.2.0.0²,⁴]octane-8-carboxylate (888 mg, 3.94 mmol) in THF (4 mL) was added to the reaction mixture and the reaction mixture was stirred at rt for 3 hr. Sat aq NH₄Cl was added to the reaction mixture and the mixture was filtered to give titled compound (809 mg, 46%). The filtrate was extracted with EtOAc twice and the combined organic layer was concentrated in vacuo. The crude product was triturated with IPA to give additional titled compound (549 mg, 31%). MS (ESI) m/z 449.4 [M–H]–

Step B: Intermediate 209: rac-tert-Butyl ((1R,2S,3S,5R)-3-bromo-2-hydroxy-5-((3-((trifluoromethyl)sulfonyl)phenyl)carbamoyl)cyclopentyl)carbamate

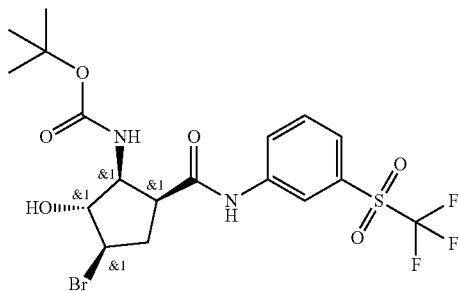 [SMILES: CC(C)(C)OC(=O)N[C@@H]1[C@@H](O)[C@H](Br)C[C@@H]1C(=O)Nc1cccc(S(=O)(=O)C(F)(F)F)c1]

Lithium bromide (289 mg, 3.33 mmol) was added to a solution of Intermediate 208 (300 mg, 0.67 mmol) in acetic acid (4.2 mL) at 0° C., then the reaction mixture was stirred at 0° C. for 1 h and rt for 5 hr. H₂O was added to the reaction mixture and filtered to give titled compound (218 mg, 62%). MS (ESI) m/z 529.2/531.2 [M–H]–

Step C: Intermediate 210: rac-tert-Butyl ((1R,2R,5R)-2-hydroxy-5-((3-((trifluoromethyl)sulfonyl)phenyl)carbamoyl)cyclopentyl)carbamate

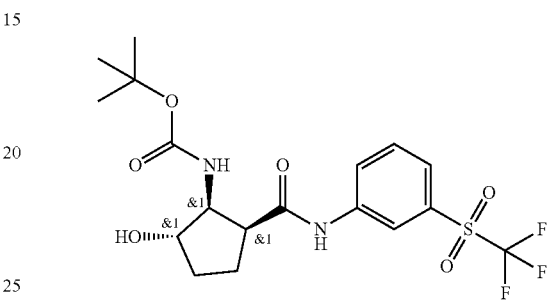

AIBN (14 mg, 0.09 mmol) was added to a solution of Intermediate 209 (455 mg, 0.86 mmol) and tributylstannane (300 mg, 1.03 mmol) in toluene (1.7 mL), then the reaction mixture was stirred at 90° C. for 4 hr. Additional tributylstannane (150 mg, 0.51 mmol) and AIBN (14 mg, 0.09 mmol) was added to the reaction mixture, then the reaction mixture was stirred at 90° C. for 1.5 hr. The reaction precipitate was collected by filtration and washed with toluene to give titled compound (335 mg, 87%). MS (ESI) m/z 451.2 [M–H]–

Step D: rac-(1R,2R,3R)-2-Amino-3-hydroxy-N-(3-((trifluoromethyl)sulfonyl)phenyl)cyclopentane-1-carboxamide hydrochloride Intermediate 210 (120 mg, 0.27 mmol) was dissolved in 2 M HCl in EtOH (3 mL) and the reaction mixture was stirred at rt for 5 hr. The reaction mixture was concentrated in vacuo to give titled compound (107 mg, 103%). MS (ESI) m/z 353.1 [M+H]⁺.

Intermediate 211: rac-(1R,2R,3R)-2-Amino-3-methoxy-N-(3-((trifluoromethyl)sulfonyl)phenyl)cyclopentane-1-carboxamide hydrochloride

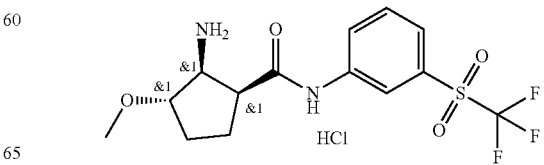

Step A: Intermediate 212: rac-tert-Butyl ((1R,2R, 5R)-2-methoxy-5-((3-((trifluoromethyl)sulfonyl) phenyl)carbamoyl)cyclopentyl)carbamate

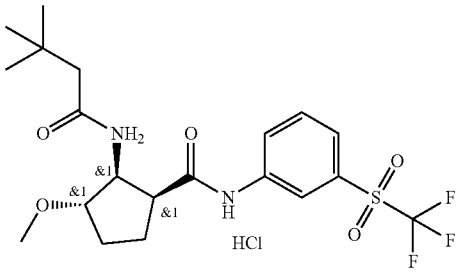 [SMILES: CO[C@H]1CC[C@H](C(=O)Nc2cccc(S(=O)(=O)C(F)(F)F)c2)[C@@H]1NC(=O)CC(C)(C)C ; Cl]

Silver oxide (131 mg, 0.57 mmol) and iodomethane (0.26 mL, 4.23 mmol) were added to a solution of Intermediate 210 (137 mg, 0.26 mmol) in MeCN (2.6 mL), then the reaction mixture was stirred at 50° C. for 6 hr. Additional silver oxide (48 mg, 0.21 mmol) and iodomethane (0.06 mL, 0.93 mmol) were added to the reaction mixture, then the reaction mixture was stirred at 50° C. for 2 h. The reaction mixture was filtered through Celite® and the filtrate was concentrated in vacuo. The crude product was triturated with Et$_2$O to give titled compound (65 mg, 43%). The filtrate was concentrated in vacuo and the residual powder was triturated with THF-hexane to give additional titled compound (50 mg, 33%). MS (ESI) m/z 465.3 [M–H]–

Step B: rac-(1R,2R,3R)-2-Amino-3-methoxy-N-(3-((trifluoromethyl)sulfonyl)phenyl)cyclopentane-1-carboxamide hydrochloride Intermediate 212 (115 mg, 0.20 mmol) was dissolved in 2 M HCl in EtOH (3 mL) and the reaction mixture was stirred at rt for 18 hr. The reaction mixture was concentrated in vacuo and the crude product was triturated with IPA to give titled compound (79 mg, 89%). MS (ESI) m/z 367.2 [M+H]$^+$.

Intermediate 213: rac-(1R,2R,3S,4S)-3-Amino-N-(3-((trifluoromethyl)sulfonyl)phenyl)bicyclo[2.2.1]hept-5-ene-2-carboxamide hydrochloride

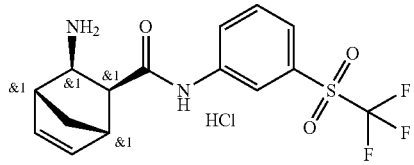 [SMILES: N[C@H]1[C@@H](C(=O)Nc2cccc(S(=O)(=O)C(F)(F)F)c2)[C@@H]2C=C[C@H]1C2 ; Cl]

The titled compound was prepared analogous to Intermediate 187, using rac-(1S,2S,3R,4R)-3-(tert-butoxycarbonylamino)bicyclo[2.2.1]hept-5-ene-2-carboxylic acid instead of Compound 1 and using 3-((trifluoromethyl)sulfonyl)aniline instead of (1-methylcyclobutyl)methylamine hydrochloride. MS (ESI) m/z 361.2 [M+H]$^+$.

Intermediate 214: rac-(1R,2R,3S,4S)-3-Amino-N-(4-fluoro-3-((trifluoromethyl)sulfonyl)phenyl)bicyclo[2.2.1]hept-5-ene-2-carboxamide hydrochloride

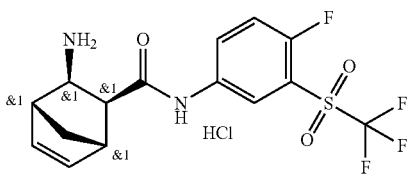 [SMILES: N[C@H]1[C@@H](C(=O)Nc2ccc(F)c(S(=O)(=O)C(F)(F)F)c2)[C@@H]2C=C[C@H]1C2 ; Cl]

The titled compound was prepared analogous to Intermediate 187, using rac-(1S,2S,3R,4R)-3-(tert-butoxycarbonylamino)bicyclo[2.2.1]hept-5-ene-2-carboxylic acid instead of Compound 1 and using 4-fluoro-3-((trifluoromethyl)sulfonyl)aniline instead of (1-methylcyclobutyl)methylamine hydrochloride. MS (APCI) m/z 379.0 [M+H]$^+$.

Intermediate 215: rac-(1R,2R,3S,4S)-3-Amino-N-(3-fluoro-5-(pentafluoro-λ6-sulfaneyl)phenyl)bicyclo[2.2.1]hept-5-ene-2-carboxamide hydrochloride

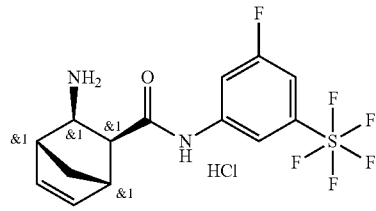 [SMILES: N[C@H]1[C@@H](C(=O)Nc2cc(F)cc(S(F)(F)(F)(F)F)c2)[C@@H]2C=C[C@H]1C2 ; Cl]

The titled compound was prepared analogous to Intermediate 187, using rac-(1S,2S,3R,4R)-3-(tert-butoxycarbonylamino)bicyclo[2.2.1]hept-5-ene-2-carboxylic acid instead of Compound 1 and using 3-fluoro-5-(pentafluoro-λ6-sulfaneyl)aniline instead of (1-methylcyclobutyl)methylamine hydrochloride. MS (ESI) m/z 373.2 [M+H]$^+$.

Intermediate 216: rac-(1R,2S)-2-Amino-N-(3-((trifluoromethyl)sulfonyl)phenyl)cyclopentane-1-carboxamide hydrochloride

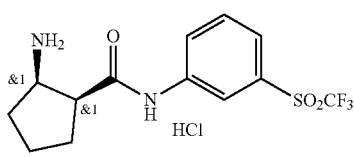

The titled compound was prepared analogous to Intermediate 187, using rac-(1S,2R)-2-(tert-butoxycarbonylamino)cyclopentane-1-carboxylic acid instead of Compound 1 and using 3-((trifluoromethyl)sulfonyl)aniline instead of (1-methylcyclobutyl)methylamine hydrochloride. MS (APCI) m/z 337.0 [M+H]$^+$.

Intermediate 217: (1S,2R)-2-Amino-N-(3-((trifluoromethyl)sulfonyl)phenyl)cyclopentane-1-carboxamide hydrochloride

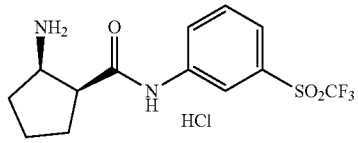

The titled compound was prepared analogous to Intermediate 187, using (1S,2R)-2-(tert-butoxycarbonylamino)cyclopentane-1-carboxylic acid instead of Compound 1 and using 3-((trifluoromethyl)sulfonyl)aniline instead of (1-methylcyclobutyl)methylamine hydrochloride. MS (ESI) m/z 337.2 [M+H]$^+$.

Intermediate 218: (1S,2R)-2-Amino-N-(4-fluoro-3-(pentafluoro-λ6-sulfaneyl)phenyl)cyclopentane-1-carboxamide hydrochloride

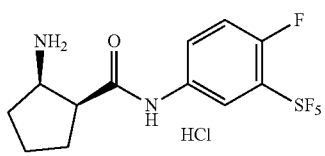

The titled compound was prepared analogous to Intermediate 187, using (1S,2R)-2-(tert-butoxycarbonylamino)cyclopentane-1-carboxylic acid instead of Compound 1 and using 4-fluoro-3-(pentafluoro-λ6-sulfaneyl)aniline instead of (1-methylcyclobutyl)methylamine hydrochloride. MS (ESI) m/z 349.1 [M+H]$^+$.

Intermediate 219: (1R,2S,3R,4S)-3-Amino-N-(4-fluoro-3-(pentafluoro-λ6-sulfaneyl)phenyl)bicyclo[2.2.1]heptane-2-carboxamide hydrochloride

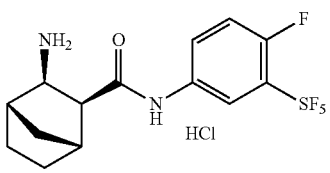

The titled compound was prepared analogous to Intermediate 187, using (1R,2S,3R,4S)-3-(tert-butoxycarbonylamino)bicyclo[2.2.1]heptane-2-carboxylic acid instead of Compound 1 and using 4-fluoro-3-(pentafluoro-λ6-sulfaneyl)aniline instead of (1-methylcyclobutyl)methylamine hydrochloride. MS (ESI) m/z 375.1 [M+H]$^+$.

Intermediate 220: (1R,2S,3R,4S)-3-Amino-N-((1-(trifluoromethyl)cyclobutyl)methyl)bicyclo[2.2.1]heptane-2-carboxamide hydrochloride

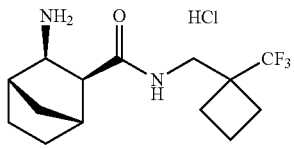 [SMILES: N[C@@H]1[C@H]2CC[C@H](C2)[C@@H]1C(=O)NCC1(C(F)(F)F)CCC1 ; Cl]

The titled compound was prepared analogous to Intermediate 187, using (1R,2S,3R,4S)-3-(tert-butoxycarbonylamino)bicyclo[2.2.1]heptane-2-carboxylic acid instead of Compound 1 and using (1-trifluoromethylcyclobutyl)methylamine hydrochloride instead of (1-methylcyclobutyl)methylamine hydrochloride.

Intermediate 221: (1S,2S,3R,4R)-3-Amino-N-((1-methylcyclobutyl)methyl)bicyclo[2.2.1]heptane-2-carboxamide hydrochloride

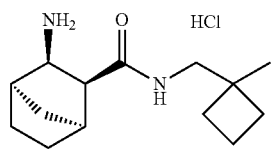 [SMILES: CC1(CNC(=O)[C@H]2[C@H]3CC[C@H](C3)[C@H]2N)CCC1 ; Cl]

The titled compound was prepared analogous to Intermediate 187, using (1S,2S,3R,4R)-3-(tert-butoxycarbonylamino)bicyclo[2.2.1]heptane-2-carboxylic acid instead of Compound 1.

Intermediate 222: (1S,2S,3R,4R)-3-Amino-N-neopentylbicyclo[2.2.1]heptane-2-carboxamide hydrochloride

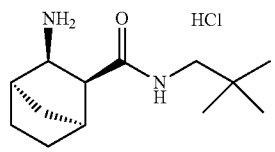 [SMILES: CC(C)(C)CNC(=O)[C@H]1[C@H]2CC[C@H](C2)[C@H]1N ; Cl]

The titled compound was prepared analogous to Intermediate 187, using (1S,2S,3R,4R)-3-(tert-butoxycarbonylamino)bicyclo[2.2.1]heptane-2-carboxylic acid instead of Compound 1 and using neopentylamine instead of (1-methylcyclobutyl)methylamine hydrochloride.

Intermediate 223: (1R,2S,3R,4S)-3-Amino-N-(3-fluorobicyclo[1.1.1]pentan-1-yl)bicyclo[2.2.1]heptane-2-carboxamide hydrochloride

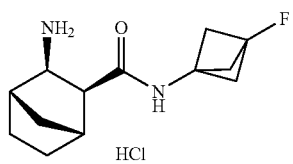 [SMILES: N[C@@H]1[C@H]2CC[C@H](C2)[C@@H]1C(=O)NC12CC(F)(C1)C2 ; Cl]

The titled compound was prepared analogous to Intermediate 187, using (1R,2S,3R,4S)-3-(tert-butoxycarbonylamino)bicyclo[2.2.1]heptane-2-carboxylic acid instead of Compound 1 and using neopentylamine instead of (1-methylcyclobutyl)methylamine hydrochloride. MS (ESI) m/z 239.2 [M+H]+.

Intermediate 224: (1R,2S,3R,4S)-3-Amino-N-neopentylbicyclo[2.2.1]heptane-2-carboxamide hydrochloride

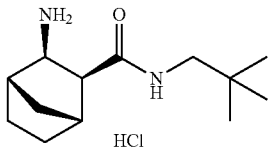 [SMILES: CC(C)(C)CNC(=O)[C@H]1[C@@H]2CC[C@@H](C2)[C@H]1N ; Cl]

The titled compound was prepared analogous to Intermediate 187, using (1R,2S,3R,4S)-3-(tert-butoxycarbonylamino)bicyclo[2.2.1]heptane-2-carboxylic acid instead of Compound 1 and using neopentylamine instead of (1-methylcyclobutyl)methylamine hydrochloride. MS (ESI) m/z 225.3 [M+H]+.

Intermediate 225: (1R,2S,3R,4S)-3-Amino-N-(3,3,3-trifluoro-2,2-dimethylpropyl)bicyclo[2.2.1]heptane-2-carboxamide hydrochloride

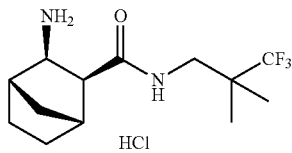 [SMILES: CC(C)(CNC(=O)[C@H]1[C@@H]2CC[C@@H](C2)[C@H]1N)C(F)(F)F ; Cl]

The titled compound was prepared analogous to Intermediate 187, using (1R,2S,3R,4S)-3-(tert-butoxycarbonylamino)bicyclo[2.2.1]heptane-2-carboxylic acid instead of Compound 1 and using 3-methyl-3-trifluoromethylpropylamine instead of (1-methylcyclobutyl)methylamine hydrochloride. MS (ESI) m/z 279.2 [M+H]+.

Intermediate 226: (1R,2S,3R,4S)-3-Amino-N-(3-((trifluoromethyl)sulfonyl)phenyl)bicyclo[2.2.1]heptane-2-carboxamide hydrochloride

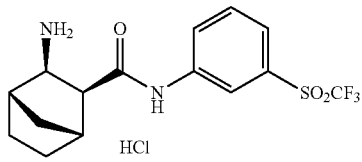

The titled compound was prepared analogous to Intermediate 187, using (1R,2S,3R,4S)-3-(tert-butoxycarbonylamino)bicyclo[2.2.1]heptane-2-carboxylic acid instead of Compound 1 and using 3-((trifluoromethyl)sulfonyl)aniline instead of (1-methylcyclobutyl)methylamine hydrochloride. MS (ESI) m/z 363.2 [M+H]+.

Intermediate 227: (1S,2S,3R,4R)-3-Amino-N-(4-fluoro-3-((trifluoromethyl)sulfonyl)phenyl)bicyclo[2.2.1]hept-5-ene-2-carboxamide hydrochloride

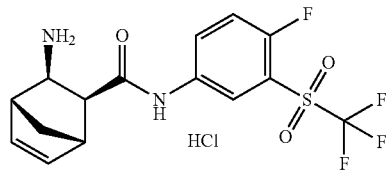 [SMILES: N[C@H]1[C@@H](C(=O)Nc2ccc(F)c(S(=O)(=O)C(F)(F)F)c2)[C@@H]2C=C[C@H]1C2 ; Cl]

The titled compound was prepared analogous to Intermediate 187, using (1S,2S,3R,4R)-3-(tert-butoxycarbonylamino)bicyclo[2.2.1]hept-5-ene-2-carboxylic acid instead of Compound 1 and using 4-fluoro-3-((trifluoromethyl)sulfonyl)aniline instead of (1-methylcyclobutyl)methylamine hydrochloride. MS (APCI) m/z 379.0 [M+H]+.

Intermediate 228: (1S,2R)-2-Amino-N-(4-fluoro-3-(trifluoromethyl)phenyl)cyclopentane-1-carboxamide hydrochloride

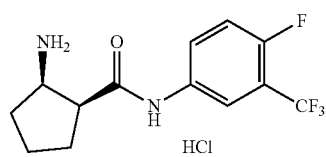 [SMILES: N[C@@H]1CCC[C@@H]1C(=O)Nc1ccc(F)c(C(F)(F)F)c1 ; Cl]

The titled compound was prepared analogous to Intermediate 187, using (1S,2R)-2-(tert-butoxycarbonylamino)cyclopentane-1-carboxylic acid instead of Compound 1 and using 4-fluoro-3-(trifluoromethyl)aniline instead of (1-methylcyclobutyl)methylamine hydrochloride. MS (APCI) m/z 291.0 [M+H]+.

Intermediate 229: (1S,2S,3R,4R)-3-Amino-N-(4-fluoro-3-(trifluoromethyl)phenyl)bicyclo[2.2.1]hept-5-ene-2-carboxamide hydrochloride

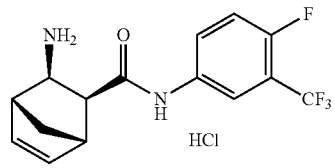 [SMILES: N[C@H]1[C@@H](C(=O)Nc2ccc(F)c(C(F)(F)F)c2)[C@@H]2C=C[C@H]1C2 ; Cl]

The titled compound was prepared analogous to Intermediate 187, using (1S,2S,3R,4R)-3-(tert-butoxycarbonylamino)bicyclo[2.2.1]hept-5-ene-2-carboxylic acid instead of Compound 1 and using 4-fluoro-3-(trifluoromethyl)aniline instead of (1-methylcyclobutyl)methylamine hydrochloride. MS (APCI) m/z 315.0 [M+H]+.

Intermediate 230: (1R,2R,3S,4S)-3-Amino-N-(4-fluoro-3-(trifluoromethyl)phenyl)bicyclo[2.2.1]hept-5-ene-2-carboxamide hydrochloride

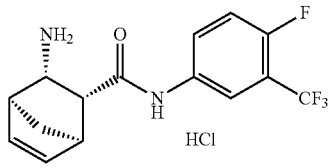 [SMILES: N[C@@H]1[C@H](C(=O)Nc2ccc(F)c(C(F)(F)F)c2)[C@H]2C=C[C@@H]1C2 ; Cl]

The titled compound was prepared analogous to Intermediate 187, using (1R,2R,3S,4S)-3-(tert-butoxycarbonylamino)bicyclo[2.2.1]hept-5-ene-2-carboxylic acid instead of Compound 1 and using 4-fluoro-3-(trifluoromethyl)aniline instead of (1-methylcyclobutyl)methylamine hydrochloride. MS (APCI) m/z 315.1 [M+H]$^+$.

Intermediate 231: rac-(1R,2R,3S,4S)-3-Amino-N-(3-((trifluoromethyl)sulfonyl)phenyl)bicyclo[2.2.1]heptane-2-carboxamide hydrochloride

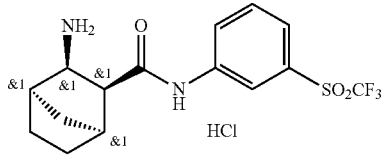

The titled compound was prepared analogous to Intermediate 187, using rac-(1R,2R,3S,4S)-3-(tert-butoxycarbonylamino)bicyclo[2.2.1]heptane-2-carboxylic acid instead of Compound 1 and using 3-(trifluoromethyl)aniline instead of (1-methylcyclobutyl)methylamine hydrochloride. MS (ESI) m/z 363.1 [M+H].

Intermediate 232: (1S,2S,3R,4R)-3-Amino-N-(3-((trifluoromethyl)sulfonyl)phenyl)bicyclo[2.2.1]heptane-2-carboxamide hydrochloride

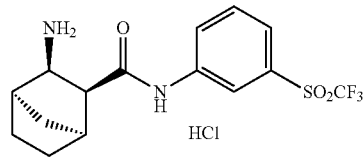

The titled compound was prepared analogous to Intermediate 187, using (1S,2S,3R,4R)-3-(tert-butoxycarbonylamino)bicyclo[2.2.1]heptane-2-carboxylic acid instead of Compound 1 and using 3-(trifluoromethyl)aniline instead of (1-methylcyclobutyl)methylamine hydrochloride. MS (ESI) m/z 363.1 [M+H]$^+$.

Intermediate 233: rac-(1R,2R,3S,4S)-3-Amino-N-(3-(pentafluoro-λ6-sulfaneyl)phenyl)bicyclo[2.2.1]heptane-2-carboxamide hydrochloride

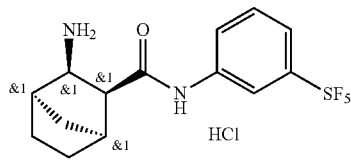

The titled compound was prepared analogous to Intermediate 187, using rac-(1R,2R,3S,4S)-3-(tert-butoxycarbonylamino)bicyclo[2.2.1]heptane-2-carboxylic acid instead of Compound 1 and using 3-(pentafluoro-λ6-sulfaneyl)aniline instead of (1-methylcyclobutyl)methylamine hydrochloride. MS (APCI) m/z 357.0 [M+H]$^+$.

Intermediate 234: (1S,2S,3R,4R)-3-Amino-N-(4-fluoro-3-(pentafluoro-λ6-sulfaneyl)phenyl)bicyclo[2.2.1]hept-5-ene-2-carboxamide hydrochloride

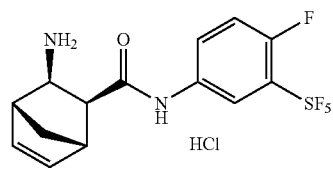

The titled compound was prepared analogous to Intermediate 187, using (1S,2S,3R,4R)-3-(tert-butoxycarbonylamino)bicyclo[2.2.1]hept-5-ene-2-carboxylic acid instead of Compound 1 and using 4-fluoro-3-(pentafluoro-λ6-sulfaneyl)aniline instead of (1-methylcyclobutyl)methylamine hydrochloride. MS (ESI) m/z 373.1 [M+H]$^+$.

Intermediate 235: rac-(1R,2R,3S,4S)-3-Amino-N-(4-fluoro-3-(pentafluoro-6-sulfaneyl)phenyl)bicyclo[2.2.1]heptane-2-carboxamide hydrochloride

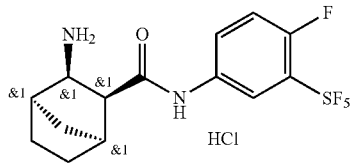

The titled compound was prepared analogous to Intermediate 187, using rac-(1R,2R,3S,4S)-3-(tert-butoxycarbonylamino)bicyclo[2.2.1]heptane-2-carboxylic acid instead of Compound 1 and using 4-fluoro-3-(pentafluoro-λ6-sulfaneyl)aniline instead of (1-methylcyclobutyl)methylamine hydrochloride. MS (ESI) m/z 375.1 [M+H]$^+$.

Intermediate 236: rac-(3R,4R)-3-Amino-N-(3-((trifluoromethyl)sulfonyl)phenyl)tetrahydro-2H-pyran-4-carboxamide hydrochloride

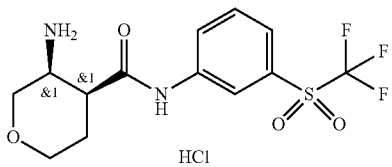 [SMILES: N[C@@H]1COCC[C@@H]1C(=O)Nc1cccc(S(=O)(=O)C(F)(F)F)c1 ; Cl]

The titled compound was prepared analogous to Intermediate 187, using rac-(3R,4R)-3-(tert-butoxycarbonylamino)tetrahydro-2H-pyran-4-carboxylic acid instead of Compound 1 and using 3-((trifluoromethyl)sulfonyl)aniline instead of (1-methylcyclobutyl)methylamine hydrochloride. MS (ESI) m/z 353.3 [M+H]$^+$.

Intermediate 237: rac-(3R,4R)-3-Amino-N-(4-fluoro-3-(pentafluoro-λ6-sulfaneyl)phenyl)tetrahydro-2H-pyran-4-carboxamide hydrochloride

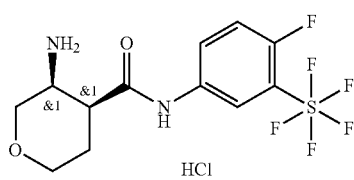 [SMILES: N[C@@H]1COCC[C@@H]1C(=O)Nc1ccc(F)c(S(F)(F)(F)(F)F)c1 ; Cl]

The titled compound was prepared analogous to Intermediate 187, using rac-(3R,4R)-3-(tert-butoxycarbonylamino)tetrahydro-2H-pyran-4-carboxylic acid instead of Compound 1 and using 4-fluoro-3-(pentafluoro-λ6-sulfaneyl)aniline instead of (1-methylcyclobutyl)methylamine hydrochloride.

Intermediate 238: (2S,3R)-3-Amino-N-(3-((trifluoromethyl)sulfonyl)phenyl)tetrahydro-2H-pyran-2-carboxamide hydrochloride

Step A: (2S,3R)-3-((tert-Butoxycarbonyl)amino)tetrahydro-2H-pyran-2-carboxylic acid

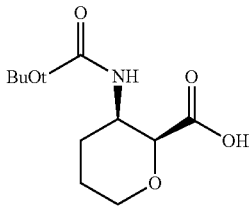

The titled compound was prepared analogous to Intermediate 196 Step B, using methyl (2S,3R)-3-((tert-butoxycarbonyl)amino)tetrahydro-2H-pyran-2-carboxylate instead of Intermediate 197.

Step B: (2S,3R)-3-Amino-N-(3-((trifluoromethyl)sulfonyl)phenyl)tetrahydro-2H-pyran-2-carboxamide hydrochloride The titled compound was prepared analogous to Intermediate 187, using (2S,3R)-3-((tert-butoxycarbonyl)amino)tetrahydro-2H-pyran-2-carboxylic acid instead of Compound 1 and using 3-((trifluoromethyl)sulfonyl)aniline instead of (1-methylcyclobutyl)methylamine hydrochloride.

Intermediate 239: rac-(1R,2S)-2-Amino-N-(3-((trifluoromethyl)sulfonyl)phenyl)cycloheptane-1-carboxamide hydrochloride

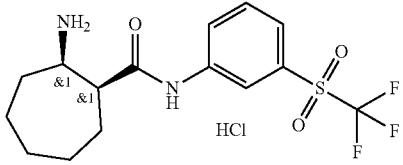 [SMILES: N[C@@H]1CCCCC[C@@H]1C(=O)Nc1cccc(S(=O)(=O)C(F)(F)F)c1 ; Cl]

The titled compound was prepared analogous to Intermediate 187, using rac-(1R,2S)-2-(tert-butoxycarbonylamino)cycloheptane-1-carboxylic acid instead of Compound 1 and using 3-((trifluoromethyl)sulfonyl)aniline instead of (1-methylcyclobutyl)methylamine hydrochloride.

Intermediate 240: rac-(3R,4R)-4-Amino-N-(3-((trifluoromethyl)sulfonyl)phenyl)tetrahydro-2H-pyran-3-carboxamide hydrochloride

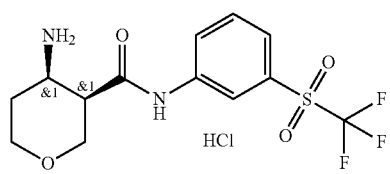 [SMILES: N[C@@H]1CCOC[C@@H]1C(=O)Nc1cccc(S(=O)(=O)C(F)(F)F)c1 ; Cl]

The titled compound was prepared analogous to Intermediate 187, using rac-(3R,4R)-4-(tert-butoxycarbonylamino)tetrahydro-2H-pyran-3-carboxylic acid instead of Compound 1 and using 3-((trifluoromethyl)sulfonyl)aniline instead of (1-methyl cyclobutyl)methylamine hydrochloride.

Intermediate 241: (2S,3R)-3-Amino-N-(3-((trifluoromethyl)sulfonyl)phenyl)tetrahydrofuran-2-carboxamide hydrochloride

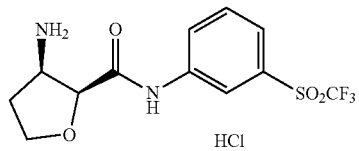

The titled compound was prepared analogous to Intermediate 187, using (2S,3R)-3-(tert-butoxycarbonylamino)tetrahydrofuran-2-carboxylic acid instead of Compound 1 and using 3-((trifluoromethyl)sulfonyl)aniline instead of (1-methylcyclobutyl)methylamine hydrochloride.

Intermediate 242: rac-(3R,4S)-4-Amino-N-((1-methylcyclobutyl)methyl)tetrahydrofuran-3-carboxamide hydrochloride

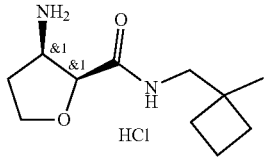

The titled compound was prepared analogous to Intermediate 187, using rac-(3R,4S)-4-(tert-butoxycarbonylamino)tetrahydrofuran-3-carboxylic acid instead of Compound 1. MS (ESI) m/z 213.2 [M+H]⁺.

Intermediate 243: rac-(3R,4S)-4-Amino-N-neopentyltetrahydrofuran-3-carboxamide hydrochloride

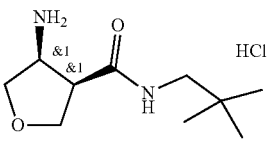

The titled compound was prepared analogous to Intermediate 187, using rac-(3R,4S)-4-(tert-butoxycarbonylamino)tetrahydrofuran-3-carboxylic acid instead of Compound 1 and using neopentylamine instead of (1-methylcyclobutyl)methylamine hydrochloride.

Intermediate 244: rac-(3R,4S)-4-Amino-N-(3-((trifluoromethyl)sulfonyl)phenyl)tetrahydrofuran-3-carboxamide hydrochloride

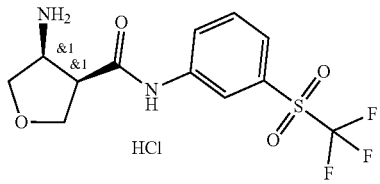 [SMILES: N[C@@H]1COC[C@@H]1C(=O)Nc1cccc(S(=O)(=O)C(F)(F)F)c1 ; Cl]

The titled compound was prepared analogous to Intermediate 187, using rac-(3R,4S)-4-(tert-butoxycarbonylamino)tetrahydrofuran-3-carboxylic acid instead of Compound 1 and using 3-((trifluoromethyl)sulfonyl)aniline instead of (1-methylcyclobutyl)methylamine hydrochloride.

Intermediate 245: rac-(3R,4S)-4-Amino-N-(4-fluoro-3-(pentafluoro-λ6-sulfaneyl)phenyl)tetrahydrofuran-3-carboxamide hydrochloride

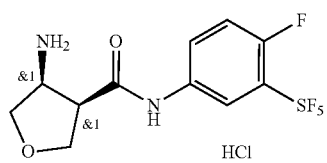

The titled compound was prepared analogous to Intermediate 187, using rac-(3R,4S)-4-(tert-butoxycarbonylamino)tetrahydrofuran-3-carboxylic acid instead of Compound 1 and using 4-fluoro-3-(pentafluoro-λ6-sulfaneyl)aniline instead of (1-methylcyclobutyl)methylamine hydrochloride.

Intermediate 246: rac-(1R,2S,4S)-2-Amino-4-hydroxy-N-(3-(((trifluoromethyl)sulfonyl)phenyl)cyclopentane-1-carboxamide

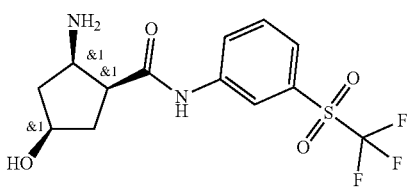 [SMILES: N[C@@H]1C[C@H](O)C[C@@H]1C(=O)Nc1cccc(S(=O)(=O)C(F)(F)F)c1]

The titled compound was prepared analogous to Intermediate 176 Step B-D, using rac-methyl (1S,2R,4R)-2-(((benzyloxy)carbonyl)amino)-4-hydroxycyclopentane-1-carboxylate instead of rac-methyl (1R,2R,3S,4S)-3-(((benzyloxy)carbonyl)amino)-7-oxabicyclo[2.2.1]heptane-2-carboxylate and using 3-((trifluoromethyl)sulfonyl)aniline instead of (1-methylcyclobutyl)methylamine hydrochloride.

Intermediate 247: rac-(1R,2S,4R)-2-Amino-4-methoxy-N-neopentylcyclopentane-1-carboxamide

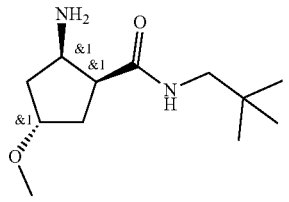 [SMILES: CO[C@@H]1C[C@@H](N)[C@@H](C(=O)NCC(C)(C)C)C1]

The titled compound was prepared analogous to Intermediate 176 Step C and D, using rac-(1R,2S,4R)-2-(((benzyloxy)carbonyl)amino)-4-methoxycyclopentane-1-carboxylic acid instead of Intermediate 178 and using neopentylamine instead of (1-methylcyclobutyl)methylamine hydrochloride.

Intermediate 248: rac-(1R,2S,4R)-2-Amino-4-methoxy-N-((1-methylcyclobutyl)methyl)cyclopentane-1-carboxamide

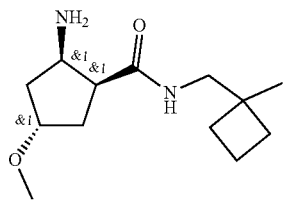 [SMILES: CO[C@@H]1C[C@@H](N)[C@@H](C(=O)NCC2(C)CCC2)C1]

The titled compound was prepared analogous to Intermediate 176 Step C and D, using rac-(1R,2S,4R)-2-(((benzyloxy)carbonyl)amino)-4-methoxycyclopentane-1-carboxylic acid instead of Intermediate 178. MS (ESI) m/z 241.2 [M+H]$^+$.

Intermediate 249: (1R,2S,3R,4S,5S,6R)-3-Amino-5,6-dihydroxy-N-(3-((trifluoromethyl)sulfonyl)phenyl)bicyclo[2.2.1]heptane-2-carboxamide hydrochloride

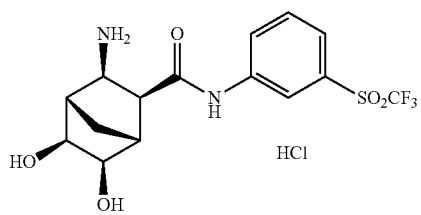

Step A: Intermediate 250: tert-Butyl ((1R,2R,3S,4S)-3-((3-((trifluoromethyl)sulfonyl)phenyl)carbamoyl)bicyclo[2.2.1]hept-5-en-2-yl)carbamate

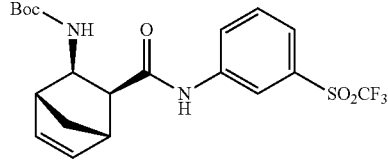

T3P (1.7 M in EtOAc, 2.30 mL, 3.90 mmol) and DIPEA (1.02 mL, 5.90 mmol) were added to a solution of (1S,2S,3R,4R)-3-(tert-butoxycarbonylamino)bicyclo[2.2.1]hept-5-ene-2-carboxylic acid (500 mg, 1.97 mmol) and 3-((trifluoromethyl)sulfonyl)aniline (489 mg, 2.17 mmol) in EtOAc (5 mL), then the reaction mixture was stirred at rt for 7 hr. Sat aq NaHCO$_3$ was added to a reaction mixture and the mixture was extracted with EtOAc three times, then the combined organic layer was concentrated in vacuo. The crude product was purified by flash chromatography using CHCl$_3$ as mobile phase to give the title compound (493 mg, 54%). MS (ESI) m/z 405.1 [M+H-tBuH]+

Step B: Intermediate 251: tert-Butyl ((1S,2R,3S,4R,5R,6S)-5,6-dihydroxy-3-((3-((trifluoromethyl)sulfonyl)phenyl)carbamoyl)bicyclo[2.2.1]heptan-2-yl)carbamate

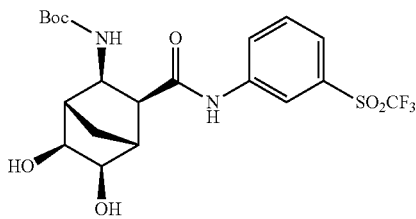

OsO4 (microcapsulated, 273 mg, 0.107 mmol) and N-methylmorpholine N-oxide (0.9 mL, 4.40 mmol) were added to a solution of Intermediate 250 (493 mg, 1.07 mmol) in MeCN (3 mL) and acetone (3 mL), and the reaction mixture was stirred at rt for 24 hr. Iodomethane (0.38 mL, 6.07 mmol) was added and the reaction mixture was stirred at 40° C. for 20 hr. The reaction mixture was filtered with Celite®, then the filtrate was concentrated in vacuo. The crude product was purified by flash chromatography using a gradient of 0-10% MeOH in CHCl$_3$ as mobile phase to give the title compound (498 mg, 94%). MS (ESI) m/z 439.1 [M+H-tBuH]+

Step C: (1R,2S,3R,4S,5S,6R)-3-Amino-5,6-dihydroxy-N-(3-((trifluoromethyl)sulfonyl)phenyl)bicyclo[2.2.1]heptane-2-carboxamide hydrochloride 4 M HCl in EtOAc (3 mL) was added to a solution of Intermediate 251 (498 mg, 1.00 mmol) in MeOH (2 mL), and the reaction mixture was stirred at rt for 18 hr. The reaction mixture was concentrated in vacuo to give titled compound (434 mg, 100%).

Intermediate 252: rac-(1R,2R,3S,4R)-2-Amino-3,4-dihydroxy-N-(3-((trifluoromethyl)sulfonyl)phenyl)cyclopentane-1-carboxamide hydrochloride

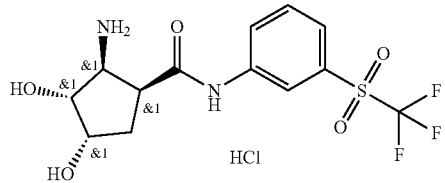 [SMILES: N[C@@H]1[C@@H](O)[C@@H](O)C[C@@H]1C(=O)Nc1cccc(S(=O)(=O)C(F)(F)F)c1 ; Cl]

The titled compound was prepared analogous to Intermediate 249, using rac-(1S,2R)-2-(tert-butoxycarbonylamino)cyclopent-3-ene-1-carboxylic acid instead of (1S,2S,3R,4R)-3-(tert-butoxycarbonylamino)bicyclo[2.2.1]hept-5-ene-2-carboxylic acid.

Intermediate 253: rac-(1R,2S)-2-Amino-4,4-difluoro-N-(4-fluoro-3-(trifluoromethyl)phenyl)cyclopentane-1-carboxamide hydrochloride

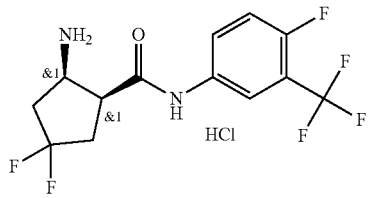 [SMILES: N[C@@H]1CC(F)(F)C[C@@H]1C(=O)Nc1ccc(F)c(C(F)(F)F)c1 ; Cl]

The titled compound was prepared analogous to Intermediate 187, using rac-(1S,2R)-2-(tert-butoxycarbonylamino)-4,4-difluoro-cyclopentanecarboxylic acid instead of Compound 1 and using 4-fluoro-3-(trifluoromethyl)aniline instead of (1-methylcyclobutyl)methylamine hydrochloride.

Intermediate 254: rac-(1R,2S,3R,4S)-3-Amino-N-((1-methylcyclobutyl)methyl)bicyclo[2.2.1]heptane-2-carboxamide hydrochloride

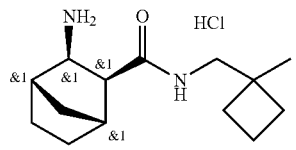 [SMILES: CC1(CNC(=O)[C@H]2[C@@H]3CC[C@@H](C3)[C@H]2N)CCC1 ; Cl]

The titled compound was prepared analogous to Intermediate 187, using rac-(1R,2S,3R,4S)-3-(tert-butoxycarbonylamino)bicyclo[2.2.1]heptane-2-carboxylic acid instead of Compound 1. MS (ESI) m/z 237.2 [M+H]⁺.

Intermediate 255: rac-(1R,2R,3S,4S)-3-Amino-N-neopentylbicyclo[2.2.1]heptane-2-carboxamide hydrochloride

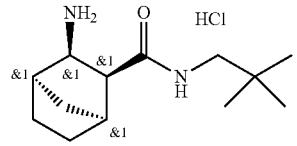 [SMILES: CC(C)(C)CNC(=O)[C@H]1[C@H]2CC[C@H](C2)[C@H]1N ; Cl]

The titled compound was prepared analogous to Intermediate 187, using rac-(1R,2R,3S,4S)-3-(tert-butoxycarbonylamino)bicyclo[2.2.1]heptane-2-carboxylic acid instead of Compound 1 and using neopentylamine instead of (1-methylcyclobutyl)methylamine hydrochloride. MS (ESI) m/z 237.2 [M+H]⁺.

Intermediate 256: (1S,2S,3R,4R)-3-Amino-N-(3-((trifluoromethyl)sulfonyl)phenyl)bicyclo[2.2.1]hept-5-ene-2-carboxamide hydrochloride

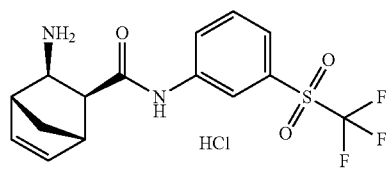 [SMILES: N[C@H]1[C@@H](C(=O)Nc2cccc(S(=O)(=O)C(F)(F)F)c2)[C@@H]2C=C[C@H]1C2 ; Cl]

The titled compound was prepared analogous to Intermediate 207 Step D, using Intermediate 250 instead of Intermediate 210. MS (APCI) m/z 361.0 [M+H]⁺.

Intermediate 257: Ethyl 1-(cyanomethyl)-4-hydroxycyclohexane-1-carboxylate

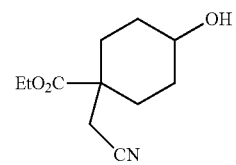

Step A: Intermediate 258: Ethyl 8-(cyanomethyl)-1,4-dioxaspiro[4.5]decane-8-carboxylate

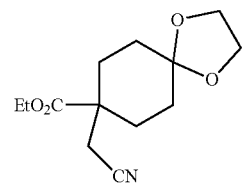

n-BuLi (2.6 M in hexane, 3.87 mL, 10.3 mmol) was added dropwise to 0° C. cooled solution of DIA (1.14 g, 11.2 mmol) in THF (12 mL) and the reaction mixture was stirred at 0° C. for 30 min. Ethyl 1,4-dioxaspiro[4.5]decane-8-carboxylate (2 g, 9.33 mmol) in THF (3 mL) was added dropwise to a reaction mixture was stirred at −78° C. for 1 hr. 2-Bromoacetonitrile (1.68 g, 14.0 mmol) was added to a reaction mixture and the mixture was stirred at rt for 4 hr. Sat aq NH$_4$Cl was added to the reaction mixture and the mixture was extracted with EtOAc twice. The combined organic layer was concentrated in vacuo. The crude product was purified by flash chromatography using a gradient of 0-35% EtOAc in hexane as mobile phase to give the title compound (900 mg, 38%). MS (ESI) m/z 254.1 [M+H]$^+$.

Step B: Ethyl 1-(cyanomethyl)-4-hydroxycyclohexane-1-carboxylate

2 M aq HCl (5 mL) was added to a solution of Intermediate 258 (900 mg, 3.55 mmol) in acetone (5 mL) and the reaction mixture was stirred at rt for 20 hr. The reaction mixture was concentrated in vacuo, and H$_2$O and EtOAc were added and the mixture was extracted with EtOAc twice. The combined organic layer was concentrated in vacuo. The crude product was dissolved in EtOH (7 mL) and NaBH$_4$ (161 mg, 4.26 mmol) was added portionwise to 0° C. cooled solution of mixture. The reaction mixture was stirred at 0° C. for 1 hr. Sat aq NH$_4$Cl was added to the reaction mixture and the mixture was extracted with EtOAc twice. The combined organic layer was concentrated in vacuo. The crude product was purified by flash chromatography using a gradient of 10-60% EtOAc in hexane as mobile phase to give the title compound (649 mg, 87%) as cis/trans mixture. MS (ESI) m/z 194.1 [M+H−H$_2$O]$^+$ Intermediate 259: tert-Butyl (1s,4s)-4-hydroxy-1-(trifluoromethyl)cyclohexane-1-carboxylate

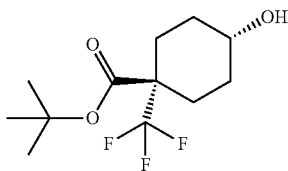 [SMILES: CC(C)(C)OC(=O)[C@]1(C(F)(F)F)CC[C@@H](O)CC1]

Step A: Intermediate 260: tert-Butyl 4-oxo-1-(trifluoromethyl)cyclohexane-1-carboxylate

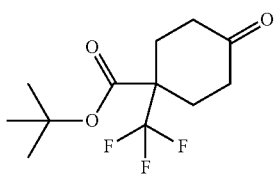 [SMILES: CC(C)(C)OC(=O)C1(C(F)(F)F)CCC(=O)CC1]

A mixture of tert-butyl 2-(trifluoromethyl)prop-2-enoate and trimethyl(1-methyleneallyloxy)silane was stirred at 140° C. for 6 hr. THF (5 mL) and 0.1 M aq HCl (5 mL) were added to the reaction mixture and the mixture was stirred at rt for 16 hr. H$_2$O was added to the reaction mixture and the mixture was extracted with EtOAc twice. The combined organic layer was washed with sat aq NaHCO$_3$ and was concentrated in vacuo. The crude product was purified by flash chromatography using a gradient of 0-50% EtOAc in hexane as mobile phase to give the title compound (880 mg, 65%).

Step B: Intermediate 261: tert-Butyl (1r,4r)-4-hydroxy-1-(trifluoromethyl)cyclohexane-1-carboxylate

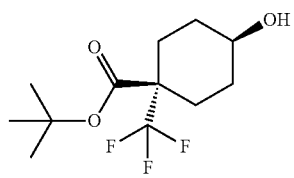 [SMILES: CC(C)(C)OC(=O)[C@]1(C(F)(F)F)CC[C@H](O)CC1]

NaBH$_4$ (150 mg, 3.97 mmol) was added portionwise to 0° C. cooled solution of Intermediate 260 (880 mg, 3.30 mmol) in EtOH (5 mL). The reaction mixture was stirred at 0° C. for 1 hr. Sat aq NH$_4$Cl was added to the reaction mixture and the mixture was extracted with EtOAc twice. The combined organic layer was concentrated in vacuo. The crude product was purified by flash chromatography using a gradient of 0-35% EtOAc in hexane as mobile phase to give the title compound (869 mg, 98%).

Step C: tert-Butyl (1s,4s)-4-hydroxy-1-(trifluoromethyl)cyclohexane-1-carboxylate Di-2-methoxyethyl azodicarboxylate (869 mg, 4.86 mmol) in THF (10 mL) was added dropwise to a solution of p-nitrobenzoic acid (812 mg, 4.86 mmol), Intermediate 261 (869 mg, 3.24 mmol) and triphenylphosphine (1.27 g, 4.84 mmol) at 0° C., and the reaction mixture was stirred at rt for 7 hr. The reaction mixture was diluted with EtOAc and the mixture was washed with H$_2$O twice, then the organic layer was concentrated in vacuo to give crude p-nitrobenzoate derivative. Potassium carbonate (1.04 g, 7.52 mmol) in H$_2$O (2 mL) was added to a mixture of above crude product in MeOH (8 mL) and the reaction mixture was stirred at reflux for 3 hr. After being concentrated the solvent, H$_2$O was added to the reaction mixture and then the mixture was extracted with CHCl$_3$, then the organic layer was concentrated in vacuo. The crude product was purified by flash chromatography using a gradient of 0-30% EtOAc in hexane as mobile phase to give the title compound (630 mg, 72%).

Intermediate 262: Benzyl (1s,4s)-4-hydroxy-1-methoxycyclohexane-1-carboxylate

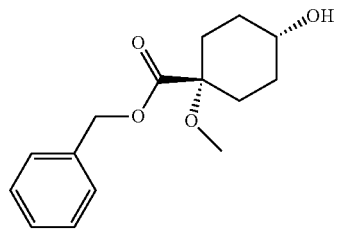 [SMILES: CO[C@]1(C(=O)OCc2ccccc2)CC[C@H](O)CC1]

NaBH$_4$ (204 mg, 5.39 mmol) was added portionwise to −78° C. cooled solution of benzyl 1-methoxy-4-oxo-cyclohexane-1-carboxylate (705 mg, 2.69 mmol) in EtOH (5 mL). The reaction mixture was stirred at 0° C. for 4 hr. Sat aq NH₄Cl was added to the reaction mixture and the mixture was extracted with EtOAc twice. The combined organic layer was concentrated in vacuo. The crude product was purified by flash chromatography using a gradient of 0-60% EtOAc in hexane as mobile phase to give the title compound (536 mg, 75%). MS (ESI) m/z 265 [M+H]⁺.

Intermediate 263: Benzyl (1r,4r)-1-((benzyloxy)methyl)-4-hydroxycyclohexane-1-carboxylate

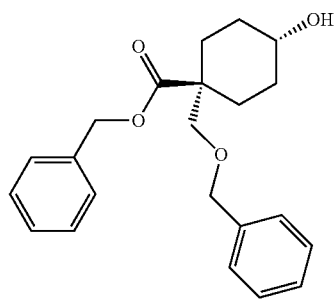 [SMILES: O=C(OCc1ccccc1)[C@]1(COCc2ccccc2)CC[C@@H](O)CC1]

Step A: Intermediate 264: Benzyl 8-((benzyloxy)methyl)-1,4-dioxaspiro[4.5]decane-8-carboxylate

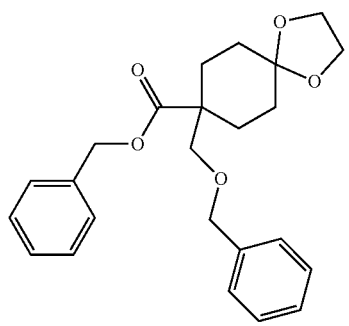 [SMILES: O=C(OCc1ccccc1)C1(COCc2ccccc2)CCC2(CC1)OCCO2]

4 M aq NaOH (13.2 mL, 52.8 mmol) was added to a solution of ethyl 8-(benzyloxymethyl)-1,4-dioxaspiro[4.5]decane-8-carboxylate (5.89 g, 17.6 mmol) in MeOH (15 mL). The reaction mixture was stirred at reflux for 6 hr. The reaction mixture was concentrated in vacuo and 6 M aq HCl was added to the mixture, and the mixture was extracted with CHCl₃ twice. The combined organic layer was concentrated in vacuo. The crude product was dissolved in DMF (20 mL). Potassium carbonate (3.65 g, 26.4 mmol) and benzyl bromide (2.20 mL, 18.5 mmol) were added to mixture, and the mixture was stirred at rt for 3 hr. H₂O was added to the mixture and the mixture was extracted with Et2O twice. The combined organic layer was washed with H₂O twice and concentrated in vacuo. The crude product was purified by flash chromatography using a gradient of 0-20% EtOAc in hexane as mobile phase to give the title compound (6.92 g, 99%). MS (ESI) m/z 397.5 [M+H]⁺.

Step B: Intermediate 265: Benzyl (1s,4s)-1-((benzyloxy)methyl)-4-hydroxycyclohexane-1-carboxylate

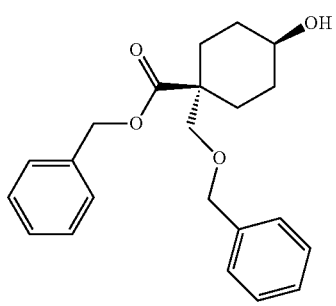 [SMILES: O=C(OCc1ccccc1)[C@]1(COCc2ccccc2)CC[C@H](O)CC1]

2 M aq HCl (70 mL) was added to a solution of Intermediate 264 (6.92 g, 17.5 mmol) in acetone (20 mL) and the reaction mixture was stirred at rt for 8 hr. The reaction mixture was concentrated in vacuo, and H₂O and EtOAc were added and the mixture was extracted with EtOAc twice. The combined organic layer was concentrated in vacuo. The crude product was dissolved in MeOH (10 mL) and THF (10 mL), and NaBH₄ (1.98 g, 52.3 mmol) was added portionwise to −78° C. cooled solution of mixture. The reaction mixture was stirred at −40° C. for 2 hr. Sat aq NH₄Cl was added to the reaction mixture and the mixture was extracted with CHCl₃ twice. The combined organic layer was concentrated in vacuo. The crude product was purified by flash chromatography using a gradient of 10-50% EtOAc in hexane as mobile phase to give the title compound (5.22 g, 84%). MS (ESI) m/z 355.4 [M+H]⁺.

Step C: Benzyl (1r,4r)-1-((benzyloxy)methyl)-4-hydroxycyclohexane-1-carboxylate

Di-2-methoxyethyl azodicarboxylate (5.17 g, 22.1 mmol) in THF (20 mL) was added dropwise to a solution of p-nitrobenzoic acid (3.69 g, 22.1 mmol), Intermediate 265 (5.22 g, 14.7 mmol) and triphenylphosphine (5.79 g, 22.1 mmol) in THF (10 mL) at 0° C., and the reaction mixture was stirred at rt for 3 hr. The reaction mixture was diluted with EtOAc and the mixture was washed with H₂O twice, then the organic layer was concentrated in vacuo to give crude p-nitrobenzoate derivative. 2 M aq LiOH (22.0 mL, 44.0 mmol) was added to a mixture of above crude product in DME (40 mL) and the reaction mixture was stirred at rt for 24 hr. H₂O was added to the reaction mixture and then the mixture was extracted with EtOAc, then the organic layer was concentrated in vacuo. The crude product was purified by flash chromatography using a gradient of 5-50% EtOAc in hexane as mobile phase to give the title compound (2.49 g, 48%). MS (ESI) m/z 355.4 [M+H]⁺.

Intermediate 266: Naphthalen-1-ylmethyl 3-hydroxy-1-methylcyclobutane-1-carboxylate

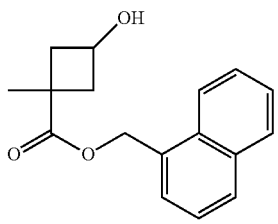 [SMILES: CC1(C(=O)OCc2cccc3ccccc23)CC(O)C1]

Step A: Intermediate 267: Naphthalen-1-ylmethyl 1-methyl-3-oxocyclobutane-1-carboxylate

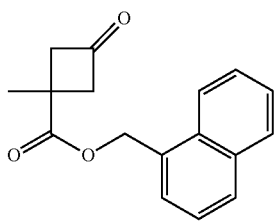 [SMILES: CC1(C(=O)OCc2cccc3ccccc23)CC(=O)C1]

Lithium iodide (3.1 g, 23 mmol) and potassium carbonate (6.7 g, 49 mmol) were added to a solution of 1-methyl-3-oxocyclobutane-1-carboxylic acid (2.5 g, 20 mmol) in DMF (50 mL), then 1-(chloromethyl)naphthalene (3.8 g, 21 mmol) was added dropwise to a reaction mixture and the mixture was stirred at rt for overnight. The mixture was added H$_2$O and extracted with EtOAc twice and the combined organic layer was concentrated in vacuo. The crude product was purified by flash chromatography using a gradient of 0-10% EtOAc in hexane as mobile phase to give the title compound (5.18 g, 99%).

Step B: Naphthalen-1-ylmethyl 3-hydroxy-1-methylcyclobutane-1-carboxylate

NaBH$_4$ (630 mg, 17 mmol) was added portionwise to −78° C. cooled solution of Intermediate 267 (1.5 g, 5.60 mmol) in MeOH (15 mL). The reaction mixture was stirred at −78° C. for 2 hr. Sat aq NH$_4$Cl was added to the reaction mixture and the mixture was concentrated in vacuo. The residue was extracted with EtOAc twice. The combined organic layer was concentrated in vacuo. The crude product was purified by flash chromatography using a gradient of 30-50% EtOAc in hexane as mobile phase to give the title compound (1.51 g, 100%) as cis/trans mixture.

Intermediate 268: rac-Benzyl (2R,5S)-5-(tosyloxy)tetrahydro-2H-pyran-2-carboxylate

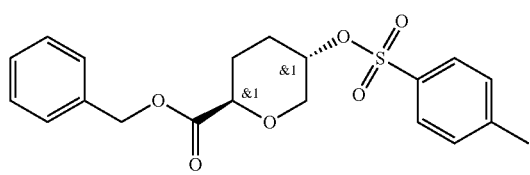 [SMILES: Cc1ccc(S(=O)(=O)O[C@H]2CC[C@H](C(=O)OCc3ccccc3)OC2)cc1]

Step A: Intermediate 269: rac-Benzyl (2R,5S)-5-hydroxytetrahydro-2H-pyran-2-carboxylate

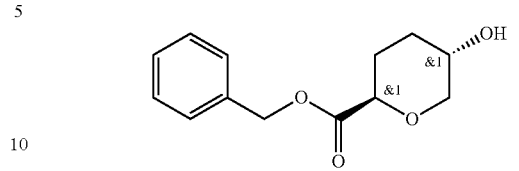

BH$_3$-THF complex (1.0 M in THF, 4.1 mL, 4.10 mmol) was added to −78° C. cooled solution of benzyl 3,4-dihydro-2H-pyran-2-carboxylate (690 mg, 3.16 mmol) in THF (16 mL) and the mixture was stirred for 30 min and rt for 6 hr. Sodium acetate (285 mg, 3.48 mmol), H$_2$O$_2$ (30% in H$_2$O, 0.72 mL, 6.32 mmol) and H$_2$O (5.27 mL) were added to a reaction mixture and the mixture was stirred at rt for 16 hr. The mixture was extracted with CHCl$_3$ twice and the combined organic layer was concentrated in vacuo. The crude product was purified by flash chromatography using a gradient of 0-65% EtOAc in hexane as mobile phase to give the title compound (203 mg, 27%). MS (ESI) m/z 237.2 [M+H]$^+$.

Step B: rac-Benzyl (2R,5S)-5-(tosyloxy)tetrahydro-2H-pyran-2-carboxylate p-Toluenesulfonyl chloride (61 mg, 0.32 mmol) and trimethylamine hydrochloride (3 mg, 0.031 mmol) were added to a mixture of Intermediate 269 (50 mg, 0.212 mmol), TEA (64 mg, 0.635 mmol) and 4-dimethylaminopyridine (2.6 mg, 0.021 mmol) in CH$_2$Cl$_2$ (1 mL) and the reaction mixture was stirred at rt for 5 hr. H$_2$O was added to a reaction mixture and the mixture was extracted with CHCl$_3$, and the organic layer was concentrated in vacuo. The crude product was purified by flash chromatography using 5-20% EtOAc in hexane as mobile phase to give the title compound (37 mg, 45%).

Intermediate 270: 4-Hydroxy-N-(4-methoxybenzyl)cyclohexane-1-sulfonamide

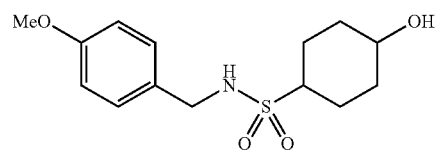 [SMILES: COc1ccc(CNS(=O)(=O)C2CCC(O)CC2)cc1]

NaBH$_4$ (35 mg, 0.93 mmol) was added portionwise to 0° C. cooled solution of N-(4-methoxybenzyl)-4-oxocyclohexane-1-sulfonamide (185 mg, 0.62 mmol) in MeOH (3 mL) and THF (2 mL). The reaction mixture was stirred at 0° C. for 1 hr. Sat aq NH$_4$Cl was added to the reaction mixture and the mixture was concentrated in vacuo. The residue was extracted with EtOAc twice. The combined organic layer was concentrated in vacuo to give titled compound which was used without further purification.

Intermediate 271: Naphthalen-1-ylmethyl (1s,4s)-1,4-dihydroxycyclohexane-1-carboxylate

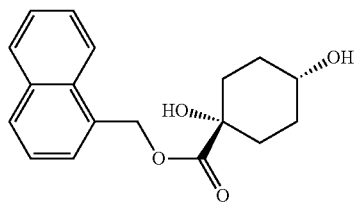 [SMILES: O=C(OCc1cccc2ccccc12)[C@]1(O)CC[C@@H](O)CC1]

The titled compound was prepared analogous to Intermediate 266 Step A, using (1s,4s)-1,4-dihydroxycyclohexane-1-carboxylic acid instead of 1-methyl-3-oxocyclobutane-1-carboxylic acid.

Intermediate 272: rac-Benzyl (1R,3S)-3-((methylsulfonyl)oxy)cyclohexane-1-carboxylate and rac-benzyl (1R,3R)-3-((methylsulfonyl)oxy)cyclohexane-1-carboxylate

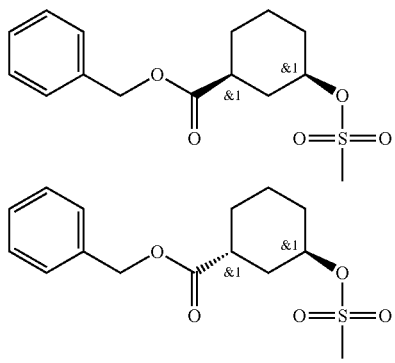

Step A: rac-Benzyl (1R,3S)-3-hydroxycyclohexane-1-carboxylate and rac-benzyl (1R,3R)-3-hydroxycyclohexane-1-carboxylate

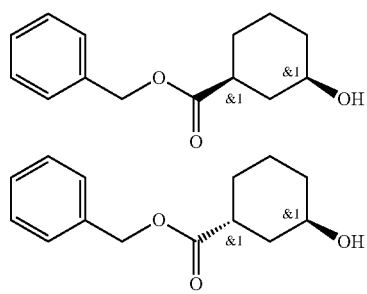

NaBH$_4$ (326 mg, 8.61 mmol) was added portionwise to 0° C. cooled solution of rac-benzyl 3-oxocyclohexane-1-carboxylate (1 g, 4.305 mmol) in THF (15 mL). The reaction mixture was stirred at rt for 4 hr. Sat aq NH$_4$Cl was added to the reaction mixture and the mixture was extracted with EtOAc, then the organic layer was concentrated in vacuo. The crude product was purified by flash chromatography using 30-50% EtOAc in hexane as mobile phase to give the first eluting compound Isomer 1: (110 mg, 11%), and the second eluting compound Isomer 2: (225 mg, 22%).

Step B: rac-Benzyl (1R,3S)-3-((methylsulfonyl)oxy)cyclohexane-1-carboxylate and rac-benzyl (1R,3R)-3-((methylsulfonyl)oxy)cyclohexane-1-carboxylate Methanesulfonyl chloride (64 mg, 0.56 mmol) was added to a solution of the first eluting compound Isomer 1 (110 mg, 0.47 mmol), obtained from Step A, and TEA (71 mg, 0.70 mmol) in CHCl$_3$ (2 mL), and the reaction mixture was stirred at rt for 12 hr. Sat aq NaHCO$_3$ was added, then the mixture was extracted with CHCl$_3$ and the combined organic layer was concentrated in vacuo to give mesylated product (146 mg, 99%).

Methanesulfonyl chloride (132 mg, 1.15 mmol) was added to a solution of the second eluting compound Isomer 2 (225 mg, 0.96 mmol), obtained from Step A, and TEA (146 mg, 1.44 mmol) in CHCl$_3$ (2 mL), and the reaction mixture was stirred at rt for 12 hr. Sat aq NaHCO$_3$ was added, then the mixture was extracted with CHCl$_3$ and the combined organic layer was concentrated in vacuo to give mesylated product (299 mg, 99%).

Intermediate 273: 1-(tert-Butyl) 1-methyl (1r,4r)-4-hydroxycyclohexane-1,1-dicarboxylate

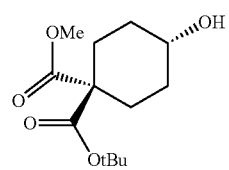 [SMILES: COC(=O)[C@]1(C(=O)OC(C)(C)C)CC[C@H](O)CC1]

Step A: Intermediate 274: (1r,4r)-4-(tert-Butoxycarbonyl)-4-(methoxymethyl)cyclohexyl 4-nitrobenzoate

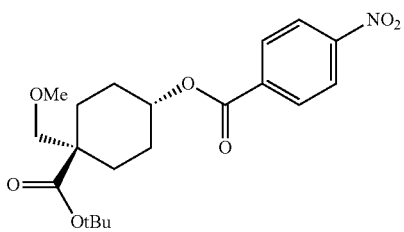 [SMILES: COC[C@]1(C(=O)OC(C)(C)C)CC[C@H](OC(=O)c2ccc([N+](=O)[O-])cc2)CC1]

Di-2-methoxyethyl azodicarboxylate (2.59 g, 11.1 mmol) in THF (10 mL) was added dropwise to a solution of p-nitrobenzoic acid (1.85 g, 11.1 mmol), tert-butyl (1s,4s)-4-hydroxy-1-(methoxymethyl)cyclohexane-1-carboxylate (1.80 g, 7.37 mmol) and triphenylphosphine (2.9 g, 11.1 mmol) in THF (10 mL) at 0° C., and the reaction mixture was stirred at rt for 24 hr. The reaction mixture was diluted with EtOAc and the mixture was washed with H$_2$O twice, then the organic layer was concentrated in vacuo. The crude product was triturated with IPA to give title compound (2.16 g, 75%).

237

Step B: Intermediate 275: 1-(tert-Butyl) 1-methyl (1r,4r)-4-(((4-nitrobenzoyl)oxy)cyclohexane-1,1-dicarboxylate

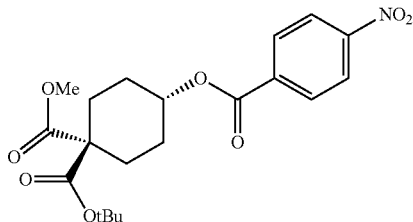 [SMILES: COC(=O)[C@]1(C(=O)OC(C)(C)C)CC[C@H](OC(=O)c2ccc([N+](=O)[O-])cc2)CC1]

Sodium periodate (784 mg, 3.67 mmol) and trichlororuthenium hydrate (82 mg, 0.367 mmol) were added to a mixture of Intermediate 274 (721 mg, 1.83 mmol) in CCl$_4$ (4.6 mL), MeCN (4.6 mL) and H$_2$O (6.1 mL), and the reaction mixture was stirred at rt for 10 hr. Sodium periodate (392 mg, 1.83 mmol) and trichlororuthenium hydrate (41 mg, 0.183 mmol) were added to a mixture and the mixture was stirred at rt for additional 12 hr. The reaction mixture was diluted with H$_2$O and extracted with CHCl$_3$, then the organic layer was concentrated in vacuo. The crude product was purified by flash chromatography using a gradient of 0-15% EtOAc in hexane as mobile phase to give the title compound (530 mg, 71%).

Step C: 1-(tert-Butyl) 1-methyl (1r,4r)-4-hydroxycyclohexane-1,1-dicarboxylate

Sodium methoxide (28% in MeOH, 50 mg, 0.259 mmol) was added to a mixture of Intermediate 275 (528 mg, 1.30 mmol) in MeOH (3.2 mL) and the reaction mixture was stirred at rt for 1 hr. The reaction mixture was neutralized with 1 M aq HCl, then the mixture was extracted with CHCl$_3$, and the organic layer was concentrated in vacuo. The crude product was purified by flash chromatography using a gradient of 0-50% EtOAc in hexane as mobile phase to give the title compound (308 mg, 92%).

Intermediate 276: Naphthalen-1-ylmethyl (1r,4r)-1-ethyl-4-hydroxycyclohexane-1-carboxylate

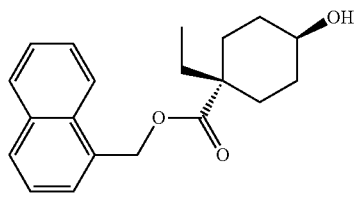 [SMILES: CC[C@]1(C(=O)OCc2cccc3ccccc23)CC[C@H](O)CC1]

238

Step A: Intermediate 277: Naphthalen-1-ylmethyl (1s,4s)-1-ethyl-4-hydroxycyclohexane-1-carboxylate

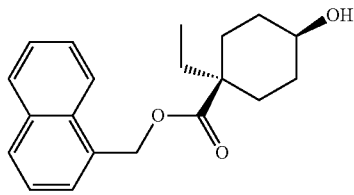 [SMILES: CC[C@]1(C(=O)OCc2cccc3ccccc23)CC[C@@H](O)CC1]

The titled compound was prepared analogous to Intermediate 266 Step A and B, using 1-ethyl-4-oxocyclohexane-1-carboxylic acid instead of 1-methyl-3-oxocyclobutane-1-carboxylic acid.

Step B: Intermediate 278: (1r,4r)-4-Ethyl-4-((naphthalen-1-ylmethoxy)carbonyl)cyclohexyl 4-nitrobenzoate

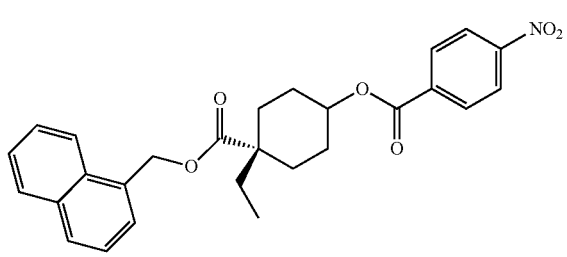

The titled compound was prepared analogous to Intermediate 273 Step A, using Intermediate 277 instead of tert-butyl (1s,4s)-4-hydroxy-1-(methoxymethyl)cyclohexane-1-carboxylate.

Step C: Naphthalen-1-ylmethyl (1r,4r)-1-ethyl-4-hydroxycyclohexane-1-carboxylate Potassium carbonate (2.39 g, 17.3 mmol) was added to a mixture of Intermediate 278 (2.66 g, 5.77 mmol) in MeOH (8 mL) and H$_2$O (2 mL), then the reaction mixture was stirred at reflux for 2 hr. The reaction mixture was cooled to rt and CHCl$_3$ was added to the mixture, and the mixture was extracted with CHCl$_3$, and the organic layer was concentrated in vacuo. The crude product was purified by flash chromatography using a gradient of 0-40% EtOAc in hexane as mobile phase to give the title compound (860 mg, 48%).

Intermediate 279: Ethyl 2-(4-hydroxy-1-methylcyclohexyl)acetate

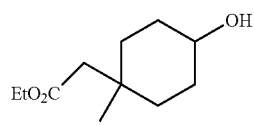

The titled compound was prepared analogous to Intermediate 266 Step B, using ethyl 2-(1-methyl-4-oxocyclohexyl)acetate instead of Intermediate 267.

Intermediate 280: Methyl 5-hydroxy-2-methoxy-6-methylnicotinate

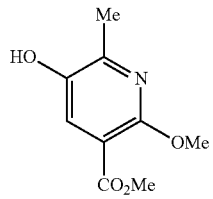 [SMILES: COC(=O)c1cc(O)c(C)nc1OC]

Bis(pinacolato)diboron (440 mg, 1.73 mmol), PdCl$_2$(dppf)$_2$·CH$_2$Cl$_2$ (50.5 mg, 0.062 mmol) and potassium acetate (243 mg, 2.48 mmol) were added to a solution of methyl 5-bromo-2-methoxy-6-methylnicotinate (Compound 3) (322 mg, 1.24 mmol) in cyclopentyl methyl ether (5 mL) and the reaction mixture was stirred at reflux temperature for 3 hr. H$_2$O and EtOAc were added to a reaction mixture and the mixture was stirred vigorously. The reaction mixture was separated, and the organic layer was concentrated in vacuo.

Ammonium hydrogen carbonate (117 mg, 1.48 mmol) and H$_2$O (0.32 mL, 3.09 mmol) were added to a solution of crude product in MeCN (5 mL) and the mixture was stirred at rt for 2 hr. 1 M aq HCl was added to a reaction mixture and the mixture was extracted with EtOAc twice, and the combined organic layer was concentrated in vacuo. The crude product was purified by flash chromatography using a gradient of 5-35% EtOAc in hexane as mobile phase to give the title compound (222 mg, 91%). MS (ESI) m/z 198.0 [M+H]$^+$.

Intermediate 281: Methyl 5-hydroxy-2-methoxy-4-(trifluoromethyl)benzoate

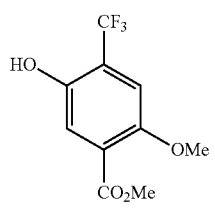

The titled compound was prepared analogous to Intermediate 280, using methyl 5-bromo-2-methoxy-4-(trifluoromethyl)benzoate instead of Compound 3. MS (ESI) m/z 251.1 [M+H]$^+$.

Intermediate 282: Ethyl 5-hydroxy-2,3-dihydrobenzofuran-7-carboxylate

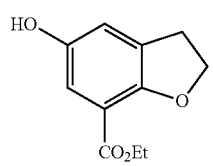

The titled compound was prepared analogous to Intermediate 280, using ethyl 5-bromo-2,3-dihydrobenzofuran-7-carboxylate instead of Compound 3. MS (ESI) m/z 209.1 [M+H]$^+$.

Intermediate 283: Methyl 4-fluoro-5-hydroxy-2-isopropoxybenzoate

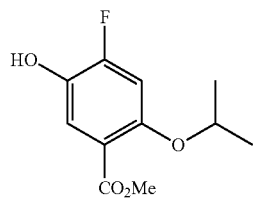

Step A: Intermediate 284: Methyl 5-bromo-4-fluoro-2-isopropoxybenzoate

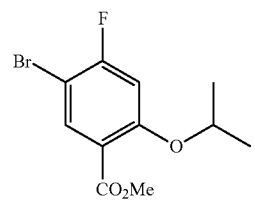

Potassium carbonate (3.55 g, 25.7 mmol) and 2-iodopropane (2.40 g, 14.1 mmol) were added to a solution of methyl 5-bromo-4-fluoro-2-hydroxybenzoate (322 mg, 1.24 mmol) in DMF (21 mL) and the reaction mixture was stirred at rt for 2 h and 50° C. for 2 hr. H$_2$O was added to a reaction mixture and the mixture was extracted with EtOAc, and the organic layer was concentrated in vacuo. The crude product was purified by flash chromatography using 10% EtOAc in hexane as mobile phase to give the title compound (2.86 g, 76%). MS (ESI) m/z 291.0/293.0 [M+H]$^+$.

Step B: Methyl 4-fluoro-5-hydroxy-2-isopropoxybenzoate

The titled compound was prepared analogous to Intermediate 280, using Intermediate 284 instead of Compound 3. MS (ESI) m/z 229.1 [M+H]$^+$.

Intermediate 285: Methyl 3-fluoro-5-hydroxy-2-methoxybenzoate

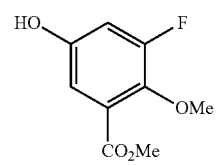

The titled compound was prepared analogous to Intermediate 280, using methyl 5-bromo-3-fluoro-2-methoxybenzoate instead of Compound 3. MS (ESI) m/z 197.1 [M+H]$^+$.

Intermediate 286: Methyl 3-chloro-5-hydroxy-2-methoxybenzoate

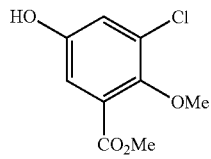 [SMILES: COC(=O)c1cc(O)cc(Cl)c1OC]

The titled compound was prepared analogous to Intermediate 280, using methyl 5-bromo-3-chloro-2-methoxybenzoate instead of Compound 3. MS (ESI) m/z 217.0/219.0 [M+H]⁺.

Intermediate 287: Methyl 5-hydroxy-2-methoxy-4-(methoxymethyl)benzoate

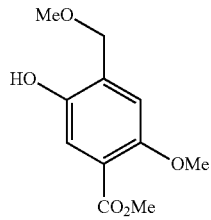 [SMILES: COCc1cc(OC)c(C(=O)OC)cc1O]

The titled compound was prepared analogous to Intermediate 280, using methyl 5-bromo-4-methoxymethyl-2-methoxybenzoate instead of Compound 3. MS (ESI) m/z 227.1 [M+H]⁺.

Intermediate 288: Methyl 4-fluoro-5-hydroxy-2-(methoxymethyl)benzoate

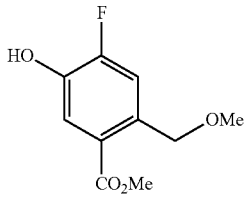 [SMILES: COCc1cc(F)c(O)cc1C(=O)OC]

Step A: Intermediate 289: Methyl 5-bromo-4-fluoro-2-(methoxymethyl)benzoate

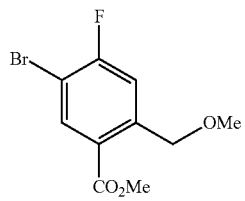 [SMILES: COCc1cc(F)c(Br)cc1C(=O)OC]

Sodium methoxide (28% in MeOH, 1.78 mL, 8.71 mmol) was added to a solution of methyl 5-bromo-4-fluoro-2-(hydroxymethyl)benzoate (1.42 g, 4.36 mmol) in MeOH (10 mL) and the reaction mixture was stirred at rt for 30 min and 80° C. for 30 min. The mixture was cooled to ambient temperature and 1 M aq HCl was added to adjust pH-2, then the mixture was extracted with EtOAc, and the organic layer was concentrated in vacuo. The crude product was purified by flash chromatography using 0-10% EtOAc in hexane as mobile phase to give the title compound (254 mg, 21%). MS (ESI) m/z 277.0/279.0 [M+H]⁺.

Step B: Methyl 4-fluoro-5-hydroxy-2-(methoxymethyl)benzoate

The titled compound was prepared analogous to Intermediate 280, using Intermediate 289 instead of Compound 3. MS (ESI) m/z 213.1 [M−H]−

Intermediate 290: Methyl 2-(2-((tert-butyldiphenylsilyl)oxy)ethoxy)-4-fluoro-5-hydroxybenzoate

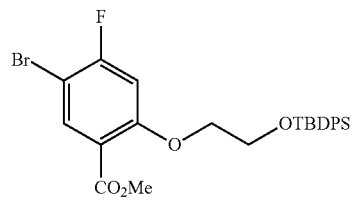

Step A: Intermediate 291: Methyl 5-bromo-2-(2-((tert-butyldiphenylsilyl)oxy)ethoxy)-4-fluorobenzoate

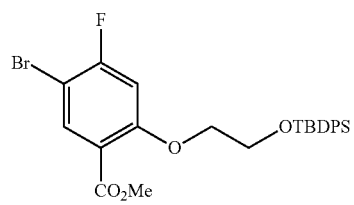

Di-2-methoxyethyl azodicarboxylate (451 mg, 1.93 mmol) in THF (15 mL) was added dropwise to a solution of methyl 5-bromo-4-fluoro-2-hydroxybenzoate (400 mg, 1.61 mmol), 2-((tert-butyldiphenylsilyl)oxy)ethan-1-ol (579 mg, 1.93 mmol) and triphenylphosphine (505 mg, 1.93 mmol) in THF (15 mL) at 0° C., and the reaction mixture was stirred at 0° C. for 12 hr. The reaction mixture was diluted with EtOAc and the mixture was washed with H₂O twice, then the organic layer was concentrated in vacuo. The crude product was purified by flash chromatography using a gradient of 0-10% EtOAc in hexane as mobile phase to give the title compound (854 mg, 100%).

Step B: Methyl 2-(2-((tert-butyldiphenylsilyl)oxy)ethoxy)-4-fluoro-5-hydroxybenzoate The titled compound was prepared analogous to Intermediate 280, using Intermediate 291 instead of Compound 3. MS (ESI) m/z 467.2[M−H]−

Intermediate 292: Benzyl 2,4-difluoro-5-hydroxybenzoate

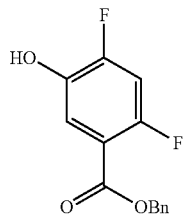 [SMILES: O=C(OCc1ccccc1)c1cc(O)c(F)cc1F]

Step A: Intermediate 293: Benzyl 5-bromo-2,4-difluorobenzoate

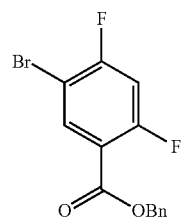

Potassium carbonate (1.30 g, 9.39 mmol) and benzyl bromide (835 mg, 4.88 mmol) were added to a solution of 5-bromo-2,4-difluorobenzoic acid (890 mg, 3.76 mmol) in DMF (10 mL) and the reaction mixture was stirred at rt for 12 h. $H_2O$ was added to a reaction mixture and the mixture was extracted with EtOAc, and the organic layer was concentrated in vacuo. The crude product was purified by flash chromatography using 0-5% EtOAc in hexane as mobile phase to give the title compound (1.22 g, 100%).

Step B: Benzyl 2,4-difluoro-5-hydroxybenzoate

The titled compound was prepared analogous to Intermediate 280, using Intermediate 293 instead of Compound 3. MS (ESI) m/z 263.1 [M–H]–

Intermediate 294: tert-Butyl 4-cyano-5-hydroxy-2-methoxybenzoate

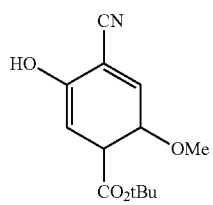

1,1-Di-tert-butoxy-N,N-dimethyl-methylamine (4.20 g, 20.9 mmol) was added to a mixture of 4-cyano-5-hydroxy-2-methoxybenzoic acid (767 mg, 3.97 mmol) in toluene (4 mL) and the reaction mixture was stirred at 80° C. for 18 hr. The mixture was cooled to ambient temperature and sat aq NaHCO$_3$ was added, then the mixture was extracted with EtOAc, and the organic layer was concentrated in vacuo. The crude product was purified by flash chromatography using 0-20% EtOAc in hexane as mobile phase to give the title compound (252 mg, 25%). MS (ESI) m/z 248.1 [M–H]–

Intermediate 295: 4-(Difluoromethyl)-2-methoxy-5-(((1s,4s)-4-methyl-4-((naphthalen-1-ylmethoxy)carbonyl)cyclohexyl)oxy)benzoic acid

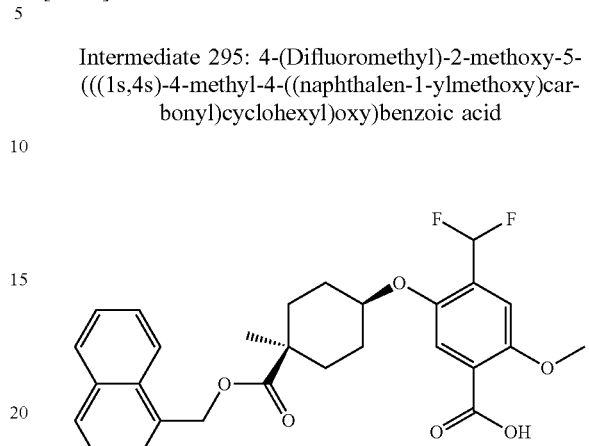

Di-2-methoxyethyl azodicarboxylate (328 mg, 1.40 mmol) in THF (5 mL) was added dropwise to a solution of methyl 4-(difluoromethyl)-5-hydroxy-2-methoxybenzoate (Compound 4) (250 mg, 1.08 mmol), Intermediate 11 (418 mg, 1.40 mmol) and triphenylphosphine (367 mg, 1.40 mmol) in THF (5 mL) at 0° C., and the reaction mixture was stirred at 0° C. for 1 hr. The reaction mixture was diluted with EtOAc and the mixture was washed with $H_2O$ twice, then the organic layer was concentrated in vacuo. The crude product was purified by flash chromatography using a gradient of 10-30% EtOAc in hexane as mobile phase to give methyl 4-(difluoromethyl)-2-methoxy-5-(((1s,4s)-4-methyl-4-((naphthalen-1-ylmethoxy)carbonyl)cyclohexyl)oxy)benzoate (432 mg, 78%). 2 M aq LiOH (1.26 mL, 2.53 mmol) was added to a solution of methyl 4-(difluoromethyl)-2-methoxy-5-(((1s,4s)-4-methyl-4-((naphthalen-1-ylmethoxy)carbonyl)cyclohexyl)oxy)benzoate (432 mg, 0.843 mmol) in DME (10 mL), and the reaction mixture was stirred at rt for 6 hr. 1 M aq HCl was added to the reaction mixture until pH<2, the reaction mixture was extracted with EtOAc twice and the combined organic layer was concentrated in vacuo to give titled compound (381 mg, 91%). MS (ESI) m/z 497.2 [M–H]–

Intermediate 296: 3-Fluoro-2-methoxy-5-(((1s,4s)-4-methyl-4-((naphthalen-1-ylmethoxy)carbonyl)cyclohexyl)oxy)benzoic acid

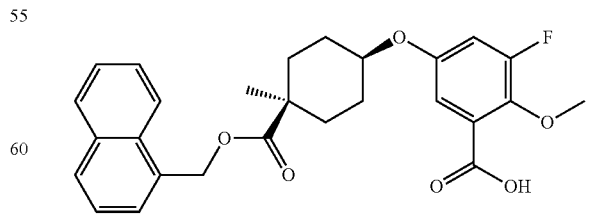

The titled compound was prepared analogous to Intermediate 295, using Intermediate 285 instead of Compound 4. MS (ESI) m/z 465.2 [M–H]–

Intermediate 297: 3-Chloro-2-methoxy-5-(((1s,4s)-4-methyl-4-((naphthalen-1-ylmethoxy)carbonyl)cyclohexyl)oxy)benzoic acid

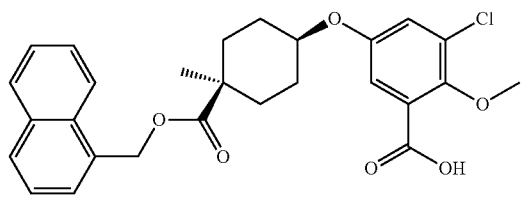 [SMILES: COc1c(Cl)cc(O[C@H]2CC[C@@](C)(C(=O)OCc3cccc4ccccc34)CC2)cc1C(=O)O]

The titled compound was prepared analogous to Intermediate 295, using Intermediate 286 instead Compound 4. MS (ESI) m/z 481.2/483.2 [M−H]−

Intermediate 298: 2-Methoxy-3-methyl-5-(((1s,4s)-4-methyl-4-((naphthalen-1-ylmethoxy)carbonyl)cyclohexyl)oxy)benzoic acid

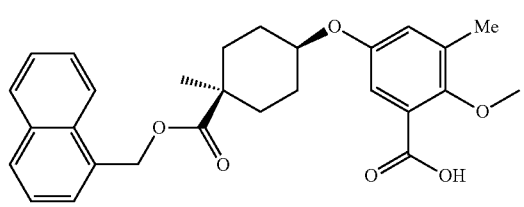 [SMILES: COc1c(C)cc(O[C@H]2CC[C@@](C)(C(=O)OCc3cccc4ccccc34)CC2)cc1C(=O)O]

The titled compound was prepared analogous to Intermediate 295, using methyl 3-methyl-5-hydroxy-2-methoxybenzoate instead of Compound 4. MS (ESI) m/z 477.3 [M+H]+.

Intermediate 299: 2-Methoxy-5-(((1s,4s)-4-methyl-4-((naphthalen-1-ylmethoxy)carbonyl)cyclohexyl)oxy)-4-(trifluoromethyl)benzoic acid

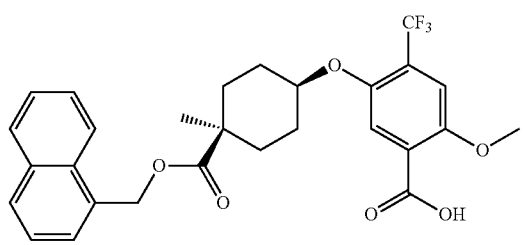

The titled compound was prepared analogous to Intermediate 295, using Intermediate 281 instead of Compound 4.

Intermediate 300: 2-Chloro-4-fluoro-5-(((1s,4s)-4-methyl-4-((naphthalen-1-ylmethoxy)carbonyl)cyclohexyl)oxy)benzoic acid

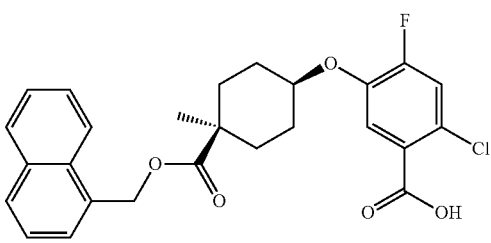 [SMILES: C[C@]1(C(=O)OCc2cccc3ccccc23)CC[C@@H](Oc2cc(C(=O)O)c(Cl)cc2F)CC1]

The titled compound was prepared analogous to Intermediate 295, using methyl 2-chloro-4-fluoro-5-hydroxybenzoate instead of Compound 4. MS (ESI) m/z 469.2/471.2 [M−H]−

Intermediate 301: 4-Chloro-2-fluoro-5-(((1s,4s)-4-methyl-4-((naphthalen-1-ylmethoxy)carbonyl)cyclohexyl)oxy)benzoic acid

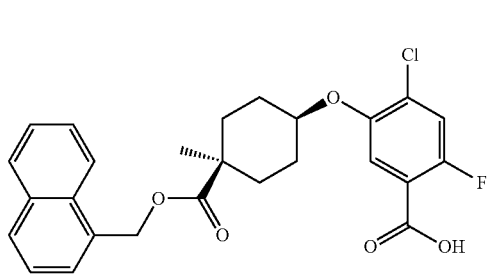

The titled compound was prepared analogous to Intermediate 295, using methyl 4-chloro-2-fluoro-5-hydroxybenzoate instead of Compound 4. MS (ESI) m/z 469.1/471.2 [M−H]−

Intermediate 302: 4-Cyano-2-fluoro-5-(((1s,4s)-4-methyl-4-((naphthalen-1-ylmethoxy)carbonyl)cyclohexyl)oxy)benzoic acid

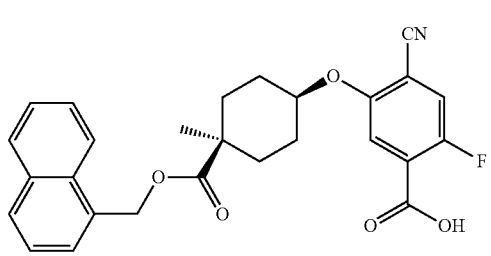

The titled compound was prepared analogous to Intermediate 295, using methyl 4-cyano-2-fluoro-5-hydroxybenzoate instead of Compound 4. MS (ESI) m/z 460.2 [M−H]−

Intermediate 303: 4-Fluoro-3-(((1s,4s)-4-methyl-4-((naphthalen-1-ylmethoxy)carbonyl)cyclohexyl)oxy)benzoic acid

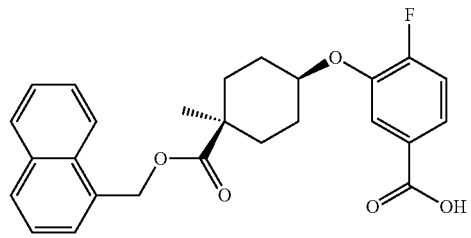 [SMILES: C[C@]1(C(=O)OCc2cccc3ccccc23)CC[C@@H](Oc2cc(C(=O)O)ccc2F)CC1]

The titled compound was prepared analogous to Intermediate 295, using methyl 4-fluoro-3-hydroxy-benzoate instead of Compound 4.

Intermediate 304: 2-Methoxy-4-(methoxymethyl)-5-(((1s,4s)-4-methyl-4-((naphthalen-1-ylmethoxy)carbonyl)cyclohexyl)oxy)benzoic acid

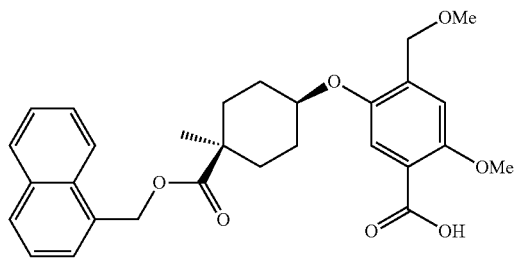 [SMILES: COCc1cc(OC)c(C(=O)O)cc1O[C@H]1CC[C@@](C)(C(=O)OCc2cccc3ccccc23)CC1]

The titled compound was prepared analogous to Intermediate 295, using Intermediate 287 instead of Compound 4. MS (ESI) m/z 507.3 [M+H]$^+$.

Intermediate 305: 2-Cyano-4-fluoro-5-(((1s,4s)-4-methyl-4-((naphthalen-1-ylmethoxy)carbonyl)cyclohexyl)oxy)benzoic acid

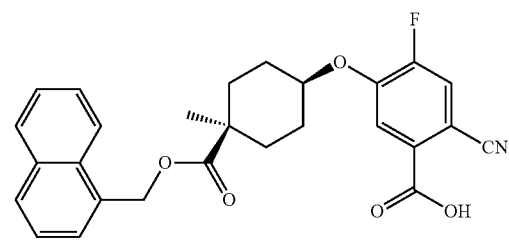 [SMILES: C[C@]1(C(=O)OCc2cccc3ccccc23)CC[C@@H](Oc2cc(C(=O)O)c(C#N)cc2F)CC1]

The titled compound was prepared analogous to Intermediate 295, using methyl 2-cyano-4-fluoro-5-hydroxybenzoate instead of Compound 4. MS (ESI) m/z 460.7 [M−H]−

Intermediate 306: 1-Methyl-7-(((1s,4s)-4-methyl-4-((naphthalen-1-ylmethoxy)carbonyl)cyclohexyl)oxy)-1H-indazole-5-carboxylic acid

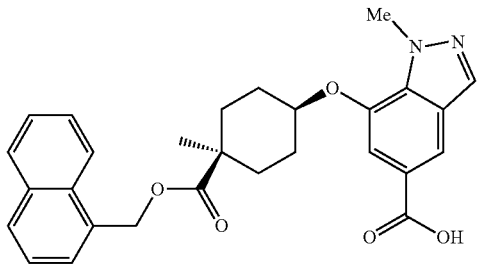 [SMILES: Cn1ncc2cc(C(=O)O)cc(O[C@H]3CC[C@@](C)(C(=O)OCc4cccc5ccccc45)CC3)c21]

The titled compound was prepared analogous to Intermediate 295, using methyl 1-methyl-7-hydroxy-1H-indazole-5-carboxylate instead of Compound 4. MS (ESI) m/z 473.3 [M+H]$^+$.

Intermediate 307: 1-Methyl-4-(((1s,4s)-4-methyl-4-((naphthalen-1-ylmethoxy)carbonyl)cyclohexyl)oxy)-1H-indazole-6-carboxylic acid

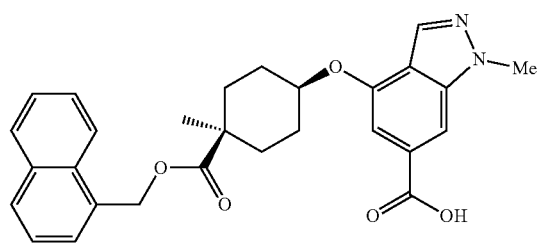 [SMILES: Cn1ncc2c(O[C@H]3CC[C@@](C)(C(=O)OCc4cccc5ccccc45)CC3)cc(C(=O)O)cc21]

The titled compound was prepared analogous to Intermediate 295, using methyl 1-methyl-4-hydroxy-1H-indazole-6-carboxylate instead of Compound 4. MS (ESI) m/z 473.3 [M+H]$^+$.

Intermediate 308: 4-Fluoro-2-(methoxymethyl)-5-(((1s,4s)-4-methyl-4-((naphthalen-1-ylmethoxy)carbonyl)cyclohexyl)oxy)benzoic acid

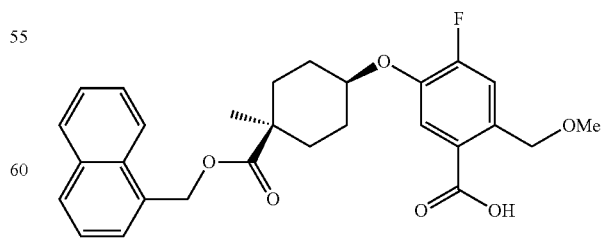

The titled compound was prepared analogous to Intermediate 295, using Intermediate 288 instead of Compound 4. MS (ESI) m/z 479.7 [M−H]−

Intermediate 309: 2-Ethoxy-4-fluoro-5-(((1s,4s)-4-methyl-4-((naphthalen-1-ylmethoxy)carbonyl)cyclohexyl)oxy)benzoic acid

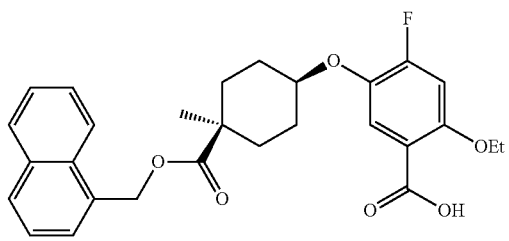 [SMILES: CCOc1cc(F)c(O[C@H]2CC[C@@](C)(C(=O)OCc3cccc4ccccc34)CC2)cc1C(=O)O]

The titled compound was prepared analogous to Intermediate 295, using methyl 2-ethoxy-4-fluoro-5-hydroxybenzoate instead of Compound 4. MS (ESI) m/z 481.3 [M+H]+.

Intermediate 310: 5-(((1s,4s)-4-Methyl-4-((naphthalen-1-ylmethoxy)carbonyl)cyclohexyl)oxy)-2,3-dihydrobenzofuran-7-carboxylic acid

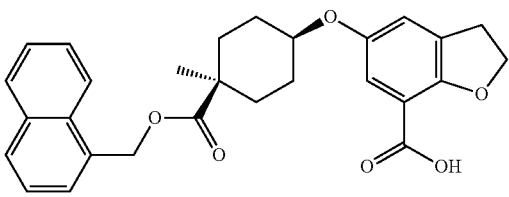 [SMILES: C[C@]1(C(=O)OCc2cccc3ccccc23)CC[C@@H](Oc2cc3c(c(C(=O)O)c2)OCC3)CC1]

The titled compound was prepared analogous to Intermediate 295, using Intermediate 282 instead of Compound 4. MS (ESI) m/z 461.3 [M+H]+.

Intermediate 311: 6-(((1s,4s)-4-Methyl-4-((naphthalen-1-ylmethoxy)carbonyl)cyclohexyl)oxy)quinoline-8-carboxylic acid

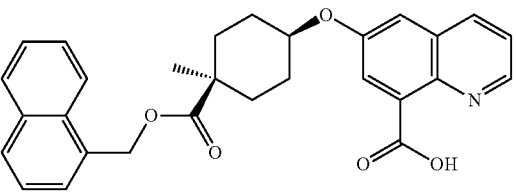 [SMILES: C[C@]1(C(=O)OCc2cccc3ccccc23)CC[C@@H](Oc2cc(C(=O)O)c3ncccc3c2)CC1]

The titled compound was prepared analogous to Intermediate 295, using methyl 6-hydroxyquinoline-8-carboxylate instead of Compound 4. MS (ESI) m/z 470.3 [M+H]+.

Intermediate 312: 4-Chloro-2-methoxy-5-(((1s,4s)-4-methyl-4-((naphthalen-1-ylmethoxy)carbonyl)cyclohexyl)oxy)benzoic acid

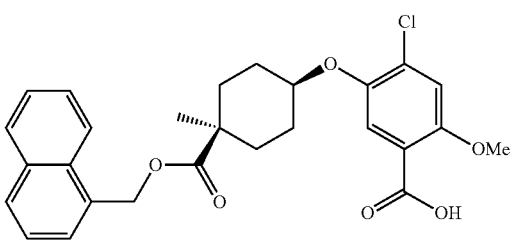

The titled compound was prepared analogous to Intermediate 295, using methyl 4-chloro-5-hydroxy-2-methoxybenzoate instead of Compound 4. MS (ESI) m/z 481.2/483.2 [M−H]−.

Intermediate 313: 3-Cyano-2-methoxy-5-(((1s,4s)-4-methyl-4-((naphthalen-1-ylmethoxy)carbonyl)cyclohexyl)oxy)benzoic acid

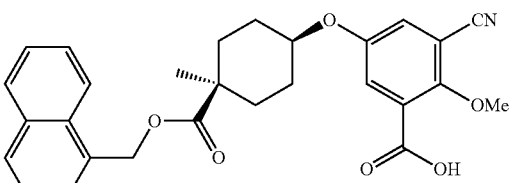

The titled compound was prepared analogous to Intermediate 295, using methyl 3-cyano-5-hydroxy-2-methoxybenzoate instead of Compound 4. MS (ESI) m/z 472.2 [M−H]−.

Intermediate 314: 4-Bromo-2-methoxy-5-(((1s,4s)-4-methyl-4-((naphthalen-1-ylmethoxy)carbonyl)cyclohexyl)oxy)benzoic acid

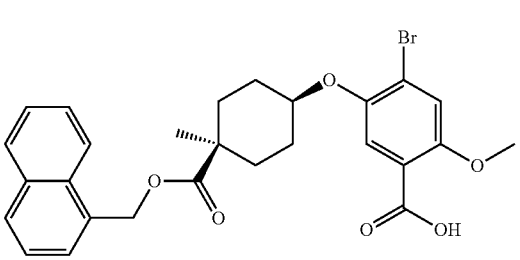

251

Step A: Intermediate 315: Methyl 4-bromo-2-methoxy-5-(((1s,4s)-4-methyl-4-((naphthalen-1-ylmethoxy)carbonyl)cyclohexyl)oxy)benzoate

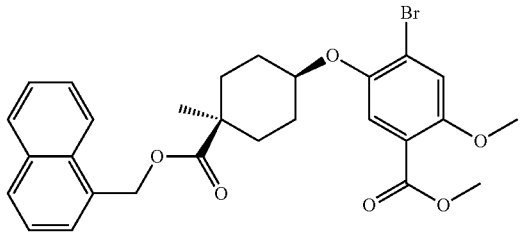

Di-2-methoxyethyl azodicarboxylate (460 mg, 1.97 mmol) in THF (5 mL) was added dropwise to a solution of methyl 4-bromo-5-hydroxy-2-methoxybenzoate (341 mg, 1.31 mmol), Intermediate 11 (456 mg, 1.45 mmol) and triphenylphosphine (514 mg, 1.96 mmol) in THF (10 mL) at 40° C., and the reaction mixture was stirred at 40° C. for 1 hr. The reaction mixture was diluted with EtOAc and the mixture was washed with $H_2O$ twice, then the organic layer was concentrated in vacuo. The crude product was purified by flash chromatography using a gradient of 0-30% EtOAc in hexane as mobile phase to give titled compound (707 mg, 99%). MS (ESI) m/z 541.2/543.2 [M+H]$^+$.

Step B: 4-Bromo-2-methoxy-5-(((1s,4s)-4-methyl-4-((naphthalen-1-ylmethoxy)carbonyl)cyclohexyl)oxy)benzoic acid 2 M aq LiOH (0.28 mL, 0.55 mmol) was added to a solution of Intermediate 315 (100 mg, 0.185 mmol) in THF (0.5 mL), and the reaction mixture was stirred at rt for 6 hr. 1 M aq HCl was added to the reaction mixture until pH<2, the reaction mixture was extracted with EtOAc twice and the combined organic layer was concentrated in vacuo to give titled compound (94 mg, 97%). MS (ESI) m/z 527.1/529.1 [M+H]$^+$.

Intermediate 316: 2-Methoxy-4-methyl-5-(((1s,4s)-4-methyl-4-((naphthalen-1-ylmethoxy)carbonyl)cyclohexyl)oxy)benzoic acid

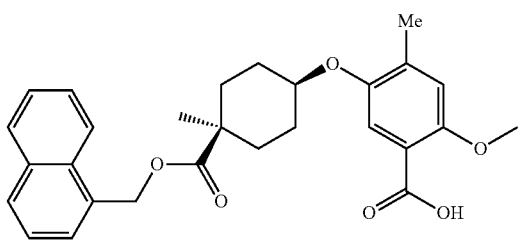 [SMILES: COc1cc(C)c(O[C@H]2CC[C@@](C)(C(=O)OCc3cccc4ccccc34)CC2)cc1C(=O)O]

252

Step A: Intermediate 317: Methyl 2-methoxy-4-methyl-5-(((1s,4s)-4-methyl-4-((naphthalen-1-ylmethoxy)carbonyl)cyclohexyl)oxy)benzoate

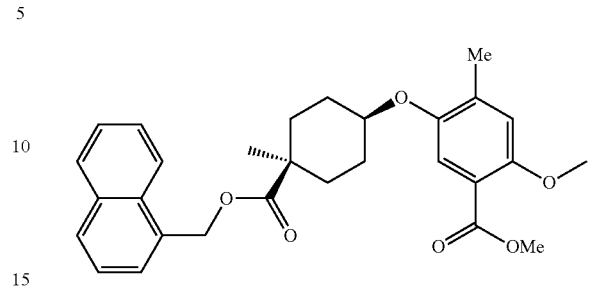

PdCl$_2$(dppf)$_2$.CH$_2$Cl$_2$ (33 mg, 0.040 mmol) was added to the mixture of Intermediate 315 (201 mg, 0.371 mmol) and trimethylboroxine (72 mg, 0.572 mmol) in potassium carbonate (157 mg, 1.138 mmol) and DME (3.7 mL), and the mixture was stirred at reflux for 1 hr. The mixture was cooled to ambient temperature and extracted with CHCl$_3$, then the combined organic layer was concentrated in vacuo. The crude product was purified by flash chromatography using 0-30% EtOAc in hexane as mobile phase to give the title compound (127 mg, 72%). MS (ESI) m/z 477.3 [M+H]$^+$.

Step B: 2-Methoxy-4-methyl-5-(((1s,4s)-4-methyl-4-((naphthalen-1-ylmethoxy)carbonyl)cyclohexyl)oxy)benzoic acid The titled compound was prepared analogous to Intermediate 314 step B, using Intermediate 317 instead of Intermediate 315. MS (ESI) m/z 463.3 [M+H]$^+$.

Intermediate 318: 4-Ethyl-2-methoxy-5-(((1s,4s)-4-methyl-4-((naphthalen-1-ylmethoxy)carbonyl)cyclohexyl)oxy)benzoic acid

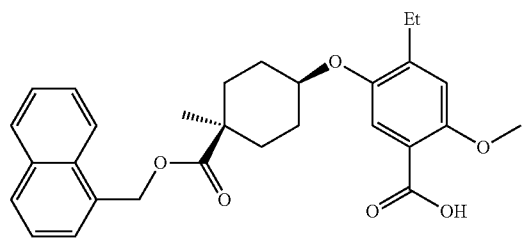 [SMILES: CCc1cc(OC)c(C(=O)O)cc1O[C@H]1CC[C@@](C)(C(=O)OCc2cccc3ccccc23)CC1]

Step A: Intermediate 319: Methyl 4-ethyl-2-methoxy-5-(((1s,4s)-4-methyl-4-((naphthalen-1-ylmethoxy)carbonyl)cyclohexyl)oxy)benzoate

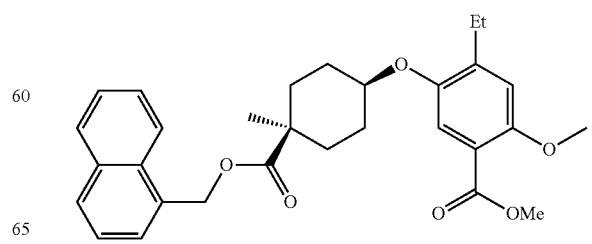

The titled compound was prepared analogous to Intermediate 316 step A, using ethylboronic acid instead of trimethylboroxine. MS (ESI) m/z 491.3 [M+H]⁺.

Step B: 4-Ethyl-2-methoxy-5-(((1s,4s)-4-methyl-4-((naphthalen-1-ylmethoxy)carbonyl)cyclohexyl)oxy)benzoic acid The titled compound was prepared analogous to Intermediate 314 step B, using Intermediate 319 instead of Intermediate 315. MS (ESI) m/z 475.2 [M+H]⁺.

Intermediate 320: 4-Cyclopropyl-2-methoxy-5-(((1s,4s)-4-methyl-4-((naphthalen-1-ylmethoxy)carbonyl)cyclohexyl)oxy)benzoic acid

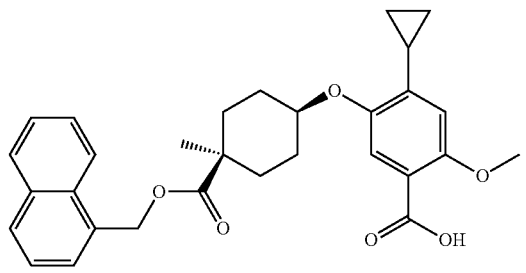 [SMILES: COc1cc(C2CC2)c(O[C@H]2CC[C@@](C)(C(=O)OCc3cccc4ccccc34)CC2)cc1C(=O)O]

Step A: Intermediate 321: Methyl 4-cyclopropyl-2-methoxy-5-(((1s,4s)-4-methyl-4-((naphthalen-1-ylmethoxy)carbonyl)cyclohexyl)oxy)benzoate

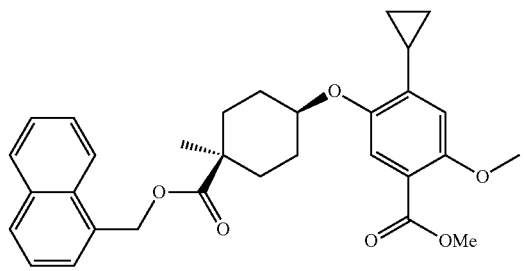 [SMILES: COC(=O)c1cc(O[C@H]2CC[C@@](C)(C(=O)OCc3cccc4ccccc34)CC2)c(C2CC2)cc1OC]

The titled compound was prepared analogous to Intermediate 316 step A, using 2-cyclopropyl-4,4,5,5-tetramethyl-1,3,2-dioxaborolane instead of trimethylboroxine. MS (ESI) m/z 503.3 [M+H]⁺.

Step B: 4-Cyclopropyl-2-methoxy-5-(((1s,4s)-4-methyl-4-((naphthalen-1-ylmethoxy)carbonyl)cyclohexyl)oxy)benzoic acid The titled compound was prepared analogous to Intermediate 314 step B, using Intermediate 321 instead of Intermediate 315. MS (ESI) m/z 489.3 [M+H]⁺.

Intermediate 322: 5-(((1r,4r)-4-(cyanomethyl)-4-(ethoxycarbonyl)cyclohexyl)oxy)-4-fluoro-2-methoxybenzoic acid

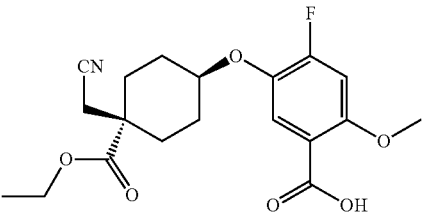 [SMILES: CCOC(=O)[C@]1(CC#N)CC[C@@H](Oc2cc(C(=O)O)c(OC)cc2F)CC1]

Step A: Intermediate 323: Benzyl 5-(((1r,4r)-4-(cyanomethyl)-4-(ethoxycarbonyl)cyclohexyl)oxy)-4-fluoro-2-methoxybenzoate and Intermediate 324: Benzyl 5-(((1s,4s)-4-(cyanomethyl)-4-(ethoxycarbonyl)cyclohexyl)oxy)-4-fluoro-2-methoxybenzoate

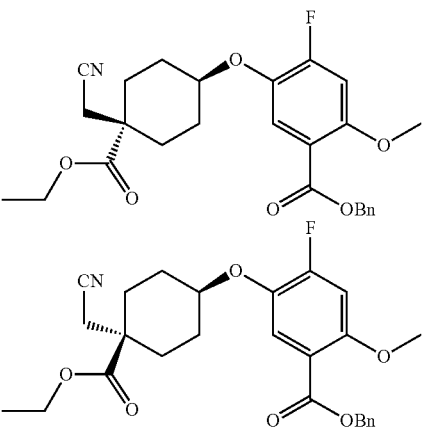

Di-2-methoxyethyl azodicarboxylate (918 mg, 3.92 mmol) in THF (5 mL) was added dropwise to a solution of benzyl 4-fluoro-5-hydroxy-2-methoxybenzoate (722 mg, 2.61 mmol), Intermediate 257 (648 mg, 3.07 mmol) and triphenylphosphine (1030 mg, 3.93 mmol) in THF (5 mL) at 0° C., and the reaction mixture was stirred at rt for 5 hr. The reaction mixture was diluted with EtOAc and the mixture was washed with H₂O twice, then the organic layer was concentrated in vacuo. The crude product was purified by flash chromatography using a gradient of 0-30% EtOAc in hexane as mobile phase to give the first eluting compound Isomer 1: Intermediate 323 (409 mg, 33%); MS (ESI) m/z 470.2 [M+H]⁺, and the second eluting compound Isomer 2: Intermediate 324 (159 mg, 13%); MS (ESI) m/z 470.2 [M+H]⁺.

Step B: 5-(((1r,4r)-4-(Cyanomethyl)-4-(ethoxycarbonyl)cyclohexyl)oxy)-4-fluoro-2-methoxybenzoic acid Palladium (10% Pd/C, moisture by 50% H₂O, 88 mg) was added to a solution of Intermediate 323 (409 mg, 0.871 mmol) in EtOH (5 mL). The reaction mixture was stirred under 1 atm of hydrogen atmosphere at rt for 4 hr. The hydrogen in the reaction vessel was replaced with argon and the reaction mixture was filtered with Celite®. After the filtrate was concentrated in vacuo, the crude product was purified by flash chromatography using a gradient of 0-5% MeOH in CHCl₃ as mobile phase to give titled compound (265 mg, 80%). MS (ESI) m/z 380.4 [M+H]⁺.

Intermediate 325: 5-(((1s,4s)-4-(Cyanomethyl)-4-(ethoxycarbonyl)cyclohexyl)oxy)-4-fluoro-2-methoxybenzoic acid

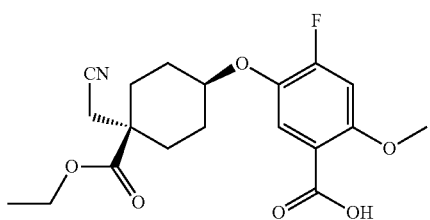 [SMILES: CCOC(=O)[C@]1(CC#N)CC[C@H](Oc2cc(C(=O)O)c(OC)cc2F)CC1]

The titled compound was prepared analogous to Intermediate 322 Step B, using Intermediate 324 of Intermediate 323. MS (ESI) m/z 380.1 [M+H]⁺.

Intermediate 326: 5-((1s,3s)-3-Carboxy-3-methylcyclobutoxy)-4-fluoro-2-methoxybenzoic acid

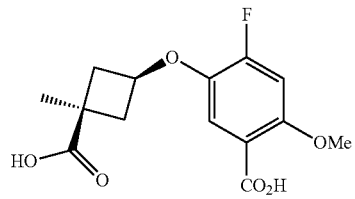 [SMILES: COc1cc(F)c(O[C@H]2C[C@@](C)(C(=O)O)C2)cc1C(=O)O]

Step A: Intermediate 327: Methyl 4-fluoro-2-methoxy-5-((1r,3r)-3-methyl-3-((naphthalen-1-ylmethoxy)carbonyl)cyclobutoxy)benzoate and Intermediate 328: Methyl 4-fluoro-2-methoxy-5-((1s,3s)-3-methyl-3-((naphthalen-1-ylmethoxy)carbonyl)cyclobutoxy)benzoate

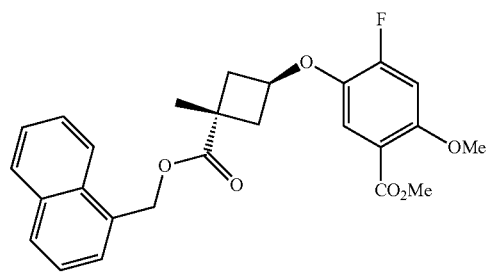

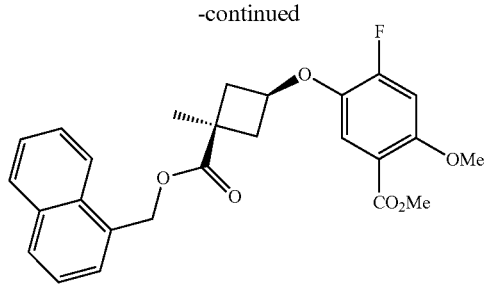

Di-2-methoxyethyl azodicarboxylate (790 mg, 3.37 mmol) in THF (10 mL) was added dropwise to a solution of Intermediate 6 (450 mg, 2.25 mmol), Intermediate 266 (699 mg, 2.59 mmol) and triphenylphosphine (885 mg, 3.37 mmol) in THF (5 mL) at 0° C., and the reaction mixture was stirred at rt for 12 h. The reaction mixture was diluted with EtOAc and the mixture was washed with H₂O twice, then the organic layer was concentrated in vacuo. The crude product was purified by flash chromatography using a gradient of 5-30% EtOAc in hexane as mobile phase to give the first eluting compound Isomer 1: Intermediate 327 (232 mg, 23%); MS (ESI) m/z 453.4 [M+H]⁺, and the second eluting compound Isomer 2: Intermediate 328 (215 mg, 21%); MS (ESI) m/z 453.2 [M+H]⁺.

Step B: 5-((1s,3s)-3-Carboxy-3-methylcyclobutoxy)-4-fluoro-2-methoxybenzoic acid The titled compound was prepared analogous to Intermediate 314 Step B, using Intermediate 328 instead of Intermediate 315. MS (ESI) m/z 299.0 [M+H]⁺.

Intermediate 329: 5-(((1r,4r)-4-Carboxy-4-methoxycyclohexyl)oxy)-4-fluoro-2-methoxybenzoic acid

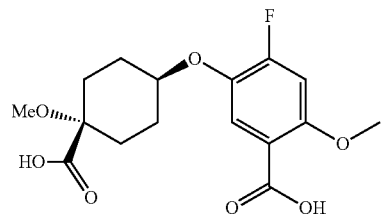 [SMILES: COc1cc(F)c(O[C@H]2CC[C@@](OC)(C(=O)O)CC2)cc1C(=O)O]

Step A: Intermediate 330: Methyl 5-(((1r,4r)-4-((benzyloxy)carbonyl)-4-methoxycyclohexyl)oxy)-4-fluoro-2-methoxybenzoate

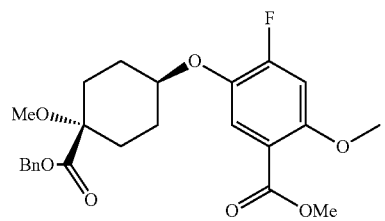 [SMILES: COC(=O)c1cc(O[C@H]2CC[C@@](OC)(C(=O)OCc3ccccc3)CC2)c(F)cc1OC]

Di-2-methoxyethyl azodicarboxylate (690 mg, 2.94 mmol) in THF (5 mL) was added dropwise to a solution of Intermediate 6 (393 mg, 1.96 mmol), Intermediate 262 (535 mg, 2.03 mmol) and triphenylphosphine (773 mg, 2.95 mmol) in THF (10 mL) at 0° C., and the reaction mixture was stirred at rt for 3 hr. The reaction mixture was diluted with EtOAc and the mixture was washed with H₂O twice, then the organic layer was concentrated in vacuo. The crude product was purified by flash chromatography using a gradient of 0-30% EtOAc in hexane as mobile phase to give titled compound (540 mg, 62%). MS (ESI) m/z 447.4 [M+H]⁺.

Step B: 5-(((1r,4r)-4-Carboxy-4-methoxycyclohexyl)oxy)-4-fluoro-2-methoxybenzoic acid The titled compound was prepared analogous to Intermediate 314 Step B, using Intermediate 330 instead of Intermediate 315. MS (ESI) m/z 343.3 [M+H]⁺.

Intermediate 331: 5-(((1R,3r,5S,6s)-6-(Ethoxycarbonyl)bicyclo[3.1.0]hexan-3-yl)oxy)-4-fluoro-2-methoxybenzoic acid

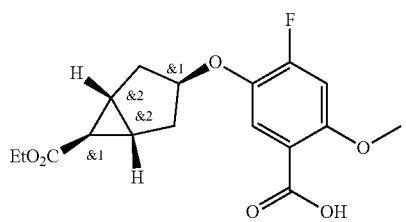 [SMILES: CCOC(=O)[C@H]1[C@@H]2C[C@@H](Oc3cc(C(=O)O)c(OC)cc3F)C[C@@H]21]

Step A: Intermediate 332: Ethyl (1R,3r,5S,6s)-3-(5-((benzyloxy)carbonyl)-2-fluoro-4-methoxyphenoxy)bicyclo[3.1.0]hexane-6-carboxylate and Intermediate 333: Ethyl (1R,3r,5S,6r)-3-(5-((benzyloxy)carbonyl)-2-fluoro-4-methoxyphenoxy)bicyclo[3.1.0]hexane-6-carboxylate

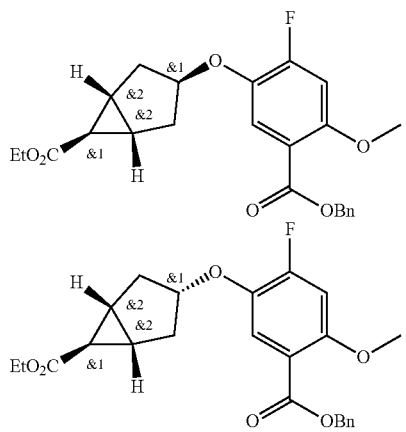

Di-2-methoxyethyl azodicarboxylate (420 mg, 1.79 mmol) in THF (4 mL) was added dropwise to a solution of Intermediate 6 (330 mg, 1.19 mmol), ethyl 3-hydroxybicyclo[3.1.0]hexane-6-carboxylate (250 mg, 1.47 mmol) and triphenylphosphine (470 mg, 1.79 mmol) in THF (4 mL) at 0° C., and the reaction mixture was stirred at rt for 4 hr. The reaction mixture was diluted with EtOAc and the mixture was washed with H₂O twice, then the organic layer was concentrated in vacuo. The crude product was purified by flash chromatography using a gradient of 0-20% EtOAc in hexane as mobile phase to give the first eluting compound Isomer 1: Intermediate 332 (87 mg, 17%); MS (ESI) m/z 429.2 [M+H]⁺, and the second eluting compound Isomer 2: Intermediate 333 (199 mg, 39%); MS (ESI) m/z 429.2 [M+H]1.

Step B: 5-(((1R,3r,5S,6s)-6-(Ethoxycarbonyl)bicyclo[3.1.0]hexan-3-yl)oxy)-4-fluoro-2-methoxybenzoic acid The titled compound was prepared analogous to Intermediate 322 Step B, using Intermediate 332 instead of Intermediate 323. MS (ESI) m/z 339.1 [M+H]⁺

Intermediate 334: 5-(((1R,3r,5S,6r)-6-(Ethoxycarbonyl)bicyclo[3.1.0]hexan-3-yl)oxy)-4-fluoro-2-methoxybenzoic acid

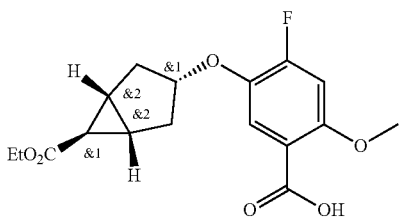 [SMILES: CCOC(=O)[C@H]1[C@@H]2C[C@H](Oc3cc(C(=O)O)c(OC)cc3F)C[C@@H]21]

The titled compound was prepared analogous to Intermediate 322 Step B, using Intermediate 333 instead of Intermediate 323. MS (ESI) m/z 339.1 [M+H]⁺

Intermediate 335: 5-(((1r,4r)-4-(tert-Butoxycarbonyl)-4-fluorocyclohexyl)oxy)-4-fluoro-2-methoxybenzoic acid

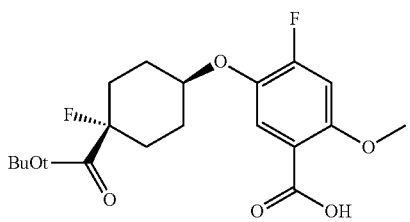

The titled compound was prepared analogous to Intermediate 329 Step A and B, using tert-butyl (1s,4s)-1-fluoro-4-hydroxycyclohexane-1-carboxylate instead of Intermediate 262. MS (ESI) m/z 331.2 [M+H-tBu+H]+

Intermediate 336: 5-(((1r,4r)-4-(tert-Butoxycarbonyl)-4-(trifluoromethyl)cyclohexyl)oxy)-4-fluoro-2-methoxybenzoic acid

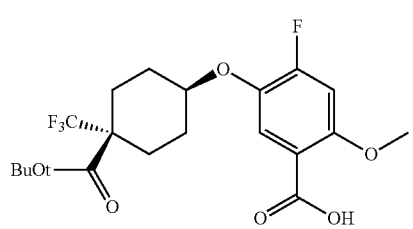

The titled compound was prepared analogous to Intermediate 329 Step A and B, using Intermediate 259 instead of Intermediate 262. MS (ESI) m/z 381.1 [M+H-tBu+H]+

Intermediate 337: 5-(((1r,4r)-4-(tert-Butoxycarbonyl)-4-hydroxycyclohexyl)oxy)-4-fluoro-2-methoxybenzoic acid

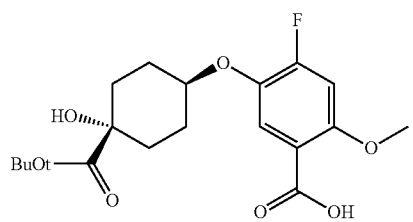

The titled compound was prepared analogous to Intermediate 329 Step A and B, using tert-butyl (1s,4s)-1,4-dihydroxycyclohexane-1-carboxylate instead of Intermediate 262. MS (ESI) m/z 329.0 [M+H-tBu+H]+

Intermediate 338: 4-Fluoro-2-methoxy-5-((4-(N-(4-methoxybenzyl)sulfamoyl)cyclohexyl)oxy)benzoic acid

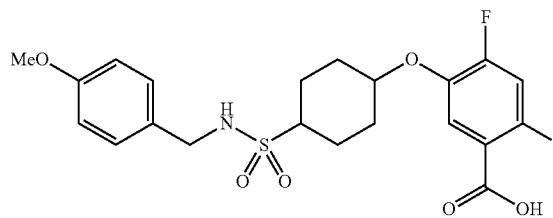

The titled compound was prepared analogous to Intermediate 329 Step A and B, using Intermediate 270 instead of Intermediate 262. MS (ESI) m/z 482.1 [M+H]+.

Intermediate 339: 5-((3-(tert-Butoxycarbonyl)cyclobutyl)methoxy)-4-fluoro-2-methoxybenzoic acid

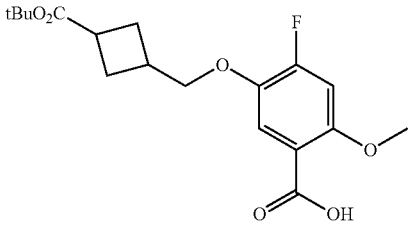 [SMILES: COc1cc(F)c(OCC2CC(C(=O)OC(C)(C)C)C2)cc1C(=O)O]

The titled compound was prepared analogous to Intermediate 329 Step A and B, using tert-butyl 3-(hydroxymethyl)cyclobutane-1-carboxylate instead of Intermediate 262. MS (ESI) m/z 299.2 [M+H-tBu]+

Intermediate 340: 4-Fluoro-2-methoxy-5-(3-(2-methoxy-2-oxoethyl)cyclobutoxy)benzoic acid

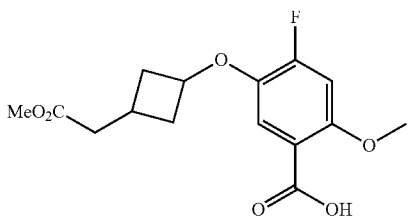 [SMILES: COC(=O)CC1CC(Oc2cc(C(=O)O)c(OC)cc2F)C1]

The titled compound (3:2 trans:cis) was prepared analogous to Intermediate 329 Step A and B, using methyl 2-(3-hydroxycyclobutyl)acetate instead of Intermediate 262. MS (ESI) m/z 313.1 [M+H]+.

Intermediate 341: 5-((4-(2-Ethoxy-2-oxoethyl)-4-methylcyclohexyl)oxy)-4-fluoro-2-methoxybenzoic acid

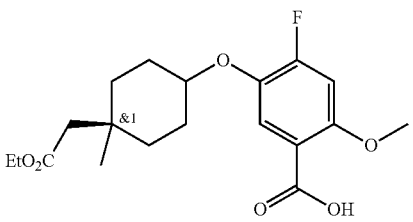

The titled compound was prepared analogous to Intermediate 329 Step A and B, using Intermediate 279 instead of Intermediate 262. MS (ESI) m/z 369.4 [M+H]+.

Intermediate 342: 5-(((1s,4s)-4-((Benzyloxy)methyl)-4-((naphthalen-1-ylmethoxy)carbonyl)cyclohexyl)oxy)-4-fluoro-2-methoxybenzoic acid

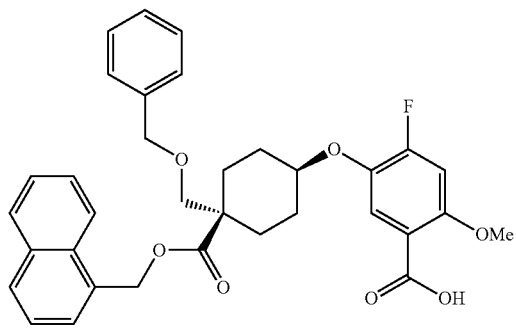 [SMILES: COc1cc(F)c(O[C@H]2CC[C@@](COCc3ccccc3)(C(=O)OCc3cccc4ccccc34)CC2)cc1C(=O)O]

The titled compound was prepared analogous to Intermediate 329 Step A and B, using Intermediate 265 instead of Intermediate 262. MS (ESI) m/z 573.1 [M+H]$^+$.

Intermediate 343: 5-(((1s,4s)-4-Ethyl-4-((naphthalen-1-ylmethoxy)carbonyl)cyclohexyl)oxy)-4-fluoro-2-methoxybenzoic acid

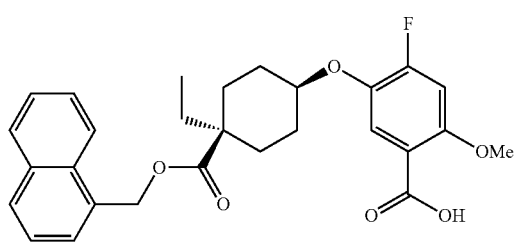

The titled compound was prepared analogous to Intermediate 329 Step A and B, using Intermediate 276 instead of Intermediate 262. MS (ESI) m/z 481.5 [M+H]$^+$.

Intermediate 344: 4-Cyano-2-methoxy-5-((5-methoxy-4,4-dimethyl-5-oxopentyl)oxy)benzoic acid

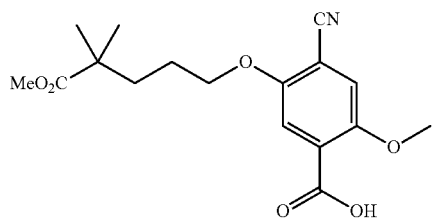 [SMILES: COC(=O)C(C)(C)CCCOc1cc(C(=O)O)c(OC)cc1C#N]

Step A: Intermediate 345: tert-Butyl 4-cyano-2-methoxy-5-((5-methoxy-4,4-dimethyl-5-oxopentyl)oxy)benzoate

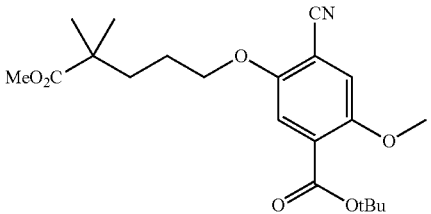

Methyl 5-bromo-2,2-dimethylpentanoate (340 mg, 1.52 mmol) was added to a mixture of Intermediate 294 (249 mg, 1.00 mmol) and potassium carbonate (279 mg, 2.02 mmol) in DMF (2 mL), then the mixture was stirred at 70 C for 1 hr. 1 M aq HCl was added to a mixture and the mixture was extracted with EtOAc, then the combined organic layer was concentrated in vacuo. The crude product was purified by flash chromatography using 0-25% EtOAc in hexane as mobile phase to give the title compound (366 mg, 94%). MS (ESI) m/z 336.2 [M−tBu]+

Step B: 4-Cyano-2-methoxy-5-((5-methoxy-4,4-dimethyl-5-oxopentyl)oxy)benzoic acid TFA (0.5 mL) was added to a mixture of Intermediate 345 (363 mg, 0.928 mmol) in CHCl$_3$ (2 mL). The reaction mixture was stirred at rt for 4 hr. The reaction mixture was concentrated, and the crude product was triturated with EtOAc-hexane to give the title compound (45 mg, 92%). MS (ESI) m/z 336.2 [M+H]$^+$.

Intermediate 346: 2,4-Difluoro-5-(((1s,4s)-4-(methoxycarbonyl)cyclohexyl)oxy)benzoic acid

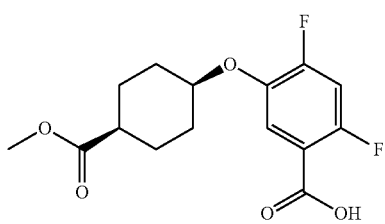 [SMILES: COC(=O)[C@H]1CC[C@@H](Oc2cc(C(=O)O)c(F)cc2F)CC1]

Step A: Intermediate 347: Benzyl 2,4-difluoro-5-(((1s,4s)-4-(methoxycarbonyl)cyclohexyl)oxy)benzoate

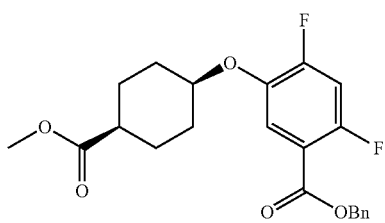 [SMILES: COC(=O)[C@H]1CC[C@@H](Oc2cc(C(=O)OCc3ccccc3)c(F)cc2F)CC1]

Trans-methyl 4-methylsulfonyloxycyclohexane-1-carboxylate (134 mg, 0.567 mmol) was added to a mixture of Intermediate 292 (100 mg, 0.379 mmol) and potassium carbonate (105 mg, 0.757 mmol) in DMF (5 mL), then the mixture was stirred at 80° C. for 12 hr. H₂O was added to a mixture and the mixture was extracted with EtOAc, then the combined organic layer was concentrated in vacuo. The crude product was purified by flash chromatography using 10-40% EtOAc in hexane as mobile phase to give the title compound (53 mg, 35%).

Step B: 2,4-Difluoro-5-(((1s,4s)-4-(methoxycarbonyl)cyclohexyl)oxy)benzoic acid

The titled compound was prepared analogous to Intermediate 322 Step B, using Intermediate 347 instead of Intermediate 323.

Intermediate 348: 4-Fluoro-2-methoxy-5-(((1s,4s)-4-(methoxycarbonyl)cyclohexyl)oxy)benzoic acid

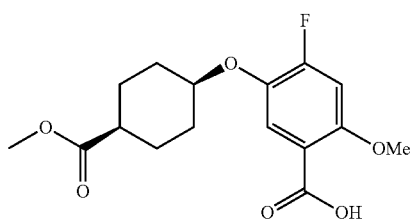 [SMILES: COc1cc(F)c(O[C@H]2CC[C@@H](C(=O)OC)CC2)cc1C(=O)O]

The titled compound was prepared analogous to Intermediate 346, using benzyl 4-fluoro-2-methoxy-5-hydroxybenzoate instead of Intermediate 292.

Intermediate 349: 5-(((1s,4s)-4-(tert-Butoxycarbonyl)-4-(methoxymethyl)cyclohexyl)oxy)-4-fluoro-2-methoxybenzoic acid

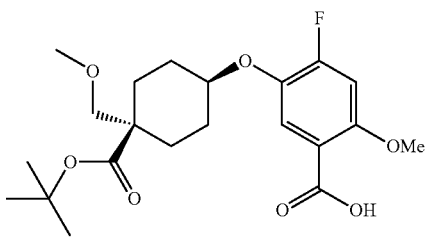 [SMILES: COC[C@]1(C(=O)OC(C)(C)C)CC[C@@H](Oc2cc(C(=O)O)c(OC)cc2F)CC1]

The titled compound was prepared analogous to Intermediate 329 step A and B, using tert-butyl (1r,4r)-4-hydroxy-1-(methoxymethyl)cyclohexane-1—instead of Intermediate 262. MS (ESI) m/z 357.2 [M+H-tBu+H]⁺.

Intermediate 350: 5-(((1r,4r)-4-(tert-Butoxycarbonyl)-4-(methoxymethyl)cyclohexyl)oxy)-4-fluoro-2-methoxybenzoic acid

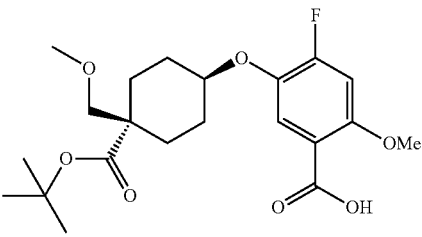 [SMILES: COC[C@]1(C(=O)OC(C)(C)C)CC[C@H](Oc2cc(C(=O)O)c(OC)cc2F)CC1]

The titled compound was prepared analogous to Intermediate 329 step A and B, using tert-butyl (1s,4s)-4-hydroxy-1-(methoxymethyl)cyclohexane-1-carboxylate instead of Intermediate 262. MS (ESI) m/z 357.2 [M+H-tBu+H]⁺.

Intermediate 351: 4-Fluoro-2-(2-methoxyethoxy)-5-(((1s,4s)-4-methyl-4-((naphthalen-1-ylmethoxy)carbonyl)cyclohexyl)oxy)benzoic acid

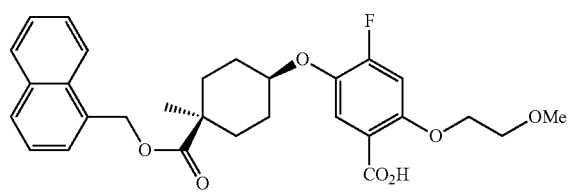 [SMILES: COCCOc1cc(F)c(O[C@H]2CC[C@@](C)(C(=O)OCc3cccc4ccccc34)CC2)cc1C(=O)O]

Step A: Intermediate 352: Methyl 2-(2-((tert-butyldiphenylsilyl)oxy)ethoxy)-4-fluoro-5-(((1s,4s)-4-methyl-4-((naphthalen-1-ylmethoxy)carbonyl)cyclohexyl)oxy)benzoate

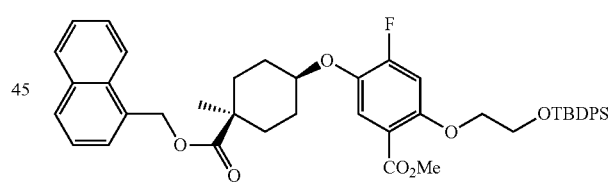

The titled compound was prepared analogous to Intermediate 295, using Intermediate 290 instead of Compound 4.

Step B: Intermediate 353: Methyl 4-fluoro-2-(2-hydroxyethoxy)-5-(((1s,4s)-4-methyl-4-((naphthalen-1-ylmethoxy)carbonyl)cyclohexyl)oxy)benzoate

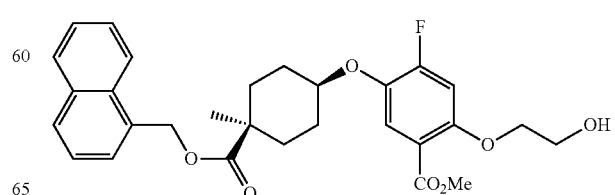

TBAF (1.0 M in THF, 0.43 mL, 0.43 mmol) was added to a solution of Intermediate 352 (217 mg, 0.290 mmol) in THF (6 mL), then the mixture was stirred at rt for 1 hr. Sat aq NH$_4$Cl and CHCl$_3$ were added to a mixture and the mixture was extracted with CHCl$_3$, then the combined organic layer was concentrated in vacuo. The crude product was purified by flash chromatography using 0-40% EtOAc in hexane as mobile phase to give the title compound (94 mg, 64%). MS (ESI) m/z 511.2 [M+H]$^+$.

Step C: Intermediate 354: Methyl 4-fluoro-2-(2-methoxyethoxy)-5-(((1s,4s)-4-methyl-4-((naphthalen-1-ylmethoxy)carbonyl)cyclohexyl)oxy)benzoate

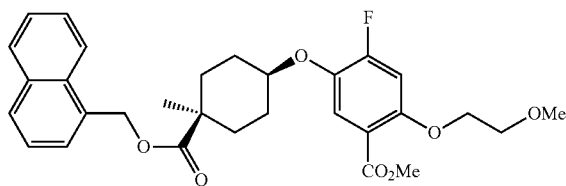 [SMILES: COCCOc1cc(F)c(O[C@H]2CC[C@@](C)(C(=O)OCc3cccc4ccccc34)CC2)cc1C(=O)OC]

Intermediate 353 (94 mg, 0.184 mmol) was added to a suspension of NaH (60% in oil suspension, 15 mg, 0.368 mmol) in THF (3 mL), then the reaction mixture was stirred at rt for 10 min. The reaction mixture was cooled to 0° C. and iodomethane (120 mg, 1.10 mmol) in DMF (3 mL) was added to the reaction mixture and the reaction mixture was stirred at rt for 3 hr. Sat aq NH$_4$Cl was added to the reaction mixture and the mixture was extracted with CHCl$_3$. The combined organic layer was concentrated in vacuo to give titled compound (96 mg, 100%). MS (ESI) m/z 525.2 [M+H]$^+$.

Step D: 4-Fluoro-2-(2-methoxyethoxy)-5-(((1s,4s)-4-methyl-4-((naphthalen-1-ylmethoxy)carbonyl)cyclohexyl)oxy)benzoic acid The titled compound was prepared analogous to Intermediate 314 Step B, using Intermediate 354 instead of Intermediate 315. MS (ESI) m/z 511.4 [M+H]$^+$.

Intermediate 355:
2-Methoxy-5-(4-(methoxycarbonyl)phenoxy)benzoic acid

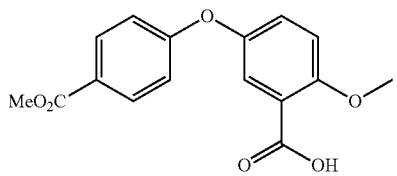 [SMILES: COC(=O)c1ccc(Oc2ccc(OC)c(C(=O)O)c2)cc1]

Step A: Intermediate 356: Methyl 4-(3-formyl-4-methoxyphenoxy)benzoate

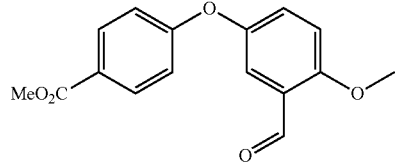 [SMILES: COC(=O)c1ccc(Oc2ccc(OC)c(C=O)c2)cc1]

CuI (89 mg, 0.465 mmol) and cesium carbonate (3.03 g, 9.30 mmol) were added to a mixture of 5-bromo-2-methoxybenzaldehyde (1 g, 4.65 mmol), methyl 4-hydroxybenzoate (1.06 g, 6.98 mmol) and N,N-dimethylglycine (195 mg, 1.40 mmol) in DME (5 mL), then the mixture was stirred at reflux for 18 hr. After being cooled to rt, aq potassium carbonate was added to the reaction mixture and the mixture was extracted with EtOAc, then the organic layer was concentrated in vacuo. The crude product was purified by flash chromatography using a gradient of 0-15% EtOAc in hexane as mobile phase to give the title compound (191 mg, 14%). MS (APCI) m/z 287.0 [M+H]$^+$.

Step B:
2-Methoxy-5-(4-(methoxycarbonyl)phenoxy)benzoic acid

Sodium chlorite (85 mg, 0.94 mmol) was added to a mixture of Intermediate 356 (191 mg, 0.67 mmol) and sodium dihydrogen phosphate (22 mg, 0.18 mmol) in DMSO (5 mL) and H$_2$O (5 mL), then the mixture was stirred at rt for 24 hr. 2 M aq HCl was added to the reaction mixture and the mixture was extracted with EtOAc, then the organic layer was concentrated in vacuo. The crude product was purified by flash chromatography using a gradient of 0-5% MeOH in CHCl$_3$ as mobile phase to give the title compound (190 mg, 99%). MS (APCI) m/z 303.0 [M+H]$^+$.

Intermediate 357:
2-Methoxy-5-(3-(methoxycarbonyl)phenoxy)benzoic acid

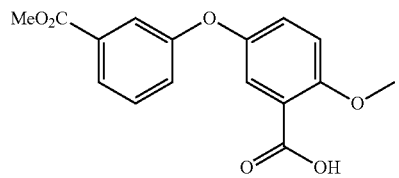 [SMILES: COC(=O)c1cccc(Oc2ccc(OC)c(C(=O)O)c2)c1]

The titled compound was prepared analogous to Intermediate 355, using methyl 3-hydroxybenzoate instead of methyl 4-hydroxybenzoate. MS (APCI) m/z 303.0 [M+H]$^+$.

Intermediate 358: 2-Methoxy-5-(2-(methoxycarbonyl)phenoxy)benzoic acid

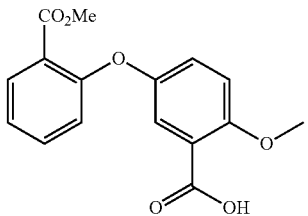 [SMILES: COC(=O)c1ccccc1Oc1ccc(OC)c(C(=O)O)c1]

The titled compound was prepared analogous to Intermediate 355, using methyl 2-hydroxybenzoate instead of methyl 4-hydroxybenzoate.

Intermediate 359: 5-(4-(tert-Butoxycarbonyl)phenoxy)-4-cyano-2-methoxybenzoic acid

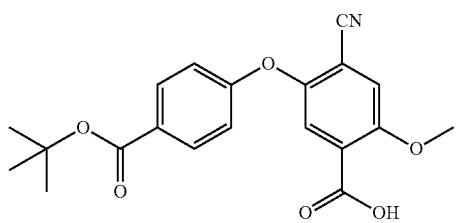 [SMILES: COc1cc(C#N)c(Oc2ccc(C(=O)OC(C)(C)C)cc2)cc1C(=O)O]

Step A: Intermediate 360: Methyl 5-(4-(tert-butoxycarbonyl)phenoxy)-4-cyano-2-methoxybenzoate

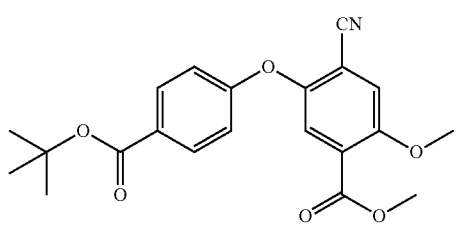 [SMILES: COC(=O)c1cc(Oc2ccc(C(=O)OC(C)(C)C)cc2)c(C#N)cc1OC]

Cu(OAc)$_2$ (88 mg, 0.483 mmol), MS4A (250 mg) and 4-(tert-butoxycarbonyl)phenylboronic acid (214 mg, 0.965 mmol) were added to a solution of methyl 4-cyano-5-hydroxy-2-methoxybenzoate (100 mg, 0.483 mmol) and pyridine (0.078 mL, 0.965 mmol) in CH$_2$Cl$_2$ (3 mL), and the reaction mixture was stirred at rt for 20 hr. The mixture was diluted with CHCl$_3$ and filtered, and the filtrate was concentrated in vacuo. The crude product was purified by NH$_2$-coated silica flash chromatography using a gradient of 25-40% EtOAc in hexane as mobile phase to give titled compound (90 mg, 49%); MS (ESI) m/z 384.1 [M+H]$^+$.

Step B: 5-(4-(tert-Butoxycarbonyl)phenoxy)-4-cyano-2-methoxybenzoic acid

The titled compound was prepared analogous to Intermediate 314 step B, using Intermediate 360 instead of Intermediate 315. MS (ESI) m/z 368.2 [M–H]–

Intermediate 361: 5-(4-(tert-Butoxycarbonyl)phenoxy)-4-fluoro-2-methoxybenzoic acid

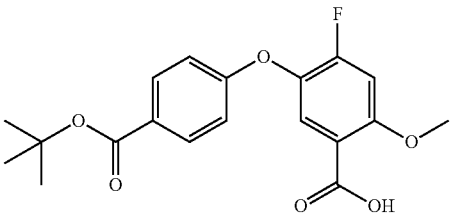 [SMILES: COc1cc(F)c(Oc2ccc(C(=O)OC(C)(C)C)cc2)cc1C(=O)O]

The titled compound was prepared analogous to Intermediate 359, using 4-fluoro-5-hydroxy-2-methoxybenzoate instead of 4-cyano-5-hydroxy-2-methoxybenzoate. MS (ESI) m/z 361.2 [M–H]–

Intermediate 362: 5-((5-(tert-Butoxycarbonyl)-1H-pyrazol-1-yl)methyl)-4-fluoro-2-methoxybenzoic acid

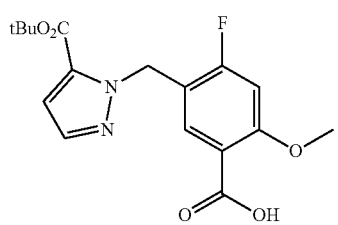 [SMILES: COc1cc(F)c(Cn2nccc2C(=O)OC(C)(C)C)cc1C(=O)O]

Step A: Intermediate 363: tert-Butyl 1-(2-fluoro-4-methoxy-5-(methoxycarbonyl)benzyl)-1H-pyrazole-5-carboxylate and Intermediate 364: tert-butyl 1-(2-fluoro-4-methoxy-5-(methoxycarbonyl)benzyl)-1H-pyrazole-3-carboxylate

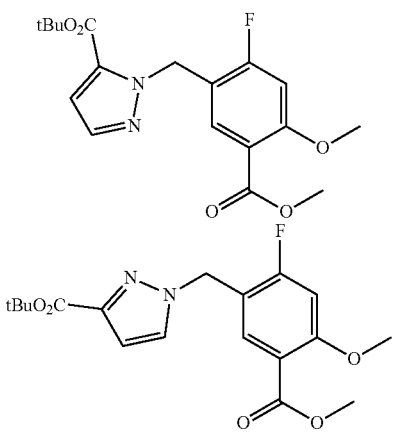

Methanesulfonyl chloride (67 mg, 0.584 mmol) was added to a solution of methyl 4-fluoro-5-(hydroxymethyl)-2-methoxybenzoate and DIPEA (94 mg, 0.728 mmol) in CHCl$_3$ (3 mL), and the reaction mixture was stirred at rt for 20 hr. Sat aq NaHCO$_3$ was added, then the mixture was extracted with CHCl$_3$ and the combined organic layer was concentrated in vacuo.

The residue and tert-butyl 1H-pyrazole-3-carboxylate (123 mg, 0.731 mmol) were dissolved in DMF (3 mL) and potassium carbonate (135 mg, 0.977 mmol) was added and the mixture was stirred at rt for 4 hr. H$_2$O was added to the reaction mixture and the mixture was extracted with EtOAc, then the organic layer was concentrated in vacuo. The crude product was purified by flash chromatography using a gradient of 0-30% EtOAc in hexane as mobile phase to give the first eluting compound Isomer 1: Intermediate 363 (74 mg, 42%); MS (ESI) m/z 365.2 [M+H]$^+$, and the second eluting compound Isomer 2: Intermediate 364 (84 mg, 47%); MS (ESI) m/z 365.2 [M+H]$^+$.

Step B: 5-((5-(tert-Butoxycarbonyl)-1H-pyrazol-1-yl)methyl)-4-fluoro-2-methoxybenzoic acid 1 M aq LiOH (0.61 mL, 0.61 mmol) was added to a solution of Intermediate 363 (74 mg, 0.202 mmol) in DME (10 mL), and the reaction mixture was stirred at rt for 4 hr. 1 M aq HCl was added to the reaction mixture, then the reaction mixture was extracted with CHCl$_3$ and the combined organic layer was concentrated in vacuo to give titled compound (70 mg, 99%).

Intermediate 365: 5-((3-(tert-Butoxycarbonyl)-1H-pyrazol-1-yl)methyl)-4-fluoro-2-methoxybenzoic acid

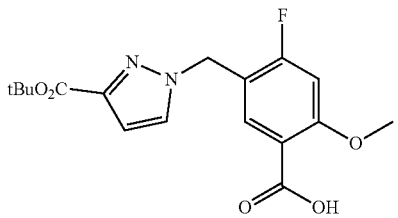 [SMILES: COc1cc(F)c(Cn2ccc(C(=O)OC(C)(C)C)n2)cc1C(=O)O]

The titled compound was prepared analogous to Intermediate 362 step B, using Intermediate 364 instead of Intermediate 363.

Intermediate 366: 5-(3-(tert-Butoxy)-3-oxopropyl)-2-methoxybenzoic acid

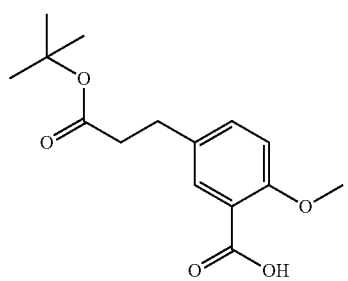 [SMILES: COc1ccc(CCC(=O)OC(C)(C)C)cc1C(=O)O]

Step A: Intermediate 367: Methyl 5-(3-(tert-butoxy)-3-oxopropyl)-2-methoxybenzoate

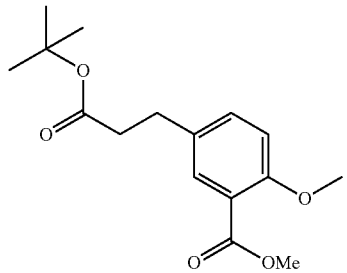 [SMILES: COC(=O)c1cc(CCC(=O)OC(C)(C)C)ccc1OC]

Palladium (10% Pd/C, moisture by 50% H$_2$O, 20 mg) was added to a solution of methyl (E)-5-(3-(tert-butoxy)-3-oxoprop-1-en-1-yl)-2-methoxybenzoate (200 mg, 0.684 mmol) in MeOH (3 mL). The reaction mixture was stirred under 1 atm of hydrogen atmosphere at rt for 20 hr. The hydrogen in the reaction vessel was replaced with argon and the reaction mixture was filtered with Celite® to give titled compound (155 mg, 77%).

Step B: 5-(3-(tert-Butoxy)-3-oxopropyl)-2-methoxybenzoic acid

The titled compound was prepared analogous to Intermediate 314 step B, using Intermediate 367 instead of Intermediate 315. MS (ESI) m/z 279.2 [M–H]–

Intermediate 368: Methyl (S)-2-(6-(4,4,5,5-tetramethyl-1,3,2-dioxaborolan-2-yl)-2,3-dihydrobenzofuran-3-yl)acetate

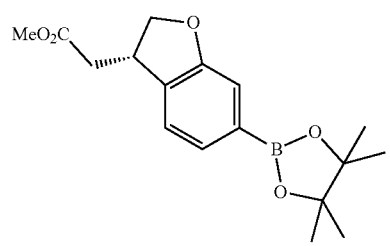 [SMILES: COC(=O)C[C@@H]1COc2cc(B3OC(C)(C)C(C)(C)O3)ccc21]

PdCl$_2$(dppf)$_2$.CH$_2$Cl$_2$ (50 mg, 0.061 mmol) and potassium acetate (242 mg, 2.47 mmol) were added to a solution of methyl 2-((3S)-6-(((trifluoromethyl)sulfonyl)oxy)-2,3-dihydrobenzofuran-3-yl)acetate (420 mg, 1.23 mmol) and bis(pinacolato)diboron (376 mg, 1.48 mmol) in cyclopentyl methyl ether (3 mL), then the mixture was stirred at reflux temperature for 1 hr. The mixture was cooled to ambient temperature and H$_2$O was added, then the mixture was extracted with CHCl$_3$ and the organic layer was concentrated in vacuo. The crude product was purified by flash chromatography using a gradient of 0-25% EtOAc in hexane as mobile phase to give the title compound (340 mg, 87%). MS (ESI) m/z 319.2 [M+H]$^+$.

Intermediate 369: Methyl (R)-2-(6-(4,4,5,5-tetramethyl-1,3,2-dioxaborolan-2-yl)-2,3-dihydrobenzofuran-3-yl)acetate

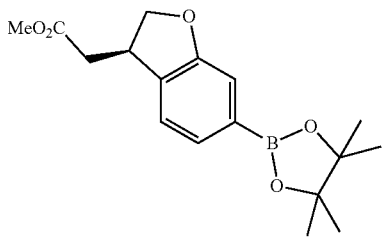 [SMILES: COC(=O)C[C@H]1COc2cc(B3OC(C)(C)C(C)(C)O3)ccc21]

The titled compound was prepared analogous to Intermediate 368, using methyl 2-[(3R)-6-(trifluoromethylsulfonyloxy)-2,3-dihydrobenzofuran-3-yl]acetate instead of methyl 2-[(3S)-6-(trifluoromethylsulfonyloxy)-2,3-dihydrobenzofuran-3-yl]acetate. MS (ESI) m/z 319.2 [M+H]$^+$.

Intermediate 370: Ethyl 3-(6-bromopyridazin-3-yl)propanoate

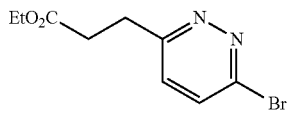

(3-Ethoxy-3-oxopropyl)zinc(II) bromide (0.5 M in THF, 3.7 mL, 1.85 mmol) was added to a solution of 3,6-dibromopyridazine (400 mg, 1.68 mmol) and tetrakis(triphenylphosphine)palladium (194 mg, 0.168 mmol) in THF (4.2 mL), then the mixture was stirred at rt for 1 hr. H$_2$O was added to the reaction mixture and the mixture was extracted with EtOAc, then the organic layer was concentrated in vacuo. The crude product was purified by flash chromatography using a gradient of 0-40% EtOAc in hexane as mobile phase to give the title compound (121 mg, 28%). MS (ESI) m/z 259.2/261.1 [M+H]$^+$.

Intermediate 371: Benzyl 3-(5-bromopyridin-2-yl)propanoate

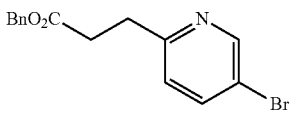

Benzyl bromide (164 mg, 0.956 mmol) was added to a mixture of 3-(5-bromo-2-pyridyl)propanoic acid (200 mg, 0.869 mmol) and potassium carbonate (180 mg, 1.304 mmol) in DMF (1.5 mL), then the mixture was stirred at rt for 1 hr. H$_2$O was added to the reaction mixture and the mixture was extracted with EtOAc/hexane (2/1), then the organic layer was concentrated in vacuo. The crude product was purified by flash chromatography using a gradient of 0-25% EtOAc in hexane as mobile phase to give the title compound (159 mg, 57%). MS (ESI) m/z 320.1/322.1 [M+H]$^+$.

Intermediate 372: tert-Butyl (5-(4-bromo-2-fluorophenethyl)-2,2-dimethyl-1,3-dioxan-5-yl)carbamate

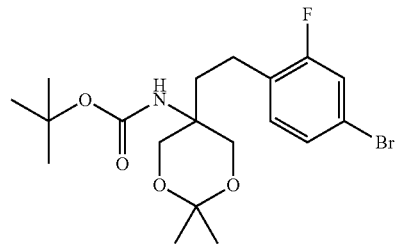 [SMILES: CC(C)(C)OC(=O)NC1(CCc2ccc(Br)cc2F)COC(C)(C)OC1]

Step A: Intermediate 373: tert-Butyl (Z)-(5-(4-bromo-2-fluorostyryl)-2,2-dimethyl-1,3-dioxan-5-yl)carbamate

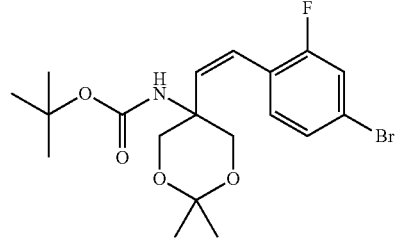 [SMILES: CC(C)(C)OC(=O)NC1(/C=C\c2ccc(Br)cc2F)COC(C)(C)OC1]

Potassium tert-butoxide (10.5 g, 93.2 mmol) was added to a mixture of (4-bromo-2-fluorobenzyl)triphenylphosphonium bromide (49.4 g, 93.2 mmol) in THF (500 mL). The reaction mixture was stirred at rt for 1 hr. tert-butyl (5-formyl-2,2-dimethyl-1,3-dioxan-5-yl)carbamate (12.1 g, 46.6 mmol) in THF (100 mL) was added to the reaction mixture and the mixture was stirred at rt for 4 hr. The mixture was poured into H$_2$O (1 L) and extracted with EtOAc, then the organic layer was concentrated in vacuo. The crude product was dissolved in Et2O and filtered off to remove triphenylphosphine oxide, then the filtrate was concentrated in vacuo and the residue was purified by flash chromatography using a gradient of 0-20% EtOAc in hexane as mobile phase to give the title compound (20.1 g, 100%).

Step B: tert-Butyl (5-(4-bromo-2-fluorophenethyl)-2,2-dimethyl-1,3-dioxan-5-yl)carbamate RhCl(PPh3)2 (200 mg, 0.22 mmol) was added to a mixture of Intermediate 373 (1.0 g, 2.32 mmol) in toluene (15 mL). The reaction mixture was stirred at rt under 1 atm of hydrogen atmosphere for 15 h and 60° C. for 10 hr. After the reaction mixture was concentrated in vacuo, acetone (20 mL), dimethoxypropane (856 uL, 6.96 mmol) and p-toluenesulfonic acid hydrate (10 mg) were added to the residue and the mixture was stirred at rt for 15 hr. After the reaction mixture was concentrated in vacuo, the crude product was purified by flash chromatography using a gradient of 0-25% EtOAc in hexane as mobile phase to give the title compound (0.99 g, 99%).

EXAMPLES

Example 1: (1S,4s)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid (Form A)

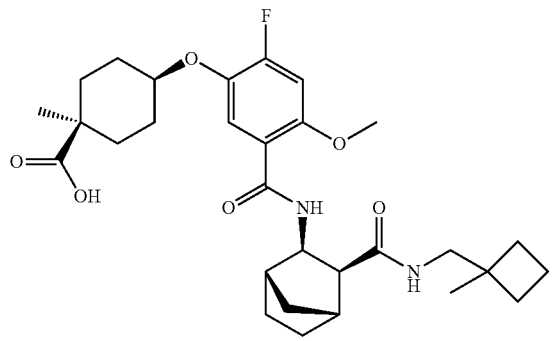 [SMILES: COc1cc(F)c(O[C@H]2CC[C@@](C)(C(=O)O)CC2)cc1C(=O)N[C@@H]1[C@H]2CC[C@H](C2)[C@@H]1C(=O)NCC1(C)CCC1]

To a solution of Intermediate 17 in EtOH (206 g, 19% w/w, 57.9 mmol) was added EtOH (385 mL) followed by 10 wt % Pd/C (3.96 g, 5% w/w). The vessel was purged with $N_2$ six times followed by $H_2$ a further six times. The vessel was pressurized to 0.4 MPa with $H_2$ and the reaction solution stirred for 20 h at between 20 and 30° C. The $H_2$ atmosphere was completely replaced with $N_2$ before the reaction mixture was filtered and the solids washed with EtOH (3×80 mL). A second identical batch was conducted and the collected EtOH solutions combined to give a single solution. The solvent was exchanged to EtOAc under reduced pressure maintaining the temperature below 45° C. The EtOAc solution (280 mL) was heated to between 70 and 75° C. for 0.5 h then cooled to between 40 and 45° C. and n-heptane (475 mL) added drop-wise over 0.5 h. The mixture was stirred for 0.5 h then cooled to between 20 and 25° C. over 2 h then held for a further 2 h. The heterogenous slurry was filtered then the solids washed twice with 1:2 EtOAc/n-heptane (160 mL) prior to drying at below 45° C. for 20 h to give crude title compound as a white solid (55.7 g, 87%).

Part 1: The crude title compound (2.50 g, 4.59 mmol) was dissolved in EtOH (15.0 mL). The temperature of the solution was maintained at 25.0±2.0° C. during the drop-wise addition of water (7.50 mL) during which a precipitate formed. The heterogenous slurry was stirred for a further 1.0 h then collected via filtration. The solids were washed with a (2:3) mixture of EtOH/Water (2×5.00 mL), collected and dried under $N_2$ to give the title compound as a white solid (1.80 g, 72%). This material was characterized as Form A and used as seed following the method described in Part 2.

Part 2: The crude title compound (50.0 g, 91.8 mmol) was dissolved in EtOH (350 mL) then passed through a filter. EtOH (100 mL) was added to vessel then passed through the filter to give a combined EtOH solution. The temperature of the solution was maintained at 25.0±2.0° C. during the slow addition of $H_2O$ (150 mL) over 0.5 h. The solution was stirred for a further 0.5 h then seed material from Part 1 (0.005 g, 0.1% w/w) was added. The solution was held for 6 h then cooled to 20.0±0.5° C. over 2 h, then held for a further 6 h. $H_2O$ (150 mL) was added slowly over 6 h then the mixture held for a further 2 h prior to filtration. EtOH (45 mL) and $H_2O$ (30 mL) was added to vessel then used to wash the filter cake. The solids were collected and dried under $N_2$ at below 45° C. for 12 h to give the title compound Form A as a white solid (42.2 g, 85%); $^1$H NMR (500 MHz, CDCl$_3$) δ 0.97 (3H, s), 1.12-1.42 (5H, m), overlapping 1.25 (3H, S), 1.43-1.82 (10H, m), 1.92-2.1 (3H, m), 2.25 (3H, dd), 2.51 (2H, dd), 2.96 (1H, dd), 3.18 (1H, dd), 3.92 (3H, s), 4.12-4.28 (1H, m), 4.41 (1H, t), 5.81 (1H, t), 6.70 (1H, d), 7.86 (1H, d), 8.60 (1H, d). HRMS (ESI) m/z [M+H]$^+$ calcd for C30H42FN2O6: 545.3022 found: 545.3019.

Form B of (1S,4s)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid Amorphous (1S,4s)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid (150 mg, 275 mmol) was placed in a beaker in a brown 250 mL glass jar. Cyclohexane (20 mL) was placed at the bottom at the glass jar and sealed with a lid. After 4 weeks, the solid in the jar was isolated as Form F (cyclohexane solvate) (173 mg, 275 mmol) as a white solid.

Form F (120 mg, 191 mmol) was heated at 80° C. on a heating block overnight (ca. 16h) resulting in Form B of the title compound (104 mg, 191 mmol) as a white solid.

Form D of (1S,4s)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid Amorphous (1S,4s)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid was slurried in MeCN (7 mL) for 1 hour. The slurry was allowed to evaporate at ambient temperature for 3 days to yield Form D of the title compound (540 mg, 991 mmol) as a white solid.

Form E of (1S,4s)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid (1S,4s)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid was dissolved in IPA (0.84 mL). Water (0.56 mL) was added and the mixture stirred for 20 min at 75° C. until dissolved. The clear solution was allowed to evaporate to dryness (2 days) at ambient temperature to yield Form E of the title compound (IPA solvate) (11 mg, 18 mmol) as a white solid.

Example 2: (1S,4s)-4-(5-(((1S,2R,3S,4R)-3-((cyclobutylmethyl)carbamoyl)bicyclo[2.2.1]heptan-2-yl)carbamoyl)-2-fluoro-4-methoxyphenoxy)-1-methylcyclohexane-1-carboxylic acid

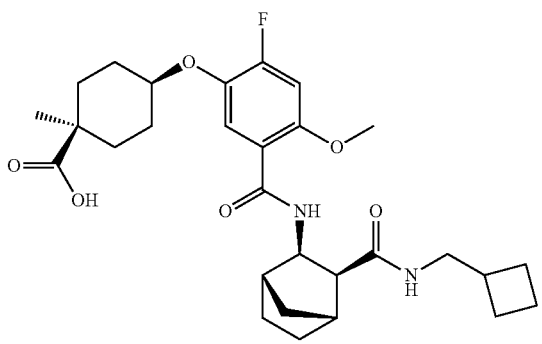 [SMILES: COc1cc(F)c(O[C@H]2CC[C@@](C)(C(=O)O)CC2)cc1C(=O)N[C@@H]1[C@H]2CC[C@H](C2)[C@@H]1C(=O)NCC1CCC1]

Step A Intermediate 18: Naphthalen-1-ylmethyl (1S,4s)-4-(5-(((1R,2R,3S,4S)-3-((cyclobutylmethyl)carbamoyl)bicyclo[2.2.1]hept-5-en-2-yl)carbamoyl)-2-fluoro-4-methoxyphenoxy)-1-methylcyclohexane-1-carboxylate To a solution of DIPEA (1.07 g, 8.31 mmol) in DCM (50.5 mL) at between 0 and 5° C. was added Intermediate 16 (5.00 g, 8.31 mmol) followed by cyclobutylmethanamine hydrochloride (1.26 g, 10.4 mmol). DIPEA (4.21 g, 32.6 mmol) was added drop-wise maintaining the temperature between 0 and 5° C., followed by the addition of T3P (8.46 g, 13.3 mmol, 50% w/w in EtOAc) over 0.5 h. The solution was warmed to between 15 and 25° C. and stirred for 2 h followed by the drop-wise addition of water (25.0 mL) maintaining the temperature below 30° C. The biphasic solution was separated and the organic phase washed with water (2×25.0 mL) then the solvent exchanged to EtOH (75.0 mL) under reduced pressure to give the title compound as a solution in EtOH that was used directly in the next step.

Step B: (1S,4s)-4-(5-(((1S,2R,3S,4R)-3-((cyclobutylmethyl)carbamoyl)bicyclo[2.2.1]heptan-2-yl)carbamoyl)-2-fluoro-4-methoxyphenoxy)-1-methylcyclohexane-1-carboxylic acid To the EtOH solution of Intermediate 18 was added 10 wt % Pd/C (290 mg, 5% w/w). The vessel was purged with $N_2$ six times followed by $H_2$ a further six times. The vessel was pressurized to 0.4 MPa with $H_2$ and the reaction solution stirred for 20 h at between 20 and 30° C. The $H_2$ atmosphere was completely replaced with $N_2$ before the reaction mixture was filtered and the solids washed with EtOH (2×12.2 ml). The solvent was exchanged to EtAOc under reduced pressure maintaining the temperature below 45° C. The EtAOc solution (41.0 mL) was heated to between 70 and 75° C. for 0.5 h then cooled to between 40 and 45° C. and n-heptane (34.8 mL) added drop-wise over 0.5 h. The mixture was stirred for 0.5 h then cooled to between 20 and 25° C. over 2 h then held for a further 2 h. The heterogenous slurry was filtered then the solids washed twice with 1:2 EtOAc/n-heptane (11.6 mL) prior to drying at below 45° C. for 20 h to give the title compound as a white solid (3.28 g, 74%). $^1$H NMR (500 MHz, DMSO-$d_6$) δ 1.04-1.30 (6H, m), overlapping 1.10 (3H, s), 1.35-1.58 (5H, m), 1.59-1.69 (2H, m), 1.71-1.82 (2H, m), 1.83-1.92 (2H, m), 1.95-2.02 (1H, m), 2.01-2.10 (3H, d), 2.18-2.31 (2H, m), 2.50-2.55 (1H, d), 2.92-3.00 (1H, m), 3.06-3.14 (1H, m), 3.89 (3H, s), 4.07-4.17 (2H, m), 7.11 (1H, d), 7.67 (1H, d), 7.94 (1H, t), 8.83 (1H, d). MS (ESI): m/z [M+H]$^+$ 531.3.

Example 3: (1R,4s)-4-(2-Fluoro-4-methoxy-5-(((1R,2S,3R,4S)-3-(((1-methylcyclobutyl)methyl)carbamoyl)bicyclo[2.2.1]heptan-2-yl)carbamoyl)phenoxy)-1-methylcyclohexane-1-carboxylic acid

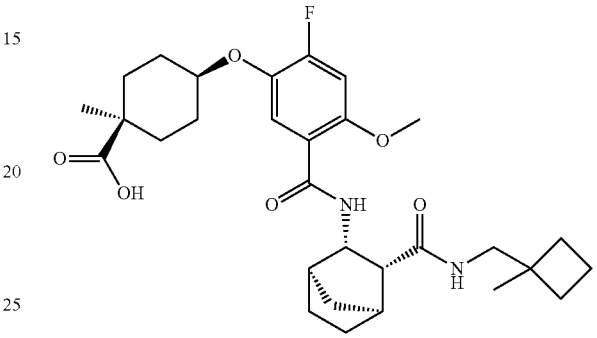

TFA (4.00 mL, 51.9 mmol) was added dropwise to Intermediate 138 (1.56 g, 2.60 mmol) in DCM (150 mL) cooled to 0° C. in 1 min under nitrogen. The resulting solution was stirred at 20° C. for 7 h. The solvents were evaporated under reduced pressure to afford the title compound (1.40 g, 97%) as a white solid after lyophilization; HRMS (ESI) m/z [M+H]$^+$ calcd for C30H42FN2O6: 545.3022 found: 545.3036.

Example 4: (1S,4s)-4-(2-Fluoro-4-(fluoromethoxy)-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid

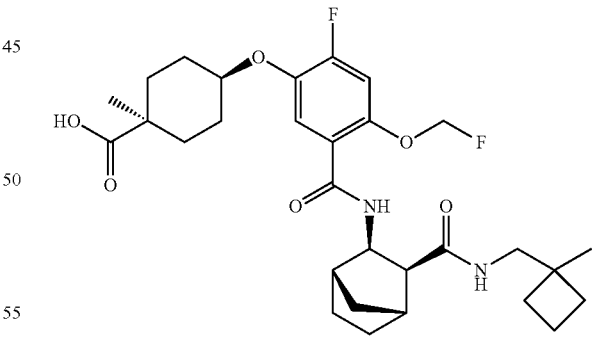

Pd—C (50 mg, 0.05 mmol, 10%) was added to Intermediate 30 (227 mg, 0.32 mmol) in MeOH (20 mL) at 20° C. The reaction suspension was stirred at 20° C. for 14 h under an atmosphere of hydrogen (1.3 atm). The reaction mixture was filtered through a pad of Celite® and the solvent was removed under reduced pressure. The crude product was purified by preparative HPLC, Method PrepAcidic-B, (gradient: 70-80%). Compound containing fractions were collected, evaporated to dryness and purified by preparative HPLC, Method PrepBasic-B, (gradient: 5-95%), to give the title compound (36 mg, 20%); HRMS (ESI) m/z [M+H]+ calcd for C30H41F2N2O6: 563.2928 found: 563.2962.

Example 5: (1S,4s)-4-(2-Fluoro-4-methyl-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid

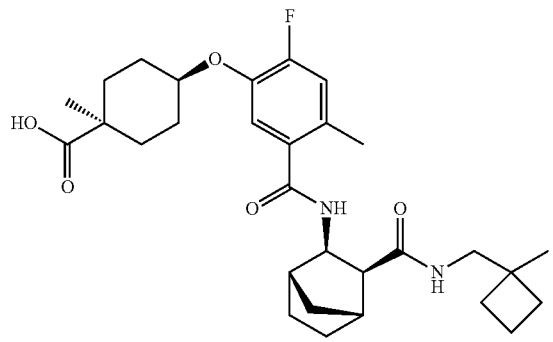 [SMILES: Cc1cc(F)c(O[C@H]2CC[C@@](C)(C(=O)O)CC2)cc1C(=O)N[C@@H]1[C@H]2CC[C@H](C2)[C@@H]1C(=O)NCC1(C)CCC1]

Pd—C (96 mg, 0.90 mmol) was added to a solution of Intermediate 33 (150 mg, 0.22 mmol) in EtOAc (10 mL) and the suspension was stirred at rt for 12 h. The reaction mixture was filtered and the solvents were removed under reduced pressure. The crude product was dissolved in DCM (20 mL), and the organic layer was washed with $H_2O$ (3×10 mL), dried over $Na_2SO_4$, filtered, and evaporated. The crude product was purified by reversed phase flash chromatography on a C18 column using a gradient of 0-70% MeCN in $H_2O$ as mobile phase, to give the title compound (50 mg, 42%) as a white solid; HRMS (ESI) m/z [M+H]+ calcd for C30H42FN2O5: 529.3072 found: 529.3076.

Example 6: (2R*,4r,6R)-6-(2-Cyano-4-methoxy-5-(((1S,2R,3S,4R)-3-(((1-methylcyclobutyl)methyl)carbamoyl)bicyclo[2.2.1]heptan-2-yl)carbamoyl)phenoxy)spiro[3.3]heptane-2-carboxylic acid ISOMER 2

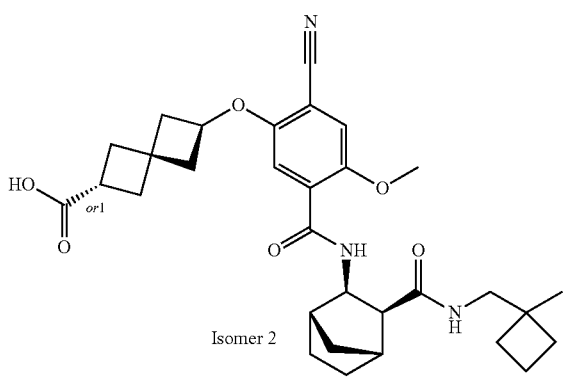

Intermediate 38 was dissolved in FA (5 mL) at rt. The reaction mixture was stirred at 100° C. for 4 h. The solvent was removed under reduced pressure and the crude product was purified by preparative HPLC to afford the title compound Example 6 (30 mg, 50%); HRMS (ESI) m/z [M+H]+ calcd for C31H40N3O6: 550.2912 found: 550.2916. The compound was analysed by chiral SFC on a Lux Cellulose 4 column (3 μm, 100×4.6 mm ID) using 30% of MeOH/DEA (99.9:0.1) in $CO_2$ as mobile phase; $t_r$=2.022 min which corresponds to the second eluting compound compared to a mixture of Example 6 and Example 7.

Example 7: (2R*,4r,6R)-6-(2-Cyano-4-methoxy-5-(((1S,2R,3S,4R)-3-(((1-methylcyclobutyl)methyl)carbamoyl)bicyclo[2.2.1]heptan-2-yl)carbamoyl)phenoxy)spiro[3.3]heptane-2-carboxylic acid Isomer 1

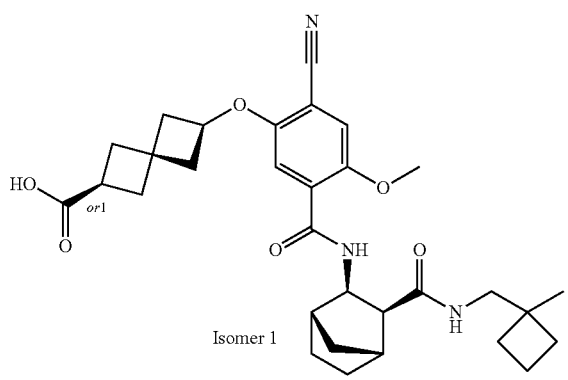

The title compound Example 7 was prepared from Intermediate 37 as described for Example 6 affording (30 mg, 44%); HRMS (ESI) m/z [M+H]+ calcd for C31H40N3O6: 550.2912 found: 550.2900. The compound was analysed by chiral SFC on a Lux Cellulose 4 column (3 μm 100×4.6 mm ID) using 30% of MeOH/DEA (99.9:0.1) in $CO_2$ as mobile phase. $t_R$=1.697 min which corresponds to the first eluting compound compared to a mixture of Example 6 and Example 7.

Example 8: (1S,4s)-4-(2-Fluoro-5-(((1S,2R,3S,4R)-3-(isopropylcarbamoyl)bicyclo[2.2.1]heptan-2-yl)carbamoyl)-4-methoxyphenoxy)cyclohexane-1-carboxylic acid

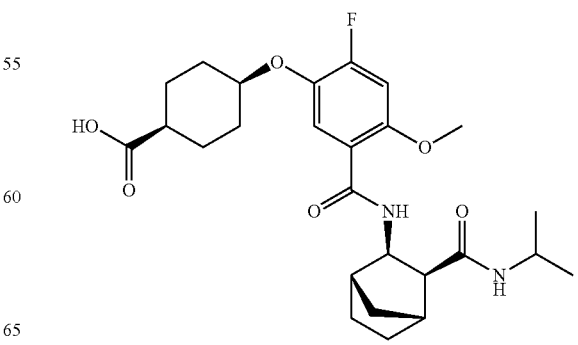

279

Step A Intermediate 374: Ethyl (1S,4s)-4-(2-fluoro-5-(((1S,2R,3S,4R)-3-(isopropylcarbamoyl)bicyclo[2.2.1]heptan-2-yl)carbamoyl)-4-methoxyphenoxy)cyclohexane-1-carboxylate

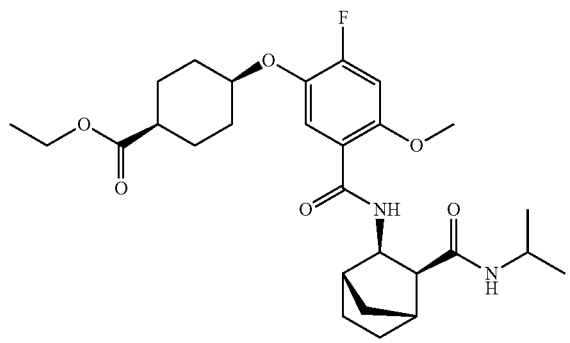 [SMILES: CCOC(=O)[C@H]1CC[C@@H](Oc2cc(C(=O)N[C@@H]3[C@H]4CC[C@H](C4)[C@@H]3C(=O)NC(C)C)c(OC)cc2F)CC1]

EDC (0.177 g, 0.92 mmol) was added slowly to a solution of Intermediate 106 (0.2 g, 0.42 mmol), propan-2-amine (0.074 g, 1.26 mmol), HOBt (0.141 g, 0.92 mmol), and TEA (0.292 mL, 2.09 mmol) in DMF (20 mL) at 20° C. and the reaction mixture was stirred at 60° C. for 14 h. The reaction mixture was diluted with EtOAc (200 mL), and the organic layer was washed sequentially with sat brine (150 mL), sat NaHCO$_3$ (150 mL), and H$_2$O (150 mL), dried over Na$_2$SO$_4$, filtered and evaporated to give the title compound (0.20 g, 92%) as a yellow oil which solidified on standing; MS (ESI) m/z [M+H]$^+$ 519.2.

Step B (1S,4s)-4-(2-Fluoro-5-(((1S,2R,3S,4R)-3-(isopropylcarbamoyl)bicyclo[2.2.1]heptan-2-yl)carbamoyl)-4-methoxyphenoxy)cyclohexane-1-carboxylic acid LiOH (0.15 g, 6.26 mmol) was added to a solution of Intermediate 374 (0.2 g, 0.39 mmol) in THF (4 mL), MeOH (1 mL) and H$_2$O (1 mL), and the reaction mixture was stirred at 20° C. for 15 h. The reaction mixture was poured into H$_2$O (150 mL) and acidified with HCl (2 M). The aq layer was extracted with EtOAc (3×50 mL), and the organic layer was dried over Na$_2$SO$_4$, filtered and evaporated under reduced pressure. The crude product was purified by Method PrepAcidic A, (gradient: 43-50%), to give the title compound (0.104 g, 55%) as a white solid; HRMS (ESI) m/z [M+H]$^+$ calcd for C26H36FN2O6: 491.2552 found: 491.2560.

280

Example 9: (1S,4s)-4-(5-(((1S,2R,3S,4R)-3-(Cyclohexylcarbamoyl)bicyclo[2.2.1]heptan-2-yl)carbamoyl)-2-fluoro-4-methoxyphenoxy)cyclohexane-1-carboxylic acid

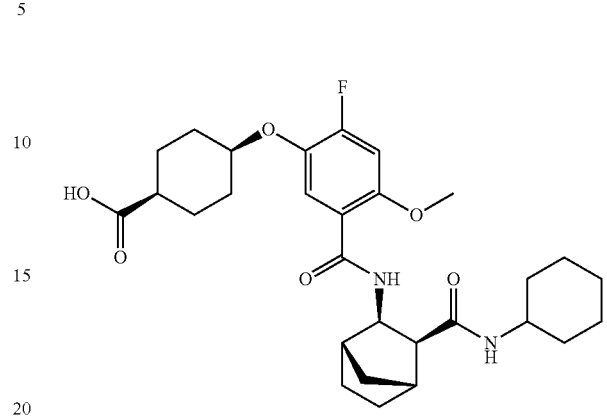

Step A Intermediate 375: Ethyl (1S,4s)-4-(5-(((1S,2R,3S,4R)-3-(cyclohexylcarbamoyl)bicyclo[2.2.1]heptan-2-yl)carbamoyl)-2-fluoro-4-methoxyphenoxy)cyclohexane-1-carboxylate

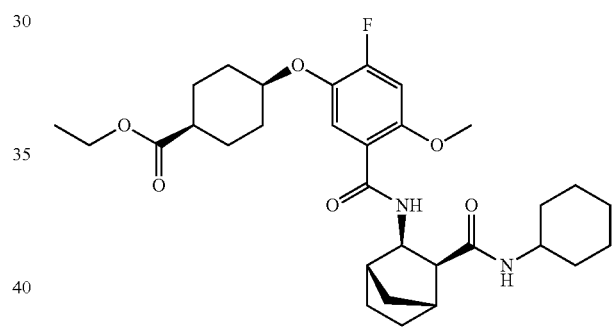

HATU (0.239 g, 0.63 mmol) was added to a solution of Intermediate 106 (0.20 g, 0.42 mmol), cyclohexanamine (0.058 g, 0.59 mmol) and DIPEA (0.219 mL, 1.26 mmol) in DMF (10 mL) at 20° C. and the reaction mixture was stirred at 60° C. for 3 h. The reaction mixture was poured into sat NaHCO$_3$ (150 mL), and the aq layer was extracted with EtOAc (3×50 mL). The combined organic layer was dried over Na$_2$SO$_4$, filtered and evaporated under reduced pressure to afford the title compound (0.20 g, 85%) as a brown oil which solidified on standing. The product was used in the next step without further purification; MS (ESI) m/z [M+H]$^+$ 559.3.

Step B (1S,4s)-4-(5-(((1S,2R,3S,4R)-3-(Cyclohexylcarbamoyl)bicyclo[2.2.1]heptan-2-yl)carbamoyl)-2-fluoro-4-methoxyphenoxy)cyclohexane-1-carboxylic acid LiOH (0.10 g, 4.18 mmol) was added to a solution of Intermediate 375 (0.20 g, 0.36 mmol) in THF (4 mL), MeOH (1 mL) and H$_2$O (1 mL) and the reaction mixture was stirred at 20° C. for 15 h. The reaction mixture was poured into H$_2$O (150 mL) and acidified with HCl (2 M). The aq layer was extracted with EtOAc (3×50 mL), and the combined organic layer was dried over Na₂SO₄, filtered and evaporated. The crude product was purified by Method PrepAcidic A, (gradient: 63-65%), to give the title compound (0.125 g, 65%) as a white solid; HRMS (ESI) m/z [M+H]⁺ calcd for C29H40FN2O6: 531.2864 found: 531.2872.

Example 10: (1S,4s)-4-(5-(((1S,2R,3S,4R)-3-((3-(Difluoromethyl)phenyl)carbamoyl)bicyclo[2.2.1]heptan-2-yl)carbamoyl)-2-fluoro-4-methoxyphenoxy)cyclohexane-1-carboxylic acid

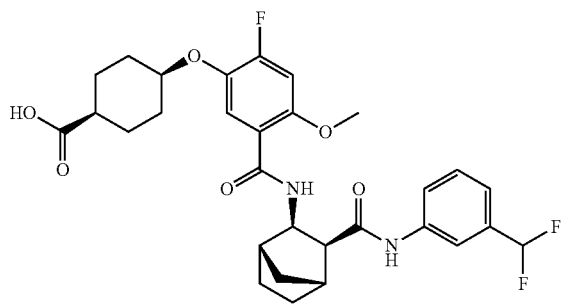 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cccc(C(F)F)c1]

Step A Intermediate 376: Ethyl (1S,4s)-4-(5-(((1S,2R,3S,4R)-3-((3-(difluoromethyl)phenyl)carbamoyl)bicyclo[2.2.1]heptan-2-yl)carbamoyl)-2-fluoro-4-methoxyphenoxy)cyclohexane-1-carboxylate

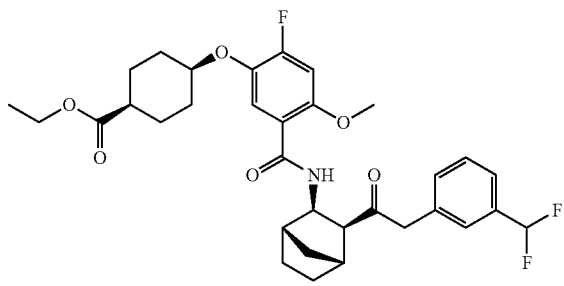 [SMILES: CCOC(=O)[C@H]1CC[C@@H](Oc2cc(C(=O)N[C@@H]3[C@H]4CC[C@H](C4)[C@@H]3C(=O)Cc3cccc(C(F)F)c3)c(OC)cc2F)CC1]

DIPEA (0.198 mL, 1.13 mmol) was added dropwise to a solution of Intermediate 106 (0.18 g, 0.38 mmol), 3-(difluoromethyl)aniline (0.081 g, 0.57 mmol) and HATU (0.430 g, 1.13 mmol) in DMF (10 mL) at 20° C., and under a nitrogen atmosphere, and the reaction mixture was stirred at 20° C. for 14 h. The reaction mixture was diluted with EtOAc (200 mL), and the organic layer was washed sequentially with sat brine (200 mL), sat NaHCO₃ (200 mL), and H₂O (200 mL), dried over Na₂SO₄, filtered and evaporated under reduced pressure. The crude product was purified by preparative TLC (EtOAc:PE, 1:1), to give the title compound (0.187 g, 82%) as a pale yellow solid; MS (ESI) m/z [M+H]⁺ 603.

Step B (1S,4s)-4-(5-(((1S,2R,3S,4R)-3-((3-(Difluoromethyl)phenyl)carbamoyl)bicyclo[2.2.1]heptan-2-yl)carbamoyl)-2-fluoro-4-methoxyphenoxy)cyclohexane-1-carboxylic acid LiOH (22 mg, 0.93 mmol) was added portion wise to Intermediate 376 (187 mg, 0.31 mmol) in EtOH (10 mL) and H₂O (10 mL) and the reaction mixture was stirred at 20° C. for 5 h. The reaction mixture was diluted with EtOAc (150 mL). The organic layer was washed sequentially with H₂O (125 mL), sat NaHCO₃ (125 mL), and sat brine (150 mL), dried over Na₂SO₄, filtered and evaporated under reduced pressure. The crude product was purified by preparative HPLC, Method PrepAcidic G, using decreasingly polar mixture of the mobile phase, to give the title compound (81 mg, 45%) as a white solid; HRMS (ESI) m/z [M+H]⁺ calcd for C30H34F3N2O6: 575.2364 found: 575.2360.

Example 11: (1S,4s)-4-(2-Fluoro-5-(((1S,2R,3S,4R)-3-((3-(fluoromethyl)phenyl)carbamoyl)bicyclo[2.2.1]heptan-2-yl)carbamoyl)-4-methoxyphenoxy)cyclohexane-1-carboxylic acid

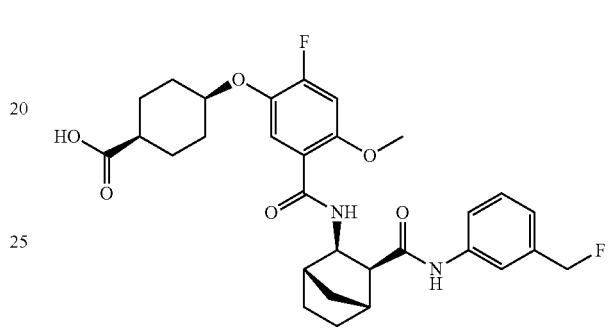 [SMILES: CCOC(=O)[C@H]1CC[C@@H](Oc2cc(C(=O)N[C@@H]3[C@H]4CC[C@H](C4)[C@@H]3C(=O)Nc3cccc(CF)c3)c(OC)cc2F)CC1]

Step A Intermediate 377: Ethyl (1S,4s)-4-(2-fluoro-5-(((1S,2R,3S,4R)-3-((3-(fluoromethyl)phenyl)carbamoyl)bicyclo[2.2.1]heptan-2-yl)carbamoyl)-4-methoxyphenoxy)cyclohexane-1-carboxylate

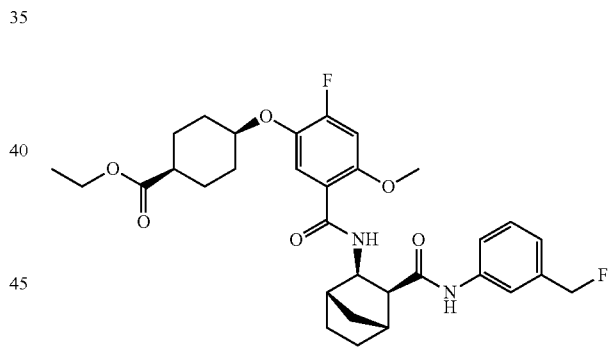

3-(Fluoromethyl)aniline (57 mg, 0.45 mmol), HATU (215 mg, 0.57 mmol), DIPEA (0.132 mL, 0.75 mmol) and DMAP (4.6 mg, 0.04 mmol) were added to a solution of Intermediate 106 (180 mg, 0.38 mmol) in DMF (5 mL). The reaction mixture was stirred at 60° C. for 2 h, and then diluted with EtOAc (75 mL). The organic layer was washed with sat brine (3×25 mL), dried over Na₂SO₄, filtered and evaporated. The crude product was purified by preparative TLC (PE:EtOAc, 1:1), to give the title compound (197 mg, 89%) as a yellow oil which solidified on standing; MS (ESI) m/z [M+H]⁺ 585.

Step B (1S,4s)-4-(2-Fluoro-5-(((1S,2R,3S,4R)-3-((3-(fluoromethyl)phenyl)carbamoyl)bicyclo[2.2.1]heptan-2-yl)carbamoyl)-4-methoxyphenoxy)cyclohexane-1-carboxylic acid LiOH (24 mg, 1.0 mmol) was added to a solution of Intermediate 377 (196 mg, 0.34 mmol) in EtOH (6 mL) and H₂O (3 mL). The reaction mixture was stirred at 20° C. for 5 h, and then diluted with EtOAc (75 mL). The organic layer was washed with sat brine (3×25 mL), dried over Na₂SO₄, filtered and evaporated. The crude product was purified by preparative HPLC, Method PrepAcidic-C, using decreasingly polar mixtures of the mobile phase, to give the title compound (77 mg, 41%) as a white solid; HRMS (ESI) m/z [M+H]⁺ calcd for C30H35F2N2O6: 557.2458 found: 557.2464.

Example 12: (1S,4s)-4-(2-Fluoro-4-methoxy-5-(((1S,2R,3S,4R)-3-((2-(trifluoromethyl)pyridin-4-yl)carbamoyl)bicyclo[2.2.1]heptan-2-yl)carbamoyl)phenoxy)cyclohexane-1-carboxylic acid

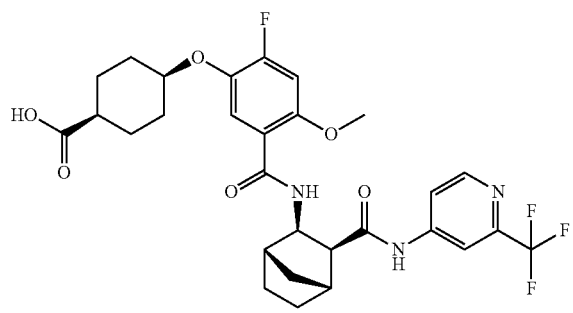

Step A Intermediate 378: Ethyl (1S,4s)-4-(2-fluoro-4-methoxy-5-(((1S,2R,3S,4R)-3-((2-(trifluoromethyl)pyridin-4-yl)carbamoyl)bicyclo[2.2.1]heptan-2-yl)carbamoyl)phenoxy)cyclohexane-1-carboxylate

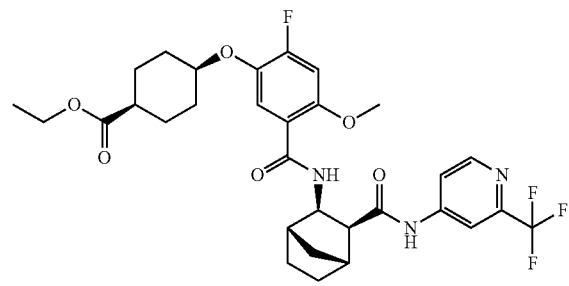

2-Chloro-1-methylpyridinium iodide (214 mg, 0.84 mmol) and DMAP (26 mg, 0.21 mmol) were added to a solution of Intermediate 106 (200 mg, 0.42 mmol), 2-(trifluoromethyl)pyridin-4-amine (102 mg, 0.63 mmol) and DIPEA (0.37 mL, 2.09 mmol) in BuOAc (10 mL) at 20° C. The reaction mixture was stirred at 120° C. for 18 h. The reaction mixture was poured into sat NaHCO₃ (150 mL) and the aq layer was extracted with EtOAc (3×50 mL). The combined organic layer was dried over Na₂SO₄, filtered and evaporated. The crude product was purified by preparative TLC (EtOAc:PE, 2:5), to give the title compound (120 mg, 46%) as a yellow oil; MS (ESI) m/z [M+H]⁺ 622.3.

Step B (1S,4s)-4-(2-Fluoro-4-methoxy-5-(((1S,2R,3S,4R)-3-((2-(trifluoromethyl)pyridin-4-yl)carbamoyl)bicyclo[2.2.1]heptan-2-yl)carbamoyl)phenoxy)cyclohexane-1-carboxylic acid LiOH (0.50 g, 20.88 mmol) was added to a solution of Intermediate 378 (0.12 g, 0.19 mmol) in THF (4 mL), MeOH (1 mL) and H₂O (1 mL) at 20° C., and the reaction mixture was stirred at 20° C. for 15 h. The reaction mixture was poured into H₂O (150 mL), and acidified with HCl (2 M). The aq layer was extracted with EtOAc (3×50 mL), and the combined organic layer was dried over Na₂SO₄, filtered and evaporated. The crude product was purified by preparative HPLC, Method PrepAcidic-G, (gradient: 54-56%), to give the title compound (0.023 g, 18%) as a white solid; MS (ESI) m/z [M+H]⁺ 594.2.

Example 13: (1S,4s)-4-(2-Fluoro-4-methoxy-5-(((1S,2R,3S,4R)-3-((5-(trifluoromethyl)pyridin-2-yl)carbamoyl)bicyclo[2.2.1]heptan-2-yl)carbamoyl)phenoxy)cyclohexane-1-carboxylic acid

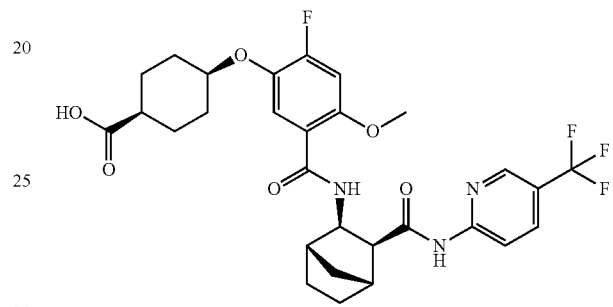 [SMILES: CCOC(=O)[C@H]1CC[C@@H](Oc2cc(C(=O)N[C@@H]3[C@H]4CC[C@H](C4)[C@@H]3C(=O)Nc3ccc(C(F)(F)F)cn3)c(OC)cc2F)CC1]

Step A Intermediate 379: Ethyl (1S,4s)-4-(2-fluoro-4-methoxy-5-(((1S,2R,3S,4R)-3-((5-(trifluoromethyl)pyridin-2-yl)carbamoyl)bicyclo[2.2.1]heptan-2-yl)carbamoyl)phenoxy)cyclohexane-1-carboxylate

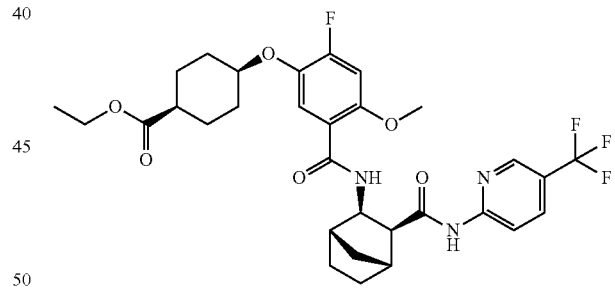

2-Chloro-1-methylpyridinium iodide (214 mg, 0.84 mmol) and DMAP (25 mg, 0.21 mmol) were added to a solution of Intermediate 106 (200 mg, 0.42 mmol), 5-(trifluoromethyl)pyridin-2-amine (102 mg, 0.63 mmol) and DIPEA (0.37 mL, 2.09 mmol) in BuOAc (10 mL) at 20° C. and the reaction mixture was stirred at 120° C. for 18 h. The reaction mixture was poured into sat NaHCO₃ (150 mL), and the organic layer was extracted with EtOAc (3×50 mL). The combined organic layer was dried over Na₂SO₄, filtered and evaporated. The crude product was purified by preparative TLC (EtOAc:PE, 2:5), to give the title compound (220 mg, 85%) as a yellow oil.

Step B (1S,4s)-4-(2-Fluoro-4-methoxy-5-(((1S,2R,3S,4R)-3-((5-(trifluoromethyl)pyridin-2-yl)carbamoyl)bicyclo[2.2.1]heptan-2-yl)carbamoyl)phenoxy)cyclohexane-1-carboxylic acid LiOH (25.04 mg, 1.05 mmol) was added to a solution of Intermediate 379 (130 mg, 0.21 mmol) in EtOH (2 mL) and H$_2$O (1 mL) at 20° C. and the reaction mixture was stirred at 20° C. for 5 h.

The reaction mixture was acidified with HCl (2 M) and diluted with EtOAc (75 mL). The organic layer was washed with sat brine (3×20 mL), dried over Na$_2$SO$_4$, filtered and evaporated. The crude product was purified by preparative HPLC, Method AcidicPrep-C, using decreasingly polar mixtures as mobile phase, to give the title compound (68 mg, 51%) as a white solid; HRMS (ESI) m/z [M+H]$^+$ calcd for C29H32F4N3O6: 594.2222 found: 594.2230.

Example 14: (1S,4s)-4-(2-Fluoro-4-methoxy-5-(((1S,2R,3S,4R)-3-((4-(trifluoromethyl)pyridin-2-yl)carbamoyl)bicyclo[2.2.1]heptan-2-yl)carbamoyl)phenoxy)cyclohexane-1-carboxylic acid

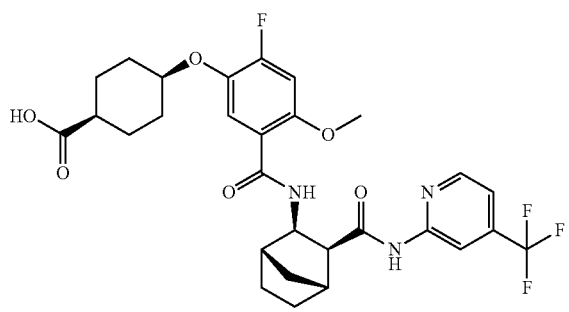 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cc(C(F)(F)F)ccn1]

Step A Intermediate 380: Ethyl (1S,4s)-4-(2-fluoro-4-methoxy-5-(((1S,2R,3S,4R)-3-((4-(trifluoromethyl)pyridin-2-yl)carbamoyl)bicyclo[2.2.1]heptan-2-yl)carbamoyl)phenoxy)cyclohexane-1-carboxylate

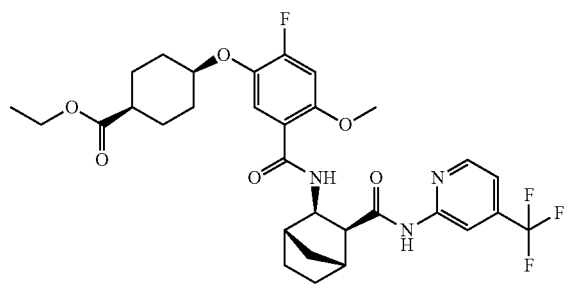 [SMILES: CCOC(=O)[C@H]1CC[C@@H](Oc2cc(C(=O)N[C@@H]3[C@H]4CC[C@H](C4)[C@@H]3C(=O)Nc3cc(C(F)(F)F)ccn3)c(OC)cc2F)CC1]

2-Chloro-1-methylpyridinium iodide (128 mg, 0.50 mmol) and DMAP (15 mg, 0.13 mmol) were added to a solution of Intermediate 106 (120 mg, 0.25 mmol), 4-(trifluoromethyl)pyridin-2-amine (81 mg, 0.50 mmol) and DIPEA (0.22 mL, 1.26 mmol) in BuOAc (10 mL) at 0-5° C. The reaction mixture was stirred at 120° C. for 15 h. The reaction mixture was poured into sat NaHCO$_3$ (150 mL), and the aq layer was extracted with EtOAc (3×50 mL). The combined organic layer was dried over Na$_2$SO$_4$, filtered and evaporated. The crude product was purified by preparative TLC (EtOAc:PE, 1:2), to give the title compound (40 mg, 26%) as a pale yellow oil; MS (ESI) m/z [M+H]$^+$ 622.3. The process above was repeated to give another 65 mg of the title compound; MS (ESI) m/z [M+H]$^+$ 622.3.

Step B (1S,4s)-4-(2-Fluoro-4-methoxy-5-(((1S,2R,3S,4R)-3-((4-(trifluoromethyl)pyridin-2-yl)carbamoyl)bicyclo[2.2.1]heptan-2-yl)carbamoyl)phenoxy)cyclohexane-1-carboxylic acid LiOH (0.50 g, 20.9 mmol) was added to a solution of Intermediate 380 (0.105 g, 0.17 mmol) in THF (4 mL), MeOH (1 mL) and H$_2$O (1 mL) and the reaction mixture was stirred at 20° C. for 15 h. The reaction mixture was poured into H$_2$O (150 mL) and acidified with HCl (2 M). The aq layer was extracted with EtOAc (3×50 mL), and the combined organic layer was dried over Na$_2$SO$_4$, filtered and evaporated. The crude product was purified by preparative HPLC, Method PrepAcidic-G, (gradient: 56-66%), to give the title compound (0.012 g, 11%) as a white solid; MS (ESI) m/z [M+H]$^+$ 594.3.

Example 15: (1S,4s)-4-(2-Fluoro-4-methoxy-5-(((1S,2R,3S,4R)-3-((4-((trifluoromethyl)sulfonyl)phenyl)carbamoyl)bicyclo[2.2.1]heptan-2-yl)carbamoyl)phenoxy)cyclohexane-1-carboxylic acid

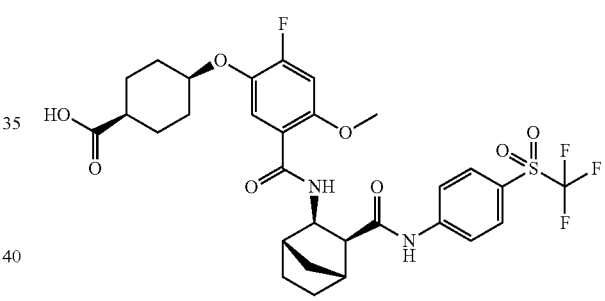 [SMILES: CCOC(=O)[C@H]1CC[C@@H](Oc2cc(C(=O)N[C@@H]3[C@H]4CC[C@H](C4)[C@@H]3C(=O)Nc3ccc(S(=O)(=O)C(F)(F)F)cc3)c(OC)cc2F)CC1]

Step A Intermediate 381: Ethyl (1S,4s)-4-(2-fluoro-4-methoxy-5-(((1S,2R,3S,4R)-3-((4-((trifluoromethyl)sulfonyl)phenyl)carbamoyl)bicyclo[2.2.1]heptan-2-yl)carbamoyl)phenoxy)cyclohexane-1-carboxylate

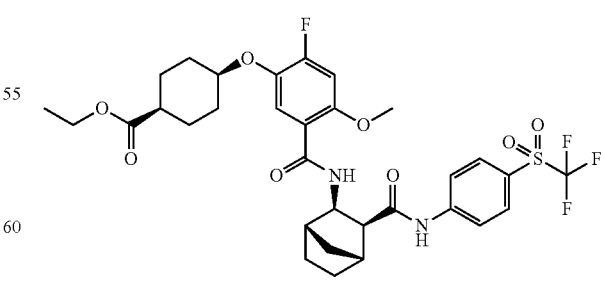

4-((Trifluoromethyl)sulfonyl)aniline (68 mg, 0.30 mmol), T3P (240 mg, 0.75 mmol, 50% in EtOAc), DIPEA (018 mL, 1.01 mmol) and DMAP (3 mg, 0.03 mmol) were added to a solution of Intermediate 106 (120 mg, 0.25 mmol) in BuOAc (5 mL) and the reaction mixture was stirred at 120° C. overnight. The reaction mixture was diluted with EtOAc (75 mL), and washed with sat brine (3×20 mL). The organic layer was dried over Na$_2$SO$_4$, filtered and evaporated. The crude product was purified by preparative TLC (PE:EtOAc, 1:1), to give the title compound (106 mg, 62%) as a pale yellow oil which solidified on standing; MS (ESI) m/z [M+H]$^+$ 685.

Step B (1S,4s)-4-(2-Fluoro-4-methoxy-5-(((1S,2R, 3S,4R)-3-((4-(((trifluoromethyl)-sulfonyl)phenyl) carbamoyl)bicyclo[2.2.1]heptan-2-yl)carbamoyl) phenoxy)cyclohexane-1-carboxylic acid LiOH (11 mg, 0.46 mmol) was added to a solution of Intermediate 381 (106 mg, 0.15 mmol) in EtOH (3 mL) and H$_2$O (1.5 mL). The reaction mixture was stirred at 20° C. for 8 h and then acidified with HCl (1 M). The reaction mixture was diluted with EtOAc (75 mL), and the organic layer was washed with sat brine (3×20 mL), dried over Na$_2$SO$_4$, filtered and evaporated. The crude product was purified by preparative HPLC, Method PrepAcidic-C, using decreasingly polar mixtures as eluents, to give the title compound (22 mg, 21%) as a white solid; MS (ESI) m/z [M+H]$^+$ 657.

Example 16: (1S,4s)-4-(2-Fluoro-4-methoxy-5-(((1S,2R,3S,4R)-3-((perfluorophenyl)carbamoyl) bicyclo[2.2.1]heptan-2-yl)carbamoyl)phenoxy)cyclohexane-1-carboxylic acid DIPEA (0.44 mL, 2.51 mmol) was added to a solution of Intermediate 106 (120 mg, 0.25 mmol), 2,3,4,5,6-pentafluoroaniline (69 mg, 0.38 mmol) and T3P (0.75 mL, 1.26 mmol, 50% in EtOAc) in BuOAc (5 mL) and the reaction mixture was stirred at 120° C. for 16 h. The reaction mixture was poured into sat NaHCO$_3$ (100 mL) and extracted with EtOAc (3×75 mL). The combined organic layer was dried over Na$_2$SO$_4$, filtered and evaporated to give the title compound (120 mg, 74%) as a white solid; MS (ESI) m/z [M+Na]$^+$665.

Step B (1S,4s)-4-(2-Fluoro-4-methoxy-5-(((1S,2R, 3S,4R)-3-((perfluorophenyl)carbamoyl)bicyclo [2.2.1]heptan-2-yl)carbamoyl)phenoxy)cyclohexane-1-carboxylic acid LiOH (22 mg, 0.93 mmol) was added to a solution of Intermediate 382 (120 mg, 0.19 mmol) in THF (4 mL) and H$_2$O (2 mL) and the reaction mixture was stirred at 20° C. for 1 h. The reaction mixture was acidified with HCl (1 M), and diluted with EtOAc (25 mL). The organic layer was washed sequentially with sat brine (3×20 mL), and H$_2$O (25 mL), dried over Na$_2$SO$_4$, filtered and evaporated. The crude product was purified by preparative HPLC, Method PrepAcidic-G, (gradient: 54-64%), to give the title compound (70 mg, 58%) as a white solid; HRMS (ESI) m/z [M+H]$^+$ calcd for C29H29F6N2O6: 615.1924 found: 615.1952.

Example 17: (1S,4s)-4-(2-Fluoro-5-(((1S,2R,3S, 4R)-3-((3-fluoro-5-(pentafluoro-6-sulfaneyl)phenyl) carbamoyl)bicyclo[2.2.1]heptan-2-yl)carbamoyl)-4-methoxyphenoxy)cyclohexane-1-carboxylic acid

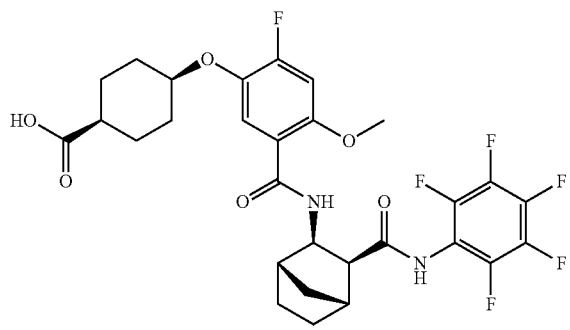 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1c(F)c(F)c(F)c(F)c1F]

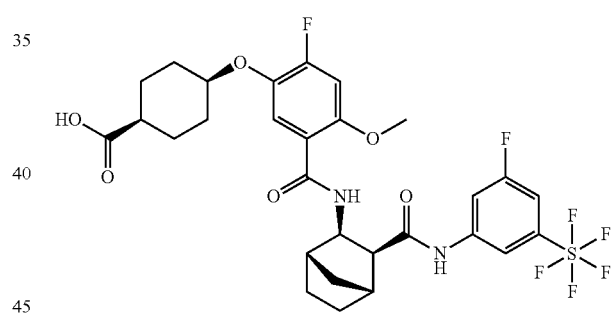

Step A Intermediate 382: Ethyl (1S,4s)-4-(2-fluoro-4-methoxy-5-(((1S,2R,3S,4R)-3-((perfluorophenyl) carbamoyl)bicyclo[2.2.1]heptan-2-yl)carbamoyl) phenoxy)cyclohexane-1-carboxylate Step A Intermediate 383: Ethyl (1S,4s)-4-(2-fluoro-5-(((1S,2R,3S,4R)-3-((3-fluoro-5-(pentafluoro-M6-sulfaneyl)phenyl)carbamoyl)bicyclo[2.2.1]heptan-2-yl)carbamoyl)-4-methoxyphenoxy)cyclohexane-1-carboxylate

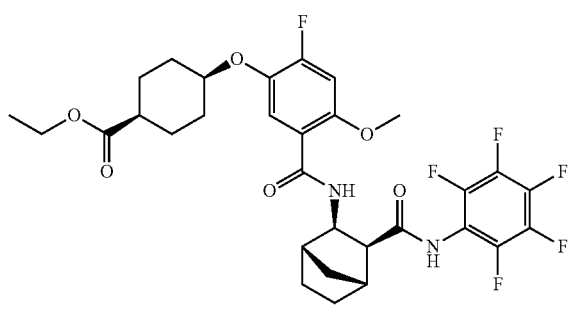 [SMILES: CCOC(=O)[C@H]1CC[C@@H](Oc2cc(C(=O)N[C@@H]3[C@H]4CC[C@H](C4)[C@@H]3C(=O)Nc3c(F)c(F)c(F)c(F)c3F)c(OC)cc2F)CC1]

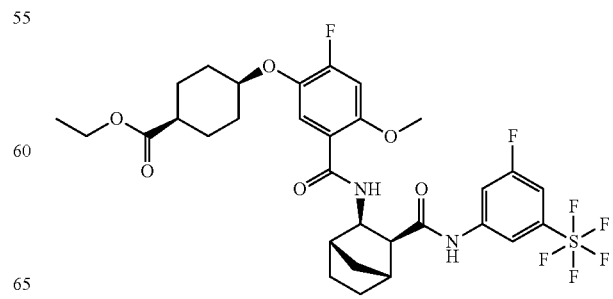

T3P (0.75 mL, 1.26 mmol, 50% in EtOAc) was added to a solution of Intermediate 106 (0.12 g, 0.25 mmol), 3-fluoro-5-(pentafluoro-λ6-sulfaneyl)aniline (0.119 g, 0.50 mmol) and DIPEA (0.439 mL, 2.51 mmol) in BuOAc (15 mL) at 20° C., and the reaction mixture was stirred at 120° C. for 15 h. The reaction mixture was poured into sat NaHCO₃ (150 mL) and extracted with EtOAc (3×50 mL). The combined organic layer was dried over Na₂SO₄, filtered and evaporated to give the title compound (0.150 g, 86%) as a brown gum; MS (ESI) m/z [M+H]⁺ 697.2.

Step B (1S,4s)-4-(2-Fluoro-5-(((1S,2R,3S,4R)-3-((3-fluoro-5-(pentafluoro-6-sulfaneyl)phenyl)carbamoyl) bicyclo[2.2.1]heptan-2-yl)carbamoyl)-4-methoxyphenoxy)cyclohexane-1-carboxylic acid LiOH (0.50 g, 20.9 mmol) was added to a solution of Intermediate 383 (0.15 g, 0.22 mmol) in THF (4 mL), MeOH (1 mL) and H₂O (1 mL) and the reaction mixture was stirred at 20° C. for 15 h. The reaction mixture was poured into H₂O (150 mL), acidified with HCl (2 M), and the aq layer was extracted with EtOAc (3×50 mL). The combined organic layer was dried over Na₂SO₄, filtered and evaporated. The crude product was purified by preparative HPLC, Method PrepAcidic-C, (gradient: 55-75%), to give the title compound (0.040 g, 26%) as a pale yellow solid; HRMS (ESI) m/z [M+H]⁺ calcd for C29H32F7N2O6S: 669.1864 found: 669.1890. The examples included in Table 1 below were synthesized and purified analogous to the procedure of Example 17 using the appropriate amines (as the free base or as the corresponding HCl salt). The amine is commercially available if not otherwise stated.

TABLE 1

| Ex No | Structure | HRMS (ESI) m/z [M + H]⁺ | Purification Method |
|---|---|---|---|
| 18 | 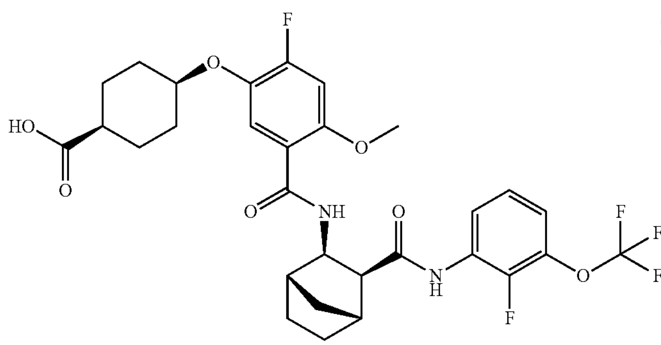 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cccc(OC(F)(F)F)c1F] | calcd for C30H32F5N2O7: 627.2124 found: 627.2142 | Step B Method PrepAcidic-G (gradient 62-64%) |
| 19 | 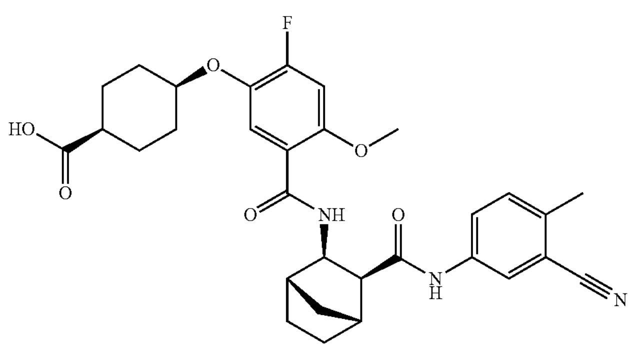 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1ccc(C)c(C#N)c1] | calcd for C31H35FN3O6: 564.2504 found: 564.2510 | Step B Method PrepAcidic-G (gradient 60-64%) |
| 20 | 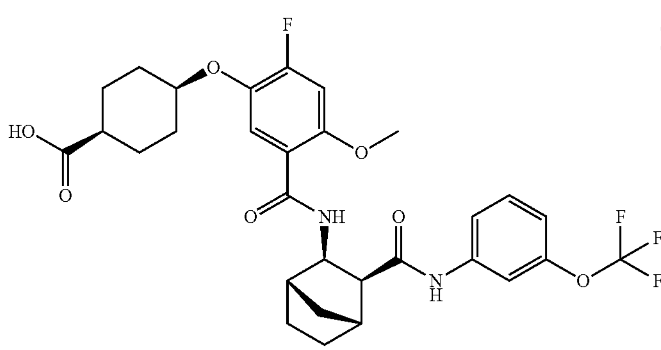 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cccc(OC(F)(F)F)c1] | calcd for C30H33F4N2O7: 609.2218 found: 609.2254 | Step B Method PrepAcidic-G (gradient 60-70%) |

TABLE 1-continued

| Ex No | Structure | HRMS (ESI) m/z [M + H]⁺ | Purification Method |
|---|---|---|---|
| 21 | 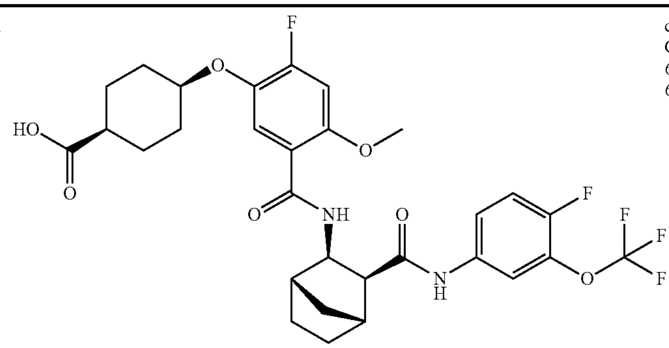 | calcd for C30H32F5N2O7: 627.2124 found: 627.2162 | Step B Method PrepAcidic-G (gradient 60-70%) |

Example 22: (1S,4s)-4-(5-(((1S,2R,3S,4R)-3-((3,5-Bis(trifluoromethyl)phenyl)carbamoyl)bicyclo[2.2.1]heptan-2-yl)carbamoyl)-2-fluoro-4-methoxyphenoxy)cyclohexane-1-carboxylic acid

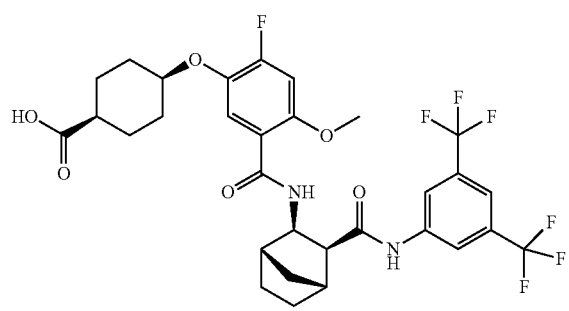 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cc(C(F)(F)F)cc(C(F)(F)F)c1]

Step A Intermediate 384: Ethyl (1S,4s)-4-(5-(((1S,2R,3S,4R)-3-((3,5-bis(trifluoromethyl)phenyl)carbamoyl)bicyclo[2.2.1]heptan-2-yl)carbamoyl)-2-fluoro-4-methoxyphenoxy)cyclohexane-1-carboxylate

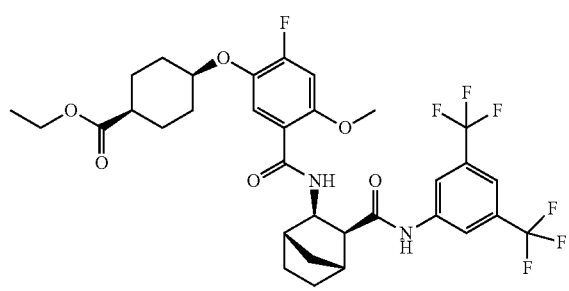 [SMILES: CCOC(=O)[C@H]1CC[C@@H](Oc2cc(C(=O)N[C@@H]3[C@H]4CC[C@H](C4)[C@@H]3C(=O)Nc3cc(C(F)(F)F)cc(C(F)(F)F)c3)c(OC)cc2F)CC1]

DIPEA (0.44 mL, 2.51 mmol) was added to a solution of Intermediate 106 (120 mg, 0.25 mmol), 3,5-bis(trifluoromethyl)aniline (86 mg, 0.38 mmol) and T3P (800 mg, 1.26 mmol, 50% in EtOAc) in BuOAc (5 mL) and the reaction mixture was stirred at 120° C. for 16 h. The reaction mixture was poured into sat NaHCO₃ (100 mL) and extracted with EtOAc (3×75 mL). The combined organic layer was dried over Na₂SO₄, filtered and evaporated to give the title compound (111 mg, 64%) as a white solid; MS (ESI) m/z [M+H]⁺ 689. The compound was used in the next step without further purification.

Step B (1S,4s)-4-(5-(((1S,2R,3S,4R)-3-((3,5-Bis(trifluoromethyl)phenyl)carbamoyl)bicyclo[2.2.1]heptan-2-yl)carbamoyl)-2-fluoro-4-methoxyphenoxy)cyclohexane-1-carboxylic acid LiOH (11 mg, 0.48 mmol) was added to a solution of Intermediate 384 (111 mg, 0.16 mmol) in EtOH (3 mL) and H₂O (1.5 mL) and the reaction mixture was stirred at 20° C. for 6 h. The reaction mixture was acidified with HCl (1 M) and diluted with EtOAc (50 mL). The organic layer was washed with sat brine (3×20 mL), dried over Na₂SO₄, filtered and evaporated. The crude product was purified by preparative HPLC, Method PrepAcidic-G, (gradient: 63-73%), to give the title compound (62 mg, 58l) as a white solid; HRMS (ESI) m/z [M+H]⁺ calcd for C31H32F7N2O6: 661.2142 found: 661.2180.

The examples included in Table 2 below were synthesized and purified analogous to the procedure of Example 22 using the appropriate amines (as the free base or as the corresponding HCl salt). The amine is commercially available if not otherwise stated

TABLE 2

| Ex No | Structure | HRMS (ESI) m/z [M + H]+ | Purification Method |
|---|---|---|---|
| 23 | 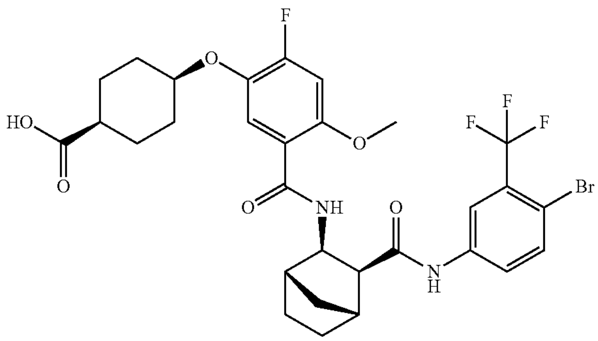 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1ccc(Br)c(C(F)(F)F)c1] | calcd for C30H32BrF4N2O6: 671.1374 found: 671.1406 | Step B Method PrepAcidic-C |
| 24 | 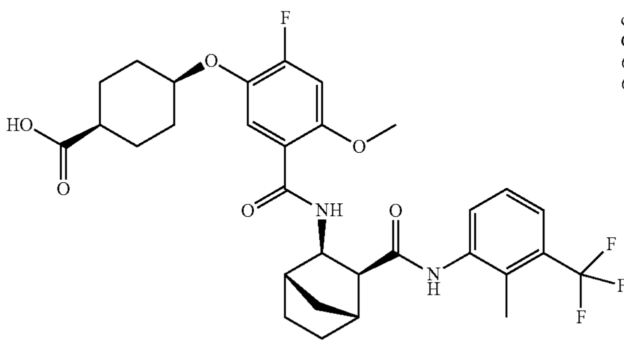 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cccc(C(F)(F)F)c1C] | calcd for C31H35F4N2O6: 607.2426 found: 607.2466 | Step B Method PrepAcidic-C |
| 25 | 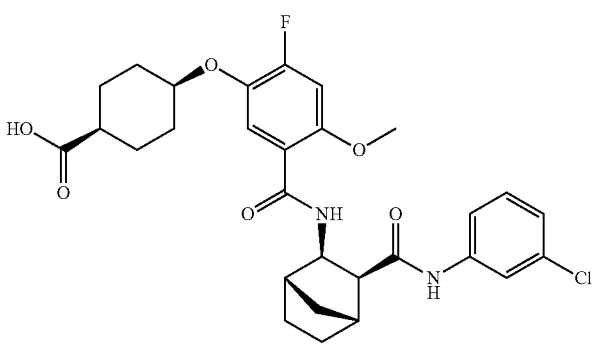 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cccc(Cl)c1] | calcd for C29H33ClFN2O6: 559.2006 found: 559.2012 | Step B Method PrepAcidic-C |
| 26 | 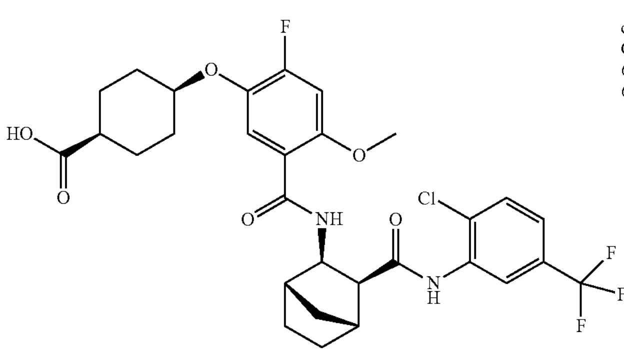 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cc(C(F)(F)F)ccc1Cl] | calcd for C30H32ClF4N2O6: 627.1880 found: 627.1912 | Step B Method PrepAcidic-C |

Example 27: (1S,4s)-4-(5-(((1S,2R,3S,4R)-3-((3-Bromo-4-cyanophenyl)carbamoyl)bicyclo[2.2.1]heptan-2-yl)carbamoyl)-2-fluoro-4-methoxyphenoxy)cyclohexane-1-carboxylic acid

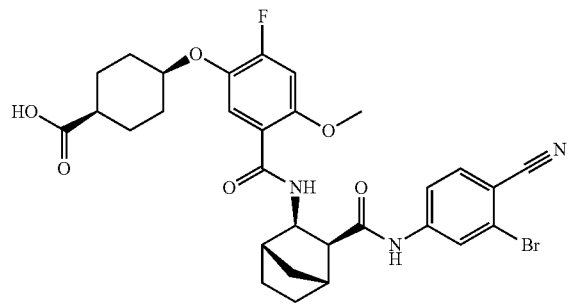 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1ccc(C#N)c(Br)c1]

Step A Intermediate 385: Ethyl (1S,4s)-4-(5-(((1S,2R,3S,4R)-3-((3-bromo-4-cyanophenyl)carbamoyl)bicyclo[2.2.1]heptan-2-yl)carbamoyl)-2-fluoro-4-methoxyphenoxy)cyclohexane-1-carboxylate

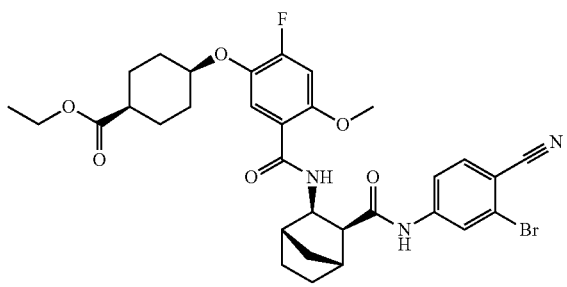 [SMILES: CCOC(=O)[C@H]1CC[C@@H](Oc2cc(C(=O)N[C@@H]3[C@H]4CC[C@H](C4)[C@@H]3C(=O)Nc3ccc(C#N)c(Br)c3)c(OC)cc2F)CC1]

T3P (0.45 mL, 0.75 mmol, 50% in EtOAc) was added dropwise to a solution of 4-amino-2-bromobenzonitrile (49 mg, 0.25 mmol), Intermediate 106 (120 mg, 0.25 mmol) and TEA (0.175 mL, 1.26 mmol) in BuOAc (10 mL) at 20° C. and under a nitrogen atmosphere, and the reaction mixture was stirred at 120° C. for 14 h. The reaction mixture was diluted with EtOAc (150 mL), and washed sequentially with sat brine (150 mL), sat NaHCO$_3$ (150 mL), and H$_2$O (150 mL). The organic layer was dried over Na$_2$SO$_4$, filtered and evaporated. The crude product was purified by preparative TLC (EtOAc:PE, 1:5), to give the title compound (130 mg, 79%) as a pale yellow solid; MS (ESI) m/z [M+H]$^+$ 657.

Step B (1S,4s)-4-(5-(((1S,2R,3S,4R)-3-((3-Bromo-4-cyanophenyl)carbamoyl)bicyclo[2.2.1]heptan-2-yl)carbamoyl)-2-fluoro-4-methoxyphenoxy)cyclohexane-1-carboxylic acid LiOH (11 mg, 0.46 mmol) was added to a solution of Intermediate 385 (100 mg, 0.15 mmol) in EtOH (3 mL) and H$_2$O (1.5 mL) and the reaction mixture was stirred at 20° C. for 5 h. The reaction mixture was acidified with HCl (1 M), diluted with EtOAc (100 mL), and washed with sat brine (3×20 mL). The organic layer was dried over Na$_2$SO$_4$, filtered and evaporated. The crude product was purified by preparative HPLC, Method PrepAcidic-C, using a gradient of decreasingly polar mixtures as mobile phase to give the title compound (24 mg, 24%) as a white solid; MS (ESI) m/z [M+H]$^+$ 630.

The examples included in Table 3 below were synthesized analogous to the procedure of Example 27 using the appropriate amines (as the free base or as the corresponding HCl salt). The amine is commercially available if not otherwise stated.

TABLE 3

| Ex No | Structure | HRMS (ESI) m/z [M + H]$^+$ | Purification Method |
|---|---|---|---|
| 28 | 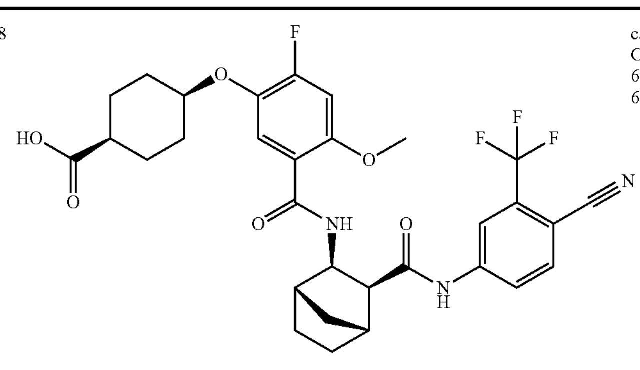 | calcd for C31H32F4N3O6: 618.2222 found: 618.2210 | Step A Preparative TLC (EtOAc:PE, 1:5) Step B Method PrepAcidic-C |

TABLE 3-continued

| Ex No | Structure | HRMS (ESI) m/z [M + H]+ | Purification Method |
|---|---|---|---|
| 29 | 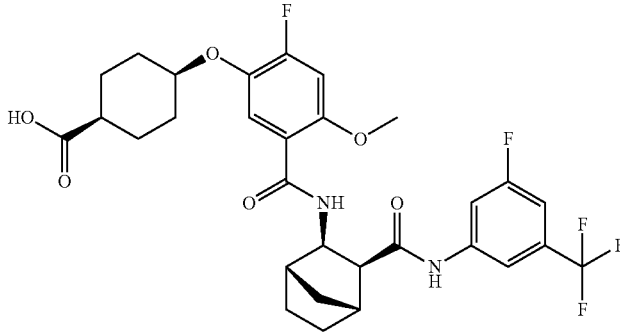 | calcd for C30H32F5N2O6: 611.2174 found: 611.2188 | Step A Preparative TLC (EtOAc:PE, 1:5) Step B Method PrepAcidic-C |

Example 30: (1S,4s)-4-(5-(((1S,2R,3S,4R)-3-((5-Chloropyridazin-3-yl)carbamoyl)bicyclo[2.2.1]heptan-2-yl)carbamoyl)-2-fluoro-4-methoxyphenoxy)cyclohexane-1-carboxylic acid T3P (0.315 mL, 0.59 mmol, 50% in EtOAc) was added dropwise to a solution of Intermediate 67 (100 mg, 0.20 mmol), 5-chloropyridazin-3-amine (31 mg, 0.24 mmol) and DIPEA (0.19 mL, 0.79 mmol) in BuOAc (3 mL) at 20° C. and the reaction mixture was stirred at 120° C. for 2 h. The solvent was removed under reduced pressure and the residue was purified by preparative TLC (EtOAc), to give the title compound (80 mg, 65%) as a brown red oil which solidified on standing; MS (ESI) m/z [M+H]+ 617.4.

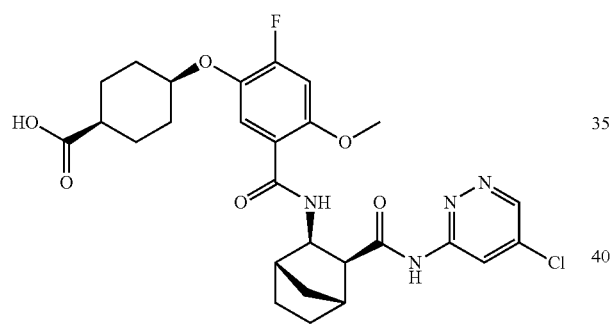

Step B (1S,4s)-4-(5-(((1S,2R,3S,4R)-3-((5-Chloropyridazin-3-yl)carbamoyl)bicyclo[2.2.1]heptan-2-yl)carbamoyl)-2-fluoro-4-methoxyphenoxy)cyclohexane-1-carboxylic acid Step A Intermediate 386: tert-Butyl (1S,4s)-4-(5-(((1S,2R,3S,4R)-3-((5-chloropyridazin-3-yl)carbamoyl)bicyclo[2.2.1]heptan-2-yl)carbamoyl)-2-fluoro-4-methoxyphenoxy)cyclohexane-1-carboxylate TFA (0.1 mL) was added to Intermediate 386 (80 mg, 0.13 mmol) in DCM (2 mL) and the reaction mixture was stirred at 20° C. for 5 h. The solvent was removed under reduced pressure and the crude product was purified by preparative HPLC, Method PrepAcidic-C, using decreasingly polar mixtures of mobile phase, to give the title compound (20 mg, 25%) as a white solid; MS (ESI) m/z [M+H]+ 561.

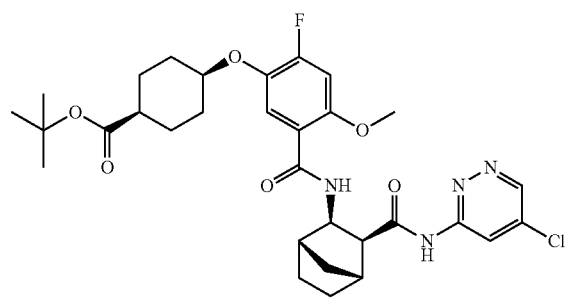 [SMILES: COc1cc(F)c(O[C@H]2CC[C@@H](C(=O)OC(C)(C)C)CC2)cc1C(=O)N[C@@H]1[C@H]2CC[C@H](C2)[C@@H]1C(=O)Nc1cc(Cl)cnn1]

The examples included in Table 4 below were synthesized and purified analogous to the procedure of Example 30 using the appropriate amines (as the free base or as the corresponding HCl salt). The amine is commercially available if not otherwise stated

TABLE 4

| Ex No | Structure | HRMS (ESI) m/z [M + H]+ | Purification Method |
|---|---|---|---|
| 31 | 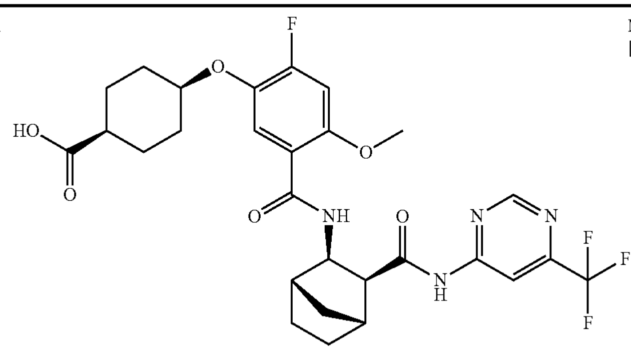 | MS (ESI) m/z [M + H]+ 595 | Step A Preparative TLC (EtOAc:PE, 1:5) Step B Method PrepAcidic-J (isocratic 49%) |
| 32 | 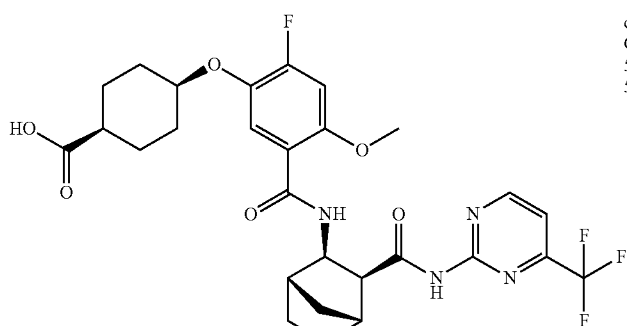 | calcd for C28H31F4N4O6: 595.2174 found: 595.2166 | Step A Preparative TLC (EtOAc:PE, 1:1) Step B Method PrepAcidic-C |

Example 33: (1S,4s)-4-(5-(((1S,2R,3S,4R)-3-((3,3-Difluorocyclobutyl)carbamoyl)bicyclo[2.2.1]heptan-2-yl)carbamoyl)-2-fluoro-4-methoxyphenoxy)cyclohexane-1-carboxylic acid Step A Intermediate 387: Ethyl (1S,4s)-4-(5-(((1S,2R,3S,4R)-3-((3,3-difluorocyclobutyl)carbamoyl)bicyclo[2.2.1]heptan-2-yl)carbamoyl)-2-fluoro-4-methoxyphenoxy)cyclohexane-1-carboxylate

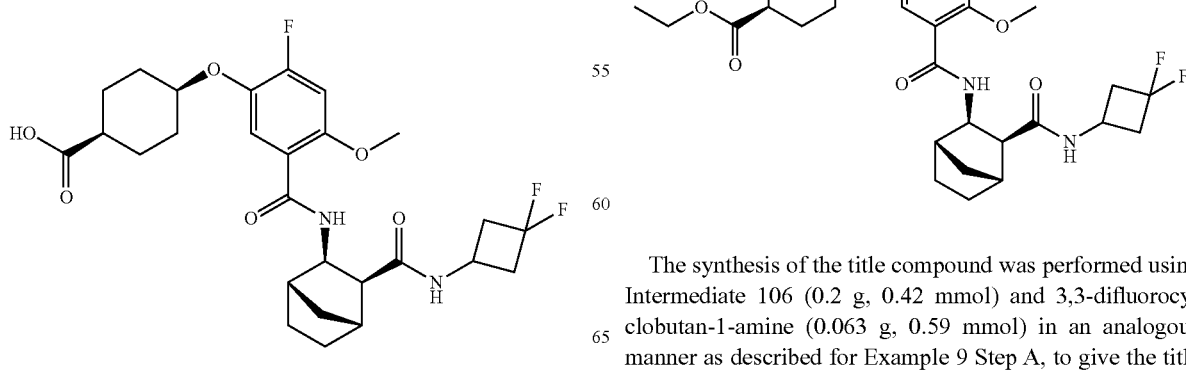

The synthesis of the title compound was performed using Intermediate 106 (0.2 g, 0.42 mmol) and 3,3-difluorocyclobutan-1-amine (0.063 g, 0.59 mmol) in an analogous manner as described for Example 9 Step A, to give the title compound (0.20 g, 84%) as a brown oil which solidified upon standing; MS (ESI) m/z [M+H]+ 567.3. The product was used in the next step directly without further purification.

Step B (1S,4s)-4-(5-(((1S,2R,3S,4R)-3-((3,3-Difluorocyclobutyl)carbamoyl)bicyclo[2.2.1]heptan-2-yl)carbamoyl)-2-fluoro-4-methoxyphenoxy)cyclohexane-1-carboxylic acid The hydrolysis of Intermediate 387 was performed in an analogous manner as described for Example 9 Step B. The crude product was purified by preparative HPLC Method PrepAcidic-A, (gradient: 44-55%), to give the title compound (0.160 g, 84%) as a white solid; HRMS (ESI) m/z [M+H]+ calcd for C27H34F3N2O6: 539.2364 found: 539.2310.

Example 34: (1S,4s)-4-(2-Fluoro-5-(((1S,2R,3S,4R)-3-(isobutylcarbamoyl)bicyclo[2.2.1]heptan-2-yl)carbamoyl)-4-methoxyphenoxy)-1-methylcyclohexane-1-carboxylic acid

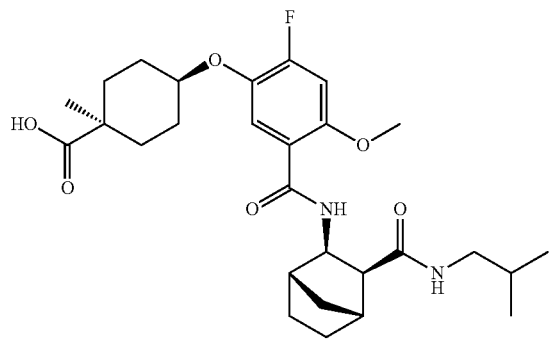 [SMILES: COc1cc(F)c(O[C@H]2CC[C@@](C)(C(=O)O)CC2)cc1C(=O)N[C@@H]1[C@H]2CC[C@H](C2)[C@@H]1C(=O)NCC(C)C]

Step A Intermediate 388: tert-Butyl (1S,4s)-4-(2-fluoro-5-(((1S,2R,3S,4R)-3-(isobutylcarbamoyl)bicyclo[2.2.1]heptan-2-yl)carbamoyl)-4-methoxyphenoxy)-1-methylcyclohexane-1-carboxylate

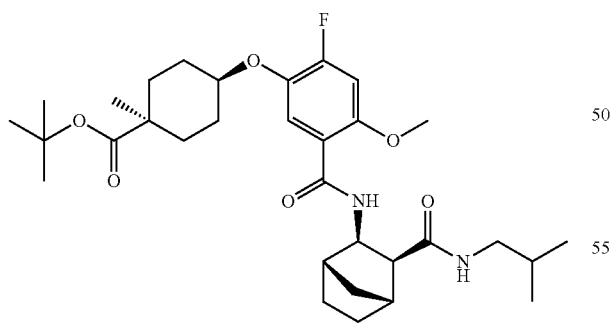

2-Methylpropan-1-amine (19.7 mg, 0.27 mmol) was added to a solution of Intermediate 75 (70 mg, 0.13 mmol), EDC (77 mg, 0.40 mmol), HOBt (62 mg, 0.40 mmol) and DIPEA (0.12 mL, 0.67 mmol) in DMF (1 mL) and the reaction mixture was stirred at 20° C. for 16 h. The reaction mixture was diluted with EtOAc (20 mL), and washed sequentially with H2O (3×20 mL) and sat brine (3×20 mL). The organic layer was dried over Na2SO4, filtered and evaporated. The crude product was purified by preparative TLC (PE:EtOAc, 5:1), to give the title compound (75 mg, 97%) as a yellow solid; MS (ESI) m/z [M+H]+ 575.

Step B (1S,4s)-4-(2-Fluoro-5-(((1S,2R,3S,4R)-3-(isobutylcarbamoyl)bicyclo[2.2.1]heptan-2-yl)carbamoyl)-4-methoxyphenoxy)-1-methylcyclohexane-1-carboxylic acid TFA (2 mL) was added to a solution of Intermediate 388 (70 mg, 0.12 mmol) in DCM (2 mL) at 20° C., and the reaction mixture was stirred at 20° C. for 30 min. The solvent was removed under reduced pressure, and the crude product was purified by preparative HPLC, Method PrepAcidic O, (gradient: 50-65%), to give the title compound (50 mg, 79%) as a white solid; HRMS (ESI) m/z [M+H]+ calcd for C28H40FN2O6: 519.2864 found: 519.2886.

Example 35: (1S,4s)-4-(2-Fluoro-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid

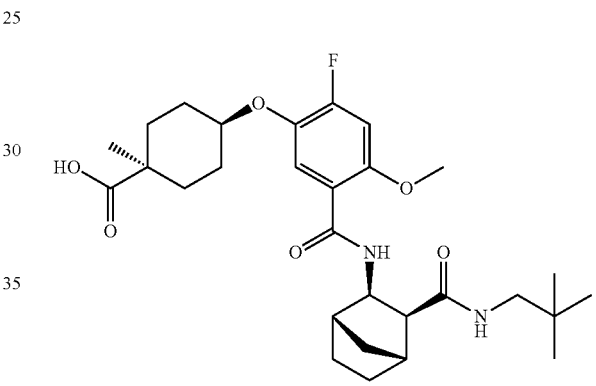

Step A Intermediate 389: tert-Butyl (1S,4s)-4-(2-fluoro-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylate

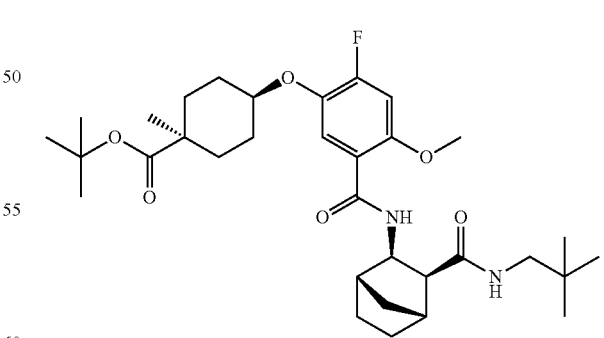

HATU (146 mg, 0.38 mmol) was added to a solution of Intermediate 75 (100 mg, 0.19 mmol), 2,2-dimethylpropan-1-amine (25 mg, 0.29 mmol) and DIPEA (75 mg, 0.58 mmol) in DMF (10 mL) at 25° C., and the reaction mixture was stirred at 25° C. for 16 h. The reaction mixture was poured into sat brine (50 mL), and extracted with EtOAc (2×50 mL). The organic layer was dried over Na₂SO₄, filtered and evaporated. The crude product was purified by flash chromatography using a gradient 0-20% EtOAc in PE as mobile phase, to give the title compound (70 mg, 62%) as a white solid; MS (ESI) m/z [M+Na]⁺611.

Step B (1S,4s)-4-(2-Fluoro-4-methoxy-5-(((1S,2R, 3S,4R)-3-(neopentylcarbamoyl)bicyclo[2.2.1]heptan-2-yl)carbamoyl)phenoxy)-1-methylcyclohexane-1-carboxylic acid TFA (0.57 mL) was added to a solution of Intermediate 389 (110 mg, 0.19 mmol) in DCM (10 mL) at 25° C., and the reaction mixture was stirred at 25° C. for 4 h. The reaction mixture was evaporated at reduced pressure and the crude product was purified by preparative HPLC, Method PrepAcidic-K, (gradient: 50-60%), to give the title compound (65 mg, 61%) as a white solid; HRMS (ESI) m/z [M+H]⁺ calcd for C29H42FN2O6: 533.3022 found: 533.3030.

Example 36: (1S,4s)-4-(5-(((1S,2R,3S,4R)-3-(((R)-3,3-Dimethylbutan-2-yl)carbamoyl)bicyclo[2.2.1]heptan-2-yl)carbamoyl)-2-fluoro-4-methoxyphenoxy)-1-methylcyclohexane-1-carboxylic acid

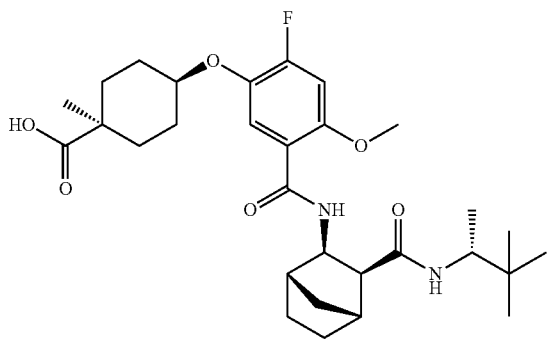 [SMILES: COc1cc(F)c(O[C@H]2CC[C@@](C)(C(=O)O)CC2)cc1C(=O)N[C@@H]1[C@H]2CC[C@H](C2)[C@@H]1C(=O)N[C@H](C)C(C)(C)C]

Step A Intermediate 390: tert-Butyl (1S,4s)-4-(5-(((1S,2R,3S,4R)-3-(((R)-3,3-dimethylbutan-2-yl)carbamoyl)bicyclo[2.2.1]heptan-2-yl)carbamoyl)-2-fluoro-4-methoxyphenoxy)-1-methylcyclohexane-1-carboxylate

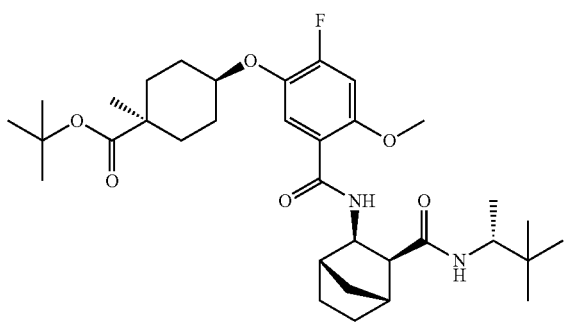 [SMILES: COc1cc(F)c(O[C@H]2CC[C@@](C)(C(=O)OC(C)(C)C)CC2)cc1C(=O)N[C@@H]1[C@H]2CC[C@H](C2)[C@@H]1C(=O)N[C@H](C)C(C)(C)C]

HATU (146 mg, 0.38 mmol) was added to a solution of Intermediate 75 (100 mg, 0.19 mmol), (R)-3,3-dimethylbutan-2-amine (29 mg, 0.29 mmol) and DIPEA (75 mg, 0.58 mmol) in DMF (10 mL) and the reaction mixture was stirred at 25° C. for 16 h. The reaction mixture was quenched with ice (75 mL), extracted with DCM (3×50 mL), and the organic layer was dried over Na₂SO₄, filtered and evaporated. The crude product was purified by flash chromatography using a gradient of 0-20% EtOAc in PE as mobile phase, to give the title compound (60 mg, 52%) as a yellow oil; MS (ESI) m/z [M+H]⁺ 603.

Step B (1S,4s)-4-(5-(((1S,2R,3S,4R)-3-(((R)-3,3-Dimethylbutan-2-yl)carbamoyl)bicyclo[2.2.1]heptan-2-yl)carbamoyl)-2-fluoro-4-methoxyphenoxy)-1-methylcyclohexane-1-carboxylic acid TFA (0.15 mL) was added to a solution of Intermediate 390 (60 mg, 0.10 mmol), TFA (0.15 mL) in DCM (10 mL) and the reaction mixture was stirred at 25° C. for 16 h. The solvent was removed under reduced pressure and the crude product was purified by preparative HPLC, Method PrepAcidic-K, (gradient: 50-60%), to give the title product (50 mg, 91%) as a white solid; HRMS (ESI) m/z [M+H]⁺ calcd for C30H44FN2O6: 547.3178 found: 547.3188.

Example 37: (1S,4s)-4-(5-(((1S,2R,3S,4R)-3-((2,2-Dimethylbutyl)carbamoyl)bicyclo[2.2.1]heptan-2-yl)carbamoyl)-2-fluoro-4-methoxyphenoxy)-1-methylcyclohexane-1-carboxylic acid

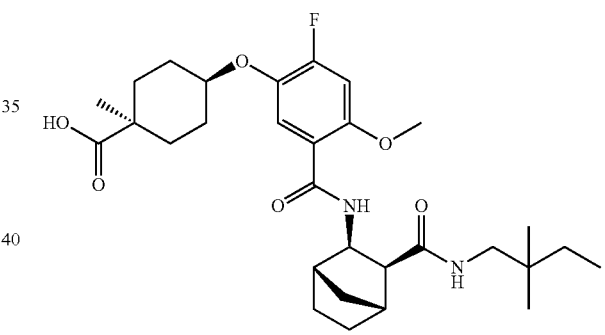

Step A Intermediate 391: tert-Butyl (1S,4s)-4-(5-(((1S,2R,3S,4R)-3-((2,2-dimethylbutyl)carbamoyl)bicyclo[2.2.1]heptan-2-yl)carbamoyl)-2-fluoro-4-methoxyphenoxy)-1-methylcyclohexane-1-carboxylate

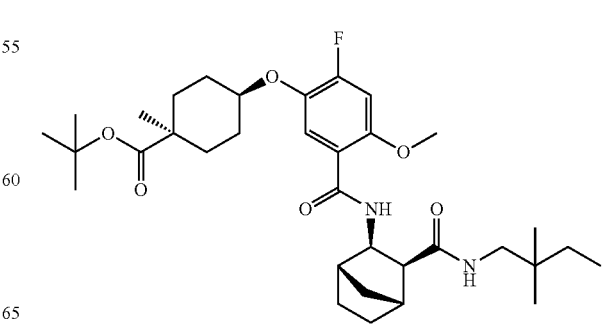

DIPEA (0.081 mL, 0.46 mmol) was added dropwise to a solution of Intermediate 75 (48 mg, 0.09 mmol), 2,2-dimethylbutan-1-amine hydrochloride (25.4 mg, 0.18 mmol) and HATU (105 mg, 0.28 mmol) in DMF (8 mL) at 20° C. under a nitrogen atmosphere, and the reaction mixture was stirred at 20° C. for 3 h. The reaction mixture was diluted with EtOAc (50 mL), and washed sequentially with sat NaHCO₃ (100 mL), and sat brine (2×100 mL). The organic layer was dried over Na₂SO₄, filtered and evaporated. The crude product was purified by preparative TLC (EtOAc:PE, 1:3), to give the title compound (48 mg, 86%) as a pale yellow oil which solidified on standing; MS (ESI) m/z [M+H]⁺ 603.

Step B (1S,4s)-4-(5-(((1S,2R,3S,4R)-3-((2,2-Dimethylbutyl)carbamoyl)bicyclo[2.2.1]heptan-2-yl)carbamoyl)-2-fluoro-4-methoxyphenoxy)-1-methylcyclohexane-1-carboxylic acid TFA (2 mL) was added dropwise to a solution of Intermediate 391 (48 mg, 0.08 mmol) in DCM (2 mL) at 20° C. and the reaction mixture was stirred at 20° C. for 5 h. The solvent was evaporated to dryness and dried by lyophilization to give the title compound (28 mg, 62%) as a white solid; HRMS (ESI) m/z [M+H]⁺ calcd for C30H44FN2O6: 547.3178 found: 547.3176.

Example 38: (1S,4s)-4-(2-Fluoro-4-methoxy-5-(((1S,2R,3S,4R)-3-((3,3,3-trifluoro-2,2-dimethylpropyl)carbamoyl)bicyclo[2.2.1]heptan-2-yl)carbamoyl)phenoxy)-1-methylcyclohexane-1-carboxylic acid

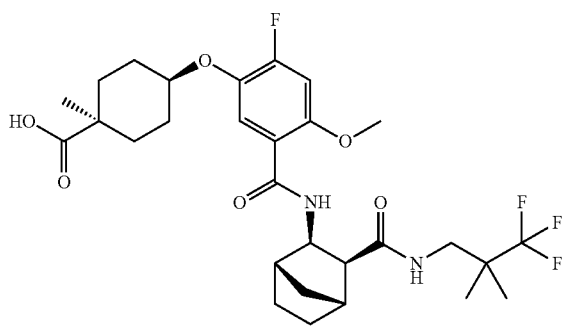

Step A Intermediate 392: tert-Butyl (1S,4s)-4-(2-fluoro-4-methoxy-5-(((1S,2R,3S,4R)-3-((3,3,3-trifluoro-2,2-dimethylpropyl)carbamoyl)bicyclo[2.2.1]heptan-2-yl)carbamoyl)phenoxy)-1-methylcyclohexane-1-carboxylate

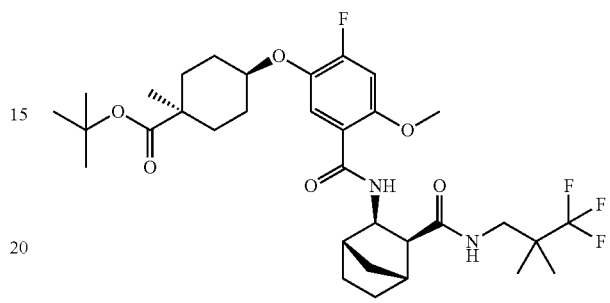

3,3,3-Trifluoro-2,2-dimethylpropan-1-amine (29 mg, 0.21 mmol), HATU (329 mg, 0.87 mmol) and DIPEA (0.27 mL, 1.56 mmol) were added to a solution of Intermediate 75 (90 mg, 0.17 mmol) in DMF (5 mL), and the reaction mixture was stirred at 20° C. for 3 h. The reaction mixture was diluted with EtOAc (75 mL), and washed with sat brine (3×20 mL). The organic layer was dried over Na₂SO₄, filtered and evaporated. The crude product was purified by preparative TLC (PE:EtOAc, 2:1), to give the title compound (110 mg, 99%) as a brown oil which solidified on standing; MS (ESI) m/z [M+H]⁺ 617.

Step B (1S,4s)-4-(2-Fluoro-4-methoxy-5-(((1S,2R,3S,4R)-3-((3,3,3-trifluoro-2,2-dimethylpropyl)carbamoyl)bicyclo[2.2.1]heptan-2-yl)carbamoyl)phenoxy)-1-methylcyclohexane-1-carboxylic acid TFA (3 mL) was added to a solution of Intermediate 392 (100 mg, 0.20 mmol) in DCM (3 mL), and the reaction mixture was stirred at 20° C. for 3h. The solvent was removed under reduced pressure and the crude product was purified by preparative HPLC, Method PrepAcidic-C, using decreasingly polar mixtures of the mobile phase to give the title compound (45 mg, 47%) as a white solid; HRMS (ESI) m/z [M+H]⁺ calcd for C29H39F4N2O6: 587.2738 found: 587.2750.

The examples included in Table 5 below were synthesized analogous to the procedure of Example 38 using the appropriate amines (as the free base or as the corresponding HCl salt). The amine is commercially available if not otherwise stated

TABLE 5

| Ex No | Structure | HRMS or MS (ESI) (m/z) [M + H]+ | Purification Method |
|---|---|---|---|
| 39 | 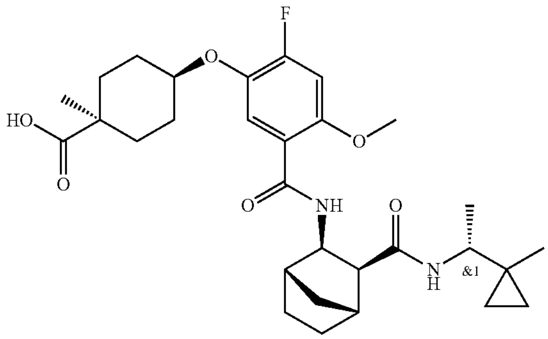 [SMILES: COc1cc(F)c(O[C@H]2CC[C@@](C)(C(=O)O)CC2)cc1C(=O)N[C@@H]1[C@H]2CC[C@H](C2)[C@@H]1C(=O)N[C@H](C)C1(C)CC1] | calcd for C30H42FN2O6: 545.3022 found: 545.3032 | Step A Preparative TLC (EtOAc:PE, 1:3) Step B Method PrepAcidic-K (gradient 28-38%) |
| 40 | 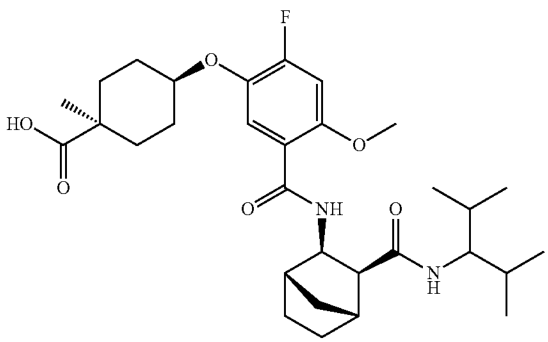 [SMILES: COc1cc(F)c(O[C@H]2CC[C@@](C)(C(=O)O)CC2)cc1C(=O)N[C@@H]1[C@H]2CC[C@H](C2)[C@@H]1C(=O)NC(C(C)C)C(C)C] | calcd for C31H46FN2O6: 561.3334 found: 561.3340 | Step A Preparative TLC (EtOAc:PE, 1:3) Step B Method PrepAcidic-K (gradient 50-80%) |
| 41 | 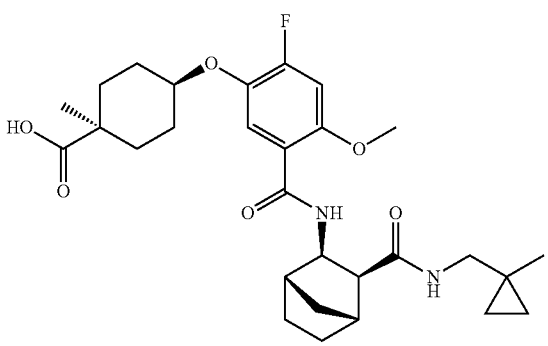 [SMILES: COc1cc(F)c(O[C@H]2CC[C@@](C)(C(=O)O)CC2)cc1C(=O)N[C@@H]1[C@H]2CC[C@H](C2)[C@@H]1C(=O)NCC1(C)CC1] | MS (ESI) m/z [M + H]+ 531 | Step A Preparative TLC (EtOAc:PE, 1:1) Step B Method PrepAcidic-K (gradient 28-38%) |
| 42 | 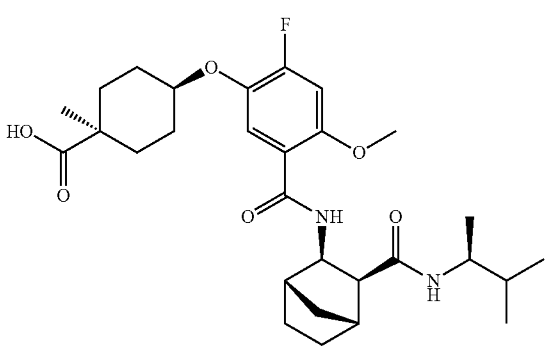 [SMILES: COc1cc(F)c(O[C@H]2CC[C@@](C)(C(=O)O)CC2)cc1C(=O)N[C@@H]1[C@H]2CC[C@H](C2)[C@@H]1C(=O)N[C@@H](C)C(C)C] | calcd for C29H42FN2O6: 533.3022 found: 533.3060 | Method PrepAcidic-K (gradient 50-60%) |

TABLE 5-continued

| Ex No | Structure | HRMS or MS (ESI) (m/z) [M + H]+ | Purification Method |
|---|---|---|---|
| 43 | 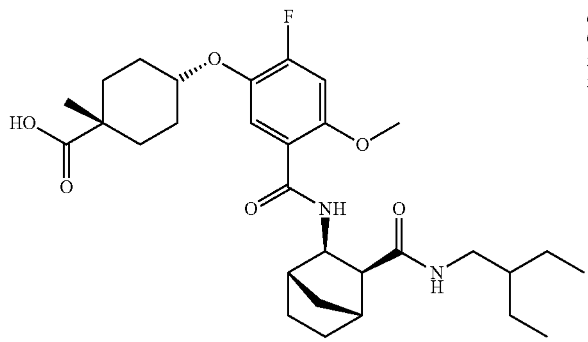 | calcd for C30H44FN2O6: 547.3178 found: 547.3204 | Step A Preparative TLC (EtOAc:PE, 1:3) Step B Method PrepAcidic-K (gradient 50-70%) |
| 44 | 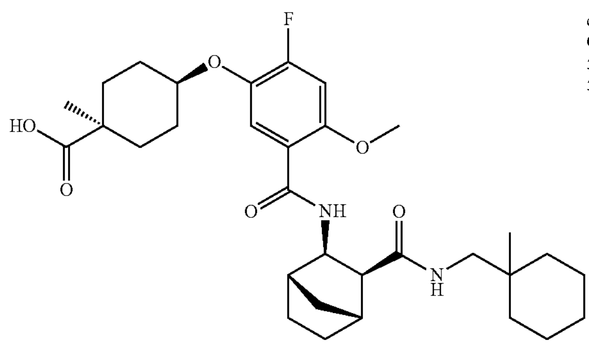 | calcd for C32H46FN2O6: 573.3334 found: 573.3348 | Step A Preparative TLC (EtOAc:PE, 1:3) Step B Method PrepAcidic-K (gradient 60-70%) |
| 45 | 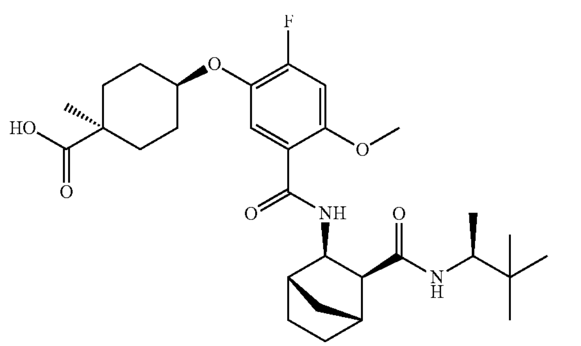 [SMILES: COc1cc(F)c(O[C@H]2CC[C@@](C)(C(=O)O)CC2)cc1C(=O)N[C@@H]1[C@H]2CC[C@H](C2)[C@@H]1C(=O)N[C@@H](C)C(C)(C)C] | calcd for C30H44FN2O6: 547.3178 found: 547.3188 | Step A Preparative TLC (EtOAc:PE, 1:3) Step B Method PrepAcidic-K (gradient 50-70%) |
| 46 | 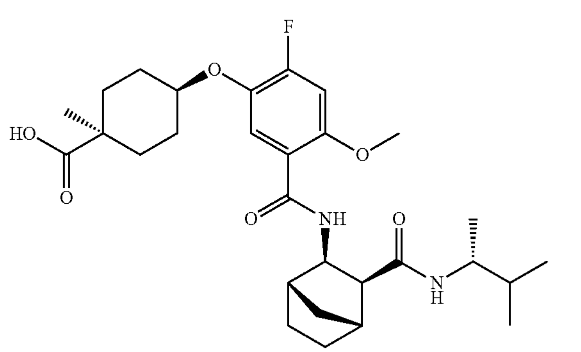 [SMILES: COc1cc(F)c(O[C@H]2CC[C@@](C)(C(=O)O)CC2)cc1C(=O)N[C@@H]1[C@H]2CC[C@H](C2)[C@@H]1C(=O)N[C@H](C)C(C)C] | calcd for C29H42FN2O6: 533.3022 found: 533.3018 | Step A Preparative TLC (EtOAc:PE, 1:3) Step B Method PrepAcidic-K (gradient 50-60%) |

TABLE 5-continued

| Ex No | Structure | HRMS or MS (ESI) (m/z) [M + H]+ | Purification Method |
|---|---|---|---|
| 47 | 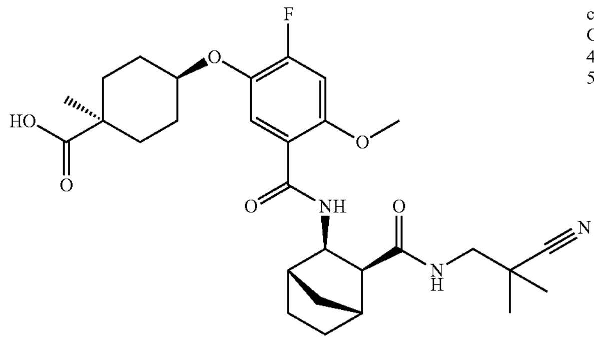 [SMILES: COc1cc(F)c(O[C@H]2CC[C@@](C)(C(=O)O)CC2)cc1C(=O)N[C@@H]1[C@H]2CC[C@H](C2)[C@@H]1C(=O)NCC(C)(C)C#N] | calcd for C29H39FN3O6: 44.2818 found: 544.2840 | Step A Preparative TLC (EtOAc:PE, 1:1) Step B Method PrepAcidic-K (gradient 42-52%) |
| 48 | 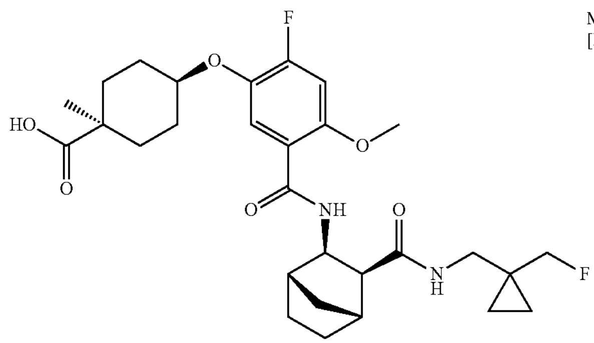 | MS (ESI) m/z [M + H]+ 549 | Step A Preparative TLC (EtOAc:PE, 1:1) Step B Method PrepAcidic-K (gradient 46-56%) |

Example 49: (1R,4s)-4-(2-Fluoro-5-(((1S,2S,3R,4R)-3-((4-fluoro-3-(trifluoromethyl)phenyl)carbamoyl)-7-oxabicyclo[2.2.1]heptan-2-yl)carbamoyl)-4-methoxyphenoxy)cyclohexane-1-carboxylic acid Step A Intermediate 393: Ethyl (1R,4s)-4-(2-fluoro-5-(((1S,2S,3R,4R)-3-((4-fluoro-3-(trifluoromethyl)phenyl)carbamoyl)-7-oxabicyclo[2.2.1]heptan-2-yl)carbamoyl)-4-methoxyphenoxy)cyclohexane-1-carboxylate

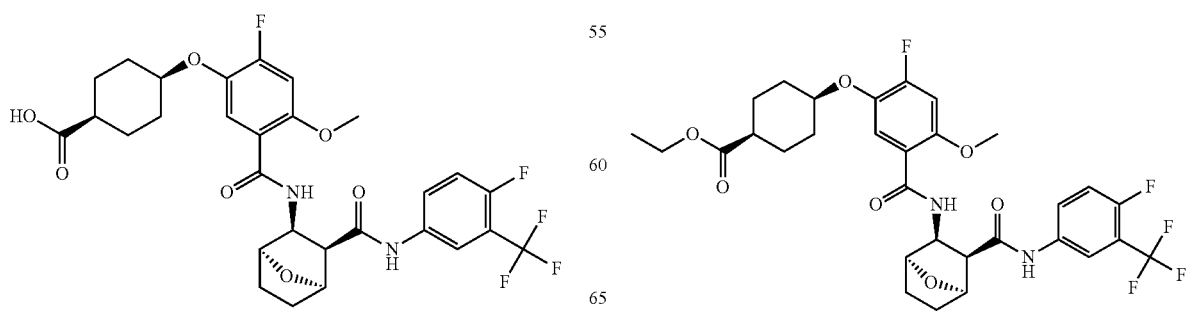

HATU (125 mg, 0.33 mmol), DIPEA (0.077 mL, 0.44 mmol), and Intermediate 111 (45 mg, 0.13 mmol) was added to a solution of Intermediate 46 (35 mg, 0.11 mmol) in DMF (5 mL) and the reaction mixture was stirred at 20° C. for 2h. The reaction mixture was diluted with EtOAc (50 mL), and washed with sat brine (3×20 mL). The organic layer was dried over $Na_2SO_4$, filtered and evaporated. The crude product was purified by preparative TLC (PE:EtOAc, 1:1), to give the title compound (60 mg, 85%) as a white solid; MS (ESI) m/z [M+Na]$^+$ 663.

Step B (1R,4s)-4-(2-Fluoro-5-((((1S,2S,3R,4R)-3-((4-fluoro-3-(trifluoromethyl)phenyl)carbamoyl)-7-oxabicyclo[2.2.1]heptan-2-yl)carbamoyl)-4-methoxyphenoxy)cyclohexane-1-carboxylic acid LiOH (2 mg, 0.09 mmol) was added to a solution of Intermediate 393 (55 mg, 0.09 mmol) in EtOH (4 mL) and $H_2O$ (2 mL) and the reaction mixture was stirred at 20° C. for 5h. The reaction mixture was acidified with HCl (1 M, aq), diluted with EtOAc (25 mL), and washed with sat brine (3×5 mL). The organic layer was dried over $Na_2SO_4$, filtered and evaporated. The crude product was purified by preparative HPLC, Method PrepAcidic-C, using decreasingly polar mixtures of mobile phase, to give the title compound (24 mg, 42%) as a white solid; MS (ESI) m/z [M+H]$^+$ 613.

Example 50: (1S,4s)-4-(2-Fluoro-5-((((1R,2R,3S,4S)-3-((4-fluoro-3-(trifluoromethyl)phenyl)carbamoyl)-7-oxabicyclo[2.2.1]heptan-2-yl)carbamoyl)-4-methoxyphenoxy)cyclohexane-1-carboxylic acid

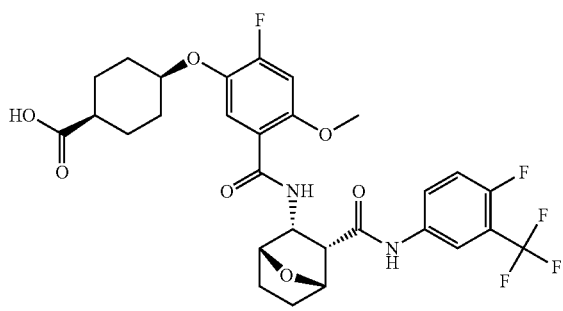 [SMILES: COc1cc(F)c(O[C@H]2CC[C@@H](C(=O)O)CC2)cc1C(=O)N[C@@H]1[C@H](C(=O)Nc2ccc(F)c(C(F)(F)F)c2)[C@@H]2CC[C@H]1O2]

The title compound was synthesized and purified in two steps from Intermediate 47 and Intermediate 111 in analogy with the synthesis described for Example 49 to give the title compound (26 mg, 52%) as a pale green solid; MS (ESI) m/z [M+H]$^+$ 613.

Example 51: (1S,4s)-4-(2-Fluoro-5-(((1R,2S)-2-((4-fluoro-3-(trifluoromethyl)phenyl)carbamoyl)cyclobutyl)carbamoyl)-4-methoxyphenoxy)-1-methylcyclohexane-1-carboxylic acid

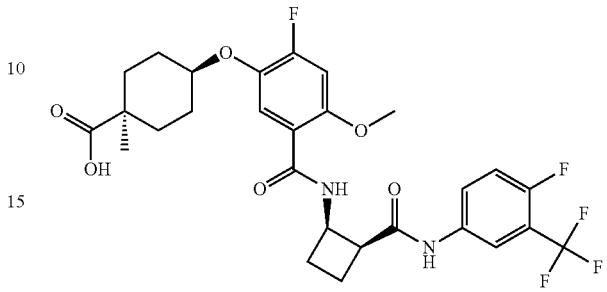

Step A Intermediate 394: tert-Butyl (1S,4s)-4-(2-fluoro-5-(((1R,2S)-2-((4-fluoro-3-(trifluoromethyl)phenyl)carbamoyl)cyclobutyl)carbamoyl)-4-methoxyphenoxy)-1-methylcyclohexane-1-carboxylate

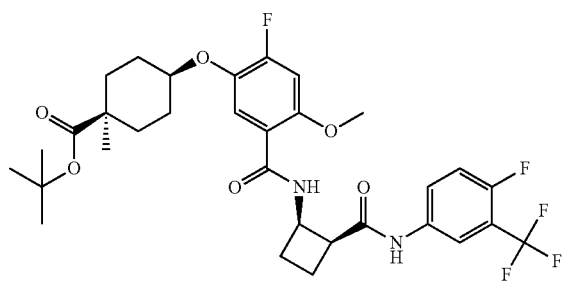 [SMILES: COc1cc(F)c(O[C@H]2CC[C@@](C)(C(=O)OC(C)(C)C)CC2)cc1C(=O)N[C@@H]1CC[C@@H]1C(=O)Nc1ccc(F)c(C(F)(F)F)c1]

Intermediate 73 (102 mg, 0.27 mmol), HATU (461 mg, 1.21 mmol) and DIPEA (0.169 mL, 0.97 mmol) were added to a solution of Intermediate 49 (67 mg, 0.24 mmol) in DMF (5 mL), and the reaction mixture was stirred at 20° C. for 3 h. The reaction mixture was diluted with EtOAc (75 mL), and washed with sat brine (6×15 mL). The organic layer was dried over $Na_2SO_4$, filtered and evaporated. The crude product was purified by preparative TLC (PE:EtOAc, 2:1), to give the title compound (110 mg, 71%) as a brown solid; MS (ESI) m/z [M+Na]$^+$ 663.

Step B (1S,4s)-4-(2-Fluoro-5-(((1R,2S)-2-((4-fluoro-3-(trifluoromethyl)phenyl)carbamoyl)cyclobutyl)carbamoyl)-4-methoxyphenoxy)-1-methylcyclohexane-1-carboxylic acid TFA (3 mL) was added to a solution of Intermediate 394 (100 mg, 0.16 mmol) in DCM (3 mL) and the reaction mixture was stirred at 20° C. for 2 h. The solvent was removed under reduced pressure, and the crude product was purified by preparative HPLC, Method PrepAcidic-C, using decreasingly polar mixtures of the mobile phase to give the title compound (45 mg, 47%) as a white solid; HRMS (ESI) m/z [M+H]$^+$ calcd for $C_{28}H_{30}F_5N_2O_6$: 585.2018 found: 585.2034.

Example 52: (1R,4s)-4-(2-fluoro-5-(((3S,4R)-4-((4-fluoro-3-(trifluoromethyl)phenyl)carbamoyl)tetrahydrofuran-3-yl)carbamoyl)-4-methoxyphenoxy)-1-methylcyclohexane-1-carboxylic acid

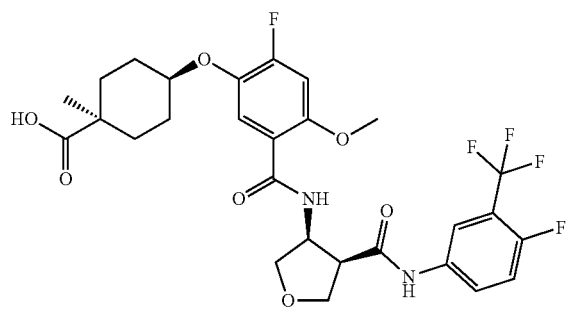 [SMILES: COc1cc(F)c(O[C@H]2CC[C@@](C)(C(=O)O)CC2)cc1C(=O)N[C@@H]1COC[C@@H]1C(=O)Nc1ccc(F)c(C(F)(F)F)c1]

Step A Intermediate 395: tert-Butyl (1S,4s)-4-(2-fluoro-5-(((3R,4R)-4-((4-fluoro-3-(trifluoromethyl)phenyl)carbamoyl)tetrahydrofuran-3-yl)carbamoyl)-4-methoxyphenoxy)-1-methylcyclohexane-1-carboxylate

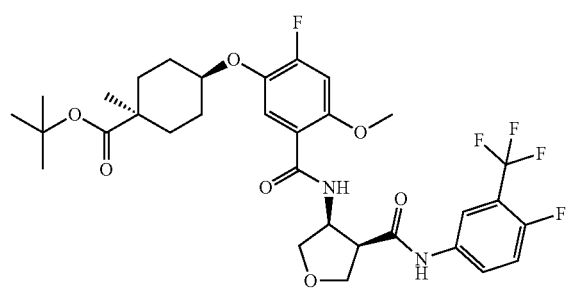 [SMILES: COc1cc(F)c(O[C@H]2CC[C@@](C)(C(=O)OC(C)(C)C)CC2)cc1C(=O)N[C@@H]1COC[C@@H]1C(=O)Nc1ccc(F)c(C(F)(F)F)c1]

HATU (312 mg, 0.82 mmol), DIPEA (0.12 mL, 0.68 mmol) and Intermediate 73 (63 mg, 0.16 mmol) were added to a solution of Intermediate 56 (40 mg, 0.14 mmol) in DMF (2 mL) and the reaction mixture was stirred at rt overnight. The reaction mixture was diluted with EtOAc (50 mL), and washed with sat brine (5×20 mL). The organic layer was dried over $Na_2SO_4$, filtered and evaporated. The crude product was purified by preparative TLC (PE:EtOAc, 1:5), to give the title compound (74 mg, 82%) as a colourless oil which solidified on standing; MS (ESI) m/z [M+H]$^+$ 657.

Step B (1S,4s)-4-(2-Fluoro-5-(((3R,4R)-4-((4-fluoro-3-(trifluoromethyl)phenyl)carbamoyl)tetrahydrofuran-3-yl)carbamoyl)-4-methoxyphenoxy)-1-methylcyclohexane-1-carboxylic acid TFA (4 mL) was added to a solution of Intermediate 395 (70 mg, 0.11 mmol) in DCM (4 mL), and the reaction mixture was stirred at rt for 6 h. The solvent was removed under reduced pressure and the crude product was purified by preparative HPLC, Method PrepAcidic-C, using decreasingly polar mixtures of the mobile phase, to give the title compound (24 mg, 38%) as a white solid; HRMS (ESI) m/z [M+H]$^+$ calcd for C28H30F5N2O7: 601.1968 found: 601.1972.

Example 53: (1R,2S,3R,4S)-3-(5-(((1s,4S)-4-Carbamoyl-4-methylcyclohexyl)oxy)-4-fluoro-2-methoxybenzamido)-N-neopentylbicyclo[2.2.1]heptane-2-carboxamide

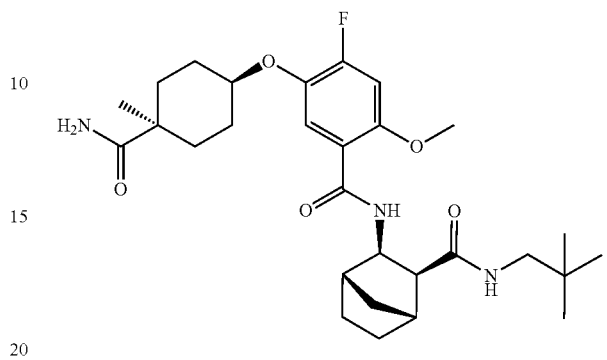

A solution of $NH_3$ (0.033 mL, 1.50 mmol, 0.5 M in THF) in THF (1 mL) was added dropwise to a solution of Example 35 (100 mg, 0.19 mmol), EDC (180 mg, 0.94 mmol), HOBt (144 mg, 0.94 mmol), and DIPEA (0.328 mL, 1.88 mmol) in DCM (1 mL) cooled to 0° C. and under a nitrogen atmosphere. The reaction mixture was stirred at 0° C. for 14 h. The reaction mixture was diluted with EtOAc (100 mL), and washed sequentially with sat brine (100 mL), sat $NaHCO_3$ (2×100 mL), and $H_2O$ (100 mL). The organic layer was dried over $Na_2SO_4$, filtered and evaporated. The crude product was purified by preparative TLC (EtOAc:PE, 1:2), and then by preparative HPLC, Method Prep-Acidic 0, (gradient: 44-54%), to give the title compound. (65 mg, 56%) as a white solid; HRMS (ESI) m/z [M+H]$^+$ calcd for C29H43FN3O5: 532.3182 found: 532.3212.

Example 54: (1s,4s)-4-(5-((3-Chloro-2-(((1-methylcyclobutyl)methyl)carbamoyl)phenyl)carbamoyl)-2-fluoro-4-methoxyphenoxy)-1-methylcyclohexane-1-carboxylic acid

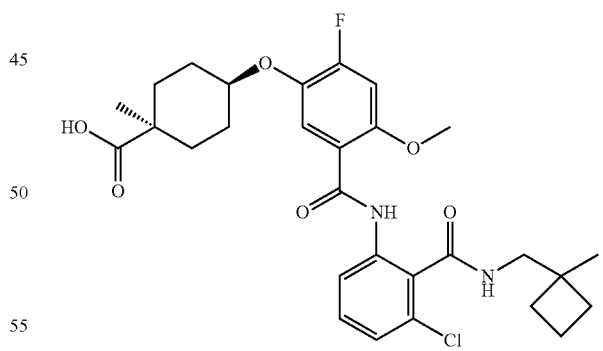

Pd—C (1.5 mg, 0.01 mmol) was added to a solution of Intermediate 59 (100 mg, 0.14 mmol) in THF (5 mL) at 20° C. and the reaction mixture was stirred under a hydrogen atmosphere for 6 h. The reaction mixture was filtered through silica, and the solvent was removed under reduced pressure. The crude product was purified by preparative HPLC, Method PrepAcidic-M, (gradient: 18-32%), to give the title compound (29 mg, 37%) as a white solid; HRMS (ESI) m/z [M+H]$^+$ calcd for C29H35ClFN2O6: 561.2162 found: 561.2194.

Example 55: (1S,4s)-4-(2-Fluoro-4-methoxy-5-(((1R,2S)-2-(((S)-3-methylbutan-2-yl)carbamoyl)cyclopentyl)carbamoyl)phenoxy)-1-methylcyclohexane-1-carboxylic acid

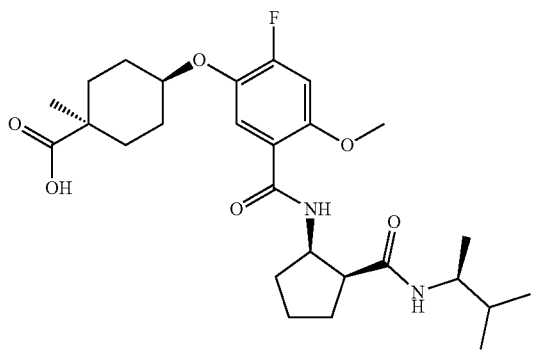 [SMILES: COc1cc(F)c(O[C@H]2CC[C@@](C)(C(=O)O)CC2)cc1C(=O)N[C@@H]1CCC[C@@H]1C(=O)N[C@@H](C)C(C)C]

Step A Intermediate 396: tert-Butyl (1S,4s)-4-(2-fluoro-4-methoxy-5-(((1R,2S)-2-(((S)-3-methylbutan-2-yl)carbamoyl)cyclopentyl)carbamoyl)phenoxy)-1-methylcyclohexane-1-carboxylate

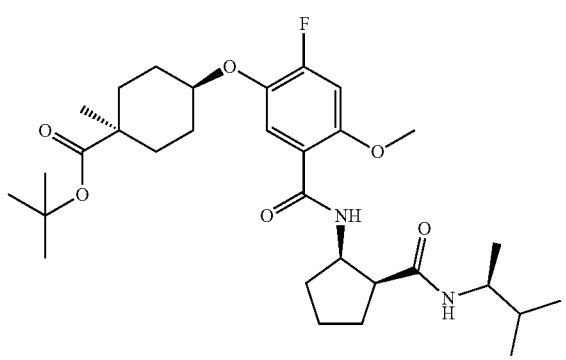 [SMILES: COc1cc(F)c(O[C@H]2CC[C@@](C)(C(=O)OC(C)(C)C)CC2)cc1C(=O)N[C@@H]1CCC[C@@H]1C(=O)N[C@@H](C)C(C)C]

Intermediate 63 (100 mg, 0.20 mmol) was added to a solution of (S)-3-methylbutan-2-amine (35 mg, 0.41 mmol), HATU (154 mg, 0.41 mmol) and DIPEA (0.071 mL, 0.41 mmol) in DMF (5 mL) and the reaction mixture was stirred at rt for 4 h. The reaction mixture was quenched with ice (75 mL), and extracted with EtOAc (3×50 mL). The organic layer was dried over $Na_2SO_4$, filtered and evaporate to give the title compound (100 mg, 88%) as yellow oil; MS (ESI) m/z [M+H]$^+$ 563.

Step B (1S,4s)-4-(2-Fluoro-4-methoxy-5-(((1R,2S)-2-(((S)-3-methylbutan-2-yl)carbamoyl)cyclopentyl)carbamoyl)phenoxy)-1-methylcyclohexane-1-carboxylic acid Intermediate 396 (100 mg, 0.18 mmol) was added to a solution of TFA (1 mL) in DCM (2 mL), and the reaction mixture was stirred at rt for 2 h. The solvent was removed under reduced pressure, and the crude product was purified by preparative HPLC, Method PrepAcidic-K, (gradient: 45-55%), to give the title compound (30 mg, 31%) as a white solid; HRMS (ESI) m/z [M+H]$^+$ calcd for C27H40FN2O6: 507.2864 found: 507.2854.

Example 56: (1S,4s)-4-(2-Fluoro-5-(((1R,2S)-2-(((1-(fluoromethyl)cyclopropyl)methyl)carbamoyl)cyclopentyl)carbamoyl)-4-methoxyphenoxy)-1-methylcyclohexane-1-carboxylic acid

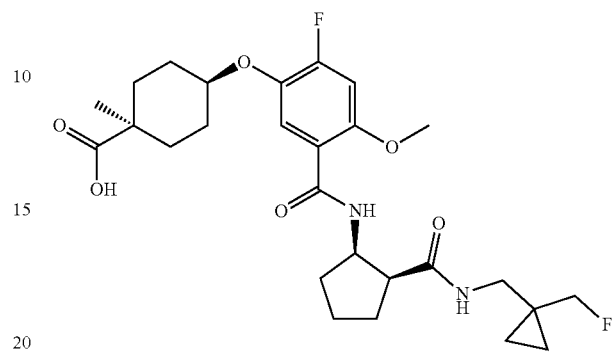

Step A Intermediate 397: tert-Butyl (1S,4s)-4-(2-fluoro-5-(((1R,2S)-2-(((1-(fluoromethyl)cyclopropyl)methyl)carbamoyl)cyclopentyl)carbamoyl)-4-methoxyphenoxy)-1-methylcyclohexane-1-carboxylate

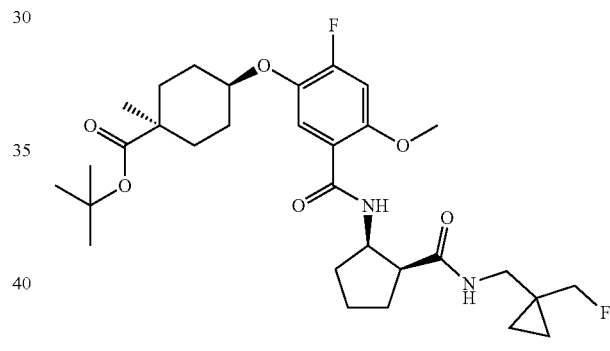

DIPEA (0.212 mL, 1.22 mmol) was added to a solution of Intermediate 63 (120 mg, 0.24 mmol), (1-(fluoromethyl)cyclopropyl)methanamine (50 mg, 0.49 mmol) and HATU (277 mg, 0.73 mmol) in DMF (4 mL) under a nitrogen atmosphere, and the reaction mixture was stirred at 20° C. for 16 h. The reaction mixture was diluted with EtOAc (50 mL), and washed sequentially with $H_2O$ (2×50 mL), sat $NaHCO_3$ (50 mL), and sat brine (2×50 mL). The organic layer was dried over $Na_2SO_4$, filtered and evaporated. The crude product was purified by preparative TLC (EtOAc:PE, 1:1) to give the title compound (135 mg, 96%) as a yellow gum; MS (ESI) m/z [M+H]$^+$ 579.

Step B (1S,4s)-4-(2-Fluoro-5-(((1R,2S)-2-(((1-(fluoromethyl)cyclopropyl)methyl)carbamoyl)cyclopentyl)carbamoyl)-4-methoxyphenoxy)-1-methylcyclohexane-1-carboxylic acid TFA (1 mL) was added to a solution of Intermediate 397 (130 mg, 0.22 mmol) in DCM (4 mL) at 20° C., and the reaction mixture was stirred at 20° C. for 1 h. The solvent was removed under reduced pressure, and the crude product was purified by preparative HPLC, Method PrepAcidic-K, (gradient: 40-50%), to give the title compound (65 mg, 51%) as a white solid; HRMS (ESI) m/z [M+H]$^+$ calcd for C27H37F2N2O6: 523.2614 found: 523.2606.

Example 57: (1S,4s)-4-(2-Fluoro-4-methoxy-5-(((1R,2S)-2-(neopentylcarbamoyl)cyclopentyl)carbamoyl)phenoxy)-1-methylcyclohexane-1-carboxylic acid

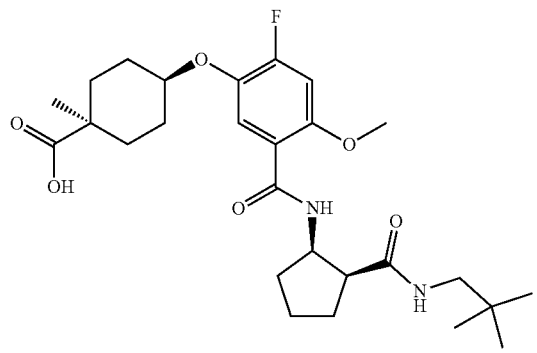 [SMILES: COc1cc(F)c(O[C@H]2CC[C@@](C)(C(=O)O)CC2)cc1C(=O)N[C@@H]1CCC[C@@H]1C(=O)NCC(C)(C)C]

Step A Intermediate 398: tert-Butyl (1S,4s)-4-(2-fluoro-4-methoxy-5-(((1R,2S)-2-(neopentylcarbamoyl)cyclopentyl)carbamoyl)phenoxy)-1-methylcyclohexane-1-carboxylate

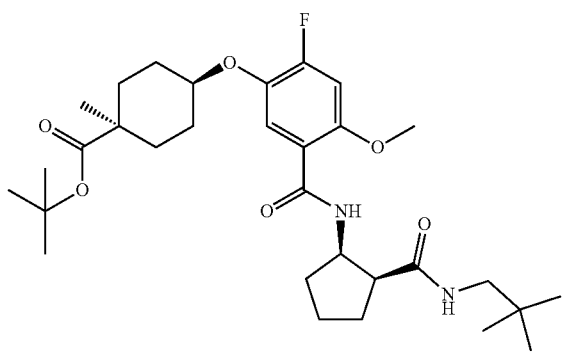 [SMILES: COc1cc(F)c(O[C@H]2CC[C@@](C)(C(=O)OC(C)(C)C)CC2)cc1C(=O)N[C@@H]1CCC[C@@H]1C(=O)NCC(C)(C)C]

DIPEA (0.106 mL, 0.61 mmol) was added dropwise to a solution of 2,2-dimethylpropan-1-amine (26 mg, 0.30 mmol), Intermediate 63 (100 mg, 0.20 mmol) and HATU (385 mg, 1.01 mmol) in DMF (8 mL) at 20° C. and under a nitrogen atmosphere, and the reaction mixture was stirred at rt for 14 h. The reaction mixture was diluted with EtOAc (100 mL), and washed sequentially with sat brine (125 mL), sat NaHCO$_3$ (125 mL), and H$_2$O (125 mL). The organic layer was dried over Na$_2$SO$_4$, filtered and evaporated. The crude product was purified by preparative TLC (EtOAc:PE, 1:2), to give the title compound (98 mg, 86%) as a pale yellow solid.

Step B (1S,4s)-4-(2-Fluoro-4-methoxy-5-(((1R,2S)-2-(neopentylcarbamoyl)cyclopentyl)carbamoyl)phenoxy)-1-methylcyclohexane-1-carboxylic acid TFA (2 mL) was added dropwise to a solution of Intermediate 398 (98 mg, 0.17 mmol) in DCM (2 mL) at 0° C. The reaction mixture was stirred at 20° C. for 5 h. The solvent was removed under reduced pressure to give the title compound (93 mg, 91%) as a colourless solid; HRMS (ESI) m/z [M+H]$^+$ calcd for C27H40FN2O6: 507.2864 found: 507.2876.

Example 58: (1S,4s)-4-(5-(((1R,2S)-2-((2,2-Dimethylbutyl)carbamoyl)cyclopentyl)carbamoyl)-2-fluoro-4-methoxyphenoxy)-1-methylcyclohexane-1-carboxylic acid

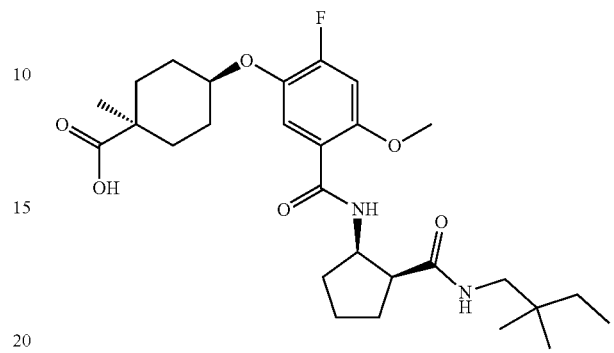

Step A Intermediate 399: tert-Butyl (1S,4s)-4-(5-(((1R,2S)-2-((2,2-dimethylbutyl)carbamoyl)cyclopentyl)carbamoyl)-2-fluoro-4-methoxyphenoxy)-1-methylcyclohexane-1-carboxylate DIPEA (0.106 mL, 0.61 mmol) was added dropwise to a solution of Intermediate 63 (100 mg, 0.20 mmol), 2,2-dimethylbutan-1-amine (20 mg, 0.20 mmol) and HATU (385 mg, 1.01 mmol) in DMF (5 mL) at 20° C. and under a nitrogen atmosphere, and the reaction mixture was stirred at 25° C. for 14 h. The reaction mixture was diluted with EtOAc (100 mL), and washed sequentially with sat brine (125 mL), sat NaHCO$_3$ (125 mL), and H$_2$O (125 mL). The organic layer was dried over Na$_2$SO$_4$, filtered and evaporated. The crude product was purified by preparative TLC (EtOAc:PE, 1:2), to give the title compound (115 mg, 98%) as a pale yellow solid; MS (ESI) m/z [M+H]$^+$ 577.

Step B (1S,4s)-4-(5-(((1R,2S)-2-((2,2-Dimethylbutyl)carbamoyl)cyclopentyl)carbamoyl)-2-fluoro-4-methoxyphenoxy)-1-methylcyclohexane-1-carboxylic acid TFA (2 mL) was added dropwise to a solution of Intermediate 399 (100 mg, 0.17 mmol) in DCM (2 mL) at 0° C. The reaction mixture was stirred at 20° C. for 5 h. The solvent was removed under reduced pressure and the crude product was purified by preparative HPLC, Method PrepAcidic-K, (gradient: 50-60%), to give the title compound (55 mg, 59%) as a white solid; HRMS (ESI) m/z [M+H]+ calcd for C28H42FN2O6: 521.3022 found: 521.3046.

Example 59: (1S,4s)-4-(5-(((1R,2S)-2-((2-Ethylbutyl)carbamoyl)cyclopentyl)carbamoyl)-2-fluoro-4-methoxyphenoxy)-1-methylcyclohexane-1-carboxylic acid

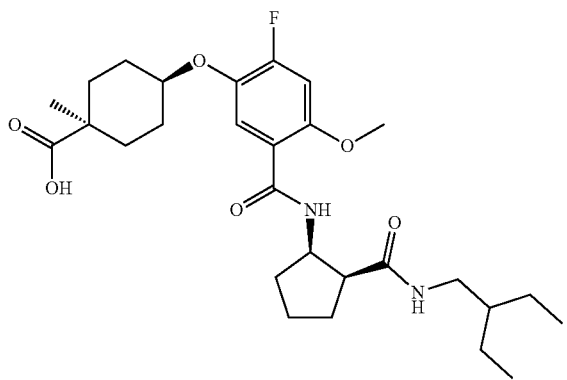 [SMILES: CCC(CC)CNC(=O)[C@H]1CCC[C@H]1NC(=O)c1cc(O[C@H]2CC[C@@](C)(C(=O)O)CC2)c(F)cc1OC]

Step A Intermediate 400: tert-Butyl (1S,4s)-4-(5-(((1R,2S)-2-((2-ethylbutyl)carbamoyl)cyclopentyl)carbamoyl)-2-fluoro-4-methoxyphenoxy)-1-methylcyclohexane-1-carboxylate

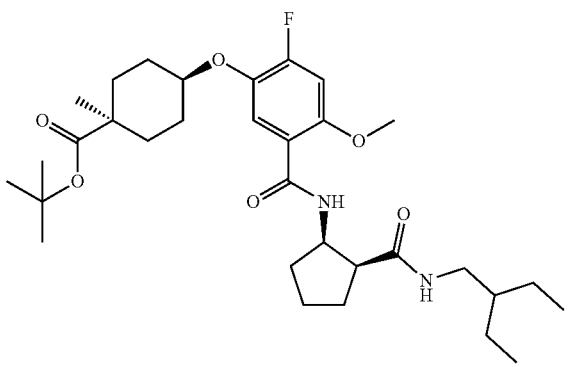 [SMILES: CCC(CC)CNC(=O)[C@H]1CCC[C@H]1NC(=O)c1cc(O[C@H]2CC[C@@](C)(C(=O)OC(C)(C)C)CC2)c(F)cc1OC]

DIPEA (0.142 mL, 0.81 mmol) was added to a solution of Intermediate 63 (100 mg, 0.20 mmol), 2-ethylbutan-1-amine (31 mg, 0.30 mmol) and HATU (154 mg, 0.41 mmol) in DMF (3 mL) at 15° C. and under a nitrogen atmosphere, and the reaction mixture was stirred at 15° C. for 3 h. The reaction mixture was diluted with EtOAc (150 mL), and washed sequentially with H2O (2×50 mL), sat NaHCO3 (50 mL), and sat brine (2×50 mL). The organic layer was dried over Na2SO4, filtered and evaporated. The crude product was purified by preparative TLC (EtOAc:PE, 1:2), to give the title compound (100 mg, 86%) as a white solid; MS (ESI) m/z [M+H]+ 577.

Step B (1S,4s)-4-(5-(((1R,2S)-2-((2-Ethylbutyl)carbamoyl)cyclopentyl)carbamoyl)-2-fluoro-4-methoxyphenoxy)-1-methylcyclohexane-1-carboxylic acid TFA (2 mL) was added to a solution of Intermediate 400 (90 mg, 0.16 mmol) in DCM (2 mL) at 15° C., and the reaction mixture was stirred at 15° C. for 4 h. The solvent was removed under reduced pressure, and the crude product was purified by preparative HPLC, Method PrepAcidic-K, (gradient: 48-58%), to give the title compound (60 mg, 70%) as a white solid; HRMS (ESI) m/z [M+H]+ calcd for C28H42FN2O6: 521.3022 found: 521.3030.

The examples included in Table 6 below were synthesized and purified analogous to the procedure of Example 59 using the appropriate amines (as the free base or as the corresponding HCl salt). The amine is commercially available if not otherwise stated.

TABLE 6

| Ex No | Structure | HRMS (ESI) m/z [M + H]+ | Purification Method |
|---|---|---|---|
| 60 | 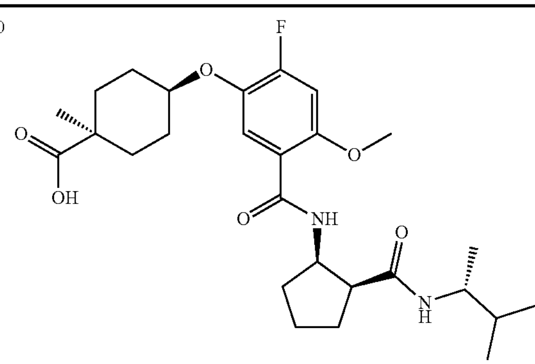 | calcd for C27H40FN2O6: 507.2864 found: 507.2860 | Step A: Preparative TLC (EtOAc:PE, 1:2) Step B: Method PrepAcidic-K (gradient 50-60%) |

TABLE 6-continued

| Ex No | Structure | HRMS (ESI) m/z [M + H]+ | Purification Method |
|---|---|---|---|
| 61 | 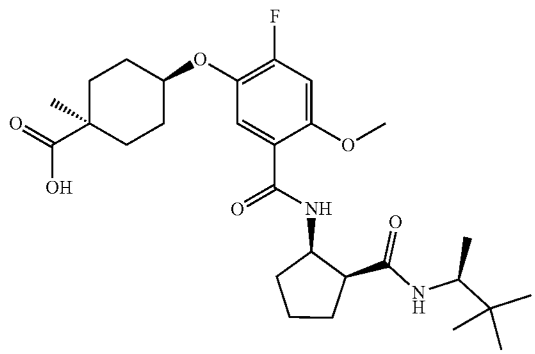 [SMILES: COc1cc(F)c(O[C@H]2CC[C@@](C)(C(=O)O)CC2)cc1C(=O)N[C@@H]1CCC[C@@H]1C(=O)N[C@@H](C)C(C)(C)C] | calcd for C28H42FN2O6: 521.3022 found: 521.3024 | Step A: Preparative TLC (EtOAc:PE, 1:2) Step B: Method PrepAcidic-K (gradient 40-55%) |
| 62 | 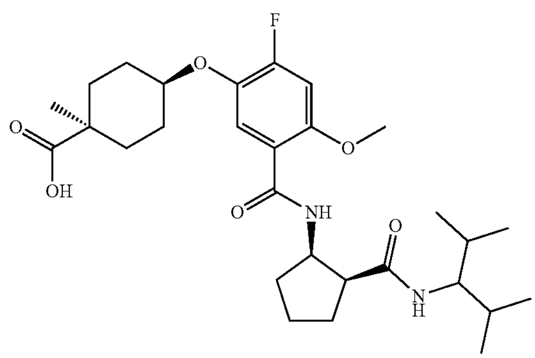 [SMILES: COc1cc(F)c(O[C@H]2CC[C@@](C)(C(=O)O)CC2)cc1C(=O)N[C@@H]1CCC[C@@H]1C(=O)NC(C(C)C)C(C)C] | calcd for C29H44FN2O6: 535.3178 found: 535.3194 | Step A: Preparative TLC (EtOAc:PE, 1:2) Step B: Method PrepAcidic-K (gradient 50-60%) |
| 63 | 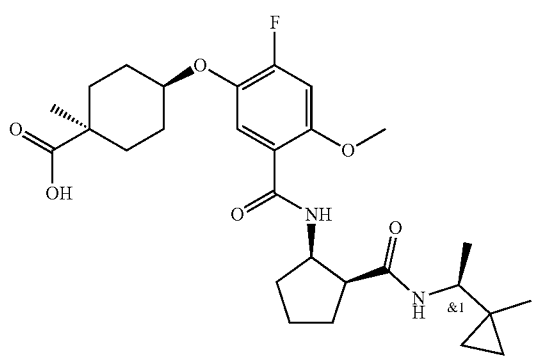 [SMILES: COc1cc(F)c(O[C@H]2CC[C@@](C)(C(=O)O)CC2)cc1C(=O)N[C@@H]1CCC[C@@H]1C(=O)N[C@@H](C)C1(C)CC1] | calcd for C28H40FN2O6: 519.2864 found: 519.2872 | Step A: Preparative TLC (EtOAc:PE, 1:2) Step B: Method PrepAcidic-K (gradient 27-37%) |
| 64 | 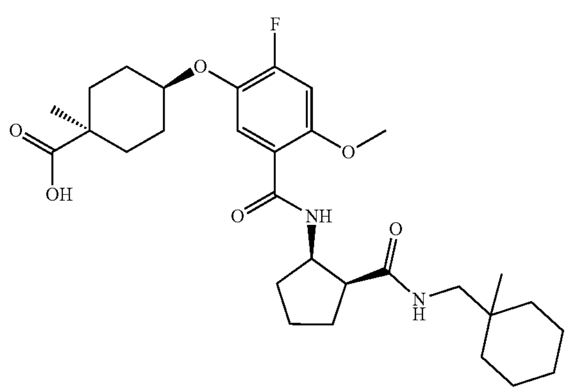 [SMILES: COc1cc(F)c(O[C@H]2CC[C@@](C)(C(=O)O)CC2)cc1C(=O)N[C@@H]1CCC[C@@H]1C(=O)NCC1(C)CCCCC1] | calcd for C30H44FN2O6: 547.3178 found: 547.3202 | Step A: Preparative TLC (EtOAc:PE, 1:2) Step B: Method PrepAcidic-K (gradient 54-64%) |

Example 65: (1S,4s)-4-(5-(((1R,2S)-2-(((R)-3,3-Dimethylbutan-2-yl)carbamoyl)cyclopentyl)carbamoyl)-2-fluoro-4-methoxyphenoxy)-1-methylcyclohexane-1-carboxylic acid

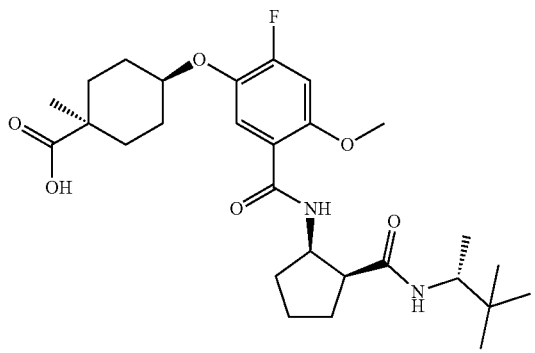 [SMILES: COc1cc(F)c(O[C@H]2CC[C@@](C)(C(=O)O)CC2)cc1C(=O)N[C@@H]1CCC[C@@H]1C(=O)N[C@H](C)C(C)(C)C]

Step A Intermediate 401: tert-Butyl (1S,4s)-4-(5-(((1R,2S)-2-(((R)-3,3-dimethylbutan-2-yl)carbamoyl)cyclopentyl)carbamoyl)-2-fluoro-4-methoxyphenoxy)-1-methylcyclohexane-1-carboxylate

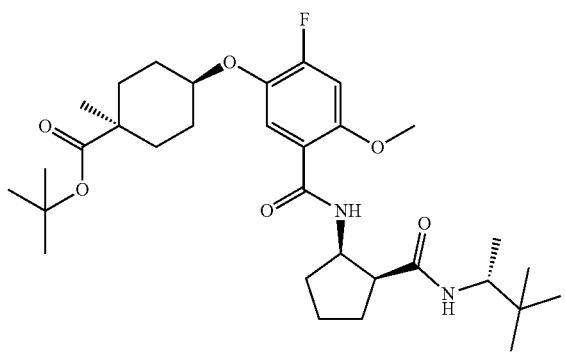 [SMILES: COc1cc(F)c(O[C@H]2CC[C@@](C)(C(=O)OC(C)(C)C)CC2)cc1C(=O)N[C@@H]1CCC[C@@H]1C(=O)N[C@H](C)C(C)(C)C]

DIPEA (0.177 mL, 1.01 mmol) was added to a solution of Intermediate 63 (100 mg, 0.20 mmol), (R)-3,3-dimethylbutan-2-amine (31 mg, 0.30 mmol) and HATU (231 mg, 0.61 mmol) in DMF (3 mL) under a nitrogen atmosphere, and the reaction mixture was stirred at 20° C. for 16 h. The reaction mixture was diluted with EtOAc (50 mL), and washed sequentially with H₂O (2×50 mL), sat NaHCO₃ (50 mL), and sat brine (2×50 mL). The organic layer was dried over Na₂SO₄, filtered and evaporated. The crude product was purified by preparative TLC (EtOAc:PE, 1:1), to give the title compound (110 mg, 94%) as a yellow gum; MS (ESI) m/z [M+H]⁺ 577.

Step B (1S,4s)-4-(5-(((1R,2S)-2-(((R)-3,3-Dimethylbutan-2-yl)carbamoyl)cyclopentyl)carbamoyl)-2-fluoro-4-methoxyphenoxy)-1-methylcyclohexane-1-carboxylic acid TFA (3 mL) was added to Intermediate 401 (105 mg, 0.18 mmol) in DCM (3 mL) at 20° C., an the reaction mixture was stirred at 20° C. for 30 min. The solvent was removed under reduced pressure, and the crude product was purified by preparative HPLC, Method PrepAcidic-K, (gradient: 50-60%), to give the title compound (75 mg, 75%) as a white solid; HRMS (ESI) m/z [M+H]⁺ calcd for C28H42FN2O6: 521.3022 found: 521.3034.

The examples included in Table 7 below were synthesized and purified analogous to the procedure of Example 65 using the appropriate amines (as the free base or as the corresponding HCl salt). The amine is commercially available if not otherwise stated.

TABLE 7

| Ex No | Structure | (m/z) [M + H]⁺ | Purification Method |
|---|---|---|---|
| 66 | (structure shown) | calcd for C26H38FN2O6: 493.2708 found: 493.2714 | Step A: Preparative TLC (EtOAc:PE, 1:1) Step B: Method PrepAcidic-K (gradient 46-56%) |

TABLE 7-continued

| Ex No | Structure | (m/z) [M + H]+ | Purification Method |
|---|---|---|---|
| 67 | 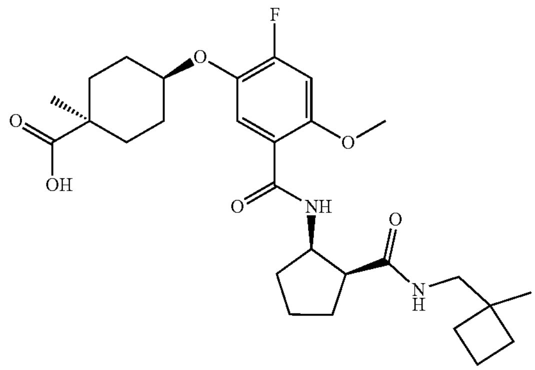 [SMILES: COc1cc(F)c(O[C@H]2CC[C@@](C)(C(=O)O)CC2)cc1C(=O)N[C@@H]1CCC[C@@H]1C(=O)NCC1(C)CCC1] | calcd for C28H40FN2O6: 519.2864 found: 519.2872 | Step A: Preparative TLC (EtOAc:PE, 1:1) Step B: Method PrepAcidic-K (gradient 45-55%) |
| 68 | 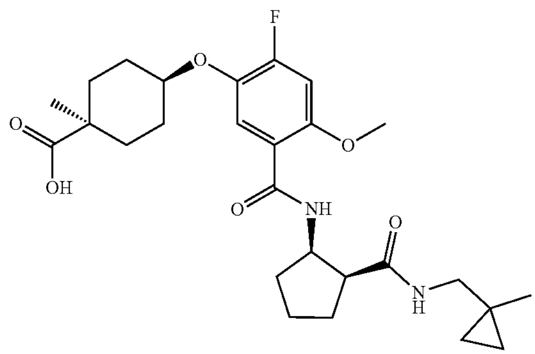 [SMILES: COc1cc(F)c(O[C@H]2CC[C@@](C)(C(=O)O)CC2)cc1C(=O)N[C@@H]1CCC[C@@H]1C(=O)NCC1(C)CC1] | calcd for C27H38FN2O6: 505.2708 found: 505.2716 | Step A: Preparative TLC (EtOAc:PE, 1:1) Step B: Method PrepAcidic-K (gradient 42-52%) |
| 69 | 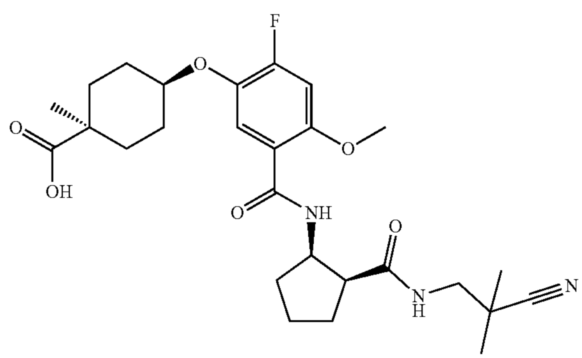 [SMILES: COc1cc(F)c(O[C@H]2CC[C@@](C)(C(=O)O)CC2)cc1C(=O)N[C@@H]1CCC[C@@H]1C(=O)NCC(C)(C)C#N] | calcd for C27H37FN3O6: 518.2660 found: 518.2644 | Step A: Preparative TLC (EtOAc:PE, 1:1) Step B: Method PrepAcidic-K (gradient 37-47%) |
| 70 | 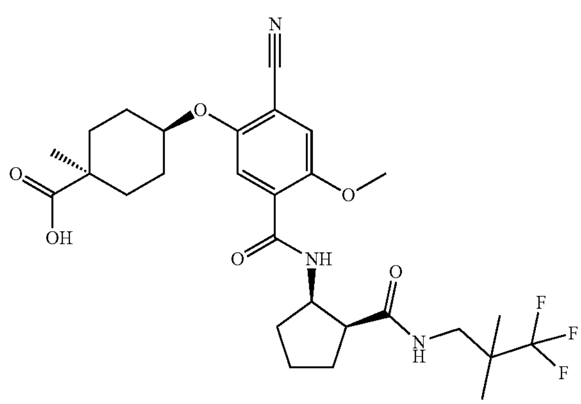 [SMILES: COc1cc(C#N)c(O[C@H]2CC[C@@](C)(C(=O)O)CC2)cc1C(=O)N[C@@H]1CCC[C@@H]1C(=O)NCC(C)(C)C(F)(F)F] | calcd for C27H37F4N2O6: 561.2582 found: 561.2568 | Step A: Preparative TLC (EtOAc:PE, 1:1) Step B: Method PrepAcidic-K (gradient 47-57%) |

Example 71. (1S,4s)-4-(2-Cyano-5-(((1S,2R,3S,4R)-3-((cyclopropylmethyl)carbamoyl)bicyclo[2.2.1]heptan-2-yl)carbamoyl)-4-methoxyphenoxy)-1-methylcyclohexane-1-carboxylic acid

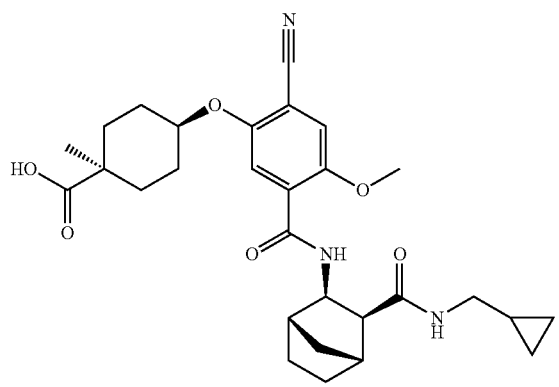 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1CC1]

A solution of Intermediate 68 (500 μL, 0.024 g, 0.05 mmol, 0.1 M in DMF), a solution of cyclopropylmethanamine (500 μL, 0.05 mmol, 0.1 M in DMF) and a solution of DIPEA (500 L, 0.15 mmol, 0.3 M in DMF) were added to a vial at rt. A solution of HATU (500 μL, 0.15 mmol, 0.3 M in DMF) was added and the reaction mixture was stirred at 40° C. overnight. The crude mixture was washed with DMSO (3×500 μL), filtered and the filtrate was evaporated under reduced pressure. The crude product was purified by Method SFC-A to afford the title compound (10.3 mg, 39%). HRMS (ESI) m/z [M+H]$^+$ calcd for $C_{29}H_{38}N_3O_6$: 524.2756 found: 524.2752.

The examples included in Table 8 below were synthesized analogous to the procedure of Example 71 using the appropriate amines (as the free base or as the corresponding HCl salt). The amine is commercially available if not otherwise stated.

TABLE 8

| Ex No. | Structure | HRMS (ESI) m/z [M + H]$^+$ | Purification Method |
|---|---|---|---|
| 72 | 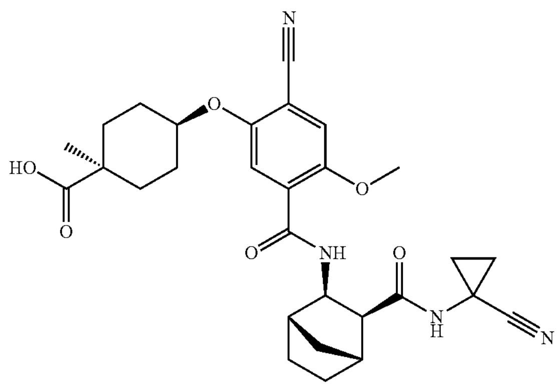 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC1(C#N)CC1] | calcd for $C_{29}H_{35}N_4O_6$: 535.2552 found: 535.2554 | SFC-A |
| 73 | 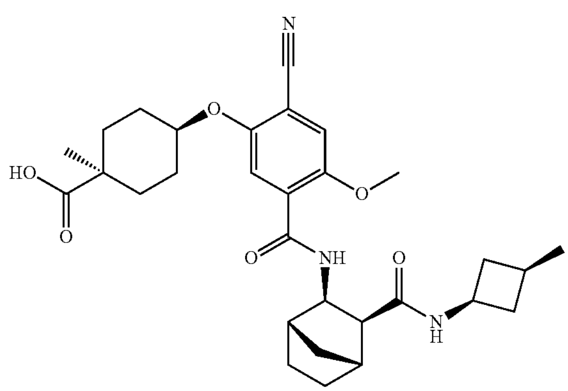 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)N[C@H]1C[C@@H](C)C1] | calcd for $C_{30}H_{40}N_3O_6$: 538.2912 found: 538.2912 | SFC-A |

TABLE 8-continued

| Ex No. | Structure | HRMS (ESI) m/z [M + H]+ | Purification Method |
|---|---|---|---|
| 74 | 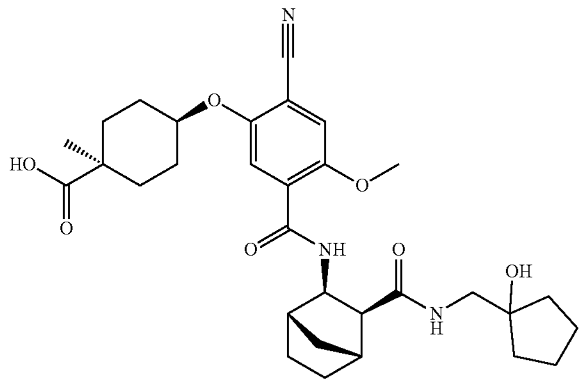 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1(O)CCCC1] | calcd for $C_{31}H_{42}N_3O_7$: 568.3016 found: 568.3014 | SFC-B |
| 75 | 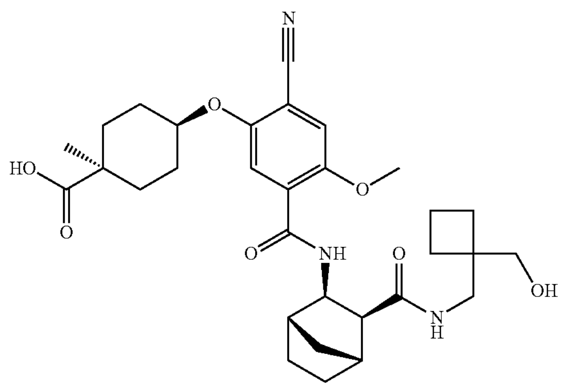 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1(CO)CCC1] | calcd for $C_{31}H_{42}N_3O_7$: 568.3016 found: 568.3020 | SFC-C |
| 76 | 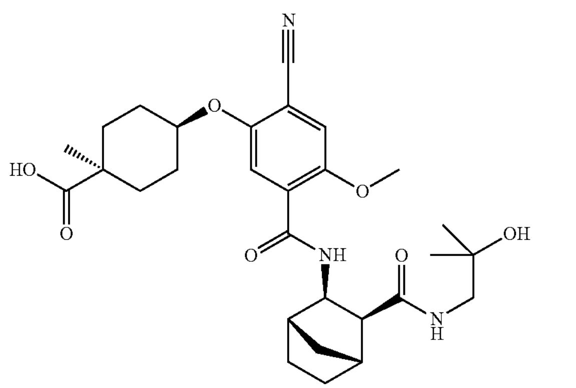 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC(C)(C)O] | calcd for $C_{29}H_{40}N_3O_7$: 542.2860 found: 542.2860 | SFC-C |
| 77 | 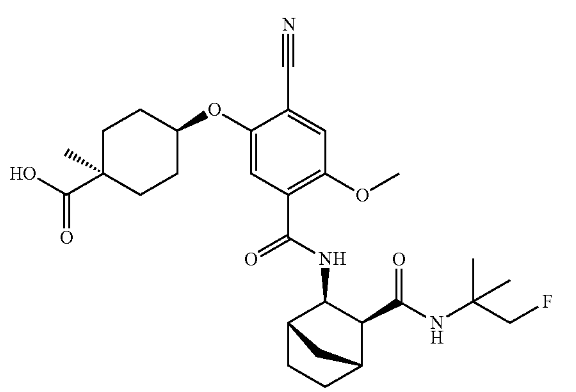 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC(C)(C)CF] | calcd for $C_{29}H_{39}FN_3O_6$: 544.2818 found: 544.2820 | SFC-C |

TABLE 8-continued

| Ex No. | Structure | HRMS (ESI) m/z [M + H]+ | Purification Method |
|---|---|---|---|
| 78 | 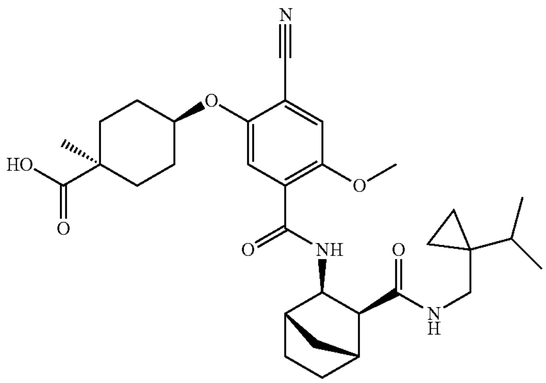 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1(C(C)C)CC1] | calcd for C$_{32}$H$_{44}$N$_3$O$_6$: 566.3224 found: 566.3232 | SFC-A |
| 79 | 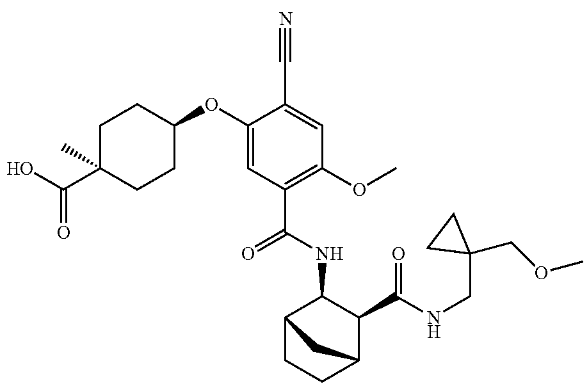 [SMILES: COCC1(CNC(=O)[C@H]2[C@@H]3CC[C@@H](C3)[C@H]2NC(=O)c2cc(O[C@H]3CC[C@@](C)(C(=O)O)CC3)c(C#N)cc2OC)CC1] | calcd for C$_{31}$H$_{42}$N$_3$O$_7$: 568.3016 found: 568.3012 | SFC-A |
| 80 | 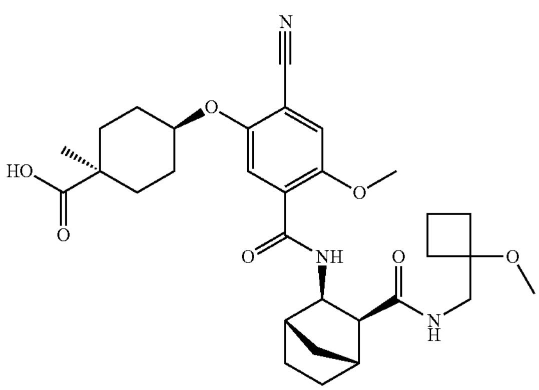 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1(OC)CCC1] | calcd for C$_{31}$H$_{42}$N$_3$O$_7$: 568.3016 found: 568.3010 | SFC-A |
| 81 | 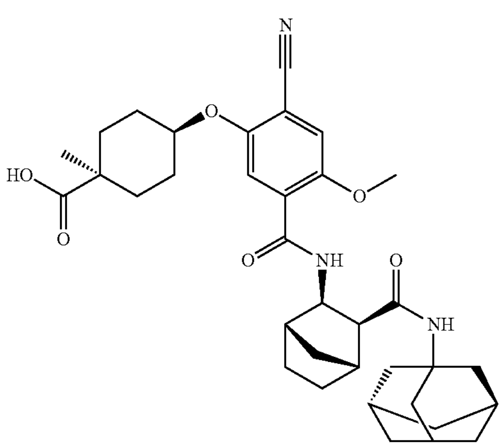 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC12CC3C[C@H](C1)C[C@H](C3)C2] | calcd for C$_{35}$H$_{46}$N$_3$O$_6$: 604.3380 found: 604.3376 | PrepBasic-C Gradient: 5-95% |

TABLE 8-continued

| Ex No. | Structure | HRMS (ESI) m/z [M + H]+ | Purification Method |
|---|---|---|---|
| 82 | 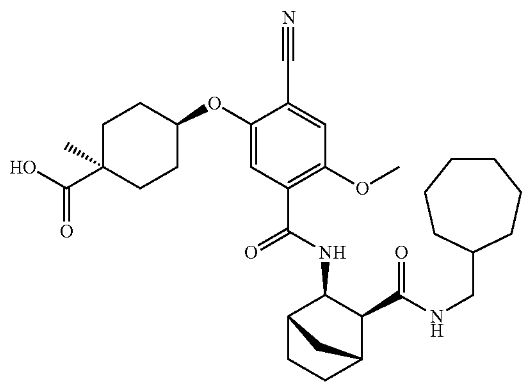 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1CCCCCC1] | calcd for $C_{33}H_{46}N_3O_6$: 580.3380 found: 580.3378 | PrepBasic-C Gradient: 5-95% |
| 83 | 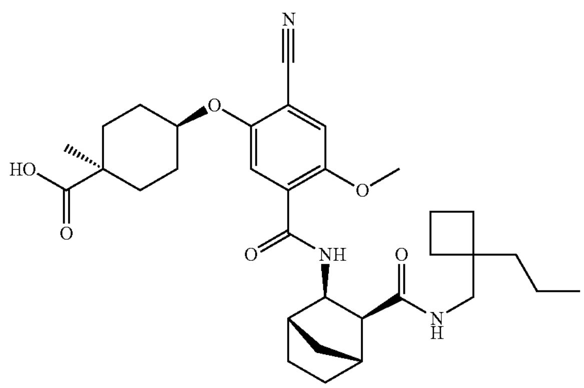 [SMILES: CCCC1(CNC(=O)[C@H]2[C@@H]3CC[C@@H](C3)[C@H]2NC(=O)c2cc(O[C@H]3CC[C@@](C)(C(=O)O)CC3)c(C#N)cc2OC)CCC1] | calcd for $C_{33}H_{46}N_3O_6$: 580.3380 found: 580.3372 | SFC-D |
| 84 | 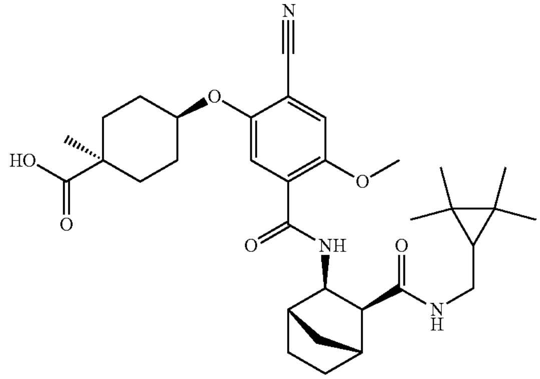 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1C(C)(C)C1(C)C] | calcd for $C_{33}H_{46}N_3O_6$: 580.3380 found: 580.3382 | SFC-D |

TABLE 8-continued

| Ex No. | Structure | HRMS (ESI) m/z [M + H]+ | Purification Method |
|---|---|---|---|
| 85 | 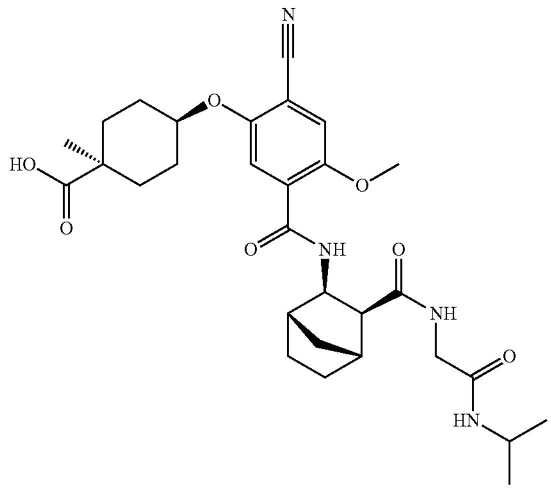 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC(=O)NC(C)C] | calcd for C30H41N4O7: 569.2970 found: 569.2974 | SFC-D |
| 86 | 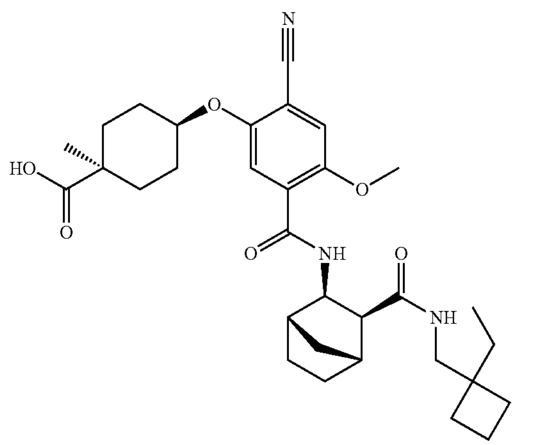 [SMILES: CCC1(CNC(=O)[C@H]2[C@@H]3CC[C@@H](C3)[C@H]2NC(=O)c2cc(O[C@H]3CC[C@@](C)(C(=O)O)CC3)c(C#N)cc2OC)CCC1] | calcd for C32H44N3O6: 566.3224 found: 566.3222 | PrepBasic-C Gradient: 5-95% |
| 87 | 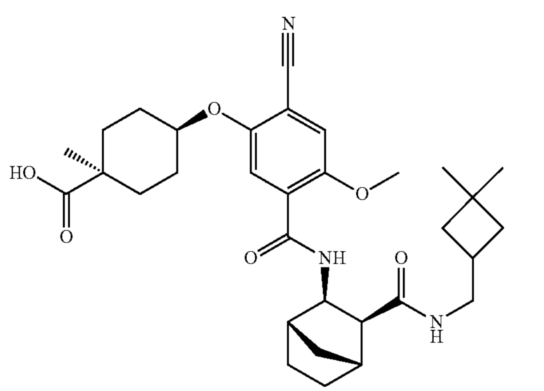 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1CC(C)(C)C1] | calcd for C32H44N3O6: 566.3224 found: 566.3240 | PrepBasic-C Gradient: 5-95% |

TABLE 8-continued

| Ex No. | Structure | HRMS (ESI) m/z [M + H]+ | Purification Method |
|---|---|---|---|
| 88 | 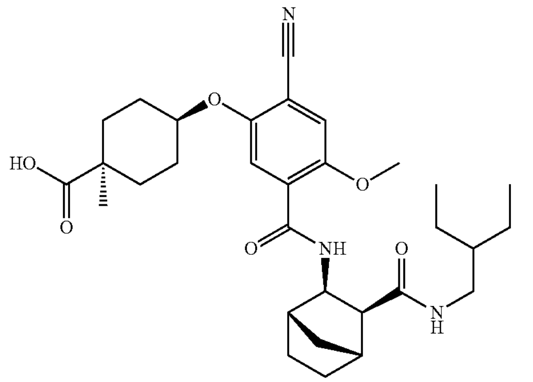 [SMILES: CCC(CC)CNC(=O)[C@H]1[C@@H]2CC[C@@H](C2)[C@H]1NC(=O)c1cc(O[C@H]2CC[C@@](C)(C(=O)O)CC2)c(C#N)cc1OC] | calcd for C31H44N3O6: 554.3224 found: 554.3222 | PrepBasic-C Gradient: 5-95% |
| 89 | 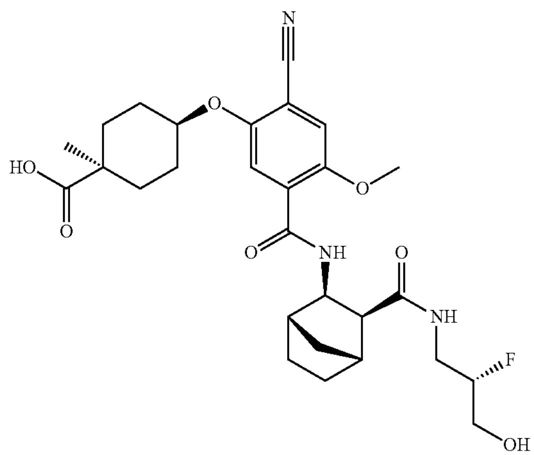 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC[C@H](F)CO] | calcd for C28H37FN3O7: 546.2610 found: 546.2614 | SFC-D |
| 90 | 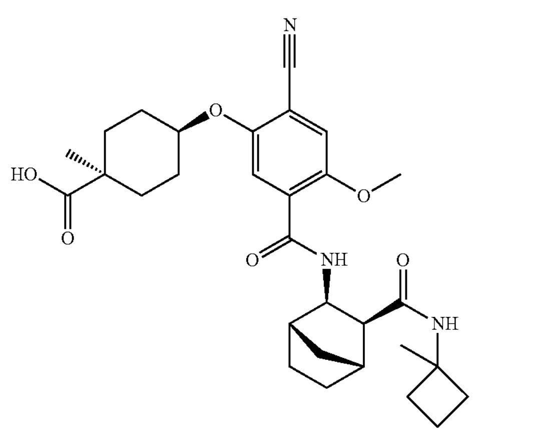 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC1(C)CCC1] | calcd for C30H40N3O6: 538.2912 found: 538.2912 | SFC-D |

TABLE 8-continued
| Ex No. | Structure | HRMS (ESI) m/z [M + H]+ | Purification Method |
|---|---|---|---|
| 91 | 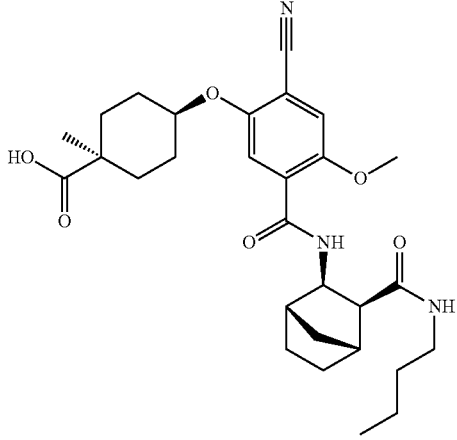 [SMILES: CCCCNC(=O)[C@H]1[C@@H]2CC[C@@H](C2)[C@H]1NC(=O)c1cc(O[C@H]2CC[C@@](C)(C(=O)O)CC2)c(C#N)cc1OC] | calcd for $C_{29}H_{40}N_3O_6$: 526.2912 found: 526.2910 | PrepBasic-C Gradient: 5-95% |
| 92 | 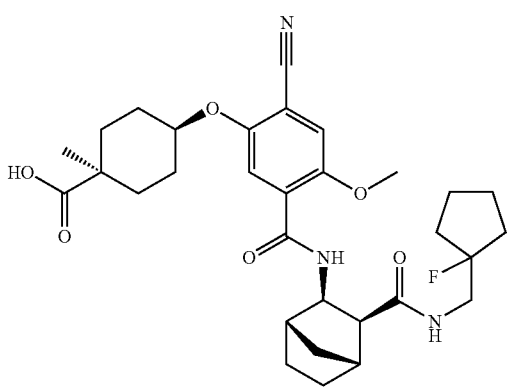 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1(F)CCCC1] | calcd for $C_{31}H_{41}FN_3O_6$: 570.2979, found: 570.2987 | SFC-E |
| 93 | 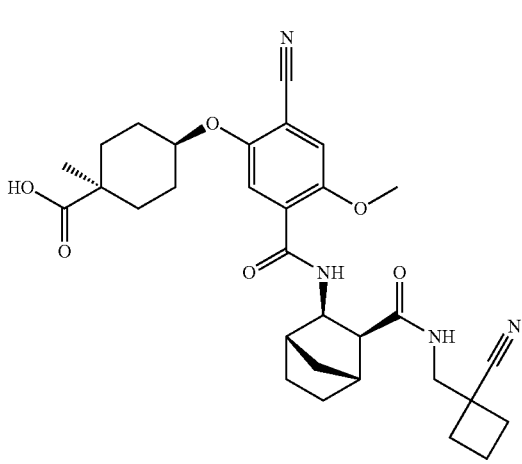 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1(C#N)CCC1] | calcd for $C_{31}H_{39}N_4O_6$: 563.2864 found: 563.2858 | PrepBasic-C Gradient: 5-95% |

TABLE 8-continued

| Ex No. | Structure | HRMS (ESI) m/z [M + H]+ | Purification Method |
|---|---|---|---|
| 94 | 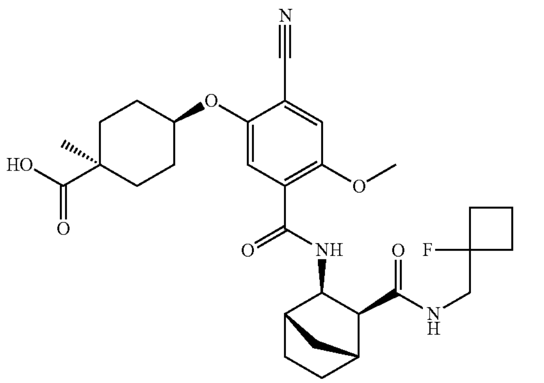 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1(F)CCC1] | calcd for $C_{30}H_{39}FN_3O_6$: 556.2818 found: 556.2810 | PrepAcidic-E Gradient: 5-95% |
| 95 | 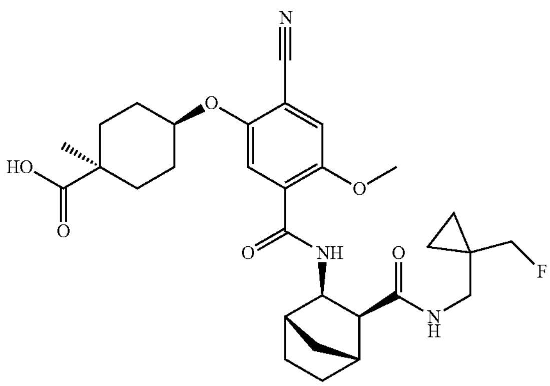 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1(CF)CC1] | calcd for $C_{30}H_{39}FN_3O_6$: 556.2818 found: 556.2816 | PrepBasic-C Gradient: 5-95% |
| 96 | 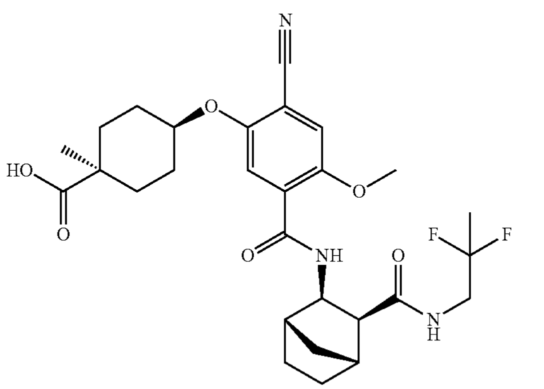 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC(C)(F)F] | calcd for $C_{28}H_{36}F_2N_3O_6$: 548.2566 found: 548.2570 | SFC-F |
| 97 | 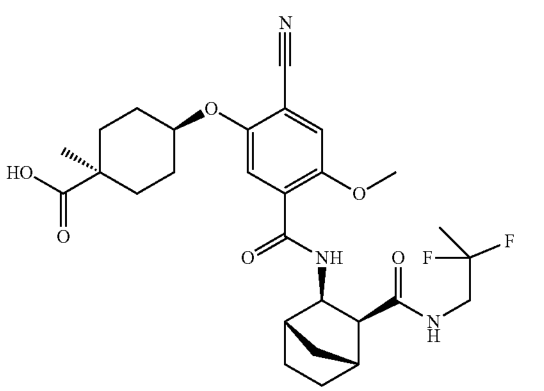 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC(C)(F)F] | calcd for $C_{29}H_{39}FN_3O_6$: 544.2818 found: 544.2818 | SFC-F |

TABLE 8-continued

| Ex No. | Structure | HRMS (ESI) m/z [M + H]+ | Purification Method |
|---|---|---|---|
| 98 | 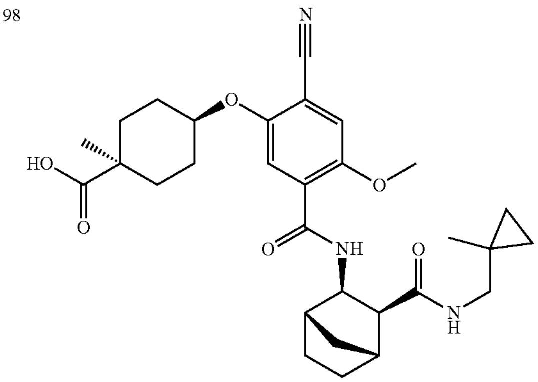 | calcd for $C_{30}H_{40}N_3O_6$: 538.2912 found: 538.2918 | SFC-D |
| 99 | 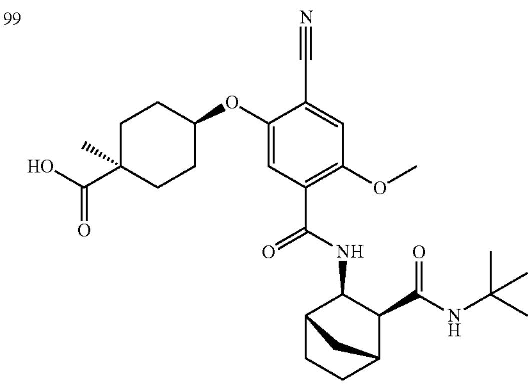 | calcd for $C_{29}H_{40}N_3O_6$: 526.2912 found: 526.2908 | SFC-F |
| 100 | 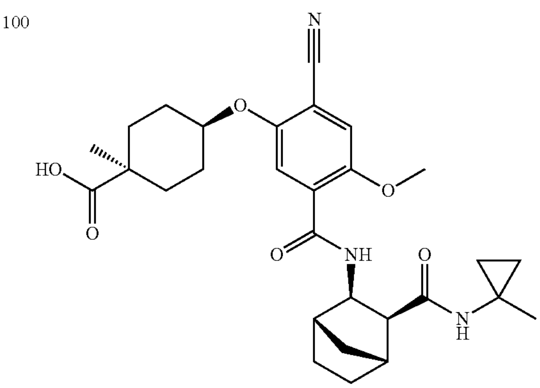 | calcd for $C_{29}H_{38}N_3O_6$: 524.2756 found: 524.2760 | SFC-D |
| 101 | 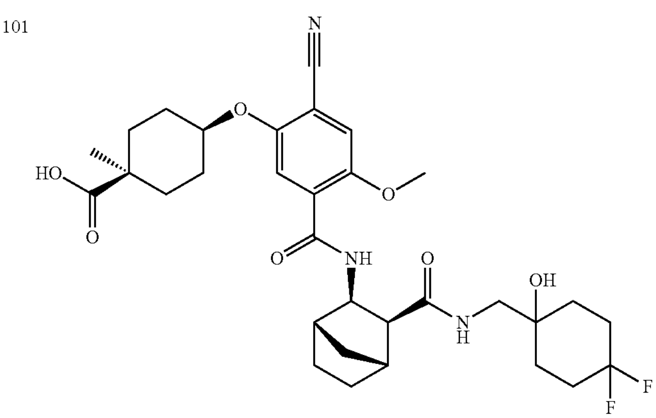 | calcd for $C_{32}H_{42}F_2N_3O_7$: 618.2986 found: 618.2980 | SFC-F |

TABLE 8-continued

| Ex No. | Structure | HRMS (ESI) m/z [M + H]+ | Purification Method |
|---|---|---|---|
| 102 | 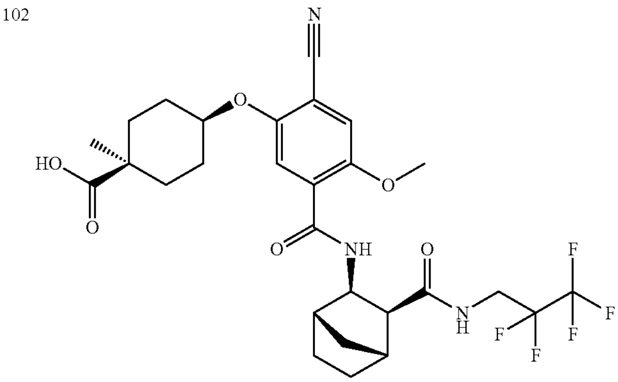 | calcd for $C_{28}H_{33}F_5N_3O_6$: 602.2284 found: 602.2280 | SFC-A |
| 103 | 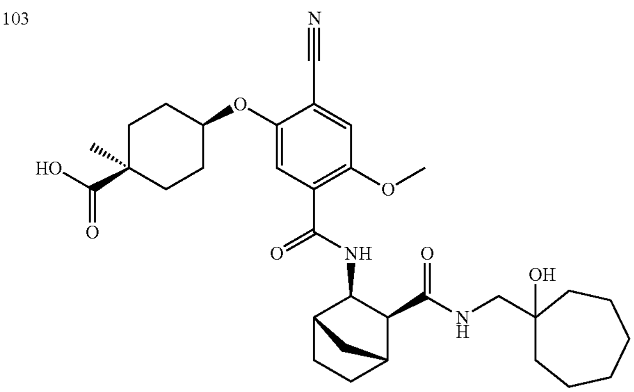 | calcd for $C_{33}H_{46}N_3O_7$: 596.3330 found: 596.3324 | SFC-F |
| 104 | 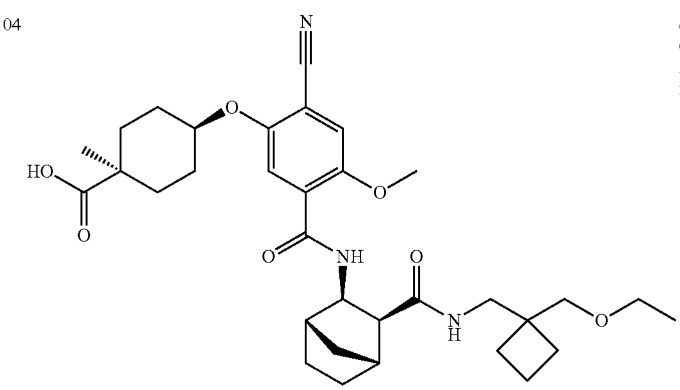 | calcd for $C_{33}H_{46}N_3O_7$: 596.3330 found: 596.3334 | SFC-F |
| 105 | 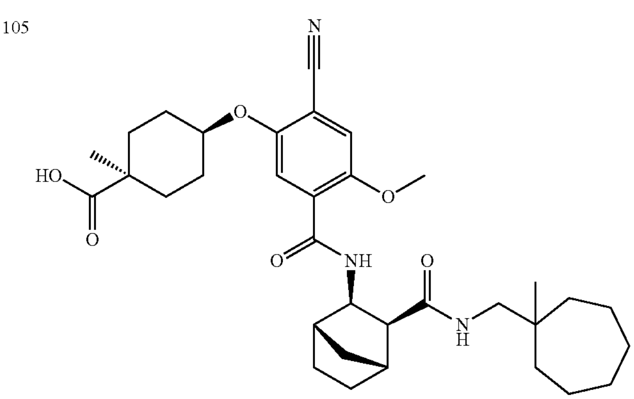 | calcd for $C_{34}H_{43}N_3O_6$: 594.3538 found: 594.3538 | SFC-F |

TABLE 8-continued

| Ex No. | Structure | HRMS (ESI) m/z [M + H]+ | Purification Method |
|---|---|---|---|
| 106 | 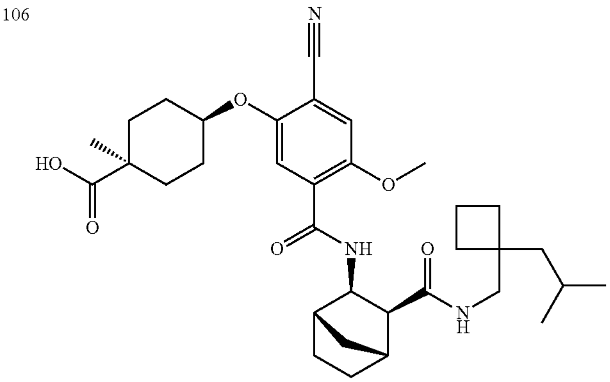 | calcd for $C_{34}H_{48}N_3O_6$: 594.3538 found: 594.3538 | SFC-A |
| 107 | 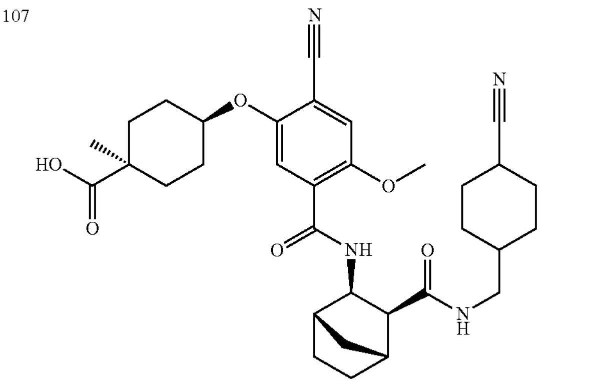 | calcd for $C_{33}H_{43}N_4O_6$: 591.3176 found: 591.3178 | SFC-A |
| 108 | 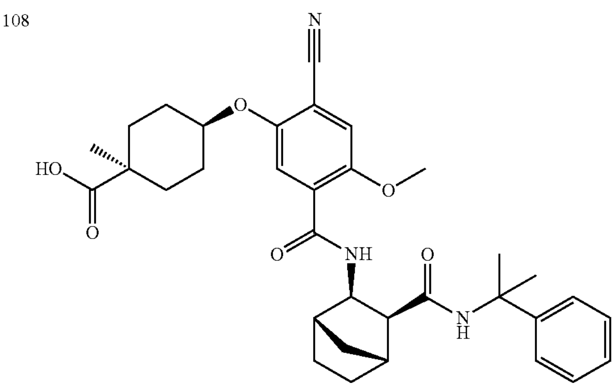 | calcd for $C_{34}H_{42}N_3O_6$: 588.3068 found: 588.3082 | SFC-F |
| 109 | 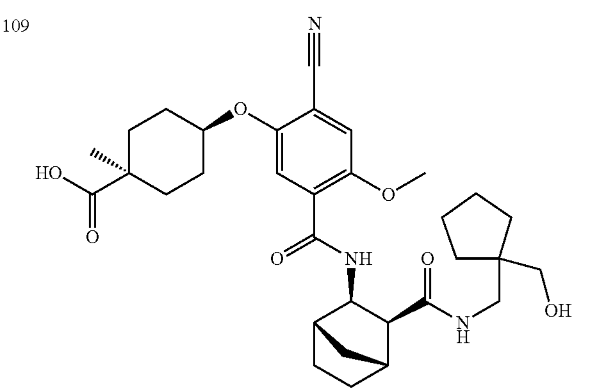 | calcd for $C_{32}H_{44}N_3O_7$: 582.3174 found: 582.3170 | SFC-F |

TABLE 8-continued

| Ex No. | Structure | HRMS (ESI) m/z [M + H]+ | Purification Method |
|---|---|---|---|
| 110 | 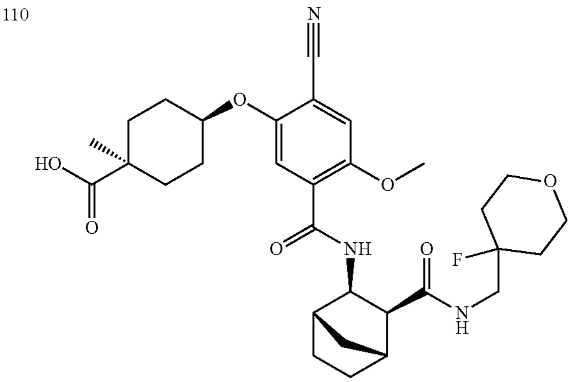 | calcd for C₃₁H₄₁FN₃O₇: 586.2922 found: 586.2920 | SFC-A |
| 111 | 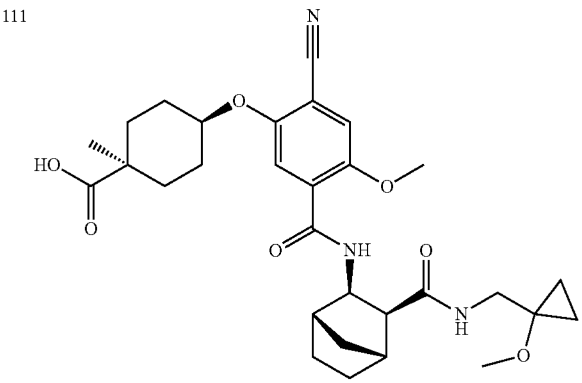 | calcd for C₃₀H₄₀N₃O₇: 554.2860 found: 554.2864 | SFC-E |
| 112 | 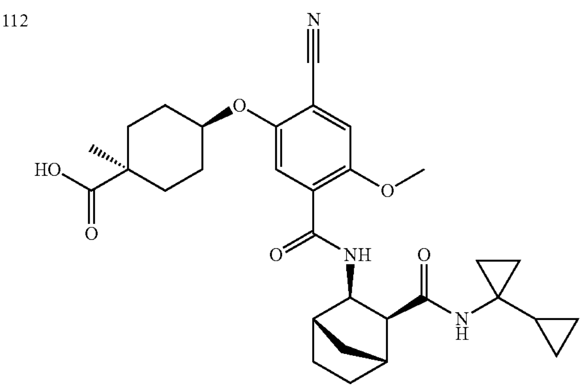 | calcd for C₃₁H₄₀N₃O₆: 550.2912 found: 550.2912 | SFC-F |
| 113 | 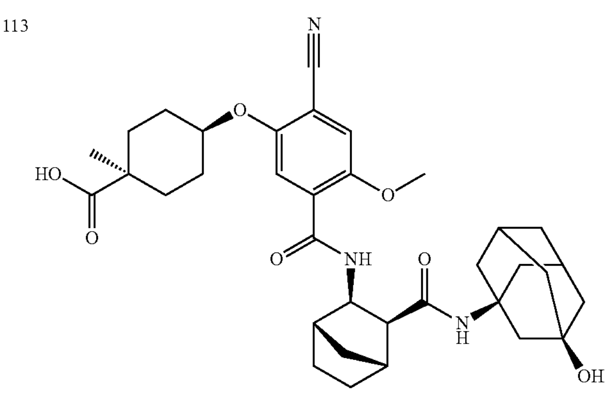 | calcd for C₃₅H₄₆N₃O₇: 620.3330 found: 620.3328 | SFC-A |

TABLE 8-continued

| Ex No. | Structure | HRMS (ESI) m/z [M + H]+ | Purification Method |
|---|---|---|---|
| 114 | 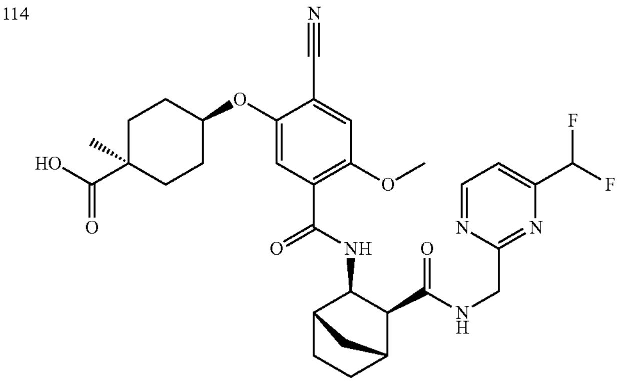 | calcd for $C_{31}H_{36}F_2N_5O_6$: 612.2628 found: 612.2616 | SFC-A |
| 115 | 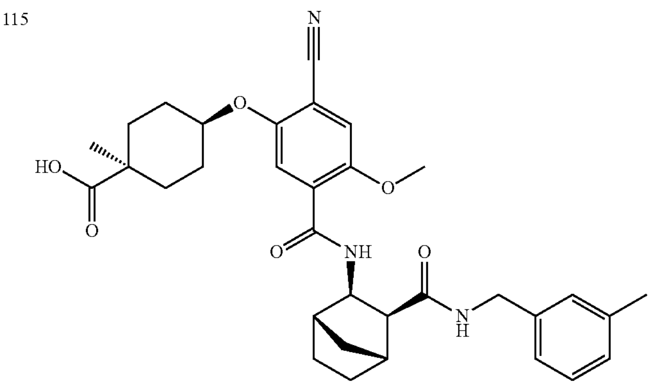 | calcd for $C_{33}H_{40}N_3O_6$: 574.2912 found: 574.2914 | Method PrepBasic-1 |

Example 116. (1S,4s)-4-(2-Cyano-4-methoxy-5-(((1S,2R,3S,4R)-3-(propylcarbamoyl)bicyclo[2.2.1]heptan-2-yl)carbamoyl)phenoxy)-1-methylcyclohexane-1-carboxylic acid

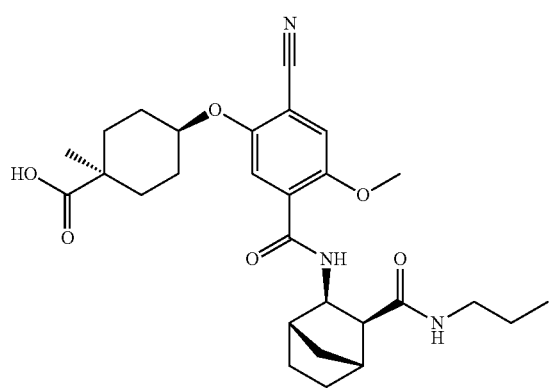 [SMILES: CCCNC(=O)[C@H]1[C@@H]2CC[C@@H](C2)[C@H]1NC(=O)c1cc(O[C@H]2CC[C@@](C)(C(=O)O)CC2)c(C#N)cc1OC]

Intermediate 68 (2.6 g, 5.5 mmol) and N-hydroxysuccinimide (636 mg, 5.5 mmol) were added to DCM (20 mL) at rt. The mixture was stirred for 30 min and cooled to 5° C. DCC (1.1 g, 5.5 mmol) was added slowly and the reaction was stirred at 5° C. for 1 h. The solvent was removed in vacuo and the residue was purified by preparative TLC with MeOH/DCM (20:1) to give 1.8 g of (1S,4s)-4-(2-cyano-5-(((1S,2R,3S,4R)-3-(((2,5-dioxopyrrolidin-1-yl)oxy)carbonyl)bicyclo[2.2.1]heptan-2-yl)carbamoyl)-4-methoxyphenoxy)-1-methylcyclohexane-1-carboxylic acid (74% purity, 42%) as a white solid.

The resulting solid (57 mg, 0.10 mmol), propan-1-amine (6.5 mg, 0.11 mmol), TEA (20.2 mg, 0.20 mmol) and DCM (2 mL) were added to a 40 mL vial. The mixture was stirred at room temperature for 16 h. The solvent was removed in vacuo and the residue was directly purified by Method PrepBasic-I to give the title compound (4.2 mg, 10%) as a solid. HRMS m/z [M+H]+ calcd for $C_{28}H_{38}N_3O_6$: 512.2756 found: 512.2754.

The examples included in Table 9 below were synthesized according to the procedure of Example 116 using the appropriate amine (as the free base or as the corresponding HCl salt) instead of propan-1-amine. The amine is commercially available if not otherwise stated.

TABLE 9

| Ex No. | Structure | HRMS (ESI) m/z [M + H]⁺ | Purification Method |
|---|---|---|---|
| 117 | 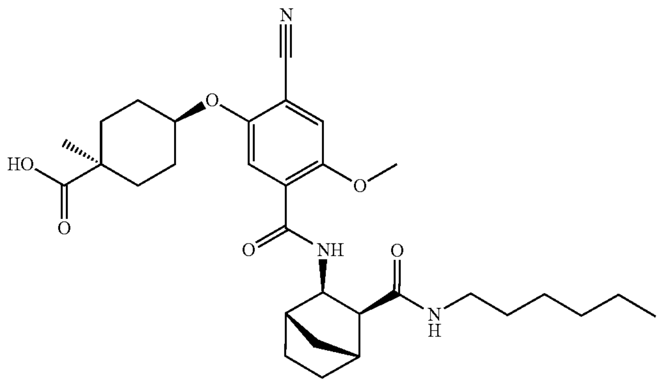 [SMILES: CCCCCCNC(=O)[C@H]1[C@@H]2CC[C@@H](C2)[C@H]1NC(=O)c1cc(O[C@H]2CC[C@@](C)(C(=O)O)CC2)c(C#N)cc1OC] | calcd for C$_{31}$H$_{44}$N$_3$O$_6$: 554.3224 found: 554.3206 | Method PrepBasic-I |
| 118 | 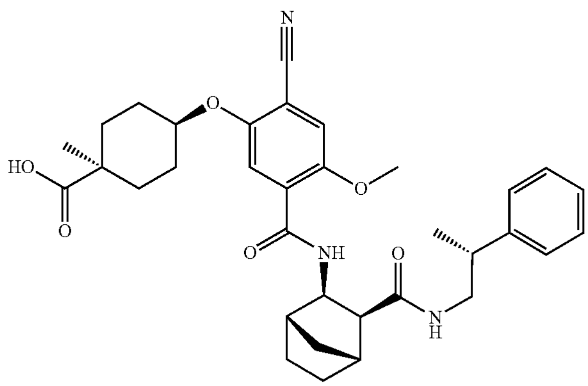 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC[C@H](C)c1ccccc1] | calcd for C$_{34}$H$_{42}$N$_3$O$_6$: 588.3068 found: 588.3056 | Method PrepBasic-Q |
| 119 | 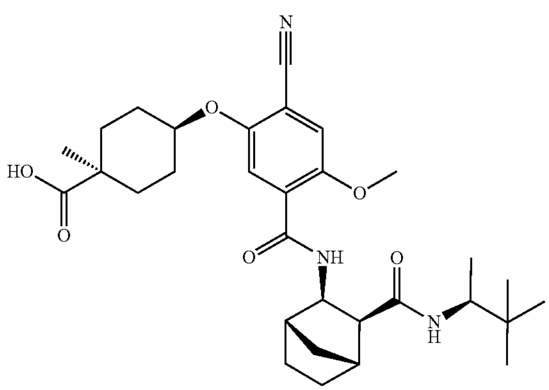 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)N[C@@H](C)C(C)(C)C] | calcd for C$_{31}$H$_{44}$N$_3$O$_6$: 554.3224 found: 554.3234 | Method PrepBasic-Q |
| 120 | 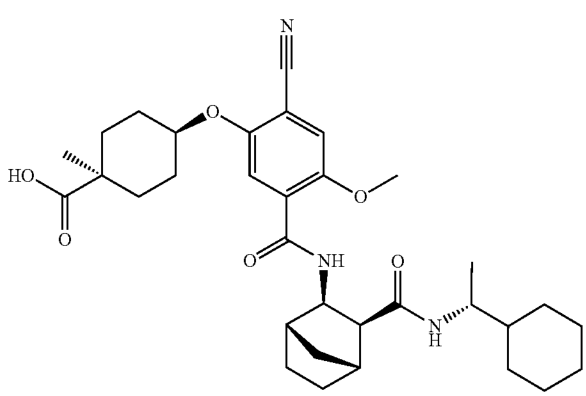 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)N[C@H](C)C1CCCCC1] | calcd for C$_{33}$H$_{46}$N$_3$O$_6$: 580.3380 found: 580.3386 | Method PrepBasic-R |

TABLE 9-continued

| Ex No. | Structure | HRMS (ESI) m/z [M + H]+ | Purification Method |
|---|---|---|---|
| 121 | 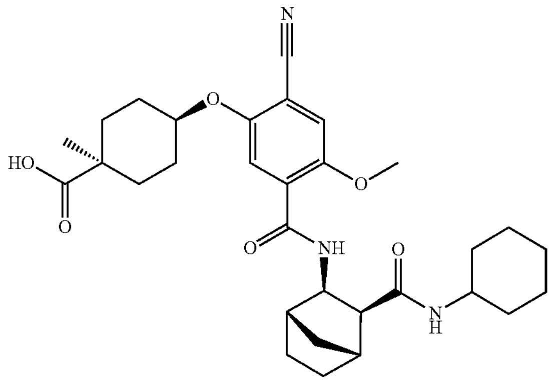 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC1CCCCC1] | calcd for $C_{31}H_{42}N_3O_6$: 552.3068 found: 552.3060 | Method PrepBasic-P |
| 122 | 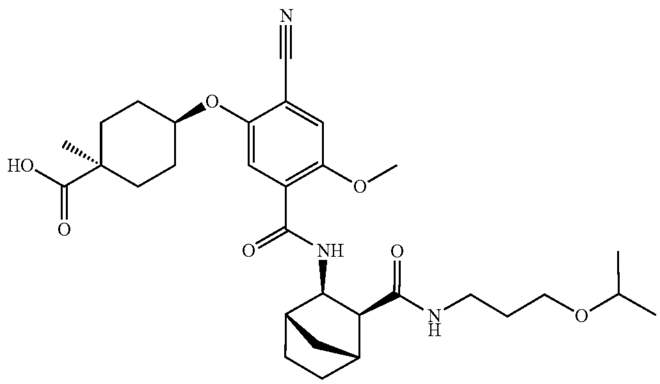 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCCCOC(C)C] | calcd for $C_{31}H_{44}N_3O_7$: 570.3174 found: 570.3178 | Method PrepBasic-W |
| 123 | 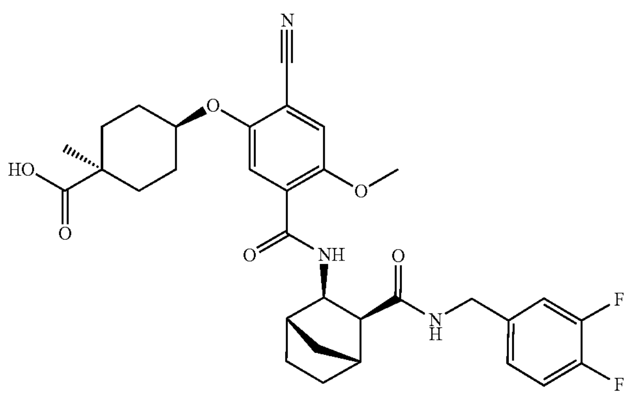 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCc1ccc(F)c(F)c1] | calcd for $C_{32}H_{36}F_2N_3O_6$: 596.2566 found: 596.2572 | Method FlashBasic-A |
| 124 | 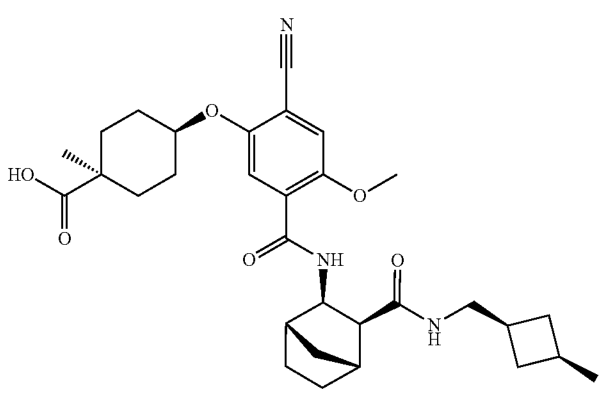 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC[C@H]1C[C@@H](C)C1] | calcd for $C_{31}H_{42}N_3O_6$: 552.3068 found: 552.3078 | Method PrepBasic-Y Prepared from amine Intermediate 99 |

TABLE 9-continued

| Ex No. | Structure | HRMS (ESI) m/z [M + H]+ | Purification Method |
|---|---|---|---|
| 125 | 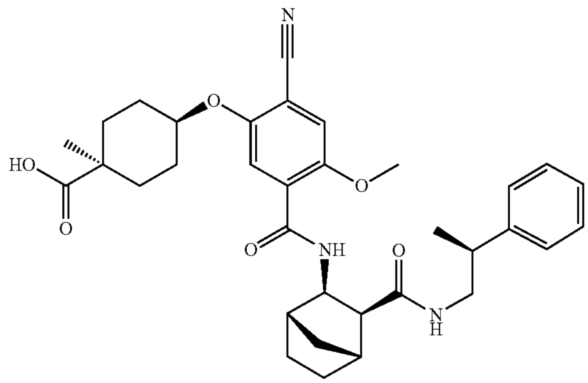 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC[C@@H](C)c1ccccc1] | calcd for $C_{34}H_{42}N_3O_6$: 588.3068 found: 588.3060 | Method PrepBasic-X |
| 126 | 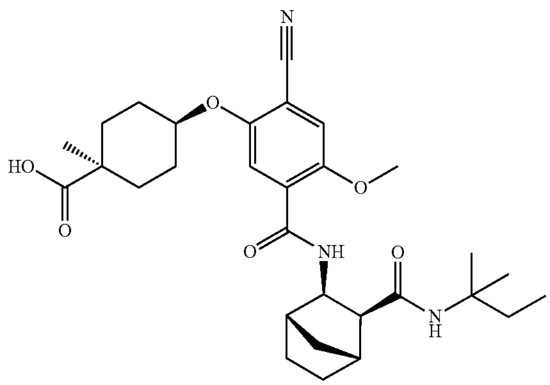 [SMILES: CCC(C)(C)NC(=O)[C@H]1[C@@H]2CC[C@@H](C2)[C@H]1NC(=O)c1cc(O[C@H]2CC[C@@](C)(C(=O)O)CC2)c(C#N)cc1OC] | calcd for $C_{30}H_{42}N_3O_6$: 540.3068 found: 540.3068 | Method PrepBasic-X |
| 127 | 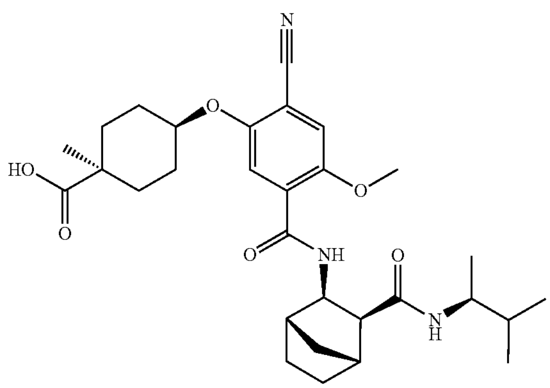 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)N[C@@H](C)C(C)C] | calcd for $C_{30}H_{42}N_3O_6$: 540.3068 found: 540.3054 | Method FlashBasic-A |
| 128 | 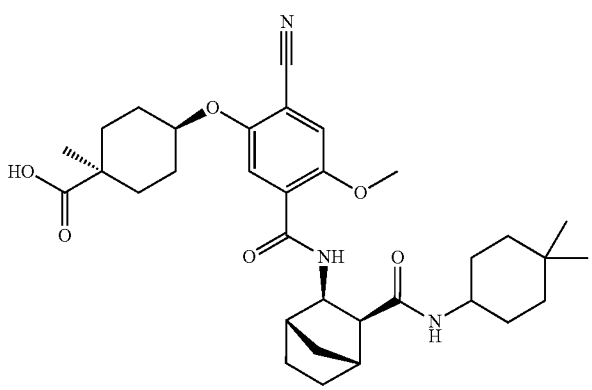 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC1CCC(C)(C)CC1] | calcd for $C_{33}H_{46}N_3O_6$: 580.3380 found: 580.3382 | Method PrepBasic-S |

TABLE 9-continued

| Ex No. | Structure | HRMS (ESI) m/z [M + H]+ | Purification Method |
|---|---|---|---|
| 129 | 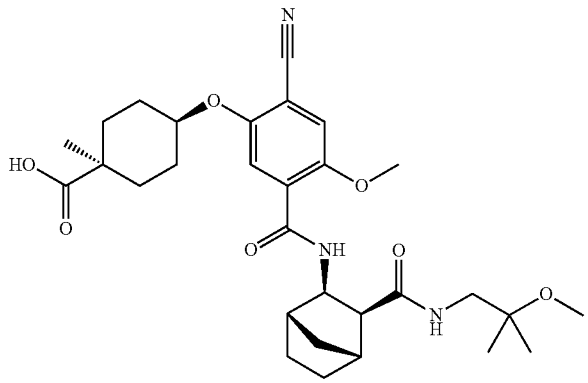 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC(C)(C)OC] | calcd for $C_{30}H_{42}N_3O_7$: 556.3016 found: 556.3014 | Method PrepBasic-O |
| 130 | 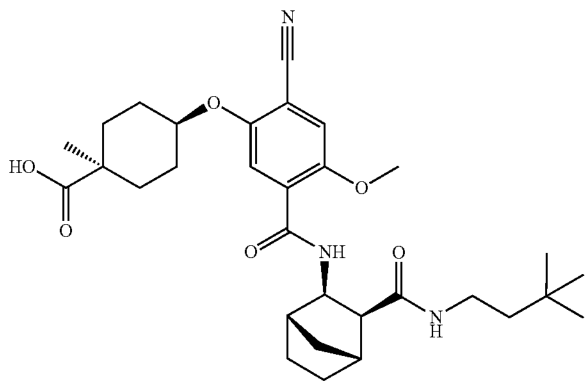 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCCC(C)(C)C] | calcd for $C_{31}H_{44}N_3O_6$: 554.3224 found: 554.3238 | Method PrepBasic-O |
| 131 | 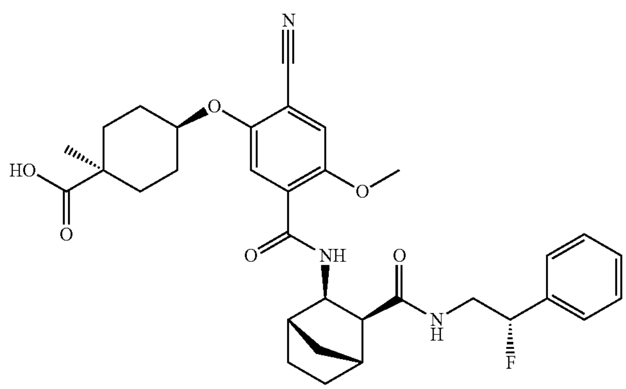 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC[C@@H](F)c1ccccc1] | calcd for $C_{33}H_{39}FN_3O_6$: 592.2818 found: 592.2826 | Method PrepBasic-U |
| 132 | 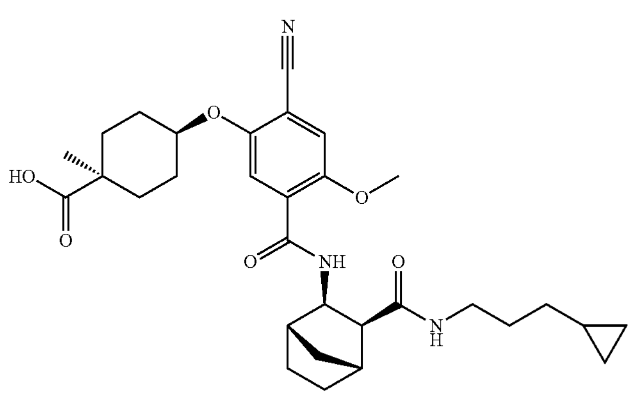 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCCCC1CC1] | calcd for $C_{31}H_{42}N_3O_6$: 552.3068 found: 552.3070 | Method FlashBasic-A |

TABLE 9-continued

| Ex No. | Structure | HRMS (ESI) m/z [M + H]+ | Purification Method |
|---|---|---|---|
| 133 | 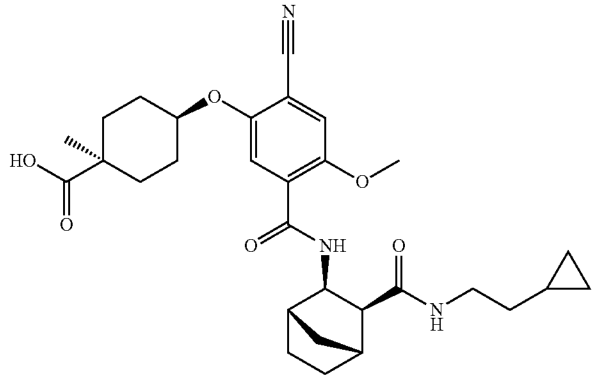 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCCC1CC1] | calcd for $C_{30}H_{40}N_3O_6$: 538.2912 found: 538.2908 | Method PrepBasic-O |
| 134 | 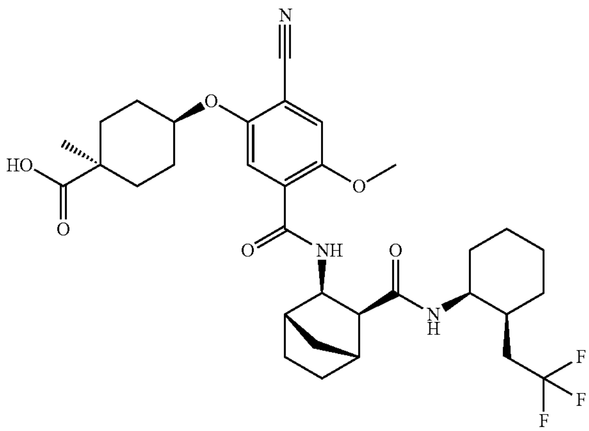 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)N[C@H]1CCCC[C@H]1CC(F)(F)F] | calcd for $C_{33}H_{43}F_3N_3O_6$: 634.3098 found: 634.3096 | Method PrepBasic-J |
| 135 | 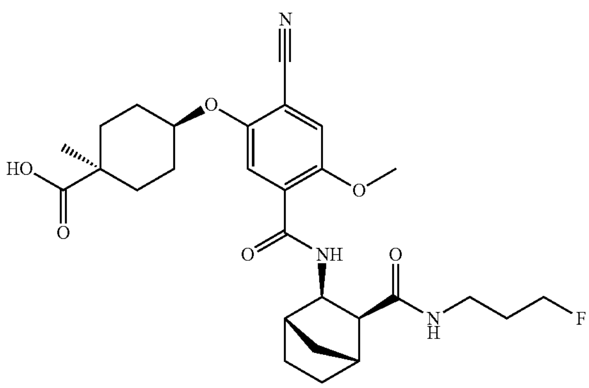 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCCCF] | calcd for $C_{28}H_{37}FN_3O_6$: 530.2660 found: 530.2660 | Method PrepBasic-I |
| 136 | 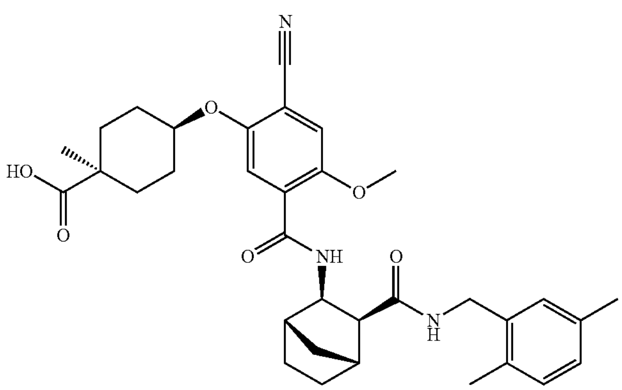 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCc1cc(C)ccc1C] | calcd for $C_{34}H_{42}N_3O_6$: 588.3068 found: 588.3066 | Method PrepBasic-I |

TABLE 9-continued

| Ex No. | Structure | HRMS (ESI) m/z [M + H]+ | Purification Method |
|---|---|---|---|
| 137 | 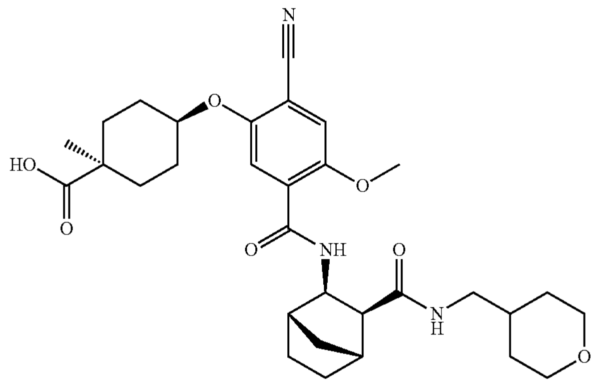 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC1CCOCC1] | calcd for $C_{31}H_{42}N_3O_7$: 568.3016 found: 568.3022 | Method PrepBasic-I |
| 138 | 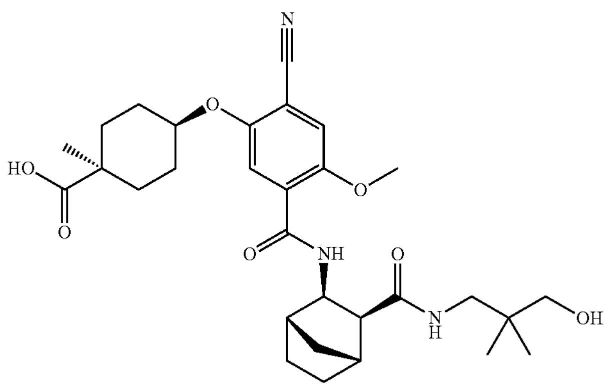 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NCC(C)(C)CO] | calcd for $C_{30}H_{42}N_3O_7$: 556.3016 found: 556.3020 | Method PrepBasic-I |
| 139 | 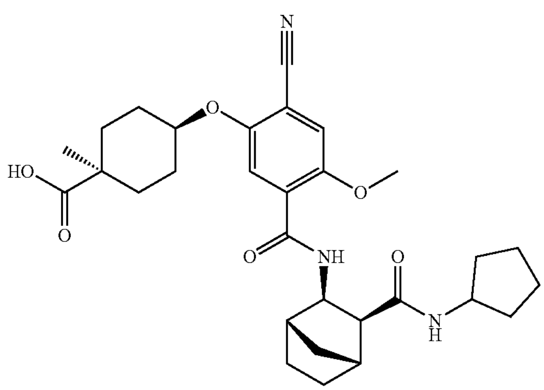 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC1CCCC1] | calcd for $C_{30}H_{40}N_3O_6$: 538.2912 found: 538.2910 | Method PrepBasic-I |
| 140 | 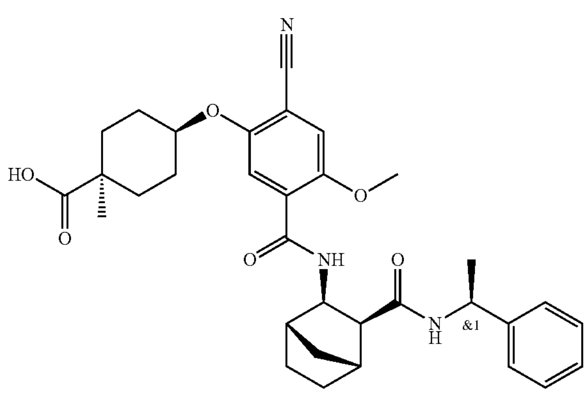 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)N[C@@H](C)c1ccccc1] | calcd for $C_{33}H_{40}N_3O_6$: 574.2912 found: 574.2908 | Method PrepBasic-X |

Example 141. (1S,4s)-4-(5-(((1S,2R,3S,4R)-3-(Bicyclo[1.1.1]pentan-1-ylcarbamoyl)-bicyclo[2.2.1]heptan-2-yl)carbamoyl)-2-cyano-4-methoxyphenoxy)-1-methylcyclohexane-1-carboxylic acid

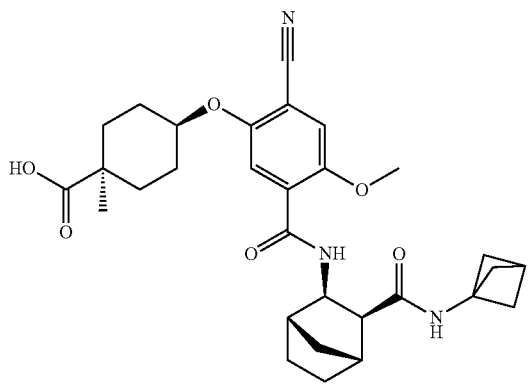 [SMILES: COc1cc(C#N)c(O[C@H]2CC[C@@](C)(C(=O)O)CC2)cc1C(=O)N[C@@H]1[C@H]2CC[C@H](C2)[C@@H]1C(=O)NC12CC(C1)C2]

Intermediate 68 (40 mg, 0.09 mmol) was dissolved in DCM (4.2 mL). DIPEA (28 µL, 0.16 mmol) was added followed by HATU (97 mg, 0.26 mmol) and bicyclo[1.1.1]pentan-1-amine hydrochloride (10 mg, 0.09 mmol). After stirring at rt for 2 h, the reaction was quenched with $Na_2CO_3$ (sat) and the biphasic mixture stirred for 2 h. The organic layer was separated and washed with DCM twice. The combined organic phase was passed through a phase separator and the solvent removed under reduced pressure. The crude material was purified by Method PrepBasic-A using a gradient of 35-75% to afford the title compound (10.5 mg, 23%). HRMS (ESI): m/z [M+H]$^+$ calcd for $C_{30}H_{38}N_3O_6$: 536.2761, found: 536.2786.

Example 142. (1s,4s)-4-(2-Fluoro-4-methoxy-5-((2-(neopentylcarbamoyl)phenyl)-carbamoyl)phenoxy)-1-methylcyclohexane-1-carboxylic acid

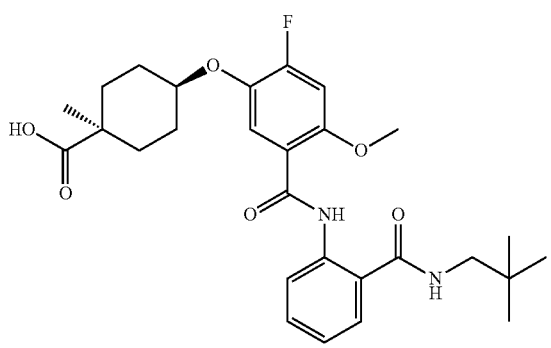 [SMILES: COc1cc(F)c(O[C@H]2CC[C@@](C)(C(=O)O)CC2)cc1C(=O)Nc1ccccc1C(=O)NCC(C)(C)C]

TFA (0.34 mL, 4.2 mmol) was added to a solution of Intermediate 74 (50.4 mg, 0.09 mmol) in DCM (1.8 mL) and the mixture was stirred for 2 h. The solvent was removed under reduced pressure. The crude material was purified by Method PrepAcidic-F using a gradient of 35-75% to afford the title compound (29.6 mg, 65%) as a white solid. HRMS (ESI) m/z [M+H]$^+$ calcd for $C_{28}H_{36}FN_2O_6$: 515.2552 found: 515.2558.

Example 143. (1s,4s)-4-(2-Fluoro-4-methoxy-5-((2-(((1-methylcyclobutyl)methyl)-carbamoyl)phenyl)carbamoyl)phenoxy)-1-methylcyclohexane-1-carboxylic acid

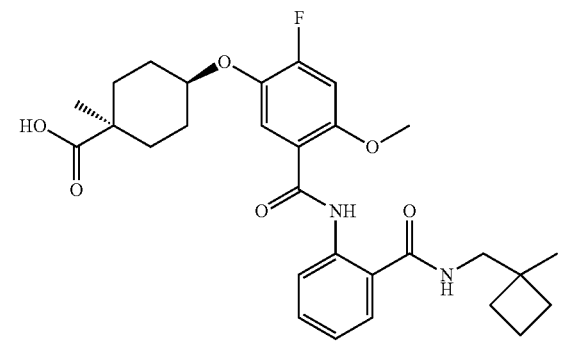 [SMILES: COc1cc(F)c(O[C@H]2CC[C@@](C)(C(=O)O)CC2)cc1C(=O)Nc1ccccc1C(=O)NCC1(C)CCC1]

Step A. Intermediate 402: Tert-Butyl (1s,4s)-4-(2-fluoro-4-methoxy-5-((2-(((1-methylcyclobutyl)methyl)carbamoyl)phenyl)carbamoyl)phenoxy)-1-methylcyclohexane-1-carboxylate

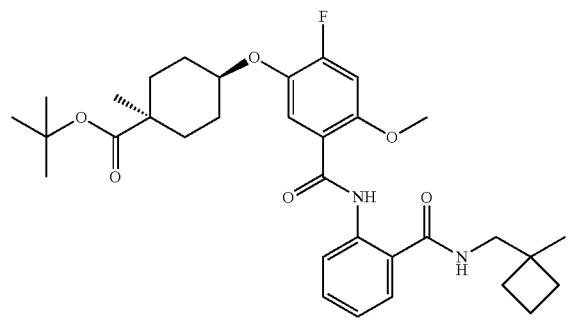 [SMILES: COc1cc(F)c(O[C@H]2CC[C@@](C)(C(=O)OC(C)(C)C)CC2)cc1C(=O)Nc1ccccc1C(=O)NCC1(C)CCC1]

DIPEA (68 µL, 0.39 mmol) was added to a solution of Intermediate 73 (50 mg, 0.13 mmol) in DCM (0.9 mL). HATU (149 mg, 0.39 mmol) was added followed by 2-amino-N-[(1-methylcyclobutyl)methyl]benzamide (34.2 mg, 0.16 mmol) and the reaction mixture stirred at rt for 5 h. $Na_2CO_3$ (sat) was added and the biphasic mixture stirred for 10 min before the two layers were separated. The aq phase was washed with DCM. The combined organic phase was passed through a phase separator and the solvent removed under reduced pressure to afford the title compound. The product was used in the next step without further purification. MS (ESI): m/z [M+H]$^+$ 583.3.

Step B. (1s,4s)-4-(2-Fluoro-4-methoxy-5-((2-(((1-methylcyclobutyl)methyl)carbamoyl)-phenyl)carbamoyl)phenoxy)-1-methylcyclohexane-1-carboxylic acid Intermediate 402 was dissolved in DCM (1.8 mL) and TFA (0.48 mL, 6.3 mmol) was added. The mixture was stirred for 2 h after which the solvent was removed under reduced pressure. The crude material was purified by Method PrepAcidic-F using a gradient of 35-75% to afford the title compound (57.4 mg, 84%) as a white solid. HRMS (ESI) m/z [M+H]+ calcd for $C_{29}H_{36}FN_2O_6$: 527.2552 found: 527.2564.

Example 144. (1S,4s)-4-(5-(((1S,2R,3S,4R)-3-(((R*)-3-Ethylpentan-2-yl)carbamoyl)bicyclo-[2.2.1]heptan-2-yl)carbamoyl)-2-fluoro-4-methoxyphenoxy)-1-methylcyclohexane-1-carboxylic acid. Isomer 1

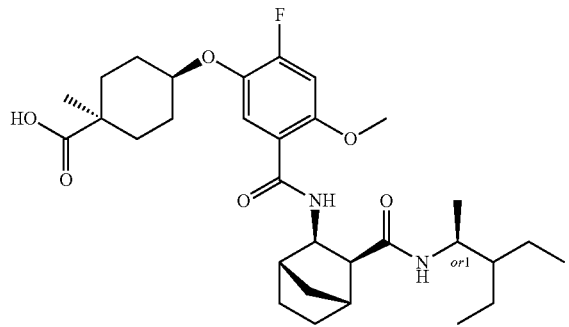 [SMILES: CCC(CC)[C@H](C)NC(=O)[C@H]1[C@@H]2CC[C@@H](C2)[C@H]1NC(=O)c1cc(O[C@H]2CC[C@@](C)(C(=O)O)CC2)c(F)cc1OC]

TFA (0.4 mL, 5.2 mmol) was added to a solution of Intermediate 78 (67 mg, 0.11 mmol) in DCM (1.8 mL) and the mixture was stirred at rt for 2 h. The solvent was removed under reduced pressure to afford the title compound (69.4 mg, 86%). HRMS (ESI) m/z [M+H]+ calcd for $C_{31}H_{46}FN_2O_6$: 561.3334 found: 561.3334.

Example 145. (1S,4s)-4-(5-(((1S,2R,3S,4R)-3-(((R*)-3-Ethylpentan-2-yl)carbamoyl)bicyclo[2.2.1]heptan-2-yl)carbamoyl)-2-fluoro-4-methoxyphenoxy)-1-methylcyclohexane-1-carboxylic acid. Isomer 2

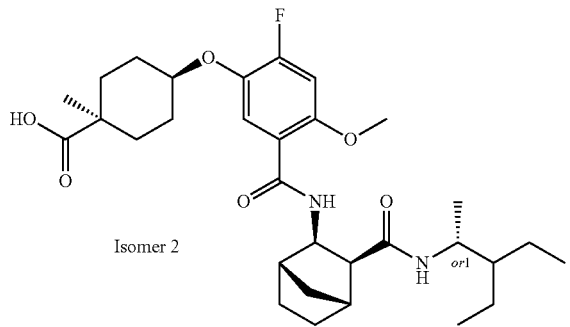 [SMILES: CCC(CC)[C@@H](C)NC(=O)[C@H]1[C@@H]2CC[C@@H](C2)[C@H]1NC(=O)c1cc(O[C@H]2CC[C@@](C)(C(=O)O)CC2)c(F)cc1OC]

TFA (0.3 mL, 4.3 mmol) was added to a solution of Intermediate 79 (55 mg, 0.09 mmol) in DCM (1.8 mL) and the mixture stirred at rt for 2 h. The solvent was removed under reduced pressure and the crude compound was purified by Method PrepAcidic-F using a gradient of 35-75% to afford the title compound (45.7 mg, 91%). HRMS (ESI) m/z [M+H]+ calcd for $C_{31}H_{46}FN_2O_6$: 561.3334 found: 561.3332.

Example 146. (1S,4s)-4-(2-Fluoro-5-(((1S,2R,3S,4R)-3-(((4-fluorotetrahydro-2H-pyran-4-yl)methyl)carbamoyl)bicyclo[2.2.1]heptan-2-yl)carbamoyl)-4-methoxyphenoxy)-1-methylcyclohexane-1-carboxylic acid Example 147. (1R,2S,3R,4S)-3-(5-(((1s,4S)-4-Carbamoyl-4-methylcyclohexyl)oxy)-4-fluoro-2-methoxybenzamido)-N-((4-fluorotetrahydro-2H-pyran-4-yl)methyl)bicyclo-[2.2.1]heptane-2-carboxamide Step A. Intermediate 403: (1R,2S,3R,4S)-3-(5-(((1s,4S)-4-Carboxy-4-methylcyclohexyl)oxy)-4-fluoro-2-methoxybenzamido)bicyclo[2.2.1]heptane-2-carboxylic acid

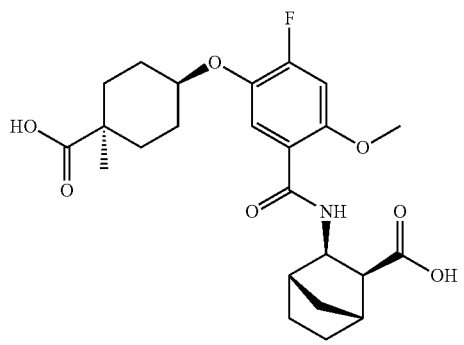 [SMILES: COc1cc(F)c(O[C@H]2CC[C@@](C)(C(=O)O)CC2)cc1C(=O)N[C@@H]1[C@H]2CC[C@H](C2)[C@@H]1C(=O)O]

TFA (0.4 mL, 5.2 mmol) was added to a solution of Intermediate 75 (56 mg, 0.11 mmol) in DCM (0.7 mL) and the mixture stirred at rt for 2 h. The solvent was removed under reduced pressure to afford the title compound as a 1:1 TFA adduct (66 mg). The product was used in the next step without further purification. MS (ESI): m/z [M+H]+ 464.4.

Step B. (1S,4s)-4-(2-Fluoro-5-(((1S,2R,3S,4R)-3-(((4-fluorotetrahydro-2H-pyran-4-yl)methyl)carbamoyl)bicyclo[2.2.1]heptan-2-yl)carbamoyl)-4-methoxyphenoxy)-1-methylcyclohexane-1-carboxylic acid (1R,2S,3R,4S)-3-(5-(((1s,4S)-4-Carbamoyl-4-methylcyclohexyl)oxy)-4-fluoro-2-methoxybenzamido)-N-((4-fluorotetrahydro-2H-pyran-4-yl)methyl)bicyclo[2.2.1]heptane-2-carboxamide Intermediate 403 (25 mg, 0.05 mmol) was dissolved in DCM. DIPEA (28 µL, 0.16 mmol) was added followed by HATU (61.5 mg, 0.16 mmol) and (4-fluorotetrahydropyran-4-yl)methanamine hydrochloride (9.15 mg, 0.05 mmol). The reaction mixture was stirred at rt for 2 h. Na$_2$CO$_3$ (sat) was added and the biphasic mixture stirred for 10 min before the two layers were separated. The aq phase was washed with DCM. The combined organic phase was passed through a phase separator and the solvent removed under reduced pressure. The crude material was purified by Method PrepBasic-D using a gradient of 15-55% to afford a first fraction containing Example 146 and a second fraction containing Example 147. The first fraction was further purified by Method PrepAcidic-E using a gradient of 5-95% to afford Example 146 (5.5 mg, 17%). HRMS (ESI) m/z [M+H]$^+$ calcd for C$_{30}$H$_{41}$F$_2$N$_2$O7: 579.2876 found: 579.2872.

The second fraction was further purified by Method PrepAcidic-E using a gradient of 5-95% to afford Example 147 (4 mg, 13%). HRMS (ESI) m/z [M+H]$^+$ calcd for C$_{30}$H$_{42}$F$_2$N$_3$O$_6$: 578.3036 found: 578.3044.

Example 148: (1S,3s)-3-(2-cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclobutane-1-carboxylic acid

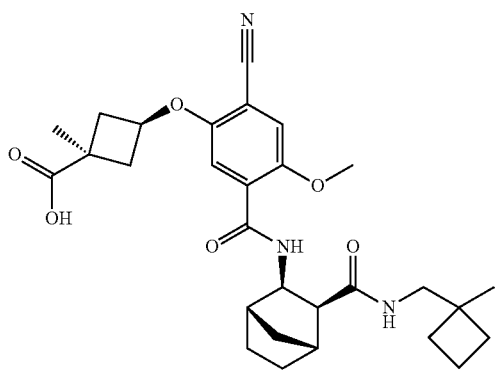 [SMILES: COc1cc(C#N)c(O[C@H]2C[C@@](C)(C(=O)O)C2)cc1C(=O)N[C@@H]1[C@H]2CC[C@H](C2)[C@@H]1C(=O)NCC1(C)CCC1]

Intermediate 80 (17.5 mg, 0.03 mmol) was dissolved in MeOH (0.7 mL) and hydrogenated in a H-cube® reactor at 1 mL/min, rt, Full H2, Pd/C (CatCart 30 mm). The solvent was removed under reduced pressure. The crude material was purified by Method PrepAcidic-H using a gradient of 15-55% to afford the title compound (2.1 mg, 12%). HRMS (ESI) m/z [M+H]$^+$ calcd for C$_{29}$H$_{38}$N$_3$O$_6$: 524.2756 found: 524.2744.

Example 149: (1S,3s)-3-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclobutane-1-carboxylic acid

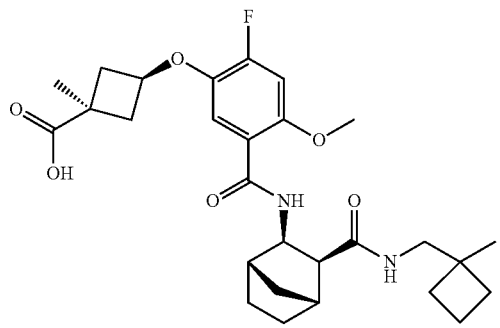 [SMILES: COc1cc(F)c(O[C@H]2C[C@@](C)(C(=O)O)C2)cc1C(=O)N[C@@H]1[C@H]2CC[C@H](C2)[C@@H]1C(=O)NCC1(C)CCC1]

Intermediate 83 (17.7 mg, 0.03 mmol) was dissolved in MeOH (0.7 mL) and hydrogenated in a H-cube® reactor at 1 mL/min, rt, Full H2, Pd/C (CatCart 30 mm). The solvent was removed under reduced pressure. The crude material was purified by Method PrepAcidic-H using a gradient of 25-65% to afford the title compound (14.8 mg, 83%). HRMS (ESI) m/z [M+H]$^+$ calcd for C$_{28}$H$_{38}$FN$_2$O$_6$: 517.2708 found: 517.2738.

Example 150: (1s,4s)-4-(2-Fluoro-4-methoxy-5-((4-(((1-methylcyclobutyl)methyl)carbamoyl)pyridin-3-yl)carbamoyl)phenoxy)-1-methylcyclohexane-1-carboxylic acid

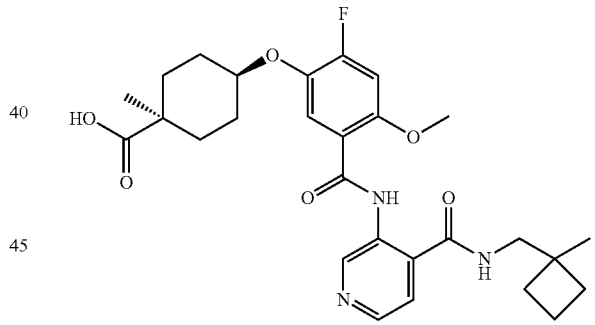

Pd(OH)$_2$/C (20 wt %, 12.1 mg, 0.02 mmol) was added to a solution of Intermediate 86 (115 mg, 0.17 mmol) in THF:MeOH (2:1, 5.7 mL). The reaction suspension was stirred at rt under an atmosphere of hydrogen (2 atm). The reaction mixture was filtered through a pad of Celite® and the solvent removed under reduced pressure. The crude material was purified by Method PrepAcidic-E using a gradient of 5-95% to afford the title compound (50.7 mg, 56%). HRMS (ESI) m/z [M+H]$^+$ calcd for C$_{28}$H$_{35}$FN$_3$O$_6$: 528.2504 found: 528.2512. $^1$H NMR (600 MHz, DMSO-d6) δ 1.12 (d, 6H), 1.29 (td, 2H), 1.4-1.5 (m, 2H), 1.61 (ddd, 2H), 1.81 (ddddd, 2H), 1.89-1.99 (m, 4H), 2.08 (d, 2H), 3.33 (s, 2H), 4.01 (s, 3H), 4.24 (tt, 1H), 7.24 (d, 1H), 7.57 (d, 1H), 7.80 (d, 1H), 8.45 (d, 1H), 8.91 (t, 1H), 9.70 (s, 1H), 11.55 (s, 1H).

The examples included in Table 10 below were synthesized analogous to the procedure of Example 150 starting from the appropriate intermediate.

TABLE 10

| Ex No. | Structure | HRMS (ESI) m/z [M + H]+ | Purification Method | Starting Intermediate | Catalyst |
|---|---|---|---|---|---|
| 151 | 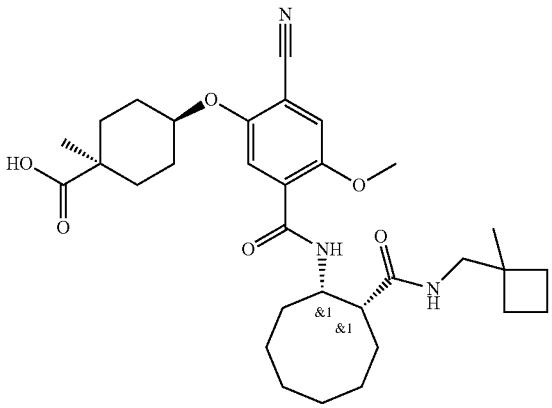 [SMILES: COc1cc(C#N)c(O[C@H]2CC[C@@](C)(C(=O)O)CC2)cc1C(=O)N[C@H]1CCCCCC[C@H]1C(=O)NCC1(C)CCC1] | calcd for C$_{31}$H$_{46}$FN$_2$O$_6$: 561.3334 found: 561.3344 | SFC-F | Int. 89 | Pd(OH)$_2$/C |
| 152 | 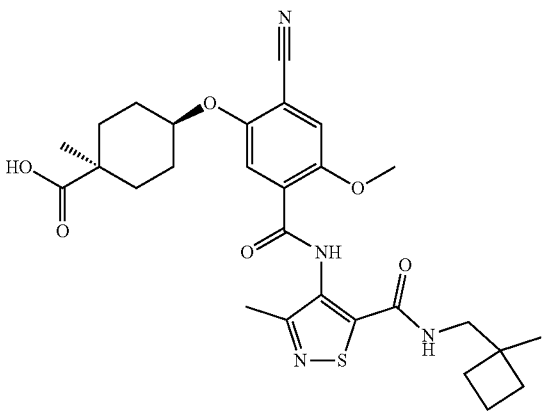 [SMILES: COc1cc(C#N)c(O[C@H]2CC[C@@](C)(C(=O)O)CC2)cc1C(=O)Nc1c(C)nsc1C(=O)NCC1(C)CCC1] | calcd for C$_{27}$H$_{35}$FN$_3$O$_6$S: 548.2224 found: 548.2242 | PrepAcidic-I Gradient: 5-95% | Int. 92 | Pd/C |
| 153 | 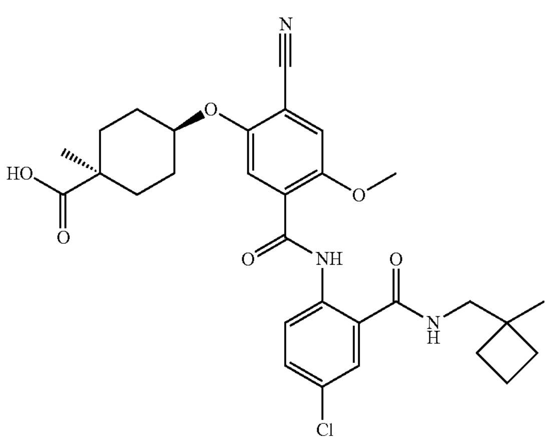 [SMILES: COc1cc(C#N)c(O[C@H]2CC[C@@](C)(C(=O)O)CC2)cc1C(=O)Nc1ccc(Cl)cc1C(=O)NCC1(C)CCC1] | calcd for C$_{29}$H$_{35}$ClFN$_2$O$_6$: 561.2162 found: 561.2178 | SFC-F | Int. 97 | Pd/C |

TABLE 10-continued

| Ex No. | Structure | HRMS (ESI) m/z [M + H]+ | Purification Method | Starting Intermediate | Catalyst |
|---|---|---|---|---|---|
| 154 | 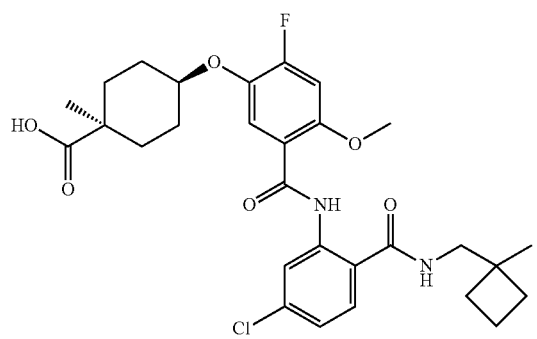 [SMILES: COc1cc(F)c(O[C@H]2CC[C@@](C)(C(=O)O)CC2)cc1C(=O)Nc1cc(Cl)ccc1C(=O)NCC1(C)CCC1] | calcd for C27H34FN2O6S: 533.2116 found: 533.2146 | PrepBasic-E Gradient 5-95% | Int. 98 | Pd/C |

Example 155: (1s,4s)-4-(5-((5-Chloro-2-(((1-methylcyclobutyl)methyl)carbamoyl)phenyl)carbamoyl)-2-fluoro-4-methoxyphenoxy)-1-methylcyclohexane-1-carboxylic acid Example 156: (1s,4s)-4-(2-Fluoro-4-methoxy-5-((2-methyl-6-(((1-methylcyclobutyl)methyl)carbamoyl)phenyl)carbamoyl)phenoxy)-1-methylcyclohexane-1-carboxylic acid

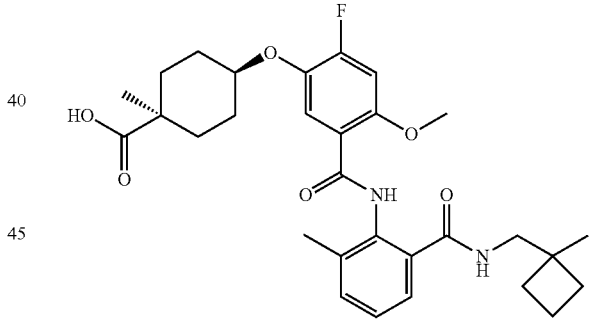

Hydrogenation of Intermediate 95 was performed analogous to the procedure described for the synthesis of Example 150 using THF:MeOH (9:1) as solvent. The crude material was purified by Method PrepAcidic-E using a gradient of 5-95% to afford the title compound (52.8 mg, 55%). HRMS (ESI) m/z [M+H]+ calcd for $C_{29}H_{35}ClFN_2O_6$: 561.2162 found: 561.2154. $^1$H NMR (600 MHz, DMSO-d6) δ 1.12 (d, 6H), 1.29 (td, 2H), 1.4-1.49 (m, 2H), 1.61 (ddd, 2H), 1.74-1.89 (m, 2H), 1.89-2 (m, 4H), 2.08 (d, 2H), 3.30 (s, 2H), 3.99 (s, 3H), 4.23 (tt, 1H), 7.22 (d, 1H), 7.29 (dd, 1H), 7.67 (d, 1H), 7.76 (d, 1H), 8.70 (d, 1H), 8.74 (t, 1H), 11.93 (s, 1H).

Intermediate 96 (91.9 mg, 0.13 mmol) was dissolved in THF:MeOH (1:1) and hydrogenated in a H-cube® reactor at 1 mL/min, 50° C., Full H2, Pd/C (CatCart 30 mm). The solvent was removed under reduced pressure. The crude material was purified by Method SFC-B to afford the title compound (53.8 mg, 73%). HRMS (ESI) m/z [M+H]+ calcd for $C_{30}H_{38}FN_2O_6$: 541.2708 found: 541.2722.

Example 157. (1s,4s)-4-(5-((5-Chloro-2-((cycloheptylmethyl)carbamoyl)phenyl)carbamoyl)-2-cyano-4-methoxyphenoxy)-1-methylcyclohexane-1-carboxylic acid

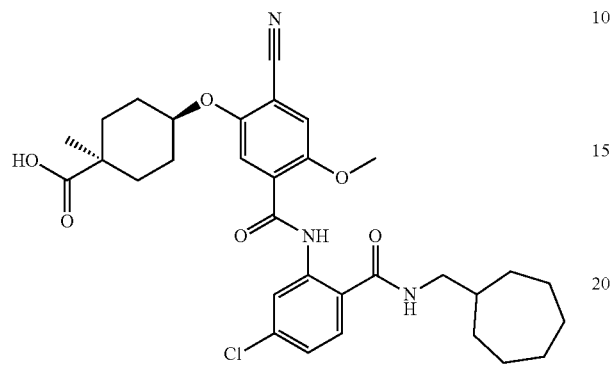

Step A. Intermediate 404: Naphthalen-1-ylmethyl (1s,4s)-4-(5-((5-chloro-2-((cycloheptyl-methyl)carbamoyl)phenyl)carbamoyl)-2-cyano-4-methoxyphenoxy)-1-methylcyclohexane-1-carboxylate

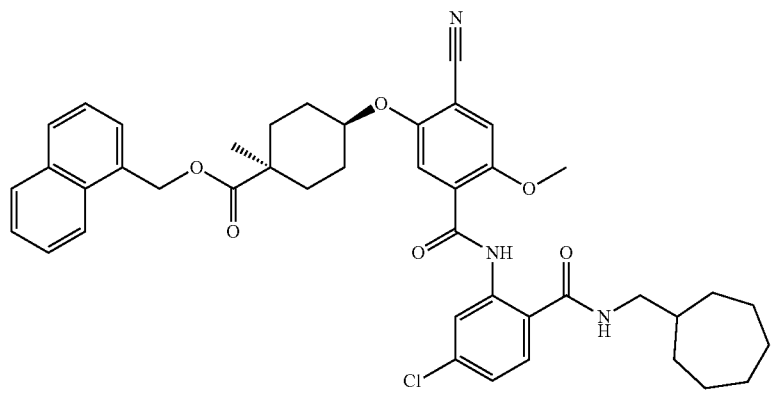 [SMILES: COc1cc(C#N)c(O[C@H]2CC[C@@](C)(C(=O)OCc3cccc4ccccc34)CC2)cc1C(=O)Nc1cc(Cl)ccc1C(=O)NCC1CCCCCC1]

Intermediate 103 (44 mg, 0.09 mmol) was dissolved in DMF (2 mL). DIPEA (31 µL, 0.18 mmol), TCFH (39 mg, 0.14 mmol) and cycloheptylmethanamine (18 mg, 0.14 mmol) were added and the mixture stirred at rt for 16 h. The crude compound was purified by Method PrepAcidic-P and used in the next step.

Step B. (1s,4s)-4-(5-((5-Chloro-2-((cycloheptylmethyl)carbamoyl)phenyl)carbamoyl)-2-cyano-4-methoxyphenoxy)-1-methylcyclohexane-1-carboxylic acid Hydrogenation of Intermediate 404 was performed analogous to the procedure described for the synthesis of Example 150. The crude material was purified by Method FlashAcid-A using a gradient of 5-100% to afford the title compound (3.8 mg, 5%). HRMS (ESI) m/z [M+H]$^+$ calcd for $C_{32}H_{39}ClN_3O_6$: 596.2522 found: 596.2518.

The examples included in Table 11 below were synthesized analogous to the procedure of Example 157 using the appropriate amines (as the free base or as the corresponding HCl salt). The amine is commercially available if not otherwise stated. All Examples except Example 159 within this table were purified by Method PrepAcidic-P in Step A and by Method FlashAcid-A in Step B. Example 159 was purified by Method PrepBasic-K in Step A and by Method FlashAcid-A in Step B.

TABLE 11

| Ex No. | Structure | HRMS (ESI) m/z [M + H]+ | Starting amine |
|---|---|---|---|
| 158 | 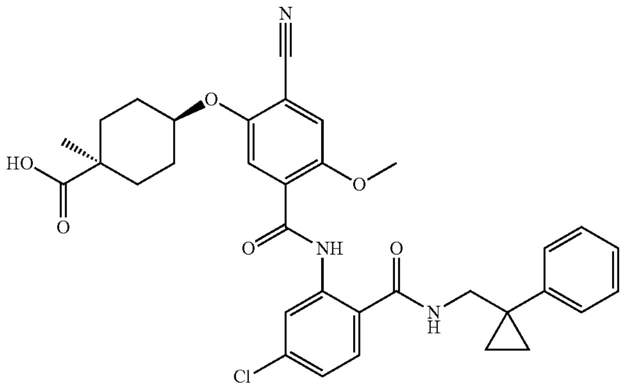 [SMILES: COc1cc(C#N)c(O[C@H]2CC[C@@](C)(C(=O)O)CC2)cc1C(=O)Nc1cc(Cl)ccc1C(=O)NCC1(c2ccccc2)CC1] | calcd for $C_{34}H_{35}ClN_3O_6$: 616.2208 found: 616.2196 | |
| 159 | 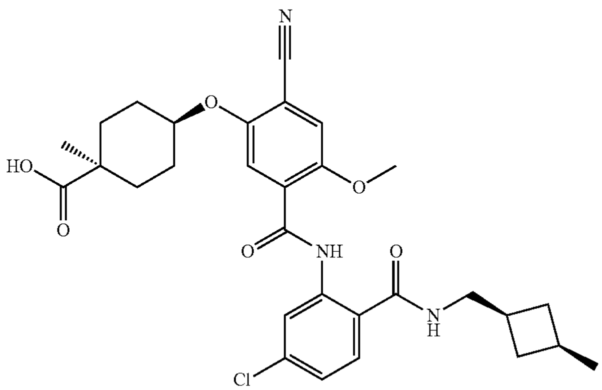 [SMILES: COc1cc(C#N)c(O[C@H]2CC[C@@](C)(C(=O)O)CC2)cc1C(=O)Nc1cc(Cl)ccc1C(=O)NC[C@H]1C[C@@H](C)C1] | calcd for $C_{30}H_{35}ClN_3O_6$: 568.2208 found: 568.2208 | Int. 99 |
| 160 | 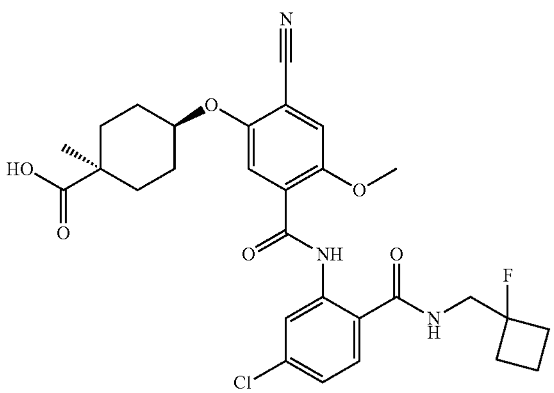 [SMILES: COc1cc(C#N)c(O[C@H]2CC[C@@](C)(C(=O)O)CC2)cc1C(=O)Nc1cc(Cl)ccc1C(=O)NCC1(F)CCC1] | calcd for $C_{29}H_{32}ClFN_3O_6$: 572.1958 found: 572.1962 | |
| 161 | 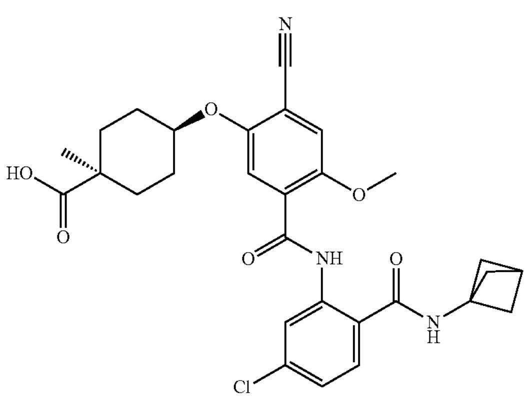 [SMILES: COc1cc(C#N)c(O[C@H]2CC[C@@](C)(C(=O)O)CC2)cc1C(=O)Nc1cc(Cl)ccc1C(=O)NC12CC(C1)C2] | calcd for $C_{29}H_{31}ClN_3O_6$: 552.1896 found: 552.1910 | |

TABLE 11-continued

| Ex No. | Structure | HRMS (ESI) m/z [M + H]+ | Starting amine |
|---|---|---|---|
| 162 | 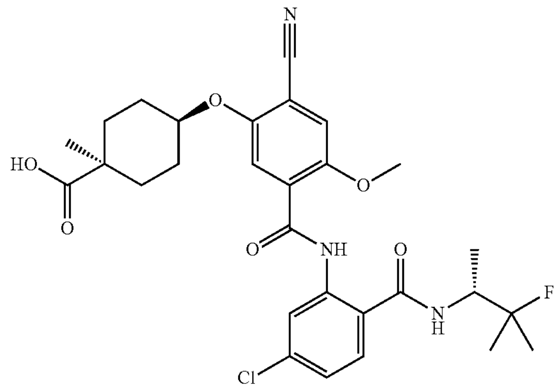 [SMILES: COc1cc(C#N)c(O[C@H]2CC[C@@](C)(C(=O)O)CC2)cc1C(=O)Nc1cc(Cl)ccc1C(=O)N[C@H](C)C(C)(C)F] | calcd for $C_{29}H_{34}ClFN_3O_6$: 574.2114 found: 574.2134 | |
| 163 | 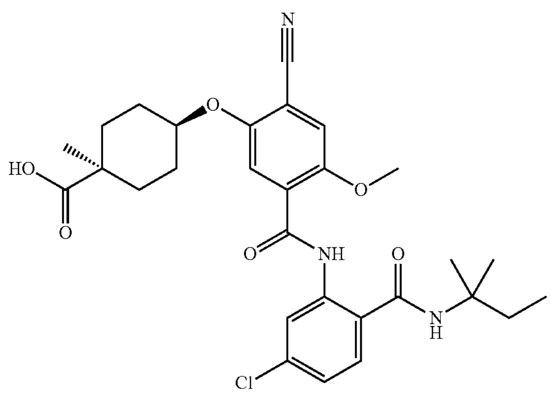 [SMILES: CCC(C)(C)NC(=O)c1ccc(Cl)cc1NC(=O)c1cc(O[C@H]2CC[C@@](C)(C(=O)O)CC2)c(C#N)cc1OC] | calcd for $C_{29}H_{35}ClN_3O_6$: 556.2208 found: 556.2212 | |
| 164 | 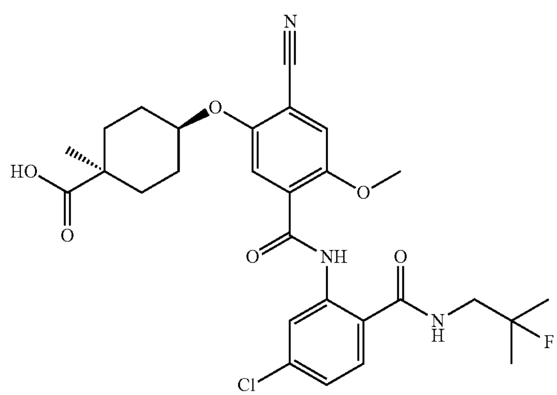 [SMILES: COc1cc(C#N)c(O[C@H]2CC[C@@](C)(C(=O)O)CC2)cc1C(=O)Nc1cc(Cl)ccc1C(=O)NCC(C)(C)F] | calcd for $C_{28}H_{32}ClFN_3O_6$: 560.1958 found: 560.1970 | |
| 165 | 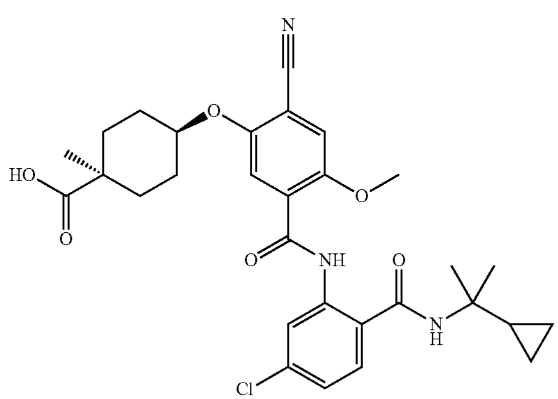 [SMILES: COc1cc(C#N)c(O[C@H]2CC[C@@](C)(C(=O)O)CC2)cc1C(=O)Nc1cc(Cl)ccc1C(=O)NC(C)(C)C1CC1] | calcd for $C_{30}H_{35}ClN_3O_6$: 568.2208 found: 568.2228 | |

Example 166. (1s,4s)-4-(2-Cyano-5-((2-((3-fluorobenzyl)carbamoyl)-5-methylphenyl)carbamoyl)-4-methoxyphenoxy)-1-methylcyclohexane-1-carboxylic acid

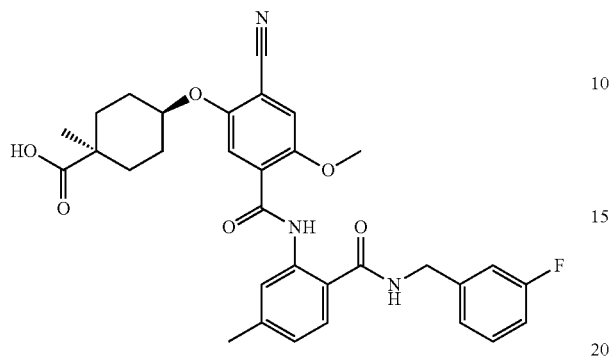

Step A. Intermediate 405: Naphthalen-1-ylmethyl (1s,4s)-4-(2-cyano-5-((2-((3-fluorobenzyl)carbamoyl)-5-methylphenyl)carbamoyl)-4-methoxyphenoxy)-1-methylcyclohexane-1-carboxylate

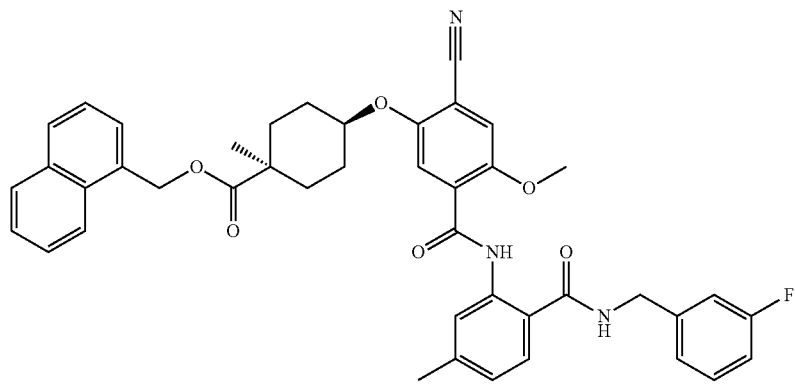 [SMILES: COc1cc(C#N)c(O[C@H]2CC[C@@](C)(C(=O)OCc3cccc4ccccc34)CC2)cc1C(=O)Nc1cc(C)ccc1C(=O)NCc1cccc(F)c1]

Intermediate 104 (39 mg, 0.064 mmol) was dissolved in DMF (2 mL). DIPEA (21 µL, 0.12 mmol), TCFH (25 mg, 0.09 mmol) and (3-fluorophenyl)methanamine (11 mg, 0.09 mmol) were added and the reaction mixture was stirred at 80° C. for 16 h. The crude compound was purified by Method PrepAcidic-P.

Step B. (1s,4s)-4-(2-Cyano-5-((2-((3-fluorobenzyl)carbamoyl)-5-methylphenyl)carbamoyl)-4-methoxyphenoxy)-1-methylcyclohexane-1-carboxylic acid Hydrogenation of Intermediate 405 was performed analogous to the procedure described for the synthesis of Example 150. The crude material was purified by Method PrepBasic-M to afford the title compound (2.3 mg, 6%). HRMS (ESI) m/z [M+H]$^+$ calcd for $C_{32}H_{33}FN_3O_6$: 574.2348 found: 574.2340.

The examples included in Table 12 below were synthesized analogous to the procedure of Example 166 using the appropriate commercially available amines (as the free base or as the corresponding HCl salt). All Examples within this table were purified by Method PrepAcidic-P in Step A and in Step B as indicated in Table 12.

TABLE 12

| Ex No. | Structure | Purification Method | HRMS (ESI) m/z [M + H]+ |
|---|---|---|---|
| 167 | 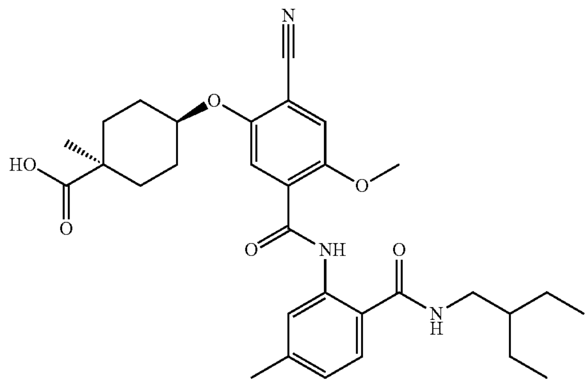 [SMILES: CCC(CC)CNC(=O)c1ccc(C)cc1NC(=O)c1cc(O[C@H]2CC[C@@](C)(C(=O)O)CC2)c(C#N)cc1OC] | Method PrepBasic-L | calcd for $C_{31}H_{40}N_3O_6$: 550.2912 found: 550.2906 |
| 168 | 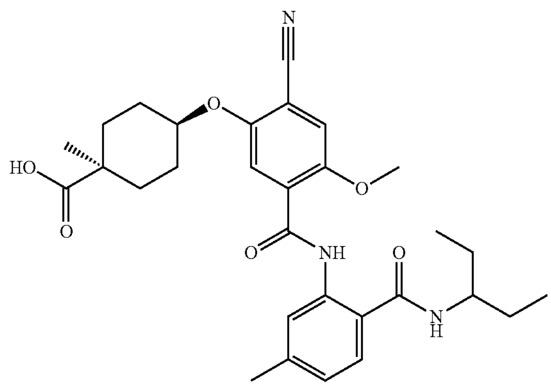 [SMILES: CCC(CC)NC(=O)c1ccc(C)cc1NC(=O)c1cc(O[C@H]2CC[C@@](C)(C(=O)O)CC2)c(C#N)cc1OC] | Method PrepBasic-M | calcd for $C_{30}H_{38}N_3O_6$: 536.2756 found: 536.2752 |
| 169 | 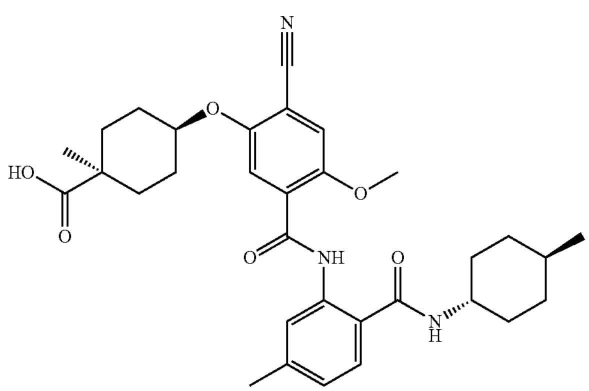 [SMILES: COc1cc(C#N)c(O[C@H]2CC[C@@](C)(C(=O)O)CC2)cc1C(=O)Nc1cc(C)ccc1C(=O)N[C@H]1CC[C@H](C)CC1] | Method PrepBasic-V | calcd for $C_{32}H_{40}N_3O_6$: 562.2912 found: 562.2906 |
| 170 | 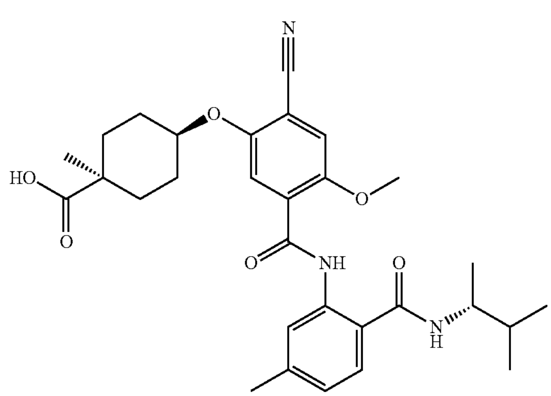 [SMILES: COc1cc(C#N)c(O[C@H]2CC[C@@](C)(C(=O)O)CC2)cc1C(=O)Nc1cc(C)ccc1C(=O)N[C@H](C)C(C)C] | Method PrepBasic-V | calcd for $C_{30}H_{38}N_3O_6$: 536.2756 found: 536.2756 |

TABLE 12-continued

| Ex No. | Structure | Purification Method | HRMS (ESI) m/z [M + H]+ |
|---|---|---|---|
| 171 | 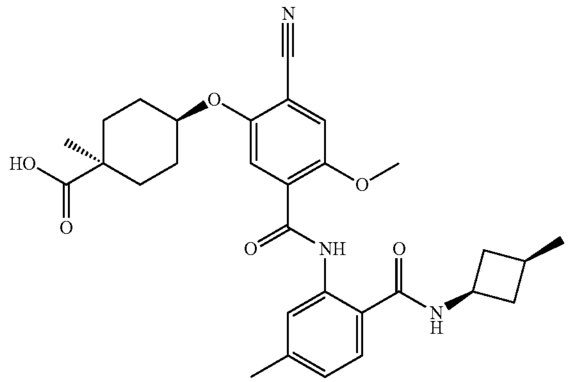 [SMILES: COc1cc(C#N)c(O[C@H]2CC[C@@](C)(C(=O)O)CC2)cc1C(=O)Nc1cc(C)ccc1C(=O)N[C@H]1C[C@@H](C)C1] | Method PrepBasic-V | calcd for $C_{30}H_{36}N_3O_6$: 534.2598 found: 534.2590 |
| 172 | 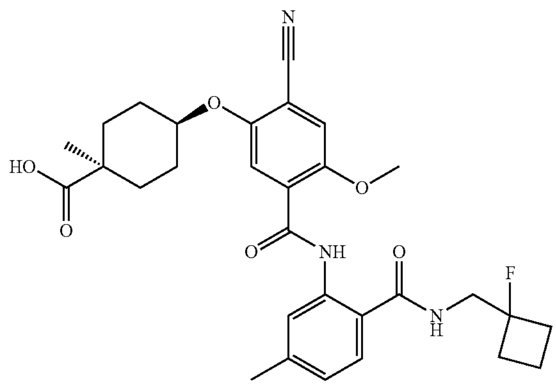 [SMILES: COc1cc(C#N)c(O[C@H]2CC[C@@](C)(C(=O)O)CC2)cc1C(=O)Nc1cc(C)ccc1C(=O)NCC1(F)CCC1] | Method PrepBasic-V | calcd for $C_{30}H_{35}FN_3O_6$: 552.2504 found: 552.2508 |
| 173 | 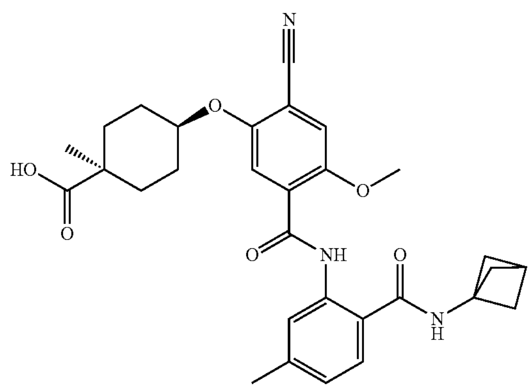 [SMILES: COc1cc(C#N)c(O[C@H]2CC[C@@](C)(C(=O)O)CC2)cc1C(=O)Nc1cc(C)ccc1C(=O)NC12CC(C1)C2] | Method PrepBasic-V | calcd for $C_{30}H_{34}N_3O_6$: 532.2442 found: 532.2446 |
| 174 | 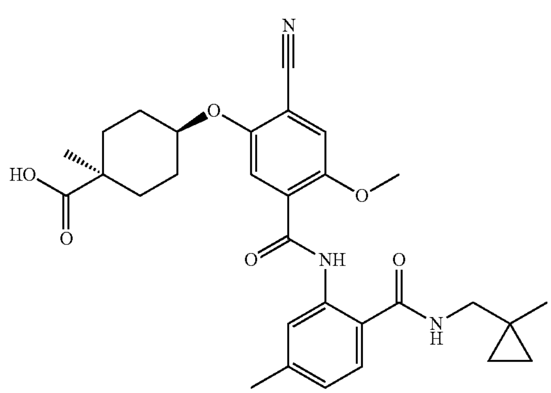 [SMILES: COc1cc(C#N)c(O[C@H]2CC[C@@](C)(C(=O)O)CC2)cc1C(=O)Nc1cc(C)ccc1C(=O)NCC1(C)CC1] | Method PrepBasic-V | calcd for $C_{30}H_{36}N_3O_6$: 534.2598 found: 534.2594 |

Example 175. (1S,4s)-4-(2-Fluoro-4-methoxy-5-((((1S,2R,3S,4R)-3-((4,4,4-trifluorobutyl)carbamoyl)bicyclo[2.2.1]heptan-2-yl)carbamoyl)phenoxy)cyclohexane-1-carboxylic acid

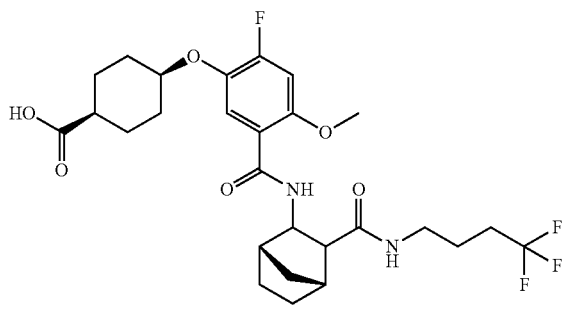 [SMILES: COc1cc(F)c(O[C@H]2CC[C@@H](C(=O)O)CC2)cc1C(=O)NC1C(C(=O)NCCCC(F)(F)F)[C@@H]2CC[C@H]1C2]

Step A. Intermediate 406: Ethyl (1S,4s)-4-(2-fluoro-4-methoxy-5-((((1S,2R,3S,4R)-3-((4,4,4-trifluorobutyl)carbamoyl)bicyclo[2.2.1]heptan-2-yl)carbamoyl)phenoxy)cyclohexane-1-carboxylate

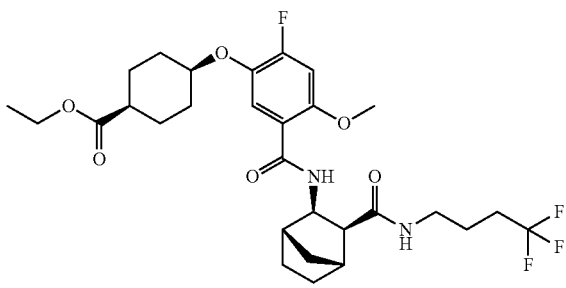 [SMILES: CCOC(=O)[C@H]1CC[C@@H](Oc2cc(C(=O)N[C@@H]3[C@H]4CC[C@H](C4)[C@@H]3C(=O)NCCCC(F)(F)F)c(OC)cc2F)CC1]

HATU (0.239 g, 0.63 mmol) was added to a mixture of Intermediate 106 (0.2 g, 0.42 mmol), 4,4,4-trifluorobutan-1-amine (0.075 g, 0.59 mmol) and DIPEA (0.219 mL, 1.26 mmol) in DMF (10 mL) at 20° C. The resulting solution was stirred at 60° C. for 3 h. The reaction mixture was poured into sat NaHCO$_3$ (150 mL), extracted with EtOAc (3×50 mL), the organic layer was dried over Na$_2$SO$_4$, filtered and evaporated to afford the title compound (0.2 g, 81%) as a yellow oil which solidified on standing. The crude product was used in the next step directly without further purification. MS (ESI): m/z [M+H]$^+$ 587.4.

Step B. (1S,4s)-4-(2-Fluoro-4-methoxy-5-((((1S,2R,3S,4R)-3-((4,4,4-trifluorobutyl)carbamoyl)bicyclo[2.2.1]heptan-2-yl)carbamoyl)phenoxy)cyclohexane-1-carboxylic acid LiOH (0.10 g, 4.18 mmol) was added to Intermediate 406 (0.20 g, 0.34 mmol) in THF (4 mL), MeOH (1 mL) and H$_2$O (1 mL) at 20° C. The resulting solution was stirred at 20° C. for 15 h.

The reaction mixture was poured into H$_2$O (150 mL) and acidified with HCl (2 M, aq). The aq layer was extracted with EtOAc (3×50 mL), the organic layer was dried over Na$_2$SO$_4$, filtered and evaporated to afford a colorless oil which solidified on standing. The crude product was purified by preparative HPLC using Method PrepAcidic-A to afford the title compound (0.165 g, 87%) as a white solid. HRMS (ESI) m/z [M+H]$^+$ calcd for C$_{27}$H$_{35}$F$_4$N$_2$O$_6$: 559.2426 found: 559.2374.

The examples included in Table 13 below were synthesized in a similar way to the procedure of Example 175 using the appropriate amines (as the free base or as the corresponding HCl salt). The amine is commercially available if not otherwise stated.

TABLE 13

| Ex No. | Structure | HRMS (ESI) m/z [M + H]$^+$ | Purification Method |
|---|---|---|---|
| 176 | 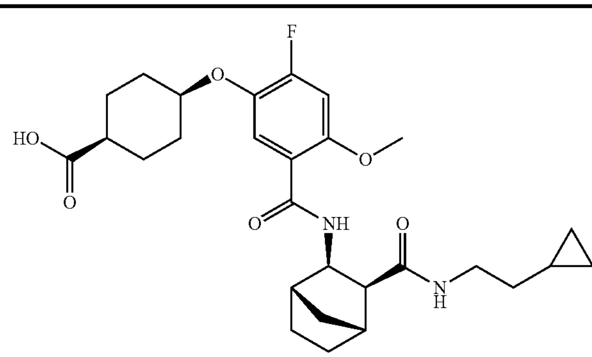 | Calcd for C$_{28}$H$_{38}$FN$_2$O$_6$: 517.2708 found: 517.2700 | Method PrepAcidic-A |

TABLE 13-continued

| Ex No. | Structure | HRMS (ESI) m/z [M + H]+ | Purification Method |
|---|---|---|---|
| 177 | 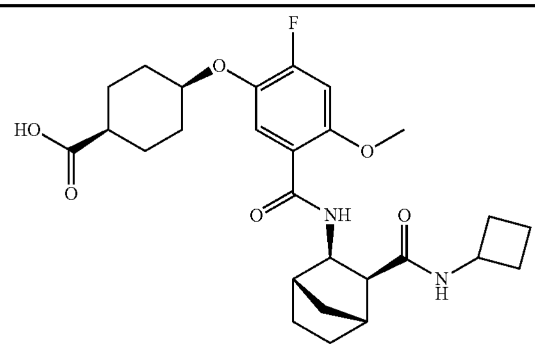 | Calcd for $C_{27}H_{36}FN_2O_6$: 503.2552 found: 503.2536 | Method PrepAcidic-A (Gradient: 44%-54%) |
| 178 | 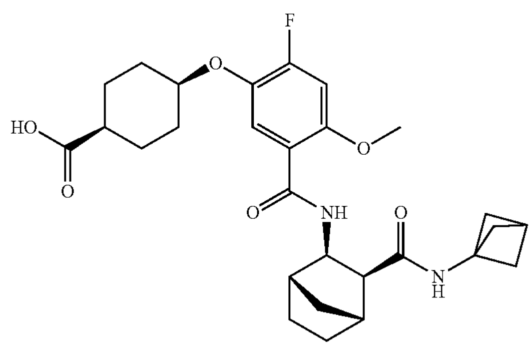 [SMILES: COc1cc(F)c(O[C@H]2CC[C@@H](C(=O)O)CC2)cc1C(=O)N[C@@H]1[C@H]2CC[C@H](C2)[C@@H]1C(=O)NC12CC(C1)C2] | Calcd for $C_{28}H_{36}FN_2O_6$: 515.2552 found: 515.2540 | Method PrepAcidic-C (Gradient: 53%-53%) |

Example 179. (1S,4s)-4-(2-Fluoro-5-(((1S,2R,3S,4R)-3-((4-fluoro-3-(trifluoromethyl)phenyl)carbamoyl)bicyclo[2.2.1]heptan-2-yl)carbamoyl)-4-methoxyphenoxy)cyclohexane-1-carboxylic acid Step A. Intermediate 407: Ethyl (1S,4s)-4-(2-fluoro-5-(((1S,2R,3S,4R)-3-((4-fluoro-3-(trifluoromethyl)phenyl)carbamoyl)bicyclo[2.2.1]heptan-2-yl)carbamoyl)-4-methoxyphenoxy)cyclohexane-1-carboxylate

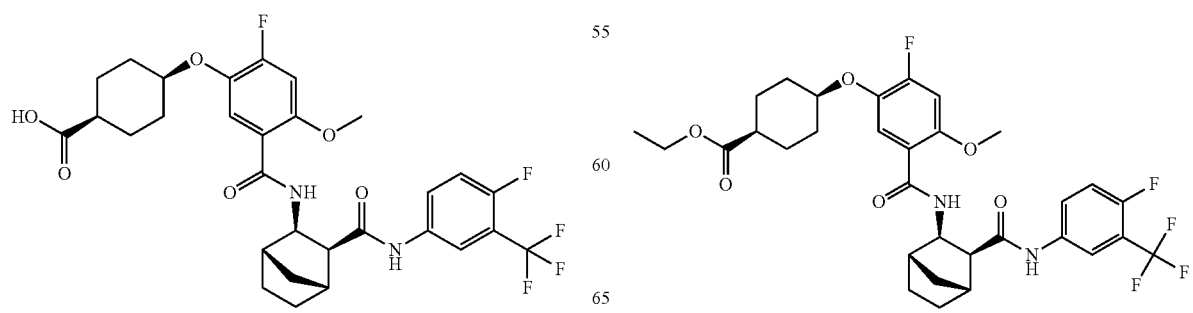

HATU (260 mg, 0.68 mmol) was added portion wise to Intermediate 111 (194 mg, 0.57 mmol), Intermediate 119 (180 mg, 0.57 mmol) and DIPEA (221 mg, 1.71 mmol) in DMF (10 mL) at Rt. The resulting solution was stirred at 60° C. for 2 h. The reaction mixture was poured into sat NaHCO$_3$ (200 mL), extracted with EtOAc (3×75 mL), the organic layer was washed with brine (2×100 mL, sat). The organic layer was dried over Na$_2$SO$_4$, filtered and evaporated to afford the title compound (260 mg, 72%) as a brown gum. The product was used in the next step directly without further purification. MS (ESI): m/z [M+H]$^+$ 661.2.

Step B. (1S,4s)-4-(2-Fluoro-5-((((1S,2R,3S,4R)-3-((4-fluoro-3-(trifluoromethyl)phenyl)carbamoyl)bicyclo[2.2.1]heptan-2-yl)carbamoyl)-4-methoxyphenoxy)cyclohexane-1-carboxylic acid The hydrolysis of Intermediate 407 was carried out in an analogous way to Example 175 Step B. Purification by Method PrepAcidic-C (Gradient: 32%-32%) afforded the title compound (0.142 g, 74.8%) as a white solid. HRMS (ESI) m/z [M+H]$^+$ calcd for C$_{30}$H$_{32}$F$_5$N$_2$O$_6$: 611.2174 found: 611.2182.

Example 180. (1S,4s)-4-(2-Fluoro-4-methoxy-5-(((1S,2R,3S,4R)-3-(neopentylcarbamoyl)bicyclo[2.2.1]heptan-2-yl)carbamoyl)phenoxy)cyclohexane-1-carboxylic acid

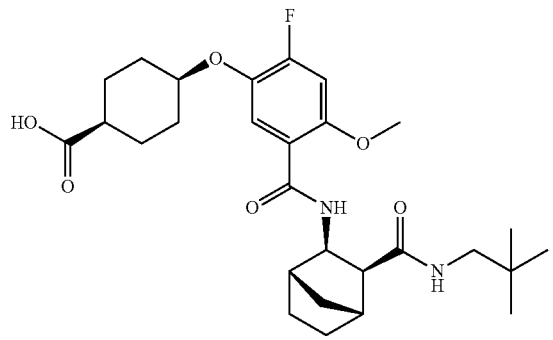 [SMILES: COc1cc(F)c(O[C@H]2CC[C@@H](C(=O)O)CC2)cc1C(=O)N[C@@H]1[C@H]2CC[C@H](C2)[C@@H]1C(=O)NCC(C)(C)C]

Step A. Intermediate 408: Ethyl (1S,4s)-4-(2-fluoro-4-methoxy-5-(((1S,2R,3S,4R)-3-(neopentylcarbamoyl)bicyclo[2.2.1]heptan-2-yl)carbamoyl)phenoxy)cyclohexane-1-carboxylate

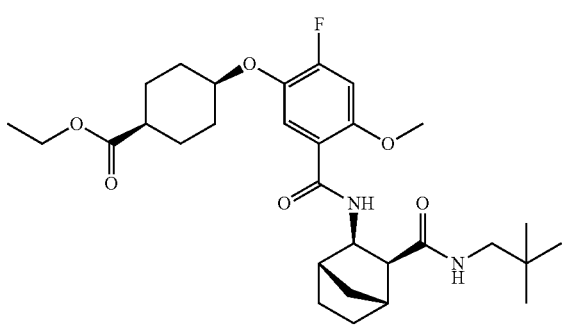 [SMILES: CCOC(=O)[C@H]1CC[C@@H](Oc2cc(C(=O)N[C@@H]3[C@H]4CC[C@H](C4)[C@@H]3C(=O)NCC(C)(C)C)c(OC)cc2F)CC1]

EDC (0.177 g, 0.92 mmol) was added slowly to a mixture of Intermediate 106 (0.2 g, 0.42 mmol), 2,2-dimethylpropan-1-amine (0.110 g, 1.26 mmol) and HOBt (0.141 g, 0.92 mmol), Et$_3$N (0.292 mL, 2.09 mmol) in DMF (20 mL) at 20° C. The resulting solution was stirred at 60° C. for 15 h. The reaction mixture was diluted with EtOAc (200 mL) and washed sequentially with brine (150 mL, sat), sat NaHCO$_3$ (150 mL), and H$_2$O (150 mL). The organic layer was dried over Na$_2$SO$_4$, filtered and evaporated to afford the title compound (0.2 g, 87%) as a yellow oil which solidified on standing. MS (ESI): m/z [M+H]$^+$ 547.5.

Step B. (1S,4s)-4-(2-Fluoro-4-methoxy-5-(((1S,2R,3S,4R)-3-(neopentylcarbamoyl)bicyclo[2.2.1]heptan-2-yl)carbamoyl)phenoxy)cyclohexane-1-carboxylic acid The hydrolysis of Intermediate 408 and following purification was carried out in an analogous way to Example 175 Step B. to afford the title compound (0.142 g, 74.8%) as a white solid. HRMS (ESI) m/z [M+H]$^+$ calcd for C$_{28}$H$_{40}$FN$_2$O$_6$: 519.2864 found: 519.2888.

Example 181 (1S,4s)-4-(5-(((1S,2R,3S,4R)-3-((4-(Difluoromethyl)phenyl)carbamoyl)bicyclo[2.2.1]heptan-2-yl)carbamoyl)-2-fluoro-4-methoxyphenoxy)cyclohexane-1-carboxylic acid

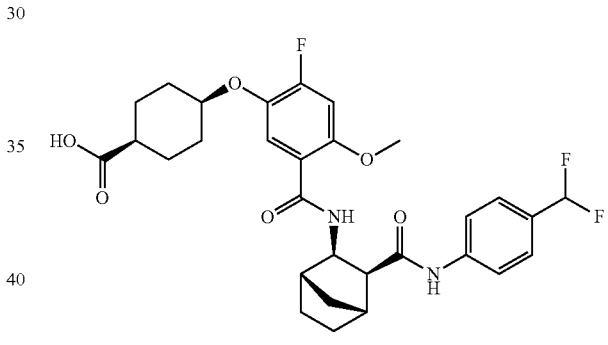

Step A. Intermediate 409: Ethyl (1S,4s)-4-(5-(((1S,2R,3S,4R)-3-((4-(difluoromethyl)phenyl)carbamoyl)bicyclo[2.2.1]heptan-2-yl)carbamoyl)-2-fluoro-4-methoxyphenoxy)cyclohexane-1-carboxylate

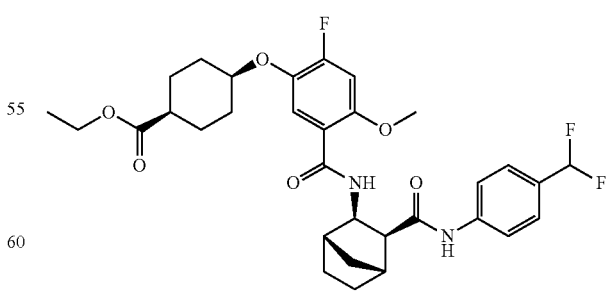

4-(Difluoromethyl)aniline (71.4 mg, 0.50 mmol), HATU (239 mg, 0.63 mmol), DIPEA (108 mg, 0.84 mmol) and DMAP (5.12 mg, 0.04 mmol) were added to Intermediate 106 (200 mg, 0.42 mmol) and the mixture was stirred at 20°

C. overnight. The reaction mixture was diluted with EtOAc (100 mL), and washed sequentially with brine (3×20 mL, sat). The organic layer was dried over Na$_2$SO$_4$, filtered and evaporated to afford the crude product. The crude product was purified by flash chromatography using a gradient of 0-10% MeOH in DCM as mobile phase to give the title compound (220 mg, 87%) as an orange solid. MS (ESI): m/z [M+H]$^+$ 603.

Step B. (1S,4s)-4-(5-(((1S,2R,3S,4R)-3-((4-(Difluoromethyl)phenyl)carbamoyl)bicyclo[2.2.1]heptan-2-yl)carbamoyl)-2-fluoro-4-methoxyphenoxy)cyclohexane-1-carboxylic acid LiOH (26.2 mg, 1.10 mmol) was added to Intermediate 409 (220 mg, 0.37 mmol) in a solution of EtOH (6 mL)/H$_2$O (3 mL). The reaction mixture was stirred at 20° C. for 5 h. The reaction mixture was acidified with 1 M HCl. Purification by Method PrepAcidic-C afforded the title compound (47.0 mg, 22%) as a light orange solid. HRMS (ESI) m/z [M+H]$^+$ calcd for C$_{30}$H$_{34}$F$_3$N$_2$O$_6$: 575.2364 found: 575.2388.

The examples included in Table 14 below were synthesized in a similar way to the procedure of Example 181 using the appropriate amines (as the free base or as the corresponding HCl salt). The amine is commercially available if not otherwise stated.

TABLE 14

| Ex No. | Structure | HRMS (ESI) m/z [M + H]$^+$ | Purification Method |
|---|---|---|---|
| 182 | 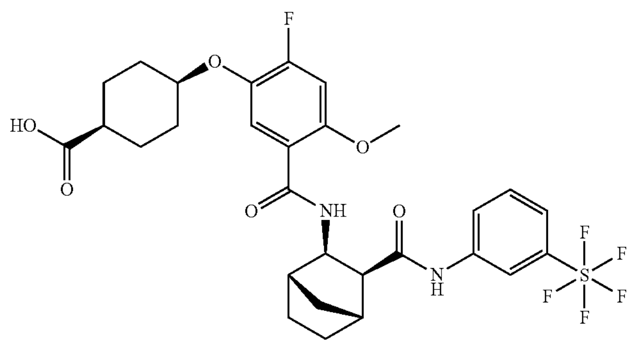 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cccc(S(F)(F)(F)(F)F)c1] | Calcd for C$_{29}$H$_{33}$F$_6$N$_2$O$_6$S: 651.1958 found: 651.1942 | Method PrepAcidic-C |
| 183 | 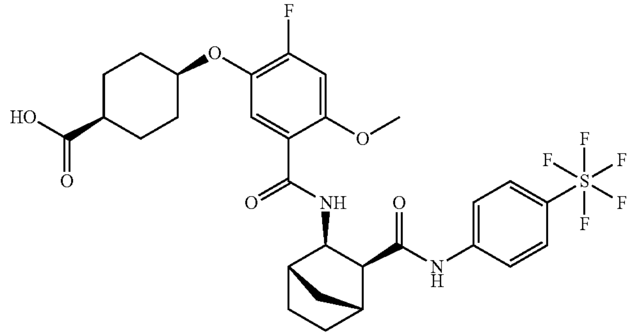 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1ccc(S(F)(F)(F)(F)F)cc1] | Calcd for C$_{29}$H$_{33}$F$_6$N$_2$O$_6$S: 651.1958 found: 651.1994 | Method PrepAcidic-C |

Example 184. (1S,4s)-4-(5-(((1S,2R,3S,4R)-3-((2,6-Difluorophenyl)carbamoyl)bicyclo[2.2.1]heptan-2-yl)carbamoyl)-2-fluoro-4-methoxyphenoxy)cyclohexane-1-carboxylic acid

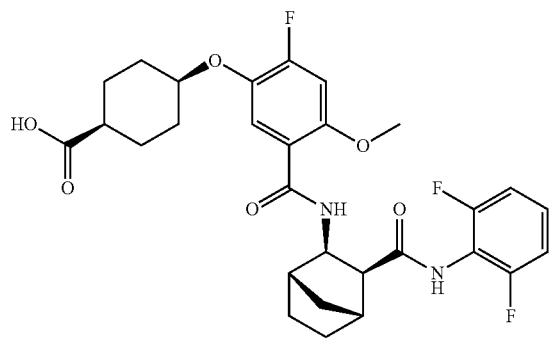 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1c(F)cccc1F]

Step A. Intermediate 410: Ethyl (1S,4s)-4-(5-(((1S,2R,3S,4R)-3-((2,6-difluorophenyl)carbamoyl)bicyclo[2.2.1]heptan-2-yl)carbamoyl)-2-fluoro-4-methoxyphenoxy)cyclohexane-1-carboxylate

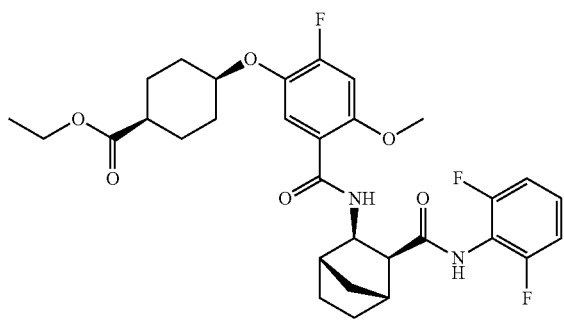 [SMILES: CCOC(=O)[C@H]1CC[C@@H](Oc2cc(C(=O)N[C@@H]3[C@H]4CC[C@H](C4)[C@@H]3C(=O)Nc3c(F)cccc3F)c(OC)cc2F)CC1]

T3P (0.800 g, 1.26 mmol) was added to Intermediate 106 (0.20 g, 0.42 mmol), 2,6-difluoroaniline (0.065 g, 0.50 mmol) and DIPEA (0.366 mL, 2.09 mmol) in butyl acetate (20 mL) at 20° C. The resulting solution was stirred at 120° C. for 15 h. The reaction mixture was poured into sat NaHCO$_3$ (150 mL), extracted with EtOAc (3×50 mL), the organic layer was dried over Na$_2$SO$_4$, filtered and evaporated to afford the title compound (0.200 g, 81%) as a brown gum. This was used in the next step without further purification. MS (ESI): m/z [M+H]$^+$ 589.2.

Step B. (1S,4s)-4-(5-(((1S,2R,3S,4R)-3-((2,6-Difluorophenyl)carbamoyl)bicyclo[2.2.1]heptan-2-yl)carbamoyl)-2-fluoro-4-methoxyphenoxy)cyclohexane-1-carboxylic acid The hydrolysis of Intermediate 410 was carried out in an analogous way to Example 175 Step B. Purification by Method PrepAcidic-A (Gradient: 49%-59%) afforded the title compound (152 mg, 80%) as a white solid. HRMS (ESI) m/z [M+H]$^+$ calcd for C$_{29}$H$_{32}$F$_3$N$_2$O$_6$: 561.2208 found: 561.2182.

The examples included in Table 15 below were synthesized in a similar way to the procedure of Example 184 using the appropriate amines (as the free base or as the corresponding HCl salt). The amine is commercially available if not otherwise stated.

TABLE 15

| Ex No. | Structure | HRMS (ESI) m/z [M + H]$^+$ | Purification Method |
|---|---|---|---|
| 185 | (structure shown) | Calcd for C$_{29}$H$_{33}$FIN$_2$O$_6$: 651.1362 found: 651.1364 | Method PrepAcidic-C (Gradient: 58%-58%) |

TABLE 15-continued

| Ex No. | Structure | HRMS (ESI) m/z [M + H]+ | Purification Method |
|---|---|---|---|
| 186 | 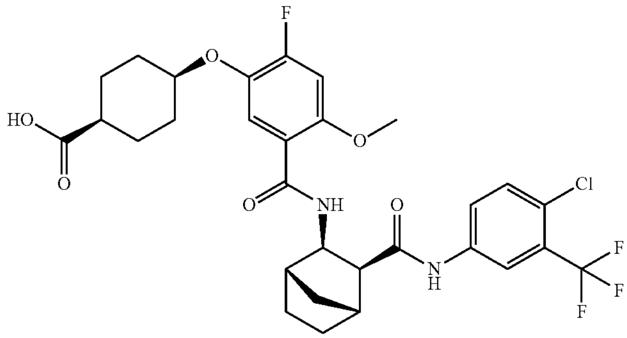 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1ccc(Cl)c(C(F)(F)F)c1] | Calcd for $C_{30}H_{32}ClF_4N_2O_6$: 627.1880 found: 627.1896 | Method PrepAcidic-A (Gradient: 60%-70%) |
| 187 | 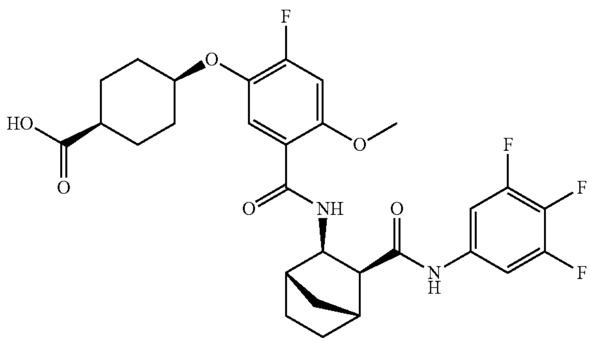 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cc(F)c(F)c(F)c1] | Calcd for $C_{29}H_{31}F_4N_2O_6$: 579.2112 found: 579.2130 | Method PrepAcidic-G (Gradient: 60%-70%) |
| 188 | 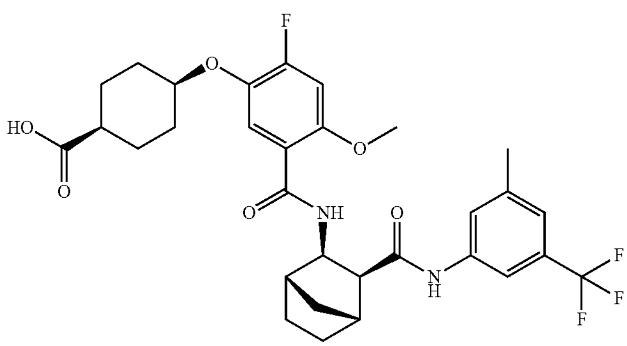 | Calcd for $C_{31}H_{35}F_4N_2O_6$: 607.2426 found: 607.2426 | Method PrepAcidic-A (Gradient: 50%-80%) |
| 189 | 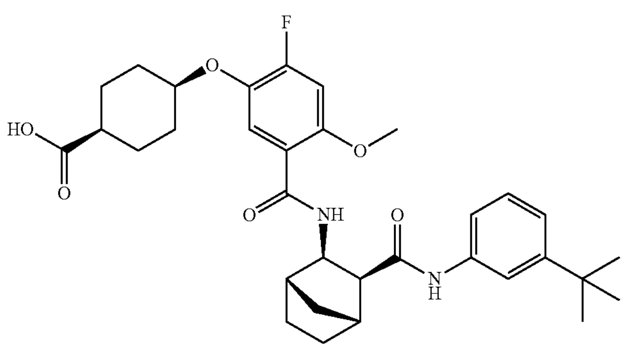 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cccc(C(C)(C)C)c1] | Calcd for $C_{33}H_{42}FN_2O_6$: 581.3022 found: 581.3032 | Method PrepAcidic-C (Gradient: 50%-75%) |

TABLE 15-continued

| Ex No. | Structure | HRMS (ESI) m/z [M + H]+ | Purification Method |
|---|---|---|---|
| 190 | 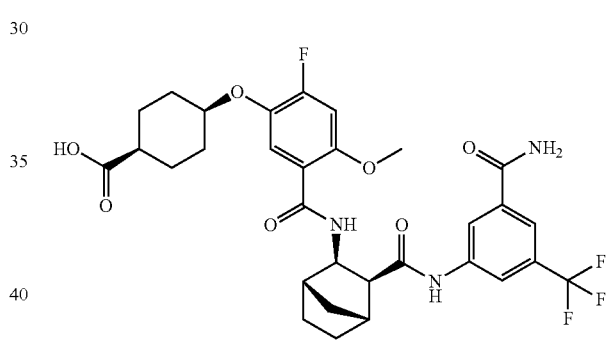 | Calcd for $C_{32}H_{38}FN_2O_6$: 565.2708 found: 565.2754 | Method PrepAcidic-A (Gradient: 40%-80%) |

Example 191 (1S,4s)-4-(5-(((1S,2R,3S,4R)-3-((3-Cyano-5-(trifluoromethyl)phenyl)carbamoyl)bicyclo[2.2.1]heptan-2-yl)carbamoyl)-2-fluoro-4-methoxyphenoxy)cyclohexane-1-carboxylic acid Step A. Intermediate 411: Ethyl (1S,4s)-4-(5-(((1S,2R,3S,4R)-3-((3-cyano-5-(trifluoromethyl)phenyl)carbamoyl)bicyclo[2.2.1]heptan-2-yl)carbamoyl)-2-fluoro-4-methoxyphenoxy)cyclohexane-1-carboxylate

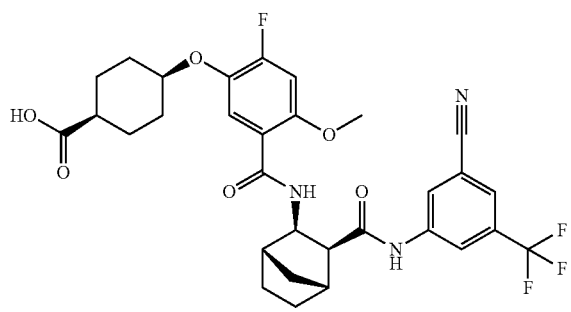 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cc(C#N)cc(C(F)(F)F)c1]

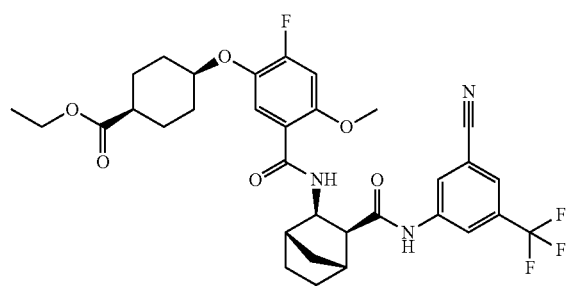 [SMILES: CCOC(=O)[C@H]1CC[C@@H](Oc2cc(C(=O)N[C@@H]3[C@H]4CC[C@H](C4)[C@@H]3C(=O)Nc3cc(C#N)cc(C(F)(F)F)c3)c(OC)cc2F)CC1]

T3P (0.800 g, 1.26 mmol) was added to Intermediate 106 (0.12 g, 0.25 mmol), 3-amino-5-(trifluoromethyl)benzonitrile (0.084 g, 0.45 mmol) and DIPEA (0.439 mL, 2.51 mmol) in butyl acetate (15 mL) at 20° C. The resulting solution was stirred at 120° C. for 15 h. The reaction mixture was poured into sat NaHCO$_3$ (150 mL), extracted with EtOAc (3×50 mL), the organic layer was dried over Na$_2$SO$_4$, filtered and evaporated to afford the title compound (0.150 g, 92%) as a brown gum which was used as such in the next step. MS (ESI): m/z [M+H]+ 646.3.

Step B. Intermediate 412: (1S,4s)-4-(5-(((1S,2R,3S,4R)-3-((3-Carbamoyl-5-(trifluoromethyl)phenyl)carbamoyl)bicyclo[2.2.1]heptan-2-yl)carbamoyl)-2-fluoro-4-methoxyphenoxy)cyclohexane-1-carboxylic acid LiOH (0.50 g, 20.88 mmol) was added to Intermediate 411 (0.15 g, 0.23 mmol) in THF (4 mL), MeOH (1 mL) and H$_2$O (1 mL) at 20° C. The resulting solution was stirred at 20° C. for 15 h. The reaction mixture was poured into H$_2$O (150 mL), the reaction mixture was acidified with 2 M HCl. The aq layer was extracted with EtOAc (3×50 mL), the organic layer was dried over Na$_2$SO$_4$, filtered and evaporated to afford colorless oil which solidified on standing. The crude product was purified by Method PrepAcidic-G (Gradient: 54%-64%) to afford the title compound (0.050 g, 34%) as a pale yellow solid along with Example 191 (10.0 mg, 7%) as a pale yellow solid. MS (ESI): m/z [M+H]+ 618.2.

Step C. (1S,4s)-4-(5-(((1S,2R,3S,4R)-3-((3-Cyano-5-(trifluoromethyl)phenyl)carbamoyl)bicyclo[2.2.1]heptan-2-yl)carbamoyl)-2-fluoro-4-methoxyphenoxy)cyclohexane-1-carboxylic acid PdCl$_2$ (13.95 mg, 0.08 mmol) was added to Intermediate 412 (50 mg, 0.08 mmol) in MeCN (4 mL) and H$_2$O (4.00 mL) at 20° C. under nitrogen. The resulting solution was stirred at 20° C. for 15 h. The reaction mixture was poured into brine (150 mL, sat), extracted with EtOAc (3×75 mL), the organic layer was dried over Na$_2$SO$_4$, filtered and evaporated to afford yellow oil. The crude product and the product isolated in the step above (10.0 mg) were combined and purified by Method PrepAcidic-G (Gradient: 60%-70%) to afford the title compound (38.0 mg, 73.2%) as a white solid. HRMS (ESI) m/z [M+H]$^+$ calcd for $C_{31}H_{32}F_4N_3O_6$: 618.2222 found: 618.2236.

Example 192 (1S,4s)-4-(2-Fluoro-4-methoxy-5-(((1S,2R,3S,4R)-3-((4-methyl-3-(trifluoromethyl)phenyl)carbamoyl)bicyclo[2.2.1]heptan-2-yl)carbamoyl)phenoxy)cyclohexane-1-carboxylic acid

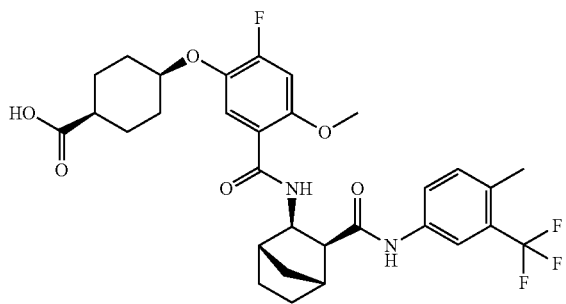 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1ccc(C)c(C(F)(F)F)c1]

Step A. Intermediate 413: Ethyl (1S,4s)-4-(2-fluoro-4-methoxy-5-(((1S,2R,3S,4R)-3-((4-methyl-3-(trifluoromethyl)phenyl)carbamoyl)bicyclo[2.2.1]heptan-2-yl)carbamoyl)phenoxy)cyclohexane-1-carboxylate

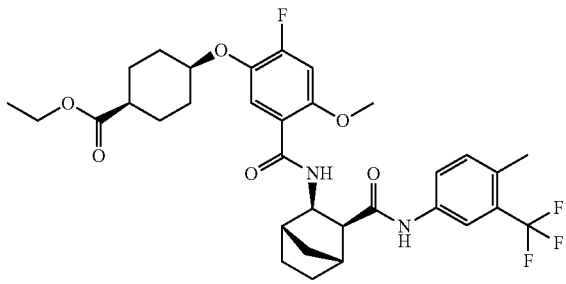 [SMILES: CCOC(=O)[C@H]1CC[C@@H](Oc2cc(C(=O)N[C@@H]3[C@H]4CC[C@H](C4)[C@@H]3C(=O)Nc3ccc(C)c(C(F)(F)F)c3)c(OC)cc2F)CC1]

DMAP (3.07 mg, 0.03 mmol) was added Intermediate 106 (120 mg, 0.25 mmol), 4-methyl-3-(trifluoromethyl)aniline (52.8 mg, 0.30 mmol), T3P (480 mg, 0.75 mmol) and DIEPA (0.176 mL, 1.01 mmol) in butyl acetate (5 mL). The resulting mixture was stirred at 120° C. for 16 h. The reaction mixture was poured into sat NaHCO$_3$ (100 mL), extracted with EtOAc (3×75 mL), the organic layer was dried over Na$_2$SO$_4$, filtered and evaporated to afford the title compound (109 mg, 68%) as a white solid. This was used without further purification in the next step. MS (ESI): m/z [M+H]$^+$ 635.

Step B. (1S,4s)-4-(2-Fluoro-4-methoxy-5-(((1S,2R,3S,4R)-3-((4-methyl-3-(trifluoromethyl)phenyl)carbamoyl)bicyclo[2.2.1]heptan-2-yl)carbamoyl)phenoxy)cyclohexane-1-carboxylic acid The hydrolysis of Intermediate 413 was carried out in an analogous way to Example 181 Step B. Purification by Method PrepAcidic-C afforded the title compound (61 mg, 57%) as a white solid. HRMS (ESI) m/z [M+H]$^+$ calcd for $C_{31}H_{35}F_4N_2O_6$: 607.2426 found: 607.2454.

The examples included in Table 16 below were synthesized in a similar way to the procedure of Example 192 using the appropriate amines (as the free base or as the corresponding HCl salt). The amine is commercially available if not otherwise stated.

TABLE 16

| Ex No. | Structure | HRMS (m/z) [M + H]$^+$ | Purification Method |
|---|---|---|---|
| 193 | (structure shown) | Calcd for $C_{30}H_{33}F_4N_2O_6$: 593.2270 found: 593.2294 | Method PrepAcidic-C |

TABLE 16-continued

| Ex No. | Structure | HRMS (m/z) [M + H]+ | Purification Method |
|---|---|---|---|
| 194 | 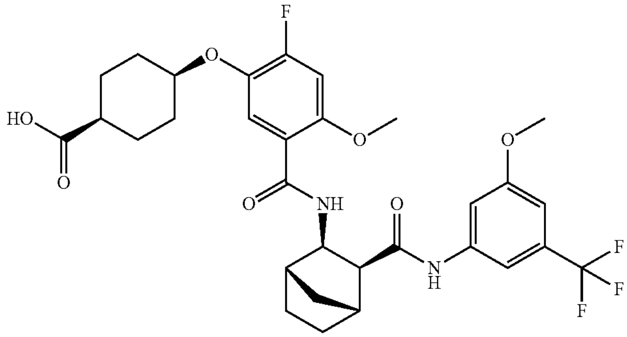 [SMILES: COc1cc(NC(=O)[C@H]2[C@@H]3CC[C@@H](C3)[C@H]2NC(=O)c2cc(O[C@H]3CC[C@@H](C(=O)O)CC3)c(F)cc2OC)cc(C(F)(F)F)c1] | Calcd for $C_{31}H_{35}F_4N_2O_7$: 623.2374 found: 623.2364 | Method PrepAcidic-C |
| 195 | 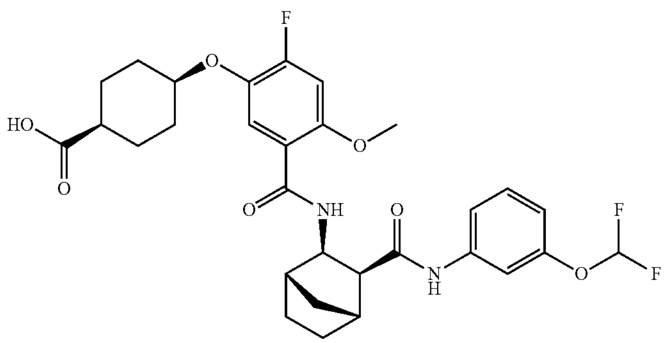 [SMILES: COc1cc(F)c(O[C@H]2CC[C@@H](C(=O)O)CC2)cc1C(=O)N[C@@H]1[C@H]2CC[C@H](C2)[C@@H]1C(=O)Nc1cccc(OC(F)F)c1] | Calcd for $C_{30}H_{34}F_3N_2O_7$: 591.2312 found: 591.2332 | Method PrepAcidic-C |

Example 196 (1S,4s)-4-(2-Fluoro-5-(((1S,2R,3S,4R)-3-((3-isopropylphenyl)carbamoyl)bicyclo[2.2.1]heptan-2-yl)carbamoyl)-4-methoxyphenoxy)cyclohexane-1-carboxylic acid Step A. Intermediate 414: Ethyl (1S,4s)-4-(2-fluoro-5-(((1S,2R,3S,4R)-3-((3-isopropylphenyl)carbamoyl)bicyclo[2.2.1]heptan-2-yl)carbamoyl)-4-methoxyphenoxy)cyclohexane-1-carboxylate

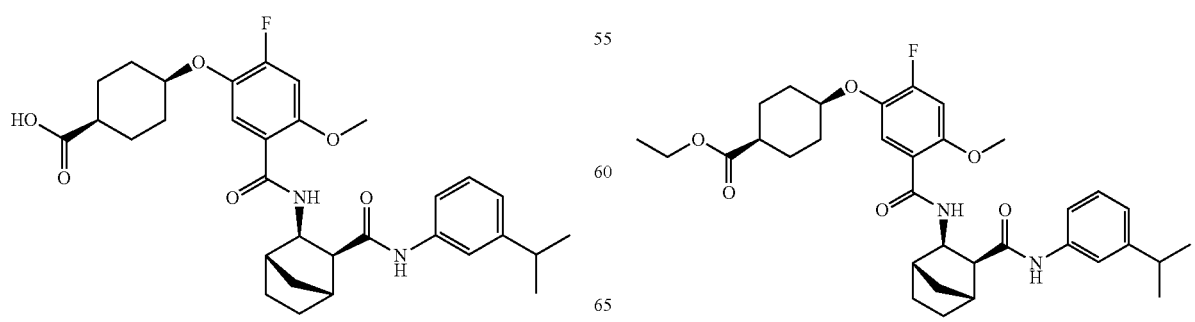

The compound was synthesized analogous to the procedure of Example 184 Step A. from Intermediate 106 and 3-isopropylaniline to afford the title compound (120 mg, 80%) as a white solid which was used without further purification in the next step. MS (ESI): m/z [M+H]$^+$ 595.

Step B. (1S,4s)-4-(2-Fluoro-5-(((1S,2R,3S,4R)-3-((3-isopropylphenyl)carbamoyl)bicyclo[2.2.1]heptan-2-yl)carbamoyl)-4-methoxyphenoxy)cyclohexane-1-carboxylic acid The hydrolysis of Intermediate 414 was carried out in an analogous way to Example 181 Step B. Purification by Method PrepAcidic-C afforded the title compound (56 mg, 48%) as a white solid. HRMS (ESI) m/z [M+H]$^+$ calcd for $C_{32}H_{40}FN_2O_6$: 567.2864 found: 567.2888.

Example 197 (1S,4s)-4-(5-(((1S,2R,3S,4R)-3-((2-ethylbutyl)carbamoyl)bicyclo[2.2.1]heptan-2-yl)carbamoyl)-2-fluoro-4-methoxyphenoxy)cyclohexane-1-carboxylic acid

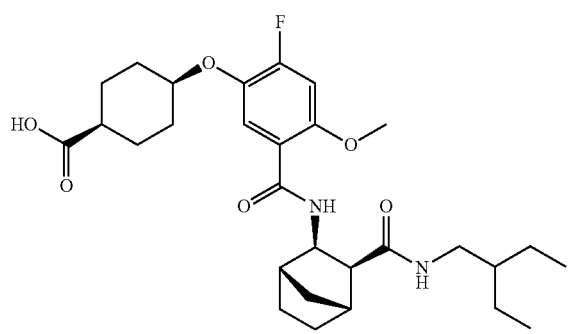 [SMILES: CCC(CC)CNC(=O)[C@H]1[C@@H]2CC[C@@H](C2)[C@H]1NC(=O)c1cc(O[C@H]2CC[C@@H](C(=O)O)CC2)c(F)cc1OC]

Step A. Intermediate 415: Ethyl (1S,4s)-4-(5-(((1S,2R,3S,4R)-3-((2-ethylbutyl)carbamoyl)bicyclo[2.2.1]heptan-2-yl)carbamoyl)-2-fluoro-4-methoxyphenoxy)cyclohexane-1-carboxylate

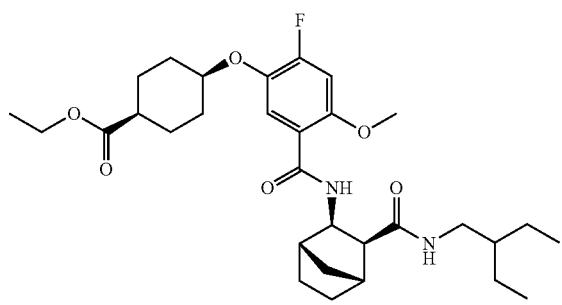 [SMILES: CCOC(=O)[C@H]1CC[C@@H](Oc2cc(C(=O)N[C@@H]3[C@H]4CC[C@H](C4)[C@@H]3C(=O)NCC(CC)CC)c(OC)cc2F)CC1]

HATU (96 mg, 0.25 mmol) was added to a solution of Intermediate 106 (100 mg, 0.21 mmol) in DMF (2 mL). The reaction mixture was stirred at ambient temperature for 5 minutes before 2-ethylbutan-1-amine (25.4 mg, 0.25 mmol) and DIPEA (73.0 µL, 0.42 mmol) was added and the reaction was stirred for 4 h. H$_2$O and EtOAc were added and the two phases were separated. The aq phase was extracted with EtOAc and the organic extracts were combined and washed with H$_2$O (two times), dried over MgSO$_4$ and evaporated. The crude product was purified by flash chromatography using heptane/EtOAc 1/2 as eluent to afford the title compound (86 mg, 73%). $^1$H NMR (400 MHz, CDCl$_3$) δ 0.69-0.8 (m, 6H), 1.18 (dq, 6H), 1.25-1.36 (m, 6H), 1.63 (d, 3H), 1.73 (dd, 2H), 1.93-2.09 (m, 5H), 2.23 (d, 1H), 2.35-2.47 (m, 2H), 2.51 (s, 1H), 2.94-3.13 (m, 2H), 3.93 (s, 3H), 4.15 (q, 2H), 4.41 (t, 2H), 5.52 (t, 1H), 6.71 (d, 1H), 7.87 (d, 1H), 8.58 (d, 1H). MS (ESI): m/z [M+H]$^+$ 561.5.

Step B. (1S,4s)-4-(5-(((1S,2R,3S,4R)-3-((2-ethylbutyl)carbamoyl)bicyclo[2.2.1]heptan-2-yl)carbamoyl)-2-fluoro-4-methoxyphenoxy)cyclohexane-1-carboxylic acid MeOH (0.4 mL) and NaOH(aq) (0.4 mL, 1.9 M) was added to a solution of Intermediate 415 (86 mg, 0.15 mmol) in THF (1.6 mL) and the mixture was stirred at ambient temperature for 18 hrs. H$_2$O was added followed by 1 M HCl to pH approximately 4. EtOAc was added and the two phases were separated. The aq phase was extracted with EtOAc and the combined organic extracts were washed with H$_2$O, dried over MgSO$_4$ and evaporated. The crude product was purified by flash chromatography using 5% MeOH in EtOAc as eluent to afford the title compound (76 mg, 93%). HRMS (ESI) m/z [M+H]$^+$ calcd for $C_{29}H_{42}FN_2O_6$: 533.3022 found: 533.2992.

The examples included in Table 17 below were synthesized in a similar way to the procedure of Example 197 using the appropriate amines (as the free base or as the corresponding HCl salt). The amine is commercially available if not otherwise stated.

TABLE 17

| Ex No. | Structure | HRMS (m/z) [M + H]+ | Purification Method |
|---|---|---|---|
| 198 | 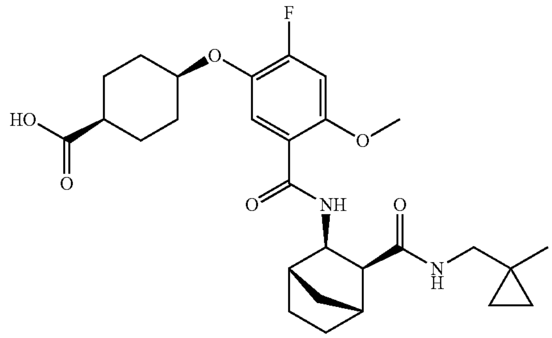 [SMILES: COc1cc(F)c(O[C@H]2CC[C@@H](C(=O)O)CC2)cc1C(=O)N[C@@H]1[C@H]2CC[C@H](C2)[C@@H]1C(=O)NCC1(C)CC1] | Calcd for C28H38FN2O6: 517.2708 found: 517.2708 | Flash chromatography using 5% MeOH in EtOAc |
| 199 | 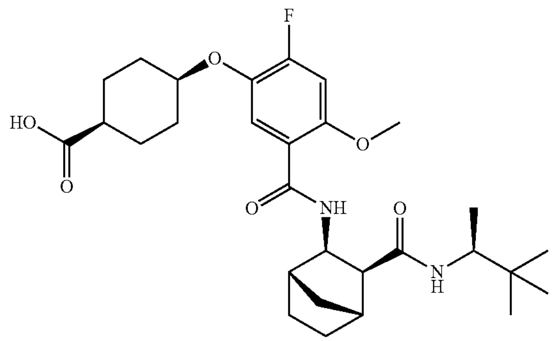 [SMILES: COc1cc(F)c(O[C@H]2CC[C@@H](C(=O)O)CC2)cc1C(=O)N[C@@H]1[C@H]2CC[C@H](C2)[C@@H]1C(=O)N[C@@H](C)C(C)(C)C] | Calcd for C29H42FN2O6: 533.3022 found: 533.3068 | Flash chromatography using 5% MeOH in EtOAc |
| 200 | 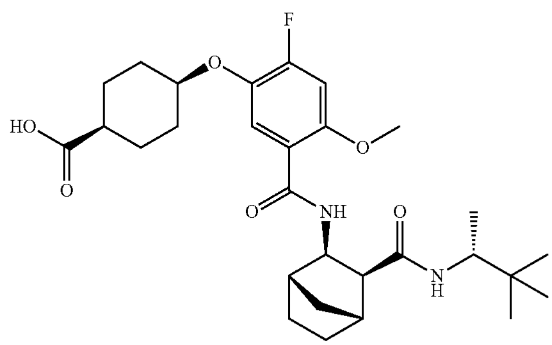 [SMILES: COc1cc(F)c(O[C@H]2CC[C@@H](C(=O)O)CC2)cc1C(=O)N[C@@H]1[C@H]2CC[C@H](C2)[C@@H]1C(=O)N[C@H](C)C(C)(C)C] | Calcd for C29H42FN2O6: 533.3022 found: 533.3054 | Flash chromatography using 5% MeOH in EtOAc |

Example 201 (1S,4s)-4-(2-Fluoro-4-methoxy-5-(((1S,2R,3S,4R)-3-(phenylcarbamoyl)bicyclo[2.2.1]heptan-2-yl)carbamoyl)phenoxy)cyclohexane-1-carboxylic acid Step A. Intermediate 416: Ethyl (1S,4s)-4-(2-fluoro-4-methoxy-5-(((1S,2R,3S,4R)-3-(phenylcarbamoyl)bicyclo[2.2.1]heptan-2-yl)carbamoyl)phenoxy)cyclohexane-1-carboxylate

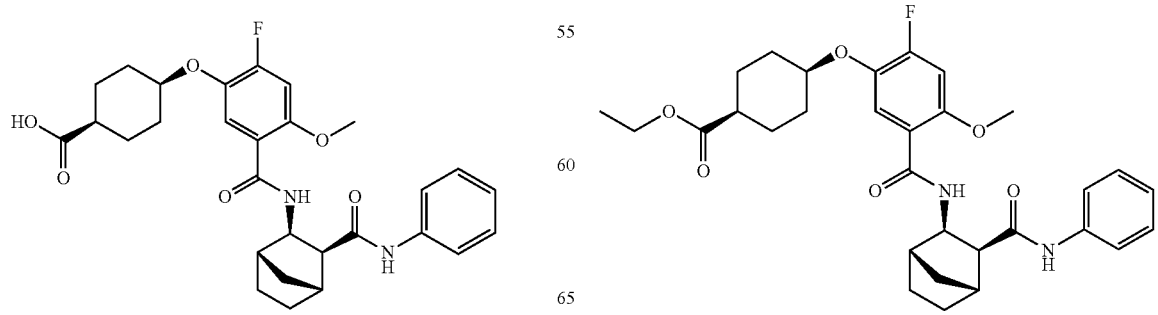

HATU (322 mg, 0.85 mmol), DIPEA (0.296 mL, 1.69 mmol) and Intermediate 111 (231 mg, 0.68 mmol) were added to Intermediate 124 (130 mg, 0.56 mmol) in DMF (5 mL). The reaction mixture was stirred at Rt for 1.5 h. The reaction mixture was diluted with EtOAc (50 mL), and washed sequentially with brine (10 mL, sat). The organic layer was dried over Na$_2$SO$_4$, filtered and evaporated to afford the crude product which was purified by preparative TLC (PE/EtOAc 1/1), to afford the title compound (240 mg, 77%) as a yellow oil. MS (ESI): m/z [M+H]$^+$ 553.

Step B. (1S,4s)-4-(2-Fluoro-4-methoxy-5-(((1S,2R, 3S,4R)-3-(phenylcarbamoyl)bicyclo[2.2.1]heptan-2-yl)carbamoyl)phenoxy)cyclohexane-1-carboxylic acid The hydrolysis of Intermediate 416 was carried out in an analogous way to Example 181 Step B. Purification by Method PrepAcidic-D afforded the title compound (106 mg, 46%) as a white solid. HRMS (ESI) m/z [M+H]$^+$ calcd for C$_{29}$H$_{34}$FN$_2$O$_6$: 525.2396 found: 525.2368.

Example 202 (1S,4s)-4-(2-Fluoro-4-methoxy-5-(((1S,2R,3S,4R)-3-(((R*)-2-methylbutyl)carbamoyl) bicyclo[2.2.1]heptan-2-yl)carbamoyl)phenoxy)cyclohexane-1-carboxylic acid (Isomer 1) & Example 203 (1S,4s)-4-(2-Fluoro-4-methoxy-5-(((1S,2R,3S, 4R)-3-(((R*)-2-methylbutyl)carbamoyl)bicyclo [2.2.1]heptan-2-yl)carbamoyl)phenoxy)cyclohexane-1-carboxylic acid (Isomer 2)

ISOMER 1

ISOMER 2

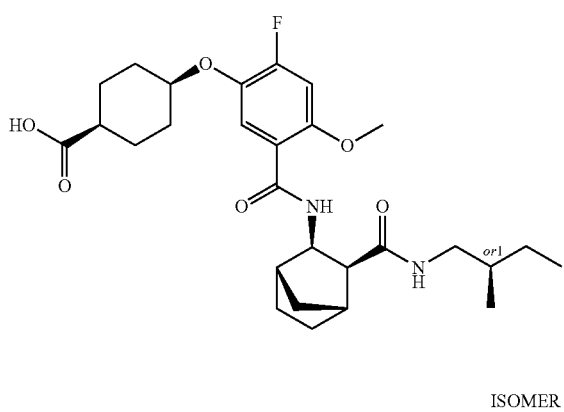

Step A. Intermediate 417: Ethyl (1S,4s)-4-(2-fluoro-4-methoxy-5-(((1S,2R,3S,4R)-3-(((RS)-2-methylbutyl)carbamoyl)bicyclo[2.2.1]heptan-2-yl)carbamoyl)phenoxy)cyclohexane-1-carboxylate

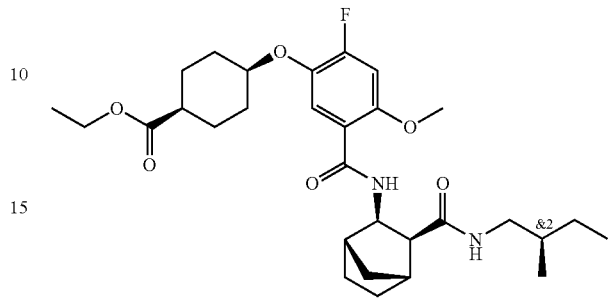

The compound was synthesized analogous to the procedure of Example 197 Step A. from Intermediate 106 and 2-methylbutan-1-amine. The crude product was purified by flash chromatography using heptane/EtOAc 1/2 as eluent to afford the title compound (85 mg, 74%). MS (ESI): m/z [M+H]$^+$ 547.5.

Step B. Intermediate 418: (1S,4s)-4-(2-Fluoro-4-methoxy-5-(((1S,2R,3S,4R)-3-(((RS)-2-methylbutyl) carbamoyl)bicyclo[2.2.1]heptan-2-yl)carbamoyl) phenoxy)cyclohexane-1-carboxylic acid

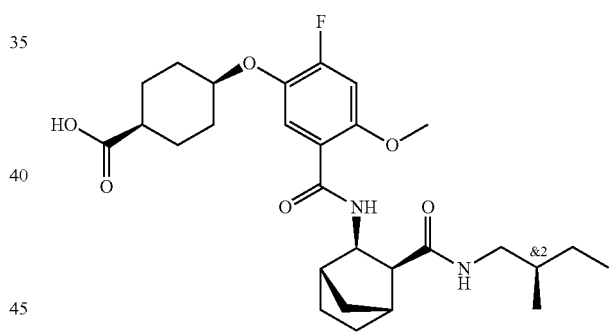

The hydrolysis of Intermediate 417 was carried out in an analogous way to Example 197 Step B. The crude product was purified by flash chromatography using 5% MeOH in EtOAc as eluent to afford the title compound (75 mg, 93%). MS (ESI): m/z [M+H]$^+$ 519.3.

Step C. Example 202 (1S,4s)-4-(2-Fluoro-4-methoxy-5-(((1S,2R,3S,4R)-3-(((R*)-2-methylbutyl) carbamoyl)bicyclo[2.2.1]heptan-2-yl)carbamoyl) phenoxy)cyclohexane-1-carboxylic acid (Isomer 1) & Example 203 (1S,4s)-4-(2-Fluoro-4-methoxy-5-(((1S,2R,3S,4R)-3-(((R*)-2-methylbutyl)carbamoyl) bicyclo[2.2.1]heptan-2-yl)carbamoyl)phenoxy)cyclohexane-1-carboxylic acid (Isomer 2)

The isomers of Intermediate 418 (75 mg, 0.14 mmol) were separated by preparative chiral HPLC on a Chiralpak IA column (5 um, 250×20 mm ID) using 0.1% of FA in a heptane:IPA (85:15) system as mobile phase to give the first eluting compound Isomer 1: Example 202 (28 mg, 37%);

HRMS (ESI) m/z [M+H]+ calcd for $C_{28}H_{40}FN_2O_6$: 519.2864 found: 519.2882 and the second eluting compound Isomer 2: Example 203 (26 mg, 35%); HRMS (ESI) m/z [M+H]+ calcd for $C_{28}H_{40}FN_2O_6$: 519.2864 found: 519.2868.

Example 204 (1S,4s)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)benzyl)-1-methylcyclohexane-1-carboxylic acid & Example 205 (1R,4r)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)benzyl)-1-methylcyclohexane-1-carboxylic acid

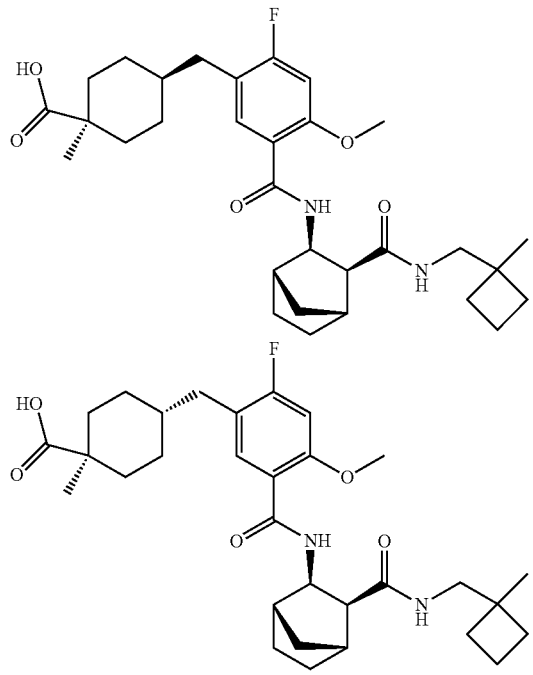

Step A. Intermediate 419: Naphthalen-1-ylmethyl 4-(2-fluoro-4-methoxy-5-(((1S,2R,3S,4R)-3-(((1-methylcyclobutyl)methyl)carbamoyl)bicyclo[2.2.1]heptan-2-yl)carbamoyl)benzylidene)-1-methylcyclohexane-1-carboxylate

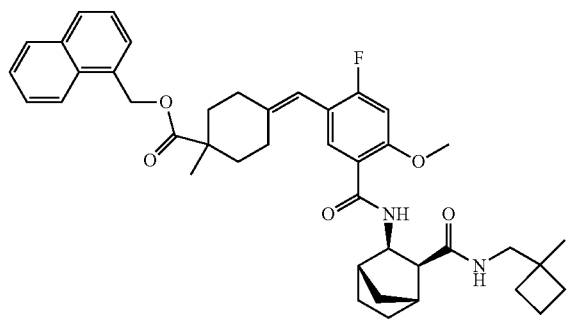 [SMILES: COc1cc(F)c(C=C2CCC(C)(C(=O)OCc3cccc4ccccc34)CC2)cc1C(=O)N[C@@H]1[C@H]2CC[C@H](C2)[C@@H]1C(=O)NCC1(C)CCC1]

DIPEA (0.129 mL, 0.74 mmol), HATU (188 mg, 0.49 mmol) and finally (1-methylcyclobutyl)methanamine hydrochloride (36.8 mg, 0.27 mmol) was added to Intermediate 126 (148 mg, 0.25 mmol) in DCM (1.10 mL) added. The reaction was stirred for 2 h. DCM and NaHCO3 (aq) was added and the phases was separated. The organic phase was evaporated and the crude product was purified by flash chromatography using a gradient of 10-50% EtOAc in heptane as mobile phase to give the title compound (136 mg, 81%) as a film/solid. $^1$H NMR (400 MHz, CDCl$_3$) δ 0.95 (s, 3H), 1.20 (d, 4H), 1.26-1.45 (m, 4H), 1.62-1.8 (m, 6H), 2.00 (s, 2H), 2.03-2.17 (m, 3H), 2.19-2.29 (m, 4H), 2.40 (dd, 1H), 2.43-2.54 (m, 2H), 2.95 (ddd, 1H), 3.18 (dd, 1H), 3.94 (s, 3H), 4.41 (t, 1H), 5.60 (q, 3H), 6.05 (s, 1H), 6.61 (d, 1H), 7.39-7.6 (m, 4H), 7.81-7.92 (m, 2H), 7.99 (dd, 2H), 8.48 (dd, 1H). MS (ESI): m/z [M+H]+ 681.7.

Step B. Intermediate 420: 4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)benzyl)-1-methylcyclohexane-1-carboxylic acid

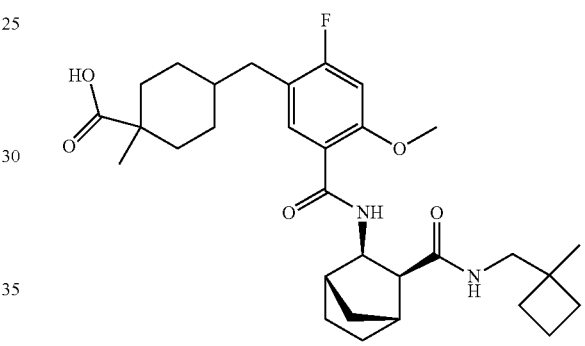

Intermediate 419 (136 mg, 0.20 mmol) was dissolved in ethanol (19.975 mL) and hydrogenated in a H-cube® reactor at 1 ml/min, rt, Full H2, Pd/C (CatCart 30 mm). The solvent was evaporated and the crude product was purified by Method PrepBasic-D (Gradient 10%-50%) to give the title compound (80 mg, 74%). $^1$H NMR (400 MHz, CDCl$_3$) δ 0.97 (d, 3H), 1.04-1.26 (m, 7H), 1.33 (d, 2H), 1.43-1.83 (m, 13H), 2.02-2.09 (m, 1H), 2.13-2.27 (m, 2H), 2.43-2.57 (m, 4H), 2.87-3 (m, 1H), 3.17 (dd, 1H), 3.94 (d, 3H), 4.44 (t, 1H), 5.80 (dt, 1H), 6.62 (dd, 1H), 7.9-8 (m, 1H), 8.49 (t, 1H). MS (ESI): m/z [M+H]+ 543.6.

Step C. Example 204 (1S,4s)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)benzyl)-1-methylcyclohexane-1-carboxylic acid & Example 205 (1R,4r)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)benzyl)-1-methylcyclohexane-1-carboxylic acid The isomers of Intermediate 420 (80 mg, 0.15 mmol) were separated by preparative SFC on a YMC SA (IA) column (5 um, 250×20 mm ID) using 31% EtOH/FA 100/0.5 in CO$_2$ (g) (123 bar) as mobile phase to give the first eluting compound Example 204 (30 mg, 40%); $^1$H NMR (400 MHz, CDCl$_3$) δ 0.97 (s, 3H), 1.05-1.25 (m, 8H), 1.32 (d, 2H), 1.47-1.63 (m, 7H), 1.66-1.83 (m, 4H), 2.05 (d, 1H), 2.21 (dd, 3H), 2.49 (dd, 4H), 2.92 (dd, 1H), 3.17 (dd, 1H), 3.94 (s, 3H), 4.43 (t, 1H), 5.88 (s, 1H), 6.61 (d, 1H), 7.95 (d, 1H), 8.47 (d, 1H). HRMS (ESI) m/z [M+H]+ calcd for $C_{31}H_{44}FN_2O_5$: 543.3228 found: 543.3218, and the second eluting compound Example 205 (30 mg, 40%); $^1$H NMR (400 MHz, CDCl$_3$) δ 0.95 (s, 3H), 1.14-1.3 (m, 7H), 1.33 (s, 2H), 1.47-1.59 (m, 6H), 1.59-1.8 (m, 8H), 2.05 (d, 1H), 2.23 (d, 1H), 2.46-2.54 (m, 4H), 2.91-2.96 (m, 1H), 3.17 (dd, 1H), 3.94 (s, 3H), 4.43 (t, 1H), 5.66 (s, 1H), 6.61 (d, 1H), 7.95 (d, 1H), 8.48 (d, 1H). HRMS (ESI) m/z [M+H]+ calcd for $C_{31}H_{44}FN_2O_5$: 543.3228 found: 543.3214.

Example 206 (1R,4s)-4-(2-Fluoro-5-(((1R,2S,3R,4S)-3-((4-fluoro-3-(pentafluoro-?6-sulfaneyl)phenyl)carbamoyl)bicyclo[2.2.1]heptan-2-yl)carbamoyl)-4-methoxyphenoxy)-1-methylcyclohexane-1-carboxylic acid

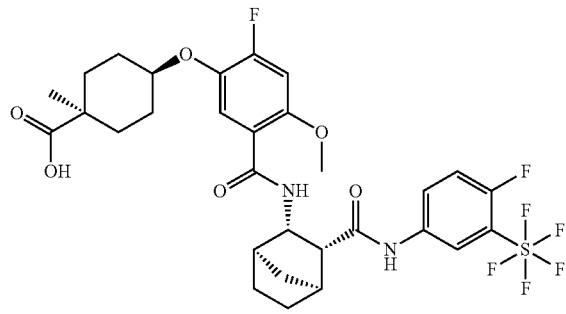 [SMILES: COc1cc(F)c(O[C@H]2CC[C@@](C)(C(=O)O)CC2)cc1C(=O)N[C@H]1[C@@H]2CC[C@@H](C2)[C@H]1C(=O)Nc1ccc(F)c(S(F)(F)(F)(F)F)c1]

Step A. Intermediate 421: tert-butyl (1R,4s)-4-(2-fluoro-5-(((1R,2S,3R,4S)-3-((4-fluoro-3-(pentafluoro-λ6-sulfaneyl)phenyl)carbamoyl)bicyclo[2.2.1]heptan-2-yl)carbamoyl)-4-methoxyphenoxy)-1-methylcyclohexane-1-carboxylate

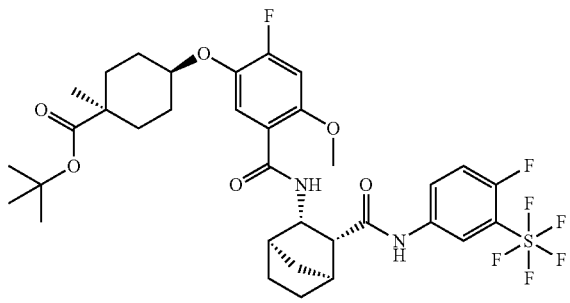 [SMILES: COc1cc(F)c(O[C@H]2CC[C@@](C)(C(=O)OC(C)(C)C)CC2)cc1C(=O)N[C@H]1[C@@H]2CC[C@@H](C2)[C@H]1C(=O)Nc1ccc(F)c(S(F)(F)(F)(F)F)c1]

DIEPA (0.822 mL, 4.71 mmol) was added dropwise to Intermediate 130 (815 mg, 1.57 mmol), 4-fluoro-3-(pentafluoro-λ6-sulfanyl)aniline (446 mg, 1.88 mmol) (Trasher, J. P. et al, J. Fluorine Chemistry (2001), 112(2), pp 287-295) and T3P (2994 mg, 4.71 mmol) in butyl acetate (30 mL) at 0° C. over a period of 1 min under nitrogen. The resulting solution was stirred at 20° C. for 14 h. The reaction mixture was diluted with EtOAc (1 L), and washed sequentially with NaHCO$_3$ (1×250 mL, sat), brine (3×300 mL, sat), and H$_2$O (2×300 mL). The organic layer was dried over Na$_2$SO$_4$, filtered and evaporated to afford crude product. The crude product was purified by reverse phase flash C-18 chromatography using a gradient of 0-75% MeCN in H$_2$O as mobile phase followed by preparative chiral SFC on a Phenomenex Lux Cellulose-4 column AXIA Packed (5 um, 250×21 mm ID) using 17% MeOH in CO$_2$ (g) as mobile phase to give the title compound (850 mg, 73%) as a pale yellow gum.

Step B. (1R,4s)-4-(2-Fluoro-5-(((1R,2S,3R,4S)-3-((4-fluoro-3-(pentafluoro-λ6-sulfaneyl)phenyl)carbamoyl)bicyclo[2.2.1]heptan-2-yl)carbamoyl)-4-methoxyphenoxy)-1-methylcyclohexane-1-carboxylic acid TFA (0.407 mL, 5.28 mmol) was added dropwise to Intermediate 421 (650 mg, 0.88 mmol) in DCM (50 mL) cooled to 0° C. over a period of 1 minute under nitrogen. The resulting solution was stirred at 20° C. for 14 h. The solvent was removed under reduced pressure to afford the title compound (570 mg, 88%) as a white solid by lyophilization. HRMS (ESI) m/z [M+H]+ calcd for $C_{30}H_{34}F_7N_2O_6S$: 683.2020 found: 683.2018.

Step C. (1R,4s)-4-(2-Fluoro-5-(((1R,2S,3R,4S)-3-((4-fluoro-3-(pentafluoro-λ6-sulfaneyl)phenyl)carbamoyl)bicyclo[2.2.1]heptan-2-yl)carbamoyl)-4-methoxyphenoxy)-1-methylcyclohexane-1-carboxylic acid Part of the material from Example 206 Step B. above (450 mg, 0.66 mmol) was submitted to further purification by preparative SFC on a YMC SA (IA) column (5 um, 250×30 mm ID) using 25% IPA/FA 100/0.5 in CO$_2$ (g) (120 bar) as mobile phase to give the title compound (351 mg, 78%). $^1$H NMR (500 MHz, DMSO-d6) δ 1.10 (s, 3H), 1.16-1.31 (m, 5H), 1.31-1.45 (m, 2H), 1.45-1.66 (m, 2H), 1.80 (t, 2H), 2.00 (dd, 3H), 2.13 (d, 1H), 2.43 (d, 1H), 2.75 (d, 1H), 3.80 (s, 3H), 4.03 (tt, 1H), 4.31 (t, 1H), 7.09 (d, 1H), 7.45 (dd, 1H), 7.50 (d, 1H), 7.62 (ddd, 1H), 8.33 (dd, 1H), 8.62 (d, 1H), 10.42 (s, 1H). HRMS (ESI) m/z [M+H]+ calcd for $C_{30}H_{34}F_7N_2O_6S$: 683.2020 found: 683.2042.

Example 207 (1S,4s)-4-(4-(Difluoromethoxy)-2-fluoro-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid

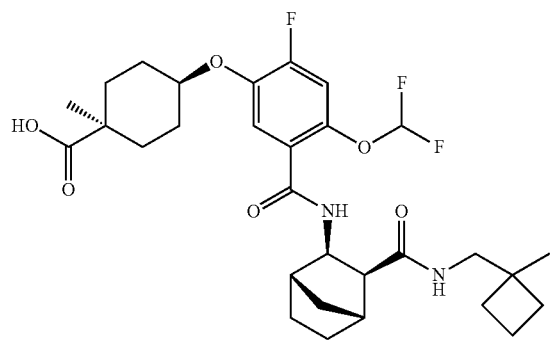 [SMILES: CC1(CNC(=O)[C@H]2[C@@H]3CC[C@@H](C3)[C@H]2NC(=O)c2cc(O[C@H]3CC[C@@](C)(C(=O)O)CC3)c(F)cc2OC(F)F)CCC1]

Step A. Intermediate 422: Naphthalen-1-ylmethyl (1S,4s)-4-(4-(difluoromethoxy)-2-fluoro-5-((((1R,2R,3S,4S)-3-(((1-methylcyclobutyl)methyl)carbamoyl)bicyclo[2.2.1]hept-5-en-2-yl)carbamoyl)phenoxy)-1-methylcyclohexane-1-carboxylate

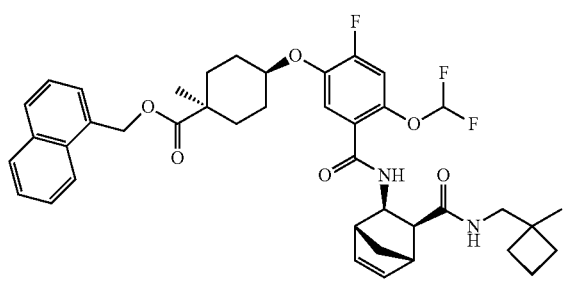 [SMILES: CC1(CNC(=O)[C@@H]2[C@H](NC(=O)c3cc(O[C@H]4CC[C@@](C)(C(=O)OCc5cccc6ccccc56)CC4)c(F)cc3OC(F)F)[C@H]3C=C[C@@H]2C3)CCC1]

DIPEA (0.305 mL, 1.75 mmol) was added dropwise to Intermediate 147 (195 mg, 0.39 mmol), Intermediate 21 (116 mg, 0.43 mmol) and EDC (186 mg, 0.97 mmol) HOBt (149 mg, 0.97 mmol) in DMF (10 mL) at 20° C. over a period of 1 min under nitrogen. The resulting solution was stirred at 25° C. for 14 h. The reaction mixture was diluted with EtOAc (100 mL), and washed sequentially with NaHCO$_3$ (1×75 mL, sat), NH$_4$Cl (1×75 mL, sat), and brine (1×100 mL, sat). The organic layer was dried over Na$_2$SO$_4$, filtered and evaporated to afford crude product. which was purified by preparative TLC (EtOAc/PE 1/4), to afford the title compound (258 mg, 92%) as a pale yellow solid. MS (ESI): m/z [M+H]$^+$ 719.

Step B. (1S,4s)-4-(4-(Difluoromethoxy)-2-fluoro-5-((((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid Intermediate 422 (258 mg, 0.36 mmol) and Pd—C (40 mg, 0.38 mmol) in MeOH (15 mL) was stirred under an atmosphere of hydrogen at 1.25 atm and 28° C. for 14 h. The solvent was removed under reduced pressure and the crude product was purified by Method PrepAcidic-L (Gradient: 70%-95%) to afford the title compound (82 mg, 39.3%) as a white solid. $^1$H NMR (400 MHz, DMSO-d6) δ 0.95 (s, 3H), 1.05-1.35 (m, 8H), 1.36-1.58 (m, 6H), 1.61-1.81 (m, 4H), 1.87-1.99 (m, 2H), 2-2.14 (m, 4H), 2.22 (s, 1H), 2.65 (d, 1H), 2.93 (dd, 1H), 3.06 (dd, 1H), 4.09 (t, 1H), 4.25-4.35 (m, 1H), 7.11 (t, 1H, OCHF2), 7.25 (d, 1H), 7.37 (d, 1H), 7.95 (t, 1H), 8.25 (d, 1H), 12.33 (s, 1H). HRMS (ESI) m/z [M+H]$^+$ calcd for C$_{30}$H$_{40}$F$_3$N$_2$O$_6$: 581.2832 found: 581.2882.

Example 208 (1S,4s)-4-(2-Fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenoxy)-1-methylcyclohexane-1-carboxylic acid

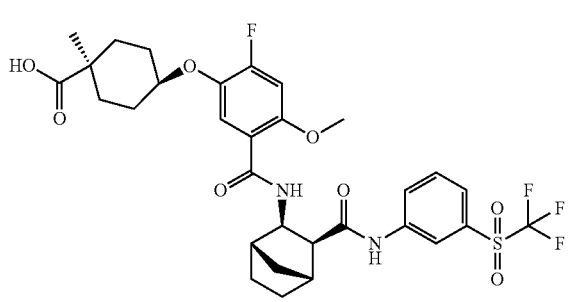 [SMILES: COc1cc(F)c(O[C@H]2CC[C@@](C)(C(=O)O)CC2)cc1C(=O)N[C@@H]1[C@H]2CC[C@H](C2)[C@@H]1C(=O)Nc1cccc(S(=O)(=O)C(F)(F)F)c1]

Step A. Intermediate 423: tert-Butyl (1S,4s)-4-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenoxy)-1-methylcyclohexane-1-carboxylate

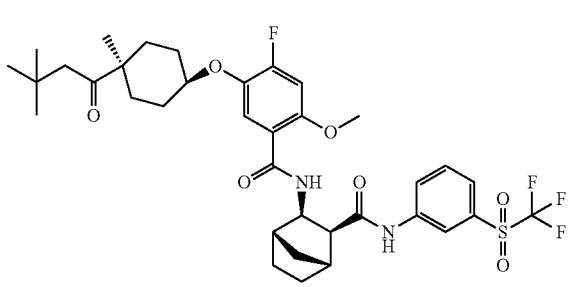 [SMILES: COc1cc(F)c(O[C@H]2CC[C@@](C)(C(=O)CC(C)(C)C)CC2)cc1C(=O)N[C@@H]1[C@H]2CC[C@H](C2)[C@@H]1C(=O)Nc1cccc(S(=O)(=O)C(F)(F)F)c1]

Intermediate 73 (2.216 g, 5.80 mmol), HATU (6.61 g, 17.39 mmol), DIEA (4.05 mL, 23.18 mmol) and Intermediate 153 (2.1 g, 5.80 mmol) in DMF (50 mL) were stirred at 20° C. for 3h. The reaction mixture was diluted with EtOAc (50 mL), and washed sequentially with brine (3×5 mL, sat), NaHCO$_3$ (3×5 mL, sat). The organic layer was dried over Na$_2$SO$_4$, filtered and evaporated to afford crude product which was purified by flash chromatography using a gradient of 0-50% EtOAc in PE as mobile phase to give the title compound (3.61 g, 86%) as a pale yellow solid. MS (ESI): m/z [M+H]$^+$ 685.

Step B. (1S,4s)-4-(2-Fluoro-4-methoxy-5-((((1S,2R, 3S,4R)-3-((3-(((trifluoromethyl)sulfonyl)phenyl)car-bamoyl)bicyclo[2.2.1]heptan-2-yl)carbamoyl)phe-noxy)-1-methylcyclohexane-1-carboxylic acid

Step A. Intermediate 424: Ethyl 2'-fluoro-4'-methoxy-5'-((((1S,2R,3S,4R)-3-((3-(pentafluoro-λ⁶-sulfaneyl)phenyl)carbamoyl)bicyclo[2.2.1]heptan-2-yl)carbamoyl)-[1,1'-biphenyl]-4-carboxylate

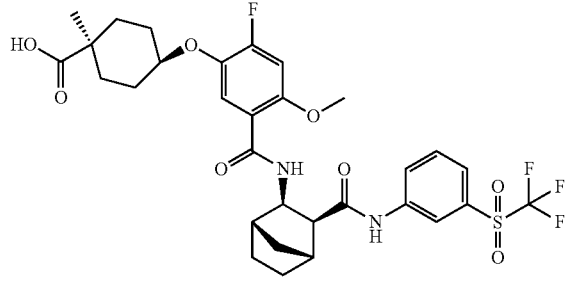 [SMILES: COc1cc(F)c(O[C@H]2CC[C@@](C)(C(=O)O)CC2)cc1C(=O)N[C@@H]1[C@H]2CC[C@H](C2)[C@@H]1C(=O)Nc1cccc(S(=O)(=O)C(F)(F)F)c1]

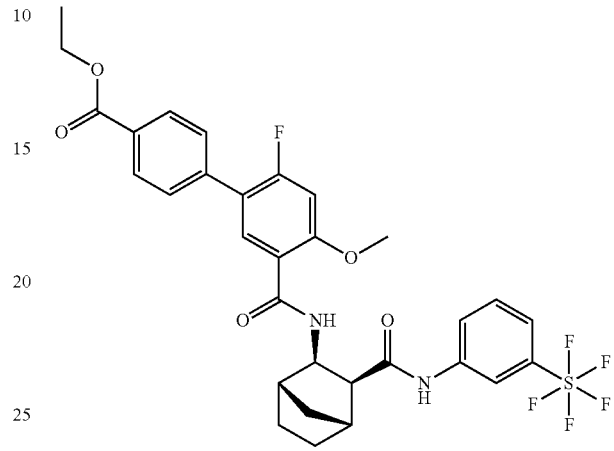

TFA (10 mL, 129.80 mmol) was added dropwise to Intermediate 423 (2.4 g, 3.30 mmol) in DCM (15 mL) at 0° C. over a period of 1 min under air. The resulting solution was stirred at rt for 14 h. The solvent was removed under reduced pressure and the crude product was purified by preparative SFC on a Lux Cellulose (Chiral-A(LUX-3)) column (5 um, 250×34.6 mm ID) using 10% IPA/DEA 100/0.1 in CO$_2$ (g) as mobile phase to afford the title compound (1.600 g, 72.2%) as a white solid. The product was combined with two other batches (2.8 g, 4.17 mmol) and purified by preparative SFC on a Chiralpak IA column (5 μm, 50×250 mm ID) using 60% MeOH/IPA 100/0.1 in CO$_2$ (g) as mobile phase to afford the title compound (2.0 g, 71%) as a white solid. HRMS (ESI) m/z [M+H]$^+$ calcd for C$_{31}$H$_{38}$F$_4$N$_2$O$_8$S: 671.2044 found: 671.2026.

3-(pentafluoro-λ⁶-sulfanyl)aniline (201 mg, 0.92 mmol), HATU (952 mg, 2.50 mmol), DIPEA (0.291 mL, 1.67 mmol) and DMAP (10.19 mg, 0.08 mmol) were added to Intermediate 157 (380 mg, 0.83 mmol) in DMF (3 mL). The reaction mixture was stirred at 20° C. overnight. The reaction mixture was diluted with EtOAc (50 mL), and washed sequentially with brine (3×25 mL, sat). The organic layer was dried over Na$_2$SO$_4$, filtered and evaporated to afford the crude product which was purified by preparative TLC (PE/EtOAc 1/1), to afford the title compound (also containing some methyl ester present in the starting material) (180 mg, 32.9%) as a yellow oil which solidified on standing. MS (ESI): m/z [M+H]$^+$ 657 (ethyl ester). MS (ESI): m/z [M+H]$^+$ 643 (methyl ester).

Example 209 2'-Fluoro-4'-methoxy-5'-((((1S,2R,3S,4R)-3-((3-(pentafluoro-λ6-sulfaneyl)phenyl)carbam-oyl)bicyclo[2.2.1]heptan-2-yl)carbamoyl)-[1,1'-bi-phenyl]-4-carboxylic acid

Step B. 2'-Fluoro-4'-methoxy-5'-((((1S,2R,3S,4R)-3-((3-(pentafluoro-λ⁶-sulfaneyl)phenyl)carbamoyl)bicyclo[2.2.1]heptan-2-yl)carbamoyl)-[1,1'-biphe-nyl]-4-carboxylic acid

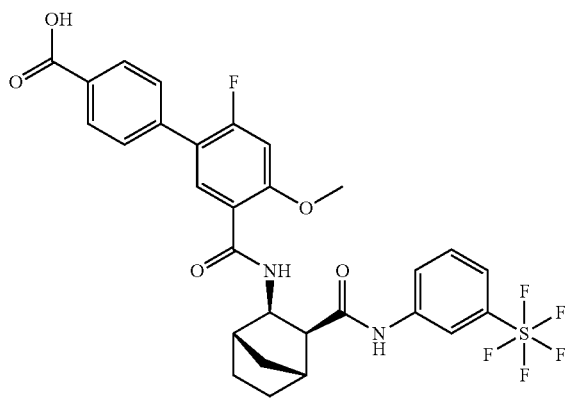 [SMILES: COc1cc(F)c(-c2ccc(C(=O)O)cc2)cc1C(=O)N[C@@H]1[C@H]2CC[C@H](C2)[C@@H]1C(=O)Nc1cccc(S(F)(F)(F)(F)F)c1]

LiOH (19.69 mg, 0.82 mmol) was added to Intermediate 424 (180 mg, 0.27 mmol) in EtOH (4 mL)/H$_2$O (2 mL). The reaction mixture was stirred at 20° C. for 5h. The reaction mixture was diluted with EtOAc (100 mL), and washed sequentially with brine (3×50 mL, sat). The organic layer was dried over Na$_2$SO$_4$, filtered and evaporated to afford crude product which was purified by Method PrepAcidic-C to afford the title compound (58.0 mg, 32%) as a white solid. $^1$H NMR (400 MHz, CD$_3$OD) δ 1.37 (dd, 3H), 1.58-1.77 (m, 2H), 2.12 (d, 1H), 2.28 (d, 1H), 2.58 (s, 1H), 2.86 (d, 1H), 3.97 (s, 3H), 4.49 (d, 1H), 7.01 (d, 1H), 7.42 (dt, 2H), 7.56 (t, 3H), 8.06 (dd, 3H), 8.27 (s, 1H). HRMS (ESI) m/z [M+H]$^+$ calcd for C$_{29}$H$_{27}$F$_6$N$_2$O$_5$S: 629.1540 found: 629.1552.

Example 210 2'-Fluoro-4'-methoxy-5'-(((1S,2R,3S,4R)-3-((4-(pentafluoro-λ⁶-sulfaneyl)phenyl)carbamoyl)bicyclo[2.2.1]heptan-2-yl)carbamoyl)-[1,1'-biphenyl]-4-carboxylic acid

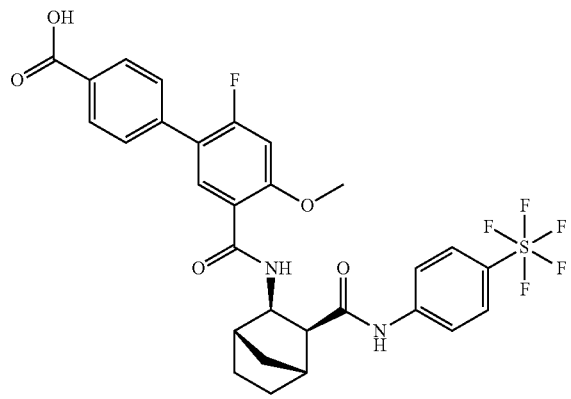 [SMILES: COc1cc(F)c(-c2ccc(C(=O)O)cc2)cc1C(=O)N[C@@H]1[C@H]2CC[C@H](C2)[C@@H]1C(=O)Nc1ccc(S(F)(F)(F)(F)F)cc1]

Step A. Intermediate 425: Ethyl 2'-fluoro-4'-methoxy-5'-(((1S,2R,3S,4R)-3-((4-(pentafluoro-λ⁶-sulfaneyl)phenyl)carbamoyl)bicyclo[2.2.1]heptan-2-yl)carbamoyl)-[1,1'-biphenyl]-4-carboxylate

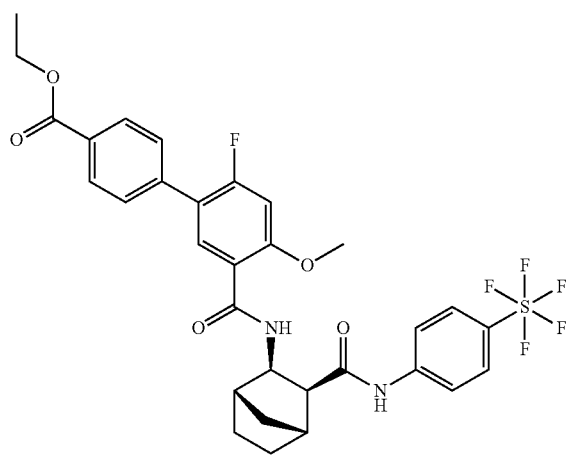 [SMILES: CCOC(=O)c1ccc(-c2cc(C(=O)N[C@@H]3[C@H]4CC[C@H](C4)[C@@H]3C(=O)Nc3ccc(S(F)(F)(F)(F)F)cc3)c(OC)cc2F)cc1]

4-(pentafluoro-λ⁶-sulfanyl)aniline (106 mg, 0.48 mmol), HATU (250 mg, 0.66 mmol), DIEA (0.153 mL, 0.88 mmol) and DMAP (5.36 mg, 0.04 mmol) were added to Intermediate 157 (200 mg, 0.44 mmol). The reaction mixture was stirred at 20° C. for 2 h. The reaction mixture was diluted with EtOAc (100 mL), and washed sequentially with brine (3×50 mL, sat). The organic layer was dried over Na$_2$SO$_4$, filtered and evaporated to afford crude product which was purified by preparative TLC (PE/EtOAc 1/1), to afford the title compound (also containing some methyl ester present in the starting material) (103 mg, 36%) as a white solid. MS (ESI): m/z [M+H]$^+$ 657 (ethyl ester) MS (ESI): m/z [M+H]$^+$ 643 (methyl ester).

Step B. 2'-Fluoro-4'-methoxy-5'-(((1S,2R,3S,4R)-3-((4-(pentafluoro-λ⁶-sulfaneyl)phenyl)carbamoyl)bicyclo[2.2.1]heptan-2-yl)carbamoyl)-[1,1'-biphenyl]-4-carboxylic acid LiOH (11.27 mg, 0.47 mmol) was added to Intermediate 425 (103 mg, 0.16 mmol) in EtOH (4 mL)/H$_2$O (2.0 mL). The reaction mixture was stirred at 20° C. for 5h. The reaction mixture was diluted with EtOAc (100 mL), and washed sequentially with brine (3×50 mL, sat). The organic layer was dried over Na$_2$SO$_4$, filtered and evaporated to afford crude product which was purified by Method PrepAcidic-C to afford the title compound (80 mg, 79%) as a white solid. HRMS (ESI) m/z [M+H]$^+$ calcd for C$_{29}$H$_{27}$F$_6$N$_2$O$_5$S: 629.1540 found: 629.1594.

Example 211 (1s,4s)-4-(5-((2,4-Dimethyl-6-(((1-methylcyclobutyl)methyl)carbamoyl)phenyl)carbamoyl)-2-fluoro-4-methoxyphenoxy)-1-methylcyclohexane-1-carboxylic acid

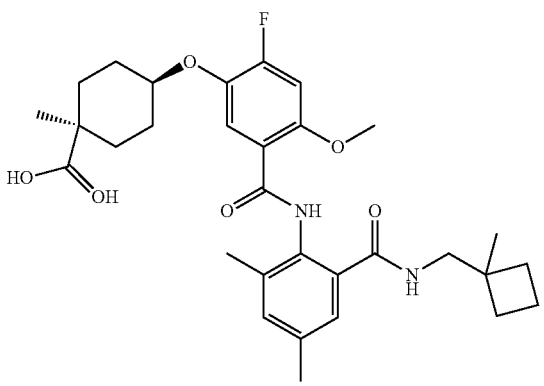 [SMILES: COc1cc(F)c(O[C@H]2CC[C@@](C)(C(=O)O)CC2)cc1C(=O)Nc1c(C)cc(C)cc1C(=O)NCC1(C)CCC1]

Step A. Intermediate 426: Naphthalen-1-ylmethyl (1s,4s)-4-(5-((2,4-dimethyl-6-(((1-methylcyclobutyl)methyl)carbamoyl)phenyl)carbamoyl)-2-fluoro-4-methoxyphenoxy)-1-methylcyclohexane-1-carboxylate

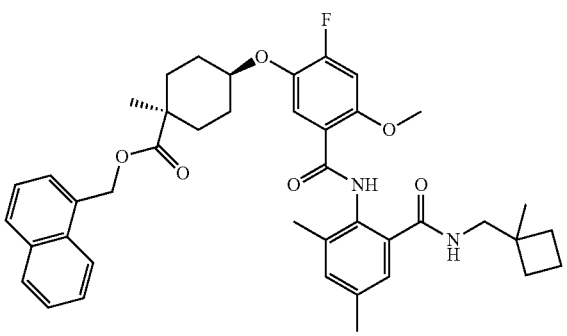 [SMILES: COc1cc(F)c(O[C@H]2CC[C@@](C)(C(=O)OCc3cccc4ccccc34)CC2)cc1C(=O)Nc1c(C)cc(C)cc1C(=O)NCC1(C)CCC1]

Intermediate 13 (121 mg, 0.26 mmol) and HATU (197 mg, 0.52 mmol) was diluted in DCM (1161 μL) and DIPEA (136 μL, 0.78 mmol) was added. The mixture was added to Intermediate 161 (81 mg, 0.29 mmol) and the reaction was stirred overnight. The crude product was purified by flash chromatography using a gradient of 10-60% EtOAc in heptane as mobile phase to give the title compound (121 mg, 38%) as a solid. $^1$H NMR (400 MHz, CDCl$_3$) δ 1.02 (s, 3H). 1.18 (s, 3H), 1.21-1.32 (m, 3H), 1.54 (s, 2H), 1.62 (s, 1H), 1.69-1.82 (m, 4H), 1.92-2.02 (m, 2H), 2.24 (s, 3H), 2.29 (d, 2H), 2.35 (s, 3H), 3.31 (d, 2H), 3.99 (s, 3H), 4.15 (td, 1H), 5.61 (s, 2H), 6.37 (t, 1H), 6.80 (d, 1H), 7.16 (s, 2H), 7.41-7.63 (m, 4H), 7.88 (dd, 3H), 8.01 (d, 1H), 9.72 (s, 1H). MS (ESI): m/z [M+H]$^+$ 695.7.

Step B. (1s,4s)-4-(5-(((2,4-Dimethyl-6-(((1-methyl-cyclobutyl)methyl)carbamoyl)phenyl)carbamoyl)-2-fluoro-4-methoxyphenoxy)-1-methylcyclohexane-1-carboxylic acid Intermediate 426 (69 mg, 0.10 mmol) was dissolved in THF/MeOH 1/9 10 mL and hydrogenated in a H-cube® reactor at 1 mL/min, rt, Full H2, Pd/C (CatCart 30 mm). The compound was purified by Method SFC-B to give the title compound (40 mg, 73%). $^1$H NMR (600 MHz, DMSO-d6) δ 0.98 (s, 3H), 1.11 (s, 3H), 1.23-1.32 (m, 2H), 1.39-1.49 (m, 4H), 1.6-1.76 (m, 2H), 1.8-1.87 (m, 2H), 1.87-1.94 (m, 2H), 2.07 (d, 2H), 2.17 (s, 3H), 2.32 (s, 3H), 3.17 (d, 2H), 3.94 (s, 3H), 4.18 (dt, 1H), 7.13 (s, 1H), 7.20 (d, 2H), 7.66 (d, 1H), 8.24 (t, 1H), 10.05 (s, 1H). HRMS (ESI) m/z [M+H]$^+$ calcd for C$_{31}$H$_{40}$FN$_2$O$_6$: 555.2864 found: 555.2874.

Example 212 (1s,4s)-4-(5-((4,5-Dimethyl-2-(((1-methylcyclobutyl)methyl)carbamoyl)phenyl)carbamoyl)-2-fluoro-4-methoxyphenoxy)-1-methylcyclohexane-1-carboxylic acid

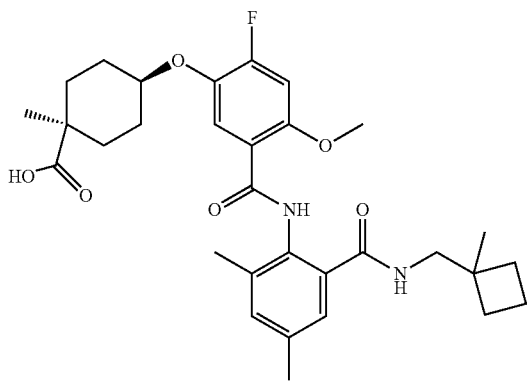 [SMILES: COc1cc(F)c(O[C@H]2CC[C@@](C)(C(=O)O)CC2)cc1C(=O)Nc1c(C)cc(C)cc1C(=O)NCC1(C)CCC1]

Step A. Intermediate 427: Naphthalen-1-ylmethyl (1s,4s)-4-(5-((4,5-dimethyl-2-(((1-methylcyclobutyl)methyl)carbamoyl)phenyl)carbamoyl)-2-fluoro-4-methoxyphenoxy)-1-methylcyclohexane-1-carboxylate

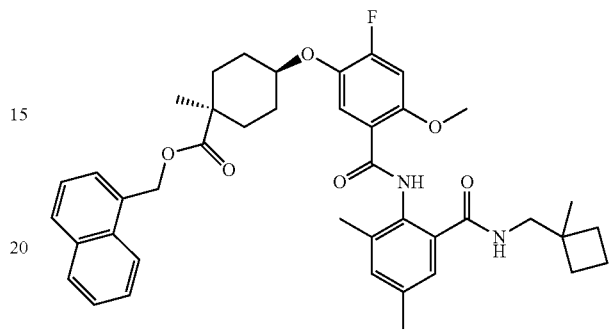

Intermediate 13 (125 mg, 0.27 mmol) and HATU (204 mg, 0.54 mmol) was diluted in DCM (1199 μL) and DIPEA (140 μL, 0.80 mmol) and the mixture was added to Intermediate 163 (83 mg, 0.29 mmol) and the reaction was stirred for 2 h. Added DCM and NaHCO$_3$ (aq) and separated the phases. The residue was purified by flash chromatography using a gradient of 5-50% EtOAc in heptane as mobile phase to give the title compound (92 mg, 49.4%) as solid. $^1$H NMR (400 MHz, CDCl$_3$) δ 1.18 (s, 6H), 1.22-1.32 (m, 3H), 1.61 (d, 2H), 1.74 (d, 2H), 1.91 (d, 3H), 1.99 (d, 2H), 2.30 (d, 8H), 3.43 (d, 2H), 4.05 (s, 3H), 4.18 (s, 1H), 5.61 (s, 2H), 6.01 (s, 1H), 6.77 (d, 1H), 7.18 (s, 1H), 7.41-7.62 (m, 4H), 7.82-7.96 (m, 3H), 8.01 (d, 1H), 8.46 (s, 1H), 11.60 (s, 1H). MS (ESI): m/z [M+H]$^+$ 695.7.

Step B. (1s,4s)-4-(5-((4,5-Dimethyl-2-(((1-methylcyclobutyl)methyl)carbamoyl)phenyl)carbamoyl)-2-fluoro-4-methoxyphenoxy)-1-methylcyclohexane-1-carboxylic acid Intermediate 427 (92 mg, 0.13 mmol) was dissolved in MeOH/THF and hydrogenated in a H-cube® reactor at 1 mL/min, rt, Full H2, Pd/C (CatCart 30 mm). Evaporated the solvent to give the crude product as a solid which was purified by Method SFC-B. $^1$H NMR (600 MHz, DMSO) δ 1.12 (d, 6H), 1.29 (td, 2H), 1.41-1.51 (m, 2H), 1.60 (ddd, 2H), 1.81 (dddd, 2H), 1.89-2 (m, 4H), 2.08 (d, 2H), 2.26 (d, 6H), 3.29 (s, 2H), 3.97 (s, 3H), 4.21 (tt, 1H), 4.21 (tt, 1H), 7.19 (d, 1H), 7.43 (s, 1H), 7.74 (d, 1H), 8.39 (s, 1H), 8.53 (t, 1H), 11.77 (s, 1H). HRMS (ESI) m/z [M+H]$^+$ calcd for C$_{31}$H$_{40}$FN$_2$O$_6$: 555.2864 found: 555.2868.

Example 213 (1s,4s)-4-(2-Fluoro-5-((2-((4-fluoro-3-(trifluoromethyl)phenyl)carbamoyl)cyclohex-1-en-1-yl)carbamoyl)-4-methoxyphenoxy)cyclohexane-1-carboxylic acid

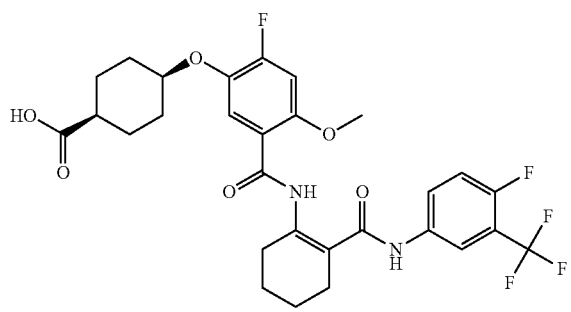 [SMILES: COc1cc(F)c(O[C@H]2CC[C@@H](C(=O)O)CC2)cc1C(=O)NC1=C(C(=O)Nc2ccc(F)c(C(F)(F)F)c2)CCCC1]

Step A. Intermediate 428: Ethyl (1s,4s)-4-(2-fluoro-5-((2-((4-fluoro-3-(trifluoromethyl)phenyl)carbamoyl)cyclohex-1-en-1-yl)carbamoyl)-4-methoxyphenoxy)cyclohexane-1-carboxylate

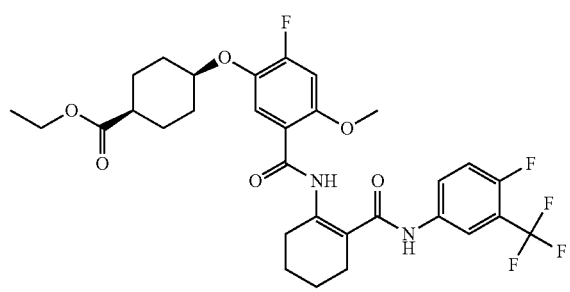 [SMILES: CCOC(=O)[C@H]1CC[C@@H](Oc2cc(C(=O)NC3=C(C(=O)Nc4ccc(F)c(C(F)(F)F)c4)CCCC3)c(OC)cc2F)CC1]

$Pd_2(dba)_3$ (40.5 mg, 0.04 mmol) and Xantphos (51.2 mg, 0.09 mmol) were added to Intermediate 165 (150 mg, 0.44 mmol), Intermediate 166 (212 mg, 0.49 mmol) and $Cs_2CO_3$ (432 mg, 1.33 mmol) in 1,4-dioxane (15 mL) at 20° C. The resulting suspension was stirred at 110° C. for 15 h under nitrogen. The reaction mixture was poured into brine (150 mL, sat), extracted with EtOAc (3×50 mL), the organic layer was dried over $Na_2SO_4$, filtered and evaporated to afford yellow oil. The residue was purified by preparative TLC (EtOAc/PE 2/5), to afford the title compound (120 mg, 43.5%) as a pale yellow oil. MS (ESI): m/z [M+H]$^+$ 647.2.

Step B. (1s,4s)-4-(2-Fluoro-5-((2-((4-fluoro-3-(trifluoromethyl)phenyl)carbamoyl)cyclohex-1-en-1-yl)carbamoyl)-4-methoxyphenoxy)cyclohexane-1-carboxylic acid LiOH (0.50 g, 20.88 mmol) was added to Intermediate 428 (0.12 g, 0.19 mmol) in THF (4 mL), MeOH (1 mL) and $H_2O$ (1 mL) at 20° C. The resulting solution was stirred at 20° C. for 15 h. The reaction mixture was poured into $H_2O$ (150 mL), the reaction mixture was acidified with 2 M HCl. The aq layer was extracted with EtOAc (3×50 mL), the organic layer was dried over $Na_2SO_4$, filtered and evaporated to afford colorless oil which solidified on standing. The crude product was purified by Method PrepAcidic-A (Gradient 50%-67%) to give the title compound (0.019 g, 16.58%) as a white solid. $^1$H NMR (400 MHz, DMSO-d6): δ 1.57-1.69 (m, 8H), 1.7-1.84 (m, 4H), 2.29-2.41 (m, 1H), 2.44-2.49 (m, 2H), 2.8-2.95 (m, 2H), 3.89 (s, 3H), 4.39 (s, 1H), 7.19 (d, 1H), 7.49 (t, 1H), 7.59 (d, 1H), 7.93-7.99 (m, 1H), 8.21 (dd, 1H), 9.70 (s, 1H), 11.97 (s, 1H), 12.16 (s, 1H). MS (ESI): m/z [M+Na]$^+$619.4.

Example 214 (1s,4s)-4-(2-Fluoro-5-((2-((4-fluoro-3-(trifluoromethyl)phenyl)carbamoyl)cyclopent-1-en-1-yl)carbamoyl)-4-methoxyphenoxy)cyclohexane-1-carboxylic acid

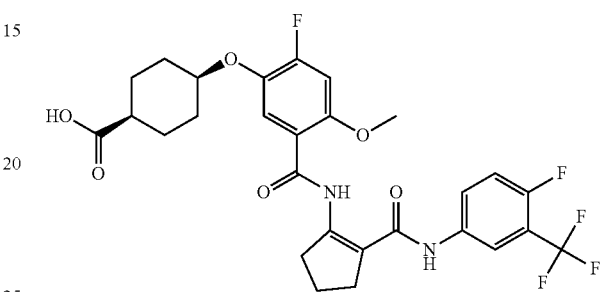

Step A. Intermediate 429: Ethyl (1s,4s)-4-(2-fluoro-5-((2-((4-fluoro-3-(trifluoromethyl)phenyl)carbamoyl)cyclopent-1-en-1-yl)carbamoyl)-4-methoxyphenoxy)cyclohexane-1-carboxylate

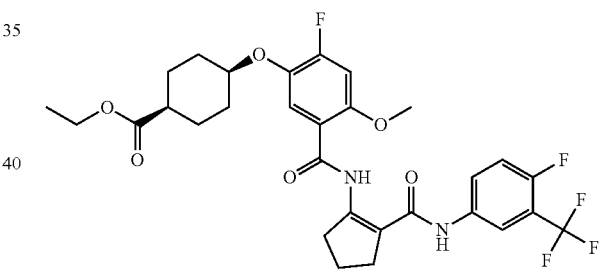

$Pd_2(dba)_3$ (40.5 mg, 0.04 mmol) and Xantphos (51.2 mg, 0.09 mmol) were added to Intermediate 165 (150 mg, 0.44 mmol), Intermediate 168 (205 mg, 0.49 mmol) and $Cs_2CO_3$ (432 mg, 1.33 mmol) in 1,4-dioxane (15 mL) at 20° C. The resulting suspension was stirred at 110° C. for 15 h under nitrogen. The reaction mixture was combined with a second batch prepared in the same way (0.59 mmol scale) were poured into brine (150 mL, sat), extracted with EtOAc (3×50 mL), the organic layer was dried over $Na_2SO_4$, filtered and evaporated to afford a brown oil. The residue was purified by preparative TLC (EtOAc/PE 1/3), to afford the title compound (160 mg, 25.4%, total yield based on the two batches combined) as a pale yellow oil which solidified on standing. MS (ESI): m/z [M+Na]$^+$633.2.

Step B. (1s,4s)-4-(2-Fluoro-5-((2-((4-fluoro-3-(trifluoromethyl)phenyl)carbamoyl)cyclopent-1-en-1-yl)carbamoyl)-4-methoxyphenoxy)cyclohexane-1-carboxylic acid LiOH (0.50 g, 20.88 mmol) was added to Intermediate 429 (0.16 g, 0.26 mmol) in THF (4 mL), MeOH (1 mL) and H₂O (1 mL) at 20° C. The resulting solution was stirred at 20° C. for 15 h. The reaction mixture was poured into H₂O (150 mL), the reaction mixture was acidified with 2 M HCl. The aq layer was extracted with EtOAc (3×50 mL), the organic layer was dried over Na₂SO₄, filtered and evaporated to afford colorless oil which solidified on standing. The crude product was purified by Method PrepAcidic-A (Gradient 72%-83%) to give the title compound (0.068 g, 44.5%) as a white solid. HRMS (ESI) m/z [M+H]⁺ calcd for C₂₈H₂₈F₅N₂O₆: 583.1862 found: 583.1844.

Example 215 (1s,4s)-4-(2-Fluoro-4-methoxy-5-((3-(((1-methylcyclobutyl)methyl)carbamoyl)naphthalen-2-yl)carbamoyl)phenoxy)-1-methylcyclohexane-1-carboxylic acid

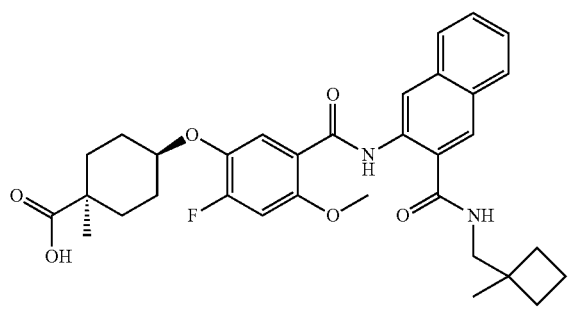 [SMILES: COc1cc(F)c(O[C@H]2CC[C@@](C)(C(=O)O)CC2)cc1C(=O)Nc1cc2ccccc2cc1C(=O)NCC1(C)CCC1]

Step A. Intermediate 430: Naphthalen-1-ylmethyl (1s,4s)-4-(2-fluoro-4-methoxy-5-((3-(((1-methylcyclobutyl)methyl)carbamoyl)naphthalen-2-yl)carbamoyl)phenoxy)-1-methylcyclohexane-1-carboxylate

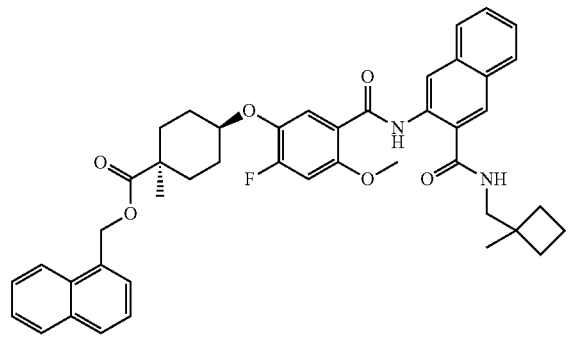 [SMILES: COc1cc(F)c(O[C@H]2CC[C@@](C)(C(=O)OCc3cccc4ccccc34)CC2)cc1C(=O)Nc1cc2ccccc2cc1C(=O)NCC1(C)CCC1]

Intermediate 170 (130 mg, 0.51 mmol) was added to Intermediate 13 (358 mg, 0.77 mmol), T3P (1626 mg, 5.11 mmol), DIPEA (198 mg, 1.53 mmol) in EtOAc (10 mL) at 20° C. The resulting solution was stirred at 30° C. for 12 h. The reaction mixture was concentrated and diluted with EtOAc (200 mL), and washed sequentially with NH₄Cl (1×200 mL, sat), H₂O (1×200 mL), and brine (1×200 mL). The organic layer was dried over Na₂SO₄, filtered and evaporated to afford crude product which was purified by preparative TLC (MeOH/DCM 1/10), to afford the title compound (90 mg, 24.6%) as a yellow solid.

Step B. (1s,4s)-4-(2-Fluoro-4-methoxy-5-((3-(((1-methylcyclobutyl)methyl)carbamoyl)-naphthalen-2-yl)carbamoyl)phenoxy)-1-methylcyclohexane-1-carboxylic acid Pd—C (1.336 mg, 0.01 mmol) was added to Intermediate 430 (90 mg, 0.13 mmol) in EtOAc (1 mL)/MeOH (2 mL)/THF (1 mL) at 20° C. and the reaction mixture was placed under an atmosphere of hydrogen and stirred at 30° C. for 2 h. The reaction mixture was filtered through silica. The solvent was removed by distillation under vacuum. The crude product was purified by preparative Method PrepAcidic-N (Gradient: 15%-25%) to afford the title compound (35.0 mg, 48%) as a white solid. HRMS (ESI) m/z [M+H]⁺ calcd for C₃₃H38FN₂O₆: 577.2708 found: 577.2714.

Example 216 (1s,4s)-4-(2-Fluoro-4-methoxy-5-((4-methyl-2-(((1-methylcyclobutyl)methyl)-carbamoyl)phenyl)carbamoyl)phenoxy)-1-methylcyclohexane-1-carboxylic acid

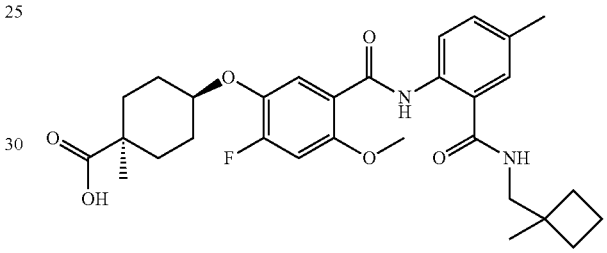

Step A. Intermediate 431: Naphthalen-1-ylmethyl (1s,4s)-4-(2-fluoro-4-methoxy-5-((4-methyl-2-(((1-methylcyclobutyl)methyl)carbamoyl)phenyl)carbamoyl)phenoxy)-1-methylcyclohexane-1-carboxylate

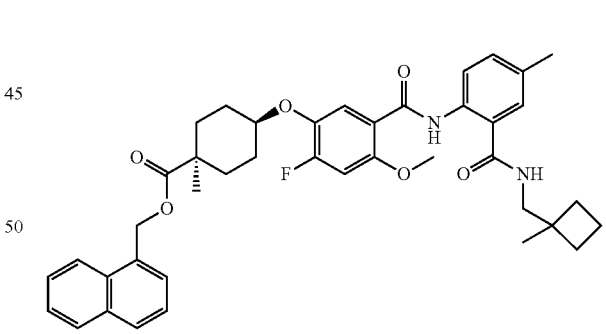

Intermediate 172 (130 mg, 0.48 mmol) was added to Intermediate 13 (271 mg, 0.58 mmol), T3P (1539 mg, 4.84 mmol) and DIPEA (188 mg, 1.45 mmol) in n-Butyl acetate (10 mL) at 20° C. The resulting solution was stirred at 120° C. for 3 h. The reaction mixture was concentrated and diluted with EtOAc (150 mL) and washed sequentially with NH₄Cl (1×200 mL, sat), H₂O (1×200 mL) and brine (1×200 mL, sat). The organic layer was dried over Na₂SO₄, filtered and evaporated to afford the crude product which was purified by preparative TLC (PE/EtOAc 3/1), to afford the title compound (100 mg, 30.4%) as a yellow solid. MS (ESI): m/z [M+Na]⁺703.3.

Step B. (1s,4s)-4-(2-Fluoro-4-methoxy-5-((4-methyl-2-(((1-methylcyclobutyl)methyl)-carbamoyl)phenyl)carbamoyl)phenoxy)-1-methylcyclohexane-1-carboxylic acid Pd—C (1.563 mg, 0.01 mmol) was added to Intermediate 431 (100 mg, 0.15 mmol) in MeOH (1 mL)/THF (0.5 mL)EtOAc (0.5 mL)/at 20° C. and the reaction mixture was placed under an atmosphere of hydrogen and stirred at 30° C. for 2 h. The reaction mixture was filtered through silica. The solvent was removed by distillation under vacuum to give the crude product which was purified by Method PrepBasic-H (Gradient 47-65%) to afford the title compound (40.0 mg, 50.4%) as a white solid. HRMS (ESI) m/z [M+H]+ calcd for $C_{30}H_{38}FN_2O_6$: 541.2708 found: 541.2736.

Example 217 (1s,4s)-4-(2-Fluoro-4-methoxy-5-((3-(((1-methylcyclobutyl)methyl)carbamoyl)pyrazolo[1,5-a]pyrimidin-2-yl)carbamoyl)phenoxy)-1-methylcyclohexane-1-carboxylic acid

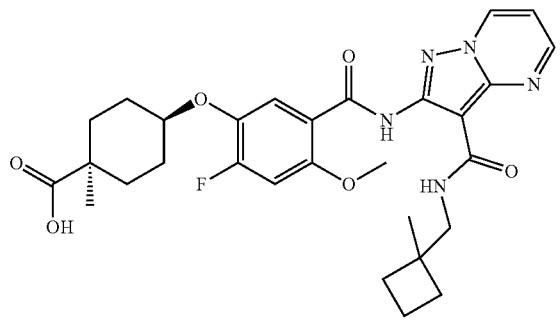 [SMILES: COc1cc(F)c(O[C@H]2CC[C@@](C)(C(=O)O)CC2)cc1C(=O)Nc1nn2cccnc2c1C(=O)NCC1(C)CCC1]

Step A. Intermediate 432: Naphthalen-1-ylmethyl (1s,4s)-4-(2-fluoro-4-methoxy-5-((3-(((1-methylcyclobutyl)methyl)carbamoyl)pyrazolo[1,5-a]pyrimidin-2-yl)carbamoyl)phenoxy)-1-methylcyclohexane-1-carboxylate

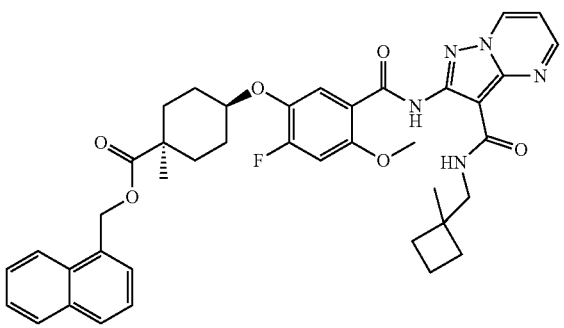 [SMILES: COc1cc(F)c(O[C@H]2CC[C@@](C)(C(=O)OCc3cccc4ccccc34)CC2)cc1C(=O)Nc1nn2cccnc2c1C(=O)NCC1(C)CCC1]

Intermediate 174 (100 mg, 0.34 mmol) was added to Intermediate 13 (189 mg, 0.41 mmol), T3P (1076 mg, 3.38 mmol) and DIPEA (131 mg, 1.01 mmol) in n-butyl acetate (8 mL) at 20° C. The resulting solution was stirred at 120° C. for 12 h. The reaction mixture was concentrated and diluted with EtOAc (150 mL), and washed sequentially with NH4Cl (1×150 mL, sat), H2O (1×150 mL), and brine (1×150 mL). The organic layer was dried over Na2SO4, filtered and evaporated to afford crude product which was purified by preparative TLC (EtOAc:PE, 1:3), to afford the title compound (100 mg, 41.8%) as a yellow solid. MS (ESI): m/z [M+H]+ 708.

Step B. (1s,4s)-4-(2-Fluoro-4-methoxy-5-((3-(((1-methylcyclobutyl)methyl)carbamoyl)-pyrazolo[1,5-a]pyrimidin-2-yl)carbamoyl)phenoxy)-1-methylcyclohexane-1-carboxylic acid Palladium (1.504 mg, 0.010 mmol) was added to Intermediate 432 (100 mg, 0.14 mmol) in THF (1 mL)/MeOH (2 mL)/EtOAc (1 mL) at 20° C. was placed under an atmosphere of hydrogen and stirred at 30° C. for 2 h. The reaction mixture was filtered through silica. The solvent was removed by distillation under vacuum to give the crude product which was purified by Method PrepAcidic-E (Gradient: 22%-32%) to afford the title compound (40.0 mg, 49.9%) as a white solid. HRMS (ESI) m/z [M+H]+ calcd for $C_{29}H_{35}FN_5O_6$: 568.2566 found: 568.2574.

Example 218: rac-3-(4-Methoxy-3-(((1R,2R,3S,4S)-3-((3-((trifluoromethyl)sulfonyl)phenyl)carbamoyl)bicyclo[2.2.1]hept-5-en-2-yl)carbamoyl)phenyl)propanoic acid

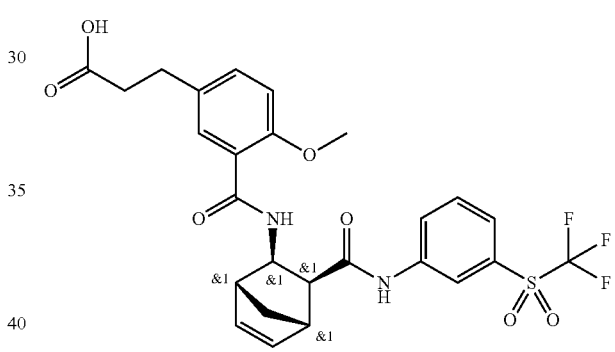

Step A: Intermediate 433: rac-tert-Butyl 3-(4-methoxy-3-(((1R,2R,3S,4S)-3-((3-((trifluoromethyl)sulfonyl)phenyl)carbamoyl)bicyclo[2.2.1]hept-5-en-2-yl)carbamoyl)phenyl)propanoate

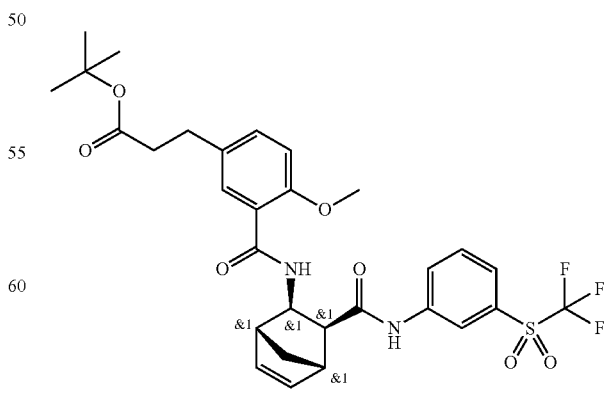

HATU (29 mg, 0.075 mmol) and DIPEA (0.033 mL, 0.19 mmol) were added to a solution of Intermediate 213 (25 mg, 0.069 mmol) and Intermediate 366 (19 mg, 0.069 mmol) in DMF (0.3 mL), then the mixture was stirred at rt for 18 h. H₂O was added to the reaction mixture and the mixture was extracted with EtOAc, then the organic layer was concentrated in vacuo. The crude product was purified by flash chromatography using a gradient of 0-45% EtOAc in hexane as mobile phase to give the title compound (17 mg, 43%). MS (ESI) m/z 623.3 [M+H]⁺.

Step B: rac-3-(4-methoxy-3-(((1R,2R,3S,4S)-3-((3-((trifluoromethyl)sulfonyl)phenyl)carbamoyl)bicyclo[2.2.1]hept-5-en-2-yl)carbamoyl)phenyl)propanoic acid A mixture of TFA (0.1 mL) and Intermediate 433 (12 mg, 0.019 mmol) was stirred at rt for 1 hr. The reaction mixture was concentrated in vacuo to give the title compound (10 mg, 92%). MS (ESI) m/z 567.3 [M+H]⁺.

Example 219: (1R,2S,3R,4S)-3-(5-((1H-Pyrazol-4-yl)methyl)-4-fluoro-2-methoxybenzamido)-N-(3-((trifluoromethyl)sulfonyl)phenyl)bicyclo[2.2.1]heptane-2-carboxamide

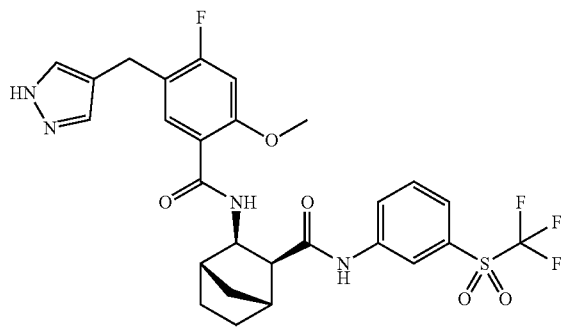 [SMILES: COc1cc(F)c(Cc2cn[nH]c2)cc1C(=O)N[C@@H]1[C@H]2CC[C@H](C2)[C@@H]1C(=O)Nc1cccc(S(=O)(=O)C(F)(F)F)c1]

Step A: Intermediate 434: Methyl 5-((1-benzyl-1H-pyrazol-4-yl)(hydroxy)methyl)-4-fluoro-2-methoxybenzoate

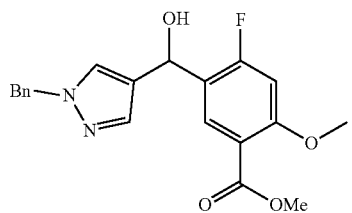 [SMILES: COC(=O)c1cc(C(O)c2cnn(Cc3ccccc3)c2)c(F)cc1OC]

Isopropylmagnesium chloride-lithium chloride complex (1.0 M in THF, 1.2 mL, 1.2 mmol) was added to a solution of methyl 4-fluoro-5-iodo-2-methoxybenzoate (300 mg, 0.968 mmol) in THF (5 mL) at −78° C., then the mixture was stirred at −78° C. for 15 min. 1-Benzylpyrazole-4-carbaldehyde (200 mg, 1.074 mmol) in THF (5 mL) was added dropwise, then the mixture was stirred at rt for 12 hr. Aq potassium carbonate was added to the reaction mixture, then the mixture was extracted with CHCl₃ and the organic layer was concentrated in vacuo. The crude product was purified by flash chromatography using a gradient of 30-60% EtOAc in hexane as mobile phase to give the title compound (110 mg, 31%). MS (API) m/z 371.1 [M+H]⁺.

Step B: Intermediate 435: (1S,2S,3R,4R)-3-(5-((RS)-(1-Benzyl-1H-pyrazol-4-yl)(hydroxy)methyl)-4-fluoro-2-methoxybenzamido)-N-(3-((trifluoromethyl)sulfonyl)phenyl)bicyclo[2.2.1]hept-5-ene-2-carboxamide

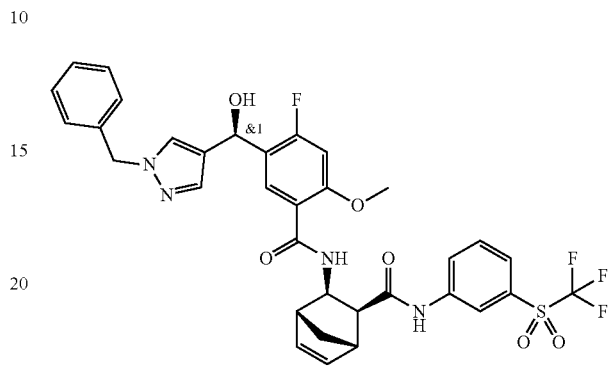

2 M aq NaOH (0.4 mL, 0.80 mmol) was added to a solution of Intermediate 434 (110 mg, 0.297 mmol) in MeOH (2 mL) and the mixture was stirred at rt for 5 hr. 2 M aq HCl was added to the reaction mixture and the mixture was concentrated in vacuo to give 5-((1-benzyl-1H-pyrazol-4-yl)(hydroxy)methyl)-4-fluoro-2-methoxybenzoic acid, to which EDC (120 mg, 0.626 mmol), HOAt (42 mg, 0.309 mmol) and TEA (0.2 mL, 1.0 mmol) were added, followed by Intermediate 256 (100 mg, 0.899 mmol) in DMF (2 mL), then the mixture was stirred at rt for 12 hr. H₂O was added to the reaction mixture and the mixture was extracted with CHCl₃, then organic layer was separated and concentrated in vacuo. The crude product was purified by flash chromatography using a gradient of 0-3% MeOH in CHCl₃ as mobile phase to give the title compound (88 mg, 41%). MS (ESI) m/z 699.2 [M+H]⁺.

Step C: (1R,2S,3R,4S)-3-(5-((1H-Pyrazol-4-yl)methyl)-4-fluoro-2-methoxybenzamido)-N-(3-((trifluoromethyl)sulfonyl)phenyl)bicyclo[2.2.1]heptane-2-carboxamide Acetic anhydride (2.0 mL) was added to a solution of Intermediate 435 (88 mg, 0.126 mmol) in pyridine (2 mL) and the mixture was stirred at rt for 1 hr. The mixture was concentrated in vacuo and aq citric acid was added, then the mixture was extracted with EtOAc and the combined organic layer was concentrated in vacuo to give (RS)-(1-benzyl-1H-pyrazol-4-yl)(2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenyl)methyl acetate. The solid was dissolved in EtOAc (10 mL) and acetic acid (10 mL), then Palladium (10% Pd/C, moisture by 50% H₂O, 50 mg) added. The reaction mixture was stirred under 7 atm of hydrogen atmosphere at 50 C for 12 hr. The hydrogen in the reaction vessel was replaced with argon and the reaction mixture was filtered with Celite®. The filtrate was concentrated in vacuo and aq potassium carbonate was added, then the mixture was extracted with CHCl₃ and the combined organic layer was concentrated in vacuo. The crude product was purified by flash chromatography using a gradient of 0-10% MeOH in CHCl₃ as mobile phase to give Example 220: 2-(4-(2-Fluoro-4-methoxy-5-(((1S, 2R,3S,4R)-3-((3-((trifluoromethyl)sulfonyl)phenyl) carbamoyl)bicyclo[2.2.1]heptan-2-yl)carbamoyl) benzyl)-1H-pyrazol-1-yl)acetic acid

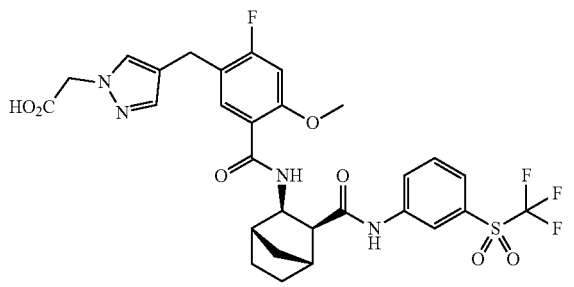 [SMILES: COc1cc(F)c(Cc2cnn(CC(=O)O)c2)cc1C(=O)N[C@@H]1[C@H]2CC[C@H](C2)[C@@H]1C(=O)Nc1cccc(S(=O)(=O)C(F)(F)F)c1]

Step A: Intermediate 436: tert-Butyl 2-(4-(2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)benzyl)-1H-pyrazol-1-yl) acetate

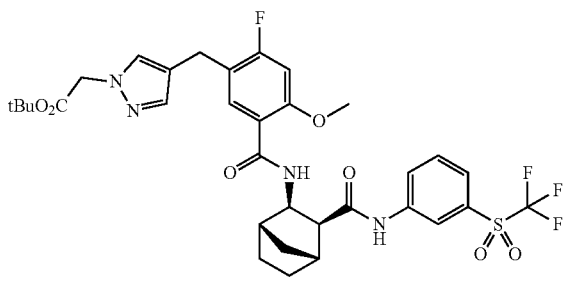 [SMILES: COc1cc(F)c(Cc2cnn(CC(=O)OC(C)(C)C)c2)cc1C(=O)N[C@@H]1[C@H]2CC[C@H](C2)[C@@H]1C(=O)Nc1cccc(S(=O)(=O)C(F)(F)F)c1]

tert-Butyl bromoacetate (0.011 mL, 0.074 mmol) was added to a mixture of Example 219 (40 mg, 0.0673 mmol) and cesium carbonate (33 mg, 0.101 mmol) in DMF (1 mL) and the mixture was stirred at 70° C. for 2 hr. The mixture was concentrated in vacuo and the crude product was purified by flash chromatography using a gradient of 0-5% MeOH in CHCl₃ as mobile phase to give titled compound (19 mg, 39%). MS (ESI) m/z 709.6 [M+H]⁺.

Step B: 2-(4-(2-Fluoro-4-methoxy-5-(((1S,2R,3S, 4R)-3-((3-((trifluoromethyl)sulfonyl)phenyl)carbamoyl)bicyclo[2.2.1]heptan-2-yl)carbamoyl)benzyl)-1H-pyrazol-1-yl)acetic acid A mixture of Intermediate 436 (19 mg, 0.0261 mmol) in TFA (1 mL) was stirred at rt for 1 hr. The mixture was concentrated in vacuo to give titled compound (20 mg, 99%). HRMS (ESI) m/z [M+H]⁺ calcd for C29H29F4N4O7S: 653.1688 found: 653.1708.

Example 221: 1-(2-Fluoro-4-methoxy-5-(((1S,2R, 3S,4R)-3-((3-((trifluoromethyl)sulfonyl)phenyl)carbamoyl)bicyclo[2.2.1]heptan-2-yl)carbamoyl)benzyl)-1H-pyrazole-5-carboxylic acid

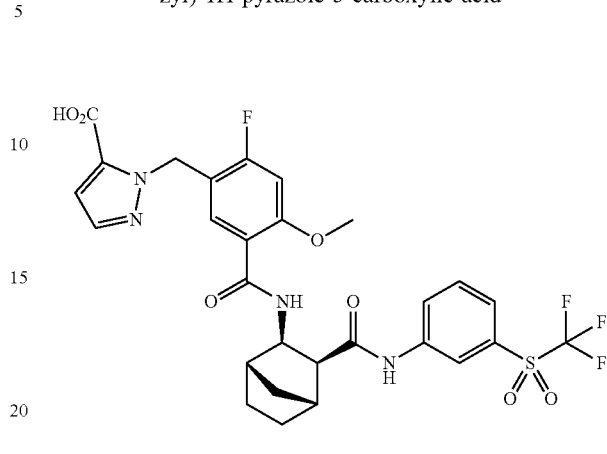

Step A: Intermediate 437: tert-Butyl 1-(2-fluoro-4-methoxy-5-(((1S,2R,3S,4R)-3-((3-((trifluoromethyl) sulfonyl)phenyl)carbamoyl)bicyclo[2.2.1]heptan-2-yl)carbamoyl)benzyl)-1H-pyrazole-5-carboxylate

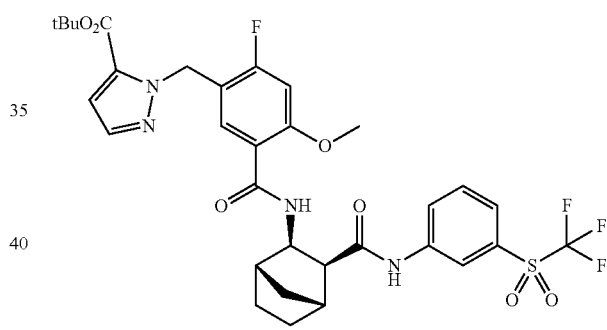

EDC (39 mg, 0.201 mmol), HOAt (28 mg, 0.201 mmol) and TEA (0.028 mL, 0.201 mmol) were added to a solution of Intermediate 362 (71 mg, 0.201 mmol) and Intermediate 226 (67 mg, 0.168 mmol) in DMF (3 mL), then the mixture was stirred at rt for 4 hr. 1 M aq HCl was added to the reaction mixture and the mixture was extracted with CHCl₃, then organic layer was concentrated in vacuo. The crude product was purified by flash chromatography using a gradient of 0-50% EtOAc in hexane as mobile phase to give the title compound (43 mg, 37%). MS (ESI) m/z 695.3 [M+H]⁺.

Step B: 1-(2-Fluoro-4-methoxy-5-(((1S,2R,3S,4R)-3-((3-((trifluoromethyl)sulfonyl)phenyl)carbamoyl) bicyclo[2.2.1]heptan-2-yl)carbamoyl)benzyl)-1H-pyrazole-5-carboxylic acid The titled compound was prepared analogous to Example 218 Step B, using Intermediate 437 instead of Intermediate 433. MS (ESI) m/z 639.3 [M+H]⁺.

Example 222: 1-(2-Fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)benzyl)-1H-pyrazole-3-carboxylic acid

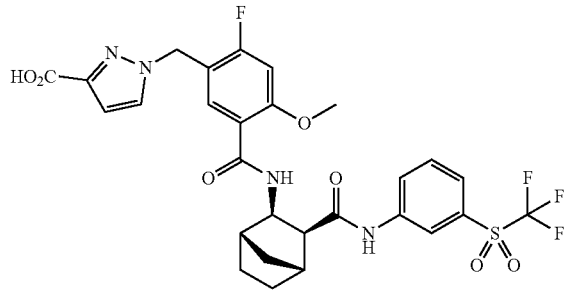 [SMILES: COc1cc(F)c(Cn2ccc(C(=O)O)n2)cc1C(=O)N[C@@H]1[C@H]2CC[C@H](C2)[C@@H]1C(=O)Nc1cccc(S(=O)(=O)C(F)(F)F)c1]

Step A: Intermediate 438: tert-Butyl 1-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)benzyl)-1H-pyrazole-3-carboxylate

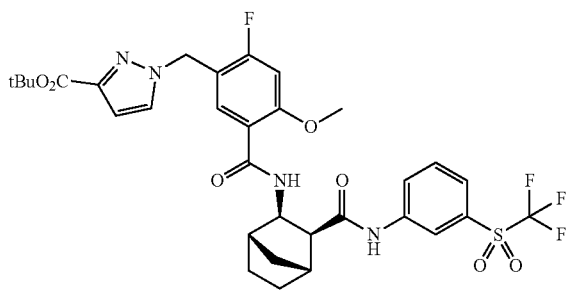 [SMILES: COc1cc(F)c(Cn2ccc(C(=O)OC(C)(C)C)n2)cc1C(=O)N[C@@H]1[C@H]2CC[C@H](C2)[C@@H]1C(=O)Nc1cccc(S(=O)(=O)C(F)(F)F)c1]

The titled compound was prepared analogous to Example 221 Step A, using Intermediate 365 instead of Intermediate 362. MS (ESI) m/z 695.4 [M+H]$^+$.

Step B: 1-(2-Fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)benzyl)-1H-pyrazole-3-carboxylic acid The titled compound was prepared analogous to Example 218 Step B, using Intermediate 438 instead of Intermediate 433. MS (ESI) m/z 639.3 [M+H]$^+$.

Example 223: rac-2-(4-Methoxy-3-((((1R,2R,3S,4S)-3-((3-((trifluoromethyl)sulfonyl)phenyl)carbamoyl)bicyclo[2.2.1]hept-5-en-2-yl)carbamoyl)benzyl)benzoic acid

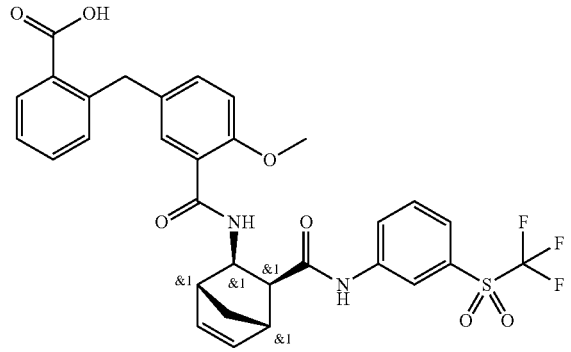 [SMILES: COc1ccc(Cc2ccccc2C(=O)O)cc1C(=O)N[C@H]1[C@@H](C(=O)Nc2cccc(S(=O)(=O)C(F)(F)F)c2)[C@@H]2C=C[C@H]1C2]

Step A: Intermediate 439: Methyl 5-((2-(1,3-dioxolan-2-yl)phenyl)(acetoxy)methyl)-2-methoxybenzoate

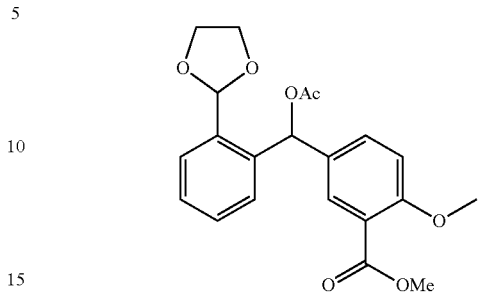

Magnesium (49 mg, 2.008 mmol) was added to a solution of 2-(2-bromophenyl)-1,3-dioxolane (425 mg, 1.854 mmol) in THF (3 mL), then the mixture was stirred at reflux for 30 min. After the mixture was cooled to −78 C, methyl 5-formyl-2-methoxybenzoate (300 mg, 1.545 mmol) in THF (7 mL) was added to the mixture and the mixture was stirred at rt for 12 hr. H$_2$O was added to the mixture and the mixture was extracted with EtOAc, then the organic layer was concentrated in vacuo.

The residue was dissolved in pyridine (4 mL), and Ac$_2$O (2 mL) was added. The reaction mixture was stirred at rt for 2 hr, then the mixture was concentrated in vacuo. The crude product was purified by flash chromatography using a gradient of 40% EtOAc in hexane as mobile phase to give the title compound (542 mg, 91%).

Step B: Intermediate 440: 5-(2-formylbenzyl)-2-methoxybenzoic acid

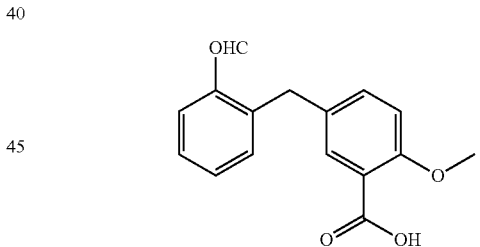

Palladium (10% Pd/C, moisture by 50% H$_2$O, 30 mg) was added to a solution of Intermediate 439 (542 mg, 1.403 mmol) in EtOAc (10 mL). The reaction mixture was stirred under 1 atm of hydrogen atmosphere at rt for 12 hr. The hydrogen in the reaction vessel was replaced with argon and the reaction mixture was filtered with Celite®®. After the filtrate was concentrated in vacuo.

The residue was dissolved in MeOH (10 mL), and 2 M aq NaOH (1.4 mL, 2.8 mmol) was added and the mixture was stirred at rt for 12 hr. The mixture was acidified with aq citric acid (acetal was removed in this process) and extracted with EtOAc, then the organic layer was concentrated in vacuo. The crude product was purified by flash chromatography using 5% MeOH in CHCl$_3$ as mobile phase to give the title compound (290 mg, 77%). MS (ESI) m/z 270.9 [M+H]$^+$ Step C: Intermediate 441: rac-(1R,2R,3S,4S)-3-(5-(2-Formylbenzyl)-2-methoxybenzamido)-N-(3-((trifluoromethyl)sulfonyl)phenyl)bicyclo[2.2.1]hept-5-ene-2-carboxamide

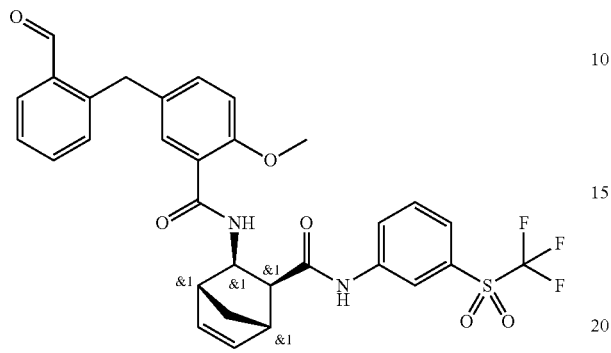

The titled compound was prepared analogous to Example 218 Step A, using Intermediate 440 instead of Intermediate 366. MS (ESI) m/z 613.3 [M+H]$^+$.

Step D: rac-2-(4-Methoxy-3-(((1R,2R,3S,4S)-3-((3-((trifluoromethyl)sulfonyl)phenyl)carbamoyl)bicyclo[2.2.1]hept-5-en-2-yl)carbamoyl)benzyl)benzoic acid Sodium chlorite (10 mg, 0.111 mmol) was added to a mixture of Intermediate 441 (39 mg, 0.064 mmol) and sodium dihydrogen phosphate (20 mg, 0.167 mmol) in DMSO (0.4 mL) and H$_2$O (0.4 mL), then the mixture was stirred at rt for 30 min. Aq citric acid was added to the reaction mixture and the precipitate was collected by filtration to give the title compound (38 mg, 95%). MS (APCI) m/z 629.0 [M+H]$^+$.

Example 224: rac-2'-Fluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid

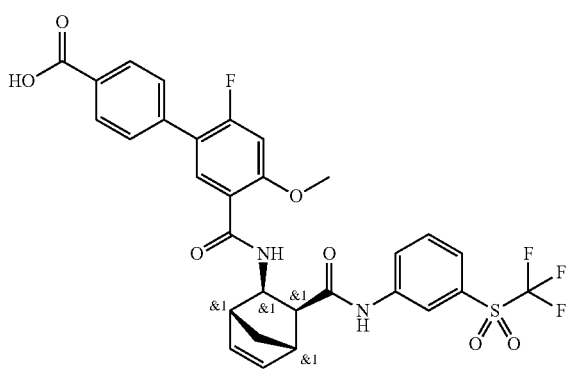 [SMILES: COc1cc(F)c(-c2ccc(C(=O)O)cc2)cc1C(=O)N[C@H]1[C@@H](C(=O)Nc2cccc(S(=O)(=O)C(F)(F)F)c2)[C@@H]2C=C[C@H]1C2]

Step A: Intermediate 442: rac-(1R,2R,3S,4S)-3-(5-Bromo-4-fluoro-2-methoxybenzamido)-N-(3-((trifluoromethyl)sulfonyl)phenyl)bicyclo[2.2.1]hept-5-ene-2-carboxamide

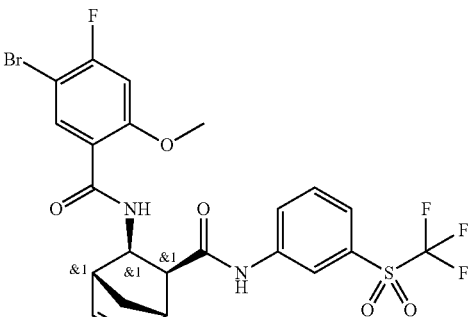

EDC (205 mg, 1.07 mmol), HOAt (145 mg, 1.07 mmol) and TEA (0.30 mL, 2.14 mmol) were added to a solution of Intermediate 213 (350 mg, 0.97 mmol) and 5-bromo-4-fluoro-2-methoxybenzoic acid (254 mg, 1.02 mmol) in CHCl$_3$ (15 mL), then the mixture was stirred at rt for 5 hr. H$_2$O was added to the reaction mixture, then organic layer was separated and concentrated in vacuo. The crude product was purified by flash chromatography using a gradient of 20-50% EtOAc in hexane as mobile phase to give the title compound (436 mg, 76%). MS (ESI) m/z 589.0/591.0 [M−H]−

Step B: Intermediate 443: rac-tert-Butyl 2'-fluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylate

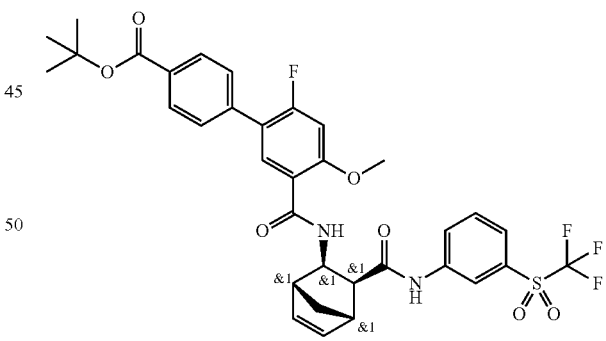

Tetrakis(triphenylphosphine)palladium (7 mg, 0.006 mmol) was added to the mixture of Intermediate 442 (35 mg, 0.059 mmol) and (4-tert-butoxycarbonylphenyl)boronic acid (26 mg, 0.118 mmol) in sat aq NaHCO$_3$ (0.6 mL) and DME (0.6 mL), and the mixture was stirred at reflux for 1 hr. The mixture was cooled to ambient temperature and extracted with CHCl$_3$, then the combined organic layer was concentrated in vacuo. The crude product was purified by flash chromatography using 20-80% EtOAc in hexane as mobile phase to give the title compound (29 mg, 71%). MS (ESI) m/z 689.3 [M+H]$^+$.

Step C: rac-2'-Fluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid The mixture of Intermediate 443 (180 mg, 0.017 mmol) and TFA (1 mL, 13 mmol) were stirred at rt for 4 hr. After the reaction mixture was concentrated in vacuo, the crude product was purified by flash chromatography using 0-10% MeOH in CHCl₃ as mobile phase to give the title compound (82 mg, 50%). MS (ESI) m/z 633.3 [M+H]⁺.

Example 225: rac-2'-Fluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid

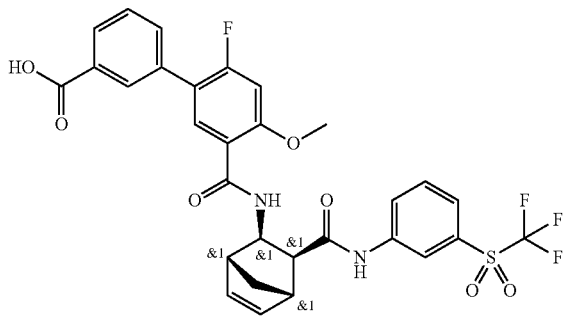 [SMILES: COc1cc(F)c(-c2cccc(C(=O)O)c2)cc1C(=O)N[C@H]1[C@@H](C(=O)Nc2cccc(S(=O)(=O)C(F)(F)F)c2)[C@@H]2C=C[C@H]1C2]

The titled compound was prepared analogous to Example 224 Step B and C, (3-tert-butoxycarbonylphenyl)boronic acid instead of (4-tert-butoxycarbonylphenyl)boronic acid. MS (ESI) m/z 633.3 [M+H]⁺.

Example 226: rac-2'-Fluoro-3,4'-dimethoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid

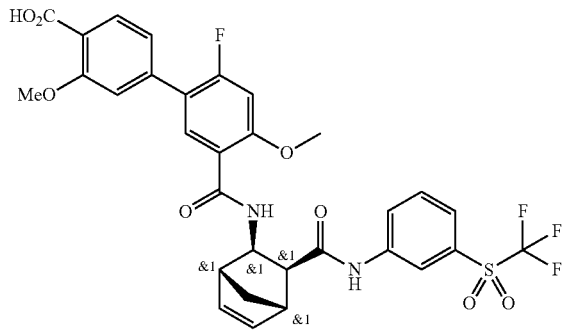 [SMILES: COc1cc(-c2cc(C(=O)N[C@H]3[C@@H](C(=O)Nc4cccc(S(=O)(=O)C(F)(F)F)c4)[C@@H]4C=C[C@H]3C4)c(OC)cc2F)ccc1C(=O)O]

Tetrakis(triphenylphosphine)palladium (10 mg, 0.008 mmol) was added to the mixture of Intermediate 442 (50 mg, 0.084 mmol) and methyl 2-methoxy-4-(4,4,5,5-tetramethyl-1,3,2-dioxaborolan-2-yl)benzoate (Compound 5) (50 mg, 0.171 mmol) in sat aq NaHCO₃ (1 mL) and DME (1 mL), and the mixture was stirred at reflux for 24 hr. The mixture was cooled to ambient temperature and acidified by 2 M aq HCl, then extracted with EtOAc and the combined organic layer was concentrated in vacuo. The crude product was purified by flash chromatography using a gradient of 7% MeOH in CHCl₃ as mobile phase to give the title compound (37 mg, 66%). 1H NMR (400 MHz, DMSO-d6) δ 1.31 (s, 2H), 1.53 (br d, J=9.07 Hz, 1H), 2.22 (br d, J=9.07 Hz, 1H), 2.76 (s, 1H), 3.03 (br s, 1H), 3.83 (s, 3H), 3.89 (s, 3H), 4.32 (t, J=8.16 Hz, 1H), 6.99 (d, J=7.86 Hz, 1H), 7.10 (s, 1H), 7.17 (d, J=12.70 Hz, 1H), 7.67 (d, J=7.56 Hz, 1H), 7.70-7.78 (m, 2H), 7.85-7.95 (m, 2H), 8.61 (s, 1H), 8.67 (d, J=8.77 Hz, 1H), 10.75 (s, 1H). HRMS (ESI) m/z [M+H]⁺. calcd for C31H27F4N2O8S: 663.1418 found: 663.1446.

The examples included in Table 18 below were synthesized analogously to the procedure of Example 226 using the specified boronic acid or boronate ester instead of Compound 5. The boronic acid or boronate ester is commercially available if not otherwise stated.

TABLE 18

| Ex No. | Boronic acid/Boronate ester | Product | MS (ESI) |
|---|---|---|---|
| 227 | [structure] | [structure] | m/z 651.3 [M + H]⁺ |

TABLE 18-continued

| Ex No. | Boronic acid/Boronate ester | Product | MS (ESI) |
| --- | --- | --- | --- |
| 228 | | | m/z 634.2 [M + H]+ |
| 229 | | | m/z 622.0 [M + H]+ |
| 230 | | | m/z 662.9 [M + H]+ |
| 231 | | | HRMS m/z [M + H]+ 651.1220 |

TABLE 18-continued

| Ex No. | Boronic acid/Boronate ester | Product | MS (ESI) |
|---|---|---|---|
| 232 | | | m/z 651.3 [M + H]+ |
| 233 | | | m/z 651.3 [M + H]+ |
| 234 | | | HRMS m/z [M + H]+ 647.1494 |
| 235 | | | m/z 647.3 [M + H]+ |

Example 236: 2',3-Difluoro-4'-methoxy-5'-(((1S,2R,3S,4R)-3-((3-(((trifluoromethyl)sulfonyl)phenyl)carbamoyl)bicyclo[2.2.1]heptan-2-yl)carbamoyl)-[1,1'-biphenyl]-4-carboxylic acid

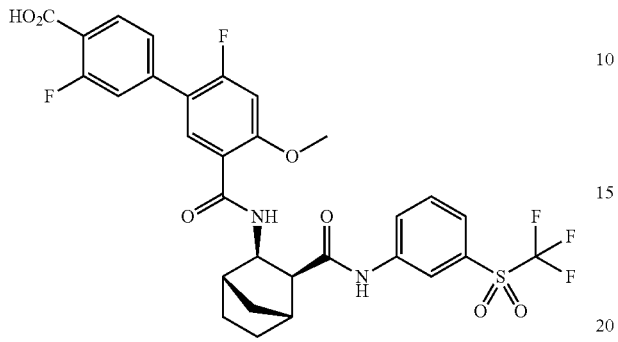

Step A-1: Intermediate 444: benzyl 5-bromo-4-fluoro-2-methoxybenzoate

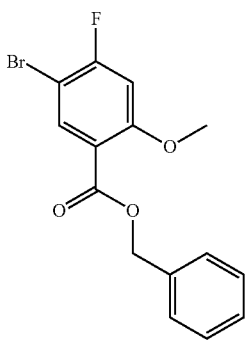 [SMILES: COc1cc(F)c(Br)cc1C(=O)OCc1ccccc1]

Oxalyl chloride (1.02 mL, 12.05 mmol) was added to a mixture of 5-bromo-4-fluoro-2-methoxybenzoic acid (2.0 g, 8.03 mmol) and DMF (0.05 mL, 0.6 mmol), then the mixture was stirred at rt for 2 hr. The mixture was concentrated in vacuo and dissolved in toluene (20 mL). Benzyl alcohol (1.73 g, 16.06 mmol), 4-(dimethylamino)pyridine (50 mg, 0.41 mmol) and TEA (2.0 mL, 14.4 mmol) were added to the reaction mixture and the mixture was stirred at rt for 1 hr. The reaction mixture was washed with sat aq NaHCO$_3$ and the organic layer was concentrated in vacuo. The crude product was purified by flash chromatography using a gradient of 10% EtOAc in hexane as mobile phase to give the title compound (2.45 g, 90%). MS (APCI) m/z 338.9/340.9 [M+H]$^+$.

Step A-2: Intermediate 445: benzyl 4-fluoro-2-methoxy-5-(4,4,5,5-tetramethyl-1,3,2-dioxaborolan-2-yl)benzoate

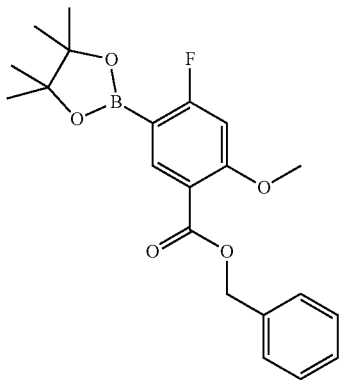 [SMILES: COc1cc(F)c(B2OC(C)(C)C(C)(C)O2)cc1C(=O)OCc1ccccc1]

PdCl$_2$(dppf)$_2$.CH$_2$Cl$_2$ (38 mg, 0.05 mmol) and potassium acetate (309 mg, 3.1 mmol) were added to a solution of Intermediate 444 (350 mg, 1.03 mmol) and bis(pinacolato)diboron (314 mg, 1.24 mmol) in cyclopentyl methyl ether (2.5 mL), then the mixture was stirred at reflux temperature for 1 hr. The mixture was cooled to ambient temperature and H$_2$O was added, then the mixture was extracted with CHCl$_3$ and the organic layer was concentrated in vacuo. The crude product was purified by flash chromatography using a gradient of 40% EtOAc in hexane as mobile phase to give the title compound (362 mg, 91%).

Step B: Intermediate 446: 4-fluoro-2-methoxy-5-(4,4,5,5-tetramethyl-1,3,2-dioxaborolan-2-yl)benzoic acid

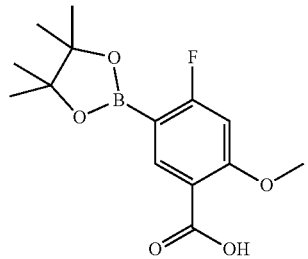

Palladium (10% Pd/C, moisture by 50% H$_2$O, 88 mg) was added to a solution of Intermediate 445 (876 mg, 2.27 mmol) in EtOH (12 mL). The reaction mixture was stirred under 1 atm of hydrogen atmosphere at rt for 1 hr. The hydrogen in the reaction vessel was replaced with argon and the reaction mixture was filtered with Celite®®. The filtrate was concentrated in vacuo to give titled compound (650 mg, 97%). MS (ESI) m/z 297.1 [M+H]$^+$.

Step C: Intermediate 447: (1R,2S,3R,4S)-3-(4-fluoro-2-methoxy-5-(4,4,5,5-tetramethyl-1,3,2-dioxaborolan-2-yl)benzamido)-N-(3-((trifluoromethyl)sulfonyl)phenyl)bicyclo[2.2.1]heptane-2-carboxamide

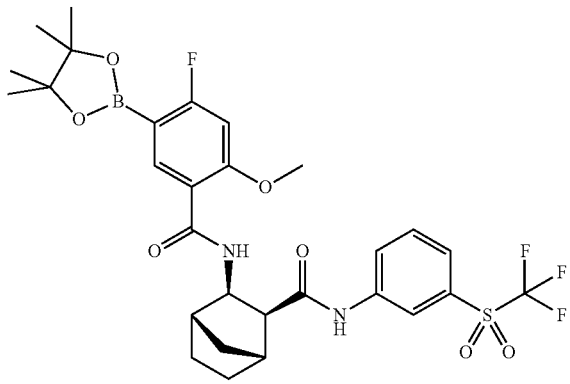 [SMILES: COc1cc(F)c(B2OC(C)(C)C(C)(C)O2)cc1C(=O)N[C@@H]1[C@H]2CC[C@H](C2)[C@@H]1C(=O)Nc1cccc(S(=O)(=O)C(F)(F)F)c1]

HATU (493 mg, 1.16 mmol) and DIPEA (0.41 mL, 2.36 mmol) were added to a solution of Intermediate 226 (350 mg, 0.97 mmol) and Intermediate 446 (346 mg, 1.17 mmol) in DMF (2 mL), then the mixture was stirred at rt for 1 hr. $H_2O$ was added to the reaction mixture, then the precipitate was collected by filtration and dried under pump vacuum to give titled compound (740 mg, 98%). MS (ESI) m/z 641.3 [M+H]$^+$.

Step D: Intermediate 448: methyl 2',3-difluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-carboxylate

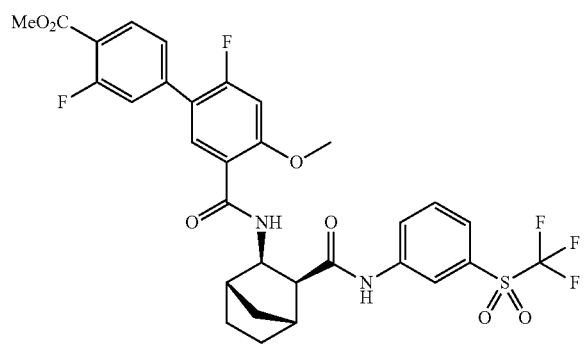 [SMILES: COC(=O)c1ccc(-c2cc(C(=O)N[C@@H]3[C@H]4CC[C@H](C4)[C@@H]3C(=O)Nc3cccc(S(=O)(=O)C(F)(F)F)c3)c(OC)cc2F)cc1F]

Bis(di-tert-butyl(4-dimethylaminophenyl)phosphine)dichloropalladium(II) (4 mg, 0.005 mmol) was added to the mixture of Intermediate 447 (70 mg, 0.11 mmol) and methyl 4-bromo-2-fluorobenzoate (Compound 6) (38 mg, 0.16 mmol) in 2 M aq $Na_2CO_3$ (0.5 mL) and DME (2 mL), and the mixture was stirred at reflux for 2 hr. The mixture was cooled to ambient temperature and diluted with EtOAc, then the mixture was filtered and the filtrate was concentrated in vacuo. The crude product was purified by flash chromatography using a gradient of 0-40% EtOAc in hexane as mobile phase to give the title compound (38 mg, 53%). MS (ESI) m/z 667.3 [M+H]$^+$.

Step E: 2',3-difluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-carboxylic acid 1 M aq LiOH (0.58 mL, 0.58 mmol) was added to a solution of Intermediate 448 (38 mg, 0.058 mmol) in DME (2 mL) and the mixture was stirred at rt for 18 hr. 1 M aq HCl and $CHCl_3$ were added to the reaction mixture and the layer was separated. Combined organic layer was concentrated in vacuo. The crude product was purified by flash chromatography using a gradient of 0-15% MeOH in $CHCl_3$ as mobile phase to give the title compound (19 mg, 51%). 1H NMR (400 MHz, DMSO-d6) δ 1.20-1.35 (m, 3H), 1.45-1.66 (m, 2H), 2.00-2.07 (m, 1H), 2.15-2.19 (m, 1H), 2.45-2.50 (m, 1H), 2.81-2.86 (m, 1H), 3.88 (s, 3H), 4.38 (t, J=8.8 Hz, 1H), 7.17 (d, J=13.0 Hz, 1H), 7.22-7.31 (m, 1H), 7.68-7.73 (m, 2H), 7.81 (d, J=9.4 Hz, 1H), 7.82-7.92 (m, 2H), 8.54-8.62 (m, 2H), 10.63 (s, 1H). HRMS (ESI) m/z [M+H]$^+$ calcd for $C_{30}H_{26}F_5N_2O_7S$: 653.1376 found: 653.1402.

The examples included in Table 19 below were synthesized analogously to the procedure of Example 236 steps D and E using the specified starting material instead of Compound 6. Step E was not conducted for Example 244 or Example 248.

TABLE 19

| Ex No. | Step D SM | Product | MS (ESI) |
|---|---|---|---|
| 237 | 5-bromopyrimidine propanoic acid ethyl ester | pyrimidine-phenyl-methoxy-benzamide-norbornene-trifluoromethylsulfonyl-phenyl product | HRMS m/z [M + H]+ 665.1700 |
| 238 | 5-bromopyrazine propanoic acid ethyl ester | pyrazine-phenyl-methoxy-benzamide-norbornane-trifluoromethylsulfonyl-phenyl product | HRMS m/z [M + H]+ 665.1676 |
| 239 | methyl 4-bromo-2-(dimethylamino)benzoate | dimethylamino-biphenyl-methoxy-benzamide-norbornane-trifluoromethylsulfonyl-phenyl product | m/z 678.2 [M + H]+ |
| 240 | ethyl 2-((5-bromopyridin-2-yl)amino)acetate | aminopyrimidine-phenyl-methoxy-benzamide-norbornane-trifluoromethylsulfonyl-phenyl product | HRMS m/z [M + H]+ 666.1644 |

TABLE 19-continued

| Ex No. | Step D SM | Product | MS (ESI) |
|---|---|---|---|
| 241 | 5-bromo-2-(methoxycarbonylmethoxy)pyridine | (structure) | HRMS m/z [M + H]⁺ 666.1536 |
| 242 | ethyl 3-(6-bromopyridin-3-yl)propanoate | (structure) | HRMS m/z [M + H]⁺ 664.1752 |
| 243 | methyl 3-(2-bromothiazol-5-yl)propanoate | (structure) | HRMS m/z [M + H]⁺ 670.1294 |
| 244 | 3-(4-bromophenyl)propanoic acid | (structure) | HRMS m/z [M + H]⁺ 663.1820 |

TABLE 19-continued

| Ex No. | Step D SM | Product | MS (ESI) |
|---|---|---|---|
| 245 | Intermediate 370 | (structure) | HRMS m/z [M + H]+ 665.1714 |
| 246 | methyl 4-bromo-2-methylbenzoate | (structure) | HRMS m/z [M + H]+ 649.1652 |
| 247 | methyl 4-bromo-2-hydroxybenzoate | (structure) | HRMS m/z [M + H]+ 651.1426 |
| 248 | 4-bromobenzenesulfonamide | (structure) | HRMS m/z [M + H]+ 670.1346 |

TABLE 19-continued
| Ex No. | Step D SM | Product | MS (ESI) |
|---|---|---|---|
| 249 | 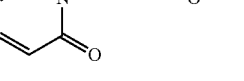 | 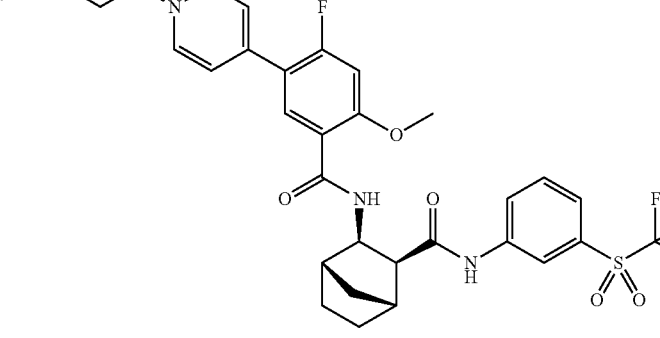 | HRMS m/z [M + H]+ 680.1642 |
| 250 | 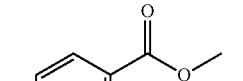 | 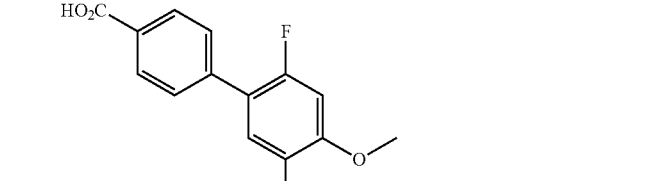 | HRMS m/z [M + H]+ 635.1462 |

Example 251: 4-((2'-Fluoro-4'-methoxy-5'-(((1S,2R,3S,4R)-3-((3-(((trifluoromethyl)sulfonyl)phenyl)carbamoyl)bicyclo[2.2.1]heptan-2-yl)carbamoyl)-[1,1'-biphenyl]-4-yl)oxy)butanoic acid

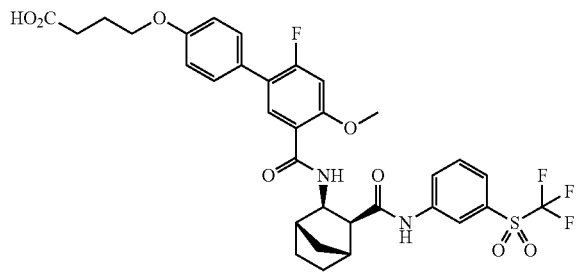 [SMILES: COc1cc(F)c(-c2ccc(OCCCC(=O)O)cc2)cc1C(=O)N[C@@H]1[C@H]2CC[C@H](C2)[C@@H]1C(=O)Nc1cccc(S(=O)(=O)C(F)(F)F)c1]

Step A: Intermediate 449: (1R,2S,3R,4S)-3-(5-bromo-4-fluoro-2-methoxybenzamido)-N-(3-((trifluoromethyl)sulfonyl)phenyl)bicyclo[2.2.1]heptane-2-carboxamide

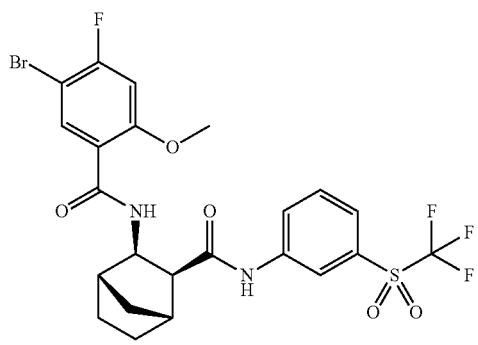 [SMILES: COc1cc(F)c(Br)cc1C(=O)N[C@@H]1[C@H]2CC[C@H](C2)[C@@H]1C(=O)Nc1cccc(S(=O)(=O)C(F)(F)F)c1]

HATU (686 mg, 1.81 mmol) and DIPEA (0.78 mL, 4.51 mmol) were added to a mixture of Intermediate 226 (600 mg, 1.50 mmol) and 5-bromo-4-fluoro-2-methoxybenzoic acid (412 mg, 1.65 mmol) in DMF (4 mL), then the mixture was stirred at rt for 1 hr. H$_2$O was added to the reaction mixture, then the precipitate was filtered and dried under air to give crude product. The crude product was purified by flash chromatography using a gradient of 0-50% EtOAc in hexane as mobile phase to give the title compound (722 mg, 81%). MS (ESI) m/z 593.1/595.1 [M+H]$^+$.

Step B: Intermediate 450: methyl 4-((2'-fluoro-4'-methoxy-5'-(((1S,2R,3S,4R)-3-((3-(((trifluoromethyl)sulfonyl)phenyl)carbamoyl)bicyclo[2.2.1]heptan-2-yl)carbamoyl)-[1,1'-biphenyl]-4-yl)oxy)butanoate

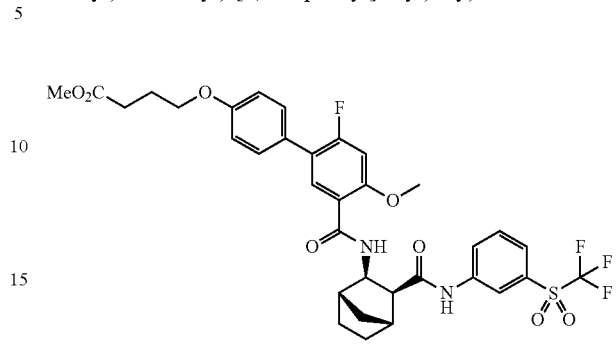

Bis(di-tert-butyl(4-dimethylaminophenyl)phosphine)dichloropalladium(II) (5 mg, 0.007 mmol) was added to the mixture of Intermediate 449 (80 mg, 0.135 mmol) and methyl 4-(4-(4,4,5,5-tetramethyl-1,3,2-dioxaborolan-2-yl)phenoxy)butanoate (Compound 7) (65 mg, 0.20 mmol) in 2 M aq Na$_2$CO$_3$ (0.5 mL) and DME (2 mL), and the mixture was stirred at reflux for 2 hr. The mixture was cooled to ambient temperature and diluted with EtOAc, then the mixture was filtered and the filtrate was concentrated in vacuo. The crude product was purified by flash chromatography using a gradient of 20-60% EtOAc in hexane as mobile phase to give the title compound (68 mg, 71%). MS (ESI) m/z 707.5 [M+H]$^+$.

Step C: 4-((2'-fluoro-4'-methoxy-5'-(((1S,2R,3S,4R)-3-((3-(((trifluoromethyl)sulfonyl)phenyl)carbamoyl)bicyclo[2.2.1]heptan-2-yl)carbamoyl)-[1,1'-biphenyl]-4-yl)oxy)butanoic acid The titled compound was prepared analogous to Example 236 step E, using Intermediate 450 instead of Intermediate 448. MS (ESI) m/z 693.6 [M+H]$^+$.

Example 252: 2'-Fluoro-4'-methoxy-3,5-dimethyl-5'-(((1S,2R,3S,4R)-3-((3-(((trifluoromethyl)sulfonyl)phenyl)carbamoyl)bicyclo[2.2.1]heptan-2-yl)carbamoyl)-[1,1'-biphenyl]-4-carboxylic acid

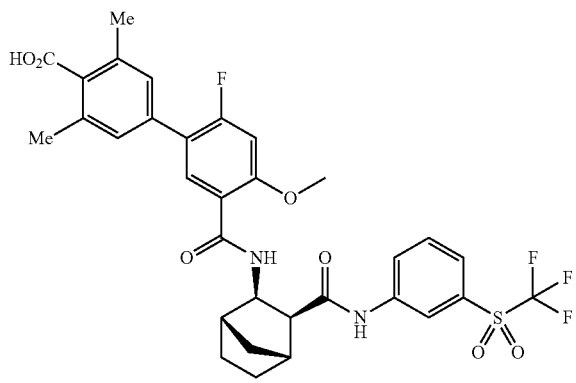 [SMILES: COc1cc(F)c(-c2cc(C)c(C(=O)O)c(C)c2)cc1C(=O)N[C@@H]1[C@H]2CC[C@H](C2)[C@@H]1C(=O)Nc1cccc(S(=O)(=O)C(F)(F)F)c1]

459

Step A: Intermediate 451: methyl 2'-fluoro-4'-methoxy-3,5-dimethyl-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-carboxylate

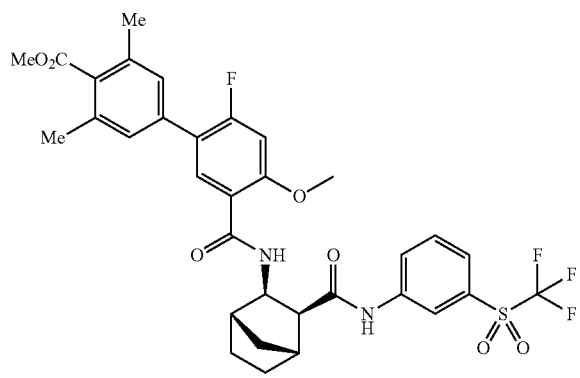 [SMILES: COC(=O)c1c(C)cc(-c2cc(C(=O)N[C@@H]3[C@H]4CC[C@H](C4)[C@@H]3C(=O)Nc3cccc(S(=O)(=O)C(F)(F)F)c3)c(OC)cc2F)cc1C]

460

The titled compound was prepared analogous to Example 251 step B, using (4-methoxycarbonyl-3,5-dimethyl-phenyl)boronic acid instead of Compound 7. MS (ESI) m/z 677.3 [M+H]⁺.

Step B: 2'-fluoro-4'-methoxy-3,5-dimethyl-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-carboxylic acid Lithium iodide (50 mg, 0.37 mmol) was added to a solution of Intermediate 451 (50 mg, 0.074 mmol) in pyridine (3 mL), then the mixture was stirred at 80° C. for 17.5 hr. The mixture was concentrated in vacuo and 1 M aq HCl was added to the reaction mixture, then the mixture was extracted with CHCl₃ and the organic layer was concentrated in vacuo. The crude product was purified by flash chromatography using a gradient of 0-10% MeOH in EtOAc as mobile phase to give the title compound (10 mg, 20%). MS (ESI) m/z 663.2 [M+H]⁺.

The examples included in Table 20 below were synthesized analogously to the procedure of Example 251 steps B and C using the specified starting material instead of Compound 7.

TABLE 20

| Ex No. | Step B SM | Product | MS (ESI) |
|---|---|---|---|
| 253 | | | HRMS m/z [M + H]⁺ 691.1788 |
| 254 | | | HRMS m/z [M + H]⁺ 691.1702 |

TABLE 20-continued

| Ex No. | Step B SM | Product | MS (ESI) |
|---|---|---|---|
| 255 | | | HRMS m/z [M + H]+ 653.1704 |

Example 256: 2-((2'-Fluoro4'-methoxy-5'-((((1S,2R,3S,4R)-3-((3-(((trifluoromethyl)sulfonyl)phenyl)carbamoyl)bicyclo[2.2.1]heptan-2-yl)carbamoyl-[1,1'-biphenyl]-r-yl)oxy)-2-methylpropanoic acid

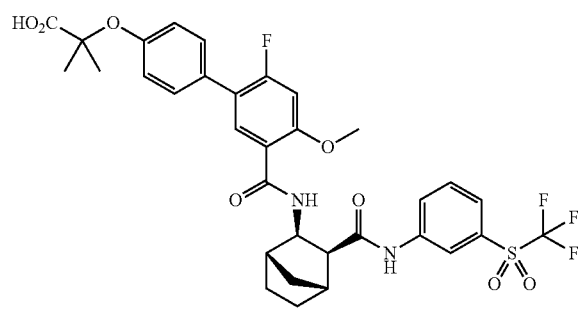 [SMILES: COc1cc(F)c(-c2ccc(OC(C)(C)C(=O)O)cc2)cc1C(=O)N[C@@H]1[C@H]2CC[C@H](C2)[C@@H]1C(=O)Nc1cccc(S(=O)(=O)C(F)(F)F)c1]

Step A: Intermediate 452: tert-butyl 2-((2'-fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)oxy)-2-methylpropanoate

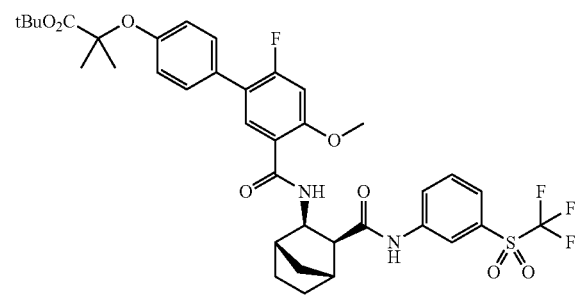 [SMILES: COc1cc(F)c(-c2ccc(OC(C)(C)C(=O)OC(C)(C)C)cc2)cc1C(=O)N[C@@H]1[C@H]2CC[C@H](C2)[C@@H]1C(=O)Nc1cccc(S(=O)(=O)C(F)(F)F)c1]

The titled compound was prepared analogous to Example 251 step B, using tert-butyl 2-methyl-2-[4-(4,4,5,5-tetramethyl-1,3,2-dioxaborolan-2-yl)phenoxy]propanoate instead of Compound 7. MS (ESI) m/z 749.7 [M+H]+.

Step B: 2-((2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)oxy)-2-methylpropanoic acid TFA (0.35 mL) was added to a solution of Intermediate 452 (104 mg, 0.14 mmol) in CHCl3 (0.35 mL). The mixture was stirred at rt for 3 hr, then the mixture was concentrated in vacuo to give titled compound (90 mg, 94%). HRMS (ESI) m/z [M+H]+ calcd for C33H33F4N2O8S: 693.1888 found: 693.1920.

Example 257: 2-((2'-Fluoro-4'-methoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)oxy)acetic acid

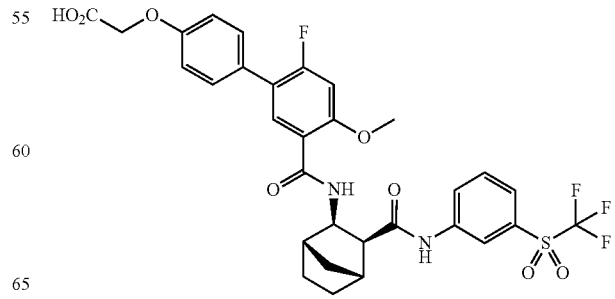

Step A: Intermediate 453: tert-butyl 2-((2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)oxy)acetate

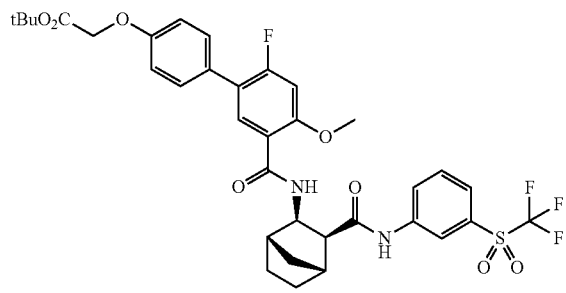

The titled compound was prepared analogous to Example 251 Step B, using tert-butyl 2-[4-(4,4,5,5-tetramethyl-1,3,2-dioxaborolan-2-yl)phenoxy]acetate instead of Compound 7. MS (ESI) m/z 721.3 [M+H]⁺.

Step B: 2-((2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)oxy)acetic acid The titled compound was prepared analogous to Example 256 Step B, using Intermediate 453 instead of Intermediate 452. HRMS (ESI) m/z [M+H]⁺ calcd for C31H29F4N2O8S: 665.1576 found: 665.1562.

Example 258: 3-(5-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)propanoic acid

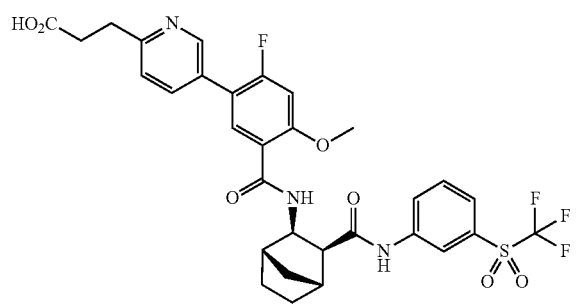 [SMILES: COc1cc(F)c(-c2ccc(CCC(=O)O)nc2)cc1C(=O)N[C@@H]1[C@H]2CC[C@H](C2)[C@@H]1C(=O)Nc1cccc(S(=O)(=O)C(F)(F)F)c1]

Step A: Intermediate 454: benzyl 3-(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)propanoate

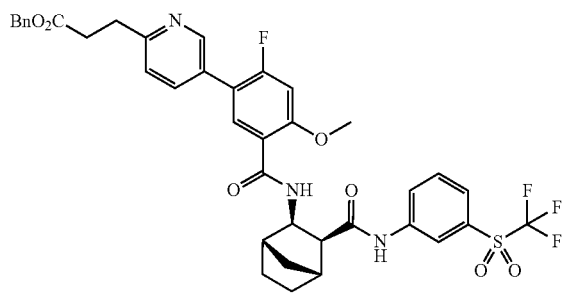

The titled compound was prepared analogous to Example 236 step D, using benzyl 3-(5-bromo-2-pyridyl)propanoate instead of Compound 6. MS (ESI) m/z 754.3 [M+H]⁺.

Step B: 3-(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)propanoic acid Palladium (10% Pd/C, moisture by 50% H₂O, 10 mg) was added to a solution of Intermediate 454 (46 mg, 0.062 mmol) in MeOH (3 mL). The reaction mixture was stirred under 1 atm of hydrogen atmosphere at rt for 1 hr. The hydrogen in the reaction vessel was replaced with argon and the reaction mixture was filtered with Celite®®. The filtrate was concentrated in vacuo to give the title compound (41 mg, 100%). HRMS (ESI) m/z [M+H]⁺ calcd for C31H30F4N3O7S: 664.1736 found: 664.1756.

Example 259: 3-(2'-Fluoro-3,4'-dimethoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoic acid

465

Step A: Intermediate 455: tert-butyl 3-(2'-fluoro-3,4'-dimethoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoate

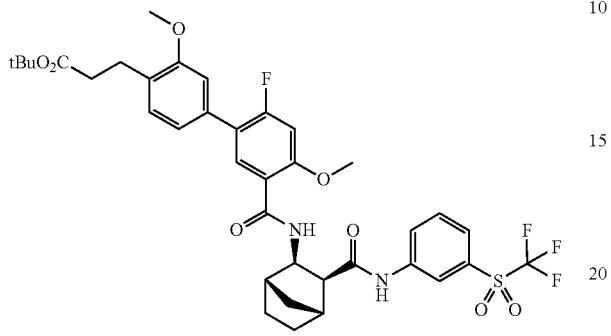

The titled compound was prepared analogous to Example 236 Step D, using tert-butyl 3-(4-bromo-2-methoxyphenyl)propanoate instead of Compound 6. MS (ESI) m/z 749.4 [M+H]$^+$.

Step B: 3-(2'-fluoro-3,4'-dimethoxy-5'-((((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoic acid The titled compound was prepared analogous to Example 256 Step B, using Intermediate 455 instead of Intermediate 452. MS (ESI) m/z 693.3 [M+H]$^+$.

Example 260: (E)-3-(5-(2-Fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)acrylic acid

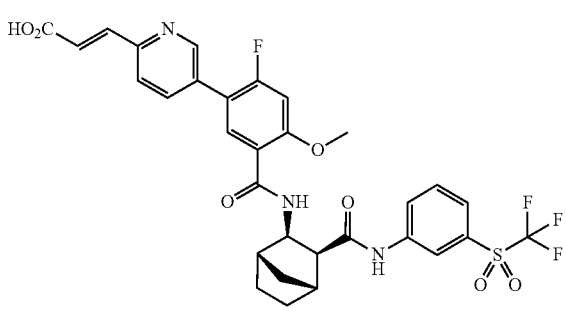 [SMILES: COc1cc(F)c(-c2ccc(/C=C/C(=O)O)nc2)cc1C(=O)N[C@@H]1[C@H]2CC[C@H](C2)[C@@H]1C(=O)Nc1cccc(S(=O)(=O)C(F)(F)F)c1]

466

Step A: Intermediate 456: tert-butyl (E)-3-(5-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)acrylate

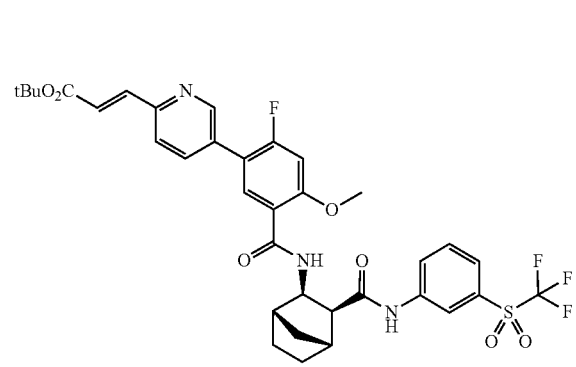 [SMILES: COc1cc(F)c(-c2ccc(/C=C/C(=O)OC(C)(C)C)nc2)cc1C(=O)N[C@@H]1[C@H]2CC[C@H](C2)[C@@H]1C(=O)Nc1cccc(S(=O)(=O)C(F)(F)F)c1]

The titled compound was prepared analogous to Example 236 Step D, using tert-butyl (E)-3-(5-bromo-2-pyridyl)prop-2-enoate instead of Compound 6. MS (ESI) m/z 718.4 [M+H]$^+$.

Step B: (E)-3-(5-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)acrylic acid

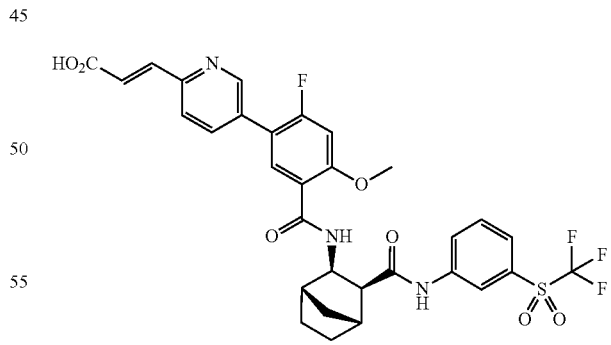

The titled compound was prepared analogous to Example 256 Step B, using Intermediate 456 instead of Intermediate 452. HRMS (ESI) m/z [M+H]$^+$ calcd for C31H28F4N3O7S: 662.1578 found: 662.1608.

Example 261: (1R*,2R*)-2-(5-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)cyclopropane-1-carboxylic acid (Isomer 2) and Example 262: (1R*,2R*)-2-(5-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)cyclopropane-1-carboxylic acid (Isomer 1)

Step B: Intermediate 458: tert-Butyl (1R*,2R*)-2-(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)cyclopropane-1-carboxylate (Isomer 1) and Intermediate 459: tert-Butyl (1R*,2R*)-2-(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)cyclopropane-1-carboxylate (Isomer 2)

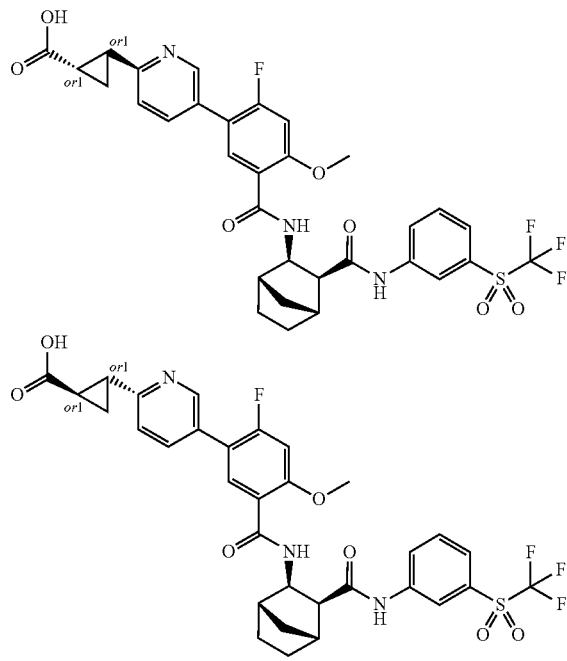

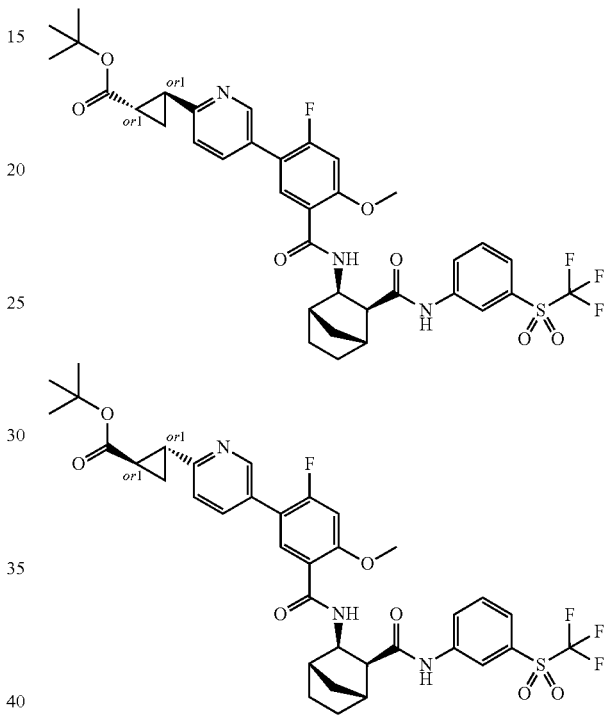

Step A: Intermediate 457: rac-tert-Butyl (1R,2R)-2-(5-bromopyridin-2-yl)cyclopropane-1-carboxylate

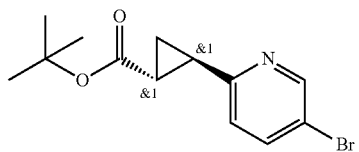 [SMILES: CC(C)(C)OC(=O)[C@@H]1C[C@H]1c1ccc(Br)cn1]

Sodium hydride (60% in oil suspension, 68 mg, 1.69 mmol) was added to DMSO (3.5 mL), then the mixture was stirred at rt for 15 min. Trimethylsulfoxonium iodide (372 mg, 1.69 mmol) was added to a reaction mixture and the mixture was stirred at rt for 5 min. tert-Butyl (E)-3-(5-bromopyridin-2-yl)acrylate (400 mg, 1.41 mmol) was added to a reaction mixture and the mixture was stirred at rt for 1 hr. Ice $H_2O$ was added to a reaction mixture and the mixture was extracted with $CHCl_3$. The combined organic layer was concentrated in vacuo and the crude product was purified by flash chromatography using 0-10% EtOAc in hexane as mobile phase to give titled compound (224 mg, 53%). MS (ESI) m/z 298.1/300.1 [M+H]+.

Bis(di-tert-butyl(4-dimethylaminophenyl)phosphine)dichloropalladium(II) (7.8 mg, 0.011 mmol) and cesium carbonate (71 mg, 0.22 mmol) were added to a solution of Intermediate 457 (66 mg, 0.22 mmol) and Intermediate 447 (70 mg, 0.11 mmol) in DME (0.5 mL) and $H_2O$ (0.1 mL), then the mixture was stirred at reflux temperature for 1 hr. The mixture was cooled to ambient temperature and $H_2O$ was added, then the mixture was extracted with $CHCl_3$ and the organic layer was concentrated in vacuo. The crude product was purified by flash chromatography using a gradient of 0-50% EtOAc in hexane as mobile phase to give the first eluting compound Intermediate 458 (30 mg, 38%); MS (ESI) m/z 732.3 [M+H]+, and the second eluting compound Intermediate 459 (9 mg, 11%); MS (ESI) m/z 732.4 [M+H]+.

Step C: (1R*,2R*)-2-(5-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyridin-2-yl)cyclopropane-1-carboxylic acid The titled compounds were prepared analogous to Example 256 Step B, using Intermediate 458 instead of Intermediate 452 to give Example 261, and Intermediate 459 instead of Intermediate 452 to give Example 262. HRMS (ESI) m/z [M+H]+ calcd for C32H30F4N3O7S: 676.1736 found: 676.1752.

Example 263: (1R*,2R*)-2-(5-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyrazin-2-yl)cyclopropane-1-carboxylic acid (Isomer 1) and Example 264: (1R*, 2R*)-2-(5-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyrazin-2-yl)cyclopropane-1-carboxylic acid (Isomer 2)

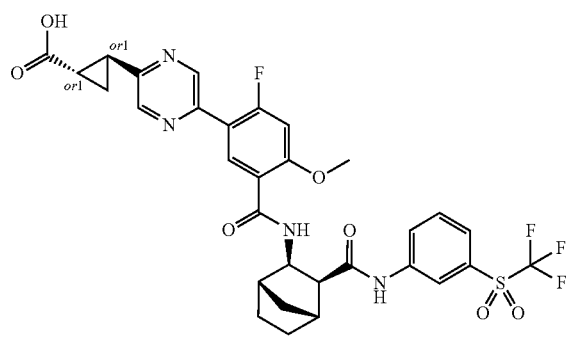

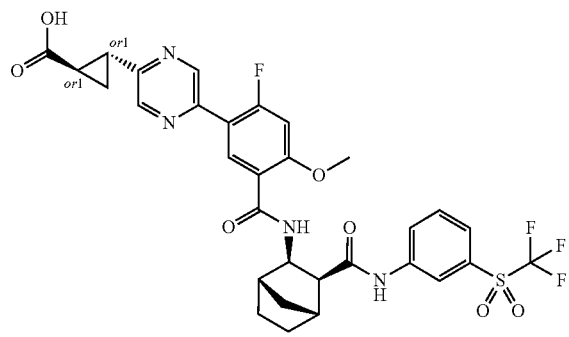

Step A: Intermediate 460: rac-tert-Butyl (1R,2R)-2-(5-chloropyrazin-2-yl)cyclopropane-1-carboxylate

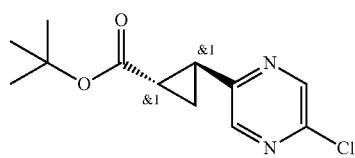 [SMILES: CC(C)(C)OC(=O)[C@H]1C[C@@H]1c1cnc(Cl)cn1]

The titled compound was prepared analogous to Example 261 Step A, using tert-butyl (E)-3-(5-chloropyrazin-2-yl) acrylate instead of tert-butyl (E)-3-(5-bromopyridin-2-yl) acrylate. MS (ESI) m/z 255.1/257.1 [M+H]+.

Step B: Intermediate 461: rac-Benzyl 5-(5-((1R, 2R)-2-(tert-butoxycarbonyl)cyclopropyl)pyrazin-2-yl)-4-fluoro-2-methoxybenzoate

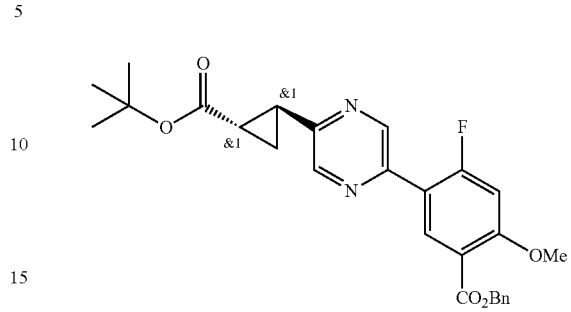

(2-Dicyclohexylphosphino-2',4',6'-triisopropyl-1,1'-biphenyl)[2-(2'-amino-1,1'-biphenyl)]palladium(II) methanesulfonate (9 mg, 0.011 mmol) was added to the mixture of cesium carbonate (69 mg, 0.212 mmol), Intermediate 460 (27 mg, 0.106 mmol) and Intermediate 445 (45 mg, 0.116 mmol) in H2O (0.1 mL) and DME (0.5 mL), then the mixture was stirred at reflux for 4 hr. The mixture was cooled to ambient temperature and extracted with CHCl3, then the combined organic layer was concentrated in vacuo. The crude product was purified by flash chromatography using 0-25% EtOAc in hexane as mobile phase to give the title compound (51 mg, 43%). MS (ESI) m/z 479.2 [M+H]+.

Step C: Intermediate 462: rac-5-(5-((1R,2R)-2-(tert-Butoxycarbonyl)cyclopropyl)pyrazin-2-yl)-4-fluoro-2-methoxybenzoic acid

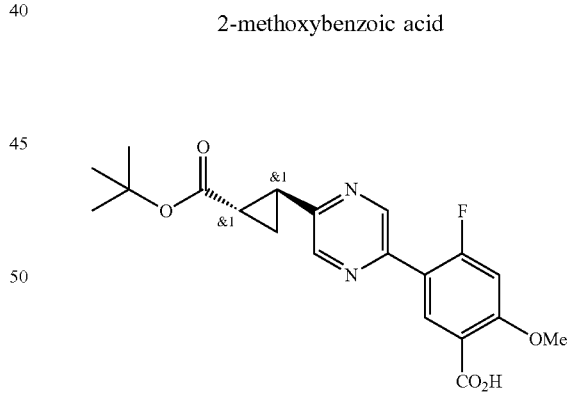

Palladium (10% Pd/C, moisture by 50% H2O, 10 mg) was added to a solution of Intermediate 461 (19 mg, 0.039 mmol) in EtOH (12 mL). The reaction mixture was stirred under 1 atm of hydrogen atmosphere at rt for 1 hr. The hydrogen in the reaction vessel was replaced with argon and the reaction mixture was filtered with Celite®®. The filtrate was concentrated in vacuo to give titled compound (15 mg, 100%). MS (ESI) m/z 389.1 [M+H]+.

Step D: Intermediate 463: tert-butyl (1R*,2R*)-2-(5-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyrazin-2-yl)cyclopropane-1-carboxylate

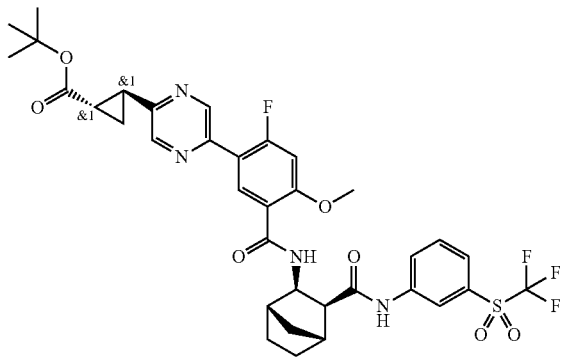

The titled compound was prepared analogous to Example 236 step C, using Intermediate 462 instead of Intermediate 446. MS (ESI) m/z 733.3 [M+H]$^+$.

Step E: Intermediate 464: tert-Butyl (1RS,2RS)-2-(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyrazin-2-yl)cyclopropane-1-carboxylate (Isomer 1) and Intermediate 465: tert-butyl (1RS,2RS)-2-(5-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)pyrazin-2-yl)cyclopropane-1-carboxylate (Isomer 2)

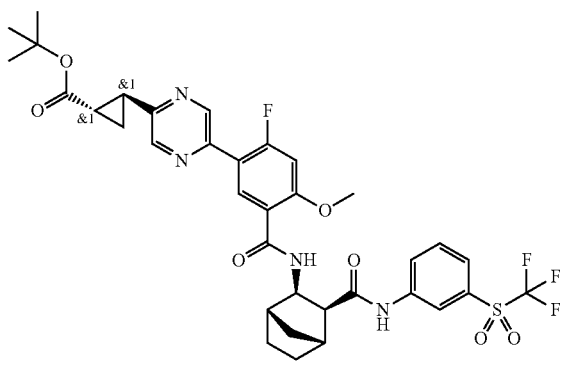 [SMILES: COc1cc(F)c(-c2cnc([C@H]3C[C@@H]3C(=O)OC(C)(C)C)cn2)cc1C(=O)N[C@@H]1[C@H]2CC[C@H](C2)[C@@H]1C(=O)Nc1cccc(S(=O)(=O)C(F)(F)F)c1]

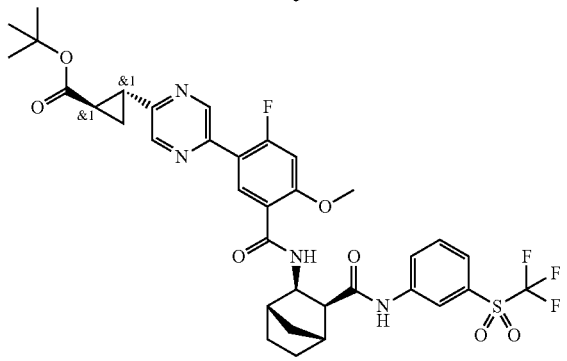

Intermediate 463 obtained in Example 263 step D (29 mg) was separated by chiral HPLC (column: CHIRALPAK IC (250 mm*30 mm); mobile phase: [MeOH/MeCN/DEA=70/30/0.1]) to give the first eluting compound Intermediate 464 (10 mg, 48%); MS (ESI) m/z 733.3 [M+H]$^+$, and the second eluting compound Intermediate 465 (10 mg, 48%); MS (ESI) m/z 733.3 [M+H]$^+$.

Step F: (1R*,2R*)-2-(5-(2-Fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)pyrazin-2-yl)cyclopropane-1-carboxylic acid The titled compounds were prepared analogous to Example 256 Step B, using Intermediate 464 instead of Intermediate 452 to give Example 263, and Intermediate 465 instead of Intermediate 452 to give Example 264. MS (ESI) m/z 677.6 [M+H]$^+$.

Example 265: (1R,2S,3R,4S)-3-(4'-(2-Amino-1,3-dihydroxypropan-2-yl)-6-fluoro-4-methoxy-[1,1'-biphenyl]-3-carboxamido)-N-(3-((trifluoromethyl)sulfonyl)phenyl)bicyclo[2.2.1]heptane-2-carboxamide

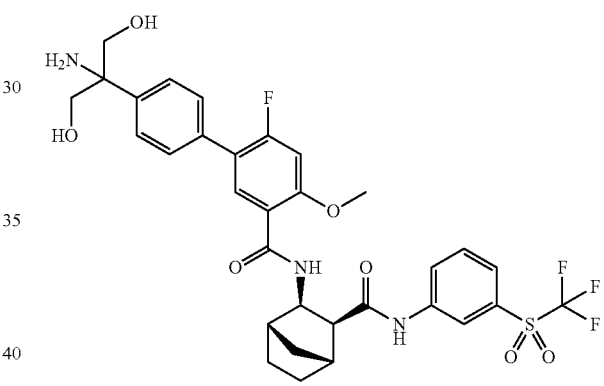

Step A: Intermediate 466: (1R,2S,3R,4S)-3-(4'-(1,3-dihydroxy-2-nitropropan-2-yl)-6-fluoro-4-methoxy-[1,1'-biphenyl]-3-carboxamido)-N-(3-((trifluoromethyl)sulfonyl)phenyl)bicyclo[2.2.1]heptane-2-carboxamide

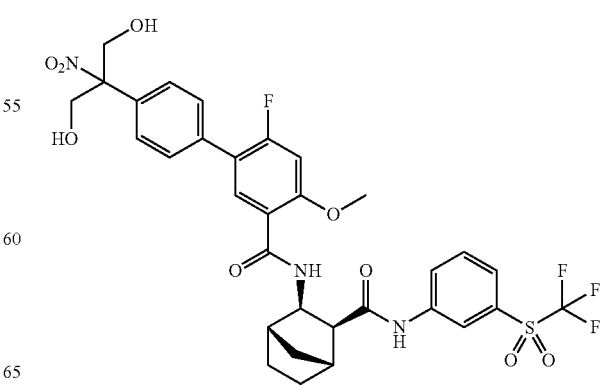

The titled compound was prepared analogous to Example 236 step D, using 2-(4-bromophenyl)-2-nitropropane-1,3-diol instead of Compound 6. MS (ESI) m/z 710.2 [M+H]⁺.

Step B: (1R,2S,3R,4S)-3-(4'-(2-amino-1,3-dihydroxypropan-2-yl)-6-fluoro-4-methoxy-[1,1'-biphenyl]-3-carboxamido)-N-(3-((trifluoromethyl)sulfonyl)phenyl)bicyclo[2.2.1]heptane-2-carboxamide NaBH$_4$ (30 mg, 0.791 mmol) was added to a mixture of Intermediate 466 (56 mg, 0.079 mmol) and NiCl2 (12 mg, 0.095 mmol) in MeOH (1.6 mL). The reaction mixture was stirred at rt for 1 hr. CHCl$_3$ and 2 M aq HCl were added to the reaction mixture and the mixture was basified with sat aq NaHCO$_3$. The mixture was extracted with CHCl$_3$ and the organic layer was concentrated in vacuo. The crude product was purified by flash chromatography using a gradient of 0-20% MeOH in CHCl$_3$ as mobile phase to give the title compound (8 mg, 15%). MS (ESI) m/z 680.4 [M+H]⁺.

Example 266: (1R,2S,3R,4S)-3-(4'-(3-Amino-4-hydroxy-3-(hydroxymethyl)butyl)-3',6-difluoro-4-methoxy-[1,1'-biphenyl]-3-carboxamido)-N-(3-((trifluoromethyl)sulfonyl)phenyl)bicyclo[2.2.1]heptane-2-carboxamide

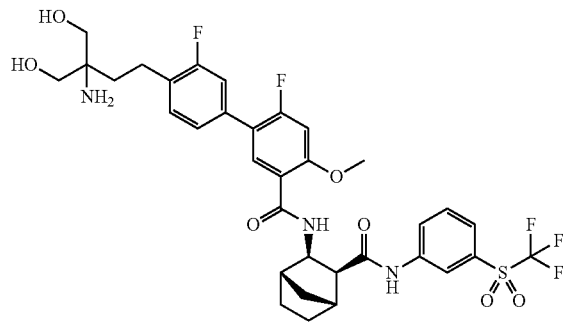 [SMILES: COc1cc(F)c(-c2ccc(CCC(N)(CO)CO)c(F)c2)cc1C(=O)N[C@@H]1[C@H]2CC[C@H](C2)[C@@H]1C(=O)Nc1cccc(S(=O)(=O)C(F)(F)F)c1]

Step A: Intermediate 467: tert-Butyl (5-(2-(2',3-difluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)ethyl)-2,2-dimethyl-1,3-dioxan-5-yl)carbamate

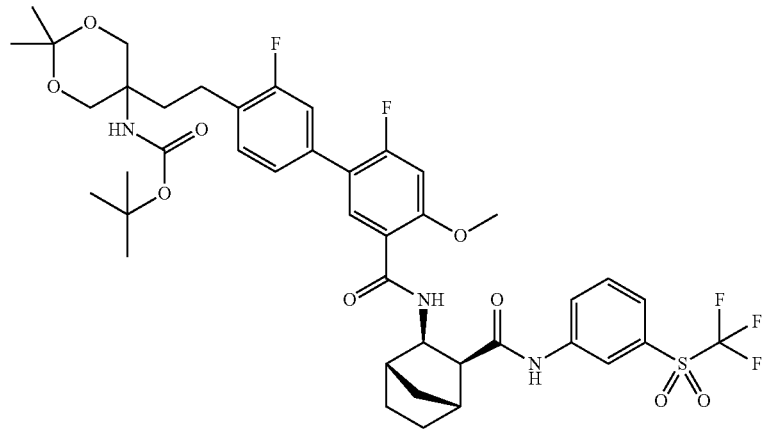 [SMILES: COc1cc(F)c(-c2ccc(CCC3(NC(=O)OC(C)(C)C)COC(C)(C)OC3)c(F)c2)cc1C(=O)N[C@@H]1[C@H]2CC[C@H](C2)[C@@H]1C(=O)Nc1cccc(S(=O)(=O)C(F)(F)F)c1]

The titled compound was prepared analogous to Example 236 step D, using Intermediate 372 instead of Compound 6.

Step B: (1R,2S,3R,4S)-3-(4'-(3-Amino-4-hydroxy-3-(hydroxymethyl)butyl)-3',6-difluoro-4-methoxy-[1,1'-biphenyl]-3-carboxamido)-N-(3-((trifluoromethyl)sulfonyl)phenyl)bicyclo[2.2.1]heptane-2-carboxamide A mixture of Intermediate 467 (77 mg, 0.090 mmol) in TFA (0.2 mL) was stirred at rt for 12 hr. Aq potassium carbonate was added to the reaction mixture and the mixture was extracted with CHCl$_3$. The combined organic layer was concentrated in vacuo. The crude product was purified by NH flash chromatography using a gradient of 0-5% MeOH in CHCl$_3$ as mobile phase to give the title compound (40 mg, 62%). HRMS (ESI) m/z [M+H]⁺ calcd for C34H37F5N3O7S: 726.2266 found: 726.2288.

Example 267: (RS)-2'-Fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-2,3,4,5-tetrahydro-[1,1'-biphenyl]-4-carboxylic acid

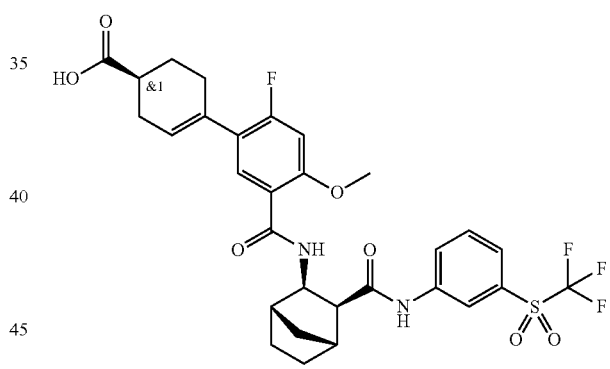

475

Step A: Intermediate 468: Ethyl (RS)-2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-2,3,4,5-tetrahydro-[1,1'-biphenyl]-4-carboxylate

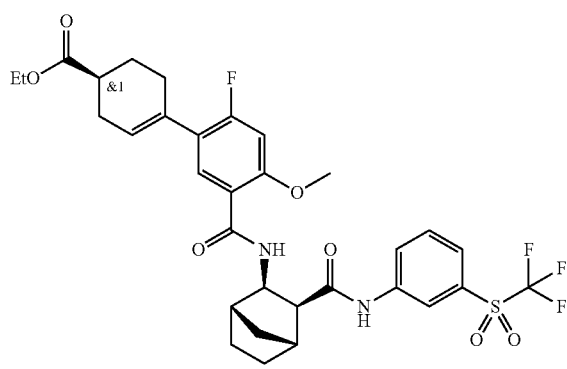 [SMILES: CCOC(=O)[C@@H]1CC=C(c2cc(C(=O)N[C@@H]3[C@H]4CC[C@H](C4)[C@@H]3C(=O)Nc3cccc(S(=O)(=O)C(F)(F)F)c3)c(OC)cc2F)CC1]

The titled compound was prepared analogous to Example 251 step B, using ethyl 4-(4,4,5,5-tetramethyl-1,3,2-dioxaborolan-2-yl)cyclohex-3-ene-1-carboxylate instead of Compound 7. MS (ESI) m/z 667.3 [M+H]$^+$.

Step B: (RS)-2'-Fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-2,3,4,5-tetrahydro-[1,1'-biphenyl]-4-carboxylic acid The titled compound was prepared analogous to Example 236 step E, using Intermediate 468 instead of Intermediate 448. MS (ESI) m/z 639.3 [M+H]$^+$.

Example 268: (1S,4s)-4-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)cyclohexane-1-carboxylic acid and Example 269: (1S,4s)-4-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)cyclohexane-1-carboxylic acid and (1R,4r)-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)cyclohexane-1-carboxylic acid and

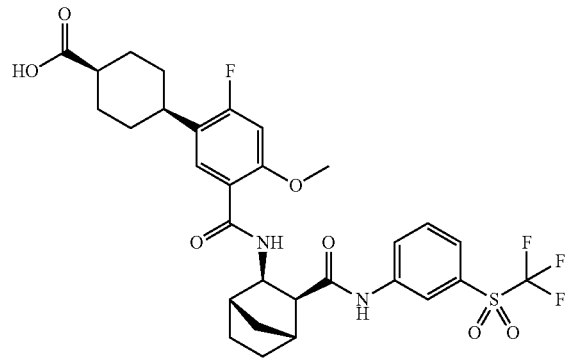

476

-continued

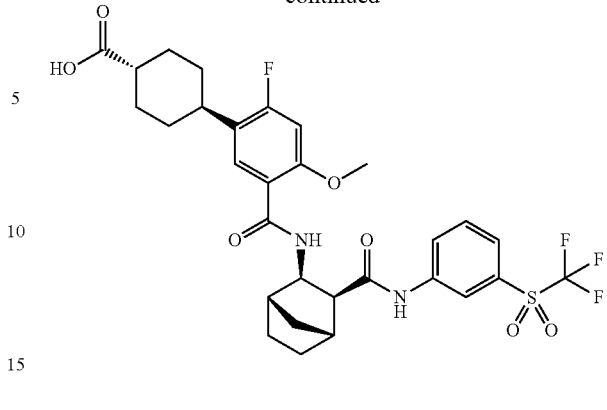

Step A: Intermediate 469: Ethyl 4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)cyclohexane-1-carboxylate

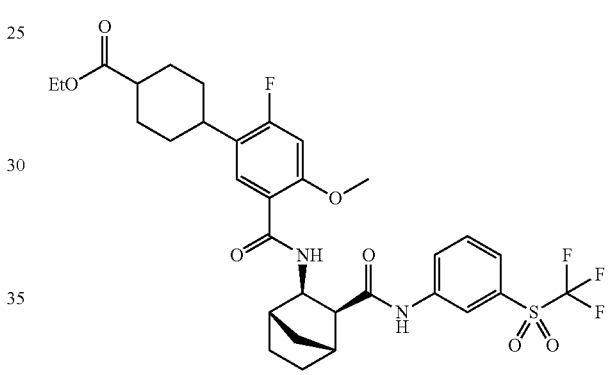

Palladium (10% Pd/C, moisture by 50% H$_2$O, 88 mg) was added to a solution of Intermediate 468 (120 mg, 0.18 mmol) in EtOH (3 mL). The reaction mixture was stirred under 1 atm of hydrogen atmosphere at rt for 5 hr. The hydrogen in the reaction vessel was replaced with argon and the reaction mixture was filtered with Celite®®. The filtrate was concentrated in vacuo and the crude product was purified by flash chromatography using 20-60% EtOAc in hexane as mobile phase to give titled compound (100 mg, 83%). MS (ESI) m/z 669.3 [M+H]$^+$.

Step B: (1S,4s)-4-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)cyclohexane-1-carboxylic acid and (1R,4r)-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenyl)cyclohexane-1-carboxylic acid 1 M aq LiOH (1.49 mL, 1.49 mmol) was added to a solution of Intermediate 469 (100 mg, 0.15 mmol) in DME (2 mL) and the mixture was stirred at rt for 12 hr. 1 M aq HCl and EtOAc were added to the reaction mixture and the layer was separated. Combined organic layer was concentrated in vacuo. The crude product was purified by reversed phase HPLC on a C18 column using a gradient of 50-60% MeCN in TFA (0.05% in H$_2$O) as mobile phase to give the first eluting compound Isomer 1: Example 268 (8 mg, 8%); MS (ESI) m/z 641.3 [M+H]+, and the second eluting compound Isomer 2: Example 269 (28 mg, 29%); MS (ESI) m/z 641.3 [M+H]+.

Example 270: 6-Fluoro-4-methoxy-N3-((1R,2R,3S,4S)-3-((3-((trifluoromethyl)sulfonyl)phenyl)carbamoyl)bicyclo[2.2.1]hept-5-en-2-yl)-[1,1'-biphenyl]-3,4'-dicarboxamide

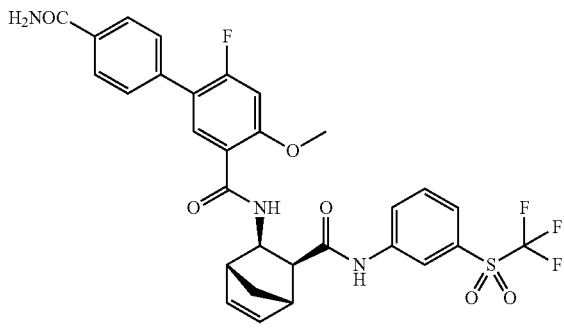 [SMILES: COc1cc(F)c(-c2ccc(C(N)=O)cc2)cc1C(=O)N[C@H]1[C@@H](C(=O)Nc2cccc(S(=O)(=O)C(F)(F)F)c2)[C@@H]2C=C[C@H]1C2]

Step A: Intermediate 470: (1S,2S,3R,4R)-3-(5-Bromo-4-fluoro-2-methoxybenzamido)-N-(3-((trifluoromethyl)sulfonyl)phenyl)bicyclo[2.2.1]hept-5-ene-2-carboxamide

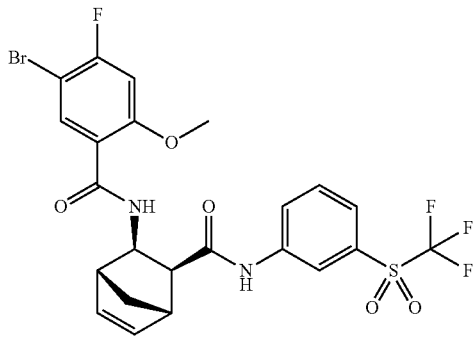 [SMILES: COc1cc(F)c(Br)cc1C(=O)N[C@H]1[C@@H](C(=O)Nc2cccc(S(=O)(=O)C(F)(F)F)c2)[C@@H]2C=C[C@H]1C2]

The titled compound was prepared analogous to Example 224 step A, using Intermediate 256 instead of Intermediate 213. MS (APCI) m/z 590.9/593.0 [M+H]+.

Step B: 6-Fluoro-4-methoxy-N3-((1R,2R,3S,4S)-3-((3-((trifluoromethyl)sulfonyl)phenyl)carbamoyl)bicyclo[2.2.1]hept-5-en-2-yl)-[1,1'-biphenyl]-3,4'-dicarboxamide PdCl$_2$(dppf)$_2$·CH$_2$Cl$_2$ (18 mg, 0.022 mmol) was added to the mixture of Intermediate 470 (130 mg, 0.22 mmol) and 4-carbamoylbenzeneboronic acid (73 mg, 0.44 mmol) in sat aq NaHCO$_3$ (0.4 mL) and DME (3 mL), and the mixture was stirred at reflux for 3 hr. The mixture was cooled to ambient temperature and extracted with CHCl$_3$, then the combined organic layer was concentrated in vacuo. The crude product was purified by flash chromatography using 0-5% MeOH in CHCl$_3$ as mobile phase to give the title compound (50 mg, 36%). HRMS (ESI) m/z [M+H]+ calcd for C30H26F4N3O6S: 632.1472 found: 632.1432.

Example 271: 2-(4-(2-Fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenyl)-1H-pyrazol-1-yl)acetic acid

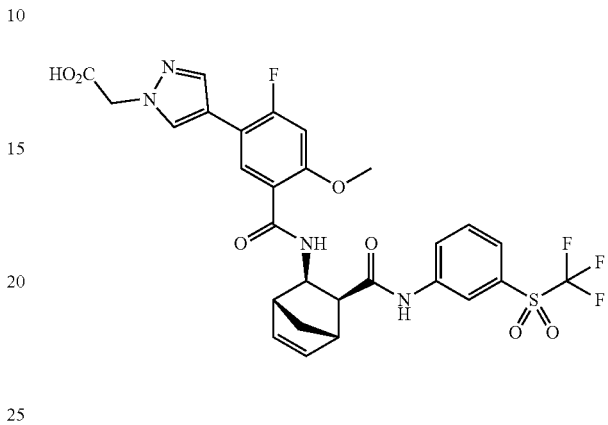

Step A: Intermediate 471: tert-Butyl 2-(4-(2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenyl)-1H-pyrazol-1-yl)acetate

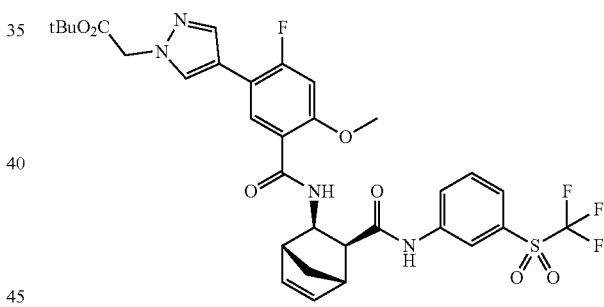

The titled compound was prepared analogous to Example 270 step B, using tert-butyl 2-[4-(4,4,5,5-tetramethyl-1,3,2-dioxaborolan-2-yl)pyrazol-1-yl]acetate instead of 4-carbamoylbenzeneboronic acid.

Step B: 2-(4-(2-Fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenyl)-1H-pyrazol-1-yl)acetic acid A mixture of TFA (1 mL) and Intermediate 471 (84 mg, 0.12 mmol) was stirred at rt for 1 hr. After the reaction mixture was concentrated in vacuo, the crude product was purified by reversed phase HPLC on a C18 column using a gradient of 25-55% MeCN in TFA (0.05% in H$_2$O) as mobile phase to give the title compound (85 mg, 93%). HRMS (ESI) m/z [M+H]+ calcd for C28H25F4N4O7S: 637.1374 found: 637.1362.

Example 272: rac-4-(2-Fluoro-4-methoxy-5-(((1R, 2R,3S,4S)-3-((3-((trifluoromethyl)sulfonyl)phenyl) carbamoyl)bicyclo[2.2.1]hept-5-en-2-yl)carbamoyl) phenyl)picolinic acid

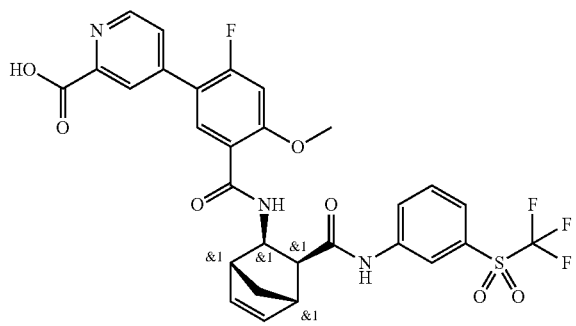 [SMILES: COc1cc(F)c(-c2ccnc(C(=O)O)c2)cc1C(=O)N[C@H]1[C@@H](C(=O)Nc2cccc(S(=O)(=O)C(F)(F)F)c2)[C@@H]2C=C[C@H]1C2]

Step A: Intermediate 472: rac-(1R,2R,3S,4S)-3-(4- Fluoro-2-methoxy-5-(4,4,5,5-tetramethyl-1,3,2-di- oxaborolan-2-yl)benzamido)-N-(3-((trifluoromethyl) sulfonyl)phenyl)bicyclo[2.2.1]hept-5-ene-2- carboxamide

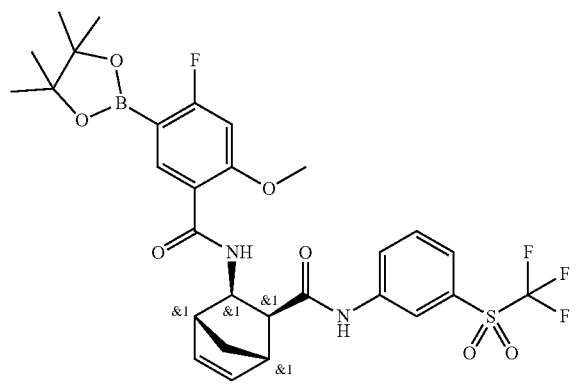 [SMILES: COc1cc(F)c(B2OC(C)(C)C(C)(C)O2)cc1C(=O)N[C@H]1[C@@H](C(=O)Nc2cccc(S(=O)(=O)C(F)(F)F)c2)[C@@H]2C=C[C@H]1C2]

The titled compound was prepared analogous to Example 236 step C, using Intermediate 213 instead of Intermediate 226. MS (ESI) m/z 639.3 [M+H]⁺.

Step B: Intermediate 473: rac-tert-Butyl 4-(2- fluoro-4-methoxy-5-(((1R,2R,3S,4S)-3-((3-((trifluo- romethyl)sulfonyl)phenyl)carbamoyl)bicyclo[2.2.1] hept-5-en-2-yl)carbamoyl)phenyl)picolinate

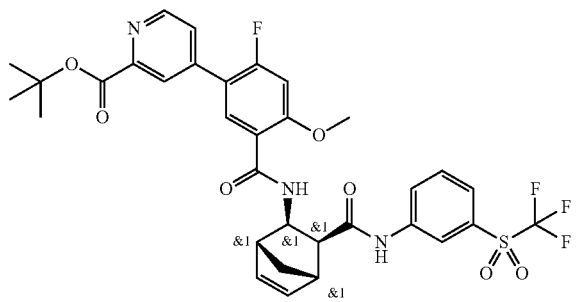 [SMILES: COc1cc(F)c(-c2ccnc(C(=O)OC(C)(C)C)c2)cc1C(=O)N[C@H]1[C@@H](C(=O)Nc2cccc(S(=O)(=O)C(F)(F)F)c2)[C@@H]2C=C[C@H]1C2]

Tris(dibenzylideneacetone)dipalladium(0) (5.0 mg, 0.005 mmol) and ((2,4,6-tri-isopropyl)phenyl)dicyclohexylphos- phine (6.5 mg, 0.014 mmol) were added to the mixture of Intermediate 472 (35 mg, 0.055 mmol), tert-butyl 4-chloro- pyridine-2-carboxylate (18 mg, 0.082 mmol) and CsF (25 mg, 0.165 mmol) in cyclopentyl methyl ether (0.5 mL), and the mixture was stirred at reflux for 3 hr. The mixture was cooled to ambient temperature, then H₂O and CHCl₃ was added to the reaction mixture. The mixture was extracted with CHCl₃ and combined organic layer was concentrated in vacuo. The crude product was purified by flash chromatog- raphy using a gradient of 0-50% EtOAc in hexane as mobile phase to give the title compound (25 mg, 66%). MS (ESI) m/z 690.3 [M+H]⁺.

Step C: rac-4-(2-Fluoro-4-methoxy-5-(((1R,2R,3S, 4S)-3-((3-((trifluoromethyl)sulfonyl)phenyl)carbam- oyl)bicyclo[2.2.1]hept-5-en-2-yl)carbamoyl)phenyl) picolinic acid A mixture of TFA (0.2 mL) and Intermediate 473 (24 mg, 0.034 mmol) was stirred at rt for 2 hr. After the reaction mixture was concentrated in vacuo, the crude product was purified by flash chromatography using a gradient of 0-20% MeOH in CHCl₃ as mobile phase to give the title compound (10 mg, 45%). MS (ESI) m/z 634.3 [M+H]⁺.

Example 273: rac-2'-Fluoro-4'-methoxy-5'-(((1R,2R, 3S,4S)-3-((3-((trifluoromethyl)sulfonyl)phenyl)car- bamoyl)bicyclo[2.2.1]hept-5-en-2-yl)carbamoyl)-[1, 1'-biphenyl]-2-carboxylic acid

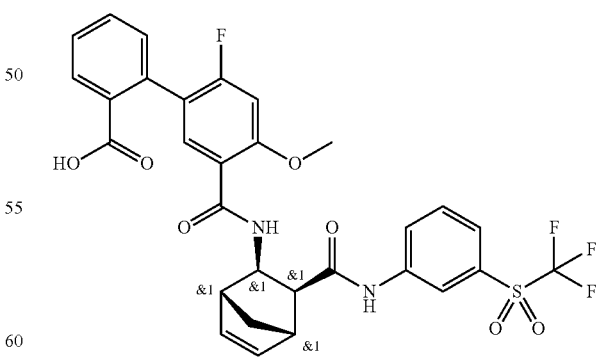

The titled compound was prepared analogous to Example 272 Step B and C, using tert-butyl 2-bromobenzoate instead of tert-butyl 4-chloropyridine-2-carboxylate. MS (ESI) m/z 633.3 [M+H]⁺.

Example 274: rac-5-(2-Fluoro-4-methoxy-5-(((1R, 2R,3S,4S)-3-((3-((trifluoromethyl)sulfonyl)phenyl) carbamoyl)bicyclo[2.2.1]hept-5-en-2-yl)carbamoyl) phenyl)picolinic acid Example 275: rac-2-(2-Fluoro-4-methoxy-5-(((1R, 2R,3S,4S)-3-((3-((trifluoromethyl)sulfonyl)phenyl) carbamoyl)bicyclo[2.2.1]hept-5-en-2-yl)carbamoyl) phenyl)oxazole-4-carboxylic acid

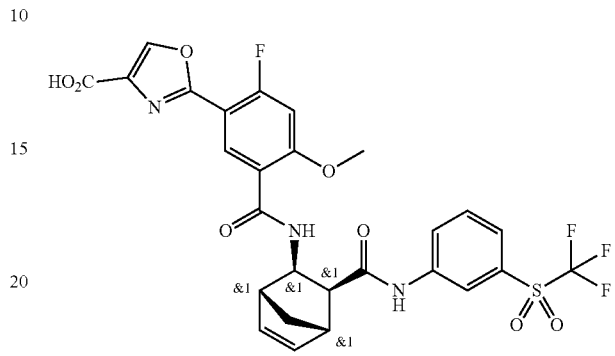

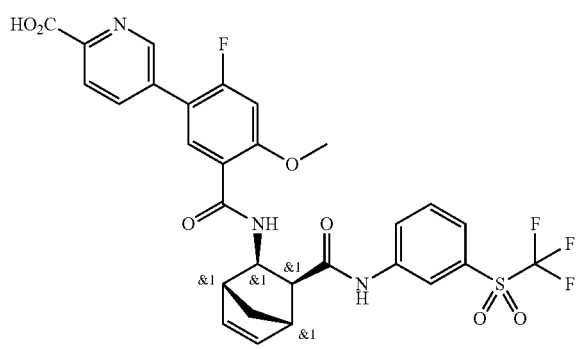 [SMILES: COc1cc(F)c(-c2ccc(C(=O)O)nc2)cc1C(=O)N[C@H]1[C@@H](C(=O)Nc2cccc(S(=O)(=O)C(F)(F)F)c2)[C@@H]2C=C[C@H]1C2]

Tetrakis(triphenylphosphine)palladium (7.2 mg, 0.006 mmol) was added to the mixture of Intermediate 472 (40 mg, 0.063 mmol), ethyl 2-chlorooxazole-4-carboxylate (Compound 8) (14 mg, 0.082 mmol) in sat aq $NaHCO_3$ (0.3 mL) and DME (0.3 mL), and the mixture was stirred at reflux for 4 hr. The mixture was cooled to ambient temperature, then 1 M aq HCl was added to the reaction mixture until pH<2. The mixture was extracted with $CHCl_3$ and combined organic layer was concentrated in vacuo. The crude product was purified by flash chromatography using a gradient of 0-20% MeOH in $CHCl_3$ as mobile phase to give the title compound (8 mg, 20%). MS (ESI) m/z 624.3 [M+H]$^+$.

The titled compound was prepared analogous to Example 272 Step B and C, using tert-butyl 5-bromopyridine-2-carboxylate instead of tert-butyl 4-chloropyridine-2-carboxylate. MS (ESI) m/z 634.1 [M+H]$^+$.

The examples included in Table 21 below were synthesized analogously to Example 275, using the specified starting material instead of Compound 8.

TABLE 21

| Ex No. | SM | Product | MS (ESI) |
|---|---|---|---|
| 276 | | | m/z 635.3 [M + H]$^+$ |

TABLE 21-continued
| Ex No. | SM | Product | MS (ESI) |
|---|---|---|---|
| 277 | 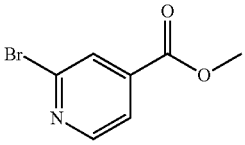 | 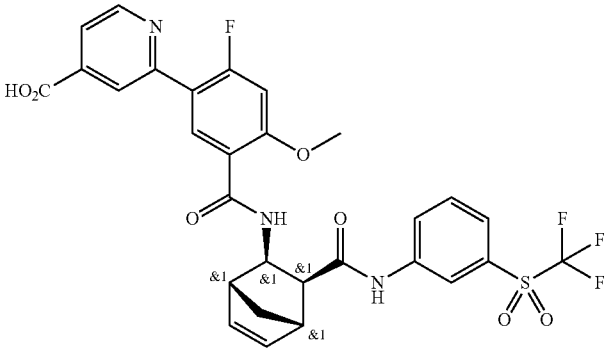 | m/z 634.3 [M + H]+ |
| 278 | 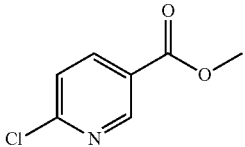 | 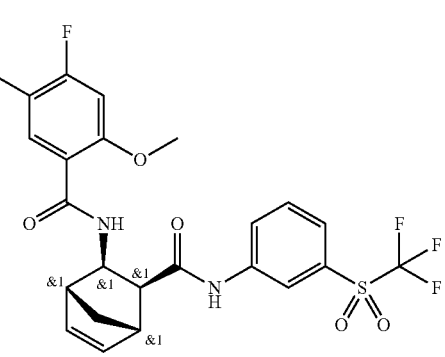 | m/z 634.2 [M + H]+ |
| 279 | 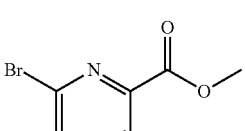 | 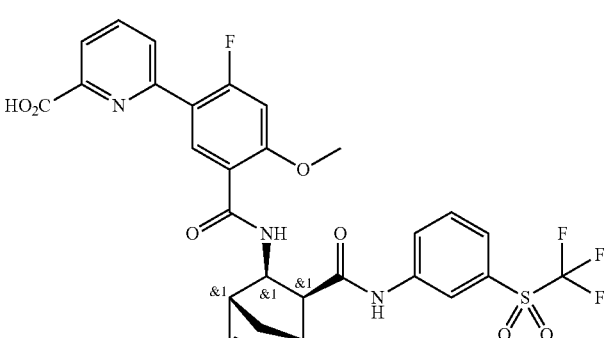 | m/z 634.3 [M + H]+ |
| 280 | 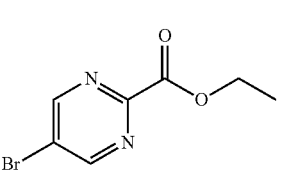 | 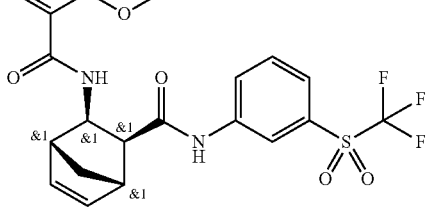 | m/z 635.3 [M + H]+ |

TABLE 21-continued
| Ex No. | SM | Product | MS (ESI) |
|---|---|---|---|
| 281 | 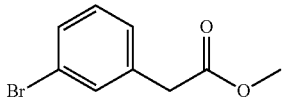 | 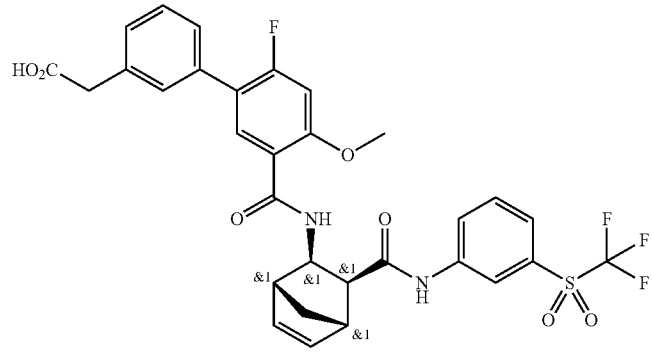 [SMILES: COc1cc(F)c(-c2cccc(CC(=O)O)c2)cc1C(=O)N[C@H]1[C@@H](C(=O)Nc2cccc(S(=O)(=O)C(F)(F)F)c2)[C@@H]2C=C[C@H]1C2] | HRMS m/z [M + H]+ 647.1512 |
| 282 | 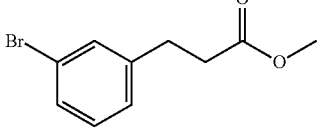 | 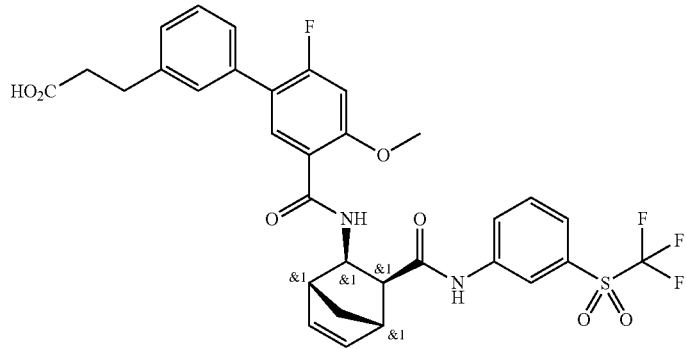 [SMILES: COc1cc(F)c(-c2cccc(CCC(=O)O)c2)cc1C(=O)N[C@H]1[C@@H](C(=O)Nc2cccc(S(=O)(=O)C(F)(F)F)c2)[C@@H]2C=C[C@H]1C2] | HRMS m/z [M + H]+ 661.1606 |
| 283 | 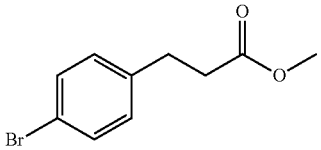 | 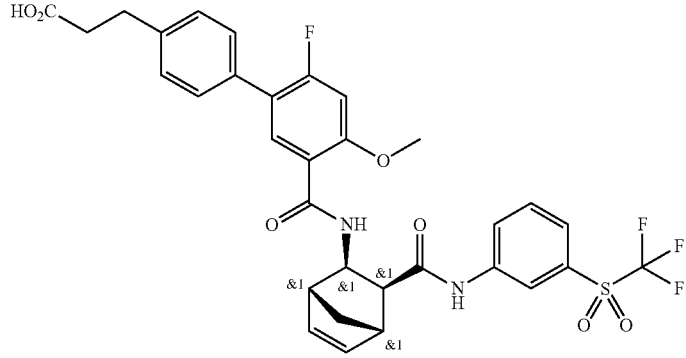 [SMILES: COc1cc(F)c(-c2ccc(CCC(=O)O)cc2)cc1C(=O)N[C@H]1[C@@H](C(=O)Nc2cccc(S(=O)(=O)C(F)(F)F)c2)[C@@H]2C=C[C@H]1C2] | HRMS m/z [M + H]+ 661.1640 |

Example 284: rac-5-(2-Fluoro-4-methoxy-5-((((1R, 2R,3S,4S)-3-((3-((trifluoromethyl)sulfonyl)phenyl) carbamoyl)bicyclo[2.2.1]hept-5-en-2-yl)carbamoyl) phenyl)thiophene-3-carboxylic acid

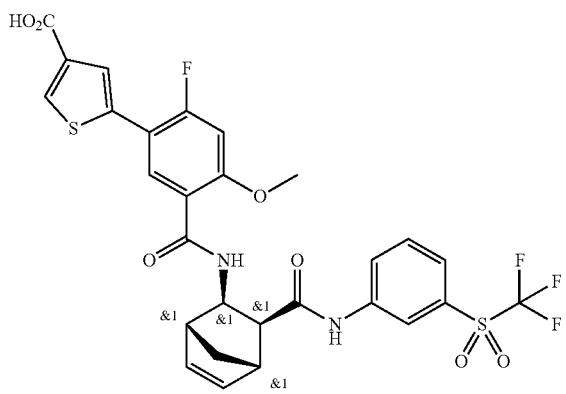

Step A: Intermediate 474: rac-Methyl 5-(2-fluoro-4-methoxy-5-((((1R,2R,3S,4S)-3-((3-((trifluoromethyl)sulfonyl)phenyl)carbamoyl)bicyclo[2.2.1]hept-5-en-2-yl)carbamoyl)phenyl)thiophene-3-carboxylate

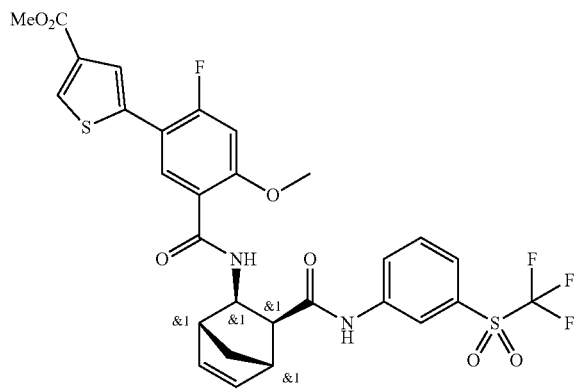 [SMILES: COC(=O)c1csc(-c2cc(C(=O)N[C@H]3[C@@H](C(=O)Nc4cccc(S(=O)(=O)C(F)(F)F)c4)[C@@H]4C=C[C@H]3C4)c(OC)cc2F)c1]

Tetrakis(triphenylphosphine)palladium (5.4 mg, 0.005 mmol) was added to the mixture of Intermediate 472 (30 mg, 0.047 mmol), methyl 5-bromothiophene-3-carboxylate (Compound 9) (12 mg, 0.056 mmol) in sat aq NaHCO$_3$ (0.5 mL) and DME (0.5 mL), and the mixture was stirred at reflux for 2 hr. After the mixture was cooled to ambient temperature the mixture was extracted with CHCl$_3$ and combined organic layer was concentrated in vacuo. The crude product was purified by flash chromatography using a gradient of 0-4% MeOH in CHCl$_3$ as mobile phase to give the title compound (31 mg, 75%). MS (ESI) m/z 653.2 [M+H]$^+$.

Step B: rac-5-(2-Fluoro-4-methoxy-5-((((1R,2R,3S, 4S)-3-((3-((trifluoromethyl)sulfonyl)phenyl)carbamoyl)bicyclo[2.2.1]hept-5-en-2-yl)carbamoyl)phenyl) thiophene-3-carboxylic acid The titled compound was prepared analogous to Example 236 step E, using Intermediate 474 instead of Intermediate 448. MS (ESI) m/z 639.2 [M+H]$^+$.

The examples included in Table 22 below were synthesized analogously to Example 284, using the specified starting material instead of Compound 9.

TABLE 22

| Ex No. | SM | Product | MS (ESI) |
|---|---|---|---|
| 285 | ![SM] | ![Product] | m/z 639.2 [M + H]$^+$ |

TABLE 22-continued
| Ex No. | SM | Product | MS (ESI) |
|---|---|---|---|
| 286 | 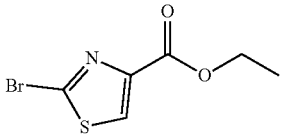 | 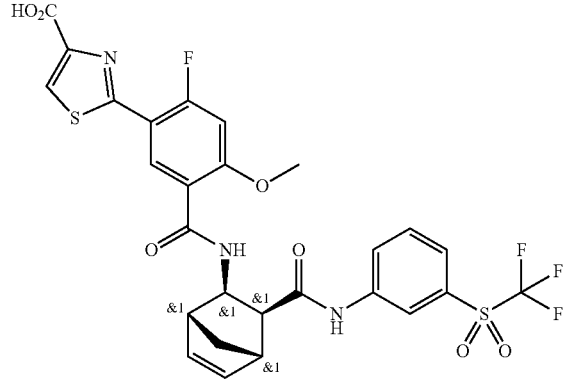 [SMILES: COc1cc(F)c(-c2nc(C(=O)O)cs2)cc1C(=O)N[C@H]1[C@@H](C(=O)Nc2cccc(S(=O)(=O)C(F)(F)F)c2)[C@@H]2C=C[C@H]1C2] | m/z 640.2 [M + H]+ |
| 287 | 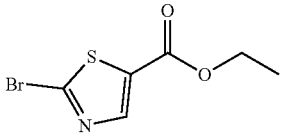 | 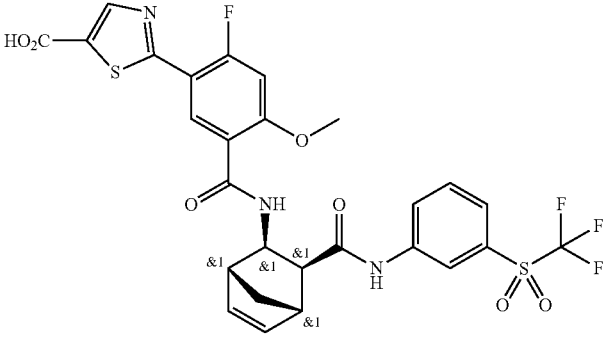 [SMILES: COc1cc(F)c(-c2ncc(C(=O)O)s2)cc1C(=O)N[C@H]1[C@@H](C(=O)Nc2cccc(S(=O)(=O)C(F)(F)F)c2)[C@@H]2C=C[C@H]1C2] | m/z 640.2 [M + H]+ |
| 288 | 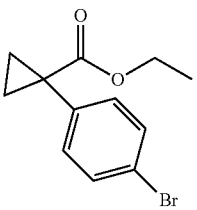 | 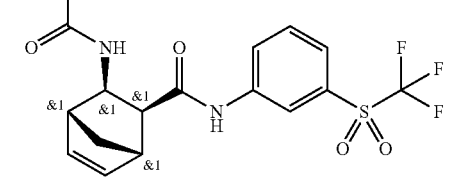 | HRMS m/z [M + H]+ 673.1642 |

Example 289: (S)-2-(Dimethylamino)-3-(2'-fluoro-4'-methoxy-5'-(((1RS,2SR,3RS,4SR)-3-((3-((trifluoromethyl)sulfonyl)phenyl)carbamoyl)bicyclo[2.2.1]heptan-2-yl)carbamoyl)-[1,1'-biphenyl]-4-yl)propanoic acid

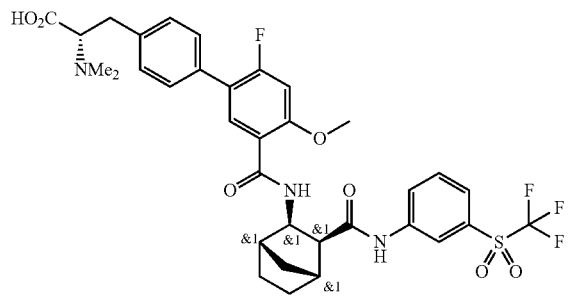 [SMILES: COc1cc(F)c(-c2ccc(C[C@@H](C(=O)O)N(C)C)cc2)cc1C(=O)N[C@@H]1[C@H]2CC[C@H](C2)[C@@H]1C(=O)Nc1cccc(S(=O)(=O)C(F)(F)F)c1]

Step A: Intermediate 475: (S)-2-((tert-Butoxycarbonyl)amino)-3-(2'-fluoro-4'-methoxy-5'-(((1RS,2RS,3SR,4SR)-3-((3-((trifluoromethyl)sulfonyl)phenyl)carbamoyl)bicyclo[2.2.1]hept-5-en-2-yl)carbamoyl)-[1,1'-biphenyl]-4-yl)propanoic acid

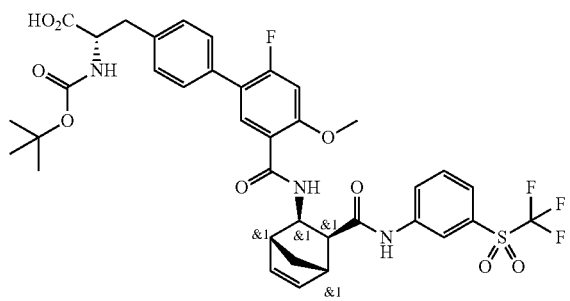 [SMILES: COc1cc(F)c(-c2ccc(C[C@H](NC(=O)OC(C)(C)C)C(=O)O)cc2)cc1C(=O)N[C@H]1[C@@H](C(=O)Nc2cccc(S(=O)(=O)C(F)(F)F)c2)[C@@H]2C=C[C@H]1C2]

Tetrakis(triphenylphosphine)palladium (9 mg, 0.008 mmol) was added to the mixture of Intermediate 472 (50 mg, 0.078 mmol), (2S)-3-(4-bromophenyl)-2-(tert-butoxycarbonylamino)propanoic acid (54 mg, 0.157 mmol) in sat aq NaHCO₃ (1 mL) and DME (1 mL), and the mixture was stirred at reflux for 3 hr. The mixture was cooled to ambient temperature, then aq citric acid was added to the reaction mixture. The mixture was extracted with EtOAc and combined organic layer was concentrated in vacuo. The crude product was purified by flash chromatography using a gradient of 0-10% MeOH in CHCl₃ as mobile phase to give the title compound (50 mg, 82%).

Step B: (S)-2-(Dimethylamino)-3-(2'-fluoro-4'-methoxy-5'-(((1RS,2SR,3RS,4SR)-3-((3-((trifluoromethyl)sulfonyl)phenyl)carbamoyl)bicyclo[2.2.1]heptan-2-yl)carbamoyl)-[1,1'-biphenyl]-4-yl)propanoic acid A mixture of Intermediate 475 (50 mg, 0.064 mmol) in 4 M HCl in EtOAc (1 mL) was stirred at rt for 12 hr. MeCN (1 mL) and H₂O (1 mL) were added to the reaction mixture, then HCHO (37% in H₂O, 21 mg, 0.258 mmol) and NaBH(OAc)₃ (41 mg, 0.193 mmol) were added and the mixture was stirred at rt for 3 hr. The mixture was concentrated in vacuo and the crude product was purified by reversed phase HPLC on a C18 column using a gradient of 20-45% MeCN in TFA (0.05% in H₂O) as mobile phase to give the title compound (50 mg, 82%). HRMS (ESI) m/z [M+H]⁺ calcd for C34H36F4N3O7S: 706.2204 found: 706.2212.

Example 290: (R)-2-(Dimethylamino)-3-(2'-fluoro-4'-methoxy-5'-(((1RS,2SR,3RS,4SR)-3-((3-((trifluoromethyl)sulfonyl)phenyl)carbamoyl)bicyclo[2.2.1]heptan-2-yl)carbamoyl)-[1,1'-biphenyl]-4-yl)propanoic acid

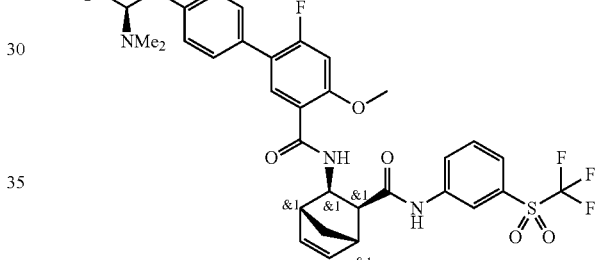

The titled compound was prepared analogous to Example 289, using (2R)-3-(4-bromophenyl)-2-(tert-butoxycarbonylamino)propanoic acid instead of (2S)-3-(4-bromophenyl)-2-(tert-butoxycarbonylamino)propanoic acid. HRMS (ESI) m/z [M+H]⁺ calcd for C34H36F4N3O7S: 706.2204 found: 706.2202.

Example 291: (R)-2-Amino-3-(2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoic acid

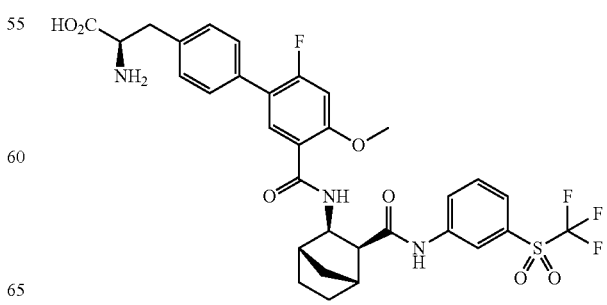

Step A: Intermediate 476: (R)-2-((tert-Butoxycarbonyl)amino)-3-(2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoic acid

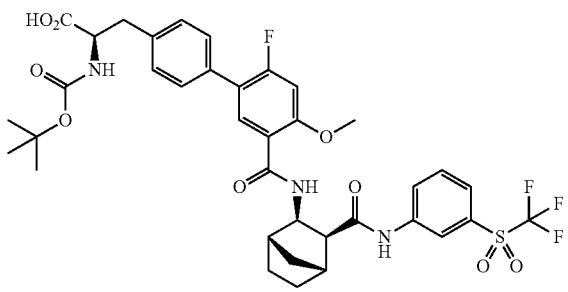 [SMILES: COc1cc(F)c(-c2ccc(C[C@@H](NC(=O)OC(C)(C)C)C(=O)O)cc2)cc1C(=O)N[C@@H]1[C@H]2CC[C@H](C2)[C@@H]1C(=O)Nc1cccc(S(=O)(=O)C(F)(F)F)c1]

Tetrakis(triphenylphosphine)palladium (20 mg, 0.097 mmol) was added to the mixture of Intermediate 447 (100 mg, 0.179 mmol), (2R)-3-(4-bromophenyl)-2-(tert-butoxycarbonylamino)propanoic acid (123 mg, 0.358 mmol) in sat aq NaHCO₃ (1 mL) and DME (1 mL), and the mixture was stirred at reflux for 3 hr. The mixture was cooled to ambient temperature, then aq citric acid was added to the reaction mixture. The mixture was extracted with CHCl₃ and combined organic layer was concentrated in vacuo. The crude product was purified by flash chromatography using a gradient of 0-5% MeOH in CHCl₃ as mobile phase to give the title compound (86 mg, 62%).

Step B: (R)-2-Amino-3-(2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoic acid A mixture of Intermediate 476 (86 mg, 0.11 mmol) in 4 M HCl in EtOAc (1 mL) was stirred at rt for 1 hr. The mixture was concentrated and the crude product was purified by reversed phase HPLC on a C18 column using a gradient of 20-50% MeCN in TFA (0.05% in H₂O) as mobile phase to give the title compound (41 mg, 47%). HRMS (ESI) m/z [M+H]⁺ calcd for C32H32F4N3O7S: 678.1892 found: 678.1902.

Example 292: (R)-2-(Dimethylamino)-3-(2'-fluoro-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)propanoic acid

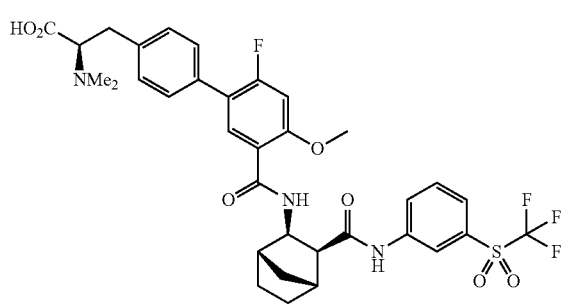 [SMILES: COc1cc(F)c(-c2ccc(C[C@H](C(=O)O)N(C)C)cc2)cc1C(=O)N[C@@H]1[C@H]2CC[C@H](C2)[C@@H]1C(=O)Nc1cccc(S(=O)(=O)C(F)(F)F)c1]

NaBH(OAc)₃ (36 mg, 0.171 mmol) was added to a mixture of HCHO (37% in H₂O, 0.013 mL, 0.171 mmol) and Example 291 (45 mg, 0.057 mmol) in MeCN (1 mL), and the mixture was stirred at rt for 12 hr. The mixture was concentrated and the crude product was purified by reversed phase HPLC on a C18 column using a gradient of 25-55% MeCN in TFA (0.05% in H₂O) as mobile phase to give the title compound (45 mg, 97%). HRMS (ESI) m/z [M+H]⁺ calcd for C34H36F4N3O7S: 706.2204 found: 706.2186.

The examples included in Table 23 below were synthesized analogously to Example 291 followed by Example 292, using the specified starting material instead of (2R)-3-(4-bromophenyl)-2-(tert-butoxycarbonylamino)propanoic acid for Example 291 Step A.

TABLE 23

| Ex No. | SM (Step A) | Product | MS (ESI) |
|---|---|---|---|
| 293 | ![SM structure] | ![Product structure] | HRMS m/z [M + H]⁺ 706.2256 |

TABLE 23-continued

| Ex No. | SM (Step A) | Product | MS (ESI) |
|---|---|---|---|
| 294 | | | m/z 692.1 [M + H]+ |
| 295 | | | m/z 692.1 [M + H]+ |

Example 296: rac-2'-Fluoro-5'-(((1R,2R,3S,4S)-3-((4-fluoro-3-((trifluoromethyl)sulfonyl)phenyl)carbamoyl)bicyclo[2.2.1]hept-5-en-2-yl)carbamoyl)-4'-methoxy-[1,1'-biphenyl]-4-carboxylic acid

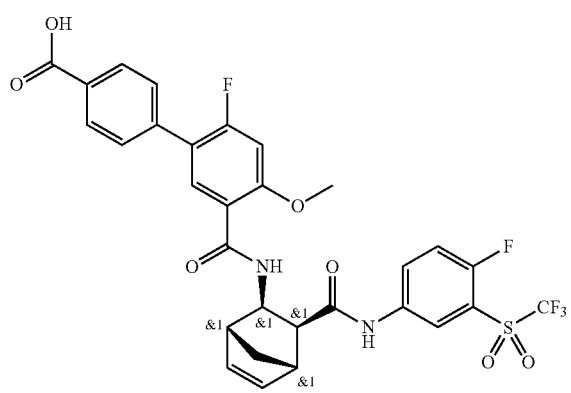 [SMILES: COc1cc(F)c(-c2ccc(C(=O)O)cc2)cc1C(=O)N[C@H]1[C@@H](C(=O)Nc2ccc(F)c(S(=O)(=O)C(F)(F)F)c2)[C@@H]2C=C[C@H]1C2]

Step A: Intermediate 477: 3-Benzyl 4'-(tert-butyl) 6-fluoro-4-methoxy-[1,1'-biphenyl]-3,4'-dicarboxylate

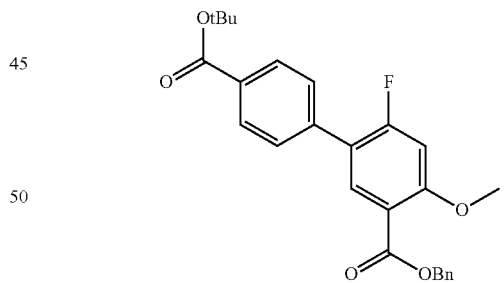

Tetrakis(triphenylphosphine)palladium (100 mg, 0.087 mmol) was added to the mixture of Intermediate 444 (300 mg, 0.884 mmol) and (4-tert-butoxycarbonylphenyl)boronic acid (300 mg, 1.35 mmol) in sat aq NaHCO₃ (3 mL) and DME (3 mL), and the mixture was stirred at reflux for 2 hr. The mixture was cooled to ambient temperature and extracted with CHCl₃, then the combined organic layer was concentrated in vacuo. The crude product was purified by flash chromatography using 15% EtOAc in hexane as mobile phase to give the title compound (386 mg, 99%). MS (APCI) m/z 381.0 [M+H]+.

Step B: Intermediate 478: 4'-(tert-Butoxycarbonyl)-6-fluoro-4-methoxy-[1,1'-biphenyl]-3-carboxylic acid

Step C: Intermediate 479: rac-tert-Butyl 2'-fluoro-5'-(((1R,2R,3S,4S)-3-((4-fluoro-3-((trifluoromethyl)sulfonyl)phenyl)carbamoyl)bicyclo[2.2.1]hept-5-en-2-yl)carbamoyl)-4'-methoxy-[1,1'-biphenyl]-4-carboxylate

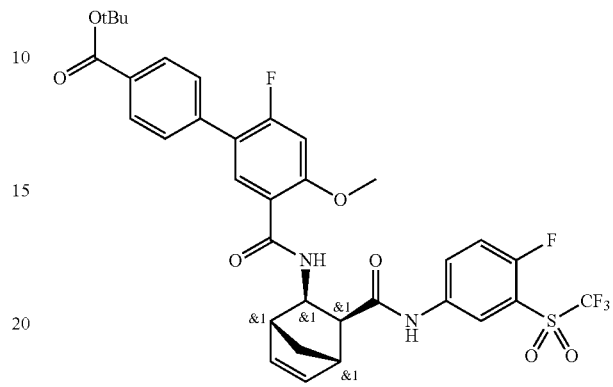

WSC.HCl (55 mg, 0.289 mmol), HOAt (20 mg, 0.145 mmol) and TEA (0.06 mL, 0.434 mmol) were added to a solution of Intermediate 214 (60 mg, 0.145 mmol) and Intermediate 478 (50 mg, 0.145 mmol) in $CHCl_3$ (1 mL), then the mixture was stirred at rt for 12 hr. The mixture was concentrated in vacuo and the crude product was used without further purification.

Step D: rac-2'-Fluoro-5'-(((1R,2R,3S,4S)-3-((4-fluoro-3-((trifluoromethyl)sulfonyl)phenyl)carbamoyl)bicyclo[2.2.1]hept-5-en-2-yl)carbamoyl)-4'-methoxy-[1,1'-biphenyl]-4-carboxylic acid The mixture of Intermediate 479 (180 mg, 0.017 mmol) and TFA (2 mL, 26 mmol) were stirred at rt for 12 hr. After the reaction mixture was concentrated in vacuo, the crude product was purified by flash chromatography using 7% MeOH in $CHCl_3$ as mobile phase to give the title compound (94 mg, 18%). HRMS (ESI) m/z [M+H]$^+$ calcd for $C_{30}H_{24}F_5N_2O_7S$: 651.1218 found: 651.1202.

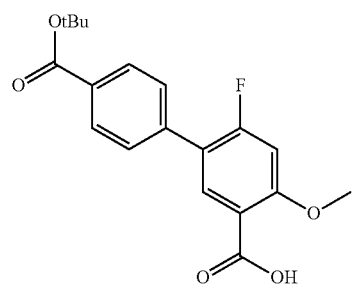 [SMILES: COc1cc(F)c(-c2ccc(C(=O)OC(C)(C)C)cc2)cc1C(=O)O]

1 M aq NaOH (2.0 mL, 2.0 mmol) was added to the solution of Intermediate 477 (386 mg, 0.88 mmol) in MeOH (10 mL), and the mixture was stirred at rt for 12 hr. The mixture was concentrated in vacuo, then 1 M aq HCl was added to the mixture and residual precipitate was collected by filtration to give the title compound (160 mg, 52%). MS (APCI) m/z 364.1 [M+H]$^+$.

The examples included in Table 24 below were synthesized analogously to Example 296, using the specified starting material for Step A instead of (4-tert-butoxycarbonylphenyl)boronic acid, and the specified starting material for Step C instead of Intermediate 214.

TABLE 24

| Ex No. | SM (Step A) | SM (Step C) | Product | MS (ESI) |
|---|---|---|---|---|
| 297 | ![boronic acid] | Int. 214 | ![product] | HRMS m/z [M + H]$^+$ 651.1230 |

TABLE 24-continued

| Ex No. | SM (Step A) | SM (Step C) | Product | MS (ESI) |
|---|---|---|---|---|
| 298 | [4-(tert-butoxycarbonyl)phenyl]boronic acid | Int. 215 | biphenyl carboxylic acid product with fluoro, methoxy, norbornene-dicarboxamide linker to 3-fluoro-5-(pentafluorosulfanyl)aniline | m/z 645.3 [M + H]+ |
| 299 | [4-(tert-butoxycarbonyl)phenyl]boronic acid | Int. 216 | biphenyl carboxylic acid product with fluoro, methoxy, cyclopentane-dicarboxamide linker to 3-(trifluoromethylsulfonyl)aniline | m/z 609.0 [M + H]+ |
| 300 | [3-(tert-butoxycarbonyl)phenyl]boronic acid | Int. 216 | biphenyl-3-carboxylic acid product with fluoro, methoxy, cyclopentane-dicarboxamide linker to 3-(trifluoromethylsulfonyl)aniline | m/z 609.0 [M + H]+ |
| 301 | [4-(tert-butoxycarbonyl)phenyl]boronic acid | Int. 183 | biphenyl carboxylic acid product with fluoro, methoxy, cyclobutane-dicarboxamide linker to 3-(trifluoromethylsulfonyl)aniline | |

TABLE 24-continued
| Ex No. | SM (Step A) | SM (Step C) | Product | MS (ESI) |
|---|---|---|---|---|
| 302 | 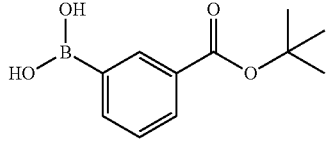 | Int. 183 | 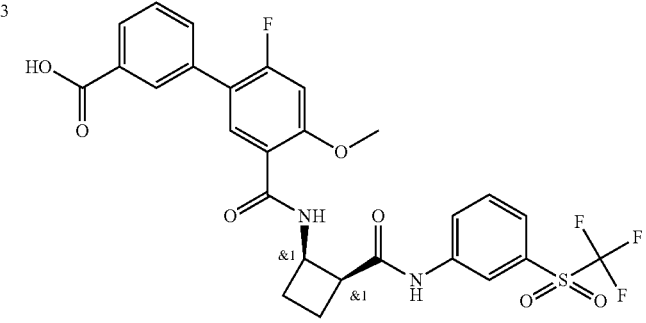 | m/z 609.0 [M + H]+ |
| 303 | 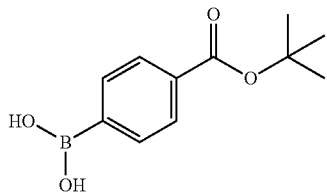 | Int. 231 | 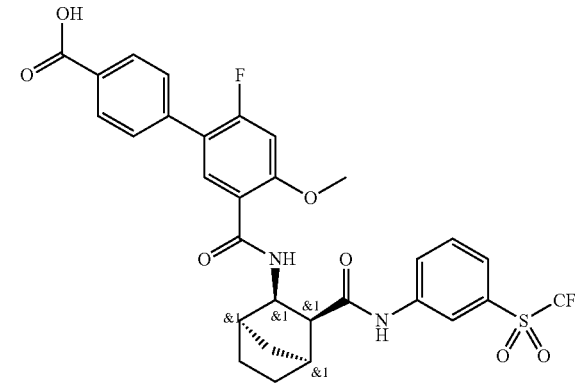 | m/z 635.2 [M + H]+ |
| 304 | 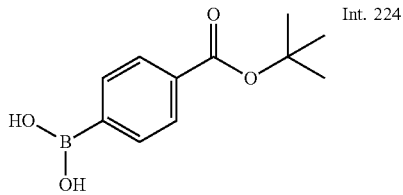 | Int. 224 | 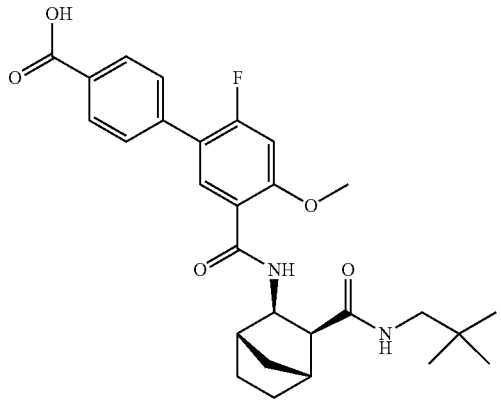 [SMILES: COc1cc(F)c(-c2ccc(C(=O)O)cc2)cc1C(=O)N[C@@H]1[C@H]2CC[C@H](C2)[C@@H]1C(=O)NCC(C)(C)C] | m/z 497.5 [M + H]+ |

503

Example 305: rac-2'-Fluoro-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid

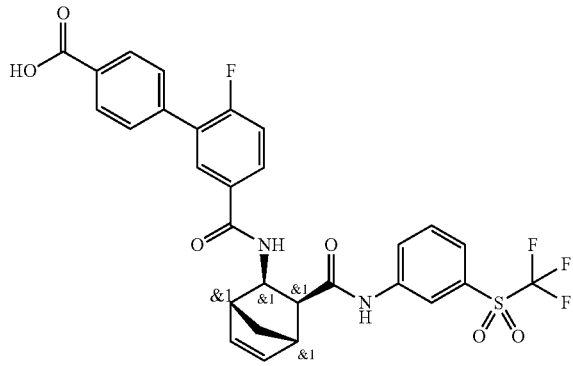 [SMILES: O=C(O)c1ccc(-c2cc(C(=O)N[C@H]3[C@@H](C(=O)Nc4cccc(S(=O)(=O)C(F)(F)F)c4)[C@@H]4C=C[C@H]3C4)ccc2F)cc1]

Step A: Intermediate 480: rac-(1R,2R,3S,4S)-3-(3-bromo-4-fluorobenzamido)-N-(3-((trifluoromethyl)sulfonyl)phenyl)bicyclo[2.2.1]hept-5-ene-2-carboxamide

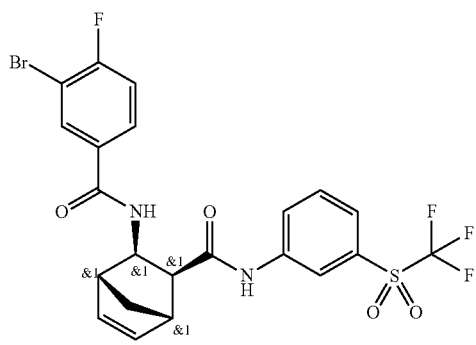 [SMILES: O=C(N[C@H]1[C@@H](C(=O)Nc2cccc(S(=O)(=O)C(F)(F)F)c2)[C@@H]2C=C[C@H]1C2)c1ccc(F)c(Br)c1]

T3P (1.7 M in EtOAc, 0.57 mL, 0.97 mmol) and DIPEA (0.25 mL, 1.46 mmol) were added to a solution of Intermediate 213 (175 mg, 0.49 mmol) and 3-bromo-4-fluorobenzoic acid (117 mg, 0.53 mmol) in EtOAc (3 mL), then the mixture was stirred at rt for 17 hr. Sat aq NaHCO$_3$ was added to the reaction mixture, then organic layer was separated and concentrated in vacuo. After H$_2$O and a few drop of THF were added to a crude mixture, residual precipitate was collected by filtration and washed with H$_2$O and MeOH to give the title compound (239 mg, 88%). MS (APCI) m/z 560.9/562.9 [M+H]$^+$.

504

Step B: Intermediate 481: rac-methyl 2'-fluoro-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylate

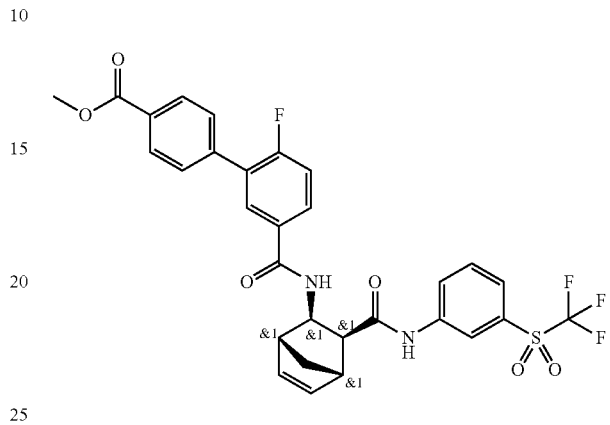

Tetrakis(triphenylphosphine)palladium (9.3 mg, 0.008 mmol) was added to the mixture of Intermediate 480 (90 mg, 0.16 mmol) and (4-methoxycarbonylphenyl)boronic acid (43 mg, 0.241 mmol) in sat aq NaHCO$_3$ (0.5 mL) and DME (2 mL), and the mixture was stirred at reflux for 7 hr. The mixture was cooled to ambient temperature and extracted with EtOAc, then the combined organic layer was concentrated in vacuo. The crude product was purified by flash chromatography using 10-35% EtOAc in hexane as mobile phase to give the title compound (58 mg, 58%). MS (APCI) m/z 617.0 [M+H]$^+$.

Step C: rac-2'-Fluoro-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid 1 M aq LiOH (0.81 mL, 0.81 mmol) was added to a solution of Intermediate 481 (50 mg, 0.81 mmol) in DME (3 mL), and the reaction mixture was stirred at rt for 6 hr. 2 M aq HCl was added to the reaction mixture to adjust pH<2 and the reaction mixture was extracted with CHCl$_3$ twice and the combined organic layer was concentrated in vacuo. The crude product was purified by flash chromatography using 0-6% MeOH in EtOAc as mobile phase to give the title compound (30 mg, 61%). MS (APCI) m/z 603.0 [M+H]$^+$.

Example 306: rac-2',4'-Difluoro-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-4-carboxylic acid

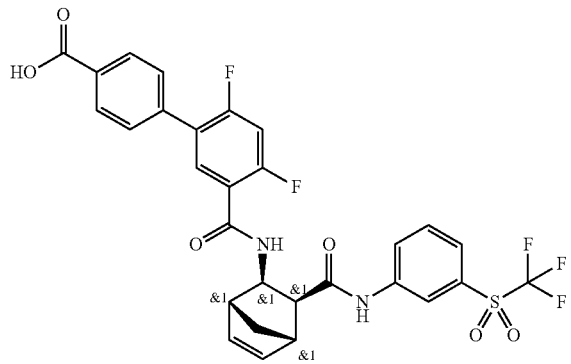

The titled compound was prepared analogous to Example 305, using 3-bromo-2,4-difluorobenzoic acid instead of 3-bromo-4-fluorobenzoic acid. MS (APCI) m/z 621.0 [M+H]⁺.

Example 307: rac-2'-Fluoro-5'-(((1R,2R,3S,4S)-3-((4-fluoro-3-(trifluoromethyl)phenyl)carbamoyl)bicyclo[2.2.1]hept-5-en-2-yl)carbamoyl)-4'-methoxy-[1,1'-biphenyl]-4-carboxylic acid

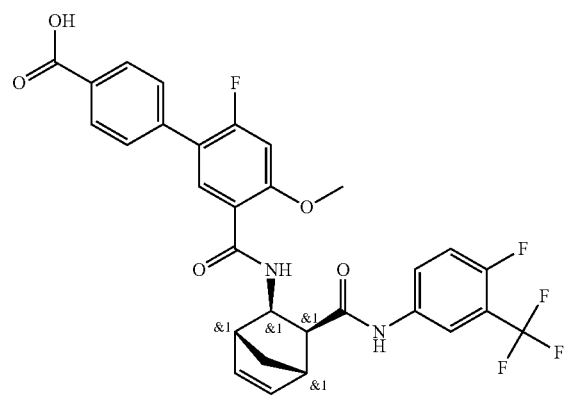 [SMILES: COc1cc(F)c(-c2ccc(C(=O)O)cc2)cc1C(=O)N[C@H]1[C@@H](C(=O)Nc2ccc(F)c(C(F)(F)F)c2)[C@@H]2C=C[C@H]1C2]

Step A: Intermediate 482: 3-Benzyl 4'-methyl 6-fluoro-4-methoxy-[1,1'-biphenyl]-3,4'-dicarboxylate

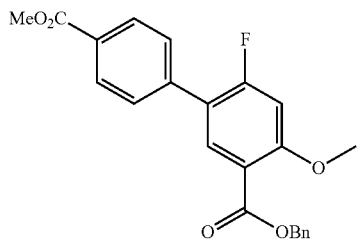 [SMILES: COC(=O)c1ccc(-c2cc(C(=O)OCc3ccccc3)c(OC)cc2F)cc1]

Bis(di-tert-butyl(4-dimethylaminophenyl)phosphine)dichloropalladium(II) (203 mg, 0.28 mmol) and $K_3PO_4$ (2.39 mg, 11.3 mmol) were added to a solution of Intermediate 444 (350 mg, 1.03 mmol) and (4-methoxycarbonylphenyl)boronic acid (2.03 g, 11.26 mmol) in toluene (28.7 mL) and $H_2O$ (5.7 mL), then the mixture was stirred at reflux temperature for 1.5 hr. The mixture was cooled to ambient temperature and $H_2O$ was added, then the mixture was extracted with EtOAc and the organic layer was concentrated in vacuo. The crude product was purified by NH flash chromatography using a gradient of 10-30% EtOAc in hexane as mobile phase to give the title compound (2.11 g, 95%). MS (ESI) m/z 287.1 [M+H]⁺.

Step B: Intermediate 483: 6-Fluoro-4-methoxy-4'-(methoxycarbonyl)-[1,1'-biphenyl]-3-carboxylic acid

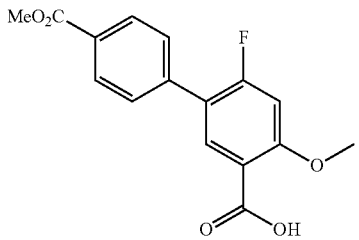 [SMILES: COC(=O)c1ccc(-c2cc(C(=O)O)c(OC)cc2F)cc1]

Palladium (10% Pd/C, moisture by 50% $H_2O$, 235 mg) was added to a solution of Intermediate 482 (2.35 g, 5.95 mmol) in MeOH (23 mL) and THF (23 mL). The reaction mixture was stirred under 1 atm of hydrogen atmosphere at rt for 15 min. The hydrogen in the reaction vessel was replaced with argon, then the reaction mixture was diluted with hot EtOAc and filtered with Celite®®. The filtrate was concentrated in vacuo and triturated with IPA to give titled compound (1.80 g, 99%). MS (ESI) m/z 305.1 [M+H]⁺.

Step C: Intermediate 484: rac-Methyl 2'-fluoro-4'-methoxy-5'-((1R,2R,5S,6S)-4-oxo-3-azatricyclo[4.2.1.02,5]non-7-ene-3-carbonyl)-[1,1'-biphenyl]-4-carboxylate

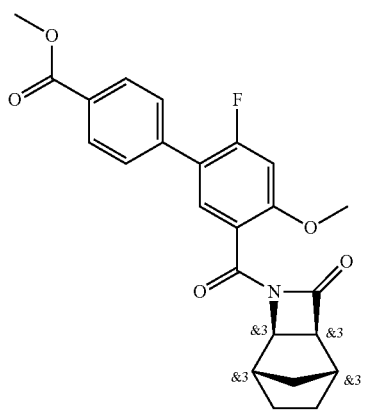 [SMILES: COC(=O)c1ccc(-c2cc(C(=O)N3C(=O)[C@H]4[C@@H]5CC[C@@H](C5)[C@H]43)c(OC)cc2F)cc1]

Oxalyl chloride (500 mg, 0.334 mmol) was added to a mixture of Intermediate 483 (600 mg, 1.97 mmol) in $CH_2Cl_2$ (12 mL) and DMF (0.02 mL), then the mixture was stirred at rt for 1 hr. The mixture was concentrated and the residue was dissolved in $CH_2Cl_2$. The reaction mixture was cooled to 0° C. and DMAP (48 mg, 0.394 mmol), TEA (0.83 mL, 5.92 mmol) and rac-(1R,2R,5S,6S)-3-azatricyclo[4.2.1.02,5]non-7-en-4-one were added, then the mixture was stirred at rt for 17 hr. Sat aq $NaHCO_3$ was added to the reaction mixture and extracted with $CHCl_3$. The organic layer was concentrated in vacuo. The crude product was purified by flash chromatography using 30% EtOAc in hexane as mobile phase to give the title compound (603 mg, 73%). MS (ESI) m/z 422.3 $[M+H]^+$.

Step D: Intermediate 485: rac-Methyl 2'-fluoro-5'-(((1R,2R,3S,4S)-3-((4-fluoro-3-(trifluoromethyl)phenyl)carbamoyl)bicyclo[2.2.1]hept-5-en-2-yl)carbamoyl)-4'-methoxy-[1,1'-biphenyl]-4-carboxylate

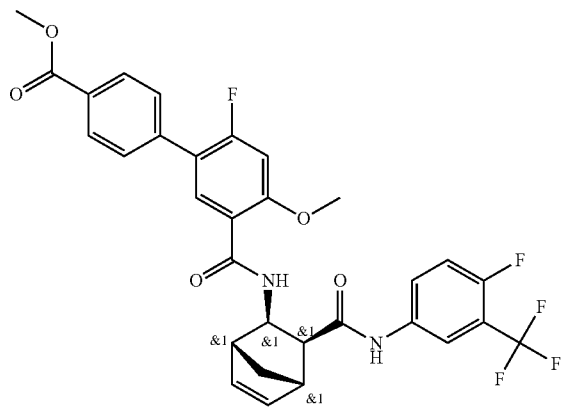 [SMILES: COC(=O)c1ccc(-c2cc(C(=O)N[C@H]3[C@@H](C(=O)Nc4ccc(F)c(C(F)(F)F)c4)[C@@H]4C=C[C@H]3C4)c(OC)cc2F)cc1]

A mixture of 4-fluoro-3-(trifluoromethyl)aniline (61 mg, 0.332 mmol) and Intermediate 484 (70 mg, 0.166 mmol) in acetic acid (1 mL) was stirred at rt for 3 hr. After the reaction mixture was concentrated, sat aq $NaHCO_3$ was added and the mixture was extracted with EtOAc. Combined organic layer was concentrated in vacuo. The crude product was purified by flash chromatography using 25-50% EtOAc in hexane as mobile phase to give the title compound (84 mg, 83%). MS (ESI) m/z 601.3 $[M+H]^+$.

Step E: rac-2'-Fluoro-5'-(((1R,2R,3S,4S)-3-((4-fluoro-3-(trifluoromethyl)phenyl)carbamoyl)bicyclo[2.2.1]hept-5-en-2-yl)carbamoyl)-4'-methoxy-[1,1'-biphenyl]-4-carboxylic acid 4 M aq NaOH (0.196 mL, 0.79 mmol) was added to a solution of Intermediate 485 (80 mg, 0.131 mmol) in MeOH (0.8 mL) and THF (0.8 mL), then the reaction mixture was stirred at rt for 17 hr. After the reaction mixture was concentrated in vacuo, 2 M aq HCl was added to the reaction mixture to adjust pH<2, then the residual precipitate was collected by filtration. The crude solid was purified by flash chromatography using 0-10% MeOH in $CHCl_3$ as mobile phase to give the title compound (63 mg, 82%). MS (ESI) m/z 587.3 $[M+H]^+$.

The examples included in Table 25 below were synthesized analogously to Example 307 steps D and E, using the specified starting material for Step D instead of 4-fluoro-3-(trifluoromethyl)aniline.

TABLE 25

| Ex No. | SM | Product | MS (ESI) |
|---|---|---|---|
| 308 | | | HRMS m/z $[M + H]^+$ 587.1630 |

TABLE 25-continued
| Ex No. | SM | Product | MS (ESI) |
|---|---|---|---|
| 309 | 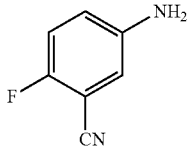 | 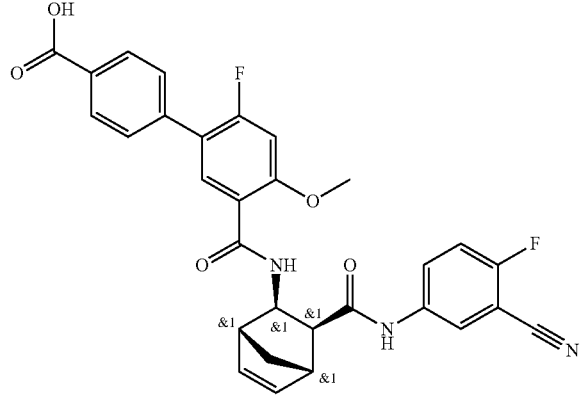 [SMILES: COc1cc(F)c(-c2ccc(C(=O)O)cc2)cc1C(=O)N[C@H]1[C@@H](C(=O)Nc2ccc(F)c(C#N)c2)[C@@H]2C=C[C@H]1C2] | m/z 544.3 [M + H]+ |
| 310 | 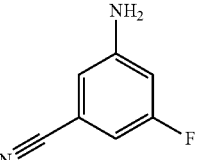 | 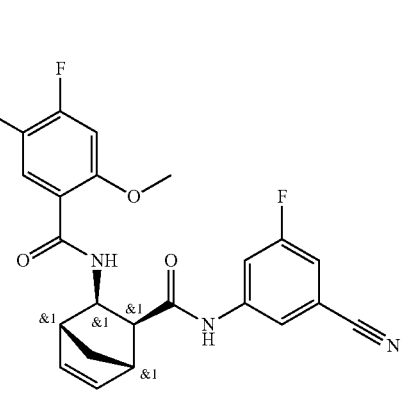 | m/z 544.5 [M + H]+ |
| 311 |  | 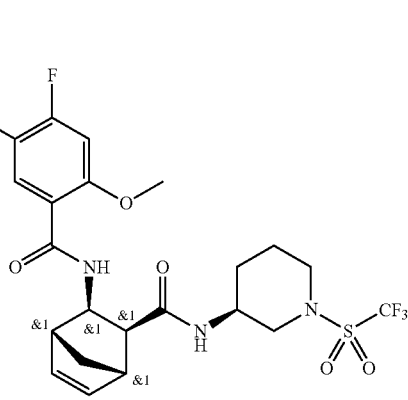 | m/z 640.3 [M + H]+ |

TABLE 25-continued

| Ex No. | SM | Product | MS (ESI) |
|---|---|---|---|
| 312 | 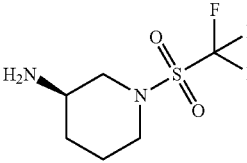 | 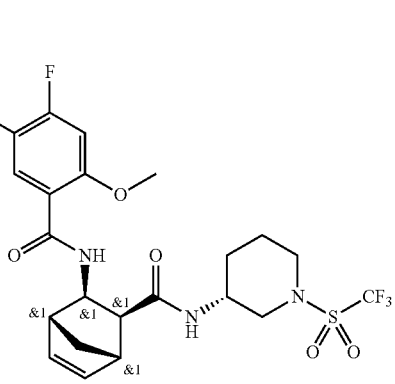 | m/z 640.3 [M + H]+ |

Example 313: 2'-Fluoro-4'-methoxy-5'-(((1R*,2S*,3R*,4S*)-3-(((S)-1-((trifluoromethyl)sulfonyl)piperidin-3-yl)carbamoyl)bicyclo[2.2.1]heptan-2-yl)carbamoyl)-[1,1'-biphenyl]-4-carboxylic acid (Isomer 1) and Example 314: 2'-Fluoro-4'-methoxy-5'-(((1R*,2S*,3R*,4S*)-3-(((S)-1-((trifluoromethyl)sulfonyl)piperidin-3-yl)carbamoyl)bicyclo[2.2.1]heptan-2-yl)carbamoyl)-[1,1'-biphenyl]-4-carboxylic acid (Isomer 2)

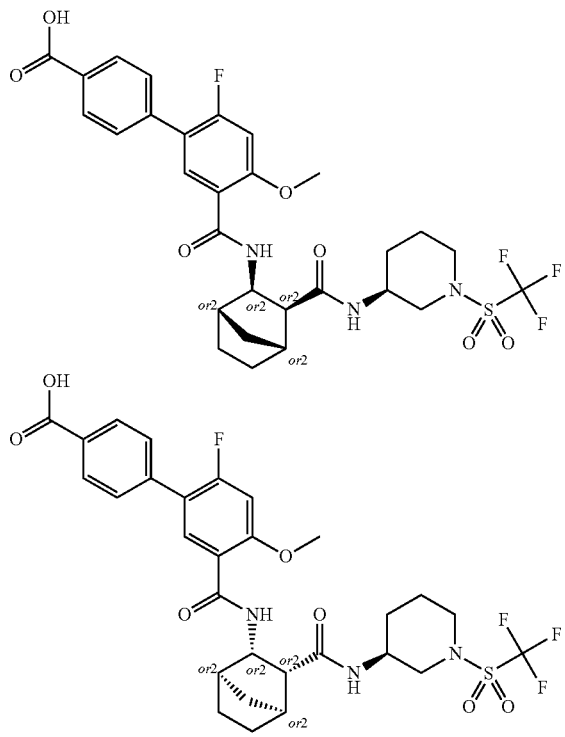

Palladium (10% Pd/C, moisture by 50% H$_2$O, 5 mg) was added to a solution of Example 311 (56 mg, 0.088 mmol) in EtOAc (1 mL). The reaction mixture was stirred under 1 atm of hydrogen atmosphere at rt for 1 hr. The hydrogen in the reaction vessel was replaced with argon and the reaction mixture was filtered with Celite®®. The filtrate was concentrated in vacuo to give titled compound (50 mg, 89%). MS (APCI) m/z 642.0 [M+H]+.

The product (50 mg) was separated by chiral HPLC (column: CHIRALPAK IA (250 mm*30 mm); mobile phase: [CO2/MeOH/AcOH=60/40/0.2]) to give the first eluting compound Isomer 1: Example 313 (18 mg, 36%); MS (APCI) m/z 642.0 [M+H]+, and the second eluting compound Isomer 2: Example 314 (15 mg, 30%); MS (APCI) m/z 642.0 [M+H]+.

Example 315: rac-2'-Fluoro-5'-(((1R,2S,3R,4S)-3-((4-fluoro-3-(trifluoromethyl)phenyl)carbamoyl)bicyclo[2.2.1]heptan-2-yl)carbamoyl)-4'-methoxy-[1,1'-biphenyl]-4-carboxylic acid

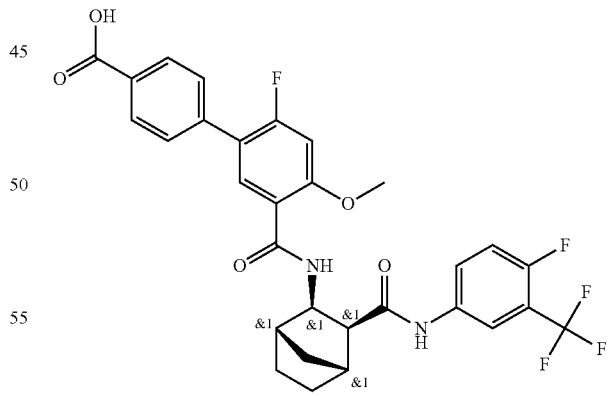

Palladium (10% Pd/C, moisture by 50% H$_2$O, 5 mg) was added to a solution of Example 307 (57 mg, 0.097 mmol) in EtOAc (1 mL). The reaction mixture was stirred under 1 atm of hydrogen atmosphere at rt for 1 hr. The hydrogen in the reaction vessel was replaced with argon and the reaction mixture was filtered with Celite®®. The filtrate was concentrated in vacuo to give titled compound (57 mg, 100%). MS (APCI) m/z 587.0 [M+H]+.

Example 316: rac-2'-Fluoro-4-hydroxy-4'-methoxy-5'-((((1R,2S,3R,4S)-3-((3-((trifluoromethyl)sulfonyl)phenyl)carbamoyl)bicyclo[2.2.1]heptan-2-yl)carbamoyl)-[1,1'-biphenyl]-3-carboxylic acid

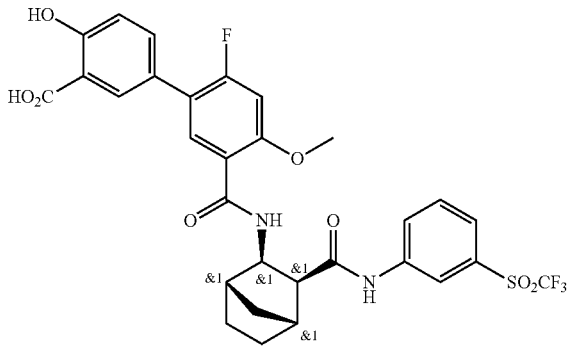

Step A: Intermediate 486: rac-4-(benzyloxy)-2'-fluoro-4'-methoxy-5'-((((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid

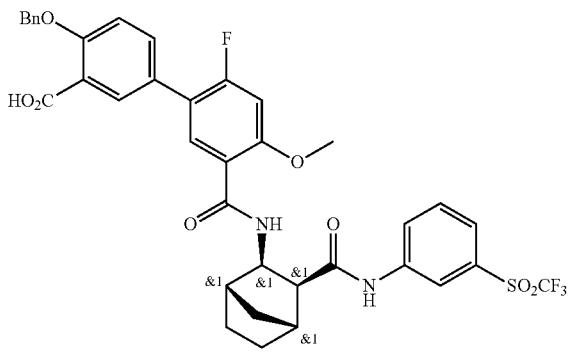

The titled compound was prepared analogous to Example 226, using methyl 2-benzyloxy-5-(4,4,5,5-tetramethyl-1,3,2-dioxaborolan-2-yl)benzoate instead of Compound 5. MS (ESI) m/z 739.4 [M+H]⁺.

Step B: rac-2'-Fluoro-4-hydroxy-4'-methoxy-5'-((((1R,2S,3R,4S)-3-((3-((trifluoromethyl)sulfonyl)phenyl)carbamoyl)bicyclo[2.2.1]heptan-2-yl)carbamoyl)-[1,1'-biphenyl]-3-carboxylic acid Palladium (10% Pd/C, moisture by 50% H₂O, 30 mg) was added to a solution of Intermediate 486 (50 mg, 0.068 mmol) in acetic acid (0.5 mL) and EtOAc (5 mL). The reaction mixture was stirred under 1 atm of hydrogen atmosphere at rt for 3 hr. The hydrogen in the reaction vessel was replaced with argon and the reaction mixture was filtered with Celite®®. The filtrate was concentrated in vacuo and the crude product was purified by flash chromatography using a gradient of 0-10% MeOH in CHCl₃ as mobile phase to give the title compound (36 mg, 65%). MS (APCI) m/z 651.0 [M+H]⁺.

Example 317: 2'-Fluoro-4'-methoxy-5'-((((1R,2S)-2-((3-((trifluoromethyl)sulfonyl)phenyl)carbamoyl)cyclopentyl)carbamoyl)-[1,1'-biphenyl]-3-carboxylic acid

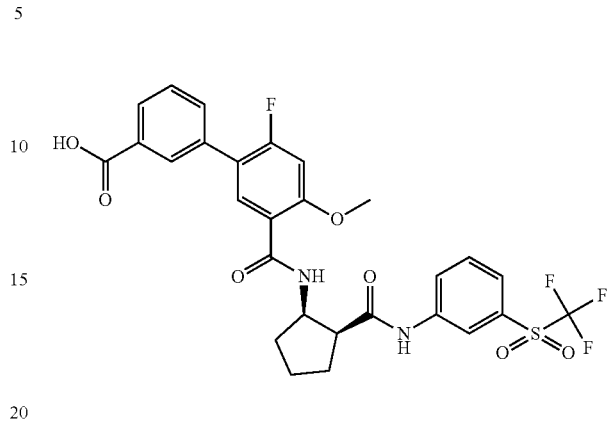

Step A: Intermediate 487: 4-Fluoro-2-methoxy-5-(4,4,5,5-tetramethyl-1,3,2-dioxaborolan-2-yl)-N-((1R,2S)-2-((3-((trifluoromethyl)sulfonyl)phenyl)carbamoyl)cyclopentyl)benzamide

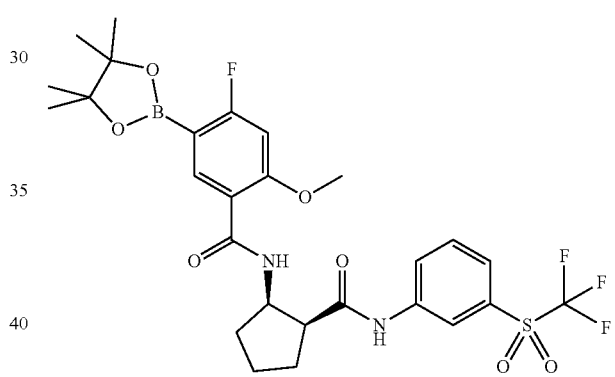

The titled compound was prepared analogous to Example 236 Step C, using Intermediate 217 instead of Intermediate 226. MS (ESI) m/z 615.5 [M+H]⁺.

Step B: 2'-Fluoro-4'-methoxy-5'-((((1R,2S)-2-((3-((trifluoromethyl)sulfonyl)phenyl)carbamoyl)cyclopentyl)carbamoyl)-[1,1'-biphenyl]-3-carboxylic acid Bis(di-tert-butyl(4-dimethylaminophenyl)phosphine)dichloropalladium(II) (12 mg, 0.016 mmol) and K3PO₄ (151 mg, 0.71 mmol) were added to the mixture of Intermediate 487 (201 mg, 0.33 mmol) and 3-bromobenzoic acid (68 mg, 0.34 mmol) in H₂O (0.5 mL) and toluene (6 mL), and the mixture was stirred at reflux for 2 hr. The mixture was cooled to ambient temperature and diluted with EtOAc, then 10% aq citric acid was added and the mixture was extracted with EtOAc. The combined organic layer was concentrated in vacuo and the crude product was purified by flash chromatography using a gradient of 0-13% MeOH in CHCl₃ as mobile phase to give the title compound (73 mg, 36%). MS (ESI) m/z 609.4 [M+H]⁺.

The examples included in Table 26 below were synthesized analogously to Example 317, using the specified starting material instead of 3-bromobenzoic acid.

TABLE 26
| Ex No. | SM | Product | MS (ESI) |
|---|---|---|---|
| 318 | 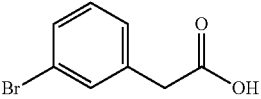 | 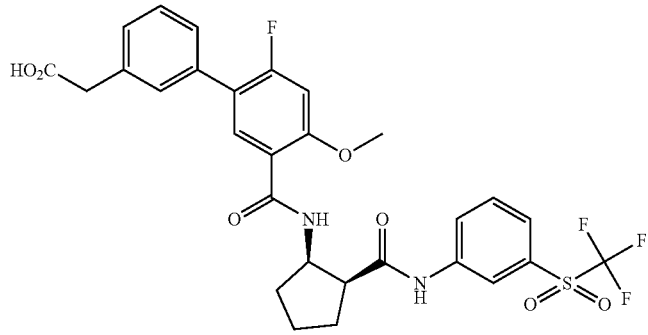 [SMILES: COc1cc(F)c(-c2cccc(CC(=O)O)c2)cc1C(=O)N[C@@H]1CCC[C@@H]1C(=O)Nc1cccc(S(=O)(=O)C(F)(F)F)c1] | HRMS m/z [M + H]+ 623.1460 |
| 319 | 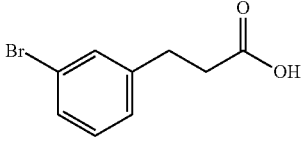 | 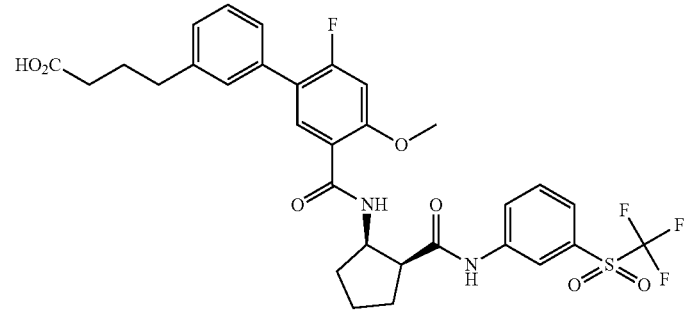 | HRMS m/z [M + H]+ 637.1616 |
| 320 | 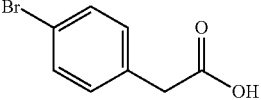 | 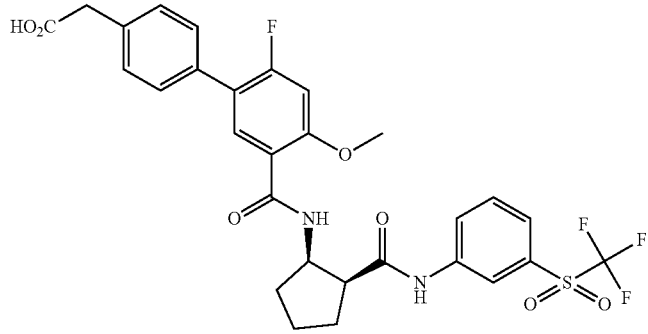 [SMILES: COc1cc(F)c(-c2ccc(CC(=O)O)cc2)cc1C(=O)N[C@@H]1CCC[C@@H]1C(=O)Nc1cccc(S(=O)(=O)C(F)(F)F)c1] | HRMS m/z [M + H]+ 623.1480 |
| 321 | 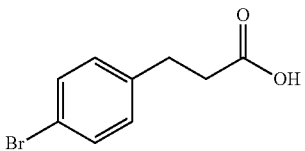 | 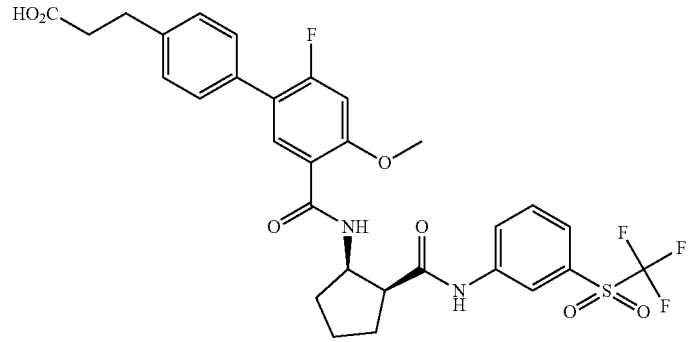 [SMILES: COc1cc(F)c(-c2ccc(CCC(=O)O)cc2)cc1C(=O)N[C@@H]1CCC[C@@H]1C(=O)Nc1cccc(S(=O)(=O)C(F)(F)F)c1] | HRMS m/z [M + H]+ 637.1630 |

Example 322: 3-(5-(2-Fluoro-4-methoxy-5-(((1S, 2R,3S,4R)-3-((3-((trifluoromethyl)sulfonyl)phenyl) carbamoyl)bicyclo[2.2.1]heptan-2-yl)carbamoyl) phenyl)-1,3-,4-thiadiazol-2-yl)propanoic acid

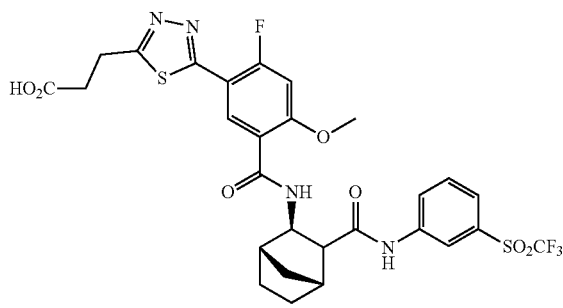

Step A. Intermediate 488: tert-Butyl (E)-3-(5- bromo-1,3,4-thiadiazol-2-yl)acrylate

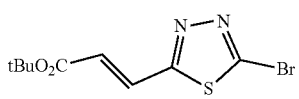 [SMILES: CC(C)(C)OC(=O)/C=C/c1nnc(Br)s1]

NaH (60% in oil suspension, 199 mg, 4.974 mmol) was added to the solution of tert-butyl 2-diethoxyphosphorylacetate (1.25 g, 4.974 mmol) in THF (10 mL) at 0° C., and the mixture was stirred at 0° C. for 1 hr. 5-bromo-1,3,4-thiadiazole-2-carbaldehyde (800 mg, 4.145 mmol) was added to the reaction mixture at 0° C., then the mixture was stirred at 0° C. for 1 hr. H$_2$O was added to the reaction mixture and extracted with CHCl$_3$, then the combined organic layer was concentrated in vacuo. The crude product was purified by flash chromatography using 0-20% EtOAc in hexane as mobile phase to give the title compound (233 mg, 19%). MS (ESI) m/z 291.0/293.0 [M+H]$^+$.

Step B: Intermediate 489: Benzyl (E)-5-(5-(3-(tert- butoxy)-3-oxoprop-1-en-1-yl)-1,3,4-thiadiazol-2-yl)- 4-fluoro-2-methoxybenzoate

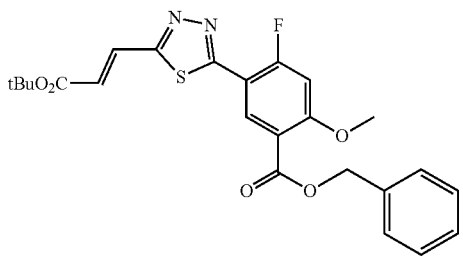 [SMILES: COc1cc(F)c(-c2nnc(/C=C/C(=O)OC(C)(C)C)s2)cc1C(=O)OCc1ccccc1]

Bis(di-tert-butyl(4-dimethylaminophenyl)phosphine)dichloropalladium(II) (24 mg, 0.034 mmol) and cesium carbonate (224 mg, 0.687 mmol) were added to the mixture of Intermediate 445 (146 mg, 0.378 mmol) and Intermediate 488 (100 mg, 0.343 mmol) in H$_2$O (0.5 mL) and DME (1 mL), and the mixture was stirred at reflux for 1 hr. The mixture was cooled to ambient temperature, the mixture was extracted with CHCl$_3$ and the combined organic layer was concentrated in vacuo. The crude product was purified by flash chromatography using a gradient of 0-35% EtOAc in hexane as mobile phase to give the title compound (69 mg, 43%).

Step C: Intermediate 490: 5-(5-(3-(tert-Butoxy)-3- oxopropyl)-1,3,4-thiadiazol-2-yl)-4-fluoro-2- methoxybenzoic acid

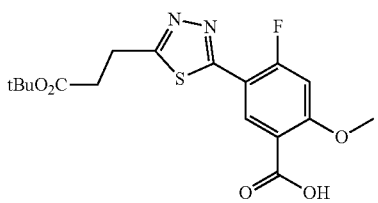 [SMILES: COc1cc(F)c(-c2nnc(CCC(=O)OC(C)(C)C)s2)cc1C(=O)O]

Palladium (10% Pd/C, moisture by 50% H$_2$O, 16 mg) was added to a solution of Intermediate 489 (60 mg, 0.128 mmol) in MeOH (3 mL). The reaction mixture was stirred under 1 atm of hydrogen atmosphere at rt for 4 days. The hydrogen in the reaction vessel was replaced with argon and the reaction mixture was filtered with Celite®®. The filtrate was concentrated in vacuo to give titled compound (25 mg, 51%). MS (ESI) m/z 383.1 [M+H]$^+$.

Step D: Intermediate 491: tert-Butyl 3-(5-(2-fluoro- 4-methoxy-5-(((1S,2R,3S,4R)-3-((3-((trifluorom- ethyl)sulfonyl)phenyl)carbamoyl)bicyclo[2.2.1]hep- tan-2-yl)carbamoyl)phenyl)-1,3,4-thiadiazol-2-yl) propanoate

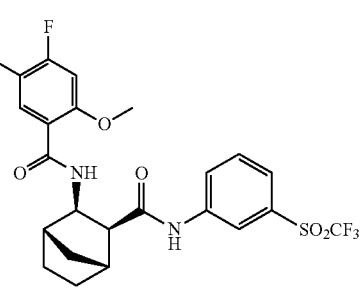

HATU (27 mg, 0.0719 mmol) was added to a solution of Intermediate 490 (25 mg, 0.0654 mmol), Intermediate 226 (29 mg, 0.0719 mmol) and DIPEA (25 mg, 0.196 mmol) in DMF (1 mL) and the reaction mixture was stirred at rt for 10 min. H$_2$O was added to the reaction mixture and the reaction mixture was stirred vigorously. The precipitate was collected by filtration and the crude material was dried under air to give titled compound (47 mg, 100%). MS (ESI) m/z 727.6 [M+H]$^+$.

Step E: 3-(5-(2-Fluoro-4-methoxy-5-(((1S,2R,3S, 4R)-3-((3-((trifluoromethyl)sulfonyl)phenyl)carbam- oyl)bicyclo[2.2.1]heptan-2-yl)carbamoyl)phenyl)-1, 3,4-thiadiazol-2-yl)propanoic acid The titled compound was prepared analogous to Example 256 Step B, using Intermediate 491 instead of Intermediate 452. MS (ESI) m/z 671.5 [M+H]$^+$.

Example 323: 3-(2-(2-Fluoro-4-methoxy-5-(((1S, 2R,3S,4R)-3-((3-((trifluoromethyl)sulfonyl)phenyl) carbamoyl)bicyclo[2.2.1]heptan-2-yl)carbamoyl) phenyl)pyrimidin-5-yl)propanoic acid

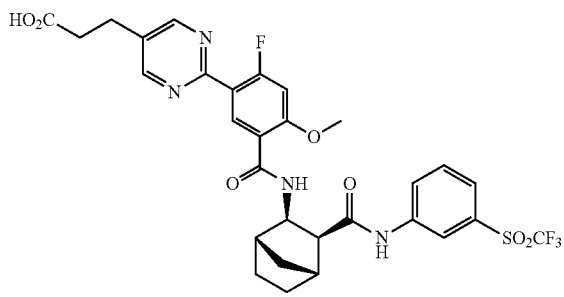

Step A: Intermediate 492: tert-butyl (E)-3-(2-chloropyrimidin-5-yl)acrylate

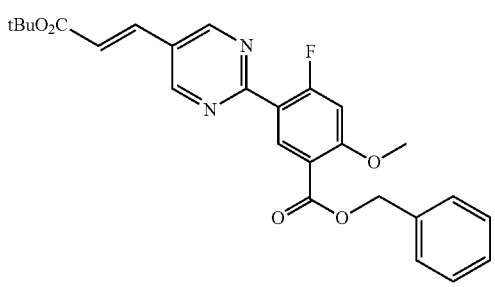 [SMILES: COc1cc(F)c(-c2ncc(/C=C/C(=O)OC(C)(C)C)cn2)cc1C(=O)OCc1ccccc1]

The titled compound was prepared analogous to Example 322 Step A, using 2-chloropyrimidine-5-carbaldehyde instead of 5-bromo-1,3,4-thiadiazole-2-carbaldehyde. MS (ESI) m/z 241.1/243.1 [M+H]⁺.

Step B: Intermediate 493: Benzyl (E)-5-(5-(3-(tert-butoxy)-3-oxoprop-1-en-1-yl)pyrimidin-2-yl)-4-fluoro-2-methoxybenzoate

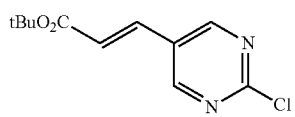

(2-Dicyclohexylphosphino-2',4',6'-triisopropyl-1,1'-biphenyl)[2-(2'-amino-1,1'-biphenyl)]palladium(II) methanesulfonate (28 mg, 0.033 mmol) and cesium carbonate (217 mg, 0.665 mmol) were added to the mixture of Intermediate 445 (141 mg, 0.366 mmol) and Intermediate 492 (80 mg, 0.332 mmol) in H₂O (0.3 mL) and DME (1.6 mL), and the mixture was stirred at reflux for 1 hr. The mixture was cooled to ambient temperature, the mixture was extracted with CHCl₃ and the combined organic layer was concentrated in vacuo. The crude product was purified by flash chromatography using a gradient of 0-35% EtOAc in hexane as mobile phase to give the title compound (105 mg, 68%). MS (ESI) m/z 465.2 [M+H]⁺.

Step C: Intermediate 494: 5-(5-(3-(tert-Butoxy)-3-oxopropyl)pyrimidin-2-yl)-4-fluoro-2-methoxybenzoic acid

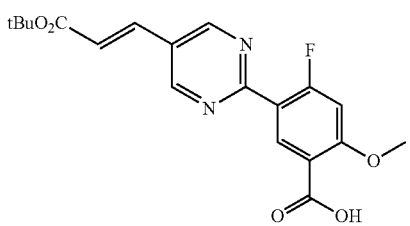 [SMILES: COc1cc(F)c(-c2ncc(/C=C/C(=O)OC(C)(C)C)cn2)cc1C(=O)O]

The titled compound was prepared analogous to Example 322 Step C, using Intermediate 493 instead of Intermediate 489. MS (ESI) m/z 377.2 [M+H]⁺

Step D: Intermediate 495: tert-Butyl 3-(2-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenyl)pyrimidin-5-yl) propanoate

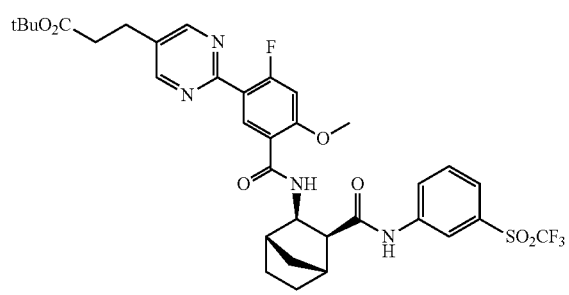

The titled compound was prepared analogous to Example 322 Step D, using Intermediate 494 instead of Intermediate 490. MS (ESI) m/z 721.3 [M+H]⁺.

Step E: 3-(2-(2-Fluoro-4-methoxy-5-(((1S,2R,3S, 4R)-3-((3-((trifluoromethyl)sulfonyl)phenyl)carbamoyl)bicyclo[2.2.1]heptan-2-yl)carbamoyl)phenyl) pyrimidin-5-yl)propanoic acid The titled compound was prepared analogous to Example 256 Step B, using Intermediate 495 instead of Intermediate 452. HRMS (ESI) m/z [M+H]⁺ calcd for C30H29F4N4O7S: 665.1688 found: 665.1694.

Example 324: rac-3-(5-(2-Fluoro-4-methoxy-5-((((1R,2R,3S,4S)-3-((3-(((trifluoromethyl)sulfonyl)phenyl)carbamoyl)bicyclo[2.2.1]heptan-2-yl)carbamoyl)phenyl)pyrazin-2-yl)propanoic acid

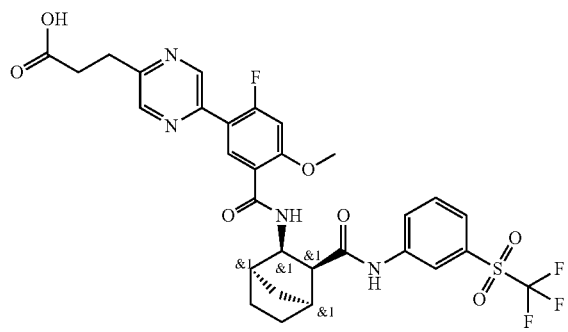 [SMILES: COc1cc(F)c(-c2cnc(CCC(=O)O)cn2)cc1C(=O)N[C@@H]1[C@@H]2CC[C@@H](C2)[C@@H]1C(=O)Nc1cccc(S(=O)(=O)C(F)(F)F)c1]

Step A: Intermediate 496: tert-Butyl (E)-3-(5-bromopyrazin-2-yl)acrylate

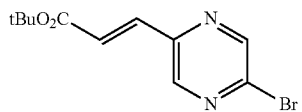

The titled compound was prepared analogous to Example 322 Step A, using 2-bromopyrazine-5-carbaldehyde instead of 5-bromo-1,3,4-thiadiazole-2-carbaldehyde. MS (ESI) m/z 285.0/287.0 [M+H]+.

Step B: Intermediate 497: 5-(5-(3-(tert-Butoxy)-3-oxopropyl)pyrazin-2-yl)-4-fluoro-2-methoxybenzoic acid

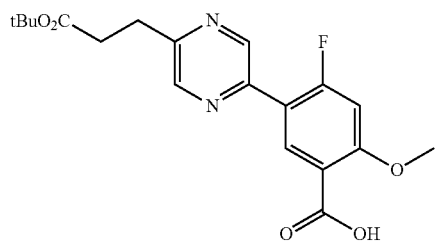 [SMILES: COc1cc(F)c(-c2cnc(CCC(=O)OC(C)(C)C)cn2)cc1C(=O)O]

The titled compound was prepared analogous to Example 322 Step B and C, using Intermediate 496 instead of Intermediate 488. MS (ESI) m/z 377.3 [M+H]+.

Step C: Intermediate 498: rac-tert-Butyl 3-(5-(2-fluoro-4-methoxy-5-(((1R,2R,3S,4S)-3-((3-(((trifluoromethyl)sulfonyl)phenyl)carbamoyl)bicyclo[2.2.1]heptan-2-yl)carbamoyl)phenyl)pyrazin-2-yl)propanoate

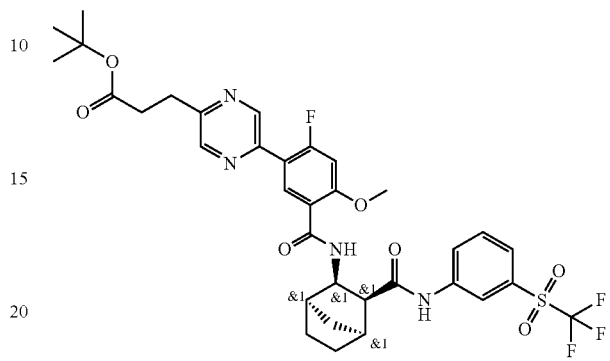

HATU (10 mg, 0.0263 mmol) was added to a solution of Intermediate 497 (9 mg, 0.0239 mmol), Intermediate 231 (11 mg, 0.0263 mmol) and DIPEA (9 mg, 0.0713 mmol) in DMF (0.5 mL) and the reaction mixture was stirred at rt for 14 hr. H2O was added to the reaction mixture and the mixture was extracted with CHCl3 and the combined organic layer was concentrated in vacuo. The crude product was purified by flash chromatography using a gradient of 20-80% EtOAc in hexane as mobile phase to give titled compound (12 mg, 70%). MS (ESI) m/z 721.2 [M+H].

Step D: rac-3-(5-(2-Fluoro-4-methoxy-5-(((1R,2R,3S,4S)-3-((3-(((trifluoromethyl)sulfonyl)phenyl)carbamoyl)bicyclo[2.2.1]heptan-2-yl)carbamoyl)phenyl)pyrazin-2-yl)propanoic acid The titled compound was prepared analogous to Example 256 Step B, using Intermediate 498 instead of Intermediate 452. MS (ESI) m/z 665.3 [M+H]+.

Example 325: (1R,2S,3R,4S)-3-(6-Fluoro-4-methoxy-4'-(1H-tetrazol-5-yl)-[1,1'-biphenyl]-3-carboxamido)-N-(3-(((trifluoromethyl)sulfonyl)phenyl)bicyclo[2.2.1]heptane-2-carboxamide

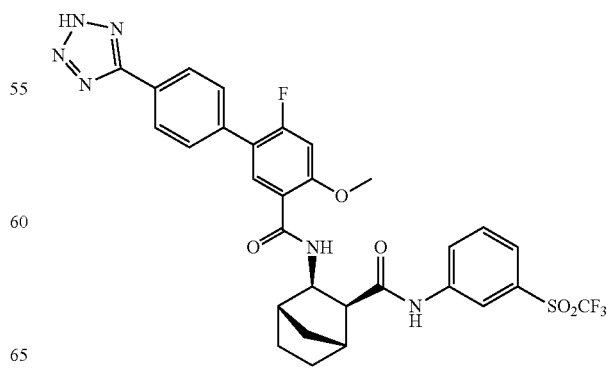

523

Step A: Intermediate 499: Methyl 4'-cyano-6-fluoro-4-methoxy-[1,1'-biphenyl]-3-carboxylate

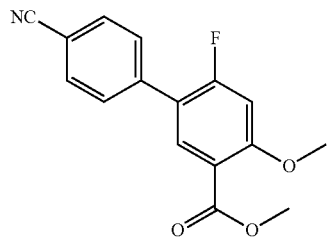 [SMILES: COC(=O)c1cc(-c2ccc(C#N)cc2)c(F)cc1OC]

Bis(di-tert-butyl(4-dimethylaminophenyl)phosphine)dichloropalladium(II) (54 mg, 0.0767 mmol) was added to the mixture of methyl 5-bromo-4-fluoro-2-methoxybenzoate (403 mg, 1.53 mmol) and 4-cyanophenylboronic acid (270 mg, 1.838 mmol) in 2 M aq $Na_2CO_3$ (2.0 mL, 4.0 mmol) and toluene (6 mL), and the mixture was stirred at reflux for 5 hr. The mixture was cooled to ambient temperature and extracted with EtOAc, then the combined organic layer was concentrated in vacuo. The crude product was purified by flash chromatography using 0-30% EtOAc in hexane as mobile phase to give the title compound (438 mg, 89%). MS (ESI) m/z 286.1 $[M+H]^+$.

Step B: Intermediate 500: Methyl 6-fluoro-4-methoxy-4'-(2H-tetrazol-5-yl)-[1,1'-biphenyl]-3-carboxylate

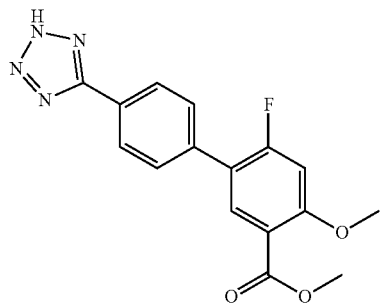

Tri-(n-butyl)tin azide (466 mg, 1.40 mmol) was added to the solution of Intermediate 499 (200 mg, 0.701 mmol) in toluene (2 mL), and the mixture was stirred at reflux for 15 hr. After the mixture was concentrated in vacuo, the crude product was purified by flash chromatography using a gradient of 0-20% MeOH in $CHCl_3$ as mobile phase to give the title compound (149 mg, 65%). MS (ESI) m/z 329.2 $[M+H]^+$.

524

Step C: Intermediate 501: 6-Fluoro-4-methoxy-4'-(2H-tetrazol-5-yl)-[1,1'-biphenyl]-3-carboxylic acid

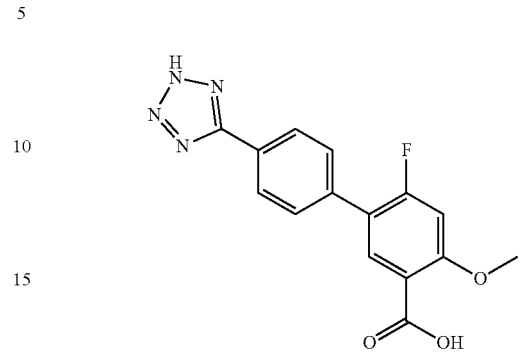

The titled compound was prepared analogous to Example 296 Step B, using Intermediate 500 instead of Intermediate 477. MS (ESI) m/z 315.2 $[M+H]^+$.

Step D: (1R,2S,3R,4S)-3-(6-Fluoro-4-methoxy-4'-(1H-tetrazol-5-yl)-[1,1'-biphenyl]-3-carboxamido)-N-(3-((trifluoromethyl)sulfonyl)phenyl)bicyclo[2.2.1]heptane-2-carboxamide The titled compound was prepared analogous to Example 322 Step D, using Intermediate 501 instead of Intermediate 490. HRMS (ESI) m/z $[M+H]^+$ calcd for $C30H27F4N6O5S$: 659.1694 found: 659.1700.

Example 326: rel-(1R,2R,3S,4S)-3-(6-Fluoro-4-methoxy-4'-(2-sulfamoylethyl)-[1,1'-biphenyl]-3-carboxamido)-N-(3-((trifluoromethyl)sulfonyl)phenyl)bicyclo[2.2.1]heptane-2-carboxamide (Isomer 1) and Example 327: rel-(1R,2R,3S,4S)-3-(6-fluoro-4-methoxy-4'-(2-sulfamoylethyl)-[1,1'-biphenyl]-3-carboxamido)-N-(3-((trifluoromethyl)sulfonyl)phenyl)bicyclo[2.2.1]heptane-2-carboxamide (Isomer 2)

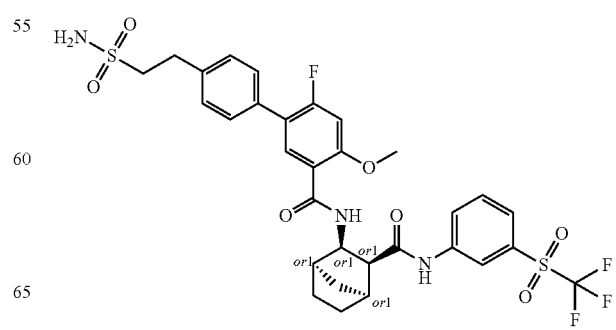

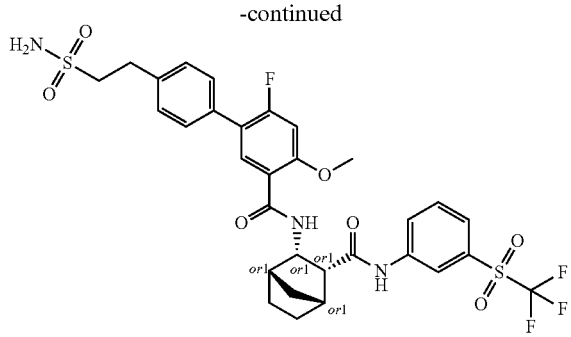

Step A: Intermediate 502: 6-Fluoro-4-methoxy-4'-(2-sulfamoylethyl)-[1,1'-biphenyl]-3-carboxylic acid

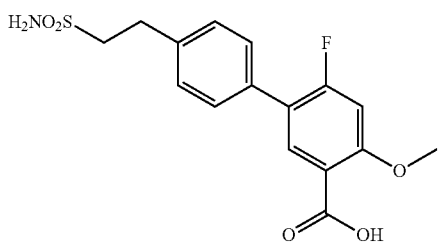 [SMILES: COc1cc(F)c(-c2ccc(CCS(N)(=O)=O)cc2)cc1C(=O)O]

The titled compound was prepared analogous to Example 322 Step B and C, using 2-(4-bromophenyl)ethane-1-sulfonamide instead of Intermediate 488. MS (ESI) m/z 354.1 [M+H]⁺.

Step B: Intermediate 503: rac-(1R,2R,3S,4S)-3-(6-Fluoro-4-methoxy-4'-(2-sulfamoylethyl)-[1,1'-biphenyl]-3-carboxamido)-N-(3-((trifluoromethyl)sulfonyl)phenyl)bicyclo[2.2.1]heptane-2-carboxamide

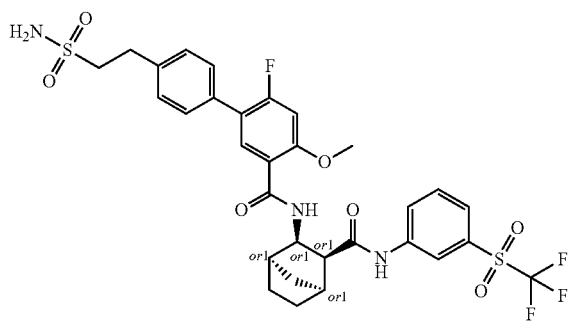 [SMILES: COc1cc(F)c(-c2ccc(CCS(N)(=O)=O)cc2)cc1C(=O)N[C@@H]1[C@@H]2CC[C@@H](C2)[C@@H]1C(=O)Nc1cccc(S(=O)(=O)C(F)(F)F)c1]

EDC (50 mg, 0.258 mmol), HOAt (35 mg, 0.258 mmol) and TEA (0.036 mL, 0.258 mmol) were added to a solution of Intermediate 231 (103 mg, 0.258 mmol) and Intermediate 502 (76 mg, 0.215 mmol) in DMF (3 mL), then the mixture was stirred at rt for 4 hr. Sat aq NaHCO₃ was added and the mixture was extracted with CHCl₃, then the combined organic layer was concentrated in vacuo. The crude product was purified by flash chromatography using a gradient of 50-90% EtOAc in hexane as mobile phase to give the title compound (144 mg, 96%). MS (ESI) m/z 698.6 [M+H]⁺.

Step C: rel-(1R,2R,3S,4S)-3-(6-Fluoro-4-methoxy-4'-(2-sulfamoylethyl)-[1,1'-biphenyl]-3-carboxamido)-N-(3-((trifluoromethyl)sulfonyl)phenyl)bicyclo[2.2.1]heptane-2-carboxamide Intermediate 503 (121 mg) was separated by chiral HPLC (column: CHIRALPAK IE (250 mm×30 mm); mobile phase: [Hex/EtOH=40/60]) to give the first eluting compound Isomer 1: Example 326 (60 mg, 50%); MS (APCI) m/z 698.5 [M+H]⁺, and the second eluting compound Isomer 2: Example 327 (60 mg, 49%); HRMS (ESI) m/z [M+H]⁺ calcd for C31H32F4N3O7S2: 698.1612 found: 698.1626.

Example 328: 2'-Fluoro-4'-methoxy-5'-((2-((3-((trifluoromethyl)sulfonyl)phenyl)carbamoyl)phenyl)carbamoyl)-[1,1'-biphenyl]-4-carboxylic acid

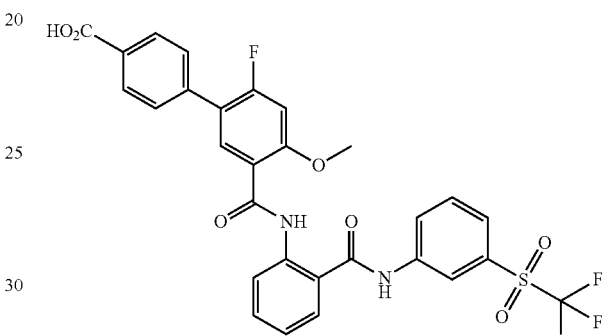

Step A: Intermediate 504: Methyl 2'-fluoro-4'-methoxy-5'-((2-((3-((trifluoromethyl)sulfonyl)phenyl)carbamoyl)phenyl)carbamoyl)-[1,1'-biphenyl]-4-carboxylate

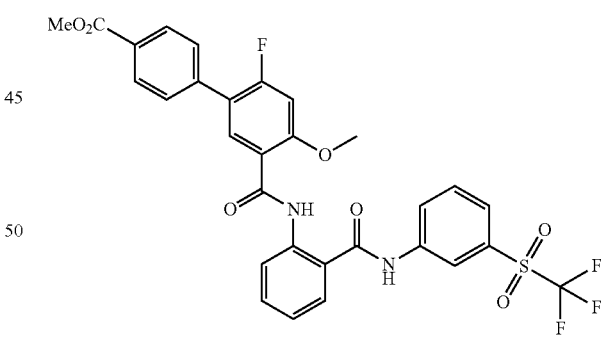

The titled compound was prepared analogous to Example 322 Step D, using Intermediate 483 instead of Intermediate 490 and using 2-amino-N-(3-((trifluoromethyl)sulfonyl)phenyl)benzamide instead of Intermediate 226. MS (ESI) m/z 629.4 [M−H]⁻.

Step B: 2'-Fluoro-4'-methoxy-5'-((2-((3-((trifluoromethyl)sulfonyl)phenyl)carbamoyl)phenyl)carbamoyl)-[1,1'-biphenyl]-4-carboxylic acid The titled compound was prepared analogous to Example 307 Step E, using Intermediate 504 instead of Intermediate 485. 1H NMR (400 MHz, DMSO-d6) δ 4.09 (s, 3H), 7.27-7.37 (m, 2H), 7.58-7.68 (m, 3H), 7.84-7.92 (m, 3H), 8.00-8.07 (m, 2H), 8.21 (d, J=9.4 Hz, 1H), 8.26 (dt, J=6.9, 2.2 Hz, 1H), 8.58 (d, J=7.7 Hz, 1H), 8.84 (s, 1H), 11.13 (s, 1H), 11.58 (s, 1H). HRMS (ESI) m/z [M+H]$^+$ calcd for C29H21F4N2O7S: 617.1000 found: 617.1002.

Example 329: 2-((2'-Cyano-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)oxy)acetic acid

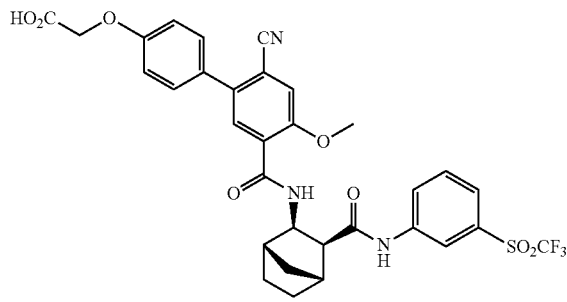

Step A: Intermediate 505: (1R,2S,3R,4S)-3-(5-Bromo-4-cyano-2-methoxybenzamido)-N-(3-((trifluoromethyl)sulfonyl)phenyl)bicyclo[2.2.1]heptane-2-carboxamide

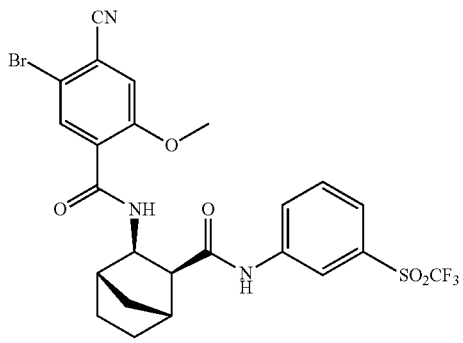

The titled compound was prepared analogous to Example 236 Step C, using 5-bromo-4-cyano-2-methoxybenzoic acid instead of Intermediate 446. MS (ESI) m/z 600.1/602.1 [M+H]$^+$.

Step B: 2-((2'-Cyano-4'-methoxy-5'-(((1S,2R,3S,4R)-3-((3-((trifluoromethyl)sulfonyl)phenyl)carbamoyl)bicyclo[2.2.1]heptan-2-yl)carbamoyl)-[1,1'-biphenyl]-4-yl)oxy)acetic acid The titled compound was prepared analogous to Example 226, using ethyl 2-[4-(4,4,5,5-tetramethyl-1,3,2-dioxaborolan-2-yl)phenoxy]acetate instead of Compound 5 and using Intermediate 505 instead of Intermediate 442. HRMS (ESI) m/z [M+H]$^+$ calcd for C32H29F3N3O8S: 672.1622 found: 672.1658.

Example 330: 2-((2'-Fluoro-4'-methoxy-5'-(((1S,2R,3S,4R)-3-(neopentylcarbamoyl)bicyclo[2.2.1]heptan-2-yl)carbamoyl)-[1,1'-biphenyl]-4-yl)oxy)acetic acid

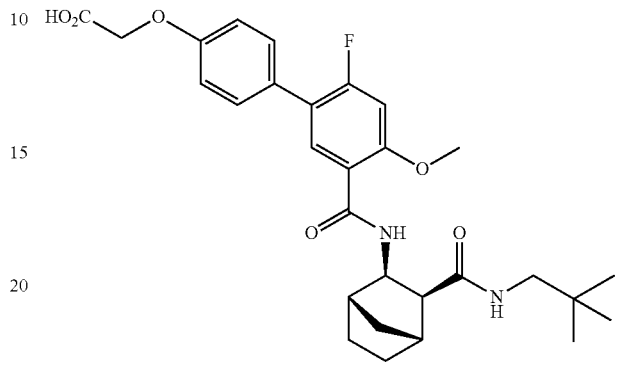

Step A: Intermediate 506: (1R,2S,3R,4S)-3-(5-Bromo-4-fluoro-2-methoxybenzamido)-N-neopentylbicyclo[2.2.1]heptane-2-carboxamide

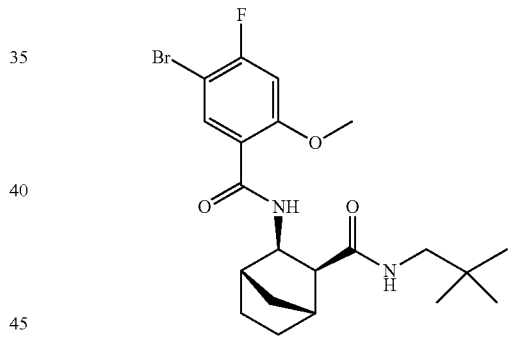

The titled compound was prepared analogous to Example 236 Step C, using 5-bromo-4-fluoro-2-methoxybenzoic acid instead of Intermediate 446 and using Intermediate 224 instead Intermediate 226. MS (ESI) m/z 455.4/457.4 [M+H]$^+$.

Step B: 2-((2'-Fluoro-4'-methoxy-5'-(((1S,2R,3S,4R)-3-(neopentylcarbamoyl)bicyclo[2.2.1]heptan-2-yl)carbamoyl)-[1,1'-biphenyl]-4-yl)oxy)acetic acid The titled compound was prepared analogous to Example 226, using ethyl 2-[4-(4,4,5,5-tetramethyl-1,3,2-dioxaborolan-2-yl)phenoxy]acetate instead of Compound 5 and using Intermediate 506 instead of Intermediate 442. MS (ESI) m/z 527.5 [M+H]$^+$ Example 331: (1R,4s)-4-(2-Fluoro-4-methoxy-5-((((1SR,2SR,3RS,4RS)-3-(((1-methylcyclobutyl)methyl)carbamoyl)-7-oxabicyclo[2.2.1]heptan-2-yl)carbamoyl)phenoxy)-1-methylcyclohexane-1-carboxylic acid

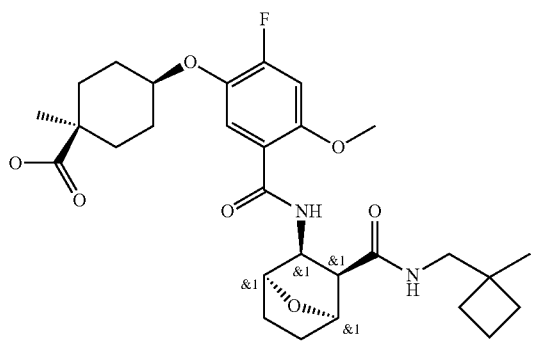 [SMILES: COc1cc(F)c(O[C@H]2CC[C@@](C)(C(=O)O)CC2)cc1C(=O)N[C@H]1[C@@H](C(=O)NCC2(C)CCC2)[C@H]2CC[C@@H]1O2]

Step A: Intermediate 507: rac-Naphthalen-1-ylmethyl (1R,4s)-4-(2-fluoro-4-methoxy-5-((((1S,2S,3R,4R)-3-(((1-methylcyclobutyl)methyl)carbamoyl)-7-oxabicyclo[2.2.1]heptan-2-yl)carbamoyl)phenoxy)-1-methylcyclohexane-1-carboxylate

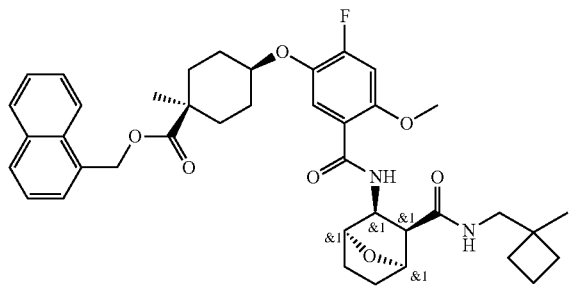 [SMILES: COc1cc(F)c(O[C@H]2CC[C@@](C)(C(=O)OCc3cccc4ccccc34)CC2)cc1C(=O)N[C@H]1[C@@H](C(=O)NCC2(C)CCC2)[C@H]2CC[C@@H]1O2]

HATU (1.82 g, 4.79 mmol) was added to a solution of Intermediate 13 (172 mg, 0.369 mmol), Intermediate 176 (123 mg, 0.516 mmol) and DIPEA (95 mg, 0.737 mmol) in DMF (1.8 mL) and the reaction mixture was stirred at rt for 1 hr. H$_2$O was added to the reaction mixture and the mixture was extracted with CHCl$_3$, then the organic layer was concentrated in vacuo. The crude product was purified by flash chromatography using a gradient of 0-70% EtOAc in hexane as mobile phase to give the title compound (235 mg, 93%). MS (ESI) m/z 687.3 [M+H]$^+$.

Step B: (1R,4s)-4-(2-Fluoro-4-methoxy-5-(((1SR,2SR,3RS,4RS)-3-(((1-methylcyclobutyl)methyl)carbamoyl)-7-oxabicyclo[2.2.1]heptan-2-yl)carbamoyl)phenoxy)-1-methylcyclohexane-1-carboxylic acid Palladium (10% Pd/C, moisture by 50% H$_2$O, 120 mg) was added to a solution of Intermediate 507 (233 mg, 0.34 mmol) in MeOH (3 mL) and THF (3 mL). The reaction mixture was stirred under 1 atm of hydrogen atmosphere at rt for 2 hr. The hydrogen in the reaction vessel was replaced with argon and the reaction mixture was filtered with Celite®®. The filtrate was concentrated in vacuo and the crude product was purified by flash chromatography using a gradient of 0-10% MeOH in CHCl$_3$ as mobile phase to give the title compound (187 mg, 1000%). MS (ESI) mz 547.3 [M+H]$^+$.

The examples included in Table 27 below were synthesized analogous to the procedure of Example 331 using indicated acids and amines.

TABLE 27

| Ex. No. | Acid | Amine | Product | MS (ESI) |
|---|---|---|---|---|
| 332 | Int. 342 | Int. 176 | | m/z 563.2 [M + H]$^+$ |

TABLE 27-continued

| Ex. No. | Acid | Amine | Product | MS (ESI) |
|---|---|---|---|---|
| 333 | Int. 70 | Int. 176 | | m/z 554.3 [M + H]+ |
| 334 | Int. 70 | Int. 182 | | m/z 653.4 [M + H]+ |
| 335 | Int. 13 | Int. 195 | | m/z 675.6 [M + H]+ |

TABLE 27-continued

| Ex. No. | Acid | Amine | Product | MS (ESI) |
|---|---|---|---|---|
| 336 | Int. 13 | Int. 191 | | m/z 675.2 [M + H]+ |
| 337 | Int. 13 | Int. 247 | | m/z 537.4 [M + H]+ |
| 338 | Int. 342 | Int. 247 | | m/z 553.4 [M + H]+ |
| 339 | Int. 342 | Int. 248 | | m/z 565.4 [M + H]+ |

TABLE 27-continued

| Ex. No. | Acid | Amine | Product | MS (ESI) |
|---|---|---|---|---|
| 340 | Int. 13 | Int. 236 | | m/z 661.6 [M + H]+ |
| 341 | Int. 13 | Int. 240 | | m/z 661.6 [M + H]+ |
| 342 | Int. 13 | Int. 244 | | m/z 647.5 [M + H]+ |
| 343 | Int. 13 | Int. 207 | | m/z 661.4 [M + H]+ |

TABLE 27-continued

| Ex. No. | Acid | Amine | Product | MS (ESI) |
|---|---|---|---|---|
| 344 | Int. 13 | Int. 245 | | m/z 659.5 [M + H]+ |
| 345 | Int. 13 | Int. 243 | | m/z 509.2 [M + H]+ |
| 346 | Int. 13 | Int. 184 | | m/z 493.5 [M + H]+ |
| 347 | Int. 13 | Int. 185 | | m/z 643.2 [M + H]+ |

TABLE 27-continued

| Ex. No. | Acid | Amine | Product | MS (ESI) |
|---|---|---|---|---|
| 348 | Int. 70 | Int. 186 | | m/z 512.3 [M + H]+ |
| 349 | Int. 13 | Int. 237 | | m/z 673.5 [M + H]+ |
| 350 | Int. 13 | Int. 242 | | m/z 521.3 [M + H]+ |
| 351 | Int. 13 | Int. 217 | | m/z 645.3 [M + H]+ |

TABLE 27-continued

| Ex. No. | Acid | Amine | Product | MS (ESI) |
|---|---|---|---|---|
| 352 | Int. 13 | Int. 218 | | HRMS m/z [M + H]+ 657.1868 m/z |
| 353 | Int. 13 | Int. 219 | | HRMS m/z [M + H]+ 683.2038 |
| 354 | Int. 13 | Int. 239 | | m/z 673.3 [M + H]+ |
| 355 | Int. 13 | Int. 196 | | HRMS m/z [M + H]+ 663.1818 |

TABLE 27-continued

| Ex. No. | Acid | Amine | Product | MS (ESI) |
|---|---|---|---|---|
| 356 | Int. 13 | Int. 241 | | m/z 647.5 [M + H]+ |
| 357 | Int. 13 | Int. 238 | | m/z 661.6 [M + H]+ |
| 358 | Int. 13 | Int. 180 | | m/z 547.5 [M + H]+ |
| 359 | Int. 13 | Int. 211 | | m/z 675.4 [M + H]+ |

TABLE 27-continued

| Ex. No. | Acid | Amine | Product | MS (ESI) |
|---|---|---|---|---|
| 360 | Int. 70 | Int. 190 | | HRMS m/z [M + H]⁺ 526.2904 |
| 361 | Int. 70 | Int. 189 | | m/z 540.2 [M + H]⁺ |
| 362 | Int. 342 | Int. 243 | | m/z 525.2 [M + H]⁺ |
| 363 | Int. 342 | Int. 242 | | m/z 537.5 [M + H]⁺ |

TABLE 27-continued
| Ex. No. | Acid | Amine | Product | MS (ESI) |
|---|---|---|---|---|
| 364 | Int. 342 | Int. 22 | 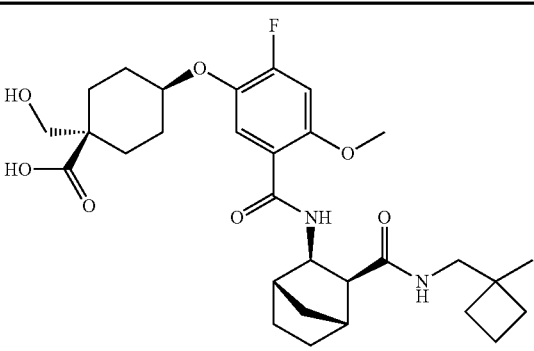 | HRMS m/z [M + H]+ 561.2940 |
| 365 | Int. 342 | Int. 220 | 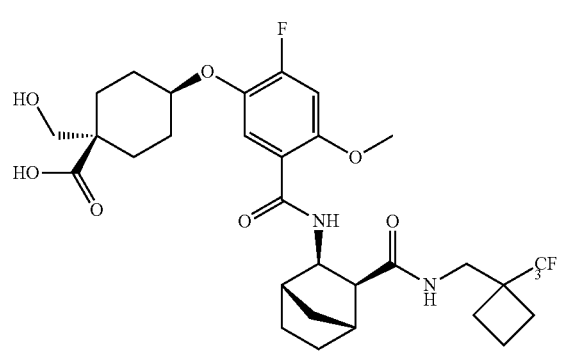 [SMILES: COc1cc(F)c(O[C@H]2CC[C@@](CO)(C(=O)O)CC2)cc1C(=O)N[C@@H]1[C@H]2CC[C@H](C2)[C@@H]1C(=O)NCC1(C(F)(F)F)CCC1] | HRMS m/z [M + H]+ 615.2712 |
| 366 | Int. 342 | Int. 231 | 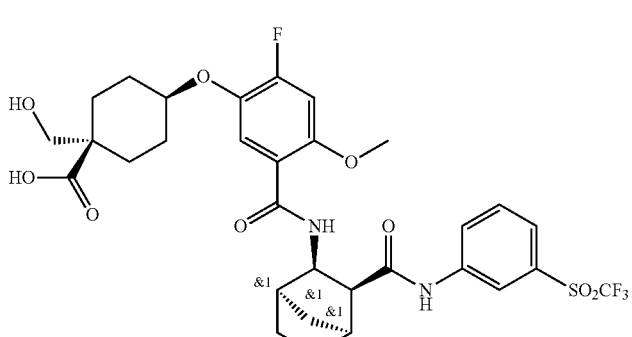 | m/z 687.4 [M + H]+ |
| 367 | Int. 13 | Int. 231 | 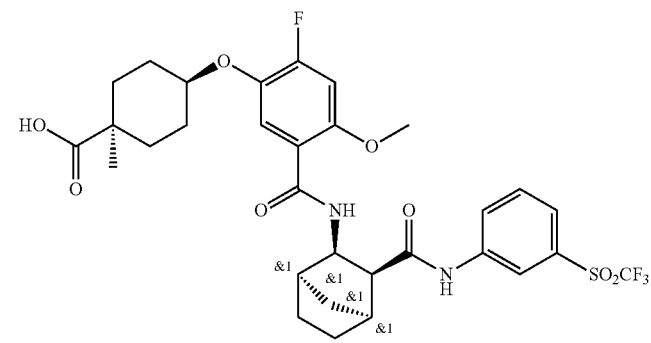 | m/z 671.6 [M + H]+ |

TABLE 27-continued

| Ex. No. | Acid | Amine | Product | MS (ESI) |
|---|---|---|---|---|
| 368 | Int. 302 | Int. 187 | | m/z 554.4 [M + H]+ |
| 369 | Int. 13 | Int. 221 | | m/z 545.3 [M + H]+ |
| 370 | Int. 13 | Int. 222 | | m/z 533.3 [M + H]+ |
| 371 | Int. 13 | Int. 235 | | m/z 683.6 [M + H]+ |

TABLE 27-continued

| Ex. No. | Acid | Amine | Product | MS (ESI) |
|---|---|---|---|---|
| 372 | Int. 299 | Int. 22 | | m/z 595.3 [M + H]+ |
| 373 | Int. 295 | Int. 22 | | HRMS m/z [M + H]+ 577.3086 |
| 374 | Int. 296 | Int. 22 | | HRMS m/z [M + H]+ 545.3040 |
| 375 | Int. 316 | Int. 22 | | HRMS m/z [M + H]+ 541.3296 |

TABLE 27-continued
| Ex. No. | Acid | Amine | Product | MS (ESI) |
|---|---|---|---|---|
| 376 | Int. 318 | Int. 22 | 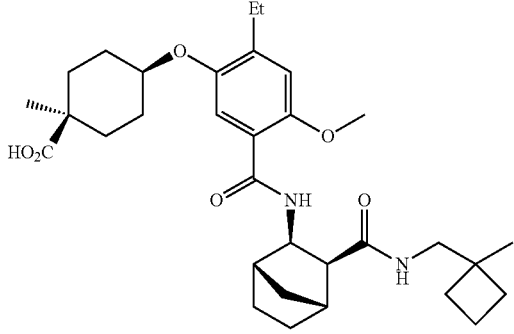 | HRMS m/z [M + H]+ 555.3410 |
| 377 | Int. 305 | Int. 22 | 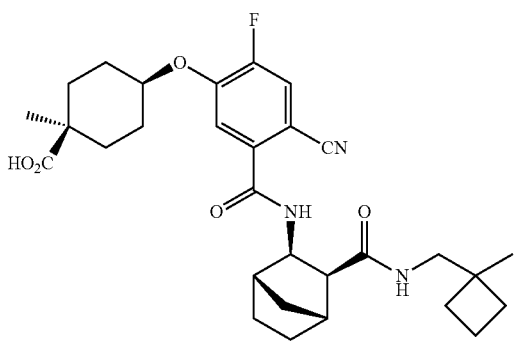 | m/z 540.4 [M + H]+ |
| 378 | Int. 306 | Int. 22 | 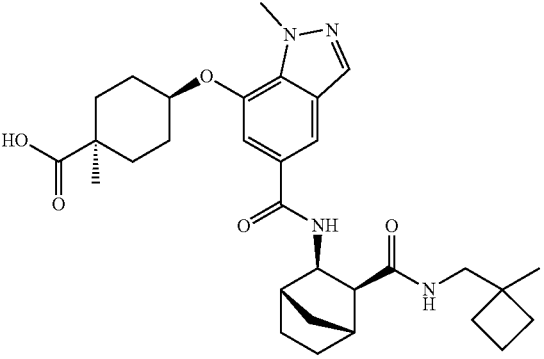 [SMILES: Cn1ncc2cc(C(=O)N[C@@H]3[C@H]4CC[C@H](C4)[C@@H]3C(=O)NCC3(C)CCC3)cc(O[C@H]3CC[C@@](C)(C(=O)O)CC3)c21] | m/z 551.4 [M + H]+ |
| 379 | Int. 307 | Int. 22 | 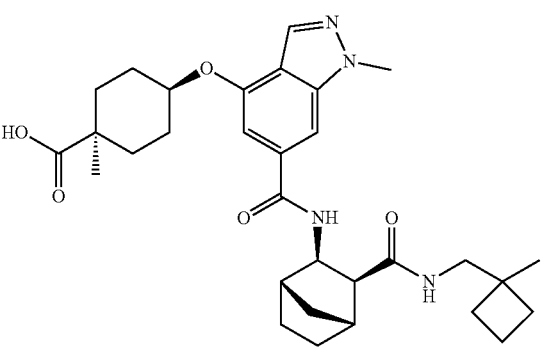 [SMILES: Cn1ncc2c(O[C@H]3CC[C@@](C)(C(=O)O)CC3)cc(C(=O)N[C@@H]3[C@H]4CC[C@H](C4)[C@@H]3C(=O)NCC3(C)CCC3)cc21] | m/z 551.4 [M + H]+ |

TABLE 27-continued

| Ex. No. | Acid | Amine | Product | MS (ESI) |
|---|---|---|---|---|
| 380 | Int. 308 | Int. 22 | | m/z 559.8 [M + H]+ |
| 381 | Int. 314 | Int. 22 | | HRMS m/z [M + H]+ 527.3142 |
| 382 | Int. 316 | Int. 223 | | m/z 543.4 [M + H]+ |
| 383 | Int. 318 | Int. 223 | | m/z 557.4 [M + H]+ |

TABLE 27-continued

| Ex. No. | Acid | Amine | Product | MS (ESI) |
|---|---|---|---|---|
| 384 | Int. 309 | Int. 223 | | m/z 561.4 [M + H]+ |
| 385 | Int. 309 | Int. 22 | | HRMS m/z [M + H]+ 559.3184 |
| 386 | Int. 343 | Int. 224 | | m/z 547.4 [M + H]+ |
| 387 | Int. 70 | Int. 254 | | m/z 552.8 [M + H]+ |

TABLE 27-continued

| Ex. No. | Acid | Amine | Product | MS (ESI) |
|---|---|---|---|---|
| 388 | Int. 70 | Int. 221 | | HRMS m/z [M + H]+ 552.3078 |
| 389 | Int. 70 | Int. 222 | | HRMS m/z [M + H]+ 540.3106 |
| 390 | Int. 296 | Int. 223 | | m/z 547.3 [M + H]+ |
| 391 | Int. 351 | Int. 22 | | m/z 589.3 [M + H]+ |

Example 392: (1S,4s)-4-(2-Chloro-4-methoxy-5-((((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid

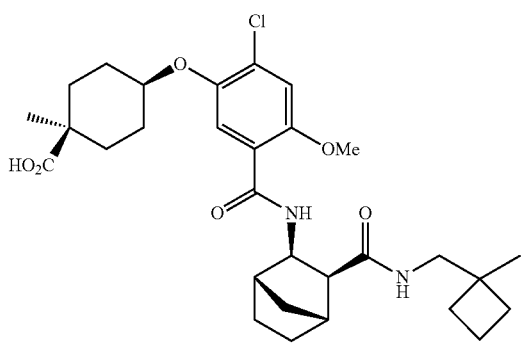

Step A: Intermediate 508: Naphthalen-1-ylmethyl (1S,4s)-4-(2-chloro-4-methoxy-5-((((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylate

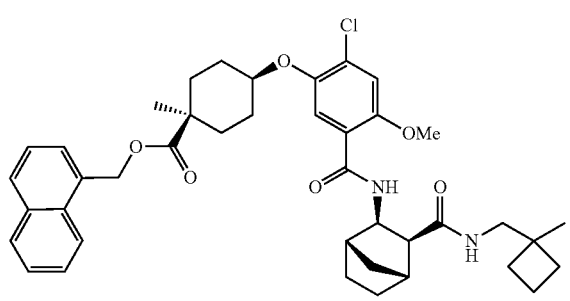 [SMILES: COc1cc(Cl)c(O[C@H]2CC[C@@](C)(C(=O)OCc3cccc4ccccc34)CC2)cc1C(=O)N[C@@H]1[C@H]2CC[C@H](C2)[C@@H]1C(=O)NCC1(C)CCC1]

The titled compound was prepared analogous to Example 331 step A, Intermediate 312 instead of Intermediate 13, and using Intermediate 22 instead of Intermediate 176. MS (ESI) m/z 701.4 [M+H]$^+$ Step B: (1S,4s)-4-(2-Chloro-4-methoxy-5-((((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid Zinc chloride (10 mg, 0.074 mmol) and palladium (10% Pd/C, moisture by 50% H$_2$O, 22 mg) were added to a solution of Intermediate 508 (125 mg, 0.18 mmol) in EtOAc (2 mL). The reaction mixture was stirred under 1 atm of hydrogen atmosphere at rt for 56 hr. The hydrogen in the reaction vessel was replaced with argon and the reaction mixture was filtered with Celite®®. CHCl$_3$ and H$_2$O were added to the filtrate and the organic layer was separated. The organic layer was concentrated in vacuo and the crude product was purified by flash chromatography using a gradient of 0-5% MeOH in CHCl$_3$ as mobile phase to give the title compound (17 mg, 17%) and unreacted starting material (75 mg, 60%). 1H NMR (400 MHz, DMSO-d6) δ 0.93 (s, 3H), 1.11 (s, 3H), 1.12-1.33 (m, 5H), 1.36-1.79 (m, 10H), 1.82-1.93 (m, 2H), 1.95-2.10 (m, 4H), 2.21-2.25 (m, 1H), 2.60-2.66 (m, 1H), 2.96 (dd, J=13.2, 5.5 Hz, 1H), 3.09 (dd, J=13.2, 6.3 Hz, 1H), 3.88 (s, 3H), 4.06-4.14 (m, 1H), 4.16-4.26 (m, 1H), 7.22 (s, 1H), 7.63 (s, 1H), 7.92-7.98 (m, 1H), 8.94 (br d, J=8.0 Hz, 1H). HRMS (ESI) m/z [M+H]$^+$ calcd for C30H42ClN2O6: 561.2726 found: 561.2764.

Example 393: (1S,4s)-4-(2,4-Difluoro-5-((((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid

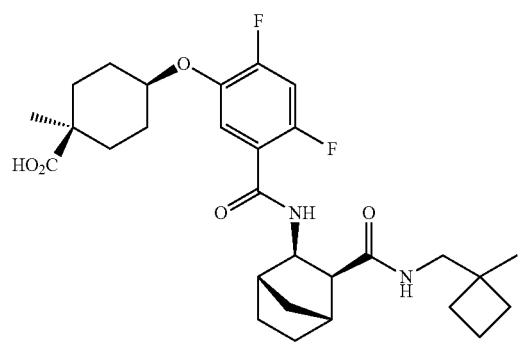

Step A: Intermediate 509: Benzyl 2,4-difluoro-5-(((1s,4s)-4-methyl-4-((naphthalen-1-ylmethoxy)carbonyl)cyclohexyl)oxy)benzoate

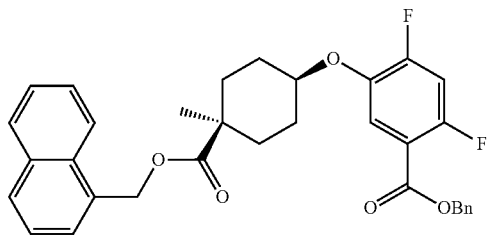 [SMILES: C[C@]1(C(=O)OCc2cccc3ccccc23)CC[C@@H](Oc2cc(C(=O)OCc3ccccc3)c(F)cc2F)CC1]

The titled compound was prepared analogous to Intermediate 314 step A, using Intermediate 292 instead of methyl 4-bromo-5-hydroxy-2-methoxybenzoate.

Step B: Intermediate 510: 5-(((1s,4s)-4-Carboxy-4-methylcyclohexyl)oxy)-2,4-difluorobenzoic acid

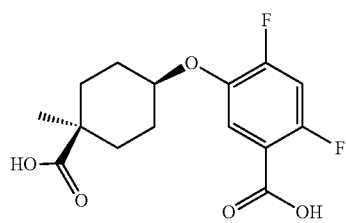 [SMILES: C[C@]1(C(=O)O)CC[C@@H](Oc2cc(C(=O)O)c(F)cc2F)CC1]

The titled compound was prepared analogous to Example 331 step B, using Intermediate 509 instead of Intermediate 507. MS (ESI) m/z 315.1 [M+H]$^+$.

Step C: (1S,4s)-4-(2,4-Difluoro-5-((((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid EDC (41 mg, 0.214 mmol) and HOAt (29 mg, 0.213 mmol) were added to a mixture of Intermediate 510 (59 mg, 0.188 mmol) in DMF (2.5 mL), then the mixture was stirred at rt for 10 min. Intermediate 22 (55 mg, 0.202 mmol) and TEA (0.03 mL, 0.216 mmol) were added to the mixture and the mixture was stirred at 0° C. for 1.5 hr. 1 M aq HCl was added to the reaction mixture to adjust pH~2 and the mixture was extracted with EtOAc, then the combined organic layer was concentrated in vacuo. The crude product was purified by flash chromatography using a gradient of 0-8% MeOH in CHCl$_3$ as mobile phase to give the title compound (67 mg, 67%). 1H NMR (400 MHz, DMSO-d6) δ 0.96 (s, 3H), 1.11 (s, 3H), 1.12-1.34 (m, 5H), 1.36-1.81 (m, 10H), 1.82-1.94 (m, 2H), 1.97-2.14 (m, 4H), 2.20-2.25 (m, 1H), 2.63-2.69 (m, 1H), 2.98 (dd, J=13.2, 6.1 Hz, 1H), 3.05 (dd, J=13.2, 6.1 Hz, 1H), 4.05-4.12 (m, 1H), 4.22-4.31 (m, 1H), 7.33-7.48 (m, 2H), 7.95-8.03 (m, 1H), 8.31-8.39 (m, 1H). HRMS (ESI) m/z [M+H]$^+$ calcd for C29H39F2N2O5: 533.2822 found: 533.2824.

Example 394: (1R,4s)-4-(5-(((1SR,2RS,3SR,5SR)-2,3-Dihydroxy-5-((3-((trifluoromethyl)sulfonyl)phenyl)carbamoyl)cyclopentyl)carbamoyl)-2-fluoro-4-methoxyphenoxy)-1-methylcyclohexane-1-carboxylic acid

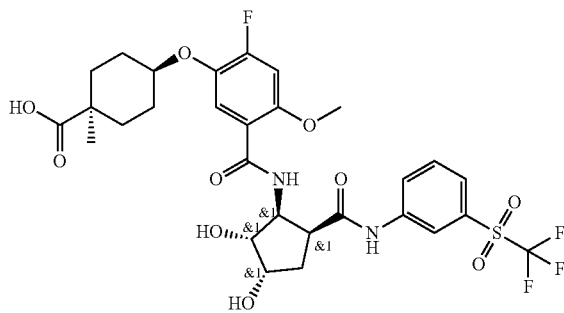 [SMILES: COc1cc(F)c(O[C@H]2CC[C@@](C)(C(=O)O)CC2)cc1C(=O)N[C@@H]1[C@@H](O)[C@@H](O)C[C@@H]1C(=O)Nc1cccc(S(=O)(=O)C(F)(F)F)c1]

Step A: Intermediate 511: Naphthalen-1-ylmethyl (1R,4s)-4-(5-(((1SR,2RS,3SR,5SR)-2,3-dihydroxy-5-((3-((trifluoromethyl)sulfonyl)phenyl)carbamoyl)cyclopentyl)carbamoyl)-2-fluoro-4-methoxyphenoxy)-1-methylcyclohexane-1-carboxylate

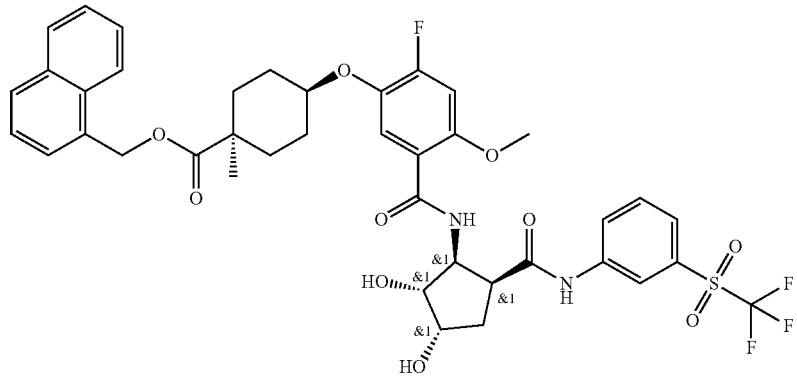 [SMILES: COc1cc(F)c(O[C@H]2CC[C@@](C)(C(=O)OCc3cccc4ccccc34)CC2)cc1C(=O)N[C@@H]1[C@@H](O)[C@@H](O)C[C@@H]1C(=O)Nc1cccc(S(=O)(=O)C(F)(F)F)c1]

The titled compound was prepared analogous to Example 331 step A, using Intermediate 252 instead of Intermediate 176. MS (ESI) m/z 817.3 [M+H]$^+$.

Step B: (1R,4s)-4-(5-(((1SR,2RS,3SR,5SR)-2,3-Dihydroxy-5-((3-((trifluoromethyl)sulfonyl)phenyl)carbamoyl)cyclopentyl)carbamoyl)-2-fluoro-4-methoxyphenoxy)-1-methylcyclohexane-1-carboxylic acid The titled compound was prepared analogous to Example 331 step B, using Intermediate 511 instead of Intermediate 507. MS (ESI) m/z 677.2 [M+H]$^+$.

Example 395: (1R,4s)-4-(2-Fluoro-4-methoxy-5-(((3aRS,4SR,5SR,6aSR)-5-((3-((trifluoromethyl)sulfonyl)phenyl)carbamoyl)tetrahydro-4H-cyclopenta[d][1,3]dioxol-4-yl)carbamoyl)phenoxy)-1-methylcyclohexane-1-carboxylic acid

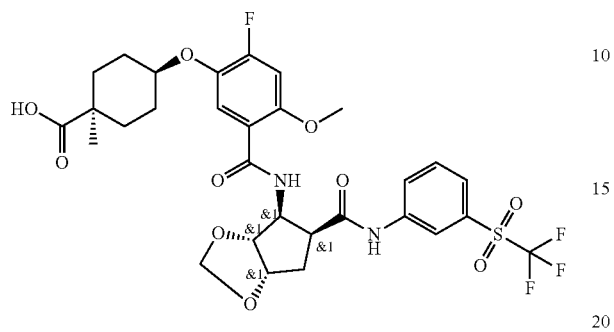

Step A: Intermediate 512: Naphthalen-1-ylmethyl (1R,4s)-4-(2-fluoro-4-methoxy-5-(((3aRS,4SR,5SR,6aSR)-5-((3-((trifluoromethyl)sulfonyl)phenyl)carbamoyl)tetrahydro-4H-cyclopenta[d][1,3]dioxol-4-yl)carbamoyl)phenoxy)-1-methylcyclohexane-1-carboxylate

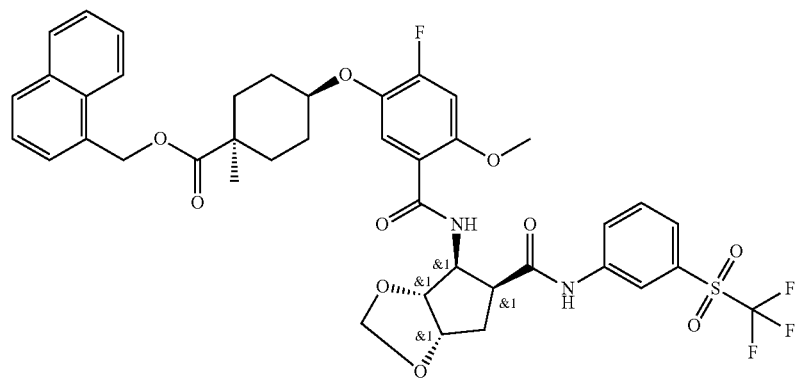 [SMILES: COc1cc(F)c(O[C@H]2CC[C@@](C)(C(=O)OCc3cccc4ccccc34)CC2)cc1C(=O)N[C@@H]1[C@H]2OCO[C@H]2C[C@@H]1C(=O)Nc1cccc(S(=O)(=O)C(F)(F)F)c1]

Dimethoxymethane (70 mg, 0.911 mmol) was added to a solution of Intermediate 511 (74 mg, 0.0911 mmol) and p-toluenesulfonic acid hydrate (2 mg, 0.011 mmol) in toluene (3 mL) and the reaction mixture was stirred at reflux for 3 hr. Sat aq NaHCO$_3$ was added to the reaction mixture and the mixture was extracted with EtOAc, then the organic layer was concentrated in vacuo. The crude product was purified by flash chromatography using a gradient of 20-60% EtOAc in hexane as mobile phase to give the title compound (68 mg, 89%). MS (ESI) m/z 829.7 [M+H]$^+$.

Step B: (1R,4s)-4-(2-Fluoro-4-methoxy-5-(((3aRS,4SR,5SR,6aSR)-5-((3-((trifluoromethyl)sulfonyl)phenyl)carbamoyl)tetrahydro-4H-cyclopenta[d][1,3]dioxol-4-yl)carbamoyl)phenoxy)-1-methylcyclohexane-1-carboxylic acid The titled compound was prepared analogous to Example 331 step B, using Intermediate 512 instead of Intermediate 507. MS (ESI) m/z 689.6 [M+H]$^+$ Example 396: (1R,4s)-4-(2-Fluoro-5-(((1SR,2RS,5SR)-2-hydroxy-5-((3-((trifluoromethyl)sulfonyl)phenyl)carbamoyl)cyclopentyl)carbamoyl)-4-methoxyphenoxy)-1-methylcyclohexane-1-carboxylic acid

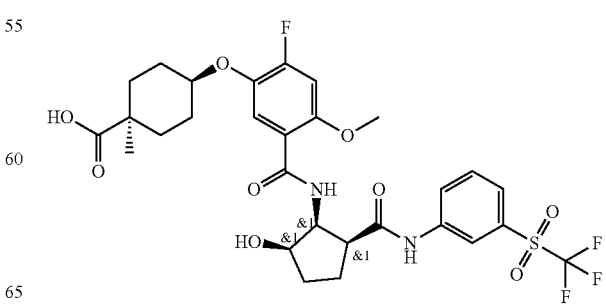

Step A: Intermediate 513: Naphthalen-1-ylmethyl (1R,4s)-4-(2-fluoro-5-(((1SR,2RS,5SR)-2-hydroxy-5-((3-((trifluoromethyl)sulfonyl)phenyl)carbamoyl)cyclopentyl)carbamoyl)-4-methoxyphenoxy)-1-methylcyclohexane-1-carboxylate

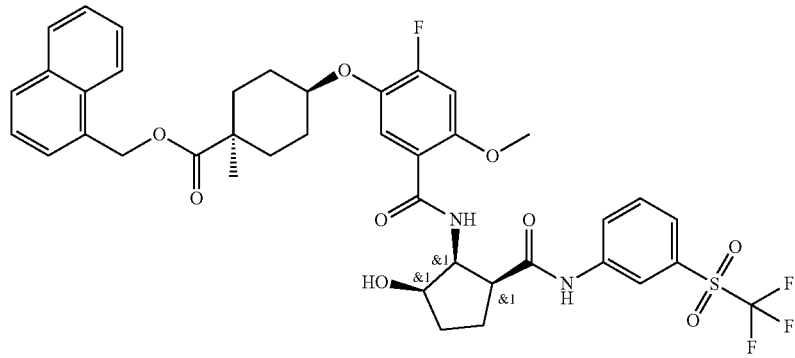 [SMILES: COc1cc(F)c(O[C@H]2CC[C@@](C)(C(=O)OCc3cccc4ccccc34)CC2)cc1C(=O)N[C@@H]1[C@H](O)CC[C@@H]1C(=O)Nc1cccc(S(=O)(=O)C(F)(F)F)c1]

The titled compound was prepared analogous to Example 331 step A, using Intermediate 200 instead of Intermediate 176. MS (ESI) m/z 801.3 [M+H]⁺.

Step B: (1R,4s)-4-(2-Fluoro-5-(((1SR,2RS,5SR)-2-hydroxy-5-((3-((trifluoromethyl)sulfonyl)phenyl)carbamoyl)cyclopentyl)carbamoyl)-4-methoxyphenoxy)-1-methylcyclohexane-1-carboxylic acid The titled compound was prepared analogous to Example 331 step B, using Intermediate 513 instead of Intermediate 507. HRMS (ESI) m/z [M+H]⁺ calcd for C29H33F4N2O9S: 661.1838 found: 661.1860.

Example 397: (1R,4s)-4-(2-Fluoro-4-methoxy-5-(((1SR,2RS,5SR)-2-methoxy-5-((3-((trifluoromethyl)sulfonyl)phenyl)carbamoyl)cyclopentyl)carbamoyl)phenoxy)-1-methylcyclohexane-1-carboxylic acid

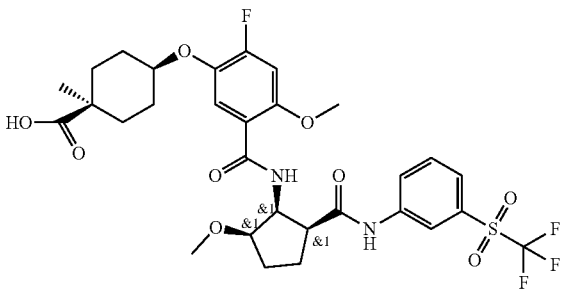 [SMILES: COc1cc(F)c(O[C@H]2CC[C@@](C)(C(=O)O)CC2)cc1C(=O)N[C@H]1[C@@H](C(=O)Nc2cccc(S(=O)(=O)C(F)(F)F)c2)CC[C@H]1OC]

Step A: Intermediate 514: Naphthalen-1-ylmethyl (1R,4s)-4-(2-fluoro-4-methoxy-5-(((1SR,2RS,5SR)-2-methoxy-5-((3-((trifluoromethyl)sulfonyl)phenyl)carbamoyl)cyclopentyl)carbamoyl)phenoxy)-1-methylcyclohexane-1-carboxylate

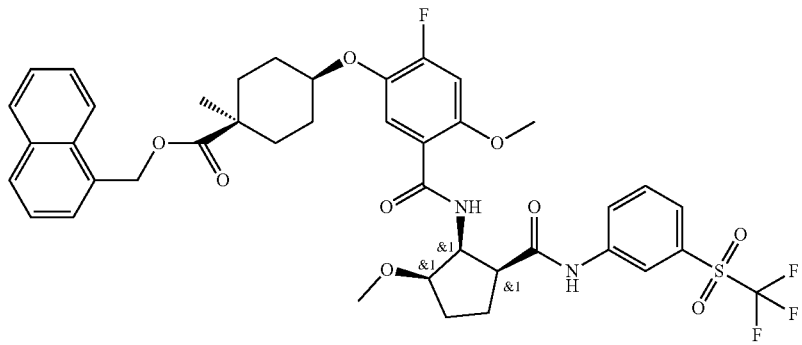 [SMILES: COc1cc(F)c(O[C@H]2CC[C@@](C)(C(=O)OCc3cccc4ccccc34)CC2)cc1C(=O)N[C@H]1[C@@H](C(=O)Nc2cccc(S(=O)(=O)C(F)(F)F)c2)CC[C@H]1OC]

Iodomethane (141 mg, 0.99 mmol) and Ag2O (12 mg, 0.049 mmol) were added to a solution of Intermediate 513 (20 mg, 0.025 mmol) in THF (0.5 mL), and the reaction mixture was stirred at 40° C. for 4 hr. The reaction mixture was cooled down to rt and the mixture was filtered, then the filtrate was concentrated in vacuo. The crude product was purified by flash chromatography using a gradient of 0-70% EtOAc in hexane as mobile phase to give the title compound (20 mg, 98%). MS (ESI) m/z 815.5 [M+H]+.

Step B: (1R,4s)-4-(2-Fluoro-4-methoxy-5-(((1SR, 2RS,5SR)-2-methoxy-5-((3-((trifluoromethyl)sulfonyl)phenyl)carbamoyl)cyclopentyl)carbamoyl)phenoxy)-1-methylcyclohexane-1-carboxylic acid The titled compound was prepared analogous to Example 331 step B, using Intermediate 514 instead of Intermediate 507. MS (ESI) m/z 675.4 [M+H]+.

Example 398: (1S,4s)-4-(4-Chloro-2-fluoro-5-(((1S, 2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid Step A: Intermediate 515: Naphthalen-1-ylmethyl (1S,4s)-4-(4-chloro-2-fluoro-5-(((1S,2R,3S,4R)-3-(((1-methylcyclobutyl)methyl)carbamoyl)bicyclo[2.2.1]heptan-2-_yl)carbamoyl)phenoxy)-1-methylcyclohexane-1-carboxylate The titled compound was prepared analogous to Example 331 step A, using Intermediate 300 instead of Intermediate 13, and using Intermediate 22 instead of Intermediate 176. MS (ESI) m/z 689.4/691.4 [M+H]+.

Step B: (1S,4s)-4-(4-Chloro-2-fluoro-5-(((1S,2R,3S, 4R)-3-(((1-methylcyclobutyl)methyl)carbamoyl) bicyclo[2.2.1]heptan-2-yl)carbamoyl)phenoxy)-1-methylcyclohexane-1-carboxylic acid TFA (3 mL) was added to a mixture of Intermediate 515 (210 mg, 0.09 mmol) and anisole (0.07 mL). The reaction mixture was stirred at rt for 1 hr. The reaction mixture was concentrated and the crude product was purified by flash chromatography using a gradient of 0-5% MeOH in CHCl3 as mobile phase to give the title compound (120 mg, 72%). 1H NMR (400 MHz, CDCl3) δ ppm 1.06 (s, 3H) 1.22-1.26 (m, 4H) 1.29 (br d, J=1.38 Hz, 3H) 1.49-1.70 (m, 5H) 1.75-1.81 (m, 2H) 1.85-1.91 (m, 1H) 1.98-2.03 (m, 1H) 2.08-2.14 (m, 1H) 2.25 (br s, 2H) 2.34 (br d, J=4.13 Hz, 1H) 2.42-2.49 (m, 2H) 2.95-3.03 (m, 1H) 3.26-3.37 (m, 1H) 4.16-4.25 (m, 1H) 4.29-4.37 (m, 1H) 5.64-5.70 (m, 1H) 7.07-7.13 (m, 1H) 7.20-7.25 (m, 1H). MS (ESI) m/z 549.3/ 551.3 [M+H].

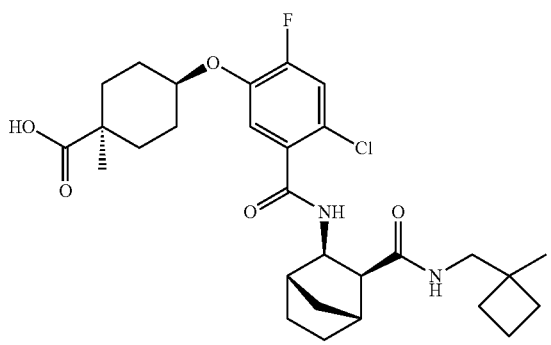 [SMILES: CC1(CNC(=O)[C@H]2[C@@H]3CC[C@@H](C3)[C@H]2NC(=O)c2cc(O[C@H]3CC[C@@](C)(C(=O)O)CC3)c(F)cc2Cl)CCC1]

The examples included in Table 28 below were synthesized analogous to the procedure of Example 398 using indicated acids and amines.

TABLE 28
| Ex. No. | Acid | Amine | Product | MS (ESI) |
|---|---|---|---|---|
| 399 | Int. 320 | Int. 22 | 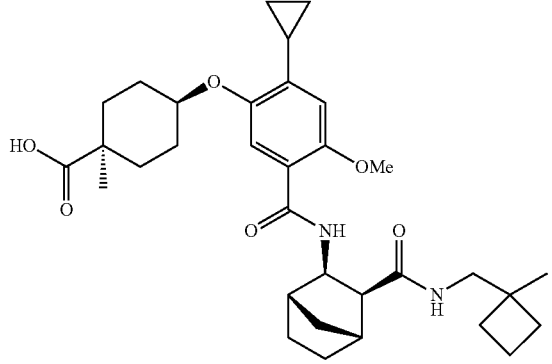 [SMILES: COc1cc(C2CC2)c(O[C@H]2CC[C@@](C)(C(=O)O)CC2)cc1C(=O)N[C@@H]1[C@H]2CC[C@H](C2)[C@@H]1C(=O)NCC1(C)CCC1] | m/z 567.4 [M + H]+ |
| 400 | Int. 303 | Int. 22 | 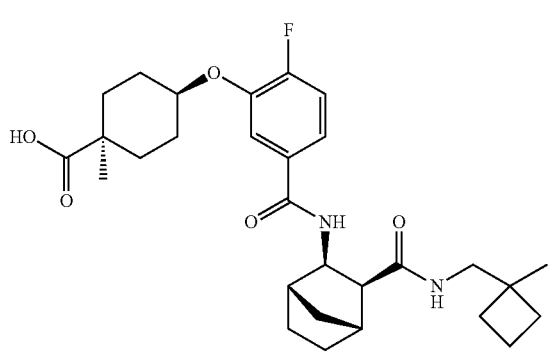 [SMILES: CC1(CNC(=O)[C@H]2[C@@H]3CC[C@@H](C3)[C@H]2NC(=O)c2ccc(F)c(O[C@H]3CC[C@@](C)(C(=O)O)CC3)c2)CCC1] | m/z 515.4 [M + H]+ |
| 401 | Int. 302 | Int. 22 | 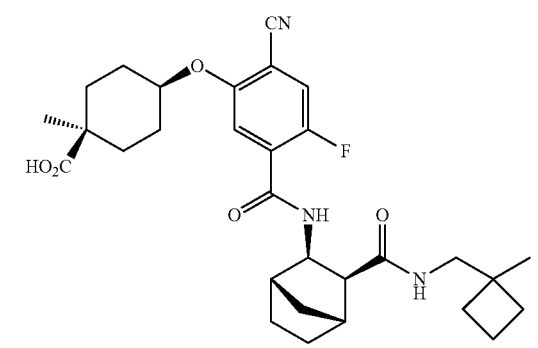 | HRMS m/z [M + H]+ 540.2868 |
| 402 | Int. 304 | Int. 22 | 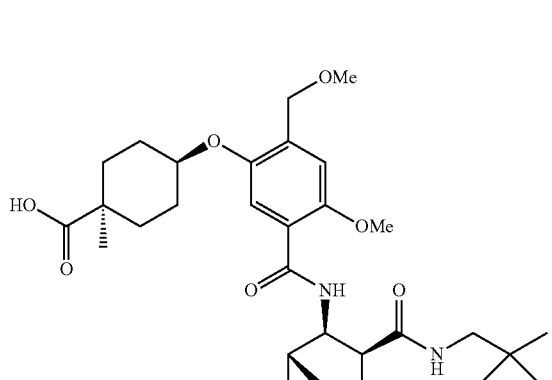 | m/z 571.5 [M + H]+ |

TABLE 28-continued

| Ex. No. | Acid | Amine | Product | MS (ESI) |
|---|---|---|---|---|
| 403 | Int. 297 | Int. 22 | | HRMS m/z [M + H]+ 561.2740 |
| 404 | Int. 313 | Int. 22 | | HRMS m/z [M + H]+ 552.3100 |
| 405 | Int. 298 | Int. 22 | | m/z 541.4 [M + H]+ |
| 406 | Int. 310 | Int. 22 | | m/z 539.3 [M + H]+ |
| 407 | Int. 311 | Int. 22 | | m/z 548.4 [M + H]+ |

TABLE 28-continued

| Ex. No. | Acid | Amine | Product | MS (ESI) |
|---|---|---|---|---|
| 408 | Int. 301 | Int. 22 | | HRMS m/z [M + H]+ 549.2528 |
| 409 | Int. 312 | Int. 225 | | HRMS m/z [M + H]+ 603.2438 |
| 410 | Int. 312 | Int. 221 | | HRMS m/z [M + H]+ 561.2720 |
| 411 | Int. 312 | Int. 223 | | HRMS m/z [M + H]+ 563.2330 |

TABLE 28-continued
| Ex. No. | Acid | Amine | Product | MS (ESI) |
|---|---|---|---|---|
| 412 | Int. 312 | Int. 224 | 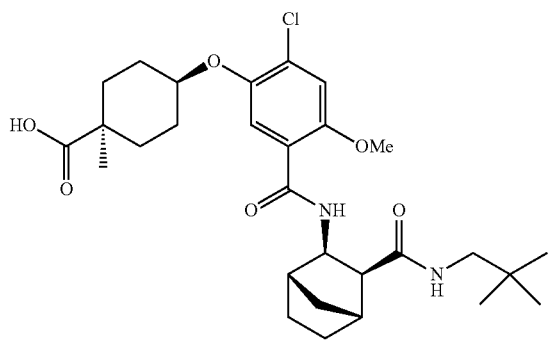 [SMILES: COc1cc(Cl)c(O[C@H]2CC[C@@](C)(C(=O)O)CC2)cc1C(=O)N[C@@H]1[C@H]2CC[C@H](C2)[C@@H]1C(=O)NCC(C)(C)C] | HRMS m/z [M + H]+ 549.2754 |
| 413 | Int. 302 | Int. 221 | 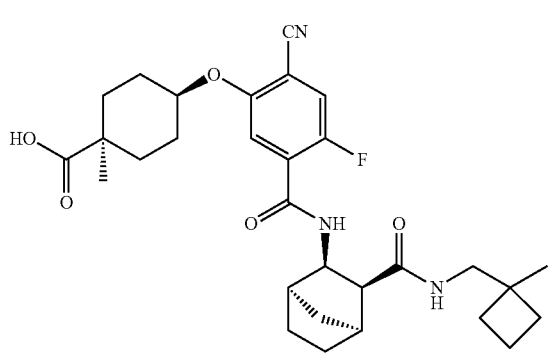 [SMILES: CC1(CNC(=O)[C@H]2[C@H]3CC[C@H](C3)[C@H]2NC(=O)c2cc(O[C@H]3CC[C@@](C)(C(=O)O)CC3)c(C#N)cc2F)CCC1] | HRMS m/z [M + H]+ 540.2880 |
| 414 | Int. 70 | Int. 255 | 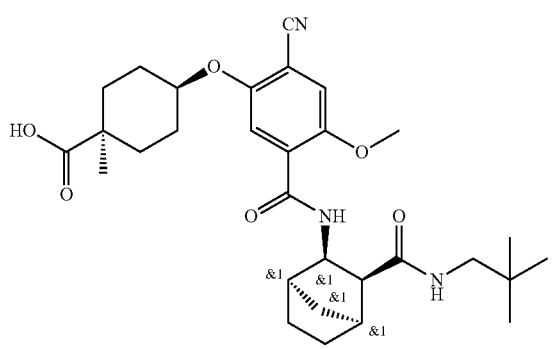 [SMILES: COc1cc(C#N)c(O[C@H]2CC[C@@](C)(C(=O)O)CC2)cc1C(=O)N[C@@H]1[C@@H]2CC[C@@H](C2)[C@@H]1C(=O)NCC(C)(C)C] | m/z 540.4 [M + H]+ |
| 415 | Int. 335 | Int. 22 | 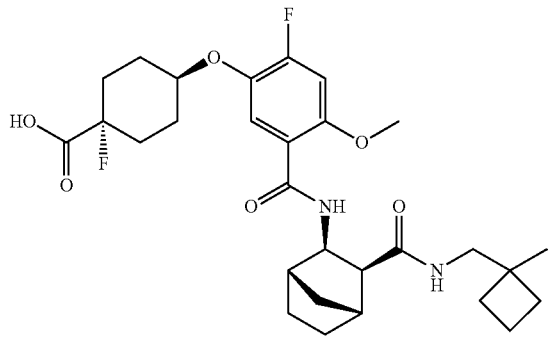 [SMILES: COc1cc(F)c(O[C@H]2CC[C@@](F)(C(=O)O)CC2)cc1C(=O)N[C@@H]1[C@H]2CC[C@H](C2)[C@@H]1C(=O)NCC1(C)CCC1] | m/z 549.5 [M + H]+ |

TABLE 28-continued

| Ex. No. | Acid | Amine | Product | MS (ESI) |
|---|---|---|---|---|
| 416 | Int. 335 | Int. 226 | | HRMS m/z [M + H]+ 675.1820 |
| 417 | Int. 13 | Int. 21 | | HRMS m/z [M + H]+ 543.2862 |

Example 418: (1R,2S,3R,4S)-3-(4-fluoro-2-methoxy-5-(((1s,4S)-4-methyl-4-(5-oxo-4,5-dihydro-1,2,4-oxadiazol-3-yl)cyclohexyl)oxy)benzamido)-N-((1-methylcyclobutyl)methyl)bicyclo[2.2.1]heptane-2-carboxamide

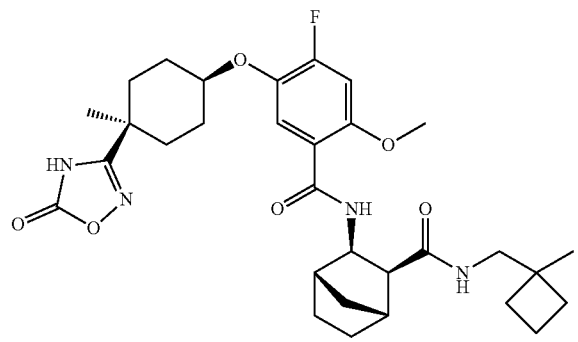 [SMILES: COc1cc(F)c(O[C@H]2CC[C@@](C)(c3noc(=O)[nH]3)CC2)cc1C(=O)N[C@@H]1[C@H]2CC[C@H](C2)[C@@H]1C(=O)NCC1(C)CCC1]

Step A: Intermediate 516: (1R,2S,3R,4S)-3-(5-(((1s,4S)-4-Carbamoyl-4-methylcyclohexyl)oxy)-4-fluoro-2-methoxybenzamido)-N-((1-methylcyclobutyl)methyl)bicyclo[2.2.1]heptane-2-carboxamide

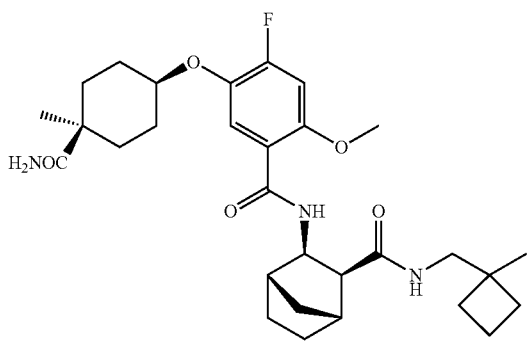

EDC (53 mg, 0.28 mmol) and HOBt (30 mg, 0.22 mmol) were added to a mixture of 1 (100 mg, 0.184 mmol) in CHCl$_3$ (1 mL), then the mixture was stirred at rt for 5 min. 28% aq NH$_3$ (0.5 mL) was added to a mixture and the mixture was stirred at rt for 12 hr. Sat aq NaHCO$_3$ was added and the mixture was extracted with CHCl$_3$, then the combined organic layer was concentrated in vacuo. The crude product was purified by flash chromatography using a gradient of 0-5% MeOH in CHCl$_3$ as mobile phase to give the title compound (96 mg, 96%). MS (ESI) m/z 544.4 [M+H]$^+$.

Step B: Intermediate 517: (1R,2S,3R,4S)-3-(5-(((1s,4S)-4-Cyano-4-methylcyclohexyl)oxy)-4-fluoro-2-methoxybenzamido)-N-((1-methylcyclobutyl)methyl)bicyclo[2.2.1]heptane-2-carboxamide

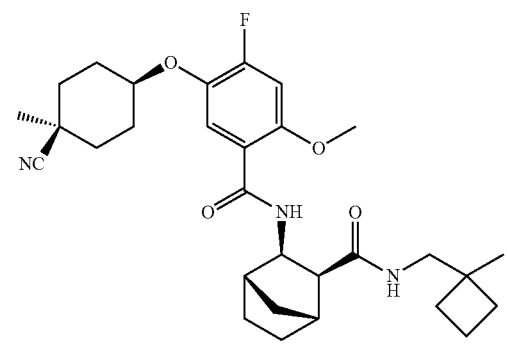

DIPEA (0.19 mL, 1.40 mmol) and trifluoroacetic anhydride (0.16 mL, 1.21 mmol) were added to a solution of Intermediate 516 (94 mg, 0.172 mmol) in THF (3 mL), then the mixture was stirred at rt for 12 hr. H$_2$O was added to the reaction mixture and the mixture was extracted with EtOAc, then the combined organic layer was concentrated in vacuo. The crude product was purified by flash chromatography using a gradient of 0-40% EtOAc in hexane as mobile phase to give the title compound (57 mg, 63%). MS (ESI) m/z 526.4 [M+H]$^+$.

Step C: Intermediate 518: (1R,2S,3R,4S)-3-(4-Fluoro-5-(((1s,4S)-4-(N'-hydroxycarbamimidoyl)-4-methylcyclohexyl)oxy)-2-methoxybenzamido)-N-((1-methylcyclobutyl)methyl)bicyclo[2.2.1]heptane-2-carboxamide

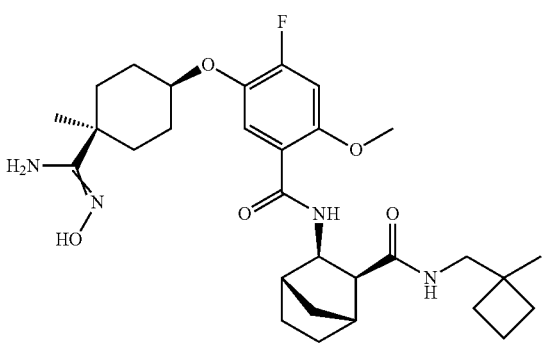 [SMILES: COc1cc(F)c(O[C@H]2CC[C@@](C)(C(N)=NO)CC2)cc1C(=O)N[C@@H]1[C@H]2CC[C@H](C2)[C@@H]1C(=O)NCC1(C)CCC1]

50% hydroxylamine solution (0.20 mL, 3.40 mmol) was added to a solution of Intermediate 517 (49 mg, 0.09 mmol) in EtOH (0.5 mL), then the mixture was stirred at 70° C. for 12 hr. Sat aq NH$_4$Cl was added to the reaction mixture and the mixture was extracted with CHCl$_3$, then the combined organic layer was concentrated in vacuo to give titled compound (50 mg, 97%). MS (ESI) m/z 559.4 [M+H]$^+$.

Step D: (1R,2S,3R,4S)-3-(4-Fluoro-2-methoxy-5-(((1s,4S)-4-methyl-4-(5-oxo-4,5-dihydro-1,2,4-oxadiazol-3-yl)cyclohexyl)oxy)benzamido)-N-((1-methylcyclobutyl)methyl)bicyclo[2.2.1]heptane-2-carboxamide 1,1'-Carbonyldiimidazole (18 mg, 0.11 mmol) was added to a solution of Intermediate 518 (50 mg, 0.09 mmol) in DME (0.5 mL), then the mixture was stirred at 100° C. for 2 hr. After the mixture was cooled to ambient temperature, 1 M aq HCl was added to the reaction mixture and the mixture was extracted with CHCl₃, then the combined organic layer was concentrated in vacuo. The crude material was purified by reversed phase HPLC on a C18 column using a gradient of 30-60% MeCN in (NH₄)₂CO₃ (10 mM in H₂O) as mobile phase to give the title compound (25 mg, 45%). 1H NMR (400 MHz, DMSO-d6) δ 0.93 (s, 3H), 1.10-1.25 (m, 3H), 1.21 (s, 3H), 1.38-1.79 (m, 12H), 1.83-1.91 (m, 2H), 1.97-2.02 (m, 1H), 2.04-2.13 (m, 3H), 2.21-2.25 (m, 1H), 2.61-2.65 (m, 1H), 2.96 (dd, J=13.2, 5.5 Hz, 1H), 3.09 (dd, J=13.2, 6.3 Hz, 1H), 3.87 (s, 3H), 4.06-4.15 (m, 1H), 4.16-4.25 (m, 1H), 7.09 (d, J=12.7 Hz, 1H), 7.67 (d, J=9.9 Hz, 1H), 7.87-7.93 (m, 1H), 8.88 (br d, J=8.0 Hz, 1H). MS (ESI) m/z 585.4 [M+H]⁺.

Example 419: (1R,2S,3R,4S)-3-(4-Fluoro-2-methoxy-5-(((1s,4S)-4-methyl-4-(5-oxo-4,5-dihydro-1,3,4-oxadiazol-2-yl)cyclohexyl)oxy)benzamido)-N-((1-methylcyclobutyl)methyl)bicyclo[2.2.1]heptane-2-carboxamide

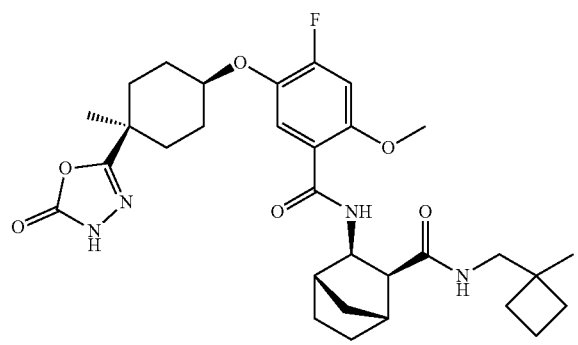 [SMILES: COc1cc(F)c(O[C@H]2CC[C@@](C)(c3n[nH]c(=O)o3)CC2)cc1C(=O)N[C@@H]1[C@H]2CC[C@H](C2)[C@@H]1C(=O)NCC1(C)CCC1]

Step A: Intermediate 519: tert-Butyl 2-((1S,4s)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carbonyl)hydrazine-1-carboxylate

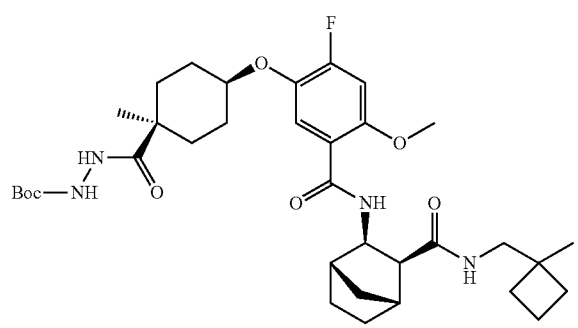 [SMILES: COc1cc(F)c(O[C@H]2CC[C@@](C)(C(=O)NNC(=O)OC(C)(C)C)CC2)cc1C(=O)N[C@@H]1[C@H]2CC[C@H](C2)[C@@H]1C(=O)NCC1(C)CCC1]

HATU (209 mg, 0.55 mmol) was added to a solution of Example 1 (200 mg, 0.37 mmol) and tert-butyl carbazate (58 mg, 0.44 mmol) in DMF (3 mL), then the mixture was stirred at rt for 12 hr. Sat aq NaHCO₃ was added and the precipitate was collected by filtration and washed with H₂O, then the material was dried to give titled compound (244 mg, 100%). MS (ESI) m/z 659.9 [M+H]⁺.

Step B: Intermediate 520: (1R,2S,3R,4S)-3-(4-Fluoro-5-(((1s,4S)-4-(hydrazinecarbonyl)-4-methylcyclohexyl)oxy)-2-methoxybenzamido)-N-((1-methylcyclobutyl)methyl)bicyclo[2.2.1]heptane-2-carboxamide

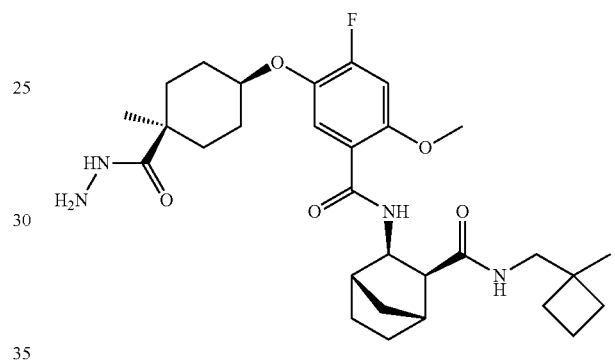

TFA (0.52 mL) was added to a solution of Intermediate 519 (241 mg, 0.37 mmol) in CHCl₃ (1 mL), then the mixture was stirred at rt for 6 hr. The reaction mixture was treated with PolaPak, then concentrated in vacuo to give titled compound (162 mg, 79%). MS (ESI) m/z 559.4 [M+H]⁺.

Step C: (1R,2S,3R,4S)-3-(4-Fluoro-2-methoxy-5-(((1s,4S)-4-methyl-4-(5-oxo-4,5-dihydro-1,3,4-oxadiazol-2-yl)cyclohexyl)oxy)benzamido)-N-((1-methylcyclobutyl)methyl)bicyclo[2.2.1]heptane-2-carboxamide 1,1'-Carbonyldiimidazole (71 mg, 0.44 mmol) was added to a solution of Intermediate 520 (162 mg, 0.29 mmol) in DME (1.2 mL), then the mixture was stirred at 100° C. for 12 hr. After the mixture was cooled to ambient temperature, 1 M aq HCl was added to the reaction mixture and the mixture was extracted with CHCl₃, then the combined organic layer was concentrated in vacuo. The crude material was purified by reversed phase HPLC on a C18 column using a gradient of 40-70% MeCN in (NH₄)₂CO₃ (10 mM in H₂O) as mobile phase to afford the title compound (125 mg, 58%). MS (ESI) m/z 585.4 [M+H]⁺.

Example 420: (1R,2S,3R,4S)-3-(4-Fluoro-2-methoxy-5-(((1s,4S)-4-methyl-4-(1H-tetrazol-5-yl)cyclohexyl)oxy)benzamido)-N-((1-methylcyclobutyl)methyl)bicyclo[2.2.1]heptane-2-carboxamide

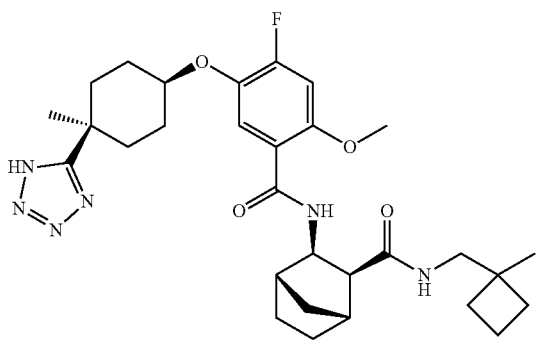 [SMILES: COc1cc(F)c(O[C@H]2CC[C@@](C)(c3nnn[nH]3)CC2)cc1C(=O)N[C@@H]1[C@H]2CC[C@H](C2)[C@@H]1C(=O)NCC1(C)CCC1]

Step A: Intermediate 521: (1s,4s)-4-(2-Fluoro-4-methoxy-5-(methoxycarbonyl)phenoxy)-1-methylcyclohexane-1-carboxylic acid

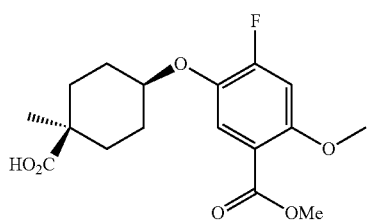

Palladium (10% Pd/C, moisture by 50% H₂O, 169 mg) was added to a solution of Intermediate 12 (845 mg, 1.76 mmol) in EtOH (10 mL). The reaction mixture was stirred under 1 atm of hydrogen atmosphere at rt for 6 hr. The hydrogen in the reaction vessel was replaced with argon and the reaction mixture was filtered through Celite®®, then the filtrate was concentrated in vacuo. The crude product was purified by flash chromatography using a gradient of 0-5% MeOH in CHCl₃ as mobile phase to give the title compound (460 mg, 77%). MS (ESI) m/z 341.2 [M+H]⁺.

Step B: Intermediate 522: Methyl 5-(((1s,4s)-4-carbamoyl-4-methylcyclohexyl)oxy)-4-fluoro-2-methoxybenzoate

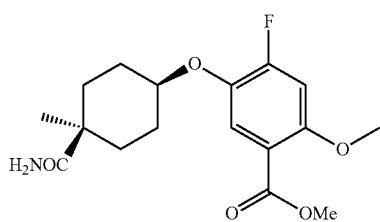

EDC (387 mg, 2.02 mmol) and HOBt (218 mg, 1.62 mmol) were added to a solution of Intermediate 521 (458 mg, 1.35 mmol) in CHCl₃ (10 mL), then the mixture was stirred at rt for 20 min. Aq NH₃ (3 mL) was added to a mixture and the mixture was stirred at rt for 12 hr. Sat aq NaHCO₃ was added and the mixture was extracted with CHCl₃, then the combined organic layer was concentrated in vacuo. The crude product was purified by flash chromatography using a gradient of 0-5% MeOH in CHCl₃ as mobile phase to give the title compound (462 mg, 100%). MS (ESI) m/z 340.2 [M+H]⁺.

Step C: Intermediate 523: Methyl 5-(((1s,4s)-4-cyano-4-methylcyclohexyl)oxy)-4-fluoro-2-methoxybenzoate

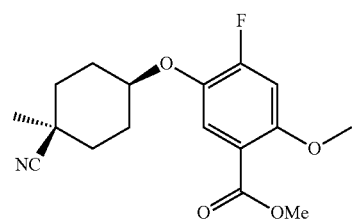

DIPEA (1.14 mL, 8.17 mmol) and trifluoroacetic anhydride (0.57 mL, 4.08 mmol) were added to a solution of Intermediate 522 (462 mg, 1.36 mmol) in THF (10 mL), then the mixture was stirred at rt for 2 hr. Sat aq NaHCO₃ was added to the reaction mixture and the mixture was extracted with EtOAc, then the combined organic layer was concentrated in vacuo. The crude product was purified by flash chromatography using a gradient of 0-30% EtOAc in hexane as mobile phase to give the title compound (192 mg, 41%). MS (ESI) m/z 322.4 [M+H]⁺.

Step D: Intermediate 524: Methyl 4-fluoro-2-methoxy-5-(((1s,4s)-4-methyl-4-(1H-tetrazol-5-yl)cyclohexyl)oxy)benzoate

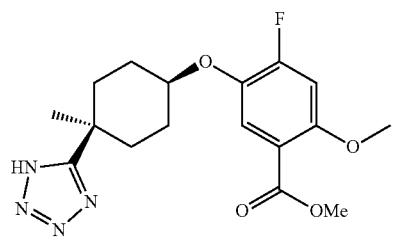 [SMILES: COC(=O)c1cc(O[C@H]2CC[C@@](C)(c3nnn[nH]3)CC2)c(F)cc1OC]

Sodium azide (202 mg, 3.11 mmol) and NH₄Cl (234 mg, 4.38 mmol) were added to a solution of Intermediate 523 (100 mg, 0.29 mmol) in DMF (1.5 mL), then the mixture was stirred at 120° C. for 6 hr. After the mixture was cooled to ambient temperature, sat aq NaHCO₃ was added to the reaction mixture and the mixture was extracted with EtOAc, then the combined organic layer was concentrated in vacuo. The crude material was purified by reversed phase HPLC on a C18 column using a gradient of 10-60% MeCN in (NH₄)₂CO₃ (10 mM in H₂O) as mobile phase to afford the title compound (31 mg, 29%). MS (ESI) m/z 365.2 [M+H]⁺.

Step E: Intermediate 525: 4-Fluoro-2-methoxy-5-
(((1s,4s)-4-methyl-4-(1H-tetrazol-5-yl)cyclohexyl)
oxy)benzoic acid

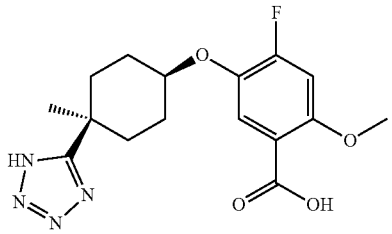 [SMILES: COc1cc(F)c(O[C@H]2CC[C@@](C)(c3nnn[nH]3)CC2)cc1C(=O)O]

2 M aq NaOH (0.12 mL, 0.23 mmol) was added to a solution of Intermediate 524 (28 mg, 0.077 mmol) in THF (0.2 mL), then the mixture was stirred at rt for 4 hr. 2 M aq HCl was added to the reaction mixture and the mixture was concentrated in vacuo. The crude material was purified by reversed phase HPLC on a C18 column using a gradient of 20-30% MeCN in $(NH_4)_2CO_3$ (10 mM in $H_2O$) as mobile phase to afford titled compound (15 mg, 57%). MS (ESI) m/z 351.2 [M+H]$^+$.

Step F: (1R,2S,3R,4S)-3-(4-Fluoro-2-methoxy-5-
(((1s,4S)-4-methyl-4-(1H-tetrazol-5-yl)cyclohexyl)
oxy)benzamido)-N-((1-methylcyclobutyl)methyl)
bicyclo[2.2.1]heptane-2-carboxamide The titled compound was prepared analogous to Example 331 step A, using Intermediate 525 instead of Intermediate 13, and using Intermediate 22 instead of Intermediate 176. HRMS m/z [M+H]$^+$ 569.3238.

Example 421: (1S,2S,3R,4R)-3-(5-(((1s,4S)-4-Car-
bamoyl-4-methylcyclohexyl)oxy)-4-fluoro-2-
methoxybenzamido)-N-((1-methylcyclobutyl)
methyl)bicyclo[2.2.1]heptane-2-carboxamide

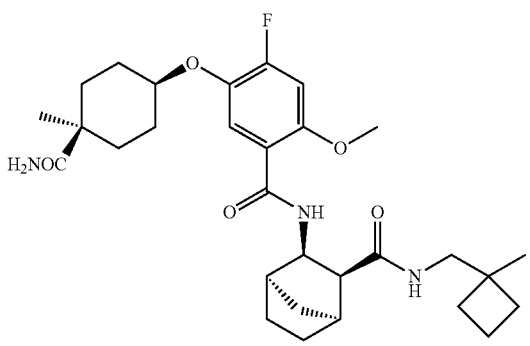

The titled compound was prepared analogous to Example 418 step A, using Example 369 instead of Example 1. MS (ESI) m/z 544.2 [M+H]$^+$.

Example 422: (1R,4r)-4-(2-Fluoro-4-methoxy-5-
(((1RS,2RS,3SR,4SR)-3-((3-((trifluoromethyl)sulfo-
nyl)phenyl)carbamoyl)bicyclo[2.2.1]heptan-2-yl)
carbamoyl)phenoxy)-1-hydroxycyclohexane-1-
carboxylic acid

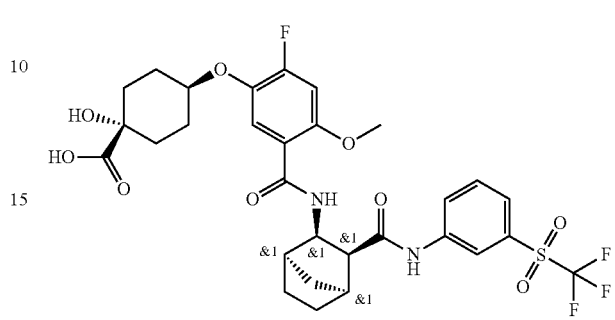

Step A: Intermediate 526: benzyl 4-fluoro-5-(((1r,
4r)-4-hydroxy-4-((naphthalen-1-ylmethoxy)carbo-
nyl)cyclohexyl)oxy)-2-methoxybenzoate

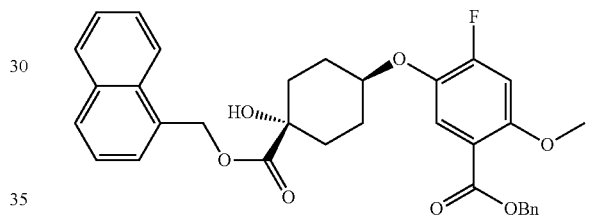

Di-2-methoxyethyl azodicarboxylate (142 mg, 0.604 mmol) was added to a solution of Intermediate 271 (121 mg, 0.403 mmol), benzyl 4-fluoro-5-hydroxy-2-methoxybenzo-ate (134 mg, 0.483 mmol) and triphenylphosphine in THF (2 mL) at 0° C., then the mixture was stirred at rt for 5 hr. $H_2O$ was added to the reaction mixture and the mixture was extracted with EtOAc, then the combined organic layer was concentrated in vacuo. The crude product was purified by flash chromatography using a gradient of 0-30% EtOAc hexane as mobile phase to afford the title compound (118 mg, 52%). MS (ESI) m/z 559.3 [M+H]$^+$.

Step B: Intermediate 527: 5-(((1r,4r)-4-Carboxy-4-
hydroxycyclohexyl)oxy)-4-fluoro-2-methoxybenzoic
acid

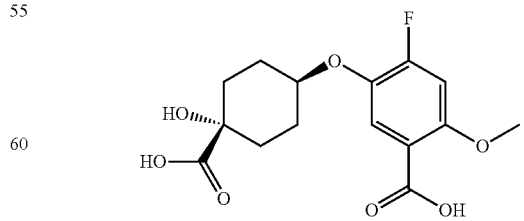

The titled compound was prepared analogous to Example 236 step B, using Intermediate 526 instead of Intermediate 445. MS (ESI) m/z 329.1 [M+H]$^+$ Step C: (1R,4r)-4-(2-Fluoro-4-methoxy-5-(((1RS,2RS,3SR,4SR)-3-((3-((trifluoromethyl)sulfonyl)phenyl)carbamoyl)bicyclo[2.2.1]heptan-2-yl)carbamoyl)phenoxy)-1-hydroxycyclohexane-1-carboxylic acid The titled compound was prepared analogous to Example 331 step A, using Intermediate 527 instead of Intermediate 13, and using Intermediate 231 instead of Intermediate 176. MS (ESI) m/z 673.3 [M+H]⁺.

Example 423: (1R,4r)-1-(Cyanomethyl)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)cyclohexane-1-carboxylic acid

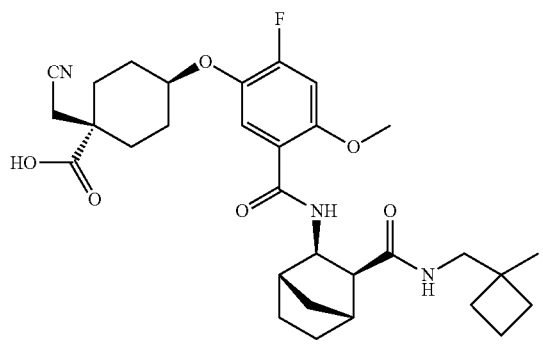 [SMILES: COc1cc(F)c(O[C@H]2CC[C@](CC#N)(C(=O)O)CC2)cc1C(=O)N[C@@H]1[C@H]2CC[C@H](C2)[C@@H]1C(=O)NCC1(C)CCC1]

Step A: Intermediate 528: ethyl (1R,4r)-1-(cyanomethyl)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)cyclohexane-1-carboxylate

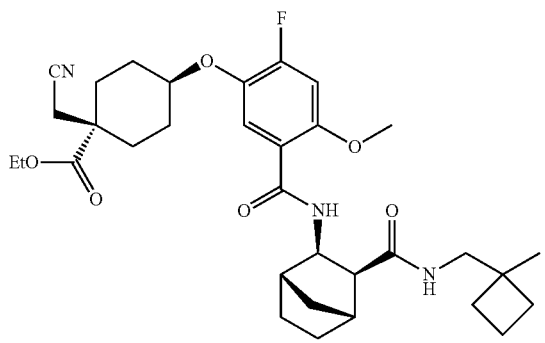 [SMILES: CCOC(=O)[C@]1(CC#N)CC[C@@H](Oc2cc(C(=O)N[C@@H]3[C@H]4CC[C@H](C4)[C@@H]3C(=O)NCC3(C)CCC3)c(OC)cc2F)CC1]

EDC (82 mg, 0.427 mmol) and HOAt (58 mg, 0.427 mmol) were added to a mixture of Intermediate 322 (135 mg, 0.356 mmol), Intermediate 22 (117 mg, 0.429 mmol) and TEA (43 mg, 0.427 mmol) in DMF (5 mL) and the reaction mixture was stirred at rt for 17 hr. H₂O was added to the reaction mixture and the mixture was extracted with EtOAc, then the organic layer was concentrated in vacuo. The crude product was purified by flash chromatography using a gradient of 10-50% EtOAc in hexane as mobile phase to give the title compound (172 mg, 81%). MS (ESI) m/z 598.3 [M+H]⁺.

Step B: (1R,4r)-1-(Cyanomethyl)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)cyclohexane-1-carboxylic acid 1 M aq LiOH (1.44 mL, 1.44 mmol) was added to a solution of Intermediate 528 (172 mg, 0.287 mmol) in DME (5 mL) and the mixture was stirred at rt for 24 hr. 1 M aq HCl and CHCl₃ were added to the reaction mixture and the layer was separated. Combined organic layer was concentrated in vacuo. The crude product was purified by flash chromatography using a gradient of 0-3% MeOH in CHCl₃ as mobile phase to give the title compound (163 mg, 100%). MS (ESI) m/z 570.6 [M+H]⁺.

Example 424: (1S,4s)-1-(Cyanomethyl)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)cyclohexane-1-carboxylic acid

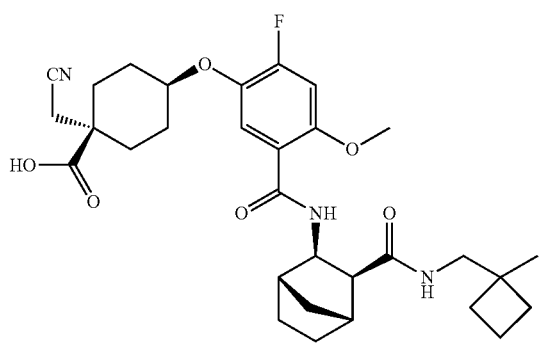 [SMILES: COc1cc(F)c(O[C@H]2CC[C@@](CC#N)(C(=O)O)CC2)cc1C(=O)N[C@@H]1[C@H]2CC[C@H](C2)[C@@H]1C(=O)NCC1(C)CCC1]

Step A: Intermediate 529: Ethyl (1S,4s)-1-(cyanomethyl)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)cyclohexane-1-carboxylate

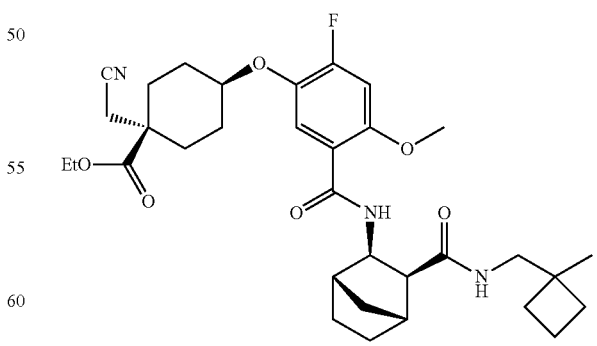

The titled compound was prepared analogous to Example 331 step A, using Intermediate 325 instead of Intermediate 13, and using Intermediate 22 instead of Intermediate 176. MS (ESI) m/z 598.3 [M+H]⁺.

Step B: (1S,4s)-1-(Cyanomethyl)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)cyclohexane-1-carboxylic acid The titled compound was prepared analogous to Example 423 step B, using Intermediate 529 instead of Intermediate 528. HRMS (ESI) m/z [M+H]+ calcd for C31H41FN3O6: 570.2974 found: 570.2998.

Example 425: (1RS,3SR,5SR,6RS)-3-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)bicyclo[3.1.0]hexane-6-carboxylic acid

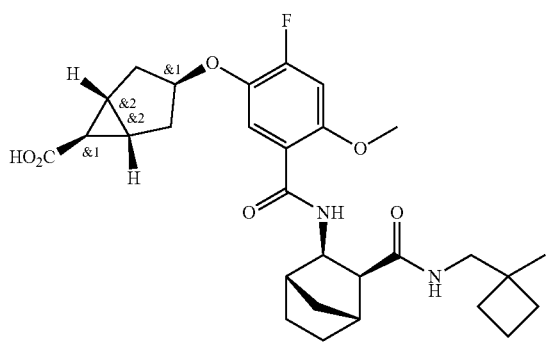 [SMILES: COc1cc(F)c(O[C@@H]2C[C@@H]3[C@H](C2)[C@H]3C(=O)O)cc1C(=O)N[C@@H]1[C@H]2CC[C@H](C2)[C@@H]1C(=O)NCC1(C)CCC1]

Step A: Intermediate 530: Ethyl (1RS,3SR,5SR,6RS)-3-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)bicyclo[3.1.0]hexane-6-carboxylate

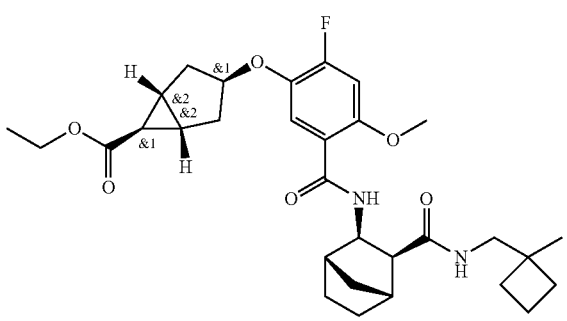 [SMILES: CCOC(=O)[C@H]1[C@@H]2C[C@@H](Oc3cc(C(=O)N[C@@H]4[C@H]5CC[C@H](C5)[C@@H]4C(=O)NCC4(C)CCC4)c(OC)cc3F)C[C@@H]21]

The titled compound was prepared analogous to Example 331 step A, using Intermediate 331 instead of Intermediate 13, and using Intermediate 22 instead of Intermediate 176. MS (ESI) m/z 557.6 [M+H]+.

Step B: (1RS,3SR,5SR,6RS)-3-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)bicyclo[3.1.0]hexane-6-carboxylic acid The titled compound was prepared analogous to Example 423 Step B, using Intermediate 530 instead of Intermediate 528. MS (ESI) m/z 529.5 [M+H]+.

Example 426: (1RS,3SR,5SR,6RS)-3-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)bicyclo[3.1.0]hexane-6-carboxylic acid

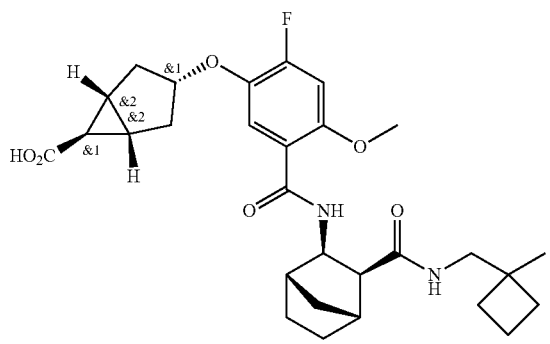 [SMILES: COc1cc(F)c(O[C@H]2C[C@@H]3[C@H](C2)[C@H]3C(=O)O)cc1C(=O)N[C@@H]1[C@H]2CC[C@H](C2)[C@@H]1C(=O)NCC1(C)CCC1]

Step A: Intermediate 531: Ethyl (1RS,3SR,5SR,6RS)-3-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)bicyclo[3.1.0]hexane-6-carboxylate

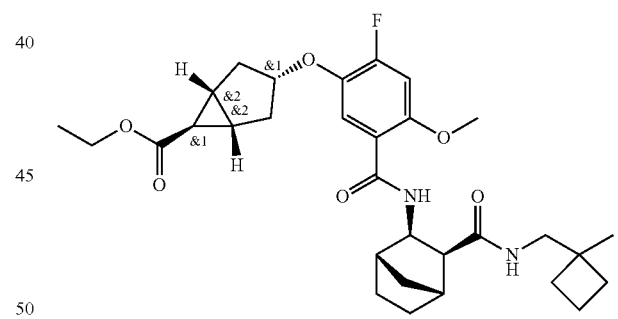

The titled compound was prepared analogous to Example 331 step A, using Intermediate 334 instead of Intermediate 13, and using Intermediate 22 instead of Intermediate 176. MS (ESI) m/z 557.3 [M+H]+.

Step B: (1RS,3SR,5SR,6RS)-3-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)bicyclo[3.1.0]hexane-6-carboxylic acid The titled compound was prepared analogous to Example 423 Step B, using Intermediate 531 instead of Intermediate 528. MS (ESI) m/z 529.2 [M+H]+.

The examples included in Table 29 below were synthesized analogous to the procedure of Example 423 using indicated acids and amines.

TABLE 29

| Example | Reagent 1 | Reagent 2 | Product | MS |
|---|---|---|---|---|
| 427 | Int. 355 | Int. 213 | | MS (APCI) m/z 631.0 [M + H]+ |
| 428 | Int. 357 | Int. 213 | | MS (APCI) m/z 631.0 [M + H]+ |
| 429 | Int. 358 | Int. 213 | | MS (APCI) m/z 631.0 [M + H]+ |
| 430 | Int. 346 | Int. 226 | | HRMS (ESI) m/z [M + H]+ 645.1724 |

TABLE 29-continued
| Example | Reagent 1 | Reagent 2 | Product | MS |
|---|---|---|---|---|
| 431 | Int. 344 | Int. 22 | 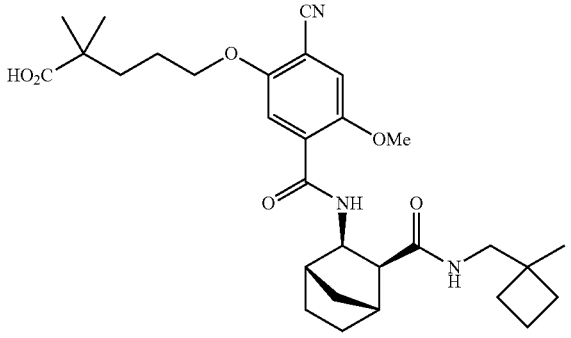 [SMILES: COc1cc(C#N)c(OCCCC(C)(C)C(=O)O)cc1C(=O)N[C@@H]1[C@H]2CC[C@H](C2)[C@@H]1C(=O)NCC1(C)CCC1] | MS (ESI) m/z 540.4 [M + H]+ |
| 432 | Int. 348 | Int. 233 | 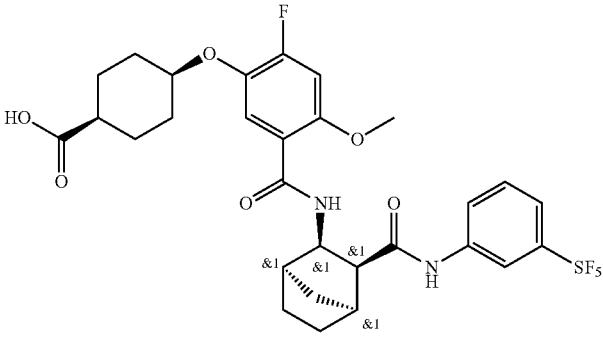 | HRMS (ESI) m/z [M + H]+ 669.1868 |
| 433 | Int. 348 | Int. 219 | 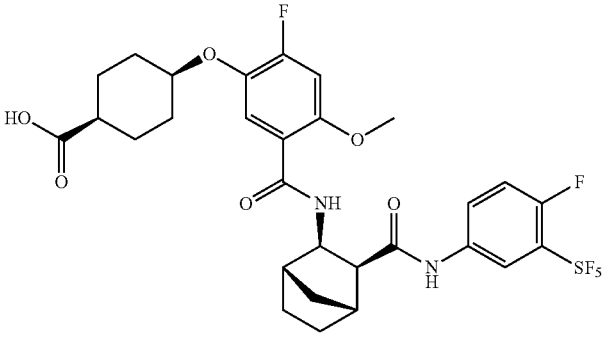 | MS (ESI) m/z 669.2 [M + H]+ |

Example 434: 6-Fluoro-4-methoxy-N3-((1S,2R,3S,4R)-3-((3-((trifluoromethyl)sulfonyl)phenyl)carbamoyl)bicyclo[2.2.1]heptan-2-yl)-[1,1'-biphenyl]-3,4'-dicarboxamide

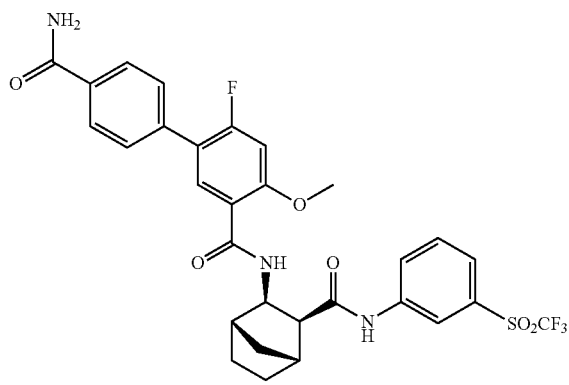

The titled compound was prepared analogous to Example 418 step A, using Example 250 instead of Example 1. MS (ESI) m/z 634.0 [M+H]⁺.

Example 435: 6-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)hexanoic acid

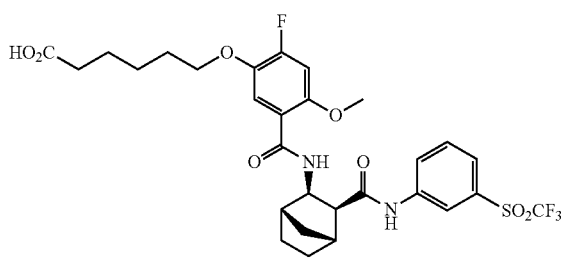

Step A: Intermediate 532: (1R,2S,3R,4S)-3-(4-Fluoro-5-hydroxy-2-methoxybenzamido)-N-(3-((trifluoromethyl)sulfonyl)phenyl)bicyclo[2.2.1]heptane-2-carboxamide

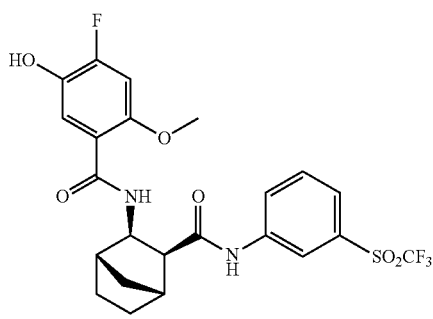

HATU (1.03 g, 2.71 mmol) and DIPEA (0.85 mL, 4.93 mmol) were added to a solution of Intermediate 226 (1.08 g, 2.71 mmol) and 4-fluoro-5-hydroxy-2-methoxybenzoic acid (459 mg, 2.47 mmol) in DMF (4 mL), then the mixture was stirred at rt for 20 min. H₂O was added to the reaction mixture and the mixture was extracted with CHCl₃, then the organic layer was concentrated in vacuo. The crude product was purified by flash chromatography using a gradient of 10-70% EtOAc in hexane as mobile phase to give the title compound (1.40 g, 100%). MS (ESI) m/z 531.2 [M+H]⁺.

Step B: Intermediate 533: Ethyl 6-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)hexanoate

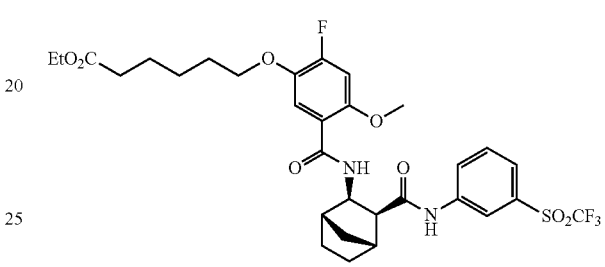

Ethyl 6-bromohexanoate (25 mg, 0.12 mmol) was added to a mixture of Intermediate 532 (40 mg, 0.075 mmol) and potassium carbonate (31 mg, 0.23 mmol) in DMF (0.2 mL), then the mixture was stirred at 80° C. for 6 hr. H₂O was added to a mixture and the mixture was extracted with CHCl₃, then the combined organic layer was concentrated in vacuo. The crude product was purified by flash chromatography using 40% EtOAc in hexane as mobile phase to give the title compound (50 mg, 100%).

Step C: 6-(2-Fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)hexanoic acid 1 M aq NaOH (1 mL, 1.00 mmol) was added to a solution of Intermediate 533 (50 mg, 0.075 mmol) in MeOH (1 mL), then the reaction mixture was stirred at rt for 20 hr. 10% Aq citric acid was added to a reaction mixture to neutralize and the mixture was extracted with CHCl₃ three times, then the combined organic layer was concentrated in vacuo. The crude product was purified by flash chromatography using a gradient of 0-4% MeOH in CHCl₃ as mobile phase to give the title compound (30 mg, 62%). 1H NMR (400 MHz, DMSO-d6) δ, 1.22-1.71 (m, 11H), 1.95-2.02 (m, 1H), 2.12-2.15 (m, 1H), 2.20 (t, J=7.7 Hz, 2H), 2.42-2.47 (m, 1H), 2.81 (d, J=8.2 Hz, 1H), 3.81 (s, 3H), 3.82-3.95 (m, 2H), 4.34 (t, J=7.9 Hz, 1H), 7.09 (d, J=13.00 Hz, 1H), 7.47 (d, J=10.0 Hz, 1H), 7.70-7.77 (m, 2H), 7.80-7.91 (m, 1H), 8.57 (br s, 1H), 8.64 (d, J=8.8 Hz, 1H), 10.63 (s, 1H). HRMS (ESI) m/z [M+H]⁺ calcd for C29H33F4N2O8S: 645.1888 found: 645.1938.

The examples included in Table 30 below were synthesized analogous to the procedure of Example 435 using the specified alkylating reagent. For Examples marked with a #, Step C was performed using Pd—C/H₂ in MeOH instead of 1 M NaOH in MeOH.

TABLE 30
| Ex. No. | Alkylating reagent | Product | MS |
|---|---|---|---|
| 436 | EtO$_2$C(CH$_2$)$_6$Br | 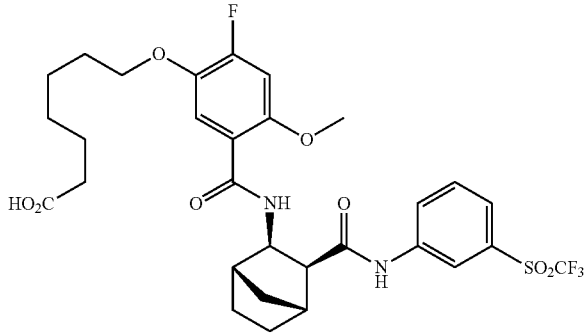 | HRMS (ESI) m/z [M + H]$^+$ 659.2056 |
| 437 | EtO$_2$C(CH$_2$)$_8$Br | 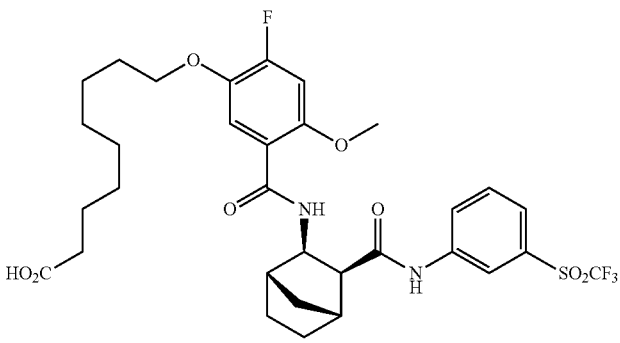 | MS (APCI) m/z 687.1 [M + H]$^+$ |
| 438 | 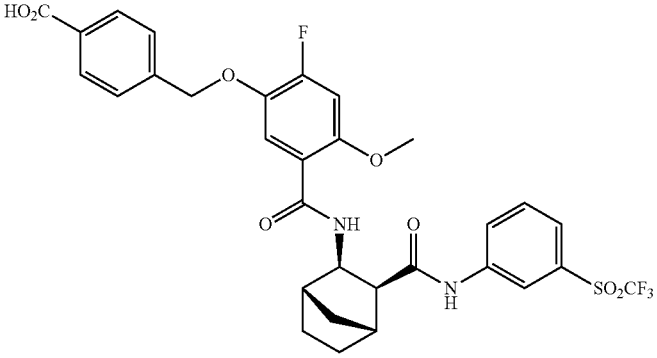 | | MS (APCI) m/z 665.0 [M + H]$^+$ |
| 439 | 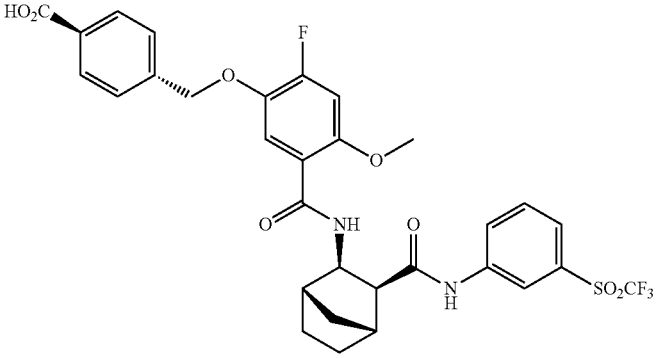 | | MS (APCI) m/z 671.0 [M + H]$^+$ |

TABLE 30-continued

| Ex. No. | Alkylating reagent | Product | MS |
|---|---|---|---|
| 440 | MeO2C-cyclohexyl-CH2-OMs | (structure) | MS (APCI) m/z 671.0 [M + H]+ |
| 441 | MeO2C-bicyclopentyl-CH2-OMs | (structure) | MS (ESI) m/z 697.3 [M + H]+ |
| 442 # | Int. 268 | (structure) | MS (ESI) m/z 659.2 [M + H]+ |
| 443 | MeO2C-cyclobutyl-OMs | (structure) | HRMS (ESI) m/z [M + H]+ 629.1610 |

TABLE 30-continued

| Ex. No. | Alkylating reagent | Product | MS |
|---|---|---|---|
| 444 | (structure: MeO2C-cyclobutyl-OMs) | (structure with HO2C-cyclobutoxy-F-methoxy-benzamide-norbornane-NH-C6H4-SO2CF3) | HRMS (ESI) m/z [M + H]+ 629.1552 |
| 445 | (structure: Me, HO2C-cyclohexyl-OMs) | (structure with Me, HO2C-cyclohexyloxy-F-methoxy-benzamide-norbornane-NH-C6H4-SO2CF3) | MS (APCI) m/z 671.1 [M + H]+ |
| 446 # | Intermediate 272, Isomer 1 | (structure with HO2C-cyclohexyloxy-F-methoxy-benzamide-norbornane-NH-C6H4-SO2CF3) First eluting diastereomers. Cis or Trans cyclohexane. | MS (ESI) m/z 657.3 [M + H]+ |
| 447 # | Intermediate 272, Isomer 2 | (structure with HO2C-cyclohexyloxy-F-methoxy-benzamide-norbornane-NH-C6H4-SO2CF3) Second eluting diastereomers. Cis or Trans cyclohexane. | MS (ESI) m/z 657.3 [M + H]+ |

Example 448: rac-2-((2-Fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)methyl)benzoic acid

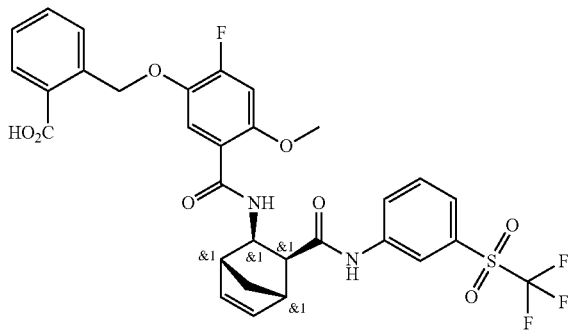 [SMILES: COc1cc(F)c(OCc2ccccc2C(=O)O)cc1C(=O)N[C@H]1[C@@H](C(=O)Nc2cccc(S(=O)(=O)C(F)(F)F)c2)[C@@H]2C=C[C@H]1C2]

Step A: Intermediate 534: rac-(1R,2R,3S,4S)-3-(4-fluoro-5-hydroxy-2-methoxybenzamido)-N-(3-((trifluoromethyl)sulfonyl)phenyl)bicyclo[2.2.1]hept-5-ene-2-carboxamide

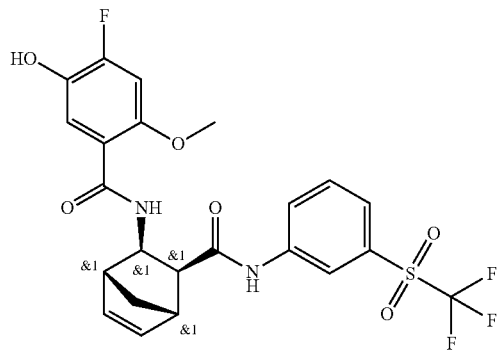 [SMILES: COc1cc(F)c(O)cc1C(=O)N[C@H]1[C@@H](C(=O)Nc2cccc(S(=O)(=O)C(F)(F)F)c2)[C@@H]2C=C[C@H]1C2]

The titled compound was prepared analogous to Example 435 Step A, using Intermediate 213 instead of Intermediate 226. MS (ESI) m/z 529.2 [M+H]$^+$.

Step B: Intermediate 535: rac-Methyl 2-((2-fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)methyl)benzoate

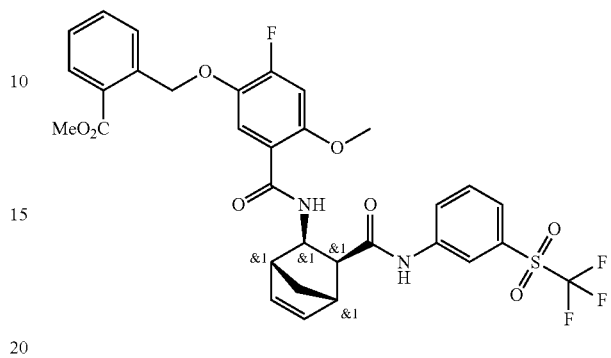

Methyl 2-(chloromethyl)benzoate (7.7 mg, 0.042 mmol) and potassium iodide (13 mg, 0.076 mmol) were added to a mixture of Intermediate 534 (20 mg, 0.038 mmol) and potassium carbonate (5.8 mg, 0.042 mmol) in DMF (0.5 mL), then the mixture was stirred at rt for 24 hr. H$_2$O was added to a mixture and the mixture was stirred vigorously for 3 hr. The residual precipitate was collected by filtration and dried under pump vacuum to give the title compound (22 mg, 86%). MS (ESI) m/z 677.3 [M+H]$^+$.

Step C: rac-2-((2-Fluoro-4-methoxy-5-(((1R,2R,3S,4S)-3-((3-((trifluoromethyl)sulfonyl)phenyl)carbamoyl)bicyclo[2.2.1]hept-5-en-2-yl)carbamoyl)phenoxy)methyl)benzoic acid LiOH (6.7 mg, 0.81 mmol) in H$_2$O (0.14 mL) was added to a solution of Intermediate 535 (19 mg, 0.028 mmol) in THF (0.3 mL), and the reaction mixture was stirred at rt for 24 hr. 2 M aq HCl was added to the reaction mixture to adjust pH<2 and the reaction mixture was extracted with CHCl$_3$ twice and the combined organic layer was concentrated in vacuo. The crude product was purified by flash chromatography using 0-5% MeOH in EtOAc as mobile phase to give the title compound (12 mg, 65%). MS (ESI) m/z 663.3 [M+H]$^+$ The examples included in Table 31 below were synthesized analogously to Example 448 Step B and C, using the specified starting material instead of methyl 2-(chloromethyl)benzoate.

TABLE 31

| Ex No. | SM | Product | MS (ESI) |
|---|---|---|---|
| 449 | ![SM] | ![Product] | m/z 663.3 [M + H]$^+$ |

TABLE 31-continued

| Ex No. | SM | Product | MS (ESI) |
|---|---|---|---|
| 450 | (structure) | (structure) | m/z 663.3 [M + H]+ |
| 451 | (structure) | (structure) | HRMS m/z [M + H]+ 629.1592 |
| 452 | (structure) | (structure) | m/z 705.4 [M + H]+ |
| 453 | (structure) | (structure) | m/z 677.3 [M + H]+ |
| 454 | (structure) | (structure) | m/z 705.4 [M + H]+ |

TABLE 31-continued

| Ex No. | SM | Product | MS (ESI) |
|---|---|---|---|
| 455 | Br-(CH2)5-C(O)-OEt | HO2C-(CH2)5-O-[2-F,4-OMe-phenyl]-C(O)-NH-[bicyclo[2.2.1]hept-5-en-2,3-diyl]-C(O)-NH-[3-(SO2CF3)phenyl] | m/z 643.3 [M + H]+ |
| 456 | Br-(CH2)3-C(O)-OMe | HO2C-(CH2)3-O-[2-F,4-OMe-phenyl]-C(O)-NH-[bicyclo[2.2.1]hept-5-en-2,3-diyl]-C(O)-NH-[3-(SO2CF3)phenyl] | m/z 615.3 [M + H]+ |
| 457 | MsO-cyclohexyl-C(O)OMe | HO2C-cyclohexyl-O-[2-F,4-OMe-phenyl]-C(O)-NH-[bicyclo[2.2.1]hept-5-en-2,3-diyl]-C(O)-NH-[3-(SO2CF3)phenyl] | m/z 655.3 [M + H]+ |

Example 458: 1-Amino-4-(2-fluoro-4-methoxy-5-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid

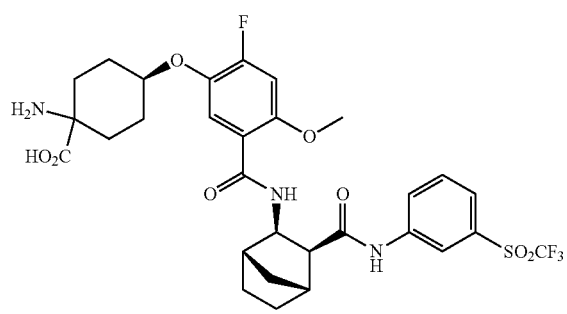

Step A: Intermediate 536: Methyl 1-((tert-butoxycarbonyl)amino)-4-((methylsulfonyl)oxy)cyclohexane-1-carboxylate

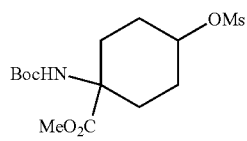 [SMILES: COC(=O)C1(NC(=O)OC(C)(C)C)CCC(OS(C)(=O)=O)CC1]

Methanesulfonyl chloride (600 mg, 5.00 mmol) was added to a solution of methyl 1-((tert-butoxycarbonyl)amino)-4-hydroxycyclohexane-1-carboxylate (100 mg, 0.366 mmol) and TEA (1.46 mL, 10.5 mmol) in CHCl₃ (2 mL), then the mixture was stirred at 0° C. for 1 hr. H₂O was added to the reaction mixture and the layer was separated. Combined organic layer was concentrated in vacuo. The crude product was purified by flash chromatography using a gradient of 0-50% EtOAc in hexane as mobile phase to give the title compound (129 mg, 79%). MS (APCI) m/z 352.1 [M+H]+.

Step B: Intermediate 537: Methyl 1-((tert-butoxy-carbonyl)amino)-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylate

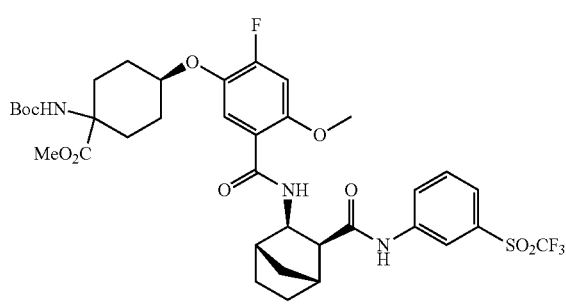

The titled compound was prepared analogous to Example 435 Step B, using Intermediate 536 instead of ethyl 6-bromohexanoate. MS (ESI) m/z 784.5 [M−H]−.

Step C: Intermediate 538: 1-((tert-Butoxycarbonyl)amino)-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid

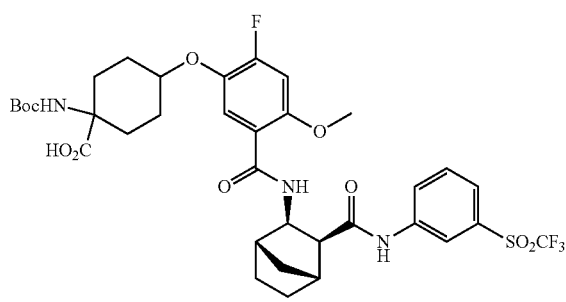

The titled compound was prepared analogous to Example 435 Step C, using Intermediate 537 instead of Intermediate 533. MS (ESI) m/z 772.5 [M+H]+.

Step D: 1-Amino-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid A mixture of Intermediate 538 (13 mg, 0.017 mmol) in 4 M HCl in EtOAc (0.5 mL) was stirred at rt for 1 hr. The mixture was concentrated and dried in vacuo to give the title compound as a mixture of trans and cis (12 mg, 100%). MS (APCI) m/z 672.0 [M+H]+.

Example 459: (1R,2S,3R,4S)-3-(4-Fluoro-2-methoxy-5-(((1s,4S)-4-(methylsulfonamido)cyclohexyl)oxy)benzamido)-N-(3-((trifluoromethyl)sulfonyl)phenyl)bicyclo[2.2.1]heptane-2-carboxamide

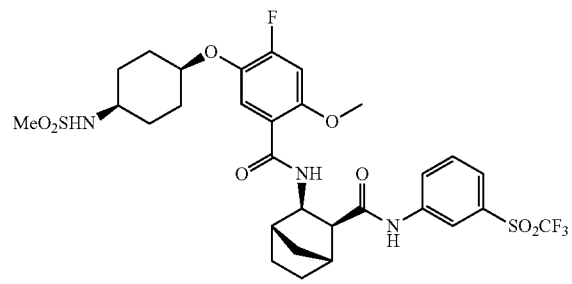

Step A: Intermediate 539: tert-Butyl ((1S,4s)-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexyl)carbamate

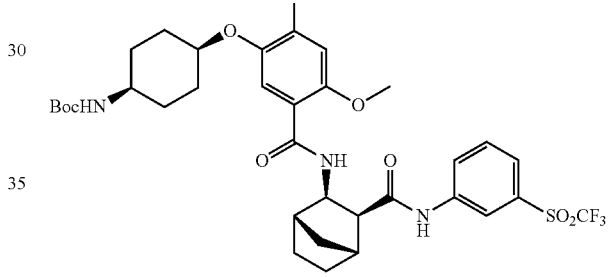

The titled compound was prepared analogous to Example 435 Step B, using (1r,4r)-4-((tert-butoxycarbonyl)amino)cyclohexyl methanesulfonate instead of ethyl 6-bromohexanoate. MS (APCI) m/z 728.1 [M+H]+.

Step B: Intermediate 540: (1R,2S,3R,4S)-3-(5-(((1s,4S)-4-Aminocyclohexyl)oxy)-4-fluoro-2-methoxybenzamido)-N-(3-((trifluoromethyl)sulfonyl)phenyl)bicyclo[2.2.1]heptane-2-carboxamide

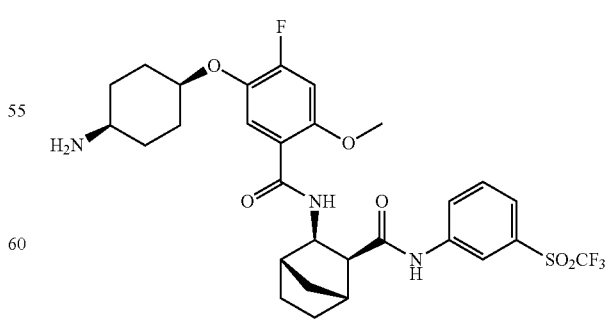

The titled compound was prepared analogous to Example 458 Step D, using Intermediate 539 instead of Intermediate 538. MS (ESI) m/z 628.3 [M+H]+.

Step C: (1R,2S,3R,4S)-3-(4-Fluoro-2-methoxy-5-(((1s,4S)-4-(methylsulfonamido)cyclohexyl)oxy)benzamido)-N-(3-((trifluoromethyl)sulfonyl)phenyl)bicyclo[2.2.1]heptane-2-carboxamide Methanesulfonyl chloride (25 mg, 0.22 mmol) was added to a solution of Intermediate 540 (92 mg, 0.146 mmol) and TEA (0.041 mL, 0.29 mmol) in CHCl$_3$ (2 mL), then the mixture was stirred at rt for 18 hr. The mixture was concentrated to remove CHCl$_3$, then H$_2$O was added to the residue and the mixture was stirred. Precipitate was collected by filtration and dried under air to give the title compound (73 mg, 71%). MS (ESI) m/z 706.3 [M+H]$^+$.

Example 460: (1R,2S,3R,4S)-3-(4-fluoro-2-methoxy-5-(((1r,4R)-4-(methylsulfonamido)cyclohexyl)oxy)benzamido)-N-(3-((trifluoromethyl)sulfonyl)phenyl)bicyclo[2.2.1]heptane-2-carboxamide

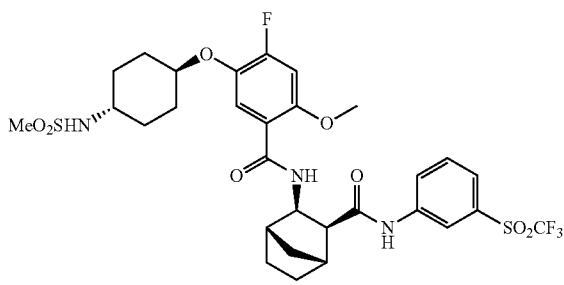

Step A: Intermediate 541: tert-Butyl ((1R,4r)-4-(2-fluoro-4-methoxy-5-(((1S,2R,3S,4R)-3-((3-((trifluoromethyl)sulfonyl)phenyl)carbamoyl)bicyclo[2.2.1]heptan-2-yl)carbamoyl)phenoxy)cyclohexyl)carbamate

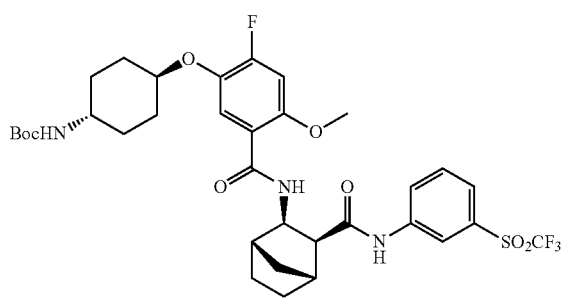

The titled compound was prepared analogous to Example 435 Step B, using (1s,4s)-4-((tert-butoxycarbonyl)amino)cyclohexyl methanesulfonate instead of ethyl 6-bromohexanoate. MS (APCI) m/z 728.1 [M+H]$^+$.

Step B: Intermediate 542: (1R,2S,3R,4S)-3-(5-(((1r,4R)-4-Aminocyclohexyl)oxy)-4-fluoro-2-methoxybenzamido)-N-(3-((trifluoromethyl)sulfonyl)phenyl)bicyclo[2.2.1]heptane-2-carboxamide

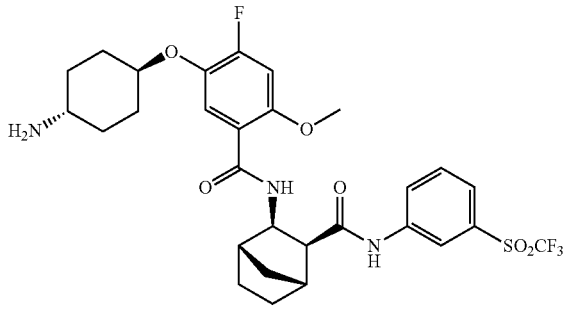

The titled compound was prepared analogous to Example 458 Step D, using Intermediate 541 instead of Intermediate 538. MS (ESI) m/z 628.4 [M+H]$^+$.

Step C: (1R,2S,3R,4S)-3-(4-Fluoro-2-methoxy-5-(((1r,4R)-4-(methylsulfonamido)cyclohexyl)oxy)benzamido)-N-(3-((trifluoromethyl)sulfonyl)phenyl)bicyclo[2.2.1]heptane-2-carboxamide The titled compound was prepared analogous to Example 459 Step C, using Intermediate 542 instead of Intermediate 540. HRMS (ESI) m/z [M+H]$^+$ calcd for C30H36F4N3O8S2: 706.1874 found: 706.1870.

Example 461: (1S,4s)-4-(2-Fluoro-4-methoxy-5-(((3aS,4S,5R,6S,7R,7aR)-6-((3-((trifluoromethyl)sulfonyl)phenyl)carbamoyl)hexahydro-4,7-methanobenzo[d][1,3]dioxol-5-yl)carbamoyl)phenoxy)cyclohexane-1-carboxylic acid

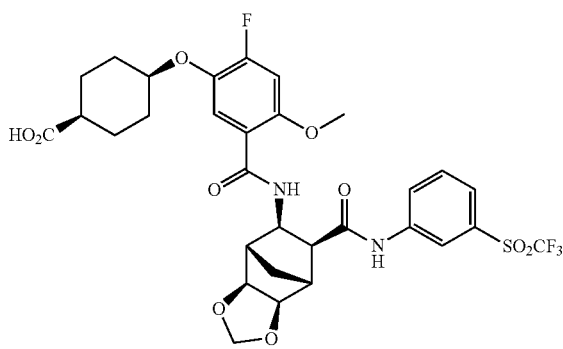

Step A: Intermediate 543: Methyl (1S,4s)-4-(5-(((1S,2R,3S,4R,5R,6S)-5,6-dihydroxy-3-((3-((trifluoromethyl)sulfonyl)phenyl)carbamoyl)bicyclo[2.2.1]heptan-2-yl)carbamoyl)-2-fluoro-4-methoxyphenoxy)cyclohexane-1-carboxylate

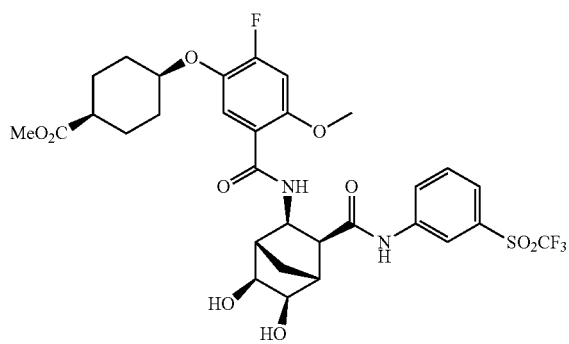

The titled compound was prepared analogous to Example 435 Step A, using Intermediate 249 instead of Intermediate 226, and using Intermediate 348 instead of 4-fluoro-5-hydroxy-2-methoxybenzoic acid. HRMS (ESI) m/z [M+H]+ calcd for C31H33F4N2O10S: 701.1786 found: 701.1804.

Step B: Intermediate 544: Methyl (1S,4s)-4-(2-fluoro-4-methoxy-5-(((3aS,4S,5R,6S,7R,7aR)-6-((3-((trifluoromethyl)sulfonyl)phenyl)carbamoyl)hexahydro-4,7-methanobenzo[d][1,3]dioxol-5-yl)carbamoyl)phenoxy)cyclohexane-1-carboxylate

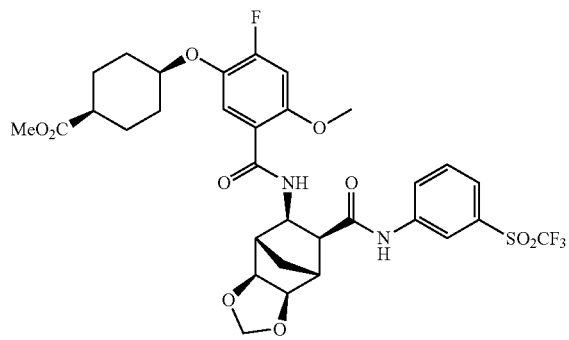

p-Toluenesulfonic acid hydrate (2.7 mg, 0.014 mmol) was added to the mixture of Intermediate 543 (99 mg, 0.141 mmol) and dimethoxymethane (0.123 mL, 1.41 mmol) in toluene (3 mL), and the mixture was stirred at reflux for 3 hr. The mixture was cooled to ambient temperature and sat aq NaHCO3 was added, then the mixture was extracted with EtOAc and combined organic layer was concentrated in vacuo. The crude product was purified by flash chromatography using a gradient of 30-90% EtOAc in hexane as mobile phase to give the title compound (89 mg, 89%). MS (ESI) m/z 715.6 [M+H]+.

Step C: (1S,4s)-4-(2-Fluoro-4-methoxy-5-(((3aS,4S,5R,6S,7R,7aR)-6-((3-((trifluoromethyl)sulfonyl)phenyl)carbamoyl)hexahydro-4,7-methanobenzo[d][1,3]dioxol-5-yl)carbamoyl)phenoxy)cyclohexane-1-carboxylic acid

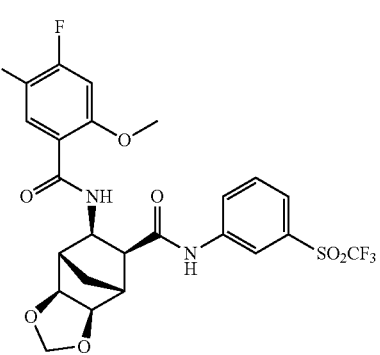

The titled compound was prepared analogous to Example 435 Step C, using Intermediate 544 instead of Intermediate 533. MS (ESI) m/z 701.2 [M+H]+.

Example 462: (1S,2S,3R,4R)-3-(4-fluoro-2-methoxy-5-(((1r,4R)-4-sulfamoylcyclohexyl)oxy)benzamido)-N-(3-((trifluoromethyl)sulfonyl)phenyl)bicyclo[2.2.1]heptane-2-carboxamide

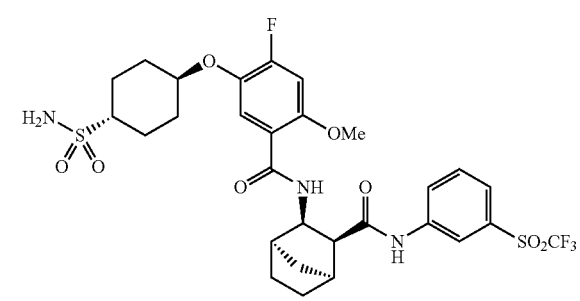

Step A: Intermediate 545: (1S,2S,3R,4R)-3-(4-Fluoro-2-methoxy-5-(((1r,4R)-4-(N-(4-methoxybenzyl)sulfamoyl)cyclohexyl)oxy)benzamido)-N-(3-((trifluoromethyl)sulfonyl)phenyl)bicyclo[2.2.1]heptane-2-carboxamide (Isomer 1) and Intermediate 546: (1S,2S,3R,4R)-3-(4-Fluoro-2-methoxy-5-(((1s,4S)-4-(N-(4-methoxybenzyl)sulfamoyl)cyclohexyl)oxy)benzamido)-N-(3-((trifluoromethyl)sulfonyl)phenyl)bicyclo[2.2.1]heptane-2-carboxamide (Isomer 2)

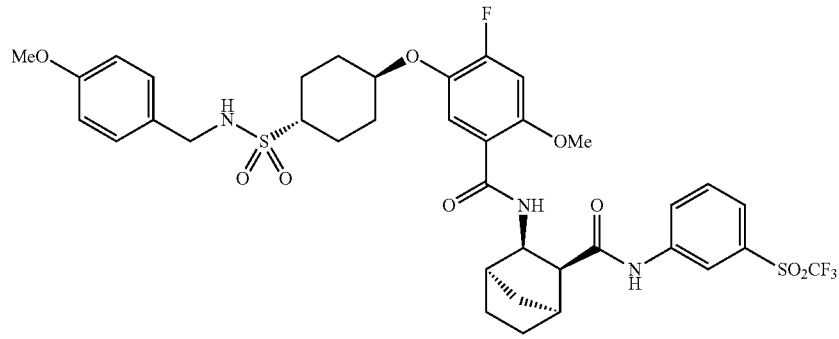

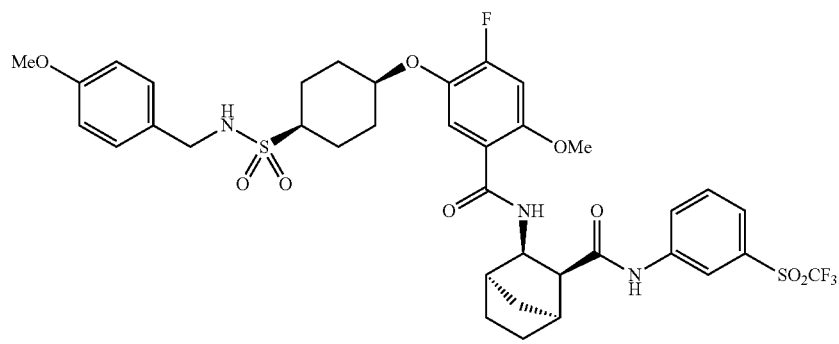

EDC (41 mg, 0.213 mmol), HOAt (29 mg, 0.213 mmol) and TEA (0.030 mL, 0.213 mmol) were added to a solution of Intermediate 232 (71 mg, 0.18 mmol) and Intermediate 338 (83 mg, 0.18 mmol) in DMF (3 mL), then the mixture was stirred at rt for 3 hr. H$_2$O was added to the reaction mixture and the mixture was extracted with EtOAc, then the organic layer was concentrated in vacuo. The crude product was purified by flash chromatography using a gradient of 30-90% EtOAc in hexane as mobile phase to give the first eluting compound Isomer 1: Intermediate 545 (29 mg, 20%); MS (ESI) m/z 812.7 [M+H]$^+$, and the second eluting compound Isomer 2: Intermediate 546 (113 mg, 79%); MS (ESI) m/z 812.3 [M+H]$^+$.

Step B: (1S,2S,3R,4R)-3-(4-Fluoro-2-methoxy-5-(((1r,4R)-4-sulfamoylcyclohexyl)oxy)benzamido)-N-(3-((trifluoromethyl)sulfonyl)phenyl)bicyclo[2.2.1]heptane-2-carboxamide TFA (1 mL) was added to a solution of Intermediate 545 (29 mg, 0.036 mmol) in CHCl$_3$ (1 mL), then the mixture was stirred at rt for 16 hrs. The reaction mixture was concentrated and azeotroped with toluene. The crude product was purified by flash chromatography using a gradient of 0-5% MeOH in CHCl$_3$ as mobile phase to give the title compound (21 mg, 84%). MS (ESI) m/z 692.2 [M+H]$^+$.

Example 463: (1S,2S,3R,4R)-3-(4-Fluoro-2-methoxy-5-(((1s,4S)-4-sulfamoylcyclohexyl)oxy)benzamido)-N-(3-((trifluoromethyl)sulfonyl)phenyl)bicyclo[2.2.1]heptane-2-carboxamide

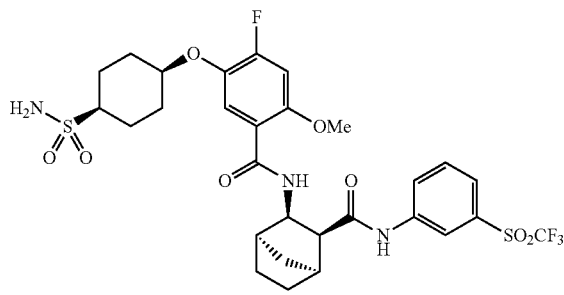

The titled compound was prepared analogous to Example 462 Step B, using Intermediate 546 instead of Intermediate 545. MS (ESI) m/z 692.2 [M+H]$^+$.

Example 464: (1S,4s)-4-(2-Bromo-4-methoxy-5-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid

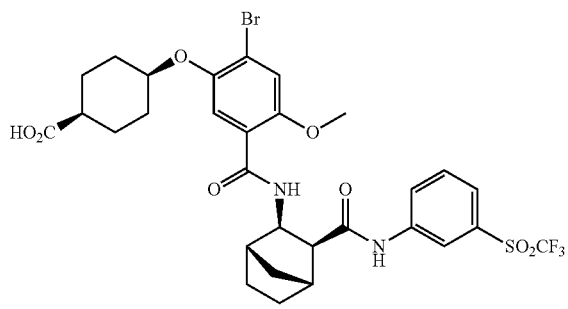

Step A: Intermediate 547: (1R,2S,3R,4S)-3-(4-bromo-5-hydroxy-2-methoxybenzamido)-N-(3-((trifluoromethyl)sulfonyl)phenyl)bicyclo[2.2.1]heptane-2-carboxamide

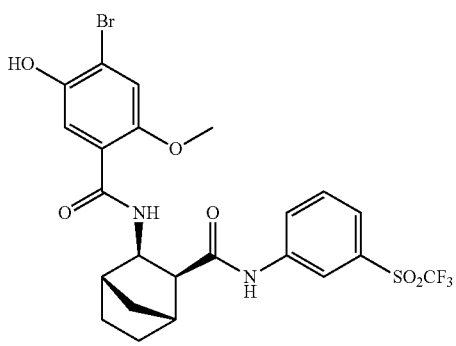

The titled compound was prepared analogous to Example 435 Step A, using 4-bromo-5-hydroxy-2-methoxybenzoic acid instead of 4-fluoro-5-hydroxy-2-methoxybenzoic acid. MS (ESI) m/z 591.1/593.1 [M+H]$^+$.

Step B: Intermediate 548: Methyl (1S,4s)-4-(2-bromo-4-methoxy-5-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylate

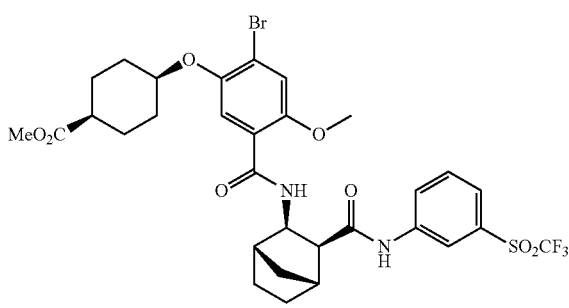

The titled compound was prepared analogous to Example 435 Step B, using methyl (1r,4r)-4-((methylsulfonyl)oxy)cyclohexane-1-carboxylate instead of ethyl 6-bromohexanoate and Intermediate 547 instead of Intermediate 532. MS (ESI) m/z 731.3/733.3 [M+H]$^+$.

Step C: (1S,4s)-4-(2-Bromo-4-methoxy-5-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid The titled compound was prepared analogous to Example 435 Step C, using Intermediate 548 instead of Intermediate 533. HRMS (ESI) m/z [M+H]$^+$ calcd for C30H33BrF3N2O8S: 717.1088 found: 717.1124.

Example 465: (1S,4s)-4-(4-Methoxy-2-methyl-5-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid

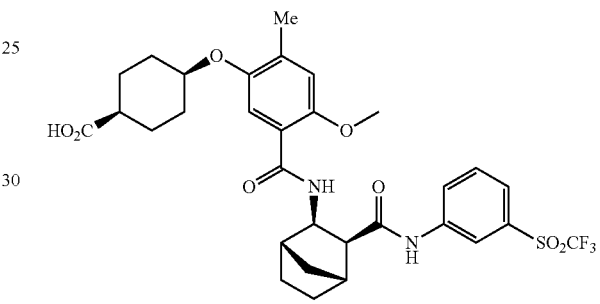

Step A: Intermediate 549: Methyl (1S,4s)-4-(4-methoxy-2-methyl-5-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylate

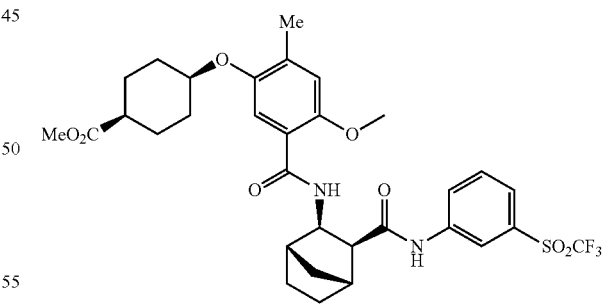

Bis(di-tert-butyl(4-dimethylaminophenyl)phosphine)dichloropalladium(II) (2.9 mg, 0.004 mmol) was added to the mixture of Intermediate 548 (60 mg, 0.082 mmol) and 2,4,6-trimethyl-1,3,5,2,4,6-trioxatriborinane (15 mg, 0.12 mmol) in 2 M aq Na$_2$CO$_3$ (0.5 mL) and DME (2 mL), and the mixture was stirred at reflux for 5 hr. The mixture was cooled to ambient temperature, then the mixture was extracted with CHCl$_3$ and combined organic layer was concentrated in vacuo. The crude product was purified by flash chromatography using a gradient of 30-70% EtOAc in hexane as mobile phase to give the title compound (48 mg, 87%). MS (ESI) m/z 667.3 [M+H]+.

Step B: (1S,4s)-4-(4-Methoxy-2-methyl-5-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid The titled compound was prepared analogous to Example 435 Step C, using Intermediate 549 instead of Intermediate 533. HRMS (ESI) m/z [M+H]+ calcd for C31H36F3N2O8S: 653.2138 found: 653.2158.

Example 466: (1S,4s)-4-(4-Methoxy-3-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid

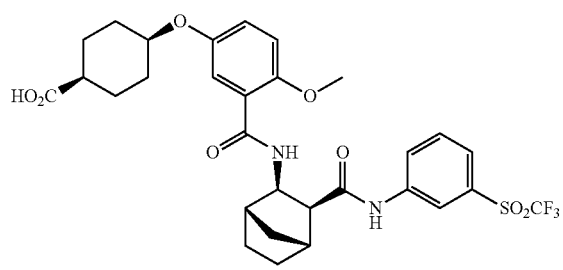

Step A: Intermediate 550: Methyl (1S,4s)-4-(4-methoxy-3-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylate

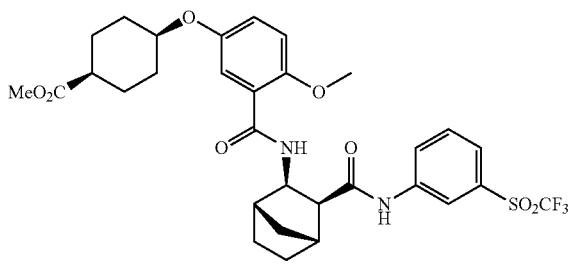

Palladium (10% Pd/C, moisture by 50% H₂O, 20 mg) was added to a solution of Intermediate 548 (60 mg, 0.082 mmol) in EtOAc (3 mL). The reaction mixture was stirred under 1 atm of hydrogen atmosphere at rt for 10 hr. The hydrogen in the reaction vessel was replaced with argon and the reaction mixture was filtered with Celite®®. The filtrate was concentrated in vacuo to give titled compound (53 mg, 99%). MS (ESI) m/z 639.2 [M+H]+.

Step B: (1S,4s)-4-(4-Methoxy-3-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid The titled compound was prepared analogous to Example 435 Step C, using Intermediate 550 instead of Intermediate 533. HRMS (ESI) m/z [M+H]+ calcd for C30H34F3N2O8S: 639.1982 found: 639.1954.

Example 467: (1S,4s)-4-(2-Cyano-4-methoxy-5-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid

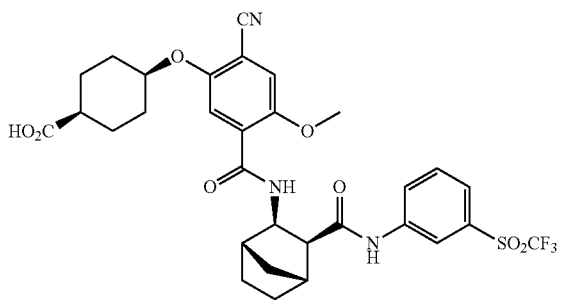

Step A: Intermediate 551: Methyl (1S,4s)-4-(2-cyano-4-methoxy-5-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylate

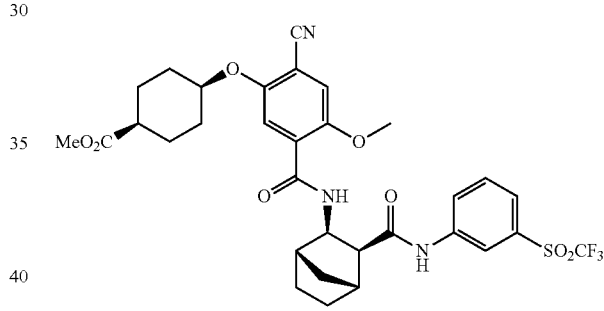

Tetrakis(triphenylphosphine)palladium (6 mg, 0.0052 mmol) was added to the mixture of Intermediate 548 (76 mg, 0.104 mmol) and dicyanozinc (18 mg, 0.157 mmol) in DMF (2 mL), and the mixture was stirred at 120° C. for 16 hr. The mixture was cooled to ambient temperature and sat aq NaHCO₃ was added, then the mixture was extracted with EtOAc and combined organic layer was concentrated in vacuo. The crude product was purified by flash chromatography using a gradient of 30-60% EtOAc in hexane as mobile phase to give the title compound (25 mg, 36%). MS (ESI) m/z 678.3 [M+H]+.

Step B: (1S,4s)-4-(2-Cyano-4-methoxy-5-((((1S,2R,3S,4R)-3-((3-((trifluoromethyl)sulfonyl)phenyl)carbamoyl)bicyclo[2.2.1]heptan-2-yl)carbamoyl)phenoxy)cyclohexane-1-carboxylic acid The titled compound was prepared analogous to Example 435 Step C, using Intermediate 551 instead of Intermediate 533. MS (ESI) m/z 664.3 [M+H]+.

Example 468: (1R,4s)-4-(2-Cyano-4-methoxy-5-((((2SR,3RS)-3-(((1-methylcyclobutyl)methyl)carbamoyl)bicyclo[2.2.2]octan-2-yl)carbamoyl)phenoxy)-1-methylcyclohexane-1-carboxylic acid

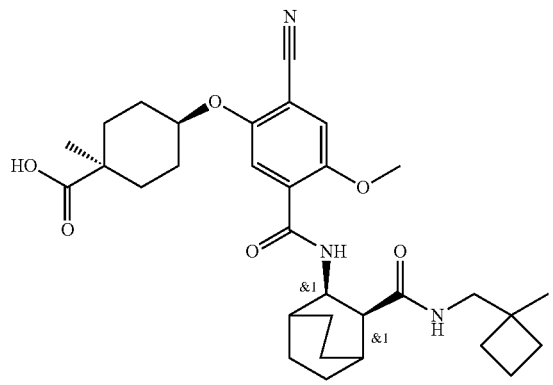 [SMILES: COc1cc(C#N)c(O[C@H]2CC[C@@](C)(C(=O)O)CC2)cc1C(=O)N[C@@H]1C2CCC(CC2)[C@@H]1C(=O)NCC1(C)CCC1]

Step A: Intermediate 552: Naphthalen-1-ylmethyl (1R,4s)-4-(2-cyano-4-methoxy-5-(((1S,2SR,3RS,4R)-3-(((1-methylcyclobutyl)methyl)carbamoyl)bicyclo[2.2.2]oct-5-en-2-yl)carbamoyl)phenoxy)-1-methylcyclohexane-1-carboxylate

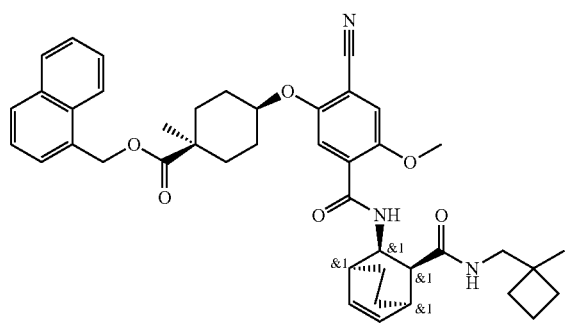 [SMILES: COc1cc(C#N)c(O[C@H]2CC[C@@](C)(C(=O)OCc3cccc4ccccc34)CC2)cc1C(=O)N[C@H]1[C@@H](C(=O)NCC2(C)CCC2)[C@H]2C=C[C@@H]1CC2]

The titled compound was prepared analogous to Example 331 Step A, using Intermediate 70 instead of Intermediate 13, and using Intermediate 187 instead of Intermediate 176. MS (ESI) m/z 704.5 [M+H]$^+$.

Step B: (1R,4s)-4-(2-Cyano-4-methoxy-5-((((2SR,3RS)-3-(((1-methylcyclobutyl)methyl)carbamoyl)bicyclo[2.2.2]octan-2-yl)carbamoyl)phenoxy)-1-methylcyclohexane-1-carboxylic acid The titled compound was prepared analogous to Example 331 Step B, using Intermediate 552 instead of Intermediate 507. MS (ESI) m/z 566.4 [M+H]$^+$.

Example 469: (1R,4s)-4-(2-Cyano-4-methoxy-5-((((1RS,2SR,3RS,4SR)-3-(((1-methylcyclobutyl)methyl)carbamoyl)bicyclo[2.2.2]oct-5-en-2-yl)carbamoyl)phenoxy)-1-methylcyclohexane-1-carboxylic acid

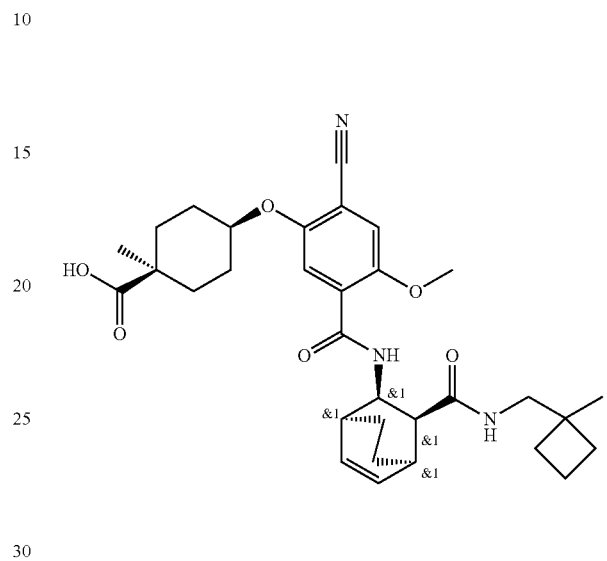

TFA (2.06 mL, 26.9 mmol) was added to a mixture of Intermediate 552 (290 mg, 0.412 mmol) and anisole (89 mg, 0.82 mmol), then the reaction mixture was stirred at rt for 1 hr. The reaction mixture was concentrated in vacuo and the crude product was purified by flash chromatography using a gradient of 0-5% MeOH in CHCl$_3$ as mobile phase to give the title compound (189 mg, 81%). MS (ESI) m/z 564.4 [M+H]$^+$.

Example 470: (1R,4s)-4-(2-Fluoro-4-methoxy-5-((((2SR,3RS)-3-(((1-methylcyclobutyl)methyl)carbamoyl)bicyclo[2.2.2]octan-2-yl)carbamoyl)phenoxy)-1-methylcyclohexane-1-carboxylic acid

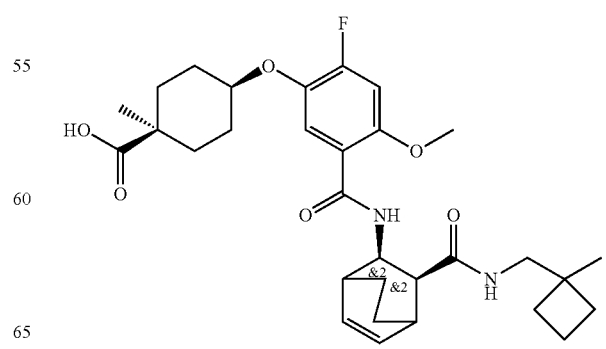

Step A: Intermediate 553: Naphthalen-1-ylmethyl (1R,4s)-4-(2-fluoro-4-methoxy-5-(((1RS,2SR,3RS,4SR)-3-(((1-methylcyclobutyl)methyl)carbamoyl)bicyclo[2.2.2]oct-5-en-2-yl)carbamoyl)phenoxy)-1-methylcyclohexane-1-carboxylate

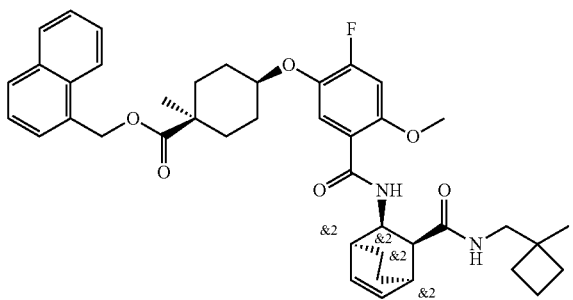 [SMILES: COc1cc(F)c(O[C@H]2CC[C@@](C)(C(=O)OCc3cccc4ccccc34)CC2)cc1C(=O)N[C@H]1[C@@H](C(=O)NCC2(C)CCC2)[C@H]2C=C[C@@H]1CC2]

The titled compound was prepared analogous to Example 331 Step A, using Intermediate 187 instead of Intermediate 176. MS (ESI) m/z 697.5 [M+H]+.

Step B: (1R,4s)-4-(2-Fluoro-4-methoxy-5-(((2SR,3RS)-3-(((1-methylcyclobutyl)methyl)carbamoyl)bicyclo[2.2.2]octan-2-yl)carbamoyl)phenoxy)-1-methylcyclohexane-1-carboxylic acid The titled compound was prepared analogous to Example 331 Step B, using Intermediate 553 instead of Intermediate 507. MS (ESI) m/z 559.4 [M+H]+.

Example 471: (1R,4s)-4-(2-Fluoro-4-methoxy-5-(((1RS,2SR,3RS,4SR)-3-(((1-methylcyclobutyl)methyl)carbamoyl)bicyclo[2.2.2]oct-5-en-2-yl)carbamoyl)phenoxy)-1-methylcyclohexane-1-carboxylic acid

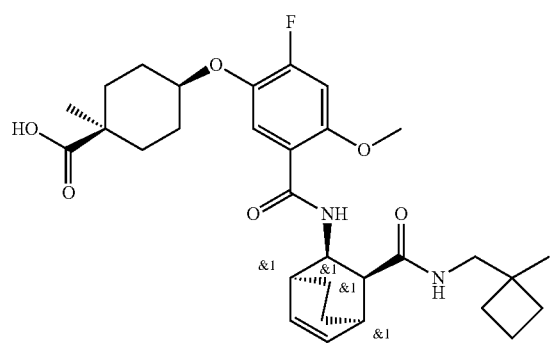 [SMILES: COc1cc(F)c(O[C@H]2CC[C@@](C)(C(=O)O)CC2)cc1C(=O)N[C@H]1[C@@H](C(=O)NCC2(C)CCC2)[C@H]2C=C[C@@H]1CC2]

The titled compound was prepared analogous to Example 469, using Intermediate 553 instead of Intermediate 552. MS (ESI) m/z 557.4 [M+H]+.

Example 472: (1R,3r)-3-((2-Fluoro-4-methoxy-5-((((1R,2R,3S,4S)-3-((3-((trifluoromethyl)sulfonyl)phenyl)carbamoyl)bicyclo[2.2.1]heptan-2-yl)carbamoyl)phenoxy)methyl)cyclobutane-1-carboxylic acid and Example 473: (1S,3s)-3-((2-Fluoro-4-methoxy-5-((((1R,2R,3S,4S)-3-((3-((trifluoromethyl)sulfonyl)phenyl)carbamoyl)bicyclo[2.2.1]heptan-2-yl)carbamoyl)phenoxy)methyl)cyclobutane-1-carboxylic acid

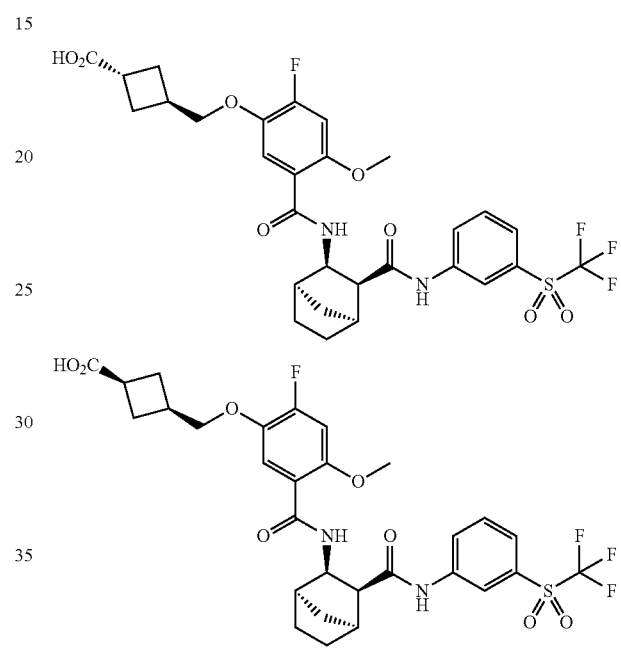

Step A: Intermediate 554: tert-Butyl 3-((2-fluoro-4-methoxy-5-((((1R,2R,3S,4S)-3-((3-((trifluoromethyl)sulfonyl)phenyl)carbamoyl)bicyclo[2.2.1]heptan-2-yl)carbamoyl)phenoxy)methyl)cyclobutane-1-carboxylate

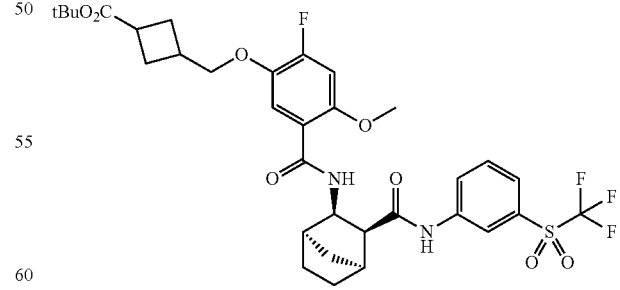

The titled compound was prepared analogous to Example 331 Step A, using Intermediate 339 instead of Intermediate 13, and using Intermediate 232 instead of Intermediate 176. MS (ESI) m/z 699.2 [M+H]+.

Step B: Intermediate 555: 3-((2-Fluoro-4-methoxy-5-((((1R,2R,3S,4S)-3-((3-((trifluoromethyl)sulfonyl)phenyl)carbamoyl)bicyclo[2.2.1]heptan-2-yl)carbamoyl)phenoxy)methyl)cyclobutane-1-carboxylic acid

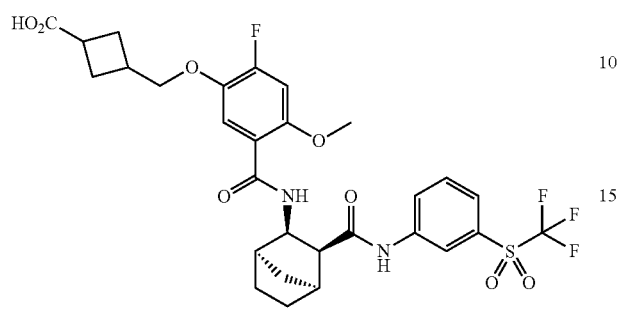

TFA (1 mL) was added to a solution of Intermediate 554 (193 mg, 0.277 mmol) in CHCl₃ (1 mL), then the reaction mixture was stirred at rt for 5 hr. The reaction mixture was concentrated in vacuo and the crude product was purified by flash chromatography using a gradient of 0-10% MeOH in CHCl₃ as mobile phase to give the title compound (153 mg, 80%). MS (ESI) m/z 643.5 [M+H]⁺.

Step C: (1R,3r)-3-((2-Fluoro-4-methoxy-5-((((1R,2R,3S,4S)-3-((3-((trifluoromethyl)sulfonyl)phenyl)carbamoyl)bicyclo[2.2.1]heptan-2-yl)carbamoyl)phenoxy)methyl)cyclobutane-1-carboxylic acid and (1S,3s)-3-((2-fluoro-4-methoxy-5-((((1R,2R,3S,4S)-3-((3-((trifluoromethyl)sulfonyl)phenyl)carbamoyl)bicyclo[2.2.1]heptan-2-yl)carbamoyl)phenoxy)methyl)cyclobutane-1-carboxylic acid Intermediate 555 (141 mg) was separated by chiral HPLC (column: CHIRALPAK IA (250 mm×30 mm); mobile phase: [CO2/MeOH=60/40]) to give the first eluting compound Isomer 1: Example 472 (76.2 mg, 54%); MS (ESI) m/z 643.5 [M+H]⁺, and the second eluting compound Isomer 2: Example 473 (65.2 mg, 46%); MS (ESI) m/z 643.2 [M+H]⁺.

Example 474: 2-((1R,3r)-3-(2-Fluoro-4-methoxy-5-((((1R,2R,3S,4S)-3-((3-((trifluoromethyl)sulfonyl)phenyl)carbamoyl)bicyclo[2.2.1]heptan-2-yl)carbamoyl)phenoxy)cyclobutyl)acetic acid and Example 475: 2-((1S,3s)-3-(2-Fluoro-4-methoxy-5-((((1R,2R,3S,4S)-3-((3-((trifluoromethyl)sulfonyl)phenyl)carbamoyl)bicyclo[2.2.1]heptan-2-yl)carbamoyl)phenoxy)cyclobutyl)acetic acid

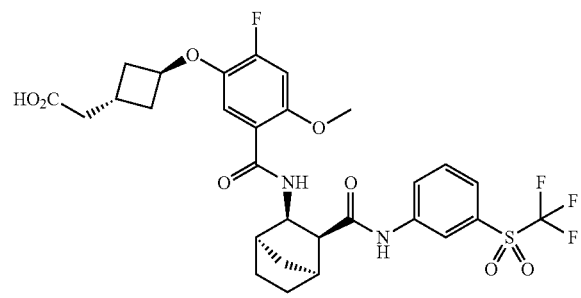 [SMILES: COc1cc(F)c(OC2CC(CC(=O)O)C2)cc1C(=O)N[C@@H]1[C@@H]2CC[C@@H](C2)[C@@H]1C(=O)Nc1cccc(S(=O)(=O)C(F)(F)F)c1]

-continued

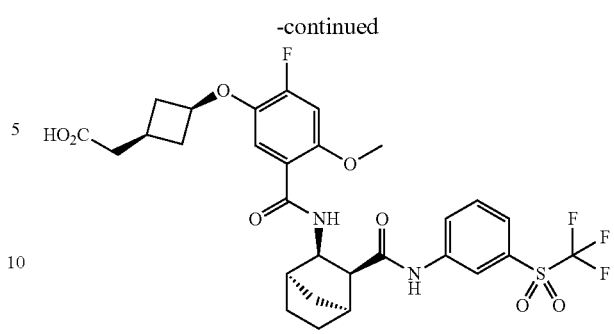

Step A: Intermediate 556: Methyl 2-(3-(2-fluoro-4-methoxy-5-((((1R,2R,3S,4S)-3-((3-((trifluoromethyl)sulfonyl)phenyl)carbamoyl)bicyclo[2.2.1]heptan-2-yl)carbamoyl)phenoxy)cyclobutyl)acetate

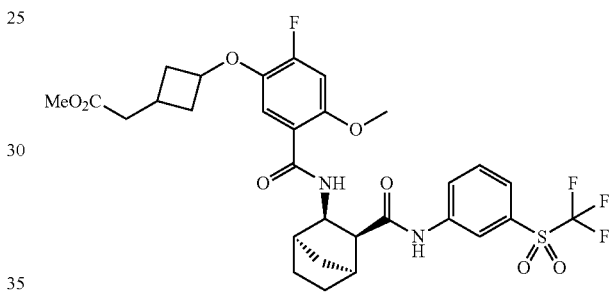

The titled compound was prepared analogous to Example 331 Step A, using Intermediate 340 instead of Intermediate 13, and using Intermediate 232 instead of Intermediate 176. MS (ESI) m/z 657.2 [M+H]⁺.

Step B: Intermediate 557: 2-(3-(2-Fluoro-4-methoxy-5-((((1R,2R,3S,4S)-3-((3-((trifluoromethyl)sulfonyl)phenyl)carbamoyl)bicyclo[2.2.1]heptan-2-yl)carbamoyl)phenoxy)cyclobutyl)acetic acid

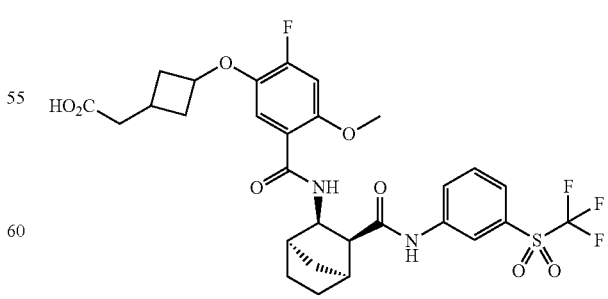

The titled compound was prepared analogous to Example 435 Step C, using Intermediate 556 instead of Intermediate 533. MS (ESI) m/z 643.5 [M+H]⁺.

Step C: 2-((1R,3r)-3-(2-Fluoro-4-methoxy-5-((((1R,2R,3S,4S)-3-((3-((trifluoromethyl)sulfonyl)phenyl)carbamoyl)bicyclo[2.2.1]heptan-2-yl)carbamoyl)phenoxy)cyclobutyl)acetic acid and 2-((1S,3s)-3-(2-fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)cyclobutyl)acetic acid Intermediate 557 (139 mg) was separated by chiral HPLC (column: CHIRALPAK IC (250 mm*30 mm); mobile phase: [CO2/MeOH=90/10]) to give the first eluting compound Isomer 1: Example 474 (72.0 mg, 52%); MS (ESI) m/z 643.2 [M+H]+, and the second eluting compound Isomer 2: Example 475 (48.9 mg, 35%); MS (ESI) m/z 643.1 [M+H]+.

Example 476: 2-((1S,4s)-4-(2-Fluoro-4-methoxy-5-((((1S,2R,3S,4R)-3-(((1-methylcyclobutyl)methyl)carbamoyl)bicyclo[2.2.1]heptan-2-yl)carbamoyl)phenoxy)-1-methylcyclohexyl)acetic acid and Example 477: 2-((1R,4r)-4-(2-Fluoro-4-methoxy-5-((((1S,2R,3S,4R)-3-(((1-methylcyclobutyl)methyl)carbamoyl)bicyclo[2.2.1]heptan-2-yl)carbamoyl)phenoxy)-1-methylcyclohexyl)acetic acid

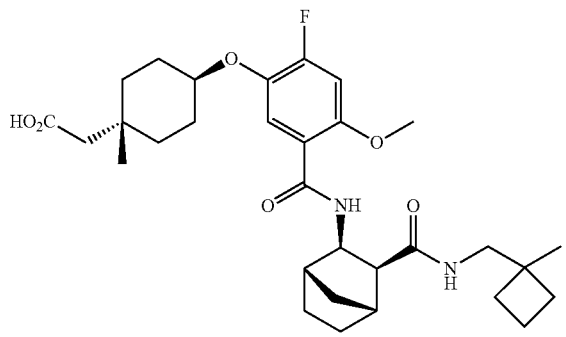

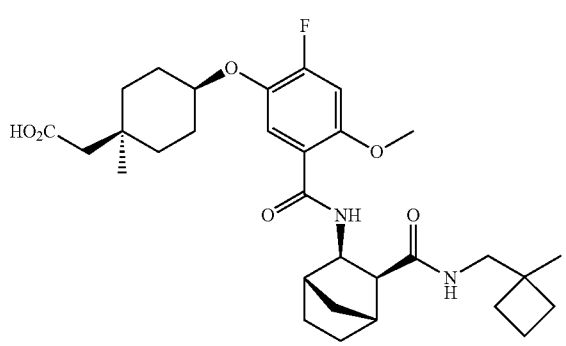 [SMILES: COc1cc(F)c(O[C@H]2CC[C@@](C)(CC(=O)O)CC2)cc1C(=O)N[C@@H]1[C@H]2CC[C@H](C2)[C@@H]1C(=O)NCC1(C)CCC1]

Step A: Intermediate 558: Ethyl 2-(4-(2-fluoro-4-methoxy-5-((((1S,2R,3S,4R)-3-(((1-methylcyclobutyl)methyl)carbamoyl)bicyclo[2.2.1]heptan-2-yl)carbamoyl)phenoxy)-1-methylcyclohexyl)acetate

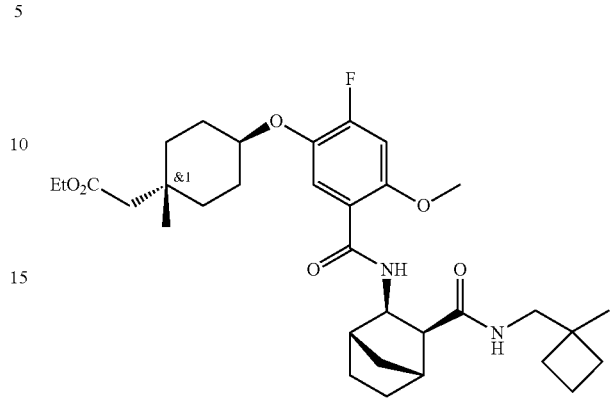

The titled compound was prepared analogous to Example 331 Step A, using Intermediate 341 instead of Intermediate 13, and using Intermediate 22 instead of Intermediate 176. MS (ESI) m/z 587.3 [M+H]+.

Step B: Intermediate 559: 2-(4-(2-Fluoro-4-methoxy-5-((((1S,2R,3S,4R)-3-(((1-methylcyclobutyl)methyl)carbamoyl)bicyclo[2.2.1]heptan-2-yl)carbamoyl)phenoxy)-1-methylcyclohexyl)acetic acid

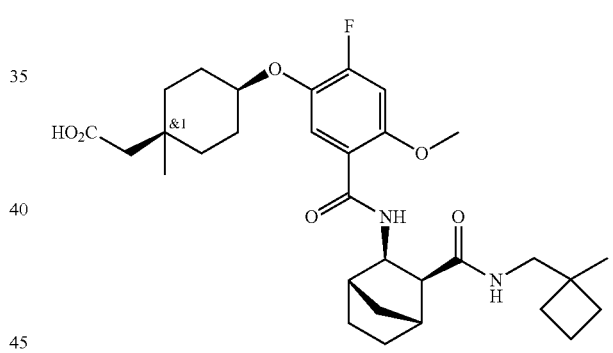

The titled compound was prepared analogous to Example 435 Step C, using Intermediate 558 instead of ethyl Intermediate 533. MS (ESI) m/z 559.6 [M+H]+.

Step C: 2-((1S,4s)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexyl)acetic acid and 2-((1R,4r)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexyl)acetic acid Intermediate 559 (160 mg) was separated by chiral HPLC (column: CHIRALPAK IE (250 mm*30 mm); mobile phase: [Hexane/2-PrOH/AcOH=75/25/0.1]) to give the first eluting compound Isomer 1: Example 476 (72 mg, 415); MS (ESI) m/z 559.3 [M+H]5, and the second eluting compound Isomer 2: Example 477 (66 mg, 380%); MS (ESI) m/z 559.3 [M+H]+.

The examples included in Table 32 below were synthesized analogously to Example 331 Step A followed by Example 472 Step B, using the specified starting materials instead of Intermediate 13 and Intermediate 176.

TABLE 32

| Ex No. | SM 1 | SM 2 | Product | MS (ESI) |
|---|---|---|---|---|
| 478 | Intermediate 336 | Intermediate 22 | | m/z 655.3 [M + H]+ |
| 479 | Intermediate 349 | Intermediate 232 | | m/z 701.6 [M + H]+ |
| 480 | Intermediate 350 | Intermediate 232 | | m/z 701.2 [M + H]+ |
| 481 | Intermediate 349 | Intermediate 224 | | m/z 563.6 [M + H]+ |

TABLE 32-continued

| Ex No. | SM 1 | SM 2 | Product | MS (ESI) |
|---|---|---|---|---|
| 482 | Intermediate 349 | Intermediate 226 | | HRMS m/z [M + H]+ 701.2184 |
| 483 | Intermediate 359 | Intermediate 22 | | m/z 532.2 [M + H]+ |
| 484 | Intermediate 361 | Intermediate 213 | | HRMS m/z [M + H]+ 649.1258 |

Example 485: (1R,4r)-4-(2-Fluoro-4-isopropoxy-5-((((1S,2R,3S,4R)-3-(((1-methylcyclobutyl)methyl)carbamoyl)bicyclo[2.2.1]heptan-2-yl)carbamoyl)phenoxy)-1-(methoxycarbonyl)cyclohexane-1-carboxylic acid

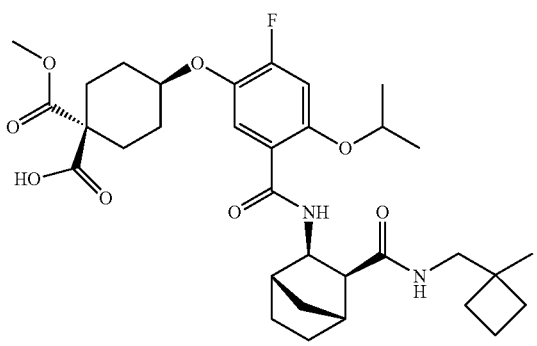 [SMILES: COC(=O)[C@]1(C(=O)O)CC[C@@H](Oc2cc(C(=O)N[C@@H]3[C@H]4CC[C@H](C4)[C@@H]3C(=O)NCC3(C)CCC3)c(OC(C)C)cc2F)CC1]

Step A: Intermediate 560: 1-(tert-Butyl) 1-methyl (1s,4s)-4-(2-fluoro-4-isopropoxy-5-(methoxycarbonyl)phenoxy)cyclohexane-1,1-dicarboxylate

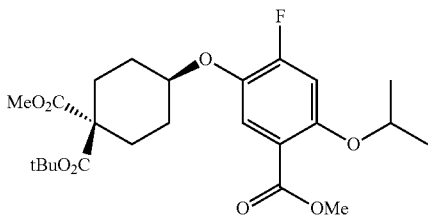 [SMILES: COC(=O)c1cc(O[C@H]2CC[C@@](C(=O)OC)(C(=O)OC(C)(C)C)CC2)c(F)cc1OC(C)C]

Di-2-methoxyethyl azodicarboxylate (154 mg, 0.66 mmol) in THF (2 mL) was added dropwise to a solution of Intermediate 283 (94 mg, 0.41 mmol), Intermediate 273 (160 mg, 0.62 mmol) and triphenylphosphine (173 mg, 0.66 mmol) in THF (2 mL) at 0° C., and the reaction mixture was stirred at 0° C. for 1 hr. The reaction mixture was diluted with EtOAc and the mixture was washed with H₂O twice, then the organic layer was concentrated in vacuo. The crude product was purified by flash chromatography using a gradient of 0-25% EtOAc in hexane as mobile phase to give title compound (122 mg, 63%).

Step B: Intermediate 561: 5-(((1s,4s)-4-(tert-Butoxycarbonyl)-4-carboxycyclohexyl)oxy)-4-fluoro-2-isopropoxybenzoic acid

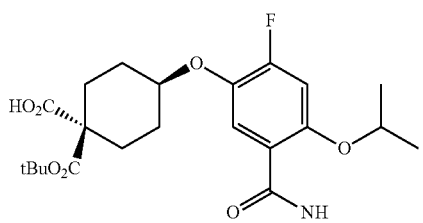 [SMILES: CC(C)Oc1cc(F)c(O[C@H]2CC[C@@](C(=O)O)(C(=O)OC(C)(C)C)CC2)cc1C(N)=O]

LiOH (15 mg, 0.62 mmol) in H₂O (0.7 mL) was added to a solution of Intermediate 560 (432 mg, 0.843 mmol) in THF (2 mL), and the reaction mixture was stirred at rt for 22 hr. 10% aq citric acid was added to the reaction mixture until pH<2, the reaction mixture was extracted with CHCl₃ twice and the combined organic layer was concentrated in vacuo. The crude product was purified by flash chromatography using a gradient of 0-10% MeOH in CHCl₃ as mobile phase to give title compound (90 mg, 79%). MS (ESI) m/z 385.2 [M+H-tBu]⁺

Step C: Intermediate 562: (1S,4s)-1-(tert-Butoxycarbonyl)-4-(2-fluoro-4-isopropoxy-5-(((1S,2R,3S,4R)-3-(((1-methylcyclobutyl)methyl)carbamoyl)bicyclo[2.2.1]heptan-2-yl)carbamoyl)phenoxy)cyclohexane-1-carboxylic acid

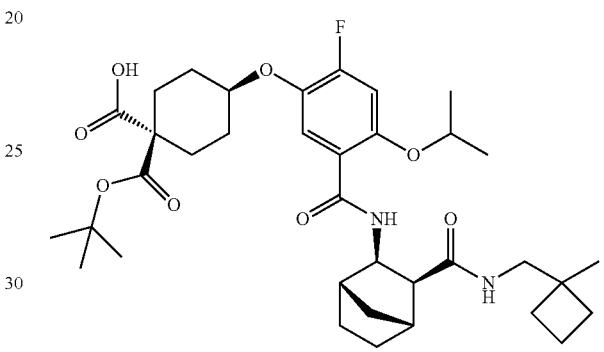

HATU (82 mg, 0.216 mmol) was added to a solution of Intermediate 561 (89 mg, 0.216 mmol), Intermediate 22 (70 mg, 0.237 mmol) and DIPEA (84 mg, 0.648 mmol) in DMF (1 mL) and the reaction mixture was stirred at rt for 1 hr. H₂O and 10% aq citric acid were added to the reaction mixture and the mixture was extracted with EtOAc, then the organic layer was concentrated in vacuo. The crude product was purified by flash chromatography using a gradient of 0-9% MeOH in CHCl₃ as mobile phase to give the title compound (46 mg, 34%). MS (ESI) m/z 659.4 [M+H]⁺.

Step D: Intermediate 563: 1-(tert-Butyl) 1-methyl (1S,4s)-4-(2-fluoro-4-isopropoxy-5-(((1S,2R,3S,4R)-3-(((1-methylcyclobutyl)methyl)carbamoyl)bicyclo[2.2.1]heptan-2-yl)carbamoyl)phenoxy)cyclohexane-1,1-dicarboxylate

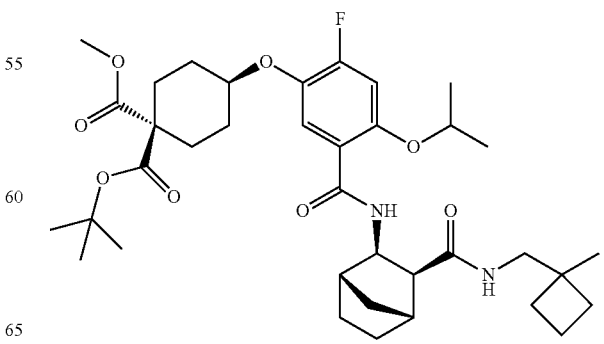

Diazomethyl(trimethyl)silane (1.0 M in hexane, 0.08 mL, 0.155 mmol) was added to toluene (0.4 mL) and MeOH (0.4 mL) and the mixture was stirred at rt for 2 min. Intermediate 562 (43 mg, 0.065 mmol) was added to the mixture, and the mixture was stirred at rt for 30 min. The mixture was concentrated in vacuo and the crude product was purified by flash chromatography using 0-50% EtOAc in hexane as mobile phase to give the title compound (32 mg, 73%). MS (ESI) m/z 673.4 [M+H]$^+$.

Step E: (1R,4r)-4-(2-Fluoro-4-isopropoxy-5-(((1S,2R,3S,4R)-3-(((1-methylcyclobutyl)methyl)carbamoyl)bicyclo[2.2.1]heptan-2-yl)carbamoyl)phenoxy)-1-(methoxycarbonyl)cyclohexane-1-carboxylic acid The titled compound was prepared analogous to Example 472 Step B, using Intermediate 563 instead of Intermediate 554. MS (ESI) m/z 617.3 [M+H]$^+$.

Example 486: (1S,4s)-4-(2-Fluoro-4-isopropoxy-5-(((1S,2R,3S,4R)-3-(((1-methylcyclobutyl)methyl)carbamoyl)bicyclo[2.2.1]heptan-2-yl)carbamoyl)phenoxy)-1-(hydroxymethyl)cyclohexane-1-carboxylic acid

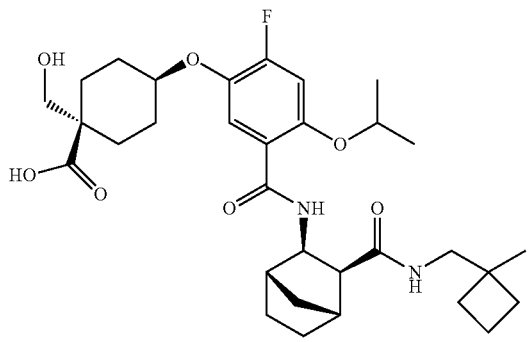 [SMILES: CC(C)Oc1cc(F)c(O[C@H]2CC[C@@](CO)(C(=O)O)CC2)cc1C(=O)N[C@@H]1[C@H]2CC[C@H](C2)[C@@H]1C(=O)NCC1(C)CCC1]

Sodium borohydride (35 mg, 0.92 mmol) and MeOH (0.5 mL) were added to a mixture of Intermediate 563 in THF (1 mL) and the mixture was stirred at rt for 2 hr. Sat aq NH$_4$Cl was added to the reaction mixture, and the mixture was extracted with CHCl$_3$ and the combined organic layer was concentrated in vacuo. The crude product was purified by flash chromatography using 0-75% EtOAc in hexane as mobile phase to give the title compound (14 mg, 47%). MS (ESI) m/z 645.4 [M+H]$^+$.

Step B: (1S,4s)-4-(2-Fluoro-4-isopropoxy-5-(((1S,2R,3S,4R)-3-(((1-methylcyclobutyl)methyl)carbamoyl)bicyclo[2.2.1]heptan-2-yl)carbamoyl)phenoxy)-1-(hydroxymethyl)cyclohexane-1-carboxylic acid The titled compound was prepared analogous to Example 472 Step B, using Intermediate 564 instead of Intermediate 554. 1H NMR (400 MHz, DMSO-d6) δ 0.85 (s, 3H), 1.10-1.71 (m, 20H), 1.80-1.93 (m, 2H), 1.97-2.12 (m, 4H), 2.24-2.28 (m, 1H), 2.59-2.64 (m, 1H), 2.79 (dd, J=13.2, 5.2 Hz, 1H), 3.07 (dd, J=13.2, 6.9 Hz, 1H), 3.16 (s, 2H), 3.18 (s, 2H), 3.36 (s, 2H), 4.02-4.11 (m, 2H), 4.24-4.32 (m, 1H), 4.67-4.76 (sep, J=6.0 Hz, 1H), 7.10 (d, J=13.2 Hz, 1H), 7.60 (d, J=9.9 Hz, 1H), 7.74 (m, 1H), 8.46 (d, J=9.3 Hz, 1H); HRMS (ESI) m/z [M+H]$^+$ calcd for C32H46FN2O7: 589.3284 found: 589.3278.

Example 487: (1R,4s)-4-(5-(((3RS,4SR)-1-Acetyl-3-((3-((trifluoromethyl)sulfonyl)phenyl)carbamoyl)piperidin-4-yl)carbamoyl)-2-fluoro-4-methoxyphenoxy)-1-methylcyclohexane-1-carboxylic acid

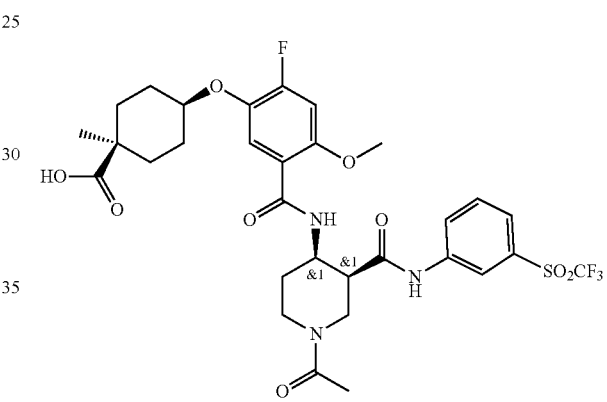

Step A: Intermediate 564: tert-Butyl (1S,4s)-4-(2-fluoro-4-isopropoxy-5-(((1S,2R,3S,4R)-3-(((1-methylcyclobutyl)methyl)carbamoyl)bicyclo[2.2.1]heptan-2-yl)carbamoyl)phenoxy)-1-(hydroxymethyl)cyclohexane-1-carboxylate Step A: Intermediate 565: 1-(tert-Butyl) 3-methyl (3RS,4SR)-4-(4-fluoro-2-methoxy-5-(((1s,4R)-4-methyl-4-((naphthalen-1-ylmethoxy)carbonyl)cyclohexyl)oxy)benzamido)piperidine-1,3-dicarboxylate

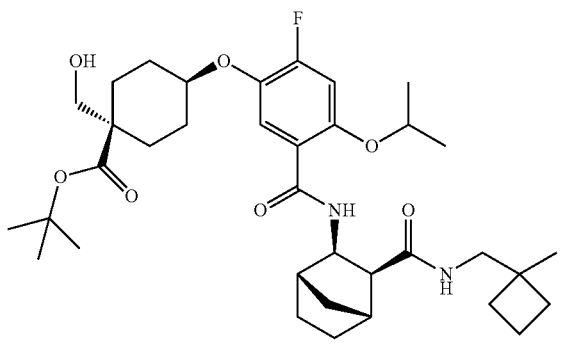 [SMILES: CC(C)Oc1cc(F)c(O[C@H]2CC[C@@](CO)(C(=O)OC(C)(C)C)CC2)cc1C(=O)N[C@@H]1[C@H]2CC[C@H](C2)[C@@H]1C(=O)NCC1(C)CCC1]

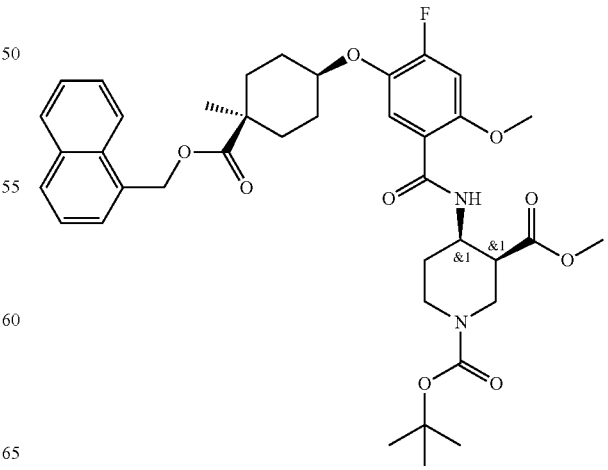

The titled compound was prepared analogous to Example 331 Step A, using rac-1-(tert-butyl) 3-methyl (3R,4S)-4-aminopiperidine-1,3-dicarboxylate instead of Intermediate 176. MS (ESI) m/z 707.4 [M+H]⁺.

Step B: Intermediate 566: rac-(3R,4S)-1-(tert-butoxycarbonyl)-4-(4-fluoro-2-methoxy-5-(((1s,4R)-4-methyl-4-((naphthalen-1-ylmethoxy)carbonyl)cyclohexyl)oxy)benzamido)piperidine-3-carboxylic acid

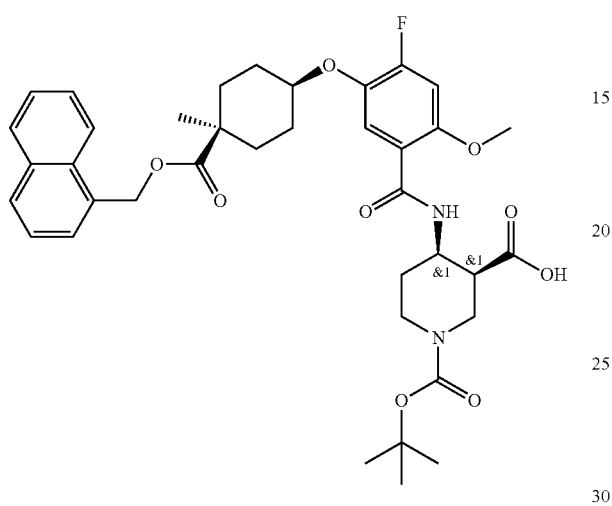

The titled compound was prepared analogous to Example 435 Step C, using Intermediate 565 instead of Intermediate 533.

Step C: Intermediate 567: tert-Butyl (3RS,4SR)-4-(4-fluoro-2-methoxy-5-(((1s,4R)-4-methyl-4-((naphthalen-1-ylmethoxy)carbonyl)cyclohexyl)oxy)benzamido)-3-((3-((trifluoromethyl)sulfonyl)phenyl)carbamoyl)piperidine-1-carboxylate

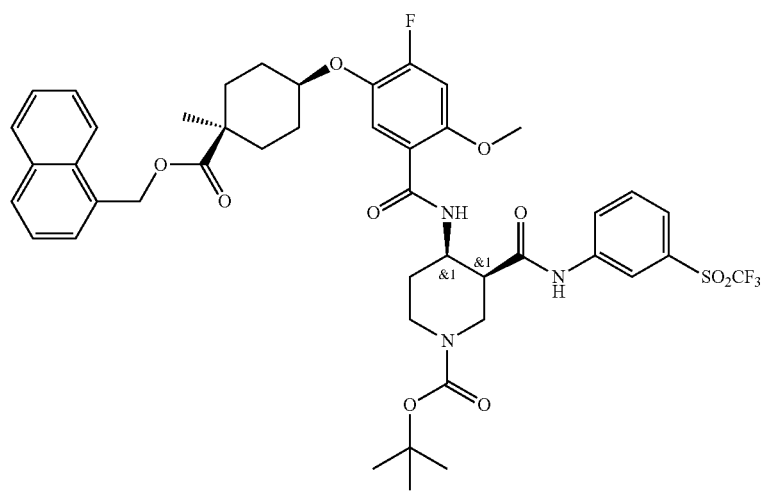

Propylphosphonic acid anhydride (1.7 M in EtOAc, 0.34 mL, 0.59 mmol) and DIPEA (0.15 mL, 0.87 mmol) were added to a solution of 3-((trifluoromethyl)sulfonyl)aniline (39 mg, 0.17 mmol) and Intermediate 566 (100 mg, 0.145 mmol) in EtOAc (3 mL), then the mixture was stirred at rt for 2 days. Sat aq NaHCO₃ was added to the reaction mixture, then organic layer was separated and concentrated in vacuo. The crude product was purified by flash chromatography using a gradient of 10-85% EtOAc in hexane as mobile phase to give the title compound (67 mg, 52%). MS (ESI) m/z 900.8 [M+H]⁺.

Step D: Intermediate 568: Naphthalen-1-ylmethyl (1R,4s)-4-(2-fluoro-4-methoxy-5-(((3RS,4SR)-3-((3-((trifluoromethyl)sulfonyl)phenyl)carbamoyl)piperidin-4-yl)carbamoyl)phenoxy)-1-methylcyclohexane-1-carboxylate hydrochloride

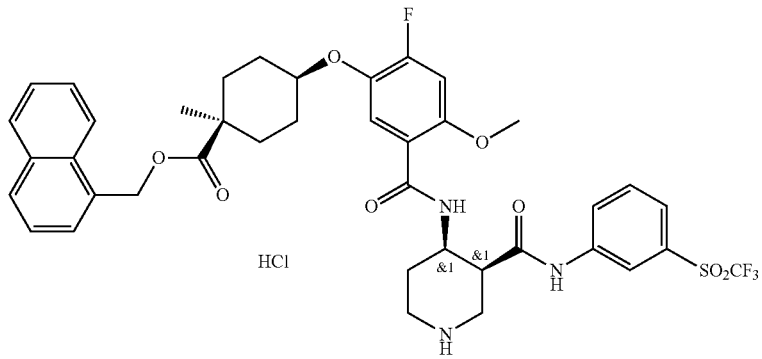

A mixture of Intermediate 567 (67 mg, 0.075 mmol) in 4 M HCl in MeOH (1 mL) was stirred at rt for 4 hr. The mixture was concentrated and dried in vacuo to give the title compound (63 mg, 100%).

Step E: Intermediate 569: Naphthalen-1-ylmethyl (1R,4s)-4-(5-(((3RS,4SR)-1-acetyl-3-((3-((trifluoromethyl)sulfonyl)phenyl)carbamoyl)piperidin-4-yl)carbamoyl)-2-fluoro-4-methoxyphenoxy)-1-methyl-cyclohexane-1-carboxylate

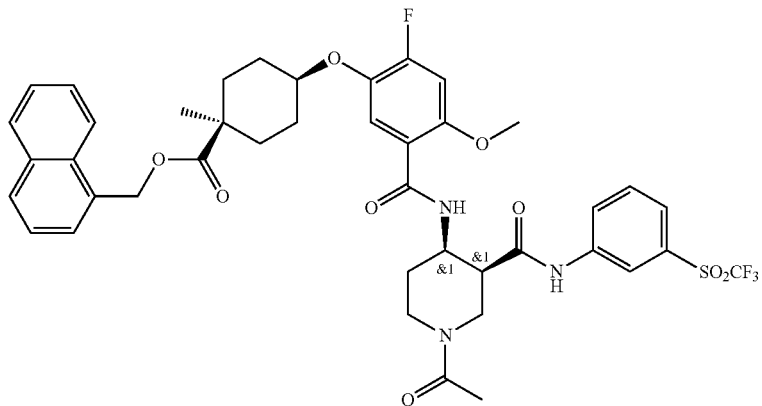

Acetic anhydride (15 mg, 0.149 mmol) was added to a solution of Intermediate 568 (62 mg, 0.075 mmol) in pyridine (2 mL), then the mixture was stirred at rt for 20 hrs. The reaction mixture was concentrated and azeotroped with toluene. The crude product was purified by flash chromatography using a gradient of 0-5% MeOH in $CHCl_3$ as mobile phase to give the title compound (65 mg, 100%). MS (ESI) m/z 842.4 [M+H]$^+$.

Step F: (1R,4s)-4-(5-(((3RS,4SR)-1-Acetyl-3-((3-((trifluoromethyl)sulfonyl)phenyl)carbamoyl)piperidin-4-yl)carbamoyl)-2-fluoro-4-methoxyphenoxy)-1-methylcyclohexane-1-carboxylic acid The titled compound was prepared analogous to Example 331 Step B, using Intermediate 569 instead of Intermediate 507. MS (ESI) m/z 702.2 [M+H]$^+$.

Example 488: (1S,4s)-4-(2-fluoro-5-(((1R,2R,3S,4S)-3-((4-fluoro-3-(pentafluoro-λ6-sulfaneyl)phenyl)carbamoyl)bicyclo[2.2.1]hept-5-en-2-yl)carbamoyl)-4-methoxyphenoxy)cyclohexane-1-carboxylic acid

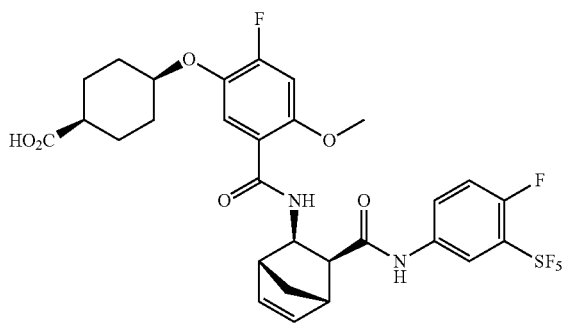

Step A: Intermediate 570: Methyl (1S,4s)-4-(2-fluoro-5-(((1R,2R,3S,4S)-3-((4-fluoro-3-(pentafluoro-M6-sulfaneyl)phenyl)carbamoyl)bicyclo[2.2.1]hept-5-en-2-yl)carbamoyl)-4-methoxyphenoxy)cyclohexane-1-carboxylate

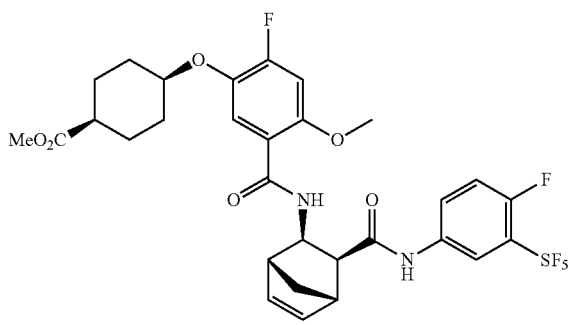

HATU (73 mg, 0.19 mmol) was added to a solution of Intermediate 234 (71 mg, 0.17 mmol), Intermediate 348 (62 mg, 0.19 mmol) and DIPEA (0.09 mL, 0.52 mmol) in DMF (0.4 mL) and the reaction mixture was stirred at rt for 5 hr. H$_2$O was added to the reaction mixture and the mixture was extracted with CHCl$_3$, then the organic layer was concentrated in vacuo. The crude product was purified by flash chromatography using a gradient of 0-60% EtOAc in hexane as mobile phase to give the title compound (109 mg, 92%). MS (ESI) m/z 681.2 [M+H]$^+$.

Step B: (1S,4s)-4-(2-Fluoro-5-(((1R,2R,3S,4S)-3-((4-fluoro-3-(pentafluoro-6-sulfaneyl)phenyl)carbamoyl)bicyclo[2.2.1]hept-5-en-2-yl)carbamoyl)-4-methoxyphenoxy)cyclohexane-1-carboxylic acid LiOH (19 mg, 0.793 mmol) in H$_2$O (0.4 mL) was added to a solution of Intermediate 570 (108 mg, 0.159 mmol) in THF (0.8 mL), then the mixture was stirred at rt for 12 hr. 1 M aq HCl and CHCl$_3$ were added to the reaction mixture and the layer was separated. Combined organic layer was concentrated in vacuo. The crude product was purified by flash chromatography using a gradient of 0-5% MeOH in CHCl$_3$ as mobile phase to give the title compound (93 mg, 88%). HRMS (ESI) m/z [M+H]$^+$ calcd for C29H30F7N2O6S: 667.1708 found: 667.1714.

The examples included in Table 33 below were synthesized analogous to the procedure of Example 488 using Intermediate 111 and indicated amines.

TABLE 33

| Example | Amine | Product | MS |
|---|---|---|---|
| 489 | Int. 227 | (structure shown) | MS (APCI) 673.0 [M + H]$^+$ |

TABLE 33-continued

| Example | Amine | Product | MS |
|---|---|---|---|
| 490 | Int. 217 | | HRMS (ESI) m/z [M + H]+ 631.1720 |
| 491 | Int. 226 | | HRMS (ESI) m/z [M + H]+ 657.1928 |
| 492 | Int. 228 | | HRMS m/z [M + H]+ 585.1992 |
| 493 | Int. 253 | | HRMS (ESI) m/z [M + H]+ 621.1848 |

TABLE 33-continued

| Example | Amine | Product | MS |
|---|---|---|---|
| 494 | Int. 249 | (structure) | MS (ESI) 689.2 [M + H]+ |
| 495 | Int. 213 | (structure) | MS (ESI) 655.3 [M + H]+ |
| 496 | Int. 246 | (structure) | MS (ESI) 661.6 [M + H]+ |

Example 497: (1S,4s)-4-(2-Fluoro-4-methoxy-5-(((1R,2R,3S,4S)-3-((4-methoxy-3-((trifluoromethyl)sulfonyl)phenyl)carbamoyl)bicyclo[2.2.1]hept-5-en-2-yl)carbamoyl)phenoxy)cyclohexane-1-carboxylic acid

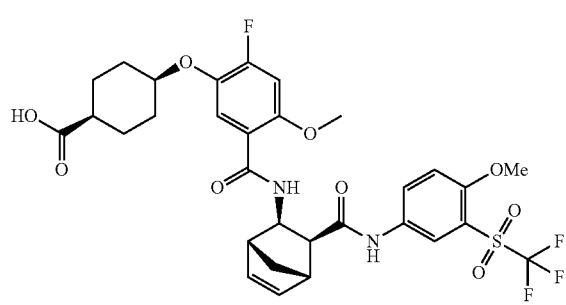 [SMILES: COc1cc(F)c(O[C@H]2CC[C@@H](C(=O)O)CC2)cc1C(=O)N[C@H]1[C@@H](C(=O)Nc2ccc(OC)c(S(=O)(=O)C(F)(F)F)c2)[C@@H]2C=C[C@H]1C2]

Step A: Intermediate 571: Ethyl (1S,4s)-4-(2-fluoro-5-(((1R,2R,3S,4S)-3-((4-fluoro-3-((trifluoromethyl)sulfonyl)phenyl)carbamoyl)bicyclo[2.2.1]hept-5-en-2-yl)carbamoyl)-4-methoxyphenoxy)cyclohexane-1-carboxylate

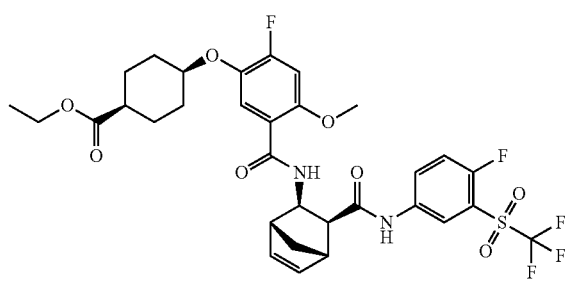 [SMILES: CCOC(=O)[C@H]1CC[C@@H](Oc2cc(C(=O)N[C@H]3[C@@H](C(=O)Nc4ccc(F)c(S(=O)(=O)C(F)(F)F)c4)[C@@H]4C=C[C@H]3C4)c(OC)cc2F)CC1]

The titled compound was prepared analogous to Example 488 Step A, using Intermediate 227 instead of Intermediate 234. MS (ESI) m/z 701.3 [M+H]$^+$.

Step B: (1S,4s)-4-(2-Fluoro-4-methoxy-5-(((1R,2R,3S,4S)-3-((4-methoxy-3-((trifluoromethyl)sulfonyl)phenyl)carbamoyl)bicyclo[2.2.1]hept-5-en-2-yl)carbamoyl)phenoxy)cyclohexane-1-carboxylic acid 2 M aq NaOH (0.65 mL, 1.3 mmol) was added to a solution of Intermediate 571 (185 mg, 0.159 mmol) in MeOH (1 mL), then the mixture was stirred at rt for 3 days. 1 M aq HCl and CHCl$_3$ were added to the reaction mixture and the layer was separated. Combined organic layer was concentrated in vacuo. The crude product was purified by flash chromatography using 5% MeOH in CHCl$_3$ as mobile phase to give the title compound (26 mg, 14%). HRMS (ESI) m/z [M+H]$^+$ calcd for C31H33F4N2O9S: 685.1838 found: 685.1810.

Example 498: (1S,4s)-4-(2-Fluoro-5-(((1R,2R,3S,4S)-3-((4-fluoro-3-(trifluoromethyl)phenyl)carbamoyl)bicyclo[2.2.1]hept-5-en-2-yl)carbamoyl)-4-methoxyphenoxy)cyclohexane-1-carboxylic acid

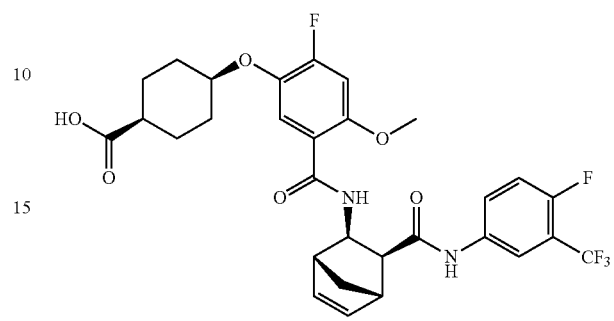

Step A: Intermediate 572: Methyl (1S,4s)-4-(2-fluoro-5-(((1R,2R,3S,4S)-3-((4-fluoro-3-(trifluoromethyl)phenyl)carbamoyl)bicyclo[2.2.1]hept-5-en-2-yl)carbamoyl)-4-methoxyphenoxy)cyclohexane-1-carboxylate

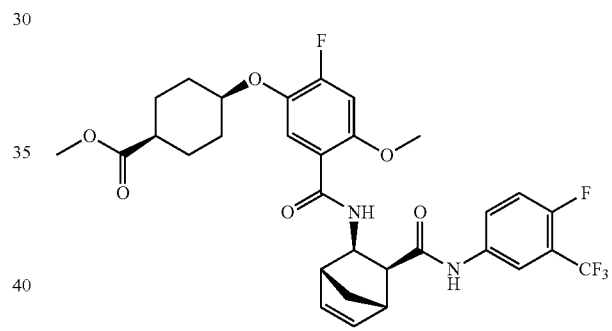

The titled compound was prepared analogous to Example 488 Step A, using Intermediate 229 instead of Intermediate 234. MS (ESI) m/z 623.3 [M+H]$^+$.

Step B: (1S,3s)-3-((2-Fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)methyl)cyclobutane-1-carboxylic acid 2 M aq NaOH (5.6 mL, 2.8 mmol) was added to a solution of Intermediate 572 (396 mg, 0.636 mmol) in MeOH (1.3 mL), then the mixture was stirred at rt for 4 days. Aq citric acid and CHCl$_3$ were added to the reaction mixture and the layer was separated. Combined organic layer was concentrated in vacuo. The crude product was purified by flash chromatography using 5% MeOH in CHCl$_3$ as mobile phase to give the first eluting trans isomer: (1S,4s)-4-(2-fluoro-5-(((1R,2R,3R,4S)-3-((4-fluoro-3-(trifluoromethyl)phenyl)carbamoyl)bicyclo[2.2.1]hept-5-en-2-yl)carbamoyl)-4-methoxyphenoxy)cyclohexane-1-carboxylic acid (18 mg, 7%); MS (APCI) m/z 609.1 [M+H]$^+$, and the second eluting cis isomer: Example 498 (285 mg, 88%); MS (APCI) m/z 609.1 [M+H]$^+$.

Example 499: (1S,2S,3R,4R)-3-(5-(((1s,4S)-4-Carbamoylcyclohexyl)oxy)-4-fluoro-2-methoxybenzamido)-N-(4-fluoro-3-(trifluoromethyl)phenyl)bicyclo[2.2.1]hept-5-ene-2-carboxamide

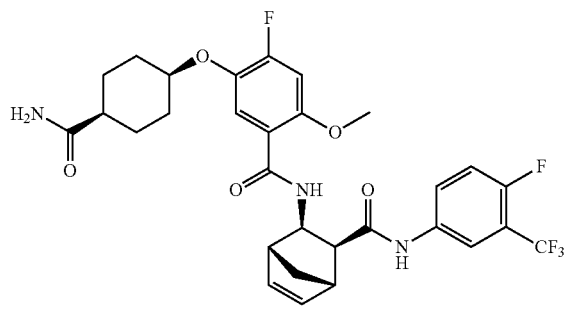 [SMILES: COc1cc(F)c(O[C@H]2CC[C@@H](C(N)=O)CC2)cc1C(=O)N[C@H]1[C@@H](C(=O)Nc2ccc(F)c(C(F)(F)F)c2)[C@@H]2C=C[C@H]1C2]

The titled compound was prepared analogous to Example 418 step A, using Example 498 instead of Example 1. HRMS (ESI) m/z [M+H]$^+$ calcd for C30H31F5N3O5: 608.2178 found: 608.2170.

Example 500: (1R,2S,3R,4S)-3-(5-(((1s,4S)-4-Carbamoylcyclohexyl)oxy)-4-fluoro-2-methoxybenzamido)-N-(4-fluoro-3-(trifluoromethyl)phenyl)bicyclo[2.2.1]heptane-2-carboxamide

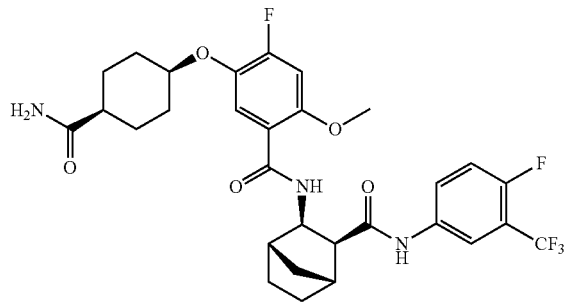 [SMILES: COc1cc(F)c(O[C@H]2CC[C@@H](C(N)=O)CC2)cc1C(=O)N[C@@H]1[C@H]2CC[C@H](C2)[C@@H]1C(=O)Nc1ccc(F)c(C(F)(F)F)c1]

The titled compound was prepared analogous to Example 418 step A, using Example 179 instead of Example 1. HRMS (ESI) m/z [M+H]$^+$ calcd for C30H33F5N3O5: 610.2334 found: 610.2348.

Example 501: (1R,4s)-4-(2-Fluoro-5-(((1S,2S,3R,4R)-3-((4-fluoro-3-(trifluoromethyl)phenyl)carbamoyl)bicyclo[2.2.1]hept-5-en-2-yl)carbamoyl)-4-methoxyphenoxy)cyclohexane-1-carboxylic acid

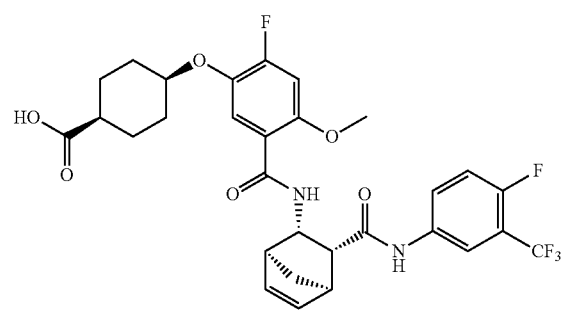 [SMILES: COc1cc(F)c(O[C@H]2CC[C@@H](C(=O)O)CC2)cc1C(=O)N[C@@H]1[C@H](C(=O)Nc2ccc(F)c(C(F)(F)F)c2)[C@H]2C=C[C@@H]1C2]

Step A: Intermediate 573: Methyl (1R,4s)-4-(2-fluoro-5-(((1S,2S,3R,4R)-3-((4-fluoro-3-(trifluoromethyl)phenyl)carbamoyl)bicyclo[2.2.1]hept-5-en-2-yl)carbamoyl)-4-methoxyphenoxy)cyclohexane-1-carboxylate

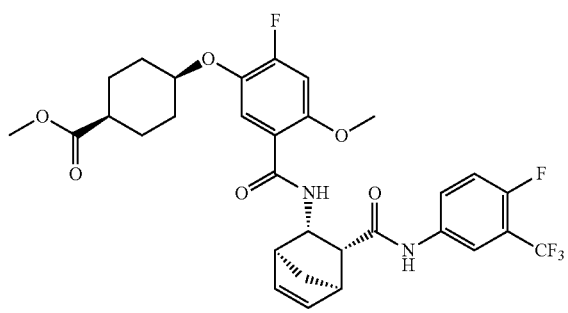 [SMILES: COc1cc(F)c(O[C@H]2CC[C@@H](C(=O)OC)CC2)cc1C(=O)N[C@@H]1[C@H](C(=O)Nc2ccc(F)c(C(F)(F)F)c2)[C@H]2C=C[C@@H]1C2]

The titled compound was prepared analogous to Example 488 Step A, using Intermediate 230 instead of Intermediate 234. MS (ESI) m/z 623.4 [M+H]$^+$.

Step B: (1R,4s)-4-(2-Fluoro-5-(((1S,2S,3R,4R)-3-((4-fluoro-3-(trifluoromethyl)phenyl)carbamoyl)bicyclo[2.2.1]hept-5-en-2-yl)carbamoyl)-4-methoxyphenoxy)cyclohexane-1-carboxylic acid The titled compound was prepared analogous to Example 488 Step B, using Intermediate 573 instead of Intermediate 570. MS (ESI) m/z 609.1 [M+H]$^+$.

Example 502: (1S,4s)-4-(2-Cyano-4-methoxy-5-(((1R,2R,3S,4S)-3-((3,3,3-trifluoro-2,2-dimethylpropyl)carbamoyl)bicyclo[2.2.1]heptan-2-yl)carbamoyl)phenoxy)-1-methylcyclohexane-1-carboxylic acid

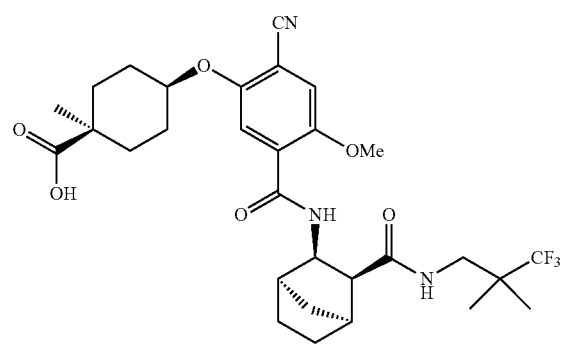 [SMILES: COc1cc(C#N)c(O[C@H]2CC[C@@](C)(C(=O)O)CC2)cc1C(=O)N[C@@H]1[C@@H]2CC[C@@H](C2)[C@@H]1C(=O)NCC(C)(C)C(F)(F)F]

Step A: Intermediate 574: Methyl (1R,2S,3R,4S)-3-(4-cyano-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylate

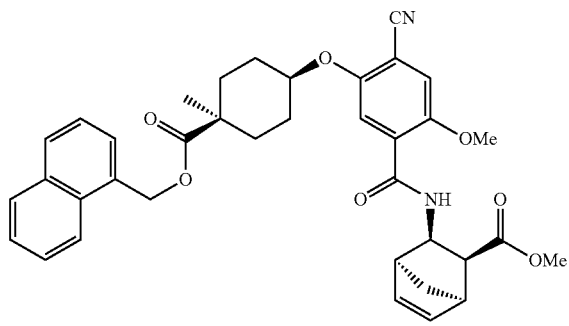 [SMILES: COC(=O)[C@@H]1[C@H](NC(=O)c2cc(O[C@H]3CC[C@@](C)(C(=O)OCc4cccc5ccccc45)CC3)c(C#N)cc2OC)[C@@H]2C=C[C@H]1C2]

HATU (289 mg, 0.76 mmol) was added to a solution of methyl (1R,2S,3R,4S)-3-aminobicyclo[2.2.1]hept-5-ene-2-carboxylate hydrochloride (155 mg, 0.76 mmol), Intermediate 70 (300 mg, 0.63 mmol) and DIPEA (0.33 mL, 1.90 mmol) in DMF (3 mL) and the reaction mixture was stirred at rt for 1 hr. H$_2$O was added to the reaction mixture and the precipitate was collected by filtration, and dried in vacuo to give the title compound (415 mg, 100%). MS (ESI) m/z 623.4 [M+H]$^+$.

Step B: Intermediate 575: (1R,2S,3R,4S)-3-(4-Cyano-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylic acid

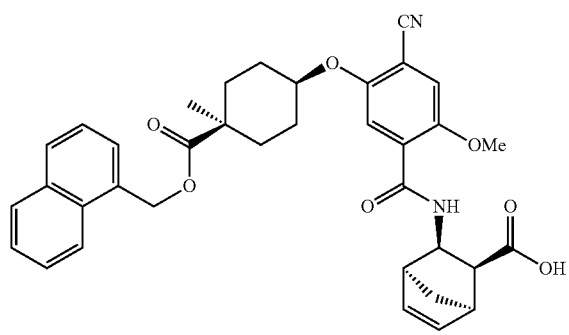 [SMILES: COc1cc(C#N)c(O[C@H]2CC[C@@](C)(C(=O)OCc3cccc4ccccc34)CC2)cc1C(=O)N[C@H]1[C@@H](C(=O)O)[C@H]2C=C[C@@H]1C2]

The titled compound was prepared analogous to Example 488 Step B, using Intermediate 574 instead of Intermediate 570. MS (ESI) m/z 609.4 [M+H]$^+$.

Step C: Intermediate 576: 3,3,3-Trifluoro-2,2-dimethylpropyl (1R,2S,3R,4S)-3-(4-cyano-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylate

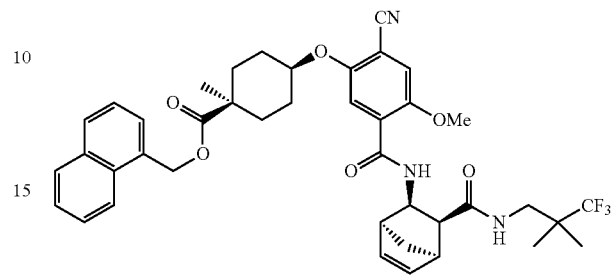

HATU (70 mg, 0.185 mmol) was added to a solution of Intermediate 575 (94 mg, 0.154 mmol), 3,3,3-trifluoro-2,2-dimethylpropylamine hydrochloride (41 mg, 0.23 mmol) and DIPEA (0.08 mL, 0.463 mmol) in DMF (0.8 mL) and the reaction mixture was stirred at rt for 1 hr. H$_2$O was added to the reaction mixture and the mixture was extracted with CHCl$_3$, then the organic layer was concentrated in vacuo. The crude product was purified by flash chromatography using a gradient of 0-50% EtOAc in hexane as mobile phase to give the title compound (85 mg, 75%). MS (ESI) m/z 732.4 [M+H]$^+$.

Step D: (1S,4s)-4-(2-Cyano-4-methoxy-5-(((1R,2R,3S,4S)-3-((3,3,3-trifluoro-2,2-dimethylpropyl)carbamoyl)bicyclo[2.2.1]heptan-2-yl)carbamoyl)phenoxy)-1-methylcyclohexane-1-carboxylic acid The titled compound was prepared analogous to Example 331 Step B, using Intermediate 576 instead of Intermediate 507. 1H NMR (400 MHz, DMSO-d6) δ 1.01 (s, 3H), 1.02 (s, 3H), 1.05 (s, 3H), 1.20-1.72 (m, 10H), 1.83-1.95 (m, 2H), 2.02-2.12 (m, 2H), 2.39-2.49 (m, 2H), 2.93 (dd, J=11.0, 6.7 Hz, 1H), 3.15 (dd, J=13.75, 6.05 Hz, 1H), 3.20-3.50 (m, 1H), 3.94 (s, 3H), 4.24-4.40 (m, 2H), 7.52 (s, 1H), 7.64 (s, 1H), 8.18 (t, J=6.33 Hz, 1H), 9.83 (d, J=7.15 Hz, 1H). HRMS (ESI) m/z [M+H]$^+$ calcd for C30H39F3N3O6: 594.2786 found: 594.2774.

Example 503: (1S,4s)-4-(5-(((1S,2R,3S,4R)-3-(((R*)-2,2-Dimethylcyclopentyl)carbamoyl)bicyclo[2.2.1]heptan-2-yl)carbamoyl)-2-fluoro-4-methoxyphenoxy)-1-methylcyclohexane-1-carboxylic acid

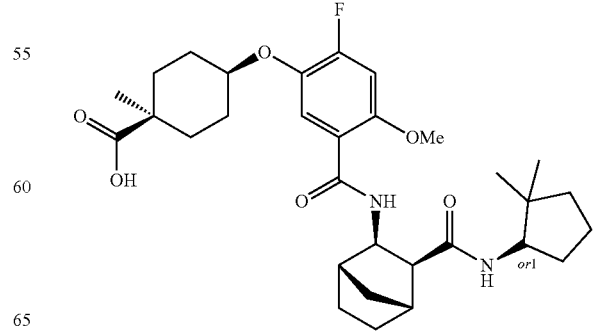

Step A: Intermediate 577: Methyl (1S,2S,3R,4R)-3-(4-fluoro-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylate

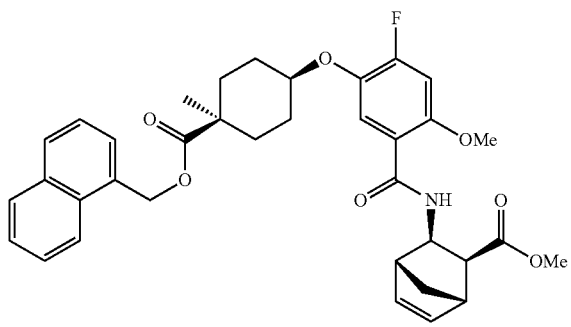 [SMILES: COC(=O)[C@@H]1[C@H](NC(=O)c2cc(O[C@H]3CC[C@@](C)(C(=O)OCc4cccc5ccccc45)CC3)c(F)cc2OC)[C@H]2C=C[C@@H]1C2]

The titled compound was prepared analogous to Example 502 Step A, Intermediate 13 instead of Intermediate 70, and using methyl (1S,2S,3R,4R)-3-aminobicyclo[2.2.1]hept-5-ene-2-carboxylate hydrochloride instead of methyl (1R,2S,3R,4S)-3-aminobicyclo[2.2.1]hept-5-ene-2-carboxylate hydrochloride. MS (ESI) m/z 616.6 [M+H]⁺.

Step B: Intermediate 578: (1S,2S,3R,4R)-3-(4-Fluoro-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylic acid

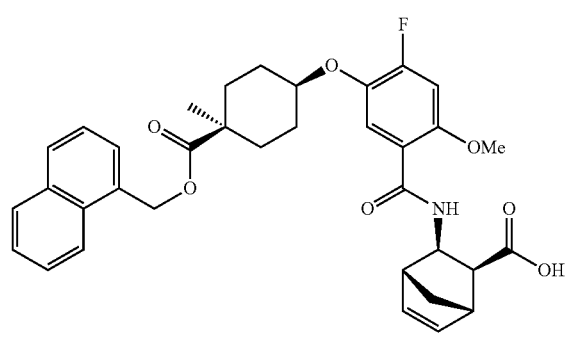

The titled compound was prepared analogous to Example 502 Step B, using Intermediate 577 instead of Intermediate 574. MS (ESI) m/z 602.5 [M+H]⁺.

Step C: Intermediate 579: Naphthalen-1-ylmethyl (1S,4s)-4-(5-(((1R,2R,3S,4S)-3-(((R*)-2,2-dimethylcyclopentyl)carbamoyl)bicyclo[2.2.1]hept-5-en-2-yl)carbamoyl)-2-fluoro-4-methoxyphenoxy)-1-methylcyclohexane-1-carboxylate (Isomer 1) and Intermediate 580: Naphthalen-1-ylmethyl (1S,4s)-4-(5-(((1R,2R,3S,4S)-3-(((R*)-2,2-dimethylcyclopentyl)carbamoyl)bicyclo[2.2.1]hept-5-en-2-yl)carbamoyl)-2-fluoro-4-methoxyphenoxy)-1-methylcyclohexane-1-carboxylate (Isomer 2)

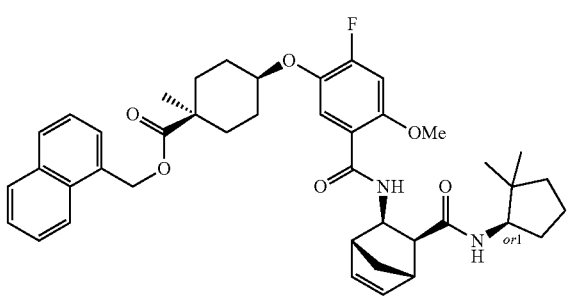

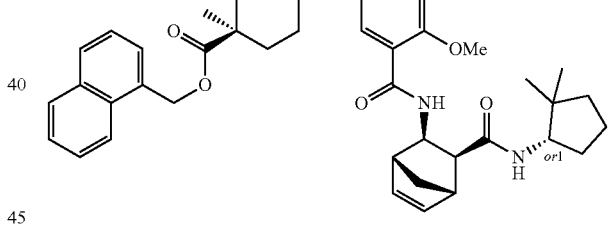

The titled compound was prepared analogous to Example 502 Step C, using Intermediate 578 instead of Intermediate 575 and using rac-2,2-dimethylcyclopentylamine instead of 3,3,3-trifluoro-2,2-dimethylpropylamine hydrochloride. The crude product was purified by flash chromatography using a gradient of 0-40% EtOAc in hexane as mobile phase to give the first eluting compound Isomer 1: Intermediate 579 (20 mg, 52%); MS (ESI) m/z 697.4 [M+H]⁺, and the second eluting compound Isomer 2: Intermediate 580 (16 mg, 41%); MS (ESI) m/z 697.4 [M+H]⁺.

Step D: (1S,4s)-4-(5-(((1S,2R,3S,4R)-3-(((R*)-2,2-Dimethylcyclopentyl)carbamoyl)bicyclo[2.2.1]heptan-2-yl)carbamoyl)-2-fluoro-4-methoxyphenoxy)-1-methylcyclohexane-1-carboxylic acid The titled compound was prepared analogous to Example 331 Step B, using Intermediate 579 instead of Intermediate 507. MS (ESI) m/z 559.3 [M+H]⁺.

Example 504: (1S,4s)-4-(5-(((1S,2R,3S,4R)-3-(((R*)-2,2-Dimethylcyclopentyl)carbamoyl)bicyclo[2.2.1]heptan-2-yl)carbamoyl)-2-fluoro-4-methoxyphenoxy)-1-methylcyclohexane-1-carboxylic acid

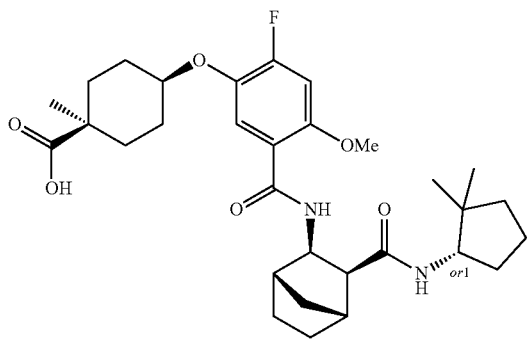 [SMILES: COc1cc(F)c(O[C@H]2CC[C@@](C)(C(=O)O)CC2)cc1C(=O)N[C@@H]1[C@H]2CC[C@H](C2)[C@@H]1C(=O)N[C@H]1CCCC1(C)C]

The titled compound was prepared analogous to Example 331 Step B, using Intermediate 580 instead of Intermediate 507. MS (ESI) m/z 559.3 [M+H]⁺.

Example 505: (1S,3s)-3-(2-Fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)-1-methylcyclobutane-1-carboxylic acid

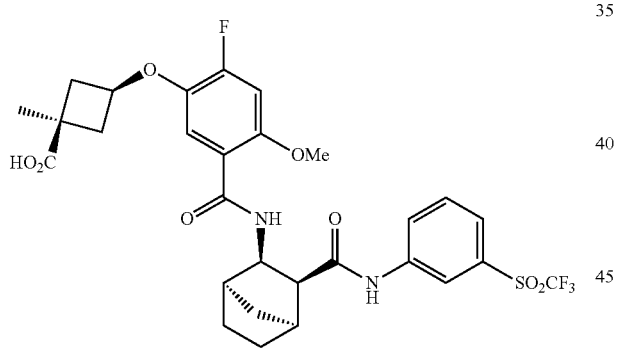

EDC (31 mg, 0.163 mmol), HOAt (22 mg, 0.163 mmol) and TEA (0.070 mL, 0.501 mmol) were added to a solution of Intermediate 326 (56 mg, 0.188 mmol) and Intermediate 232 (50 mg, 0.125 mmol) in DMF (4 mL), then the mixture was stirred at rt for 3 hr. 1 M aq HCl was added to the reaction mixture and the mixture was extracted with EtOAc, then organic layer was concentrated in vacuo. The crude product was purified by flash chromatography using a gradient of 0-10% MeOH in hexane as mobile phase to give the title compound (81 mg, 52%). 1H NMR (400 MHz, DMSO-d6) δ 1.31-1.47 (m, 3H), 1.37 (s, 3H), 1.53-1.75 (m, 3H), 2.26-2.36 (m, 2H), 2.37-2.45 (m, 2H), 2.47-2.55 (m, 1H), 2.56-2.62 (m, 1H), 3.11 (dd, J=11.2, 4.2 Hz, 1H), 3.96 (s, 3H), 4.39-4.47 (m, 1H), 4.78-4.87 (m, 1H), 7.20 (d, J=13.0 Hz, 1H), 7.55 (d, J=10.0 Hz, 1H), 7.76-7.84 (m, 2H), 7.93-7.98 (m, 1H), 8.70-8.73 (m, 1H), 9.76 (d, J=7.3 Hz, 1H), 10.76 (s, 1H). MS (ESI) m/z 643.6 [M+H]⁺.

Example 506: (1R,4r)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methoxycyclohexane-1-carboxylic acid

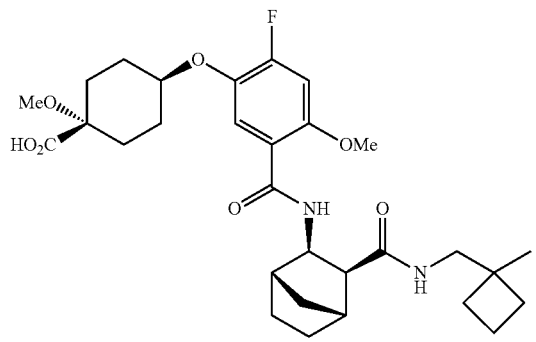 [SMILES: COc1cc(F)c(O[C@H]2CC[C@@](OC)(C(=O)O)CC2)cc1C(=O)N[C@@H]1[C@H]2CC[C@H](C2)[C@@H]1C(=O)NCC1(C)CCC1]

The titled compound was prepared analogous to Example 505, using Intermediate 329 instead of Intermediate 326, and using Intermediate 22 instead of Intermediate 232. MS (ESI) m/z 561.5 [M+H]⁺.

Example 507: (1R,4r)-4-(2-Fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-hydroxycyclohexane-1-carboxylic acid

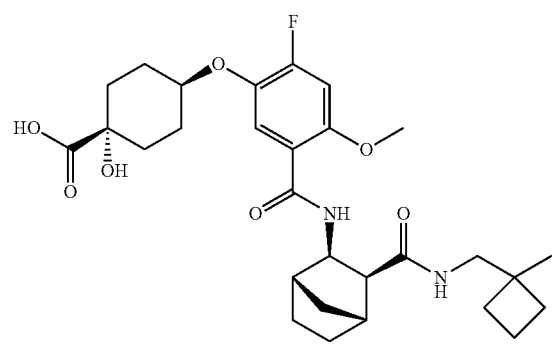 [SMILES: COc1cc(F)c(O[C@H]2CC[C@@](O)(C(=O)O)CC2)cc1C(=O)N[C@@H]1[C@H]2CC[C@H](C2)[C@@H]1C(=O)NCC1(C)CCC1]

Step A: Intermediate 581: tert-Butyl (1R,4r)-4-(2-fluoro-4-methoxy-5-(((1S,2R,3S,4R)-3-(((1-methylcyclobutyl)methyl)carbamoyl)bicyclo[2.2.1]heptan-2-yl)carbamoyl)phenoxy)-1-hydroxycyclohexane-1-carboxylate

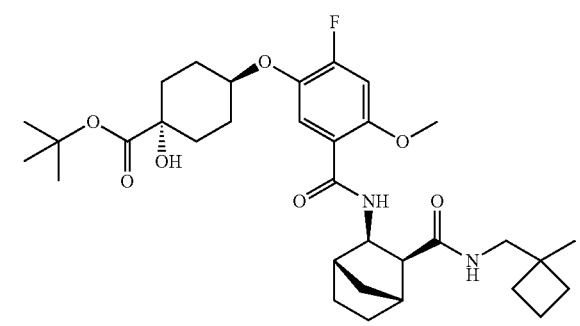 [SMILES: COc1cc(F)c(O[C@H]2CC[C@@](O)(C(=O)OC(C)(C)C)CC2)cc1C(=O)N[C@@H]1[C@H]2CC[C@H](C2)[C@@H]1C(=O)NCC1(C)CCC1]

The titled compound was prepared analogous to Example 331 step A, using Intermediate 337 instead of Intermediate 13, and using Intermediate 22 instead of Intermediate 176. MS (ESI) m/z 603.7 [M+H]⁺.

Step B: (1R,4r)-4-(2-Fluoro-4-methoxy-5-((((1S,2R,3S,4R)-3-(((1-methylcyclobutyl)methyl)carbamoyl)bicyclo[2.2.1]heptan-2-yl)carbamoyl)phenoxy)-1-hydroxycyclohexane-1-carboxylic acid The titled compound was prepared analogous to Example 398 step B, using 1-Intermediate 581 instead of Intermediate 515. MS (ESI) m/z 547.6 [M+H]⁺.

Example 508: (1R,4r)-4-(2-Fluoro-4-methoxy-5-(((1R,2R,3S,4S)-3-((3-((trifluoromethyl)sulfonyl)phenyl)carbamoyl)bicyclo[2.2.1]heptan-2-yl)carbamoyl)phenoxy)-1-methoxycyclohexane-1-carboxylic acid

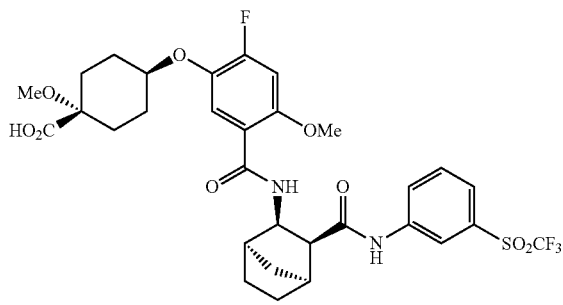

The titled compound was prepared analogous to Example 505, using Intermediate 329 instead of Intermediate 326. MS (ESI) m/z 687.2 [M+H]⁺.

Example 509: (1S,4s)-4-(2-Fluoro-4-methoxy-5-((((1R,2R,3S,4S)-3-((3-(pentafluoro-λ6-sulfaneyl)phenyl)carbamoyl)bicyclo[2.2.1]heptan-2-yl)carbamoyl)phenoxy)cyclohexane-1-carboxylic acid (Isomer 1) and Example 510: (1R,4s)-4-(2-Fluoro-4-methoxy-5-((((1S,2S,3R,4R)-3-((3-(pentafluoro-6-sulfaneyl)phenyl)carbamoyl)bicyclo[2.2.1]heptan-2-yl)carbamoyl)phenoxy)cyclohexane-1-carboxylic acid (Isomer 2)

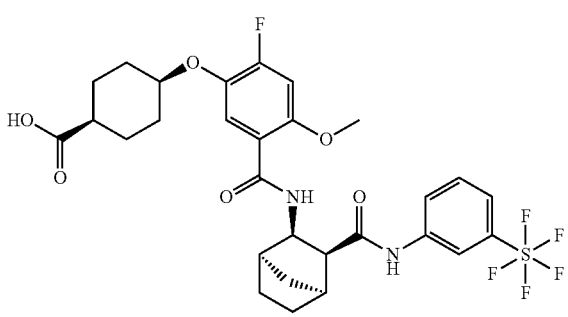

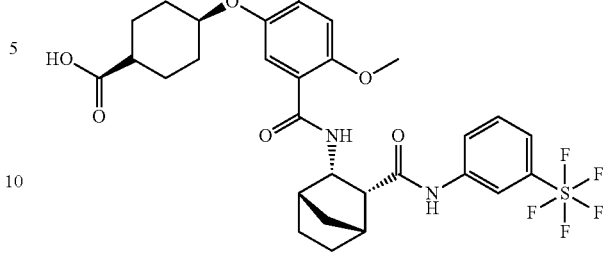

The racemic product obtained in Example 432 (201 mg) was separated by chiral HPLC (column: CHIRALPAK IA (250 mm*30 mm); mobile phase: [Hexane:2-PrOH:AcOH=70/30/0.1]) to give the first eluting compound Isomer 1: Example 509 (86.5 mg, 34%); MS (ESI) m/z 651.2 [M+H]⁺, and the second eluting compound Isomer 2: Example 510 (57 mg, 23%); HRMS (ESI) m/z [M+H]⁺ calcd for C29H33F6N2O6S: 651.1958 found: 651.1940.

Example 511: (1S,2S,3R,4R)-3-(5-(((1s,4S)-4-Carbamoylcyclohexyl)oxy)-4-fluoro-2-methoxybenzamido)-N-(3-(pentafluoro-λ6-sulfaneyl)phenyl)bicyclo[2.2.1]heptane-2-carboxamide

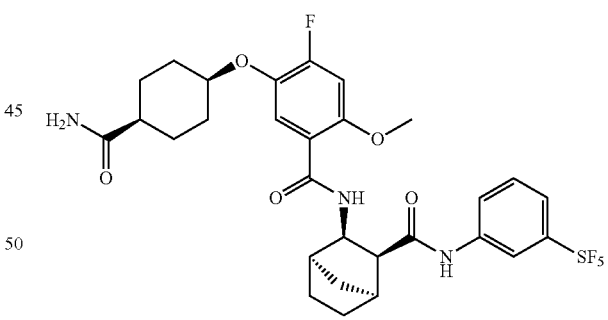

The titled compound was prepared analogous to Example 418 step A, using Example 510 instead of Example 1. 1H NMR (400 MHz, DMSO-d6) δ 1.30-1.91 (m, 14H), 2.11-2.22 (m, 1H), 2.45-2.52 (m, 1H), 2.55-2.60 (m, 1H), 3.09 (dd, J=10.9, 4.2 Hz, 1H), 3.96 (s, 3H), 4.37-4.47 (m, 2H), 6.70 (br s, 1H), 7.13-7.25 (m, 2H), 7.52-7.61 (m, 2H), 7.65-7.72 (m, 2H), 8.44-8.48 (m, 1H), 9.77 (d, J=7.3 Hz, 1H), 10.56 (s, 1H). MS (ESI) m/z 650.6 [M+H]⁺.

Example 512: (1R,4s)-4-(2-Fluoro-4-methoxy-5-(((3aR*,4S*,5S*,6aS*)-5-((3-((trifluoromethyl)sulfonyl)phenyl)carbamoyl)tetrahydro-4H-cyclopenta[d][1,3]dioxol-4-yl)carbamoyl)phenoxy)-1-methylcyclohexane-1-carboxylic acid and Example 513: (1R,4s)-4-(2-fluoro-4-methoxy-5-(((3aR*,4S*,5S*,6aS*)-5-((3-((trifluoromethyl)sulfonyl)phenyl)carbamoyl)tetrahydro-4H-cyclopenta[d][1,3]dioxol-4-yl)carbamoyl)phenoxy)-1-methylcyclohexane-1-carboxylic acid Example 514: (1R,4s)-4-(5-(((3R*,4S*)-1-Acetyl-3-((3-((trifluoromethyl)sulfonyl)phenyl)carbamoyl)piperidin-4-yl)carbamoyl)-2-fluoro-4-methoxyphenoxy)-1-methylcyclohexane-1-carboxylic acid (Isomer 1) and Example 515: (1R,4s)-4-(5-(((3R*,4S*)-1-acetyl-3-((3-((trifluoromethyl)sulfonyl)phenyl)carbamoyl)piperidin-4-yl)carbamoyl)-2-fluoro-4-methoxyphenoxy)-1-methylcyclohexane-1-carboxylic acid (Isomer 2)

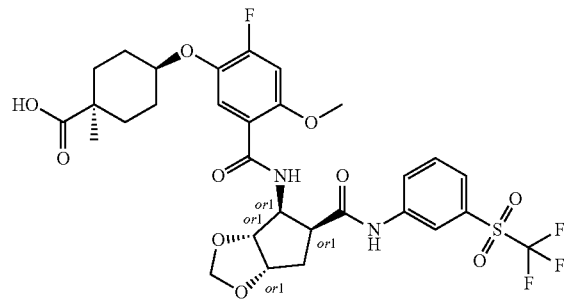

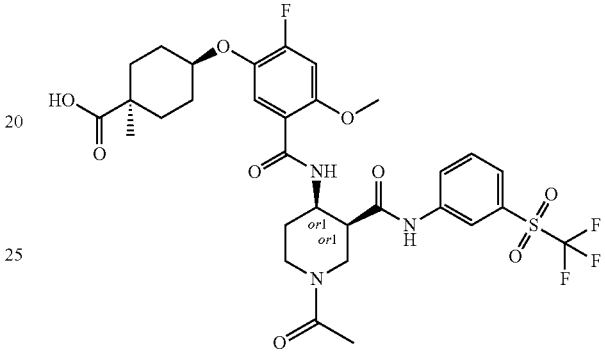

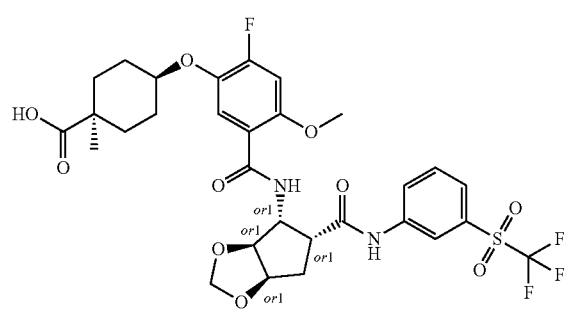

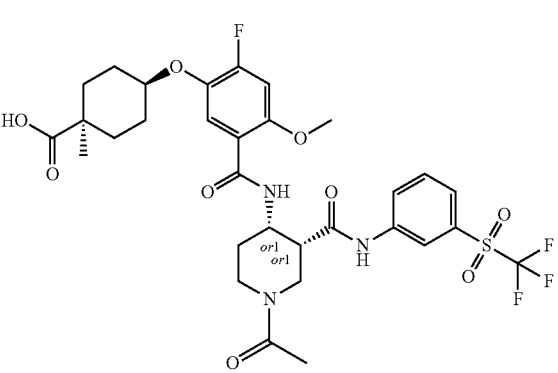

The racemic product obtained in Example 395 (39 mg) was separated by chiral HPLC (column: CHIRALPAK IA (250 mm*30 mm); mobile phase: [Hexane:EtOH:AcOH=30/70/0.1]) to give the first eluting compound Isomer 1: Example 512 (18.4 mg, 47%); MS (ESI) m/z 689.6 [M+H]+, and the second eluting compound Isomer 2: Example 513 (17.8 mg, 46%); HRMS (ESI) m/z [M+H]+ calcd for C30H33F4N2O10S: 689.1786 found: 689.1794.

The racemic product obtained in Example 487 (32.3 mg) was separated by chiral HPLC (column: CHIRALPAK IF (250 mm*30 mm); mobile phase: [MTBE/EtOH/AcOH=85/15/0.1]) to give the first eluting compound Isomer 1: Example 514 (16.6 mg, 52%); MS (ESI) m/z 702.6 [M+H]+, and the second eluting compound Isomer 2: Example 515 (15.4 mg, 48%); MS (ESI) m/z 702.2 [M+H]+.

Example 516: (1R,4s)-4-(2-Fluoro-4-methoxy-5-((((1S*,2R*)-2-((3-((trifluoromethyl)sulfonyl)phenyl)carbamoyl)cycloheptyl)carbamoyl)phenoxy)-1-methylcyclohexane-1-carboxylic acid (Isomer 1) and Example 517: (1R,4s)-4-(2-fluoro-4-methoxy-5-((((1S*,2R*)-2-((3-((trifluoromethyl)sulfonyl)phenyl)carbamoyl)cycloheptyl)carbamoyl)phenoxy)-1-methylcyclohexane-1-carboxylic acid (Isomer 2)

Example 518: (1R,4s)-4-(2-Fluoro-4-methoxy-5-(((3S*,4S*)-3-((3-((trifluoromethyl)sulfonyl)phenyl)carbamoyl)tetrahydro-2H-pyran-4-yl)carbamoyl)phenoxy)-1-methylcyclohexane-1-carboxylic acid (Isomer 1) and Example 519: (1R,4s)-4-(2-fluoro-4-methoxy-5-(((3S*,4S*)-3-((3-((trifluoromethyl)sulfonyl)phenyl)carbamoyl)tetrahydro-2H-pyran-4-yl)carbamoyl)phenoxy)-1-methylcyclohexane-1-carboxylic acid (Isomer 1)

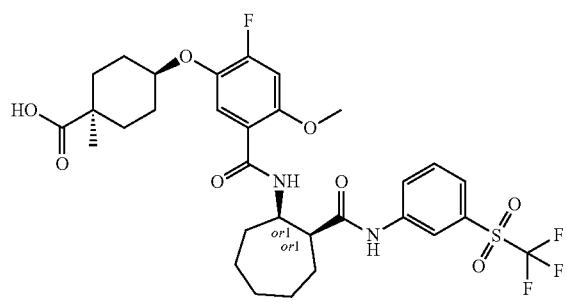

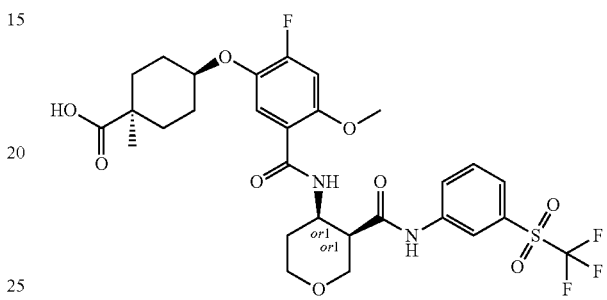

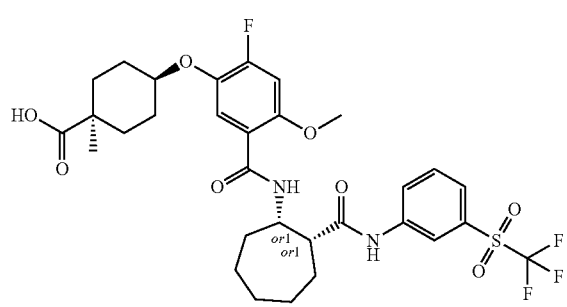

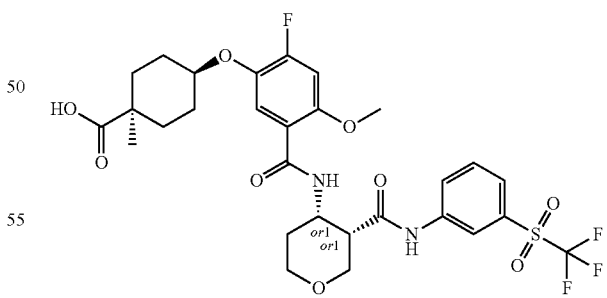

The racemic product obtained in Example 354 (100 mg) was separated by chiral HPLC (column: CHIRALPAK IA (250 mm*30 mm); mobile phase: [Hexane:2-PrOH:AcOH=65/35/0.1]) to give the first eluting compound Isomer 1: Example 516 (46.0 mg, 46%); MS (ESI) m/z 673.6 [M+H]+, and the second eluting compound Isomer 2: Example 517 (44.6 mg, 45%); MS (ESI) m/z 673.2 [M+H]+.

The racemic product obtained in Example 341 (28.5 mg) was separated by chiral HPLC (column: CHIRALPAK IF (250 mm*30 mm); mobile phase: [Hexane:EtOH:AcOH=50/50/0.1]) to give the first eluting compound Isomer 1: Example 518 (9.3 mg, 33%, 100% ee); MS (ESI) m/z 661.2 [M+H]+, and the second eluting compound Isomer 2: Example 519 (13.1 mg, 46%, 100% ee); MS (ESI) m/z 661.2 [M+H]+.

Example 520: (1R,4s)-4-(2-Fluoro-5-((((1S*,2S*,3R*,4R*)-3-((4-fluoro-3-(pentafluoro-λ6-sulfaneyl)phenyl)carbamoyl)bicyclo[2.2.1]heptan-2-yl)carbamoyl)-4-methoxyphenoxy)-1-methylcyclohexane-1-carboxylic acid (Isomer 1) and Example 521: (1R,4s)-4-(2-fluoro-5-((((1S*,2S*,3R*,4R*)-3-((4-fluoro-3-(pentafluoro-λ6-sulfaneyl)phenyl)carbamoyl)bicyclo[2.2.1]heptan-2-yl)carbamoyl)-4-methoxyphenoxy)-1-methylcyclohexane-1-carboxylic acid (Isomer 2)

Example 522: (1R,4s)-4-(2-Fluoro-4-methoxy-5-((((1S*,2R*,4S*)-4-methoxy-2-((3-((trifluoromethyl)sulfonyl)phenyl)carbamoyl)cyclopentyl)carbamoyl)phenoxy)-1-methylcyclohexane-1-carboxylic acid (Isomer 1) and Example 523: (1R,4s)-4-(2-fluoro-4-methoxy-5-((((1S*,2R*,4S*)-4-methoxy-2-((3-((trifluoromethyl)sulfonyl)phenyl)carbamoyl)cyclopentyl)carbamoyl)phenoxy)-1-methylcyclohexane-1-carboxylic acid (Isomer 2)

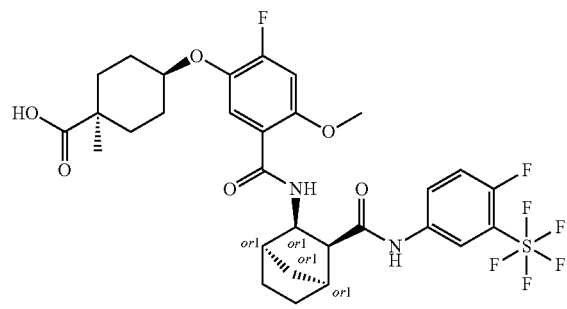

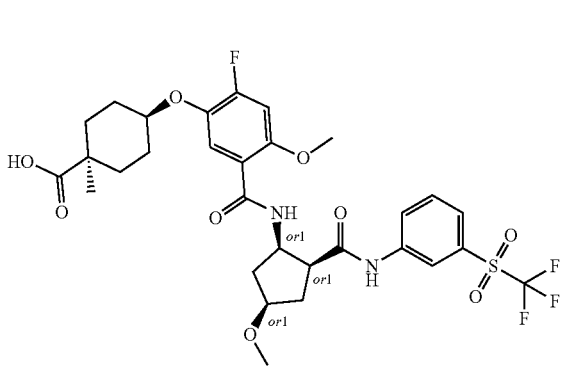

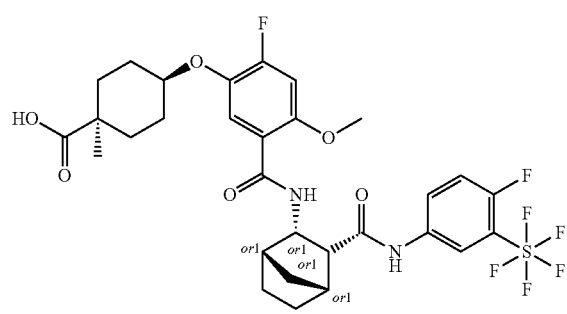

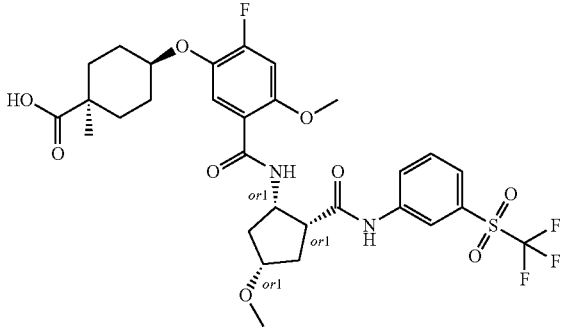

The racemic product obtained in Example 371 (95.2 mg) was separated by chiral HPLC (column: CHIRALPAK ID (250 mm*30 mm); mobile phase: [Hexane:2-PrOH:AcOH=65/35/0.1]) to give the first eluting compound Isomer 1: Example 520 (19.7 mg, 21%, 100% ee); HRMS (ESI) m/z [M+H]+ calcd for C30H34F7N2O6S: 683.2020 found: 683.2022 m/z and the second eluting compound Isomer 2: Example 521 (16.6 mg, 17%, 99.9% ee); HRMS (ESI) m/z [M+H]+ calcd for C30H34F7N2O6S: 683.2020 found: 683.2054.

The racemic product obtained in Example 335 (79.8 mg) was separated by chiral HPLC (column: CHIRALPAK IA (250 mm*30 mm); mobile phase: [Hexane/EtOH/AcOH=60/40/0.1]) to give the first eluting compound Isomer 1: Example 522 (23.9 mg, 30%, 100% ee); MS (ESI) m/z 675.2 [M+H]+, and the second eluting compound Isomer 2: Example 523 (35.3 mg, 44%, 99.8% ee); HRMS (ESI) m/z [M+H]+ calcd for C30H35F4N2O9S: 675.1994 found: 675.2002.

Example 524: (1R,4s)-4-(2-Fluoro-4-methoxy-5-
(((1S*,2R*,4R*)-4-methoxy-2-((3-((trifluoromethyl)
sulfonyl)phenyl)carbamoyl)cyclopentyl)carbamoyl)
phenoxy)-1-methylcyclohexane-1-carboxylic acid
(Isomer 1) and Example 525: (1R,4s)-4-(2-fluoro-4-methoxy-5-
(((1S*,2R*,4R*)-4-methoxy-2-((3-((trifluoromethyl)
sulfonyl)phenyl)carbamoyl)cyclopentyl)carbamoyl)
phenoxy)-1-methylcyclohexane-1-carboxylic acid
(Isomer 2)

Example 526: (1R,4s)-4-(2-Fluoro-4-methoxy-5-
(((1S*,2S*,5S*)-2-methoxy-5-((3-((trifluoromethyl)
sulfonyl)phenyl)carbamoyl)cyclopentyl)carbamoyl)
phenoxy)-1-methylcyclohexane-1-carboxylic acid
(Isomer 1) and Example 527: (1R,4s)-4-(2-fluoro-4-methoxy-5-
(((1S*,2S*,5S*)-2-methoxy-5-((3-((trifluoromethyl)
sulfonyl)phenyl)carbamoyl)cyclopentyl)carbamoyl)
phenoxy)-1-methylcyclohexane-1-carboxylic acid
(Isomer 2)

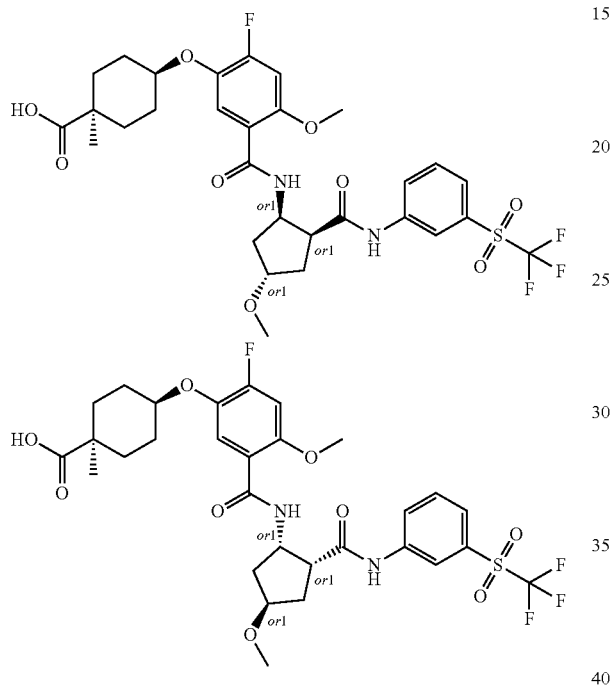

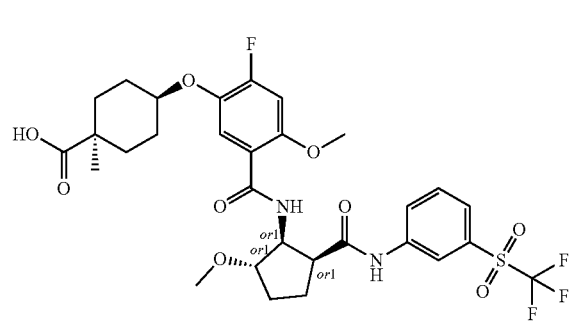

The racemic product obtained in Example 336 (35.3 mg) was separated by chiral HPLC (column: CHIRALPAK IA (250 mm*30 mm); mobile phase: [Hexane/2-PrOH/AcOH=70/30/0.1]) to give the first eluting compound Isomer 1: Example 524 (15 mg, 43%, 100% ee); 1H NMR (400 MHz, CDCl$_3$) δ ppm 1.20-1.41 (m, 4H) 1.42-1.71 (m, 2H) 1.85-2.00 (m, 2H) 2.04-2.21 (m, 2H) 2.22-2.41 (m, 3H) 2.52 (dt, J=14.31, 5.64 Hz, 1H) 3.32 (s, 3H) 3.50-3.59 (m, 1H) 3.70 (s, 3H) 4.01-4.15 (m, 2H) 4.85-5.01 (m, 1H) 6.57 (d, J=12.10 Hz, 1H) 7.41 (t, J=7.98 Hz, 1H) 7.47 (d, J=7.98 Hz, 1H) 7.62 (d, J=7.70 Hz, 1H) 7.68 (d, J=9.63 Hz, 1H) 8.22 (br d, J=7.70 Hz, 1H) 8.47 (s, 1H) 8.94 (br s, 1H); HRMS (ESI) m/z [M+H]$^+$ calcd for C30H35F4N2O9S: 675.1994 found: 675.2026, and the second eluting compound Isomer 2: Example 525 (15 mg, 42%, 99.7% ee); 1H NMR (400 MHz, CDCl$_3$) δ ppm 1.20-1.41 (m, 4H) 1.42-1.71 (m, 2H) 1.85-2.00 (m, 2H) 2.04-2.21 (m, 2H) 2.22-2.41 (m, 3H) 2.52 (dt, J=14.31, 5.64 Hz, 1H) 3.32 (s, 3H) 3.50-3.59 (m, 1H) 3.70 (s, 3H) 4.01-4.15 (m, 2H) 4.85-5.01 (m, 1H) 6.57 (d, J=12.10 Hz, 1H) 7.41 (t, J=7.98 Hz, 1H) 7.47 (d, J=7.98 Hz, 1H) 7.62 (d, J=7.70 Hz, 1H) 7.68 (d, J=9.63 Hz, 1H) 8.22 (br d, J=7.70 Hz, 1H) 8.47 (s, 1H) 8.94 (br s, 1H); MS (ESI) m/z 675.2 [M+H]$^+$.

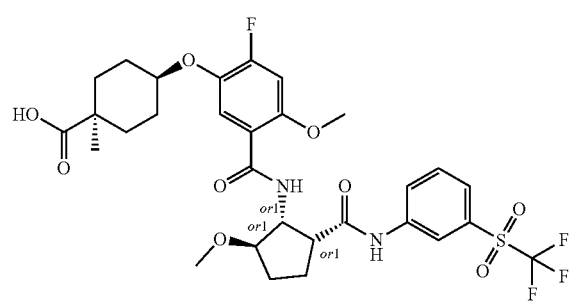

The racemic product obtained in Example 359 (30.3 mg) was separated by chiral HPLC (column: CHIRALPAK IA (250 mm*30 mm); mobile phase: [MTBE/EtOH/AcOH=96/4/0.1]) to give the first eluting compound Isomer 1: Example 526 (12.8 mg, 42%); MS (ESI) m/z 675.3 [M+H]$^+$, and the second eluting compound Isomer 2: Example 527 (5.8 mg, 19%); MS (ESI) m/z 675.2 [M+H]$^+$.

Example 528: (1R,4s)-4-(2-Fluoro-5-((((1S*,2S*,5S*)-2-hydroxy-5-((3-((trifluoromethyl)sulfonyl)phenyl)carbamoyl)cyclopentyl)carbamoyl)-4-methoxyphenoxy)-1-methylcyclohexane-1-carboxylic acid (Isomer 1) and Example 529: (1R,4s)-4-(2-Fluoro-5-((((1S*,2S*,5S*)-2-hydroxy-5-((3-((trifluoromethyl)sulfonyl)phenyl)carbamoyl)cyclopentyl)carbamoyl)-4-methoxyphenoxy)-1-methylcyclohexane-1-carboxylic acid (Isomer 2)

Example 530: (1R,4s)-4-(2-Fluoro-4-methoxy-5-((((1S*,2S*,3R*,4R*)-3-(((1-methylcyclobutyl)methyl)carbamoyl)-7-oxabicyclo[2.2.1]heptan-2-yl)carbamoyl)phenoxy)-1-methylcyclohexane-1-carboxylic acid (Isomer 1) and Example 531: (1R,4s)-4-(2-Fluoro-4-methoxy-5-((((1S*,2S*,3R*,4R*)-3-(((1-methylcyclobutyl)methyl)carbamoyl)-7-oxabicyclo[2.2.1]heptan-2-yl)carbamoyl)phenoxy)-1-methylcyclohexane-1-carboxylic acid (Isomer 2)

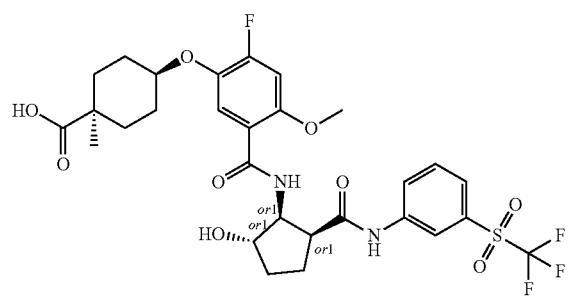

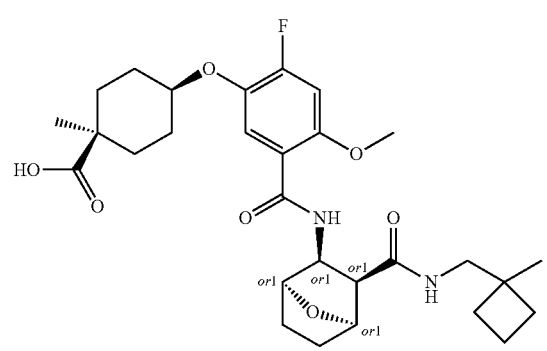

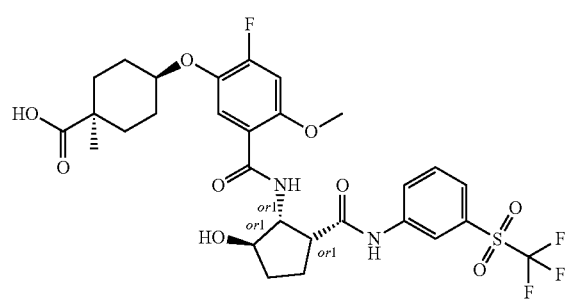

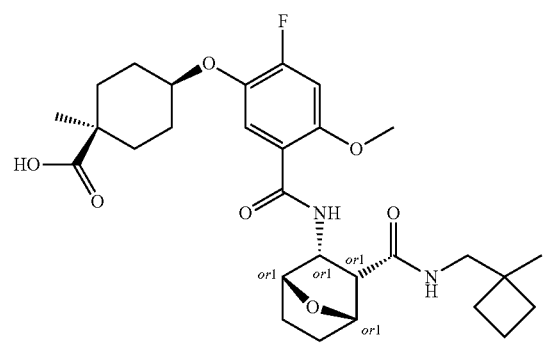

The racemic product obtained in Example 343 (149 mg) was separated by chiral HPLC (column: CHIRALPAK IA (250 mm*30 mm); mobile phase: [MTBE/EtOH/AcOH=96/4/0.1]) to give the first eluting compound Isomer 1: Example 528 (52.8 mg, 36%, 100% ee); MS (ESI) m/z 661.3 [M+H]⁺, and the second eluting compound Isomer 2: Example 529 (53.4 mg, 36%, 100% ee); MS (ESI) m/z 661.3 [M+H]⁺.

The racemic product obtained in Example 331 (170 mg) was separated by chiral HPLC (column: CHIRALPAK IC (250 mm*30 mm); mobile phase: [Hexane/2-PrOH/EtOH/AcOH=60/20/20/0.5]) to give the first eluting compound Isomer 1: Example 530 (74 mg, 44%); MS (ESI) m/z 547.3 [M+H]⁺, and the second eluting compound Isomer 2: Example 531 (72 mg, 42%); MS (ESI) m/z 547.3 [M+H]⁺.

Example 532: (1R,4s)-4-(2-Fluoro-4-methoxy-5-(((1S*,2S*,3R*,4R*)-3-(((1-methylcyclobutyl)methyl)carbamoyl)-7-oxabicyclo[2.2.1]heptan-2-yl)carbamoyl)phenoxy)-1-(hydroxymethyl)cyclohexane-1-carboxylic acid (Isomer 1) and Example 533: (1R,4s)-4-(2-Fluoro-4-methoxy-5-(((1S*,2S*,3R*,4R*)-3-(((1-methylcyclobutyl)methyl)carbamoyl)-7-oxabicyclo[2.2.1]heptan-2-yl)carbamoyl)phenoxy)-1-(hydroxymethyl)cyclohexane-1-carboxylic acid (Isomer 2)

Example 534: (1R,4s)-4-(2-Cyano-4-methoxy-5-(((1S*,2S*,3R*,4R*)-3-(((1-methylcyclobutyl)methyl)carbamoyl)-7-oxabicyclo[2.2.1]heptan-2-yl)carbamoyl)phenoxy)-1-methylcyclohexane-1-carboxylic acid (Isomer 1) and Example 535: (1R,4s)-4-(2-Cyano-4-methoxy-5-(((1S*,2S*,3R*,4R*)-3-(((1-methylcyclobutyl)methyl)carbamoyl)-7-oxabicyclo[2.2.1]heptan-2-yl)carbamoyl)phenoxy)-1-methylcyclohexane-1-carboxylic acid (Isomer 2)

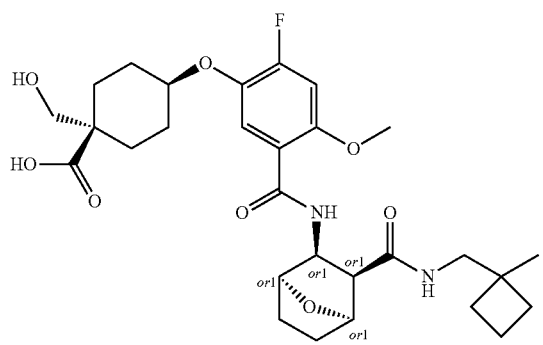

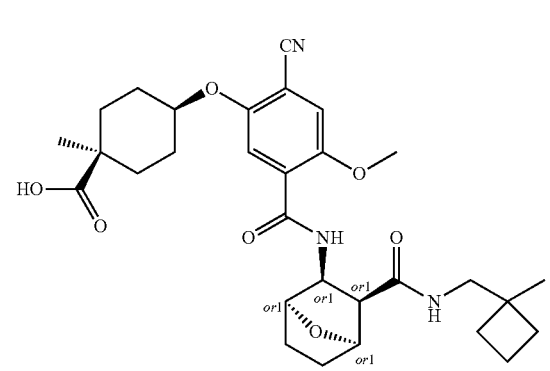

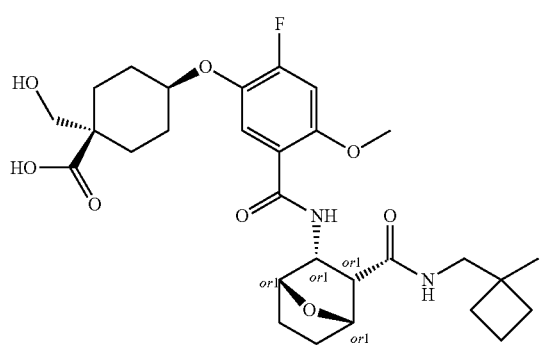

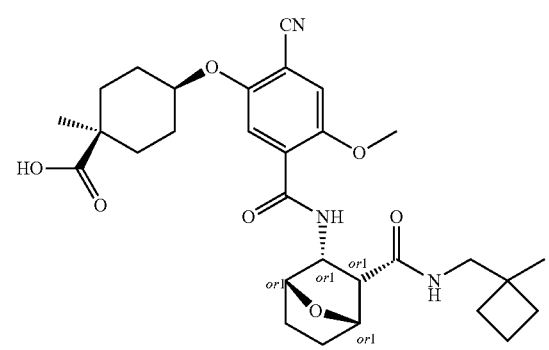

The racemic product obtained in Example 332 (85 mg) was separated by chiral HPLC (column: CHIRALPAK IB N (250 mm*30 mm); mobile phase: [Hexane/2-PrOH/AcOH=50/50/0.1]) to give the first eluting compound Isomer 1: Example 532 (16 mg, 19%); MS (ESI) m/z 563.2 [M+H]$^+$, and the second eluting compound Isomer 2: Example 533 (16 mg, 19%); MS (ESI) m/z 563.2 [M+H]$^+$.

The racemic product obtained in Example 333 (65 mg) was separated by chiral HPLC (column: CHIRALPAK IB N (250 mm*30 mm); mobile phase: [Hexane/EtOH/AcOH=50/50/0.1]) to give the first eluting compound Isomer 1: Example 534 (31 mg, 48%); HRMS (ESI) m/z [M+H]$^+$ calcd for C30H40N3O7: 554.2860 found: 554.2870, and the second eluting compound Isomer 2: Example 535 (31 mg, 48%); MS (ESI) m/z 554.3 [M+H]$^+$.

673

Example 536: (1R,4s)-4-(2-Cyano-4-methoxy-5-(((1S*,2S*,3R*,4R*)-3-(((1-methylcyclobutyl)methyl)carbamoyl)-7-(3,3,3-trifluoropropyl)-7-azabicyclo[2.2.1]heptan-2-yl)carbamoyl)phenoxy)-1-methylcyclohexane-1-carboxylic acid (Isomer 1) and Example 537: (1R,4s)-4-(2-Cyano-4-methoxy-5-(((1S*,2S*,3R*,4R*)-3-(((1-methylcyclobutyl)methyl)carbamoyl)-7-(3,3,3-trifluoropropyl)-7-azabicyclo[2.2.1]heptan-2-yl)carbamoyl)phenoxy)-1-methylcyclohexane-1-carboxylic acid (Isomer 2)

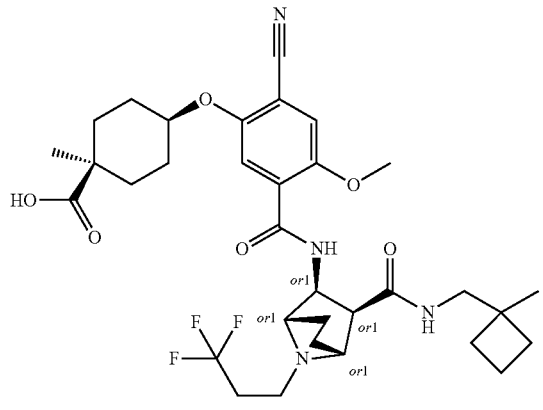

674

Step A: Intermediate 582: ((1R,4s)-4-(5-(((1S*,2S*,3R*,4R*)-7-(tert-Butoxycarbonyl)-3-(((1-methylcyclobutyl)methyl)carbamoyl)-7-azabicyclo[2.2.1]heptan-2-yl)carbamoyl)-2-cyano-4-methoxyphenoxy)-1-methylcyclohexane-1-carboxylic acid (Isomer 1) and Intermediate 583: (1R,4s)-4-(5-(((1S*,2S*,3R*,4R*)-7-(tert-Butoxycarbonyl)-3-(((1-methylcyclobutyl)methyl)carbamoyl)-7-azabicyclo[2.2.1]heptan-2-yl)carbamoyl)-2-cyano-4-methoxyphenoxy)-1-methylcyclohexane-1-carboxylic acid (Isomer 2)

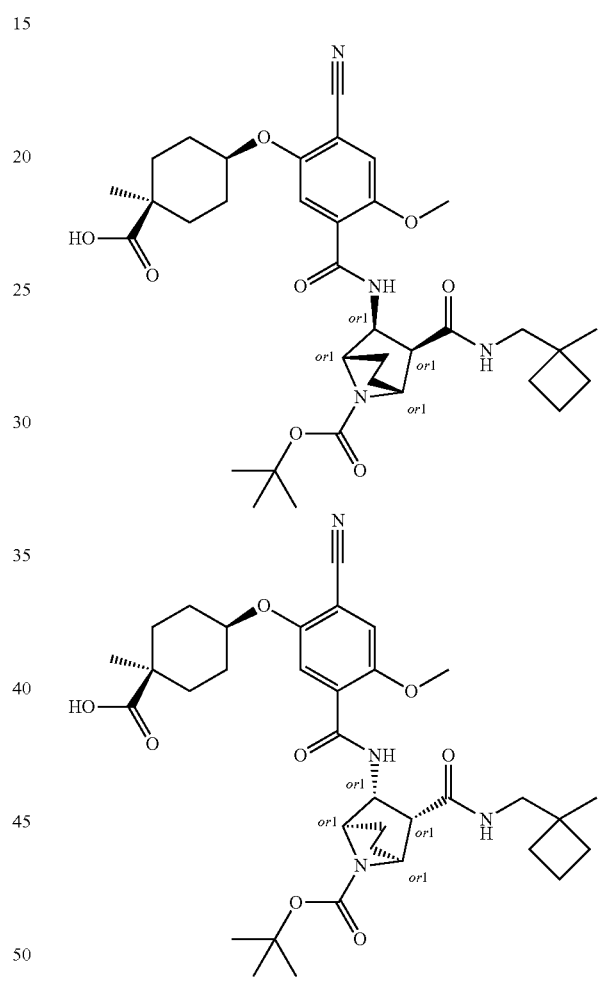

The racemic product obtained in Example 334 (145 mg) was separated by chiral HPLC (column: CHIRALPAK IC (250 mm*30 mm); mobile phase: [Hexane/EtOH/AcOH=75/25/0.5]) to give the first eluting compound Isomer 1: Intermediate 582 (74 mg, 50%); MS (ESI) m/z 653.4 [M+H]$^+$, and the second eluting compound Isomer 2: Intermediate 583 (70 mg, 48%); MS (ESI) m/z 653.3 [M+H]$^+$.

Step B: (1R,4s)-4-(2-Cyano-4-methoxy-5-(((1S*,2S*,3R*,4R*)-3-(((1-methylcyclobutyl)methyl)carbamoyl)-7-(3,3,3-trifluoropropyl)-7-azabicyclo[2.2.1]heptan-2-yl)carbamoyl)phenoxy)-1-methylcyclohexane-1-carboxylic acid A solution of Intermediate 582 (68 mg, 0.104 mmol) in 4 M HCl in cyclopentyl methyl ether (0.5 mL) was stirred at

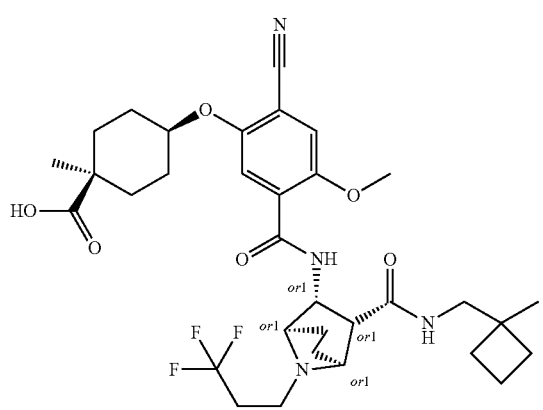

rt for 1 h and the reaction mixture was concentrated in vacuo to give the resulting amine hydrochloride (62 mg, 100%).

NaBH$_4$ (32 mg, 0.15 mmol) was added to a solution of the resulting amine hydrochloride (30 mg, 0.051 mmol), DIPEA (7 mg, 0.056 mmol) and 3,3,3-trifluoropropanal (57 mg, 0.51 mmol) in CHCl$_3$ (1 mL) and the reaction mixture was stirred at rt for 20 min. Aq citric acid (10%) was added to the reaction mixture and the mixture was extracted with CHCl$_3$, then the organic layer was concentrated in vacuo. The crude product was purified by flash chromatography using a gradient of 0-7% MeOH in CHCl$_3$ as mobile phase to give the title compound, Example 536 (31 mg, 94%). HRMS (ESI) m/z [M+H]$^+$ calcd for C33H44F3N4O6: 649.3208 found: 649.3186. Step B was repeated with Intermediate 583 instead of Intermediate 582 to give the title compound, Example 537 MS (ESI) m/z 649.3 [M+H]$^+$ Example 538: (1R,4s)-4-(2-Cyano-4-methoxy-5-(((2S*,3R*)-3-(((1-methylcyclobutyl)methyl)carbamoyl)bicyclo[2.2.2]octan-2-yl)carbamoyl)phenoxy)-1-methylcyclohexane-1-carboxylic acid (Isomer 1) and Example 539: (1R,4s)-4-(2-Cyano-4-methoxy-5-(((2S*,3R*)-3-(((1-methylcyclobutyl)methyl)carbamoyl)bicyclo[2.2.2]octan-2-yl)carbamoyl)phenoxy)-1-methylcyclohexane-1-carboxylic acid (Isomer 2)

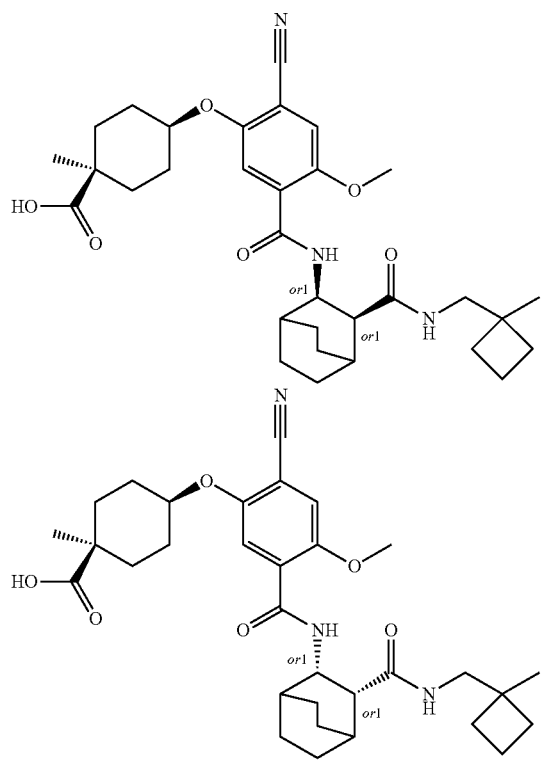

The racemic product obtained in Example 468 (260 mg) was separated by chiral HPLC (column: CHIRALPAK IA (250 mm*30 mm); mobile phase: [MTBE/EtOH/AcOH=95/5/0.1]) to give the first eluting compound Isomer 1: Example 538 (114 mg, 41%); HRMS (ESI) m/z [M+H]$^+$ calcd for C32H44N3O6: 566.3224 found: 566.3220, and the second eluting compound Isomer 2: Example 539 (114 mg, 41%); MS (ESI) m/z 566.4 [M+H]$^+$.

Example 540: (1R,4s)-4-(2-Cyano-4-methoxy-5-((((1R*,2S*,3R*,4S*)-3-(((1-methylcyclobutyl)methyl)carbamoyl)bicyclo[2.2.2]oct-5-en-2-yl)carbamoyl)phenoxy)-1-methylcyclohexane-1-carboxylic acid (Isomer 1) and Example 541: (1R,4s)-4-(2-Cyano-4-methoxy-5-((((1R*,2S*,3R*,4S*)-3-(((1-methylcyclobutyl)methyl)carbamoyl)bicyclo[2.2.2]oct-5-en-2-yl)carbamoyl)phenoxy)-1-methylcyclohexane-1-carboxylic acid (Isomer 2)

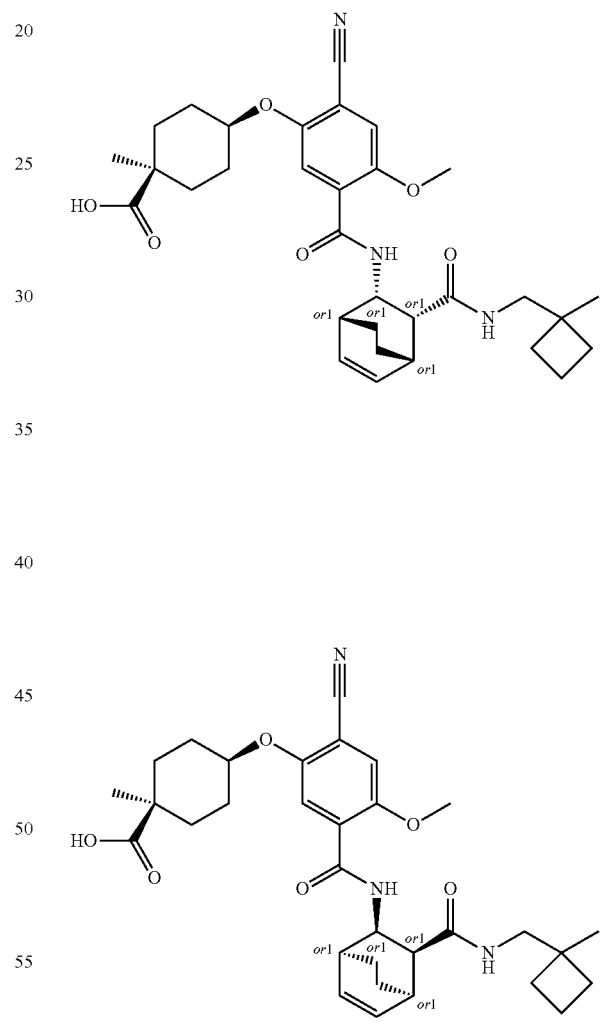

The racemic product obtained in Example 469 (180 mg) was separated by chiral HPLC (column: CHIRALPAK IA (250 mm*30 mm); mobile phase: [MTBE/EtOH/AcOH=95/5/0.1]) to give the first eluting compound Isomer 1: Example 540 (65 mg, 36%); HRMS (ESI) m/z [M+H]$^+$ calcd for C32H42N3O6: 564.3068 found: 564.3074, and the second eluting compound Isomer 2: Example 541 (64 mg, 36%); MS (ESI) m/z 564.4 [M+H]$^+$.

Example 542: (1R,4s)-4-(2-Fluoro-4-methoxy-5-(((2S*,3R*)-3-(((1-methylcyclobutyl)methyl)carbamoyl)bicyclo[2.2.2]octan-2-yl)carbamoyl)phenoxy)-1-methylcyclohexane-1-carboxylic acid (Isomer 2) and Example 543: (1R,4s)-4-(2-Fluoro-4-methoxy-5-(((2S*,3R*)-3-(((1-methylcyclobutyl)methyl)carbamoyl)bicyclo[2.2.2]octan-2-yl)carbamoyl)phenoxy)-1-methylcyclohexane-1-carboxylic acid (Isomer 1)

Example 544: (1R,4s)-4-(2-Fluoro-4-methoxy-5-((((1R*,2S*,3R*,4S*)-3-(((1-methylcyclobutyl)methyl)carbamoyl)bicyclo[2.2.2]oct-5-en-2-yl)carbamoyl)phenoxy)-1-methylcyclohexane-1-carboxylic acid (Isomer 1) and Example 545: (1R,4s)-4-(2-Fluoro-4-methoxy-5-((((1R*,2S*,3R*,4S*)-3-(((1-methylcyclobutyl)methyl)carbamoyl)bicyclo[2.2.2]oct-5-en-2-yl)carbamoyl)phenoxy)-1-methylcyclohexane-1-carboxylic acid (Isomer 2)

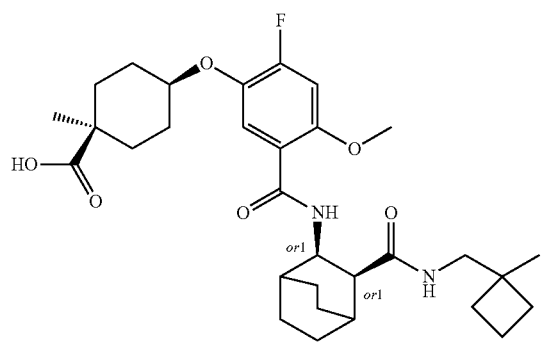

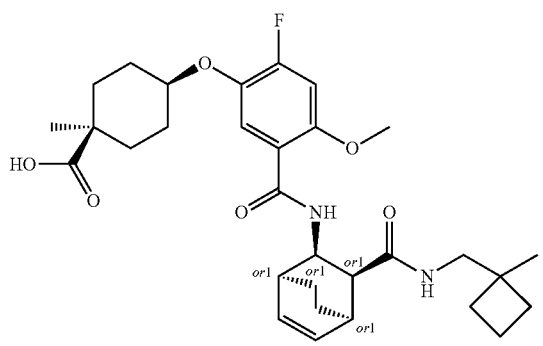

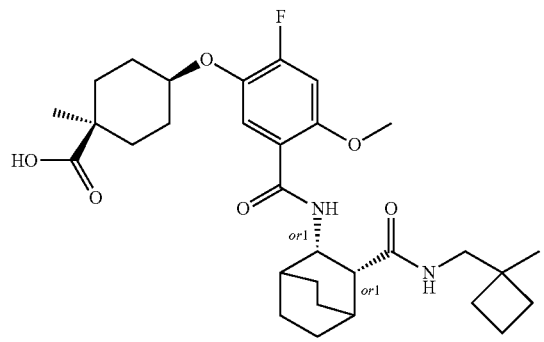

The racemic product obtained in Example 470 (207 mg) was separated by chiral HPLC (column: CHIRALPAK ID (250 mm*30 mm); mobile phase: [Hexane/2-PrOH/AcOH=60/40/0.1]) to give the first eluting compound Isomer 1: Example 542 (85 mg, 41%); HRMS (ESI) m/z [M+H]+ calcd for C31H44FN2O6: 559.3178 found: 559.3176, and the second eluting compound Isomer 2: Example 543 (78 mg, 38%); MS (ESI) m/z 559.4 [M+H]+.

The racemic product obtained in Example 471 (114 mg) was separated by chiral HPLC (column: CHIRALPAK ID (250 mm*30 mm); mobile phase: [Hexane/EtOH/AcOH=60/40/0.1]) to give the first eluting compound Isomer 1: Example 544 (53 mg, 46%); MS (ESI) m/z 557.4 [M+H]+, and the second eluting compound Isomer 2: Example 545 (40 mg, 35%); MS (ESI) m/z 557.4 [M+H]+.

Example 546: (1R,4s)-4-(2-Fluoro-4-methoxy-5-((((1S*,2R*,4R*)-4-methoxy-2-(neopentylcarbamoyl)cyclopentyl)carbamoyl)phenoxy)-1-methylcyclohexane-1-carboxylic acid (Isomer 1) and Example 547: (1R,4s)-4-(2-Fluoro-4-methoxy-5-((((1S*,2R*,4R*)-4-methoxy-2-(neopentylcarbamoyl)cyclopentyl)carbamoyl)phenoxy)-1-methylcyclohexane-1-carboxylic acid (Isomer 2)

Example 548: (1R,4s)-4-(2-Fluoro-4-methoxy-5-((((1S*,2R*,4R*)-4-methoxy-2-(neopentylcarbamoyl)cyclopentyl)carbamoyl)phenoxy)-1-(hydroxymethyl)cyclohexane-1-carboxylic acid (Isomer 1) and Example 549: (1R,4s)-4-(2-Fluoro-4-methoxy-5-((((1S*,2R*,4R*)-4-methoxy-2-(neopentylcarbamoyl)cyclopentyl)carbamoyl)phenoxy)-1-(hydroxymethyl)cyclohexane-1-carboxylic acid (Isomer 2)

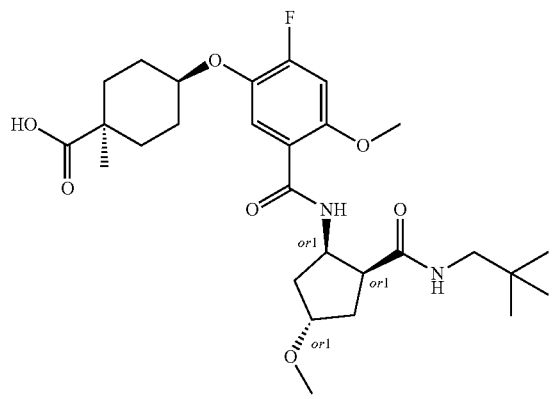

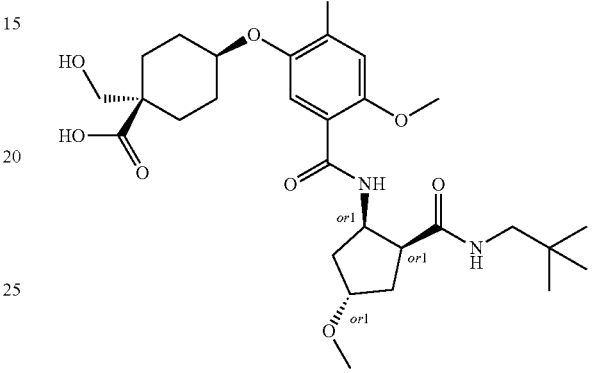

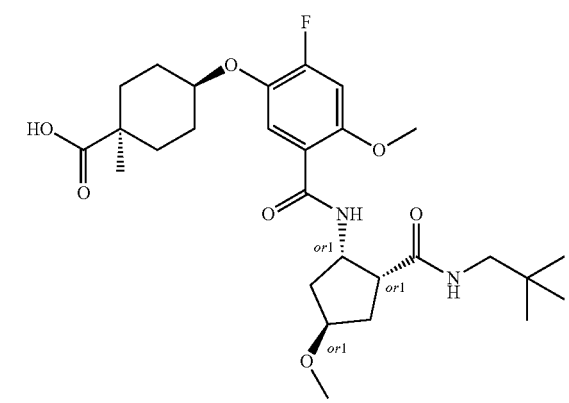

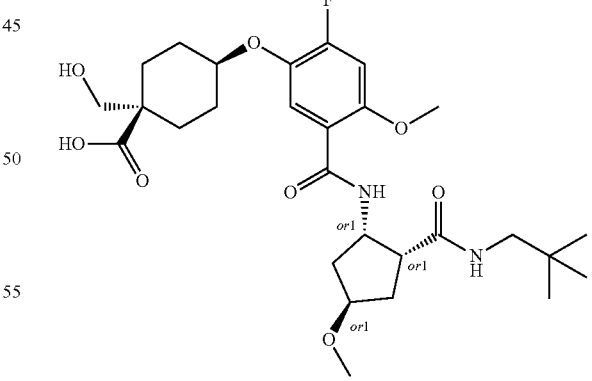

The racemic product obtained in Example 337 (155 mg) was separated by chiral HPLC (column: CHIRALPAK IG (250 mm*30 mm); mobile phase: [Hexane/2-PrOH/AcOH=60/40/0.5]) to give the first eluting compound Isomer 1: Example 546 (62.8 mg, 41%); MS (ESI) m/z 537.4 [M+H]$^+$, and the second eluting compound Isomer 2: Example 547 (62.6 mg, 40%); MS (ESI) m/z 537.4 [M+H]$^+$.

The racemic product obtained in Example 338 (101 mg) was separated by chiral HPLC (column: CHIRALPAK IA (250 mm*30 mm); mobile phase: [MTBE/EtOH/MeOH/AcOH=90/5/5/0.5]) to give the first eluting compound Isomer 1: Example 548 (40 mg, 40%); MS (ESI) m/z 553.4 [M+H]$^+$, and the second eluting compound Isomer 2: Example 549 (40 mg, 40%); MS (ESI) m/z 553.4 [M+H]$^+$.

Example 550: (1R,4s)-4-(2-Fluoro-4-methoxy-5-((((1S*,2R*,4R*)-4-methoxy-2-(((1-methylcyclobutyl)methyl)carbamoyl)cyclopentyl)carbamoyl)phenoxy)-1-(hydroxymethyl)cyclohexane-1-carboxylic acid (Isomer 1) and Example 551: (1R,4s)-4-(2-Fluoro-4-methoxy-5-((((1S*,2R*,4R*)-4-methoxy-2-(((1-methylcyclobutyl)methyl)carbamoyl)cyclopentyl)carbamoyl)phenoxy)-1-(hydroxymethyl)cyclohexane-1-carboxylic acid (Isomer 2)

Example 552: 2'-Fluoro-4'-methoxy-5'-((((1R,2R,3S,4S)-3-((3-(((trifluoromethyl)sulfonyl)phenyl)carbamoyl)bicyclo[2.2.1]hept-5-en-2-yl)carbamoyl)-[1,1'-biphenyl]-4-carboxylic acid (Isomer 1) and Example 553: 2'-Fluoro-4'-methoxy-5'-((((1S,2S,3R,4R)-3-((3-(((trifluoromethyl)sulfonyl)phenyl)carbamoyl)bicyclo[2.2.1]hept-5-en-2-yl)carbamoyl)-[1,1'-biphenyl]-4-carboxylic acid (Isomer 2)

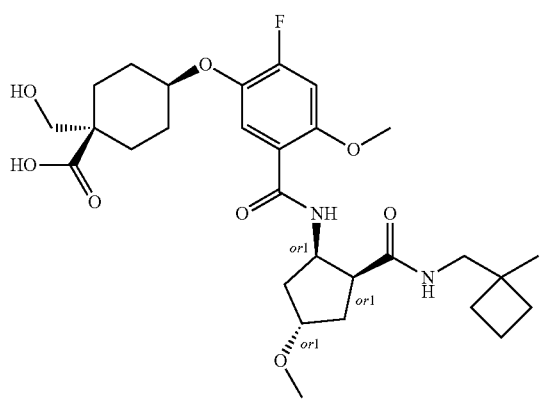

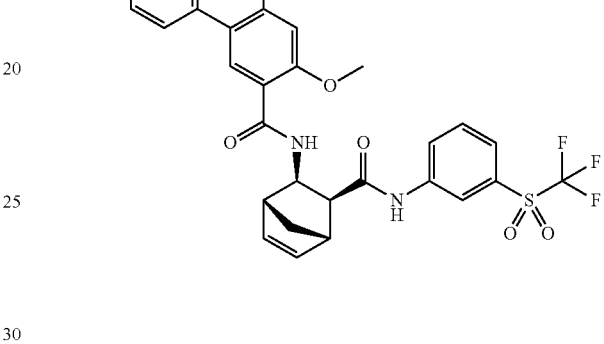

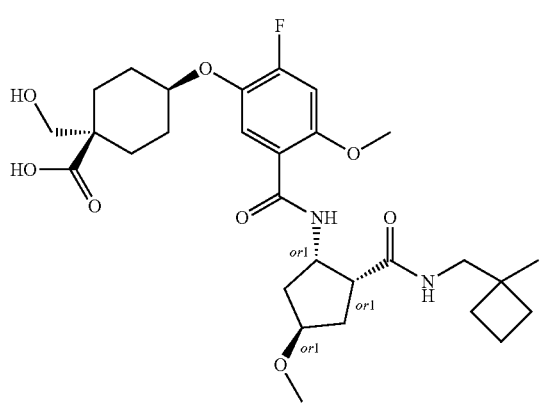

The racemic product obtained in Example 339 (74 mg) was separated by chiral HPLC (column: CHIRALPAK IA (250 mm*30 mm); mobile phase: [MTBE/EtOH/MeOH/AcOH=90/5/5/0.5]) to give the first eluting compound Isomer 1: Example 550 (28 mg, 37%); MS (ESI) m/z [M+H]⁺, and the second eluting compound Isomer 2: Example 551 (26 mg, 35%); MS (ESI) m/z [M+H]⁺.

The racemic product obtained in Example 224 (260 mg) was separated by chiral HPLC (column: CHIRALPAK IF (250 mm*30 mm); mobile phase:

[Hexane/EtOH/MeOH/AcOH=55/25/20/0.1]) to give the first eluting compound Isomer 1: Example 552 (127 mg, 49%, 100% ee); HRMS (ESI) m/z [M+H]⁺ calcd for C30H25F4N2O7S: 633.1312 found: 633.1328, and the second eluting.

compound Isomer 2: Example 553 (125 mg, 48%, 99.8% ee); HRMS (ESI) m/z [M+H]⁺ calcd for C30H25F4N2O7S: 633.1312 found: 633.1352.

Example 554: 2'-Fluoro-4'-methoxy-5'-(((1R,2R,3S,4S)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid (Isomer 1) and Example 555: 2'-Fluoro-4'-methoxy-5'-(((1S,2S,3R,4R)-3-((3-((trifluoromethyl)sulfonyl)phenyl)carbamoyl)bicyclo[2.2.1]hept-5-en-2-yl)carbamoyl)-[1,1'-biphenyl]-3-carboxylic acid (Isomer 2)

Example 556: rel-2'-Fluoro-4-hydroxy-4'-methoxy-5'-(((1R,2S,3R,4S)-3-((3-((trifluoromethyl)sulfonyl)phenyl)carbamoyl)bicyclo[2.2.1]heptan-2-yl)carbamoyl)-[1,1'-biphenyl]-3-carboxylic acid (Isomer 1) and Example 557: rel-2'-Fluoro-4-hydroxy-4'-methoxy-5'-(((1R,2S,3R,4S)-3-((3-((trifluoromethyl)sulfonyl)phenyl)carbamoyl)bicyclo[2.2.1]heptan-2-yl)carbamoyl)-[1,1'-biphenyl]-3-carboxylic acid (Isomer 2)

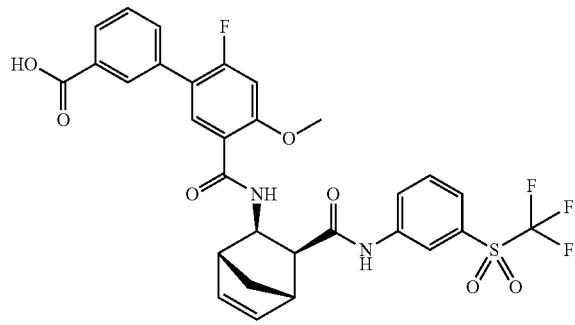

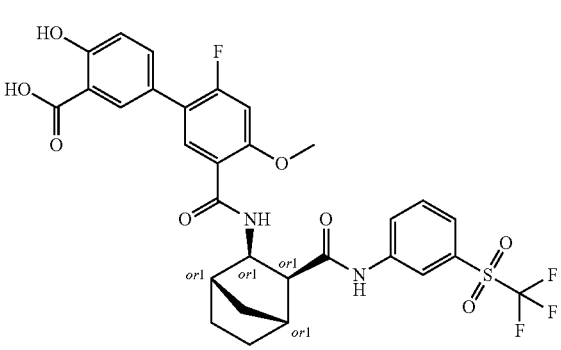

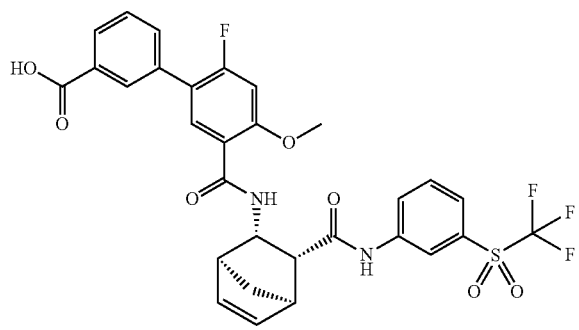

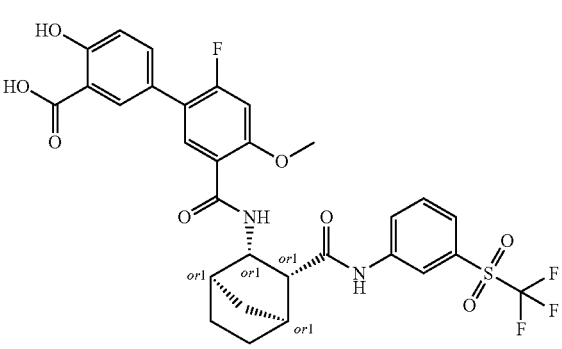

The racemic product obtained in Example 225 (260 mg) was separated by chiral HPLC (column: CHIRALPAK IF (250 mm*30 mm); mobile phase: [Hexane/MeOH/THF/AcOH=80/10/10/0.1]) to give the first eluting compound Isomer 1: Example 554 (130 mg, 50%, 99.8% ee); HRMS (ESI) m/z [M+H]$^+$ calcd for C30H25F4N2O7S: 633.1312 found: 633.1348, and the second eluting compound Isomer 2: Example 555 (130 mg, 50%, 99.8% ee); HRMS (ESI) m/z [M+H]$^+$ calcd for C30H25F4N2O7S: 633.1312 found: 633.1308.

The racemic product obtained in Example 316 (30 mg) was separated by chiral HPLC (column: CHIRALPAK IE (250 mm*30 mm); mobile phase: [Hex/EtOH/THF/TFA=80/10/10/0.1]) to give the first eluting compound Isomer 1: Example 556 (6.1 mg, 20%, 100% ee); MS (APCI) m/z 651.0 [M+H]$^+$, and the second eluting compound Isomer 2: Example 557 (8.3 mg, 28%, 99% ee); MS (APCI) m/z 651.0 [M+H]$^+$.

Example 558: (1R,4s)-4-(2-Fluoro-4-methoxy-5-
(((3S*,4S*)-4-((3-((trifluoromethyl)sulfonyl)phenyl)
carbamoyl)tetrahydro-2H-pyran-3-yl)carbamoyl)
phenoxy)-1-methylcyclohexane-1-carboxylic acid
(Isomer 1) and Example 559: (1R,4s)-4-(2-Fluoro-4-methoxy-5-
(((3S*,4S*)-4-((3-((trifluoromethyl)sulfonyl)phenyl)
carbamoyl)tetrahydro-2H-pyran-3-yl)carbamoyl)
phenoxy)-1-methylcyclohexane-1-carboxylic acid
(Isomer 2)

Example 560: (1R,4s)-4-(2-Fluoro-4-methoxy-5-
(((3S*,4R*)-4-((3-((trifluoromethyl)sulfonyl)phenyl)
carbamoyl)tetrahydrofuran-3-yl)carbamoyl)phe-
noxy)-1-methylcyclohexane-1-carboxylic acid
(Isomer 1) and Example 561: (1R,4s)-4-(2-Fluoro-4-methoxy-5-
(((3S*,4R*)-4-((3-((trifluoromethyl)sulfonyl)phenyl)
carbamoyl)tetrahydrofuran-3-yl)carbamoyl)phe-
noxy)-1-methylcyclohexane-1-carboxylic acid
(Isomer 2)

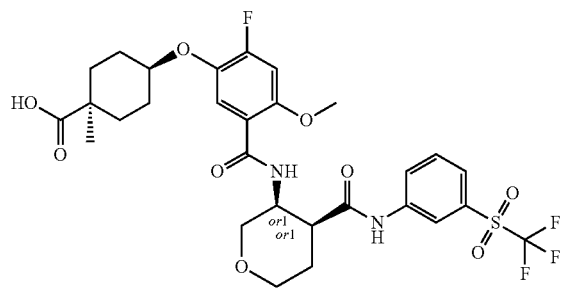

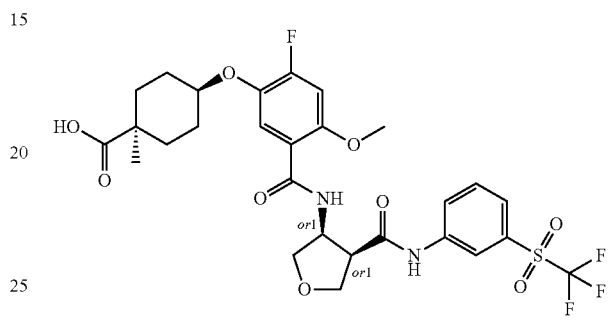

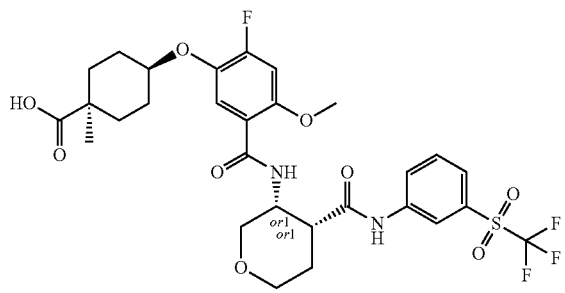

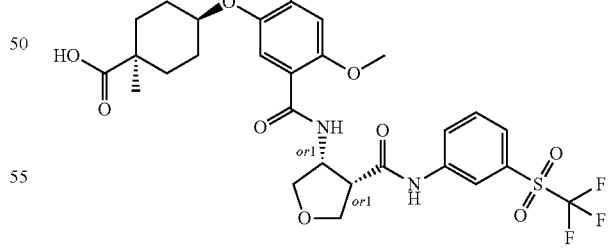

The racemic product obtained in Example 340 (56.4 mg) was separated by chiral HPLC (column: CHIRALPAK ID (250 mm*30 mm); mobile phase: [Hex/2-PrOH/AcOH=65/35/0.5]) to give the first eluting compound Isomer 1: Example 558 (28.6 mg, 50%, 100% ee); MS (ESI) m/z 661.2 [M+H]$^+$, and the second eluting compound Isomer 2: Example 559 (28.0 mg, 50%, 99.7% ee); HRMS (ESI) m/z [M+H]$^+$ calcd for C29H33F4N2O9S: 661.1838 found: 661.1848.

The racemic product obtained in Example 342 (73.4 mg) was separated by chiral HPLC (column: CHIRALPAK IA (250 mm*30 mm); mobile phase: [Hexane/EtOH/AcOH=60/40/0.1]) to give the first eluting Isomer 1: Example 560 (31.5 mg, 43%); MS (ESI) m/z 647.5 [M+H]$^+$, and the second eluting compound Isomer 2: Example 561 (30.6 mg, 42%); HRMS (ESI) m/z [M+H]$^+$ calcd for C28H31F4N2O9S: 647.1680 found: 647.1700.

Example 562: (1R,4s)-4-(5-((((1S*,2R*,3S*,5S*)-2,3-Dihydroxy-5-((3-((trifluoromethyl)sulfonyl)phenyl)carbamoyl)cyclopentyl)carbamoyl)-2-fluoro-4-methoxyphenoxy)-1-methylcyclohexane-1-carboxylic acid (Isomer 1) and Example 563: (1R,4s)-4-(5-((((1S*,2R*,3S*,5S*)-2,3-Dihydroxy-5-((3-((trifluoromethyl)sulfonyl)phenyl)carbamoyl)cyclopentyl)carbamoyl)-2-fluoro-4-methoxyphenoxy)-1-methylcyclohexane-1-carboxylic acid (Isomer 2)

Example 564: (1R,4s)-4-(2-Fluoro-5-(((3S*,4R*)-4-((4-fluoro-3-(pentafluoro-λ6-sulfaneyl)phenyl)carbamoyl)tetrahydrofuran-3-yl)carbamoyl)-4-methoxyphenoxy)-1-methylcyclohexane-1-carboxylic acid (Isomer 1) and Example 565: (1R,4s)-4-(2-Fluoro-5-(((3S*,4R*)-4-((4-fluoro-3-(pentafluoro-λ6-sulfaneyl)phenyl)carbamoyl)tetrahydrofuran-3-yl)carbamoyl)-4-methoxyphenoxy)-1-methylcyclohexane-1-carboxylic acid (Isomer 2)

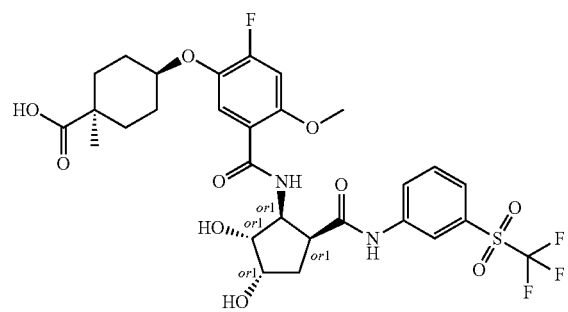

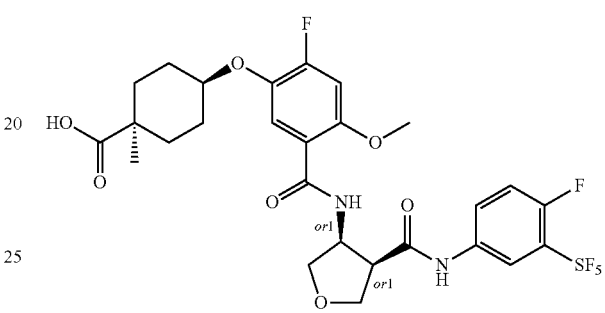

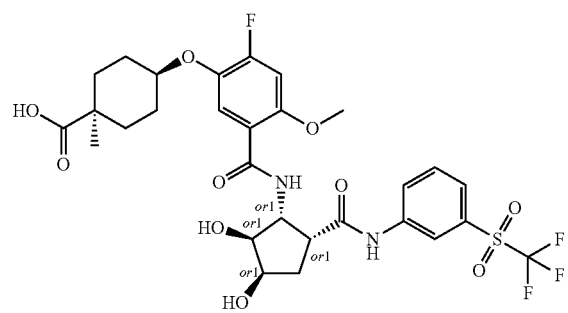

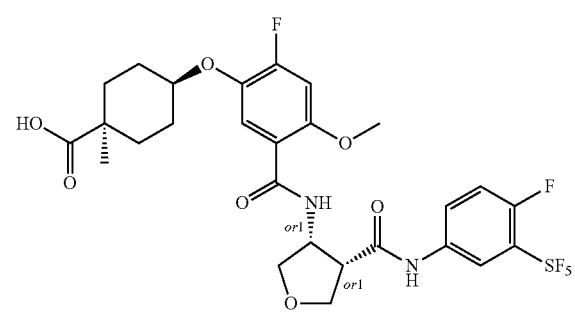

The racemic product obtained in Example 394 (139 mg) was separated by chiral HPLC (column: CHIRALPAK IF (250 mm*30 mm); mobile phase: [Hexane/EtOH/AcOH=60/40/0.1]) to give the first eluting compound Isomer 1: Example 562 (60.2 mg, 43%); MS (ESI) m/z 677.4 [M+H]$^+$, and the second eluting compound Isomer 2: Example 563 (57.0 mg, 41%); MS (ESI) m/z 677.4 [M+H]$^+$.

The racemic product obtained in Example 344 (138 mg) was separated by chiral HPLC (column: CHIRALPAK IF (250 mm*30 mm); mobile phase: [Hexane/EtOH/AcOH=60/40/0.1]) to give the first eluting compound Isomer 1: Example 564 (64.6 mg, 47%); MS (ESI) m/z 659.5 [M+H]$^+$, and the second eluting compound Isomer 2: Example 565 (64.3 mg, 47%); MS (ESI) m/z 659.2 [M+H]$^+$.

Example 566: (1R,4s)-4-(2-Fluoro-4-methoxy-5-(((3S*,4R*)-4-(neopentylcarbamoyl)tetrahydrofuran-3-yl)carbamoyl)phenoxy)-1-methylcyclohexane-1-carboxylic acid (Isomer 1) and Example 567: (1R,4s)-4-(2-Fluoro-4-methoxy-5-(((3S*,4R*)-4-(neopentylcarbamoyl)tetrahydrofuran-3-yl)carbamoyl)phenoxy)-1-methylcyclohexane-1-carboxylic acid (Isomer 2)

Example 568: (1R,4s)-4-(2-Fluoro-4-methoxy-5-(((1S*,2R*)-2-(neopentylcarbamoyl)cyclobutyl)carbamoyl)phenoxy)-1-methylcyclohexane-1-carboxylic acid (Isomer 1) and Example 569: (1R,4s)-4-(2-Fluoro-4-methoxy-5-(((1S*,2R*)-2-(neopentylcarbamoyl)cyclobutyl)carbamoyl)phenoxy)-1-methylcyclohexane-1-carboxylic acid (Isomer 2)

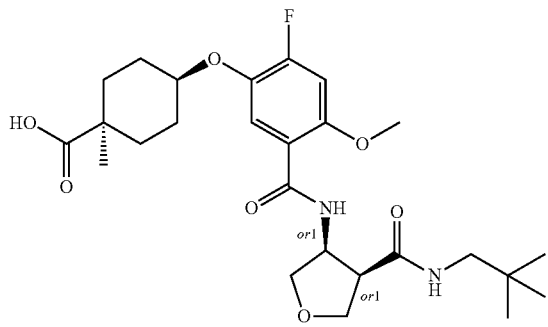

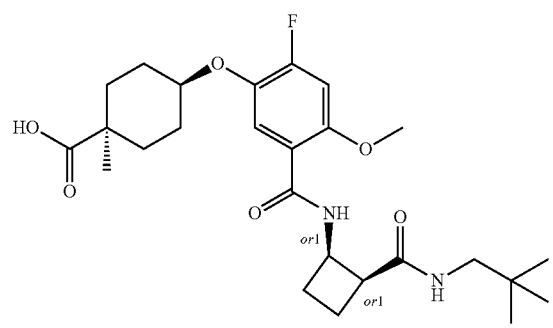

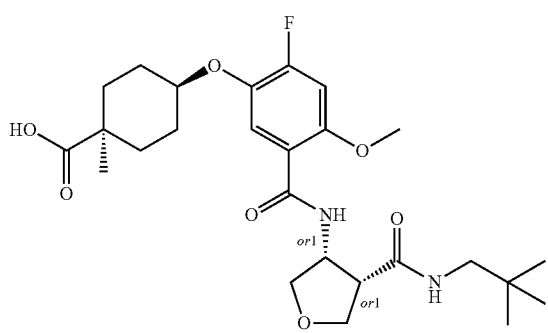

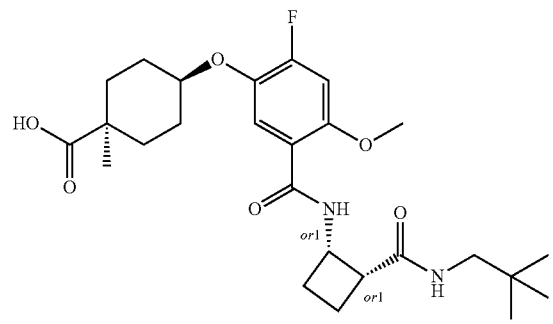

The racemic product obtained in Example 345 (193 mg) was separated by chiral HPLC (column: CHIRALPAK IA (250 mm*30 mm); mobile phase: [Hexane/2-PrOH/EtOH/AcOH=60/20/20/0.1]) to give the first eluting compound Isomer 1: Example 566 (83.1 mg, 43%); MS (ESI) m/z 509.5 [M+H]$^+$, and the second eluting compound Isomer 2: Example 567 (81.5 mg, 42%); MS (ESI) m/z 509.2 [M+H]$^+$.

The racemic product obtained in Example 346 (145 mg) was separated by chiral HPLC (column: CHIRALPAK IA (250 mm*30 mm); mobile phase: [Hexane/2-PrOH/EtOH/AcOH=65/10/25/0.1]) to give the first eluting compound Isomer 1: Example 568 (66.1 mg, 46%); MS (ESI) m/z 493.5 [M+H]$^+$, and the second eluting compound Isomer 2: Example 569 (65.4 mg, 45%); MS (ESI) m/z 493.2 [M+H]$^+$.

Example 570: (1R,4s)-4-(2-Fluoro-5-((((1S*,2R*)-2-((4-fluoro-3-(pentafluoro-λ6-sulfaneyl)phenyl)carbamoyl)cyclobutyl)carbamoyl)-4-methoxyphenoxy)-1-methylcyclohexane-1-carboxylic acid (Isomer 1) and Example 571: (1R,4s)-4-(2-Fluoro-5-((((1S*,2R*)-2-((4-fluoro-3-(pentafluoro-λ6-sulfaneyl)phenyl)carbamoyl)cyclobutyl)carbamoyl)-4-methoxyphenoxy)-1-methylcyclohexane-1-carboxylic acid (Isomer 2)

Example 572: (1R,4s)-4-(2-Cyano-4-methoxy-5-((((1S*,2R*)-2-(((1-methylcyclobutyl)methyl)carbamoyl)cyclobutyl)carbamoyl)phenoxy)-1-methylcyclohexane-1-carboxylic acid (Isomer 1) and Example 573: (1R,4s)-4-(2-Cyano-4-methoxy-5-((((1S*,2R*)-2-(((1-methylcyclobutyl)methyl)carbamoyl)cyclobutyl)carbamoyl)phenoxy)-1-methylcyclohexane-1-carboxylic acid (Isomer 2)

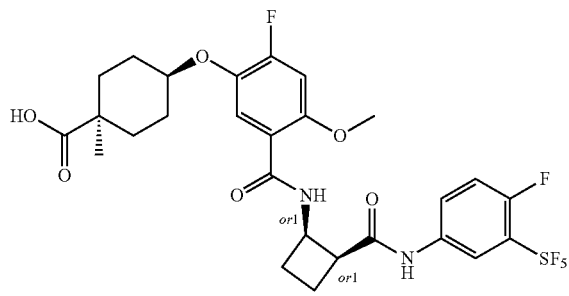

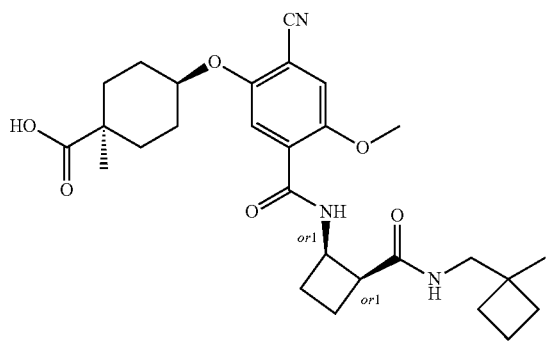

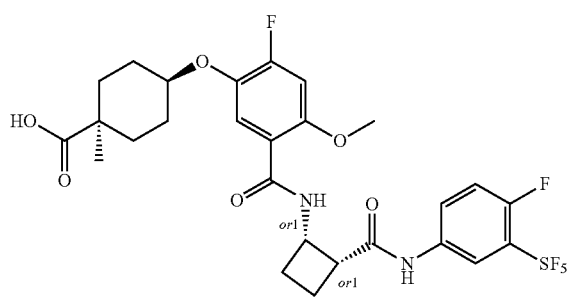

The racemic product obtained in Example 347 (214 mg) was separated by chiral HPLC (column: CHIRALPAK IA (250 mm*30 mm); mobile phase: [Hexane/2-PrOH/EtOH/AcOH=65/10/25/0.1]) to give the first eluting compound Isomer 1: Example 570 (100.6 mg, 47%); MS (ESI) m/z 643.2 [M+H]⁺, and the second eluting compound Isomer 2: Example 571 (106.2 mg, 50%); MS (ESI) m/z 643.2 [M+H]⁺.

The racemic product obtained in Example 348 (145 mg) was separated by chiral HPLC (column: CHIRALPAK IA (250 mm*30 mm); mobile phase: [Hexane/2-PrOH/EtOH/AcOH=65/10/25/0.1]) to give the first eluting compound Isomer 1: Example 572 (66.1 mg, 46%); MS (ESI) m/z 512.2 [M+H]⁺, and the second eluting compound Isomer 2: Example 573 (65.4 mg, 45%); MS (ESI) m/z 512.3 [M+H]⁺.

Example 574: (1R,4s)-4-(2-Fluoro-5-(((3S*,4S*)-4-((4-fluoro-3-(pentafluoro-λ6-sulfaneyl)phenyl)carbamoyl)tetrahydro-2H-pyran-3-yl)carbamoyl)-4-methoxyphenoxy)-1-methylcyclohexane-1-carboxylic acid (Isomer 1) and Example 575: (1R,4s)-4-(2-Fluoro-5-(((3S*,4S*)-4-((4-fluoro-3-(pentafluoro-λ6-sulfaneyl)phenyl)carbamoyl)tetrahydro-2H-pyran-3-yl)carbamoyl)-4-methoxyphenoxy)-1-methylcyclohexane-1-carboxylic acid (Isomer 2)

Example 576: (1R,4s)-4-(2-Fluoro-4-methoxy-5-(((3S*,4R*)-4-(((1-methylcyclobutyl)methyl)carbamoyl)tetrahydrofuran-3-yl)carbamoyl)phenoxy)-1-methylcyclohexane-1-carboxylic acid (Isomer 2) and Example 577: (1R,4s)-4-(2-Fluoro-4-methoxy-5-(((3S*,4R*)-4-(((1-methylcyclobutyl)methyl)carbamoyl)tetrahydrofuran-3-yl)carbamoyl)phenoxy)-1-methylcyclohexane-1-carboxylic acid (Isomer 1)

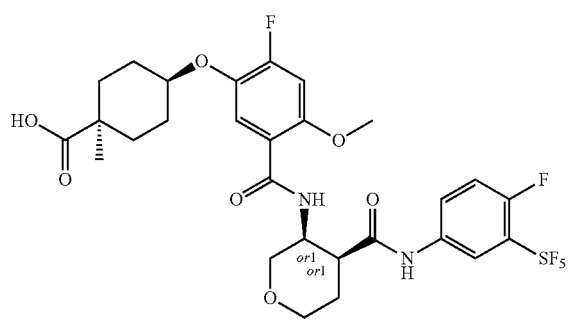

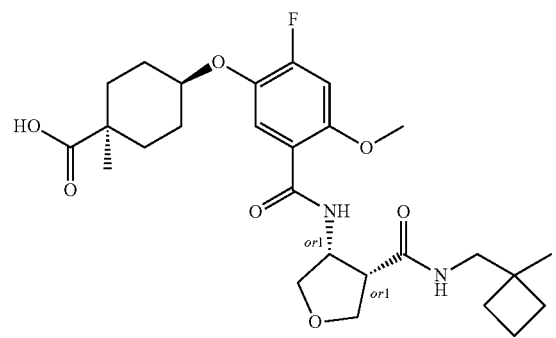

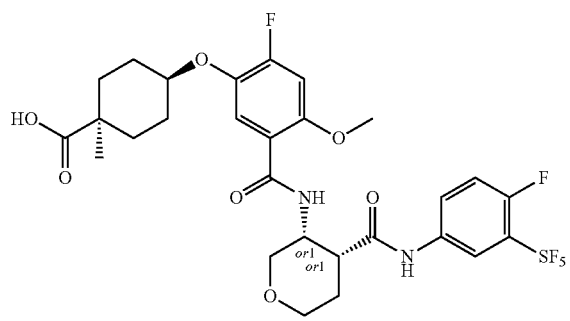

The racemic product obtained in Example 349 (161 mg) was separated by chiral HPLC (column: CHIRALPAK IG (250 mm*30 mm); mobile phase: [Hexane/2-PrOH/AcOH=70/30/0.1] to give the first eluting compound Isomer 1: Example 574 (71.5 mg, 44%); MS (ESI) m/z 673.5 [M+H]+, and the second eluting compound Isomer 2: Example 575 (80.6 mg, 50%); MS (ESI) m/z 673.2 [M+H]+.

The racemic product obtained in Example 350 (170 mg) was separated by chiral HPLC (column: CHIRALPAK IA (250 mm*30 mm); mobile phase: [Hexane/2-PrOH/EtOH/MeOH/AcOH=65/20/15/0.1]) to give the first eluting compound Isomer 1: Example 577 (72.6 mg, 43%, 100% ee); MS (ESI) m/z 521.2 [M+H]+, and the second eluting compound Isomer 2: Example 576 (74.5 mg, 44%, 99.9% ee); MS (ESI) m/z 521.2 [M+H]+.

Example 578: (1R,4s)-4-(2-Fluoro-4-methoxy-5-(((3S*,4R*)-4-(neopentylcarbamoyl)tetrahydrofuran-3-yl)carbamoyl)phenoxy)-1-(hydroxymethyl)cyclohexane-1-carboxylic acid (Isomer 1) and Example 579: (1R,4s)-4-(2-Fluoro-4-methoxy-5-(((3S*,4R*)-4-(neopentylcarbamoyl)tetrahydrofuran-3-yl)carbamoyl)phenoxy)-1-(hydroxymethyl)cyclohexane-1-carboxylic acid (Isomer 2)

Example 580: (1R,4s)-4-(2-Fluoro-4-methoxy-5-(((3S*,4R*)-4-(((1-methylcyclobutyl)methyl)carbamoyl)tetrahydrofuran-3-yl)carbamoyl)phenoxy)-1-(hydroxymethyl)cyclohexane-1-carboxylic acid (Isomer 1) and Example 581: (1R,4s)-4-(2-Fluoro-4-methoxy-5-(((3S*,4R*)-4-(((1-methylcyclobutyl)methyl)carbamoyl)tetrahydrofuran-3-yl)carbamoyl)phenoxy)-1-(hydroxymethyl)cyclohexane-1-carboxylic acid (Isomer 2)

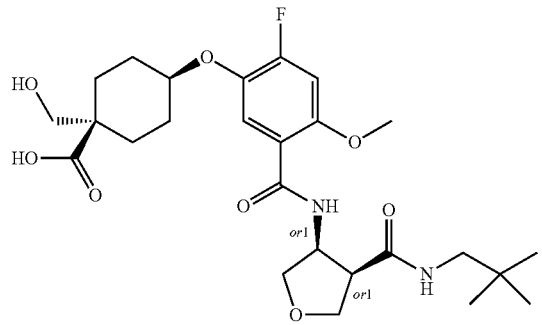

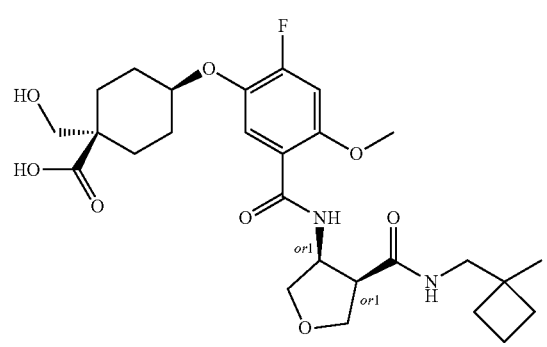

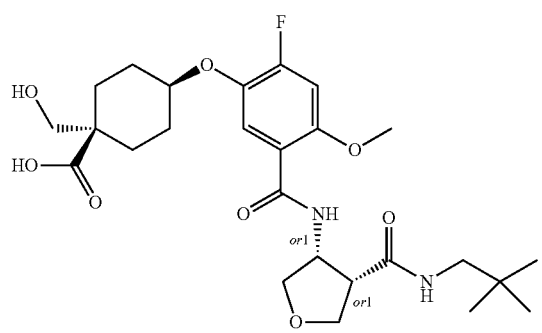

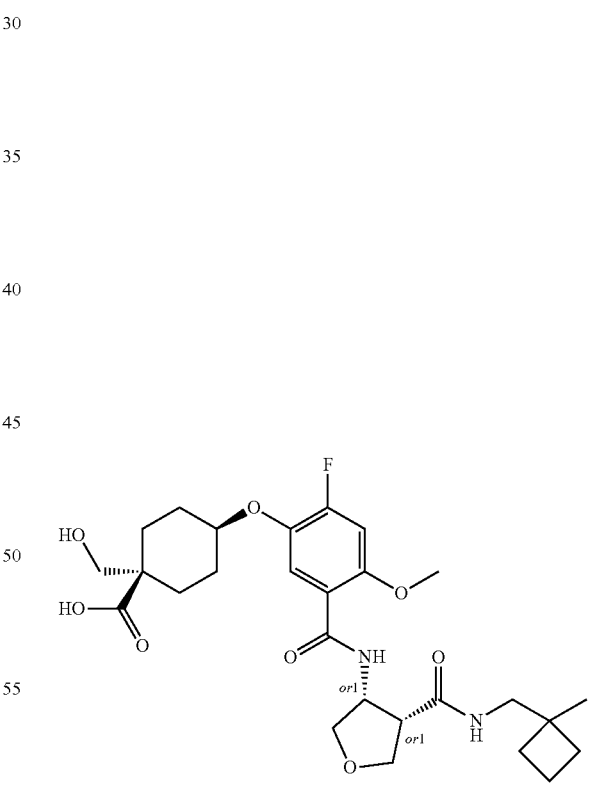

The racemic product obtained in Example 362 (102 mg) was separated by chiral HPLC (column: CHIRALPAK IA (250 mm*30 mm); mobile phase: [Hexane/2-PrOH/EtOH/MeOH/AcOH=45/10/45/0.1]) to give the first eluting compound Isomer 1: Example 578 (43.6 mg, 43%, 100% ee); MS (ESI) m/z 525.2 [M+H]+, and the second eluting compound Isomer 2: Example 579 (42.2 mg, 41%, 99.7% ee); MS (ESI) m/z 525.2 [M+H]+.

The racemic product obtained in Example 363 (40 mg) was separated by chiral HPLC (column: CHIRALPAK IA (250 mm*30 mm); mobile phase: [CO2/MeOH=60/40]) to give the first eluting compound Isomer 1: Example 580 (14.2 mg, 36%); MS (ESI) m/z 537.5 [M+H]+, and the second eluting compound Isomer 2: Example 581 (20 mg, 50%); MS (ESI) m/z 537.5 [M+H]+.

Example 582: (1R,4r)-4-(2-Fluoro-4-methoxy-5-(((1R*,2R*,3S*,4S*)-3-((3-((trifluoromethyl)sulfonyl)phenyl)carbamoyl)bicyclo[2.2.1]heptan-2-yl)carbamoyl)phenoxy)-1-hydroxycyclohexane-1-carboxylic acid (Isomer 1) and Example 583: (1R,4r)-4-(2-Fluoro-4-methoxy-5-(((1R*,2R*,3S*,4S*)-3-((3-((trifluoromethyl)sulfonyl)phenyl)carbamoyl)bicyclo[2.2.1]heptan-2-yl)carbamoyl)phenoxy)-1-hydroxycyclohexane-1-carboxylic acid (Isomer 2)

Example 584: (1R,4s)-4-(2-Fluoro-4-methoxy-5-(((1S*,2S*,3R*,4R*)-3-((3-((trifluoromethyl)sulfonyl)phenyl)carbamoyl)bicyclo[2.2.1]heptan-2-yl)carbamoyl)phenoxy)-1-(hydroxymethyl)cyclohexane-1-carboxylic acid (Isomer 1) and Example 585: (1R,4s)-4-(2-Fluoro-4-methoxy-5-(((1S*,2S*,3R*,4R*)-3-((3-((trifluoromethyl)sulfonyl)phenyl)carbamoyl)bicyclo[2.2.1]heptan-2-yl)carbamoyl)phenoxy)-1-(hydroxymethyl)cyclohexane-1-carboxylic acid (Isomer 2)

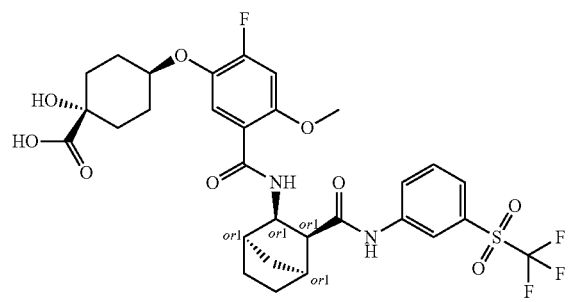

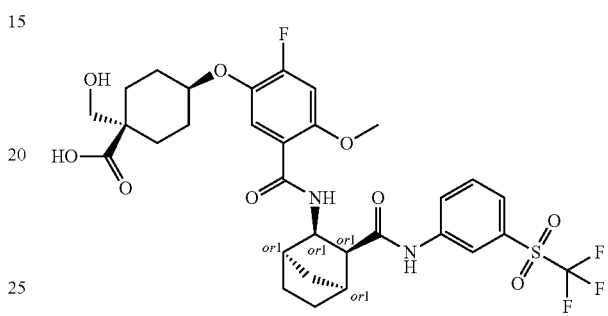

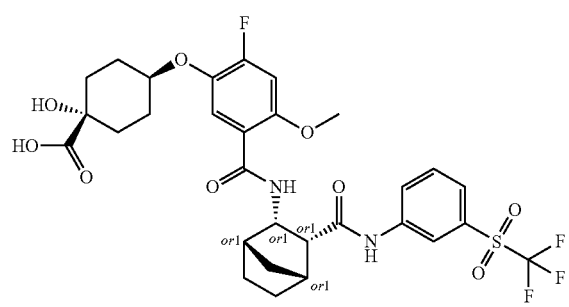

The racemic product obtained in Example 422 (16 mg) was separated by chiral HPLC (column: CHIRALPAK IE (250 mm*30 mm); mobile phase: [Hex/2-PrOH/MeOH/AcOH=65/30/5/0.5]) to give the first eluting compound Isomer 1: Example 582 (5 mg, 31%); MS (ESI) m/z 673.3 [M+H]+, and the second eluting compound Isomer 2: Example 583 (5 mg, 31%); MS (ESI) m/z 673.3 [M+H]+.

The racemic product obtained in Example 366 (13 mg) was separated by chiral HPLC (column: CHIRALPAK IA (250 mm*30 mm); mobile phase: [Hex/EtOH/AcOH=60/40/0.1]) to give the first eluting compound Isomer 1: Example 584 (6.5 mg, 50%); MS (ESI) m/z 687.6 [M+H]+, and the second eluting compound Isomer 2: Example 585 (4.2 mg, 32%); MS (ESI) m/z 687.6 [M+H]+.

Example 586: (1R,4s)-4-(2-Fluoro-4-methoxy-5-(((1S*,2S*,3R*,4R*)-3-((3-((trifluoromethyl)sulfonyl)phenyl)carbamoyl)bicyclo[2.2.1]heptan-2-yl)carbamoyl)phenoxy)-1-methylcyclohexane-1-carboxylic acid (Isomer 1) and Example 587: (1R,4s)-4-(2-Fluoro-4-methoxy-5-(((1S*,2S*,3R*,4R*)-3-((3-((trifluoromethyl)sulfonyl)phenyl)carbamoyl)bicyclo[2.2.1]heptan-2-yl)carbamoyl)phenoxy)-1-methylcyclohexane-1-carboxylic acid (Isomer 2)

Example 588: (1R,4s)-4-(2-Cyano-4-fluoro-5-(((2S*,3R*)-3-(((1-methylcyclobutyl)methyl)carbamoyl)bicyclo[2.2.2]octan-2-yl)carbamoyl)phenoxy)-1-methylcyclohexane-1-carboxylic acid (Isomer 2) and Example 589: (1R,4s)-4-(2-Cyano-4-fluoro-5-(((2S*,3R*)-3-(((1-methylcyclobutyl)methyl)carbamoyl)bicyclo[2.2.2]octan-2-yl)carbamoyl)phenoxy)-1-methylcyclohexane-1-carboxylic acid (Isomer 1)

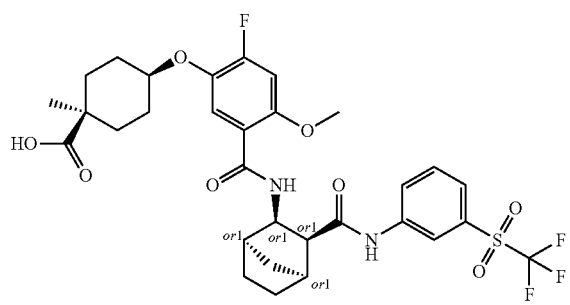

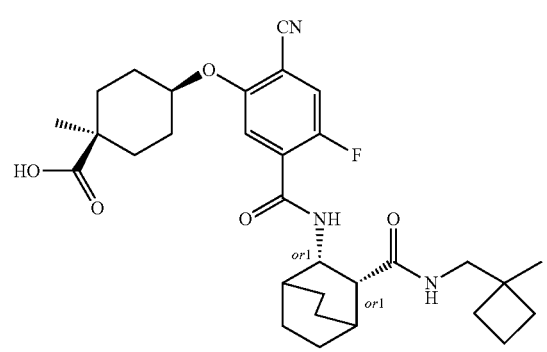

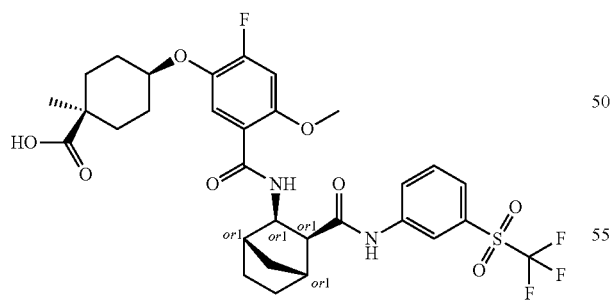

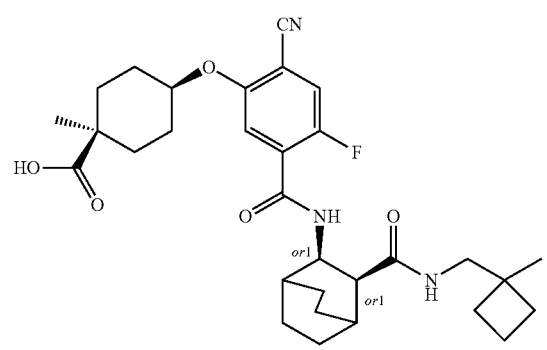

The racemic product obtained in Example 367 (133 mg) was separated by chiral HPLC (column: CHIRALPAK IE (250 mm*30 mm); mobile phase: [Hexane/EtOH/AcOH=75/25/0.1]) to give the first eluting compound Isomer 1: Example 586 (44.6 mg, 39%); MS (ESI) m/z 671.5 [M+H]$^+$, and the second eluting compound Isomer 2: Example 587 (51.7 mg, 45%); HRMS (ESI) m/z [M+H]$^+$ calcd for C31H35F4N2O8S: 671.2044 found: 671.2064.

The racemic product obtained in Example 368 (90 mg) was separated by chiral HPLC (column: CHIRALPAK IB N (250 mm*30 mm); mobile phase: [Hex/2-PrOH/AcOH=75/25/0.1]) to give the first eluting compound Isomer 1: Example 589 (39.7 mg, 41%, 99.7% ee); MS (ESI) m/z 554.4 [M+H]$^+$, and the second eluting compound Isomer 2: Example 588 (36.8 mg, 38%, 99.7% ee); MS (ESI) m/z 554.4 [M+H]$^+$.

Example 590: rel-2'-Fluoro-5'-(((1R,2S,3R,4S)-3-((4-fluoro-3-(trifluoromethyl)phenyl)carbamoyl)bicyclo[2.2.1]heptan-2-yl)carbamoyl)-4'-methoxy-[1,1'-biphenyl]-4-carboxylic acid (Isomer 1) and Example 591: rel-2'-Fluoro-5'-(((1R,2S,3R,4S)-3-((4-fluoro-3-(trifluoromethyl)phenyl)carbamoyl)bicyclo[2.2.1]heptan-2-yl)carbamoyl)-4'-methoxy-[1,1'-biphenyl]-4-carboxylic acid (Isomer 2)

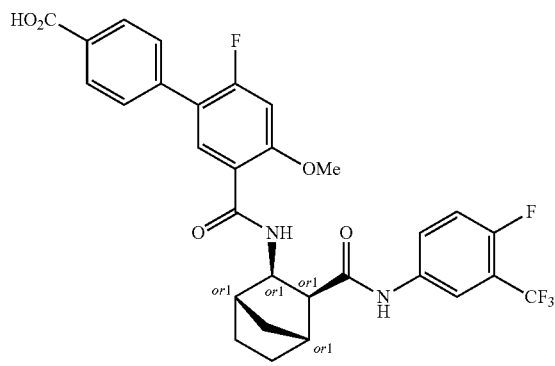

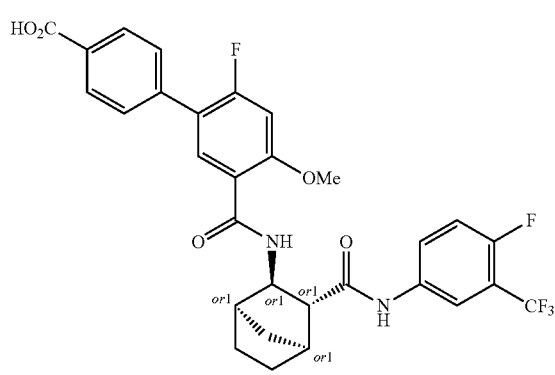

The racemic product obtained in Example 315 (57 mg) was separated by chiral HPLC (column: CHIRALPAK IF (250 mm*30 mm); mobile phase: [Hex/EtOH/THF/AcOH=75/15/10/0.1]) to give the first eluting compound Isomer 1: Example 590 (20 mg, 35%, 100% ee); MS (ESI) m/z 587.0 [M−H]−, and the second eluting compound Isomer 2: Example 591 (19 mg, 33%, 100% ee); HRMS (ESI) m/z [M+H]+ calcd for C30H26F5N2O5: 589.1756 found: 589.1774.

Example 592: (1S,4s)-4-(2-Cyano-4-methoxy-5-((((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid

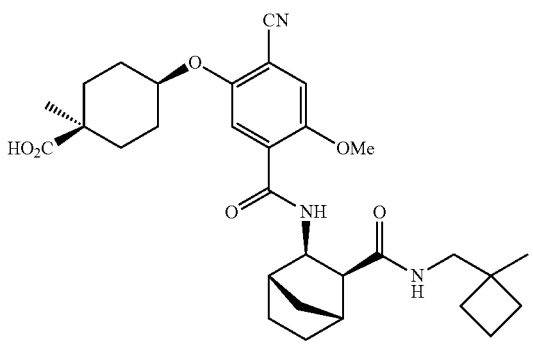

Step A: Intermediate 584: (1S,2S,3R,4R)-3-(4-Cyano-2-methoxy-5-(((1s,4S)-4-methyl-4-((naphthalen-1-ylmethoxy)carbonyl)cyclohexyl)oxy)benzamido)bicyclo[2.2.1]hept-5-ene-2-carboxylic acid

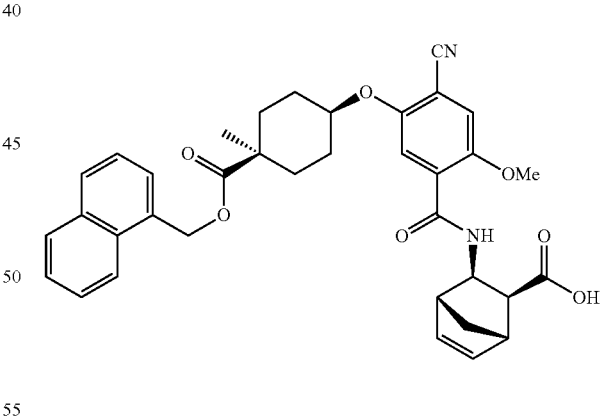

is 2 M aq LiOH (10.6 mL, 21.12 mmol) was added to a solution of Intermediate 71 (2.60 g, 4.18 mmol) in DME (50 mL), then the reaction mixture was stirred at rt for 12 hr. 10% aq citric acid was added to the reaction mixture until pH<3, then the reaction mixture was extracted with EtOAc twice and the combined organic layer was concentrated in vacuo to give titled compound (2.5 g, 97%). MS (ESI) m/z 609.3 [M+H]+.

Step B: Intermediate 585: Naphthalen-1-ylmethyl (1S,4s)-4-(5-(((1R,2R,3S,4S)-3-(((1-methylcyclobutyl)methyl)carbamoyl)bicyclo[2.2.1]hept-5-en-2-yl)carbamoyl)-2-cyano-4-methoxyphenoxy)-1-methylcyclohexane-1-carboxylate

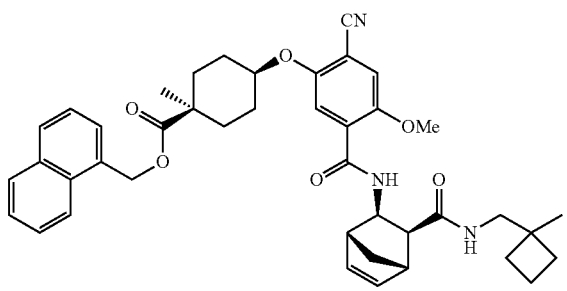

HATU (344 mg, 0.904 mmol) and DIPEA (0.43 mL, 2.46 mmol) were added to Intermediate 584 (500 mg, 0.821 mmol) and (1-methylcyclobutyl)methylamine hydrochloride (134 mg, 0.986 mmol) in DMF (4 mL), then the mixture was stirred at rt for 30 min. H$_2$O (50 mL) was added to the reaction mixture and the residual precipitate was collected by filtration, then the residue was dried under vacuum pump to give the title compound (611 mg, 100%). MS (ESI) m/z 690.4 [M+H]$^+$.

Step C: (1S,4s)-4-(2-Cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid

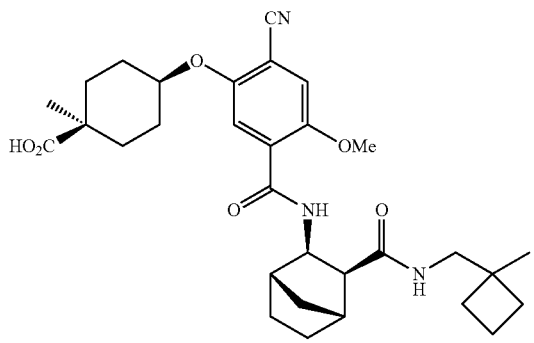

Palladium (10% Pd/C, moisture by 50% H$_2$O, 200 mg) was added to a solution of Intermediate 585 (609 mg, 0.883 mmol) in MeOH (4.4 mL). The reaction mixture was stirred under 1 atm of hydrogen atmosphere at rt for 3 hr. The hydrogen in the reaction vessel was replaced with argon and the reaction mixture was filtered with Celite®®. After the filtrate was concentrated in vacuo, the crude product was purified by flash chromatography using a gradient of 0-5% MeOH in CHCl$_3$ as mobile phase to give titled compound (389 mg, 80%). $^1$H NMR (400 MHz, DMSO-d6) δ 0.99 (s, 3H), 1.21 (s, 3H), 1.23-1.41 (m, 5H), 1.45-1.85 (m, 10H), 1.96-2.13 (m, 3H), 2.18-2.29 (m, 3H), 2.35-2.40 (m, 1H), 2.65-2.71 (m, 1H), 3.06 (dd, J=13.2, 5.8 Hz, 1H), 3.17 (dd, J=13.2, 6.3 Hz, 1H), 3.98 (s, 3H), 4.26-4.33 (m, 1H), 4.34-4.43 (m, 1H), 7.37 (s, 1H), 7.72 (s, 1H), 7.84-7.91 (m, 1H), 9.09 (d, J=8.5 Hz, 1H). HRMS (ESI) m/z [M+H]$^+$ calcd for C31H42N3O6: 552.3068 found: 552.3064.

Form A of (1S,4s)-4-(2-Cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid The product from Step C (104 mg, 0.19 mmol) was dissolved in DMSO and purified by preparative HPLC on a Kromasil C8 column (10 μm 250×50 ID mm) using a gradient of 45-80% acetonitrile in H$_2$O/MeCN/FA 95/5/0.2 buffer over 30 minutes with a flow of 100 mL/min. The desired fractions were freezedried to give Form A of the title compound (79 mg, 76%) as a white solid.

Form B of (1S,4s)-4-(2-Cyano-4-methoxy-5-(((1S,2R,3S,4R)-3-(((1-methylcyclobutyl)methyl)carbamoyl)bicyclo[2.2.1]heptan-2-yl)carbamoyl)phenoxy)-1-methylcyclohexane-1-carboxylic acid To a solution of Intermediate 585 (21.5 g, 31.2 mmol) in EtOH (260 mL) was added 10% Pd(C) (4.0 g) at 25° C. The mixture was stirred under H$_2$ (50 Psi) at 25° C. for 3 h. The reaction mixture was filtered and the filter cake was washed with EtOH (200 mL). The combined filtrate was concentrated under reduced pressure to give a residue which was triturated with PE/EtOAc (10:1, 300 mL) at 25° C. for 30 min, then filtered. The filter cake was dried in vacuum and the residue was purified by Method PrepAcidic-0, combined with a second batch prepared by the same method, and the solvent removed. The residue was purified by Method SFC-H to afford Form B of the title compound (20.0 g, 65.6%, based on the combined theoretical amount: 30.4 g) as a white solid.

Example 593: (1S,4s)-4-(2-Fluoro-4-methoxy-5-(((1S,2R,3S,4R)-3-(((1-methoxycyclobutyl)methyl)carbamoyl)bicyclo[2.2.1]heptan-2-yl)carbamoyl)phenoxy)-1-methylcyclohexane-1-carboxylic acid

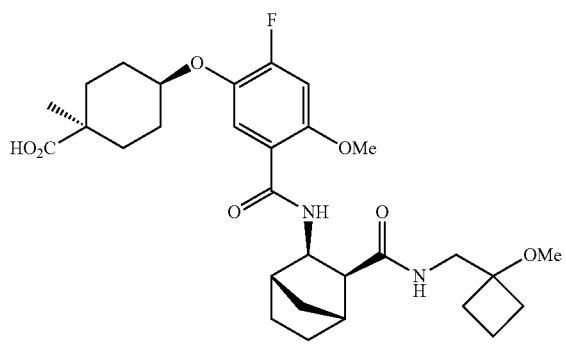 [SMILES: COc1cc(F)c(O[C@H]2CC[C@@](C)(C(=O)O)CC2)cc1C(=O)N[C@@H]1[C@H]2CC[C@H](C2)[C@@H]1C(=O)NCC1(OC)CCC1]

Step A: Intermediate 586: Naphthalen-1-ylmethyl (1S,4s)-4-(5-((((1R,2R,3S,4S)-3-(((1-methoxycyclobutyl)methyl)carbamoyl)bicyclo[2.2.1]hept-5-en-2-yl)carbamoyl)-2-fluoro-4-methoxyphenoxy)-1-methylcyclohexane-1-carboxylate

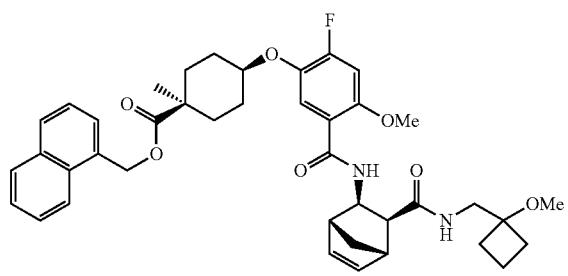 [SMILES: COc1cc(F)c(O[C@H]2CC[C@@](C)(C(=O)OCc3cccc4ccccc34)CC2)cc1C(=O)N[C@H]1[C@@H](C(=O)NCC2(OC)CCC2)[C@@H]2C=C[C@H]1C2]

HATU (104 mg, 0.274 mmol) was added to a solution of Intermediate 578 (150 mg, 0.249 mmol), (1-methoxycyclobutyl)methanamine hydrochloride (44 mg, 0.274 mmol) and DIPEA (0.13 mL, 0.75 mmol) in DMF (1 mL) and the reaction mixture was stirred at rt for 1 h. H$_2$O was added to the reaction mixture and the precipitate was collected by filtration, and dried in vacuo to give the title compound (138 mg, 79%). MS (ESI) m/z 699.3 [M+H]$^+$.

Step B: (1S,4s)-4-(2-Fluoro-4-methoxy-5-((((1S,2R,3S,4R)-3-(((1-methoxycyclobutyl)methyl)carbamoyl)bicyclo[2.2.1]heptan-2-yl)carbamoyl)phenoxy)-1-methylcyclohexane-1-carboxylic acid

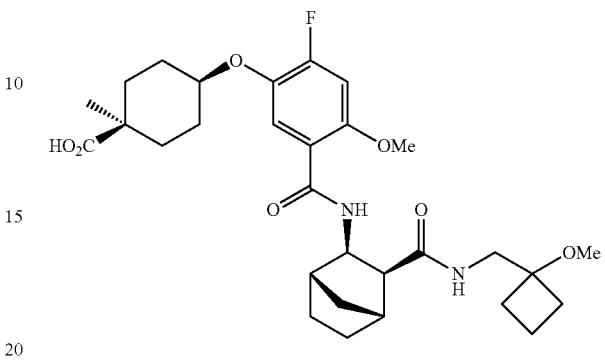

Palladium (10% Pd/C, moisture by 50% water, 70 mg) was added to a solution of Intermediate 586 (138 mg, 0.198 mmol) in EtOH (2 mL). The reaction mixture was stirred under 1 atm of hydrogen atmosphere at rt for 3 hr. The hydrogen in the reaction vessel was replaced with argon and the reaction mixture was filtered with Celite®®. After the filtrate was concentrated in vacuo, the crude product was purified by flash chromatography using a gradient of 0-5% MeOH in CHCl$_3$ as mobile phase to give titled compound (81 mg, 73%). MS (ESI) m/z 561.3 [M+H]$^+$. The Examples included in Table 34 were synthesized analogous to the procedure of Example 593 using the appropiate amines (as the free base or as the corresponding HCl salt).

TABLE 34

| Example | Amine | Product | MS (ESI) |
|---|---|---|---|
| 594 | 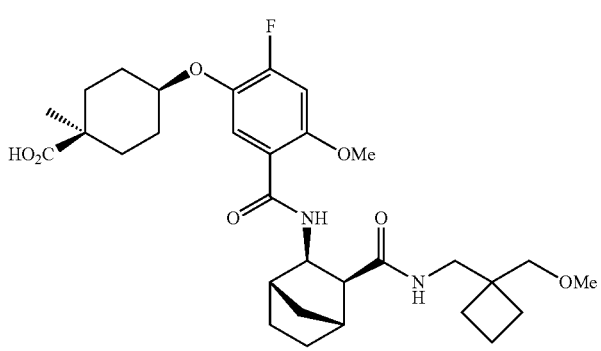 [SMILES: COCC1(CNC(=O)[C@H]2[C@@H]3CC[C@@H](C3)[C@H]2NC(=O)c2cc(O[C@H]3CC[C@@](C)(C(=O)O)CC3)c(F)cc2OC)CCC1] | 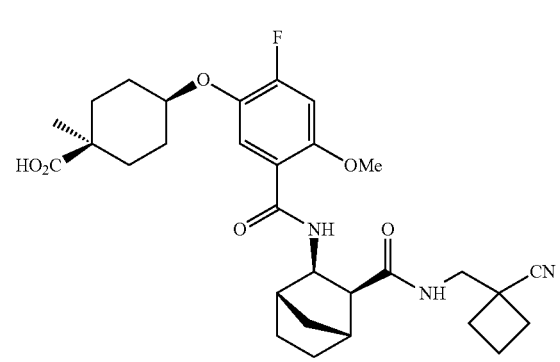 | m/z 575.3 [M + H]$^+$ |
| 595 |  |  | m/z 556.3 [M + H]$^+$ |

TABLE 34-continued

| Example | Amine | Product | MS (ESI) |
|---------|-------|---------|----------|
| 596 | H₂N−CH₂−CF₃ (2,2,2-trifluoroethylamine) | [structure] | m/z 559.2 [M + H]⁺ |
| 597 | H₂N−CH(CH₃)−CF₃ (R) | [structure] | m/z 559.2 [M + H]⁺ |
| 598 | cyclobutylamine | [structure] | m/z 517.4 [M + H]⁺ |
| 599 | cyclopentylamine | [structure] | m/z 531.2 [M + H]⁺ |

TABLE 34-continued
| Example | Amine | Product | MS (ESI) |
|---|---|---|---|
| 600 | 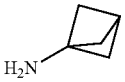 | 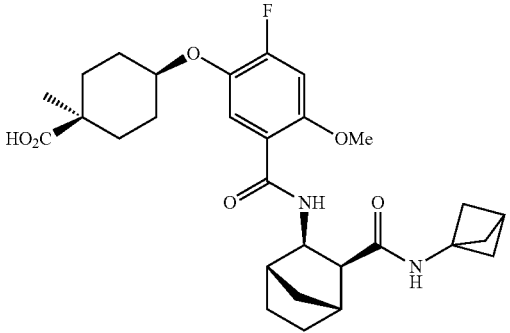 [SMILES: COc1cc(F)c(O[C@H]2CC[C@@](C)(C(=O)O)CC2)cc1C(=O)N[C@@H]1[C@H]2CC[C@H](C2)[C@@H]1C(=O)NC12CC(C1)C2] | m/z 529.3 [M + H]⁺ |
| 601 | 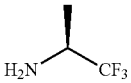 | 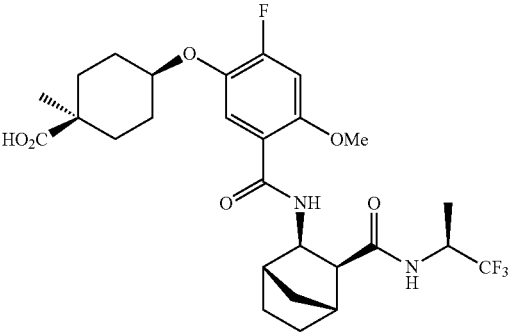 [SMILES: COc1cc(F)c(O[C@H]2CC[C@@](C)(C(=O)O)CC2)cc1C(=O)N[C@@H]1[C@H]2CC[C@H](C2)[C@@H]1C(=O)N[C@@H](C)C(F)(F)F] | m/z 559.2 [M + H]⁺ |
| 602 |  | 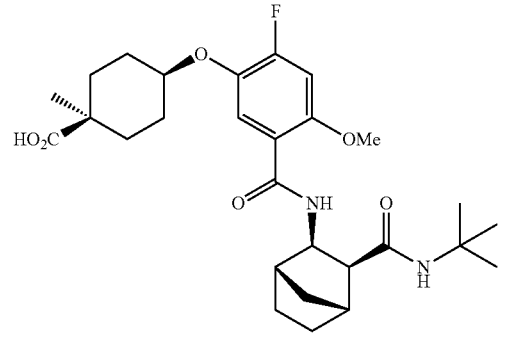 [SMILES: COc1cc(F)c(O[C@H]2CC[C@@](C)(C(=O)O)CC2)cc1C(=O)N[C@@H]1[C@H]2CC[C@H](C2)[C@@H]1C(=O)NC(C)(C)C] | m/z 519.5 [M + H]⁺ |
| 603 |  | 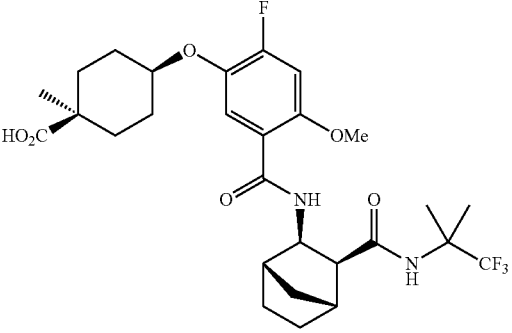 [SMILES: COc1cc(F)c(O[C@H]2CC[C@@](C)(C(=O)O)CC2)cc1C(=O)N[C@@H]1[C@H]2CC[C@H](C2)[C@@H]1C(=O)NC(C)(C)C(F)(F)F] | m/z 573.5 [M + H]⁺ |

TABLE 34-continued
| Example | Amine | Product | MS (ESI) |
|---|---|---|---|
| 604 | 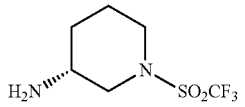 | 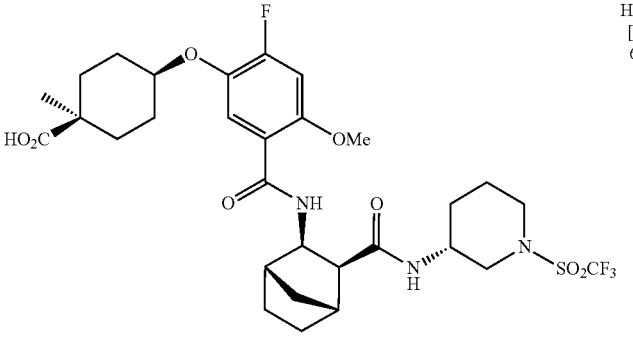 | HRMS m/z [M + H]+ 678.2504 m/z |
| 605 | 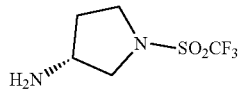 | 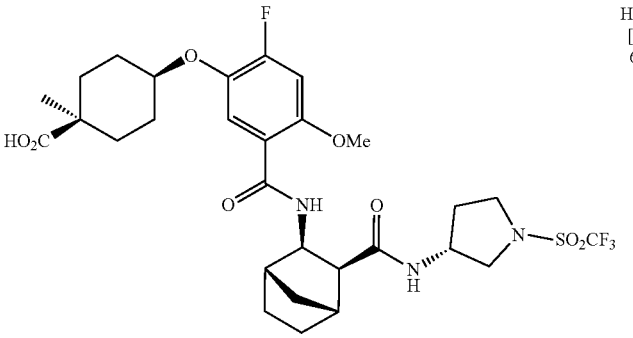 | HRMS m/z [M + H]+ 664.2340 m/z |
| 606 | 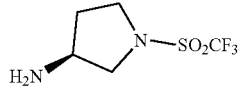 | 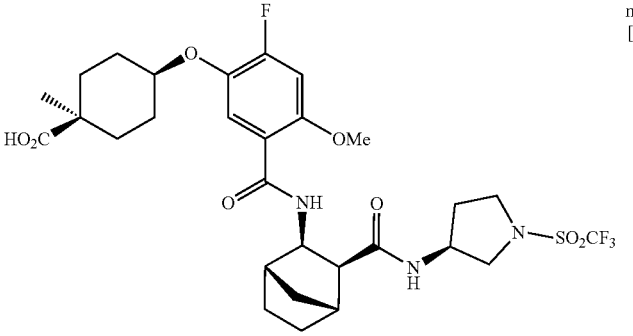 | m/z 664.1 [M + H]+ |
| 607 | 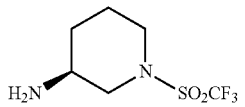 | 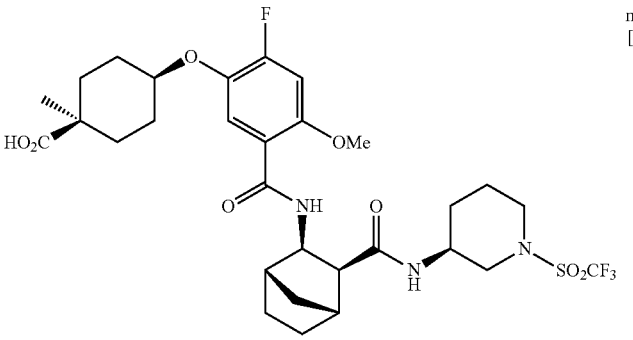 | m/z 678.2 [M + H]+ |

TABLE 34-continued

| Example | Amine | Product | MS (ESI) |
|---|---|---|---|
| 608 | 3-fluorobicyclo[1.1.1]pentan-1-amine | (structure) | HRMS m/z [M + H]+ 547.2612 m/z |
| 609 | (1-fluorocyclobutyl)methanamine | (structure) | m/z 549.3 [M + H]+ |
| 610 | 2-methoxy-2-methylpropan-1-amine | (structure) | m/z 549.3 [M + H]+ |
| 611 | 1-amino-2-methylpropan-2-ol | (structure) | m/z 535.5 [M + H]+ |

TABLE 34-continued

| Example | Amine | Product | MS (ESI) |
|---|---|---|---|
| 612 | H₂N–C(CH₃)₂–CH₂OH | (structure) | m/z 549.3 [M + H]⁺ |
| 613 | H₂N–CH₂–C(CF₃)(cyclobutyl) | (structure) | m/z 599.3 [M + H]⁺ |
| 614 | H₂N–CH₂–C(CF₃)(cyclopropyl) | (structure) | m/z 585.5 [M + H]⁺ |
| 615 | H₂N–CH(CH₃)–C(CH₃)₂–CN | (structure) | m/z 558.3 [M + H]⁺ |

TABLE 34-continued

| Example | Amine | Product | MS (ESI) |
|---|---|---|---|
| 616 | | | m/z 558.3 [M + H]+ |
| 617 | | | HRMS m/z [M + H]+ 559.3160 m/z |
| 618 | | | m/z 595.2 [M + H]+ |
| 619 | | | m/z 553.3 [M + H]+ |

TABLE 34-continued

| Example | Amine | Product | MS (ESI) |
|---|---|---|---|
| 620 | H₂N-CH₂-(3,3-difluorocyclobutyl) | (structure) | m/z 567.3 [M + H]⁺ |

Example 621: (1S,4s)-4-(2-cyano-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid

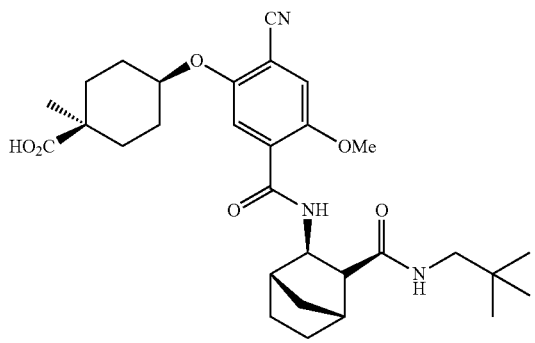

The titled compound was prepared analogously to Example 71, using 2,2-dimethylpropan-1-amine instead of cyclopropylmethanamine. HRMS (ESI) m/z [M+H]⁺ calcd for C30H42N3O6: 540.3068 found: 540.3076.

Form A of (1S,4s)-4-(2-cyano-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid Naphthalen-1-ylmethyl (1S,4s)-4-(2-cyano-4-methoxy-5-(((1R,2R,3S,4S)-3-(neopentylcarbamoyl)bicyclo[2.2.1]hept-5-en-2-yl)carbamoyl)phenoxy)-1-methylcyclohexane-1-carboxylate (0.95 g, 1.40 mmol) (which may be prepared analogously to Intermediate 585 using 2,2-dimethylpropan-1-amine instead of 1-methylcyclobutyl)methylamine hydrochloride) and Pd (C) (200 mg, 0.19 mmol) in MeOH (40 mL) was stirred at 20° C. under H₂ (g) 1.2 atm for 5 h. The mixture was filtered through a Celite® pad and the solvents were removed under reduced pressure. The crude material was purified by C18-flash chromatography, elution gradient 0 to 55% MeCN in H₂O. Pure fractions were evaporated to dryness to afford Form A of the title compound (0.580 g, 77%) as a white solid.

Form B of (1S,4s)-4-(2-cyano-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid (1S,4s)-4-(2-cyano-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid (5.1 mg) was dissolved in 50 µL of IPA at room temperature. This solution was stirred for 2 days, and then evaporated under an open condition for 6 days to give Form B seed crystals.

Further (1S,4s)-4-(2-cyano-4-methoxy-5-(((1S,2R,3S,4R)-3-(neopentylcarbamoyl)bicyclo[2.2.1]heptan-2-yl)carbamoyl)phenoxy)-1-methylcyclohexane-1-carboxylic acid (32.5 g, 60.18 mmol) was dissolved in hot EtOH (50 mL), then the mixture was cooled to room temperature. Heptane (125 mL) and above seed crystals were added, then the mixture was stirred at rt for 1 hr. The precipitate was collected by filtration and dried under reduced pressure at 50° C. for 1 day to give the title compound (20.09 g, 62%) as Form B crystals.

The examples included in Table 35 below were synthesized analogously to the procedure of Example 71 using the appropriate amines (as the free base or as the corresponding HCl salt). The amine is commercially available if not otherwise stated.

TABLE 35

| Example | Amine | Product | MS (ESI) |
|---|---|---|---|
| 622 | (3-fluorobicyclobutyl-1-amine) | | HRMS m/z [M + H]+ 554.2670 |
| 623 | (3,3-difluorocyclobutyl amine) | | m/z 560.3 [M + H]+ |
| 624 | (2,2-dimethyl-3,3,3-trifluoropropyl amine, H2N-CH2-C(CH3)2-CF3) | | HRMS m/z [M + H]+ 594.2800 |

Biological and Physicochemical Data
RXFP1 Hu cAMP (Test A)

To screen for modulators of hRXFP1, an assay identifying compounds that stimulate cAMP production via the Gs-coupled hRXFP1 receptor was used. cAMP HiRange HTRF kit (available from CisBio Bioassays, France; catalogue number 62AM6PEJ) was employed in large according to manufacturer's recommendations for detection of cAMP. The HTRF method is a competitive immunoassay between native cAMP produced by cells and cAMP labeled with the dye d2. The tracer binding is visualized with a cryptate labeled antibody for cAMP and the signal is thus inversely proportional to the amount of produced cAMP.

Preparation of Assay Reagents

Assay buffer: HBSS (ThermoFisher, 14065) with 5 mM Hepes (ThermoFisher, 15630) pH 7.4 containing 0.1% BSA (Sigma, A8806)
Cells: Jump-In™ T-REx™ CHO-K1 Cells (ThermoFisher) stably transfected with human RXFP1 was employed. Cells were induced to express human RXFP1 by treatment with 10 ng/ml doxycycline for 24 h. Cells were then cryopreserved for long term storage. At the start of each experiment, cells were thawn, washed with PBS and resuspended in assay buffer to $1.875*10^5$ cells/ml cAMP standard: stock standard cAMP provided in the CisBio kit was diluted in assay buffer to a top final concentration of 2.8 μM in the assay.

HTRF detection reagents: cAMP-d2 and anti-cAMP cryptate reconstituted according to CisBio instructions were diluted 1:40 in lysis buffer provided with the HTRF-kit.

Step by Step Procedure for Running the Assay:

1. 40 nL test compounds dissolved in DMSO were aquostically dispensed (Labcyte Echo) to white 384-well plates (Greiner; 784075), sealed and stored at room temperature until assayed.

2. 40 nL 200 nM Relaxin-2 in DMSO (1 nM final concentration) was added to 100% control wells and 40 nL DMSO added to 0% wells with Echo acoustic dispenser at the day of assay.

3. 4 μL assay buffer with 1 mM IBMX (0.5 mM final concentration) to block phosphodiesterases was added with Multidrop Combi (ThermoFisher).

4. 4 µL cell solution at 1.875*10≡cells/ml was added with Multidrop Combi to give 750 cells/well.

5. 45 min incubation at room temperature.

6. 4 µL cAMP-d2 in lysis buffer was added with Multidrop Combi.

7. 4 µL anti-cAMP cryptate in lysis buffer was added with Multidrop Combi 8. 2 h incubation at room temperature 9. Homogenous Time-Resolved Fluorescence (HTRF) signal was detected with an Envision (PerkinElmer) or Pherastar (BMG Labtech) reader ($\lambda$ex=340 nm, $\lambda$em=665 and 615 nm).

Using a cAMP standard curve, HTRF data was converted to amount cAMP produced in the samples which was subsequentially used for calculation of concentration responses. Concentration response data were fitted with a four parameter logistic fit, the Hill equation. The results from the assay are reported in Table 36 as $EC_{50}$ (µM) and $S_{inf}$ (%).

$EC_{50}$ is defined as the concentration at which the stimulatory activity reaches 50% of its maximum level. Where the assay was run multiple times for the same compound, the geometric mean is reported.

$S_{inf}$ is the fitted activity level, efficacy, at infinite concentration of test compound. To facilitate comparison of efficacy data, efficacy was normalized to % effect of the response stimulated by a saturating concentration of relaxin (1 nM). Where the assay was run multiple times for the same compound, the arithmetic mean is reported.

Human Plasma Protein Binding (Test B)

The assay was conducted according to the Human Plasma Protein Binding Assay described in pages 167-170 of Wernevik, J. et al., "*A Fully Integrated Assay Panel for Early Drug Metabolism and Pharmacokinetics Profiling*", Assay and Drug Development Technologies, 2020, 18(4), 157-179. Data are reported in Table 36 as fraction unbound ($f_u$) (% free). Where the assay was run multiple times for the same compound, the arithmetic mean is reported.

Human Liver Microsomal Stability (Test C)

The assay was conducted according to the Human Liver Microsome Stability Assay described in pages 170-174 of Wernevik, J. et al., "*A Fully Integrated Assay Panel for Early Drug Metabolism and Pharmacokinetics Profiling*", Assay and Drug Development Technologies, 2020, 18(4), 157-179. Data are reported in Table 36 as $CL_{int}$ (µl/min/mg protein). Where the assay was run multiple times for the same compound, the arithmetic mean is reported.

Human Hepatocyte Stability (Test D)

The metabolic stability of compounds in human hepatocytes was assessed using the following protocol:

1. Prepare 10 mM stock solutions of compound and control compounds in appropriate solvent (DMSO). Place incubation medium (L-15 Medium) in a 37° C. water bath, and allow warming for at least 15 minutes prior to use.

2. Add 80 µL of acetonitrile to each well of the 96-well deep well plate ("Quenching plate").

3. In a new 96-well plate, dilute the 10 mM test compounds and the control compounds to 100 µM by combining 198 µL of acetonitrile and 2 µL of 10 mM stock solution.

4. Remove a vial of cryopreserved (less than −150° C.) human hepatocytes (LiverPool™ 10-Donor Human hepatocytes obtained from Bioreclamation IVT (Product No. S01205)) from storage, ensuring that vials remain at cryogenic temperatures until thawing process ensues. As quickly as possible, thaw the cells by placing the vial in a 37° C. water bath and gently shaking the vials. Vials should remain in water bath until all ice crystals have dissolved and are no longer visible. After thawing is complete, spray vial with 70% ethanol, transfer the vial to a bio-safety cabinet.

5. Open the vial and pour the contents into the 50 mL conical tube containing thawing medium. Place the 50 mL conical tube into a centrifuge and spin at 100 g for 10 minutes (room temperature). Upon completion of spin, aspirate thawing medium and resuspend hepatocytes in enough incubation medium to yield ~1.5×$10^6$ cells/mL.

6. Using Cellometer® Vision, count cells and determine the viable cell density. Cells with poor viability (<80% viability) are not acceptable for use. Dilute cells with incubation medium to a working cell density of 1.0×$10^6$ viable cells/mL.

7. Transfer 247.5 µL of hepatocytes into each well of a 96-well cell incubation plate. Place the plate on Eppendorf Thermomixer Comfort plate shaker to allow the hepatocytes to warm for 10 minutes.

8. Add 2.5 µL of 100 µM test compound or control compounds into an incubation well containing cells to initiate the reaction.

9. Incubate the plate at 37° C. and 900 rpm on an Eppendorf Thermomixer Comfort plate shaker. At 0.5, 5, 15, 30, 45, 60, 80, 100 and 120 min, transfer 20 µL of the incubated mixture to a separate "Quenching plate", then mix the sample by vortex for 2 min.

10. Centrifuge the quenching plates for 20 minutes at 4,000 rpm. Transfer 30 µL of supernatant of each compound into a 96-well analysis plate. 4 compounds are pooled together into one cassette. Then dilute the pooled sample by adding of 180 µl of pure water. All incubations are performed in singlicate.

All calculations were carried out using Microsoft Excel. Peak areas were determined from extracted ion chromatograms. In vitro intrinsic clearance (in vitro $Cl_{int}$, in µL/min/$10^6$ cells) of parent compound was determined by regression analysis of the Ln percent parent disappearance vs. time curve. The in vitro intrinsic clearance (in vitro $Cl_{int}$, in µL/min/$10^6$ cells) reported in Table 36, and was determined from the slope value using the following equation:

$$\text{in vitro } Cl_{int} = kV/N$$

V=incubation volume (0.25 mL);

N=number of hepatocytes per well (0.25×$10^6$ cells)

Where the assay was run multiple times for the same compound, the geometric mean is reported.

Rat Hepatocyte Stability (Test E)

The assay was conducted according to the Rat Hepatocyte Stability Assay described in pages 170-174 of Wernevik, J. et al., "*A Fully Integrated Assay Panel for Early Drug Metabolism and Pharmacokinetics Profiling*", Assay and Drug Development Technologies, 2020, 18(4), 157-179. Data are reported in Table 36 as mean $Cl_{int}$(µl/min/$10^6$ cells). Where the assay was run multiple times for the same compound, the geometric mean is reported.

Solubility (Test F)

The assay was conducted according to the Solubility Assay described in pages 164-167 of Wernevik, J. et al., "*A Fully Integrated Assay Panel for Early Drug Metabolism and Pharmacokinetics Profiling*", Assay and Drug Development Technologies, 2020, 18(4), 157-179. Data are reported in Table 36 as solubility ((M). Where the assay was run multiple times for the same compound, the arithmetic mean is reported.

TABLE 36

Assay data

| Example | Test A EC$_{50}$ (uM) | Test A S$_{inf}$(%) | Test B Human Plasma Protein Binding (% free) | Test C Human Liver Microsomal Stability Cl$_{int}$ (μl/min/mg) | Test D Human Hepatocyte Stability Cl$_{int}$ (μL/min/10$^6$ cells) | Test E Rat Hepatocyte Stability Cl$_{int}$ (μL/min/10$^6$ cells) | Test F Solubility (μM) |
|---|---|---|---|---|---|---|---|
| 1 | 0.017 | 109 | 4.3 | 23 | 4.8 | 11 | >500 |
| 2 | 0.23 | 101 | 1.9 | 14 | 2 | 27 | >1000 |
| 3 | >50 | | 3.7 | 17 | 8.5 | 11 | 860 |
| 4 | 0.0047 | 103 | | 36 | | 6.9 | >1000 |
| 5 | >1.7 | 85 | 2.4 | 16 | 15 | 11 | 800 |
| 6 | 0.72 | 89 | 4.2 | 35 | | 21 | 820 |
| 7 | 1.3 | 86 | 4.4 | 23 | | 23 | 820 |
| 8 | >50 | | 23 | 1.7 | | 38 | 980 |
| 9 | >7.3 | 100 | 11 | 9.2 | | 67 | 27 |
| 10 | 0.50 | 104 | 2.2 | 32 | 11 | 130 | 750 |
| 11 | 2.3 | 104 | 3.3 | 36 | | >300 | >1000 |
| 12 | 0.41 | 107 | 2.7 | 23 | | 64 | 850 |
| 13 | 6.3 | 115 | 3.1 | 24 | | 10 | 520 |
| 14 | 0.51 | 83 | 1.8 | 18 | | 27 | 770 |
| 15 | 0.42 | 94 | 1.3 | 14 | | 13 | 390 |
| 16 | 0.33 | 93 | 2.2 | 9.3 | | 49 | 330 |
| 17 | 0.048 | 110 | <0.21 | 20 | | 11 | 150 |
| 18 | 3.2 | 105 | 1.2 | 27 | | 49 | 400 |
| 19 | 0.47 | 97 | 2.3 | 17 | | 93 | 630 |
| 20 | 0.048 | 102 | 0.74 | 28 | | 63 | 980 |
| 21 | 0.023 | 110 | 0.55 | 39 | | 28 | 850 |
| 22 | 0.29 | 130 | 0.23 | 23 | | 14 | 51 |
| 23 | 0.020 | 109 | 0.24 | 26 | | 19 | 8.7 |
| 24 | 1 | 97 | 1.8 | 29 | | 45 | 590 |
| 25 | 0.42 | 102 | 0.59 | 31 | | 130 | 440 |
| 26 | 0.19 | 105 | | 31 | | 38 | 250 |
| 27 | 0.13 | 88 | 0.40 | 29 | | >300 | 990 |
| 28 | 0.044 | 96 | 0.94 | 32 | | 51 | 690 |
| 29 | 0.11 | 111 | 0.72 | 22 | | 22 | 130 |
| 30 | >40 | | 3.6 | <3 | | 18 | >1000 |
| 31 | 0.75 | 81 | 3.7 | 18 | | 13 | 940 |
| 32 | >40 | 100 | 13 | 10 | | 26 | >1000 |
| 33 | >5 | 88 | 15 | <3 | | 110 | >1000 |
| 34 | 0.23 | 103 | 4.8 | 5.7 | <1 | 19 | 880 |
| 35 | 0.039 | 101 | 8.2 | 14 | 2.7 | 23 | >730 |
| 36 | 0.031 | 107 | 6.9 | 33 | 5.8 | 7.2 | 22 |
| 37 | 0.020 | 103 | 3.8 | 27 | 4.8 | 22 | 830 |
| 38 | 0.028 | 106 | 5.6 | 13 | 4.2 | 9 | 38 |
| 39 | 0.74 | 96 | 4.8 | 24 | 8.2 | 59 | 980 |
| 40 | 0.81 | 97 | 3.4 | 190 | 30 | 52 | 2.5 |
| 41 | >5.5 | 114 | 8 | 8.9 | | 21 | 820 |
| 42 | 4.3 | 95 | 5.4 | <3 | | 19 | >1000 |
| 43 | 0.083 | 106 | 1.3 | 33 | 5 | 25 | 770 |
| 44 | 0.016 | 107 | 2.1 | 110 | 17 | 35 | 300 |
| 45 | 1.3 | 94 | 6.9 | 15 | | 12 | 960 |
| 46 | 0.071 | 104 | 7.6 | 12 | | 12 | 380 |
| 47 | 0.20 | 111 | 21 | <3 | <1 | 17 | >1000 |
| 48 | 0.38 | 96 | 13 | <3 | | 18 | 1000 |
| 49 | >50 | | 3.2 | <3 | | <1 | 24 |
| 50 | >50 | | 1.9 | <3 | | <1 | 60 |
| 51 | 0.058 | 112 | 0.50 | 8.5 | | 55 | 170 |
| 52 | 0.15 | 108 | 0.94 | 13 | | 34 | 890 |
| 53 | 0.16 | 122 | | 130 | | 150 | 39 |
| 54 | 0.49 | 108 | 1.1 | 16 | | 13 | 2.8 |
| 55 | >8.4 | 100 | | <3 | | 16 | >1000 |
| 56 | 12 | 105 | 21 | <3 | | 17 | 980 |
| 57 | 0.66 | 99 | | 4.9 | | 11 | >1000 |
| 58 | 0.26 | 99 | 7 | 6.5 | 1.9 | 19 | >1000 |
| 59 | 0.55 | 100 | 2.4 | 22 | | 27 | 960 |
| 60 | 1.1 | 105 | | 7 | | 11 | >1000 |
| 61 | 15 | 96 | | 7.4 | | 13 | >1000 |
| 62 | >4.2 | 93 | | 94 | | 55 | >1000 |
| 63 | >50 | | | 11 | | 19 | 610 |
| 64 | 0.15 | 107 | | 74 | | 67 | 870 |
| 65 | 0.16 | 99 | | 5.5 | 3.1 | 9.7 | >1000 |
| 66 | 3.1 | 101 | | <3 | | 12 | >1000 |
| 67 | 0.27 | 105 | | <3 | 2.6 | 18 | >1000 |
| 68 | 0.84 | 97 | 14 | 4.4 | | 14 | >1000 |
| 69 | >2.7 | 93 | 33 | 6.3 | | 6.4 | 970 |

TABLE 36-continued

Assay data

| Example | Test A EC$_{50}$ (uM) | Test A S$_{inf}$(%) | Test B Human Plasma Protein Binding (% free) | Test C Human Liver Microsomal Stability Cl$_{int}$ (μl/min/mg) | Test D Human Hepatocyte Stability Cl$_{int}$ (μL/min/10$^6$ cells) | Test E Rat Hepatocyte Stability Cl$_{int}$ (μL/min/10$^6$ cells) | Test F Solubility (μM) |
|---|---|---|---|---|---|---|---|
| 70 | 0.40 | 99 | | <3 | | 9 | >1000 |
| 71 | 0.39 | 97 | 17 | <3 | | 28 | 940 |
| 72 | >3.1 | 75 | 40 | <3 | | 14 | 950 |
| 73 | 0.22 | 114 | 12 | 11 | | 18 | 850 |
| 74 | >5 | | 26 | <3 | | 10 | 920 |
| 75 | 1.1 | 110 | 25 | <3 | | 14 | 880 |
| 76 | 41 | 100 | 47 | <3 | | 12 | 790 |
| 77 | 0.23 | 108 | 21 | 4 | 3.7 | 12 | 650 |
| 78 | 0.030 | 120 | 6.9 | 44 | | 37 | 820 |
| 79 | >5 | | 28 | 7.5 | | 31 | 980 |
| 80 | 0.41 | 105 | 16 | 8 | | 23 | 890 |
| 81 | 0.031 | 111 | 2.7 | 97 | | 57 | 250 |
| 82 | 0.032 | 114 | 2.5 | 54 | | 41 | 330 |
| 83 | 0.017 | 111 | 1.6 | 130 | | 25 | 250 |
| 84 | 0.015 | 112 | 4 | 160 | | 19 | 340 |
| 85 | >9.4 | | 50 | <3 | | 15 | 920 |
| 86 | 0.020 | 115 | 4.1 | 64 | | 26 | 540 |
| 87 | 0.11 | 109 | 6.7 | 20 | | 24 | 690 |
| 88 | 0.033 | 124 | 4.4 | 40 | | 26 | 610 |
| 89 | >5 | | 50 | <3 | | 17 | 780 |
| 90 | 0.14 | 111 | 14 | <3 | <1 | 18 | 800 |
| 91 | 0.27 | 114 | 5.9 | 20 | | 59 | 830 |
| 92 | 0.14 | 122 | 12 | 8.4 | | 32 | 920 |
| 93 | 0.37 | 103 | 24 | <3 | | 16 | 920 |
| 94 | >0.71 | 111 | 14 | 9 | | 32 | 830 |
| 95 | 0.48 | 123 | 18 | 4.4 | | 21 | 880 |
| 96 | 0.44 | 97 | 26 | <3 | | 24 | 890 |
| 97 | 0.24 | 113 | 20 | 5 | <1 | 13 | 770 |
| 98 | 0.055 | 133 | 13 | 8.7 | 4.9 | 22 | 810 |
| 99 | 0.14 | 113 | 20 | 6.2 | <1 | 11 | 920 |
| 100 | >4.6 | 100 | 30 | <3 | | 9.6 | 920 |
| 101 | >3.5 | 100 | 20 | <3 | | 28 | 990 |
| 102 | 0.16 | 122 | 12 | 4.4 | 1.9 | 14 | 820 |
| 103 | >5 | | 10 | 11 | | 38 | 860 |
| 104 | 0.27 | 122 | 6.4 | 59 | | 28 | 920 |
| 105 | 0.0048 | 125 | 2.5 | >300 | | 48 | 220 |
| 106 | 0.0097 | 112 | 1.7 | >300 | | 29 | 170 |
| 107 | 8.3 | 112 | 26 | 7.9 | | 34 | 1000 |
| 108 | 0.34 | 106 | | | | | |
| 109 | 0.25 | 103 | 17 | 11 | | 26 | 810 |
| 110 | 0.74 | 102 | 44 | <3 | | 19 | 950 |
| 111 | 0.68 | 100 | 31 | <3 | | 18 | 860 |
| 112 | 0.47 | 95 | 16 | 6.8 | | 17 | 830 |
| 113 | >9.4 | | 28 | 11 | | 30 | 950 |
| 114 | >9.4 | | 17 | 17 | | 94 | 810 |
| 116 | 0.86 | 106 | | | | | |
| 117 | 0.11 | 100 | | | | | |
| 118 | 0.043 | 99 | | | | | |
| 119 | 0.56 | 99 | | | | | |
| 120 | 0.045 | 95 | | | | | |
| 121 | 0.13 | 98 | | | | | |
| 122 | 1.3 | 71 | | | | | |
| 123 | 0.72 | 107 | | | | | |
| 124 | 0.16 | 101 | | | | | |
| 125 | 0.016 | 116 | | | | | |
| 126 | 0.047 | 98 | | | | | |
| 127 | 0.99 | 71 | | | | | |
| 128 | 0.046 | 88 | | | | | |
| 129 | 0.24 | 107 | | | | | |
| 130 | 0.078 | 95 | | | | | |
| 131 | 0.084 | 99 | | | | | |
| 132 | 0.28 | 113 | | | | | |
| 133 | 0.45 | 100 | | | | | |
| 134 | 0.044 | 104 | | | | | |
| 135 | 1.1 | 76 | | | | | |
| 136 | 0.029 | 102 | | | | | |
| 137 | >2.3 | 93 | | | | | |
| 138 | 1.2 | 100 | | | | | |
| 115 | 0.22 | 94 | | | | | |

TABLE 36-continued

Assay data

| | Test A | | Test B Human Plasma Protein Binding | Test C Human Liver Microsomal Stability $Cl_{int}$ | Test D Human Hepatocyte Stability $Cl_{int}$ | Test E Rat Hepatocyte Stability $Cl_{int}$ | Test F Solubility |
|---|---|---|---|---|---|---|---|
| Example | $EC_{50}$ (uM) | $S_{inf}$ (%) | (% free) | (μl/min/mg) | (μL/min/10$^6$ cells) | (μL/min/10$^6$ cells) | (μM) |
| 139 | 0.16 | 95 | | | | | |
| 140 | 0.084 | 95 | | | | | |
| 141 | 0.074 | 107 | 16 | 8.3 | <1 | 17 | 920 |
| 142 | 0.32 | 129 | 1.2 | <3 | 3.3 | 9.8 | 6.5 |
| 143 | 0.15 | 130 | 0.68 | <3 | 6.9 | 24 | 1.6 |
| 144 | 0.093 | 106 | 3 | 240 | 17 | 29 | 29 |
| 145 | 1.3 | 95 | 0.81 | 180 | 14 | 53 | 870 |
| 146 | >1.9 | 87 | 24 | <3 | <1 | 14 | 1000 |
| 147 | >4.2 | 111 | 36 | 88 | 6.1 | 67 | 1000 |
| 148 | >5 | | 0.59 | 7.4 | | 18 | 890 |
| 149 | 0.59 | 94 | 11 | 7.6 | | 11 | 840 |
| 150 | 0.46 | 95 | 1.8 | <3 | 4.9 | 39 | 16 |
| 151 | >2.9 | 87 | 1.7 | 90 | | 56 | 570 |
| 152 | >9.4 | | 4.3 | 18 | | 17 | 38 |
| 153 | 0.13 | 146 | <0.34 | 5.6 | | 37 | 0.80 |
| 154 | >2.1 | 95 | <0.30 | 11 | | 70 | 160 |
| 155 | 0.0084 | 126 | 0.49 | 5.4 | 11 | 30 | 37 |
| 156 | 1.9 | 97 | 3.2 | 4.3 | | 22 | 770 |
| 157 | 0.088 | 118 | | | | | |
| 158 | 0.11 | 118 | | | | | |
| 159 | 0.078 | 125 | | | | | |
| 160 | 0.16 | 125 | | | | | |
| 161 | 0.13 | 170 | | | | | |
| 162 | 0.069 | 107 | | | | | |
| 163 | 0.067 | 151 | | | | | |
| 164 | 0.13 | 142 | | | | | |
| 165 | 0.012 | 111 | | | | | |
| 166 | 0.58 | 137 | | | | | |
| 167 | 0.12 | 147 | | | | | |
| 168 | >2.2 | 121 | | | | | |
| 169 | 0.27 | 111 | | | | | |
| 170 | 0.19 | 136 | | | | | |
| 171 | 0.44 | 119 | | | | | |
| 172 | 0.98 | 125 | | | | | |
| 173 | 0.19 | 126 | | | | | |
| 174 | 0.11 | 132 | | | | | |
| 175 | >5.9 | 100 | 14 | 5.8 | | 110 | >1000 |
| 176 | >4.3 | 75 | 9.3 | 8 | | 120 | 210 |
| 177 | >2.2 | 100 | 15 | 3.5 | | 130 | >1000 |
| 178 | >2.7 | 95 | 17 | 8.6 | | 39 | >1000 |
| 179 | 0.016 | 106 | 1 | 42 | 13 | 32 | >800 |
| 180 | 0.95 | 100 | 14 | 6.8 | 2.2 | 130 | >1000 |
| 181 | 0.60 | 95 | 2.3 | 13 | 4.1 | 48 | 680 |
| 182 | 0.019 | 107 | 0.45 | 34 | | 35 | 200 |
| 183 | 0.42 | 99 | 0.50 | 23 | | 13 | 50 |
| 184 | >40 | | 8.6 | 7.4 | | 70 | >1000 |
| 185 | 0.20 | 108 | 0.37 | 48 | | 83 | 270 |
| 186 | 0.018 | 110 | 0.24 | 27 | | 20 | 80 |
| 187 | 0.25 | 105 | 0.41 | 15 | | 21 | 580 |
| 188 | 0.27 | 103 | 0.64 | 36 | | 38 | 290 |
| 189 | 0.13 | 101 | 1.5 | 34 | | 23 | 83 |
| 190 | 0.68 | 110 | 1.6 | 23 | | 120 | 420 |
| 191 | >3.6 | 86 | 1.1 | 20 | | 15 | >1000 |
| 192 | 0.035 | 109 | 0.67 | 21 | | 43 | 120 |
| 193 | 0.062 | 105 | 0.93 | 29 | | 61 | >1000 |
| 194 | 0.47 | 99 | 0.53 | 31 | | 24 | 530 |
| 195 | 0.83 | 131 | 1.6 | 28 | | 130 | 860 |
| 196 | 0.22 | 103 | 1.7 | 40 | | 79 | 290 |
| 197 | 1.4 | 106 | | 45 | 12 | 28 | 1000 |
| 198 | 1.2 | 99 | | 12 | 6.6 | 77 | 920 |
| 199 | 21 | 100 | | 26 | 2.6 | 20 | 1000 |
| 200 | 0.59 | 100 | | 32 | 3.7 | 15 | 55 |
| 201 | 7.2 | 98 | 1.6 | 23 | 7.6 | 190 | 940 |
| 202 | 2.2 | 102 | | 14 | 5.6 | 57 | 890 |
| 203 | 2.9 | 118 | | 19 | 5 | 34 | 1000 |
| 204 | 0.18 | 106 | 0.29 | 78 | | 18 | 61 |
| 205 | 0.58 | 99 | 0.58 | 49 | | 26 | 180 |
| 206 | >0.15 | 99 | | 42 | 49 | 14 | 35 |
| 207 | 0.0043 | 105 | 3.5 | 34 | 26 | 10 | 560 |

TABLE 36-continued

Assay data

| Example | Test A EC$_{50}$ (uM) | S$_{inf}$ (%) | Test B Human Plasma Protein Binding (% free) | Test C Human Liver Microsomal Stability Cl$_{int}$ (μl/min/mg) | Test D Human Hepatocyte Stability Cl$_{int}$ (μL/min/10$^6$ cells) | Test E Rat Hepatocyte Stability Cl$_{int}$ (μL/min/10$^6$ cells) | Test F Solubility (μM) |
|---|---|---|---|---|---|---|---|
| 208 | <0.0020 | 108 | 1 | 54 | 15 | 35 | 130 |
| 209 | 0.088 | 101 | 0.10 | 21 | | 23 | 54 |
| 210 | >3.6 | 50 | 0.049 | <3 | | 10 | 67 |
| 211 | >9.3 | 100 | 1.4 | 5.2 | | 12 | 29 |
| 212 | 0.31 | 134 | <2.7 | 6.5 | | 17 | 4 |
| 213 | 0.18 | 98 | 0.18 | 16 | 4 | 8 | 6.5 |
| 214 | 0.29 | 115 | 0.090 | <3 | 2.3 | 5.3 | 400 |
| 215 | 0.20 | 143 | 0.20 | <3 | | 20 | <0.23 |
| 216 | 0.21 | 132 | 0.64 | <3 | 4.2 | 19 | 3.1 |
| 217 | >9.4 | | 0.19 | 43 | | 17 | <7.3 |
| 218 | >40 | | | | | | |
| 219 | 0.28 | 113 | 0.19 | >300 | 78 | 130 | 5 |
| 220 | 1.5 | 109 | 0.95 | 10 | 7.2 | 14 | 940 |
| 221 | >40 | | | | | | |
| 222 | >40 | | | | | | |
| 223 | >40 | | | | | | |
| 224 | 0.19 | 92 | 0.16 | 6.3 | | 19 | 870 |
| 225 | 0.24 | 98 | 0.10 | 6.6 | | 22 | 10 |
| 226 | 0.30 | 105 | 0.62 | 12 | 11 | 16 | 870 |
| 227 | 0.42 | 102 | | | | | |
| 228 | 1.1 | 110 | | | | | |
| 229 | 3.3 | 55 | | | | | |
| 230 | 1 | 116 | | | | | |
| 231 | 0.48 | 112 | <0.31 | <3 | 7.7 | 13 | 17 |
| 232 | 1.1 | 108 | | | | | |
| 233 | 1.7 | 105 | | | | | |
| 234 | 0.088 | 110 | <0.30 | 4.7 | 6.5 | 9.3 | 690 |
| 235 | 5 | 75 | | | | | |
| 236 | 0.21 | 103 | 0.50 | 13 | | 14 | >1000 |
| 237 | 0.38 | 101 | 4.6 | 32 | | 17 | >1000 |
| 238 | 0.14 | 102 | | 42 | 13 | 27 | 890 |
| 239 | 0.13 | 100 | | | | | |
| 240 | 0.13 | 97 | 2.3 | 19 | | 12 | 780 |
| 241 | 0.14 | 99 | 0.69 | 12 | | 12 | 550 |
| 242 | 0.20 | 109 | | 110 | 26 | 30 | 900 |
| 243 | 0.099 | 96 | 2.2 | 58 | 26 | 110 | 900 |
| 244 | 0.10 | 111 | | 53 | | 36 | 240 |
| 245 | 0.64 | 104 | 5 | 45 | 13 | 15 | 980 |
| 246 | 0.29 | 85 | | 20 | | 16 | 860 |
| 247 | 0.050 | 104 | | 14 | 9.5 | 12 | 190 |
| 248 | 0.22 | 108 | <3.3 | 74 | 18 | 32 | 2 |
| 249 | 0.32 | 113 | 3.4 | 43 | 11 | 15 | 190 |
| 250 | 0.19 | 101 | <0.32 | 16 | 32 | 18 | 900 |
| 251 | 0.033 | 101 | | | | | |
| 252 | 0.78 | 86 | | | | | |
| 253 | 0.031 | 102 | <0.32 | 24 | | 8.8 | >1000 |
| 254 | 0.034 | 114 | 0.30 | 31 | | 12 | >1000 |
| 255 | 0.55 | 101 | 2 | 26 | 13 | 12 | 1000 |
| 256 | 0.25 | 99 | 0.050 | 8.1 | | 12 | <7 |
| 257 | 0.059 | 96 | 0.35 | 16 | | 9.5 | >1000 |
| 258 | 0.12 | 106 | 1.7 | 65 | 30 | 35 | >1000 |
| 259 | 0.058 | 97 | | | | | |
| 260 | 0.28 | 108 | 0.57 | 69 | | 69 | 360 |
| 261 | 0.13 | 107 | 0.89 | 57 | | 84 | >1000 |
| 262 | 0.026 | 95 | | | | | |
| 263 | 0.084 | 106 | | | | | |
| 264 | 0.082 | 101 | | | | | |
| 265 | 0.23 | 78 | | | | | |
| 266 | 0.11 | 103 | <0.34 | 68 | 9.4 | 8.8 | |
| 267 | >0.35 | 93 | 0.39 | 32 | | 14 | 680 |
| 268 | 0.86 | 84 | | | | | |
| 269 | 2.9 | 44 | | | | | |
| 270 | 0.12 | 107 | <0.26 | 120 | 32 | 38 | 2 |
| 271 | 0.23 | 98 | 0.81 | <3 | 3.7 | 7 | 920 |
| 272 | 4.9 | 107 | | | | | |
| 273 | >40 | | | | | | |
| 274 | 5.7 | 61 | | | | | |
| 275 | 11 | 83 | | | | | |
| 276 | 3.3 | 95 | | | | | |

TABLE 36-continued

| | Assay data | | | | | | |
|---|---|---|---|---|---|---|---|
| | Test A | | Test B<br>Human<br>Plasma<br>Protein<br>Binding | Test C<br>Human Liver<br>Microsomal<br>Stability<br>$Cl_{int}$ | Test D<br>Human<br>Hepatocyte<br>Stability<br>$Cl_{int}$ | Test E<br>Rat<br>Hepatocyte<br>Stability<br>$Cl_{int}$ | Test F<br>Solubility |
| Example | $EC_{50}$ (uM) | $S_{inf}$(%) | (% free) | (μl/min/mg) | (μL/min/10$^6$ cells) | (μL/min/10$^6$ cells) | (μM) |
| 277 | 7.4 | 122 | | | | | |
| 278 | 5 | 104 | | | | | |
| 279 | >40 | | | | | | |
| 280 | >40 | | | | | | |
| 281 | 0.87 | 170 | 0.31 | 5.5 | 5 | 9.1 | 11 |
| 282 | 0.49 | 105 | <0.25 | 6.2 | | 12 | 48 |
| 283 | 0.22 | 87 | <0.29 | 12 | | 15 | 220 |
| 284 | 0.82 | 85 | | | | | |
| 285 | 0.30 | 75 | | | | | |
| 286 | 13 | 29 | | | | | |
| 287 | 0.57 | 111 | | | | | |
| 288 | 0.23 | 107 | <0.32 | 5.1 | 5 | 21 | 24 |
| 289 | 0.47 | 112 | 1 | 21 | 7.2 | 11 | 36 |
| 290 | 0.20 | 105 | | | | | |
| 291 | 0.37 | 106 | <1.2 | 18 | | 22 | 13 |
| 292 | 0.077 | 110 | 1.2 | 24 | 4.6 | 14 | 18 |
| 293 | 0.39 | 118 | | 27 | 8.4 | 41 | 21 |
| 294 | 0.37 | 95 | | | | | |
| 295 | 0.50 | 100 | | | | | |
| 296 | 0.22 | 98 | <0.32 | 15 | 22 | 17 | 640 |
| 297 | 0.12 | 98 | <0.33 | 9.1 | 9.4 | 12 | 8 |
| 298 | 0.91 | 82 | | | | | |
| 299 | 2.9 | 81 | | | | | |
| 300 | 3.9 | 78 | | | | | |
| 301 | 7.3 | 69 | | | | | |
| 302 | 5.3 | 75 | | | | | |
| 303 | 0.26 | 114 | | | | | |
| 304 | 3.1 | 95 | | | | | |
| 305 | >40 | | | | | | |
| 306 | 3.1 | 73 | | | | | |
| 307 | 0.18 | 90 | | | | | |
| 308 | 1.1 | 109 | 0.16 | 4.9 | 14 | 33 | >1000 |
| 309 | 4 | 80 | | | | | |
| 310 | >40 | | | | | | |
| 311 | 7.7 | 67 | | | | | |
| 312 | 7.5 | 50 | | | | | |
| 313 | >40 | | | | | | |
| 314 | 7.8 | 74 | | | | | |
| 316 | 0.32 | 107 | | | | | |
| 317 | 1.2 | 75 | | | | | |
| 318 | 0.60 | 89 | 0.55 | 13 | | 37 | 710 |
| 319 | 0.75 | 79 | 0.44 | 18 | | 29 | 380 |
| 320 | 0.46 | 119 | 0.67 | 14 | 11 | 9.6 | >1000 |
| 321 | 0.34 | 101 | 0.45 | 33 | | 59 | 950 |
| 322 | 0.80 | 107 | | | | | |
| 323 | 0.42 | 108 | 9.3 | 58 | 16 | 21 | 850 |
| 324 | 0.19 | 101 | | | | | |
| 325 | 0.12 | 109 | <0.30 | 18 | 5 | | 880 |
| 326 | 0.11 | 114 | <0.35 | 65 | 8 | 4.6 | 8 |
| 327 | >40 | | | | | | |
| 328 | 0.19 | 117 | <0.10 | <3 | 11 | | |
| 329 | 0.14 | 108 | 0.81 | 30 | 5.6 | 26 | 1000 |
| 330 | 0.53 | 97 | | | | | |
| 331 | 0.26 | 90 | | | | | |
| 332 | 0.29 | 103 | | | | | |
| 333 | 0.15 | 98 | | | | | |
| 334 | 0.0043 | 96 | | | | | |
| 335 | 0.54 | 104 | | | | | |
| 338 | 4.1 | 104 | | | | | |
| 340 | 1.8 | 100 | | | | | |
| 341 | 0.20 | 86 | | | | | |
| 342 | 0.55 | 132 | | | | | |
| 344 | 0.034 | 93 | | | | | |
| 345 | >40 | | | | | | |
| 346 | 2.2 | 96 | | | | | |
| 347 | 0.0064 | 115 | | | | | |
| 348 | 0.56 | 101 | | | | | |
| 349 | 1.8 | 113 | | | | | |
| 350 | 3.9 | 97 | | | | | |

TABLE 36-continued

Assay data

| Example | Test A | | Test B Human Plasma Protein Binding | Test C Human Liver Microsomal Stability $Cl_{int}$ | Test D Human Hepatocyte Stability $Cl_{int}$ | Test E Rat Hepatocyte Stability $Cl_{int}$ | Test F Solubility |
|---|---|---|---|---|---|---|---|
| | $EC_{50}$ (uM) | $S_{inf}$(%) | (% free) | (µl/min/mg) | (µL/min/10$^6$ cells) | (µL/min/10$^6$ cells) | (µM) |
| 351 | 0.018 | 109 | | 64 | 15 | 46 | 590 |
| 352 | 0.0030 | 105 | 0.26 | | 13 | 38 | 340 |
| 353 | 0.00041 | 114 | <0.23 | 61 | 21 | 23 | 45 |
| 354 | 0.011 | 95 | | | | | |
| 355 | 0.037 | 114 | 2.1 | 32 | 8 | 19 | 430 |
| 356 | 2.2 | 119 | | | | | |
| 357 | 5.4 | 101 | | | | | |
| 358 | 5.1 | 99 | | | | | |
| 359 | 0.17 | 91 | | | | | |
| 360 | 0.10 | 101 | 15 | 8.4 | 3.6 | 17 | >1000 |
| 361 | 0.78 | 91 | | | | | |
| 364 | 0.014 | 106 | 11 | <5.1 | 6.2 | 19 | >1000 |
| 365 | 0.057 | 113 | 7.8 | 14 | 9.3 | 15 | 980 |
| 366 | 0.0022 | 103 | | | | | |
| 367 | 0.0032 | 110 | | | | | |
| 369 | 0.011 | 95 | | | | | |
| 370 | 0.024 | 102 | | | | | |
| 371 | 0.0011 | 125 | | | | | |
| 372 | 0.021 | 96 | | | | | |
| 373 | 0.025 | 105 | 3.9 | 23 | 5.1 | 16 | 1000 |
| 374 | 0.044 | 102 | 2.9 | 44 | 5.3 | 21 | 680 |
| 375 | 0.10 | 115 | 4.4 | 38 | 3.1 | 32 | 240 |
| 376 | 0.088 | 103 | 2.5 | 44 | 3.9 | 28 | 300 |
| 377 | 13 | 100 | | | | | |
| 378 | >2.5 | | | | | | |
| 379 | 0.48 | 100 | | | | | |
| 380 | >2.5 | | | | | | |
| 381 | 0.11 | 114 | 3.8 | 36 | 6.1 | 21 | 1000 |
| 382 | 0.13 | 90 | | | | | |
| 383 | 0.12 | 89 | | | | | |
| 384 | 0.13 | 108 | | | | | |
| 385 | 0.030 | 106 | 4.1 | 50 | 8 | 19 | 780 |
| 386 | 0.070 | 114 | | | | | |
| 387 | 0.012 | 99 | | | | | |
| 388 | 0.0036 | 103 | 3.4 | 34 | 49 | 55 | 680 |
| 389 | 0.0095 | 106 | 6 | 5.8 | 8 | 11 | 910 |
| 390 | 0.18 | 95 | | | | | |
| 391 | 0.11 | 99 | | | | | |
| 392 | 0.0086 | 104 | 2.7 | 36 | 4.7 | 15 | 470 |
| 393 | 0.053 | 96 | 1.4 | 37 | 6.7 | 12 | 53 |
| 394 | >40 | | | | | | |
| 395 | 0.031 | 101 | | | | | |
| 396 | 0.64 | 91 | 5 | 47 | 16 | 16 | 21 |
| 397 | >40 | | | | | | |
| 398 | 0.13 | 90 | | | | | |
| 399 | 0.053 | 92 | | | | | |
| 400 | 0.18 | 91 | | | | | |
| 401 | 0.049 | 115 | 2.7 | 16 | 5.4 | 17 | 1000 |
| 402 | 0.62 | 131 | | | | | |
| 403 | 0.067 | 104 | 1.5 | 81 | 13 | 25 | 660 |
| 404 | 0.086 | 109 | 2.3 | 50 | 11 | 19 | 1000 |
| 405 | 0.20 | 92 | | | | | |
| 406 | 0.33 | 96 | | | | | |
| 407 | 0.26 | 99 | | | | | |
| 408 | 0.024 | 106 | 0.87 | 32 | 6.5 | 20 | 670 |
| 409 | 0.015 | 107 | 3.4 | 18 | 3.1 | 7.1 | 960 |
| 410 | 0.0062 | 105 | 0.48 | 20 | 49 | 21 | 280 |
| 411 | 0.024 | 108 | 1.8 | 7.9 | 2.1 | 17 | 710 |
| 412 | 0.037 | 110 | 5.3 | 13 | 2.6 | 24 | 930 |
| 413 | 0.016 | 107 | 1.5 | 9.3 | 4.5 | 21 | 820 |
| 414 | 0.021 | 100 | | | | | |
| 415 | 1.7 | 103 | | | | | |
| 416 | 0.32 | 103 | 1.2 | 9.9 | | 10 | >1000 |
| 417 | 0.0098 | 102 | 4.8 | 24 | 5.1 | 17 | 900 |
| 418 | 0.064 | 100 | | | | | |
| 419 | 0.16 | 107 | | | | | |
| 420 | 0.033 | 107 | | | | | |
| 421 | 0.044 | 96 | | | | | |
| 422 | 0.086 | 102 | | | | | |

TABLE 36-continued

Assay data

| | Test A | | Test B<br>Human<br>Plasma<br>Protein<br>Binding | Test C<br>Human Liver<br>Microsomal<br>Stability<br>$Cl_{int}$ | Test D<br>Human<br>Hepatocyte<br>Stability<br>$Cl_{int}$ | Test E<br>Rat<br>Hepatocyte<br>Stability<br>$Cl_{int}$ | Test F<br>Solubility |
|---|---|---|---|---|---|---|---|
| Example | $EC_{50}$ (uM) | $S_{inf}$(%) | (% free) | (μl/min/mg) | (μL/min/10$^6$ cells) | (μL/min/10$^6$ cells) | (μM) |
| 423 | 2.1 | 89 | | | | | |
| 424 | 0.078 | 100 | 6.7 | 13 | 10 | 21 | 990 |
| 425 | 17 | 78 | | | | | |
| 426 | >40 | | | | | | |
| 427 | 0.68 | 86 | | | | | |
| 428 | 5.1 | 80 | | | | | |
| 429 | >40 | | | | | | |
| 430 | >0.23 | 101 | 3 | 61 | | 22 | 760 |
| 431 | 0.13 | 115 | | | | | |
| 432 | 0.016 | 121 | | | | | |
| 433 | 0.0053 | 109 | 0.38 | 43 | 14 | 17 | 240 |
| 434 | 0.59 | 82 | <0.36 | 110 | | 13 | 130 |
| 435 | 0.35 | 103 | 1.4 | 63 | 150 | >300 | 880 |
| 436 | 0.54 | 115 | 0.82 | 70 | 97 | >300 | 220 |
| 437 | 0.95 | 104 | | | | | |
| 438 | 0.26 | 112 | | | | | |
| 439 | 0.17 | 104 | | | | | |
| 440 | 1.2 | 111 | | | | | |
| 441 | >40 | | | | | | |
| 442 | 0.58 | 103 | | | | | |
| 443 | 0.54 | 101 | 1.5 | 31 | 26 | 21 | 760 |
| 444 | 0.12 | 117 | 2.5 | 18 | 15 | 22 | >1000 |
| 445 | 0.15 | 101 | | | | | |
| 446 | 0.90 | 98 | | | | | |
| 447 | 0.83 | 94 | | | | | |
| 448 | 2.6 | 77 | | | | | |
| 449 | 1.6 | 108 | | | | | |
| 450 | 0.61 | 107 | | | | | |
| 451 | 0.31 | 127 | 0.93 | 15 | | 68 | 700 |
| 452 | 0.98 | 104 | | | | | |
| 453 | 2 | 155 | | | | | |
| 454 | 1.9 | 76 | | | | | |
| 455 | 0.16 | 91 | | | | | |
| 456 | 3.6 | 129 | | | | | |
| 457 | 2.9 | 56 | | | | | |
| 458 | 0.11 | 104 | | | | | |
| 459 | 0.32 | 91 | | | | | |
| 460 | 0.37 | 103 | 0.32 | 300 | | 47 | 2 |
| 461 | 0.19 | 100 | | 7.5 | 2.9 | 7.4 | 980 |
| 462 | 0.35 | 125 | | | | | |
| 463 | 0.34 | 111 | | | | | |
| 464 | 0.064 | 104 | 0.54 | 57 | | 30 | 200 |
| 465 | 0.12 | 97 | 0.76 | 74 | | 36 | 300 |
| 466 | 0.093 | 106 | 2.1 | 37 | | 29 | >1000 |
| 467 | 0.019 | 99 | 3.7 | 37 | | 47 | >1000 |
| 468 | 0.0041 | 93 | | | | | |
| 469 | 0.036 | 99 | | | | | |
| 470 | 0.017 | 102 | | | | | |
| 471 | 0.091 | 95 | | | | | |
| 472 | 0.28 | 91 | | | | | |
| 473 | 0.14 | 104 | | | | | |
| 474 | 0.65 | 118 | | | | | |
| 475 | 0.20 | 100 | | | | | |
| 476 | 0.30 | 81 | | | | | |
| 477 | 1.1 | 84 | | | | | |
| 478 | 0.0066 | 99 | | | | | |
| 479 | 0.0078 | 104 | | | | | |
| 480 | 0.098 | 100 | | | | | |
| 481 | 0.28 | 96 | | | | | |
| 482 | 0.011 | 112 | 1.5 | 56 | 18 | 78 | >1000 |
| 483 | 0.61 | 92 | | | | | |
| 484 | 0.25 | 101 | <0.31 | 9.4 | 7.2 | 13 | 400 |
| 485 | 0.28 | 95 | | | | | |
| 486 | 0.0076 | 107 | 6.8 | 35 | 22 | 28 | 950 |
| 487 | >40 | | | | | | |
| 488 | <0.0036 | 115 | 0.13 | 23 | 12 | 22 | 1000 |
| 489 | 0.012 | 115 | | | | | |
| 490 | 0.30 | 127 | 1.9 | 30 | 17 | 16 | 940 |
| 491 | 0.042 | 102 | 2.1 | 42 | 15 | 23 | 550 |

TABLE 36-continued

Assay data

| | Test A | | Test B Human Plasma Protein Binding | Test C Human Liver Microsomal Stability $Cl_{int}$ | Test D Human Hepatocyte Stability $Cl_{int}$ | Test E Rat Hepatocyte Stability $Cl_{int}$ | Test F Solubility |
|---|---|---|---|---|---|---|---|
| Example | $EC_{50}$ (uM) | $S_{inf}$(%) | (% free) | (μl/min/mg) | (μL/min/$10^6$ cells) | (μL/min/$10^6$ cells) | (μM) |
| 492 | 0.16 | 106 | 1.8 | 36 | 18 | 19 | 1000 |
| 493 | 0.42 | 108 | 1.3 | <3 | 2.4 | 4 | 38 |
| 494 | 6.9 | 90 | | | | | |
| 495 | 0.12 | 98 | | | | | |
| 496 | >40 | | | | | | |
| 497 | 0.32 | 108 | 3.3 | <3 | 4.4 | 19 | >1000 |
| 498 | >0.030 | 113 | 0.86 | 23 | 7.7 | 17 | >980 |
| 499 | 0.10 | 128 | 0.51 | 200 | 28 | 96 | 13 |
| 500 | 0.064 | 110 | 0.44 | >300 | 45 | 98 | 8 |
| 501 | 2.5 | 82 | | | | | |
| 502 | 0.0085 | 106 | 4 | <4.5 | 5.3 | 7.2 | 910 |
| 503 | 0.060 | 102 | | | | | |
| 504 | 0.60 | 91 | | | | | |
| 505 | 0.014 | 94 | | | | | |
| 506 | 0.32 | 98 | | | | | |
| 507 | 0.54 | 118 | | | | | |
| 508 | 0.013 | 112 | | | | | |
| 509 | 0.013 | 125 | <0.070 | 9.4 | 5 | 7 | 1000 |
| 510 | 1.6 | 63 | | | | | |
| 511 | 0.037 | 117 | | | | | |
| 512 | 0.023 | 104 | | 12 | 4.2 | 25 | 880 |
| 513 | >40 | | | | | | |
| 514 | 15 | 107 | | | | | |
| 515 | >40 | | | | | | |
| 516 | 0.0080 | 104 | | | | | |
| 517 | >40 | | | | | | |
| 518 | 0.13 | 95 | 2.1 | 22 | 5 | 13 | 990 |
| 519 | >17 | 101 | | | | | |
| 520 | 0.00049 | 108 | <0.070 | 12 | 5.7 | 7.5 | 460 |
| 521 | 0.71 | 99 | | | | | |
| 522 | >40 | | | | | | |
| 523 | 0.27 | 95 | 4 | >300 | 49 | 34 | 920 |
| 524 | 0.025 | 110 | 3.6 | 16 | 6.2 | 23 | 920 |
| 525 | >40 | | | | | | |
| 526 | >40 | | | | | | |
| 527 | 0.080 | 101 | | | | | |
| 528 | >40 | | | | | | |
| 529 | 0.50 | 96 | | | | | |
| 530 | 0.17 | 96 | | | | | |
| 531 | >40 | | | | | | |
| 532 | 0.14 | 104 | | | | | |
| 533 | >40 | | | | | | |
| 534 | 0.099 | 106 | 7.1 | 16 | 43 | 19 | >1000 |
| 535 | >40 | | | | | | |
| 536 | 0.0051 | 97 | 3.3 | 250 | 130 | 43 | 420 |
| 537 | 6 | 77 | | | | | |
| 538 | 11 | 100 | | | | | |
| 539 | 0.0031 | 102 | 3.2 | 63 | 64 | 28 | 700 |
| 540 | 0.020 | 104 | 6 | 20 | 8.5 | 19 | 1000 |
| 541 | 18 | 100 | | | | | |
| 542 | 0.011 | 110 | 2.5 | 66 | 32 | 12 | 800 |
| 543 | 0.45 | 88 | | | | | |
| 544 | >40 | | | | | | |
| 545 | 0.045 | 91 | | | | | |
| 546 | >40 | | | | | | |
| 547 | 1.7 | 114 | | | | | |
| 548 | 21 | 117 | | | | | |
| 549 | 1.3 | 94 | | | | | |
| 550 | >40 | | | | | | |
| 551 | 0.70 | 107 | | | | | |
| 552 | 0.14 | 98 | 0.060 | 7.2 | 12 | 16 | >1000 |
| 553 | >50 | | <0.30 | 9.9 | 9.2 | 18 | >1000 |
| 554 | 0.15 | 103 | <0.30 | <3 | 5.4 | 18 | 700 |
| 555 | >50 | | <0.30 | 21 | 13 | 18 | 560 |
| 556 | 0.13 | 114 | | | | | |
| 557 | 3.1 | 68 | | | | | |
| 558 | >40 | | | | | | |
| 559 | 1.2 | 102 | 2.5 | 9.4 | 4.1 | 8.4 | 900 |
| 560 | >40 | | | | | | |

TABLE 36-continued

Assay data

| | Test A | | Test B Human Plasma Protein Binding | Test C Human Liver Microsomal Stability $Cl_{int}$ | Test D Human Hepatocyte Stability $Cl_{int}$ | Test E Rat Hepatocyte Stability $Cl_{int}$ | Test F Solubility |
|---|---|---|---|---|---|---|---|
| Example | $EC_{50}$ (uM) | $S_{inf}$ (%) | (% free) | (µl/min/mg) | (µL/min/$10^6$ cells) | (µL/min/$10^6$ cells) | (µM) |
| 561 | 0.13 | 104 | 3.7 | 17 | 6.3 | 55 | 930 |
| 562 | >40 | | | | | | |
| 563 | >40 | | | | | | |
| 564 | >40 | | | | | | |
| 565 | 0.023 | 113 | | | | | |
| 566 | >40 | | | | | | |
| 567 | 10 | 86 | | | | | |
| 568 | >40 | | | | | | |
| 569 | 1.1 | 97 | | | | | |
| 570 | 9.2 | 128 | | | | | |
| 571 | 0.0025 | 100 | | | | | |
| 572 | >40 | | | | | | |
| 573 | 0.28 | 94 | | | | | |
| 574 | >40 | | | | | | |
| 575 | 0.29 | 101 | | | | | |
| 576 | 4.2 | 118 | | | | | |
| 577 | >40 | | | | | | |
| 578 | >40 | | | | | | |
| 579 | 13 | 120 | | | | | |
| 580 | >40 | | | | | | |
| 581 | 3.2 | 94 | | | | | |
| 582 | 0.029 | 104 | | | | | |
| 583 | 0.35 | 84 | | | | | |
| 584 | 0.00070 | 106 | | | | | |
| 585 | 0.24 | 93 | | | | | |
| 586 | 0.0015 | 105 | 0.33 | 12 | 4.3 | 17 | 190 |
| 587 | 2.2 | 113 | | | | | |
| 588 | 0.0076 | 95 | | | | | |
| 589 | 2.1 | 83 | | | | | |
| 590 | >40 | | | | | | |
| 591 | 0.15 | 111 | <0.36 | 19 | 140 | 28 | >1000 |
| 592 | 0.0058 | 100 | 6.3 | 19 | 5.6 | 18 | >890 |
| 593 | 0.52 | 118 | | | | | |
| 594 | 0.53 | 96 | | | | | |
| 595 | 0.57 | 116 | | | | | |
| 596 | 1.1 | 105 | | | | | |
| 597 | 0.40 | 106 | | | | | |
| 598 | 0.89 | 99 | | | | | |
| 599 | 0.26 | 91 | | | | | |
| 600 | 0.14 | 104 | | | | | |
| 601 | 2.1 | 116 | | | | | |
| 602 | 0.25 | 100 | | | | | |
| 603 | 0.094 | 99 | | | | | |
| 604 | 0.11 | 105 | 6.7 | 110 | 13 | 14 | 10 |
| 605 | 0.079 | 106 | 8.6 | 25 | 4.3 | 12 | 890 |
| 606 | 0.42 | 90 | | | | | |
| 607 | 0.16 | 92 | | | | | |
| 608 | 0.075 | 115 | 3.5 | 20 | 3.4 | 8.2 | 880 |
| 609 | 0.40 | 108 | | | | | |
| 610 | 0.23 | 105 | | | | | |
| 611 | >40 | | | | | | |
| 612 | 3.1 | 119 | | | | | |
| 613 | 0.076 | 109 | | | | | |
| 614 | 0.15 | 96 | | | | | |
| 615 | 0.12 | 100 | | | | | |
| 616 | 2 | 101 | | | | | |
| 617 | 0.050 | 101 | 2.4 | 120 | 12 | 13 | 810 |
| 618 | 0.10 | 93 | | | | | |
| 619 | 0.39 | 103 | | | | | |
| 620 | 0.69 | 93 | | | | | |
| 621 | 0.024 | 114 | 12 | <3 | <1.2 | 15 | 910 |
| 622 | 0.024 | 105 | 17 | <5.1 | 1.7 | 11 | >860 |
| 623 | 0.18 | 104 | | | | | |
| 624 | 0.026 | 113 | 12 | 16 | 3.3 | 7.9 | 1000 |

Human RXFP1 cGMP Production Assay (Test G)

To profile compounds for RXFP1 agonist activity with respect to cGMP production, the Green GENIe cGMP Assay (Montana Molecular; catalogue number D800G) was employed. The assay is based on an nmNeonGreen fusion protein fluorescent biosensor delivered to mammalian cells in a BacMam vector. Fluorescence is reduced when cGMP is bound to the biosensor.

Preparation of Assay Reagents

Assay buffer: DPBS (Gibco; 14040133) containing 0.100 BSA (Sigma; A8806)

Cells: HEK293s cells stably transfected with human RXFP1 in pIRESneo3 was employed. Cells were cultured in DMEM medium (Gibco; 31966) with 10% FBS complemented with 0.8 mg/mL to maintain RXFP1 expression.

Step by Step Protocol for Running the Assay:

Day 1

1. Cells were splitted one day ahead of transduction and seeded to 63 000 cells/cm2 in DMEM medium with 10% FBS without antibiotics in a tissue culture flask.

Day 2

2. After PBS wash cells were detached using accutase (Gibco; 1737341), resuspended in medium and collected in a 50 mL tube.
3. Cells were counted with a CEDEX (Innovatis) and diluted with medium to 267 000 cell/mL.
4. A viral transduction mastermix was prepared by mixing reagents in the following proportions for a single well:
   6 µL GENIe BacMAM vector
   0.2 µL 500 mM sodium butyrate
   13.8 µL DMEM medium with 10% FBS
   20 µL total volume
5. Cells and transduction mastermix were mixed in proportions 30 µL cells and 20 µL mastermix for a single well.
6. 50 µL cell-transduction mix from above was dispensed per well into Black poly-D-lysine coated µclear 384-well plates (Greiner; 781946).
7. Plate was incubated in the dark at 37° C., 5% $CO_2$ for 24 h.

Day 3

8. Medium was removed from plates using a Bluewasher (BluCatBio).
9. 20 µL assay buffer was added with a Multidrop Combi (ThermoFisher).
10. Plate was incubated in the dark at room temperature for 30 min prior to assaying.
11. Plates were assayed using a FLIPR Tetra (Molecular Devices): 10 µL compound diluted with assay buffer was added to each well by the FLIPR Tetra and measuring green fluorescence over time for up to 3 h.

Data was processed using Screener software (Genedata A G). After subtraction of background fluorescence (before addition of compounds), area under curve values from 0 to 90 min after compound addition was used for calculation of responses. Concentration response data were fitted with a four parameter logistic fit and $EC_{50}$ values (nM) are reported in Table 37.

Human RXFP1 Phospho-ERK Assay (Test H)

To profile compounds for RXFP1 agonist activity with respect to ERK phosphorylation, the advanced phospho-ERK (Thr202/Tyr204) cellular kit (CisBio; 64AERPEH) was employed. The assay uses two antibodies. One labeled with a donor fluorophore (Eu cryptate), a second with an acceptor (d2). The first antibody specific binds to phosphorylated ERK, the second binds another motif of ERK and independently of its phosphorylation state. ERK phosphorylation enables immune-complex formation involving the two antibodies, thereby generating a FRET signal. Its intensity is proportional to the concentration of phosphorylated ERK in the sample. Assay was performed according to manufacturers recommendations.

Preparation of Assay Reagents

Cells: HEK293s cells stably transfected with human RXFP1 in pIRESneo3 was employed. Cells were cultured in DMEM medium (Gibco; 31966) with 10% FBS complemented with 0.8 mg/mL to maintain RXFP1 expression. Assay was performed on cells kept in continuous culture.

Dilution of test compounds: Compounds were diluted to desired concentrations with serum-free DMEM without phenol red (Gibco; 31053-038). DMSO concentration was adjusted to 0.4%.

Antibody mix: The Eu and d2 labelled anti ERK1/2 antibodies were separately diluted 20-fold with detection buffer provided in the kit. Shortly prior to the experiment, equal volumes of each diluted antibody solution were combined to an antibody mix.

Step by Step Protocol for Running the Assay:

Day 1

1. Cells were detached from culture flasks using accutase (Gibco; 1737341), resuspended in DMEM medium without phenol red containing 10% FBS and collected in a 50 mL tube.
2. Cells were counted with a CEDEX (Innovatis) and diluted with the medium above to 320 000 cell/mL.
3. 100 µL cell suspension was dispensed per well into Black µclear poly-D-lysine coated µclear 96-well plates (Greiner; 655946).
4. Plates were incubated at 37° C., 5% $CO_2$ for 24 h.

Day 2

5. Serum starvation: Medium was removed and replaced with 50 µL serum-free DMEM without phenol red. Plates were incubated at 37° C., 5% $CO_2$ for 5 h.
6. 50 µL test compound solutions were added per well.
7. Plates were incubated at room temperature for 5 min.
8. Stimulation was stopped by rapidly removing medium and adding 50 µL lysis buffer (diluted to 1×final concentration prior to addition) per well.
9. Plates were transferred to −80° C. and lysates frozen.

Day 3

10. Plates were thawed and shaken at room temperature for 30 min.
11. Cells lysates were homogenized by pipetting.
12. 16 µL homogenate per well was transferred to white low volume 384-well plates (Greiner; 784075)
13. 4 µL antibody mix was added per well.
14. Plates were incubated at room temperature in the dark for 4 h.
15. Homogenous Time-Resolved Fluorescence (HTRF) signal was detected with a Pherastar (BMG Labtech) reader ($\lambda ex=340$ nm, $\lambda em=665$ and 615 nm).

HTRF ratio data was processed using Screener software (Genedata AG). Concentration response data were fitted with a four parameter logistic fit and $EC_{50}$ value (nM) reported in Table 37.

TABLE 37

Assay Data

| Compound | Test G cGMP assay $EC_{50}$ (nM) | Test H phospo-ERK assay $EC_{50}$ (nM) |
|---|---|---|
| Example 1 | 50 | 6.3 |
| Example 3 | 2200 | 1092 |
| Example 208 | 9.3 | 1.2 |
| Example 353 | 3.7 | 0.36 |
| Example 433 | 19 | |
| Example 552 | 300 | 81 |
| Example 592 | 29 | 2.5 |
| Example 621 | 72 | 6.8 |
| Example 622 | 107 | 5.2 |
| relaxin2 | 0.085 | 0.038 |

Those skilled in the art will appreciate that the biological assays described above may be performed using alternative equipment and minor variations to the protocol without significantly affecting the results.

The above description of illustrative embodiments is intended only to acquaint others skilled in the art with Applicant's invention, its principles, and its practical application so that others skilled in the art may readily adapt and apply the invention in its numerous forms, as they may be best suited to the requirements of a particular use. This description and its specific examples, while indicating embodiments of this invention, are intended for purposes of illustration only. This invention, therefore, is not limited to the illustrative embodiments described in this specification, and may be variously modified. In addition, it is to be appreciated that various features of the invention that are, for clarity reasons, described in the context of separate embodiments, also may be combined to form a single embodiment. Conversely, various features of the invention that are, for brevity reasons, described in the context of a single embodiment, also may be combined to form sub-combinations thereof.

Any publications disclosed within the specification are hereby incorporated by reference.

The invention claimed is:

1. A compound which is

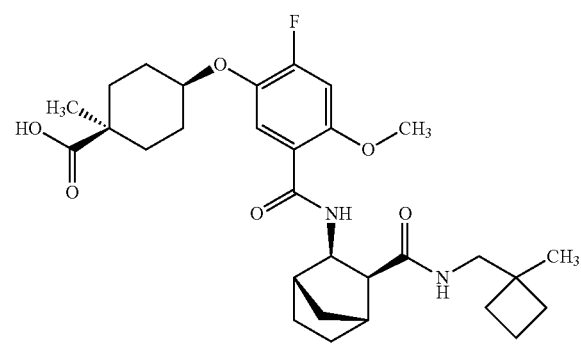 [SMILES: COc1cc(F)c(O[C@H]2CC[C@@](C)(C(=O)O)CC2)cc1C(=O)N[C@@H]1[C@H]2CC[C@H](C2)[C@@H]1C(=O)NCC1(C)CCC1]

or a pharmaceutically acceptable salt thereof.

2. A pharmaceutical composition comprising the compound of claim 1, or a pharmaceutically acceptable salt thereof, and a pharmaceutically acceptable excipient.

3. The compound of claim 1, which is

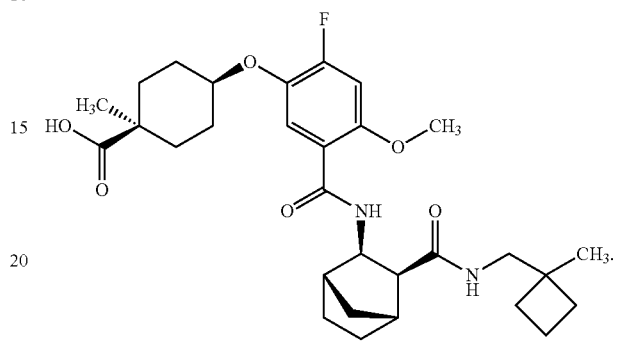

4. The compound of claim 1, which is a pharmaceutically acceptable salt of

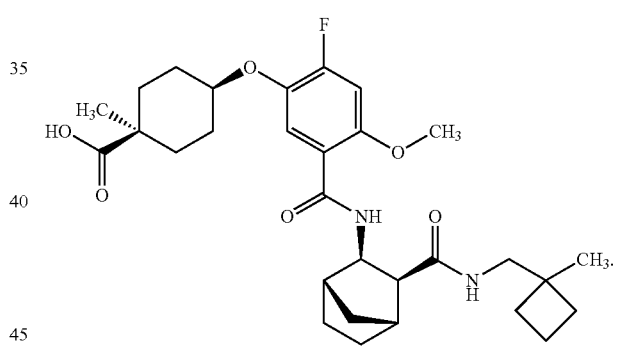

5. A pharmaceutical composition comprising the compound of claim 3 and a pharmaceutically acceptable excipient.

6. A pharmaceutical composition comprising the compound of claim 4 and a pharmaceutically acceptable excipient.

* * * * *